(12) United States Patent
Lamb et al.

(10) Patent No.: US 8,481,001 B2
(45) Date of Patent: Jul. 9, 2013

(54) COMBINATION THERAPIES COMPRISING QUINOXALINE INHIBITORS OF P13K-ALPHA FOR USE IN THE TREATMENT OF CANCER

(75) Inventors: Peter Lamb, Oakland, CA (US); David Matthews, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 541 days.

(21) Appl. No.: 12/595,236

(22) PCT Filed: Apr. 8, 2008

(86) PCT No.: PCT/US2008/004570
§ 371 (c)(1),
(2), (4) Date: Feb. 25, 2010

(87) PCT Pub. No.: WO2008/127594
PCT Pub. Date: Oct. 23, 2008

(65) Prior Publication Data
US 2011/0123434 A1  May 26, 2011

Related U.S. Application Data

(60) Provisional application No. 60/923,164, filed on Apr. 11, 2007.

(51) Int. Cl.
*A61K 31/5377* (2006.01)
*A61K 31/551* (2006.01)
*A61K 39/395* (2006.01)

(52) U.S. Cl.
USPC .......... 424/1.11; 514/157; 514/249; 514/250; 514/234.8; 514/218; 424/130.1; 424/133.1; 424/142.1; 424/138.1

(58) Field of Classification Search
None
See application file for complete search history.

(56) References Cited

U.S. PATENT DOCUMENTS

| 7,989,622 B2 | 8/2011 | Bajjalieh et al. |
| 8,044,062 B2 | 10/2011 | Baik et al. |

(Continued)

FOREIGN PATENT DOCUMENTS

| WO | WO2004/064734 | * | 8/2004 |
| WO | WO 2007/023186 A1 | | 1/2007 |

(Continued)

OTHER PUBLICATIONS

International Search Report mailed on Feb. 23, 2009, for International Application No. PCT/US2008/004570 filed on Apr. 8, 2008, 4 pages.

(Continued)

*Primary Examiner* — Mina Haghighatian
*Assistant Examiner* — Erin Hirt
(74) *Attorney, Agent, or Firm* — Honigman Miller Schwartz and Cohn LLP; Heidi M. Berven; Jonathan P. O'Brien

(57) ABSTRACT

The present invention provides methods of treating cancer by administering a compound of Formula I, optionally as a pharmaceutically acceptable salt, solvate and/or hydrate thereof, in combination with other cancer treatments.

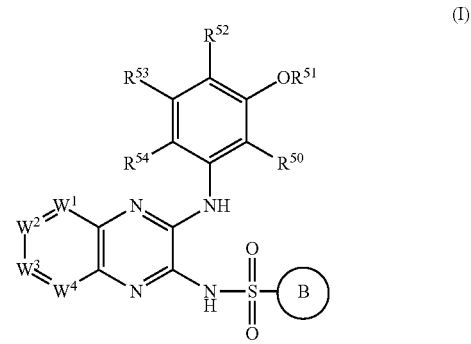

13 Claims, 6 Drawing Sheets

U.S. PATENT DOCUMENTS

| | | |
|---|---|---|
| 2010/0075947 A1 | 3/2010 | Aftab et al. |
| 2010/0209420 A1 | 8/2010 | Lamb et al. |
| 2011/0207712 A1 | 8/2011 | Bajjalieh et al. |
| 2011/0237608 A1 | 9/2011 | Baik et al. |

FOREIGN PATENT DOCUMENTS

| | | | |
|---|---|---|---|
| WO | WO2007/023186 | * | 3/2007 |
| WO | WO2007/044729 | * | 4/2007 |
| WO | WO 2007/044729 A2 | | 4/2007 |
| WO | WO 2007/044729 A3 | | 4/2007 |
| WO | WO 2008/021389 A2 | | 2/2008 |
| WO | WO 2008/021389 A3 | | 2/2008 |
| WO | WO 2008/101979 A1 | | 8/2008 |

OTHER PUBLICATIONS

U.S. Appl. No. 13/568,649, filed Aug. 7, 2012.

* cited by examiner

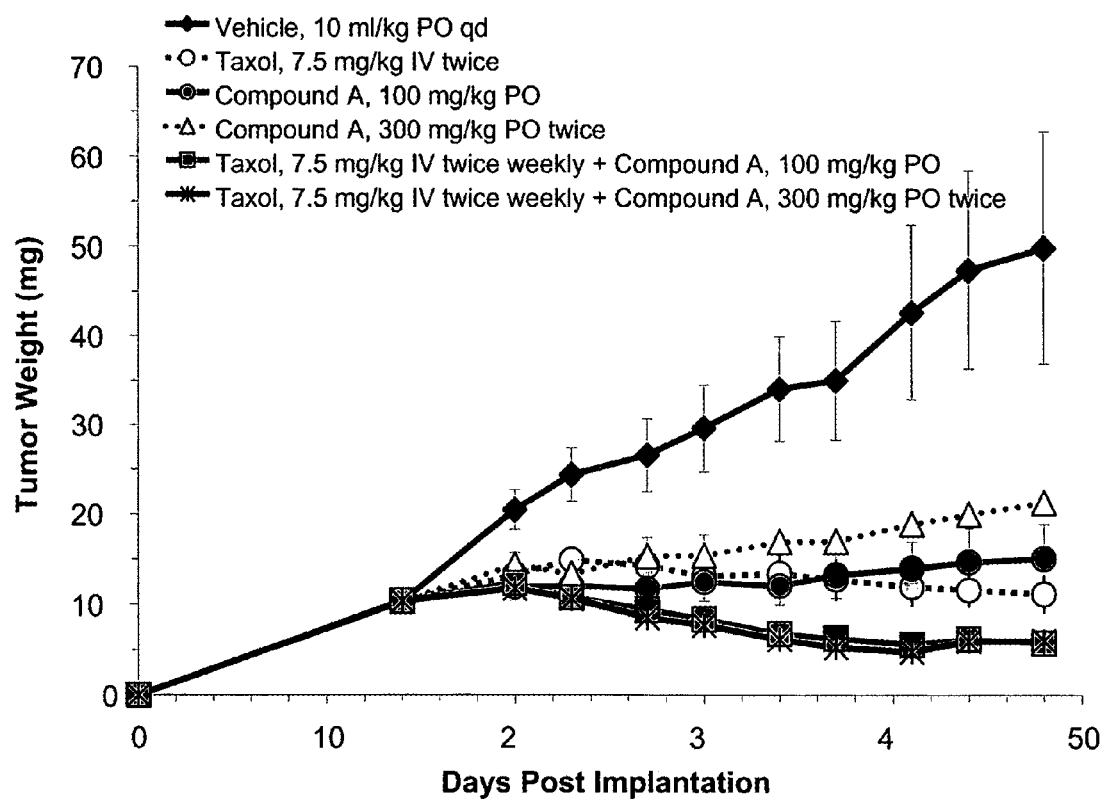
Figure 1. Compound A + Taxol in PC-3 Prostate Carcinoma Tumor Model

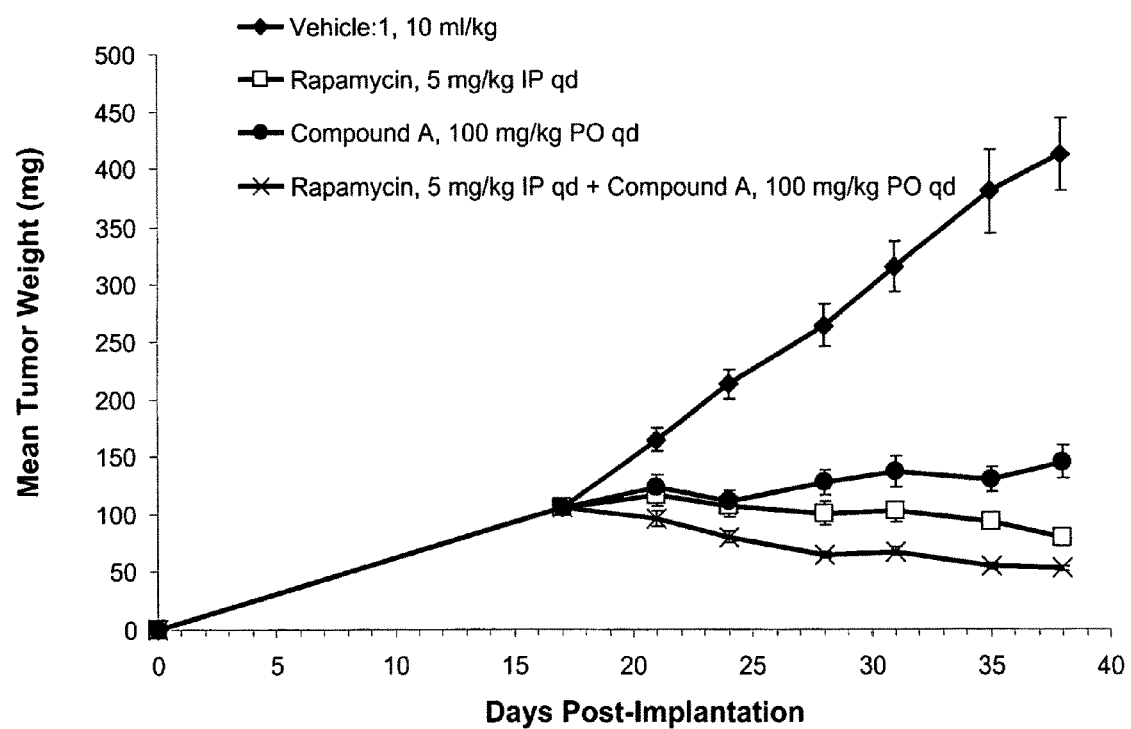
Figure 2. Compound A + Rapamycin in PC-3 Prostate Carcinoma Tumor Model

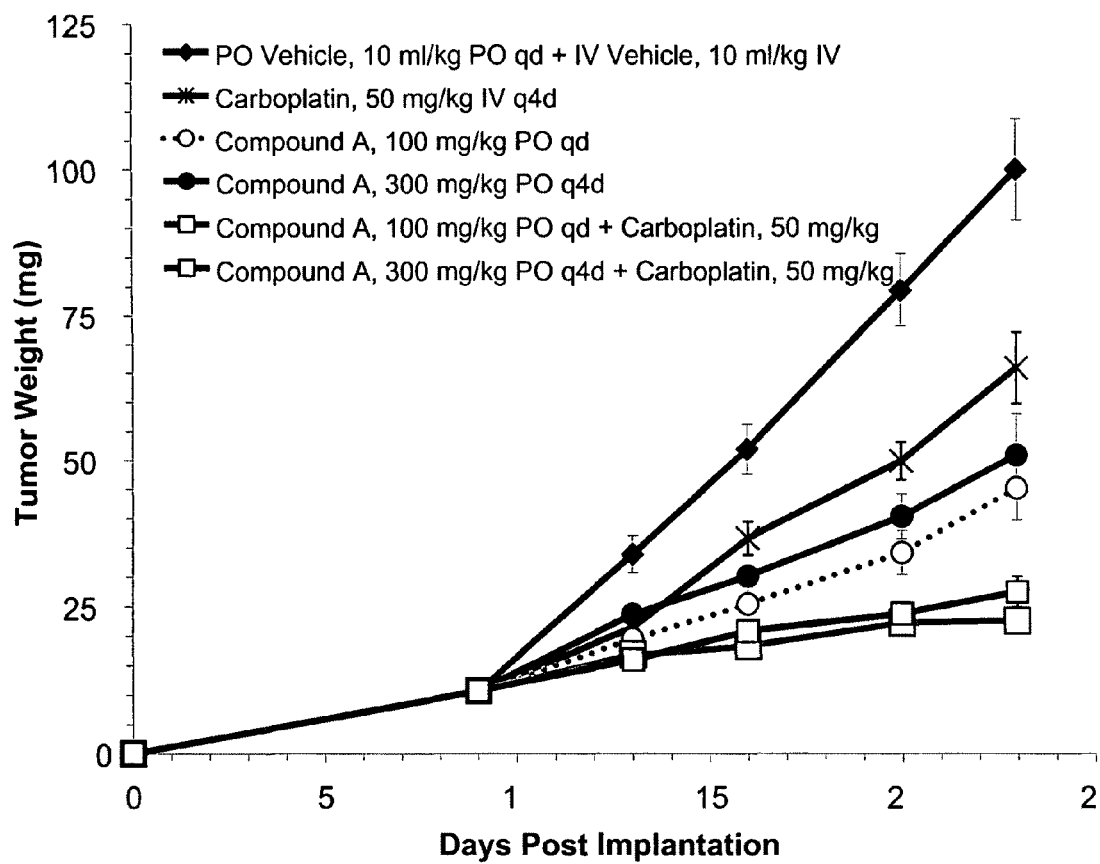
Figure 3. Compound A + Carboplatin in Calu-6 NSCLC Tumor Model

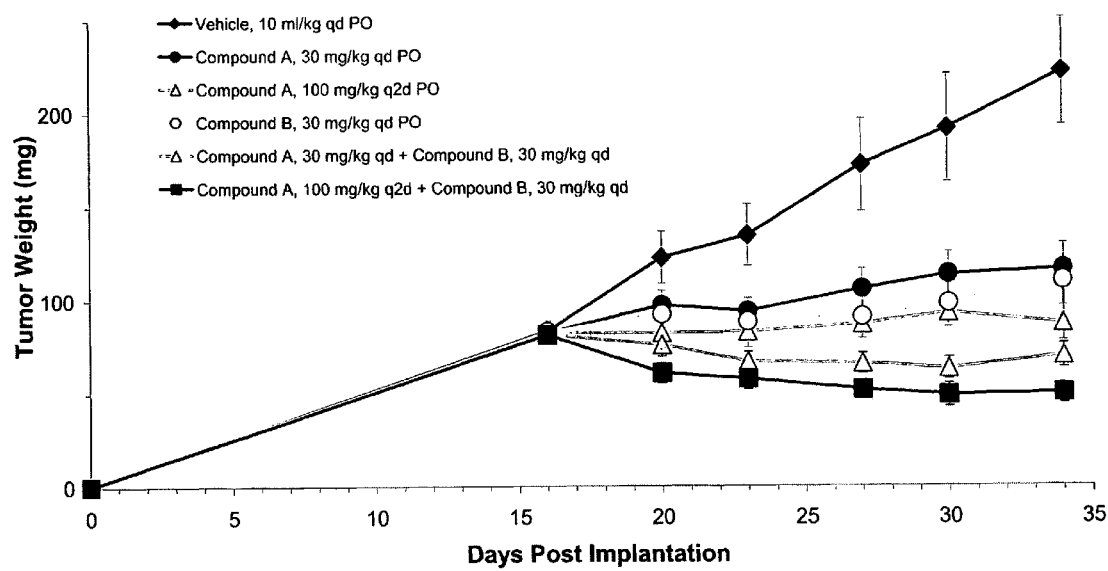
Figure 4a. Compound A + Compound B in A549 Non-small Cell Lung Cancer Tumor Model Figure 4b-1. Compound A + Compound B in MCF7 Breast Cancer Tumor Model (Study 1)
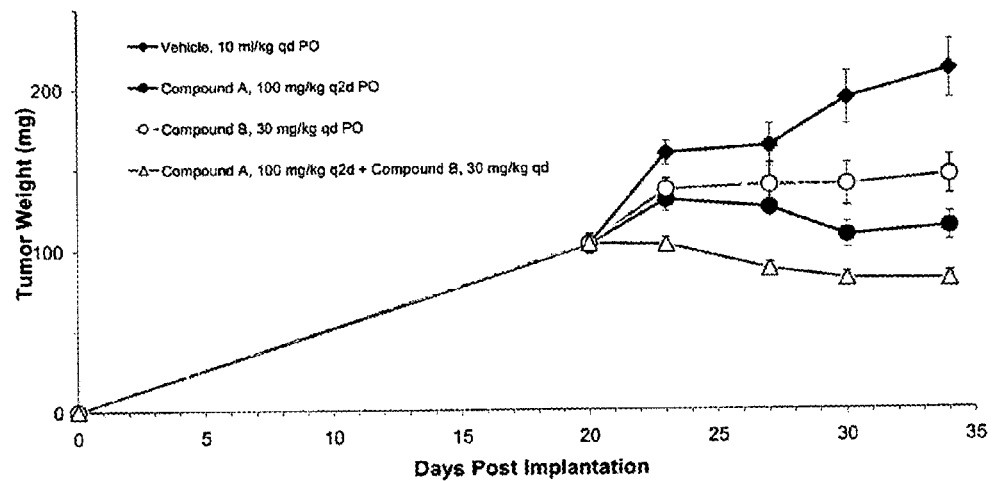
Figure 4b-2. Compound A + Compound B in MCF7 Breast Cancer Tumor Model (Study 2)
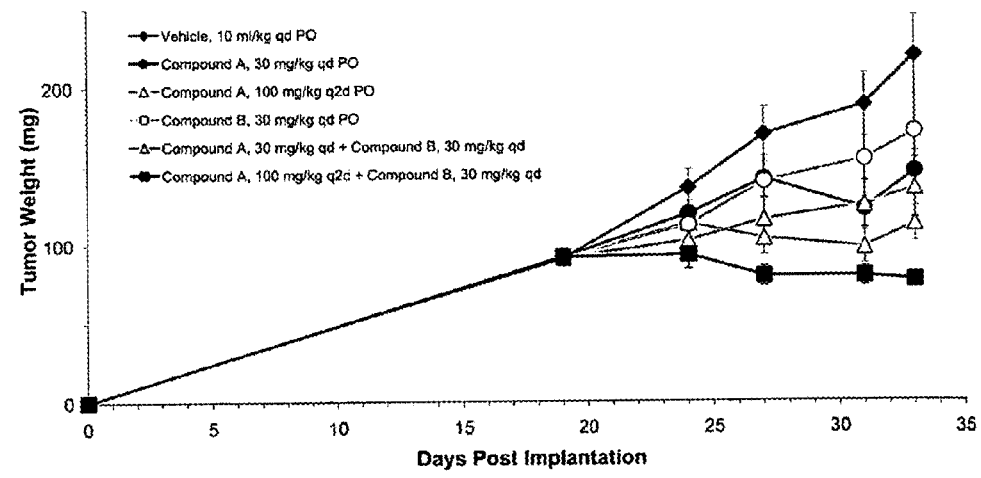

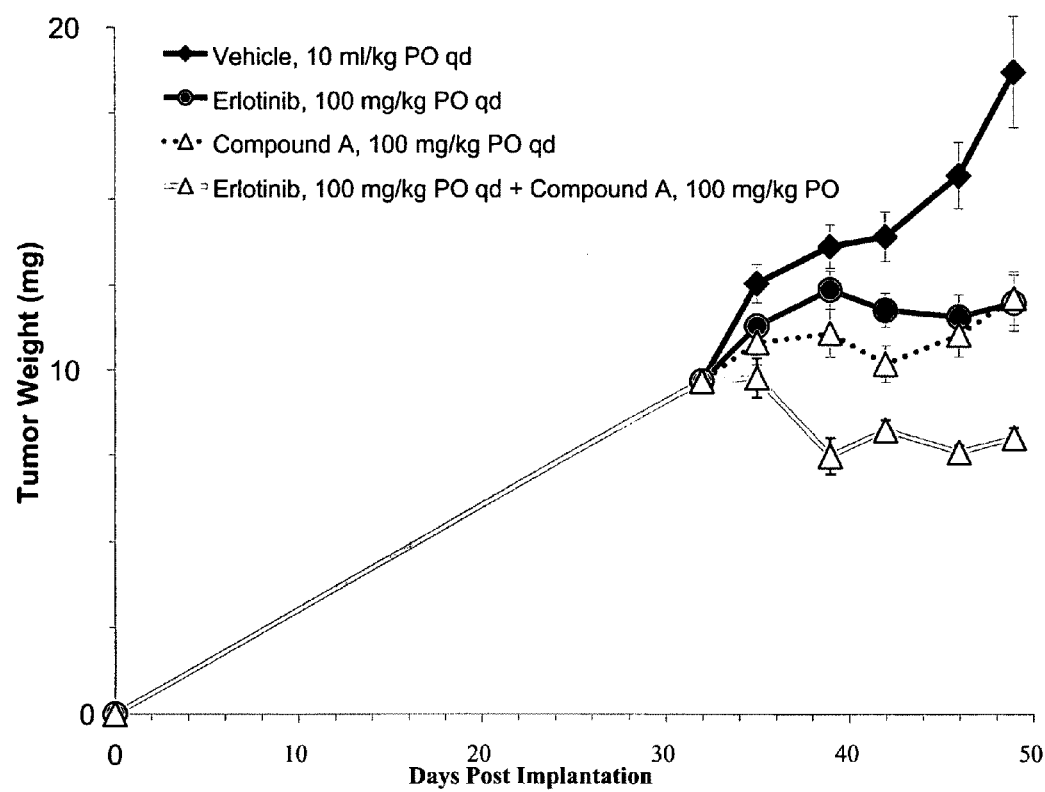
Figure 5. Compound A + Erlotinib in MDA-MB-468 Breast Carcinoma Tumor Model

COMBINATION THERAPIES COMPRISING QUINOXALINE INHIBITORS OF PI3K-ALPHA FOR USE IN THE TREATMENT OF CANCER

This application is a US national phase of international application PCT/US2008/004570 filed on Apr. 8, 2008, which claims priority to U.S. Provisional Patent Application Ser. No. 60/923,164 filed on Apr. 11, 2007, the disclosures of which are incorporated herein by reference.

CROSS-REFERENCE TO RELATED APPLICATIONS

The Applicants claim priority under 35 U.S.C. 119(e) to copending Provisional Application No. 60/923,164 filed on Apr. 11, 2007, the disclosure of which is incorporated herein by reference in its entirety.

FIELD OF THE INVENTION

This invention relates to methods of treating cancer with a compound that inhibits lipid kinase enzymatic activity and the resultant modulation of cellular activities (such as proliferation, differentiation, programmed cell death, migration, chemoinvasion and metabolism) in combination with anticancer agents.

BACKGROUND OF THE INVENTION

Improvements in the specificity of agents used to treat various disease states such as cancer, metabolic, and inflammatory diseases is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms.

Phosphatidylinositol 3-kinase (PI3K or PIK3CA) is composed of an 85 kDa regulatory subunit and a 110 kDa catalytic subunit. The protein encoded by this gene represents the catalytic subunit, which uses ATP to phosphorylate PtdIns, PtdIns4P and PtdIns(4,5)P2. PTEN, a tumor suppressor which inhibits cell growth through multiple mechanisms, can dephosphorylate PIP3, the major product of PIK3CA. PIP3, in turn, is required for translocation of protein kinase B (AKT1, PKB) to the cell membrane, where it is phosphorylated and activated by upstream kinases. The effect of PTEN on cell death is mediated through the PIK3CA/AKT1 pathway.

PI3Kα has been implicated in the control of cytoskeletal reorganization, apoptosis, vesicular trafficking, proliferation and differentiation processes. Increased copy number and expression of PIK3CA or activating mutations in the p110a catalytic subunit of PIK3CA are associated with a number of malignancies such as ovarian cancer (Campbell et al., *Cancer Res* 2004, 64, 7678-7681; Levine et al., *Clin Cancer Res* 2005, 11, 2875-2878; Wang et al., *Hum Mutat* 2005, 25, 322; Lee et al., *Gynecol Oncol* 2005, 97, 26-34), cervical cancer, breast cancer (Bachman, et al. *Cancer Biol Ther* 2004, 3, 772-775; Levine, et al., supra; Li et al., *Breast Cancer Res Treat* 2006, 96, 91-95; Saal et al., *Cancer Res* 2005, 65, 2554-2559; Samuels and Velculescu, *Cell Cycle* 2004, 3, 1221-1224), colorectal cancer (Samuels, et al. *Science* 2004, 304, 554; Velho et al. *Eur J Cancer* 2005, 41, 1649-1654), endometrial cancer (Oda et al. *Cancer Res.* 2005, 65, 10669-10673), gastric carcinomas (Byun et al., *Int J Cancer* 2003, 104, 318-327; Li et al., supra; Velho et al., supra; Lee et al., *Oncogene* 2005, 24, 1477-1480), hepatocellular carcinoma (Lee et al., id.), small and non-small cell lung cancer (Tang et al., *Lung Cancer* 2006, 51, 181-191; Massion et al., *Am J Respir Crit. Care Med* 2004, 170, 1088-1094), thyroid carcinoma (Wu et al., *J Clin Endocrinol Metab* 2005, 90, 4688-4693), acute myelogenous leukemia (AML) (Sujobert et al., *Blood* 1997, 106, 1063-1066), chronic myelogenous leukemia (CML) (Hickey and Cotter *J Biol Chem* 2006, 281, 2441-2450), and glioblastomas (Hartmann et al. *Acta Neuropathol (Berl)* 2005, 109, 639-642; Samuels et al., supra).

In view of the important role of PI3K-α in biological processes and disease states, inhibitors and/or modulators of this lipid kinase are desirable. In addition, it is well established that combining treatments with different mechanisms of action often leads to enhanced anti-tumor activity as compared to single treatments administered alone. This is true for combinations of chemotherapies (e.g. Kyrgiou M. et. al. *J Natl Cancer Inst* 2006, 98, 1655) and combinations of antibodies and chemotherapy (e.g. Pasetto L M et. al. *Anticancer Res* 2006, 26, 3973.

For example, activation of the PI3K pathway contributes to the resistance of human tumor cells to a wide variety of chemotherapeutic agents, including microtubule stabilizing agents such as taxol (Brognard, J., et. al. *Cancer Res* 2001, 61, 3986-3997; Clark, A. S., et. al. *Mol Cancer Ther* 2002, 1, 707-717; Kraus, A. C., et. al. *Oncogene* 2002, 21, 8683-8695; Krystal, G. W., et. al. *Mol Cancer Ther* 2002, 1, 913-922; and Yuan, Z. Q., et. al. *J Biol Chem* 2003, 278, 23432-23440). Taxol is widely used to treat advanced cancers including prostate carcinomas, which frequently harbor deletions in the PTEN gene, resulting in elevated signaling downstream of PI3K. A number of preclinical studies suggest that inhibiting signaling downstream of PI3K restores or enhances the ability of chemotherapeutic agents such as taxol to kill tumor cells (Brognard, J., et. al. *Cancer Res* 2001, 61, 3986-3997; Clark, A. S., et. al. *Mol Cancer Ther* 2002, 1, 707-717; Kraus, A. C., et. al. *Oncogene* 2002, 21, 8683-8695; Krystal, G. W., et. al. *Mol Cancer Ther* 2002, 1, 913-922; and Saga, Y., et. al. *Clin Cancer Res* 2002, 8, 1248-1252).

Rapamycin, another chemotherapeutic agent, is a potent inhibitor of the mTOR/Raptor complex. Inhibition of mTOR/Raptor prevents p70S6K and S6 phosphorylation, but also leads to relief of a negative feedback loop emanating from p70S6K that serves to downregulate PI3K (Sarbassov, D. D., et. al. *Science* 2005, 307, 1098-1101). As a result, rapamycin treatment can lead to upregulation of PI3K and increased phosphorylation of AKT (O'Donnell, A., et. al. paper presented at Proc Am Soc Clin Oncol. 2003; and O'Reilly, K. E., et. al. *Cancer Res* 2006, 66, 1500-1508). Thus, combining rapamycin with inhibitors of PI3K can enhance the efficacy of rapamycin (Powis, G. et. al. *Clinical Cancer Research* 2006, 12, 2964-2966; Sun, S.-Y., et. al. *Cancer Research* 2005, 65, 7052-7058).

A growing body of clinical and preclinical data indicates that activation of the PI3K pathway confers resistance to EGFR inhibitors such as erlotinib (Bianco, R., et. al. *Oncogene* 2003, 22, 2812-2822; Chakravarti, A., et. al. *Cancer Res* 2002, 62, 200-207; and Janmaat, M. L., et. al. *Clin Cancer Res* 2003, 9, 2316-2326). Both NSCLC patients with K-Ras mutations and glioblastoma patients with PTEN deletions fail to respond to erlotinib, potentially because of genetic activation of the PI3K pathway (Mellinghoff, I. K., et. al. *N. Eng. J Med.* 2006, 353, 2012-2024). Preclinical studies have shown that downregulation of PI3K signaling in EGFR-expressing tumor cells confers increased sensitivity to EGFR inhibitors (Ihle, N. T., et. al. *Mol Cancer Ther* 2005, 4, 1349-1357).

Thus, treating cancer with a PI3K inhibitor in combination with an EGFR inhibitor, such as erlotinib, is desirable.

Activation of the PI3K pathway also contributes to the resistance of human tumor cells to DNA damaging agents, such as platins. A number of preclinical studies suggest that inhibiting signaling downstream of PI3K restores or enhances the ability of chemotherapeutic agents such as platins to kill tumor cells (Brognard, J., et. al. *Cancer Res* 2001, 61, 3986-3997; and Yuan, Z. Q., et. al. *J Biol Chem* 2003, 278, 23432-23440). Carboplatin is widely used to treat advanced cancers including non-small cell lung carcinomas (NSCLC), which frequently harbor activating mutations in the K-Ras gene, resulting in activation of PI3K (Aviel-Ronen S., et. al. *Clin Lung Cancer* 2006, 8, 30-38). NSCLC patients with K-Ras mutations do not respond to EGFR inhibitors such as Tarceva, and thus represent a significant unmet medical need (Janne P A, et. al. *J Clin Oncology* 2005, 23, 3227-3234). Thus, treating NSCLC with a DNA-damaging agent such as a platin in combination with an inhibitor of PI3K is desirable in light of the lack of efficacious treatments.

Treatments that combine an inhibitor of PI3K-α with other anti-cancer agents are desirable and needed.

SUMMARY OF THE INVENTION

The following only summarizes certain aspects of the invention and is not intended to be limiting in nature. These aspects and other aspects and embodiments are described more fully below. All references cited in this specification are hereby incorporated by reference in their entirety. In the event of a discrepancy between the express disclosure of this specification and the references incorporated by reference, the express disclosure of this specification shall control.

The compositions of the invention are used to treat diseases associated with abnormal and or unregulated cellular activities. Disease states which can be treated by the methods and compositions provided herein include cancer. The invention is directed to methods of treating these diseases by administering a Compound of Formula I or II in combination with one or more treatments.

One aspect of the Invention is directed to a method of treating cancer which method comprises administering to a patient a therapeutically effective amount of a compound of Formula I:

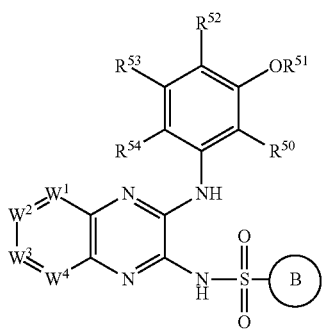

I or a single isomer thereof where the compound is optionally as a pharmaceutically acceptable salt and additionally optionally as a hydrate and additionally optionally as a solvate thereof; or administering a pharmaceutical composition comprising a therapeutically effective amount of a compound of Formula I and a pharmaceutically acceptable carrier, excipient, or diluent in combination with one or more treatments independently selected from surgery, one or more chemotherapeutic agents, one or more hormone therapies, one or more antibodies, one or more immunotherapies, radioactive iodine therapy, and radiation, where the Compound of Formula I is that wherein:

$W^1$, $W^2$, $W^3$, and $W^4$ are —C($R^1$)=; or one or two of $W^1$, $W^2$, $W^3$, and $W^4$ are independently —N= and the remaining are —C($R^1$)=; and where each $R^1$ is independently hydrogen, alkyl, haloalkyl, nitro, alkoxy, haloalkoxy, halo, hydroxy, cyano, amino, alkylamino, or dialkylamino;

$R^{51}$ is hydrogen or alkyl;

$R^{52}$ is hydrogen or halo;

$R^{50}$, $R^{53}$, and $R^{54}$ are independently hydrogen, alkyl, alkenyl, halo, haloalkyl, haloalkenyl, hydroxy, alkoxy, alkenyloxy, haloalkoxy, nitro, amino, alkylamino, dialkylamino, —N($R^{55}$)C(O)—$C_1$-$C_6$-alkylene-N($R^{55a}$)$R^{55b}$, alkylcarbonyl, alkenylcarbonyl, carboxy, alkoxycarbonyl, cyano, alkylthio, —S(O)$_2$N$R^{55}$$R^{55a}$, or alkylcarbonylamino and where $R^{55}$ and $R^{55b}$ are independently hydrogen, alkyl, or alkenyl and $R^{55a}$ is hydrogen, alkyl, alkenyl, hydroxy, or alkoxy; or $R^{53}$ and $R^{54}$ together with the carbons to which they are attached form a 5- or 6-membered heteroaryl or 5- or 6-membered heterocycloalkyl;

B is phenyl substituted with $R^{3a}$ and optionally further substituted with one, two, or three $R^3$; or B is heteroaryl optionally substituted with one, two, or three $R^3$;

$R^{3a}$ is cyano; hydroxyamino; carboxy; alkoxycarbonyl; alkylamino; dialkylamino; alkylcarbonyl; haloalkoxy; alkylsulfonyl; aminoalkyloxy; alkylaminoalkyloxy; dialkylaminoalkyloxy; or a) —N($R^7$)C(O)—$C_1$-$C_6$-alkylene-N($R^{7a}$)($R^{7b}$) where $R^7$ is hydrogen, alkyl, or alkenyl and $R^{7a}$ and $R^{7b}$ are independently hydrogen, alkyl, alkenyl, hydroxyalkyl, haloalkyl, alkoxy, alkoxyalkyl, aminoalkyl, alkylaminoalkyl, dialkylaminoalkyl, cycloalkyl, cycloalkylalkyl, heterocycloalkyl, heterocycloalkylalkyl, heteroaryl, heteroarylalkyl, aryl, arylalkyl, or arylalkyloxy and where the aryl, cycloalkyl, heterocycloalkyl and heteroaryl rings in $R^{7a}$ and $R^{7b}$ (either alone or as part of arylalkyl, cycloalkylalkyl, heterocycloalkylalkyl and heteroarylalkyl) are independently optionally substituted with 1, 2, or 3 groups independently selected from alkyl, amino, alkylamino, dialkylamino, hydroxy, halo, alkoxy, alkylthio, and oxo);

b) —C(O)N$R^8$$R^{8a}$ where $R^8$ is hydrogen, hydroxy, alkoxy, alkyl, alkenyl, haloalkyl, or haloalkoxy and $R^{8a}$ is hydrogen, alkyl, alkenyl, hydroxyalkyl, cyanoalkyl, alkoxyalkyl, alkylthioalkyl, heterocycloalkyl, heterocycloalkylalkyl, cycloalkyl, cycloalkylalkyl, heteroaryl, heteroarylalkyl, aryl, or arylalkyl and where the aryl, cycloalkyl, heteroaryl, and heterocycloalkyl rings in $R^{8a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, halo, haloalkyl, haloalkoxy, hydroxy, hydroxyalkyl, oxo, amino, alkylamino, dialkylamino, alkylcarbonyl, aminoalkyl, alkylaminoalkyl, dialkylaminoalkyl, alkoxycarbonyl, and —C(O)H;

c) —N$R^9$C(O)$R^{9a}$ where $R^9$ is hydrogen, hydroxy, alkoxy, alkyl, alkenyl, haloalkyl, or haloalkoxy and $R^{9a}$ is hydrogen, $C_2$-$C_6$-alkyl, alkenyl, hydroxyalkyl, alkoxyalkyl, cycloalkyl, cycloalkylalkyl, heterocycloalkyl, heterocycloalkylalkyl, heteroaryl, heteroarylalkyl, aryl, or arylalkyl; where the aryl, cycloalkyl, heteroaryl, and heterocycloalkyl rings in $R^{9a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, hydroxy, hydroxyalkyl, halo, haloalkyl, haloalkoxy, oxo, amino, alkylamino, dialkylamino, alkylcarbonyl, alkoxycarbonyl, —C(O)H, aryl (optionally substituted with one or two halo), arylalkyl, heteroaryl, heteroarylalkyl, heterocycloalkyl, heterocycloalkylalkyl, cyloalkyl, cyloalkylalkyl, and cycloalkylcarbonyl;

d) —C(O)N($R^{10}$)—$C_1$-$C_6$-alkylene-N($R^{10a}$)$R^{10b}$ where $R^{10a}$ is hydrogen, hydroxy, alkoxy, alkyl, alkenyl, haloalkyl, aminoalkyl, alkylaminoalkyl, dialkylaminoalkyl, or hydroxyalkyl and $R^{10}$ and $R^{10b}$ are independently hydrogen, alkyl, alkenyl, haloalkyl, aminoalkyl, alkylaminoalkyl, dialkylaminoalkyl, or hydroxyalkyl;

e) —N$R^{11}$C(O)N$R^{11a}R^{11b}$ where $R^{11a}$ is hydrogen, alkyl, alkenyl, hydroxy, or alkoxy and $R^{11}$ and $R^{11b}$ are independently hydrogen, alkyl, alkenyl, aminoalkyl, alkylaminoalkyl, or dialkylaminoalkyl;

f) —C(O)$R^{12}$ where $R^{12}$ is heterocycloalkyl optionally substituted with 1, 2, or 3 groups selected from alkyl, oxo, amino, alkylamino, and heterocycloalkylalkyl;

g) —N$R^{13}$C(O)O$R^{13a}$ where $R^{13}$ is hydrogen, alkyl, or alkenyl and $R^{13a}$ is aminoalkyl, alkylaminoalkyl, dialkylaminoalkyl, aryl, or arylalkyl;

h) —C(O)N($R^{14}$)N($R^{14a}$)($R^{14b}$) where $R^{14}$, $R^{14a}$, and $R^{14b}$ are independently hydrogen, alkyl, or alkenyl;

i) —S(O)$_2$N($R^{15}$)—$C_1$-$C_6$-alkylene-N($R^{15a}$)$R^{15b}$ where $R^{15}$, $R^{15a}$, and $R^{15b}$ are independently hydrogen, alkyl, or alkenyl;

j) —C(O)N($R^{16}$)—$C_1$-$C_6$-alkylene-C(O)O$R^{16a}$ where $R^{16}$ is hydrogen, alkyl, or alkenyl and $R^{16a}$ is alkyl or alkenyl;

k) heteroaryl optionally substituted with one or two aminoalkyl, alkylaminoalkyl, or dialkylaminoalkyl;

l) —N($R^{17}$)—C(=N($R^{17b}$)($R^{17a}$))(N$R^{17c}R^{17d}$) where $R^{17}$, $R^{17a}$, $R^{17b}$, $R^{17c}$, and $R^{17d}$ are independently hydrogen, alkyl, or alkenyl;

m) —N($R^{18}$)C(O)—$C_1$-$C_6$-alkylene-N($R^{18b}$)C(O)$R^{18a}$ where $R^{18a}$ is hydrogen, alkyl, alkenyl, or alkoxy and $R^{18}$ and $R^{18b}$ are independently hydrogen, alkyl, or alkenyl;

n) —C(O)N($R^{19}$)—$C_1$-$C_6$-alkylene-C(O)$R^{19a}$ where $R^{19}$ is hydrogen, alkyl, or alkenyl and $R^{19a}$ is amino, alkylamino, dialkylamino, or heterocycloalkyl;

o) —N($R^{20}$)C(O)—$C_1$-$C_6$-alkylene-C(O)$R^{20a}$ where $R^{20}$ is hydrogen, alkyl, or alkenyl and $R^{20a}$ is cycloalkyl or heterocycloalkyl;

p) —N$R^{21}$S(O)$_2$—$C_1$-$C_6$-alkylene-N($R^{21b}$)$R^{21a}$ where $R^{21}$ is hydrogen, alkyl, or alkenyl and $R^{21a}$ and $R^{21b}$ are independently hydrogen, alkyl, or alkenyl;

q) —N($R^{22}$)C(O)—$C_1$-$C_6$-alkylene-N($R^{22b}$)—N($R^{22c}$)($R^{22a}$) where $R^{22}$, $R^{22a}$ and $R^{22b}$ are independently hydrogen, alkyl, or alkenyl;

r) —$C_0$-$C_6$-alkylene-N($R^{23}$)—$C_1$-$C_6$-alkylene-N($R^{23b}$)$R^{23a}$ where $R^{23}$, $R^{23a}$ and $R^{23b}$ are independently hydrogen, alkyl, or alkenyl; or s) —N$R^{24}$C(O)—$C_1$-$C_6$-alkylene-O$R^{24a}$ where $R^{24}$ is hydrogen, alkyl, or alkenyl and $R^{24a}$ is alkoxyalkyl or aryl optionally substituted with one or two halo or alkyl; and where each of the alkylene in $R^{3a}$ is independently optionally further substituted with 1, 2, 3, 4, or 5 groups selected from halo, hydroxy, amino, alkylamino, and dialkylamino; and each $R^3$ (when $R^3$ is present) is independently alkyl; alkenyl; alkynyl; halo; hydroxy; oxo; alkoxy; cyano; hydroxyamino; carboxy; alkoxycarbonyl; amino; alkylamino; dialkylamino; alkylcarbonyl; haloalkoxy; alkylsulfonyl; aminoalkyloxy; alkylaminoalkyloxy; dialkylaminoalkyloxy; or a) —N($R^7$)C(O)—$C_1$-$C_6$-alkylene-N($R^{7a}$)($R^{7b}$) where $R^7$ is hydrogen, alkyl, or alkenyl and $R^{7a}$ and $R^{7b}$ are independently hydrogen, alkyl, alkenyl, hydroxyalkyl, haloalkyl, alkoxy, alkoxyalkyl, aminoalkyl, alkylaminoalkyl, dialkylaminoalkyl, cycloalkyl, cycloalkylalkyl, heterocycloalkyl, heterocycloalkylalkyl, heteroaryl, heteroarylalkyl, aryl, arylalkyl, or arylalkyloxy and where the aryl, cycloalkyl, heterocycloalkyl and heteroaryl rings in $R^{7a}$ and $R^{7b}$ (either alone or as part of arylalkyl, cycloalkylalkyl, heterocycloalkylalkyl and heteroarylalkyl) are independently optionally substituted with 1, 2, or 3 groups independently selected from alkyl, amino, alkylamino, dialkylamino, hydroxy, halo, alkoxy, alkylthio, and oxo);

b) —C(O)N$R^8R^{8a}$ where $R^8$ is hydrogen, hydroxy, alkoxy, alkyl, alkenyl, haloalkyl, or haloalkoxy and $R^{8a}$ is hydrogen, alkyl, alkenyl, hydroxyalkyl, cyanoalkyl, alkoxyalkyl, alkylthioalkyl, heterocycloalkyl, heterocycloalkylalkyl, cycloalkyl, cycloalkylalkyl, heteroaryl, heteroarylalkyl, aryl, or arylalkyl and where the aryl, cycloalkyl, heteroaryl, and heterocycloalkyl rings in $R^{8a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, halo, haloalkyl, haloalkoxy, hydroxy, hydroxyalkyl, oxo, amino, alkylamino, dialkylamino, alkylcarbonyl, aminoalkyl, alkylaminoalkyl, dialkylaminoalkyl, alkoxycarbonyl, and —C(O)H;

c) —N$R^9$C(O)$R^{9a}$ where $R^9$ is hydrogen, hydroxy, alkoxy, alkyl, alkenyl, haloalkyl, or haloalkoxy and $R^{9a}$ is hydrogen, $C_2$-$C_6$-alkyl, alkenyl, hydroxyalkyl, alkoxyalkyl, cycloalkyl, cycloalkylalkyl, heterocycloalkyl, heterocycloalkylalkyl, heteroaryl, heteroarylalkyl, aryl, or arylalkyl; where the aryl, cycloalkyl, heteroaryl, and heterocycloalkyl rings in $R^{9a}$ (either alone or as part of arylalkyl, cycloalkylalkyl, heterocycloalkylalkyl and heteroarylalkyl) are independently optionally substituted with 1, 2, or 3 groups independently selected from alkyl, alkenyl, alkoxy, hydroxy, hydroxyalkyl, halo, haloalkyl, haloalkoxy, oxo, amino, alkylamino, dialkylamino, alkylcarbonyl, alkoxycarbonyl, —C(O)H, aryl (optionally substituted with one or two halo), arylalkyl, heteroaryl, heteroarylalkyl, heterocycloalkyl, heterocycloalkylalkyl, cyloalkyl, cyloalkylalkyl, and cycloalkylcarbonyl;

d) —C(O)N($R^{10}$)—$C_1$-$C_6$-alkylene-N($R^{10a}$)$R^{10b}$ where $R^{10a}$ is hydrogen, hydroxy, alkoxy, alkyl, alkenyl, haloalkyl, or hydroxyalkyl and $R^{10}$ and $R^{10b}$ are independently hydrogen, alkyl, alkenyl, haloalkyl, or hydroxyalkyl;

e) —N$R^{11}$C(O)N$R^{11a}R^{11b}$ where $R^{11a}$ is hydrogen, alkyl, alkenyl, hydroxy, or alkoxy and $R^{11}$ and $R^{11b}$ are independently hydrogen, alkyl, alkenyl, aminoalkyl, alkylaminooalkyl, dialkylaminoalkyl;

f) —C(O)$R^{12}$ where $R^{12}$ is heterocycloalkyl optionally substituted with 1, 2, or 3 groups selected from alkyl, oxo, amino, alkylamino, and heterocycloalkylalkyl;

g) —N$R^{13}$C(O)O$R^{13a}$ where $R^{13}$ is hydrogen, alkyl, or alkenyl and $R^{13a}$ is aminoalkyl, alkylaminoalkyl, dialkylaminoalkyl, aryl, or arylalkyl);

h) —C(O)N(R$^{14}$)N(R$^{14a}$)(R$^{14b}$) where R$^{14}$, R$^{14a}$, and R$^{14b}$ are independently hydrogen, alkyl, or alkenyl;

i) —S(O)$_2$N(R$^{15}$)—C$_1$-C$_6$-alkylene-N(R$^{15a}$)R$^{15b}$ where R$^{15}$, R$^{15a}$, and R$^{15b}$ are independently hydrogen, alkyl, or alkenyl;

j) —C(O)N(R$^{16}$)—C$_1$-C$_6$-alkylene-C(O)OR$^{16a}$ where R$^{16}$ is hydrogen, alkyl, or alkenyl and R$^{16a}$ is alkyl or alkenyl;

k) heteroaryl optionally substituted with one or two aminoalkyl, alkylaminoalkyl, or dialkylaminoalkyl;

l) —N(R$^{17}$)—C(=N(R$^{17b}$)(R$^{17a}$))(NR$^{17c}$R$^{17d}$) where R$^{17}$, R$^{17a}$, R$^{17b}$, R$^{17c}$, and R$^{17d}$ are independently hydrogen, alkyl, or alkenyl;

m) —N(R$^{18}$)C(O)—C$_1$-C$_6$-alkylene-N(R$^{18b}$)C(O)R$^{18a}$ where R$^{18a}$ is hydrogen, alkyl, alkenyl, or alkoxy and R$^{18}$ and R$^{18b}$ are independently hydrogen, alkyl, or alkenyl;

n) —C(O)N(R$^{19}$)—C$_1$-C$_6$-alkylene-C(O)R$^{19a}$ where R$^{19}$ is hydrogen, alkyl, or alkenyl and R$^{19a}$ is amino, alkylamino, dialkylamino, or heterocycloalkyl;

o) —N(R$^{20}$)C(O)—C$_1$-C$_6$-alkylene-C(O)R$^{20a}$ where R$^{20}$ is hydrogen, alkyl, or alkenyl and R$^{20a}$ is cycloalkyl or heterocycloalkyl;

p) —NR$^{21}$S(O)$_2$—C$_1$-C$_6$-alkylene-N(R$^{21b}$)R$^{21a}$ where R$^{21}$ is hydrogen, alkyl, or alkenyl and R$^{21a}$ and R$^{21b}$ are independently hydrogen, alkyl, or alkenyl;

q) —N(R$^{22}$)C(O)—C$_1$-C$_6$-alkylene-N(R$^{22b}$)—N(R$^{22c}$)(R$^{22a}$), where R$^{22}$, R$^{22a}$ and R$^{22b}$ are independently hydrogen, alkyl, or alkenyl;

r) —C$_0$-C$_6$-alkylene-N(R$^{23}$)—C$_1$-C$_6$-alkylene-N(R$^{23b}$)R$^{23a}$ where R$^{23}$, R$^{23a}$ and R$^{23b}$ are independently hydrogen, alkyl, or alkenyl; or s) —NR$^{24}$C(O)—C$_1$-C$_6$-alkylene-OR$^{24a}$ where R$^{24}$ is hydrogen, alkyl, or alkenyl and R$^{24a}$ is alkoxyalkyl or aryl optionally substituted with one or two halo or alkyl;

wherein each of the alkylene in R$^3$ is independently optionally further substituted with 1, 2, 3, 4, or 5 groups selected from halo, hydroxy, amino, alkylamino, and dialkylamino; and provided that when R$^{50}$ and R$^{52}$ are hydrogen, R$^{51}$ is hydrogen or methyl, R$^{53}$ is hydrogen or methoxy, and R$^{54}$ is hydrogen or methoxy, then B is not 2,3-dihydro-1,4-benzodioxinyl, thien-2-yl, or thien-2-yl substituted with one R$^3$ where R$^3$ is halo.

A second aspect of the Invention is directed to a method of treating cancer which method comprises administering to a patient a therapeutically effective amount of a compound of Formula II:

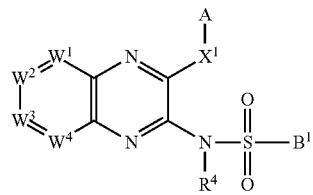

II or a pharmaceutically acceptable salt or solvate, thereof; or administering a pharmaceutical composition comprising a therapeutically effective amount of a compound of Formula II and a pharmaceutically acceptable carrier, excipient, or diluent in combination with one or more treatments independently selected from surgery, one or more chemotherapeutic agents, one or more of the hormone therapies, one or more of the antibodies, one or more immunotherapies, radioactive iodine therapy, and radiation wherein the Compound of Formula I is that wherein:

W$^1$, W$^2$, W$^3$, and W$^4$ are —C(R$^{1a}$)=; or one or two of W$^1$, W$^2$, W$^3$, and W$^4$ are independently —N= and the remaining are —C(R$^{1a}$)=;

X$^1$ is —N(R$^{5a}$)—;

A is aryl, —S(O)$_2$-aryl, heteroaryl, cycloalkyl, heterocycloalkyl, halo, haloalkyl, haloalkoxy, alkyl, alkoxy, or -alkyl-N(R$^7$)R$^{7a}$, where each of the aryl, heteroaryl, cycloalkyl, heterocycloalkyl, alkyl and alkoxy groups, each either alone or as part of another group within A, are independently optionally substituted with one, two, three, or four R$^{2a}$; or B$^1$ is aryl, arylalkyl, alkyl, heteroaryl, or heteroarylalkyl, wherein each of the aryl, heteroaryl and alkyl groups are independently optionally substituted with one, two, three, or four R$^{3d}$;

each R$^{1a}$ is independently selected from hydrogen, alkoxy, alkyl, nitro, halo, cyano, and —C$_0$-C$_6$-alkyl-N(R$^7$)R$^{7a}$, wherein each of the alkyl and alkoxy groups is optionally substituted with 1, 2, 3, 4, or 5 groups selected from alkyl, alkoxy, halo, haloalkyl, haloalkoxy, nitro, cyano, hydroxy, —N(R$^8$)R$^{8a}$, and —C(O)OR$^6$;

each R$^{2a}$ (when R$^{2a}$ is present) is independently selected from alkyl, alkenyl, -alkenyl-C(O)OR$^6$, —OR$^6$, —N(R$^7$)C(O)R$^6$, —N(R$^7$)C(O)—C$_0$-C$_6$ alkyl-N(R$^{7b}$)R$^{7a}$, —OC(O)—C$_0$-C$_6$ alkyl-N(R$^7$)R$^{7a}$, —N(R$^7$)C(O)—C$_1$-C$_6$ alkylC(O)OR$^6$, C$_0$-C$_6$-alkyl-C(O)R$^6$, oxo, dioxo, —S(O)$_2$—N(R$^7$)R$^{7a}$, —C(O)OR$^6$, —CH(R$^6$)$_2$—C(O)OR$^6$, —S(O)$_2$R$^6$, cycloalkyl, heterocycloalkyl, heteroaryl, —C(O)N(R$^7$)-alkyl-OR$^6$, —C$_0$-C$_6$ alkyl-C(O)N(R$^7$)—C$_0$-C$_6$-alkyl-C(O)OR$^6$, —C$_0$-C$_6$-alkyl-C(O)N(R$^7$)R$^{7a}$, aryl, arylalkyl, —S—(C$_1$-C$_6$ alkyl), halo, oxo, nitro, —SCN, cyano, and —C$_0$-C$_6$ alkyl-N(R$^7$)R$^{7a}$, wherein each of the alkyl (including, for example the alkyl within alkoxy), aryl, cycloalkyl, heterocycloalkyl, and heteroaryl groups, either alone or as part of another group within R$^2$, is independently optionally substituted with 1, 2, 3, 4, or 5 groups selected from alkyl, halo, haloalkyl, haloalkoxy, oxo, nitro, cyano, hydroxy, —N(R$^8$)R$^{8a}$, alkoxy, and —C(O)OR$^9$;

each R$^{3d}$ (when R$^{3d}$ is present) is independently oxo, nitro, halo, cyano, alkyl, alkenyl, alkynyl, alkoxy, C$_3$-C$_6$-cycloalkyl, —C$_0$-C$_6$-alkyl-heterocycloalkyl, —C$_0$-C$_6$ alkyl-N(R$^7$)C(O)—C$_0$-C$_6$-alkyl-N(R$^{7b}$)R$^{7a}$, —C$_0$-C$_6$ alkyl-N(R$^7$)C(O)—C$_0$-C$_6$-alkyl-N(R$^{7b}$)C(O)R$^{7a}$, —C$_0$-C$_6$ alkyl-C(O)—C$_0$-C$_6$-alkyl-N(R$^7$)R$^{7a}$, —C$_0$-C$_6$-alkyl-C(O)N(R$^7$)—C$_0$-C$_6$-alkyl-N(R$^{7b}$)R$^{7a}$, —C$_0$-C$_6$-alkyl-C(O)N(R$^7$)—C$_1$-C$_6$alkylC(O)OR$^{7a}$, —C$_0$-C$_6$ alkyl-N(R$^7$)C(O)—C$_0$-C$_6$-alkyl-(R$^{7a}$), —C$_0$-C$_6$ alkyl-N(R$^7$)—C$_0$-C$_6$-alkyl-N(R$^{7b}$)R$^{7a}$, —C$_0$-C$_6$ alkyl-N(R$^7$)C(O)—C$_0$-C$_6$-alkyl-N(R$^{7b}$)—N(R$^{7c}$)R$^{7a}$, —C$_0$-C$_6$ alkyl-N(R$^7$)C(O)O—C$_0$-C$_6$-alkyl-aryl, —C$_0$-C$_6$ alkyl-C(O)N(R$^7$)—C$_0$-C$_6$-alkyl-N(R$^{7b}$)R$^{7a}$, —C$_0$-C$_6$ alkyl-N(R$^7$)—C$_0$-C$_6$ alkyl-C(=N(R$^{7b}$)(R$^{7a}$))(NR$^{7c}$R$^{7d}$), —C$_0$-C$_6$-alkyl-aryl, —C$_0$-C$_6$-alkyl-heteroaryl, —C$_0$-C$_6$ alkyl-heterocycloalkyl, —O—C$_0$-C$_6$ alkyl-N(R$^7$)R$^{7a}$, —C$_0$-C$_6$ alkyl-OR$_6$, —C$_0$-C$_6$alkyl-C(O)OR$_6$, C$_0$-C$_6$-alkyl-N(R$^7$)R$^{7a}$, —C$_0$-C$_6$alkyl-C(O)NR$_7$R$^{7a}$, —C$_0$-C$_6$ alkyl-C(O)R$^7$, —SR$_S$, —S(O)$_2$R$_7$, —S(O)$_3$R$_7$, —S(O)R$^7$, —SO$_2$N(R$^7$)R$^{7a}$, —SO$_2$N(R$^7$)—C$_0$-C$_6$-alkyl-N(R$^{7b}$)R$^{7a}$, —C$_0$-C$_6$-alkyl-N(R$^7$)-aryl, —C$_0$-C$_6$-alkyl-N(R$^7$)-heteroaryl, —C$_0$-C$_6$-alkyl-N(R$^7$)— heterocycloalkyl, —C$_0$-C$_6$-alkyl-C(O)N(R$^7$)—C$_0$-C$_6$-alkyl-cycloalkyl, —C$_0$-C$_6$-alkyl-C(O)N(R$^7$)—C$_0$-C$_6$-alkyl-aryl, —C$_0$-C$_6$ alkyl-C(O)N(R$^7$)—C$_0$-C$_6$ alkyl-heteroaryl, C$_0$-C$_6$-alkyl-C(O)N(R$^7$)—C$_0$-C$_6$-alkyl-heterocycloalkyl, —C$_0$-C$_6$-alkyl-N(R$^7$)C(O)—C$_0$-C$_6$-alkyl-cycloalkyl, —C$_0$-C$_6$- alkyl-N(R⁷)C(O)—C₀-C₆-alkyl-aryl, C₀-C₆-alkyl-N(R⁷)C(O)—C₀-C₆-alkyl-heteroaryl, —C₀-C₆-alkyl-N(R⁷)C(O)—C₀-C₆-alkyl-heterocycloalkyl, C₀-C₆-alkyl-N(R⁷)C(O)—C₀-C₆-alkyl-heterocycloalkyl-aryl, —N(R⁷)C(O)OR⁶, or —NHC(O)H, wherein each of the alkyl, alkenyl, cycloalkyl, aryl, (including, for example the alkyl within alkoxy), heterocycloalkyl, and heteroaryl groups, either alone or as part of another group within R³ᵈ, is independently optionally substituted with 1, 2, 3, 4, or 5 groups selected from alkyl, alkenyl, cycloalkyl, halo, haloalkyl, haloalkoxy, —C(O)R⁹, nitro, cyano, oxo, —C₀-C₆-alkyl-N(R⁸)R⁸ᵃ, cycloalkyl, cycloalkylalkyl, heterocycloalkyl, heterocycloalkylalkyl, aryl, arylalkyl, heteroaryl, heteroarylalkyl, —C(O)OR⁹, alkylthio, and hydroxyalkyl;

R⁴ is hydrogen, aryl, —C₀-C₆-alkyl-N(R⁷)R⁷ᵃ, alkoxy, or C₁-C₆ alkyl, wherein each of the alkyl and aryl groups, either alone or as part of another group in R⁴, is independently optionally substituted with 1, 2, 3, 4, or 5 groups selected from alkyl, halo, haloalkyl, haloalkoxy, nitro, cyano, hydroxy, —N(R⁸)R⁸ᵃ, alkoxy, and —C(O)OR⁶; or R⁴ and X¹ together with the atoms to which they are attached form a heterocycloalkyl or heteroaryl group, wherein R⁵ᵃ is absent when X is —N(R⁵ᵃ)—, wherein each of the heterocycloalkyl or heteroaryl is optionally substituted with 1, 2, 3, 4, or 5 groups selected from alkyl, halo, haloalkyl, haloalkoxy, nitro, cyano, hydroxy, —N(R⁷)R⁷ᵃ, alkoxy, and —C(O)OR⁶;

R⁵ᵃ is hydrogen, —C₁-C₆ alkyl-N(R⁷)R⁷ᵃ, alkoxy, alkyl, or aryl, wherein each of the alkyl and aryl is optionally substituted with 1, 2, 3, 4, or 5 groups selected from alkyl, halo, haloalkyl, haloalkoxy, nitro, cyano, hydroxy, —N(R⁸)R⁸ᵃ, C₁-C₆ alkoxy, or —C(O)OR⁶; or R⁵ᵃ and R⁴ together with the atoms to which they are attached form a heterocycloalkyl or heteroaryl group, wherein the heterocycloalkyl and heteroaryl is optionally substituted with 1, 2, 3, 4, or 5 groups selected from alkyl, halo, haloalkyl, haloalkoxy, nitro, cyano, hydroxy, —N(R⁷)R⁷ᵃ, C₁-C₆ alkoxy, and —C(O)OR⁶;

R⁶ and R⁹ are independently hydrogen, hydroxy, alkyl, aryl, arylalkyl, cycloalkyl, cycloalkylalkyl, heterocycloalkyl, heterocycloalkylalkyl, heteroaryl, heteroarylalkyl, or aryl, each alkyl, aryl, cycloalkyl, heterocycloalkyl, and heteroaryl, either alone or as part of another group within R⁶ and R⁹, is independently optionally substituted with 1, 2, 3, 4, or 5 groups independently selected from amino, hydroxy, alkoxy, alkyl, and halo; and R⁷, R⁷ᵃ R⁷ᵇ, R⁷ᶜ, R⁷ᵈ, R⁸, and R⁸ᵃ are independently hydrogen, alkyl, alkenyl, hydroxy, alkyloxy, alkenyloxy, —O—C₀-C₆ alkyl-aryl, —C₀-C₆ alkyl-C(O)OR⁶, —C₀-C₆ alkyl-C(O)R⁶, aryl, arylalkyl, heteroaryl, heteroarylalkyl, cycloalkyl, cycloalkylalkyl, heterocycloalkyl, or heterocycloalkylalkyl, wherein each of the alkyl, aryl, heteroaryl, and heterocycloalkyl, either alone or part of another group within R⁷, R⁷ᵃ R⁷ᵇ, R⁷ᶜ, R⁷ᵈ, R⁸, and R⁸ᵃ is independently optionally substituted with 1, 2, 3, 4, or 5 groups selected from amino, alkylamino, dialkylamino, aminoalkyl, alkylaminoalkyl, dialkylaminoalkyl, —S—C₁-C₆ alkyl, cyano, nitro, hydroxy, C₁-C₆ alkoxy, C₁-C₆ alkyl, halo, aryl, heterocycloalkylalkyl, and heteroaryl optionally substituted with one or two C₁-C₆ alkyl.

FIG. 1 illustrates tumor growth inhibition after treatment with Compound A, a PI3K inhibitor, as a single agent and regression after treatment with Compound A in combination with taxol in a PC-3 prostate carcinoma tumor model.

FIG. 2 illustrates tumor growth inhibition after treatment with Compound A, a PI3K inhibitor, as a single agent and regression after treatment with Compound A in combination with rapamycin in a PC-3 prostate carcinoma tumor model.

FIG. 3 illustrates tumor growth inhibition after treatment with Compound A, a PI3K inhibitor, as a single agent as well as in combination with carboplatin in a Calu-6 non-small cell lung cancer tumor model.

FIG. 4a illustrates tumor growth inhibition after treatment with Compound A, a PI3K inhibitor, as a single agent and regression after treatment with Compound A in combination with Compound B, an EGFR inhibitor, in an A549 non-small cell lung cancer tumor model.

FIG. 4b-1 illustrates tumor growth inhibition after treatment with Compound A, a PI3K inhibitor, as a single agent and regression after treatment with Compound A in combination with Compound B, an EGFR inhibitor, in an MCF7 breast cancer tumor model (Study 1).

FIG. 4b-2 illustrates tumor growth inhibition after treatment with Compound A, a PI3K inhibitor, as a single agent and regression after treatment with Compound A in combination with Compound B, an EGFR inhibitor, in an MCF7 breast cancer tumor model (Study 2).

FIG. 5 illustrates tumor growth inhibition after treatment with Compound A, a PI3K inhibitor, as a single agent and regression after treatment with Compound A in combination with Erlotinib, an EGFR inhibitor, in an MDA-MB-468 breast carcinoma tumor model.

DETAILED DESCRIPTION OF THE INVENTION

Abbreviations and Definitions

The following abbreviations and terms have the indicated meanings throughout:

| Abbreviation | Meaning |
| --- | --- |
| br | broad |
| ° C. | degrees Celsius |
| CBZ | CarboBenZoxy = benzyloxycarbonyl |
| d | doublet |
| dd | doublet of doublet |
| dt | doublet of triplet |
| EI | Electron Impact ionization |
| Et | Ethyl |
| g | gram(s) |
| GC | gas chromatography |
| h or hr | hour(s) |
| HPLC | high pressure liquid chromatography |
| L | liter(s) |
| M | molar or molarity |
| m | Multiplet |
| mg | milligram(s) |
| MHz | megahertz (frequency) |
| Min | minute(s) |
| mL | milliliter(s) |
| mM | Millimolar |
| mmol | millimole(s) |
| mol | mole(s) |
| MS | mass spectral analysis |
| N | normal or normality |
| nM | Nanomolar |
| NMR | nuclear magnetic resonance spectroscopy |
| q | Quartet |
| RT | Room temperature |
| s | Singlet |
| s- | Secondary |
| t- | Tertiary |
| t or tr | Triplet |
| TFA | trifluoroacetic acid |
| THF | Tetrahydrofuran |
| μL | microliter(s) |
| μM | Micromole(s) or micromolar |

Definitions for a Compound of Formula I, Ia, and II

The symbol "—" means a single bond, "=" means a double bond, "≡" means a triple bond, and "-----" means a single bond and optionally a double bond. When chemical structures are depicted or described, unless explicitly stated otherwise, all carbons are assumed to have hydrogen substitution to conform to a valence of four.

"Administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., surgery, radiation, and chemotherapy, etc.), "administration" and its variants are each understood to include concurrent and sequential introduction of the compound or prodrug thereof and other agents.

"Alkenyl" or "lower alkenyl" means a straight or branched hydrocarbon radical having from 2 to 6 carbon atoms and at least one double bond and includes ethenyl, propenyl, 1-but-3-enyl, 1-pent-3-enyl, 1-hex-5-enyl and the like.

"Alkenylcarbonyl" means a C(O)R group where R is alkenyl, as defined herein.

"Alkenyloxy" or "lower alkenyloxy" means an —OR group where R is alkenyl, as defined herein. Representative examples include methoxy, ethoxy, 1-methoxyprop-1-en-3-yl, propoxy, isopropoxy, cyclopropyloxy, cyclohexyloxy and the like.

"Alkoxy" or "lower alkoxy" means an —OR group where R is alkyl, as defined herein. Representative examples include methoxy, ethoxy, 1-methoxyprop-1-en-3-yl, propoxy, isopropoxy, cyclopropyloxy, cyclohexyloxy and the like.

"Alkoxyalkyl" means an alkyl group, as defined herein, substituted with one, two, or three alkoxy groups, as defined herein.

"Akoxycarbonyl" means a —C(O)OR group where R is alkyl as defined herein.

"Alkoxyycarbonylalkyl" means an alkyl group, as defined herein, substituted with one, two, or three alkoxycarbonyl groups, as defined herein.

"Alkyl" or "lower alkyl" means a linear or branched hydrocarbon group having one to six carbon atoms. Examples of lower alkyl groups include methyl, ethyl, propyl, isopropyl, butyl, s-butyl, t-butyl, isobutyl, pentyl, hexyl and the like. A "$C_0$" alkyl (as in "$C_0$-$C_6$-alkyl") is a covalent bond. "$C_6$ alkyl" refers to, for example, n-hexyl, iso-hexyl, and the like.

"Alkylamino" means a —NHR radical where R is alkyl as defined herein, or an N-oxide derivative thereof, e.g., methylamino, ethylamino, n-, iso-propylamino, n-, iso-, tert-butylamino, or methylamino-N-oxide, and the like.

"Alkylaminoalkyl" means an alkyl group substituted with one or two alkylamino groups, as defined herein.

"Alkylaminoalkyloxy" means an —OR group where R is alkylaminoalkyl, as defined herein.

"Alkylcarbonyl" means a C(O)R group where R is alkyl, as defined herein.

"Alkylcarbonylamino" means a —NRC(O)R' group where R is hydrogen or alkyl, as defined herein, and R' is alkyl, as defined herein.

"Alkylene" refers to straight or branched divalent hydrocarbon, containing no unsaturation and having from two to eight carbon atoms. Examples of alkylene include eth-diyl (—$CH_2CH_2$—), prop-1,3-diyl (—$CH_2CH_2CH_2$—), 2,2-dimethylprop-1,3-diyl (—$CH_2C(CH_3)_2CH_2$—), and the like.

"Alkylsulfonyl" means a —$S(O)_2R$ group where R is alkyl, as defined herein.

"Alkylthio" means a —SR group where R is alkyl, as defined herein. Examples of alkylthio include methylthio and ethylthio, and the like.

"Alkylthioalkyl" means an alkyl group substituted with one or two alkylthio groups, as defined herein, e.g. 2-(methylthio)-ethyl and 2-(ethylthio)-ethyl.

"Alkynyl" or "lower alkynyl" means a straight or branched hydrocarbon radical having from 2 to 6 carbon atoms and at least one triple bond and includes ethynyl, propynyl, butynyl, pentyn-2-yl and the like.

"Amino" means a —$NH_2$.

"Aminoalkyl" means an alkyl group substituted with at least one, for example one, two, or three, amino groups.

"Aminoalkyloxy" means an —OR group where R is aminoalkyl, as defined herein.

"Aryl" means a monovalent six- to fourteen-membered, mono- or bi-carbocyclic ring, wherein the monocyclic ring is aromatic and at least one of the rings in the bicyclic ring is aromatic. Representative examples include phenyl, naphthyl, and indanyl, and the like.

"Arylalkyl" means an alkyl group, as defined herein, substituted with one or two aryl groups, as defined herein. Examples include benzyl, phenethyl, phenylvinyl, phenylallyl and the like.

"Aryloxy" means a —OR group where R is aryl as defined herein.

"Arylalkyloxy" means a —OR group where R is arylalkyl as defined herein.

"Arylsulfonyl" means a —$SO_2R$ group where R is aryl as defined herein.

"Carboxyalkyl" means an alkyl group, as defined herein, substituted with one, two, or three —C(O)OH groups.

"Carboxy ester" means a —C(O)OR group where R is lower alkyl, lower alkenyl, lower alkynyl, cycloalkyl, aryl or arylalkyl, each of which is defined herein. Representative examples include methoxycarbonyl, ethoxycarbonyl, and benzyloxycarbonyl, and the like.

"Cyanoalkyl" means an alkyl, alkenyl, or alkynyl radical, as defined herein, substituted with at least one, for example one, two, or three, cyano groups.

"Cycloalkyl" means a monocyclic or polycyclic hydrocarbon radical having three to thirteen carbon atoms. The cycloalkyl can be saturated or partially unsaturated, but cannot contain an aromatic ring. Cycloalkyl includes fused, bridged, and spiro ring systems. Examples of such radicals include cyclopropyl, cyclobutyl, cyclopentyl and cyclohexyl.

"Cycloalkylalkyl" means alkyl group substituted with one or two cycloalkyl groups, as defined herein. Representative examples include cyclopropylmethyl and 2-cyclobutyl-ethyl, and the like.

"Cycloalkylcarbonyl" means a —C(O)R group where R is cycloalkyl as defined herein.

"Dialkylamino" means a —NRR' radical where R and R' are independently alkyl as defined herein, or an N-oxide derivative, or a protected derivative thereof, e.g., dimethylamino, diethylamino, N,N-methylpropylamino or N,N-methylethylamino, and the like.

"Dialkylaminoalkyl" means an alkyl group substituted with one or dialkylamino groups, as defined herein.

"Dialkylaminoalkyloxy" means an —OR group where R is dialkylaminoalkyl, as defined herein.

"Fused ring system" and "fused ring" refer to a polycyclic ring system that contains bridged or fused rings; that is, where two rings have more than one shared atom in their ring structures. In this application, fused-polycyclics and fused ring systems are not necessarily all aromatic ring systems. Typically, but not necessarily, fused-polycyclics share a vicinal set of atoms, for example naphthalene or 1,2,3,4-tetrahydronaphthalene. A spiro ring system is not a fused-polycyclic by this definition, but fused polycyclic ring systems of the invention may themselves have spiro rings attached thereto via a single ring atom of the fused-polycyclic. In some examples, as appreciated by one of ordinary skill in the art, two adjacent groups on an aromatic system may be fused together to form a ring structure. The fused ring structure may contain heteroatoms and may be optionally substituted with one or more groups. It should additionally be noted that saturated carbons of such fused groups (i.e. saturated ring structures) can contain two substitution groups.

"Haloalkoxy" means an —OR' group where R' is haloalkyl as defined herein, e.g., trifluoromethoxy or 2,2,2-trifluoroethoxy, and the like.

"Haloalkoxyalkyl" means an alkyl group, as defined herein, substituted with one, two, or three haloalkoxy, as defined herein.

"Halogen" or "halo" means fluoro, chloro, bromo and iodo.

"Haloalkenyl means an alkenyl group, as defined herein, substituted with one or more halogens, for example one to five halo atoms.

"Haloalkyl" means an alkyl group, as defined herein, substituted with one or more halogens, for example one to five halo atoms. Representative examples includes 2,2-difluoroethyl, trifluoromethyl, and 2-chloro-1-fluoroethyl, and the like.

"Heteroaryl" means a monocyclic, fused bicyclic, or fused tricyclic, monovalent radical of 5 to 14 ring atoms containing one or more, for example one, two, three, or four ring heteroatoms independently selected from —O—, —S(O)$_n$—(n is 0, 1, or 2), —N—, —N(R$^x$)—, and the remaining ring atoms being carbon, wherein the ring comprising a monocyclic radical is aromatic and wherein at least one of the fused rings comprising a bicyclic or tricyclic radical is aromatic. One or two ring carbon atoms of any nonaromatic rings comprising a bicyclic or tricyclic radical may be replaced by a —C(O)—, —C(S)—, or —C(═NH)— group. R$^x$ is hydrogen, alkyl, hydroxy, alkoxy, acyl, or alkylsulfonyl. Fused bicyclic radical includes bridged ring systems. Unless stated otherwise, the valency may be located on any atom of any ring of the heteroaryl group, valency rules permitting. In particular, when the point of valency is located on the nitrogen, R$^x$ is absent. In another embodiment, the term heteroaryl includes, but is not limited to, 1,2,4-triazolyl, 1,3,5-triazolyl, phthalimidyl, pyridinyl, pyrrolyl, imidazolyl, thienyl, furanyl, indolyl, 2,3-dihydro-1H-indolyl (including, for example, 2,3-dihydro-1H-indol-2-yl or 2,3-dihydro-1H-indol-5-yl, and the like), isoindolyl, indolinyl, isoindolinyl, benzimidazolyl, benzodioxol-4-yl, benzofuranyl, cinnolinyl, indolizinyl, naphthyridin-3-yl, phthalazin-3-yl, phthalazin-4-yl, pteridinyl, purinyl, quinazolinyl, quinoxalinyl, tetrazoyl, pyrazolyl, pyrazinyl, pyrimidinyl, pyridazinyl, oxazolyl, isooxazolyl, oxadiazolyl, benzoxazolyl, quinolinyl, isoquinolinyl, tetrahydroisoquinolinyl (including, for example, tetrahydroisoquinolin-4-yl or tetrahydroisoquinolin-6-yl, and the like), pyrrolo[3,2-c]pyridinyl (including, for example, pyrrolo[3,2-c]pyridin-2-yl or pyrrolo[3,2-c]pyridin-7-yl, and the like), benzopyranyl, thiazolyl, isothiazolyl, thiadiazolyl, benzothiazolyl, benzothienyl, and the derivatives thereof, or N-oxide or a protected derivative thereof.

"Hetereoarylalkyl" means an alkyl group substituted with one or two heteroaryl groups as defined herein.

"Heterocycloalkyl" means a saturated or partially unsaturated monovalent monocyclic group of 3 to 8 ring atoms or a saturated or partially unsaturated monovalent fused bicyclic group of 5 to 12 ring atoms in which one or more, for example one, two, three, or four ring heteroatoms independently selected from —O—, —S(O)$_n$— (n is 0, 1, or 2), —N═, —N(R$^y$)— (where R$^y$ is hydrogen, alkyl, hydroxy, alkoxy, acyl, or alkylsulfonyl), the remaining ring atoms being carbon. One or two ring carbon atoms may be replaced by a —C(O)—, —C(S)—, or —C(═NH)— group. Fused bicyclic radical includes bridged ring systems. Unless otherwise stated, the valency of the group may be located on any atom of any ring within the radical, valency rules permitting. In particular, when the point of valency is located on a nitrogen atom, R$^y$ is absent. In another embodiment the term heterocycloalkyl includes, but is not limited to, azetidinyl, pyrrolidinyl, 2-oxopyrrolidinyl, 2,5-dihydro-1H-pyrrolyl, piperidinyl, 4-piperidonyl, morpholinyl, piperazinyl, 2-oxopiperazinyl, tetrahydropyranyl, 2-oxopiperidinyl, thiomorpholinyl, thiamorpholinyl, perhydroazepinyl, pyrazolidinyl, imidazolinyl, imidazolidinyl, dihydropyridinyl, tetrahydropyridinyl, oxazolinyl, oxazolidinyl, isoxazolidinyl, thiazolinyl, thiazolidinyl, quinuclidinyl, isothiazolidinyl, octahydroindolyl, octahydroisoindolyl, decahydroisoquinolyl, tetrahydrofuryl, and tetrahydropyranyl, and the derivatives thereof and N-oxide or a protected derivative thereof.

"Heterocycloalkylalkyl" means an alkyl group, as defined herein, substituted with one or two heterocycloalkyl groups, as defined herein.

"Hydroxyalkyl" means an alkyl radical, as defined herein, substituted with at least one, for example one, two, or three, hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, for example 2-hydroxyethyl, 2,3-dihydroxypropyl, or 1-(hydroxymethyl)-2-hydroxyethyl, and the like.

"Hydroxyamino" means a —NH(OH) group.

"Optional" or "optionally" means that the subsequently described event or circumstance may or may not occur, and that the description includes instances where said event or circumstance occurs and instances in which it does not. One of ordinary skill in the art would understand that with respect to any molecule described as containing one or more optional substituents, only sterically practical and/or synthetically feasible compounds are meant to be included. "Optionally substituted" refers to all subsequent modifiers in a term. So, for example, in the term "optionally substituted arylC$_{1-8}$ alkyl," both the "C$_{1-8}$ alkyl" portion and the "aryl" portion of the molecule may or may not be substituted. A list of exemplary optional substitutions is presented below in the definition of "substituted."

"Optionally substituted alkyl" means an alkyl radical, as defined herein, optionally substituted with one or more groups, for example one, two, three, four, or five groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, alkyl, optionally substituted alkenyl, optionally substituted alkynyl, hydroxy, alkoxy, alkenyloxy, or cyanoalkyl), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, alkyl, optionally substituted alkenyl, optionally substituted alkynyl, hydroxy, alkoxy, alkenyloxy, or cyanoalkyl).

"Optionally substituted alkenyl" means an alkenyl radical, as defined herein, optionally substituted with one or more groups, for example one, two, or three groups, independently selected from alkylcarbonyl, alkenylcarbonyl, cycloalkylcarbonyl, alkylcarbonyloxy, alkenylcarbonyloxy, amino, alkylamino, dialkylamino, aminocarbonyl, alkylaminocarbonyl, dialkylaminocarbonyl, cyano, cyanoalkylaminocarbonyl, alkoxy, alkenyloxy, hydroxy, hydroxyalkoxy, carboxy, alkylcarbonylamino, alkylcarbonyloxy, alkyl-S(O)$_{0-2}$—, alkenyl-S(O)$_{0-2}$—, aminosulfonyl, alkylaminosulfonyl, dialkylaminosulfonyl, alkylsulfonyl-NR$^c$— (where R$^c$ is hydrogen, optionally substituted alkyl, optionally substituted alkynyl, hydroxy, alkoxy, or alkenyloxy), alkylaminocarbonyloxy, dialkylaminocarbonyloxy, alkylaminoalkyloxy, dialkylaminoalkyloxy, alkoxycarbonyl, alkenyloxycarbonyl, alkoxycarbonylamino, alkylaminocarbonylamino, dialkylaminocarbonylamino, alkoxyalkyloxy, and —C(O)NR$^a$R$^b$ (where R$^a$ and R$^b$ are independently hydrogen, optionally substituted alkyl, alkenyl, optionally substituted alkynyl, hydroxy, alkoxy, or alkenyloxy).

"Optionally substituted aryl" means an aryl group, as defined herein, which is optionally substituted with one, two, three, four, of five groups selected from halo, haloalkyl, haloalkoxy, hydroxy, lower alkyl, lower alkenyl, lower alkynyl, alkoxy, carboxy, carboxy ester, amino, alkylamino, dialkylamino, optionally substituted cycloalkyl, optionally substituted heterocycloalkyl, optionally substituted heteroaryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted heteroaryl" means a heteroaryl group, as defined herein, optionally substituted with one, two, three, four, or five groups selected from halo, haloalkyl, haloalkoxy, lower alkyl, lower alkenyl, lower alkynyl, alkoxy, hydroxy, oxo (valency rules permitting), carboxy, carboxy ester, amino, alkylamino, dialkylamino, optionally substituted cycloalkyl, optionally substituted heterocycloalkyl, heteroaryl, optionally substituted aryl, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), and —NHS(O)$_2$R' (where R' is alkyl, aryl, or heteroaryl).

"Optionally substituted heterocycloalkyl" means a heterocycloalkyl, as defined herein, optionally substituted with one, two, three, four, or five groups selected from halo, haloalkyl, haloalkoxy, hydroxy, oxo, lower alkyl, lower alkenyl, lower alkynyl, alkoxy, optionally substituted cycloalkyl, heterocycloalkyl, optionally substituted aryl, optionally substituted heteroaryl, alkylaminoalkyl, dialkylaminoalkyl, carboxy, carboxy ester, —C(O)NR'R" (where R' is hydrogen or alkyl and R" is hydrogen, alkyl, aryl, heteroaryl, or heterocycloalkyl), —NR'C(O)R" (where R' is hydrogen or alkyl and R" is alkyl, aryl, heteroaryl, or heterocycloalkyl), amino, alkylamino, dialkylamino, and —NHS(O)$_2$R' (where R' is alkyl, aryl, or heteroaryl).

"Saturated bridged ring system" refers to a bicyclic or polycyclic ring system that is not aromatic. Such a system may contain isolated or conjugated unsaturation, but not aromatic or heteroaromatic rings in its core structure (but may have aromatic substitution thereon). For example, hexahydro-furo[3,2-b]furan, 2,3,3a,4,7,7a-hexahydro-1H-indene, 7-aza-bicyclo[2.2.1]heptane, and 1,2,3,4,4a,5,8,8a-octahydro-naphthalene are all included in the class "saturated bridged ring system."

"Spirocyclyl" or "spirocyclic ring" refers to a ring originating from a particular annular carbon of another ring. For example, as depicted below, a ring atom of a saturated bridged ring system (rings C and C'), but not a bridgehead atom, can be a shared atom between the saturated bridged ring system and a spirocyclyl (ring D) attached thereto. A spirocyclyl can be carbocyclic or heteroalicyclic.

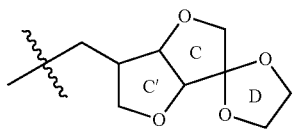

"Yield" for each of the reactions described herein is expressed as a percentage of the theoretical yield.

Definitions for the Compound of Formula 100

The terms used to describe the scope of formula 100 are defined in WO 2004/006846 (US Nat'l Stage application Ser. No. 10/522,004) which is herein incorporated by reference. For example "optionally substituted alkyl" for formula 100 has the meaning given in WO 2004/006846 (US Nat'l Stage application Ser. No. 10/522,004). Whenever a compound of formula 100 is described in this application, whether by structure or by use of the term "formula 100," the terms used to describe that compound are defined by WO 2004/006846 (US Nat'l Stage application Ser. No. 10/522,004).

Other Definitions

"AKT inhibitor" includes, for example, LY294002, PKC 412, perifosine, compounds in Table 2a, compounds in Table 2b, and compounds described in WO 2006/071819 and WO05/117909. These references also describe in vitro assays that can be used to determine the inhibitory activity of AKT.

"Alkylating agent" includes, for example, one or more of the following: Chlorambucil, Chlormethine, Cyclophosphamide, Ifosfamide, Melphalan, Carmustine, Streptozocin, Fotemustine, Lomustine, Streptozocin, Carboplatin, Cisplatin, Oxaliplatin, BBR3464, Busulfan, Dacarbazine, Mechlorethamine, Procarbazine, Temozolomide, ThioTEPA, and Uramustine.

"Antibody" includes, for example, one or more of the following: an IGF1R antibody (including, for example, $^\alpha$IGF-1R A12 MoAb, 19D12, h7C10 and CP-751871), an EGFR antibody (including, for example, Cetuximab (Erbitux®) and Panitumumab), an ErbB2 antibody (including, for example, Trastuzumab (Herceptin®)), a VEGF antibody (including, for example, Bevacizumab (Avastin®)), an IgG1 antibody (including, for example, Ibritumomab (tiuxetan)), a CD20 antibody (including, for example, Rituximab and Tositumomab), a CD33 antibody (including, for example, Gemtuzumab and Gemtuzumab ozogamicin), and a CD52 antibody (including, for example, Alemtuzumab).

"Antimetabolite" include, for example, methotrexate, Pemetrexed, Raltitrexed, Cladribine, Clofarabine, Fludarabine, Mercaptopurine, Thioguanine, Capecitabine, Cytarabine, fluorouracil (administered with or without leucovorin or folinic acid), and Gemcitabine.

"Antimicrotubule agent" includes, for example, Vincristine, Vinblastine, Vinorelbine, Vinflunine, and Vindesine.

"Aromatase inhibitor" includes, for example, one or more of the following: Aminoglutethimide, Anastrozole (Arimidex®), Letrozole (Femara®), Exemestane (Aromasin®), and Formestane (Lentaron®).

"Cancer" refers to cellular-proliferative disease states, including but not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hanlartoma, inesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma); Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformians), meninges (meningioma, meningiosarcoma, gliomatosis), brain (astrocytoma, medulloblastoma, glioma, ependymoma, germinoma [pinealoma], glioblastorna multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma); Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; Adrenal Glands: neuroblastoma; and breast cancer. Thus, the term "cancerous cell" as provided herein, includes a cell afflicted by any one of the above-identified conditions.

"Chemotherapeutic agent" includes, but is not limited to, an AKT inhibitor, an alkylating agent, an antimetabolite, an antimicrotubule agent, an aromatase inhibitor, a c-KIT inhibitor, a cMET inhibitor, an EGFR inhibitor, an ErbB2 inhibitor, a Flt-3 inhibitor, an HSP90 inhibitor, an IGF1R inhibitor, a platin, a Raf inhibitor, rapamycin, a Rapamycin analogue, a Receptor Tyrosine Kinase inhibitor, a taxane, a topoisomerase inhibitor, a SRC and/or ABL kinase inhibitor, and a VEGFR inhibitor. A pharmaceutically acceptable salt, solvate, and/or hydrate of a chemotherapeutic agent can be prepared by one of ordinary skill in the art and such salt, solvate, and/or hydrates thereof can be used to practice the invention.

"c-KIT inhibitor" includes, for example, imatinib, sunitinib, nilotinib, AMG 706, sorafenib, compounds in Table 3b, compounds in Table 3c, compounds in Table 8, compounds in Table 9, and compounds described in WO 2006/108059, WO/2005/020921, WO/2006/033943, and WO 2005/030140.

"cMET inhibitor" includes, for example, compounds in Table 3a, compounds in Table 3b, compounds in Table 3c, compounds described in WO06/108059, WO 2006/014325, and WO 2005/030140.

"EGFR inhibitor" includes, for example, one or more of the following: pelitinib, lapatinib (Tykerb®), gefitinib (Iressa®), erlotinib (Tarceva®), Zactima (ZD6474, vandetinib), AEE788 and HKI-272, EKB-569, CI-1033, N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine, N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine, compounds in Table 4, compounds in Table 7, and compounds described in WO 2004/006846 and WO 2004/050681.

"ErbB2 inhibitor" includes, for example, lapatinib (GW572016), PKI-166, canertinib, CI-1033, HKI272, and EKB-569.

"Flt-3 inhibitor" includes, for example, CEP-701, PKC 412, MLN518, sunitinib, sorafenib, compounds in Table 3a, compounds in Table 3b, compounds in Table 3c, compounds in Table 9, and compounds described in WO 2006/108059, WO/2006/033943, WO 2006/014325, and WO 2005/030140.

"Hormone therapy" or "hormonal therapy" includes, for example, treatment with one or more of the following: steroids (e.g. dexamethasone), finasteride, tamoxifen, and an aromatase inhibitor.

"HSP90 inhibitor" includes, for example, 17-AAG, 17-DMAG, Geldanamycin, 5-(2,4-dihydroxy-5-isopropylphenyl)-N-ethyl-4-(4-(morpholinomethyl)phenyl)isoxazole-3-carboxamide [NVP-AUY922 (VER 52296)], 6-chloro-9-((4-methoxy-3,5-dimethylpyridin-2-yl)methyl)-9H-purin-2-amine (CNF2024, also named BIIB021), compounds disclosed in WO2004072051 (which is herein incorporated by reference), compounds disclosed in WO2005028434 (which is herein incorporated by reference), compounds disclosed in WO2007035620 (which is herein incorporated by reference) and compounds disclosed in WO2006091963 (which is herein incorporated by reference).

"IGF1R inhibitor" includes, for example, Tyrphostin AG 1024, compounds in Table 5a, compounds in Table 5b, and compounds described in WO06/074057.

"Kinase-dependent diseases or conditions" refer to pathologic conditions that depend on the activity of one or more lipid kinases. Kinases either directly or indirectly participate in the signal transduction pathways of a variety of cellular activities including proliferation, adhesion, migration, differentiation and invasion. Diseases associated with kinase activities include tumor growth, the pathologic neovascularization that supports solid tumor growth, and associated with other diseases where excessive local vascularization is involved such as ocular diseases (diabetic retinopathy, age-related macular degeneration, and the like) and inflammation (psoriasis, rheumatoid arthritis, and the like).

While not wishing to be bound to theory, phosphatases can also play a role in "kinase-dependent diseases or conditions" as cognates of kinases; that is, kinases phosphorylate and phosphatases dephosphorylate, for example lipid substrates. Therefore compounds of the invention, while modulating kinase activity as described herein, may also modulate, either directly or indirectly, phosphatase activity. This additional modulation, if present, may be synergistic (or not) to activity of compounds of the invention toward a related or otherwise interdependent kinase or kinase family. In any case, as stated previously, the compounds of the invention are useful for treating diseases characterized in part by abnormal levels of cell proliferation (i.e. tumor growth), programmed cell death (apoptosis), cell migration and invasion and angiogenesis associated with tumor growth.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8.sup.th Ed., Pergamon Press, Gilman et al. (eds), 1990 for a discussion of biotransformation). As used herein, the metabolite of a compound of the invention or its salt may be the biologically active form of the compound in the body. In one example, a prodrug may be used such that the biologically active form, a metabolite, is released in vivo. In another example, a biologically active metabolite is discovered serendipitously, that is, no prodrug design per se was undertaken. An assay for activity of a metabolite of a compound of the present invention is known to one of skill in the art in light of the present disclosure.

"Patient" for the purposes of the present invention includes humans and other animals, particularly mammals, and other organisms. Thus the methods are applicable to both human therapy and veterinary applications. In another embodiment the patient is a mammal, and in another embodiment the patient is human.

A "pharmaceutically acceptable salt" of a compound means a salt that is pharmaceutically acceptable and that possesses the desired pharmacological activity of the parent compound. It is understood that the pharmaceutically acceptable salts are non-toxic. Additional information on suitable pharmaceutically acceptable salts can be found in *Remington's Pharmaceutical Sciences*, 17$^{th}$ ed., Mack Publishing Company, Easton, Pa., 1985, which is incorporated herein by reference or S. M. Berge, et al., "Pharmaceutical Salts," J. Pharm. Sci., 1977; 66:1-19 both of which are incorporated herein by reference.

Examples of pharmaceutically acceptable acid addition salts include those formed with inorganic acids such as hydrochloric acid, hydrobromic acid, sulfuric acid, nitric acid, phosphoric acid, and the like; as well as organic acids such as acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid and the like.

Examples of a pharmaceutically acceptable base addition salts include those formed when an acidic proton present in the parent compound is replaced by a metal ion, such as sodium, potassium, lithium, ammonium, calcium, magnesium, iron, zinc, copper, manganese, aluminum salts and the like. Preferable salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins. Examples of organic bases include isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, N-methylglucamine, polyamine resins, and the like. Exemplary organic bases are isopropylamine, diethylamine, ethanolamine, trimethylamine, dicyclohexylamine, choline, and caffeine.

"Platin," and "platin-containing agent" include, for example, cisplatin, carboplatin, and oxaliplatin.

"Prodrug" refers to compounds that are transformed (typically rapidly) in vivo to yield the parent compound of the above formulae, for example, by hydrolysis in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Raf inhibitor" includes, for example, sorafenib, RAF 265 (CHIR 265), compounds in Table 6, and compounds described in WO 2005/112932. These references also describe in vitro assays that can be used to determine the inhibitory activity of RAF.

"Rapamycin analogue" includes for example, CCI-779, AP23573, RAD 001, TAFA 93, and compounds described in WO 2004/101583 and U.S. Pat. No. 7,160,867 which are each incorporated herein by reference in their entireties.

"Receptor Tyrosine Kinase inhibitor" includes, for example, inhibitors of AKT, EGFR, ErbB2, IGF1R, KIT, Met, Raf, and VEGFR2. Examples of receptor tyrosine kinase inhibitors can be found in WO 2006/108059 (U.S. Nat'l Stage application Ser. No. 11/910,720), WO 2006/074057 (U.S. Nat'l Stage application Ser. No. 11/722,719), WO 2006/071819 (U.S. Nat'l Stage application Ser. No. 11/722,291), WO 2006/014325 (U.S. Nat'l Stage application Ser. No. 11/571,140), WO 2005/117909 (U.S. Nat'l Stage application Ser. No. 11/568,173), WO 2005/030140 (U.S. Nat'l Stage application Ser. No. 10/573,336), WO 2004/050681 U.S. Nat'l Stage application Ser. No. 10/533,555), WO 2005/112932 (U.S. Nat'l Stage application Ser. No. 11/568,789), and WO 2004/006846 (U.S. Nat'l Stage application Ser. No. 10/522,004), each of which is incorporated herein by reference for all purposes. In particular, the applications cited in this paragraph are incorporated for the purpose of providing specific examples and generic embodiments (and the definitions associated with the terms used in the embodiments) of compounds that are useful in the practice of the invention. These references also describe in vitro assays useful in the practice of this invention.

"Taxane" includes, for example, one or more of the following: Paclitaxel (Taxol®) and Docetaxel (Taxotere®).

"Therapeutically effective amount" is an amount of a compound of the invention, that when administered to a patient, ameliorates a symptom of the disease. The amount of a compound of the invention which constitutes a "therapeutically effective amount" will vary depending on the compound, the disease state and its severity, the age of the patient to be treated, and the like. The therapeutically effective amount can be determined routinely by one of ordinary skill in the art having regard to their knowledge and to this disclosure.

"Topoisomerase inhibitor" includes, for example, one or more of the following: amsacrine, camptothecin, etoposide, etoposide phosphate, exatecan, irinotecan, lurtotecan, and teniposide, and topotecan.

"Treating" or "treatment" of a disease, disorder, or syndrome, as used herein, includes (i) preventing the disease, disorder, or syndrome from occurring in a human, i.e. causing the clinical symptoms of the disease, disorder, or syndrome not to develop in an animal that may be exposed to or predisposed to the disease, disorder, or syndrome but does not yet experience or display symptoms of the disease, disorder, or syndrome; (ii) inhibiting the disease, disorder, or syndrome, i.e., arresting its development; and (iii) relieving the disease, disorder, or syndrome, i.e., causing regression of the disease, disorder, or syndrome. As is known in the art, adjustments for systemic versus localized delivery, age, body weight, general health, sex, diet, time of administration, drug interaction and the severity of the condition may be necessary, and will be ascertainable with routine experimentation by one of ordinary skill in the art.

"SRC and/or ABL kinase inhibitor" includes, for example, dasatinib, imatinib (Gleevec®), and compounds described in WO 2006/074057.

"VEGFR inhibitor" includes, for example, one or more of the following: VEGF Trap, ZD6474 (vandetanib, Zactima), sorafenib, Angiozyme, AZD2171 (cediranib), pazopanib, sorafenib, axitinib, SU5416 (semaxanib), PTK787 (vatalanib), AEE778, RAF 265, sunitinib (Sutent), N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5r,6aS)-2-methyloctahydrocyclopenta[c]pyrrol-5-yl]methyl}oxy)-6-(methyloxy)quinazolin-4-amine, N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5s,6aS)-2-methyloctahydrocyclo-penta[c]pyrrol-5-yl]methyl}oxy)-6-(methyloxy)quinazolin-4-amine, compounds in Table 7, and compounds described in WO 2004/050681 and WO 2004/006846.

Embodiments of the Invention

The following paragraphs present a number of embodiments of compounds of the invention. In each instance, the embodiment includes both the recited compounds as well as individual isomers and mixtures of isomers. In addition, in each instance, the embodiment optionally includes the pharmaceutically acceptable salts, hydrates, and/or solvates of the recited compounds and any individual isomers or mixture of isomers thereof.

For each of the following embodiments, the Compound of Formula I can, for example, be of Formula I(a) or be selected from a Compound in Table 1.

In another embodiment, the invention is directed to a method of treating cancer which method comprises administering to a patient a therapeutically effective amount of a Compound of Formula I, as defined in the Summary of the Invention, where growth and/or survival of tumor cells of the cancer is enhanced, at least in part, by the activity of PI3K; in combination with one or more treatments selected from surgery, one or more chemotherapeutic agents, one or more hormone therapies, one or more antibodies, one or more immunotherapies, radioactive iodine therapy, and radiation.

In another embodiment, the invention is directed to a method of treating cancer which method comprises administering to a patient a therapeutically effective amount of a Compound of Formula I, as defined in the Summary of the Invention, in combination with one or more treatments independently selected from surgery, one or more chemotherapeutic agents, one or more hormone therapies, one or more antibodies, one or more immunotherapies, radioactive iodine therapy, and radiation; where the cancer is selected from breast cancer, colon cancer, rectal cancer, endometrial cancer, gastric carcinoma (including gastrointestinal carcinoid tumors and gastrointestinal stromal tumors), glioblastoma, hepatocellular carcinoma, small cell lung cancer, non-small cell lung cancer (NSCLC), melanoma, ovarian cancer, cervical cancer, pancreatic cancer, prostate carcinoma, acute myelogenous leukemia (AML), chronic myelogenous leukemia (CML), non-Hodgkin's lymphoma, and thyroid carcinoma. In another embodiment, the invention is directed to a method of treating cancer which method comprises administering to a patient a therapeutically effective amount of a Compound of Formula I, as defined in the Summary of the Invention, in combination with one or more treatments independently selected from surgery, one or more chemotherapeutic agents, one or more hormone therapies, one or more antibodies, one or more immunotherapies, radioactive iodine therapy, and radiation; where the cancer is selected from prostate cancer, NSCLC, ovarian cancer, cervical cancer, breast cancer, colon cancer, rectal cancer, and glioblastoma. In another embodiment, the invention is directed to a method of treating cancer which method comprises administering to a patient a therapeutically effective amount of a Compound of Formula I, as defined in the Summary of the Invention, in combination with one or more treatments independently selected from surgery, one or more chemotherapeutic agents, one or more hormone therapies, one or more antibodies, one or more immunotherapies, radioactive iodine therapy, and radiation; where the cancer is selected from NSCLC, breast cancer, prostate cancer, glioblastoma, and ovarian cancer.

In another embodiment, the invention is directed to a method of treating cancer which method comprises administering to a patient a therapeutically effective amount of a Compound of Formula I, as defined in the Summary of the Invention, in combination with a treatment where the treatment is one or more chemotherapeutic agents.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents independently selected from rapamycin, a rapamycin analogue, an alkylating agent, a taxane, a platin, an EGFR inhibitor, and an ErbB2 inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents independently selected from rapamycin, temozolomide, paclitaxel, docetaxel, carboplatin, cisplatin, oxaliplatin, gefitinib (Iressa®), erlotinib (Tarceva®), Zactima (ZD6474), HKI-272, pelitinib, canertinib, a compound selected from Table 4, a compound in Table 7, and lapatinib. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents independently selected from rapamycin, temozolomide, paclitaxel, docetaxel, carboplatin, trastuzumab, erlotinib, N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine, N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine, a compound in Table 7, and lapatinib. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents independently selected from rapamycin, paclitaxel, carboplatin, erlotinib, and N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents independently selected from a platin and a taxane. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents independently selected from carboplatin, cisplatin, oxaliplatin, and paclitaxel.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an AKT inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an AKT inhibitor selected from perifosine, PKC 412, a compound in Table 2a, and a compound in Table 2b.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a cMET inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a cMET inhibitor selected from a compound in Table 3a, a compound in Table 3b, and a compound in Table 3c.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an EGFR inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an EGFR inhibitor selected from lapatinib (Tykerb®), gefitinib (Iressa®), erlotinib (Tarceva®), Zactima (ZD6474), AEE788, HKI-272, EKB-569, CI 1033, a compound selected from Table 4, and a compound in Table 7. In another embodiment, In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an EGFR inhibitor selected from lapatinib (Tykerb®), gefitinib (Iressa®), erlotinib (Tarceva®), Zactima (ZD6474), AEE788, HKI-272, EKB-569, CI 1033, N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine, N-(3,4-dichloro-2-fluorophenyl)-7-

({[(3aR,5s,6aS)-2-methyloctahydrocyclopenta[c]pyrrol-5-yl]methyl}oxy)-6-(methyloxy)quinazolin-4-amine, and N-(4-bromo-3-chloro-2-fluorophenyl)-7-({[(3aR,5s,6aS)-2-methyloctahydrocyclo-penta[c]pyrrol-5-yl]methyl}oxy)-6-(methyloxy)quinazolin-4-amine.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an ErbB2 inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an ErbB2 inhibitor selected from lapatinib, EKB-569, HKI272, CI 1033, PKI-166, and a compound selected from Table 4.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an HSP90 inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an HSP90 inhibitor selected from 17-AAG, 17-DMAG, Geldanamycin, and CNF2024. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an HSP90 inhibitor selected from 17-AAG, 17-DMAG, and Geldanamycin.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an IGF1R inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is an IGF1R inhibitor selected from Table 5a and Table 5b.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a Raf inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a Raf inhibitor selected from sorafenib, RAF 265 (CHIR-265), and a compound in Table 6.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a VEGFR inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a VEGFR inhibitor selected from VEGF Trap, ZD6474 (Zactima), cediranib (AZ2171), pazopanib, sunitinib, sorafenib, axitinib, AEE788, RAF 265 (CHIR-265), a compound selected from Table 4, and a compound selected from Table 7.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a cKIT inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a cKIT inhibitor selected from imatinib, sunitinib, nilotinib, AMG 706, sorafenib, a compound in Table 3b, a compound in Table 3c, a compound in Table 8, and a compound in Table 9.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a FLT3 inhibitor. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is a FLT3 inhibitor selected from CEP-701, PKC 412, sunitinib, MLN518, sunitinib, sorafenib, a compound in Table 3a, a compound in Table 3b, a compound in Table 3c, and a compound in Table 9.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from rapamycin, a rapamycin analogue, PI103, and SF 1126. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from rapamycin, CCI-779, AP23573, RAD 001, TAFA 93, PI103, and SF 1126. In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is rapamycin.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is of formula 100:

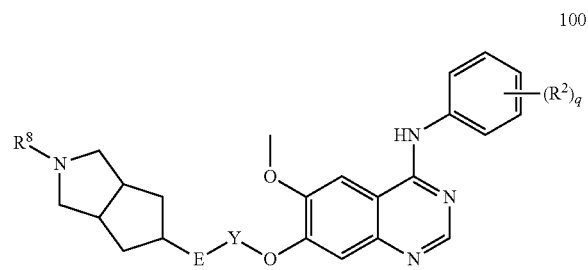

where q is 1, 2, or 3; E is —$NR^9$—, —O—, or absent and Y is —$CH_2CH_2$—, —$CH_2$—, or absent provided that when E is —$NR^5$— or —O—, then Y is —$CH_2CH_2$—; $R^2$ is selected from halogen, trihalomethyl, —CN, —$NO_2$, —$OR^3$, and lower alkyl; $R^8$ is selected from —H, lower alkyl, —C(O)$OR^3$, —C(O)N($R^3$)$R^4$, —$SO_2R^4$, and —C(O)$R^3$; $R^9$ is hydrogen or lower alkyl; $R^3$ is hydrogen or $R^4$; $R^4$ is selected from lower alkyl, aryl, lower arylalkyl, heterocyclyl, and lower heterocyclylalkyl; or $R^3$ and $R^4$, when taken together with a common nitrogen to which they are attached, form a five- to seven-membered heterocyclyl, said five- to seven-membered heterocyclyl optionally containing one or more additional heteroatom selected from N, O, S, and P; or a single geometric isomer, stereoisomer, racemate, enantiomer, or diastereomer, thereof and optionally as a pharmaceutically acceptable salt, additionally optionally as a solvate, and additionally as a hydrate thereof. The terms used to describe the scope of formula 100 are defined in WO 2004/006846 (U.S. Nat'l Stage application Ser. No. 10/522,004) which is herein incorporated by reference. Whenever a compound of formula 100 is described in this application, whether by structure or by use of the term "formula 100," the terms used to describe that compound are defined by WO 2004/006846 (U.S. Nat'l Stage application Ser. No. 10/522,004). In particular, "alkyl" in formula 100 is intended to include linear, branched, or cyclic hydrocarbon structures and combinations thereof, inclusively; "lower alkyl" means alkyl groups of from one to six carbon atoms. "Aryl" in formula 100 means an aromatic six- to fourteen-membered carbocyclic rings which include, for example, benzene, naphthalene, indane, tetralin, fluorene and the like. "Lower arylalkyl" in formula 100 means a residue in which an aryl moiety is attached to a parent structure via one of an alkylene, alkenylene, or alkynylene radical where the "alkyl" portion of the group has one to six carbons; examples include benzyl, phenethyl, phenylvinyl, phenylallyl and the like. In formula 100, "heterocyclyl" means a stable monocyclic, bicyclic or tricyclic three- to fifteen-membered ring radical (including fused or bridged ring systems) that consists of carbon atoms and from one to five heteroatoms selected from the group consisting of nitrogen, phosphorus, oxygen and sulfur where the nitrogen, phosphorus, carbon and sulfur atoms in the heterocyclyl radical may be optionally oxidized to various oxidation states and the nitrogen atom may be optionally quaternized; and the ring radical may be partially or fully saturated or aromatic. "Lower heterocyclylalkyl" means a residue in which a heterocyclyl is attached to a parent structure via one of an alkylene, alkenylene, and alkynylene radical having one to six carbons.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 2a. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 2a. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 2a.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 2b. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 2b. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 2b.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 3a. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 3a. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 3a.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 3b. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 3b. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 3b.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 3c. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 3c. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 3c.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 4. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 4. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 4.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine, N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, or N-(4-bromo-3-chloro-2-fluorophenyl)-7-({[(3aR,5s,6aS)-2-methyloctahydrocyclo-penta[c]pyrrol-5-yl]methyl}oxy)-6-(methyloxy)quinazolin-4-amine, optionally as a pharmaceutically acceptable salt and additionally optionally as a hydrate and additionally optionally as a solvate thereof. In another embodiment, the invention is directed to a method of treating cancer which method comprises administering to a patient a therapeutically effective amount of a Compound of Formula I according to Formula I(a) in combination with a treatment where the treatment is one or two chemotherapeutic agents where one of the chemotherapeutic agents is N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine, N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, or N-(4-bromo-3-chloro-2-fluorophenyl)-7-({[(3aR,5s,6aS)-2-methyloctahydrocyclo-penta[c]pyrrol-5-yl]methyl}oxy)-6-(methyloxy)quinazolin-4-amine, optionally as a pharmaceutically acceptable salt and additionally optionally as a hydrate and additionally optionally as a solvate thereof. In another embodiment, the invention is directed to a method of treating cancer which method comprises administering to a patient a therapeutically effective amount of a Compound of Formula I selected from Table 1 in combination with a treatment where the treatment is one or two chemotherapeutic agents where one of the chemotherapeutic agents is N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine, N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, or N-(4-bromo-3-chloro-2-fluorophenyl)-7-({[(3aR,5s,6aS)-2-methyloctahydrocyclo-penta[c]pyrrol-5-yl]methyl}oxy)-6-(methyloxy)quinazolin-4-amine, optionally as a pharmaceutically acceptable salt and additionally optionally as a hydrate and additionally optionally as a solvate thereof.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is N-(3,4-dichloro-2-fluorophenyl)-7-({[(3aR,5r,6aS)-2-methyloctahydrocyclopenta-[c]pyrrol-5-yl]methyl}oxy)-6-(methyloxy)quinazolin-4-amine optionally as a pharmaceutically acceptable salt and additionally optionally as a hydrate and additionally optionally as a solvate thereof. In another embodiment, the invention is directed to a method of treating cancer which method comprises administering to a patient a therapeutically effective amount of a Compound of Formula I according to Formula I(a) in combination with a treatment where the treatment is one or two chemotherapeutic agents where one of the chemotherapeutic agents is N-(3,4-dichloro-2-fluorophenyl)-7-({[(3aR,5r,6aS)-2-methyloctahydrocyclopenta-[c]pyrrol-5-yl]methyl}oxy)-6-(methyloxy)quinazolin-4-amine optionally as a pharmaceutically acceptable salt and additionally optionally as a hydrate and additionally optionally as a solvate thereof. In another embodiment, the invention is directed to a method of treating cancer which method comprises administering to a patient a therapeutically effective amount of a Compound of Formula I selected from Table 1 in combination with a treatment where the treatment is one or two chemotherapeutic agents where one of the chemotherapeutic agents is N-(3,4-dichloro-2-fluorophenyl)-7-({[3aR,5r,6aS)-2-methyloctahydrocyclopenta[c]pyrrol-5-yl]methyl}oxy)-6-(methyloxy)quinazolin-4-amine optionally as a pharmaceutically acceptable salt and additionally optionally as a hydrate and additionally optionally as a solvate thereof.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 5ac. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 5a. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 5a.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 5b. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 5b. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 5b.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 6. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 6. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 6.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 7. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 7. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 7.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 8. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 8. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 8.

In another embodiment, the invention is directed to a method of treating cancer which method comprises administering to a patient a therapeutically effective amount of a Compound of Formula I, as defined in the Summary of the Invention, in combination with a treatment where the treatment is one or two chemotherapeutic agents where one of the chemotherapeutic agents is selected from a compound in Table 9. In another embodiment, the invention is directed to a method of treating cancer which method comprises administering to a patient a therapeutically effective amount of a Compound of Formula I according to Formula I(a), in combination with a treatment where the treatment is one or two chemotherapeutic agents where one of the chemotherapeutic agents is selected from a compound in Table 9. In another embodiment, the invention is directed to a method of treating cancer which method comprises administering to a patient a therapeutically effective amount of a Compound of Formula I selected from Table 1, in combination with a treatment where the treatment is one or two chemotherapeutic agents where one of the chemotherapeutic agents is selected from a compound in Table 9.

In another embodiment, the invention is directed to a method of treating cancer which method comprises administering to a patient a therapeutically effective amount of a Compound of Formula I selected from Table 1 in combination with a treatment where the treatment is one or two chemotherapeutic agents where one of the chemotherapeutic agent is paclitaxel.

In another embodiment, the invention is directed to a method of treating cancer which method comprises administering to a patient a therapeutically effective amount of a Compound of Formula I selected from Table 1 in combination with a treatment where the treatment is one or two chemotherapeutic agents where one of the chemotherapeutic agent is rapamycin.

In another embodiment, the invention is directed to a method of treating cancer which method comprises administering to a patient a therapeutically effective amount of a Compound of Formula I selected from Table 1 in combination with a treatment where the treatment is one or two chemotherapeutic agents where one of the chemotherapeutic agent is carboplatin.

In another embodiment, the invention is directed to a method of treating cancer which method comprises administering to a patient a therapeutically effective amount of a Compound of Formula I selected from Table 1 in combination with a treatment where the treatment is one or two chemotherapeutic agents where one of the chemotherapeutic agent is erlotinib.

In another embodiment, the invention is directed to a method of treating cancer which method comprises administering to a patient a therapeutically effective amount of a Compound of Formula I selected from Table 1 in combination with a treatment where the treatment is one or two chemotherapeutic agents where one of the chemotherapeutic agent is lapatinib.

In another embodiment, the invention is directed to a method of treating cancer which method comprises administering to a patient a therapeutically effective amount of a Compound of Formula I selected from Table 1 in combination with a treatment where the treatment is one or two antibodies where one of the antibodies is trastuzumab.

In another embodiment, the invention is directed to a method of treating cancer which method comprises administering to a patient a therapeutically effective amount of a Compound of Formula I selected from Table 1 in combination with a treatment where the treatment is one or two antibodies where one of the antibodies is cetuximab.

In another embodiment, the invention is directed to a method of treating cancer which method comprises administering to a patient a therapeutically effective amount of a Compound of Formula I selected from Table 1 in combination with a treatment where the treatment is one or two antibodies where one of the antibodies is panitumumab.

In another embodiment, the invention is directed to a method of treating cancer which method comprises administering to a patient a therapeutically effective amount of a Compound of Formula I selected from Table 1 in combination with a treatment where the treatment is one or two antibodies where one of the antibodies is bevacizumab.

In another embodiment, the invention is directed to a method of treating cancer which method comprises administering to a patient a therapeutically effective amount of a Compound of Formula I, as defined in the Summary of the Invention, in combination with a treatment where the treatment is radiation. In another embodiment, the invention is directed to a method of treating cancer which method comprises administering to a patient a therapeutically effective amount of a Compound of Formula I according to Formula I(a) in combination with a treatment where the treatment is radiation. In another embodiment, the invention is directed to a method of treating cancer which method comprises administering to a patient a therapeutically effective amount of a Compound of Formula I selected from Table 1 in combination with a treatment where the treatment is radiation.

In another embodiment, the invention is directed to a method of treating cancer which method comprises administering to a patient a therapeutically effective amount of a Compound of Formula I, as defined in the Summary of the Invention, in combination with a treatment where the treatment is one or two antibodies. In another embodiment, the invention is directed to a method of treating cancer which method comprises administering to a patient a therapeutically effective amount of a Compound of Formula I, as defined in the Summary of the Invention, in combination with a treatment where the treatment is one or two antibodies independently selected from an IGF1R antibody (including, for example, $^\alpha$IGF-1R A12 MoAb, $^\alpha$IGF-1R 19D12 MoAb, $^\alpha$IGF-1R h7C10 MoAb and $^\alpha$IGF-1R CP-751871 MoAb), Alemtuzumab, Bevacizumab (Avastin®), Gemtuzumab, Gemtuzumab ozogamicin, Ibritumomab tiuxetan, Panitumumab, Rituximab, Tositumomab, Omnitarg (pertuzimab), an anti-ErbB2 antibodies (including trastuzumab (Herceptin®)), and an anti-EGFR antibodies (including, for example, cetuximab (Erbitux), panitumumab, nimotuzumab, and EMD72000)).

In another embodiment, the invention is directed to a method of treating cancer which method comprises administering to a patient a therapeutically effective amount of a Compound of Formula I according to Formula I(a) in combination with a treatment where the treatment is one or two antibodies. In another embodiment, the invention is directed to a method of treating cancer which method comprises administering to a patient a therapeutically effective amount of a Compound of Formula I according to Formula I(a) in combination with a treatment where the treatment is one or two antibodies independently selected from an IGF1R antibody (including, for example, $^\alpha$IGF-1R A12 MoAb, $^\alpha$IGF-1R 19D12 MoAb, $^\alpha$IGF-1R h7C10 MoAb and $^\alpha$IGF-1R CP-751871 MoAb), Alemtuzumab, Bevacizumab (Avastin®), Gemtuzumab, Gemtuzumab ozogamicin, Ibritumomab tiuxetan, Panitumumab, Rituximab, Tositumomab, Omnitarg (pertuzimab), an anti-ErbB2 antibodies (including trastuzumab (Herceptin®)), and an anti-EGFR antibodies (including, for example, cetuximab (Erbitux), panitumumab, nimotuzumab, and EMD72000)).

In another embodiment, the invention is directed to a method of treating cancer which method comprises administering to a patient a therapeutically effective amount of a Compound of Formula I selected from Table 1 in combination with a treatment where the treatment is one or two antibodies. In another embodiment, the invention is directed to a method of treating cancer which method comprises administering to a patient a therapeutically effective amount of a Compound of Formula I selected from Table 1 in combination with a treatment where the treatment is one or two antibodies independently selected from an IGF1R antibody (including, for example, $^a$IGF-1R A12 MoAb, $^a$IGF-1R 19D12 MoAb, $^a$IGF-1R h7C10 MoAb and $^a$IGF-1R CP-751871 MoAb), Alemtuzumab, Bevacizumab (Avastin®), Gemtuzumab, Gemtuzumab ozogamicin, Ibritumomab tiuxetan, Panitumumab, Rituximab, Tositumomab, Omnitarg (pertuzimab), an anti-ErbB2 antibodies (including trastuzumab (Herceptin®)), and an anti-EGFR antibodies (including, for example, cetuximab (Erbitux), panitumumab, nimotuzumab, and EMD72000)).

In another embodiment, the invention is directed to a method of treating cancer which method comprises administering to a patient a therapeutically effective amount of a Compound of Formula I, as defined in the Summary of the Invention, in combination with a treatment where the treatment is one or more chemotherapeutic agents where one of the chemotherapeutic agent is temozolomide. In another embodiment, the invention is directed to a method of treating cancer which method comprises administering to a patient a therapeutically effective amount of a Compound of Formula I according to Formula I(a) in combination with a treatment where the treatment is one or more chemotherapeutic agents where one of the chemotherapeutic agent is temozolomide. In another embodiment, the invention is directed to a method of treating cancer which method comprises administering to a patient a therapeutically effective amount of a Compound of Formula I selected from Table 1 in combination with a treatment where the treatment is one or more chemotherapeutic agents where one of the chemotherapeutic agent is temozolomide.

In another embodiment, the invention is directed to a method of treating cancer which method comprises administering to a patient a therapeutically effective amount of a Compound of Formula I, as defined in the Summary of the Invention, in combination with a treatment where the treatment is surgery. In another embodiment, the invention is directed to a method of treating cancer which method comprises administering to a patient a therapeutically effective amount of a Compound of Formula I according to Formula I(a) in combination with a treatment where the treatment is surgery. In another embodiment, the invention is directed to a method of treating cancer which method comprises administering to a patient a therapeutically effective amount of a Compound of Formula I selected from Table 1 in combination with a treatment where the treatment is surgery.

In another embodiment, the invention is directed to a method of treating cancer which method comprises administering to a patient a therapeutically effective amount of a Compound of Formula I, as defined in the Summary of the Invention, in combination with a treatment where the treatment is one or two hormone therapies. In another embodiment, the invention is directed to a method of treating cancer which method comprises administering to a patient a therapeutically effective amount of a Compound of Formula I or I(a), as defined in the Summary of the Invention, in combination with a treatment where the treatment is one or two hormone therapies independently selected from tamoxifen, Toremifene (Fareston), Fulvestrant (Faslodex), Megestrol acetate (Megace), ovarian ablation, Raloxifene, a luteinizing hormone-releasing hormone (LHRH) analog (including goserelin and leuprolide), Megestrol acetate (Megace), and one or more aromatase inhibitors. In another embodiment, the invention is directed to a method of treating cancer which method comprises administering to a patient a therapeutically effective amount of a Compound of Formula I or I(a), as defined in the Summary of the Invention, in combination with a treatment where the treatment is one or two hormone therapies where one of the hormone therapies is an aromatase inhibitor selected from letrozole (Femara), anastrozole (Arimidex), and exemestane (Aromasin). In another embodiment, the invention is directed to a method of treating cancer which method comprises administering to a patient a therapeutically effective amount of a Compound of Formula I or I(a), as defined in the Summary of the Invention, in combination with a treatment where the treatment is one or two hormone therapies independently selected from tamoxifen and an aromatase inhibitor.

In another embodiment, the invention is directed to a method of treating cancer which method comprises administering to a patient a therapeutically effective amount of a Compound of Formula I selected from Table 1 in combination with a treatment where the treatment is one or two hormone therapies. In another embodiment, the invention is directed to a method of treating cancer which method comprises administering to a patient a therapeutically effective amount of a Compound of Formula I selected from Table 1 in combination with a treatment where one of the treatments is one or two hormone therapies independently selected from tamoxifen, Toremifene (Fareston), Fulvestrant (Faslodex), Megestrol acetate (Megace), ovarian ablation, Raloxifene, a luteinizing hormone-releasing hormone (LHRH) analog (including goserelin and leuprolide), Megestrol acetate (Megace), and one or two aromatase inhibitors. In another embodiment, the invention is directed to a method of treating cancer which method comprises administering to a patient a therapeutically effective amount of a Compound of Formula I selected from Table 1 in combination with a treatment where one of the treatments is one or two hormone therapies where one of the hormone therapies is an aromatase inhibitors selected from letrozole (Femara), anastrozole (Arimidex), and exemestane (Aromasin). In another embodiment, the invention is directed to a method of treating cancer which method comprises administering to a patient a therapeutically effective amount of a Compound of Formula I selected from Table 1 in combination with a treatment where one of the treatments is one or two hormone therapies independently selected from tamoxifen and an aromatase inhibitor.

In another embodiment, the invention is directed to a method of treating cancer which method comprises administering to a patient a therapeutically effective amount of a Compound of Formula I, as defined in the Summary of the Invention, in combination with a treatment where one of the treatments is one antibody selected from an EGFR antibody and an ErbB2 antibody, or the treatment is one or two chemotherapeutic agents independently selected from a rapamycin, rapamycin analogue, an alkylating agent, a taxane, a platin, an EGFR inhibitor, and an ErbB2 inhibitor. In another embodiment, the invention is directed to a method of treating cancer which method comprises administering to a patient a therapeutically effective amount of a Compound of Formula I according to Formula I(a) in combination with a treatment where one of the treatments is one antibody selected from an EGFR antibody and an ErbB2 antibody, or the treatment is one or two chemotherapeutic agents independently selected from rapamycin, a rapamycin analogue, an alkylating agent, a taxane, a platin, an EGFR inhibitor, and an ErbB2 inhibitor. In another embodiment, the invention is directed to a method of treating cancer which method comprises administering to a patient a therapeutically effective amount of a Compound of Formula I selected from Table 1 in combination with a treatment where one of the treatments is one antibody selected from an EGFR antibody and an ErbB2 antibody, or the treatment is one or two chemotherapeutic agents independently selected from rapamycin, a rapamycin analogue, an alkylating agent, a taxane, a platin, an EGFR inhibitor, and an ErbB2 inhibitor.

In another embodiment, the invention is directed to a method of treating acute myelogenous leukemia (AML) which method comprises administering to a patient a therapeutically effective amount of a Compound of Formula I, as defined in the Summary of the Invention, in combination with one or more treatments independently selected from bone marrow or peripheral blood stem cell transplantation, radiation, one or two antibodies, and one or two chemotherapeutic agents. In another embodiment, the invention is directed to a method of treating acute myelogenous leukemia (AML) which method comprises administering to a patient a therapeutically effective amount of a Compound of Formula I, as defined in the Summary of the Invention, in combination with one or t treatments where one of the treatments is one antibody selected from Gemtuzumab ozogamicin (Mylotarg), $^\alpha$IGF-1R A12 MoAb, $^\alpha$IGF-1R 19D12 MoAb, $^\alpha$IGF-1R h7C10 MoAb, $^\alpha$IGF-1R CP-751871 MoAb and trastuzumab. In another embodiment, the invention is directed to a method of treating acute myelogenous leukemia (AML) which method comprises administering to a patient a therapeutically effective amount of a Compound of Formula I, as defined in the Summary of the Invention, in combination with one or more treatments where one of the treatments is one or two chemotherapeutic agents selected from Imatinib (i.e. Gleevec®), PKC 412, CEP-701, daunorubicin, doxorubicin, cytarabine (ara-C), an anthracycline drug such as daunorubicin or idarubicin (Daunomycin, Idamycin), 6-thioguanine, and a granulocyte colony-stimulating factor (such as Neupogen or Leukine).

In another embodiment, the invention is directed to a method of treating chronic myelogenous leukemia (CML) which method comprises administering to a patient a therapeutically effective amount of a Compound of Formula I, as defined in the Summary of the Invention, in combination with one or more treatments independently selected from bone marrow or peripheral blood stem cell transplantation, radiation, one or two chemotherapeutic agents, immunotherapy, and one or two antibodies. In another embodiment, the invention is directed to a method of treating chronic myelogenous leukemia (CML) which method comprises administering to a patient a therapeutically effective amount of a Compound of Formula I, as defined in the Summary of the Invention, in combination with one or more treatments where one of the treatments is one or two of the chemotherapeutic agents selected from Imatinib (i.e. Gleevec®), PKC 412, hydroxyurea (Hydrea), cytosine, cytosine arabinoside, dasatinib, AMN107, VX680 (MK0457), and cytarabine (ara-C). In another embodiment, the invention is directed to a method of treating chronic myelogenous leukemia (CML) which method comprises administering to a patient a therapeutically effective amount of a Compound of Formula I, as defined in the Summary of the Invention, in combination with one or more treatments where one of the treatments is one or two chemotherapeutic agents selected from Imatinib (i.e. Gleevec®) and dasatinib. In another embodiment, the invention is directed to a method of treating chronic myelogenous leukemia (CML) which method comprises administering to a patient a therapeutically effective amount of a Compound of Formula I, as defined in the Summary of the Invention, in combination with one or more treatments where one of the treatments is immunotherapy and the immunotherapy is interferon therapy such as interferon-$\alpha$.

In another embodiment, the invention is directed to a method of treating prostate cancer which method comprises administering to a patient a therapeutically effective amount of a Compound of Formula I, as defined in the Summary of the Invention, in combination with one or more treatments independently selected from surgery (including cryosurgery), radiation, one or two chemotherapeutic agents, one or two antibodies, and one or two hormone therapies. In another embodiment, the invention is directed to a method of treating prostate cancer which method comprises administering to a patient a therapeutically effective amount of a Compound of Formula I, as defined in the Summary of the Invention, in combination with one or more treatments where one of the treatments is an antibody selected from $^\alpha$IGF-1R A12 MoAb, $^\alpha$IGF-1R 19D12 MoAb, $^\alpha$IGF-1R h7C10 MoAb, and $^\alpha$IGF-1R CP-751871 MoAb. In another embodiment, the invention is directed to a method of treating prostate cancer which method comprises administering to a patient a therapeutically effective amount of a Compound of Formula I, as defined in the Summary of the Invention, in combination with one or more treatments where one of the treatments is one or two of the chemotherapeutic agents independently selected from rapamycin, mitoxantrone, prednisone, docetaxel (Taxotere), doxorubicin, etoposide, vinblastine, paclitaxel, and carboplatin. In another embodiment, the invention is directed to a method of treating prostate cancer which method comprises administering to a patient a therapeutically effective amount of a Compound of Formula I, as defined in the Summary of the Invention, in combination with one or more treatments where one of the treatments is one or two of the hormone therapy indeependently selected from androgen deprivation therapy and androgen suppression therapy. In another embodiment, the invention is directed to a method of treating prostate cancer which method comprises administering to a patient a therapeutically effective amount of a Compound of Formula I, as defined in the Summary of the Invention, in combination with one or more treatments where one of the treatments is one or two chemotherapeutic agents where one of the chemotherapeutic agents is a taxanes. In another embodiment, the invention is directed to a method of treating prostate cancer which method comprises administering to a patient a therapeutically effective amount of a Compound of Formula I, as defined in the Summary of the Invention, in combination with one or more treatments where one of the treatments is one or two chemotherapeutic agents where one of the chemotherapeutic agents is rapamycin.

In another embodiment, the invention is directed to a method of treating melanoma which method comprises administering to a patient a therapeutically effective amount of a Compound of Formula I, as defined in the Summary of the Invention, in combination with one or more treatments independently selected from surgery, radiation, one or two immunotherapies, one or two hormone therapies, and one or two chemotherapeutic agents. In another embodiment, the invention is directed to a method of treating melanoma which method comprises administering to a patient a therapeutically effective amount of a Compound of Formula I, as defined in the Summary of the Invention, in combination with one or more treatments where one of the treatments is one or two chemotherapeutic agents independently selected from an alkylating agent, a taxane, a platin, and a Raf inhibitor. In another embodiment, the invention is directed to a method of treating melanoma which method comprises administering to a patient a therapeutically effective amount of a Compound of Formula I, as defined in the Summary of the Invention, in combination with one or more treatments where one of the treatments is one or two chemotherapeutic agents independently selected from sorafenib, Paclitaxel (Taxol®), Docetaxel (Taxotere®), dacarbazine, rapamycin, imatinib mesylate (Gleevec®), sorafenib, cisplatin, carboplatin, dacarbazine (DTIC), carmustine (BCNU), vinblastine, temozolomide (Temodar), Melphalan, and imiquimod (Aldara). In another embodiment, the invention is directed to a method of treating melanoma which method comprises administering to a patient a therapeutically effective amount of a Compound of Formula I, as defined in the Summary of the Invention, in combination with one or more treatments where one of the treatments is one or two immunotherapies independently selected from ipilimumab, interferon-alpha and interleukin-2. In another embodiment, the invention is directed to a method of treating melanoma which method comprises administering to a patient a therapeutically effective amount of a Compound of Formula I, as defined in the Summary of the Invention, in combination with one or more treatments where one of the treatments is hormone therapy where the hormone therapy is tamoxifen.

In another embodiment, the invention is directed to a method of treating colon or rectal cancer which method comprises administering to a patient a therapeutically effective amount of a Compound of Formula I, as defined in the Summary of the Invention, in combination with one or more treatments independently selected from surgery, radiation, one or two antibodies, and one or two chemotherapeutic agents. In another embodiment, the invention is directed to a method of treating colon or rectal cancer which method comprises administering to a patient a therapeutically effective amount of a Compound of Formula I, as defined in the Summary of the Invention, in combination with one or more treatments where one of the treatments is surgery selected from local excision, electrofulguration, segmental colon resection, polypectomy, local transanal resection, low anterior resection, abdominoperineal resection, and pelvic exenteration. In another embodiment, the invention is directed to a method of treating colon or rectal cancer which method comprises administering to a patient a therapeutically effective amount of a Compound of Formula I, as defined in the Summary of the Invention, in combination with one or more treatments where one of the treatments is one or two chemotherapeutic agents independently selected from a platinum-containing compound (including cisplatin, oxaliplatin, and carboplatin), 5-fluorouracil (5-FU), leucovorin, capecitabine (Xeloda), irinotecan (Camptosar), FOLFOX (Folinic acid, 5-FU, Oxaliplatin), and leucovorin. In another embodiment, the invention is directed to a method of treating colon or rectal cancer which method comprises administering to a patient a therapeutically effective amount of a Compound of Formula I, as defined in the Summary of the Invention, in combination with one or more treatments where one of the treatments is one or two antibodies independently selected from cetuximab (Erbitux) and bevacizumab (Avastin).

In another embodiment, the invention is directed to a method of treating pancreatic cancer which method comprises administering to a patient a therapeutically effective amount of a Compound of Formula I, as defined in the Summary of the Invention, in combination with one or more treatments independently selected from surgery, radiation, one or two antibodies, and one or two chemotherapeutic agents. In another embodiment, the invention is directed to a method of treating pancreatic cancer which method comprises administering to a patient a therapeutically effective amount of a Compound of Formula I, as defined in the Summary of the Invention, in combination with one or more treatments where one of the treatments is selected from one or two chemotherapeutic agents independently selected from platinum-containing compound (including cisplatin, oxaliplatin, and carboplatin), 5-fluorouracil (5-FU), gemcitabine, a taxane (including paclitaxel and docetaxel), topotecan, irinotecan, capecitabine, streptozocin, erlotinib (Tarceva), leucovorin, and capecitabine (Xeloda). In another embodiment, the invention is directed to a method of treating pancreatic cancer which method comprises administering to a patient a therapeutically effective amount of a Compound of Formula I, as defined in the Summary of the Invention, in combination with one or more treatments where one of the treatments is an antibody where the antibody is cetuximab.

In another embodiment, the invention is directed to a method of treating breast cancer which method comprises administering to a patient a therapeutically effective amount of a Compound of Formula I, as defined in the Summary of the Invention, in combination with one or more treatments independently selected from surgery, radiation, one or two chemotherapeutic agents, one or two hormone therapies, and one or two antibodies. In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two of the chemotherapeutic agents independently selected from lapatinib (Tykerb®), Paclitaxel (Taxol®), docetaxel, capecitabine, Cyclophosphamide (Cytoxan), CMF (cyclophosphamide, fluoruracil, and methotrexate), methotrexate, fluorouracil, doxorubicin, epirubicin, gemcitabine, carboplatin (Paraplatin), cisplatin (Platinol), vinorelbine (Navelbine), capecitabine (Xeloda), pegylated liposomal doxorubicin (Doxil), albumin-bound paclitaxel (Abraxane), AC (adriamycin and Cyclophosphamide), adriamyclin, and pamidronate or zoledronic acid (to treat bone weakness). In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two hormone therapies independently selected from tamoxifen, Toremifene (Fareston), Fulvestrant (Faslodex), Megestrol acetate (Megace), ovarian ablation, Raloxifene, a luteinizing hormone-releasing hormone (LHRH) analogs (including goserelin and leuprolide), Megestrol acetate (Megace), and one or more aromatase inhibitors. In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two hormone therapies and one of the hormone therapies is an aromatase inhibitors selected from letrozole (Femara), anastrozole (Arimidex), and exemestane (Aromasin). In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two antibodies independently selected from αIGF-1R A12 MoAb, αIGF-1R 19D12 MoAb, αIGF-1R h7C10 MoAb, αIGF-1R CP-751871 MoAb, bevacizumab (Avastin), and trastuzumab.

In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two chemotherapeutic agents and one of the chemotherapeutic agents is erlotinib.

In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two of the chemotherapeutic agents and one or two of the chemotherapeutic agents are independently selected from rapamycin, lapatinib, erlotinib, N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine optionally as a pharmaceutically acceptable salt and additionally optionally as a hydrate and additionally optionally as a solvate thereof, N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine optionally as a pharmaceutically acceptable salt and additionally optionally as a hydrate and additionally optionally as a solvate thereof, N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine optionally as a pharmaceutically acceptable salt and additionally optionally as a hydrate and additionally optionally as a solvate thereof, and N-(4-bromo-3-chloro-2-fluorophenyl)-7-({[(3aR,5s,6aS)-2-methyloctahydrocyclo-penta[c]pyrrol-5-yl]methyl}oxy)-6-(methyloxy)quinazolin-4-amine optionally as a pharmaceutically acceptable salt and additionally optionally as a hydrate and additionally optionally as a solvate thereof.

In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two of the antibodies. In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two antibodies and one of the antibodies is trastuzumab.

In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two of the chemotherapeutic agents and one of the chemotherapeutic agents is selected from N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine, N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, and N-(4-bromo-3-chloro-2-fluorophenyl)-7-({[(3aR,5s,6aS)-2-methyloctahydrocyclo-penta[c]pyrrol-5-yl]methyl}oxy)-6-(methyloxy)quinazolin-4-amine; optionally as a pharmaceutically acceptable salt and additionally optionally as a hydrate and additionally optionally as a solvate thereof.

In another embodiment, the invention is directed to a method of treating breast cancer which method comprises administering to a patient a therapeutically effective amount of a Compound of Formula I, as defined in the Summary of the Invention, in combination with one or more treatments where one of the treatments is one or two of the chemotherapeutic agents and one of the chemotherapeutic agents is N-(3,4-dichloro-2-fluorophenyl)-7-({[(3aR,5r,6aS)-2-methyloctahydrocyclopenta-[c]pyrrol-5-yl]methyl}oxy)-6-(methyloxy)quinazolin-4-amine optionally as a pharmaceutically acceptable salt and additionally optionally as a hydrate and additionally optionally as a solvate thereof.

In another embodiment, the invention is directed to a method of treating non-small cell lung cancer which method comprises administering to a patient a therapeutically effective amount of a Compound of Formula I, as defined in the Summary of the Invention, in combination with one or more treatments independently selected from surgery, radiation, one or more antibodies, and one or more chemotherapeutic agents. In another embodiment, the invention is directed to a method of treating non-small cell lung cancer which method comprises administering to a patient a therapeutically effective amount of a Compound of Formula I, as defined in the Summary of the Invention, in combination with one or more treatments where one of the treatments is one or two chemotherapeutic agents independently selected from cisplatin, oxaliplatin, carboplatin, Zactima (ZD6474), Paclitaxel, Docetaxel (Taxotere®), Gemcitabine (Gemzar®), Vinorelbine, Irinotecan, Etoposide, Vinblastine, Erlotinib (Tarceva®), gefitinib (Iressa), and Pemetrexed. In another embodiment, the invention is directed to a method of treating non-small cell lung cancer which method comprises administering to a patient a therapeutically effective amount of a Compound of Formula I, as defined in the Summary of the Invention, in combination with one or more treatments where one of the treatments is an antibody and the antibody is Bevacizumab. In another embodiment, the invention is directed to a method of treating non-small cell lung cancer which method comprises administering to a patient a therapeutically effective amount of a Compound of Formula I, as defined in the Summary of the Invention, in combination with one or more treatments where one of the treatments is one or two chemotherapeutic agents independently selected from cisplatin, oxaliplatin, carboplatin, Paclitaxel, Docetaxel (Taxotere®), and erlotinib (Tarceva®).

In another embodiment, the invention is directed to a method of treating non-small cell lung cancer which method comprises administering to a patient a therapeutically effective amount of a Compound of Formula I, as defined in the Summary of the Invention, in combination with one or more treatments where one of the treatments is one or two chemotherapeutic agents and one of the chemotherapeutic agents is carboplatin.

In another embodiment, the invention is directed to a method of treating non-small cell lung cancer which method comprises administering to a patient a therapeutically effective amount of a Compound of Formula I, as defined in the Summary of the Invention, in combination with one or more treatments where one of the treatments is one or two chemotherapeutic agents and one of the chemotherapeutic agents is selected from N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine, N-(4-bromo-3-chloro-2-fluorophenyl)-7-({[(3aR,5r,6aS)-2-methyloctahydrocyclo-penta[c]pyrrol-5-yl]methyl}oxy)-6-(methyloxy)quinazolin-4-amine, N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine, and N-(4-bromo-3-chloro-2-fluorophenyl)-7-({[(3aR,5s,6aS)-2-methyloctahydrocyclo-penta[c]pyrrol-5-yl]methyl}oxy)-6-(methyloxy)quinazolin-4-amine; optionally as a pharmaceutically acceptable salt and additionally optionally as a hydrate and additionally optionally as a solvate thereof. In another embodiment, the invention is directed to a method of treating non-small cell lung cancer which method comprises administering to a patient a therapeutically effective amount of a Compound of Formula I, as defined in the Summary of the Invention, in combination with one or more treatments where one of the treatments is one or two chemotherapeutic agents and one of the chemotherapeutic agents is N-(3,4-dichloro-2-fluorophenyl)-7-({[(3aR,5r,6aS)-2-methyloctahydrocyclopenta-[c]pyrrol-5-yl]methyl}oxy)-6-(methyloxy)quinazolin-4-amine optionally as a pharmaceutically acceptable salt and additionally optionally as a hydrate and additionally optionally as a solvate thereof.

In another embodiment, the invention is directed to a method of treating small cell lung cancer which method comprises administering to a patient a therapeutically effective amount of a Compound of Formula I, as defined in the Summary of the Invention, in combination with one or more treatments independently selected from surgery, radiation, and one or two chemotherapeutic agents. In another embodiment, the invention is directed to a method of treating small cell lung cancer which method comprises administering to a patient a therapeutically effective amount of a Compound of Formula I, as defined in the Summary of the Invention, in combination with one or more treatments where one of the treatments is one or two chemotherapy agents independently selected from a platin (such as cisplatin, oxaliplatin, and carboplatin), gefitinib, vinorelbine, docetaxel, paclitaxel, etoposide, fosfamide, ifosfamide, cyclophosphamide, cyclophosphamide/doxorubicin/vincristine (CAV), doxorubicin, vincristine, gemcitabine, paclitaxel, vinorelbine, topotecan, irinotecan, methotrexate, and docetaxel.

In another embodiment, the invention is directed to a method of treating papillary or anaplastic thyroid cancer which method comprises administering to a patient a therapeutically effective amount of a Compound of Formula I, as defined in the Summary of the Invention, in combination with one or more treatments independently selected from surgery, radiation, radioactive iodine therapy, one or two hormone therapies, and one or two chemotherapeutic agents. In another embodiment, the invention is directed to a method of treating papillary or anaplastic thyroid cancer which method comprises administering to a patient a therapeutically effective amount of a Compound of Formula I, as defined in the Summary of the Invention, in combination with one or more treatments where one of the treatments is one or two chemotherapeutic agents independently selected from thyroid hormone pills, Doxorubicin and a platin. In another embodiment, the invention is directed to a method of treating papillary or anaplastic thyroid cancer which method comprises administering to a patient a therapeutically effective amount of a Compound of Formula I, as defined in the Summary of the Invention, in combination with one or more treatments where one of the treatments is hormone therapy and the hormone therapy is radioiodine ablation.

In another embodiment, the invention is directed to a method of treating endometrial cancer which method comprises administering to a patient a therapeutically effective amount of a Compound of Formula I, as defined in the Summary of the Invention, in combination with one or more treatments independently selected from surgery, radiation, one or two hormone therapies, and one or two chemotherapeutic agents. In another embodiment, the invention is directed to a method of treating endometrial cancer which method comprises administering to a patient a therapeutically effective amount of a Compound of Formula I, as defined in the Summary of the Invention, in combination with one or more treatments where one of the treatments is one or two hormone therapies independently selected from megestrol acetate, Tamoxifen, and a progestin including medroxyprogesterone acetate (Provera) and megestrol acetate (Megace). In another embodiment, the invention is directed to a method of treating endometrial cancer which method comprises administering to a patient a therapeutically effective amount of a Compound of Formula I, as defined in the Summary of the Invention, in combination with one or more treatments where one of the treatments is one or two chemotherapeutic agents independently selected from a platinum-containing compound (including cisplatin, oxaliplatin, and carboplatin, more for example cisplatin), a taxane (including paclitaxel), doxorubicin (Adriamycin), cyclophosphamide, fluorouracil (5-FU), methotrexate, and vinblastine.

In another embodiment, the invention is directed to a method of treating ovarian cancer which method comprises administering to a patient a therapeutically effective amount of a Compound of Formula I, as defined in the Summary of the Invention, in combination with one or more treatments independently selected from surgery, radiation, one or two antibodies, and one or two chemotherapeutic agents. In another embodiment, the invention is directed to a method of treating ovarian cancer which method comprises administering to a patient a therapeutically effective amount of a Compound of Formula I, as defined in the Summary of the Invention, in combination with one or more treatments where one of the treatments is an antibody and the antibody is bevacizumab. In another embodiment, the invention is directed to a method of treating ovarian cancer which method comprises administering to a patient a therapeutically effective amount of a Compound of Formula I, as defined in the Summary of the Invention, in combination with one or more treatments where one of the treatments is one or two chemotherapeutic agents independently selected from a platinum-containing compound (including cisplatin, oxaliplatin and carboplatin), a taxane (including paclitaxel and docetaxel), topotecan, an anthracyclines (including doxorubicin and liposomal doxorubicin), gemcitabine, cyclophosphamide, vinorelbine (Navelbine), hexamethylmelamine, ifosfamide, etoposide, bleomycin, vinblastine, ifosfamide, vincristine, and cyclophosphamide. In another embodiment, the invention is directed to a method of treating ovarian cancer which method comprises administering to a patient a therapeutically effective amount of a Compound of Formula I, as defined in the Summary of the Invention, in combination with one or more treatments where one of the treatments is one or two chemotherapeutic agents independently selected from a platin and a taxane. In another embodiment, the invention is directed to a method of treating ovarian cancer which method comprises administering to a patient a therapeutically effective amount of a Compound of Formula I, as defined in the Summary of the Invention, in combination with one or more treatments where one of the treatments is one or two chemotherapeutic agents independently selected from cisplatin, oxaliplatin, carboplatin, paclitaxel, and docetaxel.

In another embodiment, the invention is directed to a method of treating glioblastoma which method comprises administering to a patient a therapeutically effective amount of a Compound of Formula I, as defined in the Summary of the Invention, in combination with one or more treatments independently selected from surgery, radiation, one or two chemotherapeutic agents, one or two anti-seizure agents, and one or two agents to reduce swelling. In another embodiment, the invention is directed to a method of treating glioblastoma which method comprises administering to a patient a therapeutically effective amount of a Compound of Formula I, as defined in the Summary of the Invention, in combination with one or more treatments where one of the treatments is radiation selected from external beam radiation, interstitial radiotherapy, and stereotactic radiosurgery. In another embodiment, the invention is directed to a method of treating glioblastoma which method comprises administering to a patient a therapeutically effective amount of a Compound of Formula I, as defined in the Summary of the Invention, in combination with one or more treatments where one of the treatments is one or two chemotherapeutic agents independently selected from carmustine (BCNU), Erlotinib (Tarceva), bevacizumab, gefitinib (Iressa), rapamycin, temozolomide, cisplatin, BCNU, lomustine, procarbazine, and vincristine. In another embodiment, the invention is directed to a method of treating glioblastoma which method comprises administering to a patient a therapeutically effective amount of a Compound of Formula I, as defined in the Summary of the Invention, in combination with one or more treatments where one of the treatments is an anti-seizure agent and the anti-seizure agent is diphenylhydantoin (Dilantin). In another embodiment, the invention is directed to a method of treating glioblastoma which method comprises administering to a patient a therapeutically effective amount of a Compound of Formula I, as defined in the Summary of the Invention, in combination with one or more treatments where one of the treatments is an agents to reduce swelling and the agent is dexamethasone (Decadron). In another embodiment, the invention is directed to a method of treating glioblastoma which method comprises administering to a patient a therapeutically effective amount of a Compound of Formula I, as defined in the Summary of the Invention, in combination with one or more treatments where one of the treatments is one or two chemotherapeutic agents. In another embodiment, the invention is directed to a method of treating glioblastoma which method comprises administering to a patient a therapeutically effective amount of a Compound of Formula I, as defined in the Summary of the Invention, in combination with one or more treatments where one of the treatments is one or two chemotherapeutic agents independently selected from erlotinib and temozolomide.

In another embodiment, the invention is directed to a method of treating cervical cancer which method comprises administering to a patient a therapeutically effective amount of a Compound of Formula I, as defined in the Summary of the Invention, in combination with one or more treatments independently selected from surgery, radiation, and one or two chemotherapeutic agents. In another embodiment, the invention is directed to a method of treating cervical cancer which method comprises administering to a patient a therapeutically effective amount of a Compound of Formula I, as defined in the Summary of the Invention, in combination with one or more treatments where one of the treatments is surgery selected from cryosurgery, laser surgery, loop electrosurgical excision, conization, simple hysterectomy, and radical hysterectomy and pelvic lymph node dissection. In another embodiment, the invention is directed to a method of treating cervical cancer which method comprises administering to a patient a therapeutically effective amount of a Compound of Formula I, as defined in the Summary of the Invention, in combination with one or more treatments where one of the treatments is radiation selected from called external beam radiation therapy and brachytherapy. In another embodiment, the invention is directed to a method of treating cervical cancer which method comprises administering to a patient a therapeutically effective amount of a Compound of Formula I, as defined in the Summary of the Invention, in combination with one or more treatments where one of the treatments is one or two chemotherapeutic agents independently selected from a platinum compound (such as cisplatin, carboplatin, and oxaliplatin), paclitaxel, topotecan, ifosfamide, gemcitabine, vinorelbine, and fluorouracil.

In another embodiment, the invention is directed to a method of treating a gastrointestinal carcinoid tumor which method comprises administering to a patient a therapeutically effective amount of a Compound of Formula I, as defined in the Summary of the Invention, in combination with one or more treatments independently selected from surgery, radiation, immunotherapy, and one or two chemotherapeutic agents. In another embodiment, the invention is directed to a method of treating a gastrointestinal carcinoid tumor which method comprises administering to a patient a therapeutically effective amount of a Compound of Formula I, as defined in the Summary of the Invention, in combination with one or more treatments where one of the treatments is surgery selected from excision and electrofulguration. In another embodiment, the invention is directed to a method of treating a gastrointestinal carcinoid tumor which method comprises administering to a patient a therapeutically effective amount of a Compound of Formula I, as defined in the Summary of the Invention, in combination with one or more treatments where one of the treatments is one or two chemotherapeutic agents independently selected from cyproheptadine, SOM230, octreotide and lanreotide. In another embodiment, the invention is directed to a method of treating a gastrointestinal carcinoid tumor which method comprises administering to a patient a therapeutically effective amount of a Compound of Formula I, as defined in the Summary of the Invention, in combination with one or more treatments where one of the treatments is immunotherapy and the immunotherapy is an interferon.

In another embodiment, the invention is directed to a method of treating a gastrointestinal stromal tumor which method comprises administering to a patient a therapeutically effective amount of a Compound of Formula I, as defined in the Summary of the Invention, in combination with one or more treatments independently selected from surgery, radiation, and one or two chemotherapeutic agents. In another embodiment, the invention is directed to a method of treating a gastrointestinal stromal tumor which method comprises administering to a patient a therapeutically effective amount of a Compound of Formula I, as defined in the Summary of the Invention, in combination with one or more treatments where one of the treatments is one or two chemotherapeutic agents independently selected from imatinib mesylate (Gleevec), sunitinib (Sutent), and nilotinib (AMN107).

In another embodiment, the invention is directed to a method of treating hepatocellular carcinoma which method comprises administering to a patient a therapeutically effective amount of a Compound of Formula I, as defined in the Summary of the Invention, in combination with one or more treatments independently selected from surgery, radiofrequency ablation, ethanol ablation, cryosurgery, hepatic artery embolization, chemoembolization, radiation, and one or two chemotherapeutic agents. In another embodiment, the invention is directed to a method of treating hepatocellular carcinoma which method comprises administering to a patient a therapeutically effective amount of a Compound of Formula I, as defined in the Summary of the Invention, in combination with one or more treatments where one of the treatments is surgery selected from resection and transplantation. In another embodiment, the invention is directed to a method of treating hepatocellular carcinoma which method comprises administering to a patient a therapeutically effective amount of a Compound of Formula I, as defined in the Summary of the Invention, in combination with one or more treatments where one of the treatments is one or two chemotherapeutic agents independently selected from sorafenib, 5-fluorouracil and cisplatin.

In another embodiment, the invention is directed to a method of treating non-Hodgkin's lymphoma which method comprises administering to a patient a therapeutically effective amount of a Compound of Formula I, as defined in the Summary of the Invention, in combination with one or more treatments independently selected from radiation, one or two chemotherapeutic agents, interferon therapy, one or two antibodies, and bone marrow or peripheral blood stem cell transplantation. In another embodiment, the invention is directed to a method of treating non-Hodgkin's lymphoma which method comprises administering to a patient a therapeutically effective amount of a Compound of Formula I, as defined in the Summary of the Invention, in combination with one or more treatments where one of the treatments is one or two chemotherapeutic agents selected from CHOP (cyclophosphamide, doxorubicin, vincristine and prednisone), chlorambucil, fludarabine, and etoposide. In another embodiment, the invention is directed to a method of treating non-Hodgkin's lymphoma which method comprises administering to a patient a therapeutically effective amount of a Compound of Formula I, as defined in the Summary of the Invention, in combination with one or more treatments where one of the treatments is an antibody selected from rituximab, ibritumomab tiuxetan, tositumomab, and alemtuzumab. In another embodiment, the invention is directed to a method of treating non-Hodgkin's lymphoma which method comprises administering to a patient a therapeutically effective amount of a Compound of Formula I, as defined in the Summary of the Invention, in combination with one or more treatments where one of the treatments is an antibody and the anitbody is rituximab.

In another embodiment, the invention is directed to a method of treating cancer which method comprises administering to a patient a therapeutically effective amount of a Compound of Formula I, as defined in the Summary of the Invention, in combination with one or more treatments where one of the treatments is radiation and another treatment is surgery.

In another embodiment, the invention is directed to a method of treating cancer which method comprises administering to a patient a therapeutically effective amount of a Compound of Formula I, as defined in the Summary of the Invention, in combination with one or more treatments where one of the treatments is radiation and another treatment is one or two chemotherapeutic agents.

In another embodiment, the invention is directed to a method of treating cancer which method comprises administering to a patient a therapeutically effective amount of a Compound of Formula I, as defined in the Summary of the Invention, in combination with one or more treatments where one of the treatments is surgery and another treatment is one or two chemotherapeutic agents.

For each of the foregoing embodiments, the Compound of Formula I is selected from any of the following embodiments, including from the Representative Compounds in Table 1.

One embodiment (A) of the invention is directed to a compound of Formula I where $W^1$, $W^2$, $W^3$, and $W^4$ are $-C(R^1)$ =; or one or two of $W^1$, $W^2$, $W^3$, and $W^4$ are independently $-N=$ and the remaining are $-C(R^1)=$; where each $R^1$ is independently hydrogen, alkyl, haloalkyl, nitro, alkoxy, haloalkoxy, halo, hydroxy, cyano, amino, alkylamino, or dialkylamino; and all other groups are as defined in the Summary of the Invention. In another embodiment, $W^1$, $W^2$, $W^3$, and $W^4$ are $-C(R^1)=$ and each $R^1$ is independently hydrogen or alkyl; or one of $W^1$ and $W^4$ is $-N=$ and the other is $-C(H)=$. In another embodiment, $W^1$, $W^2$, $W^3$, and $W^4$ are $-C(R^1)=$ where each $R^1$ is independently hydrogen or alkyl. In another embodiment, $R^1$ is hydrogen.

Another embodiment (B) of the invention is a Compound of Formula I where $R^{50}$ is hydrogen, alkyl, alkenyl, halo, haloalkyl, haloalkenyl, hydroxy, alkoxy, alkenyloxy, haloalkoxy, nitro, amino, alkylamino, dialkylamino, $-N(R^{55})C(O)-C_1-C_6$-alkylene-$N(R^{55a})R^{55b}$, alkylcarbonyl, alkenylcarbonyl, carboxy, alkoxycarbonyl, cyano, alkylthio, $-S(O)_2NR^{55}R^{55a}$, or alkylcarbonylamino; where $R^{55}$ and $R^{55b}$ are independently hydrogen, alkyl, or alkenyl and $R^{55a}$ is hydrogen, alkyl, alkenyl, hydroxy, or alkoxy; and all other groups are as defined in the Summary of the Invention. In another embodiment, $R^{50}$ is hydrogen.

Another embodiment (C) of the invention is a Compound of Formula I where $R^{51}$ is hydrogen or alkyl; and all other groups are as defined in the Summary of the Invention. In another embodiment, $R^{51}$ is alkyl. In another embodiment, $R^{51}$ is methyl.

Another embodiment (D) of the invention is a Compound of Formula I where $R^{52}$ is hydrogen or halo; and all other groups are as defined in the Summary of the Invention. In another embodiment $R^{52}$ is hydrogen or fluoro. In another embodiment, $R^{52}$ is hydrogen.

Another embodiment (E) of the invention is a Compound of Formula I where $R^{53}$ is hydrogen, alkyl, alkenyl, halo, haloalkyl, haloalkenyl, hydroxy, alkoxy, alkenyloxy, haloalkoxy, nitro, amino, alkylamino, dialkylamino, $-N(R^{55})C(O)-C_1-C_6$-alkylene-$N(R^{55}a)R^{55b}$, alkylcarbonyl, alkenylcarbonyl, carboxy, alkoxycarbonyl, cyano, alkylthio, $-S(O)_2NR^{55}R^{55a}$, or alkylcarbonylamino; where $R^{55}$ and $R^{55b}$ are independently hydrogen, alkyl, or alkenyl and $R^{55a}$ is hydrogen, alkyl, alkenyl, hydroxy, or alkoxy; and all other groups are as defined in the Summary of the Invention. In another embodiment, $R^{53}$ is hydrogen, alkoxy, nitro, amino, or $-N(R^{55})C(O)-C_1-C_6$-alkylene-$N(R^{55a})R^{55b}$. In another embodiment, $R^{53}$ is hydrogen, methoxy, nitro, amino, or $-NHC(O)CH_2N(CH_3)_2$. In another embodiment, $R^{53}$ is hydrogen or methoxy.

Another embodiment (F) of the invention is a Compound of Formula I where $R^{54}$ is hydrogen, alkyl, alkenyl, halo, haloalkyl, haloalkenyl, hydroxy, alkoxy, alkenyloxy, haloalkoxy, nitro, amino, alkylamino, dialkylamino, $-N(R^{55})C(O)-C_1-C_6$-alkylene-$N(R^{55a})R^{55b}$, alkylcarbonyl, alkenylcarbonyl, carboxy, alkoxycarbonyl, cyano, alkylthio, $-S(O)_2NR^{55}R^{55a}$, or alkylcarbonylamino; where $R^{55}$ and $R^{55"}$ are independently hydrogen, alkyl, or alkenyl and $R^{55a}$ is hydrogen, alkyl, alkenyl, hydroxy, or alkoxy; and all other groups are as defined in the Summary of the Invention. In another embodiment, $R^{54}$ is hydrogen, alkyl, alkoxy, or halo. In another embodiment, $R^{54}$ is hydrogen, methyl, methoxy, bromo, or chloro. In another embodiment, $R^{54}$ is hydrogen, methoxy, or chloro.

Another embodiment (G) of the invention is directed to a compound of Formula I where $R^{50}$, $R^{52}$, and $R^{53}$ are hydrogen and $R^{54}$ is halo or alkoxy; $R^{50}$, $R^{52}$, and $R^{54}$ are hydrogen and $R^{53}$ is alkoxy; or $R^{50}$ and $R^{52}$ are hydrogen and $R^{53}$ and $R^{54}$ together with the carbons to which they are attached form a 6-membered heteroaryl; and all other groups are as defined in the Summary of the Invention. In another embodiment, $R^{50}$, $R^{52}$, and $R^{53}$ are hydrogen and $R^{54}$ is chloro or methoxy; $R^{50}$, $R^{52}$, and $R^{54}$ are hydrogen and $R^{53}$ is methoxy; or $R^{50}$ and $R^{52}$ are hydrogen and $R^{53}$ and $R^{54}$ together with the carbons to which they are attached form pyridinyl. Even more specifically, $R^{50}$, $R^{52}$, and $R^{53}$ are hydrogen and $R^{54}$ is chloro or methoxy; or $R^{50}$, $R^{52}$, and $R^{54}$ are hydrogen and $R^{53}$ is methoxy.

In another embodiment (G1) of embodiment G is a compound of Formula I where $R^{51}$ is methyl.

Another embodiment (H) of the invention is a compound of Formula I where B is phenyl substituted with $R^{3a}$ and optionally further substituted with one, two, or three $R^3$; and all other groups are as defined in the Summary of the Invention. In another embodiment, B is phenyl substituted with $R^{3a}$. In another embodiment the Compound is of Formula I(a):

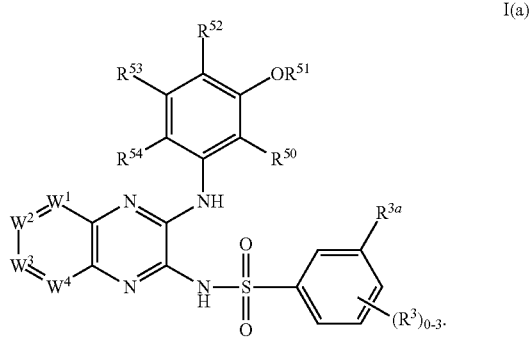

I(a)

In another embodiment, B is phenyl substituted with $R^{3a}$ as depicted in Ia and is not further substituted with $R^3$.

Another embodiment of the Invention (J) is directed to a compound of Formula I where B is heteroaryl optionally substituted with one, two, or three $R^3$. In another embodiment, B is thien-3-yl, pyridinyl, pyrimidinyl, pyridazinyl, pyrazinyl, oxazolyl, isoxazolyl, pyrrolyl, imidazolyl, pyrazolyl, or thiazolyl, each of which is optionally substituted with one or two $R^3$. In another embodiment, B is thien-3-yl, pyridin-2-yl, pyridin-3-yl, pyridin-4-yl, oxazol-2-yl, oxazol-4-yl, oxazol-5-yl, isoxazol-3-yl, isoxazol-4-yl, isoxazol-5-yl, imidazol-2-yl, pyrrol-2-yl, pyrrol-3-yl, imidazol-4-yl, imidazol-5-yl, pyrazol-3-yl, pyrazol-4-yl, or pyrazol-5-yl, each of which is optionally substituted with one or two $R^3$. In another embodiment, B is thien-3-yl, pyridin-3-yl, pyridin-4-yl, isoxazol-4-yl, or pyrazol-4-yl, each of which is optionally substituted with one or two $R^3$. In another embodiment, B is pyridin-3-yl, 2-hydroxy-pyridin-5-yl, isoxazol-4-yl, or pyrazol-4-yl, each of which is optionally substituted with one or two $R^3$.

Another embodiment (K) provides a compound of Formula I or Ia where $R^{3a}$ is cyano; hydroxyamino; carboxy; alkylsulfonyl, aminoalkyloxy; alkylaminoalkyloxy; dialkylaminoalkyloxy; —N($R^7$)C(O)—$C_1$-$C_6$-alkylene-N($R^{7a}$)($R^{7b}$); —C(O)N$R^8R^{8a}$; —N$R^9$C(O)$R^{9a}$; —C(O)N($R^{10}$—$C_1$-$C_6$-alkylene-N($R^{10a}$)$R^{10b}$; —N$R^{11}$C(O)N$R^{11a}R^{11b}$ where $R^{11a}$; —C(O)$R^{12}$; —N$R^{13}$C(O)O$R^{13a}$; —C(O)N($R^{14}$)N($R^{14a}$)($R^{14b}$); —S(O)$_2$N($R^{15}$)—$C_1$-$C_6$-alkylene-N($R^{15a}$)$R^{15b}$; —C(O)N($R^{16}$)—$C_1$-$C_6$-alkylene-C(O)O$R^{16a}$; heteroaryl optionally substituted with one or two aminoalkyl, alkylaminoalkyl, or dialkylaminoalkyl; —N($R^{17}$)—C(═N($R^{17b}$)($R^{17a}$))(N$R^{17c}R^{17d}$); —N($R^{18}$)C(O)—$C_1$-$C_6$-alkylene-N($R^{18b}$)C(O)$R^{18a}$; —C(O)N($R^{19}$)—$C_1$-$C_6$-alkylene-C(O)$R^{19a}$; —N($R^{22}$)C(O)—$C_1$-$C_6$-alkylene-N($R^{22b}$)—N($R^{22c}$)($R^{22a}$); —$C_0$-$C_6$-alkylene-N($R^{23}$)—$C_1$-$C_6$-alkylene-N($R^{23b}$)$R^{23a}$; or —N$R^{24}$C(O)—$C_1$-$C_6$-alkylene-O$R^{24a}$; where each of the alkylene in $R^{3a}$ is independently optionally further substituted with 1, 2, 3, 4, or 5 groups selected from halo, hydroxy, amino, alkylamino, and dialkylamino; and all other groups are as defined in the Summary of the Invention.

In another embodiment, $R^{3a}$ is —NHC(O)CH$_2$NH(CH$_3$), —NHC(O)CH$_2$NH(CH$_2$CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, —NHC(O)CH(CH$_3$)NH(CH$_3$), —NHC(O)CH$_2$NH$_2$, —NHC(O)H, —NHC(O)CH$_2$(azetidin-1-yl), —NHC(O)(pyrrolidin-2-yl), —NHC(O)CH(NH$_2$)CH$_2$OH, —NHC(O)(azetidin-4-yl), —NHC(O)C(CH$_3$)$_2$NH(CH$_3$), —NH$_2$, —NHC(O)CH$_2$NH(CH$_2$CH$_3$), —NHC(O)CH$_2$CH$_2$NH$_2$, —NHOH, —NHC(O)(piperidin-3-yl), —NHC(O)CH$_2$(4-methyl-1,4-diazepan-1-yl), —NHC(O)CH(NH$_2$)(CH$_2$CH$_3$), —NHC(O)CH$_2$NH(CH$_2$CH(OH)(CH$_3$)), —NHC(O)CH$_2$NHCH$_2$CH$_2$F, —NHC(O)CH$_2$NH(OCH$_2$CH(CH$_3$)$_2$), —NHC(O)(1-aminocycloprop-1-yl), —NHC(O)CH$_2$NH(CH$_2$cyclopropyl), —NHC(O)CH$_2$(3-(dimethylamino)-azetidin-1-yl), —NHC(O)(piperidin-2-yl), —NHC(O)(morpholin-4-yl), —NHC(O)CH$_2$(pyrrolidin-1-yl), —NHC(O)CH(NH$_2$)CH$_2$CH$_2$CH$_2$CH$_2$N(CH$_3$)$_2$, —NHC(O)CH$_2$N(CH$_3$)(CH$_2$CH$_3$), —NHC(O)CH$_2$(imidazol-5-yl), —NHC(O)(1-aminocyclopent-1-yl), —NHC(O)CH$_2$NH(CH$_2$CH(CH$_3$)$_2$), —NHC(O)CH$_2$N(CH$_3$)(CH$_2$CH$_3$), —NHC(O)(N-(imidazol-4-ylmethyl)-azetidin-3-yl), —NHC(O)(N-ethyl-azetidin-3-yl), —NHCH$_2$N(CH$_3$)CH$_2$CH$_2$N(CH$_3$)$_2$, —NHC(O)CH$_2$N(CH$_3$)(N-methyl-pyrrolidin-3-yl), —NHC(O)CH$_2$N(CH$_3$)(CH$_2$CH$_2$N(CH$_3$)$_2$), —NHC(O)CH$_2$(3-hydroxy-pyrrolidin-1-yl), —NHC(O)(1-amino-cyclobut-1-yl), —NHC(O)CH$_2$NH(CH$_2$)$_3$CH$_3$, —NHC(O)CH$_2$(3-piperidin-1-ylazetidin-1yl), —NHC(O)NH$_2$, —NHC(O)(1-hydroxycyclopropyl), —NHC(O)CH$_2$NHN(CH$_3$)$_2$, —NHC(O)NH(CH$_3$)$_2$N(CH$_3$)$_2$, —NHC(O)CH$_2$OH, —NHC(O)(pyridazin-4-yl), —NHC(O)(N-methyl-piperidin-4-yl), —NHC(O)CH$_2$NHCH(CH$_3$)$_3$, —NHC(O)CH$_2$(3-dimethylamino-pyrrolidin-1yl), —NHC(O)CH$_2$NH(CH$_2$)$_2$N(CH$_3$)$_2$, —NHC(O)(1-cyclopropylmethyl-azetidin-3-yl), —NHC(O)CH$_2$NH(CH$_3$)$_3$, —NHC(O)(imidazol-2-yl), —NHC(O)(imidazol-4-yl), —NHC(O)(1,2-oxazol-5-yl), —NHC(O)CH$_2$NHCH$_2$CF$_3$, —NHC(O)CH$_2$CH$_2$(piperidin-1-yl), —NHC(O)(3-oxo-cyclopent-1-yl), —NHC(O)(2-hydroxy-pyridin-6-yl), —NHC(O)CH$_2$NH(3-fluoro-4-hydroxyphenyl), —NHC(O)(CH$_2$)$_3$N(CH$_3$)$_2$, —NHC(O)(1-(furan-2-ylmethyl)-azetidin-3-yl), —NHC(O)(pyrimidin-5-yl), —NHC(O)(pyrrol-2-yl), —NHC(O)CH$_2$N(CH$_3$)CH(CH$_3$)$_2$, —NHC(O)CH$_2$N(CH$_2$CH$_3$)$_2$, —NHC(O)CH$_2$(3-methyl-1,2-oxazol-5-yl), —NHC(O)CH$_2$NHCH$_2$(3-hydroxyphenyl), —NHC(O)(N-methyl-pyrrol-2-yl), —NHC(O)(2-amino-tetrahydropyran-2-yl), —NHC(O)CH$_2$(4-methylamino-piperidin-1-yl), —NHC(O)(piperidin-1-yl), —NHC(O)(N-methyl-pyrrolidin-2-yl), —NHC(O)(thien-3-yl), —NHC(O)(N-(cyclopropylcarbonyl)azetidin-3-yl), —NHC(O)CH$_2$(4-methylpiperazin-1-yl), —NHC(O)(N-benzylazetidin-3-yl), —NHC(O)(2-chloro-pyridin-3-yl), —NHC(O)CH$_2$(Pyridin- 4-yl), —NHC(O)CH₂N(CH₃)(CH₂CH=CH₂), —NHC(O)CH₂NH(benzyl), —NHC(O)CH₂OCH₃, —NHC(O)[1-(C(O)CH₂CH₃)-azetidin-3-yl], —NHC(O)(pyridin-3-yl), —NHC(O)CH₂NHCH₂CH₂OCH₃, —NHC(O)(1-[C(O)CH₃]piperidin-4-yl), —NHC(O)CH₂(2-methyl-pyrrolidin-1-yl), —NHC(O)(furan-3-yl), —NHC(O)CH₂N(CH₃)₂, —NHC(O)(2-chloro-pyridin-5-yl), —NHC(O)(2-chlorophenyl), —NHC(O)CH₂(pyridin-2-yl), —NHC(O)CH₂(3-dimethylamino-azetidin-1-yl), —NHC(O)CH₂(pyridin-3-yl), —NHC(O)CH₂(2-chlorophenyl), —NHC(O)CH₂N(CH₃)CH₂CH₂CH₂N(CH₃)₂, —NHC(O)CH₂N(CH₂CH₃)CH₂CH₂OH, —NHC(O)CH₂(2-benzyl-pyrrolidin-1-yl), —NHC(O)(furan-2-yl, —NHC(O)(2-chloro-pyridin-4-yl), —NHC(O)CH₂NHC(O)CH₃, —NHC(O)CH₂CH₂CH₃, —NHC(O)(4-chlorophenyl), —NHC(O)(4-methyl-phenyl), —NHC(O)CH₂NHC(O)O(CH₃)₃, —NHC(O)(benzo[d][1,3]dioxol-5-yl), —NHC(O)CH₂NHOCH₂(2-methoxyphenyl), —NHC(O)(pyridin-4-yl), —NHC(O)CH₂[4-(3,4-dichlorophenyl)-piperazin-1-yl], —NHC(O)CH₂CH₂(pyridin-3-yl), —NHC(O)(tetrahydrofuran-3-yl), —NHC(O)CH₂NHCH₂(2-methylphenyl), —NHC(O)CH(CH₃)CH₂CH₃, —NHC(O)CH₂(3-fluorophenyl), —NHC(O)CH₂C(CH₃)₂phenyl, —NHC(O)(2-methyl-cycloprop-1-yl), —NHC(O)(2-methyl-4-methoxyphenyl), —NHC(O)(2-methylpyridin-3-yl), —NHC(O)(4-methoxyphenyl), —NHC(O)CH₂(4-ethylpiperazin-1-yl), —NHC(O)(thien-2-yl), —NHC(O)(3-fluoro-2-methylphenyl), —NHC(O)(2-bromo-thien-3-yl), —NHC(O)(4-fluorophenyl), —NHC(O)CH₂(3-methylpiperidin-1-yl), —NHC(O)CH(CH₃)₂, —NHC(O)(CH₂)₃CH₃, —NHC(O)CH₂OCH₂CH₃, —NHC(O)CH₂NH(2-fluorophenyl), —NHC(O)(3-dimethylaminophenyl), —NHC(O)CH₂(4-methylpiperidin-1-yl), —NHC(O)CH₂NH(2-n-propylphenyl), —NHC(O)phenyl, —NHC(O)(pyrazin2-yl), —NHC(O)(3-fluoro-4-methoxyphenyl), —NHC(O)C(CH₃)₂CH₂CH₃, —NHC(O)CH₂O(4-fluorophenyl), —NHC(O)(1-methylcarbonyl-azetidin-3-yl), —NHC(O)CH₂NH(4-methylphenyl), —NHC(O)CH₂NH(phenyl), —NHC(O)CH₂(4-allyl-piperazin-1-yl), —NHC(O)(2-methylphenyl), —NHC(O)CH₂CH₂OCH₃, —NHC(O)(3-methyl-furan-2-yl), —NHC(O)C(CH₃)₃, —NHC(O)CH₂NHObenzyl, —NHC(O)CH₂NH(3-chlorophenyl), —NHC(O)cyclobutyl, —NHC(O)CH₂(3-methoxyphenyl), —NHC(O)(1-methylcycloprop-1-yl), —NHC(O)(3-fluorophenyl), —NHC(O)(4-dimethylaminophenyl), —NHC(O)(3,4-dichlorophenyl), —NHC(O)CH₂NHCH₂(2-methylthiophenyl), —NHC(O)CH₂(2-fluorophenyl), —NHC(O)CH₂N(CH₂CH₃)CH(CH₃)₂, —NHC(O)(thiazol-4-yl), —NHC(O)CH₂N(CH₃)benzyl, —NHC(O)CH₂NHCH₂(thien-2-yl), —NHC(O)CH₂NHCH₂(pyridin-2-yl), —NHC(O)(3-methoxyphenyl), —NHC(O)CH₂NHCH₂(3-chloro-4-methylphenyl), —NHC(O)CH(CH₃)CH₂CH₂CH₃, —NHC(O)CH₂(4-chlorophenyl), —NHC(O)(3-fluoro-4-methylphenyl), —NHC(O)CH₂O(2-methylphenyl), —NHC(O)CH₂(cyclohexyl), —NHC(O)(2-phenyl-cycloprop-1-yl), —NHC(O)(3-chlorophenyl), —NHC(O)CH₂(2-methoxyphenyl), —NHC(O)CH₂CH₂(3-methoxyphenyl), —NHC(O)CH₂NH(2-fluoro-4-methylphenyl), —NHC(O)CH₂NHCH₂(3-fluoro-phenyl), —NHC(O)CH₂(4-methoxy-phenyl), —NHC(O)benzyl, —NHC(O)(2,4-dichlorophenyl), —NHC(O)(3-oxo-cyclohex-1-yl), —NHC(O)CH₂NH(3-fluorophenyl), —NHC(O)CH₂(3-chlorophenyl), —NHC(O)CH₂NHCH₂CH(CH₃)phenyl, —NHC(O)CH₂NHCH₂(2,4-dimethylphenyl), —NHC(O)CH₂(2-methyl-piperidin-1-yl), —NHC(O)CH₂NH(2-methoxyphenyl), —NHC(O)CH₂(1,2,3,4-tetrahydroisoquinolin-2-yl), —NHC(O)CH₂CH₂CH=CH₂, —NHC(O)CH₂NH(2-methylphenyl), —NHC(O)CH₂(4-oxo-piperidin-1-yl), —NHC(O)(2-fluorophenyl), —NHC(O)CH₂NHCH(CH₃)phenyl, —NHC(O)(2-fluoro-6-methoxyphenyl), —NHC(O)CH₂NH(2-isopropylphenyl), —NHC(O)CH₂CH₂(2-methoxyphenyl), —NHC(O)CH₂CH₂CH(CH₃)₂, —NHC(O)CH₂(2-phenyl-morpholin-4-yl), —NHC(O)CH₂CH₂(4-methoxyphenyl), —NHC(O)CH₂N(allyl)cyclopentyl, —NHC(O)CH₂N(CH₃)CH₂CH₂OCH₃, —NHC(O)CH₂CH₂C(O)cyclopropyl, —NHC(O)CH₂NH(3-tert-butylphenyl), —NHC(O)CH₂N(n-propyl)(cyclopropylmethyl), —NHC(O)CH₂(2-oxo-cyclopentyl), —NHC(O)CH₂NH(4-chlorophenyl), —NHC(O)CH₂(4-piperidin-1-ylpiperidin-1-yl), —NHC(O)CH₂(4-cyclopentylpiperazin-1-yl), —NHC(O)CH₂(2-methylphenyl), —NHC(O)CH₂NHCH₂(3-fluoro-6-methylphenyl), —NHC(O)CH₂C(CH₃)₃, —NHC(O)CH₂NH(2-chlorophenyl), —NHC(O)(3-fluoro-6-methylphenyl), —NHC(O)(4-fluoro-3-methylphenyl), —NHC(O)(2,3-dichlorophenyl), —NHC(O)CH₂O phenyl, —NHC(O)CH₂NH(2,3-dimethylphenyl), —NHC(O)(2-fluoro-5-methylphenyl), —NHC(O)CH₂NHOCH₂(4-methylphenyl), —NHC(O)CH₂(4-isopropylpiperazin-1-yl), —NHC(O)CH₂(4-fluorophenyl), —NHC(O)CH₂CH(CH₃)₂, —NHC(O)(2-methoxy-4-methylphenyl), —NHC(O)CH₂(4-n-propylpiperidin-1-yl), —NHC(O)CH₂O(3-methylphenyl), —NHC(O)(tetrahydrofuran-2-yl), —NHC(O)CH₂(3-hydroxymethylpiperidin-1-yl), —NHC(O)(1-tert-butoxycarbonylpiperidin-2-yl), —NHC(O)CH₂N(CH₃)CH₂(pyridin-3-yl), —NHC(O)CH₂N(CH₂CH₃)phenyl, —NHC(O)CH₂OCH₂CH₂OCH₃, —NHC(O)CH₂CH₂(cyclopentyl), —NHC(O)(2,5-dichlorophenyl), —NHC(O)CH₂(4-methylcarbonylpiperazin-1-yl), —NHC(O)(5-fluoro-2-methoxyphenyl), —NHC(O)CH₂N(CH₂CH₃)cyclohexyl, —NHC(O)(5-methyl-1,2-oxazol-3-yl), —NHC(O)(3-methylpyridin-3-yl), —NHC(O)(2-methoxypyridin-3-yl), —NHC(O)(3,5-dichlorophenyl), —NHC(O)CH₂(thiazolidin3-yl), —NHC(O)CH₂(4-[C(O)H]-piperazin-1-yl), —NHC(O)CH₂(2-pyridin-4-ylpiperidin-1-yl), —NHC(O)(2-methoxyphenyl), —NHC(O)CH₂N(CH₃)CH₂CH(CH₃)₂, —NHC(O)CH₂(4-[C(O)H]-homopiperazin-1-yl), —NHC(O)(1-phenylcycloprop-1-yl), —NHC(O)CH₂(2,6-dimethylmorpholin-4-yl), NHC(O)CH₂(2-phenylpyrrolidin-1-yl), —NHC(O)CH₂(morpholin-4-yl), —C(O)NHCH(CH₃)CH₂N(CH₃)₂, —C(O)NHCH₂CH₂N(CH₃)₂, —C(O)NH(pyrrolidin-3-yl), —C(O)NHCH₂CH₂(pyrrolidin-1-yl), —C(O)NHCH₂CH₂NH₂, —C(O)N(CH₃)CH₂CH₂N(CH₃)₂, —C(O)NHCH₂(piperidin-2-yl), —C(O)NH(1-methylazetidin-3-yl), —C(O)NHCH₂CH₂(piperidin-1-yl), —C(O)NHCH₂CH₂N(CH₂CH₃)₂, —C(O)NH(1-methylpiperidin-3-yl), —C(O)NH(piperidin-3-yl), —C(O)NHCH₂(1-methylpiperidin-3-yl), —C(O)NHCH₂CH₂N(CH₂CH₂OH)₂, —C(O)NH(1-ethylpiperidin-3-yl), —C(O)NH₂, —C(O)(3-aminopyrrolidin-1-yl), —C(O)(3-methylaminopyrrolidin-1-yl), —C(O)OH, —C(O)NHCH₂CH₂(morpholin-4-yl), —C(O)NHCH₂(1-ethylpyrrolidin-2-yl), —C(O)(4-amino-3-oxo-pyrazolidin-1-yl), —C(O)NHCH₃, —C(O)(3-aminocyclobut-1-yl), —C(O)NHCH₂(pyridin-3-yl), —C(O)NHCH₂CH₂OH, —C(O)NH(3-oxo-pyrazolidin-4-yl), —NHCH₂CH₂(imidazol-4-yl), —C(O)(3-dimethylaminopyrrolidin-1-yl), —C(O)NHCH₂(pyridin-4-yl), —C(O)N(CH₃)(1-methyl-pyrrolidin-3-yl), —C(O)(3-diethylaminopyrrolidin-1-yl), —C(O)NH(pyrrol-1-yl), —C(O)NHCH₂CH₂(pyrrolidin-1-yl), —C(O)N(CH₃)CH₂CH₂CN, —C(O)NHCH₂CH₂OCH₃, —C(O)N(CH₃)CH₂CH₂CN, —C(O)(3-aminopiperidin-1-yl), —C(O)NHCH₂CH₂N(CH₃)₂, —C(O)NH(morpholin-4-yl), —C(O)NHN(CH₃)₂, —C(O)NHCH₂CH₂(imidazol-1-yl), —C(O)NHCH₂CH₂N(CH₂CH₃)₂, —C(O)NHCH₂CH₂CN, —C(O)NHCH₂CH₂C (O)OCH$_3$, —C(O)NHCH$_2$CH$_2$SCH$_3$, —C(O)NHCH$_2$CH$_2$SCH$_2$CH$_3$, —C(O)N(CH$_2$CH$_3$)CH$_2$CH$_2$N(CH$_3$)$_2$, —C(O)NHCH$_2$CH$_2$CH$_2$(2-oxo-pyrrolidin-1-yl), —C(O)NHCH$_2$CH$_2$(pyridin-4-yl), —C(O)NHCH$_2$CH$_2$CH$_2$OCH$_3$, —C(O)NHCH$_2$CH$_2$CH$_2$(morpholin-4-yl), —C(O)NHCH$_2$CH$_2$CH$_2$OCH$_3$, —C(O)N(CH$_3$)CH$_2$CH$_2$CH$_2$N(CH$_3$)$_2$, —C(O)NHCH$_2$CH$_2$CH$_2$OCH$_2$CH$_2$CH$_3$, —C(O)NHCH$_2$CH$_2$C(O)OCH$_2$CH$_3$, —C(O)NHCH$_2$CH$_2$CH$_2$OCH(CH$_3$)$_2$, —C(O)NHC(CH$_3$)$_2$CH$_2$(piperidin-1-yl), —C(O)N(CH$_3$)CH$_2$CH$_2$CH$_3$, —C(O)NH(piperidin-1-yl), —C(O)NHCH(CH$_3$)CH$_2$OCH$_3$, —C(O)NHC(CH$_3$)$_2$CH$_2$(morpholin-4-yl), —C(O)(2-dimethylaminomethylpiperidin-1-yl), —C(O)NH(CH$_2$)$_3$—O—(CH$_2$)$_3$CH$_3$, —C(O)NHCH(CH$_3$)(CH$_2$)$_3$N(CH$_2$CH$_3$)$_2$, —C(O)NHC(CH$_3$)$_2$C(O)(piperidin-1-yl), —C(O)(4-methylpiperazin-1-yl), —C(O)(2-piperidin-1-ylmethyl-piperidin-1-yl), cyano, —NHCH$_3$, —CH(CH$_3$)NHCH$_2$CH$_2$N(CH$_3$)$_2$, —C(O)CH$_3$, —S(O)$_2$NHCH$_2$CH$_2$N(CH$_3$)$_2$, —S(O)$_2$NH(CH$_2$)$_3$N(CH$_3$)$_2$, 5-(N,N-dimethylaminomethyl)-1,3,4-oxadiazol-2-yl, —NHCH$_2$CH$_2$N(CH$_3$)$_2$, —N(CH$_3$)$_2$, —OCH$_2$CH$_2$N(CH$_3$)$_2$, —NHC[N(CH$_3$)$_2$][=N(CH$_3$)$_2$], —OCHF$_2$, —S(O)$_2$CH$_3$, —OCF$_3$, or —NHC(O)CH$_2$(4-dimethylaminopiperidin-1-yl).

In another embodiment (L), the compound of Formula I or Ia is that where R$^{1a}$ is hydroxyamino, —N(R$^7$)C(O)—C$_1$-C$_6$-alkylene-N(R$^{7a}$)(R$^{7b}$), —C(O)NR$^8$R$^{8a}$, —NR$^9$C(O)R$^{9a}$, —C(O)N(R$^{10}$)—C$_1$-C$_6$-alkylene-N(R$^{10a}$)R$^{10b}$, —NR$^{11}$C(O)NR$^{11a}$R$^{11b}$, —N(R$^{22}$)C(O)—C$_1$-C$_6$-alkyene-N(R$^{22b}$)—N(R$^{22c}$)(R$^{22a}$), —NR$^{13}$C(O)OR$^{13a}$, —N(R$^{18}$)C(O)—C$_1$-C$_6$-alkylene-N(R$^{18b}$)C(O)R$^{18a}$, —NR$^{24}$C(O)—C$_1$-C$_6$-alkylene-OR$^{24a}$, or —N(R$^{20}$)C(O)—C$_1$-C$_6$-alkylene-C(O)R$^{20a}$; where each of the alkylene in R$^{3a}$ is independently optionally further substituted with 1, 2, 3, 4, or 5 groups selected from halo, hydroxy, and amino; and all other groups are as defined in the Summary of the Invention. In another embodiment, R$^{3a}$ is —NHC(O)CH$_2$NH(CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, —NHC(O)CH(CH$_3$)NH(CH$_3$), —NHC(O)H, —NHC(O)CH$_2$(azetidin-1-yl), —NHC(O)(pyrrolidin-2-yl), —NHC(O)CH(NH$_2$)CH$_2$OH, —NHC(O)(azetidin-4-yl), —NHC(O)C(CH$_3$)$_2$NH(CH$_3$), —NH$_2$, —NHC(O)CH$_2$NH(CH$_2$CH$_2$CH$_3$), —NHC(O)CH$_2$CH$_2$NH$_2$, —NHOH, or —NHC(O)(piperidin-3-yl).

In another embodiment (M) the compound is of Formula I or Ia and R$^{3a}$—N(R$^7$)C(O)—C$_1$-C$_6$-alkylene-N(R$^{7a}$)(R$^{7b}$); and R$^7$ is hydrogen or alkyl and R$^{7a}$ and R$^{7b}$ are independently hydrogen, alkyl, aminoalkyl, alkylaminoalkyl, or dialkylaminoalkyl; and all other groups are as defined in the Summary of the Invention. In another embodiment, R$^{3a}$ is —NHC(O)CH$_2$NH(CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, or —NHC(O)CH(CH$_3$)NH(CH$_3$).

Embodiment (N) provides a compound of Formula I where each R$^3$ is independently halo; cyano; alkyl; alkenyl; alkoxy; hydroxyamino; carboxy; alkylsulfonyl; aminoalkyloxy; alkylaminoalkyloxy; dialkylaminoalkyloxy; —N(R$^7$)C(O)—C$_1$-C$_6$-alkylene-N(R$^{7a}$)(R$^{7b}$); —C(O)NR$^8$R$^{8a}$; —NR$^9$C(O)R$^{9a}$; —C(O)N(R$^{10}$)—C$_1$-C$_6$-alkylene-N(R$^{10a}$)R$^{10b}$; —(NR$^{11}$C(O)NR$^{11a}$R$^{11b}$ where R$^{11a}$; —C(O)R$^{12}$; —NR$^{13}$C(O)OR$^{13a}$; —C(O)N(R$^{14}$)N(R$^{14a}$)(R$^{14b}$); —S(O)$_2$N(R$^{15}$)—C$_1$-C$_6$-alkylene-N(R$^{15a}$)R$^{15b}$; —C(O)N(R$^{16}$)—C$_1$-C$_6$-alkylene-C(O)OR$^{16a}$; heteroaryl optionally substituted with one or two aminoalkyl, alkylaminoalkyl, or dialkylaminoalkyl; —N(R$^{17}$)—C(=N(R$^{17b}$)(R$^{17a}$))(NR$^{17c}$)(R$^{17d}$); —N(R$^{18}$)C(O)—C$_1$-C$_6$-alkylene-N(R$^{18b}$)C(O)R$^{18a}$; —C(O)N(R$^{19}$)—C$_1$-C$_6$-alkylene-C(O)R$^{19a}$; —N(R$^{22}$)C(O)—C$_1$-C$_6$-alkylene-N(R$^{22b}$)—N(R$^{22c}$)(R$^{22a}$); —C$_0$-C$_6$-alkylene-N(R$^{23}$)—C$_1$-C$_6$-alkylene-N(R$^{23b}$)R$^{23a}$; or —NR$^{24}$C(O)—C$_1$-C$_6$-alkylene-OR$^{24a}$; where each of the alkylene in R$^3$ is independently optionally further substituted with 1, 2, 3, 4, or 5 groups selected from halo, hydroxy, amino, alkylamino, and dialkylamino; and all other groups are as defined in the Summary of the Invention.

In another embodiment, each R$^3$ is independently methyl, bromo, chloro, fluoro, —NHC(O)CH$_2$NH(CH$_3$), —NHC(O)CH$_2$NH(CH$_2$CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, —NHC(O)CH(CH$_3$)NH(CH$_3$), —NHC(O)CH$_2$NH$_2$, —NHC(O)H, —NHC(O)CH$_2$(azetidin-1-yl), —NHC(O)(pyrrolidin-2-yl), —NHC(O)CH(NH$_2$)CH$_2$OH, —NHC(O)(azetidin-4-yl), —NHC(O)C(CH$_3$)$_2$NH(CH$_3$), —NH$_2$, —NHC(O)CH$_2$NH(CH$_2$CH$_2$CH$_3$), —NHC(O)CH$_2$CH$_2$NH$_2$, —NHOH, —NHC(O)(piperidin-3-yl), —NHC(O)CH$_2$(4-methyl-1,4-diazepan-1-yl), —NHC(O)CH(NH$_2$)(CH$_2$CH$_3$), —NHC(O)CH$_2$NH(CH$_2$CH(OH)(CH$_3$)), —NHC(O)CH$_2$NHCH$_2$CH$_2$F, —NHC(O)CH$_2$NH(OCH$_2$CH(CH$_3$)$_2$), —NHC(O)(1-aminocycloprop-1-yl), —NHC(O)CH$_2$NH(CH$_2$cyclopropyl), —NHC(O)CH$_2$(3-(dimethylamino)-azetidin-1-yl), —NHC(O)(piperidin-2-yl), —NHC(O)(morpholin-4-yl), —NHC(O)CH$_2$(pyrrolidin-1-yl), —NHC(O)CH(NH$_2$)CH$_2$CH$_2$CH$_2$CH$_2$N(CH$_3$)$_2$, —NHC(O)CH$_2$N(CH$_3$)(CH$_2$CH$_3$), —NHC(O)CH$_2$(imidazol-5-yl), —NHC(O)(1-aminocyclopent-1-yl), —NHC(O)CH$_2$NH(CH$_2$CH(CH$_3$)$_2$), —NHC(O)CH$_2$N(CH$_3$)(CH$_2$CH$_3$), —NHC(O)(N-(imidazol-4-ylmethyl)-azetidin-3-yl), —NHC(O)(N-ethyl-azetidin-3-yl), —NHCH$_2$N(CH$_3$)CH$_2$CH$_2$N(CH$_3$)$_2$, —NHC(O)CH$_2$N(CH$_3$)(N-methyl-pyrrolidin-3-yl), —NHC(O)CH$_2$N(CH$_3$)(CH$_2$CH$_2$N(CH$_3$)$_2$), —NHC(O)CH$_2$(3-hydroxypyrrolidin-1-yl), —NHC(O)(1-amino-cyclobut-1-yl), —NHC(O)CH$_2$NH(CH$_2$)$_3$CH$_3$, —NHC(O)CH$_2$(3-piperidin-1-ylazetidin-1-yl), —NHC(O)NH$_2$, —NHC(O)(1-hydroxycyclopropyl), —NHC(O)CH$_2$NHN(CH$_3$)$_2$, —NHC(O)NH(CH$_2$)$_2$N(CH$_3$)$_2$, —NHC(O)CH$_2$OH, —NHC(O)(pyridazin-4-yl), —NHC(O)(N-methyl-piperidin-4-yl), —NHC(O)CH$_2$NHCH(CH$_3$)$_3$, —NHC(O)CH$_2$(3-dimethylamino-pyrolidin-1-yl), —NHC(O)CH$_2$NH(CH$_2$)$_2$N(CH$_3$)$_2$, —NHC(O)(1-cyclopropylmethyl-azetidin-3-yl), —NHC(O)CH$_2$NH(CH$_3$)$_3$, —NHC(O)(imidazol-2-yl), —NHC(O)(imidazol-4-yl), —NHC(O)(1,2-oxazol-5-yl), —NHC(O)CH$_2$NHCH$_2$CF$_3$, —NHC(O)CH$_2$CH$_2$(piperidin-1-yl), —NHC(O)(3-oxo-cyclopent-1-yl), —NHC(O)(2-hydroxypyridin-6-yl), —NHC(O)CH$_2$NH(3-fluoro-4-hydroxyphenyl), —NHC(O)(CH$_2$)$_3$N(CH$_3$)$_2$, —NHC(O)(1-(furan-2-ylmethyl)-azetidin-3-yl), —NHC(O)(pyrimidin-5-yl), —NHC(O)(pyrrol-2-yl), —NHC(O)CH$_2$N(CH$_3$)CH(CH$_3$)$_2$, —NHC(O)CH$_2$N(CH$_2$CH$_3$)$_2$, —NHC(O)CH$_2$(3-methyl-1,2-oxazol-5-yl), —NHC(O)CH$_2$NHCH$_2$(3-hydroxyphenyl), —NHC(O)(N-methyl-pyrrol-2-yl), —NHC(O)(2-amino-tetrahydropyran-2-yl), —NHC(O)CH$_2$(4-methylamino-piperidin-1-yl), —NHC(O)(piperidin-1-yl), —NHC(O)(N-methyl-pyrrolidin-2-yl), —NHC(O)(thien-3-yl), —NHC(O)(N-(cyclopropylcarbonyl)azetidin-3-yl), —NHC(O)CH$_2$(4-methylpiperazin-1-yl), —NHC(O)(N-benzylazetidin-3-yl), —NHC(O)(2-chloro-pyridin-3-yl), —NHC(O)CH$_2$(pyridin-4-yl), —NHC(O)CH$_2$N(CH$_3$)(CH$_2$CH=CH$_2$), —NHC(O)CH$_2$NH(benzyl), —NHC(O)CH$_2$OCH$_3$, —NHC(O)[1-(C(O)CH$_2$CH$_3$)-azetidin-3-yl], —NHC(O)(pyridin-3-yl), —NHC(O)CH₂NHCH₂CH₂OCH₃, —NHC(O)(1-[C(O)CH₃]piperidin-4-yl), —NHC(O)CH₂(2-methyl-pyrrolidin-1-yl), —NHC(O)(furan-3-yl), —NHC(O)CH₂N(CH₃)₂, —NHC(O)(2-chloro-pyridin-5-yl), —NHC(O)(2-chlorophenyl), —NHC(O)CH₂(pyridin-2-yl), —NHC(O)CH₂(3-dimethylamino-azetidin-1-yl), —NHC(O)CH₂(pyridin-3-yl), —NHC(O)CH₂(2-chlorophenyl), —NHC(O)CH₂N(CH₃)CH₂CH₂CH₂N(CH₃)₂, —NHC(O)CH₂N(CH₂CH₃)CH₂CH₂OH, —NHC(O)CH₂(2-benzyl-pyrrolidin-1-yl), —NHC(O)(furan-2-yl, —NHC(O)(2-chloro-pyridin-4-yl), —NHC(O)CH₂NHC(O)CH₃, —NHC(O)CH₂CH₂CH₃, —NHC(O)(4-chlorophenyl), —NHC(O)(4-methyl-phenyl), —NHC(O)CH₂NHC(O)O(CH₃)₃, —NHC(O)(benzo[d][1,3]dioxol-5-yl), —NHC(O)CH₂NHOCH₂(2-methoxyphenyl), —NHC(O)(pyridin-4-yl), —NHC(O)CH₂[4-(3,4-dichlorophenyl)-piperazin-1-yl], —NHC(O)CH₂CH₂(pyridin-3-yl), —NHC(O)(tetrahydrofuran-3-yl), —NHC(O)CH₂NHCH₂(2-methylphenyl), —NHC(O)CH(CH₃)CH₂CH₃, —NHC(O)CH₂(3-fluorophenyl), —NHC(O)CH₂C(CH₃)₂-phenyl, —NHC(O)(2-methyl-cycloprop-1-yl), —NHC(O)(2-methyl-4-methoxyphenyl), —NHC(O)(2-methylpyridin-3-yl), —NHC(O)(4-methoxyphenyl), —NHC(O)CH₂(4-ethylpiperazin-1-yl), —NHC(O)(thien-2-yl), —NHC(O)(3-fluoro-2-methylphenyl), —NHC(O)(2-bromo-thien-3-yl), —NHC(O)(4-fluorophenyl), —NHC(O)CH₂(3-methylpiperidin-1-yl), —NHC(O)CH(CH₃)₂, —NHC(O)(CH₂)₃CH₃, —NHC(O)CH₂OCH₂CH₃, —NHC(O)CH₂NH(2-fluorophenyl), —NHC(O)(3-dimethylaminophenyl), —NHC(O)CH₂(4-methylpiperidin-1-yl), —NHC(O)CH₂NH(2-n-propylphenyl), —NHC(O)phenyl, —NHC(O)(pyrazin2-yl), —NHC(O)(3-fluoro-4-methoxyphenyl), —NHC(O)C(CH₃)₂CH₂CH₃, —NHC(O)CH₂O(4-fluorophenyl), —NHC(O)(1-methylcarbonyl-azetidin-3-yl), —NHC(O)CH₂NH(4-methylphenyl), —NHC(O)CH₂NH(phenyl), —NHC(O)CH₂(4-allyl-piperazin-1-yl), —NHC(O)(2-methylphenyl), —NHC(O)CH₂CH₂OCH₃, —NHC(O)(3-methyl-furan-2-yl), —NHC(O)C(CH₃)₃, —NHC(O)CH₂NHObenzyl, —NHC(O)CH₂NH(3-chlorophenyl), —NHC(O)cyclobutyl, —NHC(O)CH₂(3-methoxyphenyl), —NHC(O)(1-methylcycloprop-1-yl), —NHC(O)(3-fluorophenyl), —NHC(O)(4-dimethylaminophenyl), —NHC(O)(3,4-dichlorophenyl), —NHC(O)CH₂NHCH₂(2-methylthiophenyl), —NHC(O)CH₂(2-fluorophenyl), —NHC(O)CH₂N(CH₂CH₃)CH(CH₃)₂, —NHC(O)(thiazol-4-yl), —NHC(O)CH₂N(CH₃)benzyl, —NHC(O)CH₂NHCH₂(thien-2-yl), —NHC(O)CH₂NHCH₂(pyridin-2-yl), —NHC(O)(3-methoxyphenyl), —NHC(O)CH₂NHCH₂(3-chloro-4-methylphenyl), —NHC(O)CH(CH₃)CH₂CH₂CH₃, —NHC(O)CH₂(4-chlorophenyl), —NHC(O)(3-fluoro-4-methylphenyl), —NHC(O)CH₂O(2-methylphenyl), —NHC(O)CH₂(cyclohexyl), —NHC(O)(2-phenyl-cycloprop-1-yl), —NHC(O)(3-chlorophenyl), —NHC(O)CH₂(2-methoxyphenyl), —NHC(O)CH₂CH₂(3-methoxyphenyl), —NHC(O)CH₂NH(2-fluoro-4-methylphenyl), —NHC(O)CH₂NHCH₂(3-fluoro-phenyl), —NHC(O)CH₂(4-methoxyphenyl), —NHC(O)benzyl, —NHC(O)(2,4-dichlorophenyl), —NHC(O)(3-oxo-cyclohex-1-yl), —NHC(O)CH₂NH(3-fluorophenyl), —NHC(O)CH₂(3-chlorophenyl), —NHC(O)CH₂NHCH₂CH(CH₃)phenyl, —NHC(O)CH₂NHCH₂(2,4-dimethylphenyl), —NHC(O)CH₂(2-methyl-piperidin-1-yl), —NHC(O)CH₂NH(2-methoxyphenyl), —NHC(O)CH₂(1,2,3,4-tetrahydroisoquinolin-2-yl), —NHC(O)CH₂CH₂CH=CH₂, —NHC(O)CH₂NH(2-methylphenyl), —NHC(O)CH₂(4-oxo-piperidin-1-yl), —NHC(O)(2-fluorophenyl), —NHC(O)CH₂NHCH(CH₃)phenyl, —NHC(O)(2-fluoro-6-methoxyphenyl), —NHC(O)CH₂NH(2-isopropylphenyl), —NHC(O)CH₂CH₂(2-methoxyphenyl), —NHC(O)CH₂CH₂CH(CH₃)₂, —NHC(O)CH₂(2-phenyl-morpholin-4-yl), —NHC(O)CH₂CH₂(4-methoxyphenyl), —NHC(O)CH₂N(CH₃)CH₂CH₂OCH₃, —NHC(O)CH₂N(CH₃)CH₂CH₂OCH₃, —NHC(O)CH₂CH₂C(O)cyclopropyl, —NHC(O)CH₂NH(3-tert-butylphenyl), —NHC(O)CH₂N(n-propyl)(cyclopropylmethyl), —NHC(O)CH₂(2-oxo-cyclopentyl), —NHC(O)CH₂NH(4-chlorophenyl), —NHC(O)CH₂(4-piperidin-1-ylpiperidin-1-yl), —NHC(O)CH₂(4-cyclopentylpiperazin-1-yl), —NHC(O)CH₂(2-methylphenyl), —NHC(O)CH₂NHCH₂(3-fluoro-6-methylphenyl), —NHC(O)CH₂C(CH₃)₃, —NHC(O)CH₂NH(2-chlorophenyl), —NHC(O)(3-fluoro-6-methylphenyl), —NHC(O)(4-fluoro-3-methylphenyl), —NHC(O)(2,3-dichlorophenyl), —NHC(O)CH₂O phenyl, —NHC(O)CH₂NH(2,3-dimethylphenyl), —NHC(O)(2-fluoro-5-methylphenyl), —NHC(O)CH₂NHOCH₂(4-methylphenyl), —NHC(O)CH₂(4-isopropylpiperazin-1-yl), —NHC(O)CH₂(4-fluorophenyl), —NHC(O)CH₂CH(CH₃)₂, —NHC(O)(2-methoxy-4-methylphenyl), —NHC(O)CH₂(4-n-propylpiperidin-1-yl), —NHC(O)CH₂O(3-methylphenyl), —NHC(O)(tetrahydrofuran-2-yl), —NHC(O)CH₂(3-hydroxymethylpiperidin-1-yl), —NHC(O)(1-tert-butoxycarbonylpiperidin-2-yl), —NHC(O)CH₂N(CH₃)CH₂(pyridin-3-yl), —NHC(O)CH₂N(CH₂CH₃)phenyl, —NHC(O)CH₂OCH₂CH₂OCH₃, —NHC(O)CH₂CH₂(cyclopentyl), —NHC(O)(2,5-dichlorophenyl), —NHC(O)CH₂(4-methylcarbonylpiperazin-1-yl), —NHC(O)(5-fluoro-2-methoxyphenyl), —NHC(O)CH₂N(CH₂CH₃)cyclohexyl, —NHC(O)(5-methyl-1,2-oxazol-3-yl), —NHC(O)(3-methylpyridin-3-yl), —NHC(O)(2-methoxypyridin-3-yl), —NHC(O)(3,5-dichlorophenyl), —NHC(O)CH₂(thiazolidin3-yl), —NHC(O)CH₂(4-[C(O)H]-piperazin-1-yl), —NHC(O)CH₂(2-pyridin-4-ylpiperidin-1-yl), —NHC(O)(2-methoxyphenyl), —NHC(O)CH₂N(CH₃)CH₂CH(CH₃)₂, —NHC(O)CH₂(4-[C(O)H]-homopiperazin-1-yl), —NHC(O)(1-phenylcycloprop-1-yl), —NHC(O)CH₂(2,6-dimethylmorpholin-4-yl), NHC(O)CH₂(2-phenylpyrrolidin-1-yl), —NHC(O)CH₂(morpholin-4-yl), —C(O)NHCH(CH₃)CH₂N(CH₃)₂, —C(O)NHCH₂CH₂N(CH₃)₂, —C(O)NH(pyrrolidin-3-yl), —C(O)NHCH₂CH₂(pyrrolidin-1-yl), —C(O)NHCH₂CH₂NH₂, —C(O)N(CH₃)CH₂CH₂N(CH₃)₂, —C(O)NHCH₂(piperidin-2-yl), —C(O)NH(1-methylazetidin-3-yl), —C(O)NHCH₂CH₂(piperidin-1-yl), —C(O)NHCH₂CH₂N(CH₃)₂, —C(O)NH(1-methylpiperidin-3-yl), —C(O)NH(piperidin-3-yl), —C(O)NHCH₂(1-methylpiperidin-3-yl), —C(O)NHCH₂N(CH₂CH₂OH)₂, —C(O)NH(1-ethylpiperidin-3-yl), —C(O)NH₂, —C(O)(3-aminopyrrolidin-1-yl), —C(O)(3-methylaminopyrrolidin-1-yl), —C(O)OH, —C(O)NHCH₂CH₂(morpholin-4-yl), —C(O)NHCH₂(1-ethylpyrrolidin-2-yl), —C(O)(4-amino-3-oxo-pyrazolidin-1-yl), —C(O)NHCH₃, —C(O)(3-aminocyclobut-1-yl), —C(O)NHCH₂(pyridin-3-yl), —C(O)NHCH₂CH₂OH, —C(O)NH(3-oxo-pyrazolidin-4-yl), —NHCH₂CH₂(imidazol-4-yl), —C(O)(3-dimethylaminopyrrolidin-1-yl), —C(O)NHCH₂(pyridin-4-yl), —C(O)N(CH₃)(1-methyl-pyrrolidin-3-yl), —C(O)(3-diethylaminopyrrolidin-1-yl), —C(O)NH(pyrrol-1-yl), —C(O)NHCH₂CH₂CH₂(pyrrolidin-1-yl), —C(O)N(CH₃)CH₂CH₂CN, —C(O)NHCH₂CH₂OCH₃, —C(O)N(CH₂CH₃)CH₂CH₂CN, —C(O)(3-aminopiperidin-1-yl), —C(O)NHCH₂CH₂CH₂N(CH₃)₂, —C(O)NH(morpholin-4-yl), —C(O)NHN(CH₃)₂, —C(O)NHCH₂CH₂CH₂(imidazol-1-yl), —C(O)NHCH₂CH₂N(CH₂CH₃)₂, —C(O)NHCH₂CH₂CN, —C(O)NHCH₂CH₂C(O)OCH₃, —C(O)NHCH₂CH₂SCH₃, —C(O)NHCH₂CH₂SCH₂CH₃, —C(O)N(CH₂CH₃)CH₂CH₂N(CH₃)₂, —C(O)NHCH₂CH₂CH₂(2-oxo-pyrrolidin-1-yl), —C(O)NHCH$_2$CH$_2$(pyridin-4-yl), —C(O)NHCH$_2$CH$_2$CH$_2$OCH$_2$CH$_3$, —C(O)NHCH$_2$CH$_2$CH$_2$(morpholin-4-yl), —C(O)NHCH$_2$CH$_2$CH$_2$OCH$_3$, —C(O)N(CH$_3$)CH$_2$CH$_2$CH$_2$N(CH$_3$)$_2$, —C(O)NHCH$_2$CH$_2$CH$_2$OCH$_2$CH$_3$, —C(O)NHCH$_2$CH$_2$OCH$_2$CH$_3$, —C(O)NHCH$_2$CH$_2$CH$_2$OCH(CH$_3$)$_2$, —C(O)NHC(CH$_3$)$_2$CH$_2$(piperidin-1-yl), —C(O)N(CH$_3$)CH$_2$CH$_2$CH$_3$, —C(O)NH(piperidin-1-yl), —C(O)NHCH(CH$_3$)CH$_2$OCH$_3$, —C(O)NHC(CH$_3$)$_2$CH$_2$(morpholin-4-yl), —C(O)(2-dimethylaminomethylpiperidin-1-yl), —C(O)NH(CH$_2$)$_3$—O—(CH$_2$)$_3$CH$_3$, —C(O)NHCH(CH$_3$)(CH$_2$)$_3$N(CH$_2$CH$_3$)$_2$, —C(O)NHC(CH$_3$)$_2$C(O)(piperidin-1-yl), —C(O)(4-methylpiperazin-1-yl), —C(O)(2-piperidin-1-yl-methyl-piperidin-1-yl), cyano, —NHCH$_3$, —CH(CH$_3$)NHCH$_2$CH$_2$N(CH$_3$)$_2$, —C(O)CH$_3$, —S(O)$_2$NHCH$_2$CH$_2$N(CH$_3$)$_2$, —S(O)$_2$NH(CH$_2$)$_3$N(CH$_3$)$_2$, 5-(N,N-dimethylaminomethyl)-1,3,4-oxadiazol-2-yl, —NHCH$_2$CH$_2$N(CH$_3$)$_2$, —N(CH$_3$)$_2$, —OCH$_2$CH$_2$N(CH$_3$)$_2$, —NHC[N(CH$_3$)$_2$][=N(CH$_3$)$_2$], —OCHF$_2$, —CF$_3$, —S(O)$_2$CH$_3$, —OCF$_3$, —NHC(O)CH$_2$(4-dimethylaminopiperidin-1-yl), or methoxy.

In another embodiment (P), the Compound of Formula I is that where each R$^3$ is independently halo, alkyl, hydroxyamino, —N(R$^7$)C(O)—C$_1$-C$_6$-alkylene-N(R$^{7a}$)(R$^{7b}$), —C(O)NR$^8$R$^{8a}$, —NR$^9$C(O)R$^{9a}$, —C(O)N(R$^{10}$)—C$_1$-C$_6$-alkylene-N(R$^{10a}$)R$^{10b}$—NR$^{11}$C(O)NR$^{11a}$R$^{11b}$, —N(R$^{22}$)C(O)—C$_1$-C$_6$-alkylene-N(R$^{22b}$)—NR$^{22c}$)(R$^{22a}$), —NR$^{13}$C(O)OR$^{13a}$, —N(R$^{18}$)C(O)—C$_1$-C$_6$-alkylene-N(R$^{18b}$)C(O)R$^{18a}$, —NR$^{24}$C(O)—C$_1$-C$_6$-alkylene-OR$^{24a}$, or —N(R$^{20}$)C(O)—C$_1$-C$_6$-alkylene-C(O)R$^{20a}$; where each of the alkylene in R$^3$ is independently optionally further substituted with 1, 2, 3, 4, or 5 groups selected from halo, hydroxy, and amino; and all other groups are as defined in the Summary of the Invention. In another embodiment, each R$^3$ is independently methyl, chloro, —NHC(O)CH$_2$NH(CH$_3$), —NHC(O)CH(CH$_3$)NH$_2$, —NHC(O)C(CH$_3$)$_2$NH$_2$, —NHC(O)CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, —NHC(O)CH(CH$_3$)NH(CH$_3$), —NHC(O)H, —NHC(O)CH$_2$(azetidin-1-yl), —NHC(O)(pyrrolidin-2-yl), —NHC(O)CH(NH$_2$)CH$_2$OH, —NHC(O)(azetidin-4-yl), —NHC(O)C(CH$_3$)$_2$NH(CH$_3$), —NH$_2$, —NHC(O)CH$_2$NH(CH$_2$CH$_2$CH$_3$), —NHC(O)CH$_2$CH$_2$NH$_2$, —NHOH, or —NHC(O)(piperidin-3-yl).

In another embodiment (Q), the Compound of Formula I is that where R$^3$ is alkyl or —N(R$^7$)C(O)—C$_1$-C$_6$-alkylene-N(R$^{7a}$)(R$^{7b}$); and R$^7$ is hydrogen or alkyl and R$^{7a}$ and R$^{7b}$ are independently hydrogen, alkyl, aminoalkyl, alkylaminoalkyl, or dialkylaminoalkyl; and all other groups are as defined in the Summary of the Invention. In another embodiment, each R$^3$ is independently methyl, —NHC(O)CH$_2$NH(CH$_3$), —NHC(O)CH(CH$_3$)NH$_2$, —NHC(O)C(CH$_3$)$_2$NH$_2$, —NHC(O)—CH$_2$N(CH$_3$)$_2$, —NHC(O)CH$_2$N(CH$_3$)CH$_2$CH$_2$N(CH$_3$)$_2$, —NHC(O)CH(NH$_2$)CH$_2$CH$_3$, —NHC(O)CH$_2$N(CH$_3$)CH$_2$CH$_2$N(CH$_3$)$_2$, or —NHC(O)CH(CH$_3$)NH(CH$_3$).

In another embodiment (R), the Compound of Formula I is that where B is phenyl, R$^3$ is not present or R$^3$ is halo, alkyl, or alkoxy; R$^{3a}$ is —C(O)NR$^8$R$^{8a}$, —NR$^9$C(O)R$^{9a}$, —N(R$^7$)C(O)—C$_1$-C$_6$-alkylene-N(R$^{7a}$)(R$^{7b}$), or —C(O)N(R$^{10}$)—C$_1$-C$_6$-alkylene-N(R$^{10a}$)R$^{10b}$ where each of the alkylene in R$^{3a}$ is independently optionally further substituted with 1, 2, 3, 4, or 5 groups selected from halo, hydroxy, and amino; and all other groups are as defined in the Summary of the Invention.

In another embodiment (R1) of embodiment R, the compound is that where R$^{50}$, R$^{52}$, and R$^{53}$ are hydrogen and R$^{54}$ is halo or alkoxy; R$^{50}$, R$^{52}$, and R$^{54}$ are hydrogen and R$^{53}$ is alkoxy; or R$^{50}$ and R$^{52}$ are hydrogen and R$^{53}$ and R$^{54}$ together with the carbons to which they are attached form a 6-membered heteroaryl; and all other groups are as defined in the Summary of the Invention. In another embodiment, R$^{50}$, R$^{52}$, and R$^{53}$ are hydrogen and R$^{54}$ is halo or alkoxy; or R$^{50}$, R$^{52}$, and R$^{54}$ are hydrogen and R$^{53}$ is alkoxy.

In another embodiment of (R$^2$) of embodiment R, the compound is that where R$^{51}$ is methyl.

In another embodiment (S), the compound of Formula Ia:

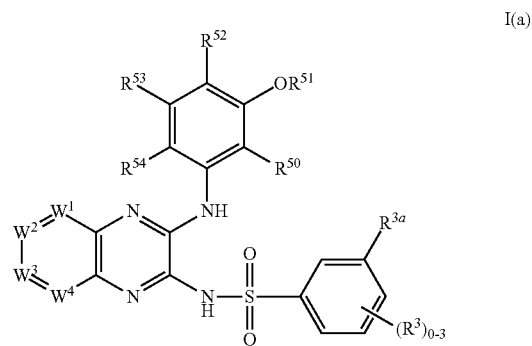

I(a)

is that where R$^3$ is not present or R$^3$ is alkyl and R$^{3a}$ is —N(R$^7$)C(O)—C$_1$-C$_6$-alkylene-N(R$^{7a}$)(R$^{7b}$), —C(O)NR$^8$R$^{8a}$, —NR$^9$C(O)R$^{9a}$, or)-C(O)N(R$^{10}$)—C$_1$-C$_6$-alkylene-N(R$^{10a}$)R$^{10b}$; where each of the alkylene in R$^{3a}$ is independently optionally further substituted with 1, 2, 3, 4, or 5 groups selected from halo, hydroxy, and amino; and all other groups are as defined in the Summary of the Invention. In another embodiment, R$^3$ is not present or is methyl. In another embodiment, R$^3$ is not present.

In another embodiment (S1) of embodiment S is that where R$^7$ is hydrogen or alkyl and R$^{7a}$, and R$^{7b}$ are independently hydrogen, alkyl, hydroxyalkyl, aminoalkyl, alkylaminoalkyl, or dialkylaminoalkyl; R$^8$ is hydrogen or alkyl and R$^{8a}$ is heterocycloalkyl or heterocycloalkylalkyl; R$^9$ is hydrogen or alkyl and R$^{9a}$ is hydrogen, heterocycloalkyl, or heterocycloalkylalkyl; and R$^{10}$, R$^{10a}$, and R$^{10b}$ are independently hydrogen, alkyl, hydroxyalkyl, aminoalkyl, alkylaminoalkyl, or dialkylaminoalkyl.

In another embodiment (S2) of embodiment S is that where R$^{50}$, R$^{52}$, and R$^{53}$ are hydrogen and R$^{54}$ is halo or alkoxy; or R$^{50}$, R$^{52}$, and R$^{54}$ are hydrogen and R$^{53}$ is alkoxy; or R$^{50}$ and R$^{52}$ are hydrogen and R$^{53}$ and R$^{54}$ together with the carbons to which they are attached form a 6-membered heteroaryl. In another embodiment, R$^{50}$, R$^{52}$, and R$^{53}$ are hydrogen and R$^{54}$ is halo or alkoxy; or R$^{50}$, R$^{52}$, and R$^{54}$ are hydrogen and R$^{53}$ is alkoxy.

In another embodiment of (S3) of embodiment S, the compound is that where R$^{51}$ is methyl.

In another embodiment (T), the Compound of Formula I is that where B is heteroaryl, one R$^3$ is halo, alkyl, or alkoxy and a second R$^3$ is —C(O)NR$^8$R$^{8a}$, —NR$^9$C(O)R$^{9a}$, —N(R$^7$)C(O)—C$_1$-C$_6$-alkylene-N(R$^{7a}$)(R$^{7b}$), or)-C(O)N(R$^{10}$)—C$_1$-C$_6$-alkylene-N(R$^{10a}$)R$^{10b}$ where each of the alkylene in R$^3$ is independently optionally further substituted with 1, 2, 3, 4, or 5 groups selected from halo, hydroxy, and amino; and all other groups are as defined in the Summary of the Invention.

In another embodiment (T1) of embodiment T, the compound is that where R$^7$ is hydrogen or alkyl and R$^{7a}$, and R$^{7b}$ are independently hydrogen, alkyl, hydroxyalkyl, aminoalkyl, alkylaminoalkyl, or dialkylaminoalkyl; R$^8$ is hydrogen or alkyl and R$^{8a}$ is heterocycloalkyl or heterocycloalkylalkyl; $R^9$ is hydrogen or alkyl and $R^{9a}$ is hydrogen, heterocycloalkyl, or heterocycloalkylalkyl; $R^{10}$, $R^{10a}$, and $R^{10b}$ are independently hydrogen, alkyl, hydroxyalkyl, aminoalkyl, alkylaminoalkyl, or dialkylaminoalkyl.

In another embodiment U, the compound of Formula I is that where B is

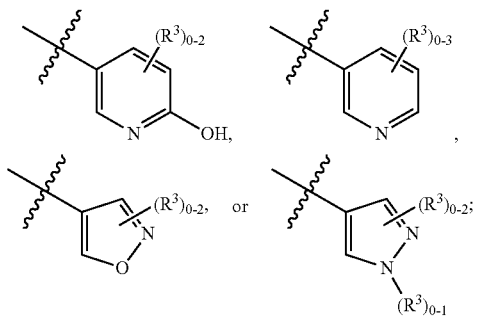

each $R^3$ (when $R^3$ is present) is independently halo, alkyl, alkoxy, aminoalkyloxy, alkylaminoalkyloxy, dialkylaminoalkyloxy, alkylamino, dialkylamino, —C(O)NR$^8$R$^{8a}$, —NR$^9$C(O)R$^{9a}$, —N(R$^7$)C(O)—C$_1$-C$_6$-alkylene-N(R$^{7a}$)(R$^{7b}$), or —C(O)N(R$^{10}$)—C$_1$-C$_6$-alkylene-N(R$^{10a}$)R$^{10b}$; and all other groups are as defined in the Summary of the Invention.

In another embodiment (U1) of embodiment U, the compound of Formula I is that where $R^{50}$, $R^{52}$, and $R^{53}$ are hydrogen and $R^{54}$ is halo or alkoxy; $R^{50}$, $R^{52}$, and $R^{54}$ are hydrogen and $R^{53}$ is alkoxy; or $R^{50}$ and $R^{52}$ are hydrogen and $R^{53}$ and $R^{54}$ together with the carbons to which they are attached form a 6-membered heteroaryl; and all other groups are as defined in the Summary of the Invention. In another embodiment, $R^{50}$, $R^{52}$, and $R^{53}$ are hydrogen and $R^{54}$ is halo or alkoxy; or $R^{50}$, $R^{52}$, and $R^{54}$ are hydrogen and $R^{53}$ is alkoxy.

In another embodiment (U2) of embodiment U1, the compound of Formula I is that where $R^{51}$ is methyl.

In another embodiment (U3) of embodiment U, the Compound of Formula I is that where $R^7$ is hydrogen or alkyl and $R^{7a}$, and $R^{7b}$ are independently hydrogen, alkyl, hydroxyalkyl, aminoalkyl, alkylaminoalkyl, or dialkylaminoalkyl; $R^8$ is hydrogen or alkyl and $R^{8a}$ is heterocycloalkyl or heterocycloalkylalkyl; $R^9$ is hydrogen or alkyl and $R^{9a}$ is hydrogen, heterocycloalkyl, or heterocycloalkylalkyl; $R^{10}$, $R^{10a}$, and $R^{10b}$ are independently hydrogen, alkyl, hydroxyalkyl, aminoalkyl, alkylaminoalkyl, or dialkylaminoalkyl In another embodiment of the Invention (V) the Compound of Formula I is that where $W^1$, $W^2$, $W^3$, and $W^4$ are —C(H)=; or $W^2$ and $W^3$ are —C(H)= and one of $W^1$ and $W^4$ is —N= and the other is —C(H)=;

$R^{50}$ is hydrogen;
$R^{51}$ is hydrogen or alkyl;
$R^{52}$ is hydrogen;
$R^{53}$ is hydrogen, alkoxy, nitro, amino, or —N(R$^{55}$)C(O)—C$_1$-C$_6$-alkylene-N(R$^{55a}$)R$^{55b}$; and $R^{54}$ is hydrogen, alkyl, alkoxy, or halo; or $R^{53}$ and $R^{54}$ together with the carbons to which they are attached form a 6-membered heteroaryl;

B is phenyl substituted with $R^{3a}$ and optionally further substituted with one $R^3$; or
B is heteroaryl optionally substituted with one or two $R^3$;
$R^{3a}$ is cyano; hydroxyamino; carboxy; alkylsulfonyl, aminoalkyloxy; alkylaminoalkyloxy; dialkylaminoalkyloxy; —N(R$^7$)C(O)—C$_1$-C$_6$-alkylene-N(R$^{7a}$)(R$^{7b}$); —C(O)NR$^8$R$^{8a}$; —NR$^9$C(O)R$^{9a}$; —C(O)N(R$^{10}$)—C$_1$-C$_6$-alkylene-N(R$^{10a}$)R$^{10b}$; —NR$^{11}$C(O)NR$^{11a}$R$^{11b}$ where R$^{11a}$; —C(O)R$^{12}$; —NR$^{13}$C(O)OR$^{13a}$; —C(O)N(R$^{14}$)N(R$^{14a}$)(R$^{14b}$); —S(O)$_2$N(R$^{15}$)—C$_1$-C$_6$-alkylene-N(R$^{15a}$)R$^{15b}$; —C(O)N(R$^{16}$)—C$_1$-C$_6$-alkylene-C(O)OR$^{16a}$; heteroaryl optionally substituted with one or two aminoalkyl, alkylaminoalkyl, or dialkylaminoalkyl; —N(R$^{17}$)— C(=N(R$^{17b}$)(R$^{17a}$))(NR$^{17c}$R$^{17d}$); —N(R$^{18}$)C(O)—C$_1$-C$_6$-alkylene-N(R$^{18b}$)C(O)R$^{18a}$; —C(O)N(R$^{19}$)—C$_1$-C$_6$-alkylene-C(O)R$^{19a}$; —N(R$^{22}$)C(O)—C$_1$-C$_6$-alkylene-N(R$^{22b}$)—N(R$^{22c}$)(R$^{22a}$); —C$_0$C$_6$-alkylene-N(R$^{23}$)—C$_1$-C$_6$-alkylene-N(R$^{23b}$)R$^{23a}$; or —NR$^{24}$C(O)—C$_1$-C$_6$-alkylene-OR$^{24a}$; where each of the alkylene in R$^{3a}$ is independently optionally further substituted with 1, 2, 3, 4, or 5 groups selected from halo, hydroxy, and amino;

each $R^3$ (when $R^3$ is present) is independently halo; cyano; alkyl; alkenyl; alkoxy; hydroxyamino; carboxy; alkylsulfonyl, aminoalkyloxy; alkylaminoalkyloxy; dialkylaminoalkyloxy; —N(R$^7$)C(O)—C$_1$-C$_6$-alkylene-N(R$^{7a}$)(R$^{7b}$); —C(O)NR$^8$R$^{8a}$; —NR$^9$C(O)R$^{9a}$; —C(O)N(R$^{10}$)—C$_1$-C$_6$-alkylene-N(R$^{10}a)R$^{10b}$; —NR$^{11}$C(O)NR$^{11a}$R$^{11b}$ where R$^{11a}$; —C(O)R$^{12}$; —NR$^{13}$C(O)OR$^{13a}$; —C(O)N(R$^{14}$)N(R$^{14a}$)(R$^{14b}$); —S(O)$_2$N(R$^{15}$)—C$_1$-C$_6$-alkylene-N(R$^{15a}$)R$^{15b}$; —C(O)N(R$^{16}$)—C$_1$-C$_6$-alkylene-C(O)OR$^{16a}$; heteroaryl optionally substituted with one or two aminoalkyl, alkylaminoalkyl, or dialkylaminoalkyl; —N(R$^{17}$)— C(=N(R$^{17}$NR$^{17a}$))(NR$^{17c}$R$^{17d}$); —N(R$^{18}$)C(O)—C$_1$-C$_6$-alkylene-N(R$^{18b}$)C(O)R$^{18a}$; —C(O)N(R$^{19}$)—C$_1$-C$_6$-alkylene-C(O)R$^{19a}$; —N(R$^{22}$)C(O)—C$_1$-C$_6$-alkylene-N(R$^{22b}$)—N(R$^{22c}$)(R$^{22a}$); —N(R$^{23b}$)R$^{23a}$; or —NR$^{24}$C(O)—C$_1$-C$_6$-alkylene-N(R$^{23}$)—C$_1$-C$_6$-alkylene or —NR$^{24}$C(O)—C$_1$-C$_6$-alkylene-OR$^{24a}$; where each of the alkylene in R$^3$ is independently optionally further substituted with 1, 2, 3, 4, or 5 groups selected from halo, hydroxy, and amino;

provided that when $R^{50}$ and $R^{52}$ are hydrogen, $R^{51}$ is hydrogen or methyl, $R^{53}$ is hydrogen or methoxy, and $R^{54}$ is hydrogen or methoxy, then B is not 2,3-dihydro-1,4-benzodioxinyl, thien-2-yl, or thien-2-yl substituted with one $R^3$ where $R^3$ is halo.

Another embodiment (W) of the invention is a Compound of Formula I where $R^{50}$, $R^{53}$, and $R^{54}$ are independently hydrogen, alkyl, alkenyl, halo, haloalkyl, haloalkenyl, hydroxy, alkoxy, alkenyloxy, haloalkoxy, nitro, amino, alkylamino, dialkylamino, —N(R$^{55}$)C(O)—C$_1$-C$_6$-alkylene-N(R$^{55a}$)R$^{55b}$, alkylcarbonyl, alkenylcarbonyl, carboxy, alkoxycarbonyl, cyano, alkylthio, —S(O)$_2$NR$^{55}$R$^{55a}$, or alkylcarbonylamino and where R$^{55}$ and R$^{55b}$ are independently hydrogen, alkyl, or alkenyl and R$^{55a}$ is hydrogen, alkyl, alkenyl, hydroxy, or alkoxy; or $R^{53}$ and $R^{54}$ together with the carbons to which they are attached form a 5- or 6-membered heteroaryl or 5- or 6-membered heterocycloalkyl.

Another embodiment (X) of the invention is a Compound of Formula I where $R^{53}$ and $R^{54}$ together with the carbons to which they are attached form a 5- or 6-membered heteroaryl or 5- or 6-membered heterocycloalkyl.

Representative Compounds

Representative compounds of Formula I and/or II are depicted below. The examples are merely illustrative and do not limit the scope of the invention in any way. Compounds of the invention are named according to systematic application of the nomenclature rules agreed upon by the International Union of Pure and Applied Chemistry (IUPAC), International Union of Biochemistry and Molecular Biology (IUBMB), and the Chemical Abstracts Service (CAS). Names in Table 1 were generated using ACD/Labs naming software 8.00 release, product version 8.08 with the exception of Compound 374 which was named using ChemDraw v. 9.0.1.

The Compounds in Table 1 can be prepared as pharmaceutically acceptable salts, solvates, hydrates, and/or isomers thereof. All such salt, solvate, hydrate, and isomer combinations of the Compounds in Table 1 can be used to practice the invention. In particular, the invention can be practiced with one or two pharmaceutically acceptable salts of a Compound of Table 1 which salt(s) are formed with one or two acids independently selected from hydrochloric acid, hydrobromic acid, sulfuric acid, nitric acid, phosphoric acid, acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid. In particular, the invention can be practiced with one or two pharmaceutically acceptable salts of a Compound of Table 1 which salt(s) are formed with one or two bases independently selected from sodium, potassium, lithium, ammonium, calcium, magnesium, iron, zinc, copper, manganese, aluminum, isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, tromethamine, and N-methylglucamine. Any individual compound (and any optional salt, optional solvate, and optional hydrate thereof) in Table 1 can be used in combination with any of the above embodiments.

TABLE 1

| Cpd. No. | Structure | Name |
|---|---|---|
| 1 | 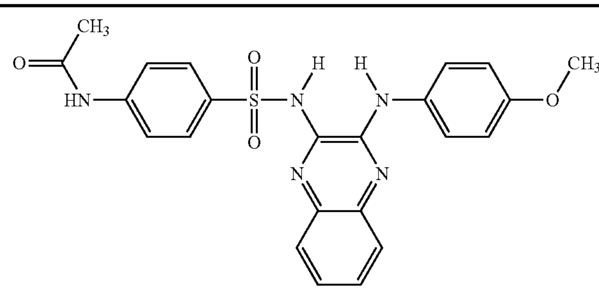 | N-(4-{[(3-{[4-(methoxy)phenyl]amino}quinoxalin-2-yl)amino]sulfonyl}phenyl)acetamide |
| 2 | 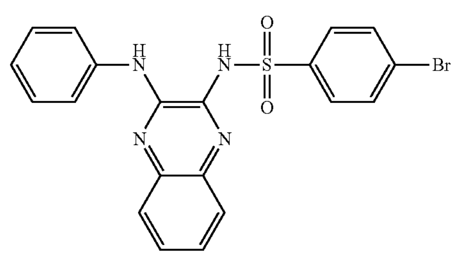 [SMILES: O=S(=O)(Nc1nc2ccccc2nc1Nc1ccccc1)c1ccc(Br)cc1] | 4-bromo-N-[3-(phenylamino)quinoxalin-2-yl]benzene sulfonamide |
| 3 | 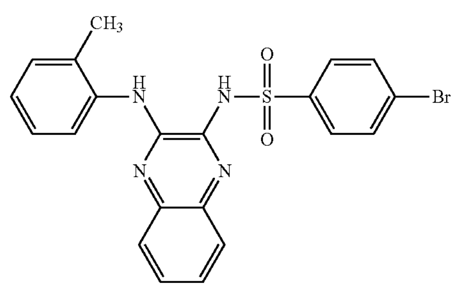 [SMILES: Cc1ccccc1Nc1nc2ccccc2nc1NS(=O)(=O)c1ccc(Br)cc1] | 4-bromo-N-{3-[(2-methylphenyl)amino]quinoxalin-2-yl}benzene sulfonamide |
| 4 | 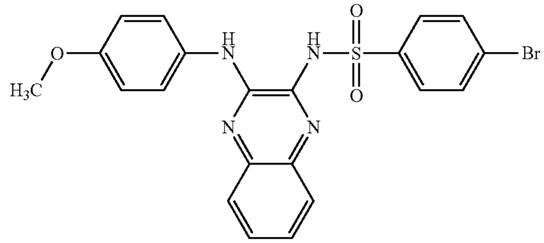 [SMILES: COc1ccc(Nc2nc3ccccc3nc2NS(=O)(=O)c2ccc(Br)cc2)cc1] | 4-bromo-N-(3-{[4-(methoxy)phenyl]amino}quinoxalin-2-yl)benzene sulfonamide |

TABLE 1-continued

| Cpd. No. | Structure | Name |
|---|---|---|
| 5 | 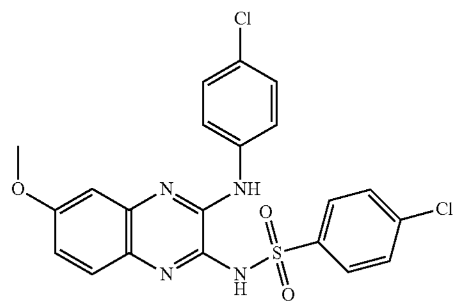 [SMILES: COc1ccc2nc(NS(=O)(=O)c3ccc(Cl)cc3)c(Nc3ccc(Cl)cc3)nc2c1] | 4-chloro-N-{3-[(4-chlorophenyl)amino]-6-(methoxy)quinoxalin-2-yl}benzenesulfonamide |
| 6 | 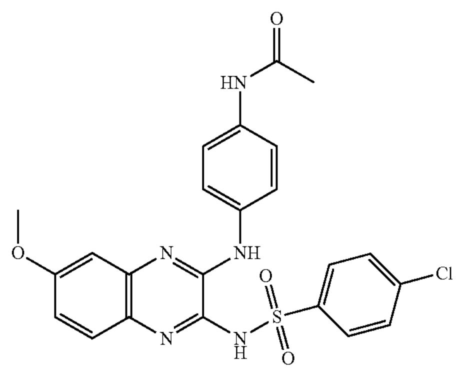 [SMILES: COc1ccc2nc(NS(=O)(=O)c3ccc(Cl)cc3)c(Nc3ccc(NC(C)=O)cc3)nc2c1] | N-(4-{[3-{[(4-chlorophenyl)sulfonyl]amino}-7-(methoxy)quinoxalin-2-yl]amino}phenyl)acetamide |
| 7 | 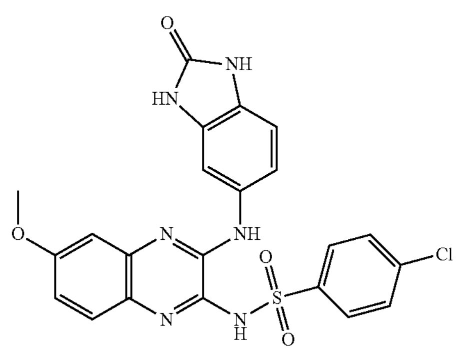 [SMILES: COc1ccc2nc(NS(=O)(=O)c3ccc(Cl)cc3)c(Nc3ccc4[nH]c(=O)[nH]c4c3)nc2c1] | 4-chloro-N-{6-(methoxy)-3-[(2-oxo-2,3-dihydro-1H-benzimidazol-5-yl)amino]quinoxalin-2-yl}benzenesulfonamide |
| 8 | 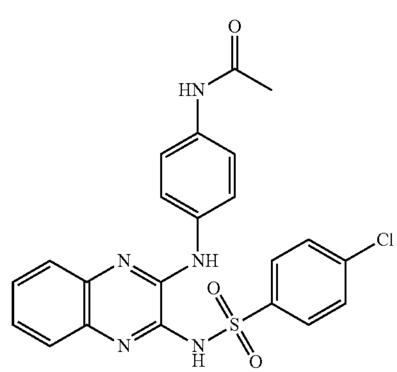 [SMILES: CC(=O)Nc1ccc(Nc2nc3ccccc3nc2NS(=O)(=O)c2ccc(Cl)cc2)cc1] | N-{4-[(3-{[(4-chlorophenyl)sulfonyl]amino}quinoxalin-2-yl)amino]phenyl}acetamide |

TABLE 1-continued

| Cpd. No. | Structure | Name |
|---|---|---|
| 9 | 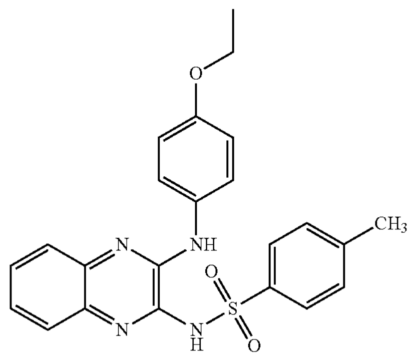 [SMILES: CCOc1ccc(Nc2nc3ccccc3nc2NS(=O)(=O)c2ccc(C)cc2)cc1] | N-(3-{[4-(ethyloxy)phenyl]amino}quinoxalin-2-yl)-4-methylbenzene sulfonamide |
| 10 | 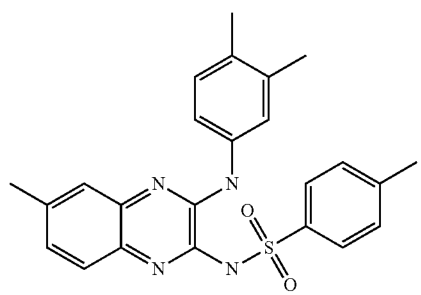 | N-{3-[(3,4-dimethylphenyl)amino]-6-methylquinoxalin-2-yl}-4-methylbenzene sulfonamide |
| 11 | 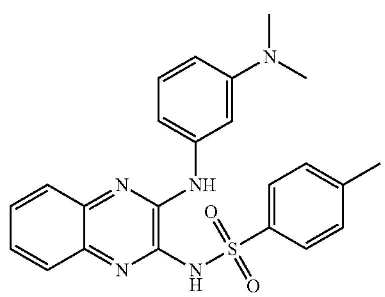 [SMILES: Cc1ccc(S(=O)(=O)Nc2nc3ccccc3nc2Nc2cccc(N(C)C)c2)cc1] | N-(3-{[3-(dimethylamino)phenyl]amino}quinoxalin-2-yl)-4-methylbenzene sulfonamide |
| 12 | 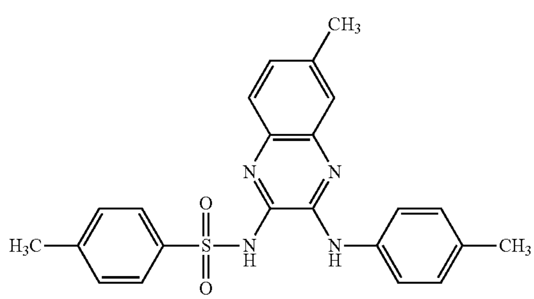 | 4-methyl-N-{6-methyl-3-[(4-methylphenyl)amino]quinoxalin-2-yl} benzene sulfonamide |
| 13 | 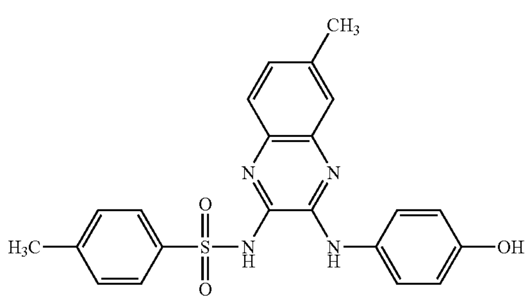 [SMILES: Cc1ccc(S(=O)(=O)Nc2nc3ccc(C)cc3nc2Nc2ccc(O)cc2)cc1] | N-{3-[(4-hydroxyphenyl)amino]-6-methylquinoxalin-2-yl}-4-methylbenzene sulfonamide |

TABLE 1-continued

| Cpd. No. | Structure | Name |
| --- | --- | --- |
| 14 | 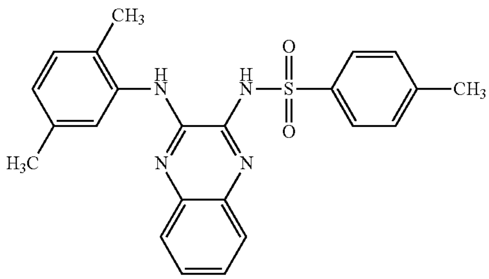 [SMILES: Cc1ccc(S(=O)(=O)Nc2nc3ccccc3nc2Nc2cc(C)ccc2C)cc1] | N-{3-[(2,5-dimethylphenyl) amino]quinoxalin-2-yl}-4-methylbenzenesulfonamide |
| 15 | 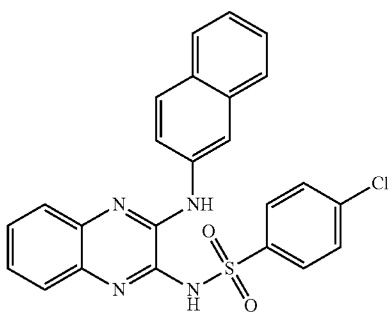 [SMILES: O=S(=O)(Nc1nc2ccccc2nc1Nc1ccc2ccccc2c1)c1ccc(Cl)cc1] | 4-chloro-N-[3-(naphthalen-2-ylamino)quinoxalin-2-yl]benzenesulfonamide |
| 16 | 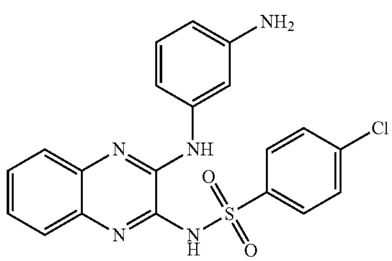 | N-{3-[(3-aminophenyl)amino] quinoxalin-2-yl}-4-chlorobenzenesulfonamide |
| 17 | 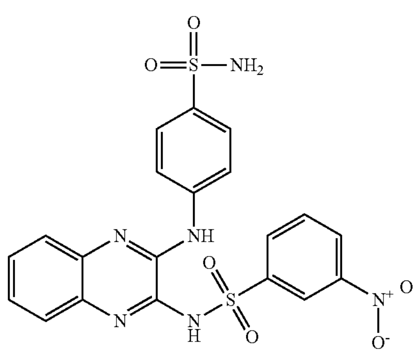 | N-(3-{[4-(aminosulfonyl)phenyl] amino}quinoxalin-2-yl)-3-nitrobenzenesulfonamide |
| 18 | 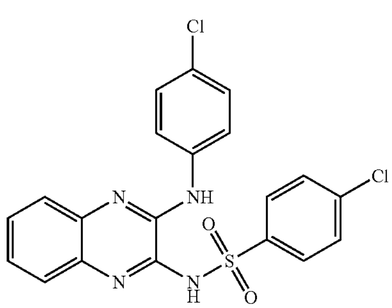 [SMILES: O=S(=O)(Nc1nc2ccccc2nc1Nc1ccc(Cl)cc1)c1ccc(Cl)cc1] | 4-chloro-N-{3-[(4-chlorophenyl) amino]quinoxalin-2-yl} benzenesulfonamide |

TABLE 1-continued

| Cpd. No. | Structure | Name |
|---|---|---|
| 19 | 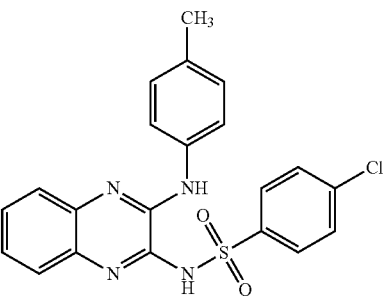 [SMILES: Cc1ccc(Nc2nc3ccccc3nc2NS(=O)(=O)c2ccc(Cl)cc2)cc1] | 4-chloro-N-{3-[(4-methylphenyl)amino]quinoxalin-2-yl}benzenesulfonamide |
| 20 | 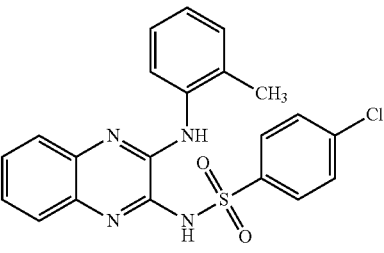 | 4-chloro-N-{3-[(2-methylphenyl)amino]quinoxalin-2-yl}benzenesulfonamide |
| 21 | 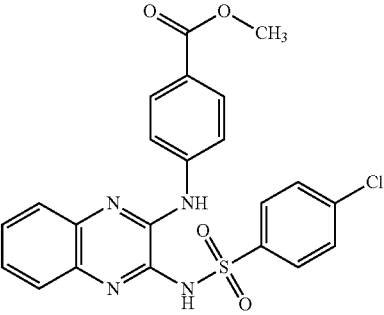 [SMILES: COC(=O)c1ccc(Nc2nc3ccccc3nc2NS(=O)(=O)c2ccc(Cl)cc2)cc1] | methyl 4-[(3-{[(4-chlorophenyl)sulfonyl]amino} quinoxalin-2-yl)amino]benzoate |
| 22 | 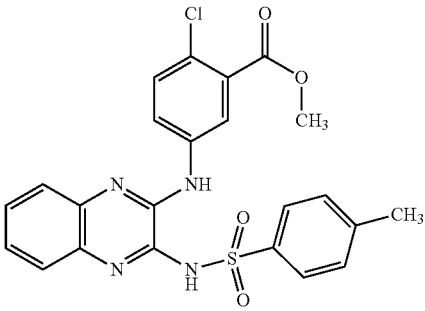 [SMILES: COC(=O)c1cc(Nc2nc3ccccc3nc2NS(=O)(=O)c2ccc(C)cc2)ccc1Cl] | methyl 2-chloro-5-[(3-{[(4-methylphenyl)sulfonyl]amino} quinoxalin-2-yl)amino]benzoate |
| 23 | 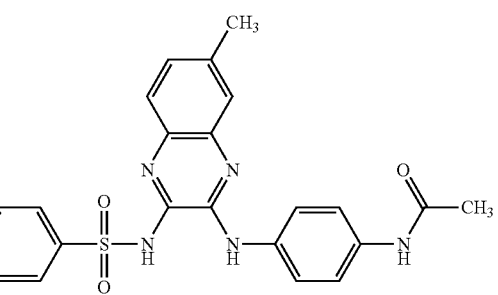 | N-{4-[(7-methyl-3-{[(4-methylphenyl)sulfonyl]amino} quinoxalin-2-yl)amino]phenyl}acetamide |

TABLE 1-continued
| Cpd. No. | Structure | Name |
|---|---|---|
| 24 | 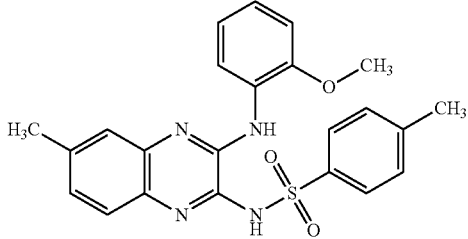 | 4-methyl-N-(6-methyl-3-{[2-(methoxy)phenyl]amino}quinoxalin-2-yl)benzenesulfonamide |
| 25 | 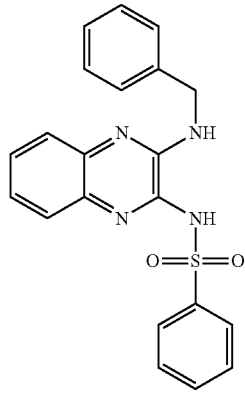 [SMILES: O=S(=O)(Nc1nc2ccccc2nc1NCc1ccccc1)c1ccccc1] | N-{3-[(phenylmethyl)amino]quinoxalin-2-yl}benzenesulfonamide |
| 26 | 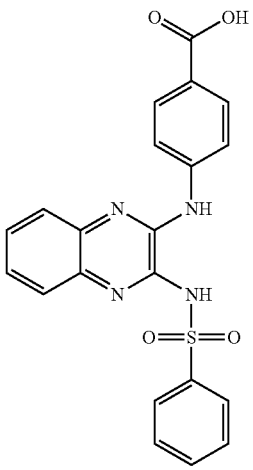 [SMILES: O=C(O)c1ccc(Nc2nc3ccccc3nc2NS(=O)(=O)c2ccccc2)cc1] | 4-({3-[(phenylsulfonyl)amino]quinoxalin-2-yl}amino)benzoic acid |
| 27 | 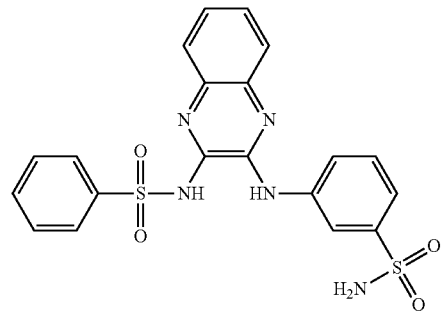 [SMILES: NS(=O)(=O)c1cccc(Nc2nc3ccccc3nc2NS(=O)(=O)c2ccccc2)c1] | 3-({3-[(phenylsulfonyl)amino]quinoxalin-2-yl}amino)benzenesulfonamide |

TABLE 1-continued
| Cpd. No. | Structure | Name |
|---|---|---|
| 28 | 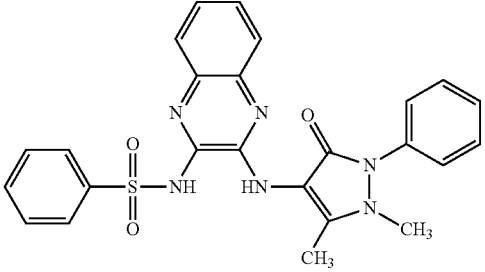 [SMILES: Cc1c(Nc2nc3ccccc3nc2NS(=O)(=O)c2ccccc2)c(=O)n(-c2ccccc2)n1C] | N-{3-[(1,5-dimethyl-3-oxo-2-phenyl-2,3-dihydro-1H-pyrazol-4-yl)amino]quinoxalin-2-yl}benzenesulfonamide |
| 29 | 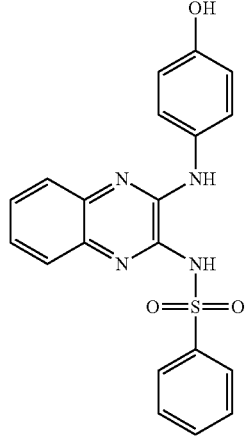 [SMILES: O=S(=O)(Nc1nc2ccccc2nc1Nc1ccc(O)cc1)c1ccccc1] | N-{3-[(4-hydroxyphenyl)amino]quinoxalin-2-yl}benzenesulfonamide |
| 30 | 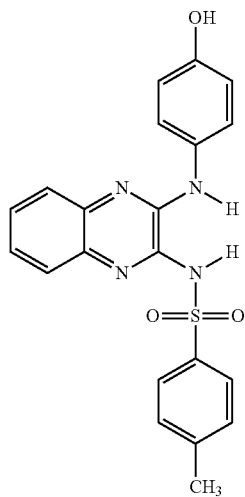 | N-{3-[(4-hydroxyphenyl)amino]quinoxalin-2-yl}-4-methylbenzenesulfonamide |
| 31 | 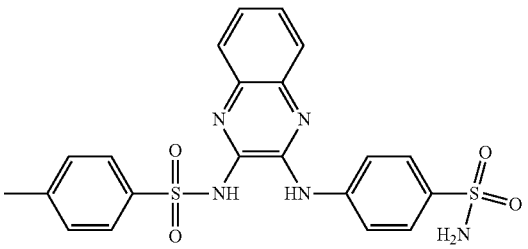 [SMILES: Cc1ccc(S(=O)(=O)Nc2nc3ccccc3nc2Nc2ccc(S(N)(=O)=O)cc2)cc1] | N-(3-{[4-(aminosulfonyl)phenyl]amino}quinoxalin-2-yl)-4-methylbenzenesulfonamide |

TABLE 1-continued
| Cpd. No. | Structure | Name |
|---|---|---|
| 32 | 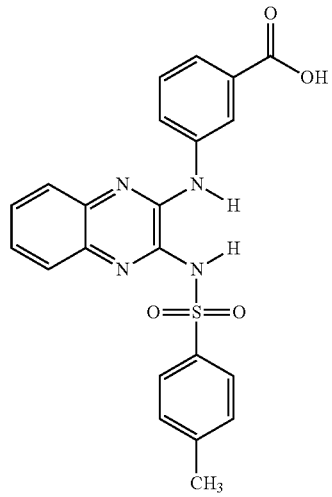 [SMILES: Cc1ccc(S(=O)(=O)Nc2nc3ccccc3nc2Nc2cccc(C(=O)O)c2)cc1] | 3-[(3-{[(4-methylphenyl)sulfonyl]amino}quinoxalin-2-yl)amino]benzoic acid |
| 33 | 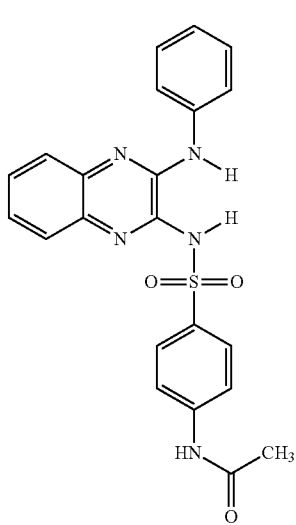 [SMILES: CC(=O)Nc1ccc(S(=O)(=O)Nc2nc3ccccc3nc2Nc2ccccc2)cc1] | N-[4-({[3-(phenylamino)quinoxalin-2-yl]amino}sulfonyl)phenyl]acetamide |
| 34 | 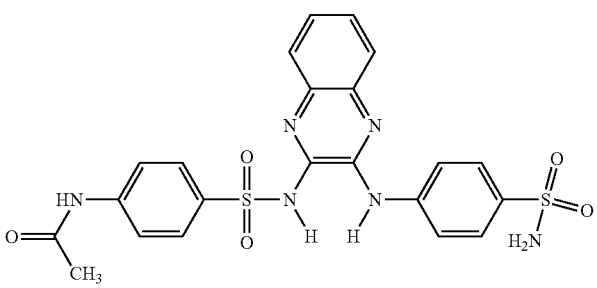 [SMILES: CC(=O)Nc1ccc(S(=O)(=O)Nc2nc3ccccc3nc2Nc2ccc(S(N)(=O)=O)cc2)cc1] | N-(4-{[(3-{[4-(aminosulfonyl)phenyl]amino}quinoxalin-2-yl)amino]sulfonyl}phenyl)acetamide |

TABLE 1-continued

| Cpd. No. | Structure | Name |
|---|---|---|
| 35 | 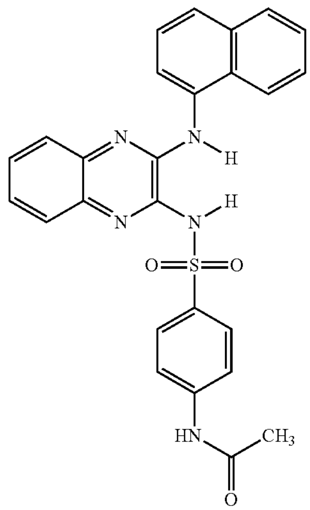 [SMILES: CC(=O)Nc1ccc(S(=O)(=O)Nc2nc3ccccc3nc2Nc2cccc3ccccc23)cc1] | N-[4-({[3-(naphthalen-1-ylamino)quinoxalin-2-yl]amino}sulfonyl)phenyl]acetamide |
| 36 | 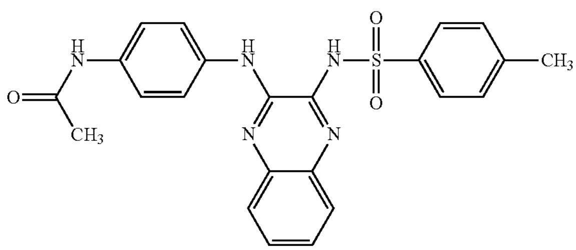 [SMILES: CC(=O)Nc1ccc(Nc2nc3ccccc3nc2NS(=O)(=O)c2ccc(C)cc2)cc1] | N-{4-[(3-{[(4-methylphenyl)sulfonyl]amino}quinoxalin-2-yl)amino]phenyl}acetamide |
| 37 | 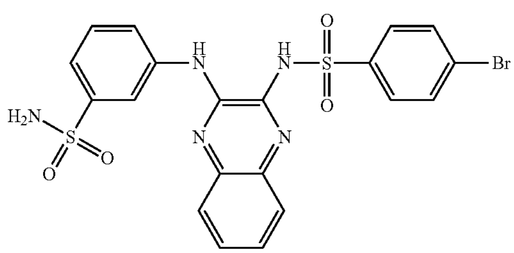 [SMILES: NS(=O)(=O)c1cccc(Nc2nc3ccccc3nc2NS(=O)(=O)c2ccc(Br)cc2)c1] | N-(3-{[3-(aminosulfonyl)phenyl]amino}quinoxalin-2-yl)-4-bromobenzenesulfonamide |
| 38 | 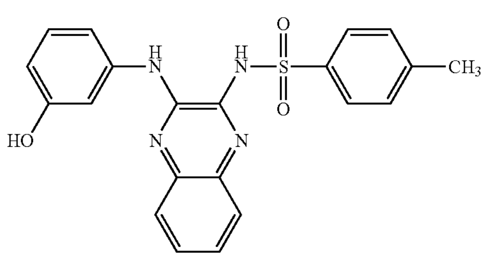 [SMILES: Cc1ccc(S(=O)(=O)Nc2nc3ccccc3nc2Nc2cccc(O)c2)cc1] | N-{3-[(3-hydroxyphenyl)amino]quinoxalin-2-yl}-4-methylbenzenesulfonamide |
| 39 | 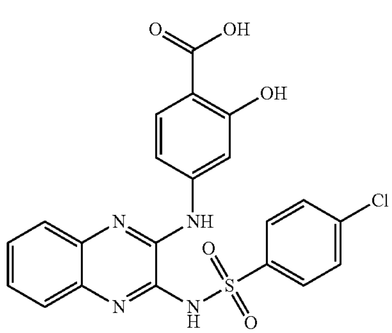 [SMILES: O=C(O)c1ccc(Nc2nc3ccccc3nc2NS(=O)(=O)c2ccc(Cl)cc2)cc1O] | 4-[(3-{[(4-chlorophenyl)sulfonyl]amino}quinoxalin-2-yl)amino]-2-hydroxybenzoic acid |

TABLE 1-continued
| Cpd. No. | Structure | Name |
|---|---|---|
| 40 | 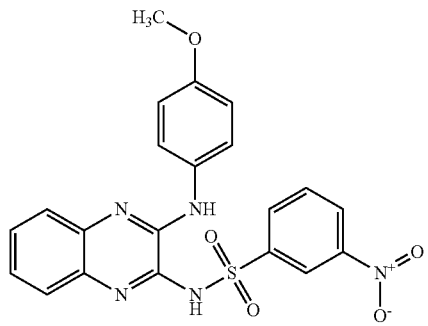 [SMILES: COc1ccc(Nc2nc3ccccc3nc2NS(=O)(=O)c2cccc([N+](=O)[O-])c2)cc1] | N-(3-{[4-(methoxy)phenyl]amino}quinoxalin-2-yl)-3-nitrobenzenesulfonamide |
| 41 | 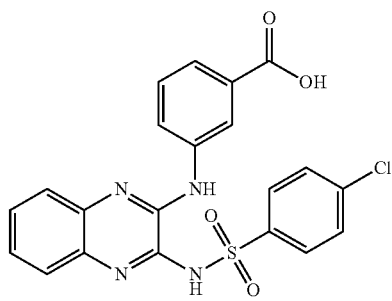 [SMILES: O=C(O)c1cccc(Nc2nc3ccccc3nc2NS(=O)(=O)c2ccc(Cl)cc2)c1] | 3-[(3-{[(4-chlorophenyl)sulfonyl]amino}quinoxalin-2-yl)amino]benzoic acid |
| 42 | 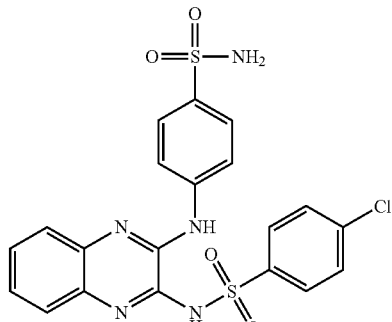 | N-(3-{[4-(aminosulfonyl)phenyl]amino}quinoxalin-2-yl)-4-chlorobenzenesulfonamide |
| 43 | 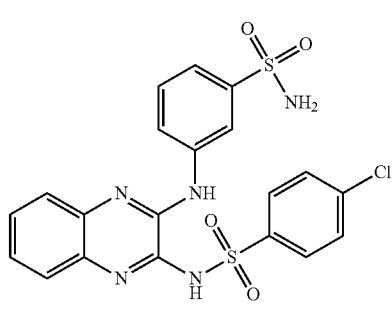 [SMILES: NS(=O)(=O)c1cccc(Nc2nc3ccccc3nc2NS(=O)(=O)c2ccc(Cl)cc2)c1] | N-(3-{[3-(aminosulfonyl)phenyl]amino}quinoxalin-2-yl)-4-chlorobenzenesulfonamide |

TABLE 1-continued

| Cpd. No. | Structure | Name |
|---|---|---|
| 44 | 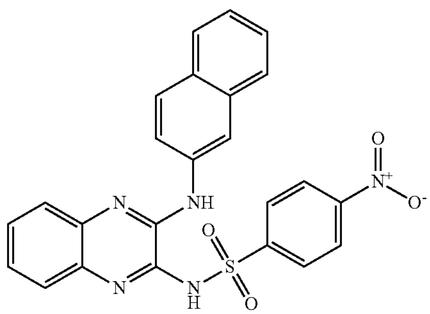 [SMILES: O=[N+]([O-])c1ccc(S(=O)(=O)Nc2nc3ccccc3nc2Nc2ccc3ccccc3c2)cc1] | N-[3-(naphthalen-2-ylamino) quinoxalin-2-yl]-4-nitrobenzenesulfonamide |
| 45 | 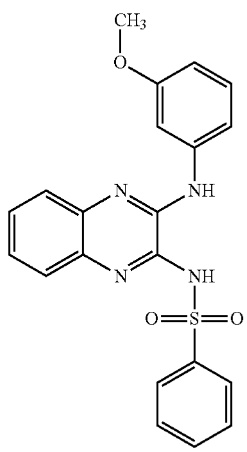 [SMILES: COc1cccc(Nc2nc3ccccc3nc2NS(=O)(=O)c2ccccc2)c1] | N-(3-{[3-(methoxy)phenyl] amino}quinoxalin-2-yl) benzenesulfonamide |
| 46 | 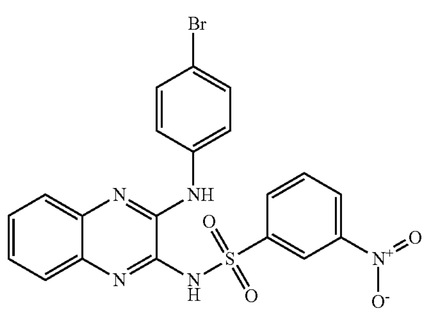 [SMILES: O=[N+]([O-])c1cccc(S(=O)(=O)Nc2nc3ccccc3nc2Nc2ccc(Br)cc2)c1] | N-{3-[(4-bromophenyl)amino] quinoxalin-2-yl}-3-nitrobenzenesulfonamide |
| 47 | 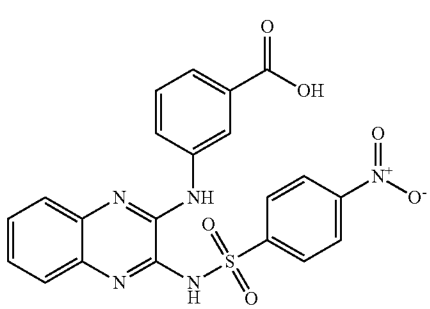 [SMILES: O=C(O)c1cccc(Nc2nc3ccccc3nc2NS(=O)(=O)c2ccc([N+](=O)[O-])cc2)c1] | 3-[(3-{[(4-nitrophenyl)sulfonyl] amino}quinoxalin-2-yl)amino]benzoic acid |

TABLE 1-continued

| Cpd. No. | Structure | Name |
|---|---|---|
| 48 | 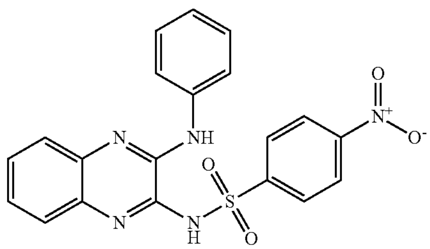 [SMILES: O=[N+]([O-])c1ccc(S(=O)(=O)Nc2nc3ccccc3nc2Nc2ccccc2)cc1] | 4-nitro-N-[3-(phenylamino)quinoxalin-2-yl]benzenesulfonamide |
| 49 | 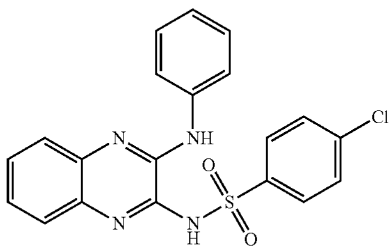 [SMILES: O=S(=O)(Nc1nc2ccccc2nc1Nc1ccccc1)c1ccc(Cl)cc1] | 4-chloro-N-[3-(phenylamino)quinoxalin-2-yl]benzenesulfonamide |
| 50 | 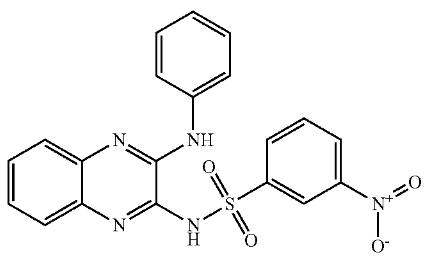 [SMILES: O=[N+]([O-])c1cccc(S(=O)(=O)Nc2nc3ccccc3nc2Nc2ccccc2)c1] | 3-nitro-N-[3-(phenylamino)quinoxalin-2-yl]benzenesulfonamide |
| 51 | 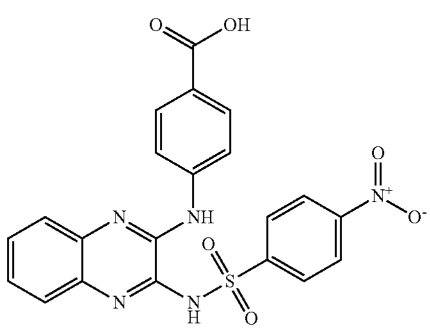 [SMILES: O=C(O)c1ccc(Nc2nc3ccccc3nc2NS(=O)(=O)c2ccc([N+](=O)[O-])cc2)cc1] | 4-[(3-{[(4-nitrophenyl)sulfonyl]amino}quinoxalin-2-yl)amino]benzoic acid |
| 52 | 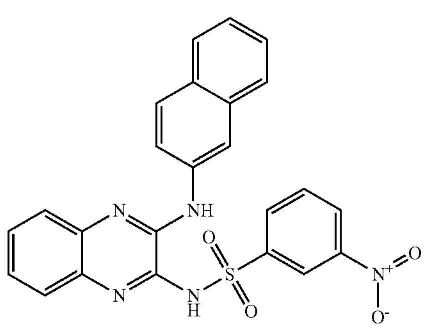 [SMILES: O=[N+]([O-])c1cccc(S(=O)(=O)Nc2nc3ccccc3nc2Nc2ccc3ccccc3c2)c1] | N-[3-(naphthalen-2-ylamino)quinoxalin-2-yl]-3-nitrobenzenesulfonamide |

TABLE 1-continued
| Cpd. No. | Structure | Name |
|---|---|---|
| 53 | 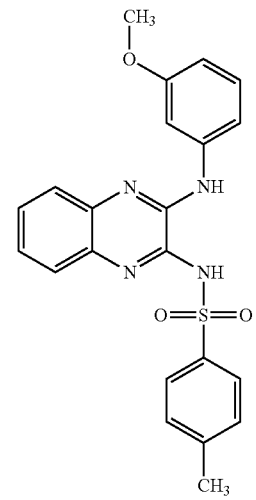 [SMILES: COc1cccc(Nc2nc3ccccc3nc2NS(=O)(=O)c2ccc(C)cc2)c1] | 4-methyl-N-(3-{[3-(methoxy)phenyl]amino}quinoxalin-2-yl)benzenesulfonamide |
| 54 | 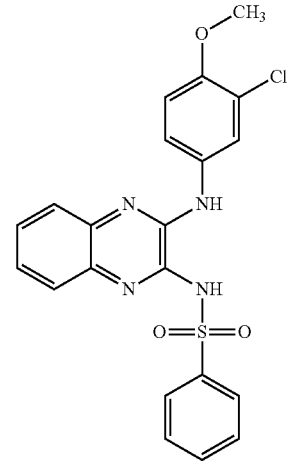 [SMILES: COc1ccc(Nc2nc3ccccc3nc2NS(=O)(=O)c2ccccc2)cc1Cl] | N-(3-{[3-chloro-4-(methoxy)phenyl]amino}quinoxalin-2-yl)benzenesulfonamide |
| 55 | 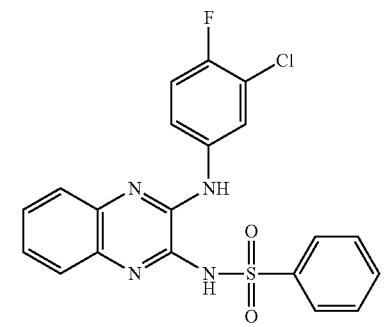 [SMILES: O=S(=O)(Nc1nc2ccccc2nc1Nc1ccc(F)c(Cl)c1)c1ccccc1] | N-{3-[(3-chloro-4-fluorophenyl)amino]quinoxalin-2-yl}benzenesulfonamide |

TABLE 1-continued
| Cpd. No. | Structure | Name |
|---|---|---|
| 56 | 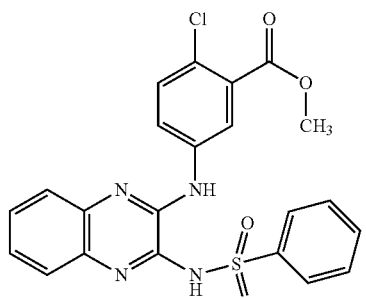 | methyl 2-chloro-5-({3-[(phenylsulfonyl)amino]quinoxalin-2-yl}amino)benzoate |
| 57 | 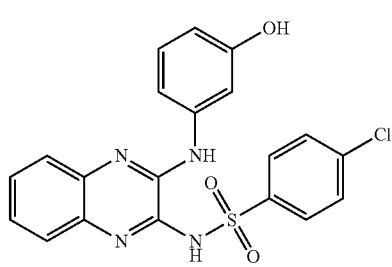 [SMILES: O=S(=O)(Nc1nc2ccccc2nc1Nc1cccc(O)c1)c1ccc(Cl)cc1] | 4-chloro-N-{3-[(3-hydroxyphenyl)amino]quinoxalin-2-yl}benzenesulfonamide |
| 58 | 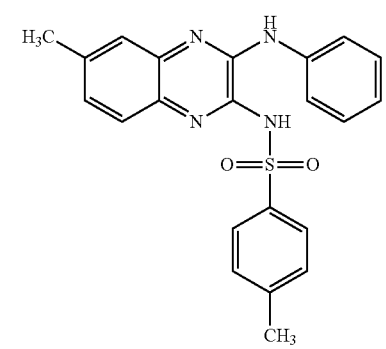 [SMILES: Cc1ccc(S(=O)(=O)Nc2nc3ccc(C)cc3nc2Nc2ccccc2)cc1] | 4-methyl-N-[6-methyl-3-(phenylamino)quinoxalin-2-yl]benzenesulfonamide |
| 59 | 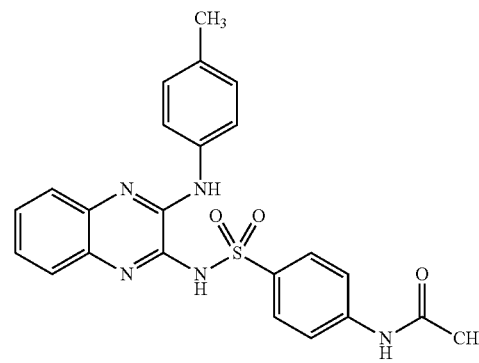 | N-{4-[({3-[(4-methylphenyl)amino]quinoxalin-2-yl}amino)sulfonyl]phenyl}acetamide |

TABLE 1-continued
| Cpd. No. | Structure | Name |
|---|---|---|
| 60 | 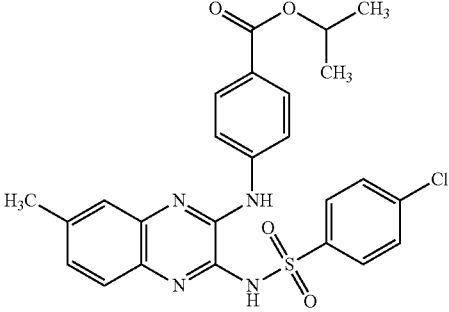 [SMILES: Cc1ccc2nc(NS(=O)(=O)c3ccc(Cl)cc3)c(Nc3ccc(C(=O)OC(C)C)cc3)nc2c1] | 1-methylethyl 4-[(3-{[(4-chlorophenyl)sulfonyl]amino}-7-methylquinoxalin-2-yl)amino]benzoate |
| 61 | 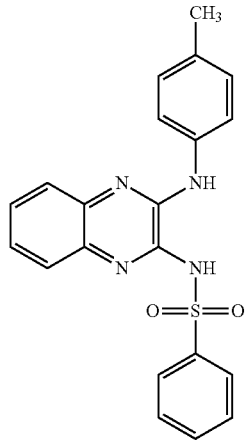 [SMILES: Cc1ccc(Nc2nc3ccccc3nc2NS(=O)(=O)c2ccccc2)cc1] | N-{3-[(4-methylphenyl)amino]quinoxalin-2-yl}benzenesulfonamide |
| 62 | 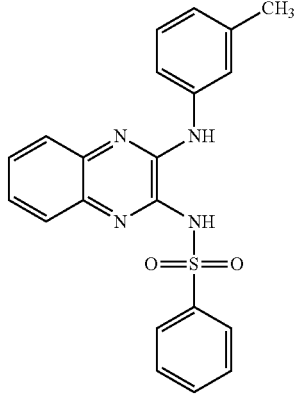 [SMILES: Cc1cccc(Nc2nc3ccccc3nc2NS(=O)(=O)c2ccccc2)c1] | N-{3-[(3-methylphenyl)amino]quinoxalin-2-yl}benzenesulfonamide |

TABLE 1-continued
| Cpd. No. | Structure | Name |
|---|---|---|
| 63 | 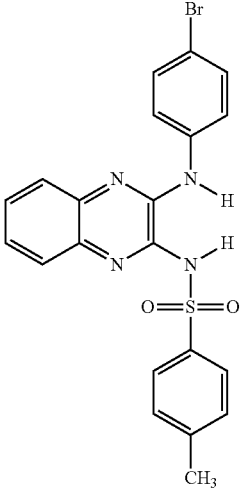 [SMILES: Cc1ccc(S(=O)(=O)Nc2nc3ccccc3nc2Nc2ccc(Br)cc2)cc1] | N-{3-[(4-bromophenyl)amino]quinoxalin-2-yl}-4-methylbenzenesulfonamide |
| 64 | 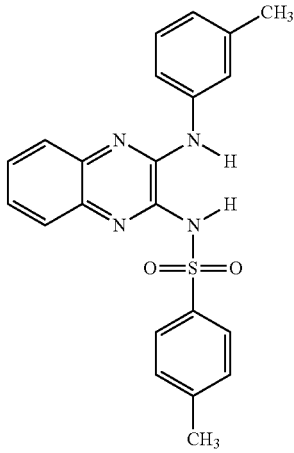 [SMILES: Cc1ccc(S(=O)(=O)Nc2nc3ccccc3nc2Nc2cccc(C)c2)cc1] | 4-methyl-N-{3-[(3-methylphenyl)amino]quinoxalin-2-yl}benzenesulfonamide |
| 65 | 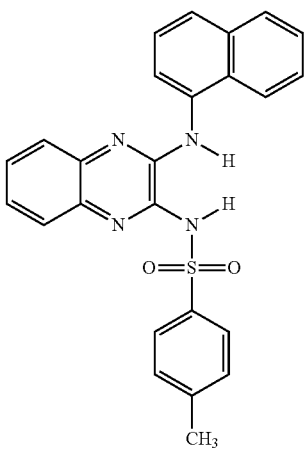 [SMILES: Cc1ccc(S(=O)(=O)Nc2nc3ccccc3nc2Nc2cccc3ccccc23)cc1] | 4-methyl-N-[3-(naphthalen-1-ylamino)quinoxalin-2-yl]benzenesulfona |

TABLE 1-continued

| Cpd. No. | Structure | Name |
|---|---|---|
| 66 | 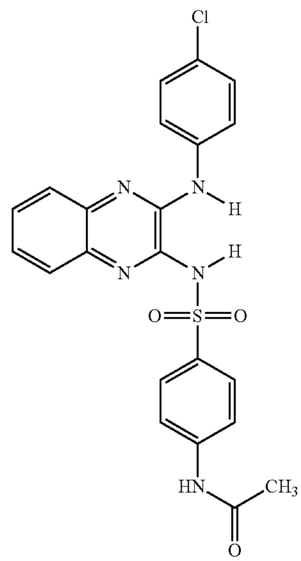 [SMILES: CC(=O)Nc1ccc(S(=O)(=O)Nc2nc3ccccc3nc2Nc2ccc(Cl)cc2)cc1] | N-{4-[({3-[(4-chlorophenyl)amino]quinoxalin-2-yl}amino)sulfonyl]phenyl}acetamide |
| 67 | 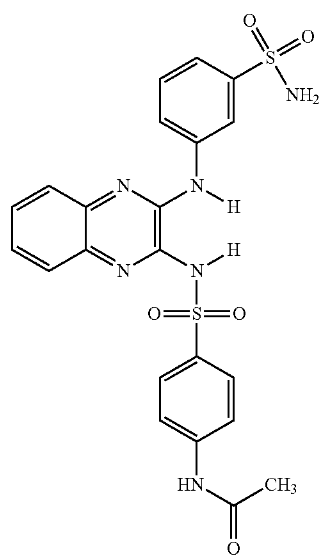 [SMILES: CC(=O)Nc1ccc(S(=O)(=O)Nc2nc3ccccc3nc2Nc2cccc(S(N)(=O)=O)c2)cc1] | N-(4-{[(3-{[3-(aminosulfonyl)phenyl]amino}quinoxalin-2-yl)amino]sulfonyl}phenyl)acetamide |
| 68 | 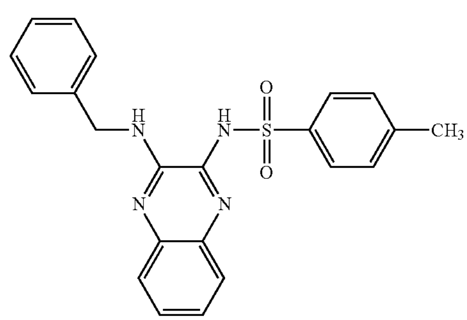 [SMILES: Cc1ccc(S(=O)(=O)Nc2nc3ccccc3nc2NCc2ccccc2)cc1] | 4-methyl-N-{3-[(phenylmethyl)amino]quinoxalin-2-yl}benzenesulfonamide |

TABLE 1-continued

| Cpd. No. | Structure | Name |
|---|---|---|
| 69 | 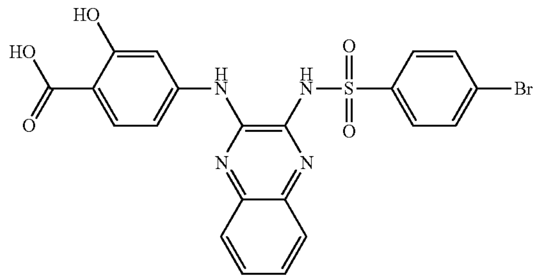 [SMILES: O=C(O)c1ccc(Nc2nc3ccccc3nc2NS(=O)(=O)c2ccc(Br)cc2)cc1O] | 4-[(3-{[(4-bromophenyl)sulfonyl]amino}quinoxalin-2-yl)amino]-2-hydroxybenzoic acid |
| 70 | 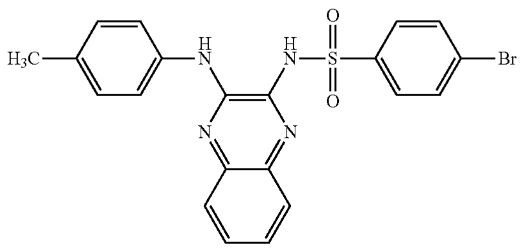 [SMILES: Cc1ccc(Nc2nc3ccccc3nc2NS(=O)(=O)c2ccc(Br)cc2)cc1] | 4-bromo-N-{3-[(4-methylphenyl)amino]quinoxalin-2-yl}benzenesulfonamide |
| 71 | 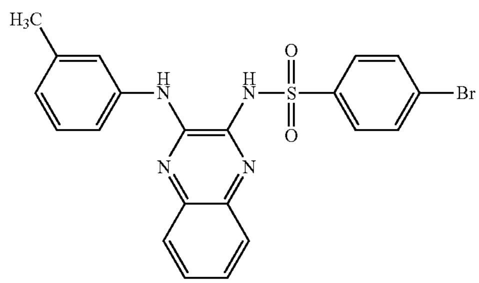 [SMILES: Cc1cccc(Nc2nc3ccccc3nc2NS(=O)(=O)c2ccc(Br)cc2)c1] | 4-bromo-N-{3-[(3-methylphenyl)amino]quinoxalin-2-yl}benzenesulfonamide |
| 72 | 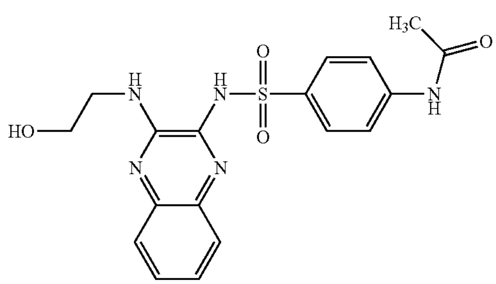 [SMILES: CC(=O)Nc1ccc(S(=O)(=O)Nc2nc3ccccc3nc2NCCO)cc1] | N-{4-[({3-[(2-hydroxyethyl)amino]quinoxalin-2-yl}amino)sulfonyl]phenyl}acetamide |
| 73 | 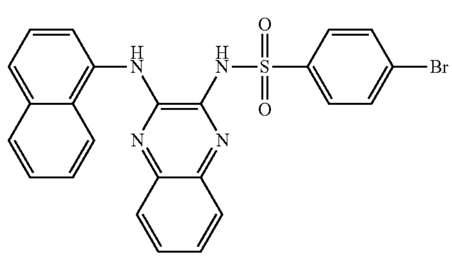 [SMILES: O=S(=O)(Nc1nc2ccccc2nc1Nc1cccc2ccccc12)c1ccc(Br)cc1] | 4-bromo-N-[3-(naphthalen-1-ylamino)quinoxalin-2-yl]benzenesulfonamide |

TABLE 1-continued
| Cpd. No. | Structure | Name |
|---|---|---|
| 74 | 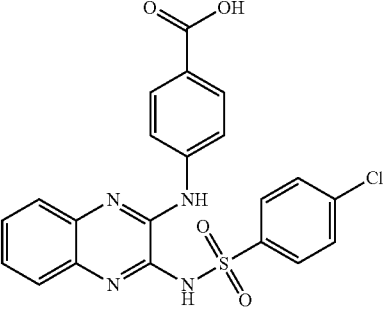 [SMILES: O=C(O)c1ccc(Nc2nc3ccccc3nc2NS(=O)(=O)c2ccc(Cl)cc2)cc1] | 4-[(3-{[(4-chlorophenyl)sulfonyl]amino}quinoxalin-2-yl)amino]benzoic acid |
| 75 | 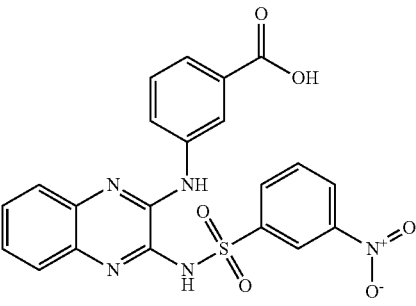 [SMILES: O=C(O)c1cccc(Nc2nc3ccccc3nc2NS(=O)(=O)c2cccc([N+](=O)[O-])c2)c1] | 3-[(3-{[(3-nitrophenyl)sulfonyl]amino}quinoxalin-2-yl)amino]benzoic acid |
| 76 | 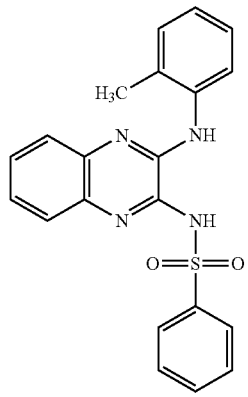 [SMILES: Cc1ccccc1Nc1nc2ccccc2nc1NS(=O)(=O)c1ccccc1] | N-{3-[(2-methylphenyl)amino]quinoxalin-2-yl}benzenesulfonamide |
| 77 | 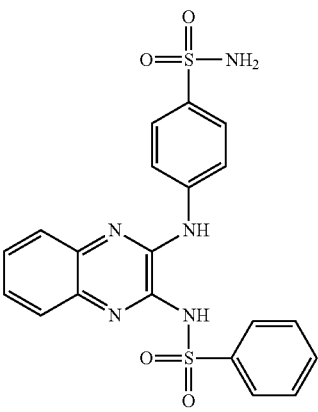 [SMILES: NS(=O)(=O)c1ccc(Nc2nc3ccccc3nc2NS(=O)(=O)c2ccccc2)cc1] | 4-({3-[(phenylsulfonyl)amino]quinoxalin-2-yl}amino)benzenesulfonamide |

TABLE 1-continued

| Cpd. No. | Structure | Name |
|---|---|---|
| 78 | 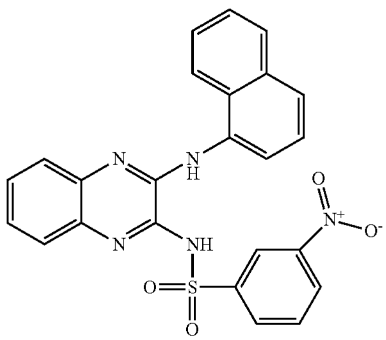 [SMILES: O=[N+]([O-])c1cccc(S(=O)(=O)Nc2nc3ccccc3nc2Nc2cccc3ccccc23)c1] | N-[3-(naphthalen-1-ylamino)quinoxalin-2-yl]-3-nitrobenzenesulfonamide |
| 79 | 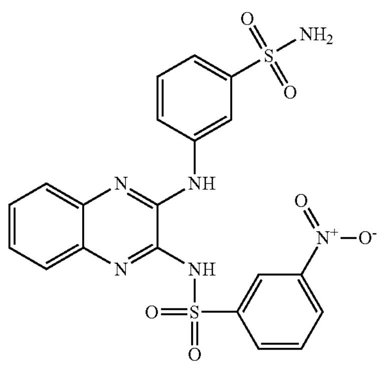 [SMILES: NS(=O)(=O)c1cccc(Nc2nc3ccccc3nc2NS(=O)(=O)c2cccc([N+](=O)[O-])c2)c1] | N-(3-{[3-(aminosulfonyl)phenyl]amino}quinoxalin-2-yl)-3-nitrobenzenesulfonamide |
| 80 | 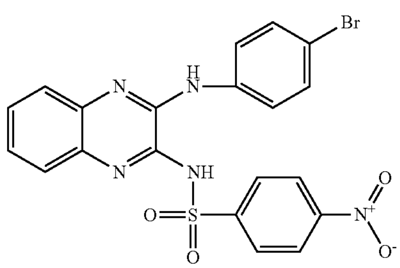 [SMILES: O=[N+]([O-])c1ccc(S(=O)(=O)Nc2nc3ccccc3nc2Nc2ccc(Br)cc2)cc1] | N-{3-[(4-bromophenyl)amino]quinoxalin-2-yl}-4-nitrobenzenesulfonamide |
| 81 | 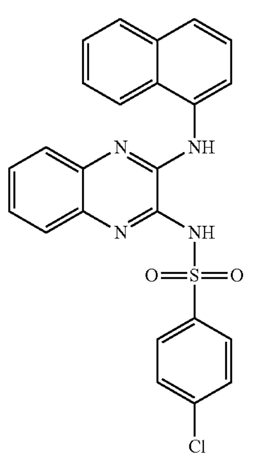 [SMILES: O=S(=O)(Nc1nc2ccccc2nc1Nc1cccc2ccccc12)c1ccc(Cl)cc1] | 4-chloro-N-[3-(naphthalen-1-ylamino)quinoxalin-2-yl]benzenesulfonamide |

| Cpd. No. | Structure | Name |
|---|---|---|
| 82 | 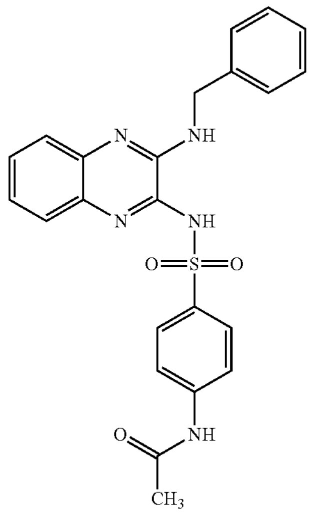 [SMILES: CC(=O)Nc1ccc(S(=O)(=O)Nc2nc3ccccc3nc2NCc2ccccc2)cc1] | N-{4-[({3-[(phenylmethyl) amino]quinoxalin-2-yl}amino) sulfonyl]phenyl}acetamide |
| 83 | 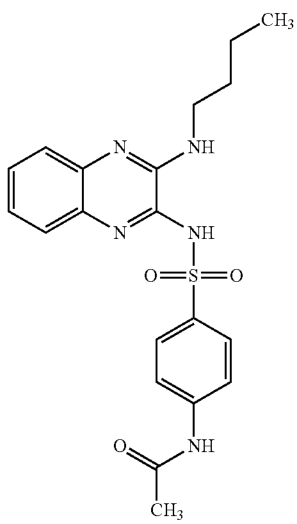 [SMILES: CCCCNc1nc2ccccc2nc1NS(=O)(=O)c1ccc(NC(C)=O)cc1] | N-[4-({[3-(butylamino) quinoxalin-2-yl]amino} sulfonyl)phenyl]acetamide |
| 84 | 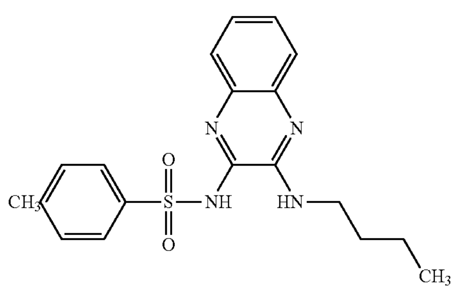 | N-[3-(butylamino)quinoxalin-2-yl]-4-methylbenzenesulfonamide |
| 85 | 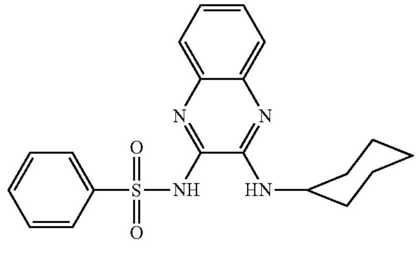 [SMILES: O=S(=O)(Nc1nc2ccccc2nc1NC1CCCCC1)c1ccccc1] | N-[3-(cyclohexylamino) quinoxalin-2-yl] benzenesulfonamide |

TABLE 1-continued

| Cpd. No. | Structure | Name |
|---|---|---|
| 86 | 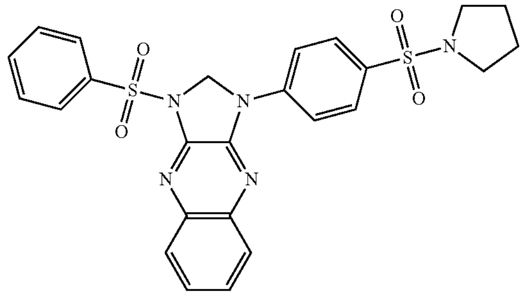 [SMILES: O=S(=O)(c1ccc(N2CN(S(=O)(=O)c3ccccc3)c3nc4ccccc4nc32)cc1)N1CCCC1] | 1-(phenylsulfonyl)-3-[4-(pyrrolidin-1-ylsulfonyl)phenyl]-2,3-dihydro-1H-imidazo[4,5-b]quinoxaline |
| 87 | 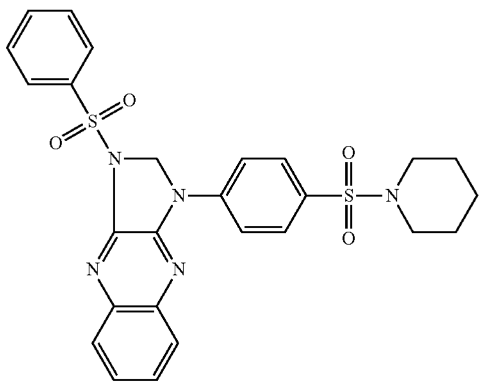 [SMILES: O=S(=O)(c1ccc(N2CN(S(=O)(=O)c3ccccc3)c3nc4ccccc4nc32)cc1)N1CCCCC1] | 1-(phenylsulfonyl)-3-[4-(piperidin-1-ylsulfonyl)phenyl]-2,3-dihydro-1H-imidazo[4,5-b]quinoxaline |
| 88 | 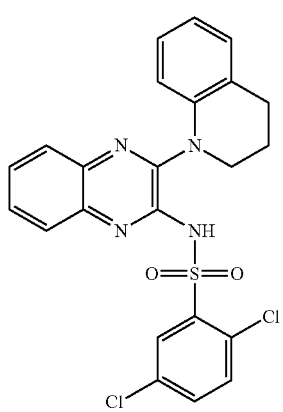 [SMILES: O=S(=O)(Nc1nc2ccccc2nc1N1CCCc2ccccc21)c1cc(Cl)ccc1Cl] | 2,5-dichloro-N-[3-(3,4-dihydroquinolin-1(2H)-yl)quinoxalin-2-yl]benzenesulfonamide |
| 89 | 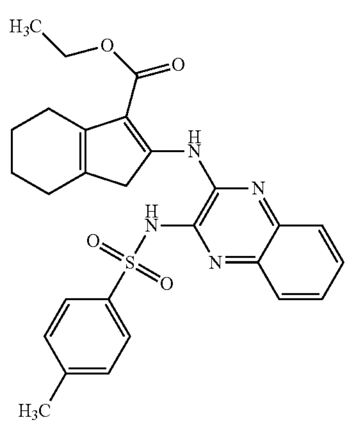 [SMILES: CCOC(=O)C1=C(Nc2nc3ccccc3nc2NS(=O)(=O)c2ccc(C)cc2)CC2=C1CCCC2] | ethyl 2-[(3-{[(4-methylphenyl)sulfonyl]amino}quinoxalin-2-yl)amino]-4,5,6,7-tetrahydro-1-benzothiophene-3-carboxylate |

TABLE 1-continued

| Cpd. No. | Structure | Name |
|---|---|---|
| 90 | 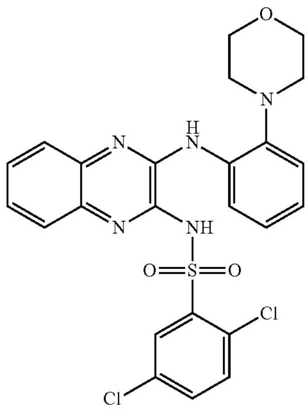 [SMILES: O=S(=O)(Nc1nc2ccccc2nc1Nc1ccccc1N1CCOCC1)c1cc(Cl)ccc1Cl] | 2,5-dichloro-N-{3-[(2-morpholin-4-ylphenyl)amino]quinoxalin-2-yl}benzenesulfonamide |
| 91 | 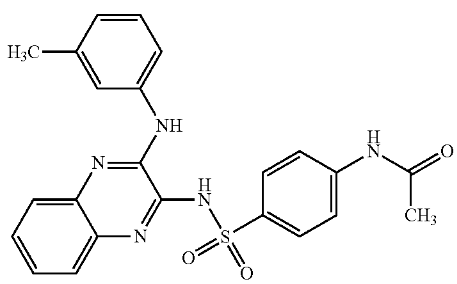 [SMILES: CC(=O)Nc1ccc(S(=O)(=O)Nc2nc3ccccc3nc2Nc2cccc(C)c2)cc1] | N-{4-[({3-[(3-methylphenyl)amino]quinoxalin-2-yl}amino)sulfonyl]phenyl}acetamide |
| 92 | 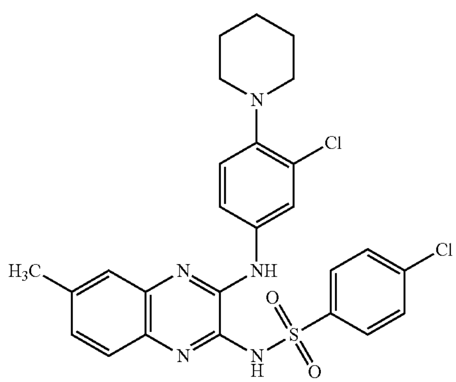 [SMILES: Cc1ccc2nc(NS(=O)(=O)c3ccc(Cl)cc3)c(Nc3ccc(N4CCCCC4)c(Cl)c3)nc2c1] | 4-chloro-N-{3-[(3-chloro-4-piperidin-1-ylphenyl)amino]-6-methylquinoxalin-2-yl}benzenesulfonamide |
| 93 | 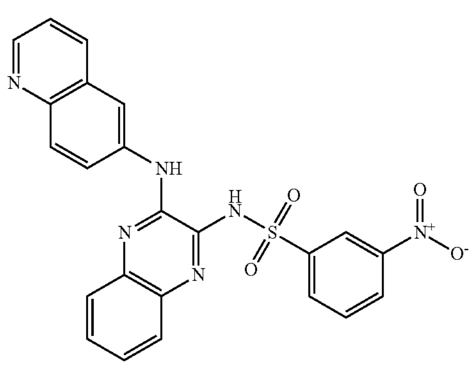 [SMILES: O=[N+]([O-])c1cccc(S(=O)(=O)Nc2nc3ccccc3nc2Nc2ccc3ncccc3c2)c1] | 3-nitro-N-[3-(quinolin-6-ylamino)quinoxalin-2-yl]benzenesulfonamide |

TABLE 1-continued

| Cpd. No. | Structure | Name |
|---|---|---|
| 94 | 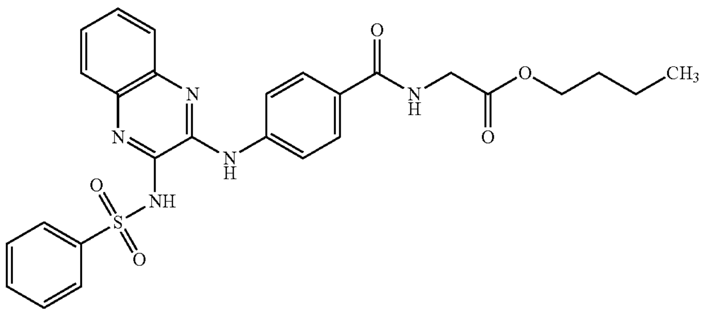 [SMILES: CCCCOC(=O)CNC(=O)c1ccc(Nc2nc3ccccc3nc2NS(=O)(=O)c2ccccc2)cc1] | butyl N-{[4-({3-[(phenylsulfonyl)amino]quinoxalin-2-yl}amino)phenyl]carbonyl}glycinate |
| 95 | 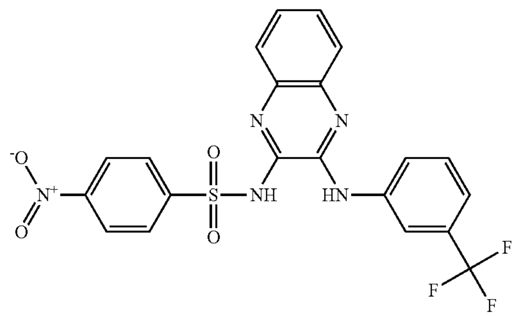 | 4-nitro-N-(3-{[3-(trifluoromethyl)phenyl]amino}quinoxalin-2-yl)benzenesulfonamide |
| 96 | 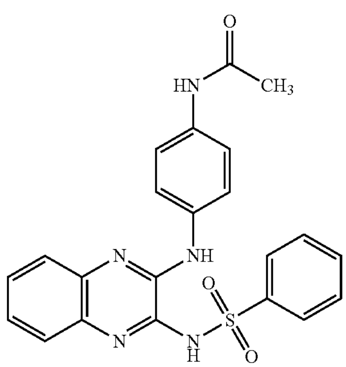 [SMILES: CC(=O)Nc1ccc(Nc2nc3ccccc3nc2NS(=O)(=O)c2ccccc2)cc1] | N-[4-({3-[(phenylsulfonyl)amino]quinoxalin-2-yl}amino)phenyl]acetamide |
| 97 | 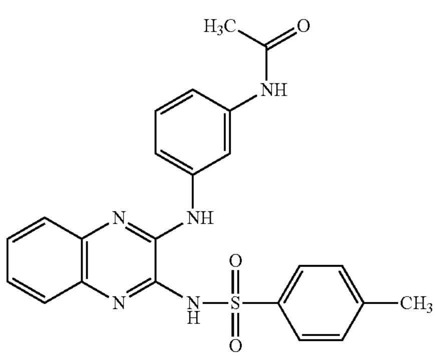 [SMILES: CC(=O)Nc1cccc(Nc2nc3ccccc3nc2NS(=O)(=O)c2ccc(C)cc2)c1] | N-{3-[(3-{[(4-methylphenyl)sulfonyl]amino}quinoxalin-2-yl)amino]phenyl}acetamide |

US 8,481,001 B2

TABLE 1-continued

| Cpd. No. | Structure | Name |
|---|---|---|
| 98 | 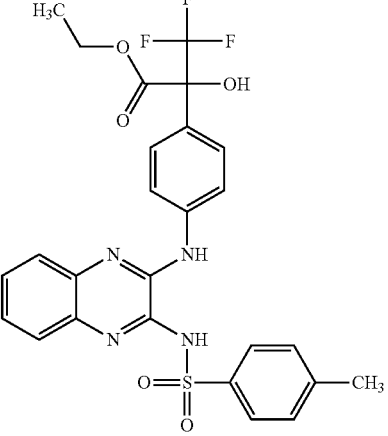 | ethyl 3,3,3-trifluoro-2-hydroxy-2-{4-[(3-{[(4-methylphenyl)sulfonyl]amino}quinoxalin-2-yl)amino]phenyl}propanoate |
| 99 | 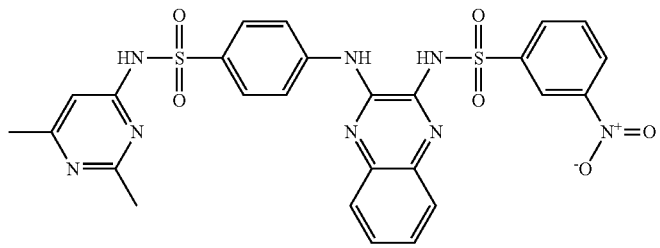 | N-{3-[(4-{[(2,6-dimethylpyrimidin-4-yl)amino]sulfonyl}phenyl)amino]quinoxalin-2-yl}-3-nitrobenzenesulfonamide |
| 100 | 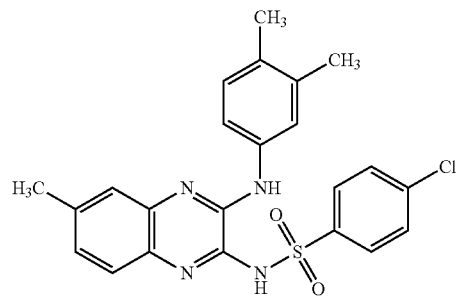 [SMILES: Cc1ccc2nc(NS(=O)(=O)c3ccc(Cl)cc3)c(Nc3ccc(C)c(C)c3)nc2c1] | 4-chloro-N-{3-[(3,4-dimethylphenyl)amino]-6-methylquinoxalin-2-yl}benzenesulfonamide |
| 101 | 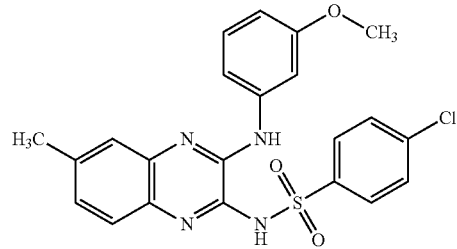 [SMILES: COc1cccc(Nc2nc3cc(C)ccc3nc2NS(=O)(=O)c2ccc(Cl)cc2)c1] | 4-chloro-N-(6-methyl-3-{[3-(methoxy)phenyl]amino}quinoxalin-2-yl)benzenesulfonamide |
| 102 | 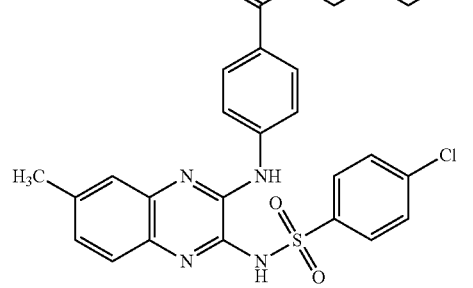 | butyl 4-[(3-{[(4-chlorophenyl)sulfonyl]amino}-7-methylquinoxalin-2-yl)amino]benzoate |

TABLE 1-continued

| Cpd. No. | Structure | Name |
|---|---|---|
| 103 | 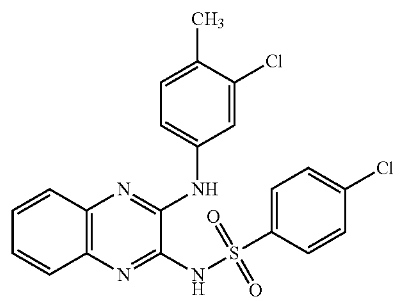 [SMILES: Cc1ccc(Nc2nc3ccccc3nc2NS(=O)(=O)c2ccc(Cl)cc2)cc1Cl] | 4-chloro-N-{3-[(3-chloro-4-methylphenyl)amino]quinoxalin-2-yl}benzenesulfonamide |
| 104 | 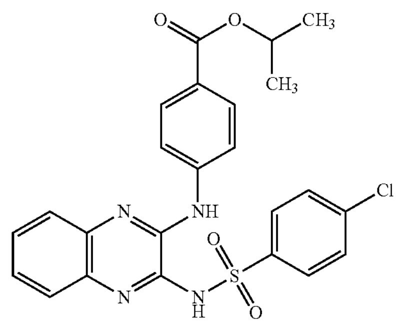 [SMILES: CC(C)OC(=O)c1ccc(Nc2nc3ccccc3nc2NS(=O)(=O)c2ccc(Cl)cc2)cc1] | 1-methylethyl 4-[(3-{[(4-chlorophenyl)sulfonyl]amino}quinoxalin-2-yl)amino]benzoate |
| 105 | 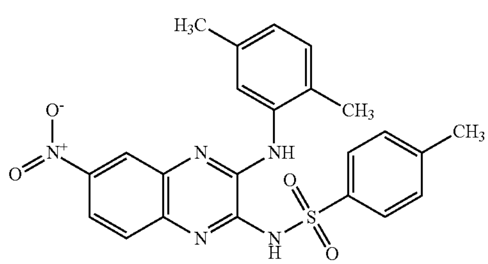 [SMILES: Cc1ccc(S(=O)(=O)Nc2nc3ccc([N+](=O)[O-])cc3nc2Nc2cc(C)ccc2C)cc1] | N-{3-[(2,5-dimethylphenyl)amino]-6-nitroquinoxalin-2-yl}-4-methylbenzenesulfonamide |
| 106 | 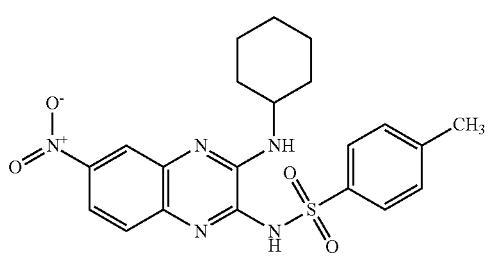 [SMILES: Cc1ccc(S(=O)(=O)Nc2nc3ccc([N+](=O)[O-])cc3nc2NC2CCCCC2)cc1] | N-[3-(cyclohexylamino)-6-nitroquinoxalin-2-yl]-4-methylbenzenesulfonamide |
| 107 | 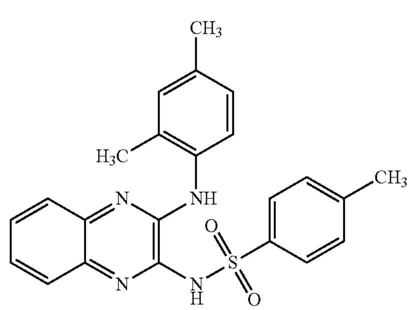 [SMILES: Cc1ccc(S(=O)(=O)Nc2nc3ccccc3nc2Nc2ccc(C)cc2C)cc1] | N-{3-[(2,4-dimethylphenyl)amino]quinoxalin-2-yl}-4-methylbenzenesulfonamide |

TABLE 1-continued

| Cpd. No. | Structure | Name |
|---|---|---|
| 108 | 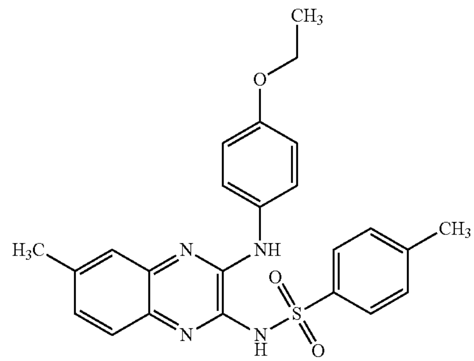 | N-(3-{[4-(ethyloxy)phenyl]amino}-6-methylquinoxalin-2-yl)-4-methylbenzenesulfonamide |
| 109 | 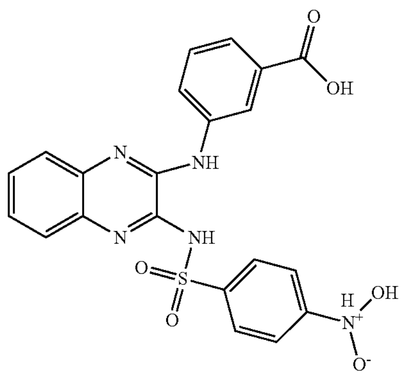 | 3-({3-[({4-[hydroxy(oxido)amino]phenyl}sulfonyl)amino]quinoxalin-2-yl}amino)benzoic acid |
| 110 | 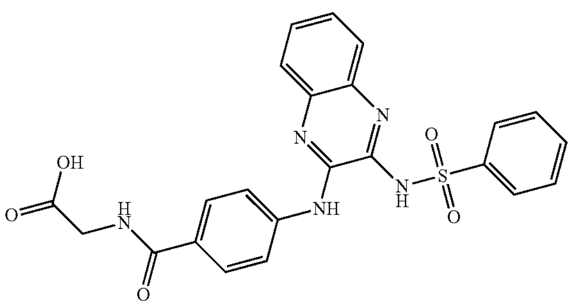 [SMILES: O=C(O)CNC(=O)c1ccc(Nc2nc3ccccc3nc2NS(=O)(=O)c2ccccc2)cc1] | N-{[4-({3-[(phenylsulfonyl)amino]quinoxalin-2-yl}amino)phenyl]carbonyl}glycine |
| 111 | 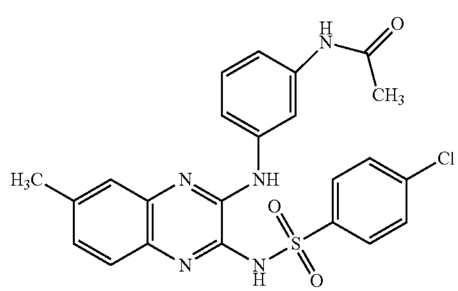 [SMILES: CC(=O)Nc1cccc(Nc2nc3cc(C)ccc3nc2NS(=O)(=O)c2ccc(Cl)cc2)c1] | N-{3-[(3-{[(4-chlorophenyl)sulfonyl]amino}-7-methylquinoxalin-2-yl)amino]phenyl}acetamide |
| 112 | 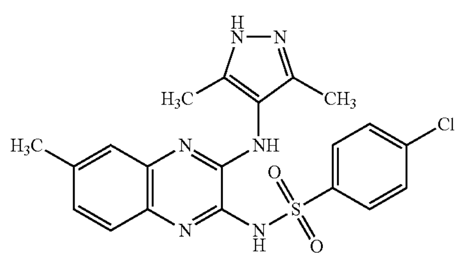 [SMILES: Cc1ccc2nc(NS(=O)(=O)c3ccc(Cl)cc3)c(Nc3c(C)n[nH]c3C)nc2c1] | 4-chloro-N-{3-[(3,5-dimethyl-1H-pyrazol-4-yl)amino]-6-methylquinoxalin-2-yl}benzenesulfonamide |

TABLE 1-continued

| Cpd. No. | Structure | Name |
|---|---|---|
| 113 | 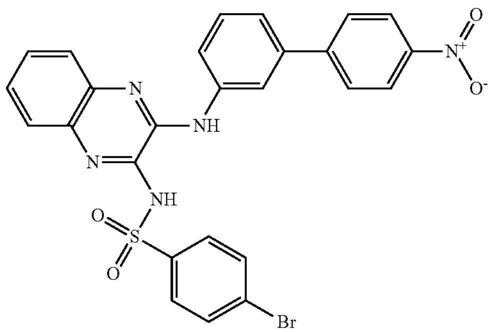 [SMILES: O=[N+]([O-])c1ccc(-c2cccc(Nc3nc4ccccc4nc3NS(=O)(=O)c3ccc(Br)cc3)c2)cc1] | 4-bromo-N-{3-[(4'-nitrobiphenyl-3-yl)amino]quinoxalin-2-yl}benzenesulfonamide |
| 114 | 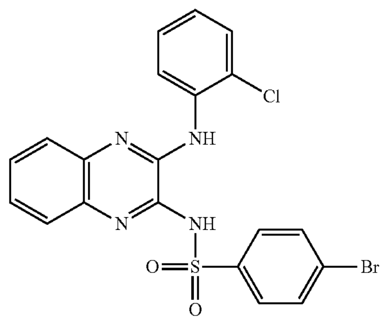 [SMILES: O=S(=O)(Nc1nc2ccccc2nc1Nc1ccccc1Cl)c1ccc(Br)cc1] | 4-bromo-N-{3-[(2-chlorophenyl)amino]quinoxalin-2-yl}benzenesulfonamide |
| 115 | 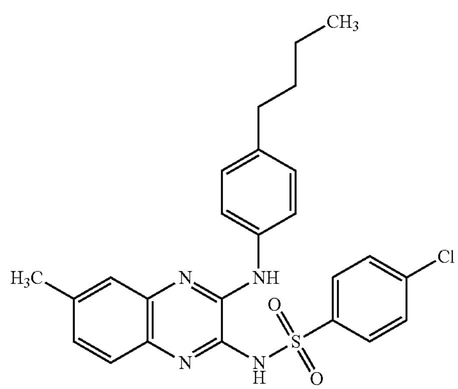 [SMILES: CCCCc1ccc(Nc2nc3cc(C)ccc3nc2NS(=O)(=O)c2ccc(Cl)cc2)cc1] | N-{3-[(4-butylphenyl)amino]-6-methylquinoxalin-2-yl}-4-chlorobenzenesulfonamide |
| 116 | 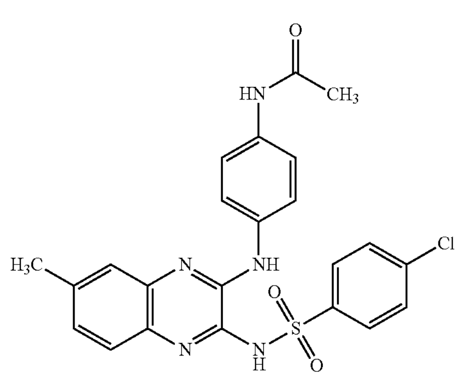 [SMILES: CC(=O)Nc1ccc(Nc2nc3cc(C)ccc3nc2NS(=O)(=O)c2ccc(Cl)cc2)cc1] | N-{4-[(3-{[(4-chlorophenyl)sulfonyl]amino}-7-methylquinoxalin-2-yl)amino]phenyl}acetamide |

TABLE 1-continued
| Cpd. No. | Structure | Name |
|---|---|---|
| 117 | 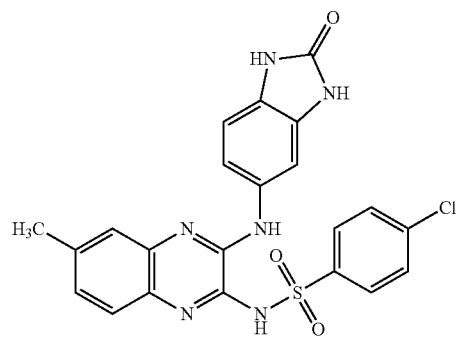 [SMILES: Cc1ccc2nc(NS(=O)(=O)c3ccc(Cl)cc3)c(Nc3ccc4[nH]c(=O)[nH]c4c3)nc2c1] | 4-chloro-N-{6-methyl-3-[(2-oxo-2,3-dihydro-1H-benzimidazol-5-yl)amino]quinoxalin-2-yl}benzenesulfonamide |
| 118 | 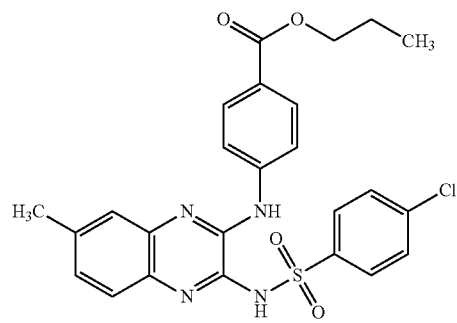 [SMILES: CCCOC(=O)c1ccc(Nc2nc3cc(C)ccc3nc2NS(=O)(=O)c2ccc(Cl)cc2)cc1] | propyl 4-[(3-{[(4-chlorophenyl)sulfonyl]amino}-7-methylquinoxalin-2-yl)amino]benzoate |
| 119 | 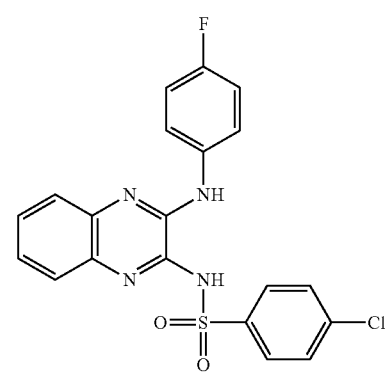 [SMILES: O=S(=O)(Nc1nc2ccccc2nc1Nc1ccc(F)cc1)c1ccc(Cl)cc1] | 4-chloro-N-{3-[(4-fluorophenyl)amino]quinoxalin-2-yl}benzenesulfonamide |
| 120 | 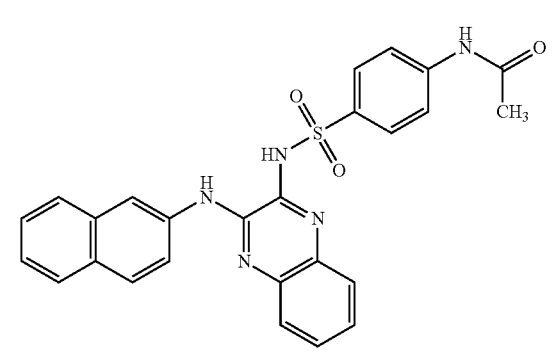 [SMILES: CC(=O)Nc1ccc(S(=O)(=O)Nc2nc3ccccc3nc2Nc2ccc3ccccc3c2)cc1] | N-[4-(({[3-(naphthalen-2-ylamino)quinoxalin-2-yl]amino}sulfonyl)phenyl]acetamide |

TABLE 1-continued

| Cpd. No. | Structure | Name |
|---|---|---|
| 121 | 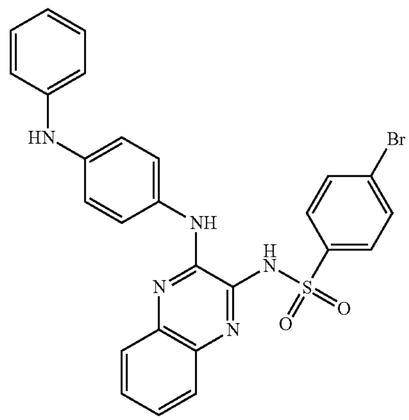 [SMILES: O=S(=O)(Nc1nc2ccccc2nc1Nc1ccc(Nc2ccccc2)cc1)c1ccc(Br)cc1] | 4-bromo-N-(3-{[4-(phenylamino)phenyl]amino}quinoxalin-2-yl)benzenesulfonamide |
| 122 | 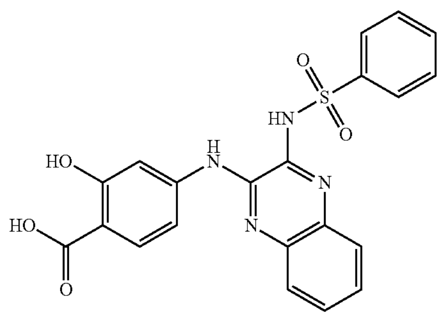 [SMILES: O=C(O)c1ccc(Nc2nc3ccccc3nc2NS(=O)(=O)c2ccccc2)cc1O] | 2-hydroxy-4-({3-[(phenylsulfonyl)amino]quinoxalin-2-yl}amino)benzoic acid |
| 123 | 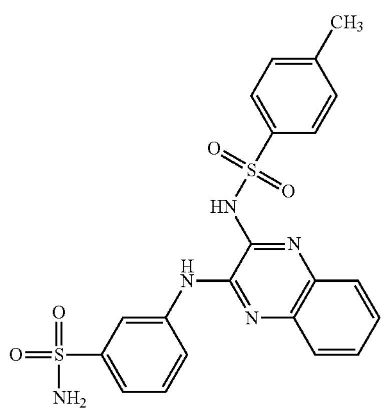 [SMILES: Cc1ccc(S(=O)(=O)Nc2nc3ccccc3nc2Nc2cccc(S(N)(=O)=O)c2)cc1] | N-(3-{[3-(aminosulfonyl)phenyl]amino}quinoxalin-2-yl)-4-methylbenzenesulfonamide |
| 124 | 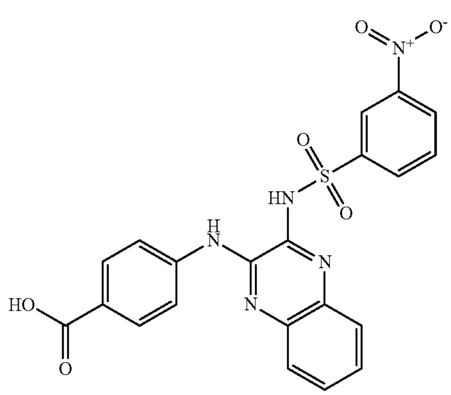 [SMILES: O=C(O)c1ccc(Nc2nc3ccccc3nc2NS(=O)(=O)c2cccc([N+](=O)[O-])c2)cc1] | 4-[(3-{[(3-nitrophenyl)sulfonyl]amino}quinoxalin-2-yl)amino]benzoic acid |

TABLE 1-continued

| Cpd. No. | Structure | Name |
|---|---|---|
| 125 | 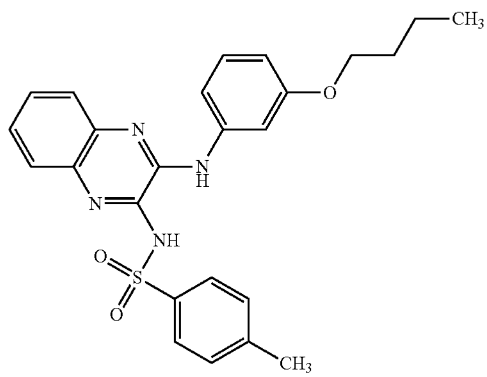 [SMILES: CCCCOc1cccc(Nc2nc3ccccc3nc2NS(=O)(=O)c2ccc(C)cc2)c1] | N-(3-{[3-(butyloxy)phenyl]amino}quinoxalin-2-yl)-4-methylbenzenesulfonamide |
| 126 | 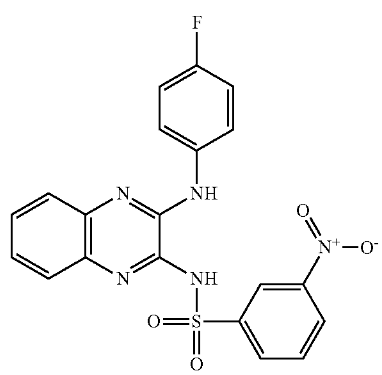 [SMILES: O=[N+]([O-])c1cccc(S(=O)(=O)Nc2nc3ccccc3nc2Nc2ccc(F)cc2)c1] | N-{3-[(4-fluorophenyl)amino]quinoxalin-2-yl}-3-nitrobenzenesulfonamide |
| 127 | 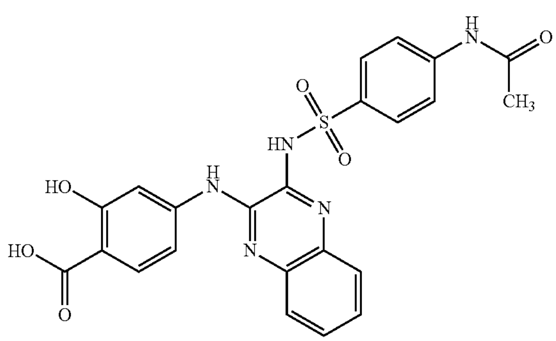 [SMILES: CC(=O)Nc1ccc(S(=O)(=O)Nc2nc3ccccc3nc2Nc2ccc(C(=O)O)c(O)c2)cc1] | 4-{[3-({[4-(acetylamino)phenyl]sulfonyl}amino)quinoxalin-2-yl]amino}-2-hydroxybenzoic acid |
| 128 | 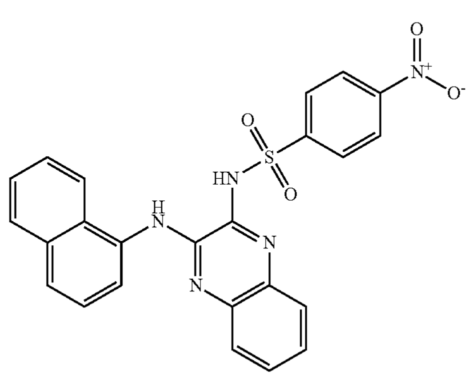 [SMILES: O=[N+]([O-])c1ccc(S(=O)(=O)Nc2nc3ccccc3nc2Nc2cccc3ccccc23)cc1] | N-[3-(naphthalen-1-ylamino)quinoxalin-2-yl]-4-nitrobenzenesulfonamide |

TABLE 1-continued
| Cpd. No. | Structure | Name |
|---|---|---|
| 129 | 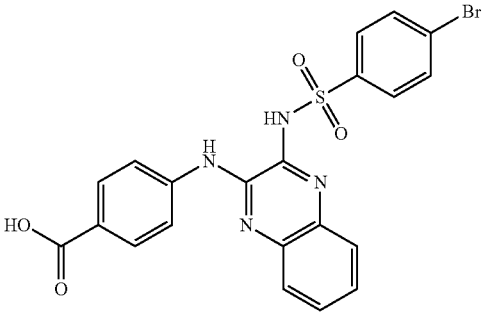 [SMILES: O=C(O)c1ccc(Nc2nc3ccccc3nc2NS(=O)(=O)c2ccc(Br)cc2)cc1] | 4-[(3-{[(4-bromophenyl)sulfonyl]amino}quinoxalin-2-yl)amino]benzoic acid |
| 130 | 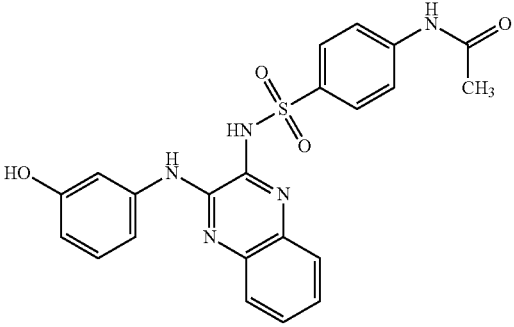 [SMILES: CC(=O)Nc1ccc(S(=O)(=O)Nc2nc3ccccc3nc2Nc2cccc(O)c2)cc1] | N-{4-[({3-[(3-hydroxyphenyl)amino]quinoxalin-2-yl}amino)sulfonyl]phenyl}acetamide |
| 131 | 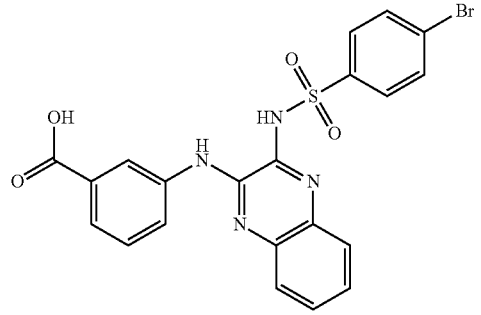 [SMILES: O=C(O)c1cccc(Nc2nc3ccccc3nc2NS(=O)(=O)c2ccc(Br)cc2)c1] | 3-[(3-{[(4-bromophenyl)sulfonyl]amino}quinoxalin-2-yl)amino]benzoic acid |
| 132 | 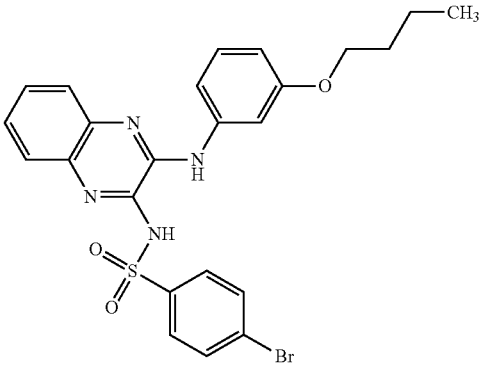 [SMILES: CCCCOc1cccc(Nc2nc3ccccc3nc2NS(=O)(=O)c2ccc(Br)cc2)c1] | 4-bromo-N-(3-{[3-(butyloxy)phenyl]amino}quinoxalin-2-yl)benzenesulfonamide |

TABLE 1-continued
| Cpd. No. | Structure | Name |
|---|---|---|
| 133 | 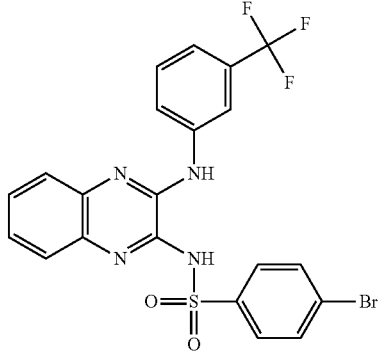 [SMILES: O=S(=O)(Nc1nc2ccccc2nc1Nc1cccc(C(F)(F)F)c1)c1ccc(Br)cc1] | 4-bromo-N-(3-{[3-(trifluoromethyl)phenyl]amino}quinoxalin-2-yl)benzenesulfonamide |
| 134 | 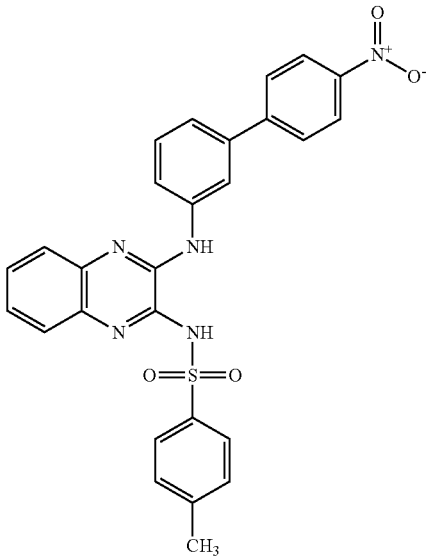 [SMILES: Cc1ccc(S(=O)(=O)Nc2nc3ccccc3nc2Nc2cccc(-c3ccc([N+](=O)[O-])cc3)c2)cc1] | 4-methyl-N-{3-[(4'-nitrobiphenyl-3-yl)amino]quinoxalin-2-yl}benzenesulfonamide |
| 135 | 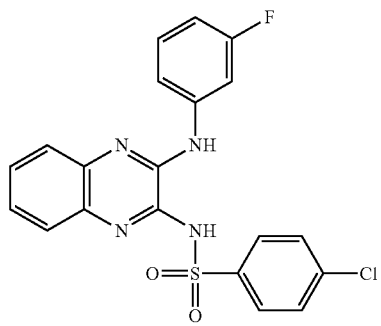 [SMILES: O=S(=O)(Nc1nc2ccccc2nc1Nc1cccc(F)c1)c1ccc(Cl)cc1] | 4-chloro-N-{3-[(3-fluorophenyl)amino]quinoxalin-2-yl}benzenesulfonamide |

TABLE 1-continued

| Cpd. No. | Structure | Name |
|---|---|---|
| 136 | 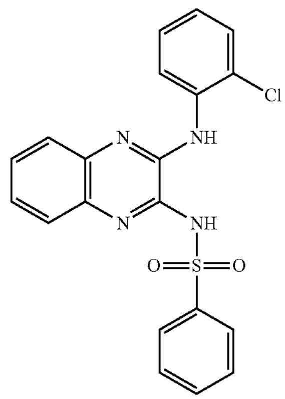 [SMILES: O=S(=O)(Nc1nc2ccccc2nc1Nc1ccccc1Cl)c1ccccc1] | N-{3-[(2-chlorophenyl)amino]quinoxalin-2-yl}benzenesulfonamide |
| 137 | 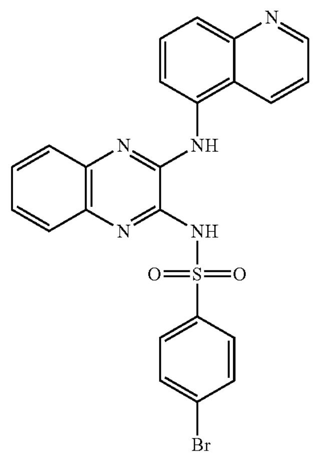 [SMILES: O=S(=O)(Nc1nc2ccccc2nc1Nc1cccc2ncccc12)c1ccc(Br)cc1] | 4-bromo-N-[3-(quinolin-5-ylamino)quinoxalin-2-yl]benzenesulfonamide |
| 138 | 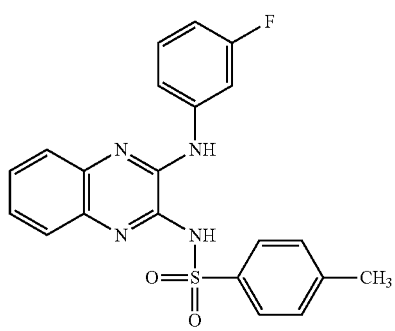 [SMILES: Cc1ccc(S(=O)(=O)Nc2nc3ccccc3nc2Nc2cccc(F)c2)cc1] | N-{3-[(3-fluorophenyl)amino]quinoxalin-2-yl}-4-methylbenzenesulfonamide |
| 139 | 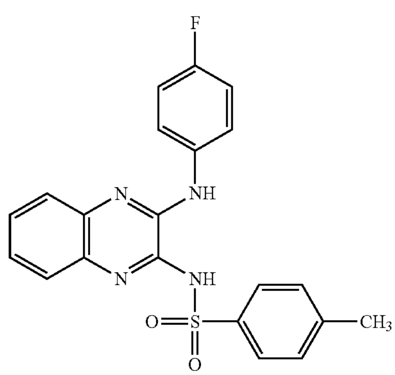 [SMILES: Cc1ccc(S(=O)(=O)Nc2nc3ccccc3nc2Nc2ccc(F)cc2)cc1] | N-{3-[(4-fluorophenyl)amino]quinoxalin-2-yl}-4-methylbenzenesulfonamide |

TABLE 1-continued

| Cpd. No. | Structure | Name |
|---|---|---|
| 140 | 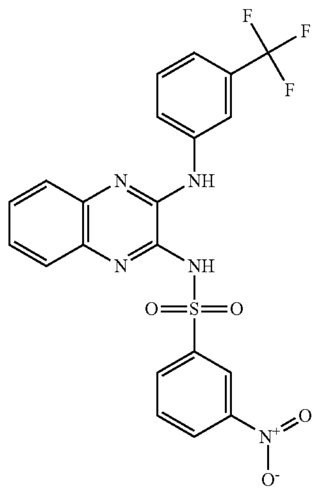 [SMILES: O=[N+]([O-])c1cccc(S(=O)(=O)Nc2nc3ccccc3nc2Nc2cccc(C(F)(F)F)c2)c1] | 3-nitro-N-(3-{[3-(trifluoromethyl)phenyl]amino}quinoxalin-2-yl)benzenesulfonamide |
| 141 | 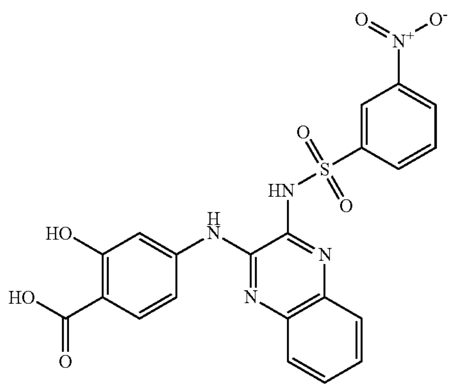 [SMILES: O=C(O)c1ccc(Nc2nc3ccccc3nc2NS(=O)(=O)c2cccc([N+](=O)[O-])c2)cc1O] | 2-hydroxy-4-[(3-{[(3-nitrophenyl)sulfonyl]amino}quinoxalin-2-yl)amino]benzoic acid |
| 142 | 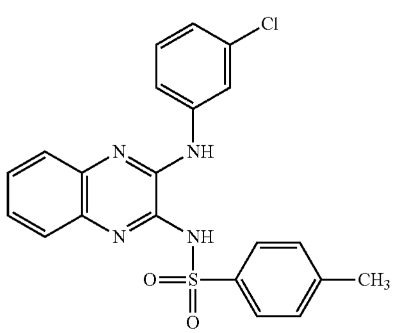 [SMILES: Cc1ccc(S(=O)(=O)Nc2nc3ccccc3nc2Nc2cccc(Cl)c2)cc1] | N-{3-[(3-chlorophenyl)amino]quinoxalin-2-yl}-4-methylbenzenesulfonamide |
| 143 | 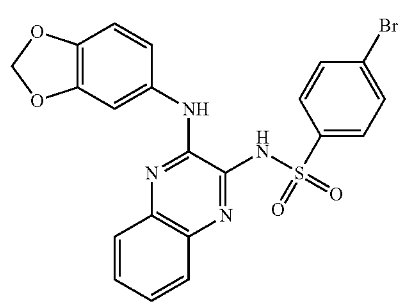 [SMILES: O=S(=O)(Nc1nc2ccccc2nc1Nc1ccc2c(c1)OCO2)c1ccc(Br)cc1] | N-[3-(1,3-benzodioxol-5-ylamino)quinoxalin-2-yl]-4-bromobenzenesulfonamide |

TABLE 1-continued
| Cpd. No. | Structure | Name |
|---|---|---|
| 144 | 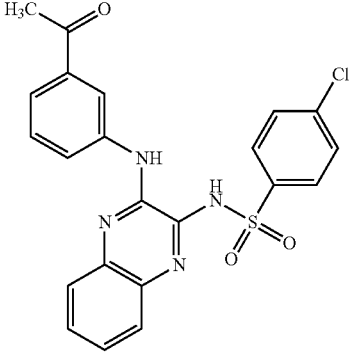 [SMILES: CC(=O)c1cccc(Nc2nc3ccccc3nc2NS(=O)(=O)c2ccc(Cl)cc2)c1] | N-{3-[(3-acetylphenyl)amino]quinoxalin-2-yl}-4-chlorobenzenesulfonamide |
| 145 | 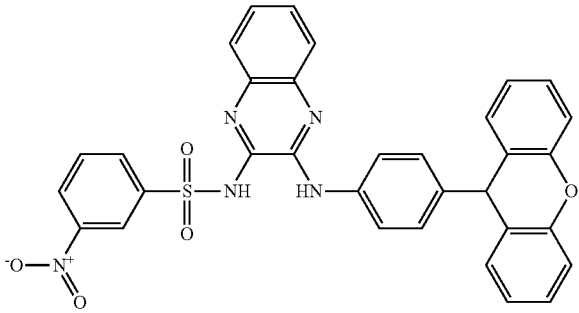 | 3-nitro-N-(3-{[4-(9H-xanthen-9-yl)phenyl]amino}quinoxalin-2-yl)benzenesulfonamide |
| 146 | 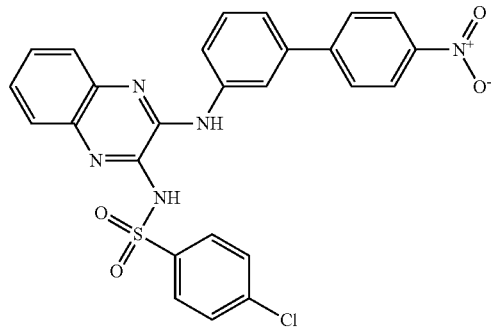 | 4-chloro-N-{3-[(4'-nitrobiphenyl-3-yl)amino]quinoxalin-2-yl}benzenesulfonamide |
| 147 | 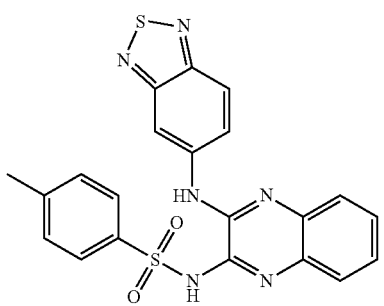 [SMILES: Cc1ccc(S(=O)(=O)Nc2nc3ccccc3nc2Nc2ccc3nsnc3c2)cc1] | N-[3-(2,1,3-benzothiadiazol-5-ylamino)quinoxalin-2-yl]-4-tolylsulfonamide |

US 8,481,001 B2
TABLE 1-continued
| Cpd. No. | Structure | Name |
|---|---|---|
| 148 | 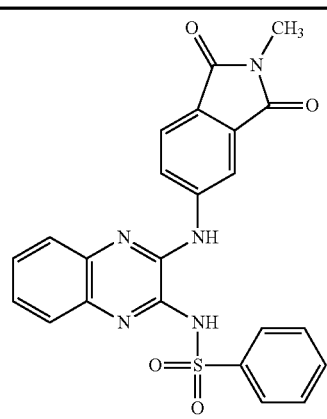 | N-{3-[(2-methyl-1,3-dioxo-2,3-dihydro-1H-isoindol-5-yl)amino]quinoxalin-2-yl}benzenesulfonamide |
| 149 | 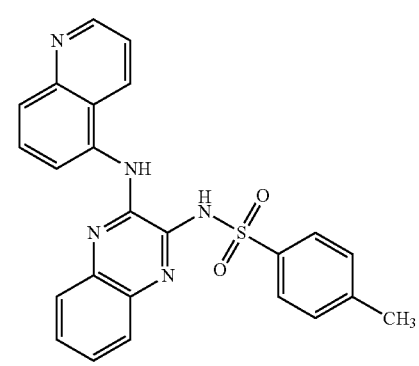 [SMILES: Cc1ccc(S(=O)(=O)Nc2nc3ccccc3nc2Nc2cccc3ncccc23)cc1] | 4-methyl-N-[3-(quinolin-5-ylamino)quinoxalin-2-yl]benzenesulfonamide |
| 150 | 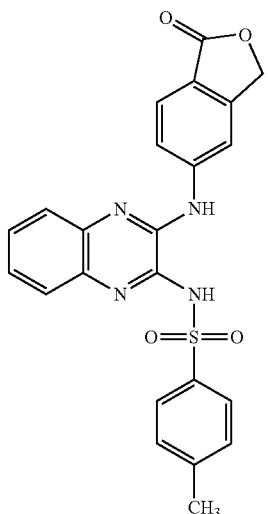 [SMILES: Cc1ccc(S(=O)(=O)Nc2nc3ccccc3nc2Nc2ccc3c(c2)COC3=O)cc1] | 4-methyl-N-{3-[(1-oxo-1,3-dihydro-2-benzofuran-5-yl)amino]quinoxalin-2-yl}benzenesulfonamide |
| 151 | 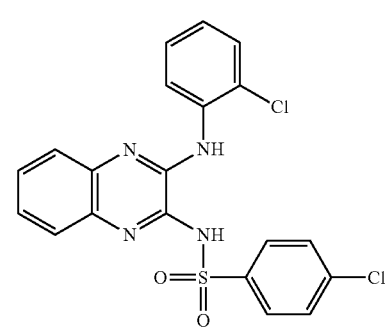 [SMILES: O=S(=O)(Nc1nc2ccccc2nc1Nc1ccccc1Cl)c1ccc(Cl)cc1] | 4-chloro-N-{3-[(2-chlorophenyl)amino]quinoxalin-2-yl]benzenesulfonamide |

TABLE 1-continued
| Cpd. No. | Structure | Name |
|---|---|---|
| 152 | 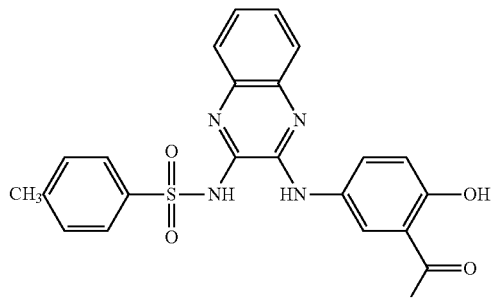 | 2-hydroxy-5-[(3-{[(4-methylphenyl)sulfonyl]amino}quinoxalin-2-yl)amino]benzoic acid |
| 153 | 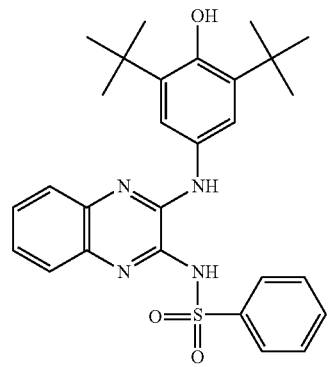 [SMILES: CC(C)(C)c1cc(Nc2nc3ccccc3nc2NS(=O)(=O)c2ccccc2)cc(C(C)(C)C)c1O] | N-(3-{[3,5-bis(1,1-dimethylethyl)-4-hydroxyphenyl]amino}quinoxalin-2-yl)benzenesulfonamide |
| 154 | 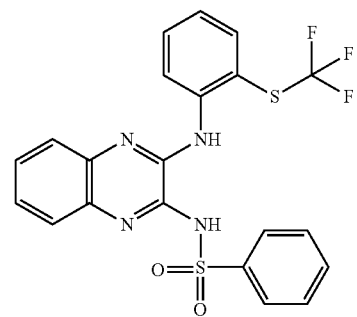 [SMILES: O=S(=O)(Nc1nc2ccccc2nc1Nc1ccccc1SC(F)(F)F)c1ccccc1] | N-[3-({2-[(trifluoromethyl)thio]phenyl}amino)quinoxalin-2-yl]benzenesulfonamide |
| 155 | 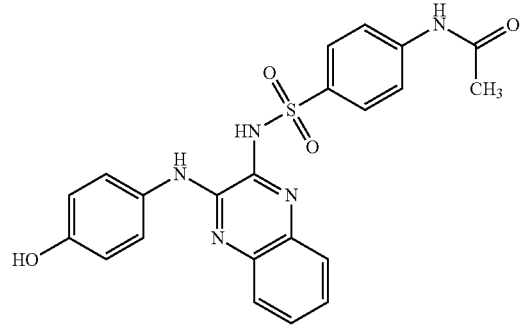 [SMILES: CC(=O)Nc1ccc(S(=O)(=O)Nc2nc3ccccc3nc2Nc2ccc(O)cc2)cc1] | N-{4-[({3-[(4-hydroxyphenyl)amino]quinoxalin-2-yl}amino)sulfonyl]phenyl}acetamide |

TABLE 1-continued

| Cpd. No. | Structure | Name |
|---|---|---|
| 156 | 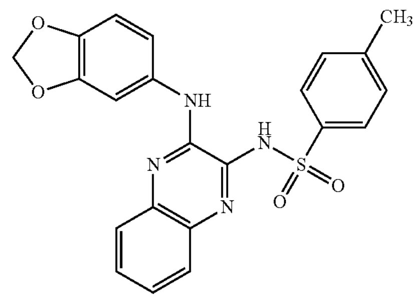 [SMILES: Cc1ccc(S(=O)(=O)Nc2nc3ccccc3nc2Nc2ccc3c(c2)OCO3)cc1] | N-[3-(1,3-benzodioxol-5-ylamino)quinoxalin-2-yl]-4-methylbenzenesulfonamide |
| 157 | 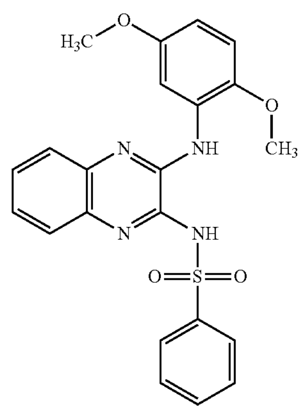 [SMILES: COc1ccc(OC)c(Nc2nc3ccccc3nc2NS(=O)(=O)c2ccccc2)c1] | N-(3-{[2,5-bis(methoxy)phenyl]amino}quinoxalin-2-yl)benzenesulfonamide |
| 158 | 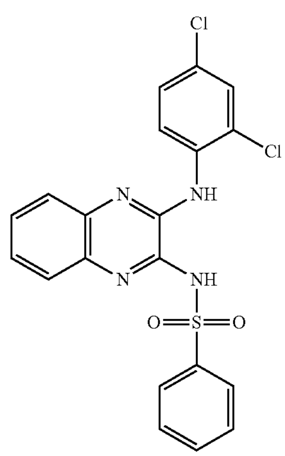 [SMILES: O=S(=O)(Nc1nc2ccccc2nc1Nc1ccc(Cl)cc1Cl)c1ccccc1] | N-{3-[(2,4-dichlorophenyl)amino]quinoxalin-2-yl}benzenesulfonamide |
| 159 | 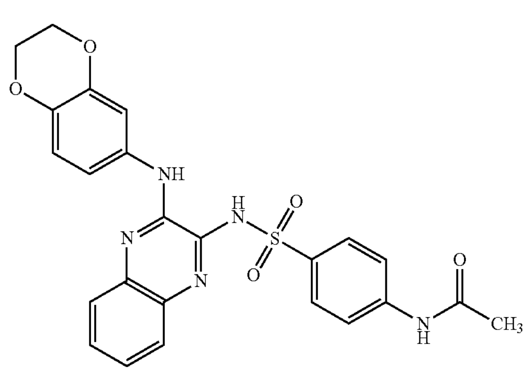 [SMILES: CC(=O)Nc1ccc(S(=O)(=O)Nc2nc3ccccc3nc2Nc2ccc3c(c2)OCCO3)cc1] | N-[4-({[3-(2,3-dihydro-1,4-benzodioxin-6-ylamino)quinoxalin-2-yl]amino}sulfonyl)phenyl]acetamide |

TABLE 1-continued
| Cpd. No. | Structure | Name |
|---|---|---|
| 160 | 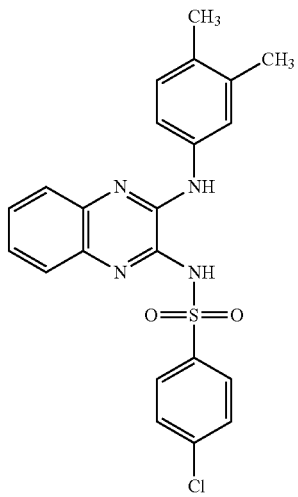 | 4-chloro-N-{3-[(3,4-dimethylphenyl)amino]quinoxalin-2-yl}benzenesulfonamide |
| 161 | 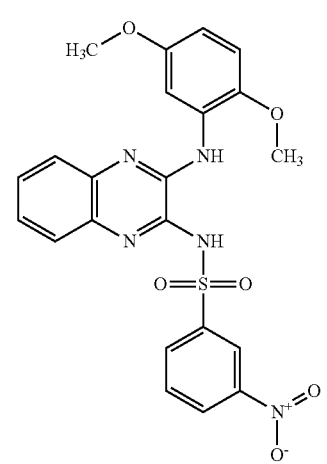 [SMILES: COc1ccc(OC)c(Nc2nc3ccccc3nc2NS(=O)(=O)c2cccc([N+](=O)[O-])c2)c1] | N-(3-{[2,5-bis(methoxy)phenyl]amino}quinoxalin-2-yl)-3-nitrobenzenesulfonamide |
| 162 | 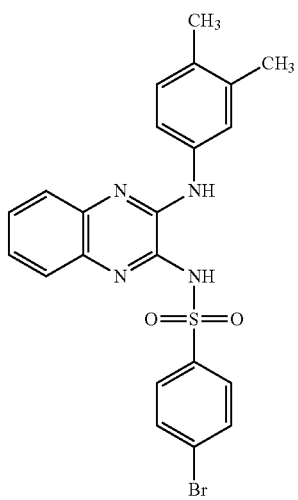 [SMILES: Cc1ccc(Nc2nc3ccccc3nc2NS(=O)(=O)c2ccc(Br)cc2)cc1C] | 4-bromo-N-{3-[(3,4-dimethylphenyl)amino]quinoxalin-2-yl}benzenesulfonamide |

TABLE 1-continued
| Cpd. No. | Structure | Name |
|---|---|---|
| 163 | 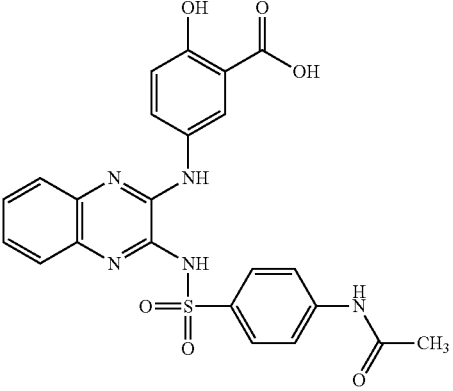 [SMILES: CC(=O)Nc1ccc(S(=O)(=O)Nc2nc3ccccc3nc2Nc2ccc(O)c(C(=O)O)c2)cc1] | 5-{[3-({[4-(acetylamino)phenyl]sulfonyl}amino)quinoxalin-2-yl]amino}-2-hydroxybenzoic acid |
| 164 | 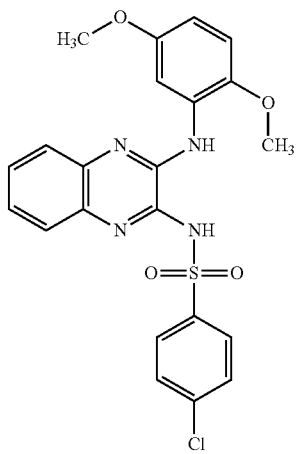 [SMILES: COc1ccc(OC)c(Nc2nc3ccccc3nc2NS(=O)(=O)c2ccc(Cl)cc2)c1] | N-(3-{[2,5-bis(methoxy)phenyl]amino}quinoxalin-2-yl)-4-chlorobenzenesulfonamide |
| 165 | 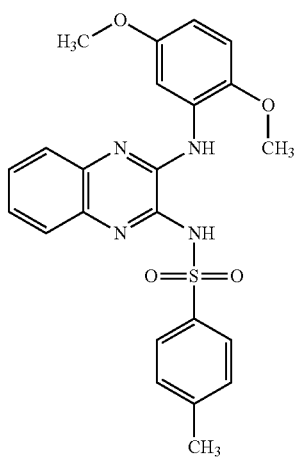 [SMILES: COc1ccc(OC)c(Nc2nc3ccccc3nc2NS(=O)(=O)c2ccc(C)cc2)c1] | N-(3-{[2,5-bis(methoxy)phenyl]amino}quinoxalin-2-yl)-4-methylbenzenesulfonamide |

TABLE 1-continued

| Cpd. No. | Structure | Name |
|---|---|---|
| 166 | 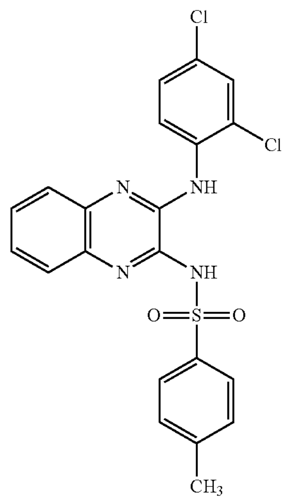 [SMILES: Cc1ccc(S(=O)(=O)Nc2nc3ccccc3nc2Nc2ccc(Cl)cc2Cl)cc1] | N-{3-[(2,4-dichlorophenyl)amino]quinoxalin-2-yl}-4-methylbenzenesulfonamide |
| 167 | 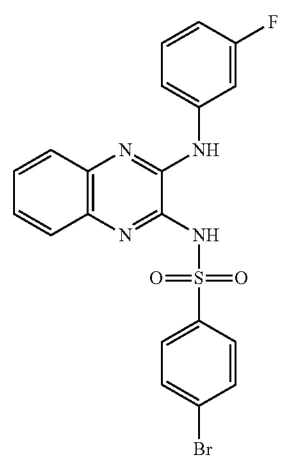 [SMILES: O=S(=O)(Nc1nc2ccccc2nc1Nc1cccc(F)c1)c1ccc(Br)cc1] | 4-bromo-N-{3-[(3-fluorophenyl)amino]quinoxalin-2-yl}benzenesulfonamide |
| 168 | 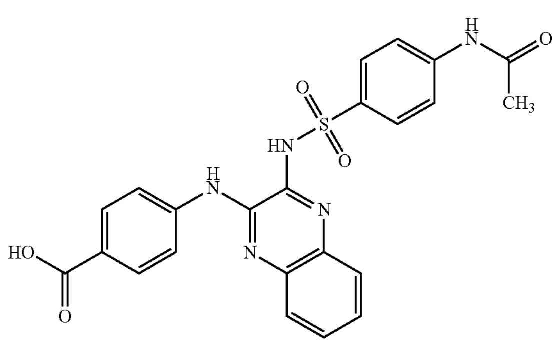 [SMILES: CC(=O)Nc1ccc(S(=O)(=O)Nc2nc3ccccc3nc2Nc2ccc(C(=O)O)cc2)cc1] | 4-{[3-({[4-(acetylamino)phenyl]sulfonyl}amino)quinoxalin-2-yl]amino}benzoic acid |
| 169 | 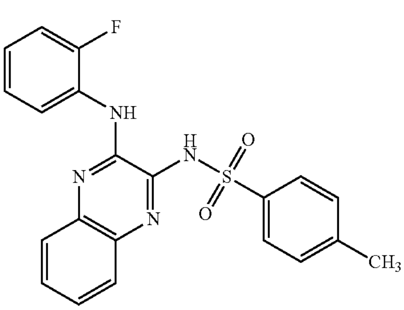 [SMILES: Cc1ccc(S(=O)(=O)Nc2nc3ccccc3nc2Nc2ccccc2F)cc1] | N-{3-[(2-fluorophenyl)amino]quinoxalin-2-yl}-4-methylbenzenesulfonamide |

TABLE 1-continued

| Cpd. No. | Structure | Name |
| --- | --- | --- |
| 170 | 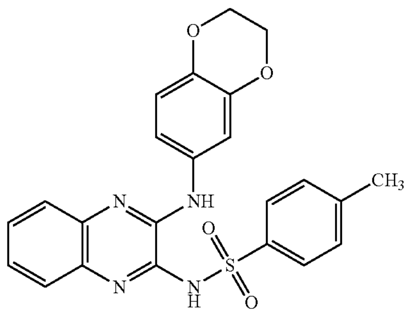 [SMILES: Cc1ccc(S(=O)(=O)Nc2nc3ccccc3nc2Nc2ccc3c(c2)OCCO3)cc1] | N-[3-(2,3-dihydro-1,4-benzodioxin-6-ylamino)quinoxalin-2-yl]-4-methylbenzenesulfonamide |
| 171 | 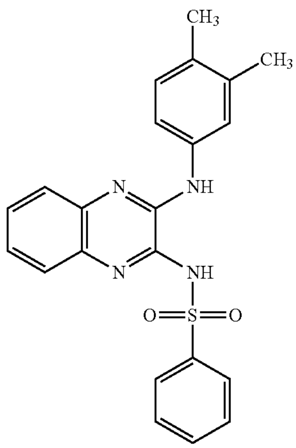 [SMILES: Cc1ccc(Nc2nc3ccccc3nc2NS(=O)(=O)c2ccccc2)cc1C] | N-{3-[(3,4-dimethylphenyl)amino]quinoxalin-2-yl}benzenesulfonamide |
| 172 | 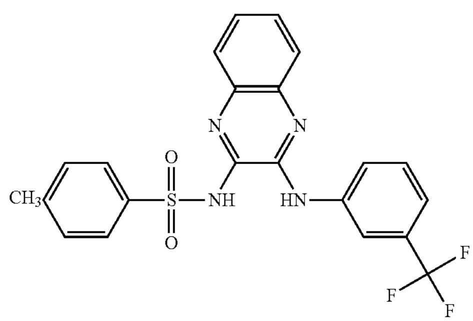 | 4-methyl-N-(3-{[3-(trifluoromethyl)phenyl]amino}quinoxalin-2-yl)benzenesulfonamide |
| 173 | 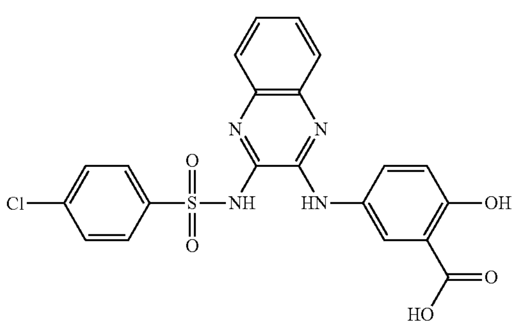 [SMILES: O=C(O)c1cc(Nc2nc3ccccc3nc2NS(=O)(=O)c2ccc(Cl)cc2)ccc1O] | 5-[(3-{[(4-chlorophenyl)sulfonyl]amino}quinoxalin-2-yl)amino]-2-hydroxybenzoic acid |

TABLE 1-continued

| Cpd. No. | Structure | Name |
|---|---|---|
| 174 | 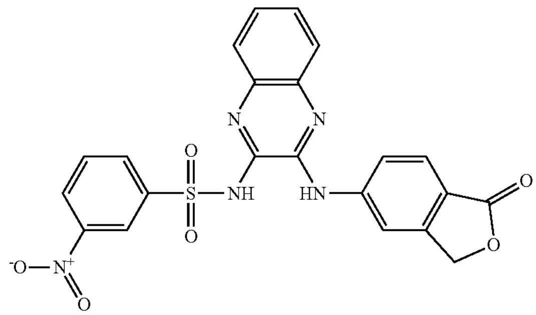 | 3-nitro-N-{3-[(1-oxo-1,3-dihydro-2-benzofuran-5-yl)amino]quinoxalin-2-yl}benzenesulfonamide |
| 175 | 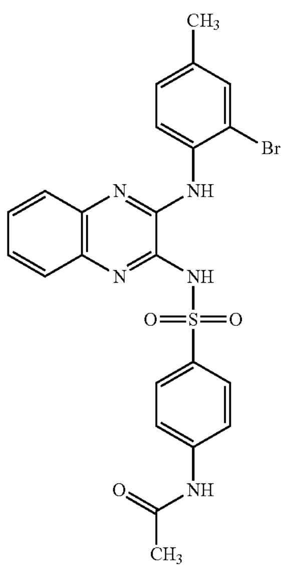 [SMILES: CC(=O)Nc1ccc(S(=O)(=O)Nc2nc3ccccc3nc2Nc2ccc(C)cc2Br)cc1] | N-{4-[({3-[(2-bromo-4-methylphenyl)amino]quinoxalin-2-yl}amino)sulfonyl]phenyl}acetamide |
| 176 | 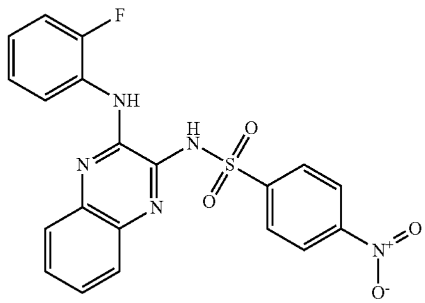 [SMILES: O=[N+]([O-])c1ccc(S(=O)(=O)Nc2nc3ccccc3nc2Nc2ccccc2F)cc1] | N-{3-[(2-fluorophenyl)amino]quinoxalin-2-yl}-4-nitrobenzenesulfonamide |

US 8,481,001 B2
149                                                                                                 150
TABLE 1-continued
| Cpd. No. | Structure | Name |
|---|---|---|
| 177 | 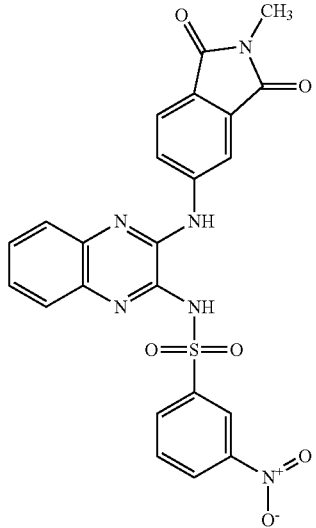 [SMILES: CN1C(=O)c2ccc(Nc3nc4ccccc4nc3NS(=O)(=O)c3cccc([N+](=O)[O-])c3)cc2C1=O] | N-{3-[(2-methyl-1,3-dioxo-2,3-dihydro-1H-isoindol-5-yl)amino]quinoxalin-2-yl}-3-nitrobenzenesulfonamide |
| 178 | 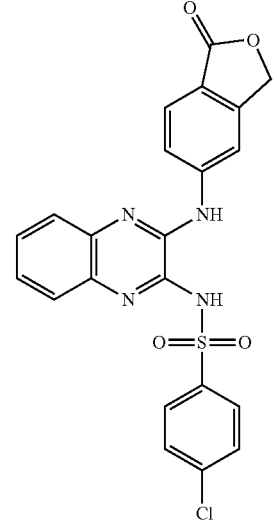 [SMILES: O=C1OCc2cc(Nc3nc4ccccc4nc3NS(=O)(=O)c3ccc(Cl)cc3)ccc21] | 4-chloro-N-{3-[(1-oxo-1,3-dihydro-2-benzofuran-5-yl)amino]quinoxalin-2-yl}benzenesulfonamide |
| 179 | 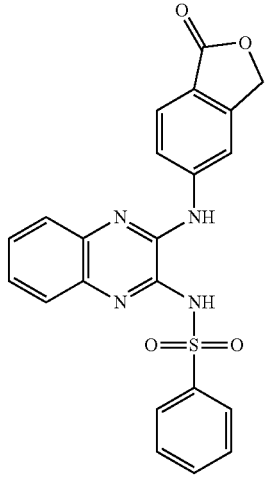 [SMILES: O=C1OCc2cc(Nc3nc4ccccc4nc3NS(=O)(=O)c3ccccc3)ccc21] | N-{3-[(1-oxo-1,3-dihydro-2-benzofuran-5-yl)amino]quinoxalin-2-yl}benzenesulfonamide |

TABLE 1-continued

| Cpd. No. | Structure | Name |
|---|---|---|
| 180 | 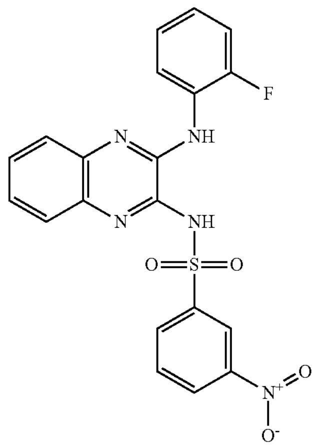 [SMILES: O=[N+]([O-])c1cccc(S(=O)(=O)Nc2nc3ccccc3nc2Nc2ccccc2F)c1] | N-{3-[(2-fluorophenyl)amino]quinoxalin-2-yl}-3-nitrobenzenesulfonamide |
| 181 | 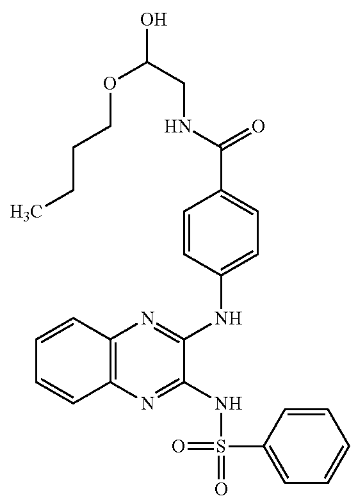 [SMILES: CCCCOC(O)CNC(=O)c1ccc(Nc2nc3ccccc3nc2NS(=O)(=O)c2ccccc2)cc1] | N-[2-(butyloxy)-2-hydroxyethyl]-4-({3-[(phenylsulfonyl)amino]quinoxalin-2-yl}amino)benzamide |
| 182 | 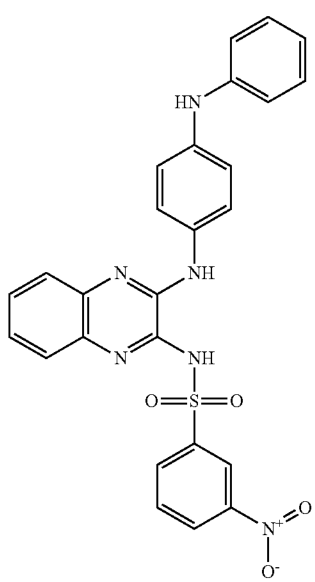 [SMILES: O=[N+]([O-])c1cccc(S(=O)(=O)Nc2nc3ccccc3nc2Nc2ccc(Nc3ccccc3)cc2)c1] | 3-nitro-N-(3-{[4-(phenylamino)phenyl]amino}quinoxalin-2-yl)benzenesulfonamide |

| Cpd. No. | Structure | Name |
|---|---|---|
| 183 | 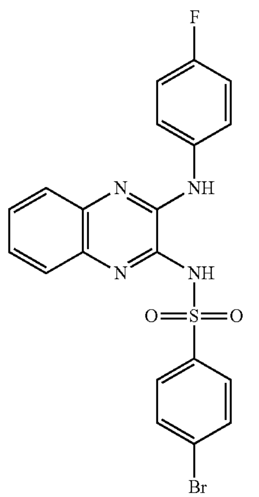 [SMILES: O=S(=O)(Nc1nc2ccccc2nc1Nc1ccc(F)cc1)c1ccc(Br)cc1] | 4-bromo-N-{3-[(4-fluorophenyl)amino]quinoxalin-2-yl}benzenesulfonamide |
| 184 | 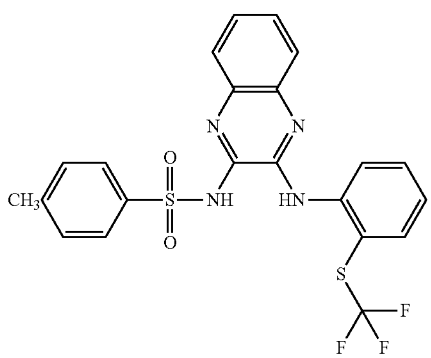 | 4-methyl-N-[3-({2-[(trifluoromethyl)thio]phenyl}amino)quinoxalin-2-yl]benzenesulfonamide |
| 185 | 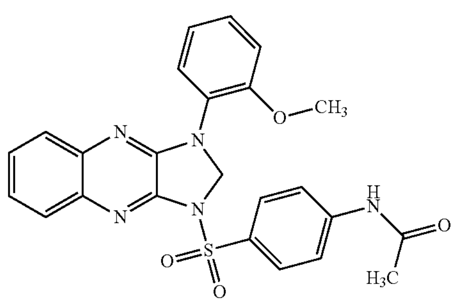 [SMILES: COc1ccccc1N1CN(S(=O)(=O)c2ccc(NC(C)=O)cc2)c2nc3ccccc3nc21] | N-[4-({3-[2-(methoxy)phenyl]-2,3-dihydro-1H-imidazo[4,5-b]quinoxalin-1-yl}sulfonyl)phenyl]acetamide |
| 186 | 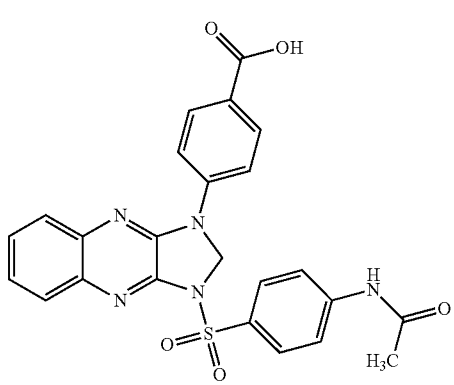 [SMILES: CC(=O)Nc1ccc(S(=O)(=O)N2CN(c3ccc(C(=O)O)cc3)c3nc4ccccc4nc32)cc1] | 4-(3-{[4-(acetylamino)phenyl]sulfonyl}-2,3-dihydro-1H-imidazo[4,5-b]quinoxalin-1-yl)benzoic acid |

TABLE 1-continued

| Cpd. No. | Structure | Name |
|---|---|---|
| 187 | 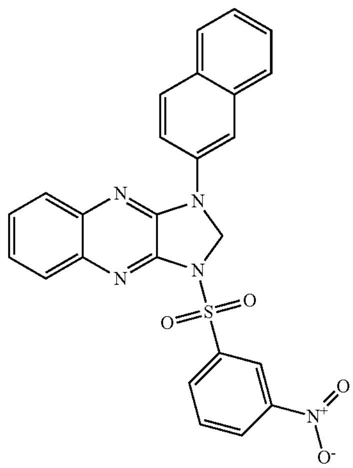 [SMILES: O=[N+]([O-])c1cccc(S(=O)(=O)N2CN(c3ccc4ccccc4c3)c3nc4ccccc4nc32)c1] | 1-naphthalen-2-yl-3-[(3-nitrophenyl)sulfonyl]-2,3-dihydro-1H-imidazo[4,5-b]quinoxaline |
| 188 | 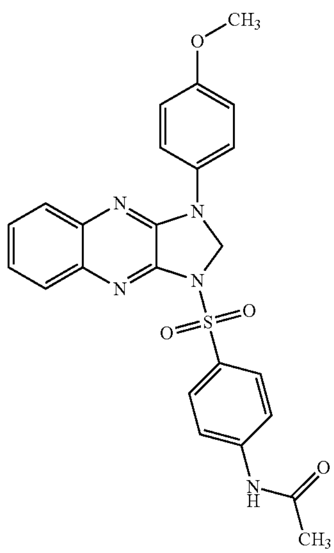 [SMILES: COc1ccc(N2CN(S(=O)(=O)c3ccc(NC(C)=O)cc3)c3nc4ccccc4nc32)cc1] | N-[4-({3-[4-(methoxy)phenyl]-2,3-dihydro-1H-imidazo[4,5-b]quinoxalin-1-yl}sulfonyl)phenyl]acetamide |
| 189 | 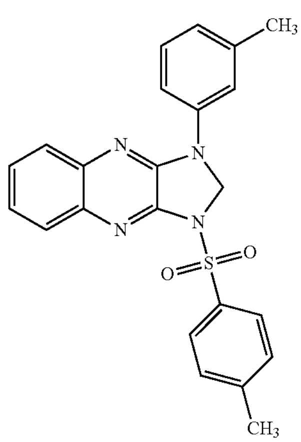 [SMILES: Cc1ccc(S(=O)(=O)N2CN(c3cccc(C)c3)c3nc4ccccc4nc32)cc1] | 1-(3-methylphenyl)-3-[(4-methylphenyl)sulfonyl]-2,3-dihydro-1H-imidazo[4,5-b]quinoxaline |

TABLE 1-continued

| Cpd. No. | Structure | Name |
|---|---|---|
| 190 | 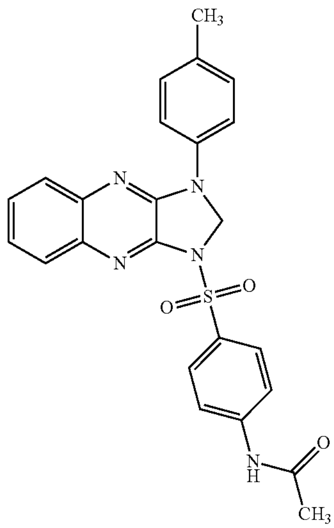 [SMILES: CC(=O)Nc1ccc(S(=O)(=O)N2CN(c3ccc(C)cc3)c3nc4ccccc4nc32)cc1] | N-(4-{[3-(4-methylphenyl)-2,3-dihydro-1H-imidazo[4,5-b]quinoxalin-1-yl]sulfonyl}phenyl)acetamide |
| 191 | 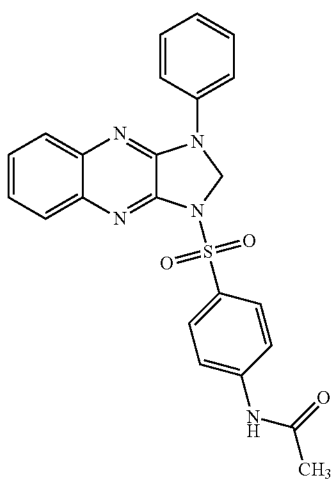 [SMILES: CC(=O)Nc1ccc(S(=O)(=O)N2CN(c3ccccc3)c3nc4ccccc4nc32)cc1] | N-{4-[(3-phenyl-2,3-dihydro-1H-imidazo[4,5-b]quinoxalin-1-yl)sulfonyl]phenyl}acetamide |
| 192 | 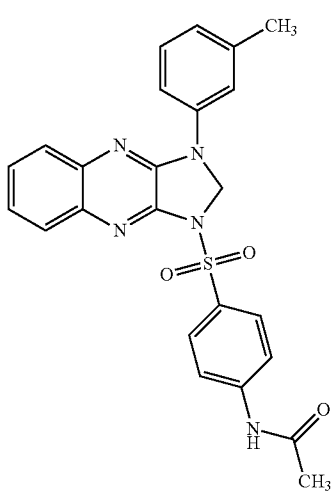 [SMILES: CC(=O)Nc1ccc(S(=O)(=O)N2CN(c3cccc(C)c3)c3nc4ccccc4nc32)cc1] | N-(4-{[3-(3-methylphenyl)-2,3-dihydro-1H-imidazo[4,5-b]quinoxalin-1-yl]sulfonyl}phenyl)acetamide |

TABLE 1-continued
| Cpd. No. | Structure | Name |
|---|---|---|
| 193 | 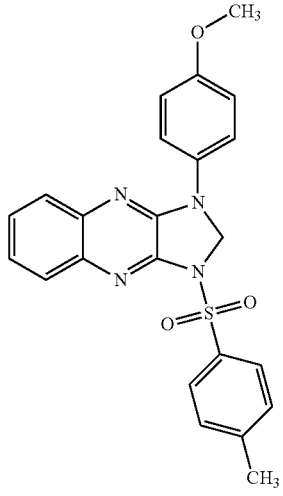 [SMILES: COc1ccc(N2CN(S(=O)(=O)c3ccc(C)cc3)c3nc4ccccc4nc32)cc1] | 1-[4-(methoxy)phenyl]-3-[(4-methylphenyl)sulfonyl]-2,3-dihydro-1H-imidazo[4,5-b]quinoxaline |
| 194 | 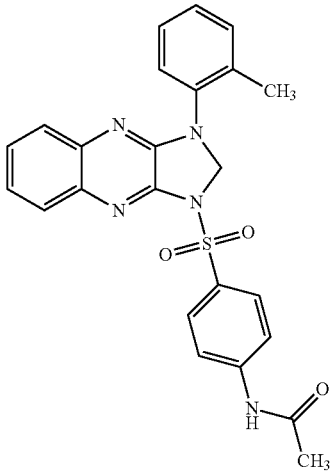 [SMILES: CC(=O)Nc1ccc(S(=O)(=O)N2CN(c3ccccc3C)c3nc4ccccc4nc32)cc1] | N-(4-{[3-(2-methylphenyl)-2,3-dihydro-1H-imidazo[4,5-b]quinoxalin-1-yl]sulfonyl}phenyl)acetamide |
| 195 | 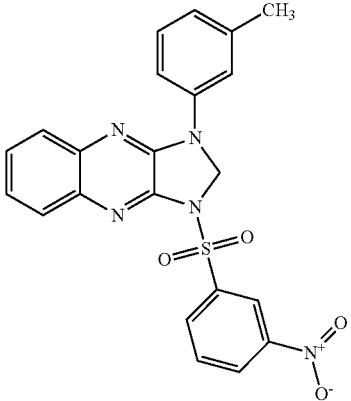 [SMILES: Cc1cccc(N2CN(S(=O)(=O)c3cccc([N+](=O)[O-])c3)c3nc4ccccc4nc32)c1] | 1-(3-methylphenyl)-3-[(3-nitrophenyl)sulfonyl]-2,3-dihydro-1H-imidazo[4,5-b]quinoxaline |

TABLE 1-continued
| Cpd. No. | Structure | Name |
|---|---|---|
| 196 | 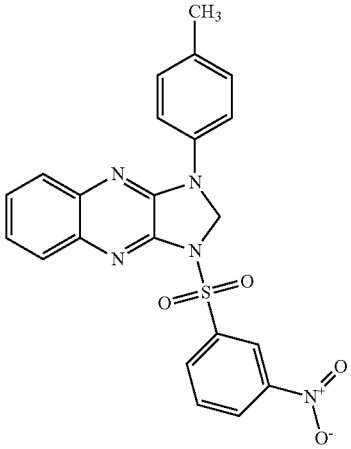 [SMILES: Cc1ccc(N2CN(S(=O)(=O)c3cccc([N+](=O)[O-])c3)c3nc4ccccc4nc32)cc1] | 1-(4-methylphenyl)-3-[(3-nitrophenyl)sulfonyl]-2,3-dihydro-1H-imidazo[4,5-b]quinoxaline |
| 197 | 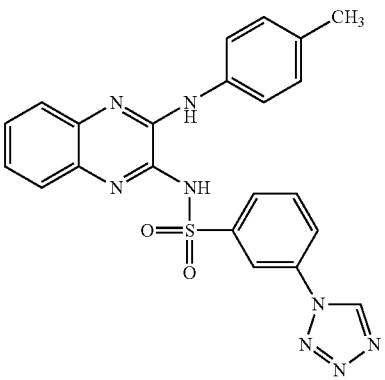 [SMILES: Cc1ccc(Nc2nc3ccccc3nc2NS(=O)(=O)c2cccc(-n3cnnn3)c2)cc1] | N-{3-[(4-methylphenyl)amino]quinoxalin-2-yl}-3-(1H-tetrazol-1-yl)benzenesulfonamide |
| 198 | 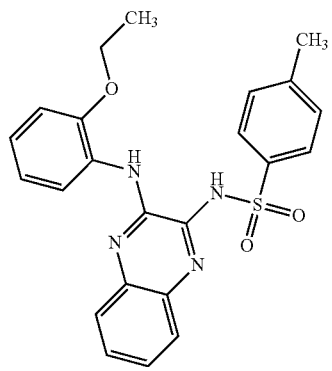 [SMILES: CCOc1ccccc1Nc1nc2ccccc2nc1NS(=O)(=O)c1ccc(C)cc1] | N-(3-{[2-(ethyloxy)phenyl]amino}quinoxalin-2-yl)-4-methylbenzenesulfonamide |

TABLE 1-continued

| Cpd. No. | Structure | Name |
|---|---|---|
| 199 | 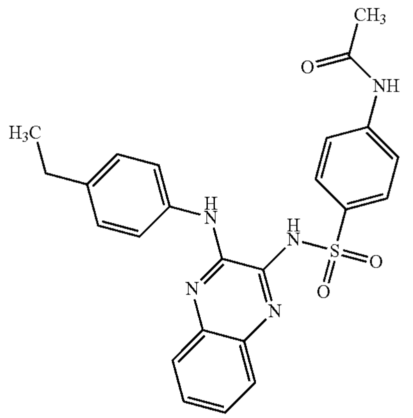 [SMILES: CCc1ccc(Nc2nc3ccccc3nc2NS(=O)(=O)c2ccc(NC(C)=O)cc2)cc1] | N-{4-[({3-[(4-ethylphenyl) amino]quinoxalin-2-yl}amino) sulfonyl]phenyl}acetamide |
| 200 | 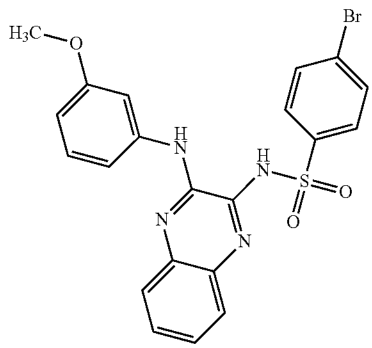 [SMILES: COc1cccc(Nc2nc3ccccc3nc2NS(=O)(=O)c2ccc(Br)cc2)c1] | 4-bromo-N-(3-{[3-(methoxy) phenyl]amino}quinoxalin-2-yl)benzenesulfonamide |
| 201 | 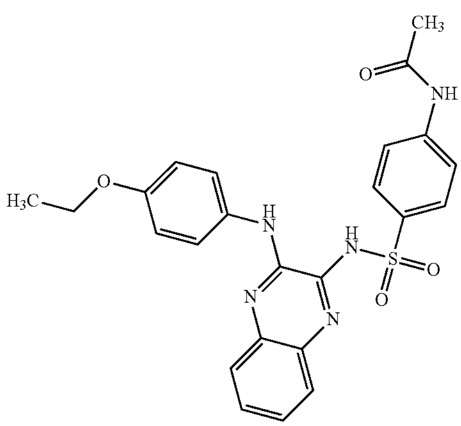 [SMILES: CCOc1ccc(Nc2nc3ccccc3nc2NS(=O)(=O)c2ccc(NC(C)=O)cc2)cc1] | N-(4-{[(3-{[4-(ethyloxy) phenyl]amino}quinoxalin-2-yl)amino]sulfonyl} phenyl)acetamide |
| 202 | 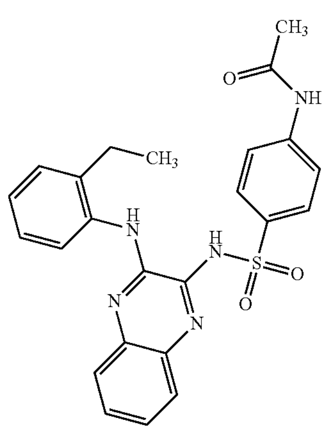 [SMILES: CCc1ccccc1Nc1nc2ccccc2nc1NS(=O)(=O)c1ccc(NC(C)=O)cc1] | N-{4-[({3-[(2-ethylphenyl) amino]quinoxalin-2-yl}amino) sulfonyl]phenyl}acetamide |

TABLE 1-continued
| Cpd. No. | Structure | Name |
|---|---|---|
| 203 | 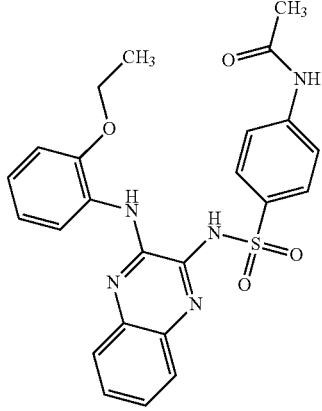 [SMILES: CCOc1ccccc1Nc1nc2ccccc2nc1NS(=O)(=O)c1ccc(NC(C)=O)cc1] | N-(4-{[(3-{[2-(ethyloxy) phenyl]amino}quinoxalin-2-yl)amino]sulfonyl}phenyl) acetamide |
| 204 | 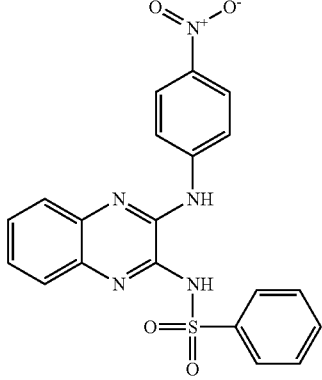 [SMILES: O=[N+]([O-])c1ccc(Nc2nc3ccccc3nc2NS(=O)(=O)c2ccccc2)cc1] | N-{3-[(4-nitrophenyl)amino] quinoxalin-2-yl} benzenesulfonamide |
| 205 | 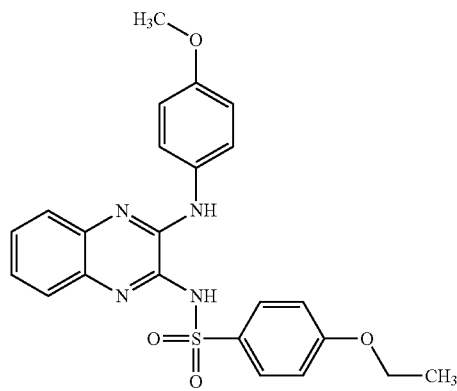 [SMILES: CCOc1ccc(S(=O)(=O)Nc2nc3ccccc3nc2Nc2ccc(OC)cc2)cc1] | 4-(ethyloxy)-N-(3-{[4-(methoxy) phenyl]amino}quinoxalin-2-yl)benzenesulfonamide |

TABLE 1-continued
| Cpd. No. | Structure | Name |
|---|---|---|
| 206 | 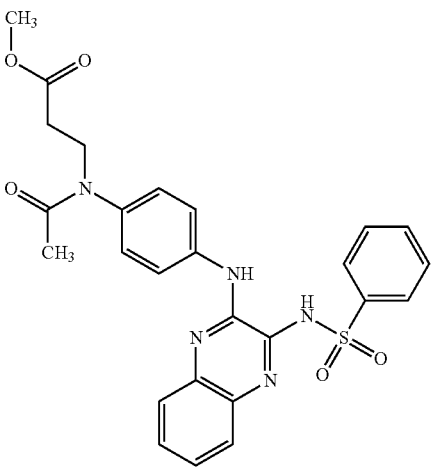 [SMILES: COC(=O)CCN(C(C)=O)c1ccc(Nc2nc3ccccc3nc2NS(=O)(=O)c2ccccc2)cc1] | methyl N-acetyl-N-[4-({3-[(phenylsulfonyl)amino]quinoxalin-2-yl}amino)phenyl]-beta-alaninate |
| 207 | 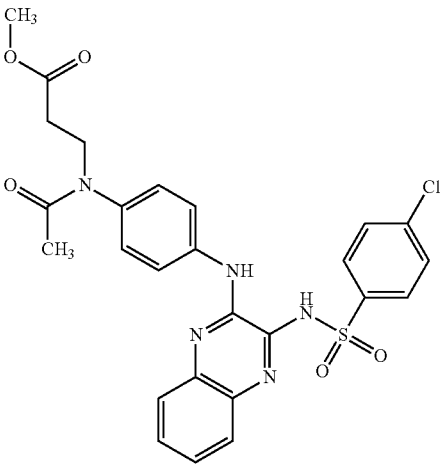 [SMILES: COC(=O)CCN(C(C)=O)c1ccc(Nc2nc3ccccc3nc2NS(=O)(=O)c2ccc(Cl)cc2)cc1] | methyl N-acetyl-N-{4-[(3-{[(4-chlorophenyl)sulfonyl]amino}quinoxalin-2-yl)amino]phenyl}-beta-alaninate |
| 208 | 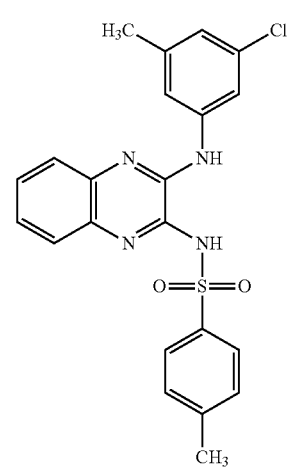 [SMILES: Cc1ccc(S(=O)(=O)Nc2nc3ccccc3nc2Nc2cc(C)cc(Cl)c2)cc1] | N-{3-[(3-chloro-5-methylphenyl)amino]quinoxalin-2-yl}-4-methylbenzenesulfonamide |

TABLE 1-continued

| Cpd. No. | Structure | Name |
| --- | --- | --- |
| 209 | 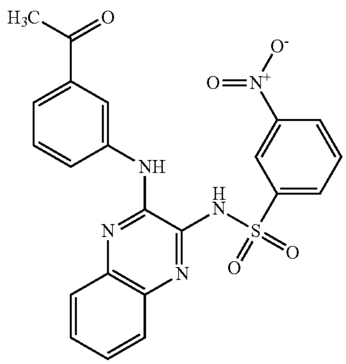 [SMILES: CC(=O)c1cccc(Nc2nc3ccccc3nc2NS(=O)(=O)c2cccc([N+](=O)[O-])c2)c1] | N-{3-[(3-acetylphenyl)amino] quinoxalin-2-yl}-3-nitrobenzenesulfonamide |
| 210 | 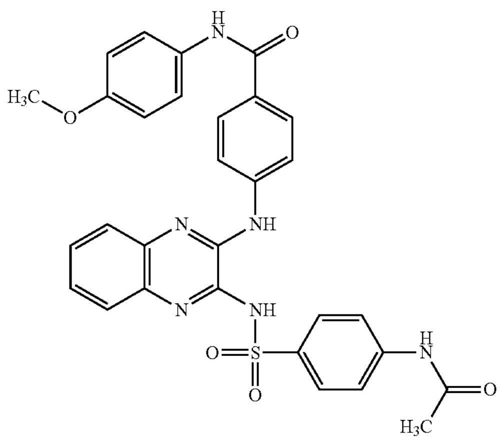 [SMILES: COc1ccc(NC(=O)c2ccc(Nc3nc4ccccc4nc3NS(=O)(=O)c3ccc(NC(C)=O)cc3)cc2)cc1] | 4-{[3-({[4-(acetylamino)phenyl] sulfonyl}amino)quinoxalin-2-yl]amino}-N-[4-(methoxy) phenyl]benzamide |
| 211 | 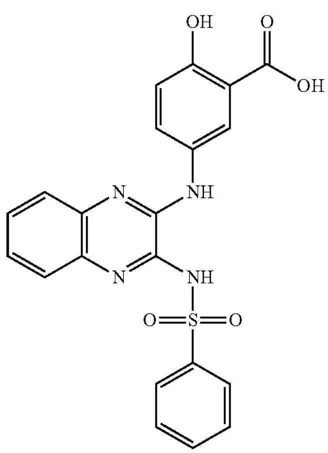 [SMILES: O=C(O)c1cc(Nc2nc3ccccc3nc2NS(=O)(=O)c2ccccc2)ccc1O] | 2-hydroxy-5-({3-[(phenylsulfonyl)amino] quinoxalin-2-yl}amino) benzoic acid |
| 212 | 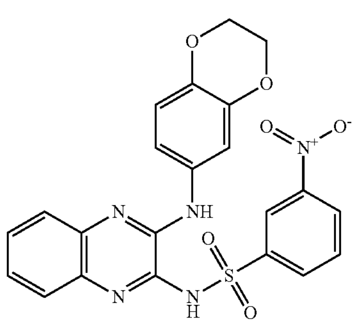 [SMILES: O=[N+]([O-])c1cccc(S(=O)(=O)Nc2nc3ccccc3nc2Nc2ccc3c(c2)OCCO3)c1] | N-[3-(2,3-dihydro-1,4-benzodioxin-6-ylamino) quinoxalin-2-yl]-3-nitrobenzenesulfonamide |

TABLE 1-continued
| Cpd. No. | Structure | Name |
|---|---|---|
| 213 | 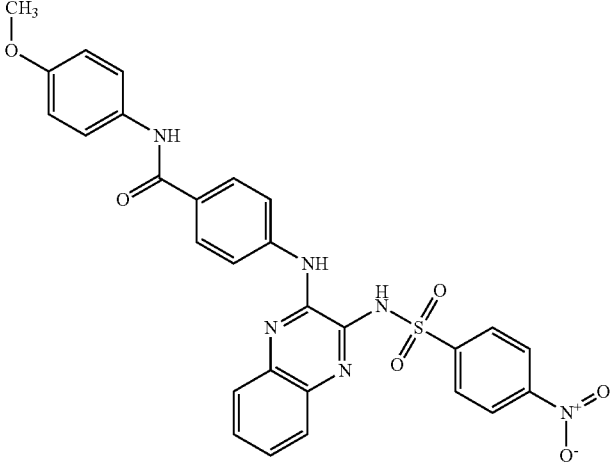 [SMILES: COc1ccc(NC(=O)c2ccc(Nc3nc4ccccc4nc3NS(=O)(=O)c3ccc([N+](=O)[O-])cc3)cc2)cc1] | N-[4-(methoxy)phenyl]-4-[(3-{[(4-nitrophenyl)sulfonyl]amino}quinoxalin-2-yl)amino]benzamide |
| 214 | 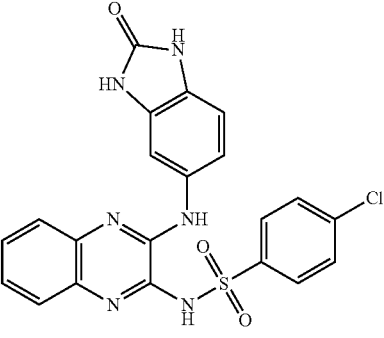 [SMILES: O=c1[nH]c2ccc(Nc3nc4ccccc4nc3NS(=O)(=O)c3ccc(Cl)cc3)cc2[nH]1] | 4-chloro-N-{3-[(2-oxo-2,3-dihydro-1H-benzimidazol-5-yl)amino]quinoxalin-2-yl}benzenesulfonamide |
| 215 | 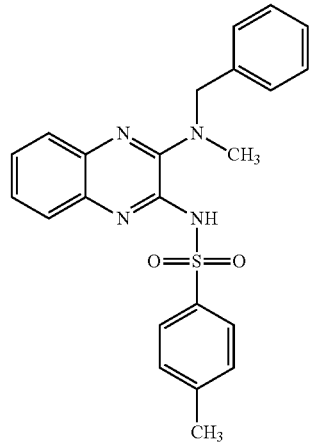 [SMILES: Cc1ccc(S(=O)(=O)Nc2nc3ccccc3nc2N(C)Cc2ccccc2)cc1] | 4-methyl-N-{3-[methyl(phenylmethyl)amino]quinoxalin-2-yl}benzenesulfonamide |

TABLE 1-continued

| Cpd. No. | Structure | Name |
|---|---|---|
| 216 | 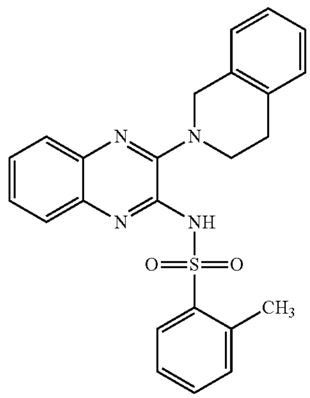 [SMILES: Cc1ccccc1S(=O)(=O)Nc1nc2ccccc2nc1N1CCc2ccccc2C1] | N-[3-(3,4-dihydroisoquinolin-2(1H)-yl)quinoxalin-2-yl]-2-methylbenzenesulfonamide |
| 217 | 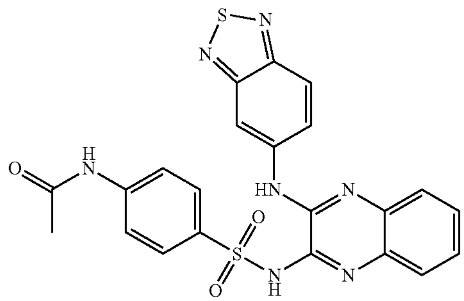 [SMILES: CC(=O)Nc1ccc(S(=O)(=O)Nc2nc3ccccc3nc2Nc2ccc3nsnc3c2)cc1] | N-[4-({[3-(2,1,3-benzothiadiazol-5-ylamino)quinoxalin-2-yl]amino}sulfonyl)phenyl]acetamide |
| 218 | 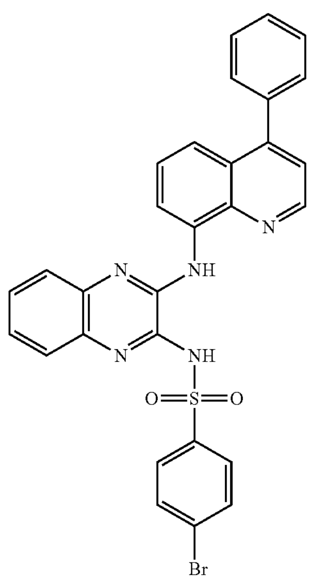 [SMILES: O=S(=O)(Nc1nc2ccccc2nc1Nc1cccc2c(-c3ccccc3)ccnc12)c1ccc(Br)cc1] | 4-bromo-N-{3-[(4-phenylquinolin-8-yl)amino]quinoxalin-2-yl}benzenesulfonamide |
| 219 | 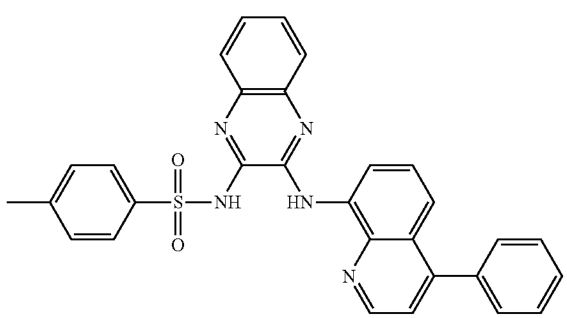 [SMILES: Cc1ccc(S(=O)(=O)Nc2nc3ccccc3nc2Nc2cccc3c(-c4ccccc4)ccnc23)cc1] | 4-methyl-N-{3-[(4-phenylquinolin-8-yl)amino]quinoxalin-2-yl}benzenesulfonamide |

TABLE 1-continued

| Cpd. No. | Structure | Name |
|---|---|---|
| 220 | 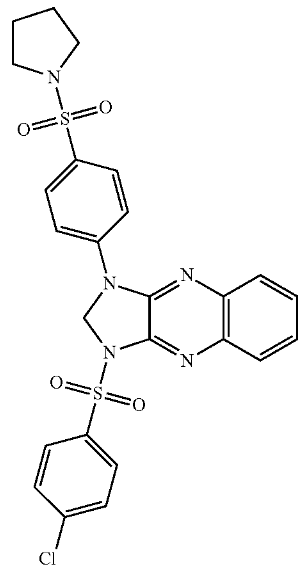 [SMILES: O=S(=O)(c1ccc(N2CN(S(=O)(=O)c3ccc(Cl)cc3)c3nc4ccccc4nc32)cc1)N1CCCC1] | 1-[(4-chlorophenyl)sulfonyl]-3-[4-(pyrrolidin-1-ylsulfonyl)phenyl]-2,3-dihydro-1H-imidazo[4,5-b]quinoxaline |
| 221 | 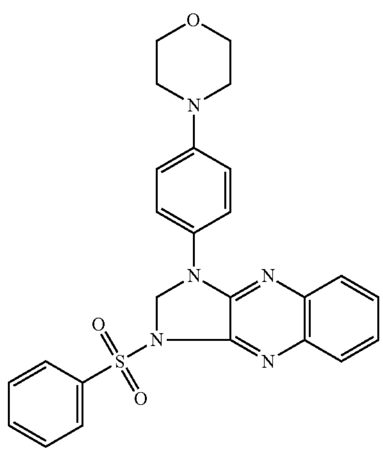 [SMILES: O=S(=O)(c1ccccc1)N1CN(c2ccc(N3CCOCC3)cc2)c2nc3ccccc3nc21] | 1-(4-morpholin-4-ylphenyl)-3-(phenylsulfonyl)-2,3-dihydro-1H-imidazo[4,5-b]quinoxaline |
| 222 | 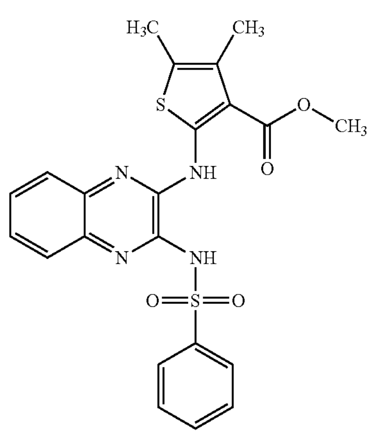 [SMILES: COC(=O)c1c(Nc2nc3ccccc3nc2NS(=O)(=O)c2ccccc2)sc(C)c1C] | methyl 4,5-dimethyl-2-({3-[(phenylsulfonyl)amino]quinoxalin-2-yl}amino)thiophene-3-carboxylate |

TABLE 1-continued

| Cpd. No. | Structure | Name |
|---|---|---|
| 223 | 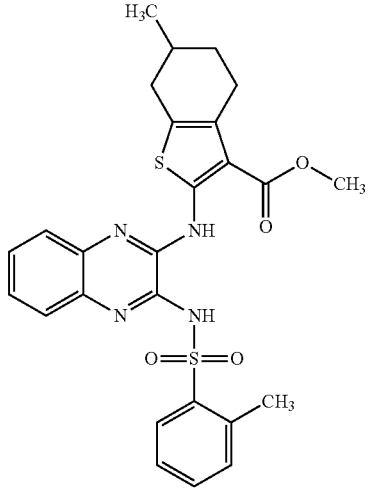 [SMILES: COC(=O)c1c(Nc2nc3ccccc3nc2NS(=O)(=O)c2ccccc2C)sc2c1CCC(C)C2] | ethyl 6-methyl-2-[(3-{[(2-methylphenyl)sulfonyl]amino}quinoxalin-2-yl)amino]-4,5,6,7-tetrahydro-1-benzothiophene-3-carboxylate |
| 224 | 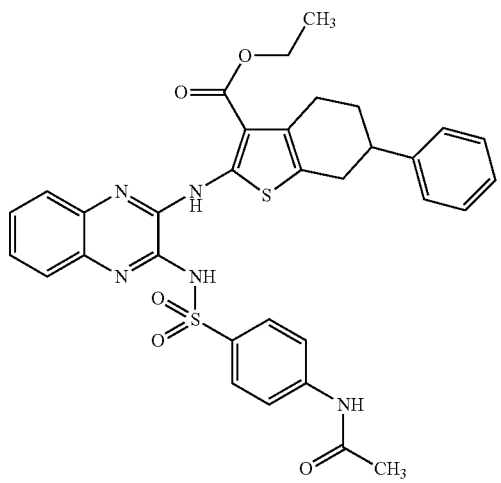 [SMILES: CCOC(=O)c1c(Nc2nc3ccccc3nc2NS(=O)(=O)c2ccc(NC(C)=O)cc2)sc2c1CCC(c1ccccc1)C2] | ethyl 2-{[3-({[4-(acetylamino)phenyl]sulfonyl}amino)quinoxalin-2-yl]amino}-6-phenyl-4,5,6,7-tetrahydro-1-benzothiophene-3-carboxylate |
| 225 | 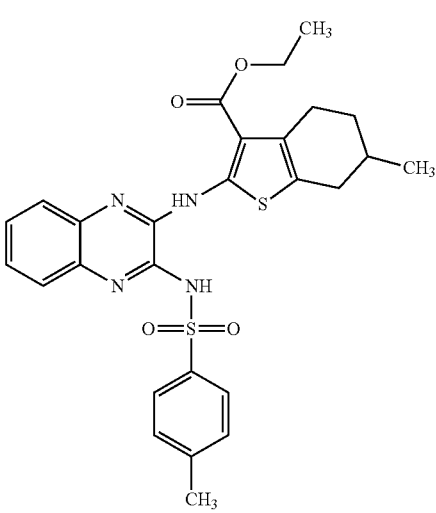 [SMILES: CCOC(=O)c1c(Nc2nc3ccccc3nc2NS(=O)(=O)c2ccc(C)cc2)sc2c1CCC(C)C2] | ethyl 6-methyl-2-[(3-{[(4-methylphenyl)sulfonyl]amino}quinoxalin-2-yl)amino]-4,5,6,7-tetrahydro-1-benzothiophene-3-carboxylate |

TABLE 1-continued
| Cpd. No. | Structure | Name |
|---|---|---|
| 226 | 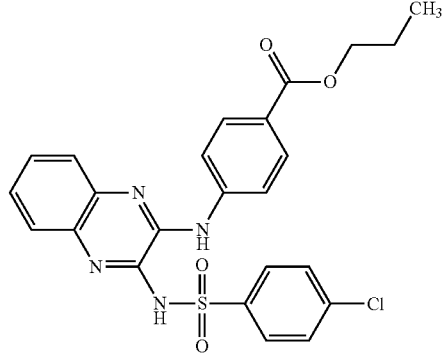 [SMILES: CCCOC(=O)c1ccc(Nc2nc3ccccc3nc2NS(=O)(=O)c2ccc(Cl)cc2)cc1] | propyl 4-[(3-{[(4-chlorophenyl)sulfonyl]amino}quinoxalin-2-yl)amino]benzoate |
| 227 | 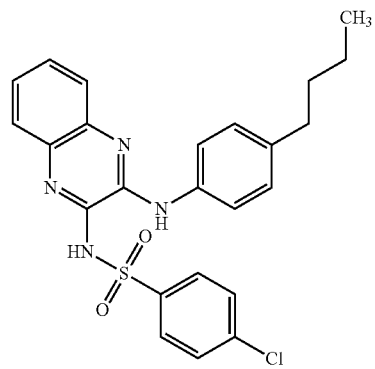 [SMILES: CCCCc1ccc(Nc2nc3ccccc3nc2NS(=O)(=O)c2ccc(Cl)cc2)cc1] | N-{3-[(4-butylphenyl)amino]quinoxalin-2-yl}-4-chlorobenzenesulfonamide |
| 228 | 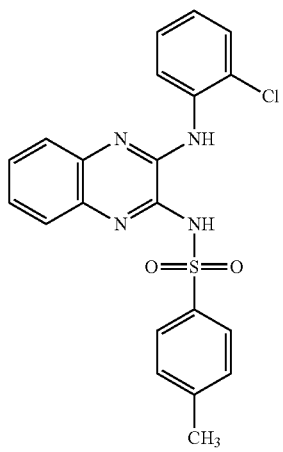 [SMILES: Cc1ccc(S(=O)(=O)Nc2nc3ccccc3nc2Nc2ccccc2Cl)cc1] | N-{3-[(2-chlorophenyl)amino]quinoxalin-2-yl}-4-methylbenzenesulfonamide |

TABLE 1-continued

| Cpd. No. | Structure | Name |
|---|---|---|
| 229 | 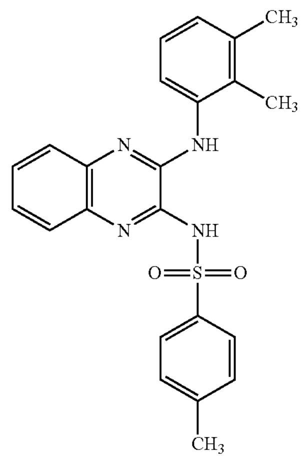 [SMILES: Cc1ccc(S(=O)(=O)Nc2nc3ccccc3nc2Nc2cccc(C)c2C)cc1] | N-{3-[(2,3-dimethylphenyl)amino]quinoxalin-2-yl}-4-methylbenzenesulfonamide |
| 230 | 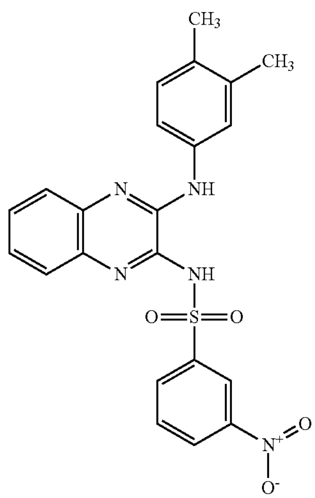 [SMILES: Cc1ccc(Nc2nc3ccccc3nc2NS(=O)(=O)c2cccc([N+](=O)[O-])c2)cc1C] | N-{3-[(3,4-dimethylphenyl)amino]quinoxalin-2-yl}-3-nitrobenzenesulfonamide |
| 231 | 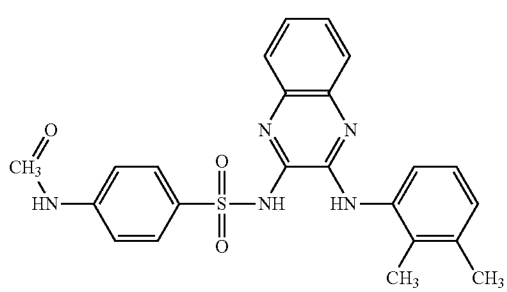 [SMILES: Cc1cccc(Nc2nc3ccccc3nc2NS(=O)(=O)c2ccc(NC=O)cc2)c1C] | N-{4-[({3-[(2,3-dimethylphenyl)amino]quinoxalin-2-yl}amino)sulfonyl]phenyl}acetamide |
| 232 | 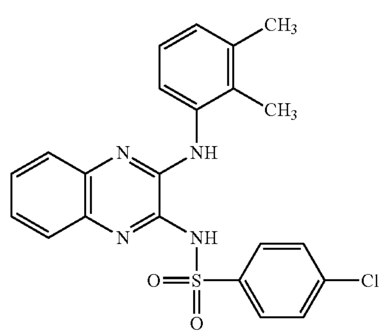 [SMILES: Cc1cccc(Nc2nc3ccccc3nc2NS(=O)(=O)c2ccc(Cl)cc2)c1C] | 4-chloro-N-{3-[(2,3-dimethylphenyl)amino]quinoxalin-2-yl}benzenesulfonamide |

TABLE 1-continued

| Cpd. No. | Structure | Name |
|---|---|---|
| 233 | 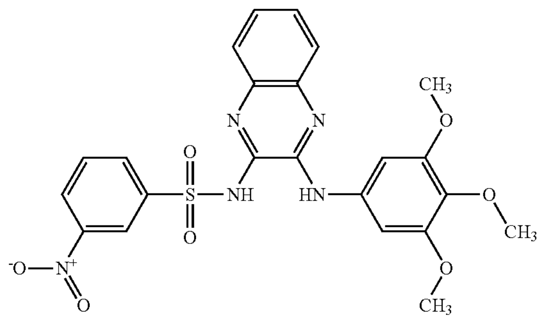 | 3-nitro-N-(3-{[3,4,5-tris(methoxy)phenyl]amino}quinoxalin-2-yl)benzenesulfonamide |
| 234 | 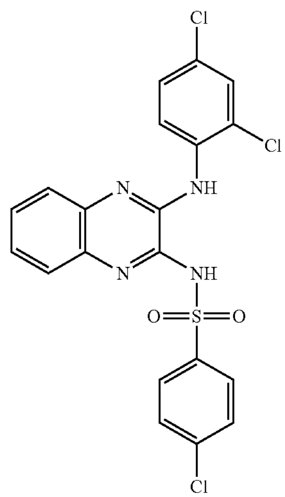 [SMILES: O=S(=O)(Nc1nc2ccccc2nc1Nc1ccc(Cl)cc1Cl)c1ccc(Cl)cc1] | 4-chloro-N-{3-[(2,4-dichlorophenyl)amino]quinoxalin-2-yl}benzenesulfonamide |
| 235 | 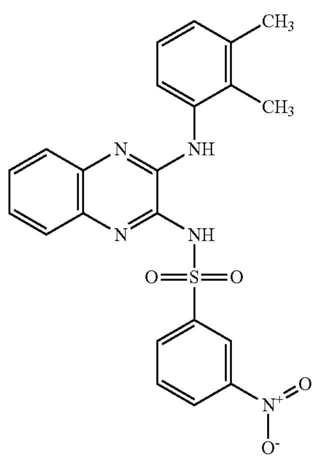 [SMILES: Cc1cccc(Nc2nc3ccccc3nc2NS(=O)(=O)c2cccc([N+](=O)[O-])c2)c1C] | N-{3-[(2,3-dimethylphenyl)amino]quinoxalin-2-yl}-3-nitrobenzenesulfonamide |
| 236 | 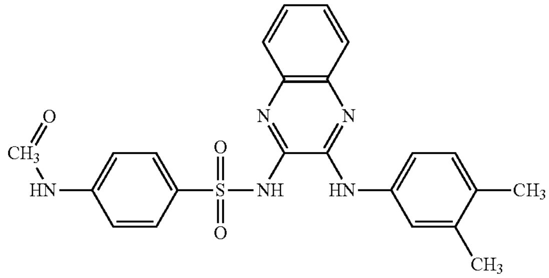 [SMILES: Cc1ccc(Nc2nc3ccccc3nc2NS(=O)(=O)c2ccc(NC=O)cc2)cc1C] | N-{4-[({3-[(3,4-dimethylphenyl)amino]quinoxalin-2-yl}amino)sulfonyl]phenyl}acetamide |

TABLE 1-continued

| Cpd. No. | Structure | Name |
|---|---|---|
| 237 | 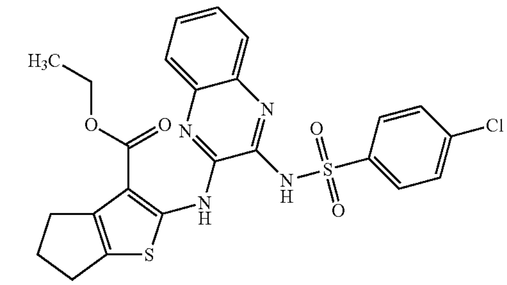 [SMILES: CCOC(=O)c1c(Nc2nc3ccccc3nc2NS(=O)(=O)c2ccc(Cl)cc2)sc2c1CCC2] | ethyl 2-[(3-{[(4-chlorophenyl)sulfonyl]amino}quinoxalin-2-yl)amino]-5,6-dihydro-4H-cyclopenta[b]thiophene-3-carboxylate |
| 238 | 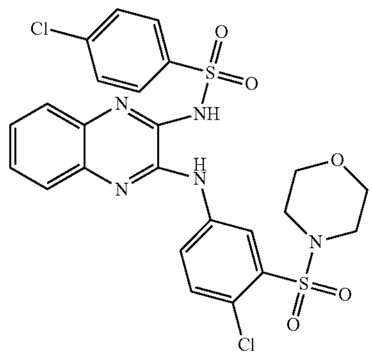 [SMILES: O=S(=O)(Nc1nc2ccccc2nc1Nc1ccc(Cl)c(S(=O)(=O)N2CCOCC2)c1)c1ccc(Cl)cc1] | 4-chloro-N-(3-{[4-chloro-3-(morpholin-4-ylsulfonyl)phenyl]amino}quinoxalin-2-yl)benzenesulfonamide |
| 239 | 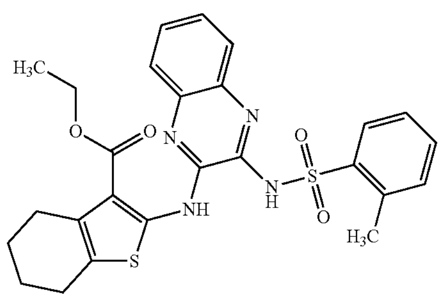 [SMILES: CCOC(=O)c1c(Nc2nc3ccccc3nc2NS(=O)(=O)c2ccccc2C)sc2c1CCCC2] | ethyl 2-[(3-{[(2-methylphenyl)sulfonyl]amino}quinoxalin-2-yl)amino]-4,5,6,7-tetrahydro-1-benzothiophene-3-carboxylate |
| 240 | 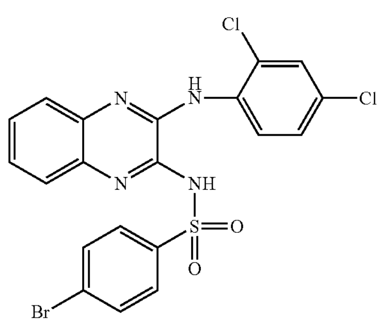 [SMILES: O=S(=O)(Nc1nc2ccccc2nc1Nc1ccc(Cl)cc1Cl)c1ccc(Br)cc1] | 4-bromo-N-{3-[(2,4-dichlorophenyl)amino]quinoxalin-2-yl}benzenesulfonamide |
| 241 | 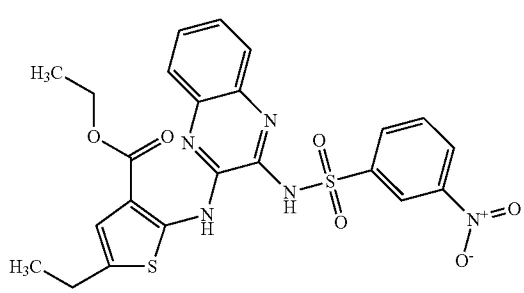 [SMILES: CCOC(=O)c1cc(CC)sc1Nc1nc2ccccc2nc1NS(=O)(=O)c1cccc([N+](=O)[O-])c1] | ethyl 5-ethyl-2-[(3-{[(3-nitrophenyl)sulfonyl]amino}quinoxalin-2-yl)amino]thiophene-3-carboxylate |

TABLE 1-continued

| Cpd. No. | Structure | Name |
|---|---|---|
| 242 | 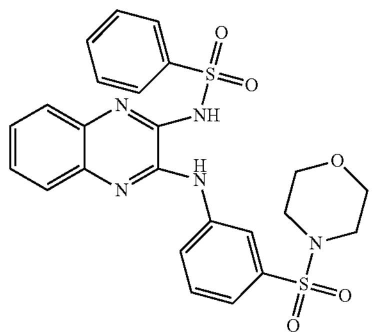 [SMILES: O=S(=O)(Nc1nc2ccccc2nc1Nc1cccc(S(=O)(=O)N2CCOCC2)c1)c1ccccc1] | N-(3-{[3-(morpholin-4-ylsulfonyl)phenyl]amino}quinoxalin-2-yl)benzenesulfonamide |
| 243 | 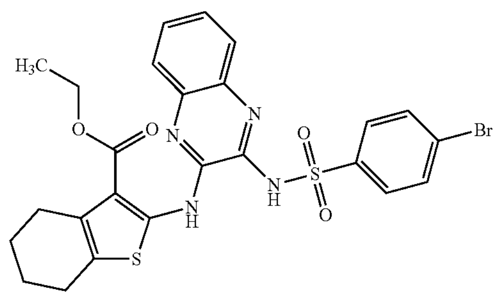 [SMILES: CCOC(=O)c1c(Nc2nc3ccccc3nc2NS(=O)(=O)c2ccc(Br)cc2)sc2c1CCCC2] | ethyl 2-[(3-{[(4-bromophenyl)sulfonyl]amino}quinoxalin-2-yl)amino]-4,5,6,7-tetrahydro-1-benzothiophene-3-carboxylate |
| 244 | 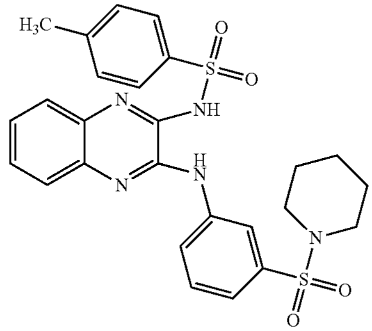 [SMILES: Cc1ccc(S(=O)(=O)Nc2nc3ccccc3nc2Nc2cccc(S(=O)(=O)N3CCCCC3)c2)cc1] | 4-methyl-N-(3-{[3-(piperidin-1-ylsulfonyl)phenyl]amino}quinoxalin-2-yl)benzenesulfonamide |
| 245 | 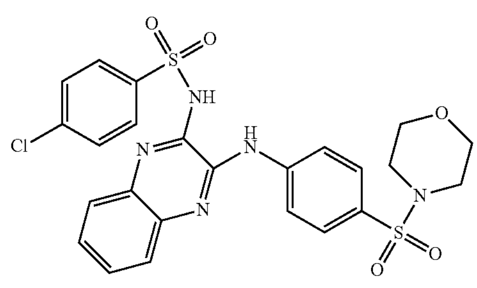 [SMILES: O=S(=O)(Nc1nc2ccccc2nc1Nc1ccc(S(=O)(=O)N2CCOCC2)cc1)c1ccc(Cl)cc1] | 4-chloro-N-(3-{[4-(morpholin-4-ylsulfonyl)phenyl]amino}quinoxalin-2-yl)benzenesulfonamide |
| 246 | 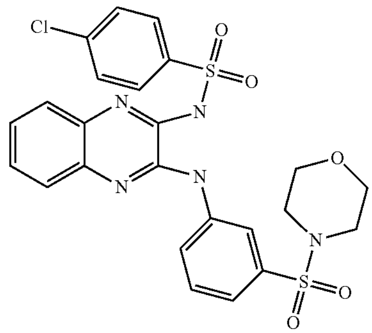 [SMILES: O=S(=O)(Nc1nc2ccccc2nc1Nc1cccc(S(=O)(=O)N2CCOCC2)c1)c1ccc(Cl)cc1] | 4-chloro-N-(3-{[3-(morpholin-4-ylsulfonyl)phenyl]amino}quinoxalin-2-yl)benzenesulfonamide |

TABLE 1-continued

| Cpd. No. | Structure | Name |
|---|---|---|
| 247 | 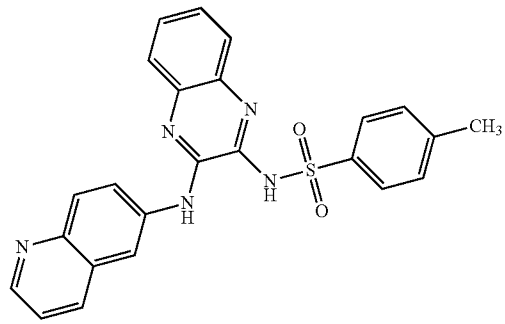 [SMILES: Cc1ccc(S(=O)(=O)Nc2nc3ccccc3nc2Nc2ccc3ncccc3c2)cc1] | 4-methyl-N-[3-(quinolin-6-ylamino)quinoxalin-2-yl]benzenesulfonamide |
| 248 | 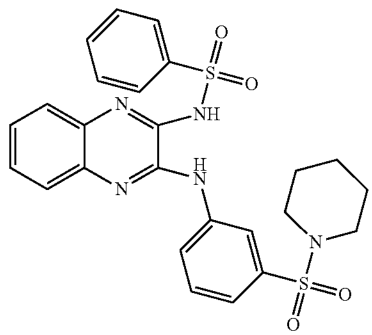 | N-(3-{[3-(piperidin-1-ylsulfonyl)phenyl]amino}quinoxalin-2-yl)benzenesulfonamide |
| 249 | 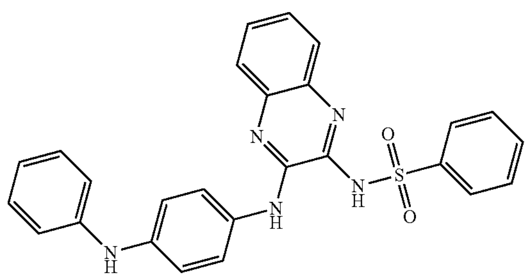 [SMILES: O=S(=O)(Nc1nc2ccccc2nc1Nc1ccc(Nc2ccccc2)cc1)c1ccccc1] | N-(3-{[4-(phenylamino)phenyl]amino}quinoxalin-2-yl)benzenesulfonamide |
| 250 | 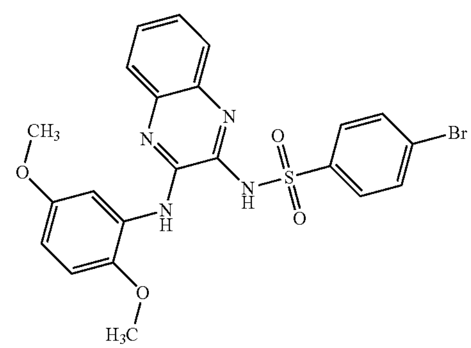 [SMILES: COc1ccc(OC)c(Nc2nc3ccccc3nc2NS(=O)(=O)c2ccc(Br)cc2)c1] | N-(3-{[2,5-bis(methoxy)phenyl]amino}quinoxalin-2-yl)-4-bromobenzenesulfonamide |
| 251 | 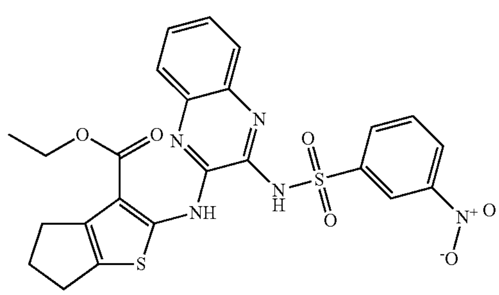 | ethyl 2-[(3-{[(3-nitrophenyl)sulfonyl]amino}quinoxalin-2-yl)amino]-5,6-dihydro-4H-cyclopenta[b]thiophene-3-carboxylate |

TABLE 1-continued

| Cpd. No. | Structure | Name |
|---|---|---|
| 252 | 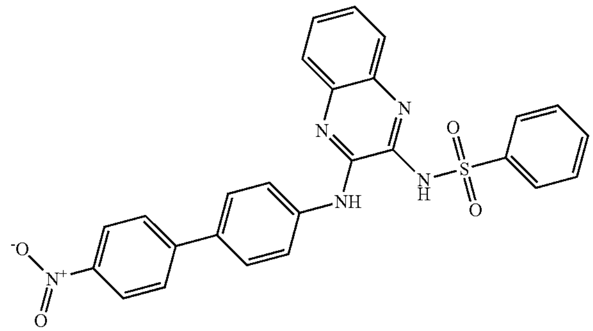 | N-{3-[(4'-nitrobiphenyl-4-yl)amino]quinoxalin-2-yl}benzenesulfonamide |
| 253 | 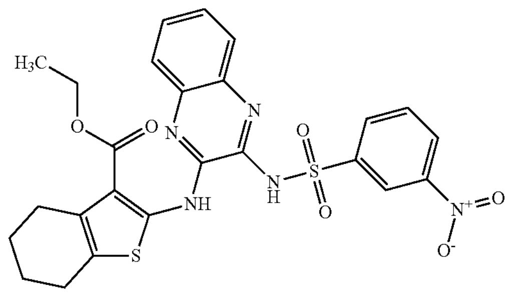 [SMILES: CCOC(=O)c1c(Nc2nc3ccccc3nc2NS(=O)(=O)c2cccc([N+](=O)[O-])c2)sc2c1CCCC2] | ethyl 2-[(3-{[(3-nitrophenyl)sulfonyl]amino}quinoxalin-2-yl)amino]-4,5,6,7-tetrahydro-1-benzothiophene-3-carboxylate |
| 254 | 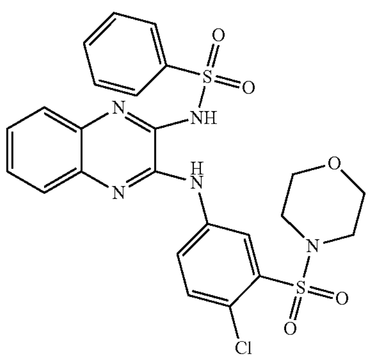 [SMILES: O=S(=O)(Nc1nc2ccccc2nc1Nc1ccc(Cl)c(S(=O)(=O)N2CCOCC2)c1)c1ccccc1] | N-(3-{[4-chloro-3-(morpholin-4-ylsulfonyl)phenyl]amino}quinoxalin-2-yl)benzenesulfonamide |
| 255 | 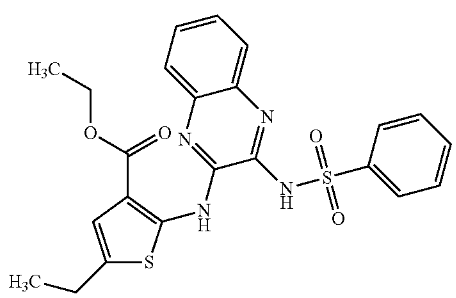 [SMILES: CCOC(=O)c1cc(CC)sc1Nc1nc2ccccc2nc1NS(=O)(=O)c1ccccc1] | ethyl 5-ethyl-2-({3-[(phenylsulfonyl)amino]quinoxalin-2-yl}amino)thiophene-3-carboxylate |
| 256 | 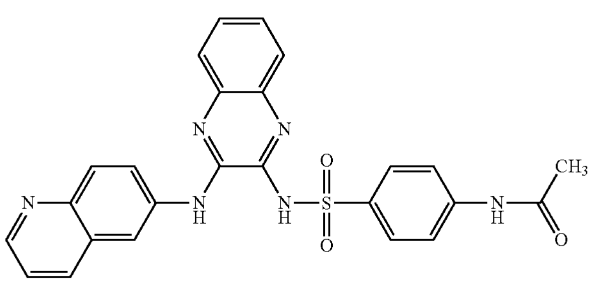 [SMILES: CC(=O)Nc1ccc(S(=O)(=O)Nc2nc3ccccc3nc2Nc2ccc3ncccc3c2)cc1] | N-[4-({[3-(quinolin-6-ylamino)quinoxalin-2-yl]amino}sulfonyl)phenyl]acetamide |

TABLE 1-continued

| Cpd. No. | Structure | Name |
|---|---|---|
| 257 | 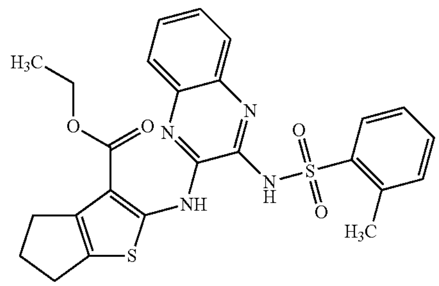 [SMILES: CCOC(=O)c1c(Nc2nc3ccccc3nc2NS(=O)(=O)c2ccccc2C)sc2c1CCC2] | ethyl 2-[(3-{[(2-methylphenyl)sulfonyl]amino}quinoxalin-2-yl)amino]-5,6-dihydro-4H-cyclopenta[b]thiophene-3-carboxylate |
| 258 | 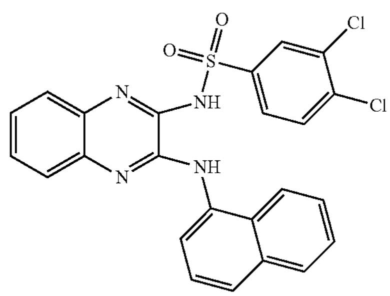 [SMILES: O=S(=O)(Nc1nc2ccccc2nc1Nc1cccc2ccccc12)c1ccc(Cl)c(Cl)c1] | 3,4-dichloro-N-[3-(naphthalen-1-ylamino)quinoxalin-2-yl]benzenesulfonamide |
| 259 | 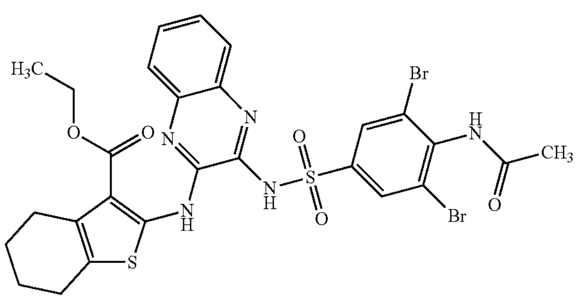 [SMILES: CCOC(=O)c1c(Nc2nc3ccccc3nc2NS(=O)(=O)c2cc(Br)c(NC(C)=O)c(Br)c2)sc2c1CCCC2] | ethyl 2-{[3-({[4-(acetylamino)-3,5-dibromophenyl]sulfonyl}amino)quinoxalin-2-yl]amino}-4,5,6,7-tetrahydro-1-benzothiophene-3-carboxylate |
| 260 | 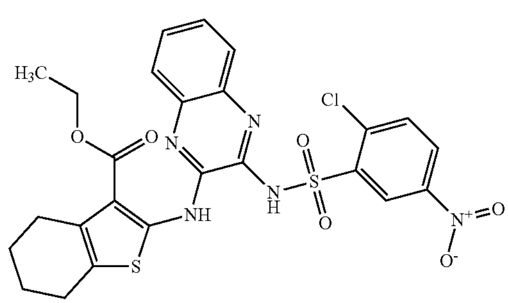 [SMILES: CCOC(=O)c1c(Nc2nc3ccccc3nc2NS(=O)(=O)c2cc([N+](=O)[O-])ccc2Cl)sc2c1CCCC2] | ethyl 2-[(3-{[(2-chloro-5-nitrophenyl)sulfonyl]amino}quinoxalin-2-yl)amino]-4,5,6,7-tetrahydro-1-benzothiophene-3-carboxylate |
| 261 | 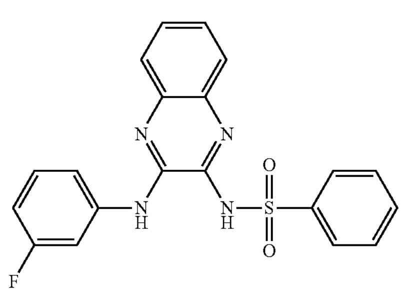 [SMILES: O=S(=O)(Nc1nc2ccccc2nc1Nc1cccc(F)c1)c1ccccc1] | N-{3-[(3-fluorophenyl)amino]quinoxalin-2-yl}benzenesulfonamide |

TABLE 1-continued

| Cpd. No. | Structure | Name |
|---|---|---|
| 262 | 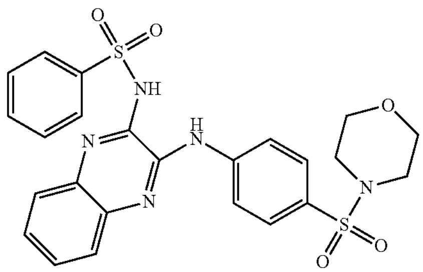 [SMILES: O=S(=O)(Nc1nc2ccccc2nc1Nc1ccc(S(=O)(=O)N2CCOCC2)cc1)c1ccccc1] | N-(3-{[4-(morpholin-4-ylsulfonyl)phenyl]amino}quinoxalin-2-yl)benzenesulfonamide |
| 263 | 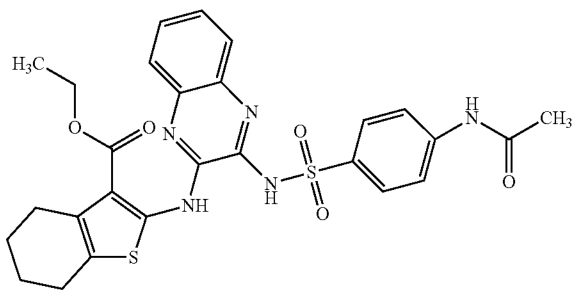 [SMILES: CCOC(=O)c1c(Nc2nc3ccccc3nc2NS(=O)(=O)c2ccc(NC(C)=O)cc2)sc2c1CCCC2] | ethyl 2-{[3-({[4-(acetylamino)phenyl]sulfonyl}amino)quinoxalin-2-yl]amino}-4,5,6,7-tetrahydro-1-benzothiophene-3-carboxylate |
| 264 | 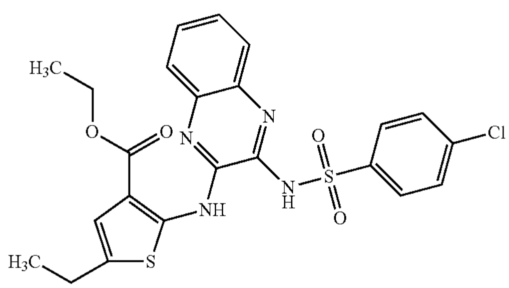 [SMILES: CCOC(=O)c1cc(CC)sc1Nc1nc2ccccc2nc1NS(=O)(=O)c1ccc(Cl)cc1] | ethyl 2-[(3-{[(4-chlorophenyl)sulfonyl]amino}quinoxalin-2-yl)amino]-5-ethylthiophene-3-carboxylate |
| 265 | 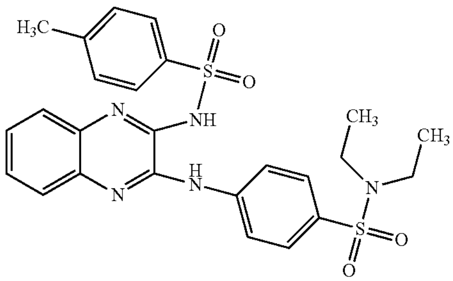 [SMILES: CCN(CC)S(=O)(=O)c1ccc(Nc2nc3ccccc3nc2NS(=O)(=O)c2ccc(C)cc2)cc1] | N,N-diethyl-4-[(3-{[(4-methylphenyl)sulfonyl]amino}quinoxalin-2-yl)amino]benzenesulfonamide |
| 266 | 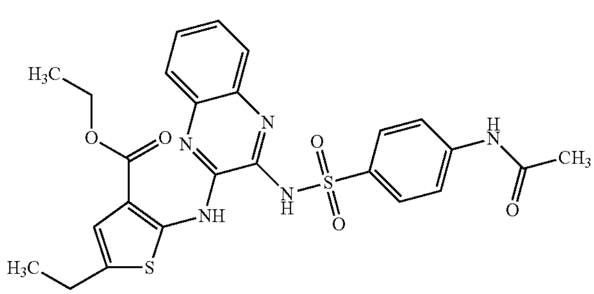 [SMILES: CCOC(=O)c1cc(CC)sc1Nc1nc2ccccc2nc1NS(=O)(=O)c1ccc(NC(C)=O)cc1] | ethyl 2-{[3-({[4-(acetylamino)phenyl]sulfonyl}amino)quinoxalin-2-yl]amino}-5-ethylthiophene-3-carboxylate |

| Cpd. No. | Structure | Name |
|---|---|---|
| 267 | 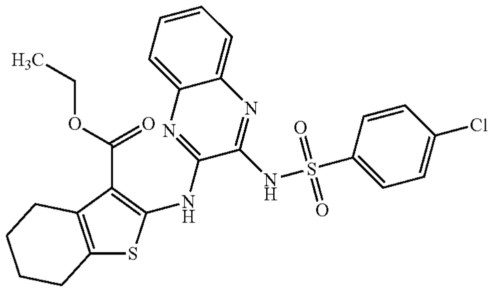 [SMILES: CCOC(=O)c1c(Nc2nc3ccccc3nc2NS(=O)(=O)c2ccc(Cl)cc2)sc2c1CCCC2] | ethyl 2-[(3-{[(4-chlorophenyl)sulfonyl]amino}quinoxalin-2-yl)amino]-4,5,6,7-tetrahydro-1-benzothiophene-3-carboxylate |
| 268 | 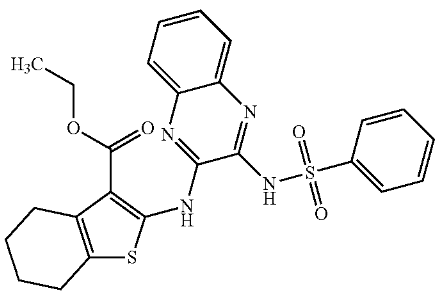 [SMILES: CCOC(=O)c1c(Nc2nc3ccccc3nc2NS(=O)(=O)c2ccccc2)sc2c1CCCC2] | ethyl 2-({3-[(phenylsulfonyl)amino]quinoxalin-2-yl}amino)-4,5,6,7-tetrahydro-1-benzothiophene-3-carboxylate |
| 269 | 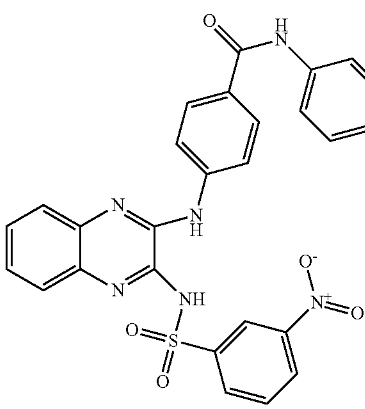 | N-[4-(methoxy)phenyl]-4-[(3-{[(3-nitrophenyl)sulfonyl]amino}quinoxalin-2-yl)amino]benzamide |
| 270 | 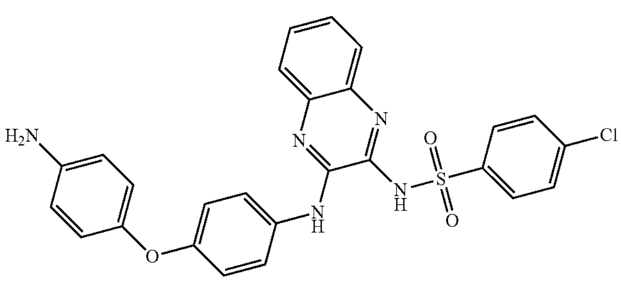 [SMILES: Nc1ccc(Oc2ccc(Nc3nc4ccccc4nc3NS(=O)(=O)c3ccc(Cl)cc3)cc2)cc1] | N-{3-({4-[(4-aminophenyl)oxy]phenyl}amino)quinoxalin-2-yl}-4-chlorobenzenesulfonamide |

| Cpd. No. | Structure | Name |
|---|---|---|
| 271 | 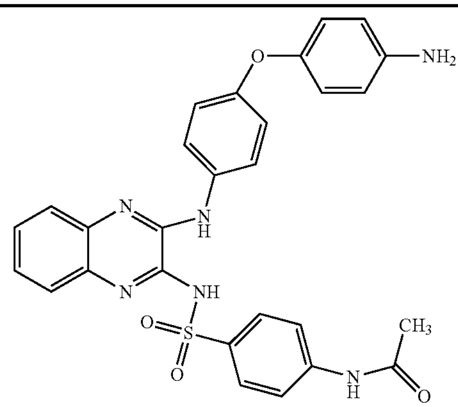 | N-[4-({[3-({4-[(4-aminophenyl)oxy]phenyl}amino)quinoxalin-2-yl]amino}sulfonyl)phenyl]acetamide |
| 272 | 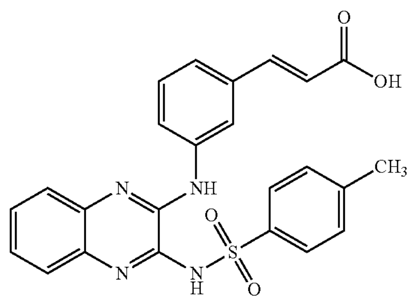 [SMILES: Cc1ccc(S(=O)(=O)Nc2nc3ccccc3nc2Nc2cccc(/C=C/C(=O)O)c2)cc1] | (2E)-3-{3-[(3-{[(4-methylphenyl)sulfonyl]amino}quinoxalin-2-yl)amino]phenyl}prop-2-enoic acid |
| 273 | 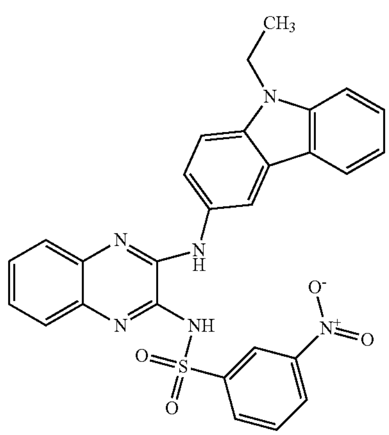 [SMILES: CCn1c2ccccc2c2cc(Nc3nc4ccccc4nc3NS(=O)(=O)c3cccc([N+](=O)[O-])c3)ccc21] | N-{3-[(9-ethyl-9H-carbazol-3-yl)amino]quinoxalin-2-yl}-3-nitrobenzenesulfonamide |
| 274 | 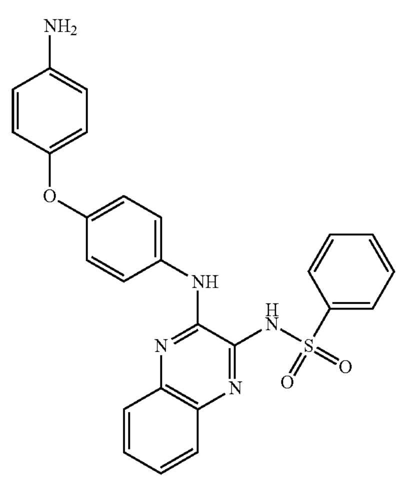 [SMILES: Nc1ccc(Oc2ccc(Nc3nc4ccccc4nc3NS(=O)(=O)c3ccccc3)cc2)cc1] | N-[3-({4-[(4-aminophenyl)oxy]phenyl}amino)quinoxalin-2-yl]benzenesulfonamide |

| Cpd. No. | Structure | Name |
|---|---|---|
| 275 | 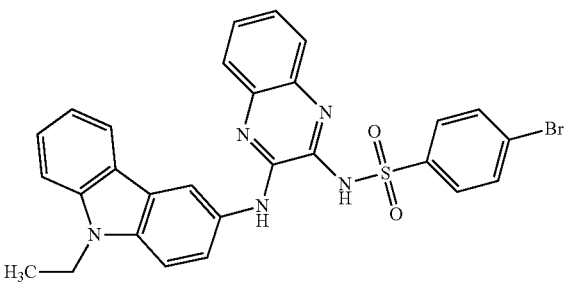 [SMILES: CCn1c2ccccc2c2cc(Nc3nc4ccccc4nc3NS(=O)(=O)c3ccc(Br)cc3)ccc21] | 4-bromo-N-{3-[(9-ethyl-9H-carbazol-3-yl)amino]quinoxalin-2-yl}benzenesulfonamide |
| 276 | 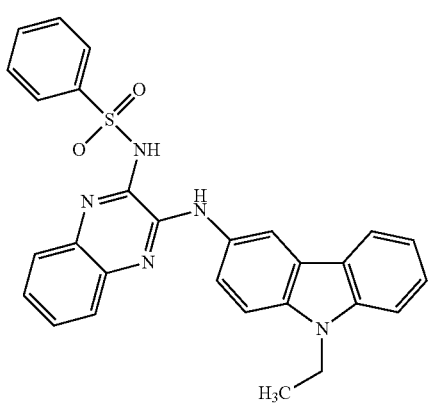 | N-{3-[(9-ethyl-9H-carbazol-3-yl)amino]quinoxalin-2-yl}benzenesulfonamide |
| 277 | 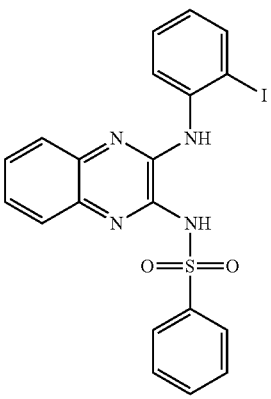 [SMILES: O=S(=O)(Nc1nc2ccccc2nc1Nc1ccccc1I)c1ccccc1] | N-{3-[(2-iodophenyl)amino]quinoxalin-2-yl}benzenesulfonamide |
| 278 | 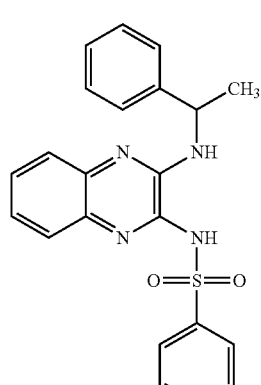 | N-{3-[(1-phenylethyl)amino]quinoxalin-2-yl}benzenesulfonamide |

| Cpd. No. | Structure | Name |
| --- | --- | --- |
| 279 | 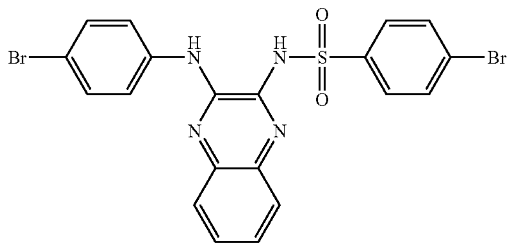 [SMILES: O=S(=O)(Nc1nc2ccccc2nc1Nc1ccc(Cl)cc1)c1ccc(Br)cc1] | 4-bromo-N-{3-[(4-bromophenyl)amino]quinoxalin-2-yl}benzenesulfonamide |
| 280 | 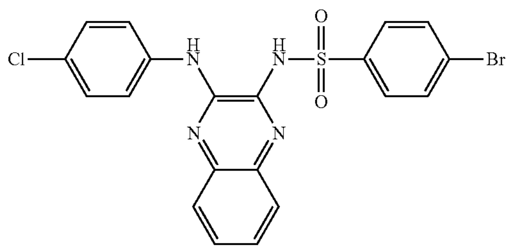 | 4-bromo-N-{3-[(4-chlorophenyl)amino]quinoxalin-2-yl}benzenesulfonamide |
| 281 | 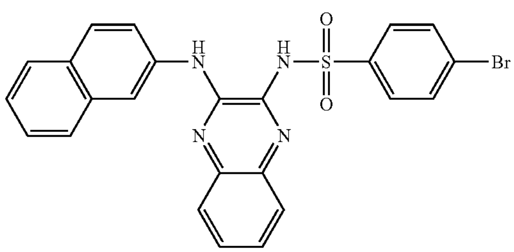 [SMILES: O=S(=O)(Nc1nc2ccccc2nc1Nc1ccc2ccccc2c1)c1ccc(Br)cc1] | 4-bromo-N-[3-(naphthalen-2-ylamino)quinoxalin-2-yl]benzenesulfonamide |
| 282 | 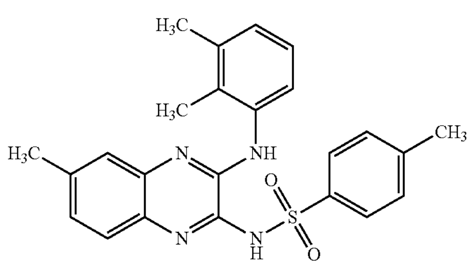 | N-{3-[(2,3-dimethylphenyl)amino]-6-methylquinoxalin-2-yl}-4-methylbenzenesulfonamide |
| 283 | 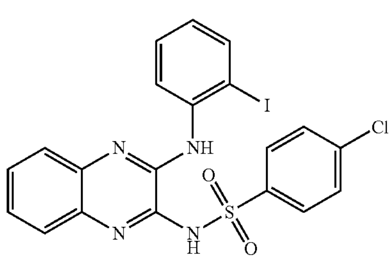 [SMILES: O=S(=O)(Nc1nc2ccccc2nc1Nc1ccccc1I)c1ccc(Cl)cc1] | 4-chloro-N-{3-[(2-iodophenyl)amino]quinoxalin-2-yl}benzenesulfonamide |

TABLE 1-continued

| Cpd. No. | Structure | Name |
|---|---|---|
| 284 | 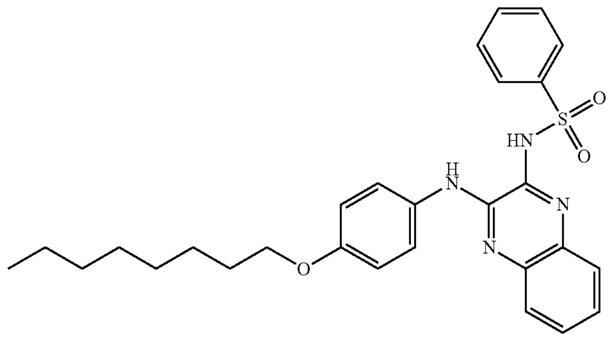 [SMILES: CCCCCCCCOc1ccc(Nc2nc3ccccc3nc2NS(=O)(=O)c2ccccc2)cc1] | N-(3-{[4-(octyloxy)phenyl]amino}quinoxalin-2-yl)benzenesulfonamide |
| 285 | 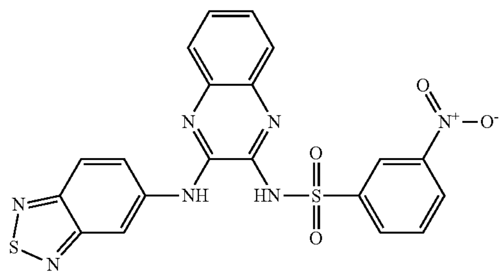 [SMILES: O=[N+]([O-])c1cccc(S(=O)(=O)Nc2nc3ccccc3nc2Nc2ccc3nsnc3c2)c1] | N-[3-(2,1,3-benzothiadiazol-5-ylamino)quinoxalin-2-yl]-3-nitrobenzenesulfonamide |
| 286 | 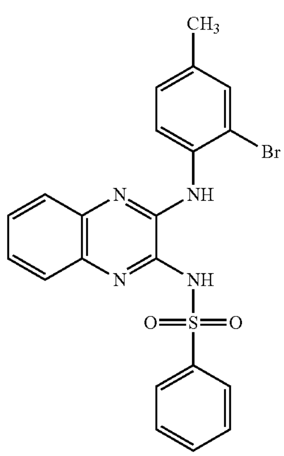 [SMILES: Cc1ccc(Nc2nc3ccccc3nc2NS(=O)(=O)c2ccccc2)c(Br)c1] | N-{3-[(2-bromo-4-methylphenyl)amino]quinoxalin-2-yl}benzenesulfonamide |
| 287 | 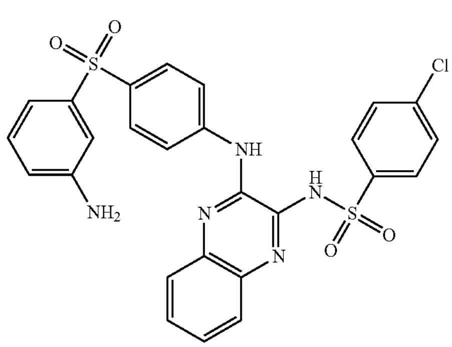 [SMILES: Nc1cccc(S(=O)(=O)c2ccc(Nc3nc4ccccc4nc3NS(=O)(=O)c3ccc(Cl)cc3)cc2)c1] | N-[3-({4-[(3-aminophenyl)sulfonyl]phenyl}amino)quinoxalin-2-yl]-4-chlorobenzenesulfonamide |

TABLE 1-continued
| Cpd. No. | Structure | Name |
|---|---|---|
| 288 | 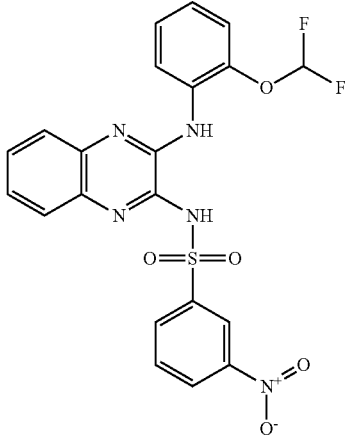 [SMILES: O=[N+]([O-])c1cccc(S(=O)(=O)Nc2nc3ccccc3nc2Nc2ccccc2OC(F)F)c1] | N-[3-({2-[(difluoromethyl)oxy]phenyl}amino)quinoxalin-2-yl]-3-nitrobenzenesulfonamide |
| 289 | 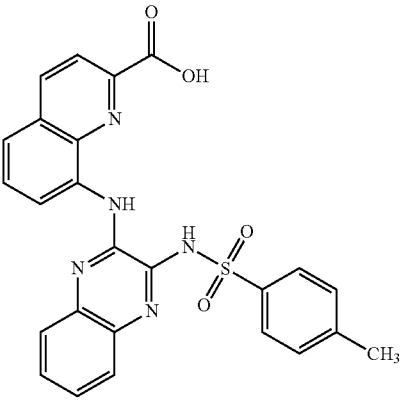 [SMILES: Cc1ccc(S(=O)(=O)Nc2nc3ccccc3nc2Nc2cccc3ccc(C(=O)O)nc23)cc1] | 8-[(3-{[(4-methylphenyl)sulfonyl]amino}quinoxalin-2-yl)amino]quinoline-2-carboxylic acid |
| 290 | 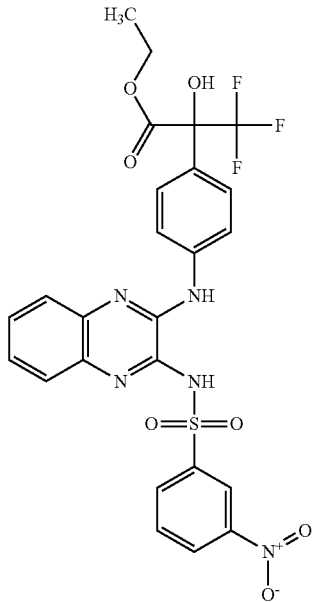 [SMILES: CCOC(=O)C(O)(c1ccc(Nc2nc3ccccc3nc2NS(=O)(=O)c2cccc([N+](=O)[O-])c2)cc1)C(F)(F)F] | ethyl 3,3,3-trifluoro-2-hydroxy-2-{4-[(3-{[(3-nitrophenyl)sulfonyl]amino}quinoxalin-2-yl)amino]phenyl}propanoate |

TABLE 1-continued

| Cpd. No. | Structure | Name |
|---|---|---|
| 291 | 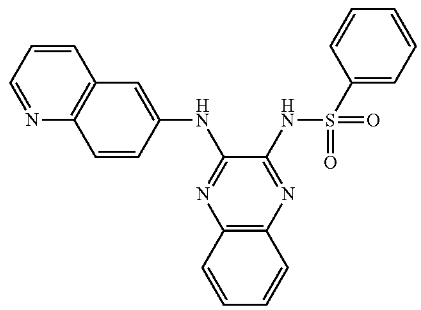 [SMILES: O=S(=O)(Nc1nc2ccccc2nc1Nc1ccc2ncccc2c1)c1ccccc1] | N-[3-(quinolin-6-ylamino)quinoxalin-2-yl]benzenesulfonaide |
| 292 | 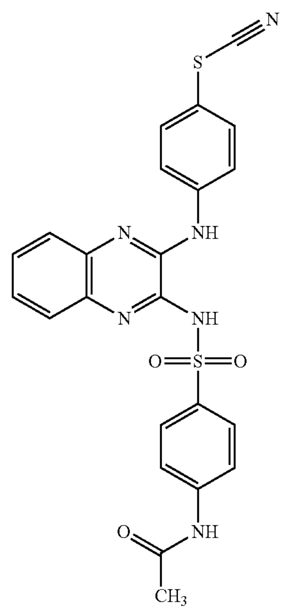 [SMILES: CC(=O)Nc1ccc(S(=O)(=O)Nc2nc3ccccc3nc2Nc2ccc(SC#N)cc2)cc1] | 4-{[3-({[4-(acetylamino)phenyl]sulfonyl}amino)quinoxalin-2-yl]amino}phenyl thiocyanate |
| 293 | 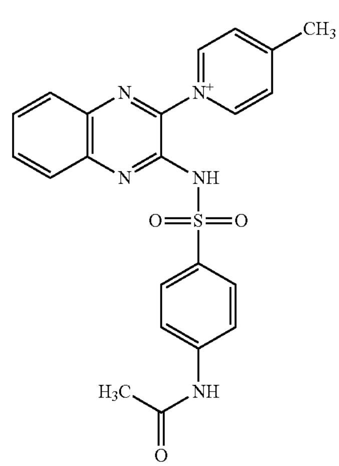 [SMILES: CC(=O)Nc1ccc(S(=O)(=O)Nc2nc3ccccc3nc2-[n+]2ccc(C)cc2)cc1] | 1-[3-({[4-(acetylamino)phenyl]sulfonyl}amino)quinoxalin-2-yl]-4-methylpyridinium |

TABLE 1-continued
| Cpd. No. | Structure | Name |
|---|---|---|
| 294 | 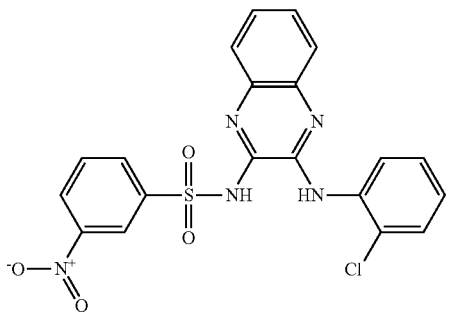 | N-{3-[(2-chlorophenyl)amino]quinoxalin-2-yl}-3-nitrobenzenesulfonamide |
| 295 | 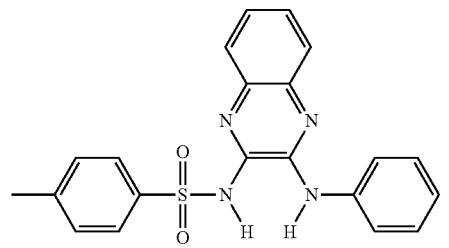 [SMILES: Cc1ccc(S(=O)(=O)Nc2nc3ccccc3nc2Nc2ccccc2)cc1] | 4-methyl-N-[3-(phenylamino)quinoxalin-2-yl]benzenesulfonamide |
| 296 | 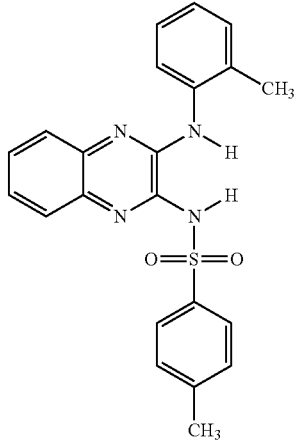 [SMILES: Cc1ccc(S(=O)(=O)Nc2nc3ccccc3nc2Nc2ccccc2C)cc1] | 4-methyl-N-{3-[(2-methylphenyl)amino]quinoxalin-2-yl}benzenesulfonamide |
| 297 | 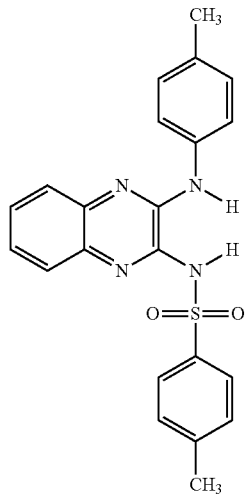 | 4-methyl-N-{3-[(4-methylphenyl)amino]quinoxalin-2-yl}benzenesulfonamide |

TABLE 1-continued

| Cpd. No. | Structure | Name |
|---|---|---|
| 298 | 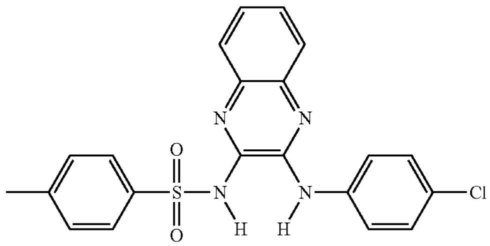 [SMILES: Cc1ccc(S(=O)(=O)Nc2nc3ccccc3nc2Nc2ccc(Cl)cc2)cc1] | N-{3-[(4-chlorophenyl)amino]quinoxalin-2-yl}-4-methylbenzenesulfonamide |
| 299 | 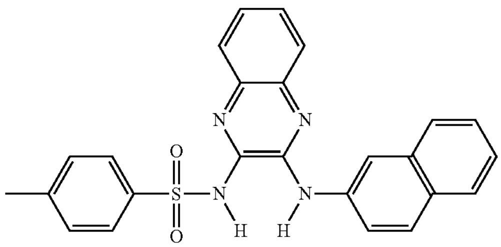 [SMILES: Cc1ccc(S(=O)(=O)Nc2nc3ccccc3nc2Nc2ccc3ccccc3c2)cc1] | 4-methyl-N-[3-(naphthalen-2-ylamino)quinoxalin-2-yl]benzenesulfonamide |
| 300 | 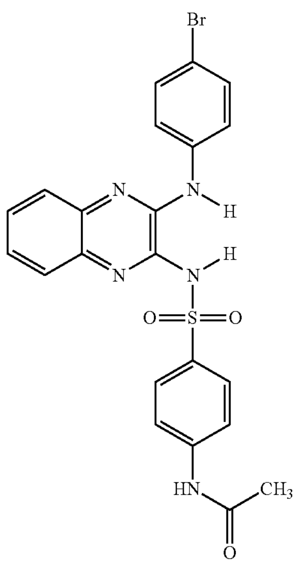 [SMILES: CC(=O)Nc1ccc(S(=O)(=O)Nc2nc3ccccc3nc2Nc2ccc(Br)cc2)cc1] | N-{4-[({3-[(4-bromophenyl)amino]quinoxalin-2-yl}amino)sulfonyl]phenyl}acetamide |
| 301 | 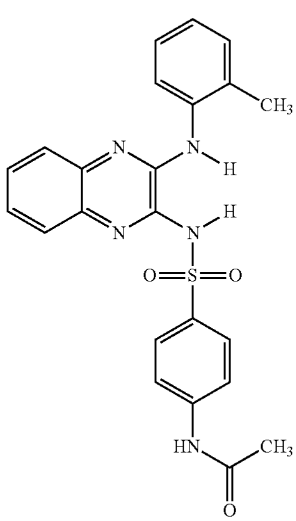 [SMILES: CC(=O)Nc1ccc(S(=O)(=O)Nc2nc3ccccc3nc2Nc2ccccc2C)cc1] | N-{4-[({3-[(2-methylphenyl)amino]quinoxalin-2-yl}amino)sulfonyl]phenyl}acetamide |

TABLE 1-continued

| Cpd. No. | Structure | Name |
|---|---|---|
| 302 | 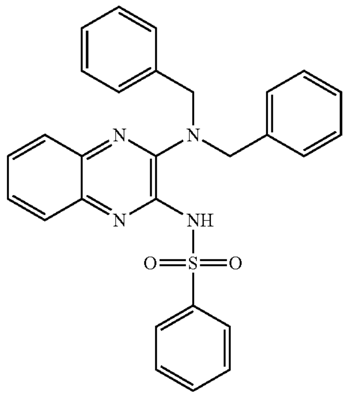 [SMILES: O=S(=O)(Nc1nc2ccccc2nc1N(Cc1ccccc1)Cc1ccccc1)c1ccccc1] | N-{3-[bis(phenylmethyl)amino]quinoxalin-2-yl}benzenesulfonamide |
| 303 | 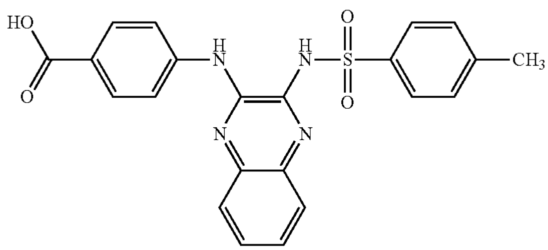 [SMILES: Cc1ccc(S(=O)(=O)Nc2nc3ccccc3nc2Nc2ccc(C(=O)O)cc2)cc1] | 4-[(3-{[(4-methylphenyl)sulfonyl]amino}quinoxalin-2-yl)amino]benzoic acid |
| 304 | 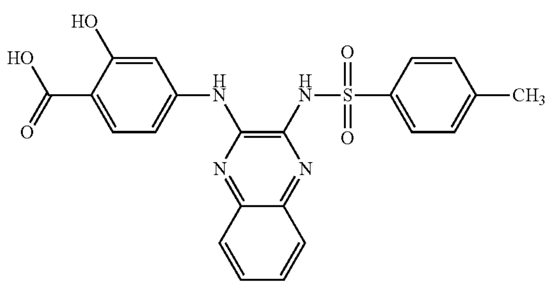 [SMILES: Cc1ccc(S(=O)(=O)Nc2nc3ccccc3nc2Nc2ccc(C(=O)O)c(O)c2)cc1] | 2-hydroxy-4-[(3-{[(4-methylphenyl)sulfonyl]amino}quinoxalin-2-yl)amino]benzoic acid |
| 305 | 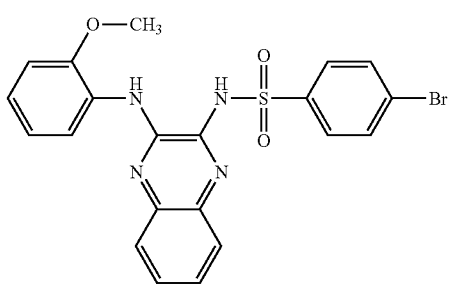 [SMILES: COc1ccccc1Nc1nc2ccccc2nc1NS(=O)(=O)c1ccc(Br)cc1] | 4-bromo-N-(3-{[2-(methoxy)phenyl]amino}quinoxalin-2-yl)benzenesulfonamide |
| 306 | 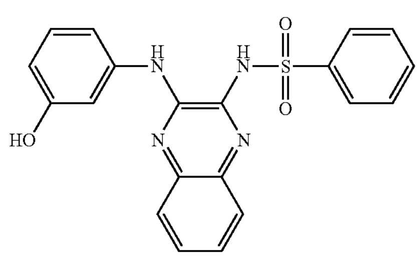 [SMILES: O=S(=O)(Nc1nc2ccccc2nc1Nc1cccc(O)c1)c1ccccc1] | N-{3-[(3-hydroxyphenyl)amino]quinoxalin-2-yl}benzenesulfonamide |

TABLE 1-continued

| Cpd. No. | Structure | Name |
|---|---|---|
| 307 | 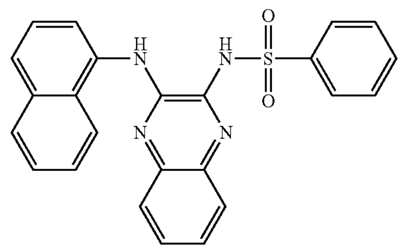 [SMILES: O=S(=O)(Nc1nc2ccccc2nc1Nc1cccc2ccccc12)c1ccccc1] | N-[3-(naphthalen-1-ylamino)quinoxalin-2-yl]benzenesulfonamide |
| 308 | 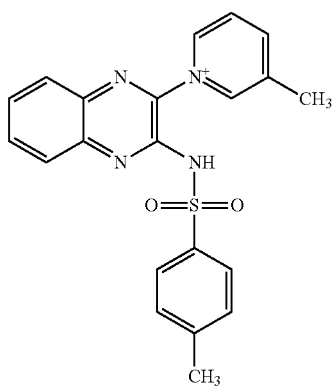 [SMILES: Cc1ccc(S(=O)(=O)Nc2nc3ccccc3nc2-[n+]2cccc(C)c2)cc1] | 3-methyl-1-(3-{[(4-methylphenyl)sulfonyl]amino}quinoxalin-2-yl)pyridinium |
| 309 | 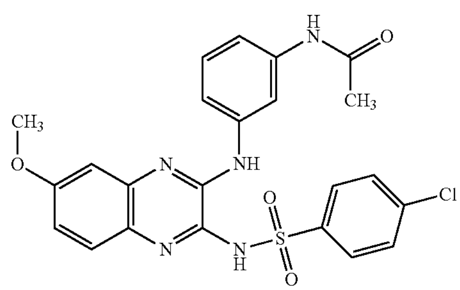 [SMILES: COc1ccc2nc(NS(=O)(=O)c3ccc(Cl)cc3)c(Nc3cccc(NC(C)=O)c3)nc2c1] | N-(3-{[3-{[(4-chlorophenyl)sulfonyl]amino}-7-(methoxy)quinoxalin-2-yl]amino}phenyl)acetamide |
| 310 | 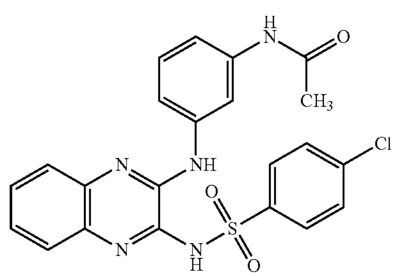 [SMILES: CC(=O)Nc1cccc(Nc2nc3ccccc3nc2NS(=O)(=O)c2ccc(Cl)cc2)c1] | N-{3-[(3-{[(4-chlorophenyl)sulfonyl]amino}quinoxalin-2-yl)amino]phenyl}acetamide |
| 311 | 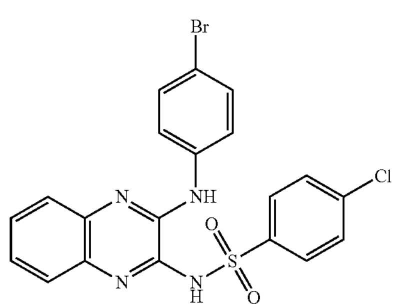 [SMILES: O=S(=O)(Nc1nc2ccccc2nc1Nc1ccc(Br)cc1)c1ccc(Cl)cc1] | N-{3-[(4-bromophenyl)amino]quinoxalin-2-yl}-4-chlorobenzenesulfonamide |

TABLE 1-continued

| Cpd. No. | Structure | Name |
|---|---|---|
| 312 | 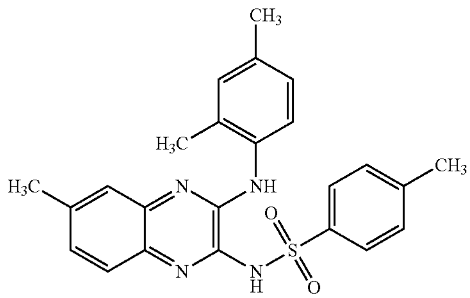 | N-{3-[(2,4-dimethylphenyl)amino]-6-methylquinoxalin-2-yl}-4-methylbenzenesulfonamide |
| 313 | 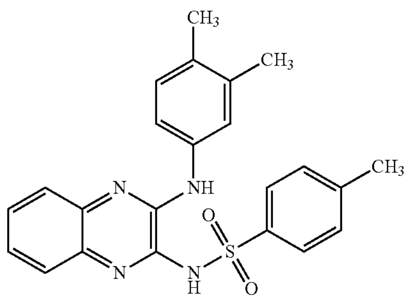 [SMILES: Cc1ccc(S(=O)(=O)Nc2nc3ccccc3nc2Nc2ccc(C)c(C)c2)cc1] | N-{3-[(3,4-dimethylphenyl)amino]quinoxalin-2-yl}-4-methylbenzenesulfonamide |
| 314 | 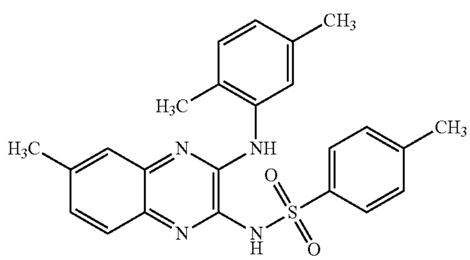 | N-{3-[(2,5-dimethylphenyl)amino]-6-methylquinoxalin-2-yl}-4-methylbenzenesulfonamide |
| 315 | 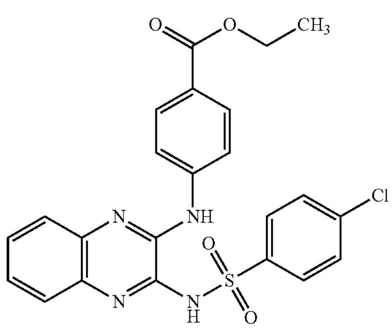 [SMILES: CCOC(=O)c1ccc(Nc2nc3ccccc3nc2NS(=O)(=O)c2ccc(Cl)cc2)cc1] | ethyl 4-[(3-{[(4-chlorophenyl)sulfonyl]amino}quinoxalin-2-yl)amino]benzoate |
| 316 | 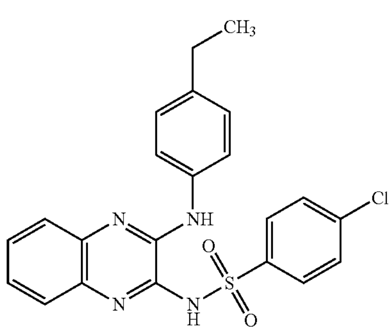 [SMILES: CCc1ccc(Nc2nc3ccccc3nc2NS(=O)(=O)c2ccc(Cl)cc2)cc1] | 4-chloro-N-{3-[(4-ethylphenyl)amino]quinoxalin-2-yl}benzenesulfonamide |

TABLE 1-continued

| Cpd. No. | Structure | Name |
|---|---|---|
| 317 | 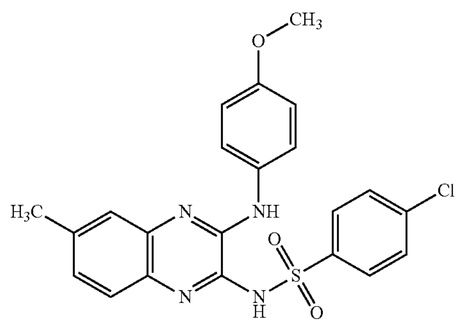 [SMILES: COc1ccc(Nc2nc3cc(C)ccc3nc2NS(=O)(=O)c2ccc(Cl)cc2)cc1] | 4-chloro-N-(6-methyl-3-{[4-(methoxy)phenyl]amino}quinoxalin-2-yl)benzenesulfonamide |
| 318 | 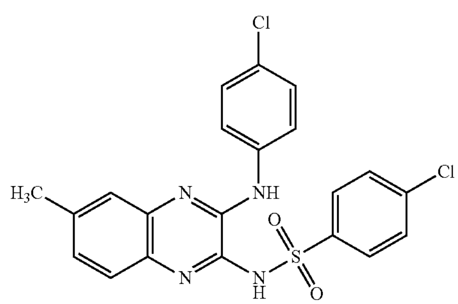 [SMILES: Cc1ccc2nc(NS(=O)(=O)c3ccc(Cl)cc3)c(Nc3ccc(Cl)cc3)nc2c1] | 4-chloro-N-{3-[(4-chlorophenyl)amino]-6-methylquinoxalin-2-yl}benzenesulfonamide |
| 319 | 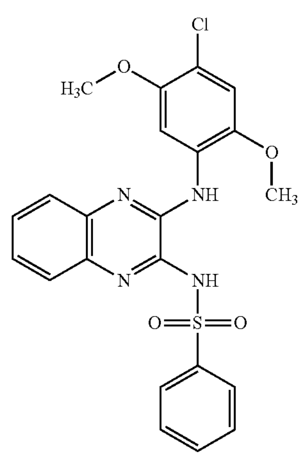 [SMILES: COc1cc(Nc2nc3ccccc3nc2NS(=O)(=O)c2ccccc2)c(OC)cc1Cl] | N-(3-{[4-chloro-2,5-bis(methoxy)phenyl]amino}quinoxalin-2-yl)benzenesulfonamide |
| 320 | 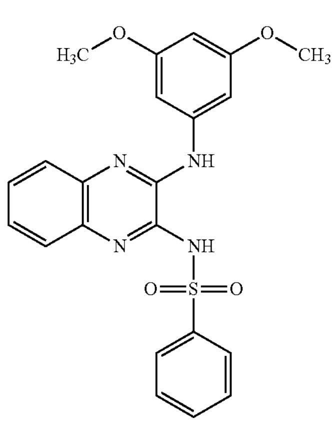 [SMILES: COc1cc(Nc2nc3ccccc3nc2NS(=O)(=O)c2ccccc2)cc(OC)c1] | N-(3-{[3,5-bis(methoxy)phenyl]amino}quinoxalin-2-yl)benzenesulfonamide |

TABLE 1-continued

| Cpd. No. | Structure | Name |
|---|---|---|
| 321 | 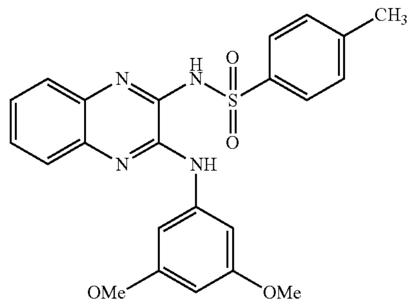 [SMILES: COc1cc(Nc2nc3ccccc3nc2NS(=O)(=O)c2ccc(C)cc2)cc(OC)c1] | N-(3-{[3,5-bis(methoxy) phenyl]amino} quinoxalin-2-yl)-4-methylbenzenesulfonamide |
| 322 | 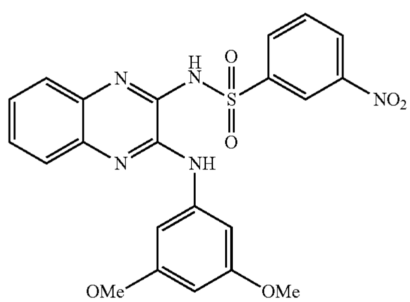 [SMILES: COc1cc(Nc2nc3ccccc3nc2NS(=O)(=O)c2cccc([N+](=O)[O-])c2)cc(OC)c1] | N-(3-{[3,5-bis(methoxy) phenyl]amino} quinoxalin-2-yl)-3-nitrobenzenesulfonamide |
| 323 | 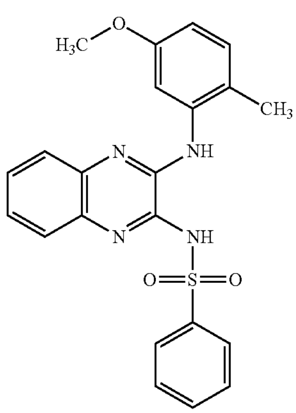 [SMILES: COc1ccc(C)c(Nc2nc3ccccc3nc2NS(=O)(=O)c2ccccc2)c1] | N-(3-{[2-methyl-5-(methoxy)phenyl] amino}quinoxalin-2-yl)benzenesulfonamide |
| 324 | 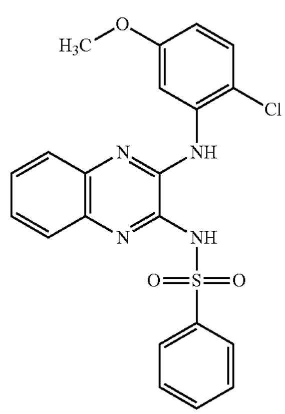 [SMILES: COc1ccc(Cl)c(Nc2nc3ccccc3nc2NS(=O)(=O)c2ccccc2)c1] | N-[3-(2-Chloro-5-methoxy-phenylamino)-quinoxalin-2-yl]-benzensulfonamide |

TABLE 1-continued

| Cpd. No. | Structure | Name |
| --- | --- | --- |
| 325 | 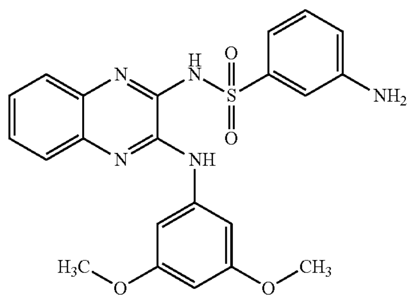 [SMILES: COc1cc(Nc2nc3ccccc3nc2NS(=O)(=O)c2cccc(N)c2)cc(OC)c1] | 3-amino-N-(3-{[3,5-bis(methoxy)phenyl]amino}quinoxalin-2-yl)benzenesulfonamide |
| 326 | 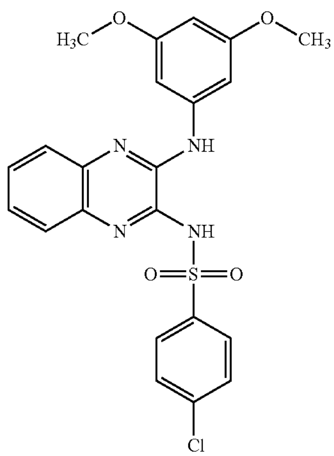 [SMILES: COc1cc(Nc2nc3ccccc3nc2NS(=O)(=O)c2ccc(Cl)cc2)cc(OC)c1] | N-(3-{[3,5-bis(methoxy)phenyl]amino}quinoxalin-2-yl)-4-chlorobenzenesulfonamide |
| 327 | 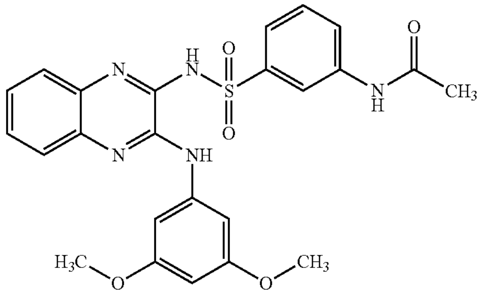 [SMILES: COc1cc(Nc2nc3ccccc3nc2NS(=O)(=O)c2cccc(NC(C)=O)c2)cc(OC)c1] | N-(3-{[(3-{[3,5-bis(methoxy)phenyl]amino}quinoxalin-2-yl)amino]sulfonyl}phenyl)acetamide |
| 328 | 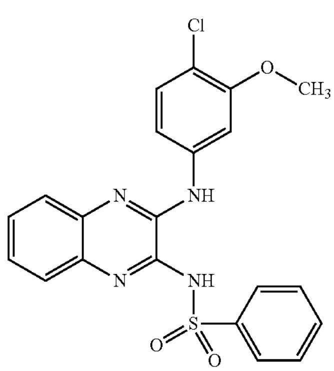 | N-(3-{[4-chloro-3-(methoxy)phenyl]amino}quinoxalin-2-yl)benzenesulfonamide |

TABLE 1-continued

| Cpd. No. | Structure | Name |
|---|---|---|
| 329 | 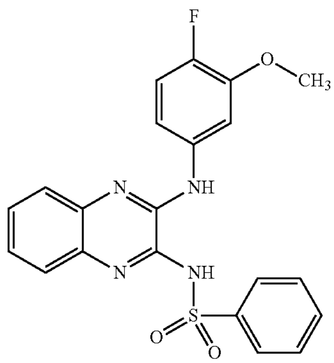 [SMILES: COc1cc(Nc2nc3ccccc3nc2NS(=O)(=O)c2ccccc2)ccc1F] | N-(3-{[4-fluoro-3-(methoxy) phenyl]amino}quinoxalin-2-yl)benzenesulfonamide |
| 330 | 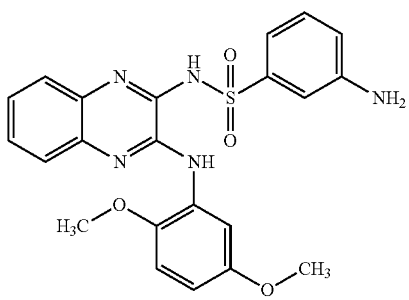 [SMILES: COc1ccc(OC)c(Nc2nc3ccccc3nc2NS(=O)(=O)c2cccc(N)c2)c1] | 3-amino-N-(3-{[2,5-bis(methoxy)phenyl] amino}quinoxalin-2-yl)benzenesulfonamide |
| 331 | 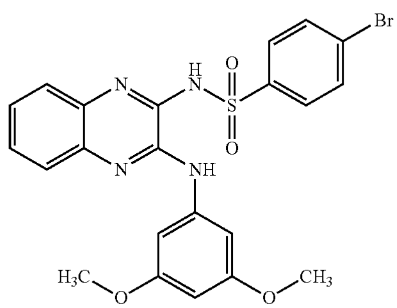 [SMILES: COc1cc(Nc2nc3ccccc3nc2NS(=O)(=O)c2ccc(Br)cc2)cc(OC)c1] | N-(3-{[3,5-bis(methoxy) phenyl]amino} quinoxalin-2-yl)-4-bromobenzenesulfonamide |
| 332 | 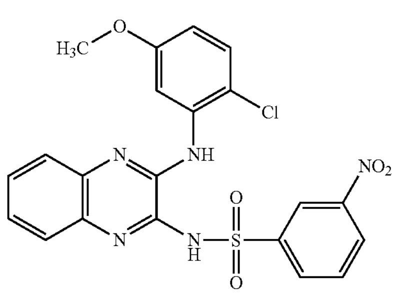 | N-(3-{[2-chloro-5-(methoxy)phenyl]amino} quinoxalin-2-yl)-3-nitrobenzenesulfonamide |
| 333 | 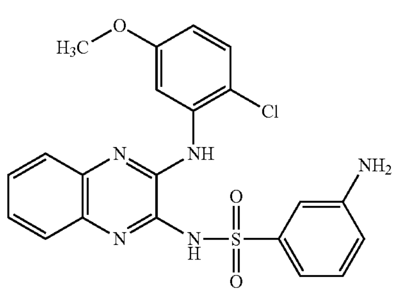 [SMILES: COc1ccc(Cl)c(Nc2nc3ccccc3nc2NS(=O)(=O)c2cccc([N+](=O)[O-])c2)c1] | 3-amino-N-(3-{[2-chloro-5-(methoxy)phenyl] amino}quinoxalin-2-yl)benzenesulfonamide |

TABLE 1-continued

| Cpd. No. | Structure | Name |
|---|---|---|
| 334 | 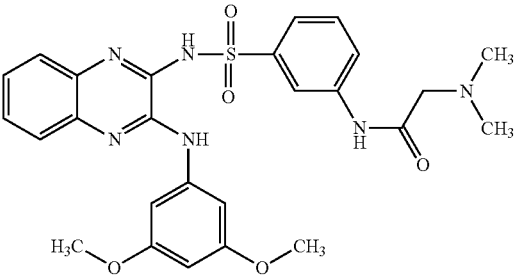 [SMILES: COc1cc(Nc2nc3ccccc3nc2NS(=O)(=O)c2cccc(NC(=O)CN(C)C)c2)cc(OC)c1] | N-(3-{[(3-{[3,5-bis(methoxy)phenyl]amino}quinoxalin-2-yl)amino]sulfonyl}phenyl)-N-2-,N-2-dimethylglycinamide |
| 335 | 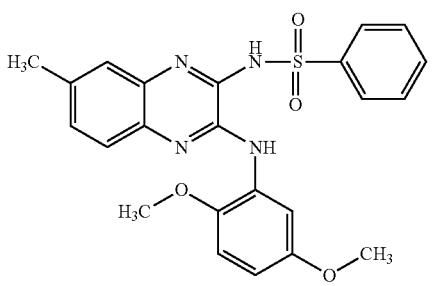 [SMILES: COc1ccc(OC)c(Nc2nc3ccc(C)cc3nc2NS(=O)(=O)c2ccccc2)c1] | N-(3-{[2,5-bis(methoxy)phenyl]amino}-7-methylquinoxalin-2-yl)benzenesulfonamide |
| 336 | 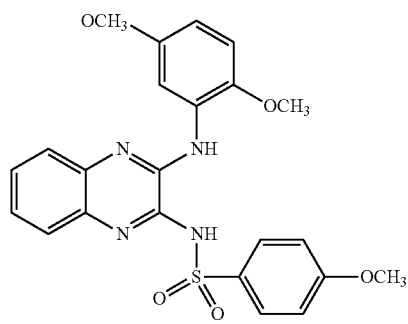 [SMILES: COc1ccc(S(=O)(=O)Nc2nc3ccccc3nc2Nc2cc(OC)ccc2OC)cc1] | N-(3-{[2,5-bis(methoxy)phenyl]amino}quinoxalin-2-yl)-4-(methoxy)benzenesulfonamide |
| 337 | 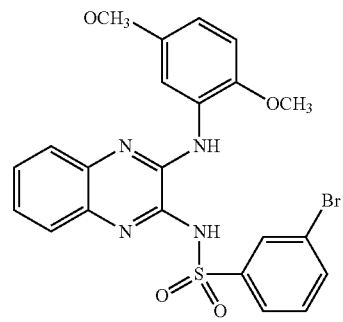 [SMILES: COc1ccc(OC)c(Nc2nc3ccccc3nc2NS(=O)(=O)c2cccc(Br)c2)c1] | N-(3-{[2,5-bis(methoxy)phenyl]amino}quinoxalin-2-yl)-3-bromobenzenesulfonamide |
| 338 | 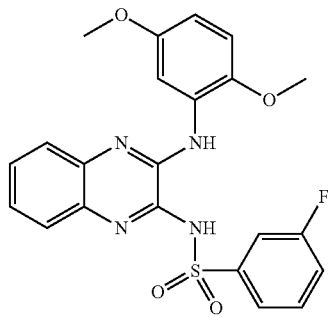 [SMILES: COc1ccc(OC)c(Nc2nc3ccccc3nc2NS(=O)(=O)c2cccc(F)c2)c1] | N-(3-{[2,5-bis(methoxy)phenyl]amino}quinoxalin-2-yl)-3-fluorobenzenesulfonamide |

TABLE 1-continued

| Cpd. No. | Structure | Name |
|---|---|---|
| 339 | 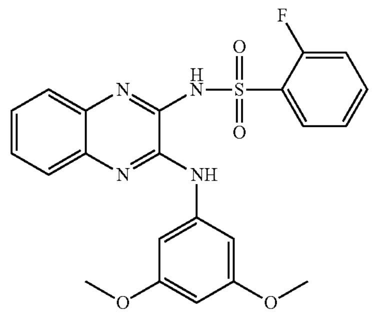 [SMILES: COc1cc(Nc2nc3ccccc3nc2NS(=O)(=O)c2ccccc2F)cc(OC)c1] | N-(3-{[3,5-bis(methoxy)phenyl]amino}quinoxalin-2-yl)-2-fluorobenzenesulfonamide |
| 340 | 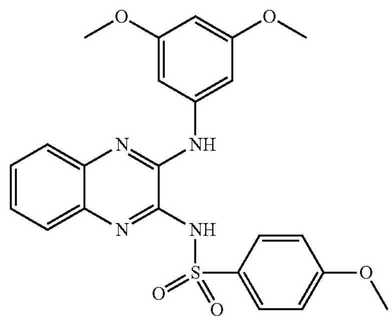 [SMILES: COc1ccc(S(=O)(=O)Nc2nc3ccccc3nc2Nc2cc(OC)cc(OC)c2)cc1] | N-(3-{[3,5-bis(methoxy)phenyl]amino}quinoxalin-2-yl)-4-(methoxy)benzenesulfonamide |
| 341 | 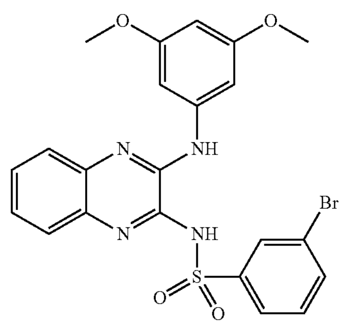 [SMILES: COc1cc(Nc2nc3ccccc3nc2NS(=O)(=O)c2cccc(Br)c2)cc(OC)c1] | N-(3-{[3,5-bis(methoxy)phenyl]amino}quinoxalin-2-yl)-3-bromobenzenesulfonamide |
| 342 | 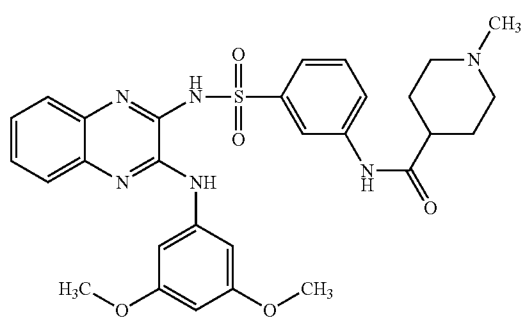 [SMILES: COc1cc(Nc2nc3ccccc3nc2NS(=O)(=O)c2cccc(NC(=O)C3CCN(C)CC3)c2)cc(OC)c1] | N-(3-{[(3-{[3,5-bis(methoxy)phenyl]amino}quinoxalin-2-yl)amino]sulfonyl}phenyl)-1-methylpiperidine-4-carboxamide |
| 343 | 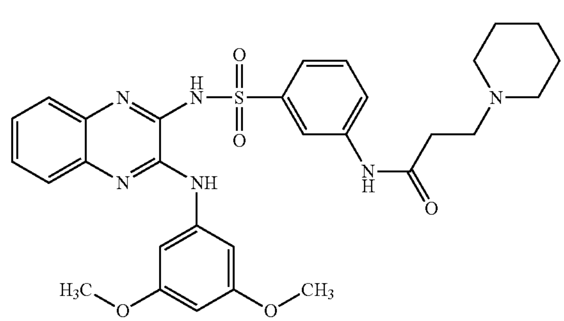 [SMILES: COc1cc(Nc2nc3ccccc3nc2NS(=O)(=O)c2cccc(NC(=O)CCN3CCCCC3)c2)cc(OC)c1] | N-(3-{[(3-{[3,5-bis(methoxy)phenyl]amino}quinoxalin-2-yl)amino]sulfonyl}phenyl)-3-piperidin-1-ylpropanamide |

TABLE 1-continued

| Cpd. No. | Structure | Name |
|---|---|---|
| 344 | 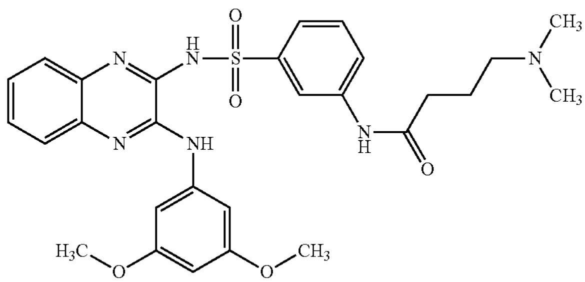 [SMILES: COc1cc(Nc2nc3ccccc3nc2NS(=O)(=O)c2cccc(NC(=O)CCCN(C)C)c2)cc(OC)c1] | N-(3-{[(3-{[3,5-bis(methoxy)phenyl]amino}quinoxalin-2-yl)amino]sulfonyl}phenyl)-4-(dimethylamino)butanamide |
| 345 | 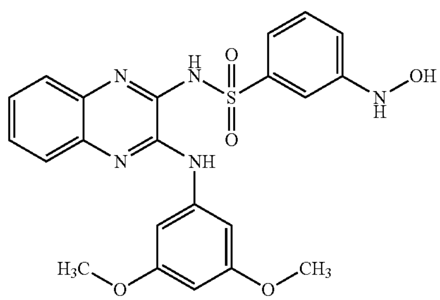 [SMILES: COc1cc(Nc2nc3ccccc3nc2NS(=O)(=O)c2cccc(NO)c2)cc(OC)c1] | N-(3-{[3,5-bis(methoxy)phenyl]amino}quinoxalin-2-yl)-3-(hydroxyamino)benzenesulfonamide |
| 346 | 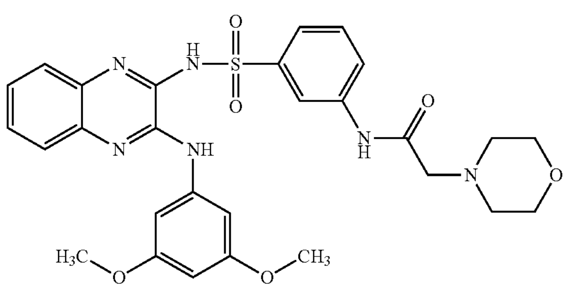 [SMILES: COc1cc(Nc2nc3ccccc3nc2NS(=O)(=O)c2cccc(NC(=O)CN3CCOCC3)c2)cc(OC)c1] | N-(3-{[(3-{[3,5-bis(methoxy)phenyl]amino}quinoxalin-2-yl)amino]sulfonyl}phenyl)-2-morpholin-4-ylacetamide |
| 347 | 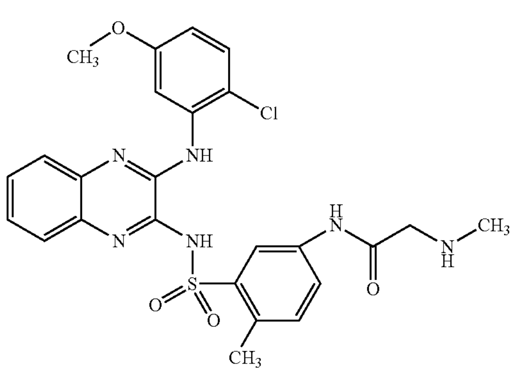 [SMILES: CNCC(=O)Nc1ccc(C)c(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}-4-methylphenyl)-N-2-methylglycinamide |

TABLE 1-continued

| Cpd. No. | Structure | Name |
|---|---|---|
| 348 | 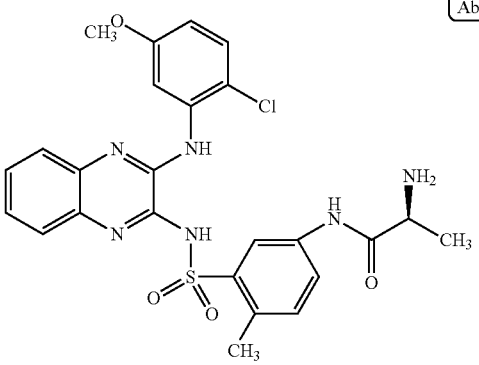 | N-(3-{[(3-{[2-chloro-5-(methoxy)phenyl]amino}quinoxalin-2-yl)amino]sulfonyl}-4-methylphenyl)-L-alaninamide |
| 349 | 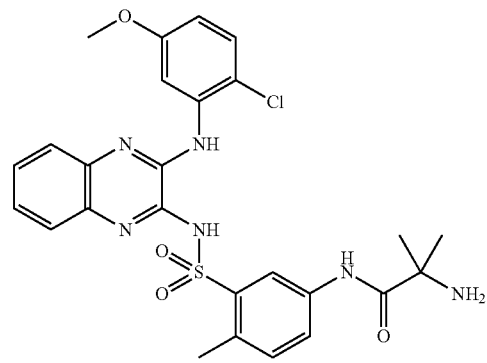 [SMILES: COc1ccc(Cl)c(Nc2nc3ccccc3nc2NS(=O)(=O)c2cc(NC(=O)C(C)(C)N)ccc2C)c1] | N-(3-{[(3-{[2-chloro-5-(methoxy)phenyl]amino}quinoxalin-2-yl)amino]sulfonyl}-4-methylphenyl)-2-methylalaninamide |
| 350 | 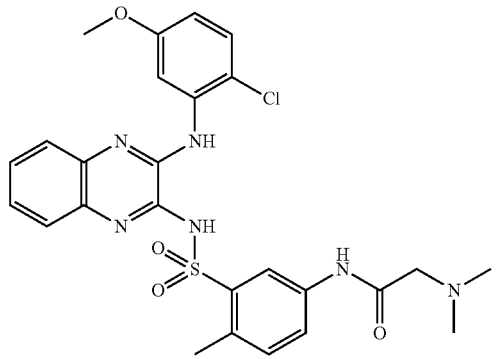 [SMILES: COc1ccc(Cl)c(Nc2nc3ccccc3nc2NS(=O)(=O)c2cc(NC(=O)CN(C)C)ccc2C)c1] | N-(3-{[(3-{[2-chloro-5-(methoxy)phenyl]amino}quinoxalin-2-yl)amino]sulfonyl}-4-methylphenyl)-N-2-,N-2-dimethylglycinamide |
| 351 | 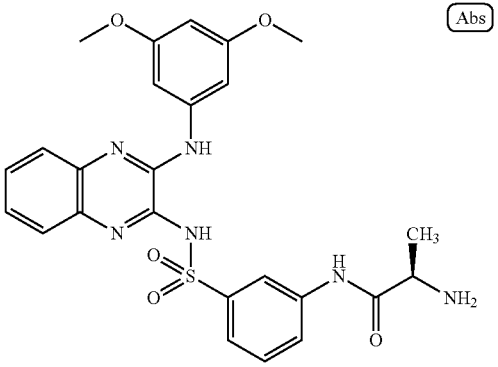 [SMILES: COc1cc(Nc2nc3ccccc3nc2NS(=O)(=O)c2cccc(NC(=O)[C@@H](C)N)c2)cc(OC)c1] | N-(3-{[(3-{[3,5-bis(methoxy)phenyl]amino}quinoxalin-2-yl)amino]sulfonyl}phenyl)-D-alaninamide |

TABLE 1-continued

| Cpd. No. | Structure | Name |
|---|---|---|
| 352 | 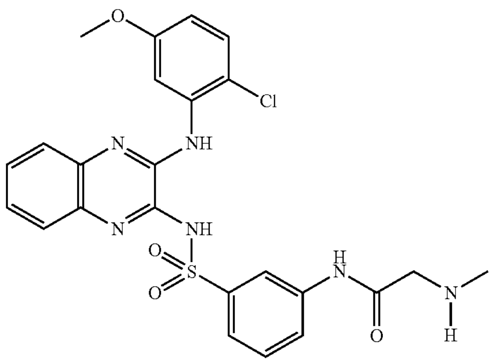 [SMILES: CNCC(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-methylglycinamide |
| 353 | 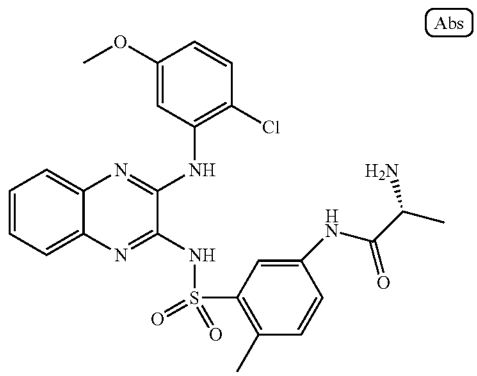 [SMILES: COc1ccc(Cl)c(Nc2nc3ccccc3nc2NS(=O)(=O)c2cc(NC(=O)[C@@H](C)N)ccc2C)c1] | N-(3-{[(3-{[2-chloro-5-(methoxy)phenyl]amino}quinoxalin-2-yl)amino]sulfonyl}-4-methylphenyl)-D-alaninamide |
| 354 | 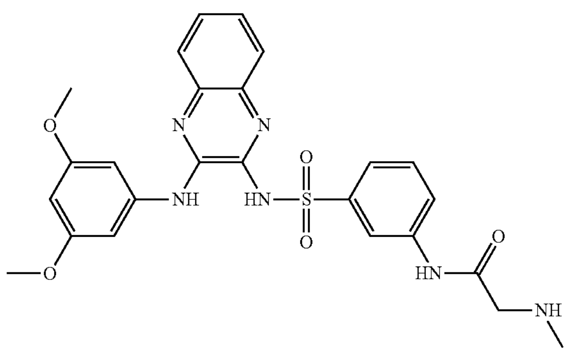 | N-(3-{[(3-{[3,5-bis(methoxy)phenyl]amino}quinoxalin-2-yl)amino]sulfonyl}phenyl)-N-2-methylglycinamide |
| 355 | 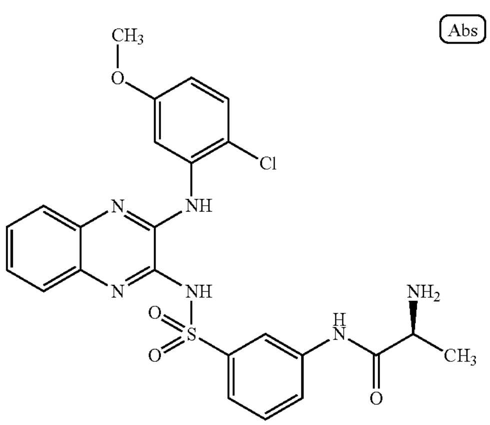 [SMILES: COc1ccc(Cl)c(Nc2nc3ccccc3nc2NS(=O)(=O)c2cccc(NC(=O)[C@H](C)N)c2)c1] | N-(3-{[(3-{[2-chloro-5-(methoxy)phenyl]amino}quinoxalin-2-yl)amino]sulfonyl}phenyl)-L-alaninamide |

TABLE 1-continued

| Cpd. No. | Structure | Name |
|---|---|---|
| 356 | 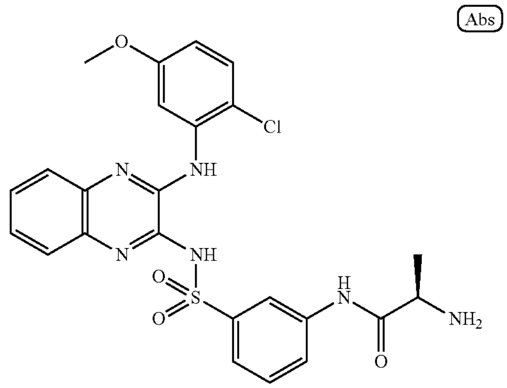 [SMILES: COc1ccc(Cl)c(Nc2nc3ccccc3nc2NS(=O)(=O)c2cccc(NC(=O)[C@@H](C)N)c2)c1] | N-(3-{[(3-{[2-chloro-5-(methoxy)phenyl]amino}quinoxalin-2-yl)amino]sulfonyl}phenyl)-D-alaninamide |
| 357 | 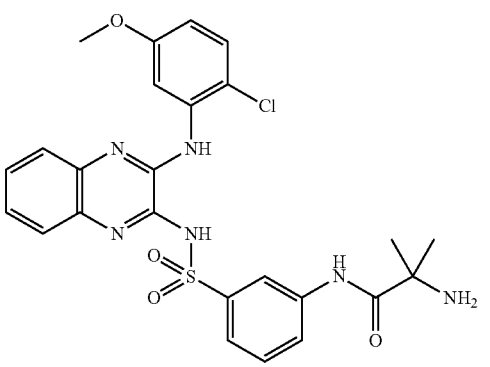 [SMILES: COc1ccc(Cl)c(Nc2nc3ccccc3nc2NS(=O)(=O)c2cccc(NC(=O)C(C)(C)N)c2)c1] | N-(3-{[(3-{[2-chloro-5-(methoxy)phenyl]amino}quinoxalin-2-yl)amino]sulfonyl}phenyl)-2-methylalaninamide |
| 358 | 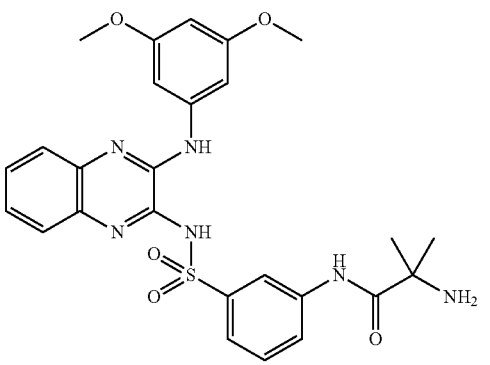 [SMILES: COc1cc(Nc2nc3ccccc3nc2NS(=O)(=O)c2cccc(NC(=O)C(C)(C)N)c2)cc(OC)c1] | N-(3-{[(3-{[3,5-bis(methoxy)phenyl]amino}quinoxalin-2-yl)amino]sulfonyl}phenyl)-2-methylalaninamide |
| 359 | 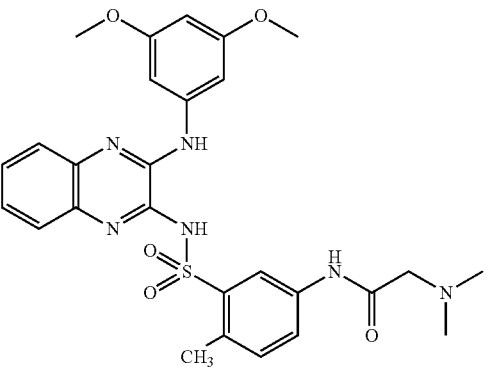 [SMILES: COc1cc(Nc2nc3ccccc3nc2NS(=O)(=O)c2cc(NC(=O)CN(C)C)ccc2C)cc(OC)c1] | N-(3-{[(3-{[3,5-bis(methoxy)phenyl]amino}quinoxalin-2-yl)amino]sulfonyl}-4-methylphenyl)-N-2-,N-2-dimethylglycinamide |

TABLE 1-continued

| Cpd. No. | Structure | Name |
|---|---|---|
| 360 | 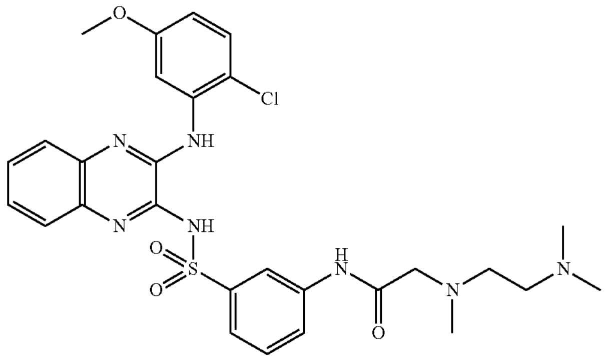 [SMILES: COc1ccc(Cl)c(Nc2nc3ccccc3nc2NS(=O)(=O)c2cccc(NC(=O)CN(C)CCN(C)C)c2)c1] | N-(3-{[(3-{[2-chloro-5-(methoxy)phenyl]amino}quinoxalin-2-yl)amino]sulfonyl}phenyl)-N-2-[2-(dimethylamino)ethyl]-N-2-methylglycinamide |
| 361 | 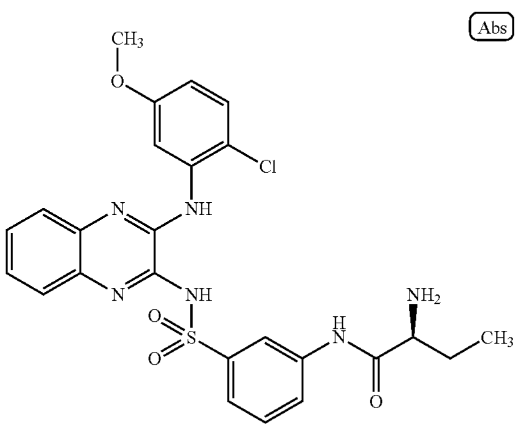 [SMILES: CC[C@H](N)C(=O)Nc1cccc(S(=O)(=O)Nc2nc3ccccc3nc2Nc2cc(OC)ccc2Cl)c1] | (2S)-2-amino-N-(3-{[(3-{[2-chloro-5-(methoxy)phenyl]amino}quinoxalin-2-yl)amino]sulfonyl}phenyl)butanamide |
| 362 | 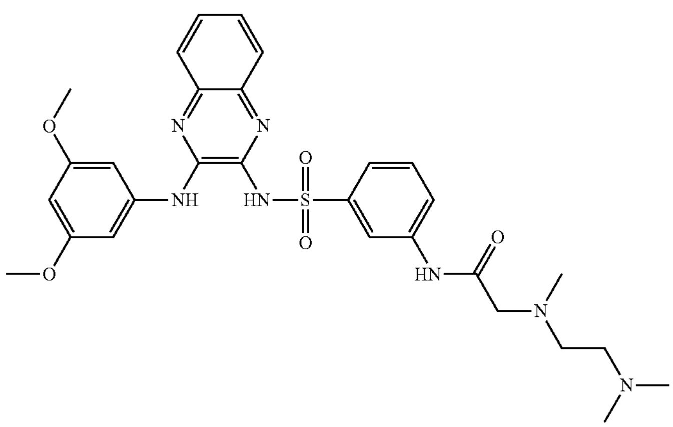 | N-(3-{[(3-{[3,5-bis(methoxy)phenyl]amino}quinoxalin-2-yl)amino]sulfonyl}phenyl)-N-2-[2-(dimethylamino)ethyl]-N-2-methylglycinamide |
| 363 | 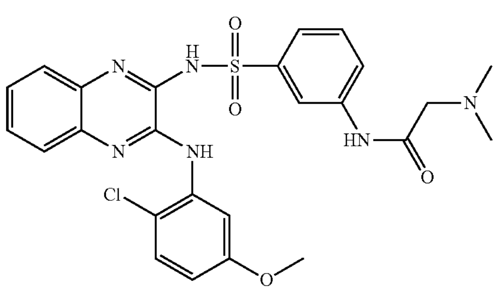 [SMILES: COc1ccc(Cl)c(Nc2nc3ccccc3nc2NS(=O)(=O)c2cccc(NC(=O)CN(C)C)c2)c1] | N-(3-{[(3-{[2-chloro-5-(methoxy)phenyl]amino}quinoxalin-2-yl)amino]sulfonyl}phenyl)-N-2-,N-2-dimethylglycinamide |

TABLE 1-continued

| Cpd. No. | Structure | Name |
|---|---|---|
| 364 | 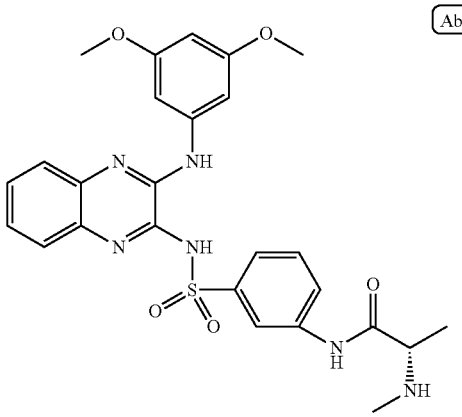 | N-(3-{[(3-{[3,5-bis(methoxy)phenyl]amino}quinoxalin-2-yl)amino]sulfonyl}phenyl)-N-2-methyl-L-alaninamide |
| 365 | 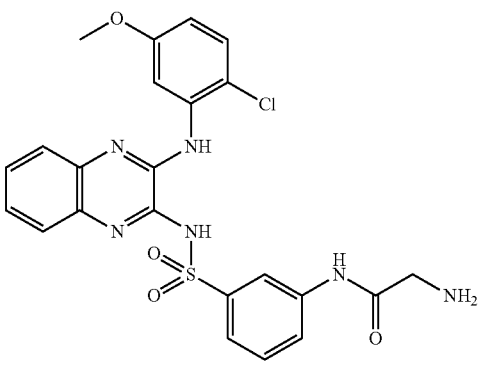 [SMILES: COc1ccc(Cl)c(Nc2nc3ccccc3nc2NS(=O)(=O)c2cccc(NC(=O)CN)c2)c1] | N-(3-{[(3-{[2-chloro-5-(methoxy)phenyl]amino}quinoxalin-2-yl)amino]sulfonyl}phenyl)glycinamide |
| 366 | 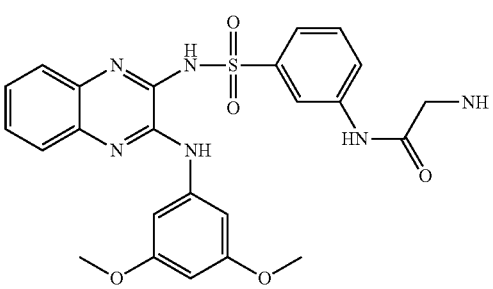 [SMILES: COc1cc(Nc2nc3ccccc3nc2NS(=O)(=O)c2cccc(NC(=O)CN)c2)cc(OC)c1] | N-(3-{[(3-{[3,5-bis(methoxy)phenyl]amino}quinoxalin-2-yl)amino]sulfonyl}phenyl)glycinamide |
| 367 | 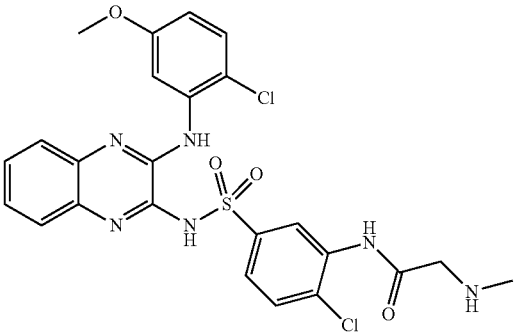 [SMILES: CNCC(=O)Nc1cc(S(=O)(=O)Nc2nc3ccccc3nc2Nc2cc(OC)ccc2Cl)ccc1Cl] | N-(2-chloro-5-{[(3-{[2-chloro-5-(methoxy)phenyl]amino}quinoxalin-2-yl)amino]sulfonyl}phenyl)-N-2-methylglycinamide |

TABLE 1-continued

| Cpd. No. | Structure | Name |
|---|---|---|
| 368 | 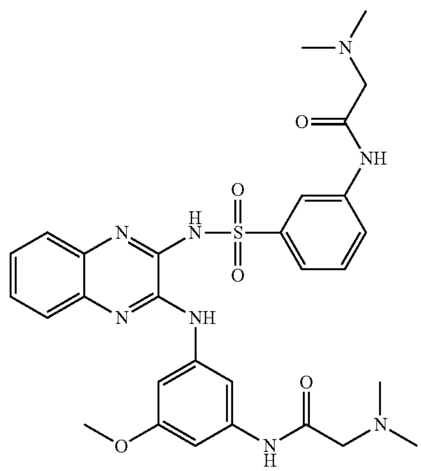 [SMILES: COc1cc(NC(=O)CN(C)C)cc(Nc2nc3ccccc3nc2NS(=O)(=O)c2cccc(NC(=O)CN(C)C)c2)c1] | 2-(dimethylamino)-N-(3-(N-(3-(3-(2-(dimethylamino)acetamido)-5-methoxyphenylamino)quinoxalin-2-yl)sulfamoyl)phenyl)acetamide |
| 369 | 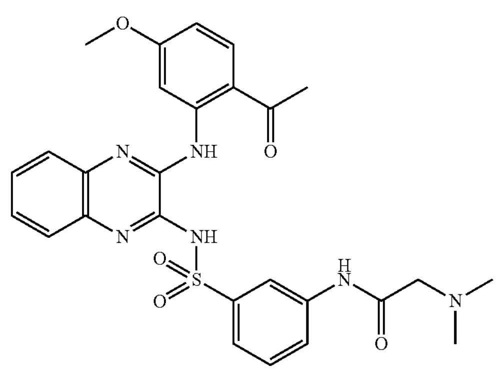 [SMILES: COc1ccc(C(C)=O)c(Nc2nc3ccccc3nc2NS(=O)(=O)c2cccc(NC(=O)CN(C)C)c2)c1] | N-(3-{[(3-{[2-acetyl-5-(methoxy)phenyl]amino}quinoxalin-2-yl)amino]sulfonyl}phenyl)-N-2-,N-2-dimethylglycinamide |
| 370 | 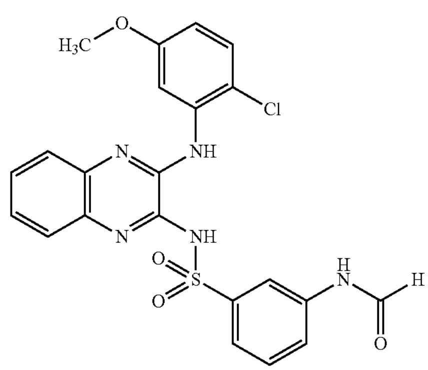 [SMILES: COc1ccc(Cl)c(Nc2nc3ccccc3nc2NS(=O)(=O)c2cccc(NC=O)c2)c1] | N-(3-{[2-chloro-5-(methoxy)phenyl]amino}quinoxalin-2-yl)-3-(formylamino)benzenesulfonamide |
| 371 | 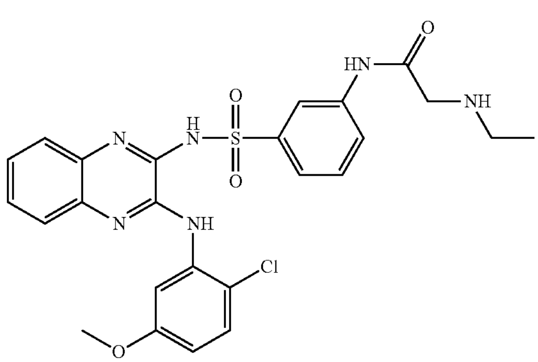 [SMILES: CCNCC(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-ethylglycinamide |

TABLE 1-continued

| Cpd. No. | Structure | Name |
|---|---|---|
| 372 | 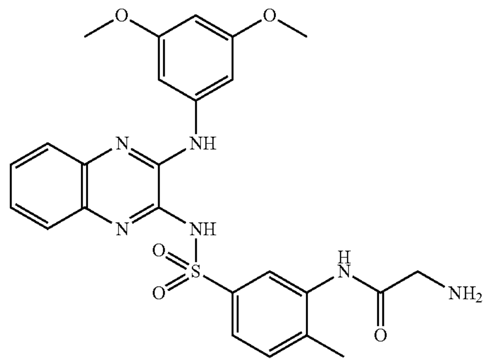 [SMILES: COc1cc(Nc2nc3ccccc3nc2NS(=O)(=O)c2ccc(C)c(NC(=O)CN)c2)cc(OC)c1] | N-(5-{[(3-{[3,5-bis(methoxy)phenyl]amino}quinoxalin-2-yl)amino]sulfonyl}-2-methylphenyl)glycinamide |
| 373 | 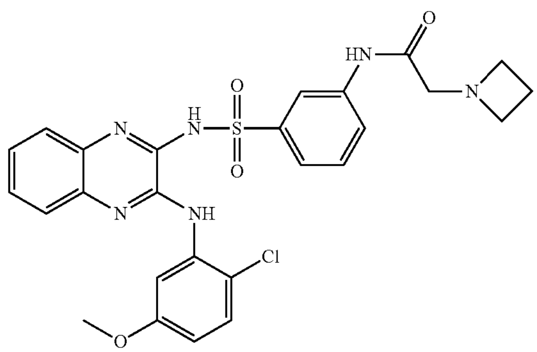 [SMILES: COc1ccc(Cl)c(Nc2nc3ccccc3nc2NS(=O)(=O)c2cccc(NC(=O)CN3CCC3)c2)c1] | 2-azetidin-1-yl-N-(3-{[(3-{[2-chloro-5-(methoxy)phenyl]amino}quinoxalin-2-yl)amino]sulfonyl}phenyl)acetamide |
| 374 | 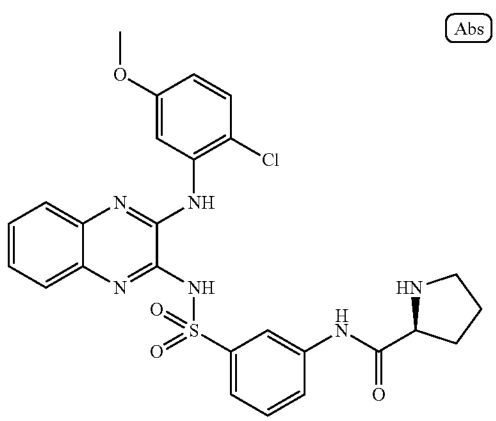 [SMILES: COc1ccc(Cl)c(Nc2nc3ccccc3nc2NS(=O)(=O)c2cccc(NC(=O)[C@@H]3CCCN3)c2)c1] | N-(3-{[(3-{[2-chloro-5-(methoxy)phenyl]amino}quinoxalin-2-yl)amino]sulfonyl}phenyl)-L-prolinamide |
| 375 | 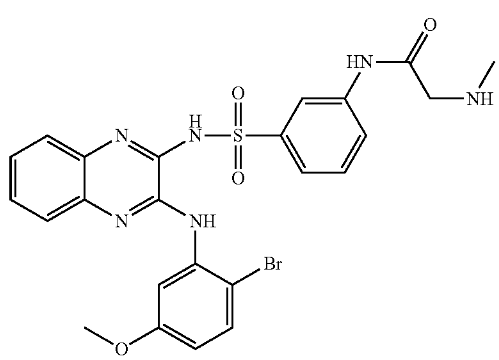 [SMILES: CNCC(=O)Nc1cccc(S(=O)(=O)Nc2nc3ccccc3nc2Nc2cc(OC)ccc2Br)c1] | N-(3-{[(3-{[2-bromo-5-(methoxy)phenyl]amino}quinoxalin-2-yl)amino]sulfonyl}phenyl)-N-2-methylglycinamide |

| Cpd. No. | Structure | Name |
|---|---|---|
| 376 | 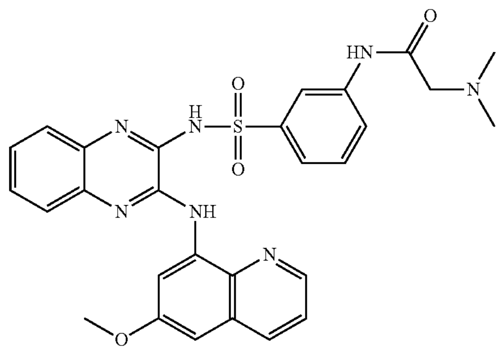 [SMILES: COc1cc(Nc2nc3ccccc3nc2NS(=O)(=O)c2cccc(NC(=O)CN(C)C)c2)c2ncccc2c1] | N-2-,N-2-dimethyl-N-(3-{[(3-{[6-(methoxy) quinolin-8-yl]amino} quinoxalin-2-yl)amino] sulfonyl}phenyl) glycinamide |
| 377 | 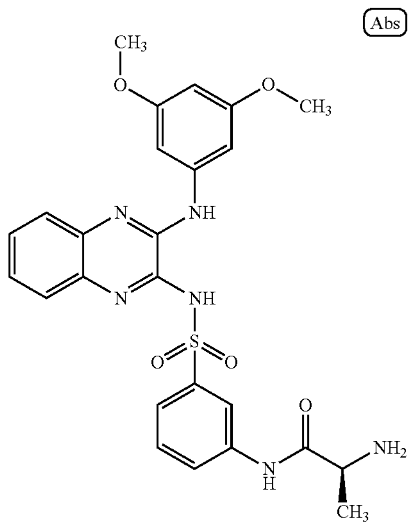 [SMILES: COc1cc(Nc2nc3ccccc3nc2NS(=O)(=O)c2cccc(NC(=O)[C@H](C)N)c2)cc(OC)c1] | N-(3-{[(3-{[3,5-bis (methoxy)phenyl]amino} quinoxalin-2-yl)amino] sulfonyl}phenyl)-L-alaninamide |
| 378 | 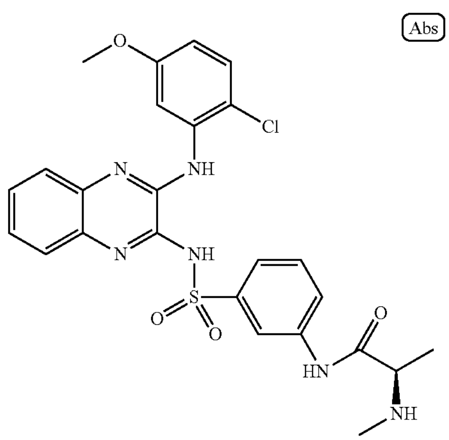 [SMILES: CN[C@H](C)C(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino} quinoxalin-2-yl)amino] sulfonyl}phenyl)-N-2-methyl-D-alaninamide |

US 8,481,001 B2

TABLE 1-continued

| Cpd. No. | Structure | Name |
|---|---|---|
| 379 | 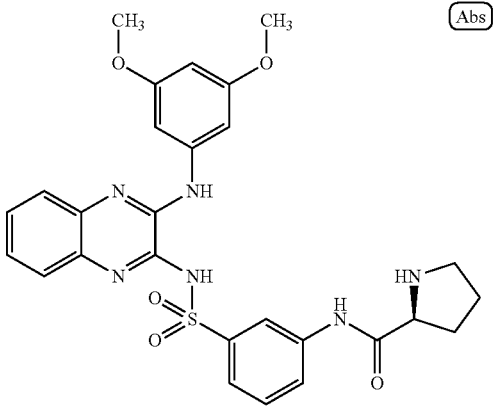 [SMILES: COc1cc(Nc2nc3ccccc3nc2NS(=O)(=O)c2cccc(NC(=O)[C@@H]3CCCN3)c2)cc(OC)c1] | N-(3-{[(3-{[3,5-bis(methoxy)phenyl]amino}quinoxalin-2-yl)amino]sulfonyl}phenyl)-L-prolinamide |
| 380 | 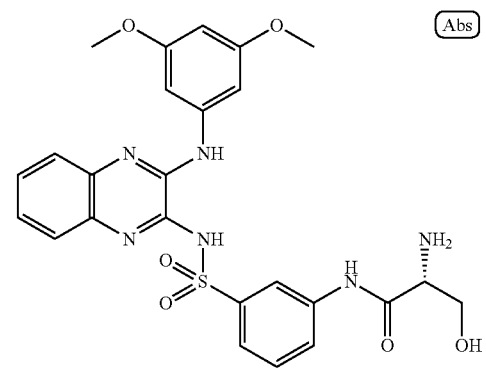 [SMILES: COc1cc(Nc2nc3ccccc3nc2NS(=O)(=O)c2cccc(NC(=O)[C@H](N)CO)c2)cc(OC)c1] | N-(3-{[(3-{[3,5-bis(methoxy)phenyl]amino}quinoxalin-2-yl)amino]sulfonyl}phenyl)-D-serinamide |
| 381 | 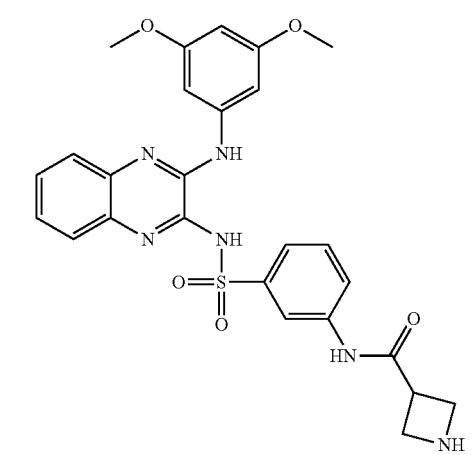 [SMILES: COc1cc(Nc2nc3ccccc3nc2NS(=O)(=O)c2cccc(NC(=O)C3CNC3)c2)cc(OC)c1] | N-(3-{[(3-{[3,5-bis(methoxy)phenyl]amino}quinoxalin-2-yl)amino]sulfonyl}phenyl)azetidine-3-carboxamide |
| 382 | 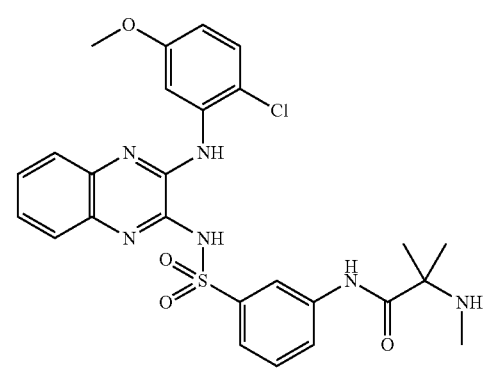 [SMILES: CNC(C)(C)C(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-,2-dimethylalaninamide |

TABLE 1-continued

| Cpd. No. | Structure | Name |
|---|---|---|
| 383 | 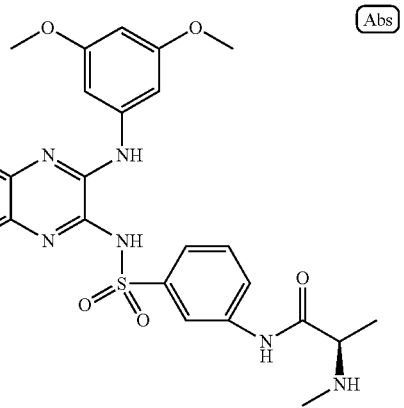 | N-(3-{[(3-{[3,5-bis(methoxy)phenyl]amino}quinoxalin-2-yl)amino]sulfonyl}phenyl)-N-2-methyl-D-alaninamide |
| 384 | 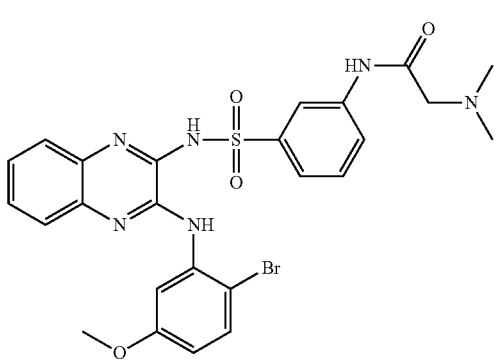 [SMILES: COc1ccc(Br)c(Nc2nc3ccccc3nc2NS(=O)(=O)c2cccc(NC(=O)CN(C)C)c2)c1] | N-(3-{[(3-{[2-bromo-5-(methoxy)phenyl]amino}quinoxalin-2-yl)amino]sulfonyl}phenyl)-N-2-,N-2-dimethylglycinamide |
| 385 | 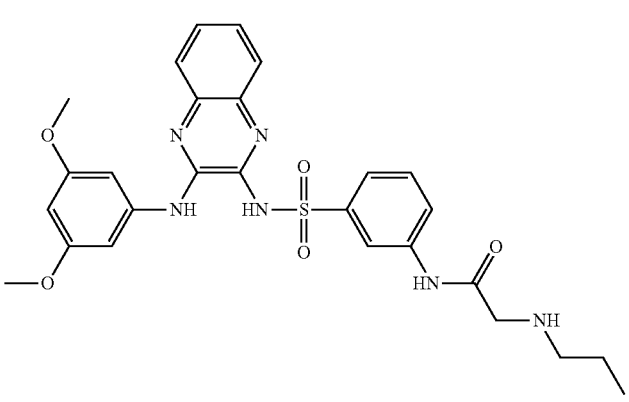 [SMILES: CCCNCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-propylglycinamide |
| 386 | 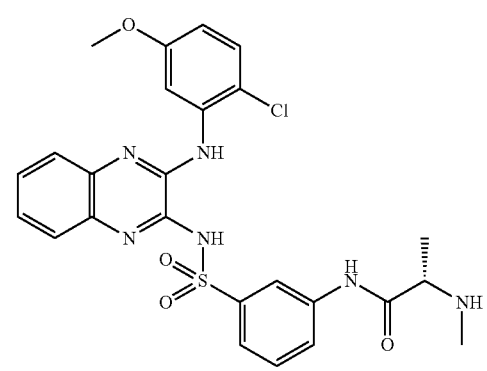 [SMILES: CN[C@@H](C)C(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-methyl-L-alaninamide |

TABLE 1-continued

| Cpd. No. | Structure | Name |
|---|---|---|
| 387 | 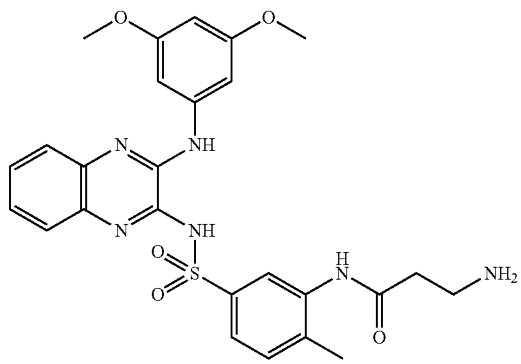 [SMILES: COc1cc(Nc2nc3ccccc3nc2NS(=O)(=O)c2ccc(C)c(NC(=O)CCN)c2)cc(OC)c1] | N-(5-{[(3-{[3,5-bis(methoxy)phenyl]amino}quinoxalin-2-yl)amino]sulfonyl}-2-methylphenyl)-beta-alaninamide |
| 388 | 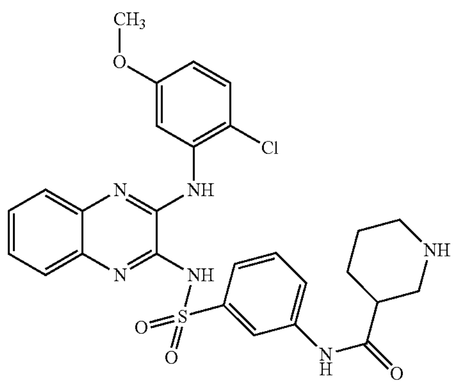 [SMILES: COc1ccc(Cl)c(Nc2nc3ccccc3nc2NS(=O)(=O)c2cccc(NC(=O)C3CCCNC3)c2)c1] | N-(3-{[(3-{[2-chloro-5-(methoxy)phenyl]amino}quinoxalin-2-yl)amino]sulfonyl}phenyl)piperidine-3-carboxamide |
| 389 | 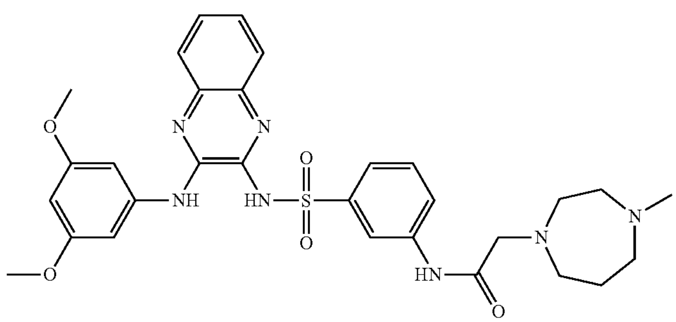 | N-(3-{[(3-{[3,5-bis(methoxy)phenyl]amino}quinoxalin-2-yl)amino]sulfonyl}phenyl)-2-(4-methyl-1,4-diazepan-1-yl)acetamide |
| 390 | 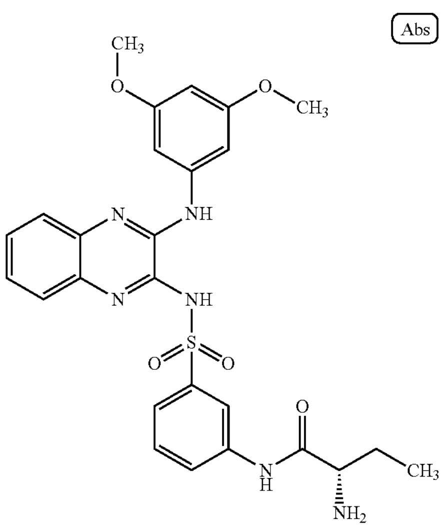 [SMILES: CC[C@H](N)C(=O)Nc1cccc(S(=O)(=O)Nc2nc3ccccc3nc2Nc2cc(OC)cc(OC)c2)c1] | (2S)-2-amino-N-(3-{[(3-{[3,5-bis(methoxy)phenyl]amino}quinoxalin-2-yl)amino]sulfonyl}phenyl)butanamide |

TABLE 1-continued

| Cpd. No. | Structure | Name |
|---|---|---|
| 391 | 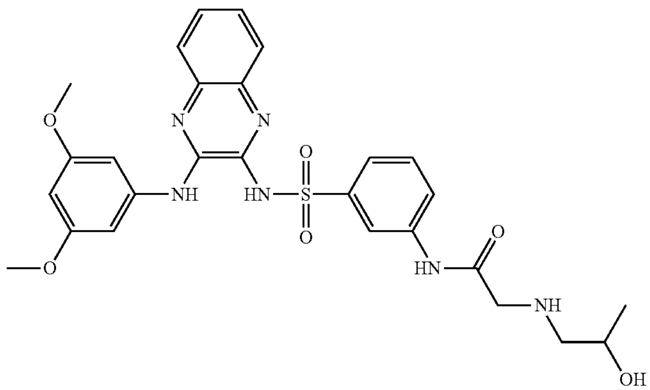 [SMILES: COc1cc(Nc2nc3ccccc3nc2NS(=O)(=O)c2cccc(NC(=O)CNCC(C)O)c2)cc(OC)c1] | N-(3-{[(3-{[3,5-bis (methoxy)phenyl] amino}quinoxalin-2-yl) amino]sulfonyl}phenyl)-N-2-(2-hydroxypropyl) glycinamide |
| 392 | 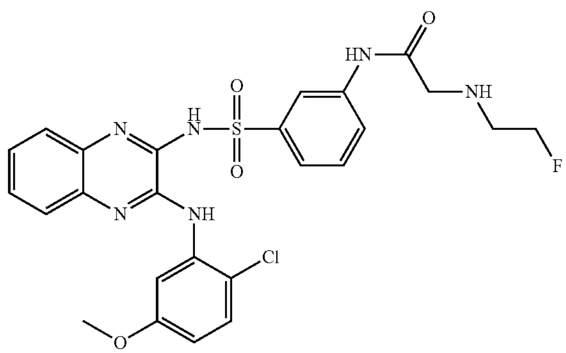 [SMILES: COc1ccc(Cl)c(Nc2nc3ccccc3nc2NS(=O)(=O)c2cccc(NC(=O)CNCCF)c2)c1] | N-(3-{[(3-{[2-chloro-5-(methoxy)phenyl]amino} quinoxalin-2-yl)amino] sulfonyl}phenyl)-N-2-(2-fluoroethyl)glycinamide |
| 393 | 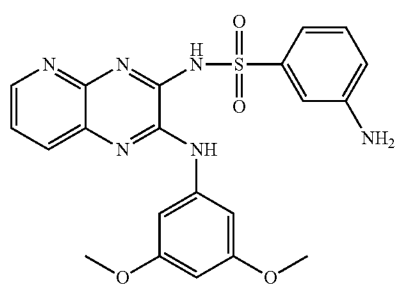 | 3-amino-N-(2-{[3,5-bis (methoxy)phenyl]amino} pyrido[2,3-b]pyrazin-3-yl) benzenesulfonamide |
| 394 | 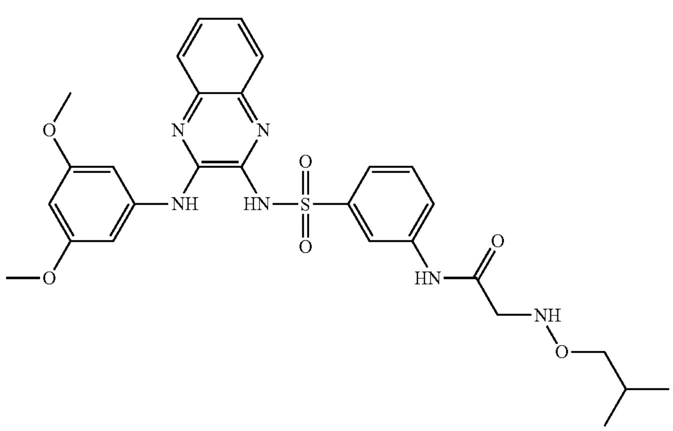 [SMILES: COc1cc(Nc2nc3ccccc3nc2NS(=O)(=O)c2cccc(NC(=O)CNOCC(C)C)c2)cc(OC)c1] | N-(3-{[(3-{[3,5-bis (methoxy)phenyl]amino} quinoxalin-2-yl)amino] sulfonyl}phenyl)-N-2-[(2-methylpropyl)oxy] glycinamide |

TABLE 1-continued

| Cpd. No. | Structure | Name |
|---|---|---|
| 395 | 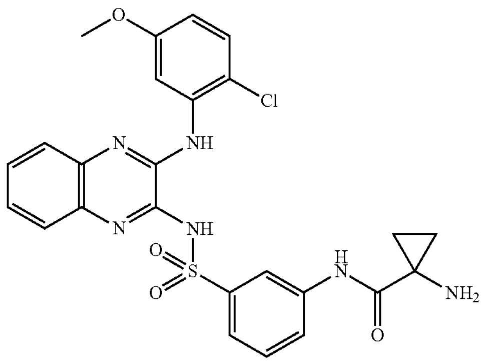 [SMILES: COc1ccc(Cl)c(Nc2nc3ccccc3nc2NS(=O)(=O)c2cccc(NC(=O)C3(N)CC3)c2)c1] | 1-amino-N-(3-{[(3-{[2-chloro-5-(methoxy)phenyl]amino}quinoxalin-2-yl)amino]sulfonyl}phenyl)cyclopropanecarboxamide |
| 396 | 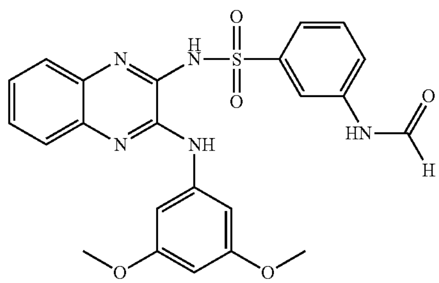 [SMILES: COc1cc(Nc2nc3ccccc3nc2NS(=O)(=O)c2cccc(NC=O)c2)cc(OC)c1] | N-(3-{[3,5-bis(methoxy)phenyl]amino}quinoxalin-2-yl)-3-(formylamino)benzenesulfonamide |
| 397 | 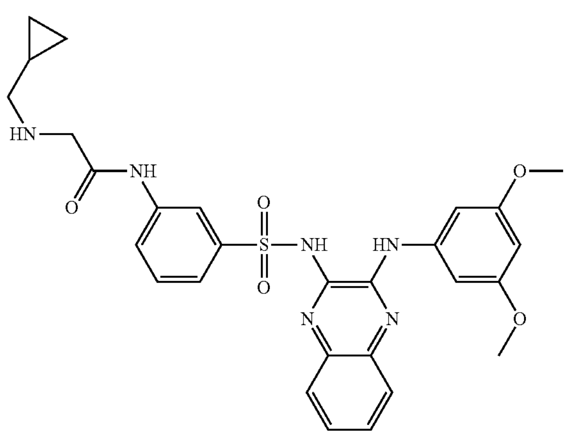 [SMILES: COc1cc(Nc2nc3ccccc3nc2NS(=O)(=O)c2cccc(NC(=O)CNCC3CC3)c2)cc(OC)c1] | N-(3-{[(3-{[3,5-bis(methoxy)phenyl]amino}quinoxalin-2-yl)amino]sulfonyl}phenyl)-N-2-(cyclopropylmethyl)glycinamide |
| 398 | 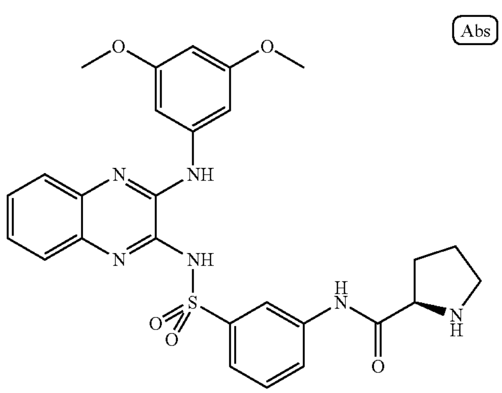 [SMILES: COc1cc(Nc2nc3ccccc3nc2NS(=O)(=O)c2cccc(NC(=O)[C@H]3CCCN3)c2)cc(OC)c1] | N-(3-{[(3-{[3,5-bis(methoxy)phenyl]amino}quinoxalin-2-yl)amino]sulfonyl}phenyl)-D-prolinamide |

TABLE 1-continued

| Cpd. No. | Structure | Name |
|---|---|---|
| 399 | 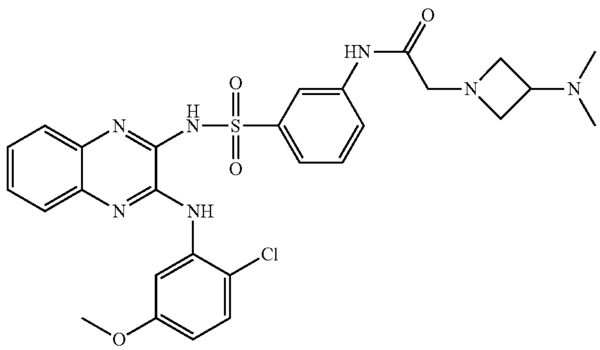 [SMILES: COc1ccc(Cl)c(Nc2nc3ccccc3nc2NS(=O)(=O)c2cccc(NC(=O)CN3CC(N(C)C)C3)c2)c1] | N-(3-{[(3-{[2-chloro-5-(methoxy)phenyl]amino}quinoxalin-2-yl)amino]sulfonyl}phenyl)-2-[3-(dimethylamino)azetidin-1-yl]acetamide |
| 400 | 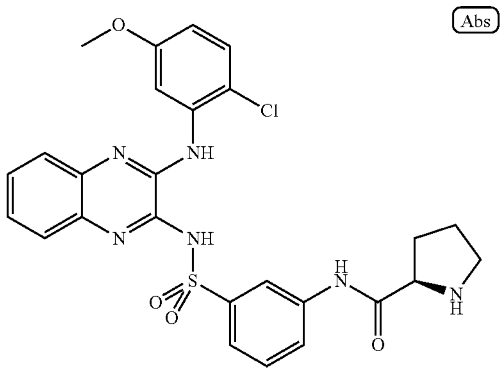 [SMILES: COc1ccc(Cl)c(Nc2nc3ccccc3nc2NS(=O)(=O)c2cccc(NC(=O)[C@H]3CCCN3)c2)c1] | N-(3-{[(3-{[2-chloro-5-(methoxy)phenyl]amino}quinoxalin-2-yl)amino]sulfonyl}phenyl)-D-prolinamide |
| 401 | 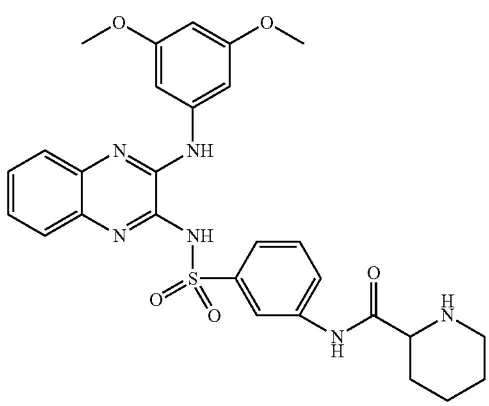 [SMILES: COc1cc(Nc2nc3ccccc3nc2NS(=O)(=O)c2cccc(NC(=O)C3CCCCN3)c2)cc(OC)c1] | N-(3-{[(3-{[3,5-bis(methoxy)phenyl]amino}quinoxalin-2-yl)amino]sulfonyl}phenyl)piperidine-2-carboxamide |
| 402 | 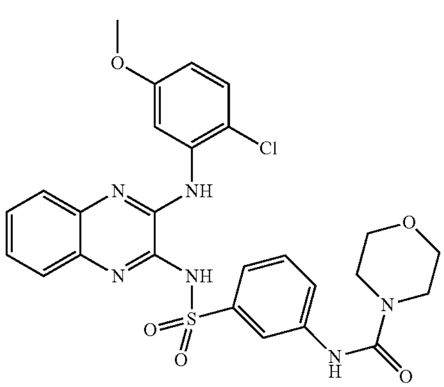 [SMILES: COc1ccc(Cl)c(Nc2nc3ccccc3nc2NS(=O)(=O)c2cccc(NC(=O)N3CCOCC3)c2)c1] | N-(3-{[(3-{[2-chloro-5-(methoxy)phenyl]amino}quinoxalin-2-yl)amino]sulfonyl}phenyl)morpholine-4-carboxamide |

TABLE 1-continued

| Cpd. No. | Structure | Name |
|---|---|---|
| 403 | 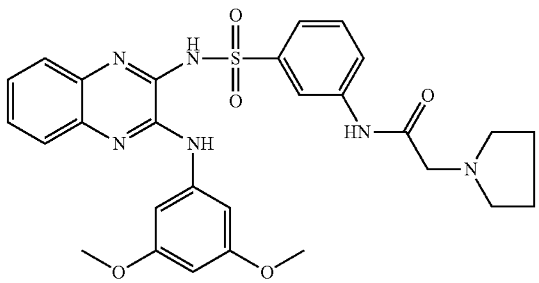 [SMILES: COc1cc(Nc2nc3ccccc3nc2NS(=O)(=O)c2cccc(NC(=O)CN3CCCC3)c2)cc(OC)c1] | N-(3-{[(3-{[3,5-bis(methoxy)phenyl]amino}quinoxalin-2-yl)amino]sulfonyl}phenyl)-2-pyrrolidin-1-ylacetamide |
| 404 | 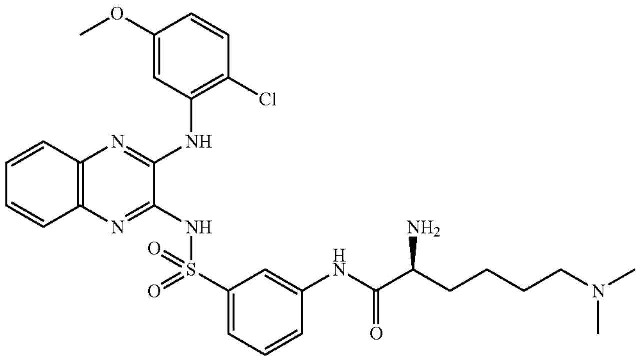 [SMILES: COc1ccc(Cl)c(Nc2nc3ccccc3nc2NS(=O)(=O)c2cccc(NC(=O)[C@@H](N)CCCCN(C)C)c2)c1] | N-(3-{[(3-{[2-chloro-5-(methoxy)phenyl]amino}quinoxalin-2-yl)amino]sulfonyl}phenyl)-N-6-,N-6-dimethyl-L-lysinamide |
| 405 | 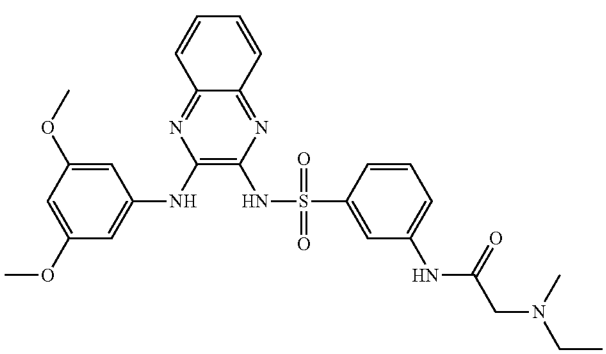 [SMILES: CCN(C)CC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-ethyl-N-2-methylglycinamide |
| 406 | 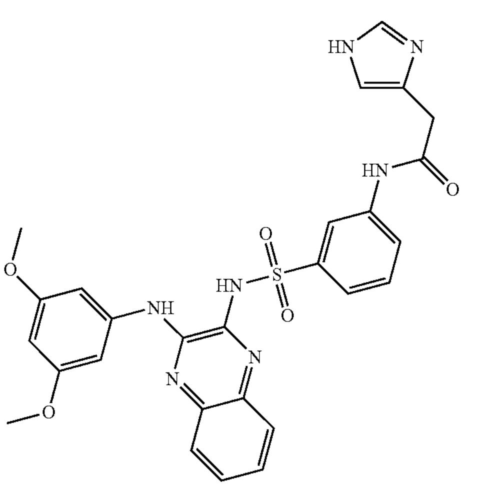 [SMILES: COc1cc(Nc2nc3ccccc3nc2NS(=O)(=O)c2cccc(NC(=O)Cc3c[nH]cn3)c2)cc(OC)c1] | N-(3-{[(3-{[3,5-bis(methoxy)phenyl]amino}quinoxalin-2-yl)amino]sulfonyl}phenyl)-2-(1H-imidazol-4-yl)acetamide |

TABLE 1-continued

| Cpd. No. | Structure | Name |
|---|---|---|
| 407 | 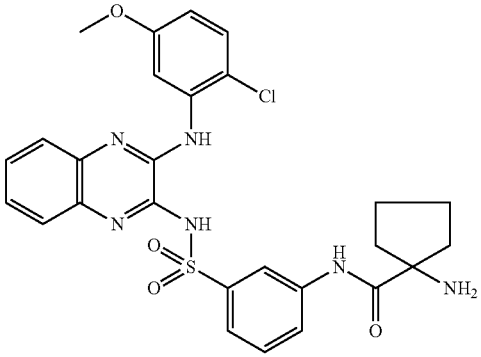 [SMILES: COc1ccc(Cl)c(Nc2nc3ccccc3nc2NS(=O)(=O)c2cccc(NC(=O)C3(N)CCCC3)c2)c1] | 1-amino-N-(3-{[(3-{[2-chloro-5-(methoxy)phenyl]amino}quinoxalin-2-yl)amino]sulfonyl}phenyl)cyclopentanecarboxamide |
| 408 | 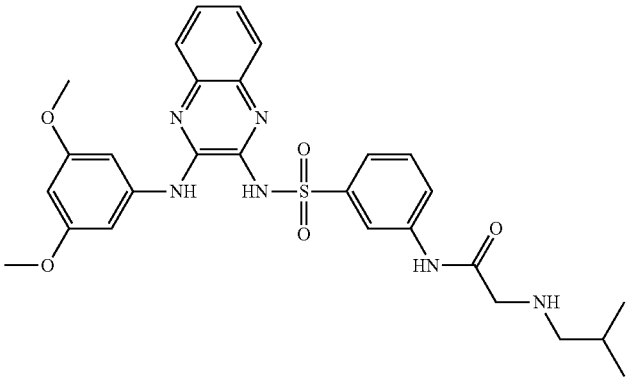 [SMILES: COc1cc(Nc2nc3ccccc3nc2NS(=O)(=O)c2cccc(NC(=O)CNCC(C)C)c2)cc(OC)c1] | N-(3-{[(3-{[3,5-bis(methoxy)phenyl]amino}quinoxalin-2-yl)amino]sulfonyl}phenyl)-N-2-(2-methylpropyl)glycinamide |
| 409 | 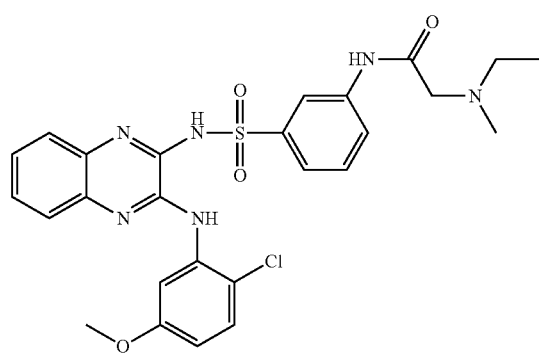 [SMILES: CCN(C)CC(=O)Nc1cccc(S(=O)(=O)Nc2nc3ccccc3nc2Nc2cc(OC)ccc2Cl)c1] | N-(3-{[(3-{[2-chloro-5-(methoxy)phenyl]amino}quinoxalin-2-yl)amino]sulfonyl}phenyl)-N-2-ethyl-N-2-methylglycinamide |
| 410 | 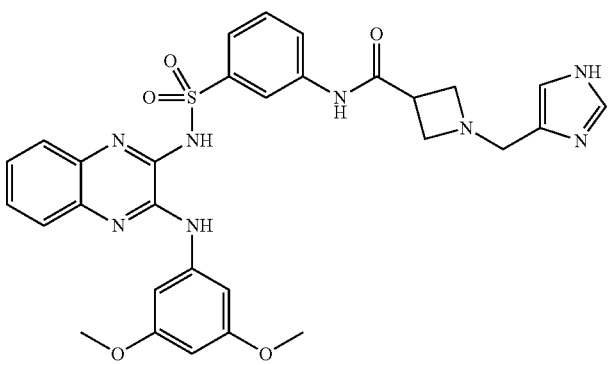 [SMILES: COc1cc(Nc2nc3ccccc3nc2NS(=O)(=O)c2cccc(NC(=O)C3CN(Cc4c[nH]cn4)C3)c2)cc(OC)c1] | N-(3-{[(3-{[3,5-bis(methoxy)phenyl]amino}quinoxalin-2-yl)amino]sulfonyl}phenyl)-1-(1H-imidazol-4-ylmethyl)azetidine-3-carboxamide |

| Cpd. No. | Structure | Name |
|---|---|---|
| 411 | 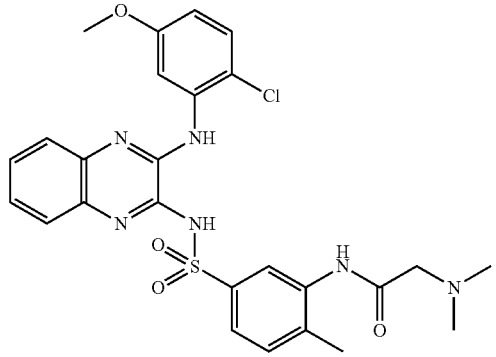 [SMILES: COc1ccc(Cl)c(Nc2nc3ccccc3nc2NS(=O)(=O)c2ccc(C)c(NC(=O)CN(C)C)c2)c1] | N-(5-{[(3-{[2-chloro-5-(methoxy)phenyl]amino}quinoxalin-2-yl)amino]sulfonyl}-2-methylphenyl)-N-2-,N-2-dimethylglycinamide |
| 412 | 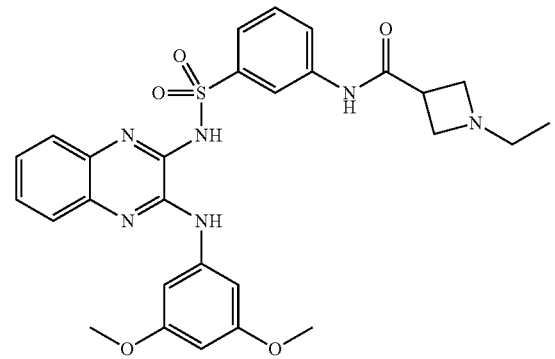 [SMILES: CCN1CC(C(=O)Nc2cccc(S(=O)(=O)Nc3nc4ccccc4nc3Nc3cc(OC)cc(OC)c3)c2)C1] | N-(3-{[(3-{[3,5-bis(methoxy)phenyl]amino}quinoxalin-2-yl)amino]sulfonyl}phenyl)-1-ethylazetidine-3-carboxamide |
| 413 | 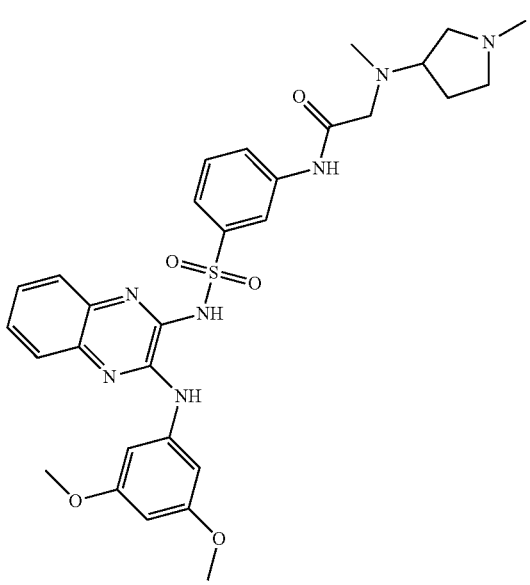 [SMILES: COc1cc(Nc2nc3ccccc3nc2NS(=O)(=O)c2cccc(NC(=O)CN(C)C3CCN(C)C3)c2)cc(OC)c1] | N-(3-{[(3-{[3,5-bis(methoxy)phenyl]amino}quinoxalin-2-yl)amino]sulfonyl}phenyl)-N-2-methyl-N-2-(1-methylpyrrolidin-3-yl)glycinamide |

TABLE 1-continued

| Cpd. No. | Structure | Name |
|---|---|---|
| 414 | 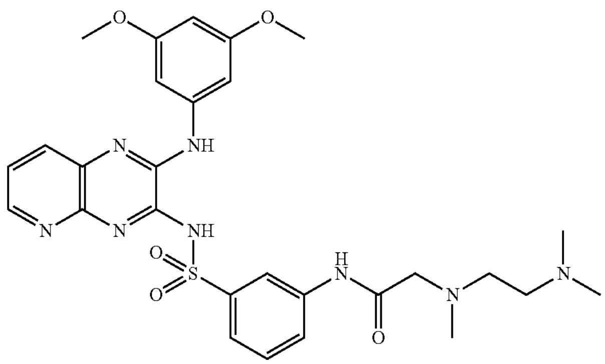 [SMILES: COc1cc(Nc2nc3cccnc3nc2NS(=O)(=O)c2cccc(NC(=O)CN(C)CCN(C)C)c2)cc(OC)c1] | N-(3-{[(2-{[3,5-bis(methoxy)phenyl]amino}pyrido[2,3-b]pyrazin-3-yl)amino]sulfonyl}phenyl)-N-2-[2-(dimethylamino)ethyl]-N-2-methylglycinaide |
| 415 | 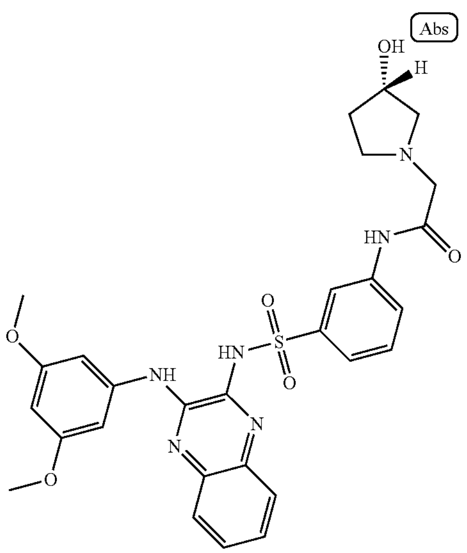 [SMILES: COc1cc(Nc2nc3ccccc3nc2NS(=O)(=O)c2cccc(NC(=O)CN3CC[C@H](O)C3)c2)cc(OC)c1] | N-(3-{[(3-{[3,5-bis(methoxy)phenyl]amino}quinoxalin-2-yl)amino]sulfonyl}phenyl)-2-[(3S)-3-hydroxypyrrolidin-1-yl]acetamide |
| 416 | 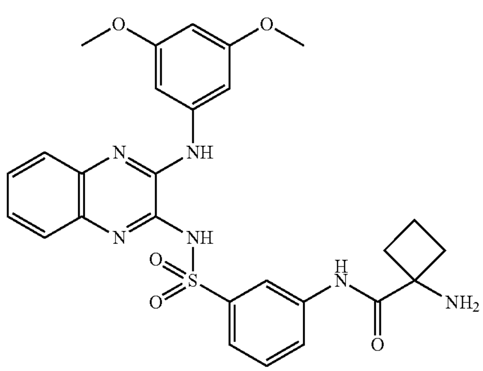 [SMILES: COc1cc(Nc2nc3ccccc3nc2NS(=O)(=O)c2cccc(NC(=O)C3(N)CCC3)c2)cc(OC)c1] | 1-amino-N-(3-{[(3-{[3,5-bis(methoxy)phenyl]amino}quinoxalin-2-yl)amino]sulfonyl}phenyl)cyclobutanecarboxamide |

TABLE 1-continued

| Cpd. No. | Structure | Name |
|---|---|---|
| 417 | 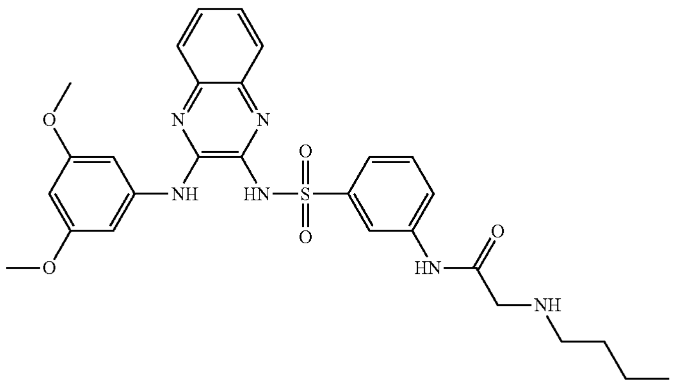 [SMILES: CCCCNCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-butylglycinamide |
| 418 | 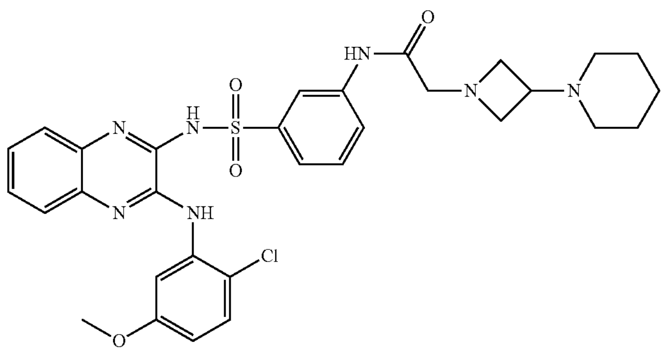 [SMILES: COc1ccc(Cl)c(Nc2nc3ccccc3nc2NS(=O)(=O)c2cccc(NC(=O)CN3CC(N4CCCCC4)C3)c2)c1] | N-(3-{[(3-{[2-chloro-5-(methoxy)phenyl]amino}quinoxalin-2-yl)amino]sulfonyl}phenyl)-2-(3-piperidin-1-ylazetidin-1-yl)acetamide |
| 419 | 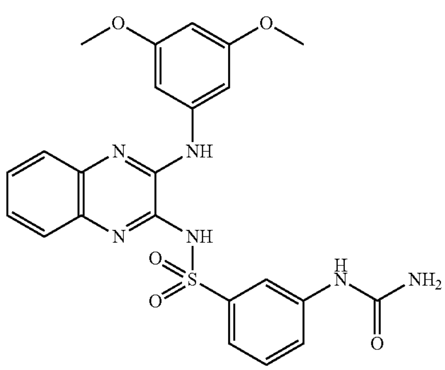 [SMILES: COc1cc(Nc2nc3ccccc3nc2NS(=O)(=O)c2cccc(NC(N)=O)c2)cc(OC)c1] | 3-[(aminocarbonyl)amino]-N-(3-{[3,5-bis(methoxy)phenyl]amino}quinoxalin-2-yl)benzenesulfonamide |
| 420 | 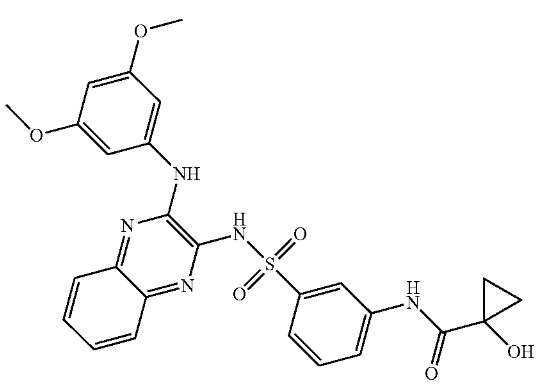 [SMILES: COc1cc(Nc2nc3ccccc3nc2NS(=O)(=O)c2cccc(NC(=O)C3(O)CC3)c2)cc(OC)c1] | N-(3-{[(3-{[3,5-bis(methoxy)phenyl]amino}quinoxalin-2-yl)amino]sulfonyl}phenyl)-1-hydroxycyclopropanecarboxamide |

TABLE 1-continued

| Cpd. No. | Structure | Name |
| --- | --- | --- |
| 421 | 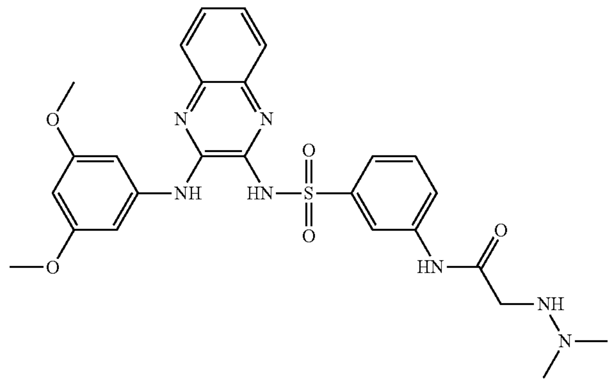 | N-(3-{[(3-{[3,5-bis(methoxy)phenyl]amino}quinoxalin-2-yl)amino]sulfonyl}phenyl)-2-(2,2-dimethylhydrazino)acetamide |
| 422 | 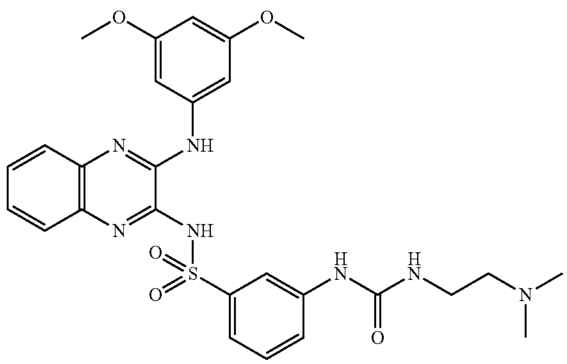 [SMILES: COc1cc(Nc2nc3ccccc3nc2NS(=O)(=O)c2cccc(NC(=O)NCCN(C)C)c2)cc(OC)c1] | N-(3-{[3,5-bis(methoxy)phenyl]amino}quinoxalin-2-yl)-3-[({[2-(dimethylamino)ethyl]amino}carbonyl)amino]benzenesulfonamide |
| 423 | 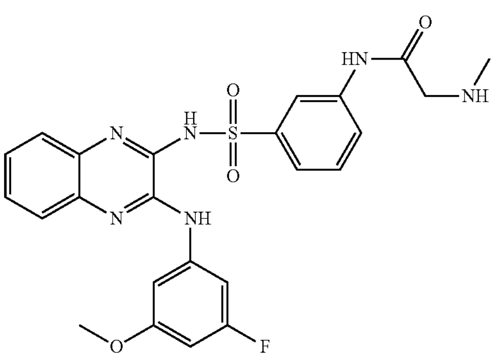 [SMILES: CNCC(=O)Nc1cccc(S(=O)(=O)Nc2nc3ccccc3nc2Nc2cc(F)cc(OC)c2)c1] | N-(3-{[(3-{[3-fluoro-5-(methoxy)phenyl]amino}quinoxalin-2-yl)amino]sulfonyl}phenyl)-N-2-methylglycinamide |
| 424 | 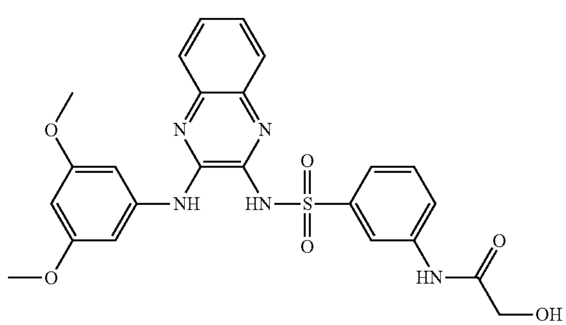 [SMILES: COc1cc(Nc2nc3ccccc3nc2NS(=O)(=O)c2cccc(NC(=O)CO)c2)cc(OC)c1] | N-(3-{[(3-{[3,5-bis(methoxy)phenyl]amino}quinoxalin-2-yl)amino]sulfonyl}phenyl)-2-hydroxyacetamide |

TABLE 1-continued

| Cpd. No. | Structure | Name |
|---|---|---|
| 425 | 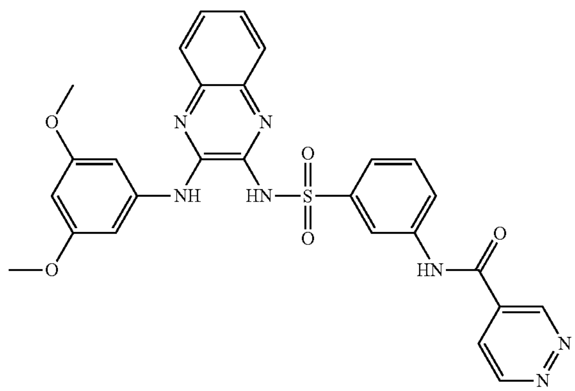 [SMILES: COc1cc(Nc2nc3ccccc3nc2NS(=O)(=O)c2cccc(NC(=O)c3ccnnc3)c2)cc(OC)c1] | N-(3-{[(3-{[3,5-bis(methoxy) phenyl]amino}quinoxalin-2-yl) amino]sulfonyl}phenyl) pyridazine-4-carboxamide |
| 426 | 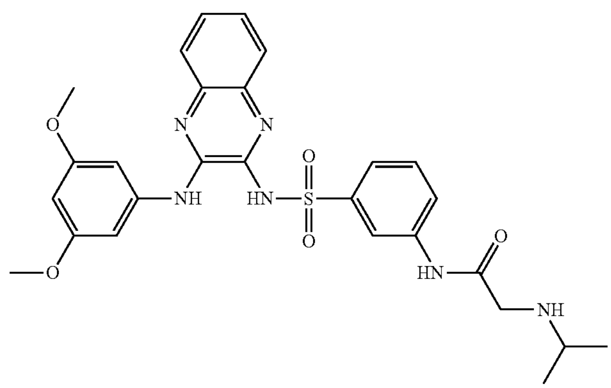 [SMILES: COc1cc(Nc2nc3ccccc3nc2NS(=O)(=O)c2cccc(NC(=O)CNC(C)C)c2)cc(OC)c1] | N-(3-{[(3-{[3,5-bis(methoxy) phenyl]amino}quinoxalin-2-yl) amino]sulfonyl}phenyl)-N-2-(1-methylethyl)glycinamide |
| 427 | 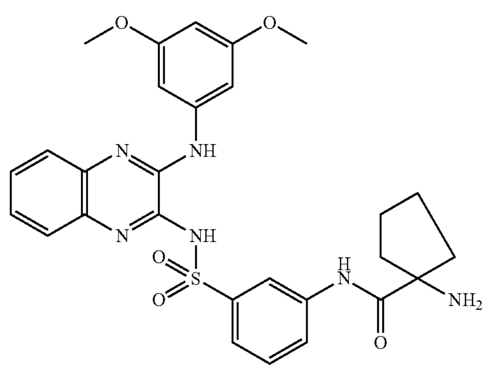 [SMILES: COc1cc(Nc2nc3ccccc3nc2NS(=O)(=O)c2cccc(NC(=O)C3(N)CCCC3)c2)cc(OC)c1] | 1-amino-N-(3-{[(3-{[3,5-bis (methoxy)phenyl]amino} quinoxalin-2-yl)amino] sulfonyl}phenyl) cyclopentanecarboxamide |
| 428 | 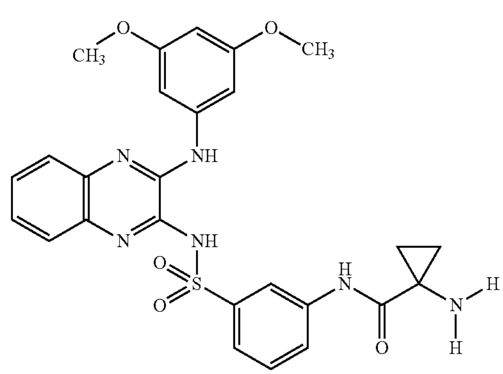 [SMILES: COc1cc(Nc2nc3ccccc3nc2NS(=O)(=O)c2cccc(NC(=O)C3(N)CC3)c2)cc(OC)c1] | 1-amino-N-(3-{[(3-{[3,5-bis (methoxy)phenyl]amino} quinoxalin-2-yl)amino] sulfonyl}phenyl) cyclopropanecarboxamide |

TABLE 1-continued

| Cpd. No. | Structure | Name |
|---|---|---|
| 429 | 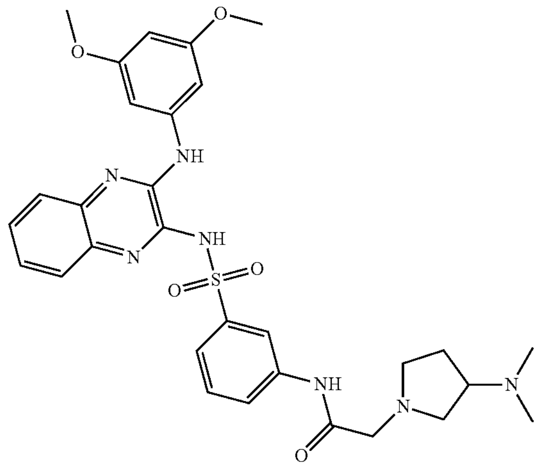 [SMILES: COc1cc(Nc2nc3ccccc3nc2NS(=O)(=O)c2cccc(NC(=O)CN3CCC(N(C)C)C3)c2)cc(OC)c1] | N-(3-{[(3-{[3,5-bis(methoxy)phenyl]amino}quinoxalin-2-yl)amino]sulfonyl}phenyl)-2-[3-(dimethylamino)pyrrolidin-1-yl]acetamide |
| 430 | 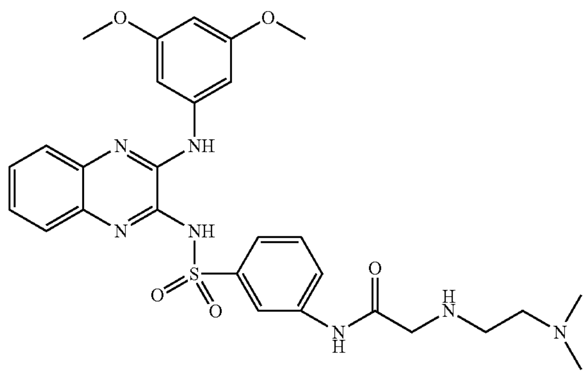 [SMILES: COc1cc(Nc2nc3ccccc3nc2NS(=O)(=O)c2cccc(NC(=O)CNCCN(C)C)c2)cc(OC)c1] | N-(3-{[(3-{[3,5-bis(methoxy)phenyl]amino}quinoxalin-2-yl)amino]sulfonyl}phenyl)-N-2-[2-(dimethylamino)ethyl]glycinamide |
| 431 | 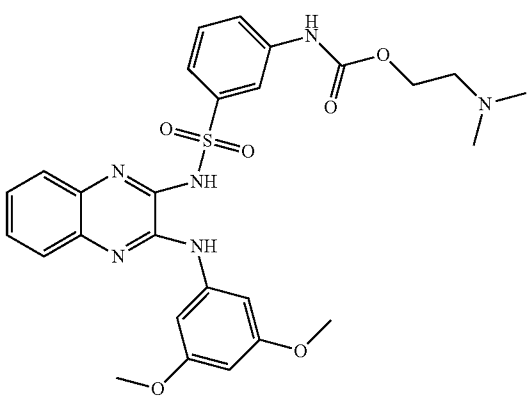 [SMILES: COc1cc(Nc2nc3ccccc3nc2NS(=O)(=O)c2cccc(NC(=O)OCCN(C)C)c2)cc(OC)c1] | 2-(dimethylamino)ethyl(3-{[(3-{[3,5-bis(methoxy)phenyl]amino}quinoxalin-2-yl)amino]sulfonyl}phenyl)carbamate |
| 432 | 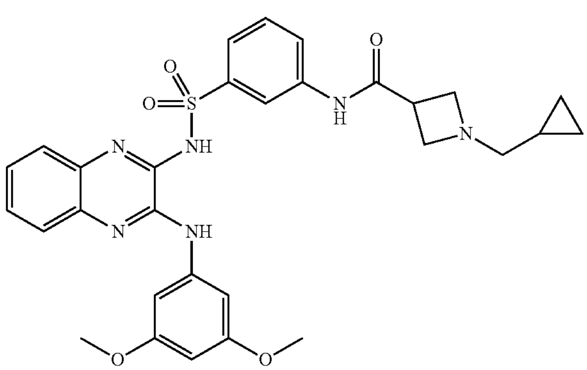 [SMILES: COc1cc(Nc2nc3ccccc3nc2NS(=O)(=O)c2cccc(NC(=O)C3CN(CC4CC4)C3)c2)cc(OC)c1] | N-(3-{[(3-{[3,5-bis(methoxy)phenyl]amino}quinoxalin-2-yl)amino]sulfonyl}phenyl)-1-(cyclopropylmethyl)azetidine-3-carboxamide |

TABLE 1-continued

| Cpd. No. | Structure | Name |
|---|---|---|
| 433 | 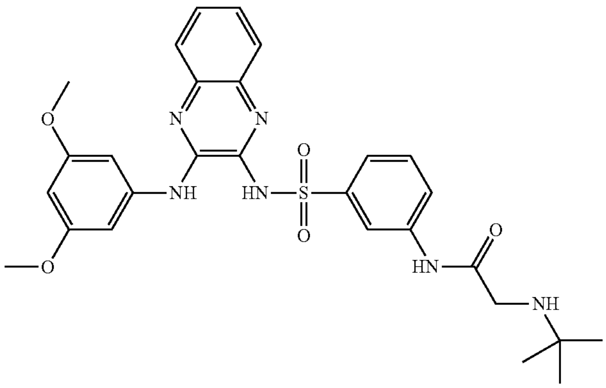 [SMILES: COc1cc(Nc2nc3ccccc3nc2NS(=O)(=O)c2cccc(NC(=O)CNC(C)(C)C)c2)cc(OC)c1] | N-(3-{[(3-{[3,5-bis(methoxy)phenyl]amino}quinoxalin-2-yl)amino]sulfonyl}phenyl)-N-2-(1,1-dimethylethyl)glycinamide |
| 434 | 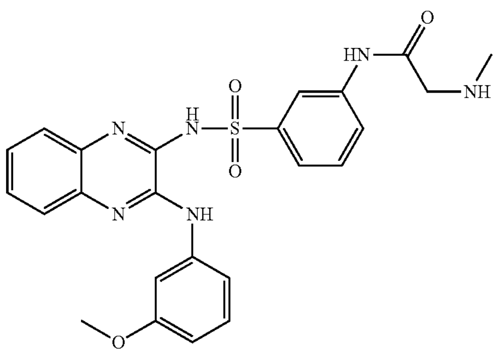 [SMILES: CNCC(=O)Nc1cccc(S(=O)(=O)Nc2nc3ccccc3nc2Nc2cccc(OC)c2)c1] | N-2-methyl-N-(3-{[(3-{[3-(methoxy)phenyl]amino}quinoxalin-2-yl)amino]sulfonyl}phenyl)glycinamide |
| 435 | 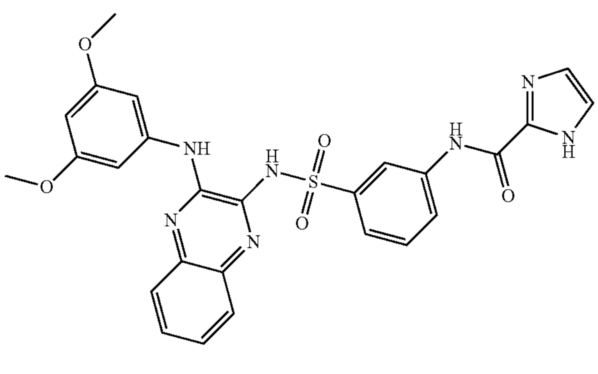 [SMILES: COc1cc(Nc2nc3ccccc3nc2NS(=O)(=O)c2cccc(NC(=O)c3ncc[nH]3)c2)cc(OC)c1] | N-(3-{[(3-{[3,5-bis(methoxy)phenyl]amino}quinoxalin-2-yl)amino]sulfonyl}phenyl)-1H-imidazole-2-carboxamide |
| 436 | 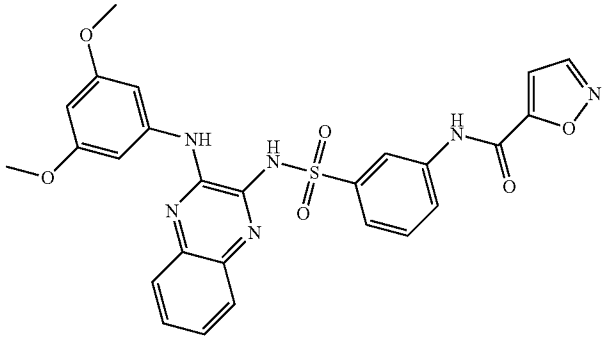 [SMILES: COc1cc(Nc2nc3ccccc3nc2NS(=O)(=O)c2cccc(NC(=O)c3ccno3)c2)cc(OC)c1] | N-(3-{[(3-{[3,5-bis(methoxy)phenyl]amino}quinoxalin-2-yl)amino]sulfonyl}phenyl)isoxazole-5-carboxamide |

| Cpd. No. | Structure | Name |
|---|---|---|
| 437 | 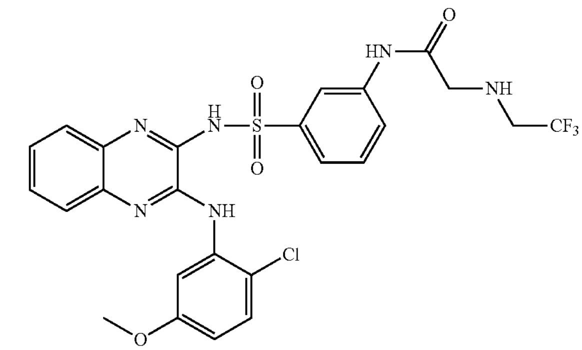 [SMILES: COc1ccc(Cl)c(Nc2nc3ccccc3nc2NS(=O)(=O)c2cccc(NC(=O)CNCC(F)(F)F)c2)c1] | N-(3-{[(3-{[2-chloro-5-(methoxy)phenyl]amino}quinoxalin-2-yl)amino]sulfonyl}phenyl)-N-2-(2,2,2-trifluoroethyl)glycinamide |
| 438 | 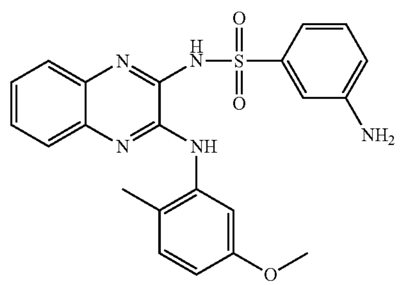 | 3-amino-N-(3-{[2-methyl-5-(methoxy)phenyl]amino}quinoxalin-2-yl)benzenesulfonamide |
| 439 | 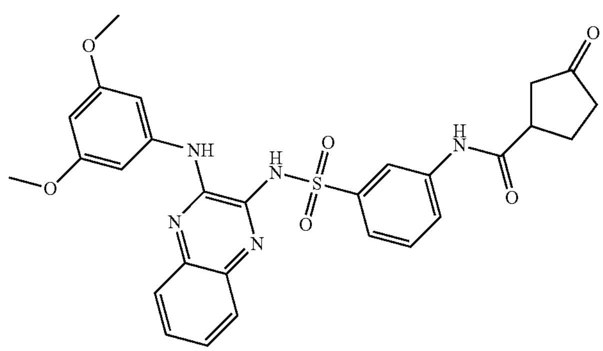 [SMILES: COc1cc(Nc2nc3ccccc3nc2NS(=O)(=O)c2cccc(NC(=O)C3CCC(=O)C3)c2)cc(OC)c1] | N-(3-{[(3-{[3,5-bis(methoxy)phenyl]amino}quinoxalin-2-yl)amino]sulfonyl}phenyl)-3-oxocyclopentanecarboxamide |
| 440 | 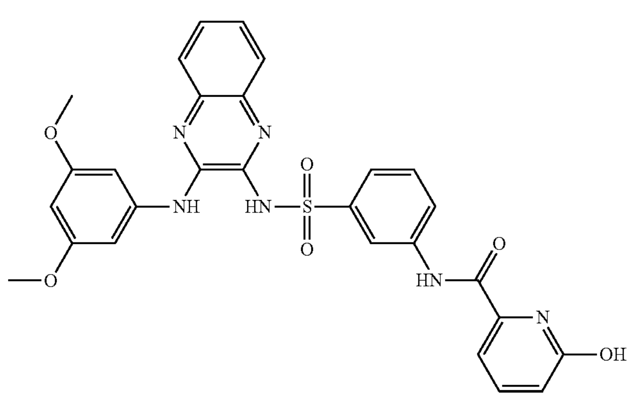 [SMILES: COc1cc(Nc2nc3ccccc3nc2NS(=O)(=O)c2cccc(NC(=O)c3cccc(O)n3)c2)cc(OC)c1] | N-(3-{[(3-{[3,5-bis(methoxy)phenyl]amino}quinoxalin-2-yl)amino]sulfonyl}phenyl)-6-hydroxypyridine-2-carboxamide |

TABLE 1-continued

| Cpd. No. | Structure | Name |
|---|---|---|
| 441 | 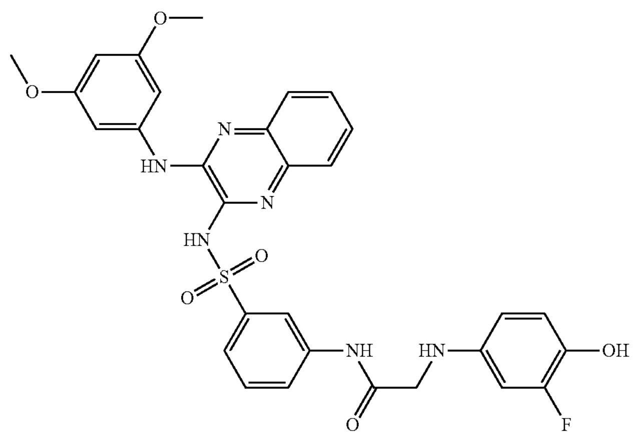 [SMILES: COc1cc(Nc2nc3ccccc3nc2NS(=O)(=O)c2cccc(NC(=O)CNc3ccc(O)c(F)c3)c2)cc(OC)c1] | N-(3-{[(3-{[3,5-bis(methoxy) phenyl]amino}quinoxalin-2-yl)amino]sulfonyl}phenyl)-N-2-(3-fluoro-4-hydroxyphenyl) glycinamide |
| 442 | 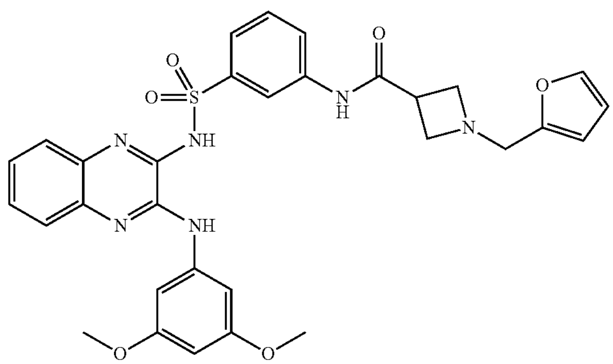 [SMILES: COc1cc(Nc2nc3ccccc3nc2NS(=O)(=O)c2cccc(NC(=O)C3CN(Cc4ccco4)C3)c2)cc(OC)c1] | N-(3-{[(3-{[3,5-bis(methoxy) phenyl]amino}quinoxalin-2-yl)amino]sulfonyl}phenyl)-1-(furan-2-ylmethyl)azetidine-3-carboxamide |
| 443 | 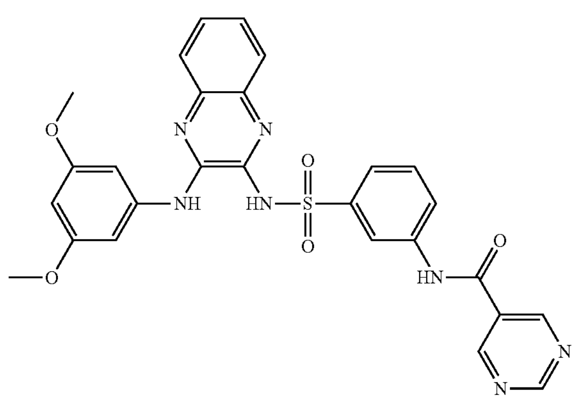 | N-(3-{[(3-{[3,5-bis(methoxy) phenyl]amino}quinoxalin-2-yl)amino]sulfonyl}phenyl) pyrimidine-5-carboxamide |
| 444 | 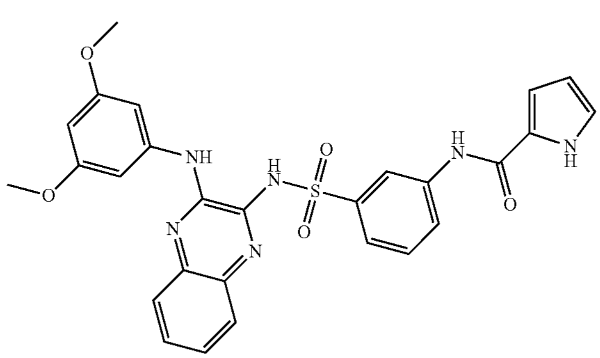 | N-(3-{[(3-{[3,5-bis(methoxy) phenyl]amino}quinoxalin-2-yl)amino]sulfonyl}phenyl)-1H-pyrrole-2-carboxamide |

TABLE 1-continued

| Cpd. No. | Structure | Name |
|---|---|---|
| 445 | 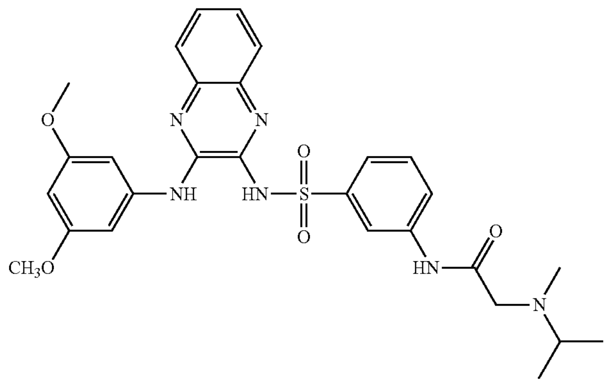 | N-(3-{[(3-{[3,5-bis(methoxy)phenyl]amino}quinoxalin-2-yl)amino]sulfonyl}phenyl)-N-2-methyl-N-2-(1-methylethyl)glycinamide |
| 446 | 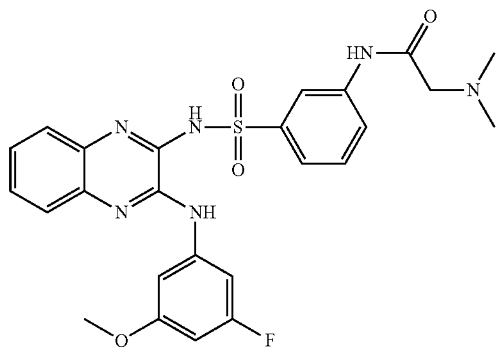 [SMILES: COc1cc(F)cc(Nc2nc3ccccc3nc2NS(=O)(=O)c2cccc(NC(=O)CN(C)C)c2)c1] | N-(3-{[(3-{[3-fluoro-5-(methoxy)phenyl]amino}quinoxalin-2-yl)amino]sulfonyl}phenyl)-N-2-,N-2-dimethylglycinamide |
| 447 | 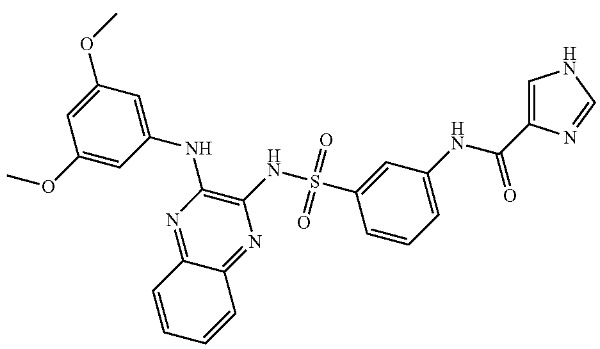 [SMILES: COc1cc(Nc2nc3ccccc3nc2NS(=O)(=O)c2cccc(NC(=O)c3c[nH]cn3)c2)cc(OC)c1] | N-(3-{[(3-{[3,5-bis(methoxy)phenyl]amino}quinoxalin-2-yl)amino]sulfonyl}phenyl)-1H-imidazole-4-carboxamide |
| 448 | 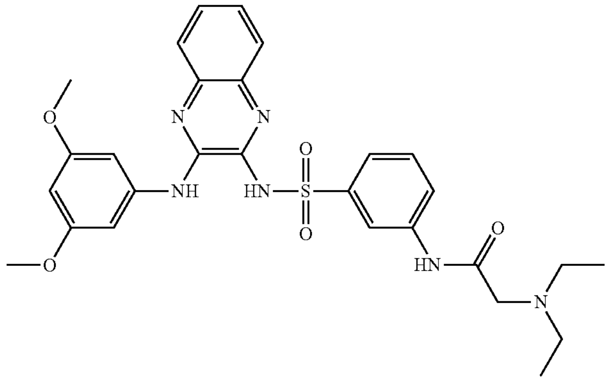 [SMILES: CCN(CC)CC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-,N-2-diethylglycinamide |

TABLE 1-continued

| Cpd. No. | Structure | Name |
|---|---|---|
| 449 | 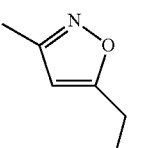 | N-(3-{[(3-{[3,5-bis(methoxy)phenyl]amino}quinoxalin-2-yl)amino]sulfonyl}phenyl)-2-(3-methylisoxazol-5-yl)acetamide |
| 450 | 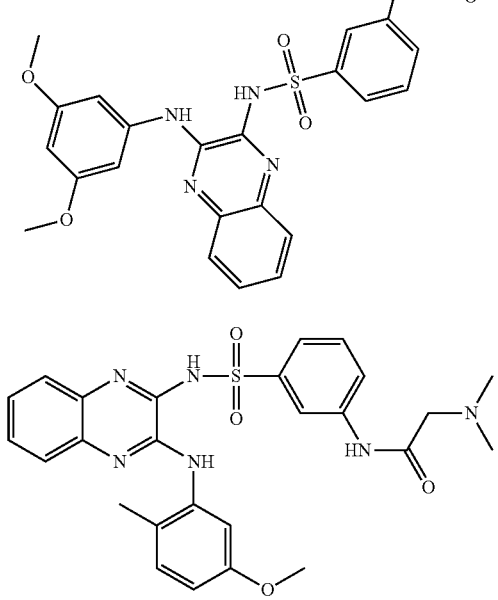 | N-2-,N-2-dimethyl-N-(3-{[(3-{[2-methyl-5-(methoxy)phenyl]amino}quinoxalin-2-yl)amino]sulfonyl}phenyl)glycinamide |
| 451 | 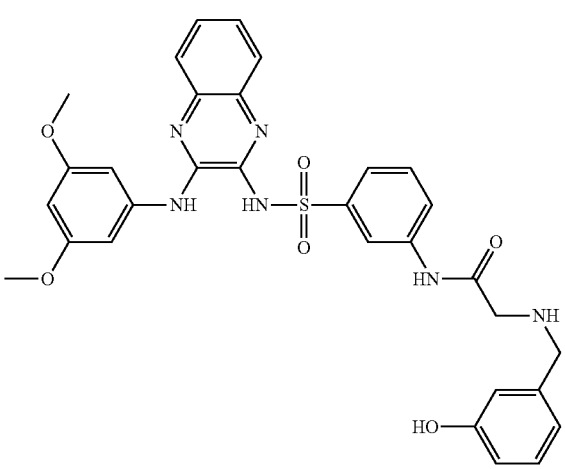 [SMILES: COc1cc(Nc2nc3ccccc3nc2NS(=O)(=O)c2cccc(NC(=O)CNCc3cccc(O)c3)c2)cc(OC)c1] | N-(3-{[(3-{[3,5-bis(methoxy)phenyl]amino}quinoxalin-2-yl)amino]sulfonyl}phenyl)-N-2-[(3-hydroxyphenyl)methyl]glycinamide |
| 452 | 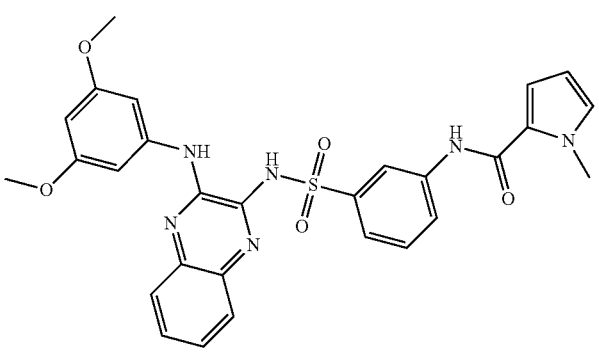 [SMILES: COc1cc(Nc2nc3ccccc3nc2NS(=O)(=O)c2cccc(NC(=O)c3cccn3C)c2)cc(OC)c1] | N-(3-{[(3-{[3,5-bis(methoxy)phenyl]amino}quinoxalin-2-yl)amino]sulfonyl}phenyl)-1-methyl-1H-pyrrole-2-carboxamide |

TABLE 1-continued

| Cpd. No. | Structure | Name |
|---|---|---|
| 453 | 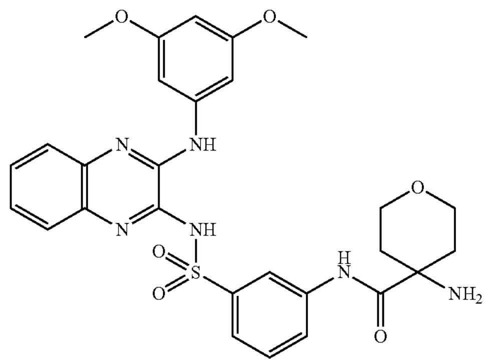 [SMILES: COc1cc(Nc2nc3ccccc3nc2NS(=O)(=O)c2cccc(NC(=O)C3(N)CCOCC3)c2)cc(OC)c1] | 4-amino-N-(3-{[(3-{[3,5-bis(methoxy)phenyl]amino}quinoxalin-2-yl)amino]sulfonyl}phenyl)tetrahydro-2H-pyran-4-carboxamide |
| 454 | 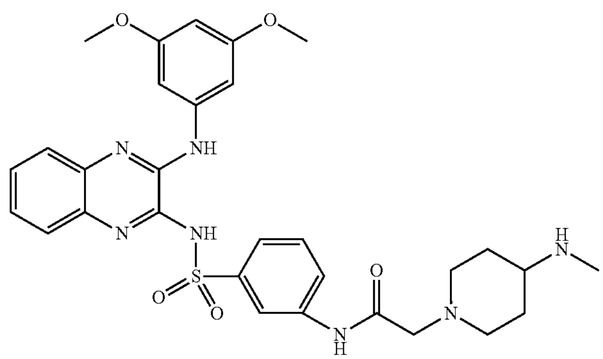 [SMILES: CNC1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methoxy)phenyl]amino}quinoxalin-2-yl)amino]sulfonyl}phenyl)-2-[4-(methylamino)piperidin-1-yl]acetamide |
| 455 | 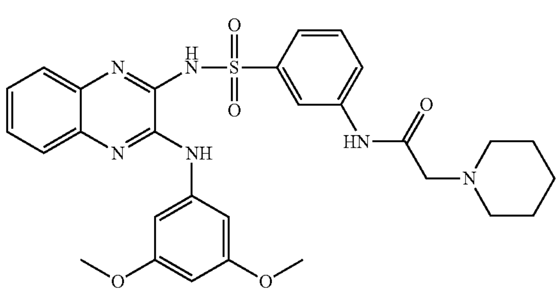 [SMILES: COc1cc(Nc2nc3ccccc3nc2NS(=O)(=O)c2cccc(NC(=O)CN3CCCCC3)c2)cc(OC)c1] | N-(3-{[(3-{[3,5-bis(methoxy)phenyl]amino}quinoxalin-2-yl)amino]sulfonyl}phenyl)-2-piperidin-1-ylacetamide |
| 456 | 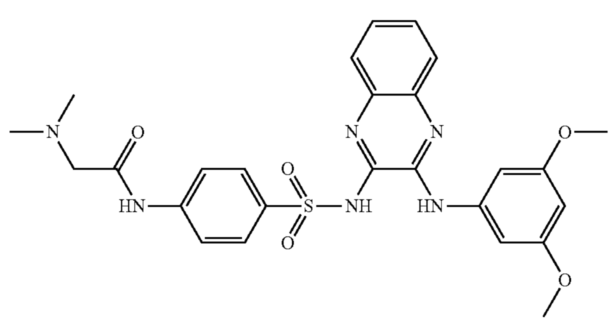 | N-(4-{[(3-{[3,5-bis(methoxy)phenyl]amino}quinoxalin-2-yl)amino]sulfonyl}phenyl)-N-2-,N-2-dimethylglycinamide |

| Cpd. No. | Structure | Name |
|---|---|---|
| 457 | 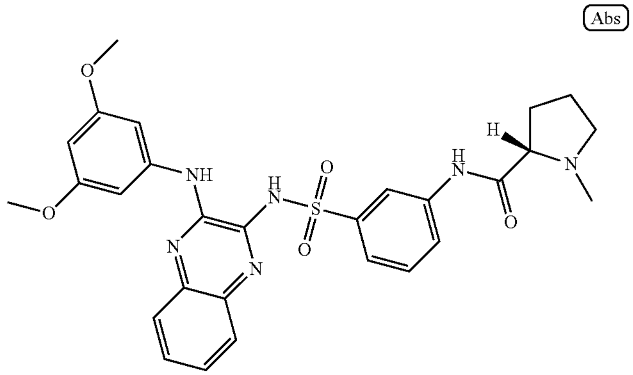 [SMILES: COc1cc(Nc2nc3ccccc3nc2NS(=O)(=O)c2cccc(NC(=O)[C@@H]3CCCN3C)c2)cc(OC)c1] | N-(3-{[(3-{[3,5-bis(methoxy)phenyl]amino}quinoxalin-2-yl)amino]sulfonyl}phenyl)-1-methyl-L-prolinamide |
| 458 | 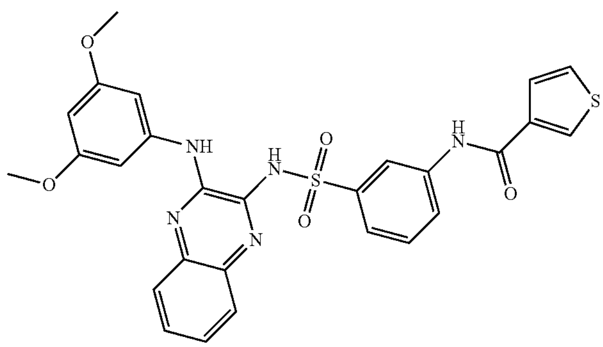 [SMILES: COc1cc(Nc2nc3ccccc3nc2NS(=O)(=O)c2cccc(NC(=O)c3ccsc3)c2)cc(OC)c1] | N-(3-{[(3-{[3,5-bis(methoxy)phenyl]amino}quinoxalin-2-yl)amino]sulfonyl}phenyl)thiophene-3-carboxamide |
| 459 | 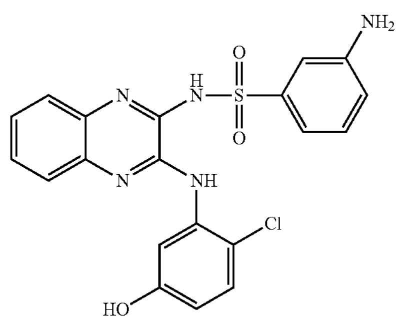 [SMILES: Nc1cccc(S(=O)(=O)Nc2nc3ccccc3nc2Nc2cc(O)ccc2Cl)c1] | 3-amino-N-{3-[(2-chloro-5-hydroxyphenyl)amino]quinoxalin-2-yl}benzenesulfonamide |
| 460 | 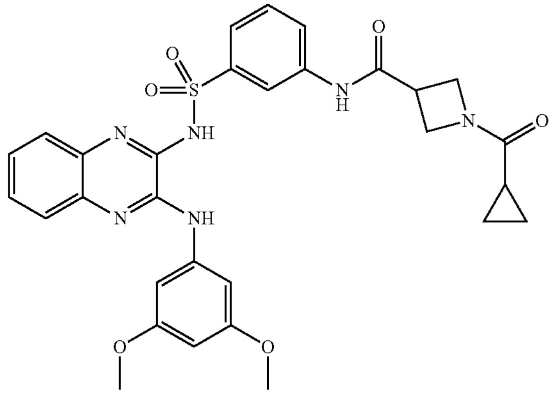 [SMILES: COc1cc(Nc2nc3ccccc3nc2NS(=O)(=O)c2cccc(NC(=O)C3CN(C(=O)C4CC4)C3)c2)cc(OC)c1] | N-(3-{[(3-{[3,5-bis(methoxy)phenyl]amino}quinoxalin-2-yl)amino]sulfonyl}phenyl)-1-(cyclopropylcarbonyl)azetidine-3-carboxamide |

| Cpd. No. | Structure | Name |
|---|---|---|
| 461 | 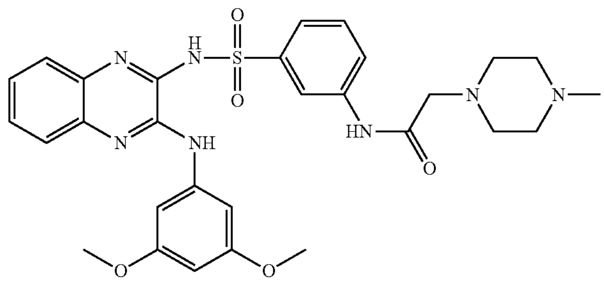 [SMILES: COc1cc(Nc2nc3ccccc3nc2NS(=O)(=O)c2cccc(NC(=O)CN3CCN(C)CC3)c2)cc(OC)c1] | N-(3-{[(3-{[3,5-bis(methoxy)phenyl]amino}quinoxalin-2-yl)amino]sulfonyl}phenyl)-2-(4-methylpiperazin-1-yl)acetamide |
| 462 | 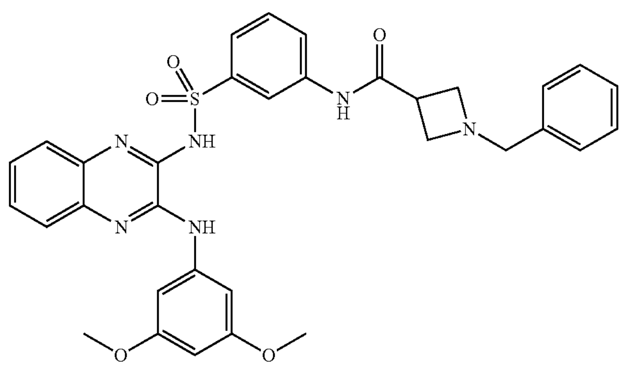 [SMILES: COc1cc(Nc2nc3ccccc3nc2NS(=O)(=O)c2cccc(NC(=O)C3CN(Cc4ccccc4)C3)c2)cc(OC)c1] | N-(3-{[(3-{[3,5-bis(methoxy)phenyl]amino(quinoxalin-2-yl)amino]sulfonyl}phenyl)-1-(phenylmethyl)azetidine-3-carboxamide |
| 463 | 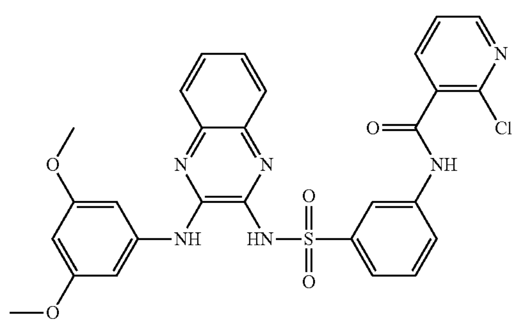 [SMILES: COc1cc(Nc2nc3ccccc3nc2NS(=O)(=O)c2cccc(NC(=O)c3cccnc3Cl)c2)cc(OC)c1] | N-(3-{[(3-{[3,5-bis(methoxy)phenyl]amino}quinoxalin-2-yl])amino]sulfonyl}phenyl)-2-chloropyridine-3-carboxamide |
| 464 | 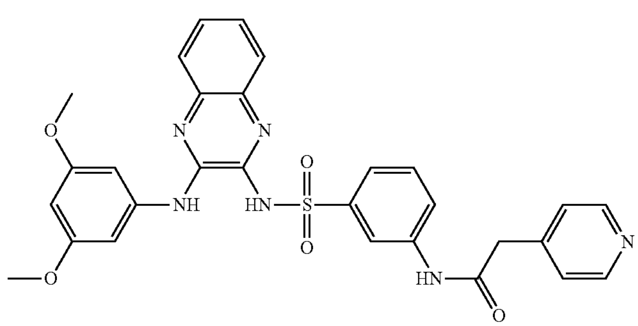 [SMILES: COc1cc(Nc2nc3ccccc3nc2NS(=O)(=O)c2cccc(NC(=O)Cc3ccncc3)c2)cc(OC)c1] | N-(3-{[(3-{[3,5-bis(methoxy)phenyl]amino}quinoxalin-2-yl)amino]sulfonyl}phenyl)-2-pyridin-4-ylacetamide |

TABLE 1-continued

| Cpd. No. | Structure | Name |
|---|---|---|
| 465 | 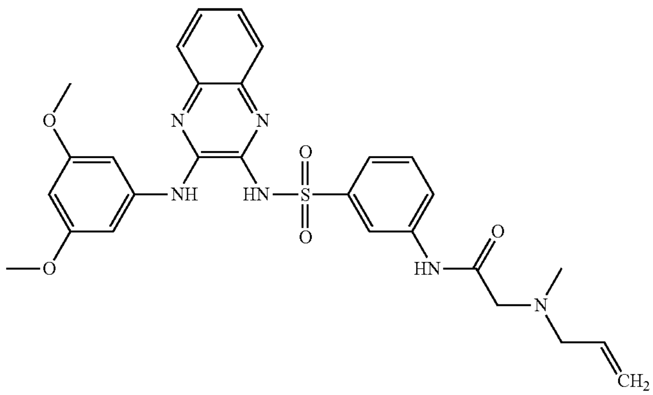 [SMILES: C=CCN(C)CC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-methyl-N-2-prop-2-en-1-ylglycinamide |
| 466 | 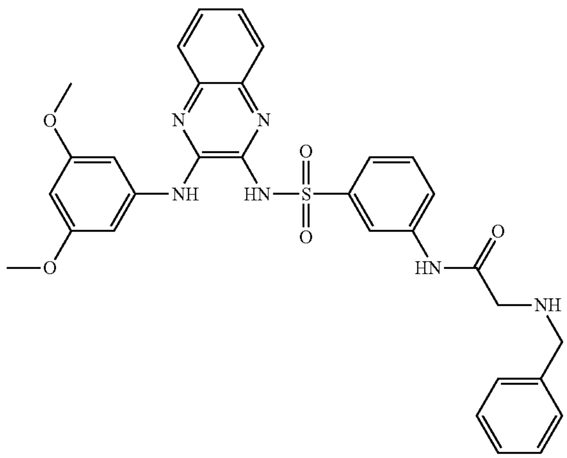 [SMILES: COc1cc(Nc2nc3ccccc3nc2NS(=O)(=O)c2cccc(NC(=O)CNCc3ccccc3)c2)cc(OC)c1] | N-(3-{[(3-{[3,5-bis(methoxy)phenyl]amino}quinoxalin-2-yl)amino]sulfonyl}phenyl)-N-2-(phenylmethyl)glycinamide |
| 467 | 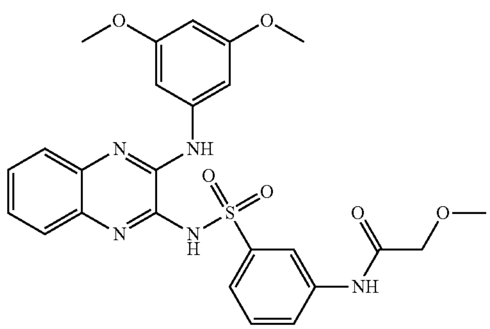 [SMILES: COCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-2-(methoxy)acetamide |
| 468 | 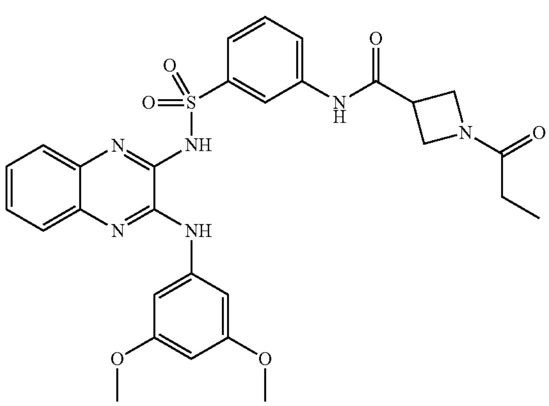 [SMILES: CCC(=O)N1CC(C(=O)Nc2cccc(S(=O)(=O)Nc3nc4ccccc4nc3Nc3cc(OC)cc(OC)c3)c2)C1] | N-(3-{[(3-{[3,5-bis(methoxy)phenyl]amino}quinoxalin-2-yl)amino]sulfonyl}phenyl)-1-propanoylazetidine-3-carboxamide |

TABLE 1-continued

| Cpd. No. | Structure | Name |
|---|---|---|
| 469 | 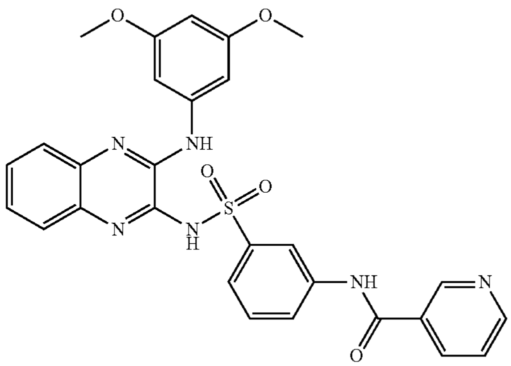 [SMILES: COc1cc(Nc2nc3ccccc3nc2NS(=O)(=O)c2cccc(NC(=O)c3cccnc3)c2)cc(OC)c1] | N-(3-{[(3-{[3,5-bis(methoxy)phenyl]amino}quinoxalin-2-yl)amino]sulfonyl}phenyl)pyridine-3-carboxamide |
| 470 | 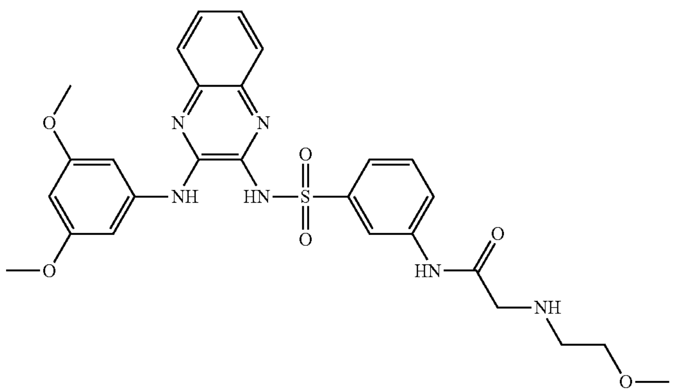 | N-(3-{[(3-{[3,5-bis(methoxy)phenyl]amino}quinoxalin-2-yl)amino]sulfonyl}phenyl)-N-2-[2-(methoxy)ethyl]glycinamide |
| 471 | 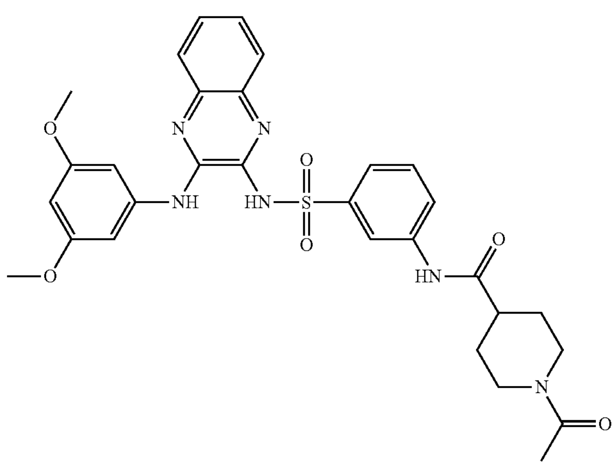 [SMILES: COc1cc(Nc2nc3ccccc3nc2NS(=O)(=O)c2cccc(NC(=O)C3CCN(C(C)=O)CC3)c2)cc(OC)c1] | 1-acetyl-N-3-{[(3-{[3,5-bis(methoxy)phenyl]amino}quinoxalin-2-yl)amino]sulfonyl}phenyl)piperidine-4-carboxamide |

TABLE 1-continued

| Cpd. No. | Structure | Name |
|---|---|---|
| 472 | 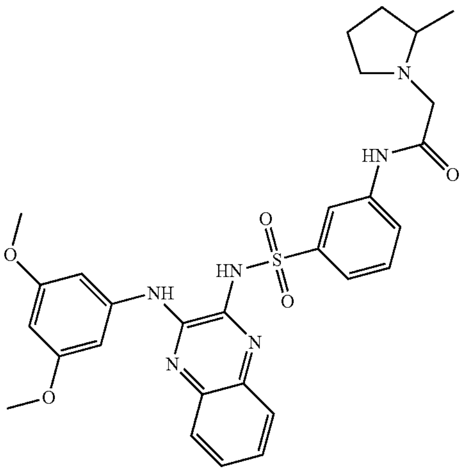 | N-(3-{[(3-{[3,5-bis (methoxy)phenyl]amino} quinoxalin-2-yl)amino] sulfonyl}phenyl)-2-(2-methylpyrrolidin-1-yl) acetamide |
| 473 | 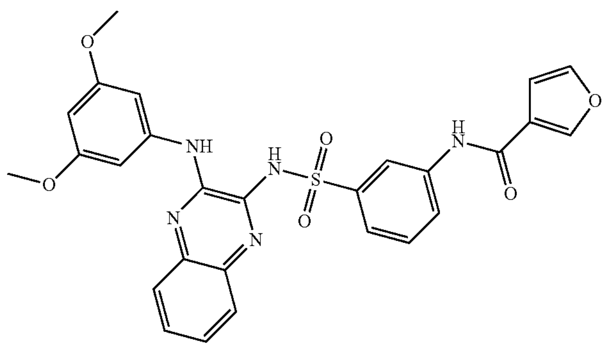 [SMILES: COc1cc(Nc2nc3ccccc3nc2NS(=O)(=O)c2cccc(NC(=O)c3ccoc3)c2)cc(OC)c1] | N-(3-{[(3-{[3,5-bis (methoxy)phenyl]amino} quinoxalin-2-yl)amino] sulfonyl}phenyl)furan-3-carboxamide |
| 474 | 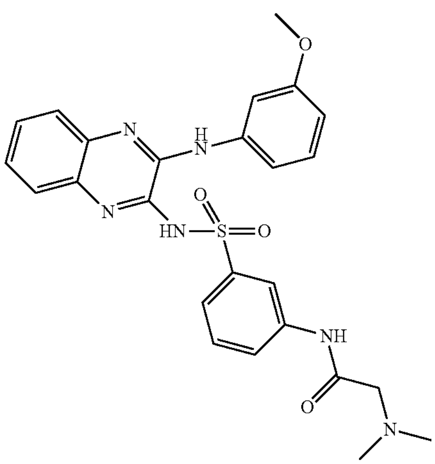 [SMILES: COc1cccc(Nc2nc3ccccc3nc2NS(=O)(=O)c2cccc(NC(=O)CN(C)C)c2)c1] | N-2-,N-2-dimethyl-N-(3-{[(3-{[3-(methoxy)phenyl] amino}quinoxalin-2-yl) amino]sulfonyl}phenyl) glycinamide |
| 475 | 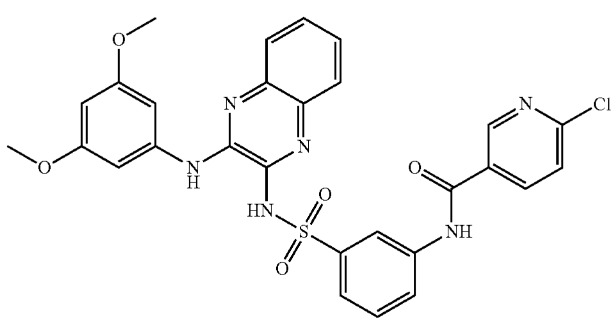 [SMILES: COc1cc(Nc2nc3ccccc3nc2NS(=O)(=O)c2cccc(NC(=O)c3ccc(Cl)nc3)c2)cc(OC)c1] | N-(3-{[(3-{[3,5-bis (methoxy)phenyl]amino} quinoxalin-2-yl)amino] sulfonyl}phenyl)-6-chloropyridine-3-carboxamide |

TABLE 1-continued

| Cpd. No. | Structure | Name |
|---|---|---|
| 476 | 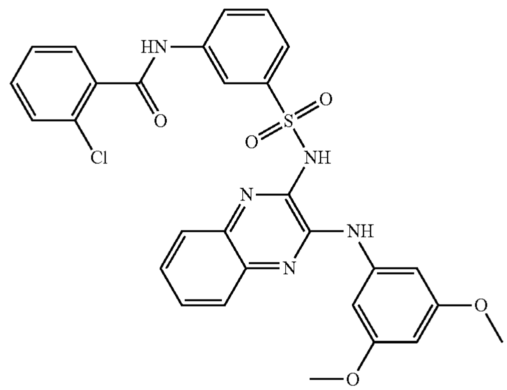 | N-(3-{[(3-{[3,5-bis(methoxy)phenyl]amino}quinoxalin-2-yl)amino]sulfonyl}phenyl)-2-chlorobenzamide |
| 477 | 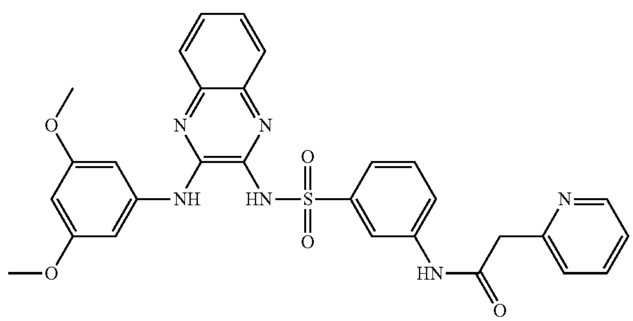 [SMILES: COc1cc(Nc2nc3ccccc3nc2NS(=O)(=O)c2cccc(NC(=O)Cc3ccccn3)c2)cc(OC)c1] | N-(3-{[(3-{[3,5-bis(methoxy)phenyl]amino}quinoxalin-2-yl)amino]sulfonyl}phenyl)-2-pyridin-2-ylacetamide |
| 478 | 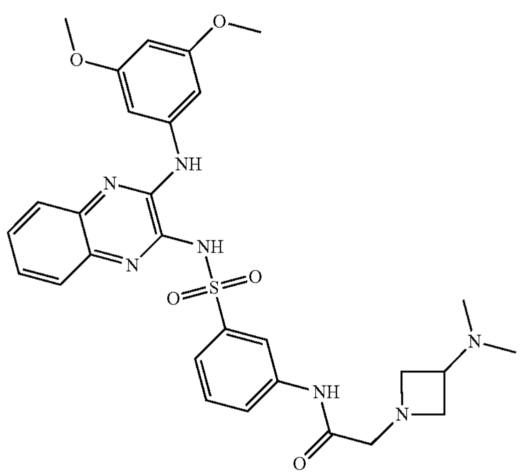 [SMILES: COc1cc(Nc2nc3ccccc3nc2NS(=O)(=O)c2cccc(NC(=O)CN3CC(N(C)C)C3)c2)cc(OC)c1] | N-(3-{[(3-{[3,5-bis(methoxy)phenyl]amino}quinoxalin-2-yl)amino]sulfonyl}phenyl)-2-[3-(dimethylamino)azetidin-1-yl]acetamide |
| 479 | 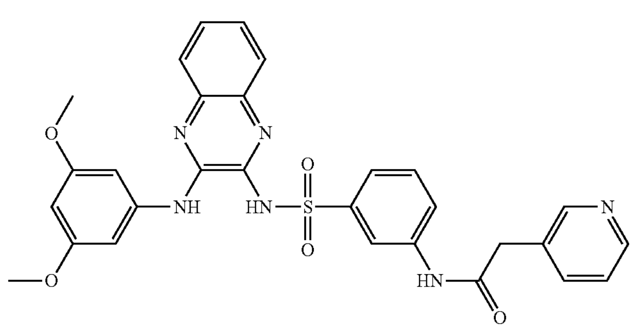 [SMILES: COc1cc(Nc2nc3ccccc3nc2NS(=O)(=O)c2cccc(NC(=O)Cc3cccnc3)c2)cc(OC)c1] | N-(3-{[(3-{[3,5-bis(methoxy)phenyl]amino}quinoxalin-2-yl)amino]sulfonyl}phenyl)-2-pyridin-3-ylacetamide |

TABLE 1-continued

| Cpd. No. | Structure | Name |
|---|---|---|
| 480 | 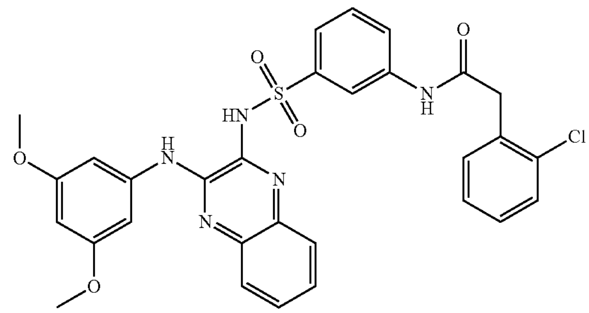 [SMILES: COc1cc(Nc2nc3ccccc3nc2NS(=O)(=O)c2cccc(NC(=O)Cc3ccccc3Cl)c2)cc(OC)c1] | N-(3-{[(3-{[3,5-bis(methoxy)phenyl]amino}quinoxalin-2-yl)amino]sulfonyl}phenyl)-2-(2-chlorophenyl)acetamide |
| 481 | 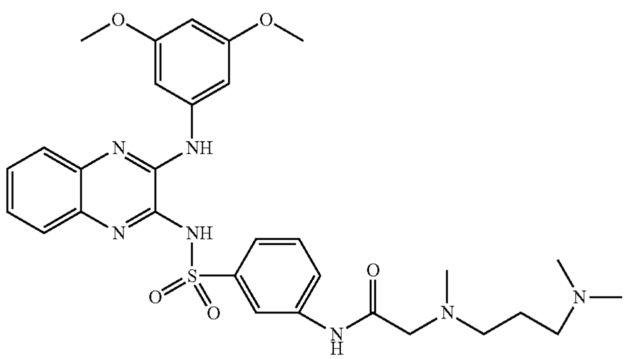 [SMILES: COc1cc(Nc2nc3ccccc3nc2NS(=O)(=O)c2cccc(NC(=O)CN(C)CCCN(C)C)c2)cc(OC)c1] | N-(3-{[(3-{[3,5-bis(methoxy)phenyl]amino}quinoxalin-2-yl)amino]sulfonyl}phenyl)-N-2-[3-(dimethylamino)propyl]-N-2-methylglycinamide |
| 482 | 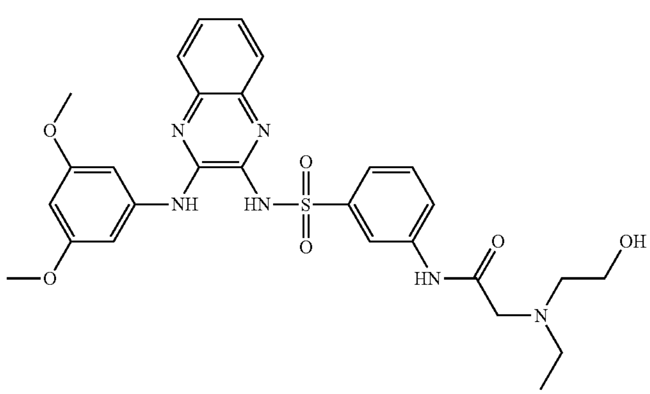 [SMILES: CCN(CCO)CC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-ethyl-N-2-(2-hydroxyethyl)glycinamide |

TABLE 1-continued

| Cpd. No. | Structure | Name |
|---|---|---|
| 483 | 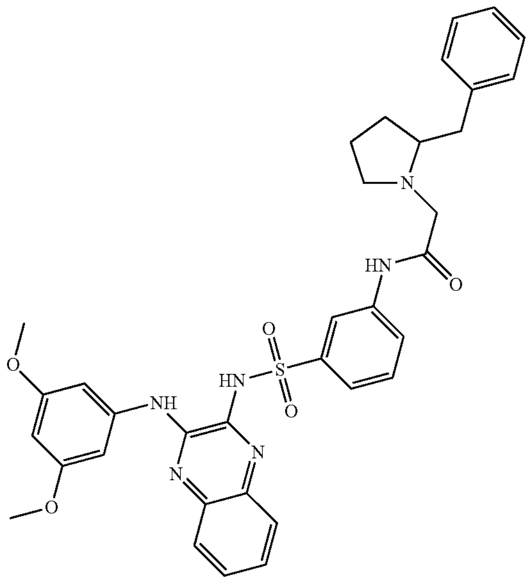 [SMILES: COc1cc(Nc2nc3ccccc3nc2NS(=O)(=O)c2cccc(NC(=O)CN3CCCC3Cc3ccccc3)c2)cc(OC)c1] | N-(3-{[(3-{[3,5-bis (methoxy)phenyl]amino} quinoxalin-2-yl)amino] sulfonyl}phenyl)-2-[2-(phenylmethyl) pyrrolidin-1-yl]acetamide |
| 484 | 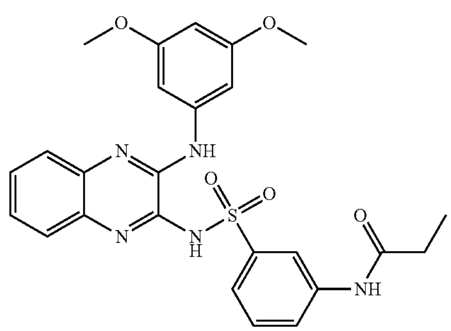 [SMILES: CCC(=O)Nc1cccc(S(=O)(=O)Nc2nc3ccccc3nc2Nc2cc(OC)cc(OC)c2)c1] | N-(3-{[(3-{[3,5-bis (methoxy)phenyl]amino} quinoxalin-2-yl)amino] sulfonyl}phenyl) propanamide |
| 485 | 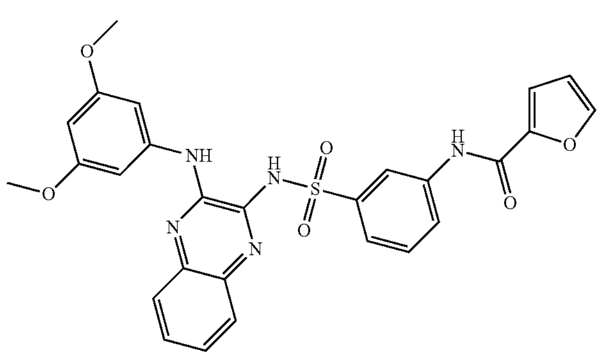 [SMILES: COc1cc(Nc2nc3ccccc3nc2NS(=O)(=O)c2cccc(NC(=O)c3ccco3)c2)cc(OC)c1] | N-(3-{[(3-{[3,5-bis (methoxy)phenyl]amino} quinoxalin-2-yl)amino] sulfonyl}phenyl)furan-2-carboxamide |

| Cpd. No. | Structure | Name |
|---|---|---|
| 486 | 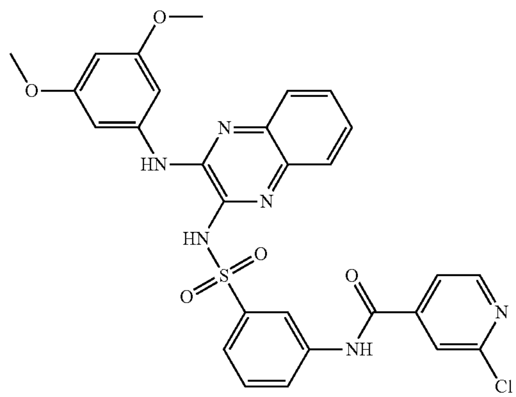 [SMILES: COc1cc(Nc2nc3ccccc3nc2NS(=O)(=O)c2cccc(NC(=O)c3ccnc(Cl)c3)c2)cc(OC)c1] | N-(3-{[(3-{[3,5-bis(methoxy)phenyl]amino}quinoxalin-2-yl)amino]sulfonyl}phenyl)-2-chloropyridine-4-carboxamide |
| 487 | 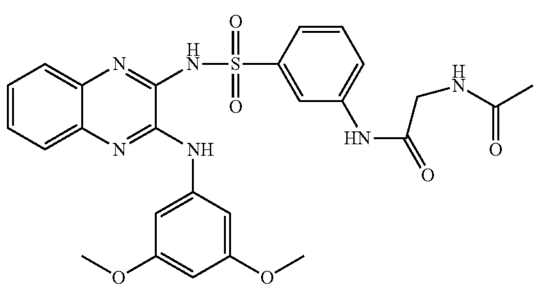 [SMILES: COc1cc(Nc2nc3ccccc3nc2NS(=O)(=O)c2cccc(NC(=O)CNC(C)=O)c2)cc(OC)c1] | N-2-acetyl-N-(3-{[(3-{[3,5-bis(methoxy)phenyl]amino}quinoxalin-2-yl)amino]sulfonyl}phenyl)glycinamide |
| 488 | 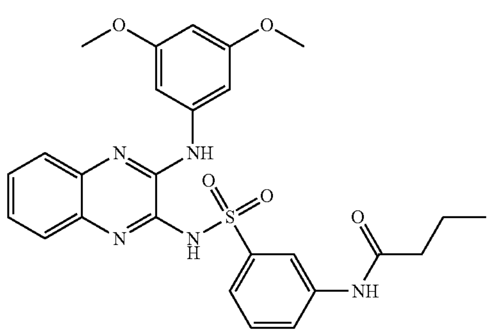 | N-(3-{[(3-{[3,5-bis(methoxy)phenyl]amino}quinoxalin-2-yl)amino]sulfonyl}phenyl)butanamide |
| 489 | 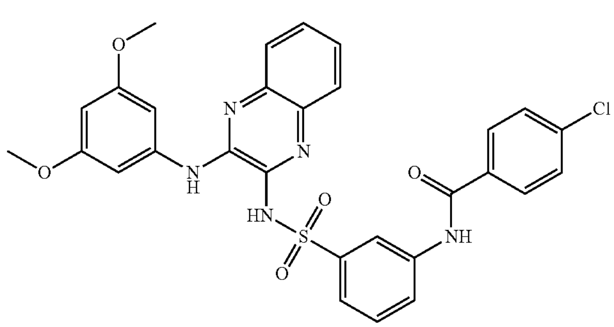 [SMILES: COc1cc(Nc2nc3ccccc3nc2NS(=O)(=O)c2cccc(NC(=O)c3ccc(Cl)cc3)c2)cc(OC)c1] | N-(3-{[(3-{[3,5-bis(methoxy)phenyl]amino}quinoxalin-2-yl)amino]sulfonyl}phenyl)-4-chlorobenzamide |

TABLE 1-continued

| Cpd. No. | Structure | Name |
|---|---|---|
| 490 | 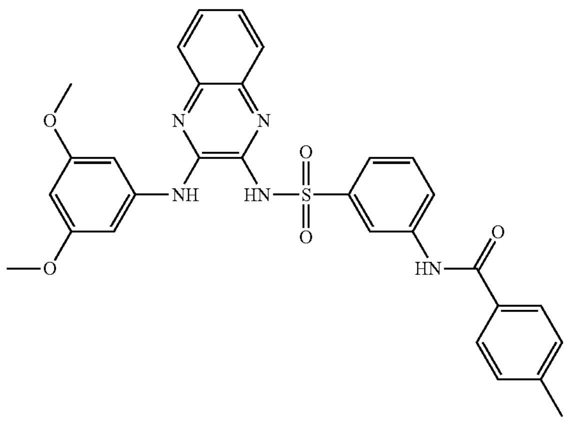 | N-(3-{[(3-{[3,5-bis(methoxy)phenyl]amino}quinoxalin-2-yl)amino]sulfonyl}phenyl)-4-methylbenzamide |
| 491 | 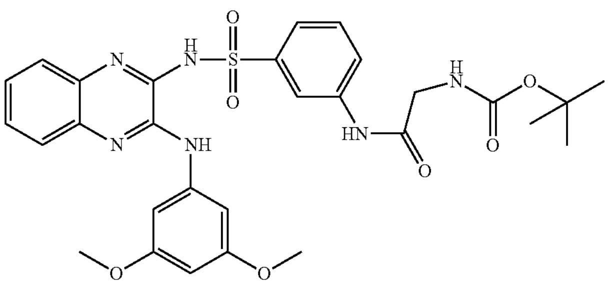 [SMILES: COc1cc(Nc2nc3ccccc3nc2NS(=O)(=O)c2cccc(NC(=O)CNC(=O)OC(C)(C)C)c2)cc(OC)c1] | 1,1-dimethylethyl{2-[(3-{[(3-{[3,5-bis(methoxy)phenyl]amino}quinoxalin-2-yl)amino]sulfonyl}phenyl)amino]-2-oxoethyl}carbamate |
| 492 | 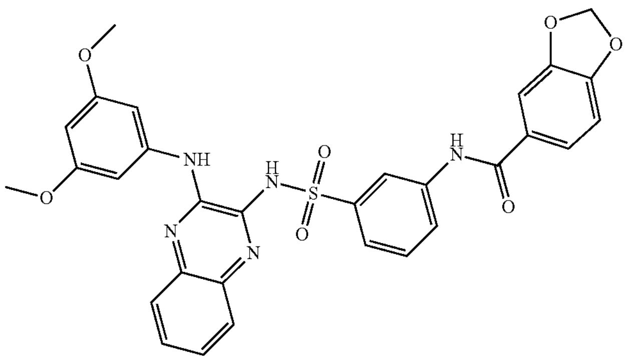 [SMILES: COc1cc(Nc2nc3ccccc3nc2NS(=O)(=O)c2cccc(NC(=O)c3ccc4c(c3)OCO4)c2)cc(OC)c1] | N-(3-{[(3-{[3,5-bis(methoxy)phenyl]amino}quinoxalin-2-yl)amino]sulfonyl}phenyl)-1,3-benzodioxole-5-carboxamide |
| 493 | 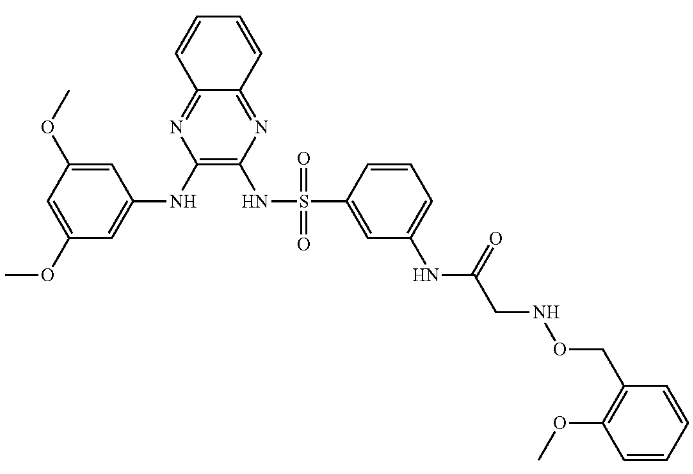 [SMILES: COc1cc(Nc2nc3ccccc3nc2NS(=O)(=O)c2cccc(NC(=O)CNOCc3ccccc3OC)c2)cc(OC)c1] | N-(3-{[(3-{[3,5-bis(methoxy)phenyl]amino}quinoxalin-2-yl)amino]sulfonyl}phenyl)-N-2-({[2-(methoxy)phenyl]methyl}oxy)glycinamid |

| Cpd. No. | Structure | Name |
|---|---|---|
| 494 | 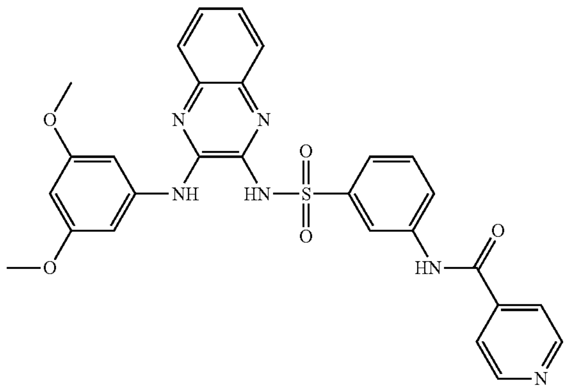 [SMILES: COc1cc(Nc2nc3ccccc3nc2NS(=O)(=O)c2cccc(NC(=O)c3ccncc3)c2)cc(OC)c1] | N-(3-{[(3-{[3,5-bis(methoxy)phenyl]amino}quinoxalin-2-yl)amino]sulfonyl}phenyl)pyridine-4-carboxamide |
| 495 | 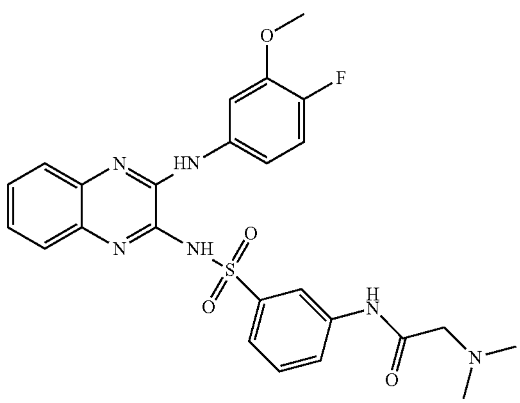 [SMILES: COc1cc(Nc2nc3ccccc3nc2NS(=O)(=O)c2cccc(NC(=O)CN(C)C)c2)ccc1F] | N-(3-{[(3-{[4-fluoro-3-(methoxy)phenyl]amino}quinoxalin-2-yl)amino]sulfonyl}phenyl)-N-2-,N-2-dimethylglycinamide |
| 496 | 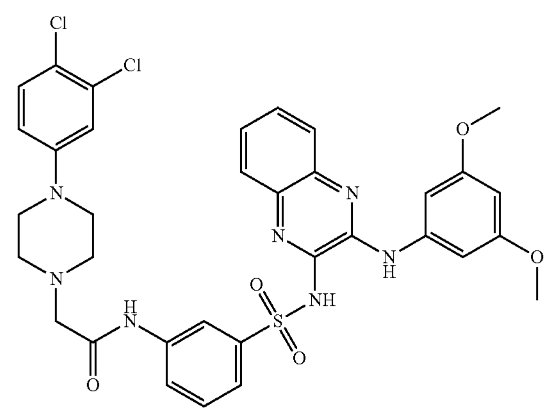 [SMILES: COc1cc(Nc2nc3ccccc3nc2NS(=O)(=O)c2cccc(NC(=O)CN3CCN(c4ccc(Cl)c(Cl)c4)CC3)c2)cc(OC)c1] | N-(3-{[(3-{[3,5-bis(methoxy)phenyl]amino}quinoxalin-2-yl)amino]sulfonyl}phenyl)-2-[4-(3,4-dichlorophenyl)piperazin-1-yl]acetamide |

TABLE 1-continued

| Cpd. No. | Structure | Name |
|---|---|---|
| 497 | 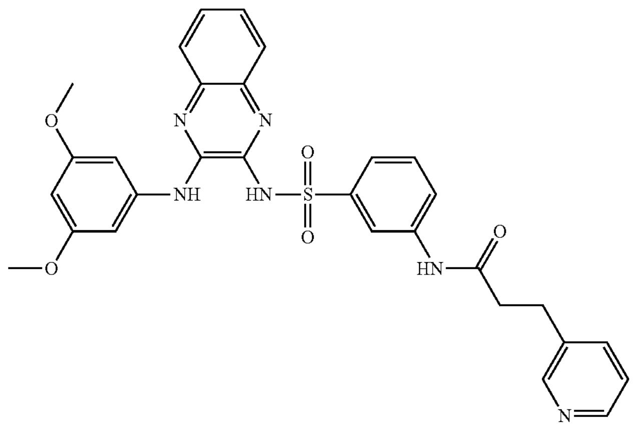 [SMILES: COc1cc(Nc2nc3ccccc3nc2NS(=O)(=O)c2cccc(NC(=O)CCc3cccnc3)c2)cc(OC)c1] | N-(3-{[(3-{[3,5-bis(methoxy)phenyl]amino}quinoxalin-2-yl)amino]sulfonyl}phenyl)-3-pyridin-3-ylpropanamide |
| 498 | 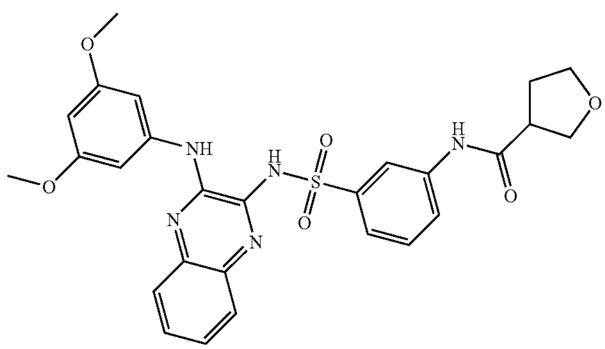 [SMILES: COc1cc(Nc2nc3ccccc3nc2NS(=O)(=O)c2cccc(NC(=O)C3CCOC3)c2)cc(OC)c1] | N-(3-{[(3-{[3,5-bis(methoxy)phenyl]amino}quinoxalin-2-yl)amino]sulfonyl}phenyl)tetrahydrofuran-3-carboxamide |
| 499 | 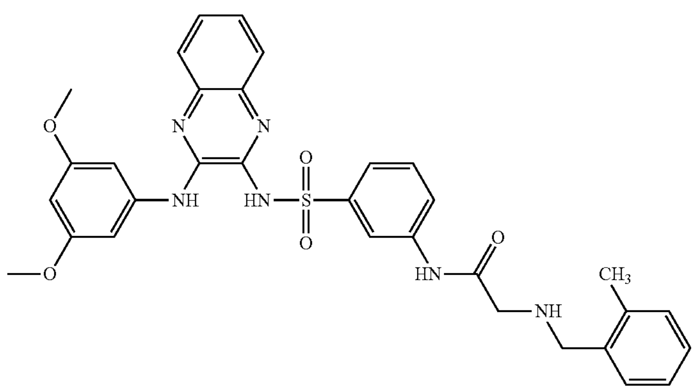 [SMILES: COc1cc(Nc2nc3ccccc3nc2NS(=O)(=O)c2cccc(NC(=O)CNCc3ccccc3C)c2)cc(OC)c1] | N-(3-{[(3-{[3,5-bis(methoxy)phenyl]amino}quinoxalin-2-yl)amino]sulfonyl}phenyl)-N-2-[(2-methylphenyl)methyl]glycinamide |
| 500 | 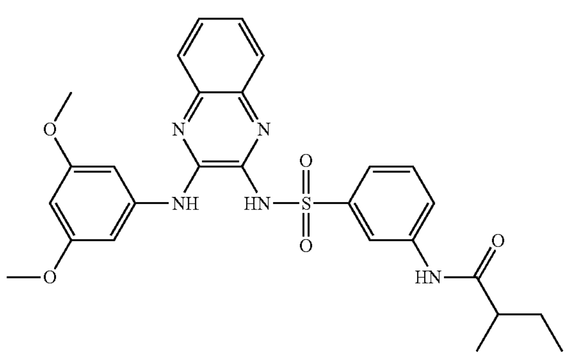 [SMILES: CCC(C)C(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-2-methylbutanamide |

TABLE 1-continued

| Cpd. No. | Structure | Name |
|---|---|---|
| 501 | 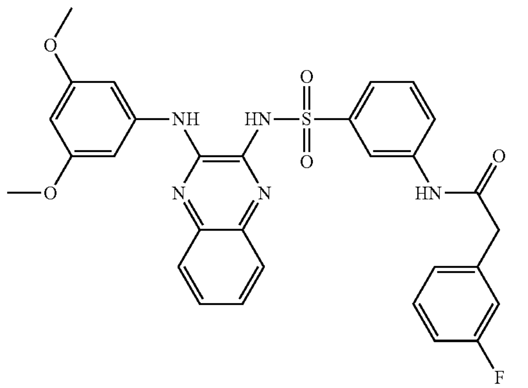 [SMILES: COc1cc(Nc2nc3ccccc3nc2NS(=O)(=O)c2cccc(NC(=O)Cc3cccc(F)c3)c2)cc(OC)c1] | N-(3-{[(3-{[3,5-bis(methoxy)phenyl]amino}quinoxalin-2-yl)amino]sulfonyl}phenyl)-2-(3-fluorophenyl)acetamide |
| 502 | 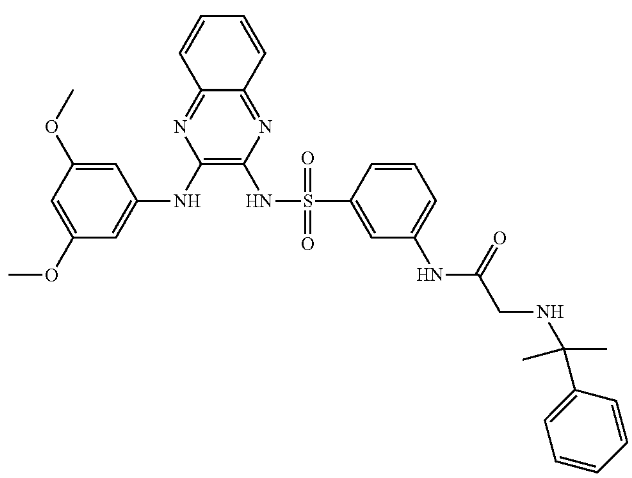 [SMILES: COc1cc(Nc2nc3ccccc3nc2NS(=O)(=O)c2cccc(NC(=O)CNC(C)(C)c3ccccc3)c2)cc(OC)c1] | N-(3-{[(3-{[3,5-bis(methoxy)phenyl]amino}quinoxalin-2-yl)amino]sulfonyl}phenyl)-N-2-(1-methyl-1-phenylethyl)glycinamide |
| 503 | 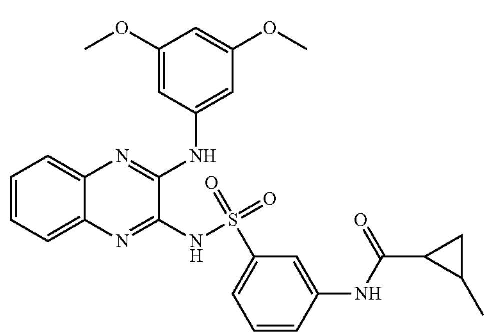 [SMILES: COc1cc(Nc2nc3ccccc3nc2NS(=O)(=O)c2cccc(NC(=O)C3CC3C)c2)cc(OC)c1] | N-(3-{[(3-{[3,5-bis(methoxy)phenyl]amino}quinoxalin-2-yl)amino]sulfonyl}phenyl)-2-methylcyclopropanecarboxamide |

TABLE 1-continued

| Cpd. No. | Structure | Name |
|---|---|---|
| 504 | 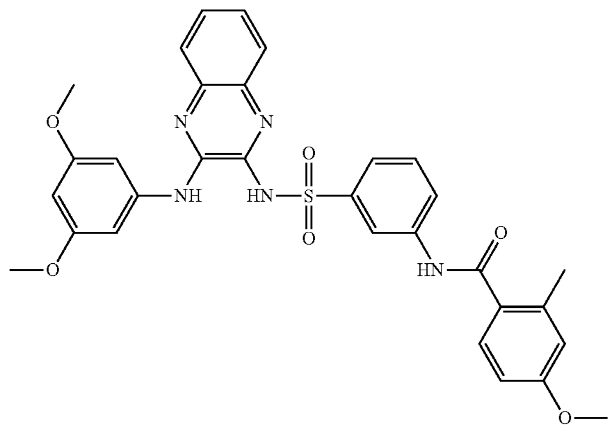 | N-(3-{[(3-{[3,5-bis(methoxy)phenyl]amino}quinoxalin-2-yl)amino]sulfonyl}phenyl)-2-methyl-4-(methoxy)benzamide |
| 505 | 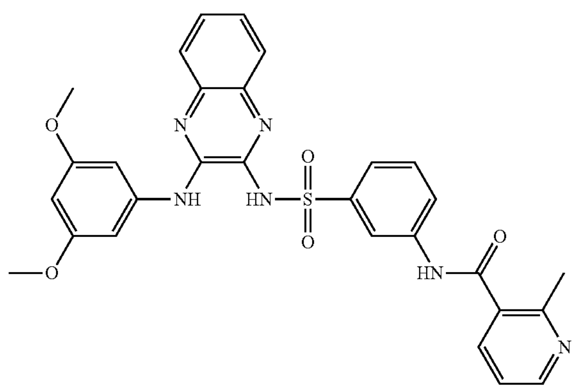 | N-(3-{[(3-{[3,5-bis(methoxy)phenyl]amino}quinoxalin-2-yl)amino]sulfonyl}phenyl)-2-methylpyridine-3-carboxamide |
| 506 | 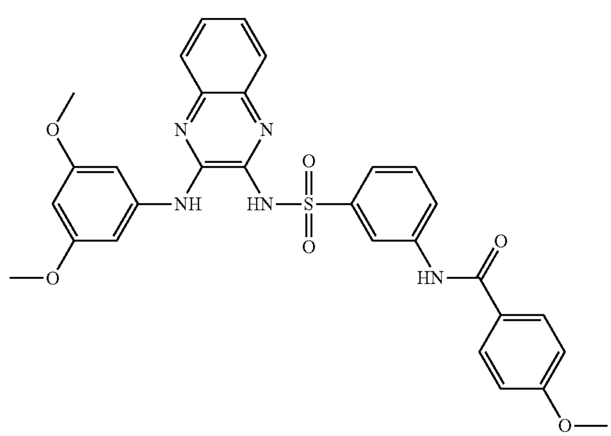 | N-(3-{[(3-{[3,5-bis(methoxy)phenyl]amino}quinoxalin-2-yl)amino]sulfonyl}phenyl)-4-(methoxy)benzamide |
| 507 | 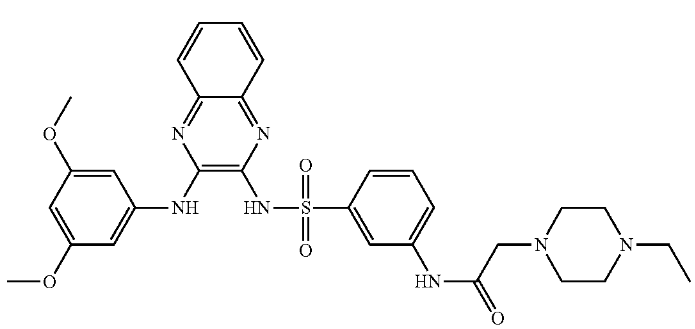 [SMILES: CCN1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methoxy)phenyl]amino}quinoxalin-2-yl)amino]sulfonyl}phenyl)-2-(4-ethylpiperazin-1-yl)acetamide |

| Cpd. No. | Structure | Name |
|---|---|---|
| 508 | 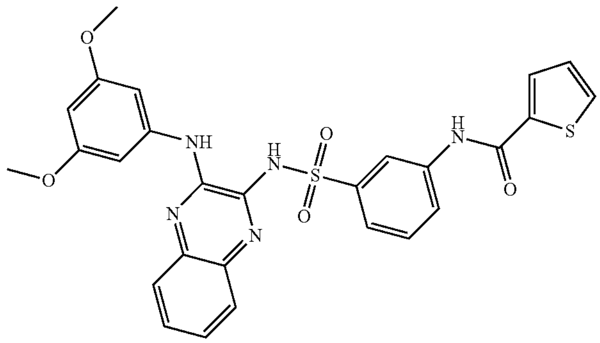 [SMILES: COc1cc(Nc2nc3ccccc3nc2NS(=O)(=O)c2cccc(NC(=O)c3cccs3)c2)cc(OC)c1] | N-(3-{[(3-{[3,5-bis(methoxy)phenyl]amino}quinoxalin-2-yl)amino]sulfonyl}phenyl)thiophene-2-carboxamide |
| 509 | 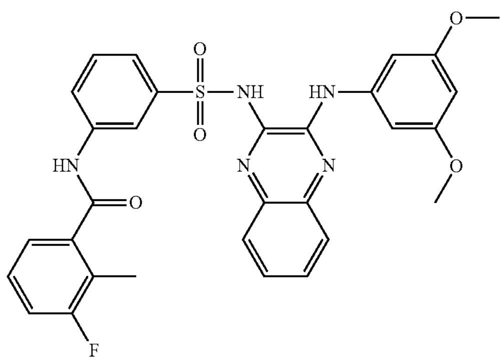 [SMILES: COc1cc(Nc2nc3ccccc3nc2NS(=O)(=O)c2cccc(NC(=O)c3cccc(F)c3C)c2)cc(OC)c1] | N-(3-{[(3-{[3,5-bis(methoxy)phenyl]amino}quinoxalin-2-yl)amino]sulfonyl}phenyl)-3-fluoro-2-methylbenzamide |
| 510 | 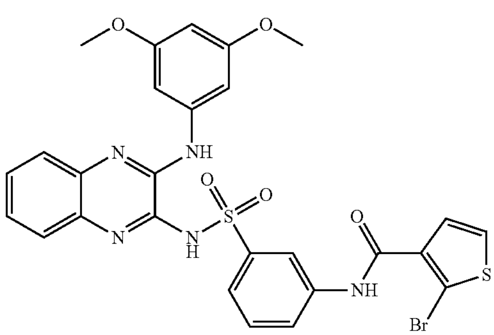 [SMILES: COc1cc(Nc2nc3ccccc3nc2NS(=O)(=O)c2cccc(NC(=O)c3ccsc3Br)c2)cc(OC)c1] | N-(3-{[(3-{[3,5-bis(methoxy)phenyl]amino}quinoxalin-2-yl)amino]sulfonyl}phenyl)-2-bromothiophene-3-carboxamide |
| 511 | 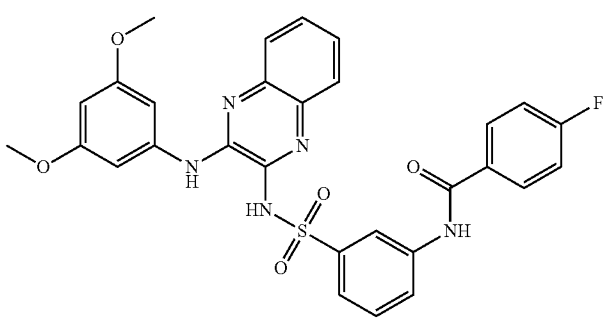 [SMILES: COc1cc(Nc2nc3ccccc3nc2NS(=O)(=O)c2cccc(NC(=O)c3ccc(F)cc3)c2)cc(OC)c1] | N-(3-{[(3-{[3,5-bis(methoxy)phenyl]amino}quinoxalin-2-yl)amino]sulfonyl}phenyl)-4-fluorobenzamide |

TABLE 1-continued

| Cpd. No. | Structure | Name |
|---|---|---|
| 512 | 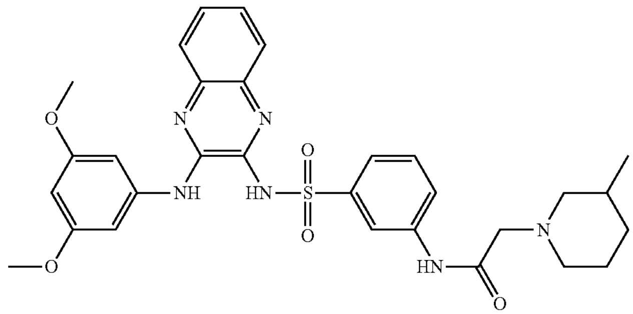 | N-(3-{[(3-{[3,5-bis(methoxy)phenyl]amino}quinoxalin-2-yl)amino]sulfonyl}phenyl)-2-(3-methylpiperidin-1-yl)acetamide |
| 513 | 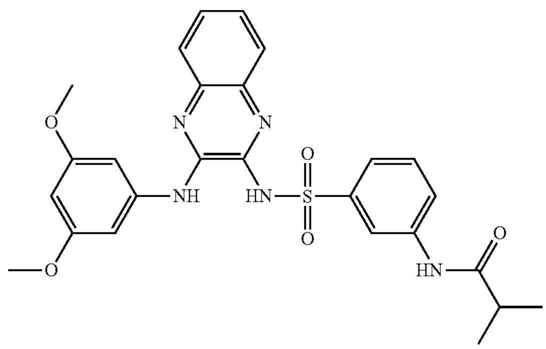 [SMILES: COc1cc(Nc2nc3ccccc3nc2NS(=O)(=O)c2cccc(NC(=O)C(C)C)c2)cc(OC)c1] | N-(3-{[(3-{[3,5-bis(methoxy)phenyl]amino}quinoxalin-2-yl)amino]sulfonyl}phenyl)-2-methylpropanide |
| amp;2p 514 | 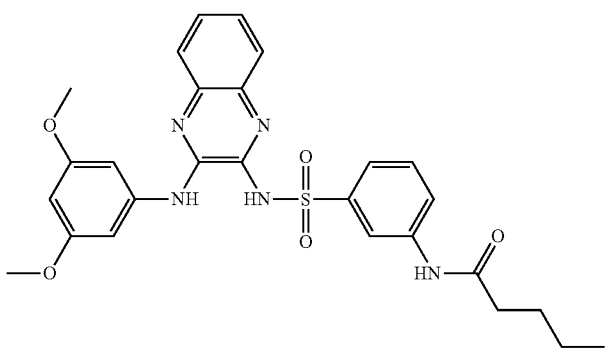 [SMILES: CCCCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)pentanamide |
| 515 | 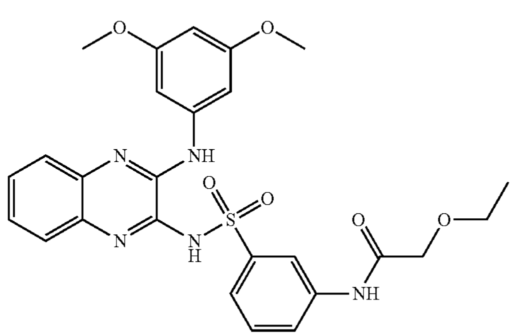 [SMILES: CCOCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-2-(ethyloxy)acetamide |

TABLE 1-continued

| Cpd. No. | Structure | Name |
|---|---|---|
| 516 | 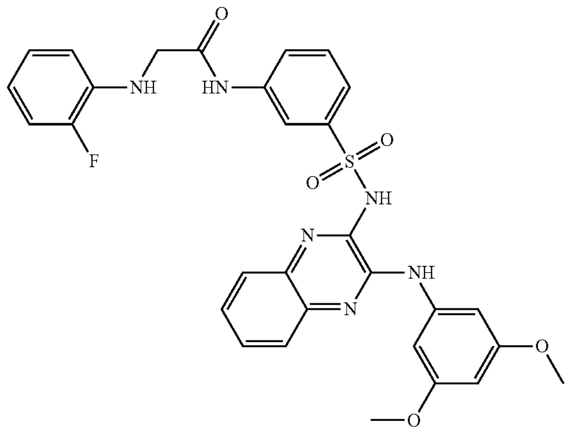 | N-(3-{[(3-{[3,5-bis(methoxy)phenyl]amino}quinoxalin-2-yl)amino]sulfonyl}phenyl)-N-2-(2-fluorophenyl)glycinamide |
| 517 | 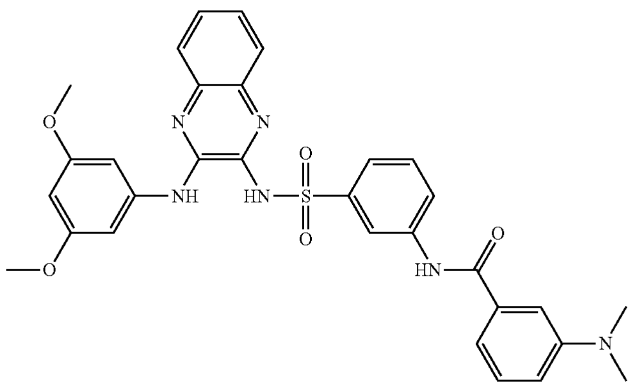 | N-(3-{[(3-{[3,5-bis(methoxy)phenyl]amino}quinoxalin-2-yl)amino]sulfonyl}phenyl)-3-(dimethylamino)benzamide |
| 518 | 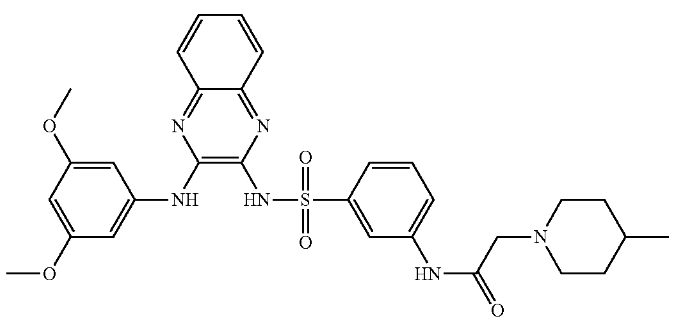 | N-(3-{[(3-{[3,5-bis(methoxy)phenyl]amino}quinoxalin-2-yl)amino]sulfonyl}phenyl)-2-(4-methylpiperidin-1-yl)acetamide |
| 519 | 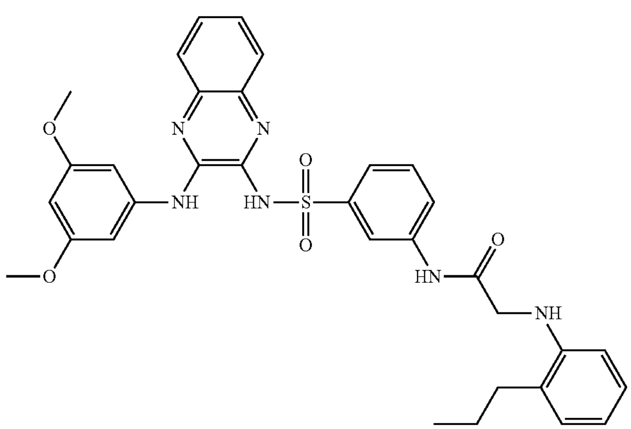 [SMILES: CCCc1ccccc1NCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-N-2-(2-propylphenyl)glycinamide |

TABLE 1-continued

| Cpd. No. | Structure | Name |
|---|---|---|
| 520 | 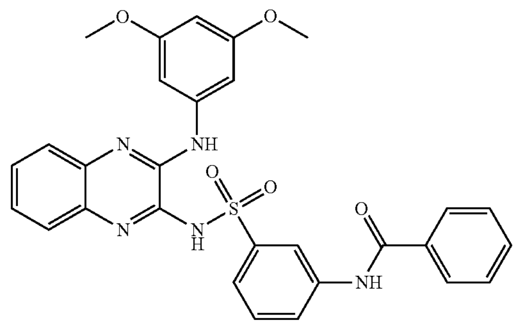 [SMILES: COc1cc(Nc2nc3ccccc3nc2NS(=O)(=O)c2cccc(NC(=O)c3ccccc3)c2)cc(OC)c1] | N-(3-{[(3-{[3,5-bis(methoxy)phenyl]amino}quinoxalin-2-yl)amino]sulfonyl}phenyl)benzamide |
| 521 | 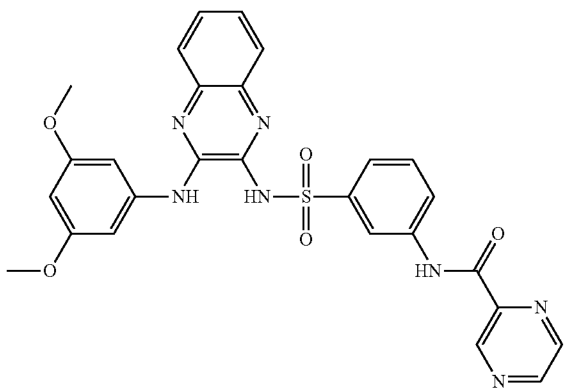 [SMILES: COc1cc(Nc2nc3ccccc3nc2NS(=O)(=O)c2cccc(NC(=O)c3cnccn3)c2)cc(OC)c1] | N-(3-{[(3-{[3,5-bis(methoxy)phenyl]amino}quinoxalin-2-yl)amino]sulfonyl}phenyl)pyrazine-2-carboxamide |
| 522 | 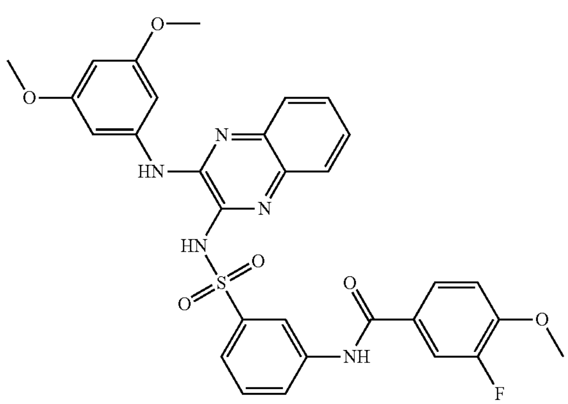 | N-(3-{[(3-{[3,5-bis(methoxy)phenyl]amino}quinoxalin-2-yl)amino]sulfonyl}phenyl)-3-fluoro-4-(methoxy)benzamide |
| 523 | 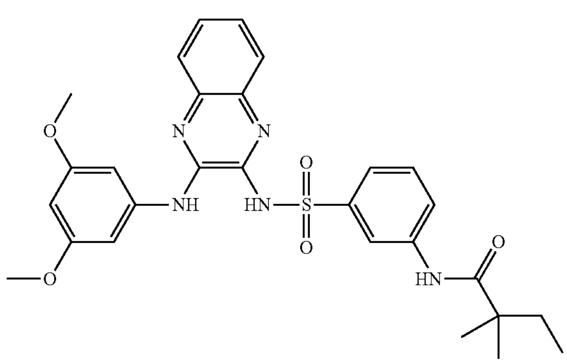 [SMILES: CCC(C)(C)C(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)-2,2-dimethylbutanami |

TABLE 1-continued

| Cpd. No. | Structure | Name |
|---|---|---|
| 524 | 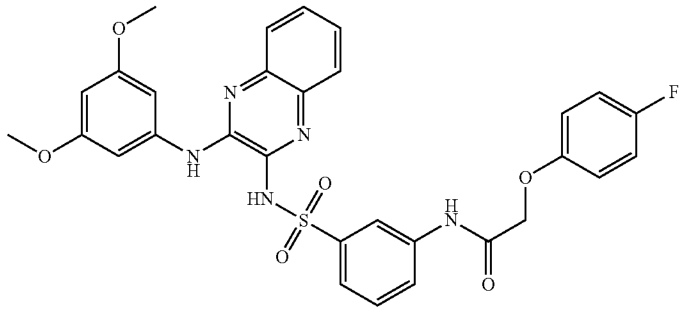 [SMILES: COc1cc(Nc2nc3ccccc3nc2NS(=O)(=O)c2cccc(NC(=O)COc3ccc(F)cc3)c2)cc(OC)c1] | N-(3-{[(3-{[3,5-bis(methoxy)phenyl]amino}quinoxalin-2-yl)amino]sulfonyl}phenyl)-2-[(4-fluorophenyl)oxy]acetamide |
| 525 | 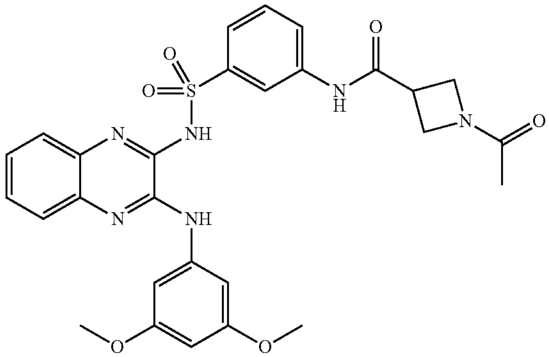 [SMILES: COc1cc(Nc2nc3ccccc3nc2NS(=O)(=O)c2cccc(NC(=O)C3CN(C(C)=O)C3)c2)cc(OC)c1] | 1-acetyl-N-(3-{[(3-{[3,5-bis(methoxy)phenyl]amino}quinoxalin-2-yl)amino]sulfonyl}phenyl)azetidine-3-carboxamide |
| 526 | 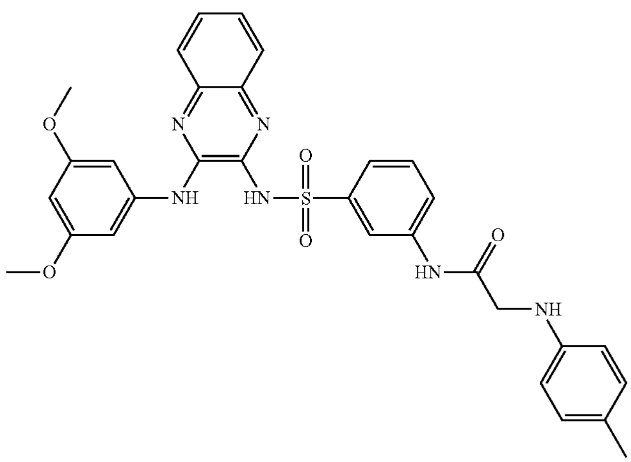 | N-(3-{[(3-{[3,5-bis(methoxy)phenyl]amino}quinoxalin-2-yl)amino]sulfonyl}phenyl)-N-2-(4-methylphenyl)glycinamide |
| 527 | 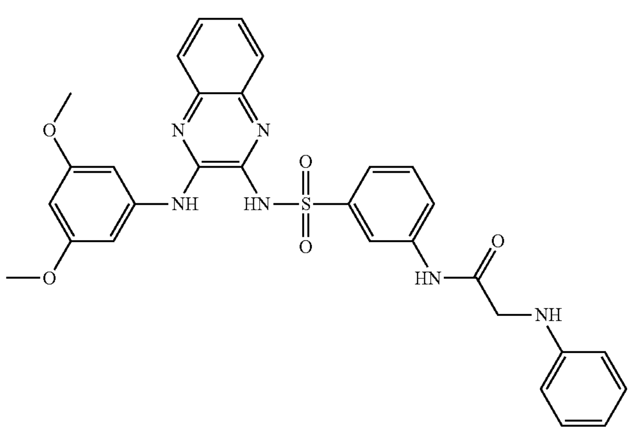 [SMILES: COc1cc(Nc2nc3ccccc3nc2NS(=O)(=O)c2cccc(NC(=O)CNc3ccccc3)c2)cc(OC)c1] | N-(3-{[(3-{[3,5-bis(methoxy)phenyl]amino}quinoxalin-2-yl)amino]sulfonyl}phenyl)-N-2-phenylglycinamide |

TABLE 1-continued

| Cpd. No. | Structure | Name |
|---|---|---|
| 528 | 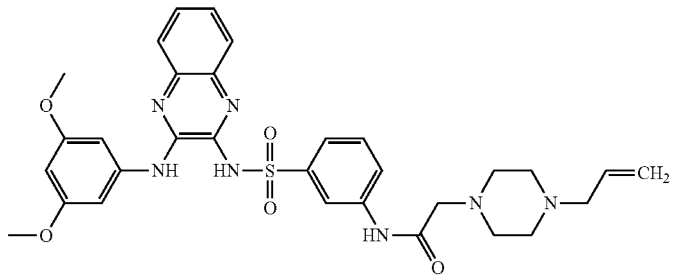 [SMILES: C=CCN1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methoxy)phenyl]amino}quinoxalin-2-yl)amino]sulfonyl}phenyl)-2-(4-prop-2-en-1-ylpiperazin-1-yl)acetamide |
| 529 | 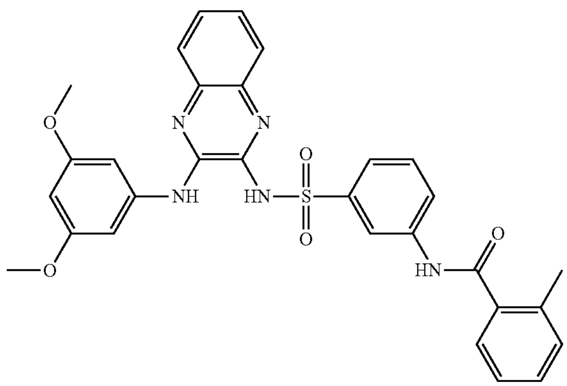 | N-(3-{[(3-{[3,5-bis(methoxy)phenyl]amino}quinoxalin-2-yl)amino]sulfonyl}phenyl)-2-methylbenzamide |
| 530 | 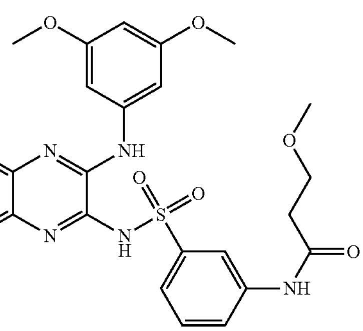 | N-(3-{[(3-{[3,5-bis(methoxy)phenyl]amino}quinoxalin-2-yl)amino]sulfonyl}phenyl)-3-(methoxy)propanamie |
| 531 | 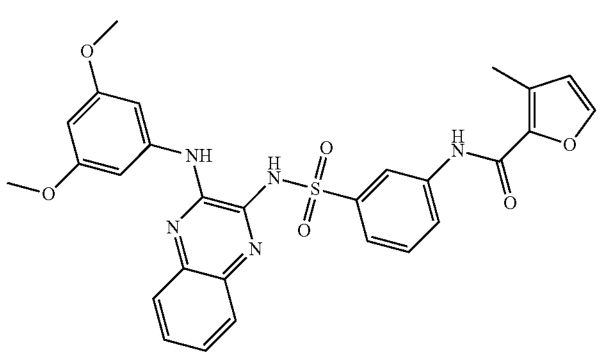 [SMILES: COc1cc(Nc2nc3ccccc3nc2NS(=O)(=O)c2cccc(NC(=O)c3occc3C)c2)cc(OC)c1] | N-(3-{[(3-{[3,5-bis(methoxy)phenyl]amino}quinoxalin-2-yl)amino]sulfonyl}phenyl)-3-methylfuran-2-carboxamide |

| Cpd. No. | Structure | Name |
|---|---|---|
| 532 | 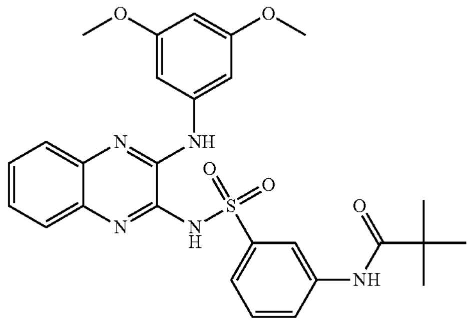 [SMILES: COc1cc(Nc2nc3ccccc3nc2NS(=O)(=O)c2cccc(NC(=O)C(C)(C)C)c2)cc(OC)c1] | N-(3-{[(3-{[3,5-bis(methoxy)phenyl]amino}quinoxalin-2-yl)amino]sulfonyl}phenyl)-2,2-dimethylpropanamide |
| 533 | 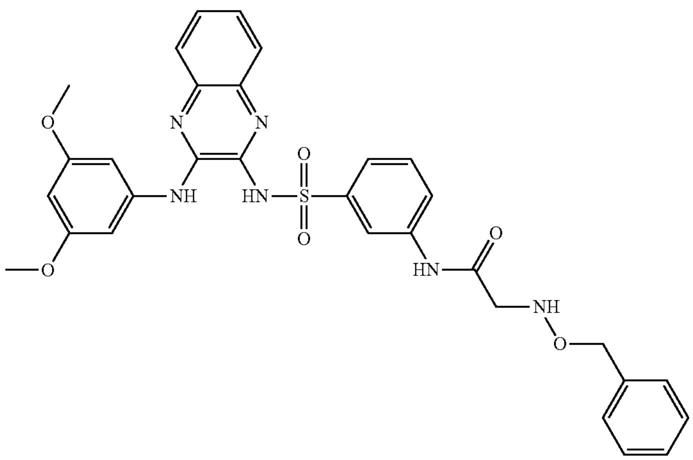 [SMILES: COc1cc(Nc2nc3ccccc3nc2NS(=O)(=O)c2cccc(NC(=O)CNOCc3ccccc3)c2)cc(OC)c1] | N-(3-{[(3-{[3,5-bis(methoxy)phenyl]amino}quinoxalin-2-yl)amino]sulfonyl}phenyl)-N-2-[(phenylmethyl)oxy]glycinamide |
| 534 | 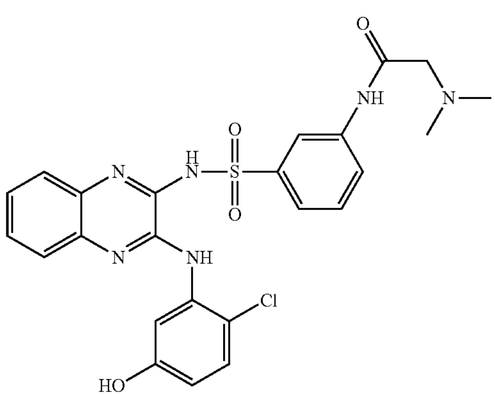 [SMILES: CN(C)CC(=O)Nc1cccc(S(=O)(=O)Nc2nc3ccccc3nc2Nc2cc(O)ccc2Cl)c1] | N-(3-[({3-[(2-chloro-5-hydroxyphenyl)amino]quinoxalin-2-yl}amino)sulfonyl]phenyl}-N-2-,N-2-dimethylglycinamide |
| 535 | 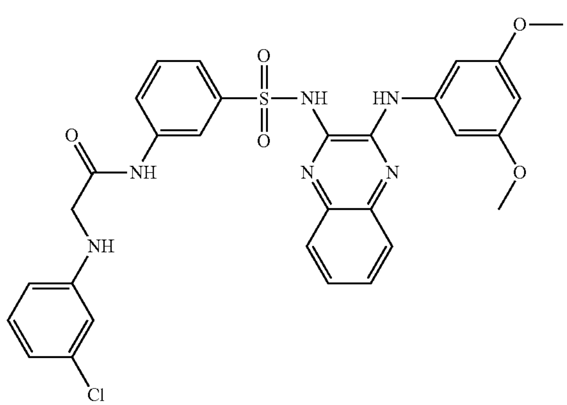 [SMILES: COc1cc(Nc2nc3ccccc3nc2NS(=O)(=O)c2cccc(NC(=O)CNc3cccc(Cl)c3)c2)cc(OC)c1] | N-(3-{[(3-{[3,5-bis(methoxy)phenyl]amino}quinoxalin-2-yl)amino]sulfonyl}phenyl)-N-2-(3-chlorophenyl)glycinamide |

TABLE 1-continued

| Cpd. No. | Structure | Name |
|---|---|---|
| 536 | 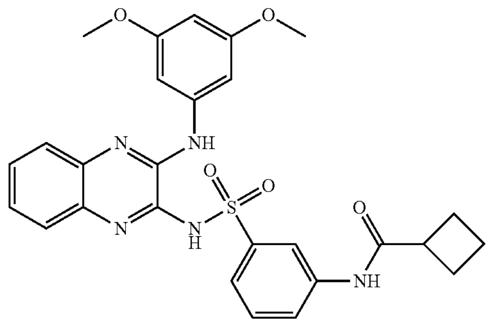 [SMILES: COc1cc(Nc2nc3ccccc3nc2NS(=O)(=O)c2cccc(NC(=O)C3CCC3)c2)cc(OC)c1] | N-(3-{[(3-{[3,5-bis(methoxy)phenyl]amino}quinoxalin-2-yl)amino]sulfonyl}phenyl)cyclobutanecarboxamide |
| 537 | 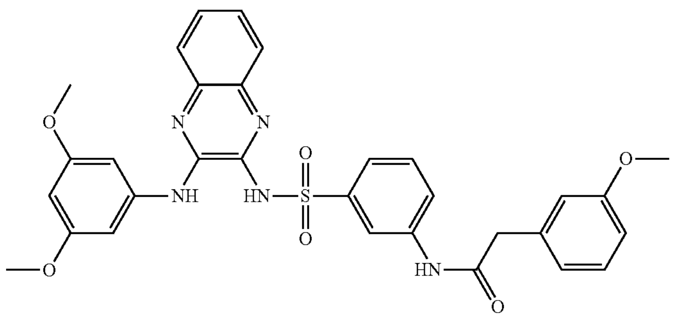 | N-(3-{[(3-{[3,5-bis(methoxy)phenyl]amino}quinoxalin-2-yl)amino]sulfonyl}phenyl)-2-[3-(methoxy)phenyl]acetamide |
| 538 | 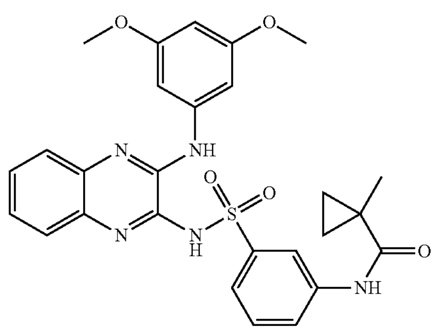 [SMILES: COc1cc(Nc2nc3ccccc3nc2NS(=O)(=O)c2cccc(NC(=O)C3(C)CC3)c2)cc(OC)c1] | N-(3-{[(3-{[3,5-bis(methoxy)phenyl]amino}quinoxalin-2-yl)amino]sulfonyl}phenyl)-1-methylcyclopropanecarboxamide |
| 539 | 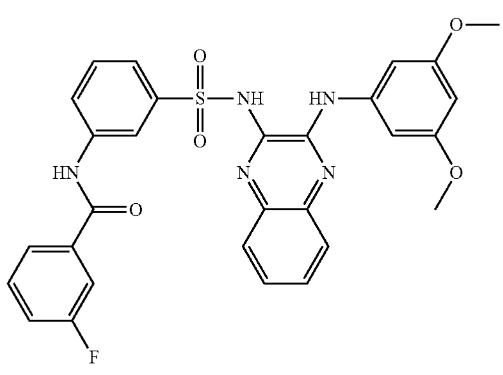 [SMILES: COc1cc(Nc2nc3ccccc3nc2NS(=O)(=O)c2cccc(NC(=O)c3cccc(F)c3)c2)cc(OC)c1] | N-(3-{[(3-{[3,5-bis(methoxy)phenyl]amino}quinoxalin-2-yl)amino]sulfonyl}phenyl)-3-fluorobenzamide |

TABLE 1-continued

| Cpd. No. | Structure | Name |
|---|---|---|
| 540 | 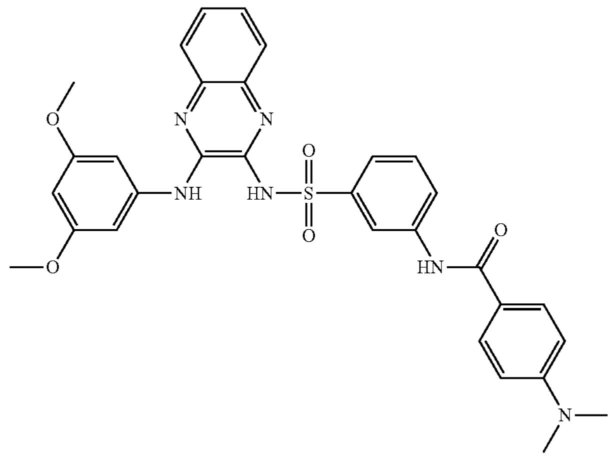 | N-(3-{[(3-{[3,5-bis(methoxy) phenyl]amino}quinoxalin-2-yl)amino]sulfonyl}phenyl)-4-(dimethylamino)benzamide |
| 541 | 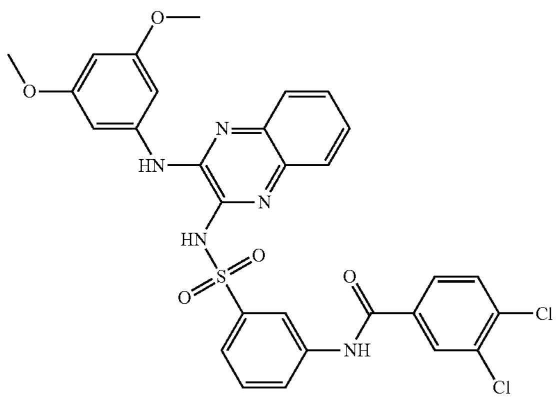 [SMILES: COc1cc(Nc2nc3ccccc3nc2NS(=O)(=O)c2cccc(NC(=O)c3ccc(Cl)c(Cl)c3)c2)cc(OC)c1] | N-(3-{[(3-{[3,5-bis(methoxy) phenyl]amino}quinoxalin-2-yl)amino]sulfonyl}phenyl)-3,4-dichlorobenzamide |
| 542 | 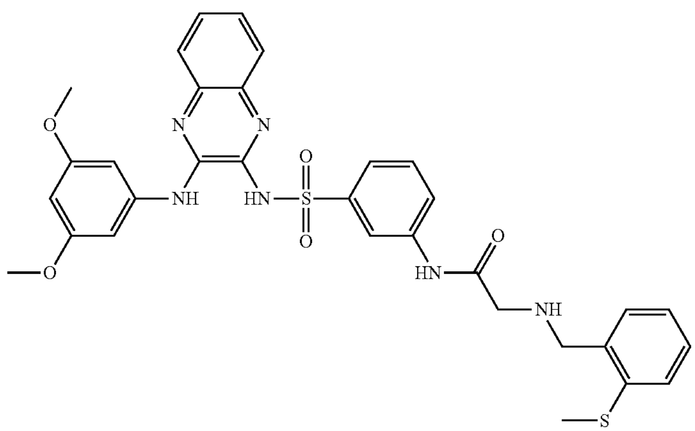 [SMILES: COc1cc(Nc2nc3ccccc3nc2NS(=O)(=O)c2cccc(NC(=O)CNCc3ccccc3SC)c2)cc(OC)c1] | N-(3-{[(3-{[3,5-bis(methoxy) phenyl]amino}quinoxalin-2-yl)amino]sulfonyl}phenyl)-N-2-{[2-(methylthio)phenyl]methyl} glycinamide |
| 543 | 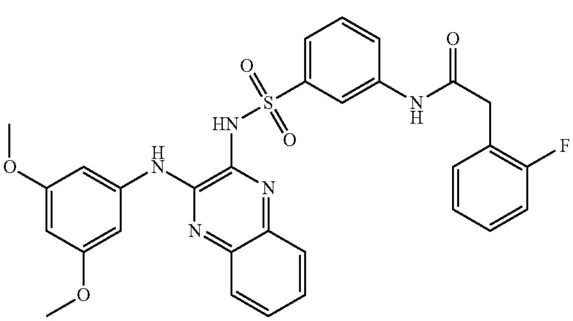 [SMILES: COc1cc(Nc2nc3ccccc3nc2NS(=O)(=O)c2cccc(NC(=O)Cc3ccccc3F)c2)cc(OC)c1] | N-(3-{[(3-{[3,5-bis(methoxy) phenyl]amino}quinoxalin-2-yl)amino]sulfonyl}phenyl)-2-(2-fluorophenyl)acetamide |

TABLE 1-continued
| Cpd. No. | Structure | Name |
|---|---|---|
| 544 | 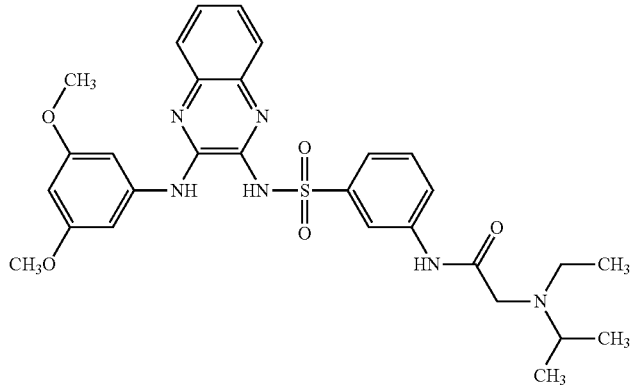 | N-(3-{[(3-{[3,5-bis(methoxy)phenyl]amino}quinoxalin-2-yl)amino]sulfonyl}phenyl)-N-2-ethyl-N-2-(1-methylethyl)glycinamide |
| 545 | 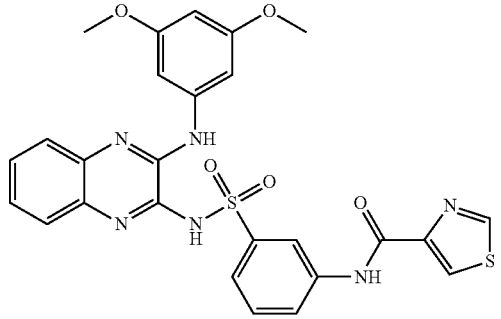 [SMILES: COc1cc(Nc2nc3ccccc3nc2NS(=O)(=O)c2cccc(NC(=O)c3cscn3)c2)cc(OC)c1] | N-(3-{[(3-{[3,5-bis(methoxy)phenyl]amino}quinoxalin-2-yl)amino]sulfonyl}phenyl)-1,3-thiazole-4-carboxamide |
| 546 | 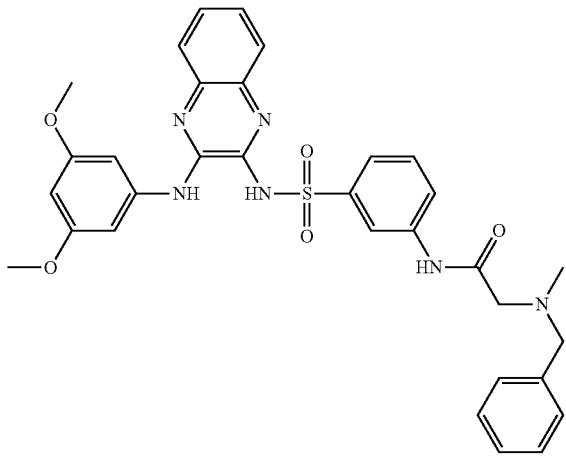 [SMILES: COc1cc(Nc2nc3ccccc3nc2NS(=O)(=O)c2cccc(NC(=O)CN(C)Cc3ccccc3)c2)cc(OC)c1] | N-(3-{[(3-{[3,5-bis(methoxy)phenyl]amino}quinoxalin-2-yl)amino]sulfonyl}phenyl)-N-2-methyl-N-2-(phenylmethyl)glycinamide |

TABLE 1-continued

| Cpd. No. | Structure | Name |
|---|---|---|
| 547 | 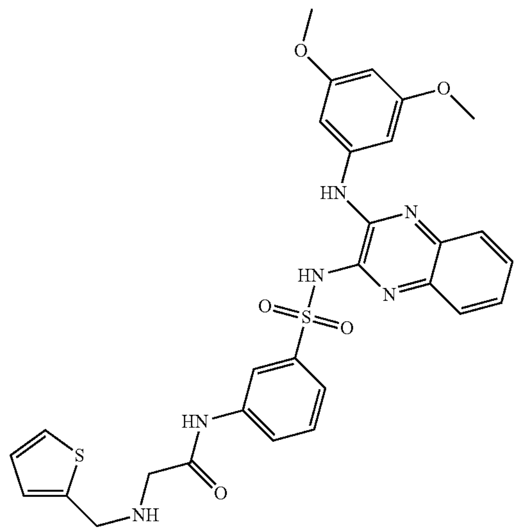 [SMILES: COc1cc(Nc2nc3ccccc3nc2NS(=O)(=O)c2cccc(NC(=O)CNCc3cccs3)c2)cc(OC)c1] | N-(3-{[(3-{[3,5-bis(methoxy)phenyl]amino}quinoxalin-2-yl)amino]sulfonyl}phenyl)-N-2-(2-thienylmethyl)glycinamide |
| 548 | 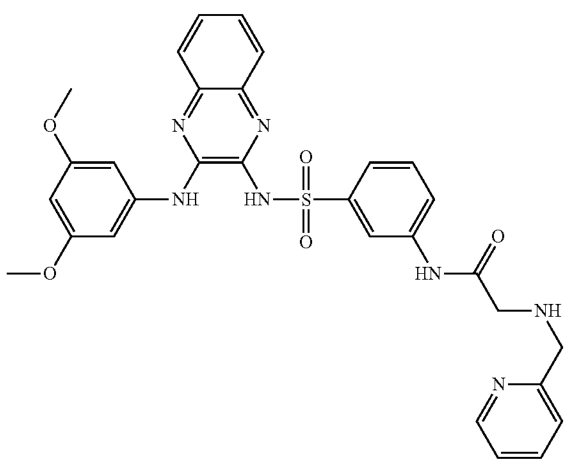 [SMILES: COc1cc(Nc2nc3ccccc3nc2NS(=O)(=O)c2cccc(NC(=O)CNCc3ccccn3)c2)cc(OC)c1] | N-(3-{[(3-{[3,5-bis(methoxy)phenyl]amino}quinoxalin-2-yl)amino]sulfonyl}phenyl)-N-2-(pyridin-2-ylmethyl)glycinamide |
| 549 | 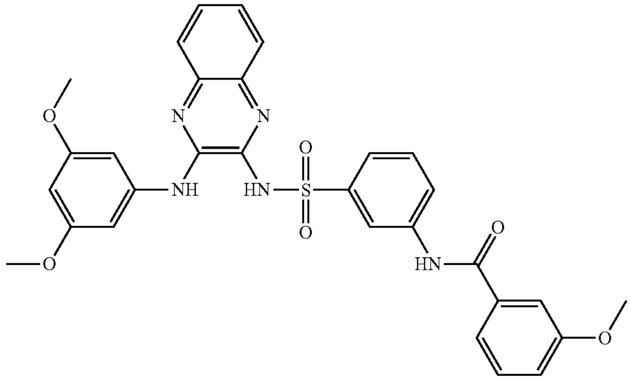 | N-(3-{[(3-{[3,5-bis(methoxy)phenyl]amino}quinoxalin-2-yl)amino]sulfonyl}phenyl)-3-(methoxy)benzamide |

TABLE 1-continued

| Cpd. No. | Structure | Name |
|---|---|---|
| 550 | 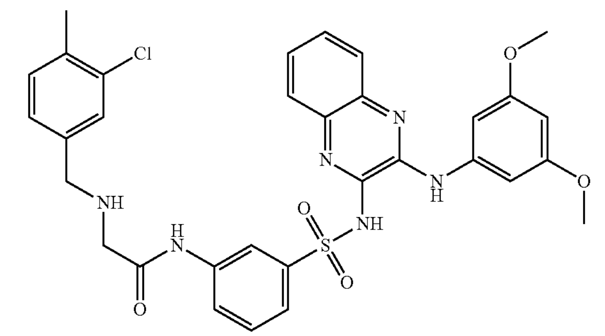 [SMILES: COc1cc(Nc2nc3ccccc3nc2NS(=O)(=O)c2cccc(NC(=O)CNCc3ccc(C)c(Cl)c3)c2)cc(OC)c1] | N-(3-{[(3-{[3,5-bis(methoxy) phenyl]amino}quinoxalin-2-yl)amino]sulfonyl}phenyl)-N-2-[(3-chloro-4-methylphenyl) methyl]glycinamide |
| 551 | 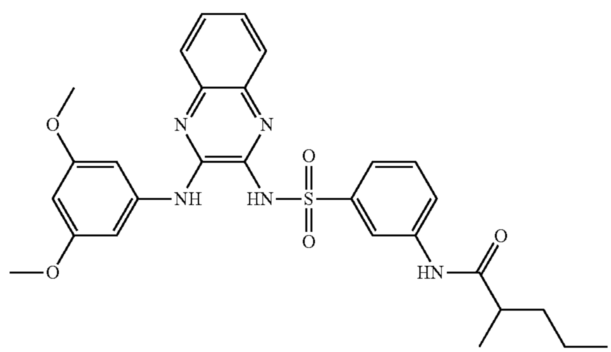 [SMILES: CCCC(C)C(=O)Nc1cccc(S(=O)(=O)Nc2nc3ccccc3nc2Nc2cc(OC)cc(OC)c2)c1] | N-(3-{[(3-{[3,5-bis(methoxy) phenyl]amino}quinoxalin-2-yl)amino]sulfonyl}phenyl)-2-methylpentanamide |
| 552 | 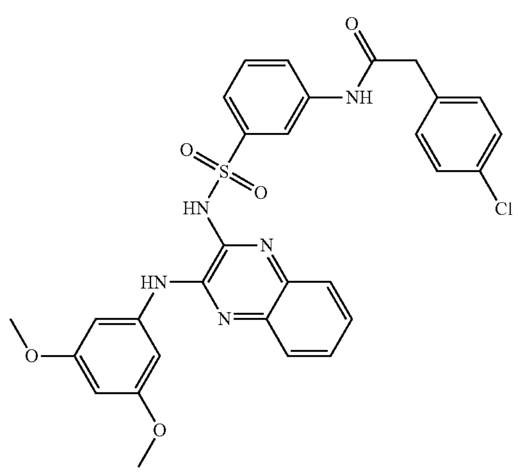 [SMILES: COc1cc(Nc2nc3ccccc3nc2NS(=O)(=O)c2cccc(NC(=O)Cc3ccc(Cl)cc3)c2)cc(OC)c1] | N-(3-{[(3-{[3,5-bis(methoxy) phenyl]amino}quinoxalin-2-yl)amino]sulfonyl}phenyl)-2-(4-chlorophenyl)acetamide |
| 553 | 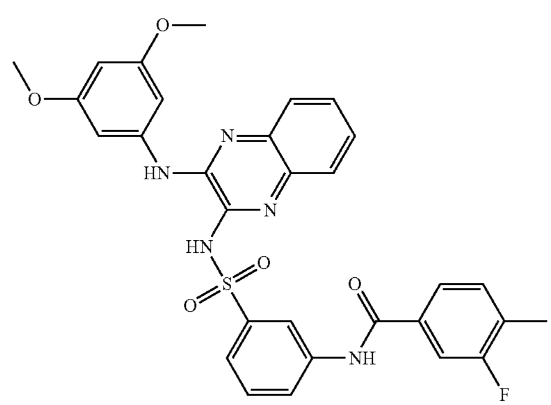 | N-(3-{[(3-{[3,5-bis(methoxy) phenyl]amino}quinoxalin-2-yl)amino]sulfonyl}phenyl)-3-fluoro-4-methylbenzami |

TABLE 1-continued

| Cpd. No. | Structure | Name |
|---|---|---|
| 554 | 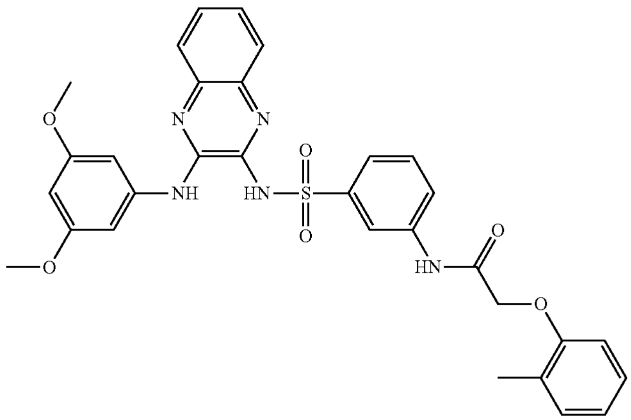 [SMILES: COc1cc(Nc2nc3ccccc3nc2NS(=O)(=O)c2cccc(NC(=O)COc3ccccc3C)c2)cc(OC)c1] | N-(3-{[(3-{[3,5-bis(methoxy) phenyl]amino}quinoxalin-2-yl) amino]sulfonyl}phenyl)-2-[(2-methylphenyl)oxy]acetamide |
| 555 | 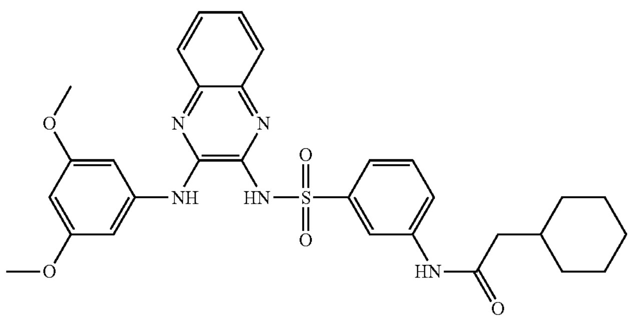 [SMILES: COc1cc(Nc2nc3ccccc3nc2NS(=O)(=O)c2cccc(NC(=O)CC3CCCCC3)c2)cc(OC)c1] | N-(3-{[(3-{[3,5-bis(methoxy) phenyl]amino}quinoxalin-2-yl)amino]sulfonyl}phenyl)-2-cyclohexylacetamide |
| 556 | 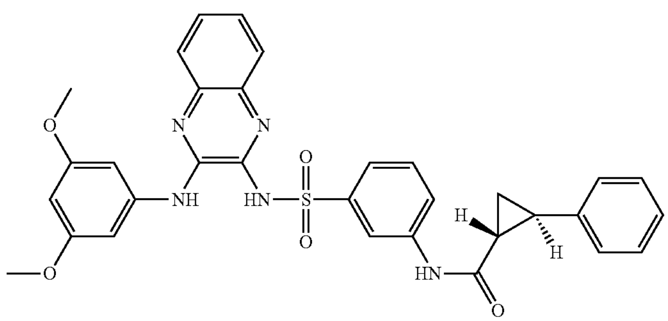 [SMILES: COc1cc(Nc2nc3ccccc3nc2NS(=O)(=O)c2cccc(NC(=O)[C@@H]3C[C@H]3c3ccccc3)c2)cc(OC)c1] | (1R,2R)-N-(3-{[(3-{[3,5-bis(methoxy)phenyl]amino}quinoxalin-2-yl)amino]sulfonyl}phenyl)-2-phenylcyclopropanecarboxamide |
| 557 | 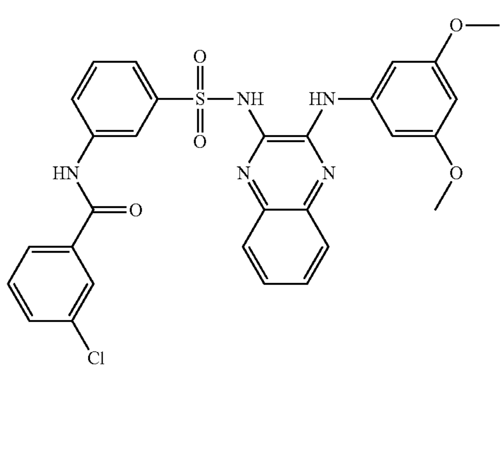 [SMILES: COc1cc(Nc2nc3ccccc3nc2NS(=O)(=O)c2cccc(NC(=O)c3cccc(Cl)c3)c2)cc(OC)c1] | N-(3-{[(3-{[3,5-bis(methoxy)phenyl]amino}quinoxalin-2-yl)amino]sulfonyl}phenyl)-3-chlorobenzamide |

TABLE 1-continued
| Cpd. No. | Structure | Name |
|---|---|---|
| 558 | 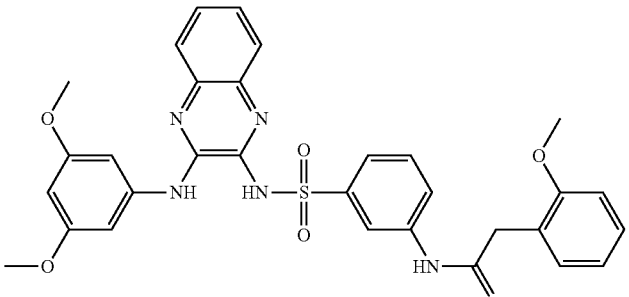 | N-(3-{[(3-{[3,5-bis(methoxy)phenyl]amino}quinoxalin-2-yl)amino]sulfonyl}phenyl)-2-[2-(methoxy)phenyl]acetamide |
| 559 | 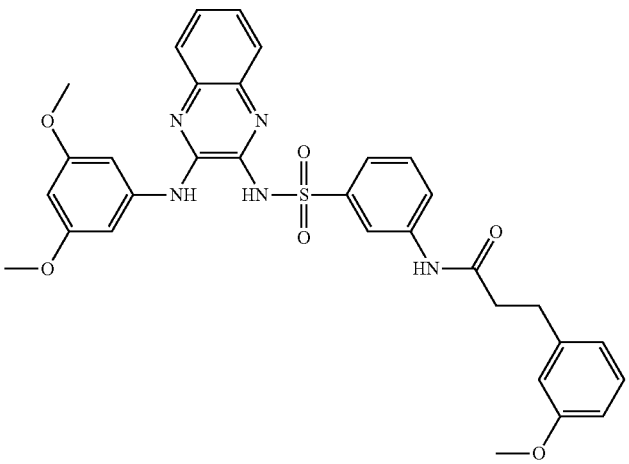 [SMILES: COc1cccc(CCC(=O)Nc2cccc(S(=O)(=O)Nc3nc4ccccc4nc3Nc3cc(OC)cc(OC)c3)c2)c1] | N-(3-{[(3-{[3,5-bis(methoxy)phenyl]amino}quinoxalin-2-yl)amino]sulfonyl}phenyl)-3-[3-(methoxy)phenyl]propanamide |
| 560 | 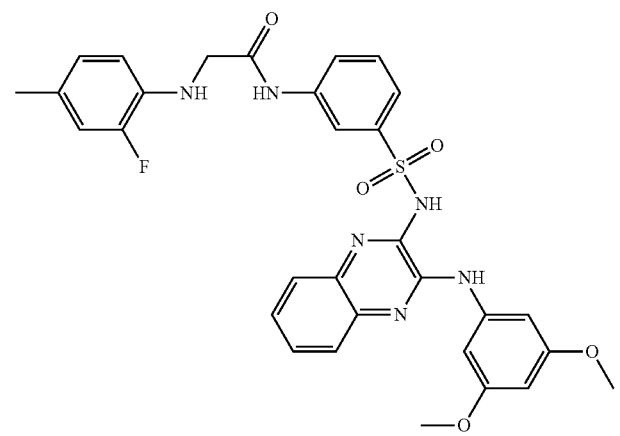 | N-(3-{[(3-{[3,5-bis(methoxy)phenyl]amino}quinoxalin-2-yl)amino]sulfonyl}phenyl)-N-2-(2-fluoro-4-methylphenyl)glycinamide |

TABLE 1-continued

| Cpd. No. | Structure | Name |
|---|---|---|
| 561 | 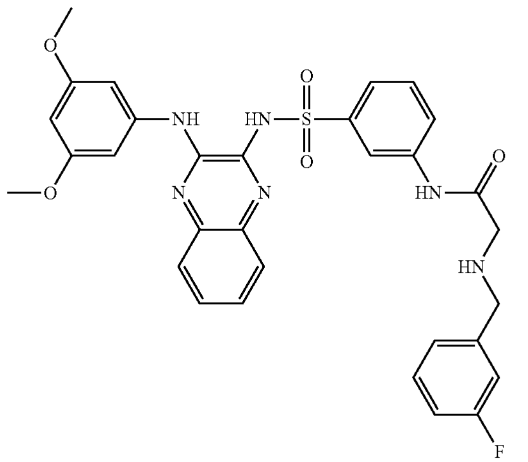 [SMILES: COc1cc(Nc2nc3ccccc3nc2NS(=O)(=O)c2cccc(NC(=O)CNCc3cccc(F)c3)c2)cc(OC)c1] | N-(3-{[(3-{[3,5-bis(methoxy) phenyl]amino}quinoxalin-2-yl)amino]sulfonyl}phenyl)-N-2-[(3-fluorophenyl)methyl] glycinamide |
| 562 | 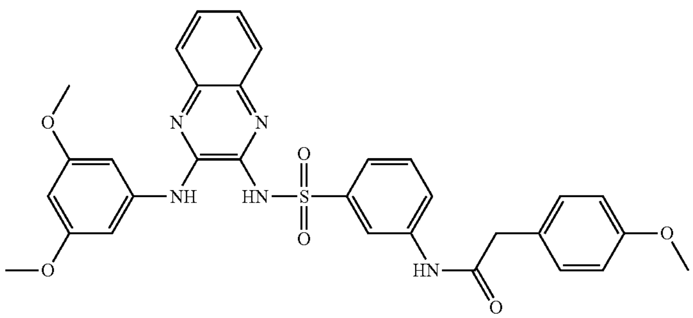 | N-(3-{[(3-{[3,5-bis(methoxy) phenyl]amino}quinoxalin-2-yl)amino]sulfonyl}phenyl)-2-[4-(methoxy)phenyl]acetamide |
| 563 | 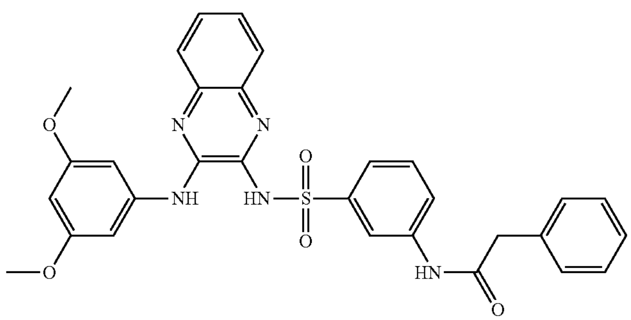 | N-(3-{[(3-{[3,5-bis(methoxy) phenyl]amino}quinoxalin-2-yl)amino]sulfonyl}phenyl)-2-phenylacetamide |
| 564 | 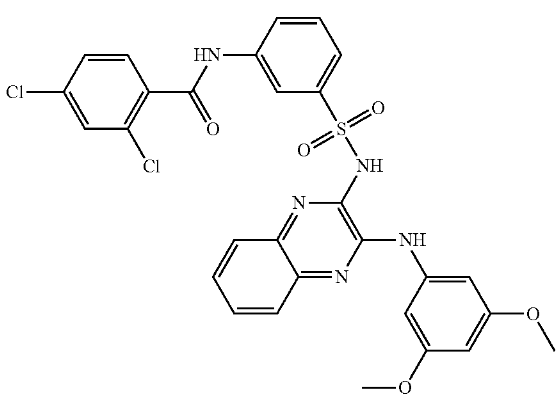 [SMILES: COc1cc(Nc2nc3ccccc3nc2NS(=O)(=O)c2cccc(NC(=O)c3ccc(Cl)cc3Cl)c2)cc(OC)c1] | N-(3-{[(3-{[3,5-bis(methoxy) phenyl]amino}quinoxalin-2-yl)amino]sulfonyl}phenyl)-2,4-dichlorobenzamide |

TABLE 1-continued

| Cpd. No. | Structure | Name |
| --- | --- | --- |
| 565 | 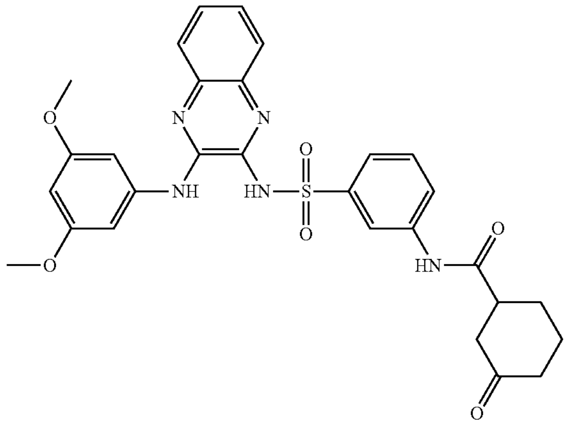 [SMILES: COc1cc(Nc2nc3ccccc3nc2NS(=O)(=O)c2cccc(NC(=O)C3CCCC(=O)C3)c2)cc(OC)c1] | N-(3-{[(3-{[3,5-bis(methoxy)phenyl]amino}quinoxalin-2-yl)amino]sulfonyl}phenyl)-3-oxocyclohexanecarboxamide |
| 566 | 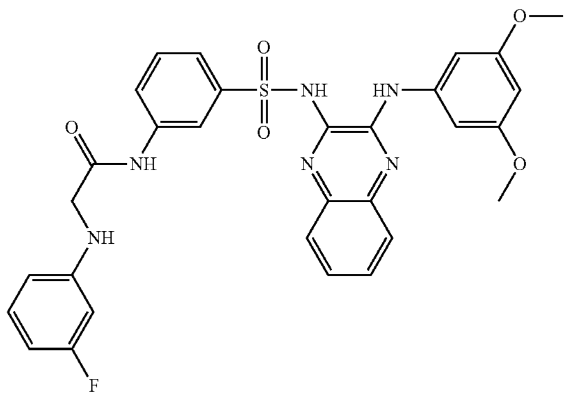 | N-(3-{[(3-{[3,5-bis(methoxy)phenyl]amino}quinoxalin-2-yl)amino]sulfonyl}phenyl)-N-2-(3-fluorophenyl)glycinamide |
| 567 | 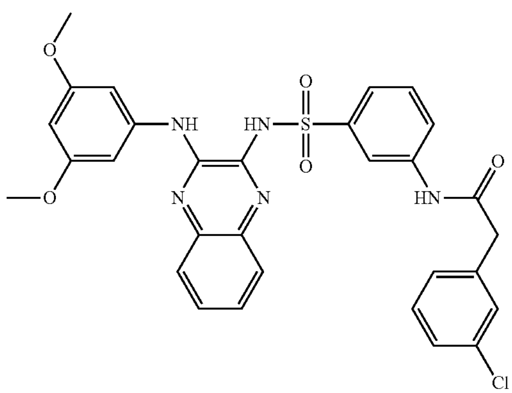 [SMILES: COc1cc(Nc2nc3ccccc3nc2NS(=O)(=O)c2cccc(NC(=O)Cc3cccc(Cl)c3)c2)cc(OC)c1] | N-(3-{[(3-{[3,5-bis(methoxy)phenyl]amino}quinoxalin-2-yl)amino]sulfonyl}phenyl)-2-(3-chlorophenyl)acetamide |
| 568 | 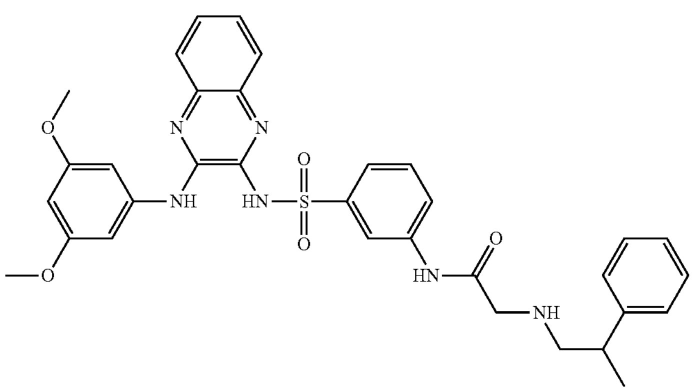 [SMILES: COc1cc(Nc2nc3ccccc3nc2NS(=O)(=O)c2cccc(NC(=O)CNCC(C)c3ccccc3)c2)cc(OC)c1] | N-(3-{[(3-{[3,5-bis(methoxy)phenyl]amino}quinoxalin-2-yl)amino]sulfonyl}phenyl)-N-2-(2-phenylpropyl)glycinamide |

TABLE 1-continued

| Cpd. No. | Structure | Name |
|---|---|---|
| 569 | 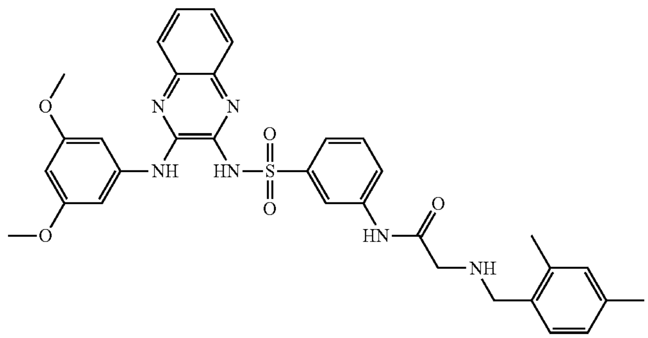 | N-(3-{[(3-{[3,5-bis(methoxy)phenyl]amino}quinoxalin-2-yl)amino]sulfonyl}phenyl)-N-2-[(2,4-dimethylphenyl)methyl]glycinamide |
| 570 | 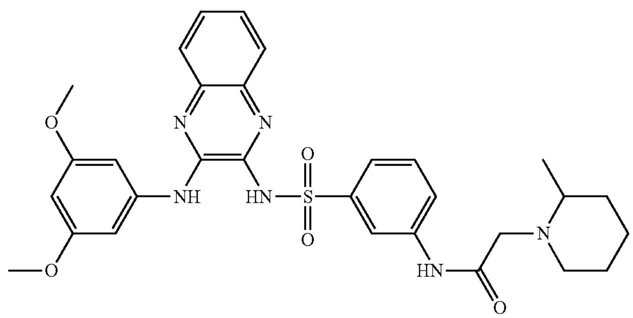 [SMILES: COc1cc(Nc2nc3ccccc3nc2NS(=O)(=O)c2cccc(NC(=O)CN3CCCCC3C)c2)cc(OC)c1] | N-(3-{[(3-{[3,5-bis(methoxy)phenyl]amino}quinoxalin-2-yl)amino]sulfonyl}phenyl)-2-(2-methylpiperidin-1-yl)acetamide |
| 571 | 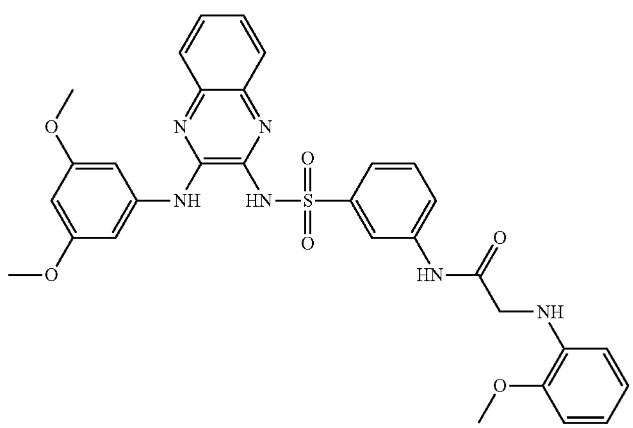 [SMILES: COc1cc(Nc2nc3ccccc3nc2NS(=O)(=O)c2cccc(NC(=O)CNc3ccccc3OC)c2)cc(OC)c1] | N-(3-{[(3-{[3,5-bis(methoxy)phenyl]amino}quinoxalin-2-yl)amino]sulfonyl}phenyl)-N-2-[2-(methoxy)phenyl]glycinamide |
| 572 | 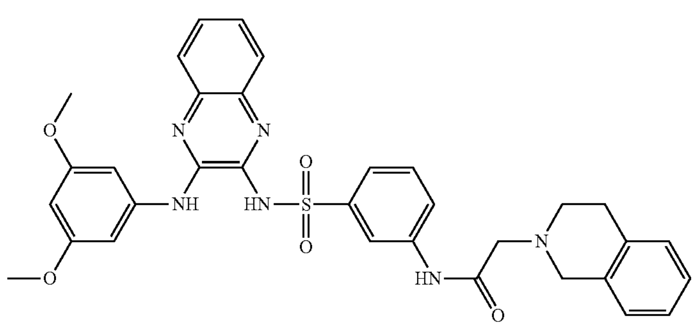 [SMILES: COc1cc(Nc2nc3ccccc3nc2NS(=O)(=O)c2cccc(NC(=O)CN3CCc4ccccc4C3)c2)cc(OC)c1] | N-(3-{[(3-{[3,5-bis(methoxy)phenyl]amino}quinoxalin-2-yl)amino]sulfonyl}phenyl)-2-(3,4-dihydroisoquinolin-2-(1H)-yl)acetamide |

TABLE 1-continued

| Cpd. No. | Structure | Name |
|---|---|---|
| 573 | 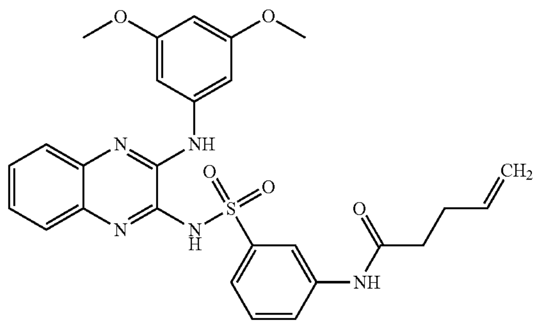 [SMILES: C=CCCC(=O)Nc1cccc(S(=O)(=O)Nc2nc3ccccc3nc2Nc2cc(OC)cc(OC)c2)c1] | N-(3-{[(3-{[3,5-bis(methoxy)phenyl]amino}quinoxalin-2-yl)amino]sulfonyl}phenyl)pent-4-enamide |
| 574 | 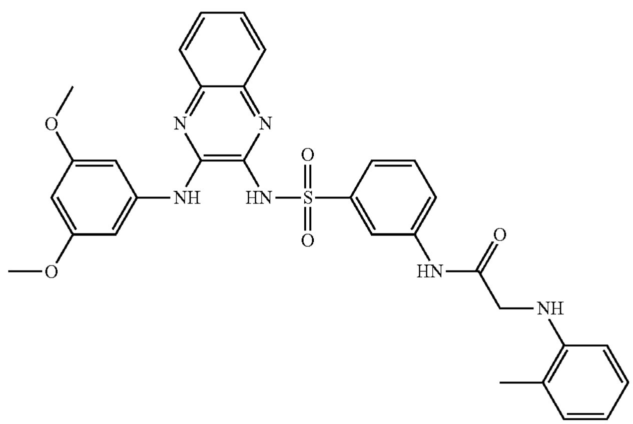 [SMILES: COc1cc(Nc2nc3ccccc3nc2NS(=O)(=O)c2cccc(NC(=O)CNc3ccccc3C)c2)cc(OC)c1] | N-3-{[(3-{[3,5-bis(methoxy)phenyl]amino}quinoxalin-2-yl)amino]sulfonyl}phenyl)-N-2-(2-methylphenyl)glycinamide |
| 575 | 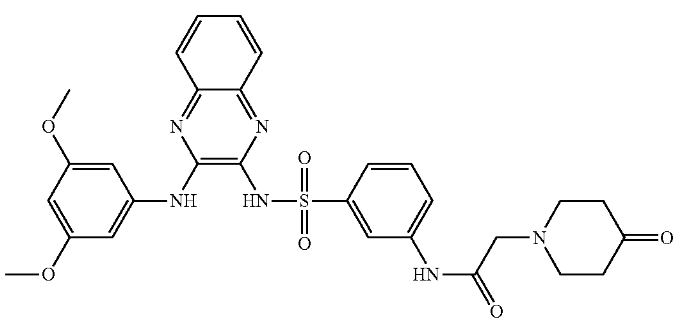 [SMILES: COc1cc(Nc2nc3ccccc3nc2NS(=O)(=O)c2cccc(NC(=O)CN3CCC(=O)CC3)c2)cc(OC)c1] | N-(3-{[(3-{[3,5-bis(methoxy)phenyl]amino}quinoxalin-2-yl)amino]sulfonyl}phenyl)-2-(4-oxopiperidin-1-yl)acetamide |
| 576 | 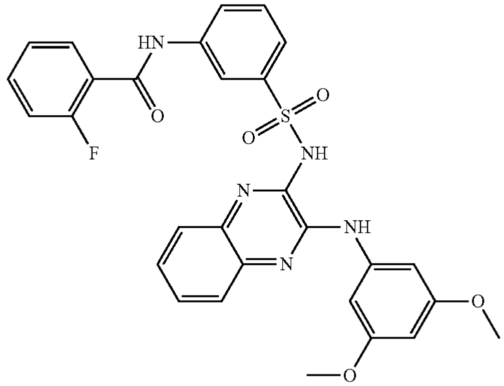 [SMILES: COc1cc(Nc2nc3ccccc3nc2NS(=O)(=O)c2cccc(NC(=O)c3ccccc3F)c2)cc(OC)c1] | N-(3-{[(3-{[3,5-bis(methoxy)phenyl]amino}quinoxalin-2-yl)amino]sulfonyl}phenyl)-2-fluorobenzamide |

TABLE 1-continued
| Cpd. No. | Structure | Name |
|---|---|---|
| 577 | 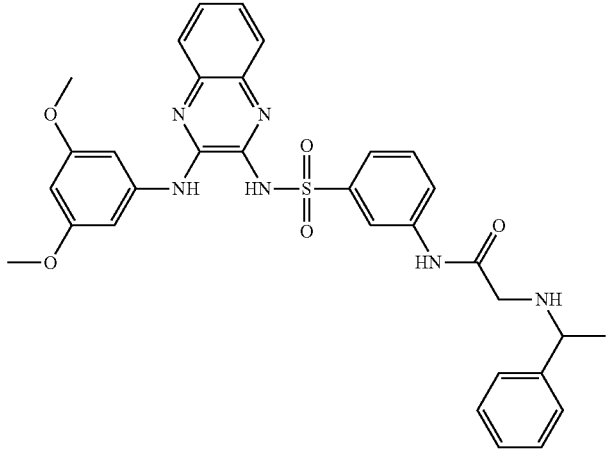 [SMILES: COc1cc(Nc2nc3ccccc3nc2NS(=O)(=O)c2cccc(NC(=O)CNC(C)c3ccccc3)c2)cc(OC)c1] | N-(3-{[(3-{[3,5-bis(methoxy)phenyl]amino}quinoxalin-2-yl])amino]sulfonyl}phenyl)-N-2-(1-phenylethyl)glycinamide |
| 578 | 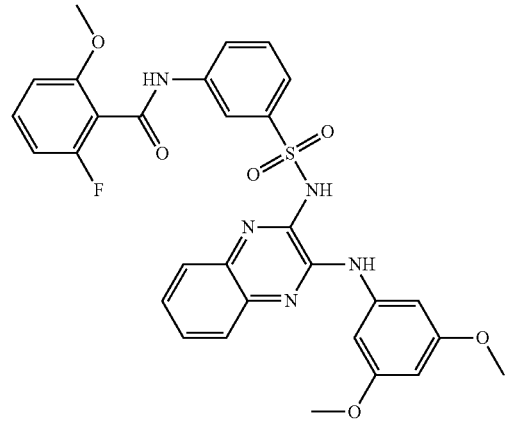 [SMILES: COc1cc(Nc2nc3ccccc3nc2NS(=O)(=O)c2cccc(NC(=O)c3c(F)cccc3OC)c2)cc(OC)c1] | N-(3-{[(3-{[3,5-bis(methoxy)phenyl]amino}quinoxalin-2-yl)amino]sulfonyl}phenyl)-2-fluoro-6-(methoxy)benzamide |
| 579 | 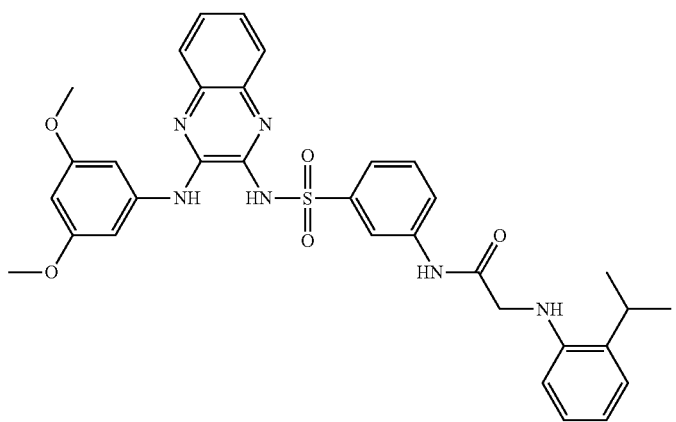 [SMILES: COc1cc(Nc2nc3ccccc3nc2NS(=O)(=O)c2cccc(NC(=O)CNc3ccccc3C(C)C)c2)cc(OC)c1] | N-(3-{[(3-{[3,5-bis(methoxy)phenyl]amino}quinoxalin-2-yl)amino]sulfonyl}phenyl)-N-2-[2-(1-methylethyl)phenyl]glycinamide |

TABLE 1-continued
| Cpd. No. | Structure | Name |
|---|---|---|
| 580 | 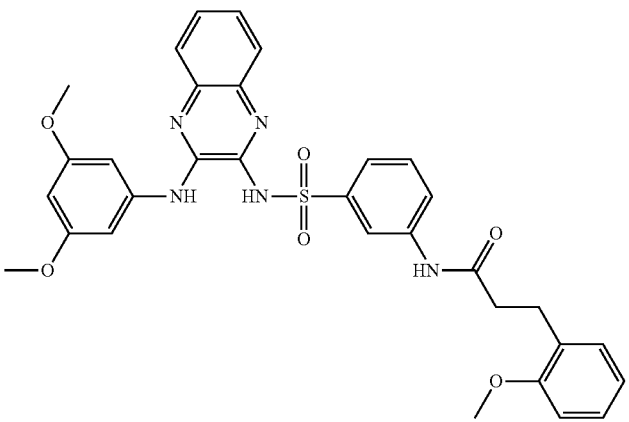 [SMILES: COc1cc(Nc2nc3ccccc3nc2NS(=O)(=O)c2cccc(NC(=O)CCc3ccccc3OC)c2)cc(OC)c1] | N-(3-{[(3-{[3,5-bis(methoxy)phenyl]amino}quinoxalin-2-yl)amino]sulfonyl}phenyl)-3-[2-(methoxy)phenyl]propanamide |
| 581 | 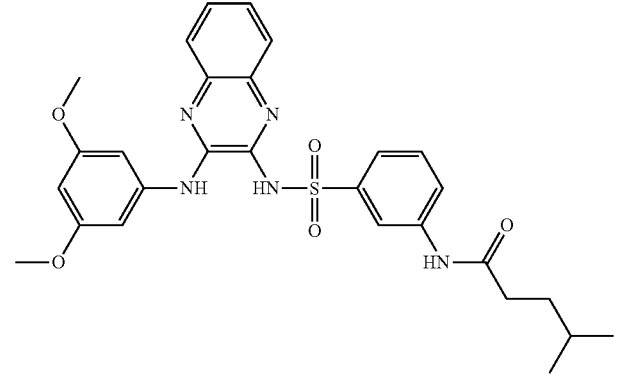 [SMILES: COc1cc(Nc2nc3ccccc3nc2NS(=O)(=O)c2cccc(NC(=O)CCC(C)C)c2)cc(OC)c1] | N-(3-{[(3-{[3,5-bis(methoxy)phenyl]amino}quinoxalin-2-yl)amino]sulfonyl}phenyl)-4-methylpentanamide |
| 582 | 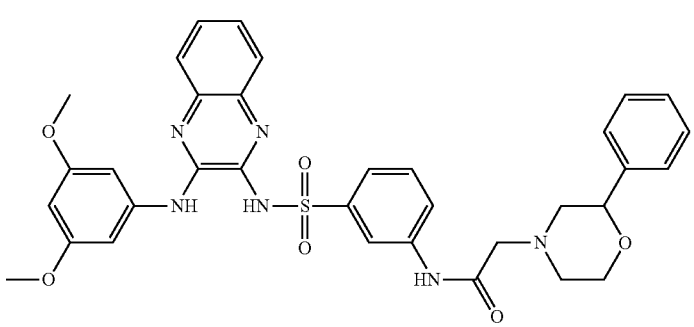 [SMILES: COc1cc(Nc2nc3ccccc3nc2NS(=O)(=O)c2cccc(NC(=O)CN3CCOC(c4ccccc4)C3)c2)cc(OC)c1] | N-(3-{[(3-{[3,5-bis(methoxy)phenyl]amino}quinoxalin-2-yl)amino]sulfonyl}phenyl)-2-(2-phenylmorpholin-4-yl)acetamide |

TABLE 1-continued

| Cpd. No. | Structure | Name |
|---|---|---|
| 583 | 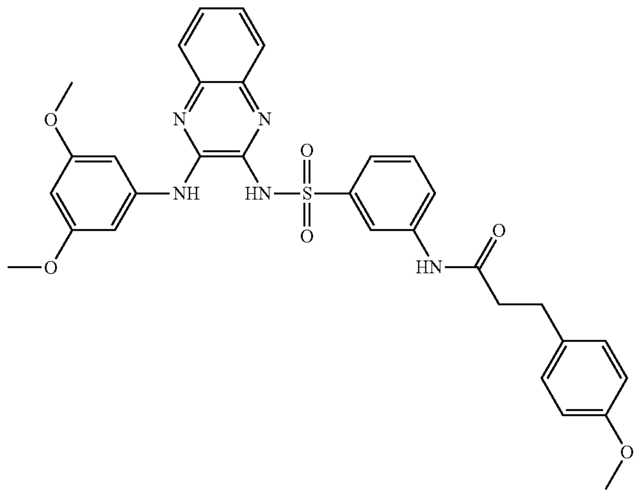 [SMILES: COc1ccc(CCC(=O)Nc2cccc(S(=O)(=O)Nc3nc4ccccc4nc3Nc3cc(OC)cc(OC)c3)c2)cc1] | N-(3-{[(3-{[3,5-bis(methoxy)phenyl]amino}quinoxalin-2-yl)amino]sulfonyl}phenyl)-3-[4-(methoxy)phenyl]propanamide |
| 584 | 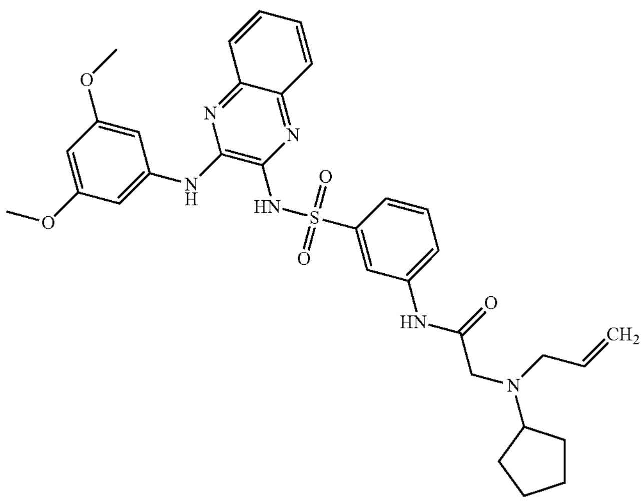 [SMILES: C=CCN(CC(=O)Nc1cccc(S(=O)(=O)Nc2nc3ccccc3nc2Nc2cc(OC)cc(OC)c2)c1)C1CCCC1] | N-(3-{[(3-{[3,5-bis(methoxy)phenyl]amino}quinoxalin-2-yl)amino]sulfonyl}phenyl)-N-2-cyclopentyl-N-2-prop-2-en-1-ylglycinamide |
| 585 | 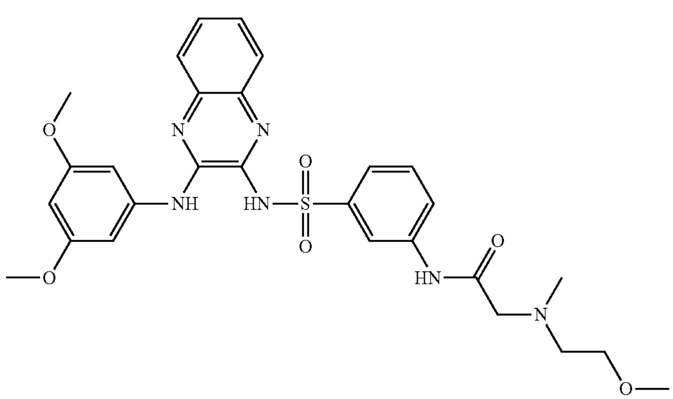 | N-(3-{[(3-{[3,5-bis(methoxy)phenyl]amino}quinoxalin-2-yl)amino]sulfonyl}phenyl)-N-2-methyl-N-2-[2-(methoxy)ethyl]glycinamide |

TABLE 1-continued

| Cpd. No. | Structure | Name |
|---|---|---|
| 586 | 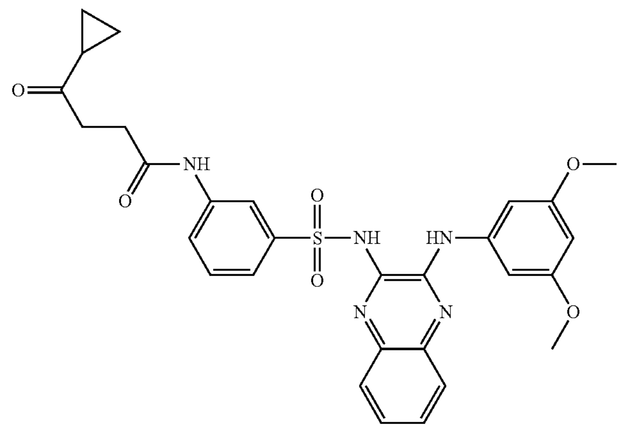 [SMILES: COc1cc(Nc2nc3ccccc3nc2NS(=O)(=O)c2cccc(NC(=O)CCC(=O)C3CC3)c2)cc(OC)c1] | N-(3-{[(3-{[3,5-bis(methoxy)phenyl]amino}quinoxalin-2-yl)amino]sulfonyl}phenyl)-4-cyclopropyl-4-oxobutanamide |
| 587 | 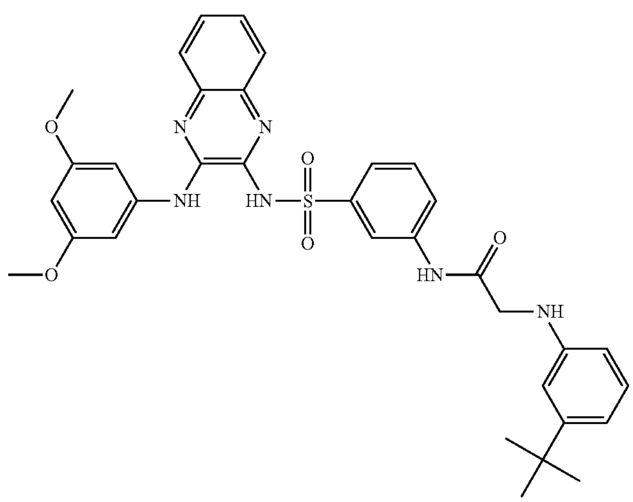 [SMILES: COc1cc(Nc2nc3ccccc3nc2NS(=O)(=O)c2cccc(NC(=O)CNc3cccc(C(C)(C)C)c3)c2)cc(OC)c1] | N-(3-{[(3-{[3,5-bis(methoxy)phenyl]amino}quinoxalin-2-yl)amino]sulfonyl}phenyl)-N-2-[3-(1,1-dimethylethyl)phenyl]glycinamide |
| 588 | 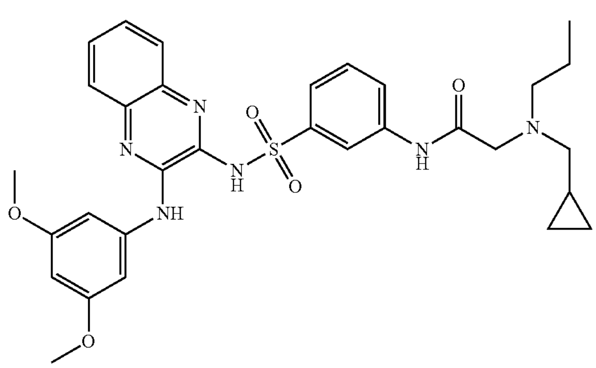 [SMILES: CCCN(CC(=O)Nc1cccc(S(=O)(=O)Nc2nc3ccccc3nc2Nc2cc(OC)cc(OC)c2)c1)CC1CC1] | N-(3-{[(3-{[3,5-bis(methoxy)phenyl]amino}quinoxalin-2-yl)amino]sulfonyl}phenyl)-N-2-(cyclopropylmethyl)-N-2-propylglycinamide |

TABLE 1-continued
| Cpd. No. | Structure | Name |
|---|---|---|
| 589 | 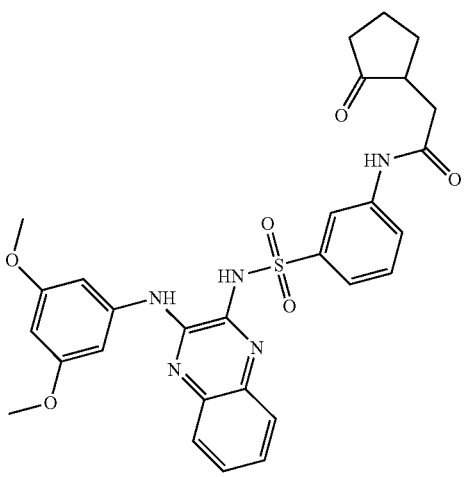 [SMILES: COc1cc(Nc2nc3ccccc3nc2NS(=O)(=O)c2cccc(NC(=O)CC3CCCC3=O)c2)cc(OC)c1] | N-(3-{[(3-{[3,5-bis(methoxy)phenyl]amino}quinoxalin-2-yl)amino]sulfonyl}phenyl)-2-(2-oxocyclopentyl)acetamide |
| 590 | 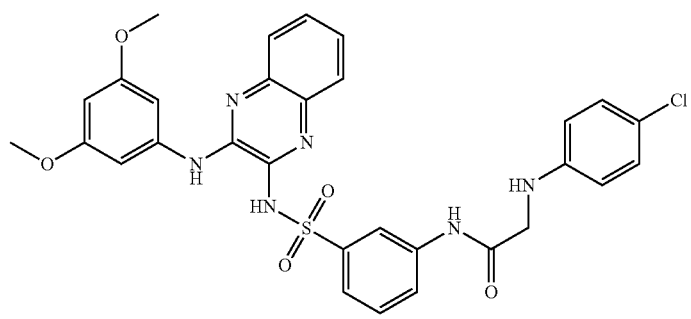 [SMILES: COc1cc(Nc2nc3ccccc3nc2NS(=O)(=O)c2cccc(NC(=O)CNc3ccc(Cl)cc3)c2)cc(OC)c1] | N-(3-{[(3-{[3,5-bis(methoxy)phenyl]amino}quinoxalin-2-yl)amino]sulfonyl}phenyl)-N-2-(4-chlorophenyl)glycinamide |
| 591 | 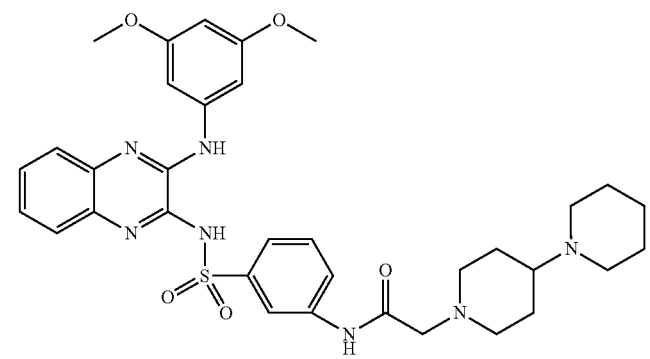 [SMILES: COc1cc(Nc2nc3ccccc3nc2NS(=O)(=O)c2cccc(NC(=O)CN3CCC(N4CCCCC4)CC3)c2)cc(OC)c1] | 2-(1,4'-bipiperidin-1'-yl)-N-(3-{[(3-{[3,5-bis(methoxy)phenyl]amino}quinoxalin-2-yl)amino]sulfonyl}phenyl)acetamide |

TABLE 1-continued

| Cpd. No. | Structure | Name |
|---|---|---|
| 592 | 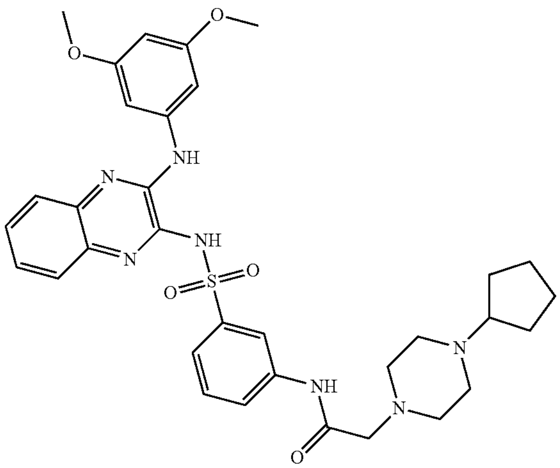 [SMILES: COc1cc(Nc2nc3ccccc3nc2NS(=O)(=O)c2cccc(NC(=O)CN3CCN(C4CCCC4)CC3)c2)cc(OC)c1] | N-(3-{[(3-{[3,5-bis(methoxy) phenyl]amino}quinoxalin-2-yl)amino]sulfonyl}phenyl)-2-(4-cyclopentylpiperazin-1-yl)acetamide |
| 593 | 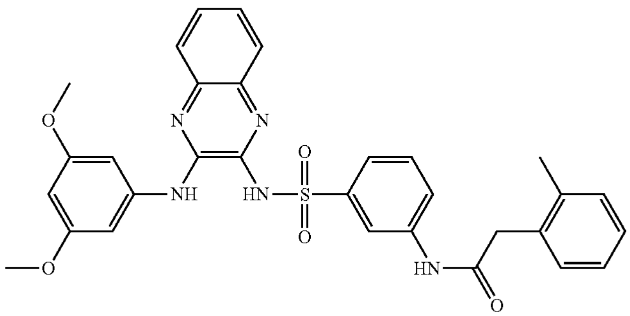 [SMILES: COc1cc(Nc2nc3ccccc3nc2NS(=O)(=O)c2cccc(NC(=O)Cc3ccccc3C)c2)cc(OC)c1] | N-(3-{[(3-{[3,5-bis(methoxy) phenyl]amino}quinoxalin-2-yl)amino]sulfonyl}phenyl)-2-(2-methylphenyl)acetamide |
| 594 | 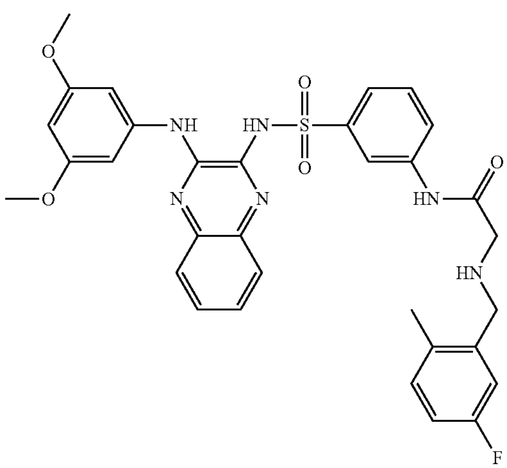 [SMILES: COc1cc(Nc2nc3ccccc3nc2NS(=O)(=O)c2cccc(NC(=O)CNCc3cc(F)ccc3C)c2)cc(OC)c1] | N-(3-{[(3-{[3,5-bis(methoxy) phenyl]amino}quinoxalin-2-yl)amino]sulfonyl}phenyl)-N-2-[(5-fluoro-2-methylphenyl) methyl]glycinamide |
| 595 | 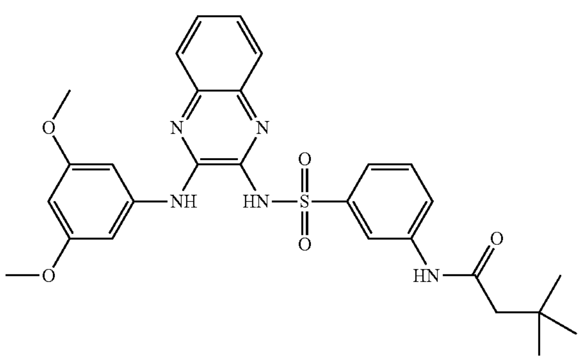 [SMILES: COc1cc(Nc2nc3ccccc3nc2NS(=O)(=O)c2cccc(NC(=O)CC(C)(C)C)c2)cc(OC)c1] | N-(3-{[(3-{[3,5-bis(methoxy) phenyl]amino}quinoxalin-2-yl)amino]sulfonyl}phenyl)-3,3-dimethylbutanamide |

TABLE 1-continued

| Cpd. No. | Structure | Name |
| --- | --- | --- |
| 596 | 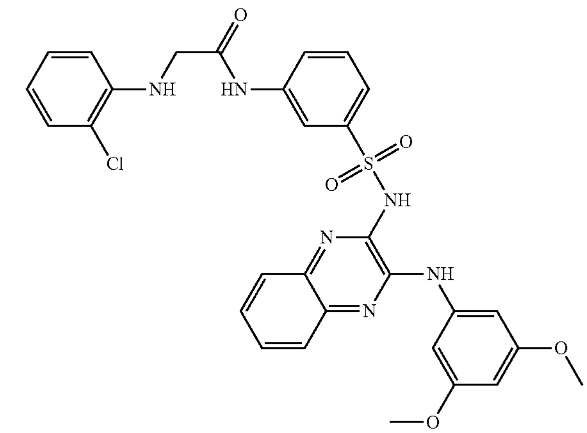 [SMILES: COc1cc(Nc2nc3ccccc3nc2NS(=O)(=O)c2cccc(NC(=O)CNc3ccccc3Cl)c2)cc(OC)c1] | N-(3-{[(3-{[3,5-bis(methyloxy)phenyl]amino}quinoxalin-2-yl)amino]sulfonyl}phenyl)-N$^2$-(2-chlorophenyl)glycinamide |
| 597 | 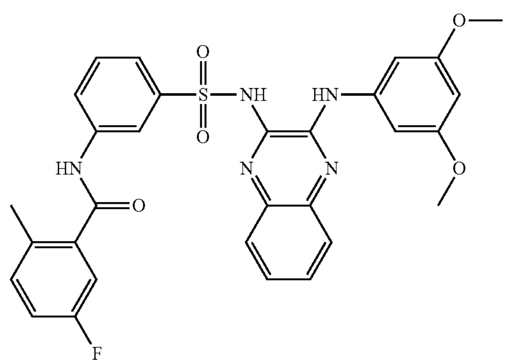 [SMILES: COc1cc(Nc2nc3ccccc3nc2NS(=O)(=O)c2cccc(NC(=O)c3cc(F)ccc3C)c2)cc(OC)c1] | N-(3-{[(3-{[3,5-bis(methoxy)phenyl]amino}quinoxalin-2-yl)amino]sulfonyl}phenyl)-5-fluoro-2-methylbenzamide |
| 598 | 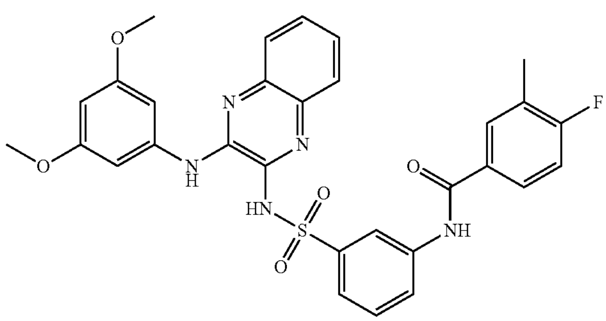 [SMILES: COc1cc(Nc2nc3ccccc3nc2NS(=O)(=O)c2cccc(NC(=O)c3ccc(F)c(C)c3)c2)cc(OC)c1] | N-(3-{[(3-{[3,5-bis(methoxy)phenyl]amino}quinoxalin-2-yl)amino]sulfonyl}phenyl)-4-fluoro-3-methylbenzamide |
| 599 | 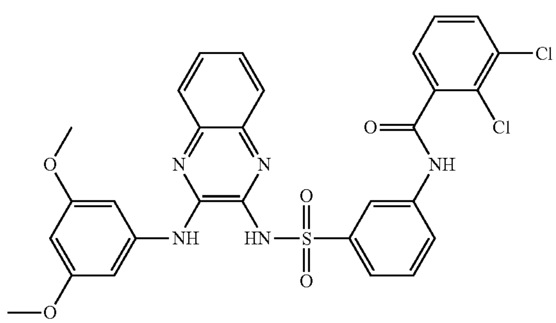 [SMILES: COc1cc(Nc2nc3ccccc3nc2NS(=O)(=O)c2cccc(NC(=O)c3cccc(Cl)c3Cl)c2)cc(OC)c1] | N-(3-{[(3-{[3,5-bis(methoxy)phenyl]amino}quinoxalin-2-yl)amino]sulfonyl}phenyl)-2,3-dichlorobenzamide |

| Cpd. No. | Structure | Name |
|---|---|---|
| 600 | 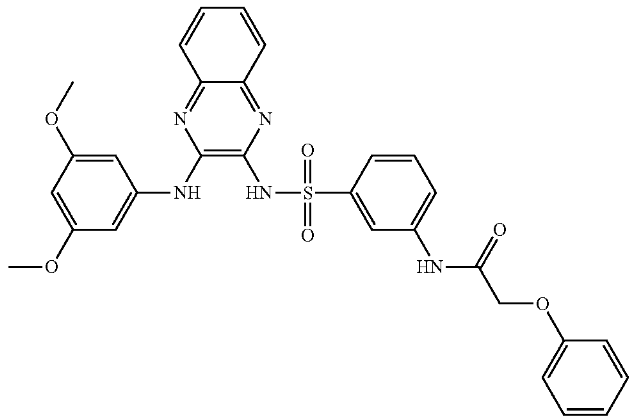 [SMILES: COc1cc(Nc2nc3ccccc3nc2NS(=O)(=O)c2cccc(NC(=O)COc3ccccc3)c2)cc(OC)c1] | N-(3-{[(3-{[3,5-bis(methoxy) phenyl]amino}quinoxalin-2-yl)amino]sulfonyl}phenyl)-2-(phenyloxy)acetamide |
| 601 | 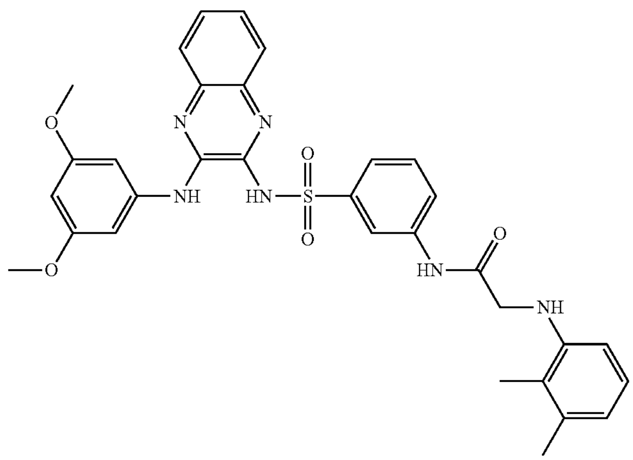 [SMILES: COc1cc(Nc2nc3ccccc3nc2NS(=O)(=O)c2cccc(NC(=O)CNc3cccc(C)c3C)c2)cc(OC)c1] | N-(3-{[(3-{[3,5-bis(methoxy) phenyl]amino}quinoxalin-2-yl) amino]sulfonyl}phenyl)-N-2-(2,3-dimethylphenyl)glycinamide |
| 602 | 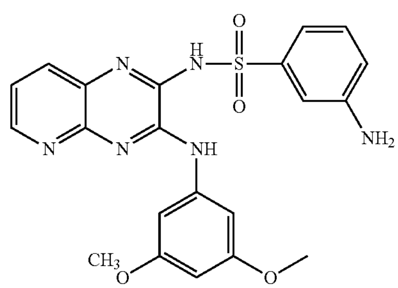 | 3-amino-N-(3-{[3,5-bis(methoxy) phenyl]amino}pyrido[2,3-b] pyrazin-2-yl)benzenesulfonamide |
| 603 | 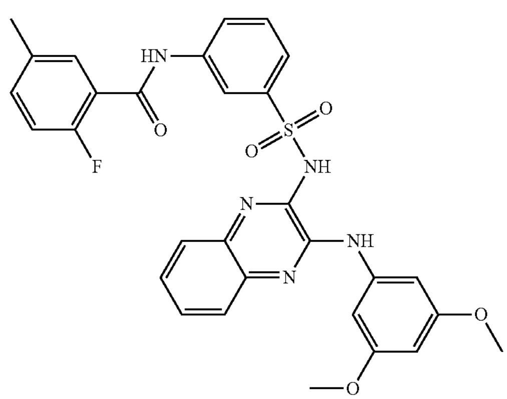 [SMILES: COc1cc(Nc2nc3ccccc3nc2NS(=O)(=O)c2cccc(NC(=O)c3cc(C)ccc3F)c2)cc(OC)c1] | N-(3-{[(3-{[3,5-bis(methoxy) phenyl]amino}quinoxalin-2-yl)amino]sulfonyl}phenyl)-2-fluoro-5-methylbenza |

TABLE 1-continued

| Cpd. No. | Structure | Name |
|---|---|---|
| 604 | 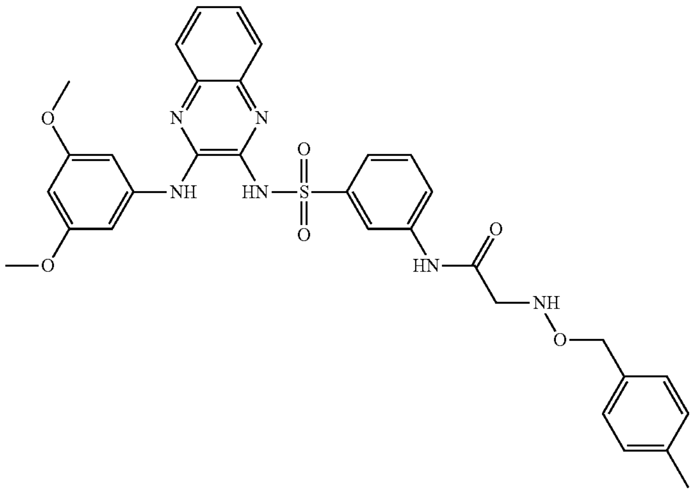 | N-(3-{[(3-{[3,5-bis(methoxy)phenyl]amino}quinoxalin-2-yl)amino]sulfonyl}phenyl)-N-2-{[(4-methylphenyl)methyl]oxy}glycinamide |
| 605 | 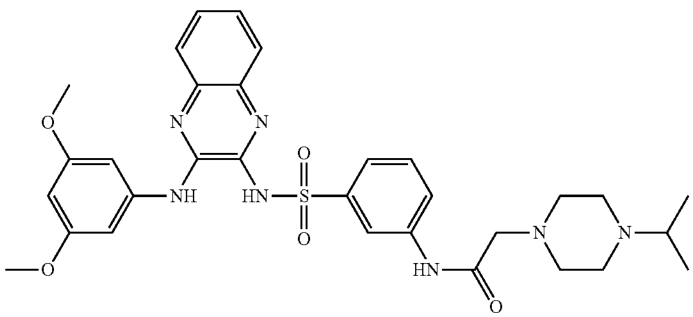 | N-(3-{[(3-{[3,5-bis(methoxy)phenyl]amino}quinoxalin-2-yl)amino]sulfonyl}phenyl)-2-[4-(1-methylethyl)piperazin-1-yl]acetamide |
| 606 | 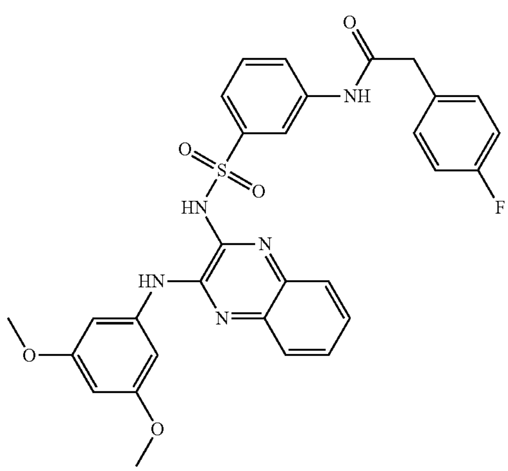 [SMILES: COc1cc(Nc2nc3ccccc3nc2NS(=O)(=O)c2cccc(NC(=O)Cc3ccc(F)cc3)c2)cc(OC)c1] | N-(3-{[(3-{[3,5-bis(methoxy)phenyl]amino}quinoxalin-2-yl)amino]sulfonyl}phenyl)-2-(4-fluorophenyl)acetamide |
| 607 | 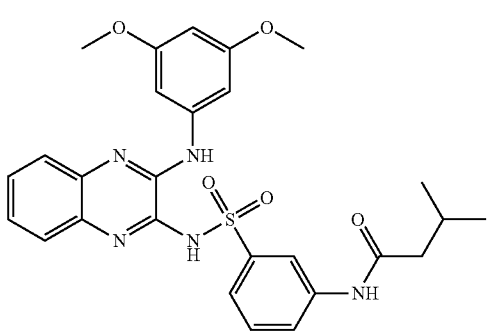 [SMILES: COc1cc(Nc2nc3ccccc3nc2NS(=O)(=O)c2cccc(NC(=O)CC(C)C)c2)cc(OC)c1] | N-(3-{[(3-{[3,5-bis(methoxy)phenyl]amino}quinoxalin-2-yl)amino]sulfonyl}phenyl)-3-methylbutanamide |

TABLE 1-continued

| Cpd. No. | Structure | Name |
| --- | --- | --- |
| 608 | 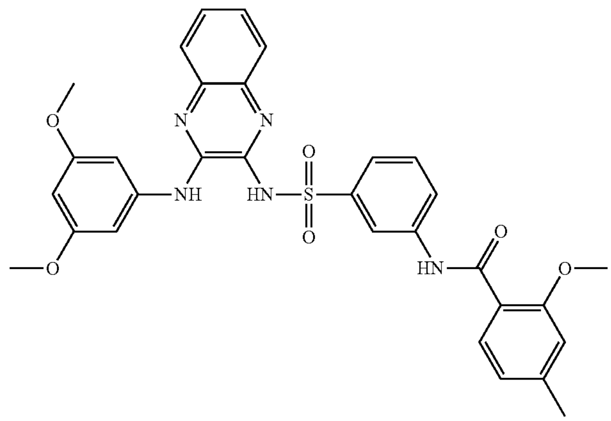 | N-(3-{[(3-{[3,5-bis(methoxy) phenyl]amino}quinoxalin-2-yl)amino]sulfonyl}phenyl)-4-methyl-2-(methoxy)benzamide |
| 609 | 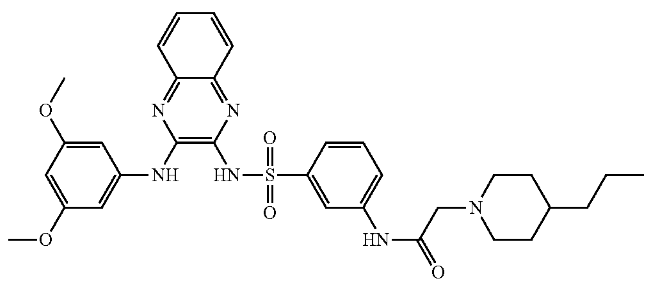 [SMILES: CCCC1CCN(CC(=O)Nc2cccc(S(=O)(=O)Nc3nc4ccccc4nc3Nc3cc(OC)cc(OC)c3)c2)CC1] | N-(3-{[(3-{[3,5-bis(methoxy) phenyl]amino}quinoxalin-2-yl)amino]sulfonyl}phenyl)-2-(4-propylpiperidin-1-yl)acetamide |
| 610 | 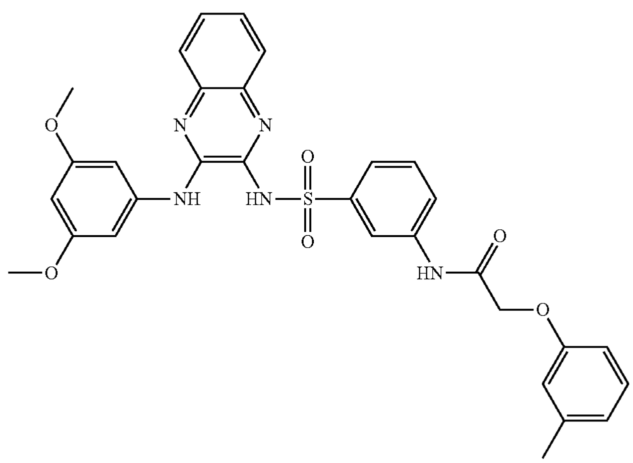 [SMILES: COc1cc(Nc2nc3ccccc3nc2NS(=O)(=O)c2cccc(NC(=O)COc3cccc(C)c3)c2)cc(OC)c1] | N-(3-{[(3-{[3,5-bis(methoxy) phenyl]amino}quinoxalin-2-yl)amino]sulfonyl}phenyl)-2-[(3-methylphenyl)oxy]acetamide |
| 611 | 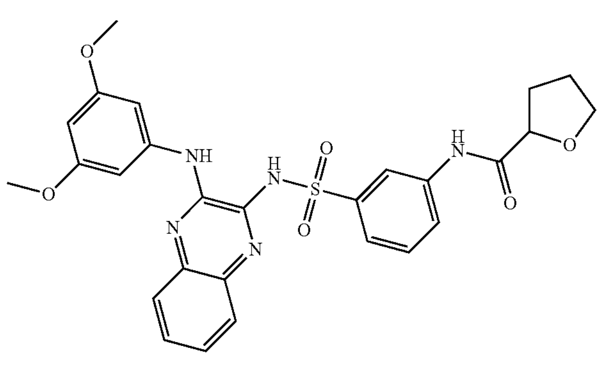 [SMILES: COc1cc(Nc2nc3ccccc3nc2NS(=O)(=O)c2cccc(NC(=O)C3CCCO3)c2)cc(OC)c1] | N-(3-{[(3-{[3,5-bis(methoxy) phenyl]amino}quinoxalin-2-yl)amino]sulfonyl}phenyl) tetrahydrofuran-2-carboxamide |

TABLE 1-continued

| Cpd. No. | Structure | Name |
|---|---|---|
| 612 | 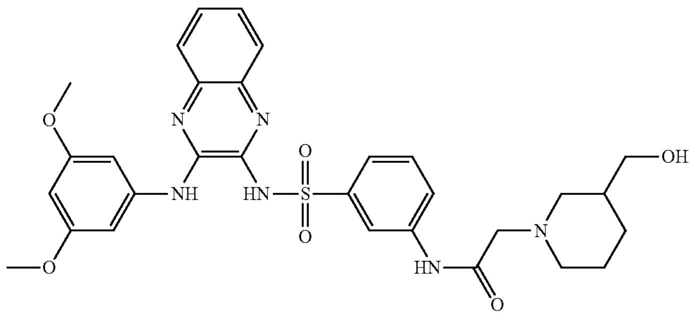 [SMILES: COc1cc(Nc2nc3ccccc3nc2NS(=O)(=O)c2cccc(NC(=O)CN3CCCC(CO)C3)c2)cc(OC)c1] | N-(3-{[(3-{[3,5-bis(methoxy) phenyl]amino}quinoxalin-2-yl)amino]sulfonyl}phenyl)-2-[3-(hydroxymethyl)piperidin-1-yl]acetamide |
| 613 | 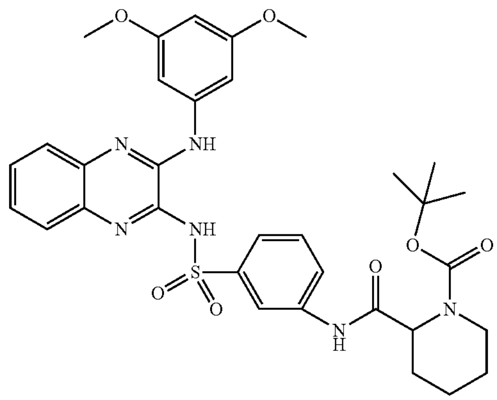 [SMILES: COc1cc(Nc2nc3ccccc3nc2NS(=O)(=O)c2cccc(NC(=O)C3CCCCN3C(=O)OC(C)(C)C)c2)cc(OC)c1] | 1,1-dimethylethyl2-{[(3-{[(3-{[3,5-bis(methoxy)phenyl] amino}quinoxalin-2-yl)amino] sulfonyl}phenyl)amino]carbonyl} piperidine-1-carboxylate |
| 614 | 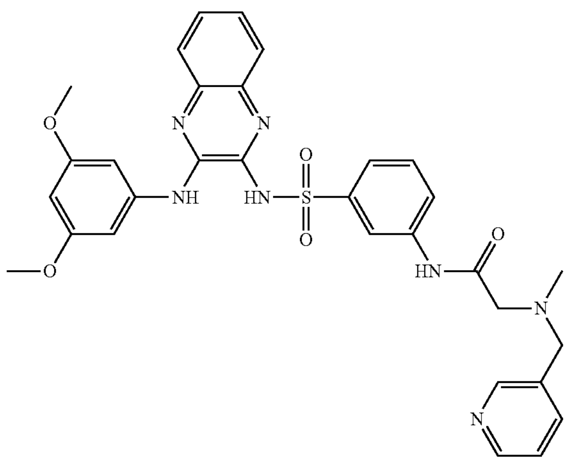 | N-(3-{[(3-{[3,5-bis(methoxy) phenyl]amino}quinoxalin-2-yl)amino]sulfonyl}phenyl)-N-2-methyl-N-2-(pyridin-3-ylmethyl)glycinamide |
| 615 | 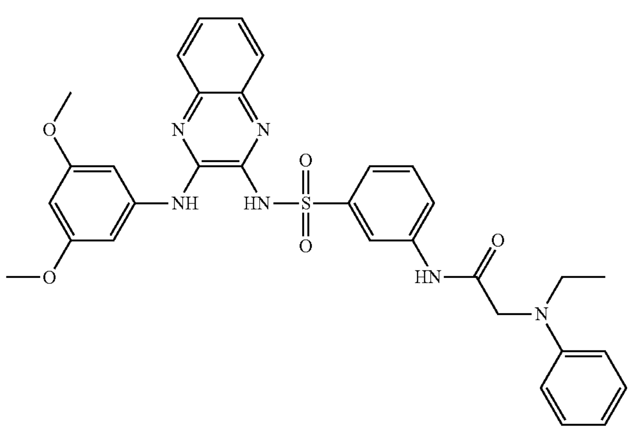 [SMILES: CCN(CC(=O)Nc1cccc(S(=O)(=O)Nc2nc3ccccc3nc2Nc2cc(OC)cc(OC)c2)c1)c1ccccc1] | N-(3-{[(3-{[3,5-bis(methoxy) phenyl]amino}quinoxalin-2-yl)amino]sulfonyl}phenyl)-N-2-ethyl-N-2-phenylglycinamide |

TABLE 1-continued

| Cpd. No. | Structure | Name |
| --- | --- | --- |
| 616 | 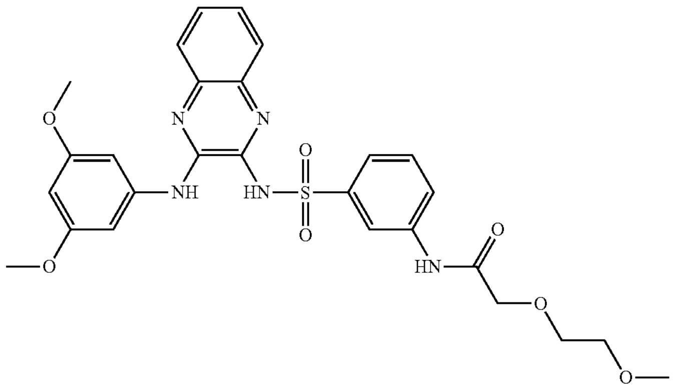 | N-(3-{[(3-{[3,5-bis(methoxy)phenyl]amino}quinoxalin-2-yl)amino]sulfonyl}phenyl)-2-{[2-(methoxy)ethyl]oxy}acetamide |
| 617 | 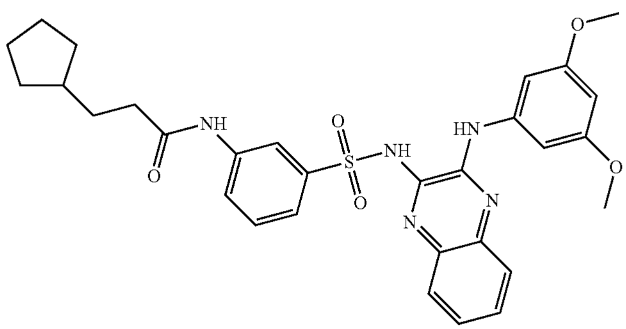 [SMILES: COc1cc(Nc2nc3ccccc3nc2NS(=O)(=O)c2cccc(NC(=O)CCC3CCCC3)c2)cc(OC)c1] | N-(3-{[(3-{[3,5-bis(methoxy)phenyl]amino}quinoxalin-2-yl)amino]sulfonyl}phenyl)-3-cyclopentylpropanamide |
| 618 | 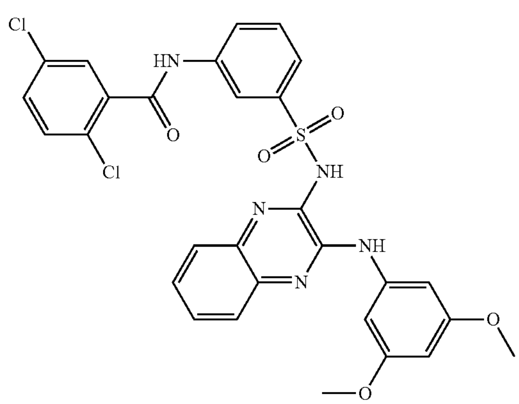 [SMILES: COc1cc(Nc2nc3ccccc3nc2NS(=O)(=O)c2cccc(NC(=O)c3cc(Cl)ccc3Cl)c2)cc(OC)c1] | N-(3-{[(3-{[3,5-bis(methoxy)phenyl]amino}quinoxalin-2-yl)amino]sulfonyl}phenyl)-2,5-dichlorobenzamide |
| 619 | 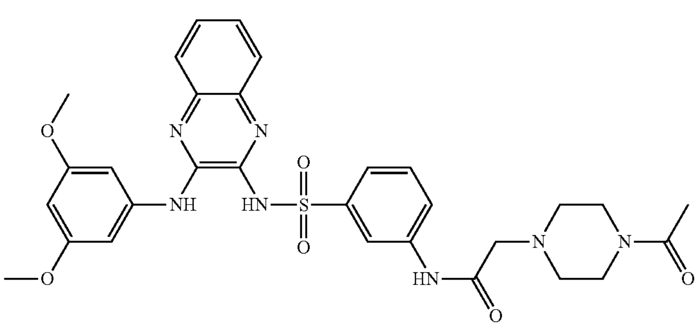 [SMILES: COc1cc(Nc2nc3ccccc3nc2NS(=O)(=O)c2cccc(NC(=O)CN3CCN(C(C)=O)CC3)c2)cc(OC)c1] | 2-(4-acetylpiperazin-1-yl)-N-(3-{[(3-{[3,5-bis(methoxy)phenyl]amino}quinoxalin-2-yl)amino]sulfonyl}phenyl)acetamide |

TABLE 1-continued

| Cpd. No. | Structure | Name |
|---|---|---|
| 620 | 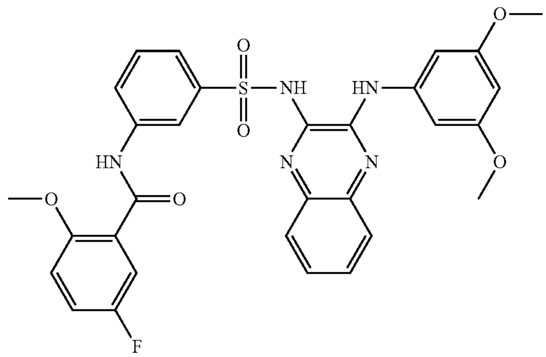 | N-(3-{[(3-{[3,5-bis(methoxy)phenyl]amino}quinoxalin-2-yl)amino]sulfonyl}phenyl)-5-fluoro-2-(methoxy)benzamide |
| 621 | 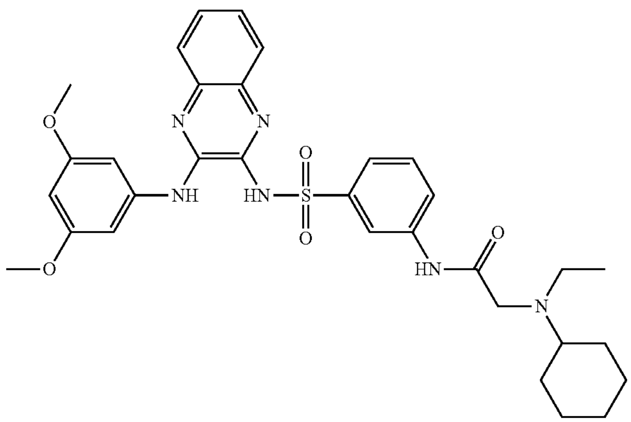 [SMILES: CCN(CC(=O)Nc1cccc(S(=O)(=O)Nc2nc3ccccc3nc2Nc2cc(OC)cc(OC)c2)c1)C1CCCCC1] | N-(3-{[(3-{[3,5-bis(methoxy)phenyl]amino}quinoxalin-2-yl)amino]sulfonyl}phenyl)-N-2-cyclohexyl-N-2-ethylglycinamide |
| 622 | 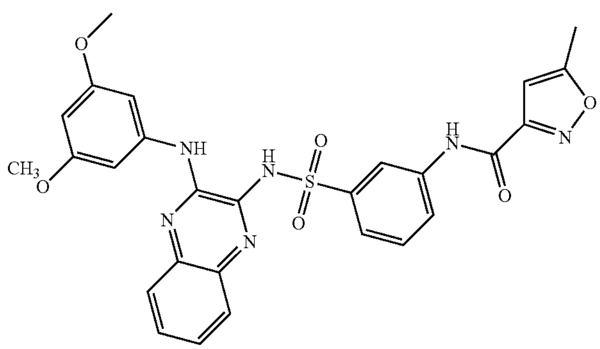 | N-(3-{[(3-{[3,5-bis(methoxy)phenyl]amino}quinoxalin-2-yl)amino]sulfonyl}phenyl)-5-methylisoxazole-3-carboxamide |
| 623 | 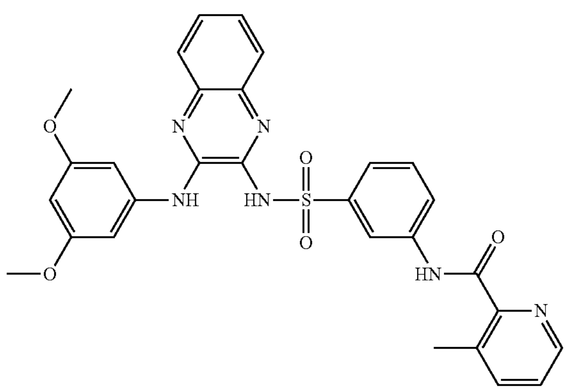 [SMILES: COc1cc(Nc2nc3ccccc3nc2NS(=O)(=O)c2cccc(NC(=O)c3ncccc3C)c2)cc(OC)c1] | N-(3-{[(3-{[3,5-bis(methoxy)phenyl]amino}quinoxalin-2-yl)amino]sulfonyl}phenyl)-3-methylpyridine-2-carboxamide |

TABLE 1-continued

| Cpd. No. | Structure | Name |
|---|---|---|
| 624 | 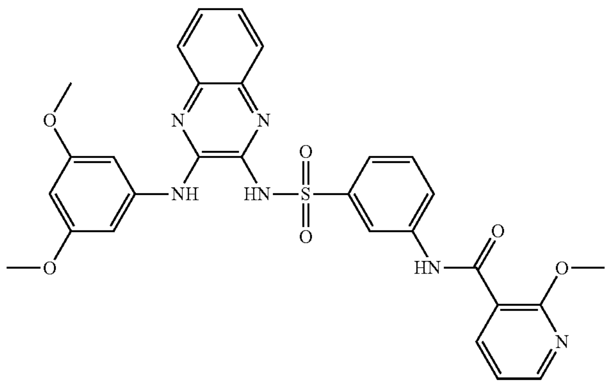 | N-(3-{[(3-{[3,5-bis(methoxy)phenyl]amino}quinoxalin-2-yl)amino]sulfonyl}phenyl)-2-(methoxy)pyridine-3-carboxamide |
| 625 | 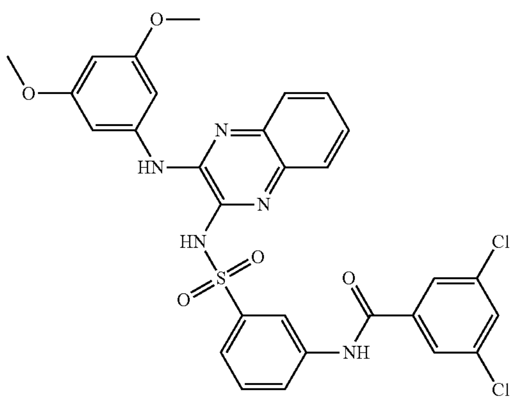 [SMILES: COc1cc(Nc2nc3ccccc3nc2NS(=O)(=O)c2cccc(NC(=O)c3cc(Cl)cc(Cl)c3)c2)cc(OC)c1] | N-(3-{[(3-{[3,5-bis(methoxy)phenyl]amino}quinoxalin-2-yl)amino]sulfonyl}phenyl)-3,5-dichlorobenzamide |
| 626 | 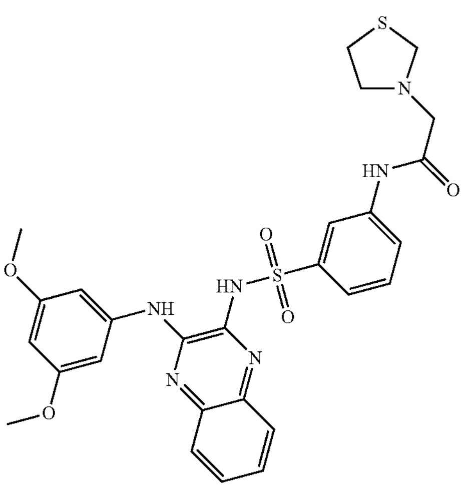 [SMILES: COc1cc(Nc2nc3ccccc3nc2NS(=O)(=O)c2cccc(NC(=O)CN3CCSC3)c2)cc(OC)c1] | N-(3-{[(3-{[3,5-bis(methoxy)phenyl]amino}quinoxalin-2-yl)amino]sulfonyl}phenyl)-2-(1,3-thiazolidin-3-yl)acetamide |
| 627 | 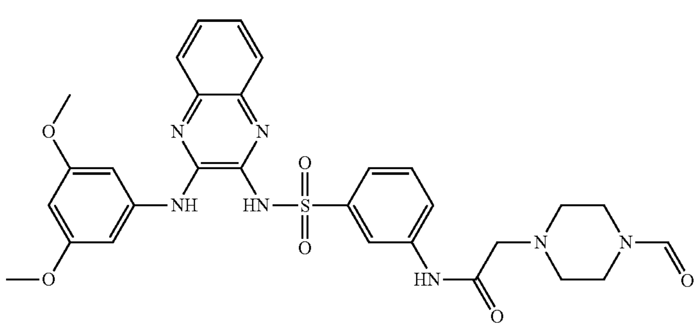 [SMILES: COc1cc(Nc2nc3ccccc3nc2NS(=O)(=O)c2cccc(NC(=O)CN3CCN(C=O)CC3)c2)cc(OC)c1] | N-(3-{[(3-{[3,5-bis(methoxy)phenyl]amino}quinoxalin-2-yl)amino]sulfonyl}phenyl)-2-(4-formylpiperazin-1-yl)acetamide |

TABLE 1-continued

| Cpd. No. | Structure | Name |
|---|---|---|
| 628 | 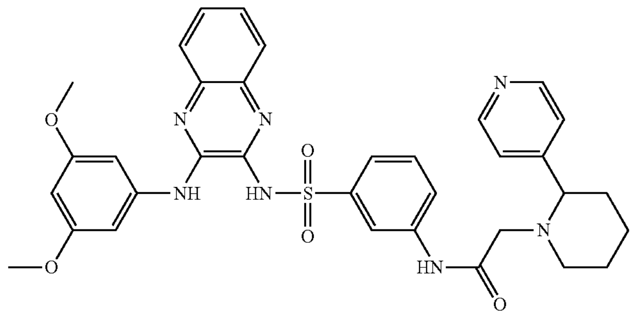 [SMILES: COc1cc(Nc2nc3ccccc3nc2NS(=O)(=O)c2cccc(NC(=O)CN3CCCCC3c3ccncc3)c2)cc(OC)c1] | N-(3-{[(3-{[3,5-bis(methoxy)phenyl]amino}quinoxalin-2-yl)amino]sulfonyl}phenyl)-2-(2-pyridin-4-ylpiperidin-1-yl)acetamide |
| 629 | 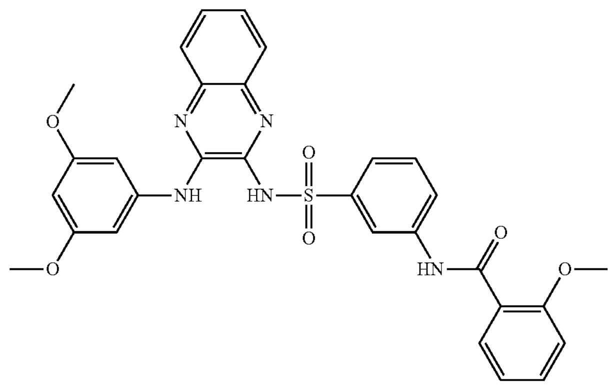 | N-(3-{[(3-{[3,5-bis(methoxy)phenyl]amino}quinoxalin-2-yl)amino]sulfonyl}phenyl)-2-(methoxy)benzamide |
| 630 | 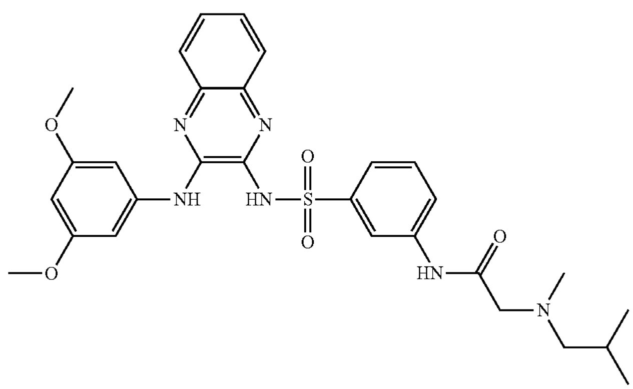 [SMILES: COc1cc(Nc2nc3ccccc3nc2NS(=O)(=O)c2cccc(NC(=O)CN(C)CC(C)C)c2)cc(OC)c1] | N-(3-{[(3-{[3,5-bis(methoxy)phenyl]amino}quinoxalin-2-yl)amino]sulfonyl}phenyl)-N-2-methyl-N-2-(2-methylpropyl)glycinamide |
| 631 | 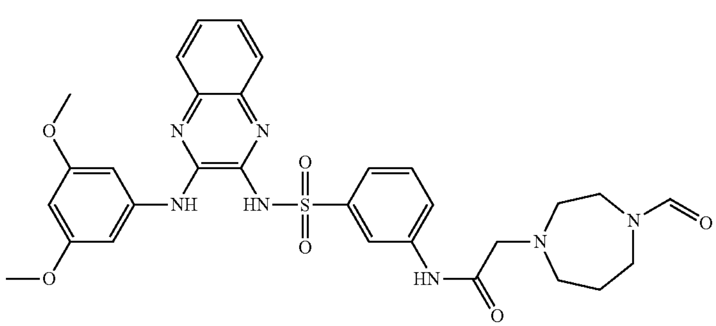 [SMILES: COc1cc(Nc2nc3ccccc3nc2NS(=O)(=O)c2cccc(NC(=O)CN3CCCN(C=O)CC3)c2)cc(OC)c1] | N-(3-{[(3-{[3,5-bis(methoxy)phenyl]amino}quinoxalin-2-yl)amino]sulfonyl}phenyl)-2-(4-formyl-1,4-diazepan-1-yl)acetamide |

TABLE 1-continued

| Cpd. No. | Structure | Name |
|---|---|---|
| 632 | 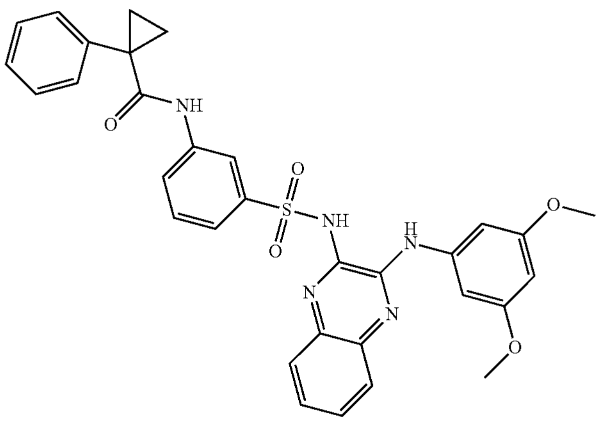 [SMILES: COc1cc(Nc2nc3ccccc3nc2NS(=O)(=O)c2cccc(NC(=O)C3(c4ccccc4)CC3)c2)cc(OC)c1] | N-(3-{[(3-{[3,5-bis(methoxy) phenyl]amino}quinoxalin-2-yl)amino]sulfonyl}phenyl)-1-phenylcyclopropanecarboxamide |
| 633 | 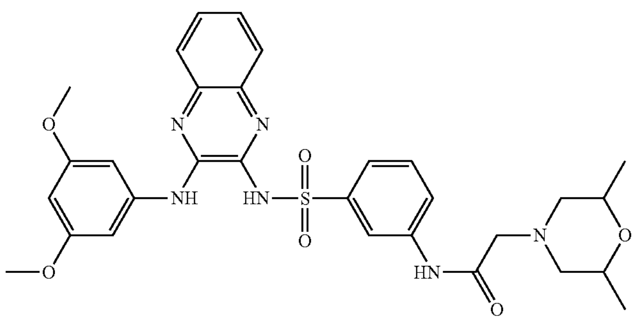 | N-(3-{[(3-{[3,5-bis(methoxy) phenyl]amino}quinoxalin-2-yl)amino]sulfonyl}phenyl)-2-(2,6-dimethylmorpholin-4-yl)acetamide |
| 634 | 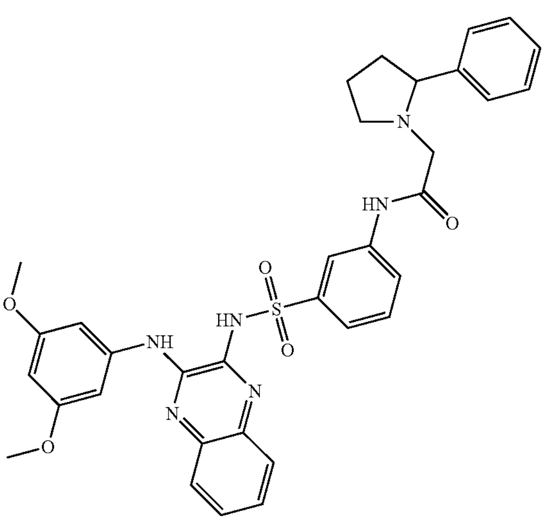 [SMILES: COc1cc(Nc2nc3ccccc3nc2NS(=O)(=O)c2cccc(NC(=O)CN3CCCC3c3ccccc3)c2)cc(OC)c1] | N-(3-{[(3-{[3,5-bis(methoxy) phenyl]amino}quinoxalin-2-yl)amino]sulfonyl}phenyl)-2-(2-phenylpyrrolidin-1-yl) acetamide |

TABLE 1-continued
| Cpd. No. | Structure | Name |
|---|---|---|
| 635 | 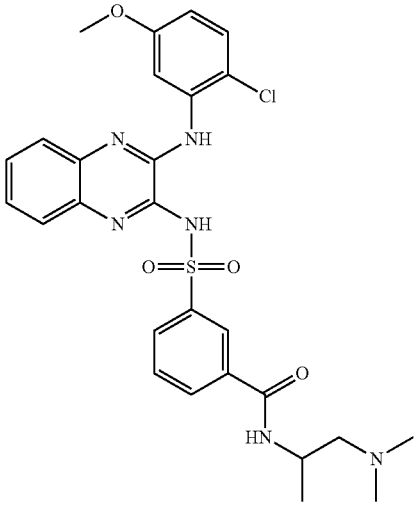 [SMILES: COc1ccc(Cl)c(Nc2nc3ccccc3nc2NS(=O)(=O)c2cccc(C(=O)NC(C)CN(C)C)c2)c1] | 3-{[(3-{[2-chloro-5-(methoxy)phenyl]amino}quinoxalin-2-yl)amino]sulfonyl}-N-[2-(dimethylamino)-1-methylethyl]benzamide |
| 636 | 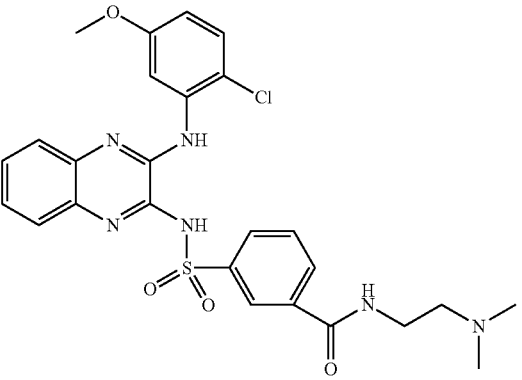 [SMILES: COc1ccc(Cl)c(Nc2nc3ccccc3nc2NS(=O)(=O)c2cccc(C(=O)NCCN(C)C)c2)c1] | 3-{[(3-{[2-chloro-5-(methoxy)phenyl]amino}quinoxalin-2-yl)amino]sulfonyl}-N-[2-(dimethylamino)ethyl]benzamide |
| 637 | 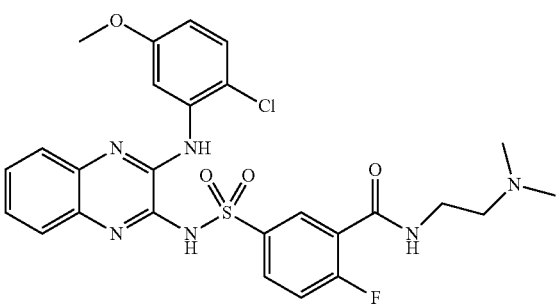 [SMILES: COc1ccc(Cl)c(Nc2nc3ccccc3nc2NS(=O)(=O)c2ccc(F)c(C(=O)NCCN(C)C)c2)c1] | 5-{[(3-{[2-chloro-5-(methoxy)phenyl]amino}quinoxalin-2-yl)amino]sulfonyl}-N-[2-(dimethylamino)ethyl]-2-fluorobenzamide |

TABLE 1-continued

| Cpd. No. | Structure | Name |
|---|---|---|
| 638 | 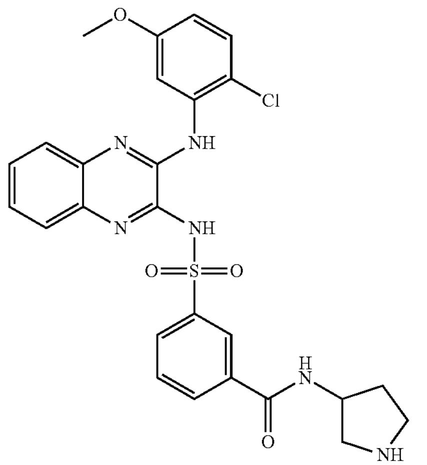 [SMILES: COc1ccc(Cl)c(Nc2nc3ccccc3nc2NS(=O)(=O)c2cccc(C(=O)NC3CCNC3)c2)c1] | 3-{[(3-{[2-chloro-5-(methoxy) phenyl]amino}quinoxalin-2-yl)amino]sulfonyl}-N-pyrrolidin-3-ylbenzamide |
| 639 | 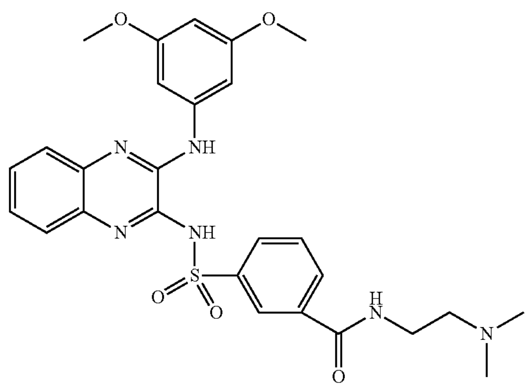 [SMILES: COc1cc(Nc2nc3ccccc3nc2NS(=O)(=O)c2cccc(C(=O)NCCN(C)C)c2)cc(OC)c1] | 3-{[(3-{[3,5-bis(methoxy) phenyl]amino}quinoxalin-2-yl)amino]sulfonyl}-N-[2-(dimethylamino)ethyl] benzamide |
| 640 | 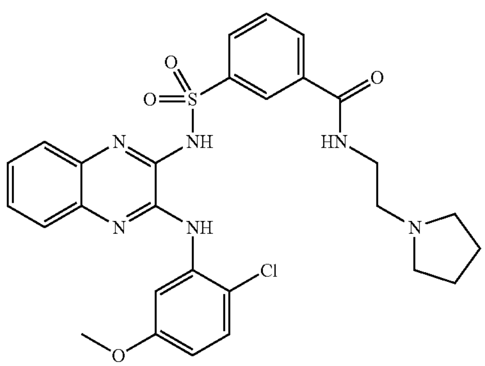 [SMILES: COc1ccc(Cl)c(Nc2nc3ccccc3nc2NS(=O)(=O)c2cccc(C(=O)NCCN3CCCC3)c2)c1] | 3-{[(3-{[2-chloro-5-(methoxy) phenyl]amino}quinoxalin-2-yl)amino]sulfonyl}-N-(2-pyrrolidin-1-ylethyl)benzamide |
| 641 | 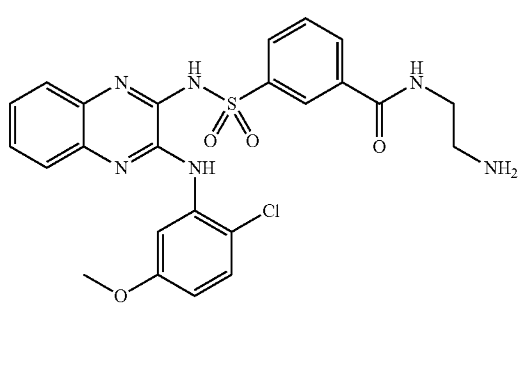 [SMILES: COc1ccc(Cl)c(Nc2nc3ccccc3nc2NS(=O)(=O)c2cccc(C(=O)NCCN)c2)c1] | N-(2-aminoethyl)-3-{[(3-{[2-chloro-5-(methoxy)phenyl] amino}quinoxalin-2-yl) amino]sulfonyl}benzamide |

TABLE 1-continued
| Cpd. No. | Structure | Name |
|---|---|---|
| 642 | 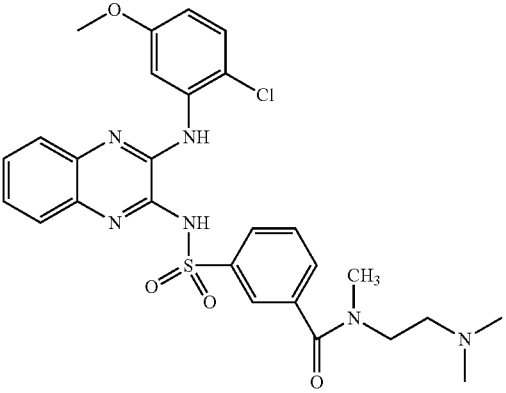 [SMILES: COc1ccc(Cl)c(Nc2nc3ccccc3nc2NS(=O)(=O)c2cccc(C(=O)N(C)CCN(C)C)c2)c1] | 3-{[(3-{[2-chloro-5-(methoxy) phenyl]amino}quinoxalin-2-yl)amino]sulfonyl}-N-[2-(dimethylamino)ethyl]-N-methylbenzamide |
| 643 | 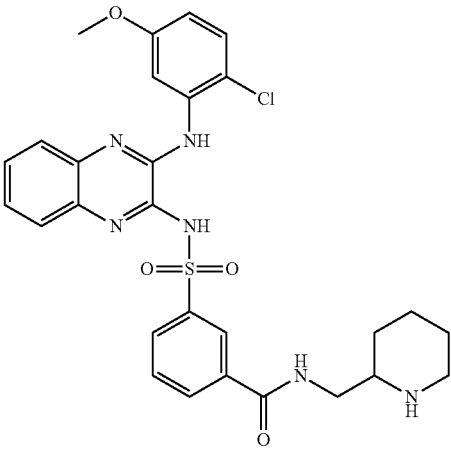 [SMILES: COc1ccc(Cl)c(Nc2nc3ccccc3nc2NS(=O)(=O)c2cccc(C(=O)NCC3CCCCN3)c2)c1] | 3-{[(3-{[2-chloro-5-(methoxy) phenyl]amino}quinoxalin-2-yl)amino]sulfonyl}-N-(piperidin-2-ylmethyl) benzamide |
| 644 | 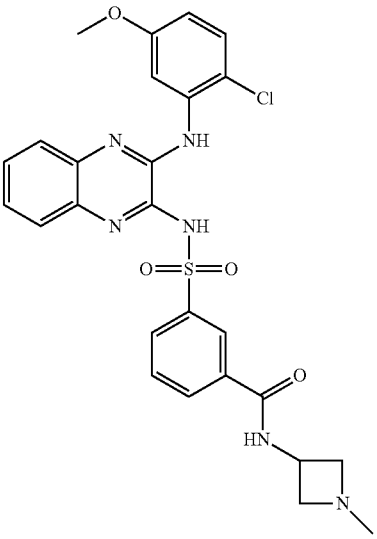 [SMILES: COc1ccc(Cl)c(Nc2nc3ccccc3nc2NS(=O)(=O)c2cccc(C(=O)NC3CN(C)C3)c2)c1] | 3-{[(3-{[2-chloro-5-(methoxy) phenyl]amino}quinoxalin-2-yl)amino]sulfonyl}-N-(1-methylazetidin-3-yl)benzamide |

TABLE 1-continued
| Cpd. No. | Structure | Name |
|---|---|---|
| 645 | 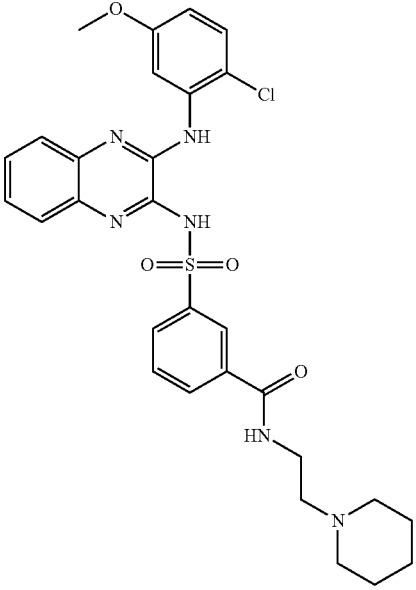 [SMILES: COc1ccc(Cl)c(Nc2nc3ccccc3nc2NS(=O)(=O)c2cccc(C(=O)NCCN3CCCCC3)c2)c1] | 3-{[(3-{[2-chloro-5-(methoxy)phenyl]amino}quinoxalin-2-yl)amino]sulfonyl}-N-(2-piperidin-1-ylethyl)benzamide |
| 646 | 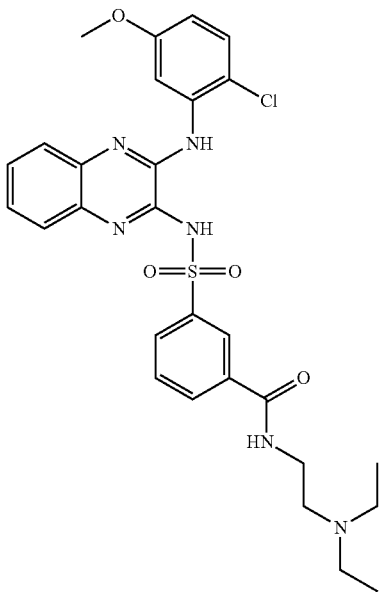 [SMILES: CCN(CC)CCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[2-(diethylamino)ethyl]benzamide |
| 647 | 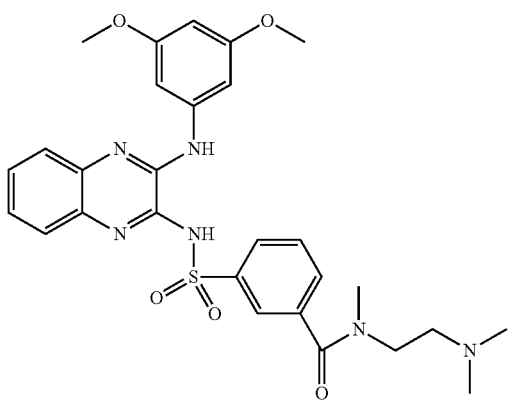 [SMILES: COc1cc(Nc2nc3ccccc3nc2NS(=O)(=O)c2cccc(C(=O)N(C)CCN(C)C)c2)cc(OC)c1] | 3-{[(3-{[3,5-bis(methoxy)phenyl]amino}quinoxalin-2-yl)amino]sulfonyl}-N-[2-(dimethylamino)ethyl]-N-methylbenzamide |

TABLE 1-continued
| Cpd. No. | Structure | Name |
|---|---|---|
| 648 | 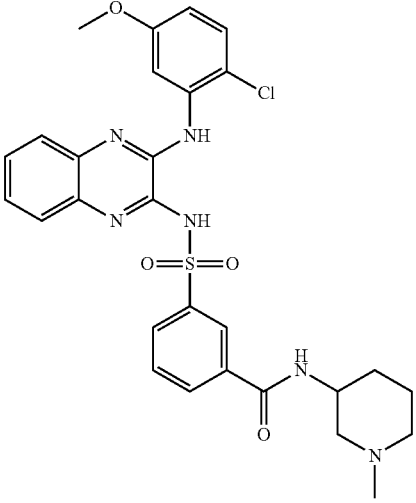 [SMILES: COc1ccc(Cl)c(Nc2nc3ccccc3nc2NS(=O)(=O)c2cccc(C(=O)NC3CCCN(C)C3)c2)c1] | 3-{[(3-{[2-chloro-5-(methoxy) phenyl]amino}quinoxalin-2-yl)amino]sulfonyl}-N-(1-methylpiperidin-3-yl)benzamide |
| 649 | 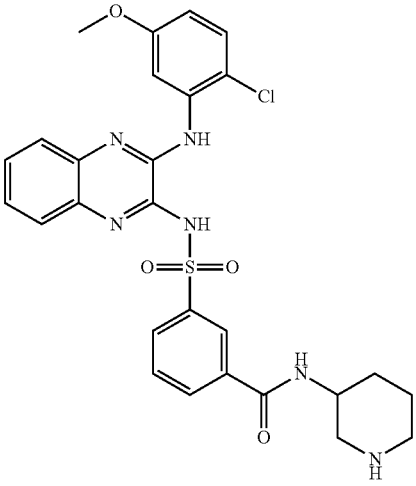 [SMILES: COc1ccc(Cl)c(Nc2nc3ccccc3nc2NS(=O)(=O)c2cccc(C(=O)NC3CCCNC3)c2)c1] | 3-{[(3-{[2-chloro-5-(methoxy) phenyl]amino}quinoxalin-2-yl)amino]sulfonyl}-N-piperidin-3-ylbenzamide |
| 650 | 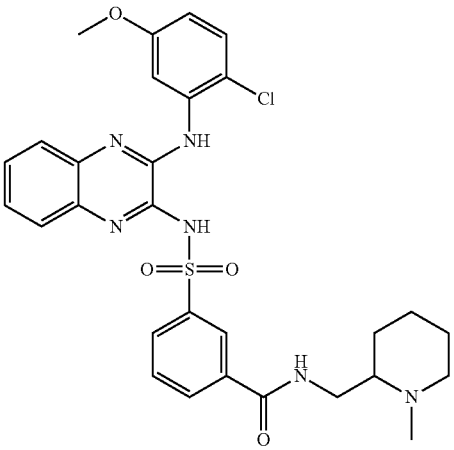 [SMILES: COc1ccc(Cl)c(Nc2nc3ccccc3nc2NS(=O)(=O)c2cccc(C(=O)NCC3CCCCN3C)c2)c1] | 3-{[(3-{[2-chloro-5-(methoxy) phenyl]amino}quinoxalin-2-yl)amino]sulfonyl}-N-[(1-methylpiperidin-2-yl)methyl]benzamide |

TABLE 1-continued
| Cpd. No. | Structure | Name |
|---|---|---|
| 651 | 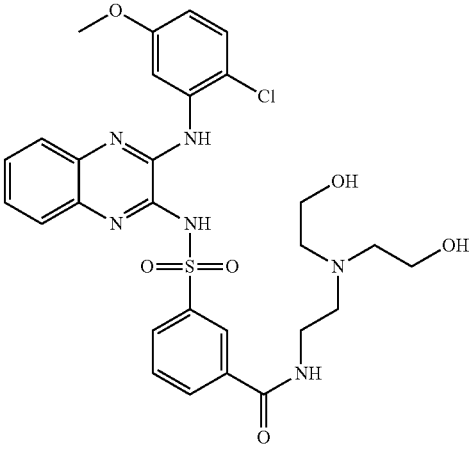 [SMILES: COc1ccc(Cl)c(Nc2nc3ccccc3nc2NS(=O)(=O)c2cccc(C(=O)NCCN(CCO)CCO)c2)c1] | N-{2-[bis(2-hydroxyethyl) amino]ethyl}-3-{[(3-{[2-chloro-5-(methoxy)phenyl] amino}quinoxalin-2-yl)amino]sulfonyl}benzamide |
| 652 | 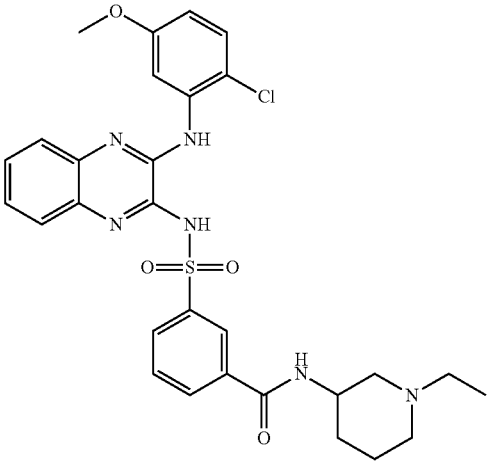 [SMILES: CCN1CCCC(NC(=O)c2cccc(S(=O)(=O)Nc3nc4ccccc4nc3Nc3cc(OC)ccc3Cl)c2)C1] | 3-{[(3-{[2-chloro-5-(methoxy) phenyl]amino}quinoxalin-2-yl)amino]sulfonyl}-N-(1-ethylpiperidin-3-yl)benzamide |
| 653 | 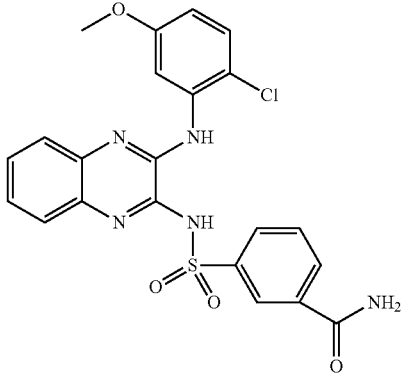 [SMILES: COc1ccc(Cl)c(Nc2nc3ccccc3nc2NS(=O)(=O)c2cccc(C(N)=O)c2)c1] | 3-{[(3-{[2-chloro-5-(methoxy) phenyl]amino}quinoxalin-2-yl)amino]sulfonyl}benzamide |

| Cpd. No. | Structure | Name |
|---|---|---|
| 654 | 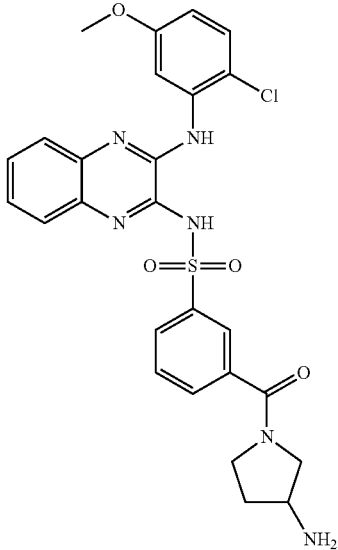 [SMILES: COc1ccc(Cl)c(Nc2nc3ccccc3nc2NS(=O)(=O)c2cccc(C(=O)N3CCC(N)C3)c2)c1] | 3-[(3-aminopyrrolidin-1-yl)carbonyl]-N-(3-{[2-chloro-5-(methoxy)phenyl]amino}quinoxalin-2-yl)benzenesulfonamide |
| 655 | 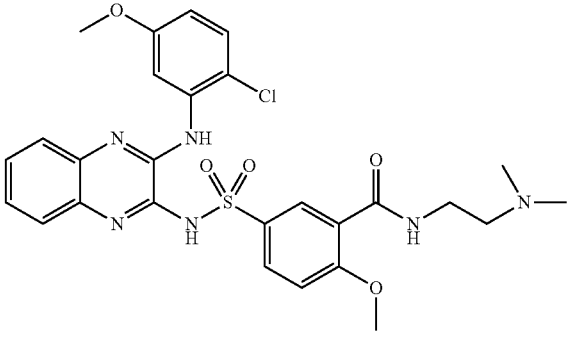 [SMILES: COc1ccc(Cl)c(Nc2nc3ccccc3nc2NS(=O)(=O)c2ccc(OC)c(C(=O)NCCN(C)C)c2)c1] | 5-{[(3-{[2-chloro-5-(methoxy)phenyl]amino}quinoxalin-2-yl)amino]sulfonyl}-N-[2-(dimethylamino)ethyl]-2-(methoxy)benzamide |
| 656 | 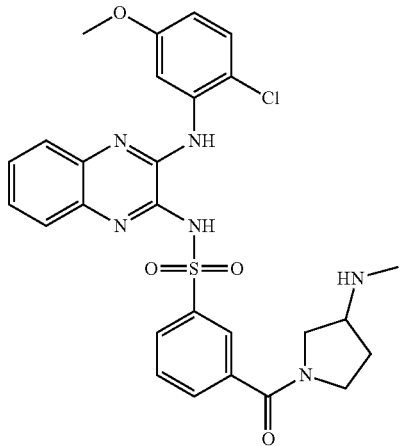 [SMILES: CNC1CCN(C(=O)c2cccc(S(=O)(=O)Nc3nc4ccccc4nc3Nc3cc(OC)ccc3Cl)c2)C1] | N-(3-{[2-chloro-5-(methoxy)phenyl]amino}quinoxalin-2-yl)-3-{[3-(methylamino)pyrrolidin-1-yl]carbonyl}benzenesulfonamide |

TABLE 1-continued

| Cpd. No. | Structure | Name |
|---|---|---|
| 657 | 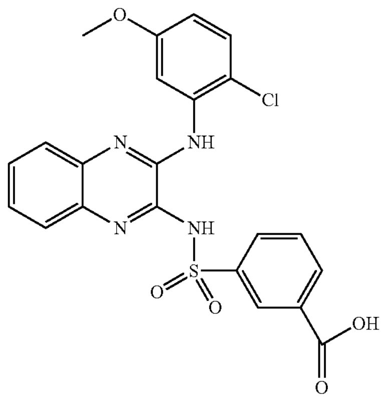 [SMILES: COc1ccc(Cl)c(Nc2nc3ccccc3nc2NS(=O)(=O)c2cccc(C(=O)O)c2)c1] | 3-{[(3-{[2-chloro-5-(methoxy) phenyl]amino}quinoxalin-2-yl)amino]sulfonyl}benzoicacid |
| 658 | 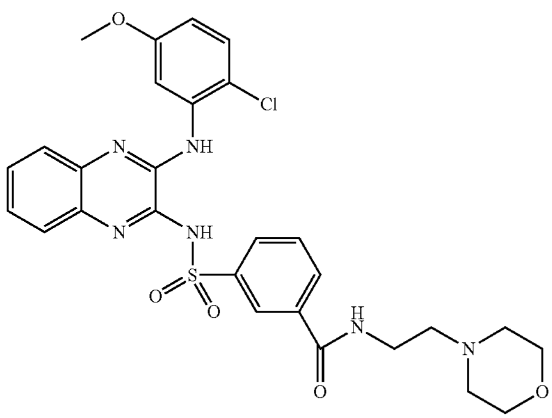 [SMILES: COc1ccc(Cl)c(Nc2nc3ccccc3nc2NS(=O)(=O)c2cccc(C(=O)NCCN3CCOCC3)c2)c1] | 3-{[(3-{[2-chloro-5-(methoxy) phenyl]amino}quinoxalin-2-yl)amino]sulfonyl}-N-(2-morpholin-4-ylethyl)benzamide |
| 659 | 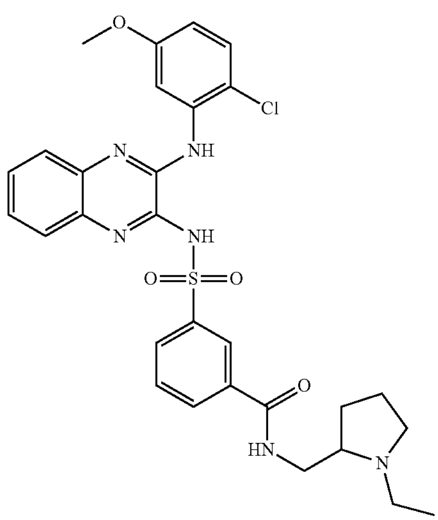 [SMILES: CCN1CCCC1CNC(=O)c1cccc(S(=O)(=O)Nc2nc3ccccc3nc2Nc2cc(OC)ccc2Cl)c1] | 3-{[(3-{[2-chloro-5-(methoxy) phenyl]amino}quinoxalin-2-yl)amino]sulfonyl}-N-[(1-ethylpyrrolidin-2-yl)methyl] benzamide |

| Cpd. No. | Structure | Name |
|---|---|---|
| 660 | 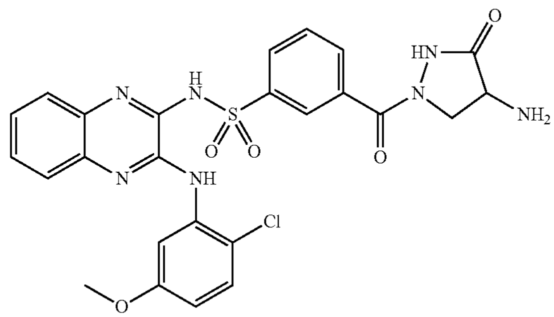 [SMILES: COc1ccc(Cl)c(Nc2nc3ccccc3nc2NS(=O)(=O)c2cccc(C(=O)N3CC(N)C(=O)N3)c2)c1] | 3-[(4-amino-3-oxopyrazolidin-1-yl)carbonyl]-N-(3-{[2-chloro-5-(methoxy)phenyl]amino}quinoxalin-2-yl)benzenesulfonamide |
| 661 | 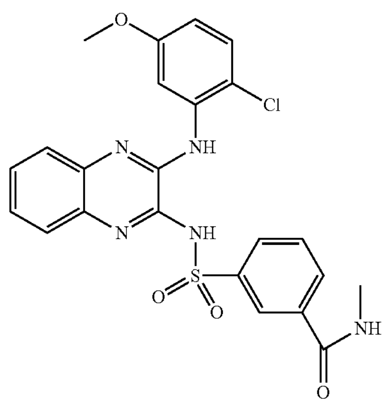 [SMILES: CNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-methylbenzamide |
| 662 | 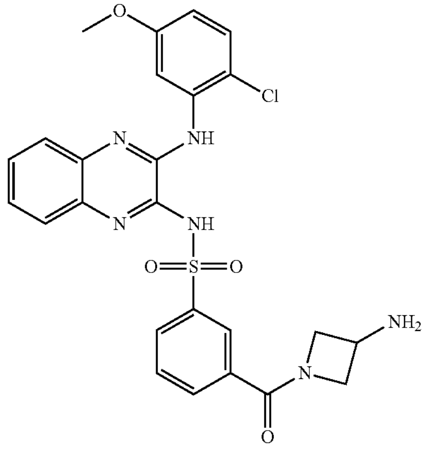 [SMILES: COc1ccc(Cl)c(Nc2nc3ccccc3nc2NS(=O)(=O)c2cccc(C(=O)N3CC(N)C3)c2)c1] | 3-[(3-aminoazetidin-1-yl)carbonyl]-N-(3-{[2-chloro-5-(methoxy)phenyl]amino}quinoxalin-2-yl)benzenesulfonamide |

TABLE 1-continued
| Cpd. No. | Structure | Name |
|---|---|---|
| 663 | 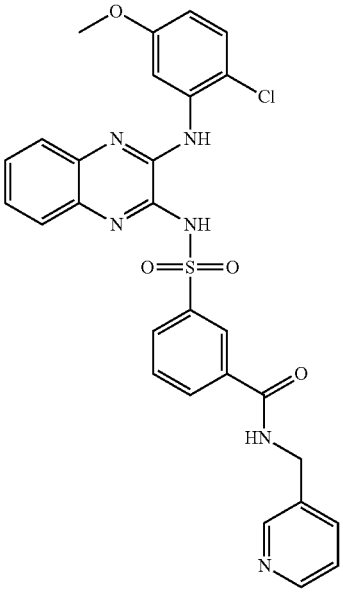 [SMILES: COc1ccc(Cl)c(Nc2nc3ccccc3nc2NS(=O)(=O)c2cccc(C(=O)NCc3cccnc3)c2)c1] | 3-{[(3-{[2-chloro-5-(methoxy) phenyl]amino}quinoxalin-2-yl)amino]sulfonyl}-N-(pyridin-3-ylmethyl)benzamide |
| 664 | 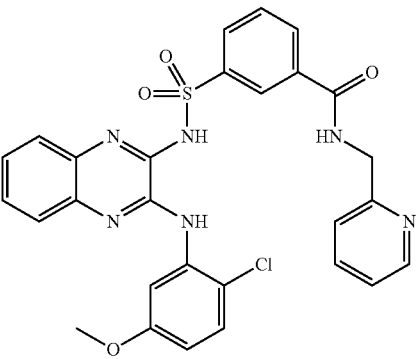 [SMILES: COc1ccc(Cl)c(Nc2nc3ccccc3nc2NS(=O)(=O)c2cccc(C(=O)NCc3ccccn3)c2)c1] | 3-{[(3-{[2-chloro-5-(methoxy) phenyl]amino}quinoxalin-2-yl)amino]sulfonyl}-N-(pyridin-2-ylmethyl)benzamide |
| 665 | 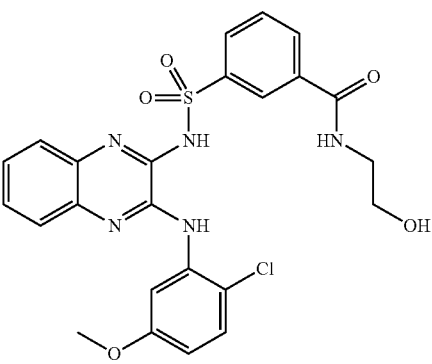 [SMILES: COc1ccc(Cl)c(Nc2nc3ccccc3nc2NS(=O)(=O)c2cccc(C(=O)NCCO)c2)c1] | 3-{[(3-{[2-chloro-5-(methoxy) phenyl]amino}quinoxalin-2-yl)amino]sulfonyl}-N-(2-hydroxyethyl)benzamide |

TABLE 1-continued

| Cpd. No. | Structure | Name |
|---|---|---|
| 666 | 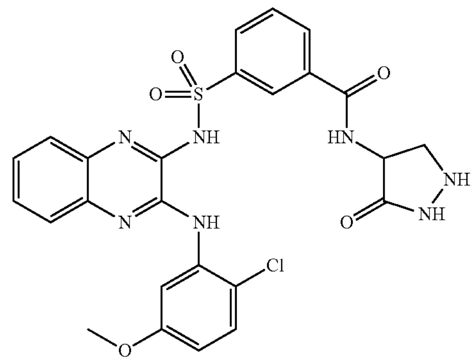 [SMILES: COc1ccc(Cl)c(Nc2nc3ccccc3nc2NS(=O)(=O)c2cccc(C(=O)NC3CNNC3=O)c2)c1] | 3-{[(3-{[2-chloro-5-(methoxy) phenyl]amino}quinoxalin-2-yl)amino]sulfonyl}-N-(3-oxopyrazolidin-4-yl)benzamide |
| 667 | 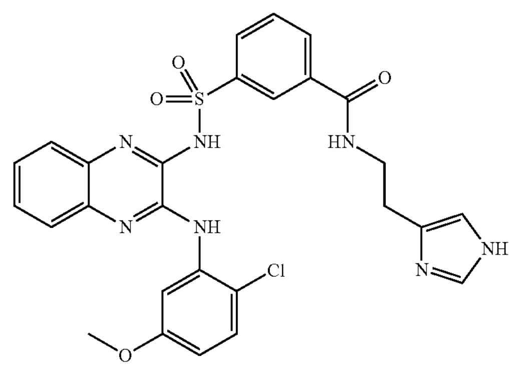 [SMILES: COc1ccc(Cl)c(Nc2nc3ccccc3nc2NS(=O)(=O)c2cccc(C(=O)NCCc3c[nH]cn3)c2)c1] | 3-{[(3-{[2-chloro-5-(methoxy) phenyl]amino}quinoxalin-2-yl)amino]sulfonyl}-N-[2-(1H-imidazol-4-yl)ethyl]benzamide |
| 668 | 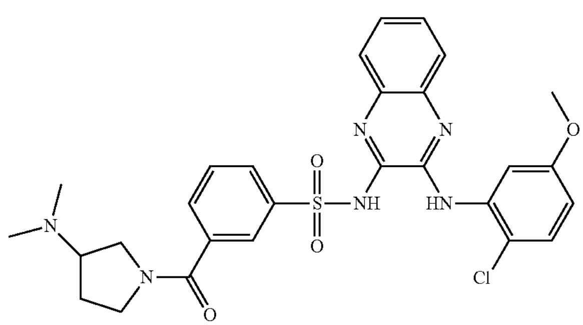 [SMILES: COc1ccc(Cl)c(Nc2nc3ccccc3nc2NS(=O)(=O)c2cccc(C(=O)N3CCC(N(C)C)C3)c2)c1] | N-(3-{[2-chloro-5-(methoxy) phenyl]amino}quinoxalin-2-yl)-3-{[3-(dimethylamino) pyrrolidin-1-yl]carbonyl} benzenesulfonamide |
| 669 | 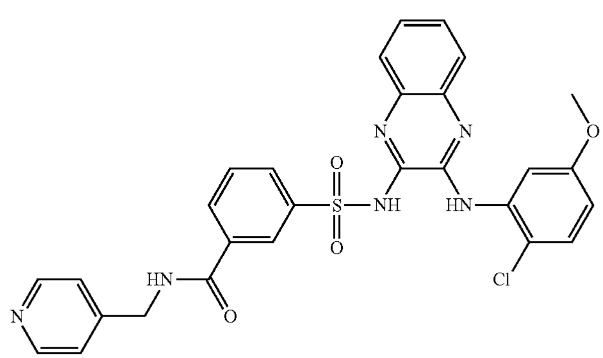 [SMILES: COc1ccc(Cl)c(Nc2nc3ccccc3nc2NS(=O)(=O)c2cccc(C(=O)NCc3ccncc3)c2)c1] | 3-{[(3-{[2-chloro-5-(methoxy) phenyl]amino}quinoxalin-2-yl)amino]sulfonyl}-N-(pyridin-4-ylmethyl)benzamide |

| Cpd. No. | Structure | Name |
|---|---|---|
| 670 | 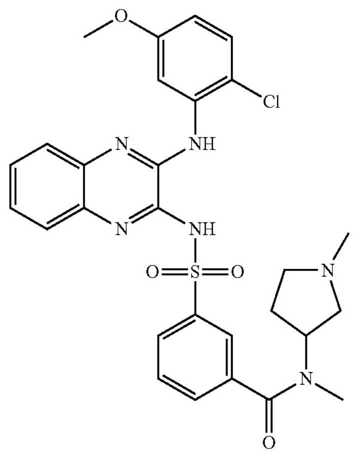 [SMILES: COc1ccc(Cl)c(Nc2nc3ccccc3nc2NS(=O)(=O)c2cccc(C(=O)N(C)C3CCN(C)C3)c2)c1] | 3-{[(3-{[2-chloro-5-(methoxy) phenyl]amino}quinoxalin-2-yl)amino]sulfonyl}-N-methyl-N-(1-methylpyrrolidin-3-yl) benzamide |
| 671 | 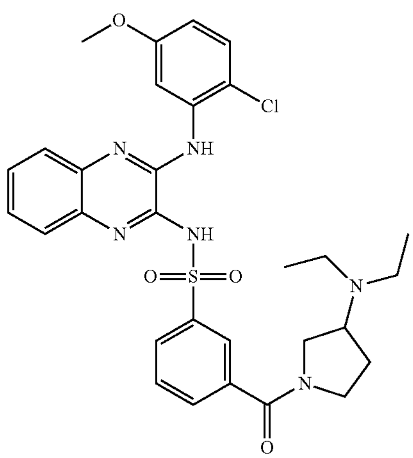 [SMILES: CCN(CC)C1CCN(C(=O)c2cccc(S(=O)(=O)Nc3nc4ccccc4nc3Nc3cc(OC)ccc3Cl)c2)C1] | N-(3-{[2-chloro-5-(methoxy) phenyl]amino}quinoxalin-2-yl)-3-{[3-(diethylamino)pyrrolidin-1-yl]carbonyl} benzenesulfonamide |
| 672 | 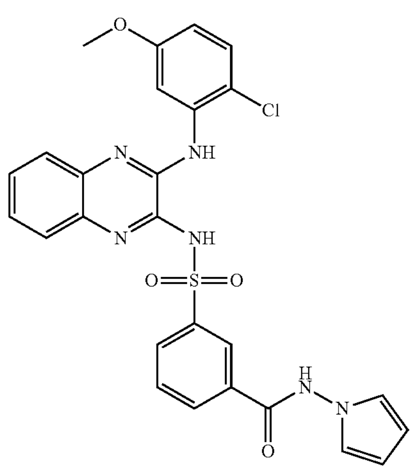 [SMILES: COc1ccc(Cl)c(Nc2nc3ccccc3nc2NS(=O)(=O)c2cccc(C(=O)Nn3cccc3)c2)c1] | 3-{[(3-{[2-chloro-5-(methoxy) phenyl]amino}quinoxalin-2-yl)amino]sulfonyl}-N-1H-pyrrol-1-ylbenzamide |

TABLE 1-continued

| Cpd. No. | Structure | Name |
| --- | --- | --- |
| 673 | 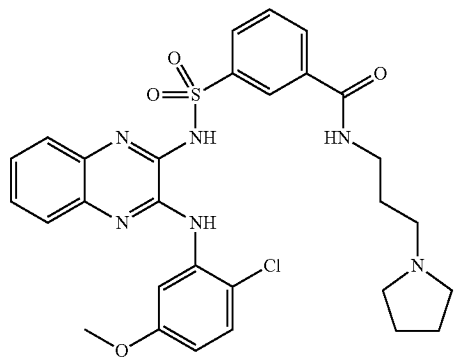 [SMILES: COc1ccc(Cl)c(Nc2nc3ccccc3nc2NS(=O)(=O)c2cccc(C(=O)NCCCN3CCCC3)c2)c1] | 3-{[(3-{[2-chloro-5-(methoxy) phenyl]amino}quinoxalin-2-yl)amino]sulfonyl}-N-(3-pyrrolidin-1-ylpropyl)benzamide |
| 674 | 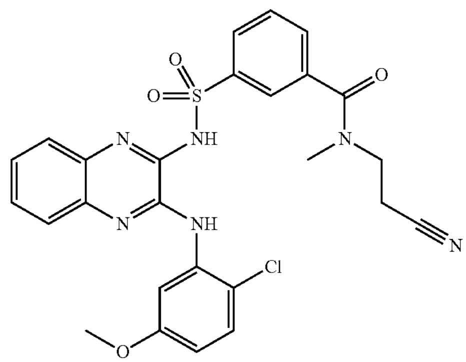 [SMILES: COc1ccc(Cl)c(Nc2nc3ccccc3nc2NS(=O)(=O)c2cccc(C(=O)N(C)CCC#N)c2)c1] | 3-{[(3-{[2-chloro-5-(methoxy) phenyl]amino}quinoxalin-2-yl) amino]sulfonyl}-N-(2-cyanoethyl)-N-methylbenzamide |
| 675 | 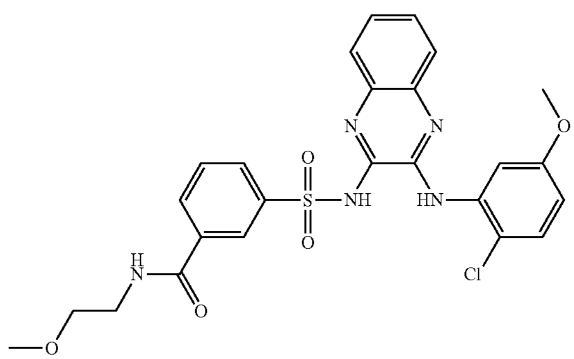 [SMILES: COCCNC(=O)c1cccc(S(=O)(=O)Nc2nc3ccccc3nc2Nc2cc(OC)ccc2Cl)c1] | 3-{[(3-{[2-chloro-5-(methoxy) phenyl]amino}quinoxalin-2-yl)amino]sulfonyl}-N-[2-(methoxy)ethyl]benzamide |
| 676 | 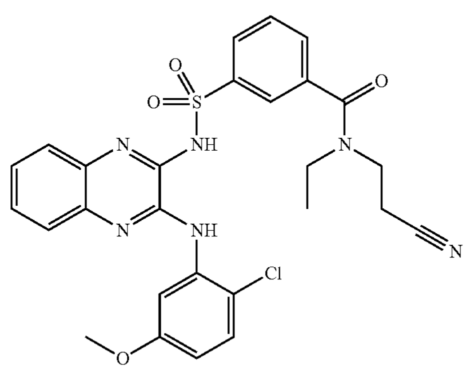 [SMILES: CCN(CCC#N)C(=O)c1cccc(S(=O)(=O)Nc2nc3ccccc3nc2Nc2cc(OC)ccc2Cl)c1] | 3-{[(3-{[2-chloro-5-(methoxy) phenyl]amino}quinoxalin-2-yl)amino]sulfonyl}-N-(2-cyanoethyl)-N-ethylbenzamide |

TABLE 1-continued

| Cpd. No. | Structure | Name |
|---|---|---|
| 677 | 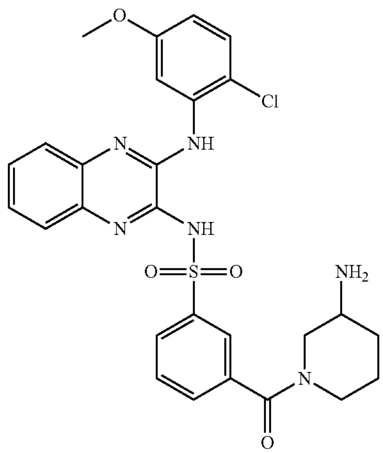 [SMILES: COc1ccc(Cl)c(Nc2nc3ccccc3nc2NS(=O)(=O)c2cccc(C(=O)N3CCCC(N)C3)c2)c1] | 3-[(3-aminopiperidin-1-yl)carbonyl]-N-(3-{[2-chloro-5-(methoxy)phenyl]amino}quinoxalin-2-yl)benzenesulfonamide |
| 678 | 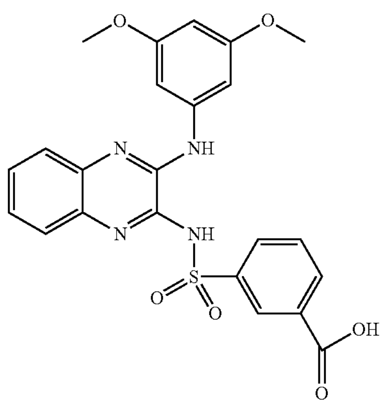 [SMILES: COc1cc(Nc2nc3ccccc3nc2NS(=O)(=O)c2cccc(C(=O)O)c2)cc(OC)c1] | 3-{[(3-{[3,5-bis(methoxy)phenyl]amino}quinoxalin-2-yl)amino]sulfony}benzoicacid |
| 679 | 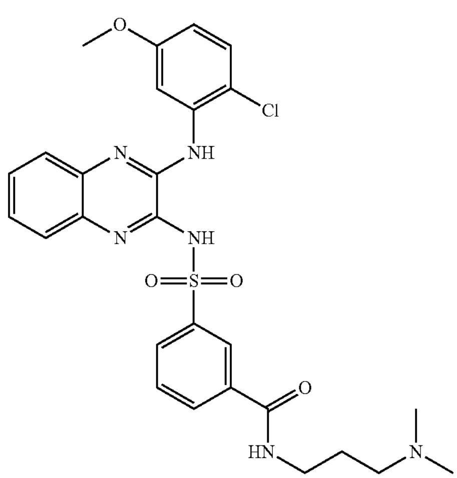 [SMILES: COc1ccc(Cl)c(Nc2nc3ccccc3nc2NS(=O)(=O)c2cccc(C(=O)NCCCN(C)C)c2)c1] | 3-{[(3-{[2-chloro-5-(methoxy)phenyl]amino}quinoxalin-2-yl)amino]sulfonyl}-N-[3-(dimethylamino)propyl]benzamide |

TABLE 1-continued

| Cpd. No. | Structure | Name |
|---|---|---|
| 680 | 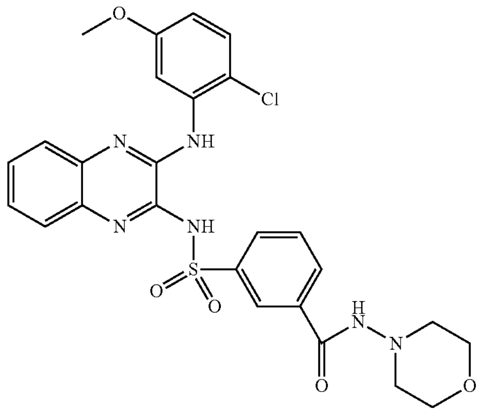 [SMILES: COc1ccc(Cl)c(Nc2nc3ccccc3nc2NS(=O)(=O)c2cccc(C(=O)NN3CCOCC3)c2)c1] | 3-{[(3-{[2-chloro-5-(methoxy)phenyl]amino}quinoxalin-2-yl)amino]sulfonyl}-N-morpholin-4-ylbenzamide |
| 681 | 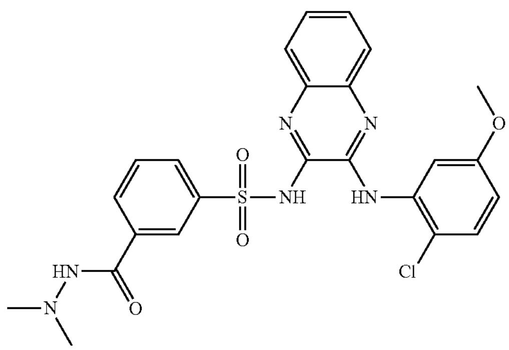 [SMILES: COc1ccc(Cl)c(Nc2nc3ccccc3nc2NS(=O)(=O)c2cccc(C(=O)NN(C)C)c2)c1] | N-(3-{[2-chloro-5-(methoxy)phenyl]amino}quinoxalin-2-yl)-3-[(2,2-dimethylhydrazino)carbonyl]benzenesulfonamide |
| 682 | 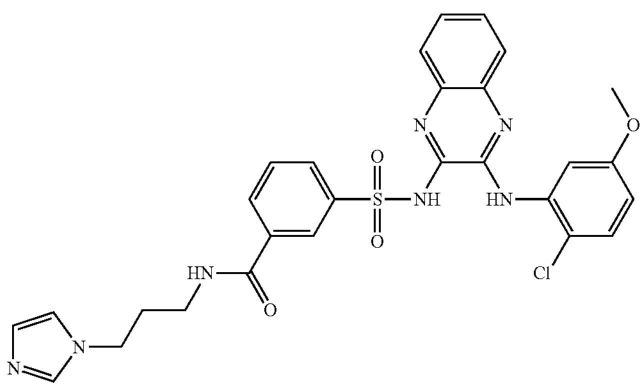 [SMILES: COc1ccc(Cl)c(Nc2nc3ccccc3nc2NS(=O)(=O)c2cccc(C(=O)NCCCn3ccnc3)c2)c1] | 3-{[(3-{[2-chloro-5-(methoxy)phenyl]amino}quinoxalin-2-yl)amino]sulfonyl}-N-[3-(1H-imidazol-1-yl)propyl]benzamide |
| 683 | 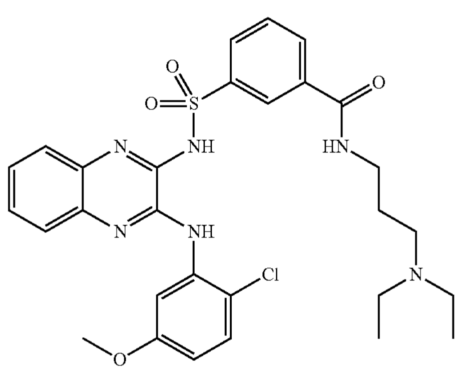 [SMILES: CCN(CC)CCCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[3-(diethylamino)propyl]benzamide |

TABLE 1-continued

| Cpd. No. | Structure | Name |
|---|---|---|
| 684 | 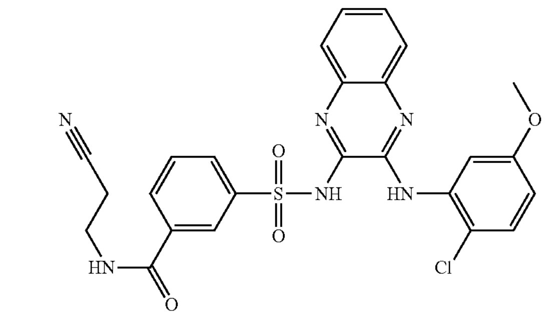 [SMILES: COc1ccc(Cl)c(Nc2nc3ccccc3nc2NS(=O)(=O)c2cccc(C(=O)NCCC#N)c2)c1] | 3-{[(3-{[2-chloro-5-(methoxy) phenyl]amino}quinoxalin-2-yl)amino]sulfonyl}-N-(2-cyanoethyl)benzamide |
| 685 | 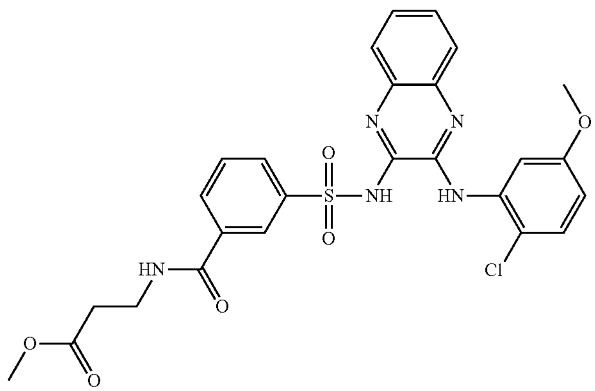 [SMILES: COC(=O)CCNC(=O)c1cccc(S(=O)(=O)Nc2nc3ccccc3nc2Nc2cc(OC)ccc2Cl)c1] | methylN-[(3-{[(3-{[2-chloro-5-(methoxy)phenyl]amino} quinoxalin-2-yl)amino]sulfonyl} phenyl)carbonyl]-beta-alaninat |
| 686 | 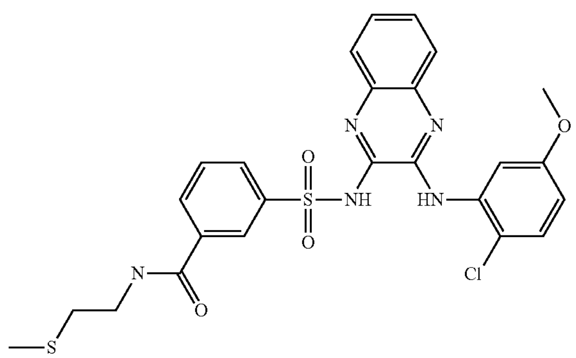 [SMILES: COc1ccc(Cl)c(Nc2nc3ccccc3nc2NS(=O)(=O)c2cccc(C(=O)NCCSC)c2)c1] | 3-{[(3-{[2-chloro-5-(methoxy) phenyl]amino}quinoxalin-2-yl)amino]sulfonyl}-N-[2-(methylthio)ethyl]benzamide |
| 687 | 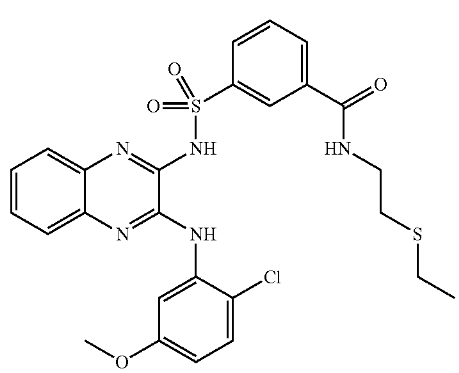 [SMILES: CCSCCNC(=O)c1cccc(S(=O)(=O)Nc2nc3ccccc3nc2Nc2cc(OC)ccc2Cl)c1] | 3-{[(3-{[2-chloro-5-(methoxy) phenyl]amino}quinoxalin-2-yl)amino]sulfonyl}-N-[2-(ethylthio)ethyl]benzamide |

TABLE 1-continued

| Cpd. No. | Structure | Name |
|---|---|---|
| 688 | 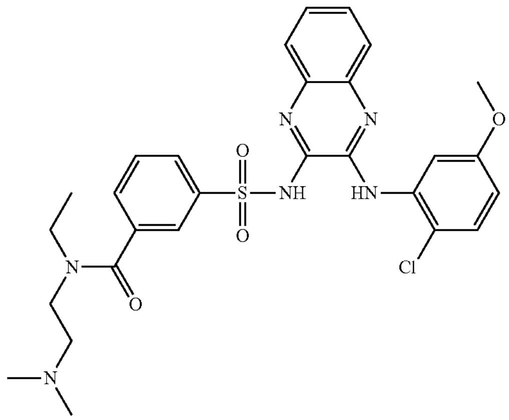 [SMILES: CCN(CCN(C)C)C(=O)c1cccc(S(=O)(=O)Nc2nc3ccccc3nc2Nc2cc(OC)ccc2Cl)c1] | 3-{[(3-{[2-chloro-5-(methoxy) phenyl]amino}quinoxalin-2-yl)amino]sulfonyl}-N-[2-(dimethylamino)ethyl]-N-ethylbenzamide |
| 689 | 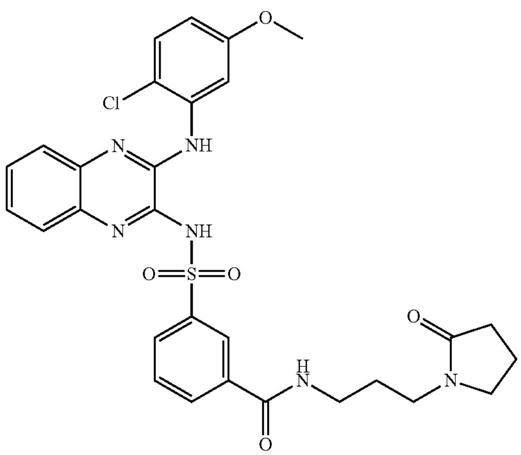 [SMILES: COc1ccc(Cl)c(Nc2nc3ccccc3nc2NS(=O)(=O)c2cccc(C(=O)NCCCN3CCCC3=O)c2)c1] | 3-{[(3-{[2-chloro-5-(methoxy) phenyl]amino}quinoxalin-2-yl)amino]sulfonyl}-N-[3-(2-oxopyrrolidin-1-yl)propyl]benzamide |
| 690 | 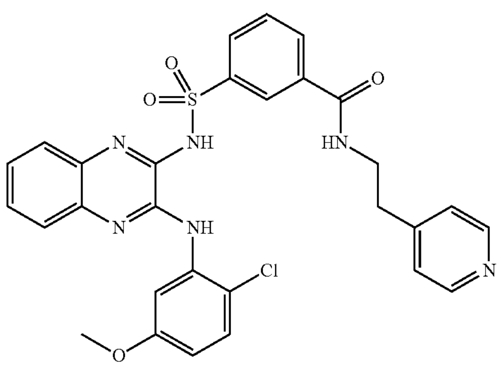 [SMILES: COc1ccc(Cl)c(Nc2nc3ccccc3nc2NS(=O)(=O)c2cccc(C(=O)NCCc3ccncc3)c2)c1] | 3-{[(3-{[2-chloro-5-(methoxy) phenyl]amino}quinoxalin-2-yl)amino]sulfonyl}-N-(2-pyridin-4-ylethyl)benzamide |
| 691 | 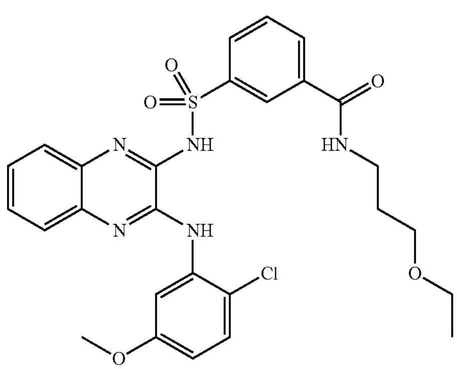 [SMILES: CCOCCCNC(=O)c1cccc(S(=O)(=O)Nc2nc3ccccc3nc2Nc2cc(OC)ccc2Cl)c1] | 3-{[(3-{[2-chloro-5-(methoxy) phenyl]amino}quinoxalin-2-yl)amino]sulfonyl}-N-[3-(ethyloxy)propyl]benzamide |

TABLE 1-continued

| Cpd. No. | Structure | Name |
|---|---|---|
| 692 | 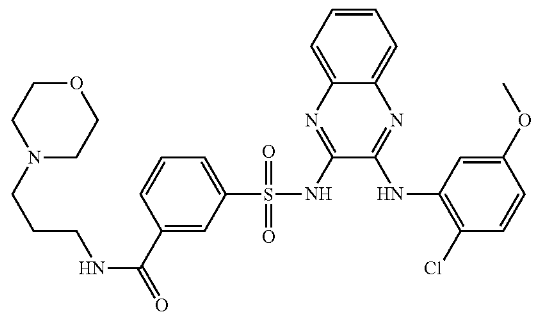 [SMILES: COc1ccc(Cl)c(Nc2nc3ccccc3nc2NS(=O)(=O)c2cccc(C(=O)NCCCN3CCOCC3)c2)c1] | 3-{[(3-{[2-chloro-5-(methoxy)phenyl]amino}quinoxalin-2-yl)amino]sulfonyl}-N-(3-morpholin-4-ylpropyl)benzamide |
| 693 | 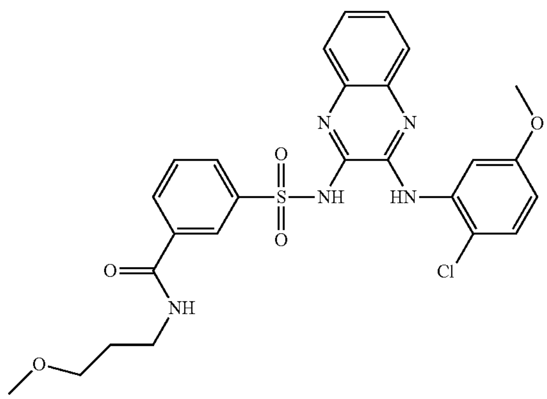 [SMILES: COCCCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[3-(methoxy)propyl]benzamide |
| 694 | 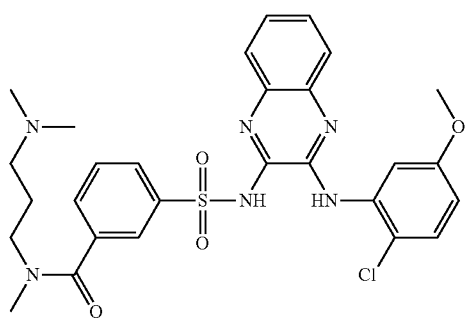 [SMILES: COc1ccc(Cl)c(Nc2nc3ccccc3nc2NS(=O)(=O)c2cccc(C(=O)N(C)CCCN(C)C)c2)c1] | 3-{[(3-{[2-chloro-5-(methoxy)phenyl]amino}quinoxalin-2-yl)amino]sulfonyl}-N-[3-(dimethylamino)propyl]-N-methylbenzamide |
| 695 | 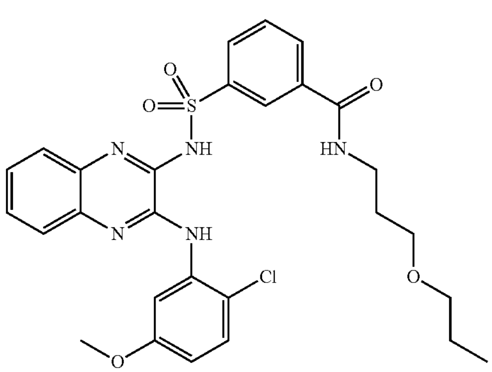 [SMILES: CCCOCCCNC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[3-(propyloxy)propyl]benzamide |

TABLE 1-continued

| Cpd. No. | Structure | Name |
|---|---|---|
| 696 | 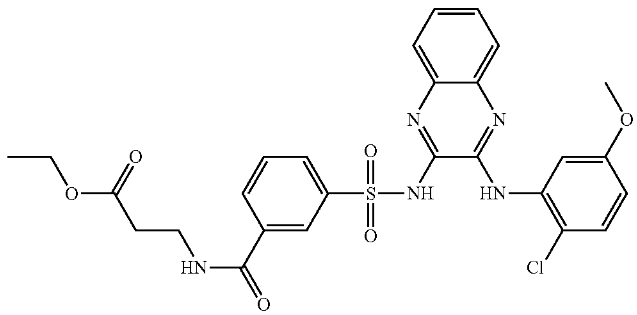 [SMILES: CCOC(=O)CCNC(=O)c1cccc(S(=O)(=O)Nc2nc3ccccc3nc2Nc2cc(OC)ccc2Cl)c1] | ethylN-[(3-{[(3-{[2-chloro-5-(methoxy)phenyl]amino}quinoxalin-2-yl)amino]sulfonyl}phenyl)carbonyl]-beta-alaninate |
| 697 | 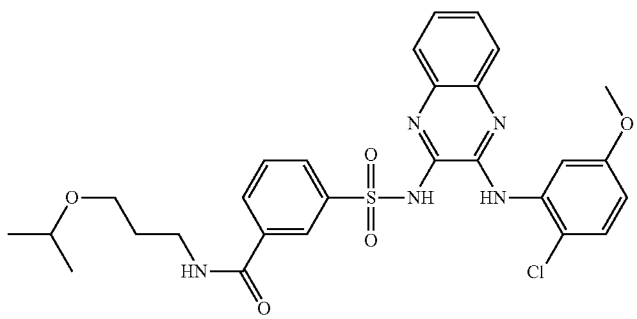 [SMILES: COc1ccc(Cl)c(Nc2nc3ccccc3nc2NS(=O)(=O)c2cccc(C(=O)NCCCOC(C)C)c2)c1] | 3-{[(3-{[2-chloro-5-(methoxy)phenyl]amino}quinoxalin-2-yl)amino]sulfonyl}-N-{3-[(1-methylethyl)oxy]propyl}benzamide |
| 698 | 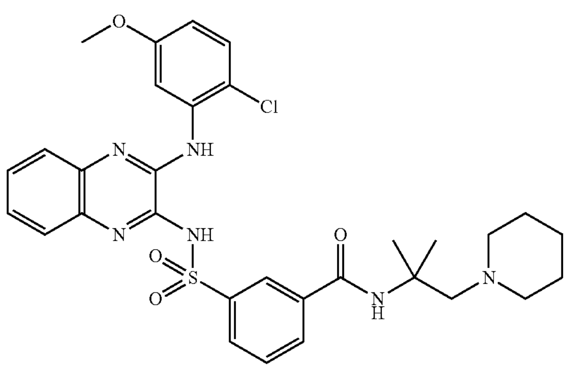 [SMILES: COc1ccc(Cl)c(Nc2nc3ccccc3nc2NS(=O)(=O)c2cccc(C(=O)NC(C)(C)CN3CCCCC3)c2)c1] | 3-{[(3-{[2-chloro-5-(methoxy)phenyl]amino}quinoxalin-2-yl)amino]sulfonyl}-N-(1,1-dimethyl-2-piperidin-1-ylethyl)benzamide |
| 699 | 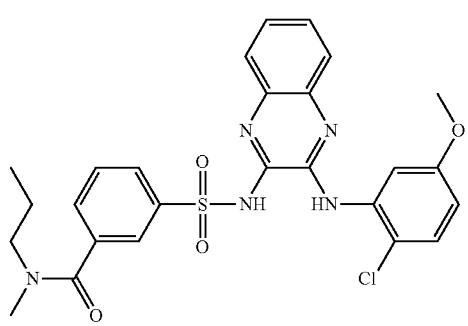 [SMILES: CCCN(C)C(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-methyl-N-propylbenzamide |

TABLE 1-continued

| Cpd. No. | Structure | Name |
|---|---|---|
| 700 | 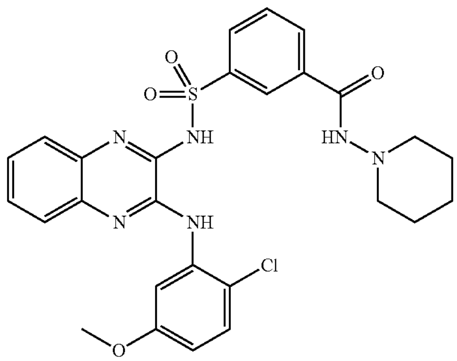 [SMILES: COc1ccc(Cl)c(Nc2nc3ccccc3nc2NS(=O)(=O)c2cccc(C(=O)NN3CCCCC3)c2)c1] | 3-{[(3-{[2-chloro-5-(methoxy) phenyl]amino}quinoxalin-2-yl)amino]sulfonyl}-N-piperidin-1-ylbenzamide |
| 701 | 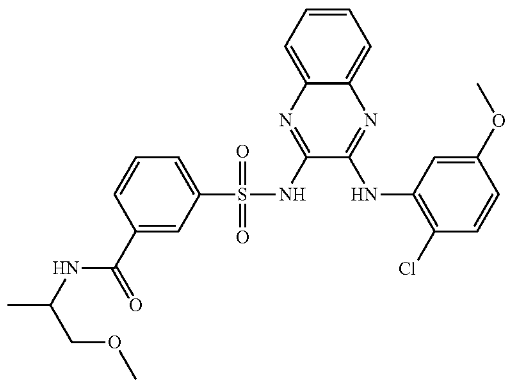 [SMILES: COCC(C)NC(=O)c1cccc(S(=O)(=O)Nc2nc3ccccc3nc2Nc2cc(OC)ccc2Cl)c1] | 3-{[(3-{[2-chloro-5-(methoxy) phenyl]amino}quinoxalin-2-yl)amino]sulfonyl}-N-[1-methyl-2-(methoxy)ethyl] benzamide |
| 702 | 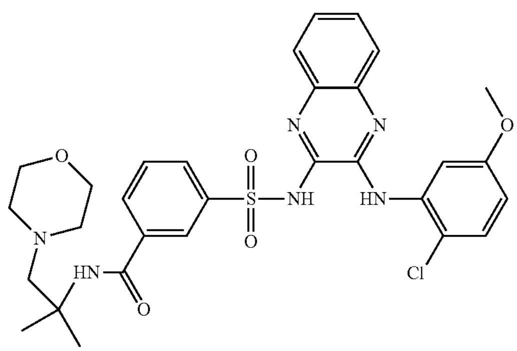 [SMILES: COc1ccc(Cl)c(Nc2nc3ccccc3nc2NS(=O)(=O)c2cccc(C(=O)NC(C)(C)CN3CCOCC3)c2)c1] | 3-{[(3-{[2-chloro-5-(methoxy) phenyl]amino}quinoxalin-2-yl) amino]sulfonyl}-N-(1,1-dimethyl-2-morpholin-4-ylethyl) benzamide |
| 703 | 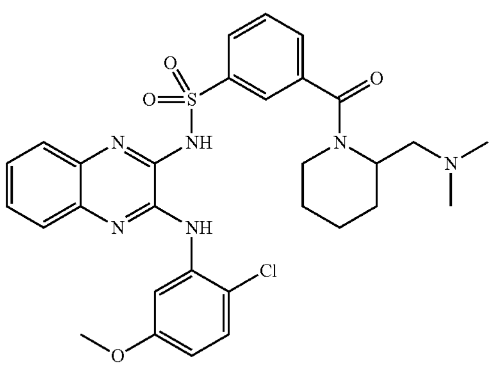 [SMILES: COc1ccc(Cl)c(Nc2nc3ccccc3nc2NS(=O)(=O)c2cccc(C(=O)N3CCCCC3CN(C)C)c2)c1] | N-(3-{[2-chloro-5-(methoxy) phenyl]amino}quinoxalin-2-yl)-3-({2-[(dimethylamino) methyl]piperidin-1-yl}carbonyl) benzenesulfonamide |

TABLE 1-continued

| Cpd. No. | Structure | Name |
|---|---|---|
| 704 | 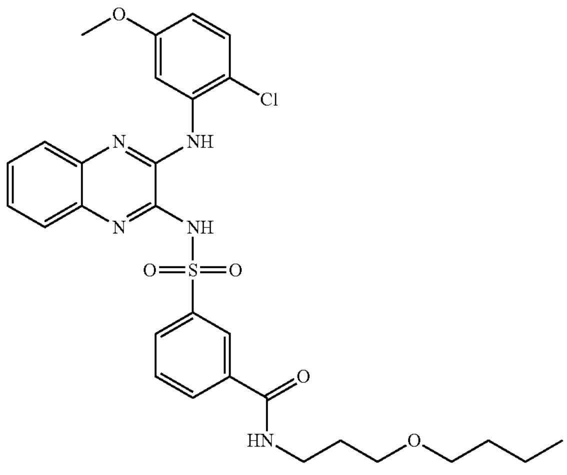 [SMILES: CCCCOCCCNC(=O)c1cccc(S(=O)(=O)Nc2nc3ccccc3nc2Nc2cc(OC)ccc2Cl)c1] | N-[3-(butyloxy)propyl]-3-{[(3-{[2-chloro-5-(methoxy)phenyl]amino}quinoxalin-2-yl)amino]sulfonyl}benzamide |
| 705 | 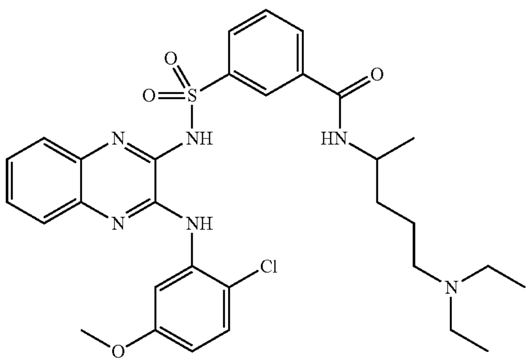 [SMILES: CCN(CC)CCCC(C)NC(=O)c1cccc(S(=O)(=O)Nc2nc3ccccc3nc2Nc2cc(OC)ccc2Cl)c1] | 3-{[(3-{[2-chloro-5-(methoxy)phenyl]amino}quinoxalin-2-yl)amino]sulfonyl}-N-[4-(diethylamino)-1-methylbutyl]benzamide |
| 706 | 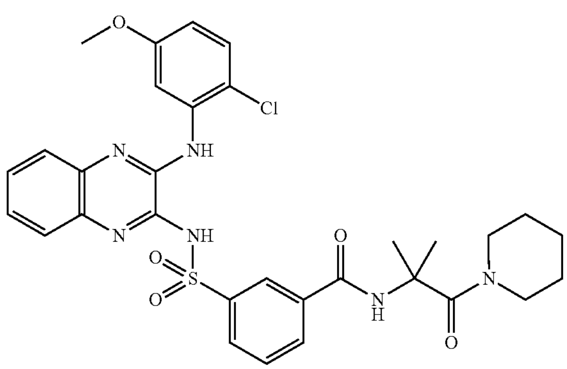 [SMILES: COc1ccc(Cl)c(Nc2nc3ccccc3nc2NS(=O)(=O)c2cccc(C(=O)NC(C)(C)C(=O)N3CCCCC3)c2)c1] | 3-{[(3-{[2-chloro-5-(methoxy)phenyl]amino}quinoxalin-2-yl)amino]sulfonyl}-N-(1,1-dimethyl-2-oxo-2-piperidin-1-ylethyl)benzamide |
| 707 | 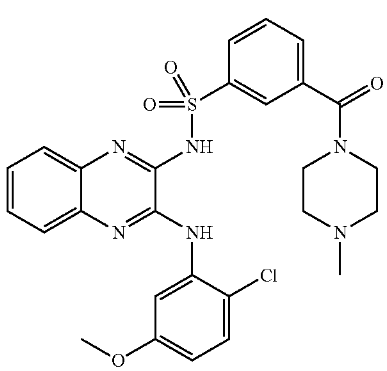 [SMILES: COc1ccc(Cl)c(Nc2nc3ccccc3nc2NS(=O)(=O)c2cccc(C(=O)N3CCN(C)CC3)c2)c1] | N-(3-{[2-chloro-5-(methoxy)phenyl]amino}quinoxalin-2-yl)-3-[(4-methylpiperazin-1-yl)carbonyl]benzenesulfonamide |

TABLE 1-continued

| Cpd. No. | Structure | Name |
|---|---|---|
| 708 | 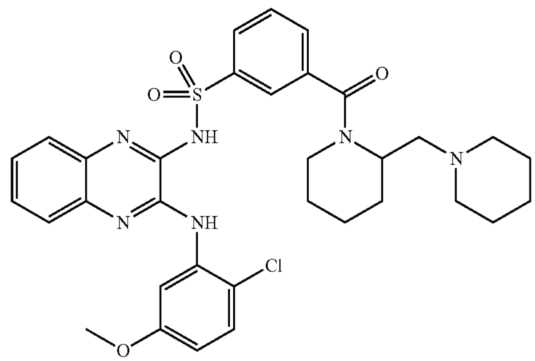 [SMILES: COc1ccc(Cl)c(Nc2nc3ccccc3nc2NS(=O)(=O)c2cccc(C(=O)N3CCCCC3CN3CCCCC3)c2)c1] | N-(3-{[2-chloro-5-(methoxy) phenyl]amino}quinoxalin-2-yl)-3-{[2-(piperidin-1-ylmethyl) piperidin-1-yl]carbonyl} benzenesulfonamide |
| 709 | 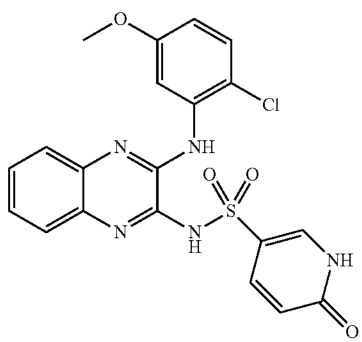 [SMILES: COc1ccc(Cl)c(Nc2nc3ccccc3nc2NS(=O)(=O)c2ccc(=O)[nH]c2)c1] | N-(3-{[2-chloro-5-(methoxy) phenyl]amino}quinoxalin-2-yl)-6-oxo-1,6-dihydropyridine-3-sulfonamide |
| 710 | 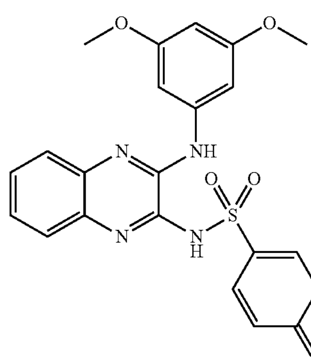 | N-(3-{[3,5-bis(methoxy)phenyl] amino}quinoxalin-2-yl)-6-oxo-1,6-dihydropyridine-3-sulfonamide |
| 711 | 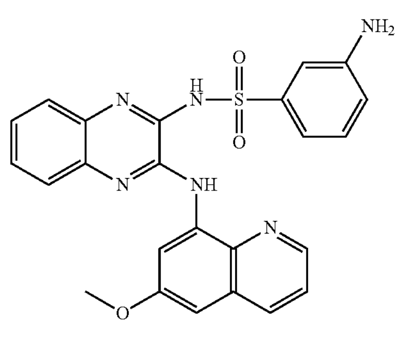 | 3-amino-N-(3-{[6-(methoxy) quinolin-8-yl]amino}quinoxalin- |

TABLE 1-continued

| Cpd. No. | Structure | Name |
|---|---|---|
| 712 | 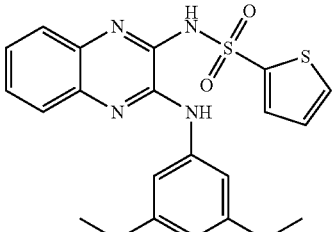 | N-(3-{[3,5-bis(methoxy)phenyl]amino}quinoxalin-2-yl)thiophene-2-sulfonamide |
| 713 | 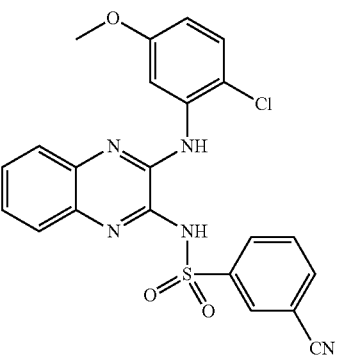 [SMILES: COc1ccc(Cl)c(Nc2nc3ccccc3nc2NS(=O)(=O)c2cccc(C#N)c2)c1] | N-(3-{[2-chloro-5-(methoxy)phenyl]amino}quinoxalin-2-yl)-3-cyanobenzenesulfonamide |
| 714 | 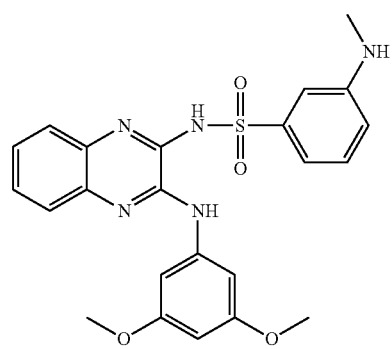 [SMILES: CNc1cccc(S(=O)(=O)Nc2nc3ccccc3nc2Nc2cc(OC)cc(OC)c2)c1] | N-(3-{[3,5-bis(methoxy)phenyl]amino}quinoxalin-2-yl)-3-(methylamino)benzenesulfonamide |
| 715 | 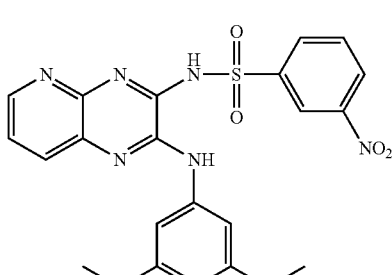 | N-(2-{[3,5-bis(methoxy)phenyl]amino}pyrido[2,3-b]pyrazin-3-yl)-3-nitrobenzenesulfonamide |
| 716 | 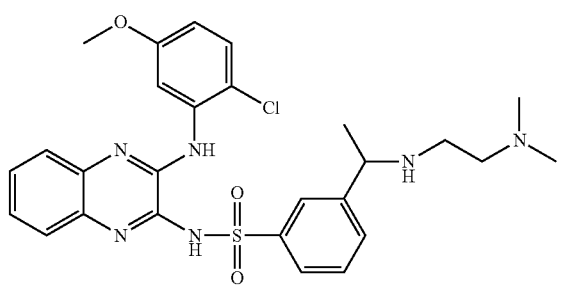 [SMILES: COc1ccc(Cl)c(Nc2nc3ccccc3nc2NS(=O)(=O)c2cccc(C(C)NCCN(C)C)c2)c1] | N-(3-{[2-chloro-5-(methoxy)phenyl]amino}quinoxalin-2-yl)-3-(1-{[2-(dimethylamino)ethyl]amino}ethyl)benzenesulfonamide |

TABLE 1-continued

| Cpd. No. | Structure | Name |
|---|---|---|
| 717 | 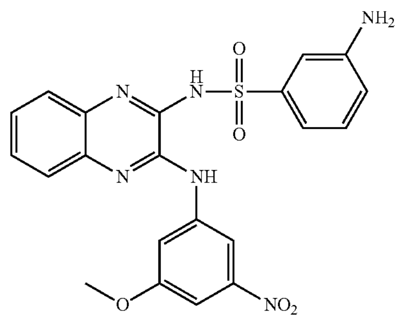 [SMILES: COc1cc(Nc2nc3ccccc3nc2NS(=O)(=O)c2cccc(N)c2)cc([N+](=O)[O-])c1] | 3-amino-N-(3-{[3-(methoxy)-5-nitrophenyl]amino}quinoxalin-2-yl)benzenesulfonamide |
| 718 | 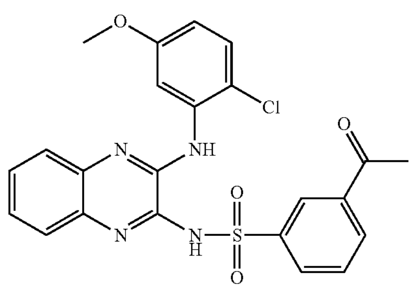 [SMILES: COc1ccc(Cl)c(Nc2nc3ccccc3nc2NS(=O)(=O)c2cccc(C(C)=O)c2)c1] | 3-acetyl-N-(3-{[2-chloro-5-(methoxy)phenyl]amino}quinoxalin-2-yl)benzenesulfonamide |
| 719 | 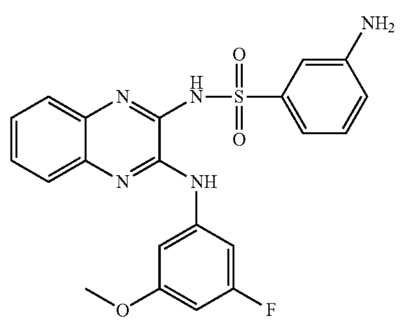 [SMILES: COc1cc(F)cc(Nc2nc3ccccc3nc2NS(=O)(=O)c2cccc(N)c2)c1] | 3-amino-N-(3-{[3-fluoro-5-(methoxy)phenyl]amino}quinoxalin-2-yl)benzenesulfonamide |
| 720 | 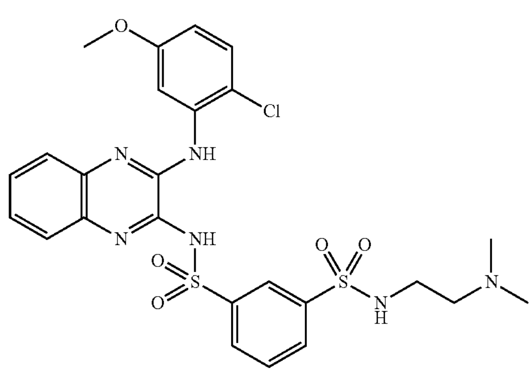 [SMILES: COc1ccc(Cl)c(Nc2nc3ccccc3nc2NS(=O)(=O)c2cccc(S(=O)(=O)NCCN(C)C)c2)c1] | N-(3-{[2-chloro-5-(methoxy)phenyl]amino}quinoxalin-2-yl)-N'-[2-(dimethylamino)ethyl]benzene-1,3-disulfonamide |

TABLE 1-continued

| Cpd. No. | Structure | Name |
|---|---|---|
| 721 | 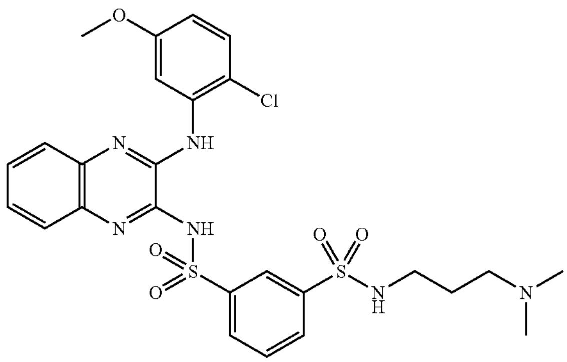 [SMILES: COc1ccc(Cl)c(Nc2nc3ccccc3nc2NS(=O)(=O)c2cccc(S(=O)(=O)NCCCN(C)C)c2)c1] | N-(3-{[2-chloro-5-(methoxy) phenyl]amino}quinoxalin-2-yl)-N'-[3-(dimethylamino)propyl] benzene-1,3-disulfonamide |
| 722 | 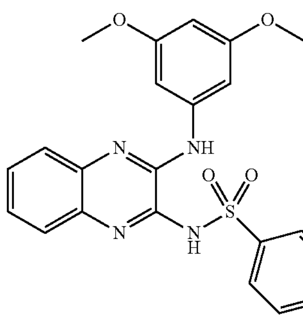 | N-(3-{[3,5-bis(methoxy)phenyl] amino}quinoxalin-2-yl)-6-chloropyridine-3-sulfonamide |
| 723 | 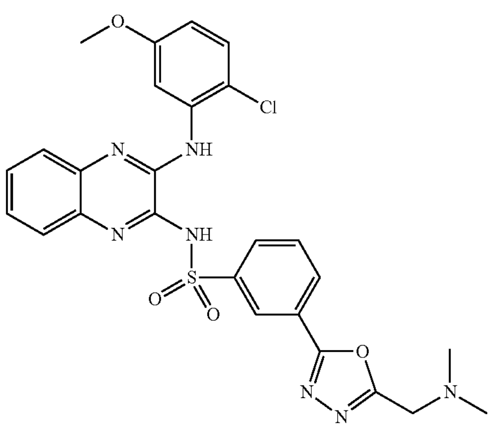 [SMILES: COc1ccc(Cl)c(Nc2nc3ccccc3nc2NS(=O)(=O)c2cccc(-c3nnc(CN(C)C)o3)c2)c1] | N-(3-{[2-chloro-5-(methoxy) phenyl]amino}quinoxalin-2-yl)-3-{5-[(dimethylamino) methyl]-1,3,4-oxadiazol-2-yl}benzenesulfonamide |
| 724 | 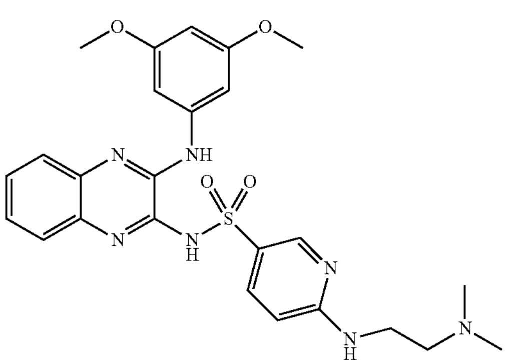 [SMILES: COc1cc(Nc2nc3ccccc3nc2NS(=O)(=O)c2ccc(NCCN(C)C)nc2)cc(OC)c1] | N-(3-{[3,5-bis(methoxy)phenyl] amino}quinoxalin-2-yl)-6-{[2-(dimethylamino)ethyl]amino} pyridine-3-sulfonamid |

TABLE 1-continued

| Cpd. No. | Structure | Name |
|---|---|---|
| 725 | 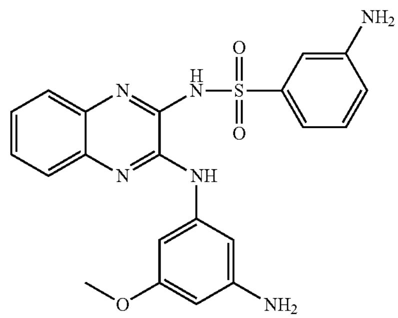 | 3-amino-N-(3-{[3-amino-5-(methoxy)phenyl]amino}quinoxalin-2-yl)benzenesulfonamide |
| 726 | 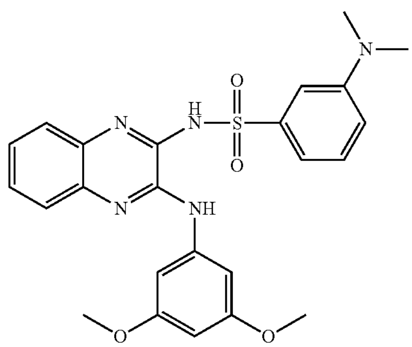 [SMILES: COc1cc(Nc2nc3ccccc3nc2NS(=O)(=O)c2cccc(N(C)C)c2)cc(OC)c1] | N-(3-{[3,5-bis(methoxy)phenyl]amino}quinoxalin-2-yl)-3-(dimethylamino)benzenesulfonamide |
| 727 | 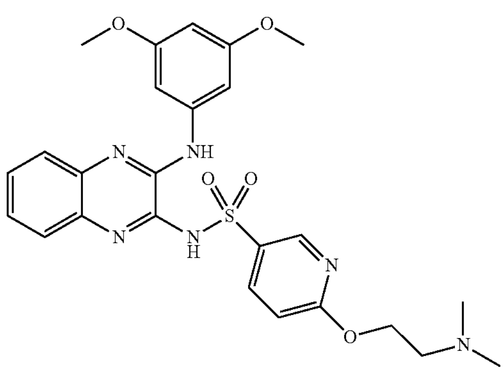 [SMILES: COc1cc(Nc2nc3ccccc3nc2NS(=O)(=O)c2ccc(OCCN(C)C)nc2)cc(OC)c1] | N-(3-{[3,5-bis(methoxy)phenyl]amino}quinoxalin-2-yl)-6-{[2-(dimethylamino)ethyl]oxy}pyridine-3-sulfonamide |
| 728 | 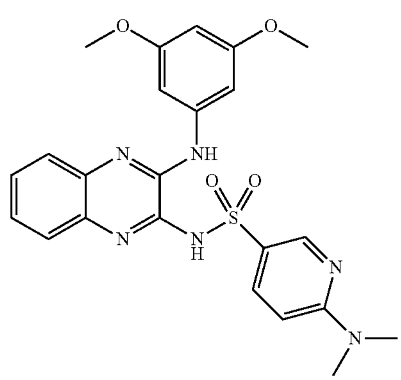 [SMILES: COc1cc(Nc2nc3ccccc3nc2NS(=O)(=O)c2ccc(N(C)C)nc2)cc(OC)c1] | N-(3-{[3,5-bis(methoxy)phenyl]amino}quinoxalin-2-yl)-6-(dimethylamino)pyridine-3-sulfonamide |

TABLE 1-continued

| Cpd. No. | Structure | Name |
|---|---|---|
| 729 | 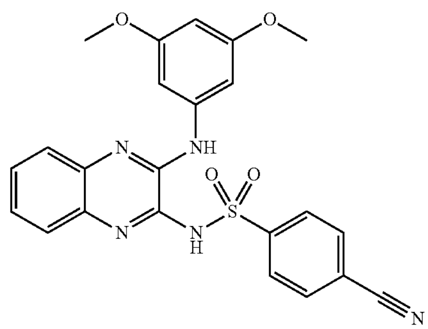 [SMILES: COc1cc(Nc2nc3ccccc3nc2NS(=O)(=O)c2ccc(C#N)cc2)cc(OC)c1] | N-(3-{[3,5-bis(methoxy)phenyl]amino}quinoxalin-2-yl)-4-cyanobenzenesulfonamide |
| 730 | 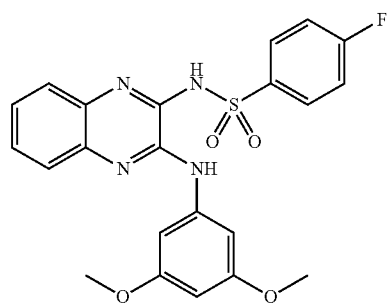 [SMILES: COc1cc(Nc2nc3ccccc3nc2NS(=O)(=O)c2ccc(F)cc2)cc(OC)c1] | N-(3-{[3,5-bis(methoxy)phenyl]amino}quinoxalin-2-yl)-4-fluorobenzenesulfonamie |
| 731 | 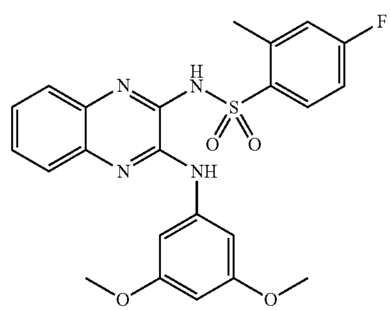 [SMILES: COc1cc(Nc2nc3ccccc3nc2NS(=O)(=O)c2ccc(F)cc2C)cc(OC)c1] | N-(3-{[3,5-bis(methoxy)phenyl]amino}quinoxalin-2-yl)-4-fluoro-2-methylbenzenesulfonamide |
| 732 | 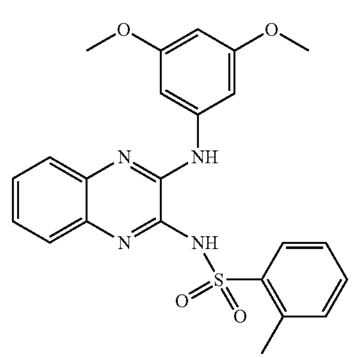 [SMILES: COc1cc(Nc2nc3ccccc3nc2NS(=O)(=O)c2ccccc2C)cc(OC)c1] | N-(3-{[3,5-bis(methoxy)phenyl]amino}quinoxalin-2-yl)-2-methylbenzenesulfonamide |

TABLE 1-continued

| Cpd. No. | Structure | Name |
|---|---|---|
| 733 | 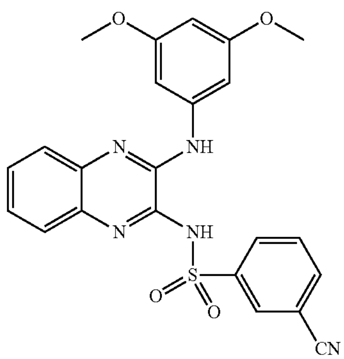 [SMILES: COc1cc(Nc2nc3ccccc3nc2NS(=O)(=O)c2cccc(C#N)c2)cc(OC)c1] | N-(3-{[3,5-bis(methoxy)phenyl]amino}quinoxalin-2-yl)-3-cyanobenzenesulfonamide |
| 734 | 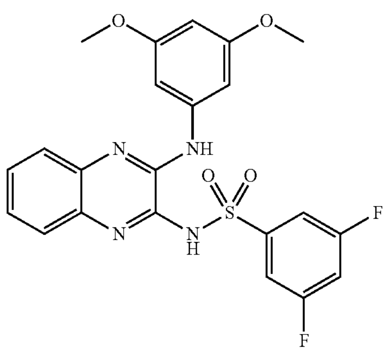 [SMILES: COc1cc(Nc2nc3ccccc3nc2NS(=O)(=O)c2cc(F)cc(F)c2)cc(OC)c1] | N-(3-{[3,5-bis(methoxy)phenyl]amino}quinoxalin-2-yl)-3,5-difluorobenzenesulfonamide |
| 735 | 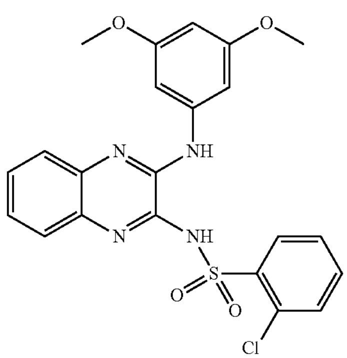 [SMILES: COc1cc(Nc2nc3ccccc3nc2NS(=O)(=O)c2ccccc2Cl)cc(OC)c1] | N-(3-{[3,5-bis(methoxy)phenyl]amino}quinoxalin-2-yl)-2-chlorobenzenesulfonamde |
| 736 | 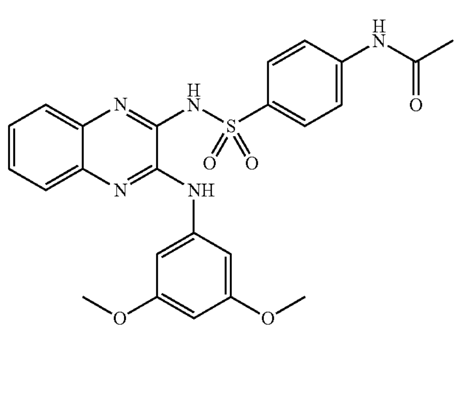 [SMILES: COc1cc(Nc2nc3ccccc3nc2NS(=O)(=O)c2ccc(NC(C)=O)cc2)cc(OC)c1] | N-(4-{[(3-{[3,5-bis(methoxy)phenyl]amino}quinoxalin-2-yl)amino]sulfonyl}phenyl)acetamide |

TABLE 1-continued

| Cpd. No. | Structure | Name |
|---|---|---|
| 737 | 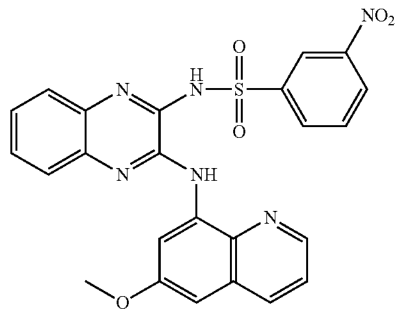 [SMILES: COc1cc(Nc2nc3ccccc3nc2NS(=O)(=O)c2cccc([N+](=O)[O-])c2)c2ncccc2c1] | N-(3-{[6-(methoxy)quinolin-8-yl]amino}quinoxalin-2-yl)-3-nitrobenzenesulfonamide |
| 738 | 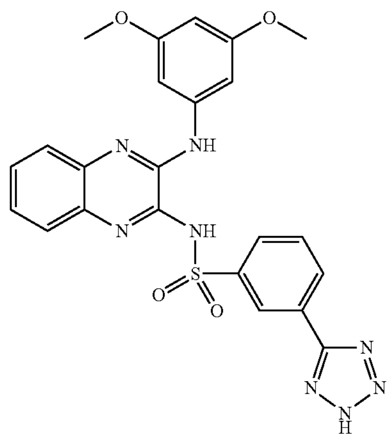 [SMILES: COc1cc(Nc2nc3ccccc3nc2NS(=O)(=O)c2cccc(-c3nn[nH]n3)c2)cc(OC)c1] | N-(3-{[3,5-bis(methoxy)phenyl]amino}quinoxalin-2-yl)-3-(2H-tetrazol-5-yl)benzenesulfonamide |
| 739 | 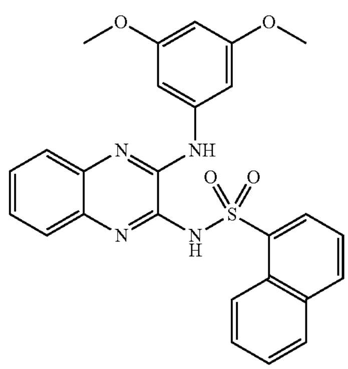 [SMILES: COc1cc(Nc2nc3ccccc3nc2NS(=O)(=O)c2cccc3ccccc23)cc(OC)c1] | N-(3-{[3,5-bis(methoxy)phenyl]amino}quinoxalin-2-yl)naphthalene-1-sulfonamide |
| 740 | 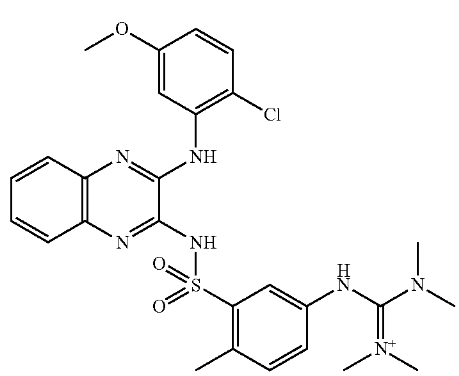 [SMILES: COc1ccc(Cl)c(Nc2nc3ccccc3nc2NS(=O)(=O)c2cc(NC(N(C)C)=[N+](C)C)ccc2C)c1] | N-{[(3-{[(3-{[2-chloro-5-(methoxy)phenyl]amino}quinoxalin-2-yl)amino]sulfonyl}-4-methylphenyl)amino](dimethylamino)methylidene}-N-methylmethanaminium |

TABLE 1-continued

| Cpd. No. | Structure | Name |
|---|---|---|
| 741 | 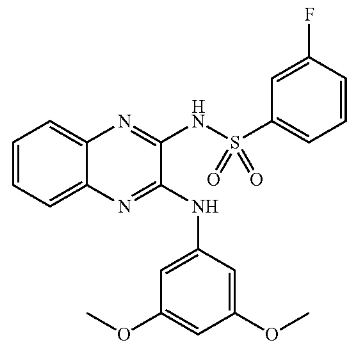 [SMILES: COc1cc(Nc2nc3ccccc3nc2NS(=O)(=O)c2cccc(F)c2)cc(OC)c1] | N-(3-{[3,5-bis(methoxy)phenyl]amino}quinoxalin-2-yl)-3-fluorobenzenesulfonamide |
| 742 | 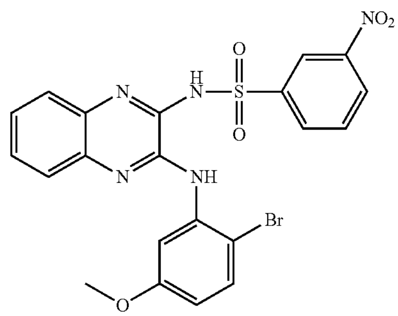 [SMILES: COc1ccc(Br)c(Nc2nc3ccccc3nc2NS(=O)(=O)c2cccc([N+](=O)[O-])c2)c1] | N-(3-{[2-bromo-5-(methoxy)phenyl]amino}quinoxalin-2-yl)-3-nitrobenzensulfonamide |
| 743 | 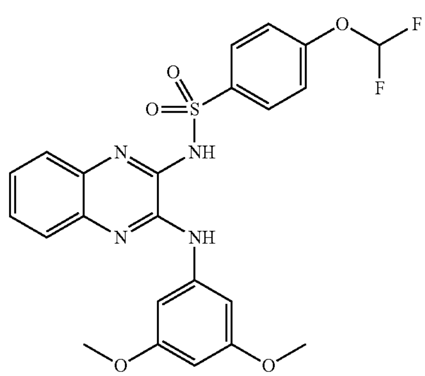 [SMILES: COc1cc(Nc2nc3ccccc3nc2NS(=O)(=O)c2ccc(OC(F)F)cc2)cc(OC)c1] | N-(3-{[3,5-bis(methoxy)phenyl]amino}quinoxalin-2-yl)-4-[(difluoromethyl)oxy]benzenesulfonamide |
| 744 | 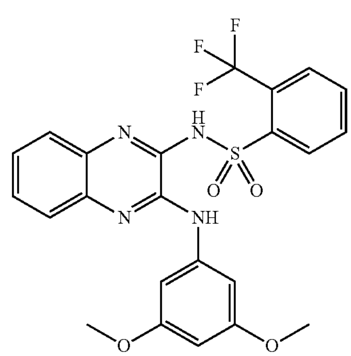 [SMILES: COc1cc(Nc2nc3ccccc3nc2NS(=O)(=O)c2ccccc2C(F)(F)F)cc(OC)c1] | N-(3-{[3,5-bis(methoxy)phenyl]amino}quinoxalin-2-yl)-2-(trifluoromethyl)benzenesulfonamide |

TABLE 1-continued

| Cpd. No. | Structure | Name |
|---|---|---|
| 745 | 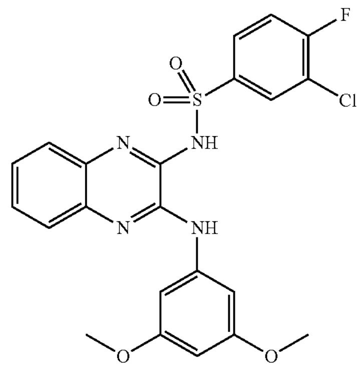 [SMILES: COc1cc(Nc2nc3ccccc3nc2NS(=O)(=O)c2ccc(F)c(Cl)c2)cc(OC)c1] | N-(3-{[3,5-bis(methoxy)phenyl]amino}quinoxalin-2-yl)-3-chloro-4-fluorobenzensulfonamide |
| 746 | 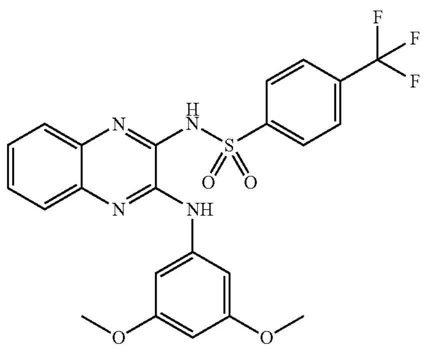 [SMILES: COc1cc(Nc2nc3ccccc3nc2NS(=O)(=O)c2ccc(C(F)(F)F)cc2)cc(OC)c1] | N-(3-{[3,5-bis(methoxy)phenyl]amino}quinoxalin-2-yl)-4-(trifluoromethyl)benzenesulfonamide |
| 747 | 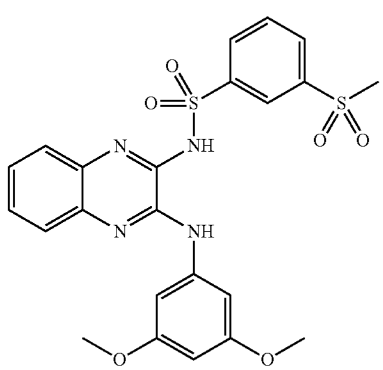 [SMILES: COc1cc(Nc2nc3ccccc3nc2NS(=O)(=O)c2cccc(S(C)(=O)=O)c2)cc(OC)c1] | N-(3-{[3,5-bis(methoxy)phenyl]amino}quinoxalin-2-yl)-3-(methylsulfonyl)benzenesulfonamide |
| 748 | 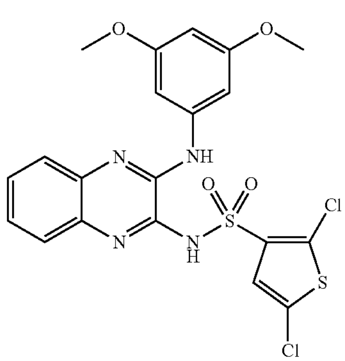 [SMILES: COc1cc(Nc2nc3ccccc3nc2NS(=O)(=O)c2cc(Cl)sc2Cl)cc(OC)c1] | N-(3-{[3,5-bis(methoxy)phenyl]amino}quinoxalin-2-yl)-2,5-dichlorthiophene-3-sulfonamide |

TABLE 1-continued

| Cpd. No. | Structure | Name |
|---|---|---|
| 749 | 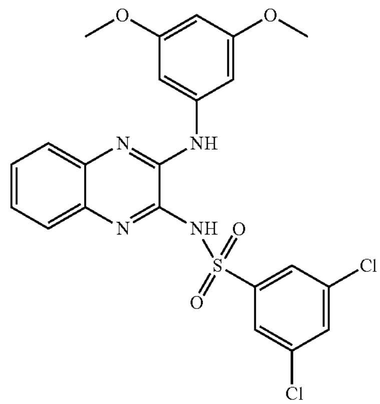 [SMILES: COc1cc(Nc2nc3ccccc3nc2NS(=O)(=O)c2cc(Cl)cc(Cl)c2)cc(OC)c1] | N-(3-{[3,5-bis(methoxy)phenyl]amino}quinoxalin-2-yl)-3,5-dichlorobenzenesulfonamide |
| 750 | 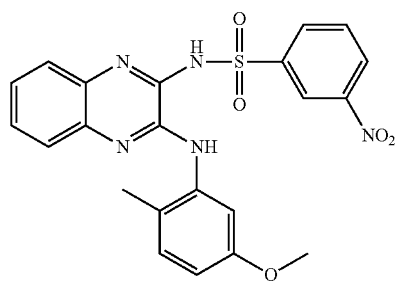 | N-(3-{[2-methyl-5-(methoxy)phenyl]amino}quinoxalin-2-yl)-3-nitrobenzenesulfonamide |
| 751 | 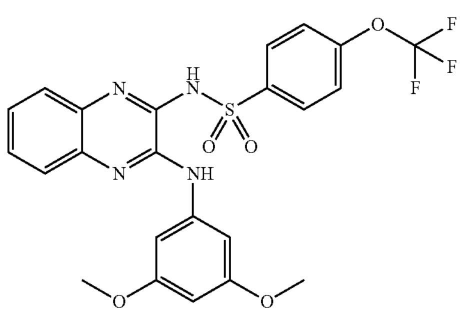 [SMILES: COc1cc(Nc2nc3ccccc3nc2NS(=O)(=O)c2ccc(OC(F)(F)F)cc2)cc(OC)c1] | N-(3-{[3,5-bis(methoxy)phenyl]amino}quinoxalin-2-yl)-4-[(trifluoromethyl)oxy]benzensulfonamide |
| 752 | 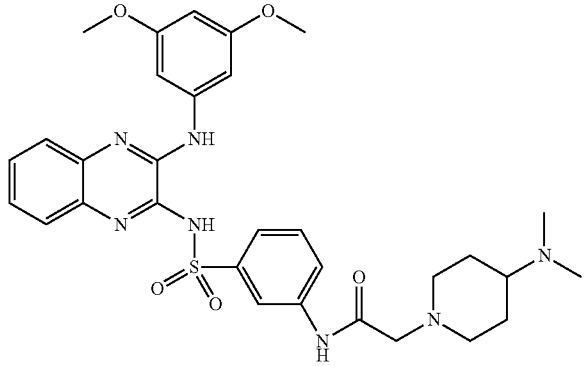 [SMILES: COc1cc(Nc2nc3ccccc3nc2NS(=O)(=O)c2cccc(NC(=O)CN3CCC(N(C)C)CC3)c2)cc(OC)c1] | N-(3-{[(3-{[3,5-bis(methoxy)phenyl]amino}quinoxalin-2-yl)amino]sulfonyl}phenyl)-2-[4-(dimethylamino)piperidin-1-yl]acetamide |

TABLE 1-continued
| Cpd. No. | Structure | Name |
|---|---|---|
| 753 | 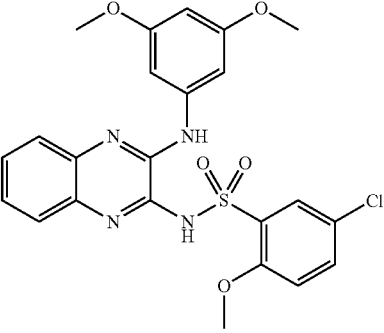 [SMILES: COc1cc(Nc2nc3ccccc3nc2NS(=O)(=O)c2cc(Cl)ccc2OC)cc(OC)c1] | N-(3-{[3,5-bis(methoxy)phenyl]amino}quinoxalin-2-yl)-5-chloro-2-(methoxy)benzenesulfoamide |
| 754 | 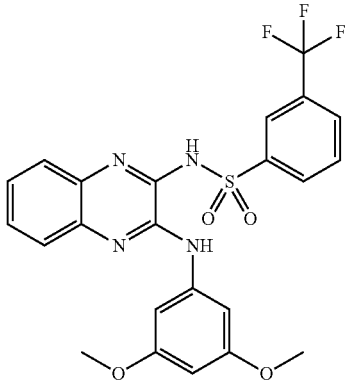 [SMILES: COc1cc(Nc2nc3ccccc3nc2NS(=O)(=O)c2cccc(C(F)(F)F)c2)cc(OC)c1] | N-(3-{[3,5-bis(methoxy)phenyl]amino}quinoxalin-2-yl)-3-(trifluoromethyl)benzenesulfonamide |
| 755 | 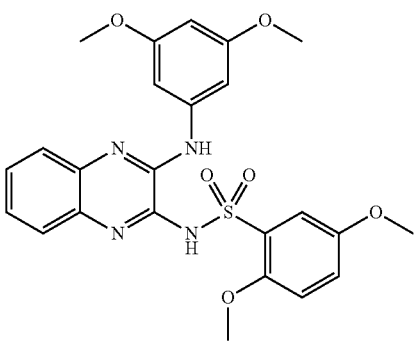 [SMILES: COc1cc(Nc2nc3ccccc3nc2NS(=O)(=O)c2cc(OC)ccc2OC)cc(OC)c1] | N-(3-{[3,5-bis(methoxy)phenyl]amino}quinoxalin-2-yl)-2,5-bis(methoxy)benzenesulfonamide |
| 756 | 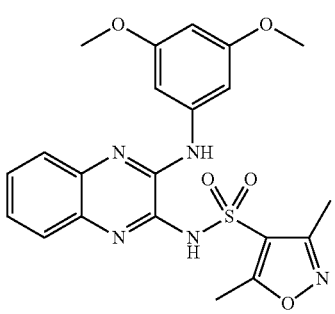 [SMILES: COc1cc(Nc2nc3ccccc3nc2NS(=O)(=O)c2c(C)noc2C)cc(OC)c1] | N-(3-{[3,5-bis(methoxy)phenyl]amino}quinoxalin-2-yl)-3,5-dimethylisoxazole-4-sulfonamide |

TABLE 1-continued

| Cpd. No. | Structure | Name |
|---|---|---|
| 757 | 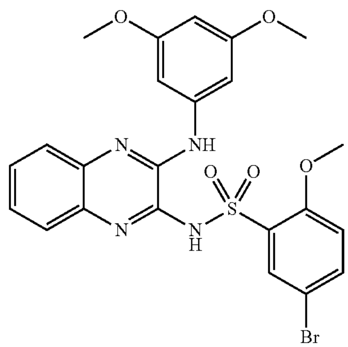 [SMILES: COc1cc(Nc2nc3ccccc3nc2NS(=O)(=O)c2cc(Br)ccc2OC)cc(OC)c1] | N-(3-{[3,5-bis(methoxy)phenyl]amino}quinoxalin-2-yl)-5-bromo-2-(methoxy)benzenesulfonamde |
| 758 | 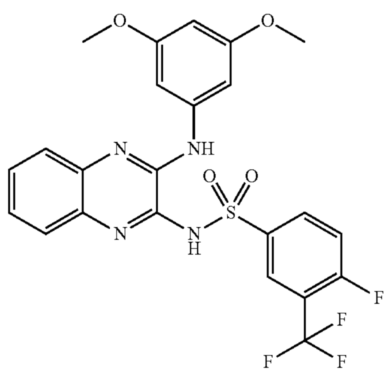 [SMILES: COc1cc(Nc2nc3ccccc3nc2NS(=O)(=O)c2ccc(F)c(C(F)(F)F)c2)cc(OC)c1] | N-(3-{[3,5-bis(methoxy)phenyl]amino}quinoxalin-2-yl)-4-fluoro-3-(trifluoromethyl)benzenesulfonamide |
| 759 | 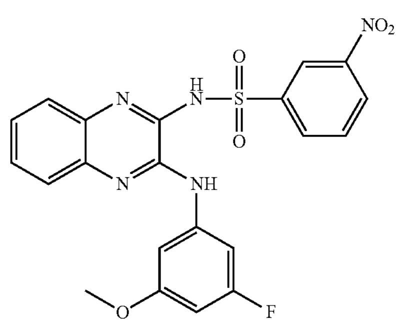 | N-(3-{[3-fluoro-5-(methoxy)phenyl]amino}quinoxalin-2-yl)-3-nitrobenzenesulfonamide |
| 760 | 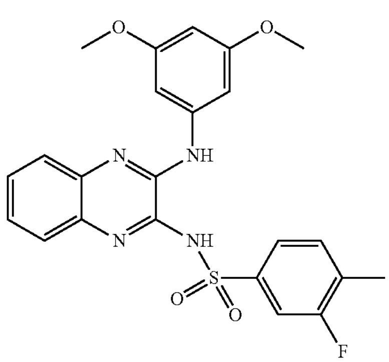 [SMILES: COc1cc(Nc2nc3ccccc3nc2NS(=O)(=O)c2ccc(C)c(F)c2)cc(OC)c1] | N-(3-{[3,5-bis(methoxy)phenyl]amino}quinoxalin-2-yl)-3-fluoro-4-methylbenzenesulfonamide |

TABLE 1-continued

| Cpd. No. | Structure | Name |
| --- | --- | --- |
| 761 | 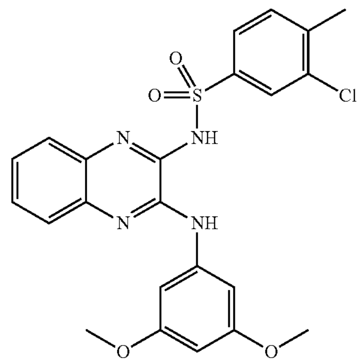 [SMILES: COc1cc(Nc2nc3ccccc3nc2NS(=O)(=O)c2ccc(C)c(Cl)c2)cc(OC)c1] | N-(3-{[3,5-bis(methoxy)phenyl]amino}quinoxalin-2-yl)-3-chloro-4-methylbenzenesulfonamide |
| 762 | 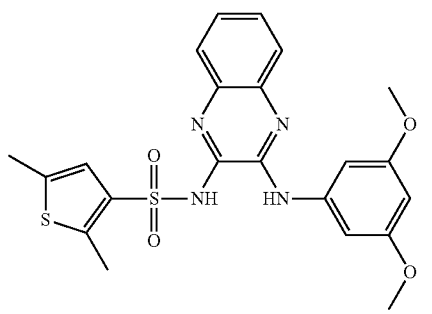 [SMILES: COc1cc(Nc2nc3ccccc3nc2NS(=O)(=O)c2cc(C)sc2C)cc(OC)c1] | N-(3-{[3,5-bis(methoxy)phenyl]amino}quinoxalin-2-yl)-2,5-dimethylthiophene-3-sulfonamide |
| 763 | 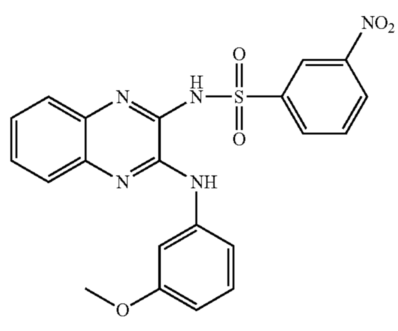 [SMILES: COc1cccc(Nc2nc3ccccc3nc2NS(=O)(=O)c2cccc([N+](=O)[O-])c2)c1] | N-(3-{[3-(methoxy)phenyl]amino}quinoxalin-2-yl)-3-nitrobenzenesulfonamide |
| 764 | 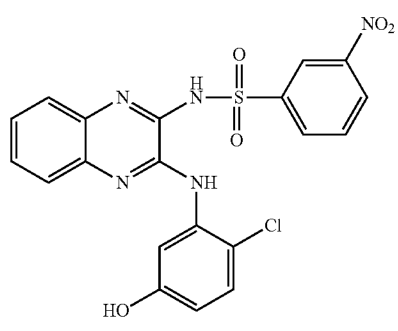 [SMILES: O=[N+]([O-])c1cccc(S(=O)(=O)Nc2nc3ccccc3nc2Nc2cc(O)ccc2Cl)c1] | N-{3-[(2-chloro-5-hydroxyphenyl)amino]quinoxalin-2-yl}-3-nitrobenzenesulfonamide |

| Cpd. No. | Structure | Name |
|---|---|---|
| 765 | 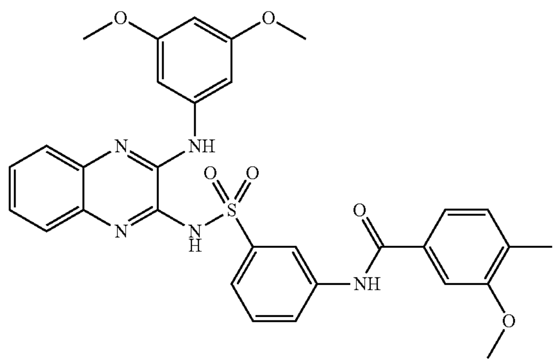 [SMILES: COc1cc(Nc2nc3ccccc3nc2NS(=O)(=O)c2cccc(NC(=O)c3ccc(C)c(OC)c3)c2)cc(OC)c1] | N-(3-{[(3-{[3,5-bis(methoxy)phenyl]amino}quinoxalin-2-yl)amino]sulfonyl}phenyl)-4-methyl-3-(methoxy)benzamide |
| 766 | 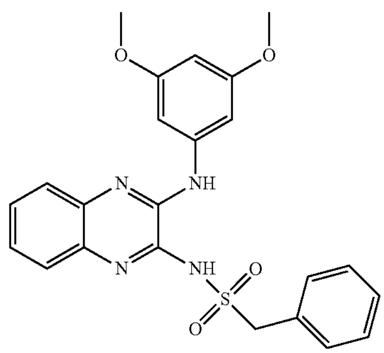 [SMILES: COc1cc(Nc2nc3ccccc3nc2NS(=O)(=O)Cc2ccccc2)cc(OC)c1] | N-(3-{[3,5-bis(methoxy)phenyl]amino}quinoxalin-2-yl)-1-phenylmethanesulfonamide |
| 767 | 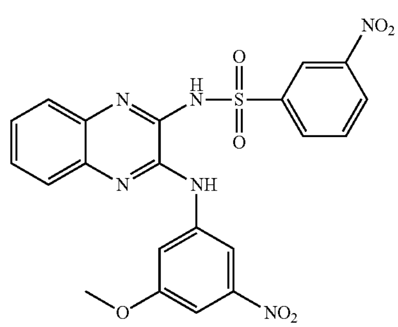 | N-(3-{[3-(methoxy)-5-nitrophenyl]amino}quinoxalin-2-yl)-3-nitrobenzenesulfonamide |
| 768 | 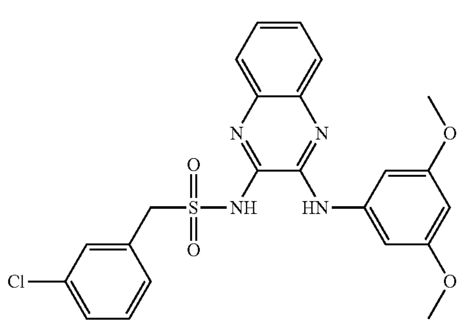 [SMILES: COc1cc(Nc2nc3ccccc3nc2NS(=O)(=O)Cc2cccc(Cl)c2)cc(OC)c1] | N-(3-{[3,5-bis(methoxy)phenyl]amino}quinoxalin-2-yl)-1-(3-chlorophenyl)methanesulfonamide |

TABLE 1-continued

| Cpd. No. | Structure | Name |
|---|---|---|
| 769 | 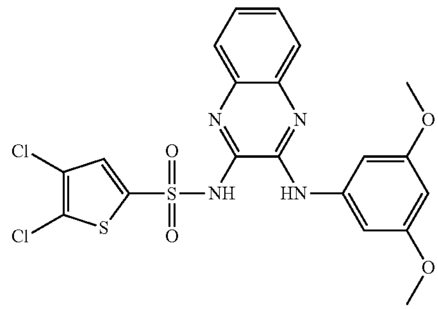 [SMILES: COc1cc(Nc2nc3ccccc3nc2NS(=O)(=O)c2cc(Cl)c(Cl)s2)cc(OC)c1] | N-(3-{[3,5-bis(methoxy)phenyl]amino}quinoxalin-2-yl)-4,5-dichlorothiophene-2-sulfonamide |
| 770 | 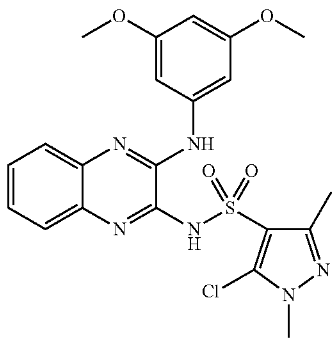 [SMILES: COc1cc(Nc2nc3ccccc3nc2NS(=O)(=O)c2c(C)nn(C)c2Cl)cc(OC)c1] | N-(3-{[3,5-bis(methoxy)phenyl]amino}quinoxalin-2-yl)-5-chloro-1,3-dimethyl-1H-pyrazole-4-sulfonamide |
| 771 | 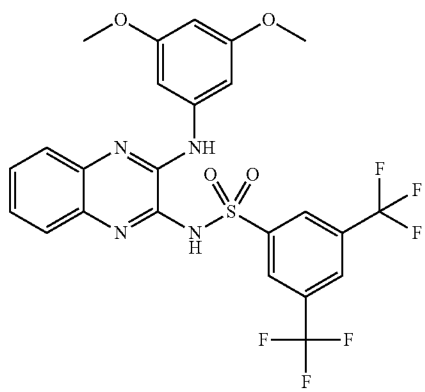 [SMILES: COc1cc(Nc2nc3ccccc3nc2NS(=O)(=O)c2cc(C(F)(F)F)cc(C(F)(F)F)c2)cc(OC)c1] | N-(3-{[3,5-bis(methoxy)phenyl]amino}quinoxalin-2-yl)-3,5-bis(trifluoromethyl)benzenesulfonamide |

The Compounds in Table 2a can be prepared as pharmaceutically acceptable salts, solvates, hydrates, and/or isomers thereof. All such salt, solvate, hydrate, and isomer combinations of the Compounds in Table 2a can be used to practice the invention.

| Cmpd No. | Name |
|---|---|
| 1 | 3-(azetidin-3-ylidenemethyl)-4-[4-(5-chloro-2-methylphenyl)piperazin-1-yl]-1H-pyrazolo[3,4-d]pyrimidine |
| 2 | 4-[4-(5-chloro-2-methylphenyl)piperazin-1-yl]-3-(3-fluoropyridin-4-yl)-1H-pyrazolo[3,4-d]pyrimidine |
| 3 | 4-[4-(5-chloro-2-methylphenyl)piperazin-1-yl]-3-(3-chloropyridin-4-yl)-1H-pyrazolo[3,4-d]pyrimidine |
| 4 | 2-({5-chloro-3-[4-(3-ethyl-1H-pyrazolo[3,4-d]pyrimidin-4-yl)piperazin-1-yl]-2-methylphenyl}oxy)-N,N-dimethylethanamine |
| 5 | 2-({5-chloro-3-[4-(3-ethyl-1H-pyrazolo[3,4-d]pyrimidin-4-yl)piperazin-1-yl]-2-methylphenyl}oxy)-N,N-diethylethanamine |
| 6 | 4-(4-{5-chloro-2-methyl-3-[(2-pyrrolidin-1-ylethyl)oxy]phenyl}piperazin-1-yl)-3-ethyl-1H-pyrazolo[3,4-d]pyrimidine |

-continued

| Cmpd No. | Name |
|---|---|
| 7 | 4-[4-(5-chloro-2-methylphenyl)piperazin-1-yl]-3-piperazin-1-yl-1H-pyrazolo[3,4-d]pyrimidine |
| 8 | N-(3-{4-[4-(5-chloro-2-methylphenyl)piperazin-1-yl]-1H-pyrazolo[3,4-d]pyrimidin-3-yl}prop-2-yn-1-yl)acetamide |
| 9 | N,N-diethyl-2-({3-[4-(3-ethyl-1H-pyrazolo[3,4-d]pyrimidin-4-yl)piperazin-1-yl]phenyl}oxy)ethanamine |
| 10 | 3-{3-[4-(3-bromo-1H-pyrazolo[3,4-d]pyrimidin-4-yl)piperazin-1-yl]-5-chloro-2-methylphenyl}-N,N-diethylpropan-1-amine |
| 11 | 3-bromo-4-{4-[5-chloro-2-methyl-3-(3-pyrrolidin-1-ylpropyl)phenyl]piperazin-1-yl}-1H-pyrazolo[3,4-d]pyrimidine |
| 12 | 3-bromo-4-(4-{5-chloro-2-methyl-3-[(2-pyrrolidin-1-ylethyl)oxy]phenyl}piperazin-1-yl)-1H-pyrazolo[3,4-d]pyrimidine |
| 13 | 2-({3-[4-(3-bromo-1H-pyrazolo[3,4-d]pyrimidin-4-yl)piperazin-1-yl]-5-chloro-2-methylphenyl}oxy)-N,N-diethylethanamine |
| 14 | 4-[4-(5-chloro-2-methyl-3-{[2-(1-methylpiperidin-4-yl)ethyl]oxy}phenyl)piperazin-1-yl]-3-ethyl-1H-pyrazolo[3,4-d]pyrimidine |
| 15 | 5-chloro-3-[4-(3-ethyl-1H-pyrazolo[3,4-d]pyrimidin-4-yl)piperazin-1-yl]-2-methyl-N-(2-pyrrolidin-1-ylethyl)aniline |
| 16 | 4-(4-{5-chloro-2-methyl-3-[(2-morpholin-4-ylethyl)oxy]phenyl}piperazin-1-yl)-3-ethyl-1H-pyrazolo[3,4-d]pyrimidine |
| 17 | 4-(4-{5-chloro-2-methyl-3-[(2-piperidin-1-ylethyl)oxy]phenyl}piperazin-1-yl)-3-ethyl-1H-pyrazolo[3,4-d]pyrimidine |
| 18 | 3-bromo-4-{4-[5-chloro-2-methyl-3-(3-morpholin-4-ylpropyl)phenyl]piperazin-1-yl}-1H-pyrazolo[3,4-d]pyrimidine |
| 19 | 3-bromo-4-(4-{5-chloro-2-methyl-3-[3-(4-methylpiperazin-1-yl)propyl]phenyl}piperazin-1-yl)-1H-pyrazolo[3,4-d]pyrimidine |
| 20 | 3-bromo-4-(4-{5-chloro-2-methyl-3-[(2-piperidin-1-ylethyl)oxy]phenyl}piperazin-1-yl)-1H-pyrazolo[3,4-d]pyrimidine |
| 21 | 3-bromo-4-(4-{5-chloro-2-methyl-3-[(2-morpholin-4-ylethyl)oxy]phenyl}piperazin-1-yl)-1H-pyrazolo[3,4-d]pyrimidine |
| 22 | 4-{4-[5-chloro-2-methyl-3-(3-morpholin-4-ylpropyl)phenyl]piperazin-1-yl}-3-ethyl-1H-pyrazolo[3,4-d]pyrimidine |
| 23 | N'-{5-chloro-3-[4-(3-ethyl-1H-pyrazolo[3,4-d]pyrimidin-4-yl)piperazin-1-yl]-2-methylphenyl}-N,N-diethylethane-1,2-diamine |
| 24 | 4-{4-[5-chloro-2-methyl-3-(3-piperidin-1-ylpropyl)phenyl]piperazin-1-yl}-3-ethyl-1H-pyrazolo[3,4-d]pyrimidine |
| 25 | 4-[4-(5-chloro-3-{[2-(4-ethylpiperazin-1-yl)ethyl]oxy}-2-methylphenyl)piperazin-1-yl]-3-ethyl-1H-pyrazolo[3,4-d]pyrimidine |
| 26 | 4-(4-{5-chloro-2-methyl-3-[(3-morpholin-4-ylpropyl)oxy]phenyl}piperazin-1-yl)-3-ethyl-1H-pyrazolo[3,4-d]pyrimidine |
| 27 | 3-bromo-4-{4-[5-chloro-2-methyl-3-(3-piperidin-1-ylpropyl)phenyl]piperazin-1-yl}-1H-pyrazolo[3,4-d]pyrimidine |
| 28 | N'-{3-[4-(3-bromo-1H-pyrazolo[3,4-d]pyrimidin-4-yl)piperazin-1-yl]-5-chloro-2-methylphenyl}-N,N-diethylethane-1,2-diamine |
| 29 | 3-[4-(3-bromo-1H-pyrazolo[3,4-d]pyrimidin-4-yl)piperazin-1-yl]-5-chloro-2-methyl-N-(2-pyrrolidin-1-ylethyl)aniline |
| 30 | 4-[4-(5-chloro-2-methyl-3-{[2-(4-methylpiperazin-1-yl)ethyl]oxy}phenyl)piperazin-1-yl]-3-ethyl-1H-pyrazolo[3,4-d]pyrimidine |
| 31 | 4-[4-(5-chloro-2-methyl-3-{[(1-methylpiperidin-4-yl)methyl]oxy}phenyl)piperazin-1-yl]-3-ethyl-1H-pyrazolo[3,4-d]pyrimidine |
| 32 | N,N-diethyl-2-({3-[4-(3-ethyl-1H-pyrazolo[3,4-d]pyrimidin-4-yl)piperazin-1-yl]-2-methylphenyl}oxy)ethanamine |
| 33 | 2-[(5-chloro-3-{4-[1-(1,1-dimethylethyl)-3-(trifluoromethyl)-1H-pyrazolo[3,4-d]pyrimidin-4-yl]piperazin-1-yl}-2-methylphenyl)oxy]-N,N-diethylethanamine |
| 34 | 2-[(5-chloro-2-methyl-3-{4-[3-(trifluoromethyl)-1H-pyrazolo[3,4-d]pyrimidin-4-yl]piperazin-1-yl}phenyl)oxy]-N,N-diethylethanamine |
| 35 | 4-(4-{5-chloro-2-methyl-3-[(3-pyrrolidin-1-ylpropyl)oxy]phenyl}piperazin-1-yl)-3-ethyl-1H-pyrazolo[3,4-d]pyrimidine |
| 36 | 4-[4-(5-chloro-2-methyl-3-{[3-(4-methylpiperazin-1-yl)propyl]oxy}phenyl)piperazin-1-yl]-3-ethyl-1H-pyrazolo[3,4-d]pyrimidine |
| 37 | 3-bromo-4-(4-{5-chloro-2-methyl-3-[(3-piperidin-1-ylpropyl)oxy]phenyl}piperazin-1-yl)-1H-pyrazolo[3,4-d]pyrimidine |
| 38 | 3-bromo-4-(4-{5-chloro-2-methyl-3-[(3-morpholin-4-ylpropyl)oxy]phenyl}piperazin-1-yl)-1H-pyrazolo[3,4-d]pyrimidine |
| 39 | 4-(4-{5-chloro-2-methyl-3-[(2-pyrrolidin-1-ylethyl)oxy]phenyl}piperazin-1-yl)-3-(trifluoromethyl)-1H-pyrazolo[3,4-d]pyrimidine |
| 40 | 4-(4-{5-chloro-2-methyl-3-[(3-morpholin-4-ylpropyl)oxy]phenyl}piperazin-1-yl)-3-(trifluoromethyl)-1H-pyrazolo[3,4-d]pyrimidine |
| 41 | 4-(4-{5-chloro-2-methyl-3-[(2-morpholin-4-ylethyl)oxy]phenyl}piperazin-1-yl)-3-(trifluoromethyl)-1H-pyrazolo[3,4-d]pyrimidine |
| 42 | 4-(4-{5-chloro-2-methyl-3-[(3-piperidin-1-ylpropyl)oxy]phenyl}piperazin-1-yl)-3-ethyl-1H-pyrazolo[3,4-d]pyrimidine |
| 43 | 4-[4-(5-chloro-3-{[3-(4-ethylpiperazin-1-yl)propyl]oxy}-2-methylphenyl)piperazin-1-yl]-3-ethyl-1H-pyrazolo[3,4-d]pyrimidine |
| 44 | 5-chloro-2-methyl-3-[4-(1H-pyrazolo[3,4-d]pyrimidin-4-yl)piperazin-1-yl]-N-(2-pyrrolidin-1-ylethyl)aniline |
| 45 | 5-chloro-2-methyl-3-[4-(3-methyl-1H-pyrazolo[3,4-d]pyrimidin-4-yl)piperazin-1-yl]-N-(2-pyrrolidin-1-ylethyl)aniline |

-continued

| Cmpd No. | Name |
| --- | --- |
| 46 | N'-(5-chloro-2-methyl-3-{4-[3-(trifluoromethyl)-1H-pyrazolo[3,4-d]pyrimidin-4-yl]piperazin-1-yl}phenyl)-N,N-dimethylethane-1,2-diamine |
| 47 | 3-({5-chloro-3-[4-(3-ethyl-1H-pyrazolo[3,4-d]pyrimidin-4-yl)piperazin-1-yl]-2-methylphenyl}oxy)-N,N-diethylpropan-1-amine |
| 48 | N'-(5-chloro-2-methyl-3-{4-[3-(trifluoromethyl)-1H-pyrazolo[3,4-d]pyrimidin-4-yl]piperazin-1-yl}phenyl)-N,N-diethylethane-1,2-diamine |
| 49 | 5-chloro-2-methyl-N-(2-pyrrolidin-1-ylethyl)-3-{4-[3-(trifluoromethyl)-1H-pyrazolo[3,4-d]pyrimidin-4-yl]piperazin-1-yl}aniline |
| 50 | 3-bromo-4-(4-{4-methyl-3-[(2-pyrrolidin-1-ylethyl)oxy]phenyl}piperazin-1-yl)-1H-pyrazolo[3,4-d]pyrimidine |
| 51 | 4-(4-{4-methyl-3-[(2-pyrrolidin-1-ylethyl)oxy]phenyl}piperazin-1-yl)-1H-pyrazolo[3,4-d]pyrimidine |
| 52 | 3-methyl-4-(4-{4-methyl-3-[(2-pyrrolidin-1-ylethyl)oxy]phenyl}piperazin-1-yl)-1H-pyrazolo[3,4-d]pyrimidine |
| 53 | 4-(4-{5-chloro-2-methyl-3-[(2-pyrrolidin-1-ylethyl)oxy]phenyl}piperazin-1-yl)-1H-pyrazolo[3,4-d]pyrimidine |
| 54 | 4-(4-{5-chloro-2-methyl-3-[(2-pyrrolidin-1-ylethyl)oxy]phenyl}piperazin-1-yl)-3-methyl-1H-pyrazolo[3,4-d]pyrimidine |
| 55 | 4-(4-{5-chloro-2-methyl-3-[(2-piperidin-1-ylethyl)oxy]phenyl}piperazin-1-yl)-3-(trifluoromethyl)-1H-pyrazolo[3,4-d]pyrimidine |
| 56 | 3-[(5-chloro-2-methyl-3-{4-[3-(trifluoromethyl)-1H-pyrazolo[3,4-d]pyrimidin-4-yl]piperazin-1-yl}phenyl)oxy]-N,N-diethylpropan-1-amine |
| 57 | 5-[4-(3-bromo-1H-pyrazolo[3,4-d]pyrimidin-4-yl)piperazin-1-yl]-2-methyl-N-(2-pyrrolidin-1-ylethyl)aniline |
| 58 | 3-[4-(3-bromo-1H-pyrazolo[3,4-d]pyrimidin-4-yl)piperazin-1-yl]-5-fluoro-2-methyl-N-(2-pyrrolidin-1-ylethyl)aniline |
| 59 | 4-{4-[5-chloro-2-methyl-3-(3-pyrrolidin-1-ylpropyl)phenyl]piperazin-1-yl}-1H-pyrazolo[3,4-d]pyrimidine |
| 60 | 3-bromo-4-{4-[5-fluoro-2-methyl-3-(3-pyrrolidin-1-ylpropyl)phenyl]piperazin-1-yl}-1H-pyrazolo[3,4-d]pyrimidine |
| 61 | 4-{4-[5-chloro-2-methyl-3-(3-pyrrolidin-1-ylpropyl)phenyl]piperazin-1-yl}-3-(trifluoromethyl)-1H-pyrazolo[3,4-d]pyrimidine |
| 62 | 4-(4-{5-chloro-2-methyl-3-[3-(4-methylpiperazin-1-yl)propyl]phenyl}piperazin-1-yl)-3-ethyl-1H-pyrazolo[3,4-d]pyrimidine |
| 63 | 3-bromo-4-(4-pyridin-2-ylpiperazin-1-yl)-1H-pyrazolo[3,4-d]pyrimidine |
| 64 | 3-bromo-4-[4-(2,4-dimethylphenyl)piperazin-1-yl]-1H-pyrazolo[3,4-d]pyrimidine |
| 65 | 3-bromo-4-{4-[3-(methyloxy)phenyl]piperazin-1-yl}-1H-pyrazolo[3,4-d]pyrimidine |
| 66 | 3-bromo-4-{4-[2-(methyloxy)phenyl]piperazin-1-yl}-1H-pyrazolo[3,4-d]pyrimidine |
| 67 | 3-bromo-4-{4-[4-methyl-3-(3-pyrrolidin-1-ylpropyl)phenyl]piperazin-1-yl}-1H-pyrazolo[3,4-d]pyrimidine |
| 68 | 4-(4-{5-chloro-2-methyl-3-[(3-pyrrolidin-1-ylpropyl)oxy]phenyl}piperazin-1-yl)-3-(trifluoromethyl)-1H-pyrazolo[3,4-d]pyrimidine |
| 69 | 4-(4-{5-chloro-2-methyl-3-[(3-piperidin-1-ylpropyl)oxy]phenyl}piperazin-1-yl)-3-(trifluoromethyl)-1H-pyrazolo[3,4-d]pyrimidine |
| 70 | 4-[4-(5-chloro-2-methyl-3-{[3-(4-methylpiperazin-1-yl)propyl]oxy}phenyl)piperazin-1-yl]-3-(trifluoromethyl)-1H-pyrazolo[3,4-d]pyrimidine |
| 71 | 4-[4-(5-chloro-3-{[3-(4-ethylpiperazin-1-yl)propyl]oxy}-2-methylphenyl)piperazin-1-yl]-3-(trifluoromethyl)-1H-pyrazolo[3,4-d]pyrimidine |
| 72 | 3-bromo-4-[4-(5-chloro-2-methyl-3-{[2-(4-methylpiperazin-1-yl)ethyl]oxy}phenyl)piperazin-1-yl]-1H-pyrazolo[3,4-d]pyrimidine |
| 73 | 4-[4-(5-chloro-2-methyl-3-{[2-(4-methylpiperazin-1-yl)ethyl]oxy}phenyl)piperazin-1-yl]-3-(trifluoromethyl)-1H-pyrazolo[3,4-d]pyrimidine |
| 74 | 3-bromo-4-[4-(5-chloro-3-{[2-(4-ethylpiperazin-1-yl)ethyl]oxy}-2-methylphenyl)piperazin-1-yl]-1H-pyrazolo[3,4-d]pyrimidine |
| 75 | 3-bromo-4-[4-(3,4-dichlorophenyl)piperazin-1-yl]-1H-pyrazolo[3,4-d]pyrimidine |
| 76 | 3-bromo-4-[4-(3,4-difluorophenyl)piperazin-1-yl]-1H-pyrazolo[3,4-d]pyrimidine |
| 77 | 3-bromo-4-[4-(2,4-dichlorophenyl)piperazin-1-yl]-1H-pyrazolo[3,4-d]pyrimidine |
| 78 | 3-[4-(3-ethyl-1H-pyrazolo[3,4-d]pyrimidin-4-yl)piperazin-1-yl]-5-fluoro-2-methyl-N-(2-pyrrolidin-1-ylethyl)aniline |
| 79 | 5-fluoro-2-methyl-N-(2-pyrrolidin-1-ylethyl)-3-{4-[3-(trifluoromethyl)-1H-pyrazolo[3,4-d]pyrimidin-4-yl]piperazin-1-yl}aniline |
| 80 | 4-{4-[3,5-bis(methyloxy)phenyl]piperazin-1-yl}-3-bromo-1H-pyrazolo[3,4-d]pyrimidine |
| 81 | 4-[4-(5-chloro-3-{[2-(4-ethylpiperazin-1-yl)ethyl]oxy}-2-methylphenyl)piperazin-1-yl]-3-(trifluoromethyl)-1H-pyrazolo[3,4-d]pyrimidine |
| 82 | N-{5-chloro-3-[4-(3-ethyl-1H-pyrazolo[3,4-d]pyrimidin-4-yl)piperazin-1-yl]-2-methylphenyl}-N,N',N'-trimethylethane-1,2-diamine |
| 83 | 3-({3-[4-(3-bromo-1H-pyrazolo[3,4-d]pyrimidin-4-yl)piperazin-1-yl]-5-chloro-2-methylphenyl}oxy)-N,N-diethylpropan-1-amine |
| 84 | 3-bromo-4-(4-{5-chloro-2-methyl-3-[(3-pyrrolidin-1-ylpropyl)oxy]phenyl}piperazin-1-yl)-1H-pyrazolo[3,4-d]pyrimidine |
| 85 | 3-bromo-4-[4-(5-chloro-2-methyl-3-{[3-(4-methylpiperazin-1-yl)propyl]oxy}phenyl)piperazin-1-yl]-1H-pyrazolo[3,4-d]pyrimidine |
| 86 | 3-bromo-4-[4-(5-chloro-3-{[3-(4-ethylpiperazin-1-yl)propyl]oxy}-2-methylphenyl)piperazin-1-yl]-1H-pyrazolo[3,4-d]pyrimidine |
| 87 | 3-(5-chloro-2-methyl-3-{4-[3-(trifluoromethyl)-1H-pyrazolo[3,4-d]pyrimidin-4-yl]piperazin-1-yl}phenyl)-N,N-diethylpropan-1-amine |
| 88 | 3-bromo-4-[4-(5-chloro-2-methyl-3-{[(1-methylpiperidin-4-yl)methyl]oxy}phenyl)piperazin-1-yl]-1H-pyrazolo[3,4-d]pyrimidine |

| Cmpd No. | Name |
|---|---|
| 89 | 3-bromo-4-[4-(5-chloro-2-methyl-3-{[2-(1-methylpiperidin-4-yl)ethyl]oxy}phenyl)piperazin-1-yl]-1H-pyrazolo[3,4-d]pyrimidine |
| 90 | 4-[4-(5-chloro-2-methyl-3-{[(1-methylpiperidin-4-yl)methyl]oxy}phenyl)piperazin-1-yl]-3-(trifluoromethyl)-1H-pyrazolo[3,4-d]pyrimidine |
| 91 | 4-[4-(5-chloro-2-methyl-3-{[2-(1-methylpiperidin-4-yl)ethyl]oxy}phenyl)piperazin-1-yl]-3-(trifluoromethyl)-1H-pyrazolo[3,4-d]pyrimidine |
| 92 | 4-(4-{5-chloro-2-methyl-3-[3-(4-methylpiperazin-1-yl)propyl]phenyl}piperazin-1-yl)-3-(trifluoromethyl)-1H-pyrazolo[3,4-d]pyrimidine |
| 93 | 3-bromo-4-[4-(3-chloro-4-fluorophenyl)piperazin-1-yl]-1H-pyrazolo[3,4-d]pyrimidine |
| 94 | 1-{4-[4-(3-bromo-1H-pyrazolo[3,4-d]pyrimidin-4-yl)piperazin-1-yl]phenyl}ethanone |
| 95 | 3-bromo-4-[4-(2,5-dichlorophenyl)piperazin-1-yl]-1H-pyrazolo[3,4-d]pyrimidine |
| 96 | 3-bromo-4-[4-(3,4-dimethylphenyl)piperazin-1-yl]-1H-pyrazolo[3,4-d]pyrimidine |
| 97 | 3-bromo-4-[4-(4-nitrophenyl)piperazin-1-yl]-1H-pyrazolo[3,4-d]pyrimidine |
| 98 | 3-ethyl-4-(4-phenylpiperazin-1-yl)-1H-pyrazolo[3,4-d]pyrimidine |
| 99 | 3-ethyl-4-{4-[3-(methyloxy)phenyl]piperazin-1-yl}-1H-pyrazolo[3,4-d]pyrimidine |
| 100 | 4-{4-[5-chloro-2-methyl-3-(3-piperidin-1-ylpropyl)phenyl]piperazin-1-yl}-3-(trifluoromethyl)-1H-pyrazolo[3,4-d]pyrimidine |
| 101 | 4-[4-(3,6-dimethylpyrazin-2-yl)piperazin-1-yl]-3-ethyl-1H-pyrazolo[3,4-d]pyrimidine |
| 102 | 1-[4-(3-ethyl-1H-pyrazolo[3,4-d]pyrimidin-4-yl)piperazin-1-yl]isoquinoline |
| 103 | 3-bromo-4-[4-(2,6-dimethylphenyl)piperazin-1-yl]-1H-pyrazolo[3,4-d]pyrimidine |
| 104 | 3-bromo-4-{4-[4-(ethyloxy)phenyl]piperazin-1-yl}-1H-pyrazolo[3,4-d]pyrimidine |
| 105 | 3-bromo-4-[4-(2-ethylphenyl)piperazin-1-yl]-1H-pyrazolo[3,4-d]pyrimidine |
| 106 | 4-{4-[2,4-bis(methyloxy)phenyl]piperazin-1-yl}-3-bromo-1H-pyrazolo[3,4-d]pyrimidine |
| 107 | 3-bromo-4-(4-pyrazin-2-ylpiperazin-1-yl)-1H-pyrazolo[3,4-d]pyrimidine |
| 108 | 3-bromo-4-(4-pyrimidin-2-ylpiperazin-1-yl)-1H-pyrazolo[3,4-d]pyrimidine |
| 109 | 4-[4-(3-bromo-1H-pyrazolo[3,4-d]pyrimidin-4-yl)piperazin-1-yl]-2-(trifluoromethyl)quinoline |
| 110 | 3-[4-(3-bromo-1H-pyrazolo[3,4-d]pyrimidin-4-yl)piperazin-1-yl]pyrazine-2-carbonitrile |
| 111 | 4-[4-(4,6-dimethylpyrimidin-2-yl)piperazin-1-yl]-3-ethyl-1H-pyrazolo[3,4-d]pyrimidine |
| 112 | ethyl 4-[4-(3-ethyl-1H-pyrazolo[3,4-d]pyrimidin-4-yl)piperazin-1-yl]-2-(trifluoromethyl)pyrimidine-5-carboxylate |
| 113 | 4-{4-[3-chloro-5-(methyloxy)phenyl]piperazin-1-yl}-3-ethyl-1H-pyrazolo[3,4-d]pyrimidine |
| 114 | 4-[4-(3-bromo-2-chloro-5-fluorophenyl)piperazin-1-yl]-3-ethyl-1H-pyrazolo[3,4-d]pyrimidine |
| 115 | 2-[4-(3-ethyl-1H-pyrazolo[3,4-d]pyrimidin-4-yl)piperazin-1-yl]pyridine-3-carboxamide |
| 116 | 3-ethyl-4-{4-[4-(trifluoromethyl)pyridin-2-yl]piperazin-1-yl}-1H-pyrazolo[3,4-d]pyrimidine |
| 117 | 3-bromo-4-{4-[4-(trifluoromethyl)pyridin-2-yl]piperazin-1-yl}-1H-pyrazolo[3,4-d]pyrimidine |
| 118 | 3-bromo-4-{4-[4-(trifluoromethyl)pyrimidin-2-yl]piperazin-1-yl}-1H-pyrazolo[3,4-d]pyrimidine |
| 119 | 2-({3-[4-(3-bromo-1H-pyrazolo[3,4-d]pyrimidin-4-yl)piperazin-1-yl]pyrazin-2-yl}oxy)-N,N-dimethylethanamine |
| 120 | 4-[4-(3-bromo-1H-pyrazolo[3,4-d]pyrimidin-4-yl)piperazin-1-yl]-2-methylquinoline |
| 121 | 3-bromo-4-[4-(2-nitrophenyl)piperazin-1-yl]-1H-pyrazolo[3,4-d]pyrimidine |
| 122 | 2-[4-(3-bromo-1H-pyrazolo[3,4-d]pyrimidin-4-yl)piperazin-1-yl]benzonitrile |
| 123 | 4-[4-(3-bromo-1H-pyrazolo[3,4-d]pyrimidin-4-yl)piperazin-1-yl]benzonitrile |
| 124 | 3-bromo-4-{4-[4-(trifluoromethyl)phenyl]piperazin-1-yl}-1H-pyrazolo[3,4-d]pyrimidine |
| 125 | 3-bromo-4-(4-{4-[(phenylmethyl)oxy]phenyl}piperazin-1-yl)-1H-pyrazolo[3,4-d]pyrimidine |
| 126 | 4-{4-[5-chloro-2-methyl-3-(methyloxy)phenyl]piperazin-1-yl}-3-ethyl-1H-pyrazolo[3,4-d]pyrimidine |
| 127 | 2-[4-(3-bromo-1H-pyrazolo[3,4-d]pyrimidin-4-yl)piperazin-1-yl]pyridine-3-carbonitrile |
| 128 | 3-bromo-4-[4-(3,5-dichlorophenyl)piperazin-1-yl]-1H-pyrazolo[3,4-d]pyrimidine |
| 129 | 3-[4-(3-bromo-1H-pyrazolo[3,4-d]pyrimidin-4-yl)piperazin-1-yl]-2-chloro-5-fluoro-N-(2-pyrrolidin-1-ylethyl)aniline |
| 130 | 2-chloro-3-[4-(3-ethyl-1H-pyrazolo[3,4-d]pyrimidin-4-yl)piperazin-1-yl]-5-fluoro-N-(2-pyrrolidin-1-ylethyl)aniline |
| 131 | 3-bromo-4-[4-(2,5-difluorophenyl)piperazin-1-yl]-1H-pyrazolo[3,4-d]pyrimidine |
| 132 | 4-[4-(2,5-difluorophenyl)piperazin-1-yl]-3-ethyl-1H-pyrazolo[3,4-d]pyrimidine |
| 133 | 3-bromo-4-{4-[3-(methyloxy)pyrazin-2-yl]piperazin-1-yl}-1H-pyrazolo[3,4-d]pyrimidine |
| 134 | 3-bromo-4-[4-(3-chlorophenyl)piperazin-1-yl]-1H-pyrazolo[3,4-d]pyrimidine |
| 135 | 3-bromo-4-{4-[3-(trifluoromethyl)pyridin-2-yl]piperazin-1-yl}-1H-pyrazolo[3,4-d]pyrimidine |
| 136 | 3-bromo-4-{4-[3-chloro-5-(trifluoromethyl)pyridin-2-yl]piperazin-1-yl}-1H-pyrazolo[3,4-d]pyrimidine |
| 137 | 4-(4-{5-chloro-2-methyl-3-[(2-pyrrolidin-1-ylethyl)oxy]phenyl}piperazin-1-yl)-3-(1-methylethyl)-1H-pyrazolo[3,4-d]pyrimidine |
| 138 | 5-chloro-2-methyl-3-{4-[3-(1-methylethyl)-1H-pyrazolo[3,4-d]pyrimidin-4-yl]piperazin-1-yl}-N-(2-pyrrolidin-1-ylethyl)aniline |
| 139 | 2-({3-[4-(3-bromo-1H-pyrazolo[3,4-d]pyrimidin-4-yl)piperazin-1-yl]phenyl}oxy)-N-ethylacetamide |
| 140 | 2-[4-(3-bromo-1H-pyrazolo[3,4-d]pyrimidin-4-yl)piperazin-1-yl]-N,N-diethylpyrimidin-4-amine |
| 141 | 3-bromo-4-[4-(3-{[(3-methylphenyl)methyl]oxy}phenyl)piperazin-1-yl]-1H-pyrazolo[3,4-d]pyrimidine |

| Cmpd No. | Name |
|---|---|
| 142 | 3-bromo-4-(4-{3-[(2-piperidin-1-ylethyl)oxy]phenyl}piperazin-1-yl)-1H-pyrazolo[3,4-d]pyrimidine |
| 143 | 3-bromo-4-[4-(4-furan-2-ylpyrimidin-2-yl)piperazin-1-yl]-1H-pyrazolo[3,4-d]pyrimidine |
| 144 | 6-{2-[4-(3-bromo-1H-pyrazolo[3,4-d]pyrimidin-4-yl)piperazin-1-yl]pyrimidin-4-yl}-2H-1,4-benzoxazin-3(4H)-one |
| 145 | 3-ethyl-4-{4-[2-methyl-3-(methyloxy)phenyl]piperazin-1-yl}-1H-pyrazolo[3,4-d]pyrimidine |
| 146 | N'-{5-chloro-3-[4-(3-ethyl-1H-pyrazolo[3,4-d]pyrimidin-4-yl)piperazin-1-yl]-2-methylphenyl}-N-methyl-N-(1-methylethyl)ethane-1,2-diamine |
| 147 | N'-{5-chloro-3-[4-(3-ethyl-1H-pyrazolo[3,4-d]pyrimidin-4-yl)piperazin-1-yl]-2-methylphenyl}-N-ethyl-N-methylethane-1,2-diamine |
| 148 | N'-{3-[4-(3-bromo-1H-pyrazolo[3,4-d]pyrimidin-4-yl)piperazin-1-yl]-5-chloro-2-methylphenyl}-N,N-dimethylethane-1,2-diamine |
| 149 | 3-({6-[4-(3-bromo-1H-pyrazolo[3,4-d]pyrimidin-4-yl)piperazin-1-yl]-2-chloro-5-methylpyrimidin-4-yl}oxy)-N,N-diethylpropan-1-amine |
| 150 | 3-bromo-4-[4-(2,3-dichlorophenyl)piperazin-1-yl]-1H-pyrazolo[3,4-d]pyrimidine |
| 151 | 3-bromo-4-{4-[2-(trifluoromethyl)phenyl]piperazin-1-yl}-1H-pyrazolo[3,4-d]pyrimidine |
| 152 | 3-bromo-4-(4-phenylpiperazin-1-yl)-1H-pyrazolo[3,4-d]pyrimidine |
| 153 | 3-bromo-4-[4-(4-fluorophenyl)piperazin-1-yl]-1H-pyrazolo[3,4-d]pyrimidine |
| 154 | 3-bromo-4-[4-(4-chlorophenyl)piperazin-1-yl]-1H-pyrazolo[3,4-d]pyrimidine |
| 155 | 3-bromo-4-{4-[3-(trifluoromethyl)phenyl]piperazin-1-yl}-1H-pyrazolo[3,4-d]pyrimidine |
| 156 | 4-[4-(5-chloro-2-methylphenyl)piperazin-1-yl]-1H-pyrazolo[3,4-d]pyrimidin-6-amine |
| 157 | 3-bromo-4-[4-(4-bromophenyl)piperazin-1-yl]-1H-pyrazolo[3,4-d]pyrimidine |
| 158 | 3-bromo-4-[3-methyl-4-(3-methylphenyl)piperazin-1-yl]-1H-pyrazolo[3,4-d]pyrimidine |
| 159 | 4-[4-(3-bromo-5-chloro-2-methylphenyl)piperazin-1-yl]-1H-pyrazolo[3,4-d]pyrimidin-6-amine |
| 160 | 4-(4-{5-chloro-2-methyl-3-[(2-pyrrolidin-1-ylethyl)oxy]phenyl}piperazin-1-yl)-3-cyclopropyl-1H-pyrazolo[3,4-d]pyrimidine |
| 161 | 5-chloro-3-[4-(3-cyclopropyl-1H-pyrazolo[3,4-d]pyrimidin-4-yl)piperazin-1-yl]-2-methyl-N-(2-pyrrolidin-1-ylethyl)aniline |
| 162 | 5-chloro-2-methyl-3-{4-[3-(2-methylpropyl)-1H-pyrazolo[3,4-d]pyrimidin-4-yl]piperazin-1-yl}-N-(2-pyrrolidin-1-ylethyl)aniline |
| 163 | 4-(4-{5-chloro-2-methyl-3-[(2-pyrrolidin-1-ylethyl)oxy]phenyl}piperazin-1-yl)-3-(2-methylpropyl)-1H-pyrazolo[3,4-d]pyrimidine |
| 164 | 3-bromo-4-[(3S)-4-(5-chloro-2-methylphenyl)-3-methylpiperazin-1-yl]-1H-pyrazolo[3,4-d]pyrimidine |
| 165 | 5-bromo-3-[4-(3-ethyl-1H-pyrazolo[3,4-d]pyrimidin-4-yl)piperazin-1-yl]-2-methylaniline |
| 166 | 2-({3-[4-(3-bromo-1H-pyrazolo[3,4-d]pyrimidin-4-yl)piperazin-1-yl]phenyl}oxy)-N-cyclopropylacetamide |
| 167 | 3-bromo-4-(4-{3-[(2-piperidin-1-ylethyl)oxy]pyrazin-2-yl}piperazin-1-yl)-1H-pyrazolo[3,4-d]pyrimidine |
| 168 | 4-[4-(3-ethyl-1H-pyrazolo[3,4-d]pyrimidin-4-yl)piperazin-1-yl]-6,7-bis(methyloxy)quinazoline |
| 169 | 2-({3-chloro-5-[4-(3-ethyl-1H-pyrazolo[3,4-d]pyrimidin-4-yl)piperazin-1-yl]phenyl}oxy)-N,N-diethylethanamine |
| 170 | 4-{4-[2-chloro-5-(trifluoromethyl)phenyl]piperazin-1-yl}-3-ethyl-1H-pyrazolo[3,4-d]pyrimidine |
| 171 | 3-[4-(3-ethyl-1H-pyrazolo[3,4-d]pyrimidin-4-yl)piperazin-1-yl]-2-methyl-5-[(2-methylpropyl)oxy]-N-(2-pyrrolidin-1-ylethyl)aniline |
| 172 | 3-({4-[4-(3-bromo-1H-pyrazolo[3,4-d]pyrimidin-4-yl)piperazin-1-yl]-6-chloro-5-methylpyrimidin-2-yl}oxy)-N,N-diethylpropan-1-amine |
| 173 | 3-[4-(3-ethyl-1H-pyrazolo[3,4-d]pyrimidin-4-yl)piperazin-1-yl]-2-methyl-5-[(phenylmethyl)oxy]-N-(2-pyrrolidin-1-ylethyl)aniline |
| 174 | 3-bromo-4-[(3R)-4-(5-chloro-2-methylphenyl)-3-methylpiperazin-1-yl]-1H-pyrazolo[3,4-d]pyrimidine |
| 175 | 3-[(2S)-4-(3-bromo-1H-pyrazolo[3,4-d]pyrimidin-4-yl)-2-methylpiperazin-1-yl]-4-methyl-N-phenylbenzamide |
| 176 | 3-[(2S)-4-(3-bromo-1H-pyrazolo[3,4-d]pyrimidin-4-yl)-2-methylpiperazin-1-yl]-4-methyl-N-(phenylmethyl)benzamide |
| 177 | methyl 3-[4-(3-bromo-1H-pyrazolo[3,4-d]pyrimidin-4-yl)piperazin-1-yl]-4-methylbenzoate |
| 178 | 3-[4-(3-bromo-1H-pyrazolo[3,4-d]pyrimidin-4-yl)piperazin-1-yl]-4-methylbenzoic acid |
| 179 | (2E)-3-(4-{4-[5-chloro-2-methyl-3-(3-pyrrolidin-1-ylpropyl)phenyl]piperazin-1-yl}-1H-pyrazolo[3,4-d]pyrimidin-3-yl)prop-2-enoic acid |
| 180 | 3-(4-{4-[5-chloro-2-methyl-3-(3-pyrrolidin-1-ylpropyl)phenyl]piperazin-1-yl}-1H-pyrazolo[3,4-d]pyrimidin-3-yl)prop-2-yn-1-ol |
| 181 | 4-(3-bromo-1H-pyrazolo[3,4-d]pyrimidin-4-yl)-1-(5-chloro-2-methylphenyl)piperazin-2-one |
| 182 | 3-[4-(3-bromo-1H-pyrazolo[3,4-d]pyrimidin-4-yl)piperazin-1-yl]-2-methyl-5-[(2-methylpropyl)oxy]-N-(2-pyrrolidin-1-ylethyl)aniline |
| 183 | N'-{3-[4-(3-bromo-1H-pyrazolo[3,4-d]pyrimidin-4-yl)piperazin-1-yl]-2-methyl-5-[(2-methylpropyl)oxy]phenyl}-N,N-diethylethane-1,2-diamine |
| 184 | methyl 3-bromo-5-[4-(3-bromo-1H-pyrazolo[3,4-d]pyrimidin-4-yl)piperazin-1-yl]-4-methylbenzoate |
| 185 | 3-[4-(3-bromo-1H-pyrazolo[3,4-d]pyrimidin-4-yl)piperazin-1-yl]-4-methyl-N-phenylbenzamide |
| 186 | 3-[4-(3-bromo-1H-pyrazolo[3,4-d]pyrimidin-4-yl)piperazin-1-yl]-N,4-dimethylbenzamide |
| 187 | 2-({3-[4-(3-bromo-1H-pyrazolo[3,4-d]pyrimidin-4-yl)piperazin-1-yl]phenyl}oxy)-N,N-diethylethanamine |

-continued

| Cmpd No. | Name |
|---|---|
| 188 | methyl 3-[4-(3-bromo-1H-pyrazolo[3,4-d]pyrimidin-4-yl)piperazin-1-yl]-4-methyl-5-[(2-pyrrolidin-1-ylethyl)amino]benzoate |
| 189 | 3-bromo-5-[4-(3-bromo-1H-pyrazolo[3,4-d]pyrimidin-4-yl)piperazin-1-yl]-4-methyl-N-phenylbenzamide |
| 190 | 3-bromo-5-[4-(3-ethyl-1H-pyrazolo[3,4-d]pyrimidin-4-yl)piperazin-1-yl]-4-methyl-N-phenylbenzamide |
| 191 | N'-{3-[4-(3-bromo-1H-pyrazolo[3,4-d]pyrimidin-4-yl)piperazin-1-yl]-5-chloro-2-methylphenyl}-N-methyl-N-(1-methylethyl)ethane-1,2-diamine |
| 192 | 3-[4-(3-bromo-1H-pyrazolo[3,4-d]pyrimidin-4-yl)piperazin-1-yl]-4-methyl-N-phenyl-5-[(2-pyrrolidin-1-ylethyl)amino]benzamide |
| 193 | N'-{3-[4-(3-bromo-1H-pyrazolo[3,4-d]pyrimidin-4-yl)piperazin-1-yl]-2-methyl-5-[(2-methylpropyl)oxy]phenyl}-N,N-dimethylethane-1,2-diamine |
| 194 | 3-[4-(3-bromo-1H-pyrazolo[3,4-d]pyrimidin-4-yl)piperazin-1-yl]-N,N,4-trimethylbenzamide |
| 195 | 3-[4-(3-chloro-1H-pyrazolo[3,4-d]pyrimidin-4-yl)piperazin-1-yl]-4-methyl-N-(2-methylpropyl)benzamide |
| 196 | 3-[4-(3-bromo-1H-pyrazolo[3,4-d]pyrimidin-4-yl)piperazin-1-yl]-N,N,4-trimethyl-5-[(2-pyrrolidin-1-ylethyl)amino]benzamide |
| 197 | 3-[4-(3-bromo-1H-pyrazolo[3,4-d]pyrimidin-4-yl)-2-oxopiperazin-1-yl]-4-methyl-N-phenylbenzamide |
| 198 | 3-[(2R)-4-(3-bromo-1H-pyrazolo[3,4-d]pyrimidin-4-yl)-2-(hydroxymethyl)piperazin-1-yl]-4-methyl-N-phenylbenzamide |
| 199 | 3-[4-(3-bromo-1H-pyrazolo[3,4-d]pyrimidin-4-yl)piperazin-1-yl]-2-methyl-5-(pyrrolidin-1-ylcarbonyl)-N-(2-pyrrolidin-1-ylethyl)aniline |
| 200 | 3-[4-(3-bromo-1H-pyrazolo[3,4-d]pyrimidin-4-yl)piperazin-1-yl]-N,4-dimethyl-5-[(2-pyrrolidin-1-ylethyl)amino]benzamide |
| 201 | 3-[4-(3-bromo-1H-pyrazolo[3,4-d]pyrimidin-4-yl)piperazin-1-yl]-N-(4-chlorophenyl)-4-methyl-5-[(2-pyrrolidin-1-ylethyl)amino]benzamide |
| 202 | 3-[4-(3-bromo-1H-pyrazolo[3,4-d]pyrimidin-4-yl)piperazin-1-yl]-N-(2-chlorophenyl)-4-methyl-5-[(2-pyrrolidin-1-ylethyl)amino]benzamide |
| 203 | 3-[4-(3-bromo-1H-pyrazolo[3,4-d]pyrimidin-4-yl)piperazin-1-yl]-5-[(cyclopropylmethyl)oxy]-2-methyl-N-(2-pyrrolidin-1-ylethyl)aniline |
| 204 | 3-[4-(3-bromo-1H-pyrazolo[3,4-d]pyrimidin-4-yl)piperazin-1-yl]-2-methyl-5-[(3-methylbutyl)oxy]-N-(2-pyrrolidin-1-ylethyl)aniline |
| 205 | 3-[4-(3-bromo-1H-pyrazolo[3,4-d]pyrimidin-4-yl)piperazin-1-yl]-5-[(2-ethylbutyl)oxy]-2-methyl-N-(2-pyrrolidin-1-ylethyl)aniline |
| 206 | 3-[4-(3-bromo-1H-pyrazolo[3,4-d]pyrimidin-4-yl)piperazin-1-yl]-5-(butyloxy)-2-methyl-N-(2-pyrrolidin-1-ylethyl)aniline |
| 207 | 3-[4-(3-bromo-1H-pyrazolo[3,4-d]pyrimidin-4-yl)piperazin-1-yl]-4-methyl-N-(1-methylethyl)-5-[(2-pyrrolidin-1-ylethyl)amino]benzamide |
| 208 | 3-[4-(3-bromo-1H-pyrazolo[3,4-d]pyrimidin-4-yl)piperazin-1-yl]-N,4-dimethyl-N-(1-methylethyl)-5-[(2-pyrrolidin-1-ylethyl)amino]benzamide |
| 209 | 3-[4-(3-bromo-1H-pyrazolo[3,4-d]pyrimidin-4-yl)piperazin-1-yl]-5-[(cyclobutylmethyl)oxy]-2-methyl-N-(2-pyrrolidin-1-ylethyl)aniline |
| 210 | 3-[4-(3-bromo-1H-pyrazolo[3,4-d]pyrimidin-4-yl)piperazin-1-yl]-5-(ethyloxy)-2-methyl-N-(2-pyrrolidin-1-ylethyl)aniline |
| 211 | 3-[4-(3-bromo-1H-pyrazolo[3,4-d]pyrimidin-4-yl)piperazin-1-yl]-N-[2-(dimethylamino)ethyl]-4-methylbenzamide |
| 212 | 3-[4-(3-bromo-1H-pyrazolo[3,4-d]pyrimidin-4-yl)piperazin-1-yl]-N-(1,1-dimethylethyl)-4-methyl-5-[(2-pyrrolidin-1-ylethyl)amino]benzamide |
| 213 | 3-[4-(3-bromo-1H-pyrazolo[3,4-d]pyrimidin-4-yl)piperazin-1-yl]-4-methyl-N-pyridin-3-yl-5-[(2-pyrrolidin-1-ylethyl)amino]benzamide |
| 214 | 3-[4-(3-bromo-1H-pyrazolo[3,4-d]pyrimidin-4-yl)piperazin-1-yl]-5-[(2-fluoro-2-methylpropyl)oxy]-2-methyl-N-(2-pyrrolidin-1-ylethyl)aniline |
| 215 | 3-[4-(3-bromo-1H-pyrazolo[3,4-d]pyrimidin-4-yl)piperazin-1-yl]-5-[(cyclohexylmethyl)oxy]-2-methyl-N-(2-pyrrolidin-1-ylethyl)aniline |
| 216 | 3-[4-(3-bromo-1H-pyrazolo[3,4-d]pyrimidin-4-yl)piperazin-1-yl]-5-[(cyclopentylmethyl)oxy]-2-methyl-N-(2-pyrrolidin-1-ylethyl)aniline |
| 217 | 3-[4-(3-bromo-1H-pyrazolo[3,4-d]pyrimidin-4-yl)piperazin-1-yl]-N-ethyl-4-methyl-5-[(2-pyrrolidin-1-ylethyl)amino]benzamide |
| 218 | 3-[4-(3-bromo-1H-pyrazolo[3,4-d]pyrimidin-4-yl)piperazin-1-yl]-2-methyl-5-[(1-methylethyl)oxy]-N-(2-pyrrolidin-1-ylethyl)aniline |
| 219 | 3-[4-(3-bromo-1H-pyrazolo[3,4-d]pyrimidin-4-yl)piperazin-1-yl]-5-[(2,2-dimethylpropyl)oxy]-2-methyl-N-(2-pyrrolidin-1-ylethyl)aniline |
| 220 | 3-[4-(3-bromo-1H-pyrazolo[3,4-d]pyrimidin-4-yl)piperazin-1-yl]-2-methyl-N-(2-pyrrolidin-1-ylethyl)-5-[(tetrahydrofuran-2-ylmethyl)oxy]aniline |
| 221 | 3-[4-(3-bromo-1H-pyrazolo[3,4-d]pyrimidin-4-yl)piperazin-1-yl]-2-methyl-5-{[2-(methyloxy)ethyl]oxy}-N-(2-pyrrolidin-1-ylethyl)aniline |
| 222 | 3-[4-(3-bromo-1H-pyrazolo[3,4-d]pyrimidin-4-yl)piperazin-1-yl]-2-methyl-5-(propyloxy)-N-(2-pyrrolidin-1-ylethyl)aniline |
| 223 | 3-[4-(3-bromo-1H-pyrazolo[3,4-d]pyrimidin-4-yl)piperazin-1-yl]-5-{[2-(dimethylamino)ethyl]amino}-4-methyl-N-phenylbenzamide |
| 224 | N'-{3-[4-(3-bromo-1H-pyrazolo[3,4-d]pyrimidin-4-yl)piperazin-1-yl]-5-[(2-fluoro-2-methylpropyl)oxy]-2-methylphenyl}-N,N-dimethylethane-1,2-diamine |
| 225 | 3-[4-(3-bromo-1H-pyrazolo[3,4-d]pyrimidin-4-yl)piperazin-1-yl]-5-{[2-(dimethylamino)ethyl]amino}-4-methyl-N-(1-methylethyl)benzamide |
| 226 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}pentan-1-one |

| Cmpd No. | Name |
|---|---|
| 227 | N'-(3-[4-(3-bromo-1H-pyrazolo[3,4-d]pyrimidin-4-yl)piperazin-1-yl]-5-{[2,3-difluoro-2-(fluoromethyl)propyl]oxy}-2-methylphenyl)-N,N-dimethylethane-1,2-diamine |
| 228 | 3-[4-(3-bromo-1H-pyrazolo[3,4-d]pyrimidin-4-yl)piperazin-1-yl]-5-{[2,3-difluoro-2-(fluoromethyl)propyl]oxy}-2-methyl-N-(2-pyrrolidin-1-ylethyl)aniline |
| 229 | 5-[4-(3-bromo-1H-pyrazolo[3,4-d]pyrimidin-4-yl)piperazin-1-yl]-4-methyl-N-(2-pyrrolidin-1-ylethyl)biphenyl-3-amine |
| 230 | 1-(3-{5-[4-(3-bromo-1H-pyrazolo[3,4-d]pyrimidin-4-yl)piperazin-1-yl]-4-methylbiphenyl-3-yl}propyl)pyridinium |
| 231 | 3-[4-(3-bromo-1H-pyrazolo[3,4-d]pyrimidin-4-yl)piperazin-1-yl]-2-methyl-N-(2-pyrrolidin-1-ylethyl)-5-(1,3-thiazol-2-yl)aniline |
| 232 | 3-[4-(3-bromo-1H-pyrazolo[3,4-d]pyrimidin-4-yl)piperazin-1-yl]-4-methyl-5-[(2-pyrrolidin-1-ylethyl)amino]benzoic acid |
| 233 | 3-[4-(3-bromo-1H-pyrazolo[3,4-d]pyrimidin-4-yl)piperazin-1-yl]-2-methyl-5-(phenylethynyl)-N-(2-pyrrolidin-1-ylethyl)aniline |
| 234 | {3-[4-(3-bromo-1H-pyrazolo[3,4-d]pyrimidin-4-yl)piperazin-1-yl]-4-methyl-5-[(2-pyrrolidin-1-ylethyl)amino]phenyl}(phenyl)methanone |
| 235 | 3-[4-(3-bromo-1H-pyrazolo[3,4-d]pyrimidin-4-yl)piperazin-1-yl]-5-ethynyl-2-methyl-N-(2-pyrrolidin-1-ylethyl)aniline |
| 236 | 3-[4-(3-bromo-1H-pyrazolo[3,4-d]pyrimidin-4-yl)piperazin-1-yl]-5-(3,3-dimethylbut-1-yn-1-yl)-2-methyl-N-(2-pyrrolidin-1-ylethyl)aniline |
| 237 | 3-bromo-4-{4-[5-{[2,3-difluoro-2-(fluoromethyl)propyl]oxy}-2-methyl-3-(3-pyrrolidin-1-ylpropyl)phenyl]piperazin-1-yl}-1H-pyrazolo[3,4-d]pyrimidine |
| 238 | 3-bromo-4-{4-[2-methyl-5-[(2-methylpropyl)oxy]-3-(3-pyrrolidin-1-ylpropyl)phenyl]piperazin-1-yl}-1H-pyrazolo[3,4-d]pyrimidine |
| 239 | 3-[4-(3-bromo-1H-pyrazolo[3,4-d]pyrimidin-4-yl)piperazin-1-yl]-2-methyl-5-(3-phenyl-1,2,4-oxadiazol-5-yl)-N-(2-pyrrolidin-1-ylethyl)aniline |
| 240 | 3-[4-(3-bromo-1H-pyrazolo[3,4-d]pyrimidin-4-yl)piperazin-1-yl]-2-methyl-5-(3-methyl-1,2,4-oxadiazol-5-yl)-N-(2-pyrrolidin-1-ylethyl)aniline |
| 241 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}propan-1-one |
| 242 | 3-[4-(3-bromo-1H-pyrazolo[3,4-d]pyrimidin-4-yl)piperazin-1-yl]-5-(3,3-dimethylbutyl)-2-methyl-N-(2-pyrrolidin-1-ylethyl)aniline |
| 243 | 3-[4-(3-bromo-1H-pyrazolo[3,4-d]pyrimidin-4-yl)piperazin-1-yl]-5-ethyl-2-methyl-N-(2-pyrrolidin-1-ylethyl)aniline |
| 244 | 3-[4-(3-bromo-1H-pyrazolo[3,4-d]pyrimidin-4-yl)piperazin-1-yl]-2-methyl-N-(2-pyrrolidin-1-ylethyl)-5-[2-(trimethylsilyl)ethyl]aniline |
| 245 | 3-[4-(3-bromo-1H-pyrazolo[3,4-d]pyrimidin-4-yl)piperazin-1-yl]-2-methyl-5-(2-phenylethyl)-N-(2-pyrrolidin-1-ylethyl)aniline |
| 246 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}butan-1-one |
| 247 | 3-[4-(3-bromo-1H-pyrazolo[3,4-d]pyrimidin-4-yl)piperazin-1-yl]-N,4-dimethyl-N-(methyloxy)-5-[(2-pyrrolidin-1-ylethyl)amino]benzamide |
| 248 | 3-bromo-4-[4-(3-bromo-5-{[2,3-difluoro-2-(fluoromethyl)propyl]oxy}-2-methylphenyl)piperazin-1-yl]-1H-pyrazolo[3,4-d]pyrimidine |
| 249 | 4-[4-(3-bromo-5-{[2,3-difluoro-2-(fluoromethyl)propyl]oxy}-2-methylphenyl)piperazin-1-yl]-3-ethyl-1H-pyrazolo[3,4-d]pyrimidine |
| 250 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}ethanone |
| 251 | 3-[4-(3-bromo-1H-pyrazolo[3,4-d]pyrimidin-4-yl)piperazin-1-yl]-5-[(difluoromethyl)oxy]-2-methyl-N-(2-pyrrolidin-1-ylethyl)aniline |
| 252 | 3-[4-(3-bromo-1H-pyrazolo[3,4-d]pyrimidin-4-yl)piperazin-1-yl]-5-{[(difluoromethyl)oxy]methyl}-2-methyl-N-(2-pyrrolidin-1-ylethyl)aniline |
| 253 | 3-[4-(3-bromo-1H-pyrazolo[3,4-d]pyrimidin-4-yl)piperazin-1-yl]-2-methyl-5-(methyloxy)-N-(2-pyrrolidin-1-ylethyl)aniline |
| 254 | 5-{[2,3-difluoro-2-(fluoromethyl)propyl]oxy}-3-[4-(3-ethyl-1H-pyrazolo[3,4-d]pyrimidin-4-yl)piperazin-1-yl]-2-methyl-N-(2-pyrrolidin-1-ylethyl)aniline |
| 255 | 2-[4-(3-bromo-1H-pyrazolo[3,4-d]pyrimidin-4-yl)piperazin-1-yl]-3,5,6-trifluoro-N-(3-methylbutyl)pyridin-4-amine |
| 256 | 3-[4-(3-bromo-1H-pyrazolo[3,4-d]pyrimidin-4-yl)piperazin-1-yl]-N-[(cyclopropylmethyl)oxy]-4-methyl-5-[(2-pyrrolidin-1-ylethyl)amino]benzamide |
| 257 | 3-[4-(3-bromo-1H-pyrazolo[3,4-d]pyrimidin-4-yl)piperazin-1-yl]-2-methyl-5-(5-methyl-1,2,4-oxadiazol-3-yl)-N-(2-pyrrolidin-1-ylethyl)aniline |
| 258 | 3-[4-(3-bromo-1H-pyrazolo[3,4-d]pyrimidin-4-yl)piperazin-1-yl]-5-(ethylsulfonyl)-2-methyl-N-(2-pyrrolidin-1-ylethyl)aniline |
| 259 | 3-[4-(3-bromo-1H-pyrazolo[3,4-d]pyrimidin-4-yl)piperazin-1-yl]-2-methyl-5-(methylsulfonyl)-N-(2-pyrrolidin-1-ylethyl)aniline |
| 260 | 1-{3-[4-(3-ethyl-1H-pyrazolo[3,4-d]pyrimidin-4-yl)piperazin-1-yl]-4-methyl-5-[(2-pyrrolidin-1-ylethyl)amino]phenyl}pentan-1-one |
| 261 | 3-bromo-4-[4-(5-{[2,3-difluoro-2-(fluoromethyl)propyl]oxy}-2-methylphenyl)piperazin-1-yl]-1H-pyrazolo[3,4-d]pyrimidine |
| 262 | 6-[4-(3-bromo-1H-pyrazolo[3,4-d]pyrimidin-4-yl)piperazin-1-yl]-3,5-difluoro-N~4~-(3-methylbutyl)-N~2~-(2-pyrrolidin-1-ylethyl)pyridine-2,4-diamine |
| 263 | 3-bromo-5-[4-(3-bromo-1H-pyrazolo[3,4-d]pyrimidin-4-yl)piperazin-1-yl]-N-(2-pyrrolidin-1-ylethyl)aniline |
| 264 | 3-bromo-4-[4-(3',4',6-trifluoro-4-methylbiphenyl-3-yl)piperazin-1-yl]-1H-pyrazolo[3,4-d]pyrimidine |
| 265 | 3-[4-(3-bromo-1H-pyrazolo[3,4-d]pyrimidin-4-yl)piperazin-1-yl]-5-chloro-N-(2-pyrrolidin-1-ylethyl)aniline |

| Cmpd No. | Name |
|---|---|
| 266 | {3-[4-(3-bromo-1H-pyrazolo[3,4-d]pyrimidin-4-yl)piperazin-1-yl]-4-methyl-5-[(2-pyrrolidin-1-ylethyl)amino]phenyl}methanol |
| 267 | 3-bromo-4-(4-{4-methyl-2'-[(2-pyrrolidin-1-ylethyl)oxy]biphenyl-3-yl}piperazin-1-yl)-1H-pyrazolo[3,4-d]pyrimidine |
| 268 | 3-[4-(3-bromo-1H-pyrazolo[3,4-d]pyrimidin-4-yl)piperazin-1-yl]-5-{[(2,2-difluorocyclopropyl)methyl]oxy}-2-methyl-N-(2-pyrrolidin-1-ylethyl)aniline |
| 269 | 5-bromo-3-[4-(3-bromo-1H-pyrazolo[3,4-d]pyrimidin-4-yl)piperazin-1-yl]-2-methyl-N-(2-pyrrolidin-1-ylethyl)aniline |
| 270 | 3-[4-(3-bromo-1H-pyrazolo[3,4-d]pyrimidin-4-yl)piperazin-1-yl]-5-[(ethyloxy)methyl]-2-methyl-N-(2-pyrrolidin-1-ylethyl)aniline |
| 271 | 3-[4-[4-(3-bromo-1H-pyrazolo[3,4-d]pyrimidin-4-yl)piperazin-1-yl]-1-methyl-6-(trifluoromethyl)-1H-benzimidazol-2-yl]propan-1-ol |
| 272 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}-4,4,4-trifluorobutan-1-one |
| 273 | {3-[4-(3-bromo-1H-pyrazolo[3,4-d]pyrimidin-4-yl)piperazin-1-yl]-4-methyl-5-[(2-pyrrolidin-1-ylethyl)amino]phenyl}(cyclopropyl)methanone |
| 274 | 3-({3'-[4-(3-bromo-1H-pyrazolo[3,4-d]pyrimidin-4-yl)piperazin-1-yl]-4'-methylbiphenyl-2-yl}oxy)-N,N-dimethylpropan-1-amine |
| 275 | 3-[4-(3-bromo-1H-pyrazolo[3,4-d]pyrimidin-4-yl)piperazin-1-yl]-5-(1,1-difluorobutyl)-2-methyl-N-(2-pyrrolidin-1-ylethyl)aniline |
| 276 | 3-bromo-4-(4-{4-methyl-2'-[(3-morpholin-4-ylpropyl)oxy]biphenyl-3-yl}piperazin-1-yl)-1H-pyrazolo[3,4-d]pyrimidine |
| 277 | 3-bromo-4-(4-{4-methyl-2'-[(2-morpholin-4-ylethyl)oxy]biphenyl-3-yl}piperazin-1-yl)-1H-pyrazolo[3,4-d]pyrimidine |
| 278 | 3-[4-(3-bromo-1H-pyrazolo[3,4-d]pyrimidin-4-yl)piperazin-1-yl]-2-methyl-N-(2-pyrrolidin-1-ylethyl)-5-{[(2,2,2-trifluoroethyl)oxy]methyl}aniline |
| 279 | 1-[2-({3'-[4-(3-bromo-1H-pyrazolo[3,4-d]pyrimidin-4-yl)piperazin-1-yl]-4'-methylbiphenyl-2-yl}oxy)ethyl]pyrrolidine-2,5-dione |
| 280 | 3-bromo-4-(4-{3'-fluoro-4-methyl-2'-[(2-pyrrolidin-1-ylethyl)oxy]biphenyl-3-yl}piperazin-1-yl)-1H-pyrazolo[3,4-d]pyrimidine |
| 281 | 1-{3-[4-(3-bromo-1H-pyrazolo[3,4-d]pyrimidin-4-yl)piperazin-1-yl]-5-[(2-pyrrolidin-1-ylethyl)amino]phenyl}butan-1-one |
| 282 | 3-[4-(3-bromo-1H-pyrazolo[3,4-d]pyrimidin-4-yl)piperazin-1-yl]-2-methyl-N-(2-pyrrolidin-1-ylethyl)-5-[(3,3,3-trifluoropropyl)oxy]aniline |
| 283 | 3-[4-(3-bromo-1H-pyrazolo[3,4-d]pyrimidin-4-yl)piperazin-1-yl]-2-methyl-N-(2-pyrrolidin-1-ylethyl)-5-[(2,2,2-trifluoroethyl)oxy]aniline |
| 284 | 1-{3-[4-(3-bromo-1H-pyrazolo[3,4-d]pyrimidin-4-yl)piperazin-1-yl]-4-methyl-5-[(2-pyrrolidin-1-ylethyl)amino]phenyl}butan-1-ol |
| 285 | 3-bromo-4-(4-{4-chloro-2'-[(2-pyrrolidin-1-ylethyl)oxy]biphenyl-3-yl}piperazin-1-yl)-1H-pyrazolo[3,4-d]pyrimidine |
| 286 | 3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-yn-1-ol |
| 287 | 3-bromo-4-(4-{4-chloro-4'-fluoro-2'-[(2-pyrrolidin-1-ylethyl)oxy]biphenyl-3-yl}piperazin-1-yl)-1H-pyrazolo[3,4-d]pyrimidine |
| 288 | 3-bromo-4-(4-{4-methyl-3'-[(2-pyrrolidin-1-ylethyl)oxy]biphenyl-3-yl}piperazin-1-yl)-1H-pyrazolo[3,4-d]pyrimidine |
| 289 | (2E)-3-[4-(4-{5-{[2,3-difluoro-2-(fluoromethyl)propyl]oxy}-2-methyl-3-[(2-pyrrolidin-1-ylethyl)amino]phenyl}piperazin-1-yl)-1H-pyrazolo[3,4-d]pyrimidin-3-yl]prop-2-enoic acid |
| 290 | 3-[4-(3-bromo-1H-pyrazolo[3,4-d]pyrimidin-4-yl)piperazin-1-yl]-2-methyl-N-(2-pyrrolidin-1-ylethyl)-5-[4,4,4-trifluoro-1,1-bis(methyloxy)butyl]aniline |
| 291 | 6-(4-phenylpiperazin-1-yl)-9H-purine |
| 292 | 6-[4-(3-chlorophenyl)piperazin-1-yl]-9H-purine |
| 293 | 4-(4-phenylpiperazin-1-yl)-7H-pyrrolo[2,3-d]pyrimidine |
| 294 | 4-[4-(3-chlorophenyl)piperazin-1-yl]-7H-pyrrolo[2,3-d]pyrimidine |
| 295 | 4-(4-phenylpiperazin-1-yl)-1H-pyrazolo[3,4-d]pyrimidine |
| 296 | 4-[4-(3-chlorophenyl)piperazin-1-yl]-1H-pyrazolo[3,4-d]pyrimidine |
| 297 | 6-[4-(2-chlorophenyl)piperazin-1-yl]-9H-purine |
| 298 | 6-[4-(2-fluorophenyl)piperazin-1-yl]-9H-purine |
| 299 | 4-[4-(2-methylphenyl)piperazin-1-yl]-7H-pyrrolo[2,3-d]pyrimidine |
| 300 | 4-{4-[2-(methyloxy)phenyl]piperazin-1-yl}-7H-pyrrolo[2,3-d]pyrimidine |
| 301 | 4-{4-[3-(methyloxy)phenyl]piperazin-1-yl}-7H-pyrrolo[2,3-d]pyrimidine |
| 302 | 4-{4-[4-(methyloxy)phenyl]piperazin-1-yl}-7H-pyrrolo[2,3-d]pyrimidine |
| 303 | 4-{4-[3-(trifluoromethyl)phenyl]piperazin-1-yl}-7H-pyrrolo[2,3-d]pyrimidine |
| 304 | 6-{4-[4-(methyloxy)phenyl]piperazin-1-yl}-9H-purine |
| 305 | 6-{4-[2-(methyloxy)phenyl]piperazin-1-yl}-9H-purine |
| 306 | 6-[4-(4-chlorophenyl)piperazin-1-yl]-9H-purine |
| 307 | 6-[4-(4-fluorophenyl)piperazin-1-yl]-9H-purine |
| 308 | 4-[4-(4-chlorophenyl)piperazin-1-yl]-7H-pyrrolo[2,3-d]pyrimidine |
| 309 | 4-[4-(2-chlorophenyl)piperazin-1-yl]-7H-pyrrolo[2,3-d]pyrimidine |
| 310 | 4-[4-(4-fluorophenyl)piperazin-1-yl]-7H-pyrrolo[2,3-d]pyrimidine |
| 311 | 4-[4-(2-fluorophenyl)piperazin-1-yl]-7H-pyrrolo[2,3-d]pyrimidine |
| 312 | 6-{4-[3-(trifluoromethyl)phenyl]piperazin-1-yl}-9H-purine |
| 313 | 6-[4-(2-methylphenyl)piperazin-1-yl]-9H-purine |
| 314 | 4-{4-[3-(trifluoromethyl)phenyl]piperazin-1-yl}-1H-pyrazolo[3,4-d]pyrimidine |
| 315 | 4-[4-(2-methylphenyl)piperazin-1-yl]-1H-pyrazolo[3,4-d]pyrimidine |
| 316 | 4-[4-(3-chlorophenyl)piperazin-1-yl]-3-methyl-1H-pyrazolo[3,4-d]pyrimidine |
| 317 | 3-methyl-4-[4-(2-methylphenyl)piperazin-1-yl]-1H-pyrazolo[3,4-d]pyrimidine |
| 318 | 4-[4-(5-chloro-2-methylphenyl)piperazin-1-yl]-1H-pyrazolo[3,4-d]pyrimidine |

| Cmpd No. | Name |
|---|---|
| 319 | 4-[4-(5-chloro-2-methylphenyl)piperazin-1-yl]-3-methyl-1H-pyrazolo[3,4-d]pyrimidine |
| 320 | 4-[4-(5-chloro-2-methylphenyl)piperazin-1-yl]-3-methyl-6-phenyl-1H-pyrazolo[3,4-d]pyrimidine |
| 321 | 4-[4-(5-chloro-2-methylphenyl)piperazin-1-yl]-3-ethyl-1H-pyrazolo[3,4-d]pyrimidine |
| 322 | 4-[4-(5-chloro-2-methylphenyl)piperazin-1-yl]-6-methyl-1H-pyrazolo[3,4-d]pyrimidine |
| 323 | 4-[4-(5-chloro-2-methylphenyl)piperazin-1-yl]-6-ethyl-1H-pyrazolo[3,4-d]pyrimidine |
| 324 | 4-[4-(5-chloro-2-methylphenyl)piperazin-1-yl]-6-(1-methylethyl)-1H-pyrazolo[3,4-d]pyrimidine |
| 325 | 4-[4-(5-chloro-2-methylphenyl)piperazin-1-yl]-3-phenyl-1H-pyrazolo[3,4-d]pyrimidine |
| 326 | 4-[4-(5-chloro-2-methylphenyl)piperazin-1-yl]-3-({[2-(methyloxy)ethyl]oxy}methyl)-1H-pyrazolo[3,4-d]pyrimidine |
| 327 | 3-bromo-4-[4-(5-chloro-2-methylphenyl)piperazin-1-yl]-1H-pyrazolo[3,4-d]pyrimidine |
| 328 | 4-[4-(5-chloro-2-methylphenyl)piperazin-1-yl]-3-propyl-1H-pyrazolo[3,4-d]pyrimidine |
| 329 | 4-{4-[4-(5-chloro-2-methylphenyl)piperazin-1-yl]-1H-pyrazolo[3,4-d]pyrimidin-3-yl}phenol |
| 330 | 4-[4-(5-chloro-2-methylphenyl)piperazin-1-yl]-N-phenyl-1H-pyrazolo[3,4-d]pyrimidin-3-amine |
| 331 | 4-[4-(3-chlorophenyl)piperazin-1-yl]-3-ethyl-1H-pyrazolo[3,4-d]pyrimidine |
| 332 | 4-{4-[5-chloro-2-(methyloxy)phenyl]piperazin-1-yl}-3-ethyl-1H-pyrazolo[3,4-d]pyrimidine |
| 333 | 3-{4-[4-(5-chloro-2-methylphenyl)piperazin-1-yl]-1H-pyrazolo[3,4-d]pyrimidin-3-yl}phenol |
| 334 | 4-[4-(5-chloro-2-methylphenyl)piperazin-1-yl]-3-{3-[(phenylmethyl)oxy]phenyl}-1H-pyrazolo[3,4-d]pyrimidine |
| 335 | 3-(1,3-benzodioxol-5-yl)-4-[4-(5-chloro-2-methylphenyl)piperazin-1-yl]-1H-pyrazolo[3,4-d]pyrimidine |
| 336 | 4-[4-(5-chloro-2-methylphenyl)piperazin-1-yl]-3-(2-thienyl)-1H-pyrazolo[3,4-d]pyrimidine |
| 337 | 3-{4-[4-(5-chloro-2-methylphenyl)piperazin-1-yl]-1H-pyrazolo[3,4-d]pyrimidin-3-yl}aniline |
| 338 | 3-{4-[4-(5-chloro-2-methylphenyl)piperazin-1-yl]-1H-pyrazolo[3,4-d]pyrimidin-3-yl}benzoic acid |
| 339 | 4-[4-(5-chloro-2-methylphenyl)piperazin-1-yl]-3-(4-methylphenyl)-1H-pyrazolo[3,4-d]pyrimidine |
| 340 | N-(4-{4-[4-(5-chloro-2-methylphenyl)piperazin-1-yl]-1H-pyrazolo[3,4-d]pyrimidin-3-yl}phenyl)acetamide |
| 341 | 4-[4-(3-chlorophenyl)-1,4-diazepan-1-yl]-3-ethyl-1H-pyrazolo[3,4-d]pyrimidine |
| 342 | 4-[5-(3-chlorophenyl)-2,5-diazabicyclo[2.2.1]hept-2-yl]-3-ethyl-1H-pyrazolo[3,4-d]pyrimidine |
| 343 | 4-(4-{3-chloro-4-[(2-morpholin-4-ylethyl)oxy]phenyl}piperazin-1-yl)-3-ethyl-1H-pyrazolo[3,4-d]pyrimidine |
| 344 | methyl 1-(3-chlorophenyl)-4-(3-ethyl-1H-pyrazolo[3,4-d]pyrimidin-4-yl)piperazine-2-carboxylate |
| 345 | 4-[4-(5-chloro-2-methylphenyl)piperazin-1-yl]-3-(3-methylbut-2-en-1-yl)-1H-pyrazolo[3,4-d]pyrimidine |
| 346 | 4-[4-(5-chloro-2-methylphenyl)piperazin-1-yl]-3-(trifluoromethyl)-1H-pyrazolo[3,4-d]pyrimidine |
| 347 | methyl 4-(3-chlorophenyl)-1-(3-ethyl-1H-pyrazolo[3,4-d]pyrimidin-4-yl)piperazine-2-carboxylate |
| 348 | 4-(4-{3-chloro-4-[(2-piperidin-1-ylethyl)oxy]phenyl}piperazin-1-yl)-3-ethyl-1H-pyrazolo[3,4-d]pyrimidine |
| 349 | 4-[4-(5-chloro-2-methylphenyl)piperazin-1-yl]-3-(1-methylethyl)-1H-pyrazolo[3,4-d]pyrimidine |
| 350 | 1-(3-chlorophenyl)-4-(3-ethyl-1H-pyrazolo[3,4-d]pyrimidin-4-yl)piperazine-2-carboxylic acid |
| 351 | 1-(3-chlorophenyl)-4-(3-ethyl-1H-pyrazolo[3,4-d]pyrimidin-4-yl)-N-methylpiperazine-2-carboxamide |
| 352 | 4-[4-(5-chloro-2-methylphenyl)piperazin-1-yl]-3-(phenylmethyl)-1H-pyrazolo[3,4-d]pyrimidine |
| 353 | 4-[4-(5-chloro-2-methylphenyl)piperazin-1-yl]-3-(2-methylpropyl)-1H-pyrazolo[3,4-d]pyrimidine |
| 354 | 4-[4-(5-chloro-2-methylphenyl)piperazin-1-yl]-3-[4-(methyloxy)phenyl]-1H-pyrazolo[3,4-d]pyrimidine |
| 355 | 4-[4-(5-chloro-2-methylphenyl)piperazin-1-yl]-3-(4-fluorophenyl)-1H-pyrazolo[3,4-d]pyrimidine |
| 356 | 4-[4-(5-chloro-2-methylphenyl)piperazin-1-yl]-3-[4-(phenyloxy)phenyl]-1H-pyrazolo[3,4-d]pyrimidine |
| 357 | 4-[4-(5-chloro-2-methylphenyl)piperazin-1-yl]-3-{4-[(piperidin-4-ylmethyl)oxy]phenyl}-1H-pyrazolo[3,4-d]pyrimidine |
| 358 | 1-(3-chlorophenyl)-N-[2-(dimethylamino)ethyl]-4-(3-ethyl-1H-pyrazolo[3,4-d]pyrimidin-4-yl)piperazine-2-carboxamide |
| 359 | 4-[4-(5-chloro-2-methyl-3-morpholin-4-ylphenyl)piperazin-1-yl]-3-ethyl-1H-pyrazolo[3,4-d]pyrimidine |
| 360 | 4-(3-chlorophenyl)-1-(3-ethyl-1H-pyrazolo[3,4-d]pyrimidin-4-yl)-N-methylpiperazine-2-carboxamide |
| 361 | 4-[4-(5-chloro-2-methylphenyl)piperazin-1-yl]-3-[2-(methyloxy)phenyl]-1H-pyrazolo[3,4-d]pyrimidine |
| 362 | 4-[4-(5-chloro-2-methylphenyl)piperazin-1-yl]-3-pyridin-4-yl-1H-pyrazolo[3,4-d]pyrimidine |

| Cmpd No. | Name |
| --- | --- |
| 363 | 4-[4-(5-chloro-2-methylphenyl)piperazin-1-yl]-3-[3-(methyloxy)phenyl]-1H-pyrazolo[3,4-d]pyrimidine |
| 364 | 4-{4-[4-(5-chloro-2-methylphenyl)piperazin-1-yl]-1H-pyrazolo[3,4-d]pyrimidin-3-yl}benzonitrile |
| 365 | [5-chloro-3-[4-(3-ethyl-1H-pyrazolo[3,4-d]pyrimidin-4-yl)piperazin-1-yl]-2-(methyloxy)phenyl]methanol |
| 366 | methyl 5-chloro-3-[4-(3-ethyl-1H-pyrazolo[3,4-d]pyrimidin-4-yl)piperazin-1-yl]-2-(methyloxy)benzoate |
| 367 | (2E)-3-{4-[4-(5-chloro-2-methylphenyl)piperazin-1-yl]-1H-pyrazolo[3,4-d]pyrimidin-3-yl}prop-2-enoic acid |
| 368 | 3-{4-[4-(5-chloro-2-methylphenyl)piperazin-1-yl]-1H-pyrazolo[3,4-d]pyrimidin-3-yl}propanoic acid |
| 369 | 3-{4-[4-(5-chloro-2-methylphenyl)piperazin-1-yl]-1H-pyrazolo[3,4-d]pyrimidin-3-yl}propan-1-ol |
| 370 | methyl (2E)-3-{4-[4-(5-chloro-2-methylphenyl)piperazin-1-yl]-1H-pyrazolo[3,4-d]pyrimidin-3-yl}prop-2-enoate |
| 371 | 4-[4-(5-chloro-2-methylphenyl)piperazin-1-yl]-3-{4-[(2-morpholin-4-ylethyl)oxy]phenyl}-1H-pyrazolo[3,4-d]pyrimidine |
| 372 | 5-chloro-N-[2-(dimethylamino)ethyl]-3-[4-(3-ethyl-1H-pyrazolo[3,4-d]pyrimidin-4-yl)piperazin-1-yl]-2-(methyloxy)benzamide |
| 373 | 4-(4-{5-chloro-2-(methyloxy)-3-[(4-methylpiperazin-1-yl)carbonyl]phenyl}piperazin-1-yl)-3-ethyl-1H-pyrazolo[3,4-d]pyrimidine |
| 374 | 2-(dimethylamino)ethyl 5-chloro-3-[4-(3-ethyl-1H-pyrazolo[3,4-d]pyrimidin-4-yl)piperazin-1-yl]-2-(methyloxy)benzoate |
| 375 | 1-[5-chloro-3-[4-(3-ethyl-1H-pyrazolo[3,4-d]pyrimidin-4-yl)piperazin-1-yl]-2-(methyloxy)phenyl]-N,N-dimethylmethanamine |
| 376 | N'-{[5-chloro-3-[4-(3-ethyl-1H-pyrazolo[3,4-d]pyrimidin-4-yl)piperazin-1-yl]-2-(methyloxy)phenyl]methyl}-N,N-dimethylethane-1,2-diamine |
| 377 | [1-(3-chlorophenyl)-4-(3-ethyl-1H-pyrazolo[3,4-d]pyrimidin-4-yl)piperazin-2-yl]methanol |
| 378 | 3-[(4-{4-[4-(5-chloro-2-methylphenyl)piperazin-1-yl]-1H-pyrazolo[3,4-d]pyrimidin-3-yl}phenyl)oxy]-N,N-dimethylpropan-1-amine |
| 379 | 2-chloro-4-[4-(3-ethyl-1H-pyrazolo[3,4-d]pyrimidin-4-yl)piperazin-1-yl]-5-methylphenol |
| 380 | 1-(3-chlorophenyl)-4-(3-ethyl-1H-pyrazolo[3,4-d]pyrimidin-4-yl)-N-(1-methylpiperidin-4-yl)piperazine-2-carboxamide |
| 381 | 1-(3-chlorophenyl)-4-(3-ethyl-1H-pyrazolo[3,4-d]pyrimidin-4-yl)-N-(2-morpholin-4-ylethyl)piperazine-2-carboxamide |
| 382 | 2-{[5-chloro-3-[4-(3-ethyl-1H-pyrazolo[3,4-d]pyrimidin-4-yl)piperazin-1-yl]-2-(methyloxy)phenyl]oxy}-N,N-dimethylethanamine |
| 383 | 3-{5-chloro-3-[4-(3-ethyl-1H-pyrazolo[3,4-d]pyrimidin-4-yl)piperazin-1-yl]-2-methylphenyl}-N,N-dimethylprop-2-yn-1-amine |
| 384 | N'-{5-chloro-3-[4-(3-ethyl-1H-pyrazolo[3,4-d]pyrimidin-4-yl)piperazin-1-yl]-2-methylphenyl}-N,N-dimethylethane-1,2-diamine |
| 385 | 1,1-dimethylethyl (2E)-3-{4-[4-(5-chloro-2-methylphenyl)piperazin-1-yl]-1H-pyrazolo[3,4-d]pyrimidin-3-yl}prop-2-enoate |
| 386 | 3-({2-chloro-4-[4-(3-ethyl-1H-pyrazolo[3,4-d]pyrimidin-4-yl)piperazin-1-yl]-5-methylphenyl}oxy)-N,N-dimethylpropan-1-amine |
| 387 | 2-({2-chloro-4-[4-(3-ethyl-1H-pyrazolo[3,4-d]pyrimidin-4-yl)piperazin-1-yl]-5-methylphenyl}oxy)-N,N-dimethylethanamine |
| 388 | 4-{4-[5-chloro-2-methyl-4-(methyloxy)phenyl]piperazin-1-yl}-3-ethyl-1H-pyrazolo[3,4-d]pyrimidine |
| 389 | 4-[4-(5-chloro-2-methylphenyl)piperazin-1-yl]-3-(4-methylpiperazin-1-yl)-1H-pyrazolo[3,4-d]pyrimidine |
| 390 | 3-{4-[4-(5-chloro-2-methylphenyl)piperazin-1-yl]-1H-pyrazolo[3,4-d]pyrimidin-3-yl}-N,N-diethylprop-2-yn-1-amine |
| 391 | 3-{4-[4-(5-chloro-2-methylphenyl)piperazin-1-yl]-1H-pyrazolo[3,4-d]pyrimidin-3-yl}prop-2-yn-1-ol |
| 392 | 4-[4-(5-chloro-2-methylphenyl)piperazin-1-yl]-3-(piperidin-4-ylmethyl)-1H-pyrazolo[3,4-d]pyrimidine |
| 393 | phenylmethyl (3aR,6aS)-5-({4-[4-(5-chloro-2-methylphenyl)piperazin-1-yl]-1H-pyrazolo[3,4-d]pyrimidin-3-yl}methylidene)hexahydrocyclopenta[c]pyrrole-2(1H)-carboxylate |
| 394 | 4-[4-(5-chloro-2-methylphenyl)piperazin-1-yl]-3-[(E)-(3aR,6aS)-hexahydrocyclopenta[c]pyrrol-5(1H)-ylidenemethyl]-1H-pyrazolo[3,4-d]pyrimidine |
| 395 | 4-[4-(5-chloro-2-methylphenyl)piperazin-1-yl]-3-(3-pyrrolidin-1-ylprop-1-yn-1-yl)-1H-pyrazolo[3,4-d]pyrimidine |
| 396 | 4-[4-(5-chloro-2-methylphenyl)piperazin-1-yl]-3-[3-(4-methylpiperazin-1-yl)prop-1-yn-1-yl]-1H-pyrazolo[3,4-d]pyrimidine |
| 397 | 3-{4-[4-(5-chloro-2-methylphenyl)piperazin-1-yl]-1H-pyrazolo[3,4-d]pyrimidin-3-yl}-N,N-diethylpropan-1-amine |
| 398 | 4-[4-(5-chloro-2-methylphenyl)piperazin-1-yl]-3-(3-pyrrolidin-1-ylpropyl)-1H-pyrazolo[3,4-d]pyrimidine |
| 399 | 4-[4-(5-chloro-2-methylphenyl)piperazin-1-yl]-3-(1,2,3,6-tetrahydropyridin-4-yl)-1H-pyrazolo[3,4-d]pyrimidine |
| 400 | 3-{5-chloro-3-[4-(3-ethyl-1H-pyrazolo[3,4-d]pyrimidin-4-yl)piperazin-1-yl]-2-methylphenyl}-N,N-diethylpropan-1-amine |
| 401 | 4-{4-[5-chloro-2-methyl-3-(3-pyrrolidin-1-ylpropyl)phenyl]piperazin-1-yl}-3-ethyl-1H-pyrazolo[3,4-d]pyrimidine |

The Compounds in Table 2b can be prepared as pharmaceutically acceptable salts, solvates, hydrates, and/or isomers thereof. All such salt, solvate, hydrate, and isomer combinations of the Compounds in Table 2b can be used to practice the invention.

| Entry | Name |
|---|---|
| 1 | [1-(3-bromo-1H-pyrazolo[3,4-d]pyrimidin-4-yl)piperidin-4-yl](4-chlorophenyl)methanol |
| 2 | 2-{[[1-(3-bromo-1H-pyrazolo[3,4-d]pyrimidin-4-yl)piperidin-4-yl](4-chlorophenyl)methyl]oxy}-N,N-dimethylethanamine |
| 3 | 3-{[[1-(3-bromo-1H-pyrazolo[3,4-d]pyrimidin-4-yl)piperidin-4-yl](4-chlorophenyl)methyl]oxy}-N,N-dimethylpropan-1-amine |
| 4 | 3-bromo-4-{4-[(4-bromophenyl)methyl]piperazin-1-yl}-1H-pyrazolo[3,4-d]pyrimidine |
| 5 | {4-(3-bromo-1H-pyrazolo[3,4-d]pyrimidin-4-yl)-1-[(4-chlorophenyl)methyl]piperazin-2-yl}methanol |
| 6 | N'-[[1-(3-bromo-1H-pyrazolo[3,4-d]pyrimidin-4-yl)piperidin-4-yl](4-chlorophenyl)methyl]-N,N-diethylethane-1,2-diamine |
| 7 | 3-bromo-4-(4-{[4-(1,1-dimethylethyl)phenyl]methyl}piperazin-1-yl)-1H-pyrazolo[3,4-d]pyrimidine |
| 8 | 4-(3-bromo-1H-pyrazolo[3,4-d]pyrimidin-4-yl)-1-[(4-chlorophenyl)methyl]piperazin-2-one |
| 9 | 2-[4-(3-bromo-1H-pyrazolo[3,4-d]pyrimidin-4-yl)piperazin-1-yl]-2-(4-chlorophenyl)-N-[2-(dimethylamino)ethyl]acetamide |
| 10 | N-[1-(3-bromo-1H-pyrazolo[3,4-d]pyrimidin-4-yl)piperidin-4-yl]-N-(4-chlorophenyl)-N',N'-diethylpropane-1,3-diamine |
| 11 | 3-bromo-4-(4-{[4-(trifluoromethyl)phenyl]methyl}piperazin-1-yl)-1H-pyrazolo[3,4-d]pyrimidine |
| 12 | N-[1-(3-bromo-1H-pyrazolo[3,4-d]pyrimidin-4-yl)piperidin-4-yl]-N-(4-chlorophenyl)-N'-[2-(dimethylamino)ethyl]urea |
| 13 | N-[[1-(3-bromo-1H-pyrazolo[3,4-d]pyrimidin-4-yl)piperidin-4-yl](4-chlorophenyl)methyl]-N'-[2-(dimethylamino)ethyl]urea |
| 14 | 2-[4-(3-bromo-1H-pyrazolo[3,4-d]pyrimidin-4-yl)-2-oxopiperazin-1-yl]-2-(4-chlorophenyl)-N-[2-(dimethylamino)ethyl]acetamide |
| 15 | 2-(dimethylamino)ethyl [1-(3-bromo-1H-pyrazolo[3,4-d]pyrimidin-4-yl)piperidin-4-yl](4-chlorophenyl)carbamate |
| 16 | 3-bromo-4-{4-[(4-chloro-3-fluorophenyl)methyl]piperazin-1-yl}-1H-pyrazolo[3,4-d]pyrimidine |
| 17 | 3-bromo-4-{4-[(4-chloro-2-fluorophenyl)methyl]piperazin-1-yl}-1H-pyrazolo[3,4-d]pyrimidine |
| 18 | N-[1-(3-bromo-1H-pyrazolo[3,4-d]pyrimidin-4-yl)piperidin-4-yl]-N-(4-chlorophenyl)-N',N'-diethylethane-1,2-diamine |
| 19 | 3-bromo-4-{4-[(4-chlorophenyl)methyl]piperazin-1-yl}-1H-pyrazolo[3,4-d]pyrimidine |
| 20 | [1-(3-bromo-1H-pyrazolo[3,4-d]pyrimidin-4-yl)piperidin-4-yl](4-fluorophenyl)methanone |
| 21 | N-[[1-(3-bromo-1H-pyrazolo[3,4-d]pyrimidin-4-yl)piperidin-4-yl](4-chlorophenyl)methyl]-N',N'-diethyl-N-methylethane-1,2-diamine |
| 22 | [1-(3-bromo-1H-pyrazolo[3,4-d]pyrimidin-4-yl)piperidin-4-yl](4-fluorophenyl)methanol |
| 23 | 3-bromo-4-(4-{[2-fluoro-4-(trifluoromethyl)phenyl]methyl}piperazin-1-yl)-1H-pyrazolo[3,4-d]pyrimidine |
| 24 | N-[1-(3-bromo-1H-pyrazolo[3,4-d]pyrimidin-4-yl)piperidin-4-yl]-N-(4-chlorophenyl)-N~3~,N~3~-diethyl-beta-alaninamide |
| 25 | 2-{[[1-(3-bromo-1H-pyrazolo[3,4-d]pyrimidin-4-yl)piperidin-4-yl](4-fluorophenyl)methyl]oxy}-N,N-dimethylethanamine |
| 26 | N-[[1-(3-bromo-1H-pyrazolo[3,4-d]pyrimidin-4-yl)piperidin-4-yl](4-chlorophenyl)methyl]-N~3~,N~3~-diethyl-beta-alaninamide |
| 27 | 3-bromo-4-{4-[(3,4-dichlorophenyl)methyl]piperazin-1-yl}-1H-pyrazolo[3,4-d]pyrimidine |
| 28 | N-[1-(3-bromo-1H-pyrazolo[3,4-d]pyrimidin-4-yl)piperidin-4-yl]-N-(4-chlorophenyl)-N'-[2-(dimethylamino)ethyl]ethanediamide |
| 29 | N-[1-(3-bromo-1H-pyrazolo[3,4-d]pyrimidin-4-yl)piperidin-4-yl]-N-(4-chlorophenyl)-2-(diethylamino)ethanesulfonamide |
| 30 | 4-[4-(biphenyl-4-ylmethyl)piperazin-1-yl]-3-bromo-1H-pyrazolo[3,4-d]pyrimidine |
| 31 | 3-bromo-4-{(3S)-4-[(4-chlorophenyl)methyl]-3-methylpiperazin-1-yl}-1H-pyrazolo[3,4-d]pyrimidine |
| 32 | 3-bromo-4-(4-{[4-(methyloxy)phenyl]methyl}piperazin-1-yl)-1H-pyrazolo[3,4-d]pyrimidine |
| 33 | 4-(3-bromo-1H-pyrazolo[3,4-d]pyrimidin-4-yl)-N-[3-(trifluoromethyl)phenyl]piperazine-1-carboxamide |
| 34 | 3-bromo-4-{4-[(4-fluorophenyl)methyl]piperazin-1-yl}-1H-pyrazolo[3,4-d]pyrimidine |
| 35 | N-[1-(3-bromo-1H-pyrazolo[3,4-d]pyrimidin-4-yl)piperidin-4-yl]-N-(4-chlorophenyl)pent-4-enamide |

-continued

| Entry | Name |
|---|---|
| 36 | 3-bromo-4-[4-(2,3-dihydro-1,4-benzodioxin-6-ylmethyl)piperazin-1-yl]-1H-pyrazolo[3,4-d]pyrimidine |
| 37 | 4-[4-(1,3-benzodioxol-5-ylmethyl)piperazin-1-yl]-3-bromo-1H-pyrazolo[3,4-d]pyrimidine |
| 38 | [1-(3-bromo-1H-pyrazolo[3,4-d]pyrimidin-4-yl)piperidin-4-yl](4-chlorophenyl)methanone |
| 39 | 3-bromo-4-(4-{[4-(phenyloxy)phenyl]methyl}piperazin-1-yl)-1H-pyrazolo[3,4-d]pyrimidine |
| 40 | 3-bromo-4-{4-[(3,4-dichlorophenyl)methyl]piperidin-1-yl}-1H-pyrazolo[3,4-d]pyrimidine |
| 41 | 4-{[4-(3-bromo-1H-pyrazolo[3,4-d]pyrimidin-4-yl)piperazin-1-yl]methyl}-N,N-dimethylaniline |
| 42 | methyl 4-{[4-(3-bromo-1H-pyrazolo[3,4-d]pyrimidin-4-yl)piperazin-1-yl]methyl}benzoate |
| 43 | 3-bromo-4-{4-[(2E)-3-phenylprop-2-enoyl]piperazin-1-yl}-1H-pyrazolo[3,4-d]pyrimidine |
| 44 | 1-(3-bromo-1H-pyrazolo[3,4-d]pyrimidin-4-yl)-4-[(4-chlorophenyl)methyl]-N-[3-(diethylamino)propyl]piperidine-4-carboxamide |
| 45 | 3-bromo-4-{4-[(2-bromophenyl)methyl]piperazin-1-yl}-1H-pyrazolo[3,4-d]pyrimidine |
| 46 | 3-bromo-4-{4-[(2-chlorophenyl)methyl]piperazin-1-yl}-1H-pyrazolo[3,4-d]pyrimidine |
| 47 | 3-bromo-4-{4-[(2,4-dichlorophenyl)methyl]piperazin-1-yl}-1H-pyrazolo[3,4-d]pyrimidine |
| 48 | 3-bromo-4-{4-[(2-chloro-4-fluorophenyl)methyl]piperazin-1-yl}-1H-pyrazolo[3,4-d]pyrimidine |
| 49 | 1-(3-bromo-1H-pyrazolo[3,4-d]pyrimidin-4-yl)-4-(4-chlorophenyl)-N-[3-(diethylamino)propyl]piperidine-4-carboxamide |
| 50 | 3-bromo-4-[4-(phenylmethyl)piperazin-1-yl]-1H-pyrazolo[3,4-d]pyrimidine |
| 51 | 2-[4-(3-bromo-1H-pyrazolo[3,4-d]pyrimidin-4-yl)piperazin-1-yl]-N-pyridin-2-ylacetamide |
| 52 | 3-bromo-4-[4-(1H-imidazol-2-ylmethyl)piperazin-1-yl]-1H-pyrazolo[3,4-d]pyrimidine |
| 53 | 3-bromo-4-(4-{[3-(phenyloxy)phenyl]methyl}piperazin-1-yl)-1H-pyrazolo[3,4-d]pyrimidine |
| 54 | 3-bromo-4-{4-[(3-methylphenyl)methyl]piperazin-1-yl}-1H-pyrazolo[3,4-d]pyrimidine |
| 55 | 3-{[4-(3-bromo-1H-pyrazolo[3,4-d]pyrimidin-4-yl)piperazin-1-yl]methyl}benzonitrile |
| 56 | 3-bromo-4-{4-[(2-chloro-6-fluorophenyl)methyl]piperazin-1-yl}-1H-pyrazolo[3,4-d]pyrimidine |
| 57 | 3-bromo-4-[4-(1-phenylethyl)piperazin-1-yl]-1H-pyrazolo[3,4-d]pyrimidine |
| 58 | 3-bromo-4-[4-(pyridin-4-ylmethyl)piperazin-1-yl]-1H-pyrazolo[3,4-d]pyrimidine |
| 59 | 1-(3-bromo-1H-pyrazolo[3,4-d]pyrimidin-4-yl)-N-(4-chlorophenyl)piperidin-4-amine |
| 60 | 3-bromo-4-[4-(pyridin-3-ylmethyl)piperazin-1-yl]-1H-pyrazolo[3,4-d]pyrimidine |
| 61 | 3-bromo-4-(4-{[2,3,4-tris(methyloxy)phenyl]methyl}piperazin-1-yl)-1H-pyrazolo[3,4-d]pyrimidine |
| 62 | 3-bromo-4-(4-{[3-(phenylmethyl)oxy]phenyl}methyl}piperazin-1-yl)-1H-pyrazolo[3,4-d]pyrimidine |
| 63 | 3-bromo-4-[4-(naphthalen-1-ylmethyl)piperazin-1-yl]-1H-pyrazolo[3,4-d]pyrimidine |
| 64 | 3-bromo-4-(4-{[5-(4-chlorophenyl)furan-2-yl]methyl}piperazin-1-yl)-1H-pyrazolo[3,4-d]pyrimidine |
| 65 | 3-bromo-4-(4-({4-[(4-fluorophenyl)oxy]-3-nitrophenyl}methyl)piperazin-1-yl]-1H-pyrazolo[3,4-d]pyrimidine |
| 66 | 3-bromo-4-[4-(furan-2-ylcarbonyl)piperazin-1-yl]-1H-pyrazolo[3,4-d]pyrimidine |
| 67 | 3-bromo-4-[4-(1H-indol-6-ylcarbonyl)piperazin-1-yl]-1H-pyrazolo[3,4-d]pyrimidine |
| 68 | 3-bromo-4-{4-[2-(2-thienyl)ethyl]piperazin-1-yl}-1H-pyrazolo[3,4-d]pyrimidine |
| 69 | 3-bromo-4-[4-(3-pyrrolidin-1-ylpropyl)piperazin-1-yl]-1H-pyrazolo[3,4-d]pyrimidine |
| 70 | 3-bromo-4-[4-(cyclohexylmethyl)piperazin-1-yl]-1H-pyrazolo[3,4-d]pyrimidine |
| 71 | 3-bromo-4-{4-[(10-chloroanthracen-9-yl)methyl]piperazin-1-yl}-1H-pyrazolo[3,4-d]pyrimidine |
| 72 | 3-bromo-4-[4-(1-methylpropyl)piperazin-1-yl]-1H-pyrazolo[3,4-d]pyrimidine |
| 73 | 4-(4-{[4,6-bis(methyloxy)pyrimidin-2-yl]methyl}piperazin-1-yl)-3-bromo-1H-pyrazolo[3,4-d]pyrimidine |
| 74 | 3-bromo-4-{4-[2-(methyloxy)ethyl]piperazin-1-yl}-1H-pyrazolo[3,4-d]pyrimidine |
| 75 | 3-bromo-4-[4-(2-morpholin-4-yl-2-oxoethyl)piperazin-1-yl]-1H-pyrazolo[3,4-d]pyrimidine |
| 76 | 3-bromo-4-{4-[3-(methyloxy)propyl]piperazin-1-yl}-1H-pyrazolo[3,4-d]pyrimidine |

| Entry | Name |
|---|---|
| 77 | 4-{4-[[4,6-bis(methyloxy)pyrimidin-2-yl](phenyl)methyl]piperazin-1-yl}-3-bromo-1H-pyrazolo[3,4-d]pyrimidine |
| 78 | 3-bromo-4-[4-(6,7,8,9-tetrahydro-5H-benzocyclohepten-5-yl)piperazin-1-yl]-1H-pyrazolo[3,4-d]pyrimidine |
| 79 | 3-bromo-4-[4-({4-[(phenylmethyl)oxy]phenyl}methyl)piperazin-1-yl]-1H-pyrazolo[3,4-d]pyrimidine |
| 80 | 3-bromo-4-[4-({3-chloro-4-[(phenylmethyl)oxy]phenyl}methyl)piperazin-1-yl]-1H-pyrazolo[3,4-d]pyrimidine |
| 81 | 4-{[4-(3-bromo-1H-pyrazolo[3,4-d]pyrimidin-4-yl)piperazin-1-yl]methyl}-N-(3-morpholin-4-ylpropyl)benzamide |
| 82 | 4-{[4-(3-bromo-1H-pyrazolo[3,4-d]pyrimidin-4-yl)piperazin-1-yl]methyl}-N-[3-(methyloxy)propyl]benzamide |
| 83 | 2-[({4-(3-bromo-1H-pyrazolo[3,4-d]pyrimidin-4-yl)-1-[(4-chlorophenyl)methyl]piperazin-2-yl}methyl)oxy]-N,N-dimethylethanamine |
| 84 | 3-bromo-4-[4-({4-[(4-chlorophenyl)oxy]-3-nitrophenyl}methyl)piperazin-1-yl]-1H-pyrazolo[3,4-d]pyrimidine |
| 85 | 2-[4-(3-bromo-1H-pyrazolo[3,4-d]pyrimidin-4-yl)piperazin-1-yl]-N,N-dimethylacetamide |
| 86 | 2-{[(R)-[1-(3-bromo-1H-pyrazolo[3,4-d]pyrimidin-4-yl)piperidin-4-yl](4-chlorophenyl)methyl]oxy}-N,N-dimethylethanamine |
| 87 | N-(4-bromo-3-fluorophenyl)-N-[1-(3-bromo-1H-pyrazolo[3,4-d]pyrimidin-4-yl)piperidin-4-yl]-N'-[2-(dimethylamino)ethyl]urea |
| 88 | 2-({(R)-(4-chlorophenyl)[1-(3-ethyl-1H-pyrazolo[3,4-d]pyrimidin-4-yl)piperidin-4-yl]methyl}oxy)-N,N-dimethylethanamine |
| 89 | 2-{[(S)-[1-(3-bromo-1H-pyrazolo[3,4-d]pyrimidin-4-yl)piperidin-4-yl](4-chlorophenyl)methyl]oxy}-N,N-dimethylethanamine |
| 90 | 3-bromo-4-(4-{(R)-(4-chlorophenyl)[(2-pyrrolidin-1-ylethyl)oxy]methyl}piperidin-1-yl)-1H-pyrazolo[3,4-d]pyrimidine |
| 91 | 1-[1-(3-bromo-1H-pyrazolo[3,4-d]pyrimidin-4-yl)piperidin-4-yl]-1-(4-chlorophenyl)-4-(dimethylamino)butan-1-ol |
| 92 | 2-{[(R)-[1-(3-bromo-1H-pyrazolo[3,4-d]pyrimidin-4-yl)piperidin-4-yl](4-chloro-3-fluorophenyl)methyl]oxy}-N,N-dimethylethanamine |
| 93 | 3-bromo-4-(4-{(R)-(4-chlorophenyl)[(2-piperidin-1-ylethyl)oxy]methyl}piperidin-1-yl)-1H-pyrazolo[3,4-d]pyrimidine |
| 94 | 4-[1-(3-bromo-1H-pyrazolo[3,4-d]pyrimidin-4-yl)piperidin-4-yl]-4-(4-chlorophenyl)-N,N-dimethylbutan-1-amine |
| 95 | 3-bromo-4-(4-{(R)-(4-chlorophenyl)[(2-morpholin-4-ylethyl)oxy]methyl}piperidin-1-yl)-1H-pyrazolo[3,4-d]pyrimidine |
| 96 | 1-[1-(3-bromo-1H-pyrazolo[3,4-d]pyrimidin-4-yl)piperidin-4-yl]-1-(4-fluorophenyl)-N-(furan-2-ylmethyl)-N-methylmethanamine |
| 97 | 1-[1-(3-bromo-1H-pyrazolo[3,4-d]pyrimidin-4-yl)piperidin-4-yl]-1-(4-fluorophenyl)-N-methyl-N-(pyridin-2-ylmethyl)methanamine |
| 98 | 4-{[{[1-(3-bromo-1H-pyrazolo[3,4-d]pyrimidin-4-yl)piperidin-4-yl](4-fluorophenyl)methyl}(methyl)amino]methyl}-N,N-dimethylaniline |
| 99 | [4-(3-bromo-1H-pyrazolo[3,4-d]pyrimidin-4-yl)piperazin-1-yl](1H-indol-6-yl)methanol |
| 100 | 3-bromo-4-(4-{(R)-(4-chloro-3-fluorophenyl)[(2-pyrrolidin-1-ylethyl)oxy]methyl}piperidin-1-yl)-1H-pyrazolo[3,4-d]pyrimidine |
| 101 | 3-bromo-4-{4-[(4-chlorophenyl)oxy]piperidin-1-yl}-1H-pyrazolo[3,4-d]pyrimidine |
| 102 | 2-{[(R)-[1-(3-bromo-1H-pyrazolo[3,4-d]pyrimidin-4-yl)piperidin-4-yl](4-chlorophenyl)methyl]oxy}-N,N-diethylethanamine |
| 103 | 2-{[1-(3-bromo-1H-pyrazolo[3,4-d]pyrimidin-4-yl)piperidin-4-yl]oxy}-5-chloro-N-(2-pyrrolidin-1-ylethyl)aniline |

The Compounds in Table 3a can be prepared as pharmaceutically acceptable salts, solvates, hydrates, and/or isomers thereof. All such salt, solvate, hydrate, and isomer combinations of the Compounds in Table 3a can be used to practice the invention.

| Cmpd No. | Name |
|---|---|
| 1 | N-(4-fluorophenyl)-N'-[3-fluoro-4-(7H-pyrrolo[2,3-d]pyrimidin-4-yloxy)phenyl]propanediamide |
| 2 | N-(4-fluorophenyl)-N'-[3-fluoro-4-(7H-pyrrolo[2,3-d]pyrimidin-4-yloxy)phenyl]cyclopropane-1,1-dicarboxamide |
| 3 | N-({[3-fluoro-4-(7H-pyrrolo[2,3-d]pyrimidin-4-yloxy)phenyl]amino}carbonothioyl)-2-phenylacetamide |
| 4 | N-(4-fluorophenyl)-N'-(4-{[1-(tetrahydro-2H-pyran-2-yl)-1H-pyrazolo[3,4-d]pyrimidin-4-yl]oxy}phenyl)cyclopropane-1,1-dicarboxamide |
| 5 | 2-phenyl-N-{[(4-{[1-(tetrahydro-2H-pyran-2-yl)-1H-pyrazolo[3,4-d]pyrimidin-4-yl]oxy}phenyl)amino]carbonothioyl}acetamide |
| 6 | N-(4-fluorophenyl)-N'-[4-(1H-pyrazolo[3,4-d]pyrimidin-4-yloxy)phenyl]cyclopropane-1,1-dicarboxamide |
| 7 | 2-phenyl-N-({[4-(1H-pyrazolo[3,4-d]pyrimidin-4-yloxy)phenyl]amino}carbonothioyl)acetamide |
| 8 | N-(4-fluorophenyl)-N'-(4-{[9-(tetrahydro-2H-pyran-2-yl)-9H-purin-6-yl]oxy}phenyl)cyclopropane-1,1-dicarboxamide |
| 9 | 2-phenyl-N-{[(4-{[9-(tetrahydro-2H-pyran-2-yl)-9H-purin-6-yl]oxy}phenyl)amino]carbonothioyl}acetamide |
| 10 | N-(4-fluorophenyl)-N'-[4-(9H-purin-6-yloxy)phenyl]cyclopropane-1,1-dicarboxamide |
| 11 | 2-phenyl-N-({[4-(9H-purin-6-yloxy)phenyl]amino}carbonothioyl)acetamide |
| 12 | N-{3-fluoro-4-[(6-{[(2-morpholin-4-ylethyl)amino]carbonyl}-7H-pyrrolo[2,3-d]pyrimidin-4-yl)oxy]phenyl}-N'-(4-fluorophenyl)cyclopropane-1,1-dicarboxamide |

The Compounds in Table 3b can be prepared as pharmaceutically acceptable salts, solvates, hydrates, and/or isomers thereof. All such salt, solvate, hydrate, and isomer combinations of the Compounds in Table 3b can be used to practice the invention.

| Entry | Name |
|---|---|
| 1 | N-[({3-fluoro-4-[(6-(methyloxy)-7-{[(3aR,6aS)-octahydrocyclopenta[c]pyrrol-5-ylmethyl]oxy}quinazolin-4-yl)oxy]phenyl}amino)carbonothioyl]-2-phenylacetamide |
| 2 | N-{[(3-fluoro-4-{[7-({[(3aR,6aS)-2-methyloctahydrocyclopenta[c]pyrrol-5-yl]methyl}oxy)-6-(methyloxy)quinazolin-4-yl]oxy}phenyl)amino]carbonothioyl}-2-phenylacetamide |
| 3 | N-{[(4-{[6,7-bis(methyloxy)quinolin-4-yl]oxy}-3-fluorophenyl)(methyl)amino]carbonothioyl}-2-phenylacetamide |
| 4 | 1-(4-{[6,7-bis(methyloxy)quinolin-4-yl]oxy}-3-fluorophenyl)imidazolidin-2-one |
| 5 | 1-(4-{[6,7-bis(methyloxy)quinolin-4-yl]oxy}-3-fluorophenyl)-3-(phenylmethyl)imidazolidin-2-one |
| 6 | 1-(4-{[6,7-bis(methyloxy)quinolin-4-yl]oxy}-3-fluorophenyl)-3-(phenylacetyl)imidazolidin-2-one |
| 7 | ethyl [(4-{[6,7-bis(methyloxy)quinolin-4-yl]oxy}-3-fluorophenyl)amino](oxo)acetate |
| 8 | N-{[(4-{[6,7-bis(methyloxy)quinazolin-4-yl]amino}-3-fluorophenyl)amino]carbonothioyl}-2-phenylacetamide |
| 9 | N'-(4-{[6,7-bis(methyloxy)quinolin-4-yl]oxy}-3-fluorophenyl)-N-methyl-N-(2-phenylethyl)sulfamide |
| 10 | N-(4-{[6,7-bis(methyloxy)quinolin-4-yl]oxy}-3-fluorophenyl)-3-(phenylmethyl)-1,2,4-oxadiazol-5-amine |
| 11 | 1-(4-{[6,7-bis(methyloxy)quinolin-4-yl]oxy}-3-fluorophenyl)piperidin-2-one |
| 12 | N-(4-{[6,7-bis(methyloxy)quinolin-4-yl]oxy}-3-fluorophenyl)-N'-(phenylmethyl)ethanediamide |
| 13 | N-(4-{[6,7-bis(methyloxy)quinolin-4-yl]oxy}-3-fluorophenyl)-4-phenyl-1,3-thiazol-2-amine |
| 14 | N-(4-{[6,7-bis(methyloxy)quinolin-4-yl]oxy}-3-fluorophenyl)-N'-(2-phenylethyl)ethanediamide |
| 15 | N-(4-{[6,7-bis(methyloxy)quinolin-4-yl]oxy}-3-fluorophenyl)-1-phenylmethanesulfonamide |
| 16 | N-(4-{[6,7-bis(methyloxy)quinolin-4-yl]oxy}-3-fluorophenyl)-2-phenylethanesulfonamide |
| 17 | 4-{[6,7-bis(methyloxy)quinolin-4-yl]oxy}-3-fluoro-N-(phenylmethyl)benzenesulfonamide |
| 18 | 4-{[6,7-bis(methyloxy)quinolin-4-yl]oxy}-3-fluoro-N-methyl-N-(phenylmethyl)benzenesulfonamide |
| 19 | 4-{[6,7-bis(methyloxy)quinolin-4-yl]oxy}-3-fluoro-N-(2-phenylethyl)benzenesulfonamide |
| 20 | 4-{[6,7-bis(methyloxy)quinolin-4-yl]oxy}-3-fluoro-N-methyl-N-(2-phenylethyl)benzenesulfonamide |
| 21 | 4-{[6,7-bis(methyloxy)quinolin-4-yl]oxy}-3-fluoro-N-(3-phenylpropyl)benzenesulfonamide |
| 22 | 1-(4-{[6,7-bis(methyloxy)quinolin-4-yl]oxy}-3-fluorophenyl)pyrrolidin-2-one |
| 23 | 4-{[6,7-bis(methyloxy)quinolin-4-yl]oxy}phenyl (phenylmethyl)carbamate |
| 24 | 4-{[6,7-bis(methyloxy)quinolin-4-yl]oxy}phenyl (2-phenylethyl)carbamate |
| 25 | 4-{[6,7-bis(methyloxy)quinolin-4-yl]oxy}-3-fluoro-N-methyl-N-(3-phenylpropyl)benzenesulfonamide |
| 26 | N-(4-{[6,7-bis(methyloxy)quinolin-4-yl]oxy}-3-fluorophenyl)-N'-phenylethanediamide |
| 27 | N-{[(3-fluoro-4-{[7-{[(2-methyloctahydrocyclopenta[c]pyrrol-5-yl)methyl]oxy}-6-(methyloxy)quinolin-4-yl]oxy}phenyl)amino]carbonothioyl}-2-phenylacetamide |
| 28 | N-[(Z)-[(4-{[6,7-bis(methyloxy)quinolin-4-yl]oxy}-3-fluorophenyl)amino](imino)methyl]-2-phenylacetamide |
| 29 | 4-{[6,7-bis(methyloxy)quinolin-4-yl]oxy}-3-fluoro-N-[2-(phenyloxy)ethyl]benzenesulfonamide |
| 30 | N,N-(4-{[6,7-bis(methyloxy)quinolin-4-yl]oxy}-3-fluorophenyl)-bis-(3-phenylpropane-1-sulfonamide) |
| 31 | N-(4-{[6,7-bis(methyloxy)quinolin-4-yl]oxy}-3-fluorophenyl)-3-phenylpropane-1-sulfonamide |
| 32 | N2-[(4-{[6,7-bis(methyloxy)quinolin-4-yl]oxy}-3-fluorophenyl)sulfonyl]-N1-phenylglycinamide |
| 33 | N-(6-{[6,7-bis(methyloxy)quinolin-4-yl]oxy}pyridin-3-yl)-2-phenylacetamide |
| 34 | N-{[(6-{[6,7-bis(methyloxy)quinolin-4-yl]oxy}pyridin-3-yl)amino]carbonothioyl}-2-phenylacetamide |
| 35 | 6-{[6,7-bis(methyloxy)quinolin-4-yl]oxy}-1,3-benzothiazol-2-amine |
| 36 | 6-{[6,7-bis(methyloxy)quinolin-4-yl]oxy}-5-fluoro-1,3-benzothiazol-2-amine |

-continued

| Entry | Name |
|---|---|
| 37 | N-(6-{[6,7-bis(methyloxy)quinolin-4-yl]oxy}-5-fluoro-1,3-benzothiazol-2-yl)-2-phenylacetamide |
| 38 | N-(4-{[6,7-bis(methyloxy)quinolin-4-yl]oxy}-3-fluorophenyl)-N'-(2-morpholin-4-ylethyl)ethanediamide |
| 39 | benzyl-{[4-(6,7-dimethoxy-quinolin-4-yloxy)-3-fluoro-phenylcarbamoyl]-methyl}-carbamic acid tert-butyl ester |
| 40 | N1-(4-{[6,7-bis(methyloxy)quinolin-4-yl]oxy}-3-fluorophenyl)-N2-(phenylmethyl)glycinamide |
| 41 | N2-acetyl-N1-(4-{[6,7-bis(methyloxy)quinolin-4-yl]oxy}-3-fluorophenyl)-N2-(phenylmethyl)glycinamide |
| 42 | N-(6-{[6,7-bis(methyloxy)quinolin-4-yl]oxy}-1,3-benzothiazol-2-yl)-2-phenylacetamide |
| 43 | benzyl-{[6-(6,7-dimethoxy-quinolin-4-yloxy)-pyridin-3-ylcarbamoyl]-methyl}-carbamic acid tert-butyl ester |
| 44 | N1-(6-{[6,7-bis(methyloxy)quinolin-4-yl]oxy}pyridin-3-yl)-N2-(phenylmethyl)glycinamide |
| 45 | N2-acetyl-N1-(6-{[6,7-bis(methyloxy)quinolin-4-yl]oxy}pyridin-3-yl)-N2-(phenylmethyl)glycinamide |
| 46 | N-(6-{[6,7-bis(methyloxy)quinolin-4-yl]oxy}pyridin-3-yl)-3-phenylpropanamide |
| 47 | N-(6-{[6,7-bis(methyloxy)quinolin-4-yl]oxy}pyridin-3-yl)-4-phenylbutanamide |
| 48 | N1-(6-{[6,7-bis(methyloxy)quinolin-4-yl]oxy}pyridin-3-yl)-N2-methyl-N2-(phenylmethyl)glycinamide |
| 49 | N-(4-{[6,7-bis(methyloxy)quinolin-4-yl]oxy}-3-fluorophenyl)-N'-{2-[4-(methyloxy)phenyl]ethyl}ethanediamide |
| 50 | N1-(4-{[6,7-bis(methyloxy)quinolin-4-yl]oxy}-3-fluorophenyl)-N2-methyl-N2-(phenylmethyl)glycinamide |
| 51 | 4-[(2-amino-1,3-benzothiazol-6-yl)oxy]-6,7-bis(methyloxy)-1-(2-oxo-2-phenylethyl)quinolinium |
| 52 | N-{[(4-{[6,7-bis(methyloxy)quinolin-4-yl]amino}phenyl)amino]carbonothioyl}-2-phenylacetamide |
| 53 | N-(6-{[6,7-bis(methyloxy)quinolin-4-yl]oxy}-5-fluoro-1,3-benzothiazol-2-yl)-3-phenylpropanamide |
| 54 | N-{[(6-{[6,7-bis(methyloxy)quinolin-4-yl]oxy}-5-chloropyridin-3-yl)amino]carbonothioyl}-2-phenylacetamide |
| 55 | N-(4-{[6,7-bis(methyloxy)quinolin-4-yl]oxy}-3-fluorophenyl)-N'-(2,3-dihydro-1H-inden-1-yl)ethanediamide |
| 56 | N-(4-{[6,7-bis(methyloxy)quinolin-4-yl]oxy}-3-fluorophenyl)-N'-(2,3-dihydro-1H-inden-2-yl)ethanediamide |
| 57 | N-(4-{[6,7-bis(methyloxy)quinolin-4-yl]oxy}-3-fluorophenyl)-N'-(1,2,3,4-tetrahydronaphthalen-1-yl)ethanediamide |
| 58 | N'-(4-{[6,7-bis(methyloxy)quinolin-4-yl]oxy}-3-fluorophenyl)-N-(2-phenylethyl)-N-(phenylmethyl)sulfamide |
| 59 | N1-(4-{[6,7-bis(methyloxy)quinolin-4-yl]oxy}-3-fluorophenyl)-N2-(trifluoroacetyl)glycinamide |
| 60 | N-{[4-(6,7-dimethoxy-quinolin-4-yloxy)-3-fluoro-phenylcarbamoyl]-methyl}-benzamide |
| 61 | N-(6-{[6,7-bis(methyloxy)quinolin-4-yl]oxy}pyridin-3-yl)-N'-(4-fluorophenyl)propanediamide |
| 62 | N-(4-{[6,7-bis(methyloxy)quinolin-4-yl]oxy}-3-fluorophenyl)-N'-[(2S)-1,2,3,4-tetrahydronaphthalen-2-yl]ethanediamide |
| 63 | N-(4-{[6,7-bis(methyloxy)quinolin-4-yl]oxy}-3-fluorophenyl)-N'-[2-(4-methylphenyl)ethyl]ethanediamide |
| 64 | N-(4-{[6,7-bis(methyloxy)quinolin-4-yl]oxy}-3-fluorophenyl)-N'-(2-phenylpropyl)ethanediamide |
| 65 | N-(4-{[6,7-bis(methyloxy)quinolin-4-yl]oxy}-3-fluorophenyl)-N'-[2-(4-chlorophenyl)ethyl]ethanediamide |
| 66 | N-(4-{[6,7-bis(methyloxy)quinolin-4-yl]oxy}-3-fluorophenyl)-N,N'-bis(phenylmethyl)sulfamide |
| 67 | N-(4-{[6,7-bis(methyloxy)quinolin-4-yl]oxy}-3-fluorophenyl)-N,N'-bis(2-phenylethyl)sulfamide |
| 68 | ethyl [(6-{[6,7-bis(methyloxy)quinolin-4-yl]oxy}-5-chloropyridin-3-yl)amino](oxo)acetate |
| 69 | N-(6-{[6,7-bis(methyloxy)quinolin-4-yl]oxy}-5-chloropyridin-3-yl)-N'-(2-phenylethyl)ethanediamide |
| 70 | N-(6-{[6,7-bis(methyloxy)quinolin-4-yl]oxy}-5-chloropyridin-3-yl)-N'-(4-fluorophenyl)propanediamide |
| 71 | N-(4-{[6,7-bis(methyloxy)quinolin-4-yl]oxy}-3-fluorophenyl)-N'-(1,2,3,4-tetrahydronaphthalen-2-yl)ethanediamide |
| 72 | N-(4-{[6,7-bis(methyloxy)quinolin-4-yl]oxy}-3-fluorophenyl)-N'-[2-(1-methylpyrrolidin-2-yl)ethyl]ethanediamide |
| 73 | N-(4-{[6,7-bis(methyloxy)quinolin-4-yl]oxy}-3-fluorophenyl)-N'-[2-(phenyloxy)ethyl]ethanediamide |
| 74 | N-(4-{[6,7-bis(methyloxy)quinolin-4-yl]oxy}-3-fluorophenyl)-N'-[2-hydroxy-1-(phenylmethyl)ethyl]urea |
| 75 | 1-(4-{[6,7-bis(methyloxy)quinolin-4-yl]oxy}-3-fluorophenyl)-3-[(4-methylphenyl)sulfonyl]-4-(phenylmethyl)imidazolidin-2-one |

| Entry | Name |
|---|---|
| 76 | N'-(4-{[6,7-bis(methyloxy)quinolin-4-yl]oxy}-3-fluorophenyl)-N-methyl-N-(2-phenylethyl)ethanediamide |
| 77 | N-(4-{[6,7-bis(methyloxy)quinolin-4-yl]oxy}-3-fluorophenyl)-N'-{[3-(trifluoromethyl)phenyl]methyl}ethanediamide |
| 78 | N-(4-{[6,7-bis(methyloxy)quinolin-4-yl]oxy}-3-fluorophenyl)-N'-{2-[3-(trifluoromethyl)phenyl]ethyl}ethanediamide |
| 79 | N-(6-{[6,7-bis(methyloxy)quinolin-4-yl]oxy}-5-chloropyridin-3-yl)-3-oxo-4-phenylbutanamide |
| 80 | N-(6-{[6,7-bis(methyloxy)quinolin-4-yl]oxy}-5-chloropyridin-3-yl)-2-[3-(trifluoromethyl)phenyl]acetamide |
| 81 | 6-{[6,7-bis(methyloxy)quinolin-4-yl]oxy}-5-fluoro-N-[2-(phenyloxy)ethyl]-1,3-benzothiazol-2-amine |
| 82 | 6-{[6,7-bis(methyloxy)quinolin-4-yl]oxy}-5-fluoro-N-(2-piperidin-1-ylethyl)-1,3-benzothiazol-2-amine |
| 83 | 6-{[6,7-bis(methyloxy)quinolin-4-yl]oxy}-5-fluoro-N-methyl-N-(2-phenylethyl)-1,3-benzothiazol-2-amine |
| 84 | 6-{[6,7-bis(methyloxy)quinolin-4-yl]oxy}-5-fluoro-N-(2-pyrrolidin-1-ylethyl)-1,3-benzothiazol-2-amine |
| 85 | 6-{[6,7-bis(methyloxy)quinolin-4-yl]oxy}-5-fluoro-N-{[3-(trifluoromethyl)phenyl]methyl}-1,3-benzothiazol-2-amine |
| 86 | 6-{[6,7-bis(methyloxy)quinolin-4-yl]oxy}-5-fluoro-N-{2-[3-(trifluoromethyl)phenyl]ethyl}-1,3-benzothiazol-2-amine |
| 87 | N-(6-{[6,7-bis(methyloxy)quinolin-4-yl]oxy}-5-chloropyridin-3-yl)-N'-[3-(trifluoromethyl)phenyl]propanediamide |
| 88 | N-(6-{[6,7-bis(methyloxy)quinolin-4-yl]oxy}-5-fluoro-1,3-benzothiazol-2-yl)-2-[3-(trifluoromethyl)phenyl]acetamide |
| 89 | N1-(4-{[6,7-bis(methyloxy)quinolin-4-yl]oxy}-3-fluorophenyl)-N2-{[3-(trifluoromethyl)phenyl]methyl}glycinamide |
| 90 | N1-(4-{[6,7-bis(methyloxy)quinolin-4-yl]oxy}-3-fluorophenyl)-N2-(2-phenylethyl)glycinamide |
| 91 | N1-(4-{[6,7-bis(methyloxy)quinolin-4-yl]oxy}-3-fluorophenyl)-N2-{2-[3-(trifluoromethyl)phenyl]ethyl}glycinamide |
| 92 | benzyl-{[5-chloro-6-(6,7-dimethoxy-quinolin-4-yloxy)-pyridin-3-ylcarbamoyl]-methyl}-carbamic acid tert-butyl ester |
| 93 | N1-(6-{[6,7-bis(methyloxy)quinolin-4-yl]oxy}-5-chloropyridin-3-yl)-N2-(phenylmethyl)glycinamide |
| 94 | N-(6-{[6,7-bis(methyloxy)quinolin-4-yl]oxy}-5-fluoro-1,3-benzothiazol-2-yl)-2-[3,5-bis(trifluoromethyl)phenyl]acetamide |
| 95 | N-(6-{[6,7-bis(methyloxy)quinolin-4-yl]oxy}-5-fluoro-1,3-benzothiazol-2-yl)-2-[2-chloro-5-(trifluoromethyl)phenyl]acetamide |
| 96 | N-{3-fluoro-4-[(6-(methyloxy)-7-{[(1-methylpiperidin-4-yl)methyl]oxy}quinolin-4-yl)oxy]phenyl}-N'-(2-phenylethyl)ethanediamide |
| 97 | N-(4-{[6,7-bis(methyloxy)quinolin-4-yl]oxy}-3-fluorophenyl)-N'-(1,2,3,4-tetrahydroisoquinolin-1-ylmethyl)ethanediamide |
| 98 | N-(4-{[6,7-bis(methyloxy)quinolin-4-yl]oxy}-3-fluorophenyl)-N'-[(2-methyl-1,2,3,4-tetrahydroisoquinolin-1-yl)methyl]ethanediamide |
| 99 | N1-(4-{[6,7-bis(methyloxy)quinolin-4-yl]oxy}-3-fluorophenyl)-N2-methyl-N2-{[3-(trifluoromethyl)phenyl]methyl}glycinamide |
| 100 | N1-(4-{[6,7-bis(methyloxy)quinolin-4-yl]oxy}-3-fluorophenyl)-N2-methyl-N2-{2-[3-(trifluoromethyl)phenyl]ethyl}glycinamide |
| 101 | N1-(4-{[6,7-bis(methyloxy)quinolin-4-yl]oxy}-3-fluorophenyl)-N2-methyl-N2-(2-phenylethyl)glycinamide |
| 102 | 1-(4-{[6,7-bis(methyloxy)quinolin-4-yl]oxy}-3-fluorophenyl)-4-(phenylmethyl)imidazolidin-2-one |
| 103 | N-(6-{[6,7-bis(methyloxy)quinolin-4-yl]oxy}pyridazin-3-yl)-N'-(4-fluorophenyl)propanediamide |
| 104 | N-(6-{[6,7-bis(methyloxy)quinolin-4-yl]oxy}-5-chloropyridin-3-yl)-N'-(2-chlorophenyl)propanediamide |
| 105 | N-(6-{[6,7-bis(methyloxy)quinolin-4-yl]oxy}-5-chloropyridin-3-yl)-N'-(3-chlorophenyl)propanediamide |
| 106 | N1-(6-{[6,7-bis(methyloxy)quinolin-4-yl]oxy}-5-chloropyridin-3-yl)-N2-methyl-N2-(phenylmethyl)glycinamide |
| 107 | N-(6-{[6,7-bis(methyloxy)quinolin-4-yl]oxy}-5-chloropyridin-3-yl)-N'-(4-chlorophenyl)propanediamide |
| 108 | (2E)-N-(4-{[6,7-bis(methyloxy)quinolin-4-yl]oxy}phenyl)-2-[(methyloxy)imino]propanamide |
| 109 | (2E)-N-(4-{[6,7-bis(methyloxy)quinolin-4-yl]oxy}phenyl)-2-[(ethyloxy)imino]propanamide |
| 110 | (2E)-N-(4-{[6,7-bis(methyloxy)quinolin-4-yl]oxy}phenyl)-2-{[(phenylmethyl)oxy]imino}propanamide |
| 111 | N-(4-{[6,7-bis(methyloxy)quinolin-4-yl]oxy}phenyl)-1-(phenylmethyl)prolinamide |
| 112 | 1-(4-{[6,7-bis(methyloxy)quinolin-4-yl]oxy}phenyl)-3-[(4-methylphenyl)sulfonyl]-4-(phenylmethyl)imidazolidin-2-one |
| 113 | 1-(4-{[6,7-bis(methyloxy)quinolin-4-yl]oxy}phenyl)-4-(phenylmethyl)imidazolidin-2-one |

| Entry | Name |
|---|---|
| 114 | N-(4-{[6,7-bis(methyloxy)quinolin-4-yl]oxy}phenyl)-4-(phenylmethyl)-4,5-dihydro-1,3-oxazol-2-amine |
| 115 | 6,7-bis(methyloxy)-4-({4-[4-(phenylmethyl)piperazin-1-yl]phenyl}oxy)quinoline |
| 116 | 1-(4-{[6,7-bis(methyloxy)quinolin-4-yl]oxy}phenyl)-4-(phenylmethyl)piperazin-2-one |
| 117 | N1-(4-{[6,7-bis(methyloxy)quinolin-4-yl]oxy}phenyl)-N2-(phenylmethyl)alaninamide |
| 118 | N1-(4-{[6,7-bis(methyloxy)quinolin-4-yl]oxy}phenyl)-N2-methyl-N2-(phenylmethyl)alaninamide |
| 119 | N1-(4-{[6,7-bis(methyloxy)quinolin-4-yl]oxy}phenyl)-N2-(phenylmethyl)leucinamide |
| 120 | N1-(4-{[6,7-bis(methyloxy)quinolin-4-yl]oxy}phenyl)-N2-methyl-N2-(phenylmethyl)leucinamide |
| 121 | N1-(4-{[6,7-bis(methyloxy)quinolin-4-yl]oxy}phenyl)-N2-(phenylmethyl)valinamide |
| 122 | 4-(6,7-dimethoxy-quinolin-4-ylamino)-N-(3-phenyl-propyl)-benzamide |
| 123 | 4-benzyl-1-[4-(6,7-dimethoxy-quinolin-4-yloxy)-phenyl]-tetrahydro-pyrimidin-2-one |
| 124 | N-{3-Fluoro-4-[6-methoxy-7-(piperidin-4-ylmethoxy)-quinolin-4-yloxy]-phenyl}-N'-phenethyl-oxalamide |
| 125 | 2-(Benzyl-methyl-amino)-N-[4-(6,7-dimethoxy-quinolin-4-yloxy)-phenyl]-3-methyl-butyramide<br>(note: Alphabetic order of prefixes ignored while selecting parent chain) |
| 126 | N-[4-(6,7-Dimethoxy-quinolin-4-yloxy)-phenyl]-2-phenoxyimino-propionamide |
| 127 | 2-Benzyloxyimino-N-[4-(6,7-dimethoxy-quinolin-4-yloxy)-phenyl]-2-phenyl-acetamide |
| 128 | 4-[4-(4-Benzyl-piperidin-1-yl)-phenoxy]-6,7-dimethoxy-quinoline |
| 129 | N-[4-(6,7-Dimethoxy-quinolin-4-yloxy)-3-fluoro-phenyl]-N'-(2-isopropyl-1,2,3,4-tetrahydro-isoquinolin-1-ylmethyl)-oxalamide |
| 130 | N-[4-(6,7-Dimethoxy-quinolin-4-yloxy)-3-fluoro-phenyl]-N'-(2-ethyl-1,2,3,4-tetrahydro-isoquinolin-1-ylmethyl)-oxalamide |
| 131 | 4-(4-{3-Chloro-5-[2-(4-fluoro-phenylcarbamoyl)-acetylamino]-pyridin-2-yloxy}-6-methoxy-quinolin-7-yloxymethyl)-piperidine-1-carboxylic acid tert-butyl ester |
| 132 | N-{5-Chloro-6-[6-methoxy-7-(piperidin-4-ylmethoxy)-quinolin-4-yloxy]-pyridin-3-yl}-N'-(4-fluoro-phenyl)-malonamide |
| 133 | N-{5-Chloro-6-[6-methoxy-7-(1-methyl-piperidin-4-ylmethoxy)-quinolin-4-yloxy]-pyridin-3-yl}-N'-(4-fluoro-phenyl)-malonamide |
| 134 | N-{4-[7-(3-Diethylamino-propoxy)-6-methoxy-quinolin-4-yloxy]-3-fluoro-phenyl}-N'-phenethyl-oxalamide |
| 135 | N-{3-Fluoro-4-[6-methoxy-7-(3-morpholin-4-yl-propoxy)-quinolin-4-yloxy]-phenyl}-N'-phenethyl-oxalamide |
| 136 | N-{3-Fluoro-4-[6-methoxy-7-(3-piperidin-1-yl-propoxy)-quinolin-4-yloxy]-phenyl}-N'-phenethyl-oxalamide |
| 137 | N-{4-[7-(2-Diethylamino-ethoxy)-6-methoxy-quinolin-4-yloxy]-3-fluoro-phenyl}-N'-phenethyl-oxalamide |
| 138 | N-{3-Fluoro-4-[6-methoxy-7-(1-methyl-piperidin-4-ylmethoxy)-quinolin-4-yloxy]-phenyl}-N'-methyl-N'-phenethyl-oxalamide |
| 139 | N-{3-Fluoro-4-[6-methoxy-7-(2-methyl-octahydro-cyclopenta[c]pyrrol-5-ylmethoxy)-quinolin-4-yloxy]-phenyl}-N'-phenethyl-oxalamide |
| 140 | N-{3-Fluoro-4-[6-methoxy-7-(2-methyl-octahydro-cyclopenta[c]pyrrol-5-ylmethoxy)-quinazolin-4-yloxy]-phenyl}-N'-phenethyl-oxalamide |
| 141 | 2-(3,4-Dihydro-1H-isoquinolin-2-yl)-N-{3-fluoro-4-[6-methoxy-7-(1-methyl-piperidin-4-ylmethoxy)-quinolin-4-yloxy]-phenyl}-2-oxo-acetamide |
| 142 | N-{3-Fluoro-4-[6-methoxy-7-(piperidin-4-ylmethoxy)-quinolin-4-yloxy]-phenyl}-2-oxo-2-(3-phenyl-pyrrolidin-1-yl)-acetamide |
| 143 | N-{3-Fluoro-4-[6-methoxy-7-(piperidin-4-ylmethoxy)-quinolin-4-yloxy]-phenyl}-2-oxo-2-(2-phenyl-morpholin-4-yl)-acetamide |
| 144 | N-(2-Dimethylamino-2-phenyl-ethyl)-N'-{3-fluoro-4-[6-methoxy-7-(piperidin-4-ylmethoxy)-quinolin-4-yloxy]-phenyl}-oxalamide |
| 145 | N-{3-Fluoro-4-[6-methoxy-7-(piperidin-4-ylmethoxy)-quinolin-4-yloxy]-phenyl}-N'-(2-oxo-2-phenyl-ethyl)-oxalamide |
| 146 | N-[5-Chloro-6-(6,7-dimethoxy-quinolin-4-yloxy)-pyridin-3-yl]-2,2-difluoro-N'-(4-fluoro-phenyl)-malonamide |
| 147 | N-Benzyl-N'-{3-fluoro-4-[6-methoxy-7-(1-methyl-piperidin-4-ylmethoxy)-quinolin-4-yloxy]-phenyl}-oxalamide |
| 148 | N-{3-Fluoro-4-[6-methoxy-7-(piperidin-4-ylmethoxy)-quinolin-4-yloxy]-phenyl}-N'-[2-(2-fluoro-phenyl)-ethyl]-oxalamide |
| 149 | N-[2-(3-Chloro-phenyl)-ethyl]-N'-{3-fluoro-4-[6-methoxy-7-(piperidin-4-ylmethoxy)-quinolin-4-yloxy]-phenyl}-oxalamide |
| 150 | N-{3-Fluoro-4-[6-methoxy-7-(piperidin-4-ylmethoxy)-quinolin-4-yloxy]-phenyl}-N'-[2-(2-methoxy-phenyl)-ethyl]-oxalamide |
| 151 | N-{3-Fluoro-4-[6-methoxy-7-(piperidin-4-ylmethoxy)-quinolin-4-yloxy]-phenyl}-N'-(2-pyridin-3-yl-ethyl)-oxalamide |

-continued

| Entry | Name |
|---|---|
| 152 | N-Benzyl-N'-{3-fluoro-4-[6-methoxy-7-(piperidin-4-ylmethoxy)-quinolin-4-yloxy]-phenyl}-oxalamide |
| 153 | N-[2-(2,5-Dimethoxy-phenyl)-ethyl]-N'-{3-fluoro-4-[6-methoxy-7-(piperidin-4-ylmethoxy)-quinolin-4-yloxy]-phenyl}-oxalamide |
| 154 | N-{3-Fluoro-4-[6-methoxy-7-(piperidin-4-ylmethoxy)-quinolin-4-yloxy]-phenyl}-N'-[2-(2-trifluoromethyl-phenyl)-ethyl]-oxalamide |
| 155 | N-[2-(2-Ethoxy-phenyl)-ethyl]-N'-{3-fluoro-4-[6-methoxy-7-(piperidin-4-ylmethoxy)-quinolin-4-yloxy]-phenyl}-oxalamide |
| 156 | N-[2-(2,4-Dimethyl-phenyl)-ethyl]-N'-{3-fluoro-4-[6-methoxy-7-(piperidin-4-ylmethoxy)-quinolin-4-yloxy]-phenyl}-oxalamide |
| 157 | N-{3-Fluoro-4-[6-methoxy-7-(piperidin-4-ylmethoxy)-quinolin-4-yloxy]-phenyl}-N'-(1S-phenyl-2-p-tolyl-ethyl)-oxalamide |
| 158 | N-[2-(4-Chloro-phenyl)-ethyl]-N'-{3-fluoro-4-[6-methoxy-7-(piperidin-4-ylmethoxy)-quinolin-4-yloxy]-phenyl}-oxalamide |
| 159 | N-{3-Fluoro-4-[6-methoxy-7-(1-methyl-piperidin-4-ylmethoxy)-quinolin-4-yloxy]-phenyl}-oxalamic acid |
| 160 | N-{3-Fluoro-4-[6-methoxy-7-(piperidin-4-ylmethoxy)-quinolin-4-yloxy]-phenyl}-N'-[2-(3-fluoro-phenyl)-ethyl]-oxalamide |
| 161 | N-[2-(2-Chloro-phenyl)-ethyl]-N'-{3-fluoro-4-[6-methoxy-7-(piperidin-4-ylmethoxy)-quinolin-4-yloxy]-phenyl}-oxalamide |
| 162 | N-{3-Fluoro-4-[6-methoxy-7-(piperidin-4-ylmethoxy)-quinolin-4-yloxy]-phenyl}-N'-[2-(3-methoxy-phenyl)-ethyl]-oxalamide |
| 163 | N-(1,2-Diphenyl-ethyl)-N'-{3-fluoro-4-[6-methoxy-7-(piperidin-4-ylmethoxy)-quinolin-4-yloxy]-phenyl}-oxalamide |
| 164 | N-[2-(2,4-Dichloro-phenyl)-ethyl]-N'-{3-fluoro-4-[6-methoxy-7-(piperidin-4-ylmethoxy)-quinolin-4-yloxy]-phenyl}-oxalamide |
| 165 | N-[2-(3,4-Dimethoxy-phenyl)-ethyl]-N'-{3-fluoro-4-[6-methoxy-7-(piperidin-4-ylmethoxy)-quinolin-4-yloxy]-phenyl}-oxalamide |
| 166 | N-[2-(4-Ethyl-phenyl)-ethyl]-N'-{3-fluoro-4-[6-methoxy-7-(piperidin-4-ylmethoxy)-quinolin-4-yloxy]-phenyl}-oxalamide |
| 167 | N-[2-(4-Ethoxy-phenyl)-ethyl]-N'-{3-fluoro-4-[6-methoxy-7-(piperidin-4-ylmethoxy)-quinolin-4-yloxy]-phenyl}-oxalamide |
| 168 | N-[2-(4-Ethoxy-3-methoxy-phenyl)-ethyl]-N'-{3-fluoro-4-[6-methoxy-7-(piperidin-4-ylmethoxy)-quinolin-4-yloxy]-phenyl}-oxalamide |
| 169 | N-{3-Fluoro-4-[6-methoxy-7-(piperidin-4-ylmethoxy)-quinolin-4-yloxy]-phenyl}-N'-[2-(4-phenoxy-phenyl)-ethyl]-oxalamide |
| 170 | N-[2-(3-Ethoxy-4-methoxy-phenyl)-ethyl]-N'-{3-fluoro-4-[6-methoxy-7-(piperidin-4-ylmethoxy)-quinolin-4-yloxy]-phenyl}-oxalamide |
| 171 | N-{3-Fluoro-4-[6-methoxy-7-(piperidin-4-ylmethoxy)-quinolin-4-yloxy]-phenyl}-N'-(2-pyridin-2-yl-ethyl)-oxalamide |
| 172 | N-{3-Fluoro-4-[6-methoxy-7-(piperidin-4-ylmethoxy)-quinolin-4-yloxy]-phenyl}-N'-(2-pyridin-4-yl-ethyl)-oxalamide |
| 173 | N-{3-Fluoro-4-[6-methoxy-7-(piperidin-4-ylmethoxy)-quinolin-4-yloxy]-phenyl}-N'-[2-(4-fluoro-phenyl)-ethyl]-oxalamide |
| 174 | N-[2-(2-Bromo-phenyl)-ethyl]-N'-{3-fluoro-4-[6-methoxy-7-(piperidin-4-ylmethoxy)-quinolin-4-yloxy]-phenyl}-oxalamide |
| 175 | N-[2-(2-Chloro-6-fluoro-phenyl)-ethyl]-N'-{3-fluoro-4-[6-methoxy-7-(piperidin-4-ylmethoxy)-quinolin-4-yloxy]-phenyl}-oxalamide |
| 176 | N-{3-Fluoro-4-[6-methoxy-7-(piperidin-4-ylmethoxy)-quinolin-4-yloxy]-phenyl}-N'-(2R-phenyl-propyl)-oxalamide |
| 177 | N-{3-Fluoro-4-[6-methoxy-7-(piperidin-4-ylmethoxy)-quinolin-4-yloxy]-phenyl}-N'-indan-1-yl-oxalamide |
| 178 | N-{3-Fluoro-4-[6-methoxy-7-(1-methyl-piperidin-4-ylmethoxy)-quinolin-4-yloxy]-phenyl}-N'-isobutyl-oxalamide |
| 179 | N-{3-Fluoro-4-[6-methoxy-7-(1-methyl-piperidin-4-ylmethoxy)-quinolin-4-yloxy]-phenyl}-N'-(3-methyl-butyl)-oxalamide |
| 180 | N-{3-Fluoro-4-[6-methoxy-7-(1-methyl-piperidin-4-ylmethoxy)-quinolin-4-yloxy]-phenyl}-N'-(2R-phenyl-propyl)-oxalamide |
| 181 | N-{3-Fluoro-4-[6-methoxy-7-(1-methyl-piperidin-4-ylmethoxy)-quinolin-4-yloxy]-phenyl}-N'-(2-phenyl-propyl)-oxalamide |
| 182 | N-{3-Fluoro-4-[6-methoxy-7-(1-methyl-piperidin-4-ylmethoxy)-quinolin-4-yloxy]-phenyl}-N'-indan-2-yl-oxalamide |
| 183 | N-{3-Fluoro-4-[6-methoxy-7-(piperidin-4-ylmethoxy)-quinolin-4-yloxy]-phenyl}-N'-(1R-phenyl-ethyl)-oxalamide |
| 184 | N-{3-Fluoro-4-[6-methoxy-7-(piperidin-4-ylmethoxy)-quinolin-4-yloxy]-phenyl}-N'-(1S-phenyl-ethyl)-oxalamide |
| 185 | N-[2-(3-Bromo-phenyl)-ethyl]-N'-{3-fluoro-4-[6-methoxy-7-(piperidin-4-ylmethoxy)-quinolin-4-yloxy]-phenyl}-oxalamide |
| 186 | N-[2-(2,6-Dichloro-phenyl)-ethyl]-N'-{3-fluoro-4-[6-methoxy-7-(piperidin-4-ylmethoxy)-quinolin-4-yloxy]-phenyl}-oxalamide |
| 187 | N-[2-(2,4-Dichloro-phenyl)-ethyl]-N'-{3-fluoro-4-[6-methoxy-7-(piperidin-4-ylmethoxy)-quinolin-4-yloxy]-phenyl}-oxalamide |
| 188 | N-(2-Benzo[1,3]dioxol-5-yl-ethyl)-N'-{3-fluoro-4-[6-methoxy-7-(piperidin-4-ylmethoxy)-quinolin-4-yloxy]-phenyl}-oxalamide |
| 189 | N-[2-(3-Bromo-4-methoxy-phenyl)-ethyl]-N'-{3-fluoro-4-[6-methoxy-7-(piperidin-4-ylmethoxy)-quinolin-4-yloxy]-phenyl}-oxalamide |
| 190 | N-[2-(3,5-Dimethoxy-phenyl)-ethyl]-N'-{3-fluoro-4-[6-methoxy-7-(piperidin-4-ylmethoxy)-quinolin-4-yloxy]-phenyl}-oxalamide |

| Entry | Name |
|---|---|
| 191 | N-{3-Fluoro-4-[6-methoxy-7-(piperidin-4-ylmethoxy)-quinolin-4-yloxy]-phenyl}-N'-(2-o-tolyl-ethyl)-oxalamide |
| 192 | N-{3-Fluoro-4-[6-methoxy-7-(piperidin-4-ylmethoxy)-quinolin-4-yloxy]-phenyl}-N'-(2-m-tolyl-ethyl)-oxalamide |
| 193 | N-[2-(3-Ethoxy-phenyl)-ethyl]-N'-{3-fluoro-4-[6-methoxy-7-(piperidin-4-ylmethoxy)-quinolin-4-yloxy]-phenyl}-oxalamide |
| 194 | N-[2-(3,4-Dimethyl-phenyl)-ethyl]-N'-{3-fluoro-4-[6-methoxy-7-(piperidin-4-ylmethoxy)-quinolin-4-yloxy]-phenyl}-oxalamide |
| 195 | N-[2-(2,5-Dimethyl-phenyl)-ethyl]-N'-{3-fluoro-4-[6-methoxy-7-(piperidin-4-ylmethoxy)-quinolin-4-yloxy]-phenyl}-oxalamide |
| 196 | N-[2-(3-Chloro-4-propoxy-phenyl)-ethyl]-N'-{3-fluoro-4-[6-methoxy-7-(piperidin-4-ylmethoxy)-quinolin-4-yloxy]-phenyl}-oxalamide |
| 197 | N-[2-(4-Butoxy-3-chloro-phenyl)-ethyl]-N'-{3-fluoro-4-[6-methoxy-7-(piperidin-4-ylmethoxy)-quinolin-4-yloxy]-phenyl}-oxalamide |
| 198 | N-[2-(4-tert-Butyl-phenyl)-ethyl]-N'-{3-fluoro-4-[6-methoxy-7-(piperidin-4-ylmethoxy)-quinolin-4-yloxy]-phenyl}-oxalamide |
| 199 | N-{3-Fluoro-4-[6-methoxy-7-(piperidin-4-ylmethoxy)-quinolin-4-yloxy]-phenyl}-N'-[2-(4-sulfamoyl-phenyl)-ethyl]-oxalamide |
| 200 | N-{3-Fluoro-4-[6-methoxy-7-(piperidin-4-ylmethoxy)-quinolin-4-yloxy]-phenyl}-N'-[2-(4-hydroxy-3-methoxy-phenyl)-ethyl]-oxalamide |
| 201 | N-{3-Fluoro-4-[6-methoxy-7-(piperidin-4-ylmethoxy)-quinolin-4-yloxy]-phenyl}-N'-[2-(3-hydroxy-4-methoxy-phenyl)-ethyl]-oxalamide |
| 202 | N-(2,4-Dichloro-benzyl)-N'-{3-fluoro-4-[6-methoxy-7-(piperidin-4-ylmethoxy)-quinolin-4-yloxy]-phenyl}-oxalamide |
| 203 | N-{3-Fluoro-4-[6-methoxy-7-(piperidin-4-ylmethoxy)-quinolin-4-yloxy]-phenyl}-N'-(4-fluoro-2-trifluoromethyl-benzyl)-oxalamide |
| 204 | N-{3-Fluoro-4-[6-methoxy-7-(piperidin-4-ylmethoxy)-quinolin-4-yloxy]-phenyl}-N'-(1-p-tolyl-ethyl)-oxalamide |
| 205 | N-{3-Fluoro-4-[6-methoxy-7-(piperidin-4-ylmethoxy)-quinolin-4-yloxy]-phenyl}-N'-(3-fluoro-4-trifluoromethyl-benzyl)-oxalamide |
| 206 | N-(3-Chloro-4-fluoro-benzyl)-N'-{3-fluoro-4-[6-methoxy-7-(piperidin-4-ylmethoxy)-quinolin-4-yloxy]-phenyl}-oxalamide |
| 207 | N-{3-Fluoro-4-[6-methoxy-7-(piperidin-4-ylmethoxy)-quinolin-4-yloxy]-phenyl}-N'-[1-(3-methoxy-phenyl)-ethyl]-oxalamide |
| 208 | N-{3-Fluoro-4-[6-methoxy-7-(piperidin-4-ylmethoxy)-quinolin-4-yloxy]-phenyl}-N'-(1-naphthalen-2-yl-ethyl)-oxalamide |
| 209 | N-(4-Chloro-3-trifluoromethyl-benzyl)-N'-{3-fluoro-4-[6-methoxy-7-(piperidin-4-ylmethoxy)-quinolin-4-yloxy]-phenyl}-oxalamide |
| 210 | N-{3-Fluoro-4-[6-methoxy-7-(piperidin-4-ylmethoxy)-quinolin-4-yloxy]-phenyl}-N'-(1-p-tolyl-ethyl)-oxalamide |
| 211 | N-{3-Fluoro-4-[6-methoxy-7-(piperidin-4-ylmethoxy)-quinolin-4-yloxy]-phenyl}-N'-(6-trifluoromethyl-pyridin-3-ylmethyl)-oxalamide |
| 212 | N-{3-Fluoro-4-[6-methoxy-7-(piperidin-4-ylmethoxy)-quinolin-4-yloxy]-phenyl}-N'-(2-methyl-benzyl)-oxalamide |
| 213 | N-{3-Fluoro-4-[6-methoxy-7-(piperidin-4-ylmethoxy)-quinolin-4-yloxy]-phenyl}-N'-(3-methyl-benzyl)-oxalamide |
| 214 | N-{3-Fluoro-4-[6-methoxy-7-(piperidin-4-ylmethoxy)-quinolin-4-yloxy]-phenyl}-N'-(4-fluoro-3-trifluoromethyl-benzyl)-oxalamide |
| 215 | N-(3,5-Dichloro-benzyl)-N'-{3-fluoro-4-[6-methoxy-7-(piperidin-4-ylmethoxy)-quinolin-4-yloxy]-phenyl}-oxalamide |
| 216 | N-{3-Fluoro-4-[6-methoxy-7-(piperidin-4-ylmethoxy)-quinolin-4-yloxy]-phenyl}-N'-(1R,2,3,4-tetrahydro-naphthalen-1-yl)-oxalamide |
| 217 | N-{3-Fluoro-4-[6-methoxy-7-(piperidin-4-ylmethoxy)-quinolin-4-yloxy]-phenyl}-N'-(1S,2,3,4-tetrahydro-naphthalen-1-yl)-oxalamide |
| 218 | N-Cyclopentyl-N'-{3-fluoro-4-[6-methoxy-7-(piperidin-4-ylmethoxy)-quinolin-4-yloxy]-phenyl}-oxalamide |
| 219 | N-[1-(4-Bromo-phenyl)-ethyl]-N'-{3-fluoro-4-[6-methoxy-7-(piperidin-4-ylmethoxy)-quinolin-4-yloxy]-phenyl}-oxalamide |
| 220 | N-(2-Fluoro-benzyl)-N'-{3-fluoro-4-[6-methoxy-7-(piperidin-4-ylmethoxy)-quinolin-4-yloxy]-phenyl}-oxalamide |
| 221 | N-[2-(3,4-Dichloro-phenyl)-ethyl]-N'-{3-fluoro-4-[6-methoxy-7-(piperidin-4-ylmethoxy)-quinolin-4-yloxy]-phenyl}-oxalamide |
| 222 | N-(4-Fluoro-benzyl)-N'-{3-fluoro-4-[6-methoxy-7-(piperidin-4-ylmethoxy)-quinolin-4-yloxy]-phenyl}-oxalamide |
| 223 | N-(2,3-Difluoro-benzyl)-N'-{3-fluoro-4-[6-methoxy-7-(piperidin-4-ylmethoxy)-quinolin-4-yloxy]-phenyl}-oxalamide |
| 224 | N-{3-Fluoro-4-[6-methoxy-7-(piperidin-4-ylmethoxy)-quinolin-4-yloxy]-phenyl}-N'-(2-phenoxy-ethyl)-oxalamide |
| 225 | N-(2,2-Diphenyl-ethyl)-N'-{3-fluoro-4-[6-methoxy-7-(piperidin-4-ylmethoxy)-quinolin-4-yloxy]-phenyl}-oxalamide |
| 226 | N-{3-Fluoro-4-[6-methoxy-7-(piperidin-4-ylmethoxy)-quinolin-4-yloxy]-phenyl}-N'-[2-(4-methoxy-phenyl)-ethyl]-oxalamide |
| 227 | N-{3-Fluoro-4-[6-methoxy-7-(piperidin-4-ylmethoxy)-quinolin-4-yloxy]-phenyl}-N'-(2-phenyl-propyl)-oxalamide |
| 228 | N-[2-(4-Bromo-phenyl)-ethyl]-N'-{3-fluoro-4-[6-methoxy-7-(piperidin-4-ylmethoxy)-quinolin-4-yloxy]-phenyl}-oxalamide |
| 229 | N-{4-[7-(1-Ethyl-piperidin-4-ylmethoxy)-6-methoxy-quinolin-4-yloxy]-3-fluoro-phenyl}-2-oxo-2-(2-phenyl-morpholin-4-yl)-acetamide |

-continued

| Entry | Name |
|---|---|
| 230 | N-{3-Fluoro-4-[6-methoxy-7-(piperidin-4-ylmethoxy)-quinolin-4-yloxy]-phenyl}-N'-(3-fluoro-5-trifluoromethyl-benzyl)-oxalamide |
| 231 | N-(3,5-Difluoro-benzyl)-N'-{3-fluoro-4-[6-methoxy-7-(piperidin-4-ylmethoxy)-quinolin-4-yloxy]-phenyl}-oxalamide |
| 232 | N-(2-Chloro-5-trifluoromethyl-benzyl)-N'-{3-fluoro-4-[6-methoxy-7-(piperidin-4-ylmethoxy)-quinolin-4-yloxy]-phenyl}-oxalamide |
| 233 | N-[4-(6,7-Dimethoxy-quinolin-4-yloxy)-3-fluoro-phenyl]-N'-(2-dimethylamino-2-phenyl-ethyl)-oxalamide |
| 234 | N-{3-Fluoro-4-[6-methoxy-7-(piperidin-4-ylmethoxy)-quinolin-4-yloxy]-phenyl}-N'-(4-methoxy-benzyl)-oxalamide |
| 235 | N-{3-Fluoro-4-[6-methoxy-7-(piperidin-4-ylmethoxy)-quinolin-4-yloxy]-phenyl}-N'-(4-trifluoromethyl-benzyl)-oxalamide |
| 236 | N-{3-Fluoro-4-[6-methoxy-7-(piperidin-4-ylmethoxy)-quinolin-4-yloxy]-phenyl}-N'-(3-methoxy-benzyl)-oxalamide |
| 237 | N-{3-Fluoro-4-[6-methoxy-7-(piperidin-4-ylmethoxy)-quinolin-4-yloxy]-phenyl}-N'-(3-trifluoromethyl-benzyl)-oxalamide |
| 238 | N-{3-Fluoro-4-[6-methoxy-7-(piperidin-4-ylmethoxy)-quinolin-4-yloxy]-phenyl}-N'-(3-trifluoromethoxy-benzyl)-oxalamide |
| 239 | N-{3-Fluoro-4-[6-methoxy-7-(piperidin-4-ylmethoxy)-quinolin-4-yloxy]-phenyl}-N'-(2-methoxy-benzyl)-oxalamide |
| 240 | N-{3-Fluoro-4-[6-methoxy-7-(piperidin-4-ylmethoxy)-quinolin-4-yloxy]-phenyl}-N'-(2-trifluoromethyl-benzyl)-oxalamide |
| 241 | N-(3-Chloro-benzyl)-N'-{3-fluoro-4-[6-methoxy-7-(piperidin-4-ylmethoxy)-quinolin-4-yloxy]-phenyl}-oxalamide |
| 242 | N-{3-Fluoro-4-[6-methoxy-7-(piperidin-4-ylmethoxy)-quinolin-4-yloxy]-phenyl}-N'-(2-trifluoromethoxy-benzyl)-oxalamide |
| 243 | N-(2-Chloro-benzyl)-N'-{3-fluoro-4-[6-methoxy-7-(piperidin-4-ylmethoxy)-quinolin-4-yloxy]-phenyl}-oxalamide |
| 244 | N-{3-Fluoro-4-[6-methoxy-7-(piperidin-4-ylmethoxy)-quinolin-4-yloxy]-phenyl}-N'-(4-trifluoromethoxy-benzyl)-oxalamide |
| 245 | N-{3-Fluoro-4-[6-methoxy-7-(1-methyl-piperidin-4-ylmethoxy)-quinolin-4-yloxy]-phenyl}-N'-(4-methoxy-benzyl)-oxalamide |
| 246 | N-{3-Fluoro-4-[6-methoxy-7-(1-methyl-piperidin-4-ylmethoxy)-quinolin-4-yloxy]-phenyl}-N'-(4-trifluoromethyl-benzyl)-oxalamide |
| 247 | N-{4-[7-(Azetidin-3-ylmethoxy)-6-methoxy-quinolin-4-yloxy]-3-fluoro-phenyl}-N'-phenethyl-oxalamide |
| 248 | N-{3-Fluoro-4-[6-methoxy-7-(1-methyl-azetidin-3-ylmethoxy)-quinolin-4-yloxy]-phenyl}-N'-phenethyl-oxalamide |
| 249 | N-{3-Fluoro-4-[6-methoxy-7-(piperidin-4-ylmethoxy)-quinolin-4-yloxy]-phenyl}-N'-(2-hydroxy-2-phenyl-ethyl)-oxalamide |
| 250 | N-[5-Chloro-6-(6,7-dimethoxy-quinolin-4-yloxy)-pyridin-3-yl]-N'-(2,4-difluoro-phenyl)-malonamide |
| 251 | N-[5-Chloro-6-(6,7-dimethoxy-quinolin-4-yloxy)-pyridin-3-yl]-N'-(4-fluoro-phenyl)-N'-methyl-malonamide |
| 252 | N-{3-Fluoro-4-[6-methoxy-7-(piperidin-4-ylmethoxy)-quinolin-4-yloxy]-phenyl}-N'-(1R-phenyl-propyl)-oxalamide |
| 253 | N-{3-Fluoro-4-[6-methoxy-7-(piperidin-4-ylmethoxy)-quinolin-4-yloxy]-phenyl}-N'-(1R-phenyl-propyl)-oxalamide |
| 254 | N-(3,4-Difluoro-benzyl)-N'-{3-fluoro-4-[6-methoxy-7-(piperidin-4-ylmethoxy)-quinolin-4-yloxy]-phenyl}-oxalamide |
| 255 | N-(2,6-Difluoro-benzyl)-N'-{3-fluoro-4-[6-methoxy-7-(piperidin-4-ylmethoxy)-quinolin-4-yloxy]-phenyl}-oxalamide |
| 256 | N-{3-Fluoro-4-[6-methoxy-7-(1-methyl-piperidin-4-ylmethoxy)-quinolin-4-yloxy]-phenyl}-N'-[2-(4-fluoro-phenyl)-ethyl]-oxalamide |
| 257 | N-{3-Fluoro-4-[6-methoxy-7-(1-methyl-piperidin-4-ylmethoxy)-quinolin-4-yloxy]-phenyl}-N'-phenyl-oxalamide |
| 258 | N-{3-Fluoro-4-[6-methoxy-7-(piperidin-4-ylmethoxy)-quinolin-4-yloxy]-phenyl}-N'-(3-fluoro-phenyl)-oxalamide |
| 259 | N-(4-Chloro-3-fluoro-phenyl)-N'-{3-fluoro-4-[6-methoxy-7-(piperidin-4-ylmethoxy)-quinolin-4-yloxy]-phenyl}-oxalamide |
| 260 | N-(3,4-Dimethoxy-phenyl)-N'-{3-fluoro-4-[6-methoxy-7-(piperidin-4-ylmethoxy)-quinolin-4-yloxy]-phenyl}-oxalamide |
| 261 | N-{3-Fluoro-4-[6-methoxy-7-(piperidin-4-ylmethoxy)-quinolin-4-yloxy]-phenyl}-N'-(3-methyl-butyl)-oxalamide |
| 262 | N-(3,3-Dimethyl-butyl)-N'-{3-fluoro-4-[6-methoxy-7-(piperidin-4-ylmethoxy)-quinolin-4-yloxy]-phenyl}-oxalamide |
| 263 | N-{5-Chloro-6-[6-methoxy-7-(3-piperidin-1-yl-propoxy)-quinolin-4-yloxy]-pyridin-3-yl}-N'-(4-fluoro-phenyl)-malonamide |
| 264 | N-{5-Chloro-6-[6-methoxy-7-(3-morpholin-4-yl-propoxy)-quinolin-4-yloxy]-pyridin-3-yl}-N'-(4-fluoro-phenyl)-malonamide |
| 265 | N-{5-Chloro-6-[7-(3-diethylamino-propoxy)-6-methoxy-quinolin-4-yloxy]-pyridin-3-yl}-N'-(4-fluoro-phenyl)-malonamide |
| 266 | N-(4-Chloro-benzyl)-N'-{3-fluoro-4-[6-methoxy-7-(piperidin-4-ylmethoxy)-quinolin-4-yloxy]-phenyl}-oxalamide |
| 267 | N-(3,5-Dimethoxy-benzyl)-N'-{3-fluoro-4-[6-methoxy-7-(piperidin-4-ylmethoxy)-quinolin-4-yloxy]-phenyl}-oxalamide |
| 268 | N-(4-Butyl-benzyl)-N'-{3-fluoro-4-[6-methoxy-7-(piperidin-4-ylmethoxy)-quinolin-4-yloxy]-phenyl}-oxalamide |

| Entry | Name |
|---|---|
| 269 | N-{3-Fluoro-4-[6-methoxy-7-(piperidin-4-ylmethoxy)-quinolin-4-yloxy]-phenyl}-N'-(2-p-tolyl-ethyl)-oxalamide |
| 270 | N-(3,5-Bis-trifluoromethyl-benzyl)-N'-{3-fluoro-4-[6-methoxy-7-(piperidin-4-ylmethoxy)-quinolin-4-yloxy]-phenyl}-oxalamide |
| 271 | N-{3-Fluoro-4-[6-methoxy-7-(piperidin-4-ylmethoxy)-quinolin-4-yloxy]-phenyl}-N'-pyrazin-2-ylmethyl-oxalamide |
| 272 | N-{3-Fluoro-4-[6-methoxy-7-(piperidin-4-ylmethoxy)-quinolin-4-yloxy]-phenyl}-N'-pyridin-2-ylmethyl-oxalamide |
| 273 | N-{3-Fluoro-4-[6-methoxy-7-(piperidin-4-ylmethoxy)-quinazolin-4-yloxy]-phenyl}-N'-phenethyl-oxalamide |
| 274 | N-{3-Fluoro-4-[6-methoxy-7-(1-methyl-piperidin-4-ylmethoxy)-quinazolin-4-yloxy]-phenyl}-N'-phenethyl-oxalamide |
| 275 | N-{3-Fluoro-4-[6-methoxy-7-(piperidin-4-ylmethoxy)-quinolin-4-yloxy]-phenyl}-N'-(2-fluoro-3-trifluoromethyl-benzyl)-oxalamide |
| 276 | N-[2-(2-Bromo-6-methoxy-phenyl)-ethyl]-N'-{3-fluoro-4-[6-methoxy-7-(piperidin-4-ylmethoxy)-quinolin-4-yloxy]-phenyl}-oxalamide |
| 277 | N-[2-(3,4-Dimethoxy-phenyl)-ethyl]-N'-{3-fluoro-4-[6-methoxy-7-(piperidin-4-ylmethoxy)-quinolin-4-yloxy]-phenyl}-N-methyl-oxalamide |
| 278 | N-[2-(5-Bromo-2-methoxy-phenyl)-ethyl]-N'-{3-fluoro-4-[6-methoxy-7-(piperidin-4-ylmethoxy)-quinolin-4-yloxy]-phenyl}-oxalamide |
| 279 | N-{3-Fluoro-4-[6-methoxy-7-(piperidin-4-ylmethoxy)-quinolin-4-yloxy]-phenyl}-N'-(2-fluoro-5-trifluoromethyl-benzyl)-oxalamide |
| 280 | N-{3-Fluoro-4-[6-methoxy-7-(piperidin-4-ylmethoxy)-quinolin-4-yloxy]-phenyl}-N'-[1-(4-fluoro-phenyl)-ethyl]-oxalamide |
| 281 | N-(1S-Benzyl-2-oxo-2-pyrrolidin-1-yl-ethyl)-N'-{3-fluoro-4-[6-methoxy-7-(piperidin-4-ylmethoxy)-quinolin-4-yloxy]-phenyl}-oxalamide |
| 282 | N-{3-Fluoro-4-[6-methoxy-7-(octahydro-cyclopenta[c]pyrrol-5-ylmethoxy)-quinazolin-4-yloxy]-phenyl}-N'-phenethyl-oxalamide |
| 283 | N-[2-(4-Amino-phenyl)-ethyl]-N'-{3-fluoro-4-[6-methoxy-7-(piperidin-4-ylmethoxy)-quinolin-4-yloxy]-phenyl}-oxalamide |
| 284 | 2-(4-Benzyl-piperidin-1-yl)-N-{3-fluoro-4-[6-methoxy-7-(piperidin-4-ylmethoxy)-quinolin-4-yloxy]-phenyl}-2-oxo-acetamide |
| 285 | N-[4-(6,7-Dimethoxy-quinolin-4-yloxy)-phenyl]-N'-(4-fluoro-phenyl)-malonamide |
| 286 | N-[5-Chloro-6-(6,7-dimethoxy-quinolin-4-yloxy)-pyridin-3-yl]-N'-(3-fluoro-phenyl)-malonamide |
| 287 | N-[5-Chloro-6-(6,7-dimethoxy-quinolin-4-yloxy)-pyridin-3-yl]-N'-phenyl-malonamide |
| 288 | N-[5-Chloro-6-(6,7-dimethoxy-quinolin-4-yloxy)-pyridin-3-yl]-N'-(4-fluoro-phenyl)-2,2-dimethyl-malonamide |
| 289 | N-Ethyl-N'-{3-fluoro-4-[6-methoxy-7-(piperidin-4-ylmethoxy)-quinolin-4-yloxy]-phenyl}-oxalamide |
| 290 | N-{3-Fluoro-4-[6-methoxy-7-(piperidin-4-ylmethoxy)-quinolin-4-yloxy]-phenyl}-N'-isopropyl-oxalamide |
| 291 | N-Butyl-N'-{3-fluoro-4-[6-methoxy-7-(piperidin-4-ylmethoxy)-quinolin-4-yloxy]-phenyl}-oxalamide |
| 292 | N-{3-Fluoro-4-[6-methoxy-7-(piperidin-4-ylmethoxy)-quinolin-4-yloxy]-phenyl}-N'-(2-methoxy-ethyl)-oxalamide |
| 293 | N-Cyclopropylmethyl-N'-{3-fluoro-4-[6-methoxy-7-(piperidin-4-ylmethoxy)-quinolin-4-yloxy]-phenyl}-oxalamide |
| 294 | N-{3-Fluoro-4-[6-methoxy-7-(piperidin-4-ylmethoxy)-quinolin-4-yloxy]-phenyl}-N'-(2-morpholin-4-yl-ethyl)-oxalamide |
| 295 | N-{3-Fluoro-4-[6-methoxy-7-(piperidin-4-ylmethoxy)-quinolin-4-yloxy]-phenyl}-2-oxo-2-pyrrolidin-1-yl-acetamide |
| 296 | N-Ethyl-N'-{3-fluoro-4-[6-methoxy-7-(piperidin-4-ylmethoxy)-quinolin-4-yloxy]-phenyl}-N-methyl-oxalamide |

The Compounds in Table 3c can be prepared as pharmaceutically acceptable salts, solvates, hydrates, and/or isomers thereof. All such salt, solvate, hydrate, and isomer combinations of the Compounds in Table 3c can be used to practice the invention.

| Entry | Name |
|---|---|
| 1 | N-(6-{[6,7-bis(methyloxy)quinolin-4-yl]oxy}-5-chloropyridin-3-yl)-N'-(4-fluorophenyl)cyclopropane-1,1-dicarboxamide |
| 2 | N-(6-{[6,7-bis(methyloxy)quinolin-4-yl]oxy}-5-chloropyridin-3-yl)-N'-(4-fluorophenyl)cyclobutane-1,1-dicarboxamide |
| 3 | N-(6-{[6,7-bis(methyloxy)quinolin-4-yl]oxy}-5-chloropyridin-3-yl)-N'-(phenylmethyl)cyclopropane-1,1-dicarboxamide |
| 4 | N-(6-{[6,7-bis(methyloxy)quinolin-4-yl]oxy}-5-chloropyridin-3-yl)-N'-phenylcyclopropane-1,1-dicarboxamide |

-continued

| Entry | Name |
|---|---|
| 5 | N-[3-fluoro-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide |
| 6 | N-[3-fluoro-4-({6-(methyloxy)-7-[(3-piperidin-1-ylpropyl)oxy]quinolin-4-yl}oxy)phenyl]-N'-(4-fluorophenyl)cyclopropane-1,1-dicarboxamide |
| 7 | N-[3-fluoro-4-({6-(methyloxy)-7-[(3-piperidin-1-ylpropyl)oxy]quinolin-4-yl}oxy)phenyl]-N'-(4-fluorophenyl)cyclobutane-1,1-dicarboxamide |
| 8 | N-(6-{[6,7-bis(methyloxy)quinolin-4-yl]oxy}-5-chloropyridin-3-yl)-N'-(2-phenylethyl)cyclopropane-1,1-dicarboxamide |
| 9 | N-(6-{[6,7-bis(methyloxy)quinolin-4-yl]oxy}-2-methylpyridin-3-yl)-N'-(4-fluorophenyl)cyclopropane-1,1-dicarboxamide |
| 10 | N-{4-[(7-chloroquinolin-4-yl)oxy]-3-fluorophenyl}-N'-(4-fluorophenyl)cyclopropane-1,1-dicarboxamide |
| 11 | N-{4-[(7-chloroquinolin-4-yl)oxy]phenyl}-N'-(4-fluorophenyl)cyclopropane-1,1-dicarboxamide |
| 12 | N-(4-{[6,7-bis(methyloxy)quinolin-4-yl]oxy}phenyl)-N'-(4-fluorophenyl)cyclopropane-1,1-dicarboxamide |
| 13 | N-(4-{[6,7-bis(methyloxy)quinazolin-4-yl]oxy}phenyl)-N'-(4-fluorophenyl)cyclopropane-1,1-dicarboxamide |
| 14 | N-(4-{[6,7-bis(methyloxy)quinazolin-4-yl]oxy}-3-fluorophenyl)-N'-(4-fluorophenyl)cyclopropane-1,1-dicarboxamide |
| 15 | N-[3-fluoro-4-({6-(methyloxy)-7-[(3-morpholin-4-ylpropyl)oxy]quinazolin-4-yl}oxy)phenyl]-N'-(4-fluorophenyl)cyclopropane-1,1-dicarboxamide |
| 16 | N-{5-chloro-6-[(6-(methyloxy)-7-{[(1-methylpiperidin-4-yl)methyl]oxy}quinolin-4-yl)oxy]pyridin-3-yl}-N'-(4-fluorophenyl)cyclopropane-1,1-dicarboxamide |
| 17 | N-[5-chloro-6-({6-(methyloxy)-7-[(piperidin-4-ylmethyl)oxy]quinolin-4-yl}oxy)pyridin-3-yl]-N'-(4-fluorophenyl)cyclopropane-1,1-dicarboxamide |
| 18 | N-[5-chloro-6-({6-(methyloxy)-7-[(phenylmethyl)oxy]quinolin-4-yl}oxy)pyridin-3-yl]-N'-(4-fluorophenyl)cyclopropane-1,1-dicarboxamide |
| 19 | N-(4-{[7-{[2-(diethylamino)ethyl]oxy}-6-(methyloxy)quinolin-4-yl]oxy}-3-fluorophenyl)-N'-(4-fluorophenyl)cyclopropane-1,1-dicarboxamide |
| 20 | N-(4-{[7-{[2-(diethylamino)ethyl]oxy}-6-(methyloxy)quinolin-4-yl]oxy}-3-fluorophenyl)-N'-(4-fluorophenyl)cyclobutane-1,1-dicarboxamide |
| 21 | N-{3-fluoro-4-[(6-(methyloxy)-7-{[(1-methylpiperidin-4-yl)methyl]oxy}quinazolin-4-yl)oxy]phenyl}-N'-(4-fluorophenyl)cyclopropane-1,1-dicarboxamide |
| 22 | N-(4-{[6,7-bis(methyloxy)quinolin-4-yl]oxy}-2-methylphenyl)-N'-(4-fluorophenyl)cyclopropane-1,1-dicarboxamide |
| 23 | N-(4-fluorophenyl)-N'-[2-methyl-6-({6-(methyloxy)-7-[(3-morpholin-4-ylpropyl)oxy]quinolin-4-yl}oxy)pyridin-3-yl]cyclopropane-1,1-dicarboxamide |
| 24 | N-(4-{[6,7-bis(methyloxy)quinolin-4-yl]oxy}-3-fluorophenyl)-N'-(4-fluorophenyl)cyclopropane-1,1-dicarboxamide |
| 25 | N-(6-{[6,7-bis(methyloxy)quinolin-4-yl]oxy}-5-chloro-2-methylpyridin-3-yl)-N'-(4-fluorophenyl)cyclopropane-1,1-dicarboxamide |
| 26 | N-[3-fluoro-4-({7-(methyloxy)-6-[(3-morpholin-4-ylpropyl)oxy]quinazolin-4-yl}oxy)phenyl]-N'-(4-fluorophenyl)cyclopropane-1,1-dicarboxamide |
| 27 | N-(4-{[6,7-bis(methyloxy)quinolin-4-yl]oxy}-3,5-difluorophenyl)-N'-(4-fluorophenyl)cyclopropane-1,1-dicarboxamide |
| 28 | N-(4-{[6,7-bis(methyloxy)quinolin-4-yl]oxy}-2,5-difluorophenyl)-N'-(4-fluorophenyl)cyclopropane-1,1-dicarboxamide |
| 29 | N-[3-fluoro-4-({7-(methyloxy)-6-[(3-morpholin-4-ylpropyl)oxy]quinolin-4-yl}oxy)phenyl]-N'-(4-fluorophenyl)cyclopropane-1,1-dicarboxamide |
| 30 | N-{3-fluoro-4-[(6-(methyloxy)-7-(2-methyl octahydrocyclo-penta[c]pyrrol-5-ylmethoxy)quinazolin-4-yl)oxy]phenyl}-N'-(4-fluorophenyl)cyclopropane-1,1-dicarboxamide |
| 31 | N-{3-fluoro-4-[(7-(methyloxy)-6-{[(1-methylpiperidin-4-yl)methyl]oxy}quinazolin-4-yl)oxy]phenyl}-N'-(4-fluorophenyl)cyclopropane-1,1-dicarboxamide |
| 32 | N-[5-fluoro-2-methyl-4-({6-(methyloxy)-7-[(3-morpholin-4-ylpropyl)oxy]quinolin-4-yl}oxy)phenyl]-N'-(4-fluorophenyl)cyclopropane-1,1-dicarboxamide |
| 33 | N-(4-{[6,7-bis(methyloxy)quinolin-4-yl]oxy}-2,3,5-trifluorophenyl)-N'-(4-fluorophenyl)cyclopropane-1,1-dicarboxamide |
| 34 | N-(4-{[6,7-bis(methyloxy)quinolin-4-yl]oxy}-5-fluoro-2-methylphenyl)-N'-(4-fluorophenyl)cyclopropane-1,1-dicarboxamide |
| 35 | N-(4-{[6,7-bis(methyloxy)quinolin-4-yl]oxy}-2-chloro-5-methylphenyl)-N'-(4-fluorophenyl)cyclopropane-1,1-dicarboxamide |
| 36 | N-(3-fluoro-4-{[6-hydroxy-7-(methyloxy)quinolin-4-yl]oxy}phenyl)-N'-(4-fluorophenyl)cyclopropane-1,1-dicarboxamide |
| 37 | N-(4-fluorophenyl)-N'-[2-methyl-4-({6-(methyloxy)-7-[(3-morpholin-4-ylpropyl)oxy]quinolin-4-yl}oxy)phenyl]cyclopropane-1,1-dicarboxamide |
| 38 | N-[3-fluoro-4-({6-(methyloxy)-7-[(3-piperazin-1-ylpropyl)oxy]quinolin-4-yl}oxy)phenyl]-N'-(4-fluorophenyl)cyclopropane-1,1-dicarboxamide |
| 39 | N-{3-fluoro-4-[(6-(methyloxy)-7-{[3-(4-methylpiperazin-1-yl)propyl]oxy}quinolin-4-yl)oxy]phenyl}-N'-(4-fluorophenyl)cyclopropane-1,1-dicarboxamide |

-continued

| Entry | Name |
|---|---|
| 40 | N-{3-fluoro-4-[(6-(methyloxy)-7-{[(1-methylpiperidin-4-yl)methyl]oxy}quinolin-4-yl)oxy]phenyl}-N'-(4-fluorophenyl)cyclopropane-1,1-dicarboxamide |
| 41 | N-(4-fluorophenyl)-N'-[4-({6-(methyloxy)-7-[(3-morpholin-4-ylpropyl)oxy]quinolin-4-yl}oxy)phenyl]cyclopropane-1,1-dicarboxamide |
| 42 | N-(4-{[7-{[3-(diethylamino)propyl]oxy}-6-(methyloxy)quinolin-4-yl]oxy}-3-fluorophenyl)-N'-(4-fluorophenyl)cyclopropane-1,1-dicarboxamide |
| 43 | N-(4-{[6,7-bis(methyloxy)quinolin-4-yl]oxy}-2-chloro-5-fluorophenyl)-N'-(4-fluorophenyl)cyclopropane-1,1-dicarboxamide |
| 44 | N-(4-{[6,7-bis(methyloxy)-2-(methylthio)quinolin-4-yl]oxy}-3-fluorophenyl)-N'-(4-fluorophenyl)cyclopropane-1,1-dicarboxamide |
| 45 | N-(4-fluorophenyl)-N'-(4-{[2-methyl-6,7-bis(methyloxy)quinazolin-4-yl]oxy}phenyl)cyclopropane-1,1-dicarboxamide |
| 46 | N-(4-{[2-amino-6,7-bis(methyloxy)quinolin-4-yl]oxy}-3-fluorophenyl)-N'-(4-fluorophenyl)cyclopropane-1,1-dicarboxamide |
| 47 | N-(3-fluoro-4-{[2-(methylamino)-6,7-bis(methyloxy)quinolin-4-yl]oxy}phenyl)-N'-(4-fluorophenyl)cyclopropane-1,1-dicarboxamide |
| 48 | (1S,2R)-N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide |
| 49 | (1R,2R)-N-[3-fluoro-4-({6-(methyloxy)-7-[(3-morpholin-4-ylpropyl)oxy]quinolin-4-yl}oxy)phenyl]-N'-(4-fluorophenyl)-2-methylcyclopropane-1,1-dicarboxamide |
| 50 | N-(4-{[6-{[3-(diethylamino)propyl]oxy}-7-(methyloxy)quinolin-4-yl]oxy}-3-fluorophenyl)-N'-(4-fluorophenyl)cyclopropane-1,1-dicarboxamide |
| 51 | N-(4-{[6-{[2-(diethylamino)ethyl]oxy}-7-(methyloxy)quinolin-4-yl]oxy}-3-fluorophenyl)-N'-(4-fluorophenyl)cyclopropane-1,1-dicarboxamide |
| 52 | 1,1-dimethylethyl 4-(3-{[4-[(2-fluoro-4-{[(1-{[(4-fluorophenyl)amino]carbonyl}cyclopropyl)carbonyl]amino}phenyl)oxy]-6-(methyloxy)quinolin-7-yl]oxy}propyl)piperazine-1-carboxylate |
| 53 | (1R,2R)-N-[3-fluoro-4-({6-(methyloxy)-7-[(3-morpholin-4-ylpropyl)oxy]quinazolin-4-yl}oxy)phenyl]-N'-(4-fluorophenyl)-2-methylcyclopropane-1,1-dicarboxamide |
| 54 | (1R,2R)-N-(4-{[7-{[2-(diethylamino)ethyl]oxy}-6-(methyloxy)quinazolin-4-yl]oxy}-3-fluorophenyl)-N'-(4-fluorophenyl)-2-methylcyclopropane-1,1-dicarboxamide |
| 55 | N-(4-{[7-{[3-(diethylamino)propyl]oxy}-6-(methyloxy)quinazolin-4-yl]oxy}-3-fluorophenyl)-N'-(4-fluorophenyl)cyclopropane-1,1-dicarboxamide |
| 56 | N-(4-{[7-{[3-(4-acetylpiperazin-1-yl)propyl]oxy}-6-(methyloxy)quinolin-4-yl]oxy}-3-fluorophenyl)-N'-(4-fluorophenyl)cyclopropane-1,1-dicarboxamide |
| 57 | 1,1-dimethylethyl 4-(3-{[4-[(2-fluoro-4-{[(((1R,2R)-1-{[(4-fluorophenyl)amino]carbonyl}-2-methylcyclopropyl)carbonyl]amino}phenyl)oxy]-6-(methyloxy)quinolin-7-yl]oxy}propyl)piperazine-1-carboxylate |
| 58 | N-(4-{[6,7-bis(methyloxy)quinolin-4-yl]oxy}phenyl)-N'-(4-fluorophenyl)-1-(phenylmethyl)azetidine-3,3-dicarboxamide |
| 59 | N-(4-{[6,7-bis(methyloxy)quinolin-4-yl]oxy}phenyl)-N'-(4-fluorophenyl)azetidine-3,3-dicarboxamide |
| 60 | (1R,2S)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2-methylcyclopropane-1,1-dicarboxamide |
| 61 | (1R,2R)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2-methylcyclopropane-1,1-dicarboxamide |
| 62 | (1R,2R)-N-[3-fluoro-4-({6-(methyloxy)-7-[(3-piperazin-1-ylpropyl)oxy]quinolin-4-yl}oxy)phenyl]-N'-(4-fluorophenyl)-2-methylcyclopropane-1,1-dicarboxamide |
| 63 | N-(3-fluoro-4-{[7-({3-[4-(1-methylethyl)piperazin-1-yl]propyl}oxy)-6-(methyloxy)quinolin-4-yl]oxy}phenyl)-N'-(4-fluorophenyl)cyclopropane-1,1-dicarboxamide |
| 64 | N-(4-{[7-{[3-(diethylamino)propyl]oxy}-6-(methyloxy)quinazolin-4-yl]oxy}-3-fluorophenyl)-N'-(4-fluorophenyl)cyclopropane-1,1-dicarboxamide |
| 65 | (1R,2R)-N-(4-{[7-{[3-(diethylamino)propyl]oxy}-6-(methyloxy)quinolin-4-yl]oxy}-3-fluorophenyl)-N'-(4-fluorophenyl)-2-methylcyclopropane-1,1-dicarboxamide |
| 66 | (1R,2R)-N-(4-{[7-{[2-(diethylamino)ethyl]oxy}-6-(methyloxy)quinolin-4-yl]oxy}-3-fluorophenyl)-N'-(4-fluorophenyl)-2-methylcyclopropane-1,1-dicarboxamide |
| 67 | (1R,2S)-N-(4-{[7-{[3-(diethylamino)propyl]oxy}-6-(methyloxy)quinolin-4-yl]oxy}-3-fluorophenyl)-N'-(4-fluorophenyl)-2-methylcyclopropane-1,1-dicarboxamide |
| 68 | (1R,2S)-N-(4-{[7-{[2-(diethylamino)ethyl]oxy}-6-(methyloxy)quinolin-4-yl]oxy}-3-fluorophenyl)-N'-(4-fluorophenyl)-2-methylcyclopropane-1,1-dicarboxamide |
| 69 | N-(4-{[7-{[2-(diethylamino)ethyl]oxy}-6-(methyloxy)quinazolin-4-yl]oxy}-3-fluorophenyl)-N'-(4-fluorophenyl)cyclobutane-1,1-dicarboxamide |

| Entry | Name |
|---|---|
| 70 | (1R,2S)-N-[3-fluoro-4-({6-(methyloxy)-7-[(3-piperazin-1-ylpropyl)oxy]quinolin-4-yl}oxy)phenyl]-N'-(4-fluorophenyl)-2-methylcyclopropane-1,1-dicarboxamide |
| 71 | (1R,2R,3S)-N-[3-fluoro-4-({6-(methyloxy)-7-[(3-morpholin-4-ylpropyl)oxy]quinolin-4-yl}oxy)phenyl]-N'-(4-fluorophenyl)-2,3-dimethylcyclopropane-1,1-dicarboxamide |
| 72 | (1R,2R,3S)-N-{3-fluoro-4-[(6-(methyloxy)-7-{[3-(4-methylpiperazin-1-yl)propyl]oxy}quinolin-4-yl)oxy]phenyl}-N'-(4-fluorophenyl)-2,3-dimethylcyclopropane-1,1-dicarboxamide |
| 73 | (1R,2R,3S)-N-[3-fluoro-4-({6-(methyloxy)-7-[(3-morpholin-4-ylpropyl)oxy]quinazolin-4-yl}oxy)phenyl]-N'-(4-fluorophenyl)-2,3-dimethylcyclopropane-1,1-dicarboxamide |
| 74 | (1R,2R,3S)-N-{3-fluoro-4-[(6-(methyloxy)-7-{[3-(4-methylpiperazin-1-yl)propyl]oxy}quinazolin-4-yl)oxy]phenyl}-N'-(4-fluorophenyl)-2,3-dimethylcyclopropane-1,1-dicarboxamide |
| 75 | N-[3-fluoro-4-({6-(methyloxy)-7-[(3-morpholin-4-ylpropyl)oxy]quinazolin-4-yl}oxy)phenyl]-N'-(4-fluorophenyl)cyclobutane-1,1-dicarboxamide |
| 76 | (2R,3R)-N-[3-fluoro-4-({6-(methyloxy)-7-[(3-morpholin-4-ylpropyl)oxy]quinolin-4-yl}oxy)phenyl]-N'-(4-fluorophenyl)-2,3-dimethylcyclopropane-1,1-dicarboxamide |
| 77 | (2R,3R)-N-(4-{[7-{[3-(diethylamino)propyl]oxy}-6-(methyloxy)quinolin-4-yl]oxy}-3-fluorophenyl)-N'-(4-fluorophenyl)-2,3-dimethylcyclopropane-1,1-dicarboxamide |
| 78 | N-(4-{[7-{[3-(diethylamino)propyl]oxy}-6-(methyloxy)quinolin-4-yl]oxy}-3-fluorophenyl)-N'-(4-fluorophenyl)-2,2-dimethylcyclopropane-1,1-dicarboxamide |
| 79 | N-[3-fluoro-4-({6-(methyloxy)-7-[(3-morpholin-4-ylpropyl)oxy]quinazolin-4-yl}oxy)phenyl]-N'-(4-fluorophenyl)-2,2-dimethylcyclopropane-1,1-dicarboxamide |
| 80 | (1R,2R,3S)-N-(4-{[7-{[3-(diethylamino)propyl]oxy}-6-(methyloxy)quinolin-4-yl]oxy}-3-fluorophenyl)-N'-(4-fluorophenyl)-2,3-dimethylcyclopropane-1,1-dicarboxamide |
| 81 | N-(4-{[7-{[2-(diethylamino)ethyl]oxy}-6-(methyloxy)quinolin-4-yl]oxy}-3-fluorophenyl)-N'-(4-fluorophenyl)-2,2-dimethylcyclopropane-1,1-dicarboxamide |
| 82 | (1R,2R,3S)-N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide |
| 83 | N-[3-fluoro-4-({6-(methyloxy)-7-[(3-morpholin-4-ylpropyl)oxy]quinolin-4-yl}oxy)phenyl]-N'-(4-fluorophenyl)-2,2-dimethylcyclopropane-1,1-dicarboxamide |
| 84 | N-(4-{[7-{[2-(diethylamino)ethyl]oxy}-6-(methyloxy)quinazolin-4-yl]oxy}-3-fluorophenyl)-N'-(4-fluorophenyl)-2,2-dimethylcyclopropane-1,1-dicarboxamide |
| 85 | N-(4-{[7-{[3-(diethylamino)propyl]oxy}-6-(methyloxy)quinazolin-4-yl]oxy}-3-fluorophenyl)-N'-(4-fluorophenyl)-2,2-dimethylcyclopropane-1,1-dicarboxamide |
| 86 | N-(4-{[7-{[3-(diethylamino)propyl]oxy}-6-(methyloxy)quinazolin-4-yl]oxy}-3-fluorophenyl)-N'-(4-fluorophenyl)cyclobutane-1,1-dicarboxamide |
| 87 | N-{3-fluoro-4-[(6-(methyloxy)-7-{[3-(4-methylpiperazin-1-yl)propyl]oxy}quinazolin-4-yl)oxy]phenyl}-N'-(4-fluorophenyl)cyclobutane-1,1-dicarboxamide |
| 88 | N-[3-fluoro-4-({6-(methyloxy)-7-[(3-piperazin-1-ylpropyl)oxy]quinazolin-4-yl}oxy)phenyl]-N'-(4-fluorophenyl)cyclobutane-1,1-dicarboxamide |
| 89 | (2R,3R)-N-[3-fluoro-4-({6-(methyloxy)-7-[(3-morpholin-4-ylpropyl)oxy]quinazolin-4-yl}oxy)phenyl]-N'-(4-fluorophenyl)-2,3-dimethylcyclopropane-1,1-dicarboxamide |
| 90 | N-(4-{[7-{[3-(diethylamino)propyl]oxy}-6-(methyloxy)quinolin-4-yl]oxy}-3-fluorophenyl)-N'-(4-fluorophenyl)cyclobutane-1,1-dicarboxamide |
| 91 | N-{3-fluoro-4-[(6-(methyloxy)-7-{[3-(4-methylpiperazin-1-yl)propyl]oxy}quinolin-4-yl)oxy]phenyl}-N'-(4-fluorophenyl)cyclobutane-1,1-dicarboxamide |
| 92 | (1R,2R)-N-(4-{[7-{[3-(diethylamino)propyl]oxy}-6-(methyloxy)quinazolin-4-yl]oxy}-3-fluorophenyl)-N'-(4-fluorophenyl)-2-methylcyclopropane-1,1-dicarboxamide |
| 93 | (1R,2R)-N-{3-fluoro-4-[(6-(methyloxy)-7-{[3-(4-methylpiperazin-1-yl)propyl]oxy}quinazolin-4-yl)oxy]phenyl}-N'-(4-fluorophenyl)-2-methylcyclopropane-1,1-dicarboxamide |
| 94 | (2R,3R)-N-(4-{[7-{[2-(diethylamino)ethyl]oxy}-6-(methyloxy)quinazolin-4-yl]oxy}-3-fluorophenyl)-N'-(4-fluorophenyl)-2,3-dimethylcyclopropane-1,1-dicarboxamide |
| 95 | (2R,3R)-N-(4-{[7-{[3-(diethylamino)propyl]oxy}-6-(methyloxy)quinazolin-4-yl]oxy}-3-fluorophenyl)-N'-(4-fluorophenyl)-2,3-dimethylcyclopropane-1,1-dicarboxamide |
| 96 | (1R,2R)-N-[3-fluoro-4-({6-(methyloxy)-7-[(3-piperazin-1-ylpropyl)oxy]quinazolin-4-yl}oxy)phenyl]-N'-(4-fluorophenyl)-2-methylcyclopropane-1,1-dicarboxamide |

| Entry | Name |
|---|---|
| 97 | (2R,3R)-N-(4-{[7-{[2-(diethylamino)ethyl]oxy}-6-(methyloxy)quinolin-4-yl]oxy}-3-fluorophenyl)-N'-(4-fluorophenyl)-2,3-dimethylcyclopropane-1,1-dicarboxamide |
| 98 | N-(4-{[6,7-bis(methyloxy)quinolin-4-yl]oxy}phenyl)-N'-[(4-fluorophenyl)methyl]cyclopropane-1,1-dicarboxamide |
| 99 | N-(4-{[6,7-bis(methyloxy)quinolin-4-yl]oxy}phenyl)-N'-(2-morpholin-4-ylethyl)cyclopropane-1,1-dicarboxamide |
| 100 | N-(4-{[6,7-bis(methyloxy)quinolin-4-yl]oxy}phenyl)-N'-[2-(piperidin-1-ylmethyl)phenyl]cyclopropane-1,1-dicarboxamide |
| 101 | N-(4-{[6,7-bis(methyloxy)quinolin-4-yl]oxy}phenyl)-N'-[2-(pyrrolidin-1-ylmethyl)phenyl]cyclopropane-1,1-dicarboxamide |
| 102 | N-(4-{[6,7-bis(methyloxy)quinolin-4-yl]oxy}phenyl)-N'-[3-(morpholin-4-ylmethyl)phenyl]cyclopropane-1,1-dicarboxamide |
| 103 | N-(4-{[6,7-bis(methyloxy)quinolin-4-yl]oxy}phenyl)-N'-[2-(morpholin-4-ylmethyl)phenyl]cyclopropane-1,1-dicarboxamide |
| 104 | N-(4-{[6,7-bis(methyloxy)quinolin-4-yl]oxy}phenyl)-N'-phenylcyclopropane-1,1-dicarboxamide |
| 105 | N-[3-(aminomethyl)phenyl]-N'-(4-{[6,7-bis(methyloxy)quinolin-4-yl]oxy}phenyl)cyclopropane-1,1-dicarboxamide |
| 106 | N-(4-{[6,7-bis(methyloxy)quinolin-4-yl]oxy}phenyl)-N'-[3-(piperidin-1-ylmethyl)phenyl]cyclopropane-1,1-dicarboxamide |
| 107 | N-(4-{[6,7-bis(methyloxy)quinolin-4-yl]oxy}phenyl)-N'-[3-(pyrrolidin-1-ylmethyl)phenyl]cyclopropane-1,1-dicarboxamide |

The Compounds in Table 4 can be prepared as pharmaceutically acceptable salts, solvates, hydrates, and/or isomers thereof. All such salt, solvate, hydrate, and isomer combinations of the Compounds in Table 4 can be used to practice the invention. In particular, the invention can be practiced with one or two pharmaceutically acceptable salts of a Compound of Table 4 which salt(s) are formed with one or two acids independently selected from hydrochloric acid, hydrobromic acid, sulfuric acid, nitric acid, phosphoric acid, acetic acid, trifluoroacetic acid, propionic acid, hexanoic acid, cyclopentanepropionic acid, glycolic acid, pyruvic acid, lactic acid, oxalic acid, maleic acid, malonic acid, succinic acid, fumaric acid, tartaric acid, citric acid, benzoic acid, cinnamic acid, 3-(4-hydroxybenzoyl)benzoic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, p-toluenesulfonic acid, and salicylic acid.

| Entry | Name |
|---|---|
| 1 | N-(3,4-dichloro-2-fluorophenyl)-7-({[(3aR,5r,6aS)-2-(1-methylethyl)octahydrocyclopenta[c]pyrrol-5-yl]methyl}oxy)-6-(methyloxy)quinazolin-4-amine |
| 2 | N-(4-bromo-3-chloro-2-fluorophenyl)-7-({[(3aR,5r,6aS)-2-(1-methylethyl)octahydrocyclopenta[c]pyrrol-5-yl]methyl}oxy)-6-(methyloxy)quinazolin-4-amine |
| 3 | 7-({[(3aR,5r,6aS)-2-acetyloctahydrocyclopenta[c]pyrrol-5-yl]methyl}oxy)-N-(4-bromo-3-chloro-2-fluorophenyl)-6-(methyloxy)quinazolin-4-amine |
| 4 | N-(4-bromo-3-chloro-2-fluorophenyl)-6-(methyloxy)-7-{[(3aR,5r,6aS)-octahydrocyclopenta[c]pyrrol-5-ylmethyl]oxy}quinazolin-4-amine |
| 5 | ethyl (3aR,6aS)-5-({[4-[(4-bromo-3-chloro-2-fluorophenyl)amino]-6-(methyloxy)quinazolin-7-yl]oxy}methyl)hexahydrocyclopenta[c]pyrrole-2(1H)-carboxylate |
| 6 | N-(4-bromo-3-chloro-2-fluorophenyl)-6-(methyloxy)-7-({[(3aR,5r,6aS)-2-(methylsulfonyl)octahydrocyclopenta[c]pyrrol-5-yl]methyl}oxy)quinazolin-4-amine |
| 7 | N-(3,4-dichloro-2-fluorophenyl)-7-({[(3aR,5r,6aS)-2-ethyloctahydrocyclopenta[c]pyrrol-5-yl]methyl}oxy)-6-(methyloxy)quinazolin-4-amine |
| 8 | N-(3,4-dichloro-2-fluorophenyl)-6-(methyloxy)-7-({[(3aR,5r,6aS)-2-(2-methylpropyl)octahydrocyclopenta[c]pyrrol-5-yl]methyl}oxy)quinazolin-4-amine |
| 9 | N-(3,4-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine |
| 10 | N-(4-bromo-3-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine |
| 11 | N-(3-chloro-2,4-difluorophenyl)-7-({[(3aR,5s,6aS)-2-methyloctahydrocyclopenta[c]pyrrol-5-yl]methyl}oxy)-6-(methyloxy)quinazolin-4-amine |

| Entry | Name |
|---|---|
| 12 | N-(4,5-dichloro-2-fluorophenyl)-7-({[(3aR,5s,6aS)-2-methyloctahydrocyclopenta[c]pyrrol-5-yl]methyl}oxy)-6-(methyloxy)quinazolin-4-amine |
| 13 | N-(4-bromo-5-chloro-2-fluorophenyl)-7-({[(3aR,5s,6aS)-2-methyloctahydrocyclopenta[c]pyrrol-5-yl]methyl}oxy)-6-(methyloxy)quinazolin-4-amine |
| 14 | N-(4-bromo-2,3-dichlorophenyl)-7-({[(3aR,5s,6aS)-2-methyloctahydrocyclopenta[c]pyrrol-5-yl]methyl}oxy)-6-(methyloxy)quinazolin-4-amine |
| 15 | N-(3,4-dichlorophenyl)-7-({[(3aR,5s,6aS)-2-methyloctahydrocyclopenta[c]pyrrol-5-yl]methyl}oxy)-6-(methyloxy)quinazolin-4-amine |
| 16 | N-(4-bromo-3-chloro-2-fluorophenyl)-7-({[(3aR,5r,6aS)-2-ethyloctahydrocyclopenta[c]pyrrol-5-yl]methyl}oxy)-6-(methyloxy)quinazolin-4-amine |
| 17 | N-(4-bromo-3-chloro-2-fluorophenyl)-6-(methyloxy)-7-({[(3aR,5r,6aS)-2-(2-methylpropyl)octahydrocyclopenta[c]pyrrol-5-yl]methyl}oxy)quinazolin-4-amine |
| 18 | N-(4-bromo-2,3-dichlorophenyl)-7-{[(3R,9aS)-hexahydro-1H-[1,4]oxazino[3,4-c][1,4]oxazin-3-ylmethyl]oxy}-6-(methyloxy)quinazolin-4-amine |
| 19 | N-(4,5-dichloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine |
| 20 | N-(4-bromo-5-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine |
| 21 | N-(3-chloro-2,4-difluorophenyl)-7-{[(3R,9aS)-hexahydro-1H-[1,4]oxazino[3,4-c][1,4]oxazin-3-ylmethyl]oxy}-6-(methyloxy)quinazolin-4-amine |
| 22 | N-(3,4-dichloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine |
| 23 | N-(4-bromo-3-chloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine |
| 24 | N-(3-chloro-2,4-difluorophenyl)-7-{[(3S,9aS)-hexahydro-1H-[1,4]oxazino[3,4-c][1,4]oxazin-3-ylmethyl]oxy}-6-(methyloxy)quinazolin-4-amine |
| 25 | N-(3,4-dichlorophenyl)-7-[(hexahydro-1H-[1,4]oxazino[3,4-c][1,4]oxazin-3-ylmethyl)oxy]-6-(methyloxy)quinazolin-4-amine |
| 26 | N-(4,5-dichloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine |
| 27 | N-(4-bromo-2,3-dichlorophenyl)-7-{[(3S,9aS)-hexahydro-1H-[1,4]oxazino[3,4-c][1,4]oxazin-3-ylmethyl]oxy}-6-(methyloxy)quinazolin-4-amine |
| 28 | N-(4-bromo-5-chloro-2-fluorophenyl)-7-{[(3S,9aS)-hexahydro-1H-[1,4]oxazino[3,4-c][1,4]oxazin-3-ylmethyl]oxy}-6-(methyloxy)quinazolin-4-amine |
| 29 | N-(3,4-dichloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine |
| 30 | N-(4-bromo-3-chloro-2-fluorophenyl)-7-{[(3R,9aS)-hexahydro-1H-[1,4]oxazino[3,4-c][1,4]oxazin-3-ylmethyl]oxy}-6-(methyloxy)quinazolin-4-amine |
| 31 | N-(3,4-dichlorophenyl)-7-{[(3R,8aR)-hexahydro-1H-pyrrolo[2,1-c][1,4]oxazin-3-ylmethyl]oxy}-6-(methyloxy)quinazolin-4-amine |
| 32 | N-(4-bromo-5-chloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine |
| 33 | N-(3,4-dichlorophenyl)-7-{[(3S,8aR)-hexahydro-1H-pyrrolo[2,1-c][1,4]oxazin-3-ylmethyl]oxy}-6-(methyloxy)quinazolin-4-amine |
| 34 | N-(3,4-dichlorophenyl)-7-{[(3S,8aS)-hexahydro-1H-pyrrolo[2,1-c][1,4]oxazin-3-ylmethyl]oxy}-6-(methyloxy)quinazolin-4-amine |
| 35 | N-(3,4-dichlorophenyl)-7-{[(3R,8aS)-hexahydro-1H-pyrrolo[2,1-c][1,4]oxazin-3-ylmethyl]oxy}-6-(methyloxy)quinazolin-4-amine |
| 36 | N-(3,4-dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine |
| 37 | N-(4-bromo-3-chloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine |
| 38 | N-(3-chloro-2,4-difluorophenyl)-7-{[(3S,8aS)-hexahydro-1H-pyrrolo[2,1-c][1,4]oxazin-3-ylmethyl]oxy}-6-(methyloxy)quinazolin-4-amine |
| 39 | N-(4-bromo-2,3-dichlorophenyl)-7-{[(3S,8aS)-hexahydro-1H-pyrrolo[2,1-c][1,4]oxazin-3-ylmethyl]oxy}-6-(methyloxy)quinazolin-4-amine |
| 40 | N-(4,5-dichloro-2-fluorophenyl)-7-{[(3S,8aS)-hexahydro-1H-pyrrolo[2,1-c][1,4]oxazin-3-ylmethyl]oxy}-6-(methyloxy)quinazolin-4-amine |
| 41 | 1,4:3,6-dianhydro-5-({[4-[(4-bromo-5-chloro-2-fluorophenyl)amino]-6-(methyloxy)quinazolin-7-yl]oxy}methyl)-5-deoxy-2-O-methyl-D-xylo-hexitol |
| 42 | 1,4:3,6-dianhydro-5-deoxy-5-({[4-[(3,4-dichlorophenyl)amino]-6-(methyloxy)quinazolin-7-yl]oxy}methyl)-2-O-methyl-D-glucitol |
| 43 | 1,4:3,6-dianhydro-5-deoxy-5-({[4-[(3,4-dichloro-2-fluorophenyl)amino]-6-(methyloxy)quinazolin-7-yl]oxy}methyl)-2-O-methyl-D-xylo-hexitol |
| 44 | 1,4:3,6-dianhydro-5-({[4-[(4-bromo-3-chloro-2-fluorophenyl)amino]-6-(methyloxy)quinazolin-7-yl]oxy}methyl)-5-deoxy-2-O-methyl-D-xylo-hexitol |
| 45 | 1,4:3,6-dianhydro-5-({[4-[(3-chloro-2,4-difluorophenyl)amino]-6-(methyloxy)quinazolin-7-yl]oxy}methyl)-5-deoxy-2-O-methyl-D-xylo-hexitol |
| 46 | 1,4:3,6-dianhydro-5-({[4-[(4-bromo-2,3-dichlorophenyl)amino]-6-(methyloxy)quinazolin-7-yl]oxy}methyl)-5-deoxy-2-O-methyl-D-glucitol |
| 47 | 1,4:3,6-dianhydro-2-deoxy-2-({[4-[(3,4-dichlorophenyl)amino]-6-(methyloxy)quinazolin-7-yl]oxy}methyl)-5-O-methyl-D-threo-hexitol |
| 48 | 1,4:3,6-dianhydro-5-deoxy-5-({[4-[(4,5-dichloro-2-fluorophenyl)amino]-6-(methyloxy)quinazolin-7-yl]oxy}methyl)-2-O-methyl-D-glucitol |

-continued

| Entry | Name |
|---|---|
| 49 | (3S,9aS)-3-({[4-[(3,4-dichloro-2-fluorophenyl)amino-6-(methyloxy)quinazolin-7-yl]oxy}methyl)hexahydro-2H-pyrido[1,2-a]pyrazin-1(6H)-one |
| 50 | (3S,9aR)-3-({[4-[(3,4-dichloro-2-fluorophenyl)amino-6-(methyloxy)quinazolin-7-yl]oxy}methyl)hexahydro-2H-pyrido[1,2-a]pyrazin-1(6H)-one |
| 51 | (3S,8aS)-3-({[4-[(3,4-dichloro-2-fluorophenyl)amino-6-(methyloxy)quinazolin-7-yl]oxy}methyl)hexahydropyrrolo[1,2-a]pyrazin-1(2H)-one |
| 52 | (3S,8aR)-3-({[4-[(3,4-dichloro-2-fluorophenyl)amino-6-(methyloxy)quinazolin-7-yl]oxy}methyl)hexahydropyrrolo[1,2-a]pyrazin-1(2H)-one |
| 53 | (3S,8aS)-3-({[4-[(4-bromo-3-chloro-2-fluorophenyl)amino]-6-(methyloxy)quinazolin-7-yl]oxy}methyl)hexahydropyrrolo[1,2-a]pyrazin-1(2H)-one |
| 54 | (3S,8aS)-3-({[4-[(3,4-dichloro-2-fluorophenyl)amino]-6-(methyloxy)quinazolin-7-yl]oxy}methyl)-2-methylhexahydropyrrolo[1,2-a]pyrazin-1(2H)-one |
| 55 | N-(3,4-dichlorophenyl)-7-({2-[(8-methyl-8-azabicyclo[3.2.1]oct-3-yl)amino]ethyl}oxy)-6-(methyloxy)quinazolin-4-amine |
| 56 | N-(3,4-dichlorophenyl)-6-(methyloxy)-7-{[(8aR)-tetrahydro-1H-[1,3]thiazolo[4,3-c][1,4]oxazin-6-ylmethyl]oxy}quinazolin-4-amine |
| 57 | N-(3,4-dichlorophenyl)-7-{[2-(8-methyl-8-azabicyclo[3.2.1]oct-3-yl)ethyl]oxy}-6-(methyloxy)quinazolin-4-amine |
| 58 | N-(3,4-dichlorophenyl)-7-{[(8-methyl-8-azabicyclo[3.2.1]oct-3-yl)methyl]oxy}-6-(methyloxy)quinazolin-4-amine |
| 59 | N-(3,4-dichlorophenyl)-7-{[(3aR,6aS)-2-methyloctahydrocyclopenta[c]pyrrol-5-yl]oxy}-6-(methyloxy)quinazolin-4-amine |
| 60 | N-(3,4-dichlorophenyl)-7-[(8-methyl-8-azabicyclo[3.2.1]oct-3-yl)oxy]-6-(methyloxy)quinazolin-4-amine |
| 61 | 1,4:3,6-dianhydro-2-O-[4-[(4-bromo-5-chloro-2-fluorophenyl)amino]-6-(methyloxy)quinazolin-7-yl]-5-O-methyl-L-iditol |
| 62 | 1,4:3,6-dianhydro-2-O-[4-[(3,4-dichloro-2-fluorophenyl)amino]-6-(methyloxy)quinazolin-7-yl]-5-O-methyl-L-iditol |
| 63 | 1,4:3,6-dianhydro-2-O-[4-[(4-bromo-3-chloro-2-fluorophenyl)amino]-6-(methyloxy)quinazolin-7-yl]-5-O-methyl-L-iditol |
| 64 | 1,4:3,6-dianhydro-2-O-methyl-5-O-{6-(methyloxy)-4-[(2,3,4-trichlorophenyl)amino]quinazolin-7-yl}-L-iditol |
| 65 | 1,4:3,6-dianhydro-5-O-[4-[(3,4-dichlorophenyl)amino]-6-(methyloxy)quinazolin-7-yl]-2-O-methyl-D-xylo-hexitol |
| 66 | 1,4:3,6-dianhydro-2-O-[4-[(4-bromo-2,3-dichlorophenyl)amino]-6-(methyloxy)quinazolin-7-yl]-5-O-methyl-L-iditol |
| 67 | 1,4:3,6-dianhydro-5-O-[4-[(4-bromo-3-chlorophenyl)amino]-6-(methyloxy)-quinazolin-7-yl]-sorbose ethylene glycol acetal |
| 68 | 1,4:3,6-dianhydro-2-O-[4-[(3-chloro-2,4-difluorophenyl)amino]-6-(methyloxy)quinazolin-7-yl]-5-O-methyl-L-iditol |
| 69 | 1,4:3,6-dianhydro-2-O-[4-[(4,5-dichloro-2-fluorophenyl)amino]-6-(methyloxy)quinazolin-7-yl]-5-O-methyl-L-iditol |
| 70 | 1,4:3,6-dianhydro-2-O-[4-[(4-bromo-3-chlorophenyl)amino]-6-(methyloxy)quinazolin-7-yl]-5-O-(difluoromethyl)-L-iditol |
| 71 | 1,4:3,6-dianhydro-2-O-[4-[(3-chloro-2-fluorophenyl)amino]-6-(methyloxy)quinazolin-7-yl]-5-O-methyl-L-iditol |
| 72 | 1,4:3,6-dianhydro-2-O-[4-[(3,4-dichlorophenyl)amino]-6-(methyloxy)quinazolin-7-yl]-5-O-methyl-L-iditol |
| 73 | 1,4:3,6-dianhydro-2-O-[4-[(4-bromo-3-chlorophenyl)amino]-6-(methyloxy)quinazolin-7-yl]-5-O-methyl-L-iditol |
| 74 | 1,4:3,6-dianhydro-2-O-[4-[(4-bromo-3-chlorophenyl)amino]-6-(methyloxy)quinazolin-7-yl]-5-O-ethyl-L-iditol |
| 75 | 1,4:3,6-dianhydro-2-O-[4-[(3-bromo-2-methylphenyl)amino]-6-(methyloxy)quinazolin-7-yl]-5-O-methyl-L-iditol |
| 76 | 1,4:3,6-dianhydro-2-O-[4-[(3-chloro-2-methylphenyl)amino]-6-(methyloxy)quinazolin-7-yl]-5-O-methyl-L-iditol |
| 77 | 1,4:3,6-dianhydro-2-O-[4-[(4-bromo-3-chlorophenyl)amino]-6-(methyloxy)quinazolin-7-yl]-5-deoxy-D-xylo-hexitol |
| 78 | 1,4:3,6-dianhydro-2-O-[4-[(4-bromo-3-chlorophenyl)amino]-6-(methyloxy)quinazolin-7-yl]-5-O-methyl-D-glucitol |
| 79 | methyl 3,6-anhydro-5-O-[4-[(4-bromo-3-chlorophenyl)amino]-6-(methyloxy)quinazolin-7-yl]-2-O-methyl-alpha-L-idofuranoside |
| 80 | 3,6-anhydro-5-O-[4-[(4-bromo-3-chlorophenyl)amino]-6-(methyloxy)quinazolin-7-yl]-1,2-O-(1-methylethylidene)-beta-L-xylo-hexofuranose |
| 81 | 1,4:3,6-dianhydro-2-O-[4-[(4-bromo-3-chlorophenyl)amino]-6-(methyloxy)quinazolin-7-yl]-5-deoxy-5-methylidene-D-xylo-hexitol |
| 82 | methyl 3,6-anhydro-5-O-[4-[(4-bromo-3-chlorophenyl)amino]-6-(methyloxy)quinazolin-7-yl]-2-O-methyl-beta-L-idofuranoside |
| 83 | N-(3,4-dichloro-2-fluorophenyl)-6-(methyloxy)-7-[(octahydro-2H-quinolizin-3-ylmethyl)oxy]quinazolin-4-amine |
| 84 | 1,4:3,6-dianhydro-2-deoxy-2-fluoro-5-O-{6-(methyloxy)-4-[(2,3,4-trifluorophenyl)amino]quinazolin-7-yl}-D-iditol |
| 85 | 1,4:3,6-dianhydro-5-O-[4-[(2-chloro-4-fluorophenyl)amino]-6-(methyloxy)quinazolin-7-yl]-2-deoxy-2-fluoro-D-iditol |
| 86 | 1,4:3,6-dianhydro-5-O-[4-[(2-bromo-4-fluorophenyl)amino]-6-(methyloxy)quinazolin-7-yl]-2-deoxy-2-fluoro-D-iditol |

| Entry | Name |
|---|---|
| 87 | 1,4:3,6-dianhydro-2-deoxy-5-O-[4-[(2,6-difluorophenyl)amino]-6-(methyloxy)quinazolin-7-yl]-2-fluoro-D-iditol |
| 88 | 1,4:3,6-dianhydro-5-O-[4-[(3-chloro-2-fluorophenyl)amino]-6-(methyloxy)quinazolin-7-yl]-2-deoxy-2-fluoro-D-iditol |
| 89 | 1,4:3,6-dianhydro-2-deoxy-2-fluoro-5-O-[4-{[4-fluoro-3-(trifluoromethyl)phenyl]amino}-6-(methyloxy)quinazolin-7-yl]-D-iditol |
| 90 | 1,4:3,6-dianhydro-2-deoxy-5-O-[4-[(2,4-difluorophenyl)amino]-6-(methyloxy)quinazolin-7-yl]-2-fluoro-D-iditol |
| 91 | 1,4:3,6-dianhydro-2-deoxy-5-O-[4-[(2,5-difluorophenyl)amino]-6-(methyloxy)quinazolin-7-yl]-2-fluoro-D-iditol |
| 92 | 1,4:3,6-dianhydro-2-deoxy-5-O-[4-[(2,3-difluorophenyl)amino]-6-(methyloxy)quinazolin-7-yl]-2-fluoro-D-iditol |
| 93 | 1,4:3,6-dianhydro-5-O-[4-[(5-chloro-2-fluorophenyl)amino]-6-(methyloxy)quinazolin-7-yl]-2-deoxy-2-fluoro-D-iditol |
| 94 | 1,4:3,6-dianhydro-2-deoxy-5-O-[4-[(3,5-difluorophenyl)amino]-6-(methyloxy)quinazolin-7-yl]-2-fluoro-D-iditol |
| 95 | 1,4:3,6-dianhydro-5-O-[4-[(3-chloro-4-fluorophenyl)amino]-6-(methyloxy)quinazolin-7-yl]-2-deoxy-2-fluoro-D-iditol |
| 96 | 1,4:3,6-dianhydro-5-O-[4-[(4-bromo-2-chlorophenyl)amino]-6-(methyloxy)quinazolin-7-yl]-2-deoxy-2-fluoro-D-iditol |
| 97 | 1,4:3,6-dianhydro-2-deoxy-5-O-[4-[(3,4-dichloro-2-fluorophenyl)amino]-6-(methyloxy)quinazolin-7-yl]-2-fluoro-D-iditol |
| 98 | 1,4:3,6-dianhydro-5-O-[4-[(4-bromo-5-chloro-2-fluorophenyl)amino]-6-(methyloxy)quinazolin-7-yl]-2-deoxy-2-fluoro-D-iditol |
| 99 | 1,4:3,6-dianhydro-2-deoxy-2-fluoro-5-O-{6-(methyloxy)-4-[(2,4,5-trifluorophenyl)amino]quinazolin-7-yl}-D-iditol |
| 100 | 1,4:3,6-dianhydro-2-deoxy-2-fluoro-5-O-{6-(methyloxy)-4-[(2,4,6-trifluorophenyl)amino]quinazolin-7-yl}-D-iditol |
| 101 | 1,4:3,6-dianhydro-5-O-[4-({4-[(4-chlorophenyl)oxy]-3,5-difluorophenyl}amino)-6-(methyloxy)quinazolin-7-yl]-2-deoxy-2-fluoro-D-iditol |
| 102 | 1,4:3,6-dianhydro-5-O-[4-[(4-bromo-3-chloro-2-fluorophenyl)amino]-6-(methyloxy)quinazolin-7-yl]-2-deoxy-2-fluoro-D-iditol |
| 103 | 1,4:3,6-dianhydro-5-O-[4-[(4-bromo-2,3-dichlorophenyl)amino]-6-(methyloxy)quinazolin-7-yl]-2-deoxy-2-fluoro-D-iditol |
| 104 | 1,4:3,6-dianhydro-5-O-[4-[(4-bromo-3-chloro-5-fluorophenyl)amino]-6-(methyloxy)quinazolin-7-yl]-2-deoxy-2-fluoro-D-iditol |
| 105 | 1,4:3,6-dianhydro-2-deoxy-5-O-[4-[(4,5-dichloro-2-fluorophenyl)amino]-6-(methyloxy)quinazolin-7-yl]-2-fluoro-D-iditol |
| 106 | 1,4:3,6-dianhydro-2-deoxy-2-fluoro-5-O-{6-(methyloxy)-4-[(2,3,4-trichlorophenyl)amino]quinazolin-7-yl}-D-iditol |
| 107 | 1,4:3,6-dianhydro-2-deoxy-2-fluoro-5-O-{6-(methyloxy)-4-[(3,4,5-trichlorophenyl)amino]quinazolin-7-yl}-D-iditol |
| 108 | 1,4:3,6-dianhydro-5-O-[4-[(4-bromo-2-fluorophenyl)amino]-6-(methyloxy)quinazolin-7-yl]-2-deoxy-2-fluoro-D-iditol |
| 109 | 1,4:3,6-dianhydro-5-O-[4-[(4-chloro-2-fluorophenyl)amino]-6-(methyloxy)quinazolin-7-yl]-2-deoxy-2-fluoro-D-iditol |
| 110 | 1,4:3,6-dianhydro-5-O-[4-[(3-chloro-2-methylphenyl)amino]-6-(methyloxy)quinazolin-7-yl]-2-deoxy-2-fluoro-D-iditol |
| 111 | 1,4:3,6-dianhydro-2-deoxy-5-O-[4-[(3,4-difluorophenyl)amino]-6-(methyloxy)quinazolin-7-yl]-2-fluoro-D-iditol |
| 112 | 1,4:3,6-dianhydro-5-O-[4-[(2-chlorophenyl)amino]-6-(methyloxy)quinazolin-7-yl]-2-deoxy-2-fluoro-D-iditol |
| 113 | 1,4:3,6-dianhydro-2-deoxy-2-fluoro-5-O-[4-[(2-fluorophenyl)amino]-6-(methyloxy)quinazolin-7-yl]-D-iditol |
| 114 | 1,4:3,6-dianhydro-5-O-[4-[(3-chlorophenyl)amino]-6-(methyloxy)quinazolin-7-yl]-2-deoxy-2-fluoro-D-iditol |
| 115 | 1,4:3,6-dianhydro-2-deoxy-2-fluoro-5-O-[4-[(4-fluorophenyl)amino]-6-(methyloxy)quinazolin-7-yl]-D-iditol |
| 116 | 1,4:3,6-dianhydro-5-O-[4-[(4-chlorophenyl)amino]-6-(methyloxy)quinazolin-7-yl]-2-deoxy-2-fluoro-D-iditol |
| 117 | 1,4:3,6-dianhydro-2-deoxy-5-O-[4-[(2,4-dichlorophenyl)amino]-6-(methyloxy)quinazolin-7-yl]-2-fluoro-D-iditol |
| 118 | 1,4:3,6-dianhydro-2-deoxy-5-O-[4-[(2,5-dichlorophenyl)amino]-6-(methyloxy)quinazolin-7-yl]-2-fluoro-D-iditol |
| 119 | 1,4:3,6-dianhydro-2-deoxy-5-O-[4-[(3,4-dichlorophenyl)amino]-6-(methyloxy)quinazolin-7-yl]-2-fluoro-D-iditol |
| 120 | 1,4:3,6-dianhydro-5-O-[4-[(2-bromo-4,6-difluorophenyl)amino]-6-(methyloxy)quinazolin-7-yl]-2-deoxy-2-fluoro-D-iditol |
| 121 | 1,4:3,6-dianhydro-5-O-[4-{[4-chloro-3-(trifluoromethyl)phenyl]amino}-6-(methyloxy)quinazolin-7-yl]-2-deoxy-2-fluoro-D-iditol |
| 122 | 1,4:3,6-dianhydro-5-O-[4-{[2-chloro-5-(trifluoromethyl)phenyl]amino}-6-(methyloxy)quinazolin-7-yl]-2-deoxy-2-fluoro-D-iditol |
| 123 | 1,4:3,6-dianhydro-2-deoxy-2-fluoro-5-O-[4-{[2-fluoro-3-(trifluoromethyl)phenyl]amino}-6-(methyloxy)quinazolin-7-yl]-D-iditol |
| 124 | 1,4:3,6-dianhydro-5-O-[4-{[2-bromo-5-(trifluoromethyl)phenyl]amino}-6-(methyloxy)quinazolin-7-yl]-2-deoxy-2-fluoro-D-iditol |
| 125 | 1,4:3,6-dianhydro-5-O-[4-{[2-bromo-4-(trifluoromethyl)phenyl]amino}-6-(methyloxy)quinazolin-7-yl]-2-deoxy-2-fluoro-D-iditol |

-continued

| Entry | Name |
|---|---|
| 126 | 1,4:3,6-dianhydro-2-deoxy-2-fluoro-5-O-[4-{[4-fluoro-2-(trifluoromethyl)phenyl]amino}-6-(methyloxy)quinazolin-7-yl]-D-iditol |
| 127 | 1,4:3,6-dianhydro-5-O-[4-{[3-bromo-5-(trifluoromethyl)phenyl]amino}-6-(methyloxy)quinazolin-7-yl]-2-deoxy-2-fluoro-D-iditol |
| 128 | 1,4:3,6-dianhydro-5-O-[4-[(2-bromophenyl)amino]-6-(methyloxy)quinazolin-7-yl]-2-deoxy-2-fluoro-D-iditol |
| 129 | 1,4:3,6-dianhydro-5-O-[4-[(3-bromophenyl)amino]-6-(methyloxy)quinazolin-7-yl]-2-deoxy-2-fluoro-D-iditol |
| 130 | 1,4:3,6-dianhydro-5-O-[4-[(4-bromophenyl)amino]-6-(methyloxy)quinazolin-7-yl]-2-deoxy-2-fluoro-D-iditol |
| 131 | 1,4:3,6-dianhydro-5-O-[4-[(3-bromo-4-methylphenyl)amino]-6-(methyloxy)quinazolin-7-yl]-2-deoxy-2-fluoro-D-iditol |
| 132 | 1,4:3,6-dianhydro-5-O-[4-[(5-chloro-2-methylphenyl)amino]-6-(methyloxy)quinazolin-7-yl]-2-deoxy-2-fluoro-D-iditol |
| 133 | 1,4:3,6-dianhydro-2-deoxy-5-O-[4-[(3,5-dimethylphenyl)amino]-6-(methyloxy)quinazolin-7-yl]-2-fluoro-D-iditol |
| 134 | 1,4:3,6-dianhydro-5-O-[4-{[2,5-bis(methyloxy)phenyl]amino}-6-(methyloxy)quinazolin-7-yl]-2-deoxy-2-fluoro-D-iditol |
| 135 | 1,4:3,6-dianhydro-5-O-[4-{[5-chloro-2,4-bis(methyloxy)phenyl]amino}-6-(methyloxy)quinazolin-7-yl]-2-deoxy-2-fluoro-D-iditol |
| 136 | 1,4:3,6-dianhydro-5-O-[4-{[4-chloro-2,5-bis(methyloxy)phenyl]amino}-6-(methyloxy)quinazolin-7-yl]-2-deoxy-2-fluoro-D-iditol |
| 137 | 1,4:3,6-dianhydro-5-O-[4-[(3-chloro-2,4-difluorophenyl)amino]-6-(methyloxy)quinazolin-7-yl]-2-deoxy-2-fluoro-D-iditol |
| 138 | N-(3,4-dichlorophenyl)-7-[({5-[(dimethylamino)methyl]-1,2,4-oxadiazol-3-yl}methyl)oxy]-6-(methyloxy)quinazolin-4-amine |
| 139 | N-(3,4-dichlorophenyl)-7-[({3-[(dimethylamino)methyl]-1,2,4-oxadiazol-5-yl}methyl)oxy]-6-(methyloxy)quinazolin-4-amine |
| 140 | N-(3,4-dichlorophenyl)-6-(methyloxy)-7-[({3-[(4-methylpiperazin-1-yl)methyl]-1,2,4-oxadiazol-5-yl}methyl)oxy]quinazolin-4-amine |
| 141 | N-(3,4-dichlorophenyl)-6-(methyloxy)-7-{[(5-piperidin-4-yl-1,2,4-oxadiazol-3-yl)methyl]oxy}quinazolin-4-amine |
| 142 | N-(3,4-dichlorophenyl)-6-(methyloxy)-7-({[5-(1-methylpiperidin-4-yl)-1,2,4-oxadiazol-3-yl]methyl}oxy)quinazolin-4-amine |
| 143 | N-(3,4-dichlorophenyl)-6-(methyloxy)-7-({[3-(morpholin-4-ylmethyl)-1,2,4-oxadiazol-5-yl]methyl}oxy)quinazolin-4-amine |
| 144 | N-(3,4-dichlorophenyl)-6-(methyloxy)-7-[(morpholin-2-ylmethyl)oxy]quinazolin-4-amine |
| 145 | N-(3,4-dichlorophenyl)-6-(methyloxy)-7-{[(5-piperidin-2-yl-1,2,4-oxadiazol-3-yl)methyl]oxy}quinazolin-4-amine |
| 146 | N-(3,4-dichlorophenyl)-7-[({2-[(dimethylamino)methyl]-1,3-thiazol-4-yl}methyl)oxy]-6-(methyloxy)quinazolin-4-amine |
| 147 | N-(3,4-dichlorophenyl)-6-(methyloxy)-7-({[4-(phenylmethyl)morpholin-2-yl]methyl}oxy)quinazolin-4-amine |
| 148 | 1,1-dimethylethyl 2-({[4-[(3,4-dichlorophenyl)amino]-6-(methyloxy)quinazolin-7-yl]oxy}methyl)morpholine-4-carboxylate |
| 149 | N-(3,4-dichlorophenyl)-6-(methyloxy)-7-({[2-(morpholin-4-ylmethyl)-1,3-thiazol-4-yl]methyl}oxy)quinazolin-4-amine |
| 150 | N-(3,4-dichlorophenyl)-6-(methyloxy)-7-[({2-[(4-methylpiperazin-1-yl)methyl]-1,3-thiazol-4-yl}methyl)oxy]quinazolin-4-amine |
| 151 | N-(3,4-dichlorophenyl)-7-{[(4-methylmorpholin-2-yl)methyl]oxy}-6-(methyloxy)quinazolin-4-amine |
| 152 | N-(3,4-dichlorophenyl)-6-(methyloxy)-7-[(1,4-oxazepan-2-ylmethyl)oxy]quinazolin-4-amine |
| 153 | N-(3,4-dichlorophenyl)-6-(methyloxy)-7-{[(5-piperidin-3-yl-1,2,4-oxadiazol-3-yl)methyl]oxy}quinazolin-4-amine |
| 154 | N-(3,4-dichlorophenyl)-6-(methyloxy)-7-({[5-(1-methylpiperidin-2-yl)-1,2,4-oxadiazol-3-yl]methyl}oxy)quinazolin-4-amine |
| 155 | N-(3,4-dichlorophenyl)-7-{[(4-methyl-1,4-oxazepan-2-yl)methyl]oxy}-6-(methyloxy)quinazolin-4-amine |
| 156 | N-(3,4-dichlorophenyl)-6-(methyloxy)-7-({[5-(1-methylpiperidin-3-yl)-1,2,4-oxadiazol-3-yl]methyl}oxy)quinazolin-4-amine |
| 157 | N-(3,4-dichlorophenyl)-7-({[5-(1,1-dimethylethyl)-1,2,4-oxadiazol-3-yl]methyl}oxy)-6-(methyloxy)quinazolin-4-amine |
| 158 | N-(3,4-dichlorophenyl)-6-(methyloxy)-7-{[(2-phenyl-1,3-thiazol-4-yl)methyl]oxy}quinazolin-4-amine |
| 159 | 7-[(2,1,3-benzothiadiazol-4-ylmethyl)oxy]-N-(3,4-dichlorophenyl)-6-(methyloxy)quinazolin-4-amine |
| 160 | N-(3,4-dichlorophenyl)-7-{[(5-methylisoxazol-3-yl)methyl]oxy}-6-(methyloxy)quinazolin-4-amine |
| 161 | N-(3,4-dichlorophenyl)-6-(methyloxy)-7-{[(5-methyl-4-phenylisoxazol-3-yl)methyl]oxy}quinazolin-4-amine |
| 162 | 7-[(1,3-benzothiazol-2-ylmethyl)oxy]-N-(3,4-dichlorophenyl)-6-(methyloxy)quinazolin-4-amine |
| 163 | 7-[(2,1,3-benzoxadiazol-5-ylmethyl)oxy]-N-(3,4-dichlorophenyl)-6-(methyloxy)quinazolin-4-amine |
| 164 | N-(3,4-dichlorophenyl)-6-(methyloxy)-7-({[2-(2-thienyl)-1,3-thiazol-4-yl]methyl}oxy)quinazolin-4-amine |

-continued

| Entry | Name |
|---|---|
| 165 | N-(3,4-dichlorophenyl)-6-(methyloxy)-7-{[(1-phenyl-1H-pyrazol-4-yl)methyl]oxy}quinazolin-4-amine |
| 166 | N-(3,4-dichlorophenyl)-6-(methyloxy)-7-[({5-[3-(trifluoromethyl)phenyl]-1,2,4-oxadiazol-3-yl}methyl)oxy]quinazolin-4-amine |
| 167 | N-(3,4-dichlorophenyl)-6-(methyloxy)-7-[({5-[4-(trifluoromethyl)phenyl]-1,2,4-oxadiazol-3-yl}methyl)oxy]quinazolin-4-amine |
| 168 | 7-({[3-(4-chlorophenyl)-1,2,4-oxadiazol-5-yl]methyl}oxy)-N-(3,4-dichlorophenyl)-6-(methyloxy)quinazolin-4-amine |
| 169 | 7-({[6-bromo-2-(methyloxy)naphthalen-1-yl]methyl}oxy)-N-(3,4-dichlorophenyl)-6-(methyloxy)quinazolin-4-amine |
| 170 | N-(3,4-dichlorophenyl)-6-(methyloxy)-7-[(1,3-thiazol-4-ylmethyl)oxy]quinazolin-4-amine |
| 171 | 7-{[(6-chloropyridin-3-yl)methyl]oxy}-N-(3,4-dichlorophenyl)-6-(methyloxy)quinazolin-4-amine |
| 172 | N-(3,4-dichlorophenyl)-6-(methyloxy)-7-[(pyridin-4-ylmethyl)oxy]quinazolin-4-amine |
| 173 | N-(3,4-dichlorophenyl)-6-(methyloxy)-7-{[(2-methyl-1,3-thiazol-4-yl)methyl]oxy}quinazolin-4-amine |
| 174 | 7-{[(6-chloro-4H-1,3-benzodioxin-8-yl)methyl]oxy}-N-(3,4-dichlorophenyl)-6-(methyloxy)quinazolin-4-amine |
| 175 | 7-{[(5-chloro-1-methyl-3-phenyl-1H-pyrazol-4-yl)methyl]oxy}-N-(3,4-dichlorophenyl)-6-(methyloxy)quinazolin-4-amine |
| 176 | N-(3,4-dichlorophenyl)-6-(methyloxy)-7-({[1-methyl-3-(trifluoromethyl)-1H-thieno[2,3-c]pyrazol-5-yl]methyl}oxy)quinazolin-4-amine |
| 177 | N-(3,4-dichlorophenyl)-6-(methyloxy)-7-{[(3-phenylisoxazol-5-yl)methyl]oxy}quinazolin-4-amine |
| 178 | N-(3,4-dichlorophenyl)-6-(methyloxy)-7-{[(2,4,6-trimethylphenyl)methyl]oxy}quinazolin-4-amine |
| 179 | N-(3,4-dichlorophenyl)-6-(methyloxy)-7-[(pyridin-3-ylmethyl)oxy]quinazolin-4-amine |
| 180 | N-(3,4-dichlorophenyl)-6-(methyloxy)-7-[({3-[4-(methyloxy)phenyl]isoxazol-5-yl}methyl)oxy]quinazolin-4-amine |
| 181 | N-(3,4-dichlorophenyl)-7-({[5-[(2,4-dichlorophenyl)oxy]-1-methyl-3-(trifluoromethyl)-1H-pyrazol-4-yl]methyl}oxy)-6-(methyloxy)quinazolin-4-amine |
| 182 | 7-[(cyclopropylmethyl)oxy]-N-(3,4-dichlorophenyl)-6-(methyloxy)quinazolin-4-amine |
| 183 | N-(3,4-dichlorophenyl)-6-(methyloxy)-7-[(tetrahydrofuran-2-ylmethyl)oxy]quinazolin-4-amine |
| 184 | 7-(cyclopentyloxy)-N-(3,4-dichlorophenyl)-6-(methyloxy)quinazolin-4-amine |
| 185 | 7-[(2-cyclohexylethyl)oxy]-N-(3,4-dichlorophenyl)-6-(methyloxy)quinazolin-4-amine |
| 186 | 7-[(cyclohexylmethyl)oxy]-N-(3,4-dichlorophenyl)-6-(methyloxy)quinazolin-4-amine |
| 187 | 7-[(cyclobutylmethyl)oxy]-N-(3,4-dichlorophenyl)-6-(methyloxy)quinazolin-4-amine |
| 188 | N-(3,4-dichlorophenyl)-7-{[2-(1,3-dioxolan-2-yl)ethyl]oxy}-6-(methyloxy)quinazolin-4-amine |
| 189 | N-(3,4-dichlorophenyl)-7-{[2-(1,3-dioxan-2-yl)ethyl]oxy}-6-(methyloxy)quinazolin-4-amine |
| 190 | N-(3,4-dichlorophenyl)-6-(methyloxy)-7-[(2-morpholin-4-ylethyl)oxy]quinazolin-4-amine |
| 191 | N-(3,4-dichlorophenyl)-6-(methyloxy)-7-[(2-pyrrolidin-1-ylethyl)oxy]quinazolin-4-amine |
| 192 | N-(3,4-dichlorophenyl)-6-(methyloxy)-7-[(2-piperidin-1-ylethyl)oxy]quinazolin-4-amine |
| 193 | 2-(2-{[4-[(3,4-dichlorophenyl)amino]-6-(methyloxy)quinazolin-7-yl]oxy}ethyl)-1H-isoindole-1,3(2H)-dione |
| 194 | methyl 6-O-[4-[(3,4-dichlorophenyl)amino]-6-(methyloxy)quinazolin-7-yl]-alpha-D-glucopyranoside |
| 195 | N-(3,4-dichlorophenyl)-6-(methyloxy)-7-[(2-morpholin-4-yl-2-oxoethyl)oxy]quinazolin-4-amine |
| 196 | 1,1-dimethylethyl 2-[3-({[4-[(3,4-dichlorophenyl)amino]-6-(methyloxy)quinazolin-7-yl]oxy}methyl)-1,2,4-oxadiazol-5-yl]piperidine-1-carboxylate |
| 197 | 1,1-dimethylethyl 4-[3-({[4-[(3,4-dichlorophenyl)amino]-6-(methyloxy)quinazolin-7-yl]oxy}methyl)-1,2,4-oxadiazol-5-yl]piperidine-1-carboxylate |
| 198 | N-(3,4-dichlorophenyl)-6-(methyloxy)-7-({[4-(4-pyrrolidin-1-ylphenyl)-1,3-thiazol-2-yl]methyl}oxy)quinazolin-4-amine |
| 199 | N-(3,4-dichlorophenyl)-7-[({4-[4-(diethylamino)phenyl]-1,3-thiazol-2-yl}methyl)oxy]-6-(methyloxy)quinazolin-4-amine |
| 200 | 5-[2-({[4-[(3,4-dichlorophenyl)amino]-6-(methyloxy)quinazolin-7-yl]oxy}methyl)-1,3-thiazol-4-yl]-2-hydroxybenzamide |
| 201 | N-(3,4-dichlorophenyl)-6-(methyloxy)-7-{[(4-pyridin-3-yl-1,3-thiazol-2-yl)methyl]oxy}quinazolin-4-amine |
| 202 | N-(3,4-dichlorophenyl)-6-(methyloxy)-7-{[(4-pyridin-2-yl-1,3-thiazol-2-yl)methyl]oxy}quinazolin-4-amine |

-continued

| Entry | Name |
|---|---|
| 203 | N-(3,4-dichlorophenyl)-6-(methyloxy)-7-{[(4-pyridin-4-yl-1,3-thiazol-2-yl)methyl]oxy}quinazolin-4-amine |
| 204 | N-(3,4-dichlorophenyl)-6-(methyloxy)-7-{[(2-morpholin-4-yl-1,3-thiazol-4-yl)methyl]oxy}quinazolin-4-amine |
| 205 | N-(3,4-dichlorophenyl)-6-(methyloxy)-7-{[(3-morpholin-4-yl-1,2,4-oxadiazol-5-yl)methyl]oxy}quinazolin-4-amine |
| 206 | N-(3,4-dichlorophenyl)-7-({[3-(dimethylamino)-1,2,4-oxadiazol-5-yl]methyl}oxy)-6-(methyloxy)quinazolin-4-amine |
| 207 | N-(3,4-dichlorophenyl)-6-(methyloxy)-7-[({4-[(4-methylpiperazin-1-yl)methyl]-1,3-thiazol-2-yl}methyl)oxy]quinazolin-4-amine |
| 208 | N-(3,4-dichlorophenyl)-6-(methyloxy)-7-[(4,5,6,7-tetrahydro[1,3]thiazolo[5,4-c]pyridin-2-ylmethyl)oxy]quinazolin-4-amine |
| 209 | N-(3,4-dichlorophenyl)-6-(methyloxy)-7-({[4-(morpholin-4-ylmethyl)-1,3-thiazol-2-yl]methyl}oxy)quinazolin-4-amine |
| 210 | N-(3,4-dichlorophenyl)-7-[({4-[(4-methyl-1,4-diazepan-1-yl)methyl]-1,3-thiazol-2-yl}methyl)oxy]-6-(methyloxy)quinazolin-4-amine |
| 211 | N-(3,4-dichlorophenyl)-6-(methyloxy)-7-{[(5-{[(phenylmethyl)oxy]methyl}-1,2,4-oxadiazol-3-yl)methyl]oxy}quinazolin-4-amine |
| 212 | N-(3,4-dichlorophenyl)-7-{[(4-ethylmorpholin-2-yl)methyl]oxy}-6-(methyloxy)quinazolin-4-amine |
| 213 | N-(3,4-dichlorophenyl)-6-(methyloxy)-7-{[(2-piperidin-4-yl-1,3-thiazol-4-yl)methyl]oxy}quinazolin-4-amine |
| 214 | N-(3,4-dichlorophenyl)-6-(methyloxy)-7-({[2-(1-methylpiperidin-4-yl)-1,3-thiazol-4-yl]methyl}oxy)quinazolin-4-amine |
| 215 | 1,1-dimethylethyl 4-[5-({[4-[(3,4-dichlorophenyl)amino]-6-(methyloxy)quinazolin-7-yl]oxy}methyl)-1,2,4-oxadiazol-3-yl]piperazine-1-carboxylate |
| 217 | N-(3,4-dichlorophenyl)-6-(methyloxy)-7-{[(3-piperazin-1-yl-1,2,4-oxadiazol-5-yl)methyl]oxy}quinazolin-4-amine |
| 218 | N-(3,4-dichlorophenyl)-6-(methyloxy)-7-({[3-(4-methylpiperazin-1-yl)-1,2,4-oxadiazol-5-yl]methyl}oxy)quinazolin-4-amine |
| 219 | N-(3,4-dichlorophenyl)-7-({[5-(1-ethylpiperidin-2-yl)-1,2,4-oxadiazol-3-yl]methyl}oxy)-6-(methyloxy)quinazolin-4-amine |
| 220 | N-(3,4-dichlorophenyl)-7-({[3-(4-ethylpiperazin-1-yl)-1,2,4-oxadiazol-5-yl]methyl}oxy)-6-(methyloxy)quinazolin-4-amine |
| 221 | N-(3,4-dichlorophenyl)-6-(methyloxy)-7-[({5-[4-(methyloxy)phenyl]-1,2,4-oxadiazol-3-yl}methyl)oxy]quinazolin-4-amine |
| 222 | N-(3,4-dichlorophenyl)-6-(methyloxy)-7-[({2-[4-(trifluoromethyl)phenyl]-1,3-thiazol-4-yl}methyl)oxy]quinazolin-4-amine |
| 223 | 7-({[2-(4-chlorophenyl)-1,3-thiazol-4-yl]methyl}oxy)-N-(3,4-dichlorophenyl)-6-(methyloxy)quinazolin-4-amine |
| 224 | N-(3,4-dichlorophenyl)-7-({[5-(3,5-dimethylisoxazol-4-yl)-1,2,4-oxadiazol-3-yl]methyl}oxy)-6-(methyloxy)quinazolin-4-amine |
| 225 | 7-{[(5-chloro-1-benzothien-3-yl)methyl]oxy}-N-(3,4-dichlorophenyl)-6-(methyloxy)quinazolin-4-amine |
| 226 | N-(3,4-dichlorophenyl)-7-[({3-[4-(1,1-dimethylethyl)phenyl]-1,2,4-oxadiazol-5-yl}methyl)oxy]-6-(methyloxy)quinazolin-4-amine |
| 227 | N-(3,4-dichlorophenyl)-6-(methyloxy)-7-[({5-[2-(methyloxy)phenyl]-1,2,4-oxadiazol-3-yl}methyl)oxy]quinazolin-4-amine |
| 228 | N-(3,4-dichlorophenyl)-6-(methyloxy)-7-({[5-(4-methylphenyl)-1,3,4-oxadiazol-2-yl]methyl}oxy)quinazolin-4-amine |
| 229 | N-(3,4-dichlorophenyl)-6-(methyloxy)-7-({[1-(phenylmethyl)-1H-imidazol-2-yl]methyl}oxy)quinazolin-4-amine |
| 230 | N-(3,4-dichlorophenyl)-7-({[3-(2,6-dichlorophenyl)-5-methylisoxazol-4-yl]methyl}oxy)-6-(methyloxy)quinazolin-4-amine |
| 231 | N-(3,4-dichlorophenyl)-7-{[(6-fluoro-4H-1,3-benzodioxin-8-yl)methyl]oxy}-6-(methyloxy)quinazolin-4-amine |
| 232 | 7-{[(3,5-dibromophenyl)methyl]oxy}-N-(3,4-dichlorophenyl)-6-(methyloxy)quinazolin-4-amine |
| 233 | N-(3,4-dichlorophenyl)-7-{[(2,6-difluorophenyl)methyl]oxy}-6-(methyloxy)quinazolin-4-amine |
| 234 | N-(3,4-dichlorophenyl)-6-(methyloxy)-7-[({3-[(pyridin-2-ylsulfonyl)methyl]-1,2,4-oxadiazol-5-yl}methyl)oxy]quinazolin-4-amine |
| 235 | N-(3,4-dichlorophenyl)-6-(methyloxy)-7-{[(5-phenyl-1,2,4-oxadiazol-3-yl)methyl]oxy}quinazolin-4-amine |
| 236 | 7-({[4-chloro-2-(trifluoromethyl)quinolin-6-yl]methyl}oxy)-N-(3,4-dichlorophenyl)-6-(methyloxy)quinazolin-4-amine |
| 237 | N-(3,4-dichlorophenyl)-6-(methyloxy)-7-{[2-(1-methylpyrrolidin-2-yl)ethyl]oxy}quinazolin-4-amine |
| 238 | N-(3,4-dichlorophenyl)-7-({[5-(1-ethylpiperidin-4-yl)-1,2,4-oxadiazol-3-yl]methyl}oxy)-6-(methyloxy)quinazolin-4-amine |
| 239 | N-(3,4-dichlorophenyl)-7-({[5-(1-ethylpiperidin-3-yl)-1,2,4-oxadiazol-3-yl]methyl}oxy)-6-(methyloxy)quinazolin-4-amine |
| 240 | N-(3,4-dichlorophenyl)-7-({[2-(dimethylamino)-1,3-thiazol-4-yl]methyl}oxy)-6-(methyloxy)quinazolin-4-amine |
| 241 | N-(3,4-dichlorophenyl)-7-{[(4-ethyl-1,4-oxazepan-2-yl)methyl]oxy}-6-(methyloxy)quinazolin-4-amine |

| Entry | Name |
|---|---|
| 242 | N-(3,4-dichlorophenyl)-7-({[2-(1-ethylpiperidin-4-yl)-1,3-thiazol-4-yl]methyl}oxy)-6-(methyloxy)quinazolin-4-amine |
| 243 | N-(3,4-dichlorophenyl)-6-(methyloxy)-7-[({3-[(2S)-pyrrolidin-2-yl]-1,2,4-oxadiazol-5-yl}methyl)oxy]quinazolin-4-amine |
| 244 | N-(3,4-dichlorophenyl)-6-(methyloxy)-7-[({2-[(2S)-pyrrolidin-2-yl]-1,3-thiazol-4-yl}methyl)oxy]quinazolin-4-amine |
| 245 | [4-({[4-[(3,4-dichlorophenyl)amino]-6-(methyloxy)quinazolin-7-yl]oxy}methyl)-1,3-thiazol-2-yl]methyl benzoate |
| 246 | [4-({[4-[(3,4-dichlorophenyl)amino]-6-(methyloxy)quinazolin-7-yl]oxy}methyl)-1,3-thiazol-2-yl]methanol |
| 247 | N-(3,4-dichlorophenyl)-6-(methyloxy)-7-{[(5-methyl-4,5,6,7-tetrahydro[1,3]thiazolo[5,4-c]pyridin-2-yl)methyl]oxy}quinazolin-4-amine |
| 248 | N-(3,4-dichlorophenyl)-6-(methyloxy)-7-[({2-[(4S)-1,3-thiazolidin-4-yl]-1,3-thiazol-4-yl}methyl)oxy]quinazolin-4-amine |
| 249 | N-(3,4-dichlorophenyl)-6-(methyloxy)-7-{[(2-piperidin-2-yl-1,3-thiazol-4-yl)methyl]oxy}quinazolin-4-amine |
| 250 | N-(3,4-dichlorophenyl)-6-(methyloxy)-7-({[2-(1-methylpiperidin-2-yl)-1,3-thiazol-4-yl]methyl}oxy)quinazolin-4-amine |
| 251 | N-(3,4-dichlorophenyl)-6-(methyloxy)-7-{[(2-piperidin-3-yl-1,3-thiazol-4-yl)methyl]oxy}quinazolin-4-amine |
| 252 | N-(3,4-dichlorophenyl)-6-(methyloxy)-7-({[2-(1-methylpiperidin-3-yl)-1,3-thiazol-4-yl]methyl}oxy)quinazolin-4-amine |
| 253 | N-(3,4-dichlorophenyl)-7-({[2-(1-ethylpiperidin-2-yl)-1,3-thiazol-4-yl]methyl}oxy)-6-(methyloxy)quinazolin-4-amine |
| 254 | N-(3,4-dichlorophenyl)-7-({[2-(1-ethylpiperidin-3-yl)-1,3-thiazol-4-yl]methyl}oxy)-6-(methyloxy)quinazolin-4-amine |
| 255 | N-(3,4-dichlorophenyl)-7-[({3-[(2S)-1-ethylpyrrolidin-2-yl]-1,2,4-oxadiazol-5-yl}methyl)oxy]-6-(methyloxy)quinazolin-4-amine |
| 256 | N-(3,4-dichlorophenyl)-7-[({2-[(2S)-1-ethylpyrrolidin-2-yl]-1,3-thiazol-4-yl}methyl)oxy]-6-(methyloxy)quinazolin-4-amine |
| 257 | N-(3,4-dichlorophenyl)-7-{[(5-ethyl-4,5,6,7-tetrahydro[1,3]thiazolo[5,4-c]pyridin-2-yl)methyl]oxy}-6-(methyloxy)quinazolin-4-amine |
| 258 | N-(3,4-dichlorophenyl)-6-(methyloxy)-7-{[(4-propyl-1,4-oxazepan-2-yl)methyl]oxy}quinazolin-4-amine |
| 259 | 7-({[4-(cyclopropylmethyl)-1,4-oxazepan-2-yl]methyl}oxy)-N-(3,4-dichlorophenyl)-6-(methyloxy)quinazolin-4-amine |
| 260 | N-(3,4-dichlorophenyl)-6-(methyloxy)-7-[({4-[2-(methyloxy)ethyl]-1,4-oxazepan-2-yl}methyl)oxy]quinazolin-4-amine |
| 261 | N-(3,4-dichlorophenyl)-7-({[4-(1-methylethyl)-1,4-oxazepan-2-yl]methyl}oxy)-6-(methyloxy)quinazolin-4-amine |
| 262 | N-(3,4-dichlorophenyl)-6-(methyloxy)-7-{[(2-piperazin-1-yl-1,3-thiazol-4-yl)methyl]oxy}quinazolin-4-amine |
| 263 | N-(3,4-dichlorophenyl)-6-(methyloxy)-7-{[(5-pyrrolidin-2-yl-1,2,4-oxadiazol-3-yl)methyl]oxy}quinazolin-4-amine |
| 264 | N-(3,4-dichlorophenyl)-7-({[5-(1-ethylpyrrolidin-2-yl)-1,2,4-oxadiazol-3-yl]methyl}oxy)-6-(methyloxy)quinazolin-4-amine |
| 265 | N-(3,4-dichlorophenyl)-6-(methyloxy)-7-[({3-[(2S)-1-methylpyrrolidin-2-yl]-1,2,4-oxadiazol-5-yl}methyl)oxy]quinazolin-4-amine |
| 266 | N-(3,4-dichlorophenyl)-6-(methyloxy)-7-[({2-[(2S)-1-methylpyrrolidin-2-yl]-1,3-thiazol-4-yl}methyl)oxy]quinazolin-4-amine |
| 267 | N-(3,4-dichlorophenyl)-7-({[2-(4-ethylpiperazin-1-yl)-1,3-thiazol-4-yl]methyl}oxy)-6-(methyloxy)quinazolin-4-amine |
| 268 | N-(3,4-dichlorophenyl)-7-{[(1,4-dimethylpiperazin-2-yl)methyl]oxy}-6-(methyloxy)quinazolin-4-amine |
| 269 | 7-{[(4-cyclopentylmorpholin-2-yl)methyl]oxy}-N-(3,4-dichlorophenyl)-6-(methyloxy)quinazolin-4-amine |
| 270 | N-(3,4-dichlorophenyl)-7-({[4-(1-methylethyl)morpholin-2-yl]methyl}oxy)-6-(methyloxy)quinazolin-4-amine |
| 271 | N-(3,4-dichlorophenyl)-6-(methyloxy)-7-({[4-(3-phenylpropyl)morpholin-2-yl]methyl}oxy)quinazolin-4-amine |
| 272 | N-(3,4-dichlorophenyl)-6-(methyloxy)-7-[({4-[2-(methyloxy)ethyl]morpholin-2-yl}methyl)oxy]quinazolin-4-amine |
| 273 | ethyl 2-[2-({[4-[(3,4-dichlorophenyl)amino]-6-(methyloxy)quinazolin-7-yl]oxy}methyl)morpholin-4-yl]propanoate |
| 274 | N-(3,4-dichlorophenyl)-7-{[(4-hex-5-en-1-ylmorpholin-2-yl)methyl]oxy}-6-(methyloxy)quinazolin-4-amine |
| 275 | 2-({2-[2-({[4-[(3,4-dichlorophenyl)amino]-6-(methyloxy)quinazolin-7-yl]oxy}methyl)morpholin-4-yl]ethyl}oxy)ethanol |
| 276 | methyl 3-[2-({[4-[(3,4-dichlorophenyl)amino]-6-(methyloxy)quinazolin-7-yl]oxy}methyl)morpholin-4-yl]propanoate |
| 277 | 6-[2-({[4-[(3,4-dichlorophenyl)amino]-6-(methyloxy)quinazolin-7-yl]oxy}methyl)morpholin-4-yl]hexanenitrile |
| 278 | N-(3,4-dichlorophenyl)-6-(methyloxy)-7-({[4-(tetrahydro-2H-pyran-2-ylmethyl)morpholin-2-yl]methyl}oxy)quinazolin-4-amine |
| 279 | 4-[2-({[4-[(3,4-dichlorophenyl)amino]-6-(methyloxy)quinazolin-7-yl]oxy}methyl)morpholin-4-yl]butanenitrile |
| 280 | N-(3,4-dichlorophenyl)-7-[({4-[(4-fluorophenyl)methyl]morpholin-2-yl}methyl)oxy]-6-(methyloxy)quinazolin-4-amine |

-continued

| Entry | Name |
|---|---|
| 281 | methyl 5-[2-({[4-[(3,4-dichlorophenyl)amino]-6-(methyloxy)quinazolin-7-yl]oxy}methyl)morpholin-4-yl]pentanoate |
| 282 | N-(3,4-dichlorophenyl)-6-(methyloxy)-7-{[(4-oct-7-en-1-ylmorpholin-2-yl)methyl]oxy}quinazolin-4-amine |
| 283 | N-(3,4-dichlorophenyl)-6-(methyloxy)-7-{[(4-propylmorpholin-2-yl)methyl]oxy}quinazolin-4-amine |
| 284 | 6-[2-({[4-[(3,4-dichlorophenyl)amino]-6-(methyloxy)quinazolin-7-yl]oxy}methyl)morpholin-4-yl]hexan-1-ol |
| 285 | 7-{[(4-acetylmorpholin-2-yl)methyl]oxy}-N-(3,4-dichlorophenyl)-6-(methyloxy)quinazolin-4-amine |
| 286 | 7-({[4-(cyclopropylmethyl)morpholin-2-yl]methyl}oxy)-N-(3,4-dichlorophenyl)-6-(methyloxy)quinazolin-4-amine |
| 287 | N-(3,4-dichlorophenyl)-6-(methyloxy)-7-{[(4-prop-2-yn-1-ylmorpholin-2-yl)methyl]oxy}quinazolin-4-amine |
| 288 | N-(3,4-dichlorophenyl)-6-(methyloxy)-7-{[(4-pyridin-4-ylmorpholin-2-yl)methyl]oxy}quinazolin-4-amine |
| 289 | N-(3,4-dichlorophenyl)-6-(methyloxy)-7-({[4-(pyridin-2-ylmethyl)morpholin-2-yl]methyl}oxy)quinazolin-4-amine |
| 290 | N-(3,4-dichlorophenyl)-6-(methyloxy)-7-{[(4-pent-2-yn-1-ylmorpholin-2-yl)methyl]oxy}quinazolin-4-amine |
| 291 | N-(3,4-dichlorophenyl)-6-(methyloxy)-7-({[2-(4-methylpiperazin-1-yl)-1,3-thiazol-4-yl]methyl}oxy)quinazolin-4-amine |
| 292 | N-(3,4-dichlorophenyl)-6-(methyloxy)-7-({[5-(1-methylpyrrolidin-2-yl)-1,2,4-oxadiazol-3-yl]methyl}oxy)quinazolin-4-amine |
| 293 | N-(3-chloro-4-fluorophenyl)-7-{[(4-methylmorpholin-2-yl)methyl]oxy}-6-(methyloxy)quinazolin-4-amine |
| 294 | 7-{[(4-butyl-1,4-oxazepan-2-yl)methyl]oxy}-N-(3,4-dichlorophenyl)-6-(methyloxy) quinazolin-4-amine |
| 295 | (3,4-dichlorophenyl)[7-(methyloxy)-6-({[4-(2-methylpropyl)-1,4-oxazepan-2-yl]methyl}oxy) quinazolin-4-amine |
| 296 | 7-{[(4-acetyl-1-ethylpiperazin-2-yl)methyl]oxy}-N-(3,4-dichlorophenyl)-6-(methyloxy)quinazolin-4-amine |
| 297 | (3,4-dichlorophenyl)(6-(methyloxy)-7-{[(4-pentyl-1,4-oxazepan-2-yl)methyl]oxy} quinazolin-4-amine |
| 298 | (3,4-dichlorophenyl)[6-(methyloxy)-7-({[4-(tetrahydro-2H-pyran-2-ylmethyl)-1,4-oxazepan-2-yl]methyl}oxy)quinazolin-4-amine |
| 299 | (3,4-dichlorophenyl)[6-(methyloxy)-7-({[4-(3-thienylmethyl)-1,4-oxazepan-2-yl]methyl}oxy) quinazolin-4-amine |
| 300 | N-[4-chloro-2,5-bis(methyloxy)phenyl]-7-{[(4-methylmorpholin-2-yl)methyl]oxy}-6-(methyloxy)quinazolin-4-amine |
| 301 | N-(3-bromo-2-methylphenyl)-7-{[(4-methylmorpholin-2-yl)methyl]oxy}-6-(methyloxy)quinazolin-4-amine |
| 302 | 7-{[(4-methylmorpholin-2-yl)methyl]oxy}-6-(methyloxy)-N-(3,4,5-trichlorophenyl)quinazolin-4-amine |
| 303 | N-(3-chloro-2-methylphenyl)-7-{[(4-methylmorpholin-2-yl)methyl]oxy}-6-(methyloxy)quinazolin-4-amine |
| 304 | N-(3,4-dichlorophenyl)-7-{[(4-ethanimidoyl-1,4-oxazepan-2-yl)methyl]oxy}-6-(methyloxy)quinazolin-4-amine |
| 305 | N-(4-bromo-2-fluorophenyl)-7-{[(4-methylmorpholin-2-yl)methyl]oxy}-6-(methyloxy)quinazolin-4-amine |
| 306 | N-(5-chloro-2-fluorophenyl)-7-{[(4-methylmorpholin-2-yl)methyl]oxy}-6-(methyloxy)quinazolin-4-amine |
| 307 | N-(4-chloro-2-fluorophenyl)-7-{[(4-methylmorpholin-2-yl)methyl]oxy}-6-(methyloxy)quinazolin-4-amine |
| 308 | N-(2,4-dichlorophenyl)-7-{[(4-methylmorpholin-2-yl)methyl]oxy}-6-(methyloxy)quinazolin-4-amine |
| 309 | N-(2,4-dibromophenyl)-7-{[(4-methylmorpholin-2-yl)methyl]oxy}-6-(methyloxy)quinazolin-4-amine |
| 310 | 7-{[(4-methylmorpholin-2-yl)methyl]oxy}-6-(methyloxy)-N-(2,3,4-trichlorophenyl)quinazolin-4-amine |
| 311 | N-(3,4-dichlorophenyl)-7-{[(1-ethyl-4-methylpiperazin-2-yl)methyl]oxy}-6-(methyloxy)quinazolin-4-amine |
| 312 | N'-cyano-2-({[4-[(3,4-dichlorophenyl)amino]-6-(methyloxy)quinazolin-7-yl]oxy}methyl)morpholine-4-carboximidamide |
| 313 | N-(3,4-dichlorophenyl)-6-(methyloxy)-7-({[2-(pyrrolidin-1-ylmethyl)-1,3-thiazol-4-yl]methyl}oxy)quinazolin-4-amine |
| 314 | N-(3,4-dichlorophenyl)-6-(methyloxy)-7-({[4-(tetrahydro-2H-pyran-4-yl)morpholin-2-yl]methyl}oxy)quinazolin-4-amine |
| 315 | N-(3,4-dichlorophenyl)-7-({[4-(2-ethylbutyl)morpholin-2-yl]methyl}oxy)-6-(methyloxy)quinazolin-4-amine |
| 316 | 7-({[4-(cyclohexylmethyl)morpholin-2-yl]methyl}oxy)-N-(3,4-dichlorophenyl)-6-(methyloxy)quinazolin-4-amine |
| 317 | 2-[2-({[4-[(3,4-dichlorophenyl)amino]-6-(methyloxy)quinazolin-7-yl]oxy}methyl)morpholin-4-yl]ethanol |
| 318 | 7-{[(4-but-2-yn-1-ylmorpholin-2-yl)methyl]oxy}-N-(3,4-dichlorophenyl)-6-(methyloxy)quinazolin-4-amine |
| 319 | 7-{[(4-cyclobutylmorpholin-2-yl)methyl]oxy}-N-(3,4-dichlorophenyl)-6-(methyloxy)quinazolin-4-amine |

-continued

| Entry | Name |
|---|---|
| 320 | N-(3,4-dichlorophenyl)-7-[({4-[2-(1,3-dioxolan-2-yl)ethyl]morpholin-2-yl}methyl)oxy]-6-(methyloxy)quinazolin-4-amine |
| 321 | 7-({[4-(2-cyclohexylethyl)morpholin-2-yl]methyl}oxy)-N-(3,4-dichlorophenyl)-6-(methyloxy)quinazolin-4-amine |
| 322 | N-(3,4-dichlorophenyl)-7-[({4-[2-(1,3-dioxan-2-yl)ethyl]morpholin-2-yl}methyl)oxy]-6-(methyloxy)quinazolin-4-amine |
| 323 | N-(3,4-dichlorophenyl)-6-(methyloxy)-7-{[(4-pent-4-en-1-ylmorpholin-2-yl)methyl]oxy}quinazolin-4-amine |
| 324 | N-(3,4-dichlorophenyl)-7-[({4-[(2R)-2-methylbutyl]morpholin-2-yl}methyl)oxy]-6-(methyloxy)quinazolin-4-amine |
| 325 | N-(3,4-dichlorophenyl)-7-({[4-(4-fluorobutyl)morpholin-2-yl]methyl}oxy)-6-(methyloxy)quinazolin-4-amine |
| 326 | 3-[2-({[4-[(3,4-dichlorophenyl)amino]-6-(methyloxy)quinazolin-7-yl]oxy}methyl)morpholin-4-yl]butan-2-one |
| 327 | 1-[2-({[4-[(3,4-dichlorophenyl)amino]-6-(methyloxy)quinazolin-7-yl]oxy}methyl)morpholin-4-yl]butan-2-one |
| 328 | N-(3,4-dichlorophenyl)-6-(methyloxy)-7-{[(4-pentylmorpholin-2-yl)methyl]oxy}quinazolin-4-amine |
| 329 | N-(3,4-dichlorophenyl)-7-{[(4-hexylmorpholin-2-yl)methyl]oxy}-6-(methyloxy)quinazolin-4-amine |
| 330 | N-(3,4-dichlorophenyl)-7-{[(4-heptylmorpholin-2-yl)methyl]oxy}-6-(methyloxy)quinazolin-4-amine |
| 331 | N-(3,4-dichlorophenyl)-6-(methyloxy)-7-{[(4-octylmorpholin-2-yl)methyl]oxy}quinazolin-4-amine |
| 332 | N-(3,4-dichlorophenyl)-6-(methyloxy)-7-({[4-(2-phenylethyl)morpholin-2-yl]methyl}oxy)quinazolin-4-amine |
| 333 | 7-{[(4-butylmorpholin-2-yl)methyl]oxy}-N-(3,4-dichlorophenyl)-6-(methyloxy)quinazolin-4-amine |
| 334 | N-(3,4-dichlorophenyl)-6-(methyloxy)-7-{[(4-prop-2-en-1-ylmorpholin-2-yl)methyl]oxy}quinazolin-4-amine |
| 335 | 2-[2-({[4-[(3,4-dichlorophenyl)amino]-6-(methyloxy)quinazolin-7-yl]oxy}methyl)morpholin-4-yl]-1-phenylethanone |
| 336 | N-(3,4-dichlorophenyl)-7-({[4-(2-fluoroethyl)morpholin-2-yl]methyl}oxy)-6-(methyloxy)quinazolin-4-amine |
| 337 | N-(3,4-dichlorophenyl)-7-({[4-(3-methylbut-2-en-1-yl)morpholin-2-yl]methyl}oxy)-6-(methyloxy)quinazolin-4-amine |
| 338 | 7-[({4-[(2E)-3-bromoprop-2-en-1-yl]morpholin-2-yl}methyl)oxy]-N-(3,4-dichlorophenyl)-6-(methyloxy)quinazolin-4-amine |
| 339 | 2-[2-({[4-[(3,4-dichlorophenyl)amino]-6-(methyloxy)quinazolin-7-yl]oxy}methyl)morpholin-4-yl]acetamide |
| 340 | N-(3,4-dichlorophenyl)-6-(methyloxy)-7-[({4-[3-(tetrahydro-2H-pyran-2-yloxy)propyl]-1,4-oxazepan-2-yl}methyl)oxy]quinazolin-4-amine |
| 341 | N-(3,4-dichlorophenyl)-7-({[4-(3-methylbutyl)-1,4-oxazepan-2-yl]methyl}oxy)-6-(methyloxy)quinazolin-4-amine |
| 342 | 7-({[4-(cyclohexylmethyl)-1,4-oxazepan-2-yl]methyl}oxy)-4-[(3,4-dichlorophenyl)methyl]-6-(methyloxy)quinazoline |
| 343 | 7-({[4-(2-cyclohexylethyl)-1,4-oxazepan-2-yl]methyl}oxy)-4-[(3,4-dichlorophenyl)methyl]-6-(methyloxy)quinazoline |
| 345 | N-(3,4-dichlorophenyl)-7-({[4-(2-ethylbutyl)-1,4-oxazepan-2-yl]methyl}oxy)-6-(methyloxy)quinazolin-4-amine |
| 346 | N-(3,4-dichlorophenyl)-6-(methyloxy)-7-({[4-(methylsulfonyl)-1,4-oxazepan-2-yl]methyl}oxy)quinazolin-4-amine |
| 347 | N-(3,4-dichlorophenyl)-6-(methyloxy)-7-({[4-(1-methylpiperidin-4-yl)morpholin-2-yl]methyl}oxy)quinazolin-4-amine |
| 348 | N-(3-chloro-2-fluorophenyl)-7-{[(4-methylmorpholin-2-yl)methyl]oxy}-6-(methyloxy)quinazolin-4-amine |
| 349 | N'-cyano-2-({[4-[(3,4-dichlorophenyl)amino]-6-(methyloxy)quinazolin-7-yl]oxy}methyl)-1,4-oxazepane-4-carboximidamide |
| 350 | N-(3-bromo-4-methylphenyl)-7-{[(4-methylmorpholin-2-yl)methyl]oxy}-6-(methyloxy)quinazolin-4-amine |
| 351 | N-(3,4-dichlorophenyl)-7-{[(1,4-diethylpiperazin-2-yl)methyl]oxy}-6-(methyloxy)quinazolin-4-amine |
| 352 | 4-({[4-[(4-bromo-2-fluorophenyl)amino]-6-(methyloxy)quinazolin-7-yl]oxy}methyl)-N'-cyanopiperidine-1-carboximidamide |
| 353 | N-(3,4-dichlorophenyl)-6-(methyloxy)-7-({[4-(methylsulfonyl)morpholin-2-yl]methyl}oxy)quinazolin-4-amine |
| 354 | N-(3,4-dichlorophenyl)-6-(methyloxy)-7-[({4-[(phenylmethyl)sulfonyl]morpholin-2-yl}methyl)oxy]quinazolin-4-amine |
| 355 | N-(3,4-dichlorophenyl)-7-[({4-[(4-fluorophenyl)sulfonyl]morpholin-2-yl}methyl)oxy]-6-(methyloxy)quinazolin-4-amine |
| 356 | N-(3,4-dichlorophenyl)-7-({[4-(ethylsulfonyl)morpholin-2-yl]methyl}oxy)-6-(methyloxy)quinazolin-4-amine |
| 357 | N-(3,4-dichlorophenyl)-6-(methyloxy)-7-({[4-(phenylsulfonyl)morpholin-2-yl]methyl}oxy)quinazolin-4-amine |
| 358 | 7-[({4-[(3-chloropropyl)sulfonyl]morpholin-2-yl}methyl)oxy]-N-(3,4-dichlorophenyl)-6-(methyloxy)quinazolin-4-amine |
| 359 | 7-({[4-(butylsulfonyl)morpholin-2-yl]methyl}oxy)-N-(3,4-dichlorophenyl)-6-(methyloxy)quinazolin-4-amine |

-continued

| Entry | Name |
|---|---|
| 360 | N-(3,4-dichlorophenyl)-6-(methyloxy)-7-[({4-[(4-methylphenyl)sulfonyl]morpholin-2-yl}methyl)oxy]quinazolin-4-amine |
| 361 | N-(3,4-dichlorophenyl)-7-[({4-[(3,5-dimethylisoxazol-4-yl)carbonyl]morpholin-2-yl}methyl)oxy]-6-(methyloxy)quinazolin-4-amine |
| 362 | N-(3,4-dichlorophenyl)-6-(methyloxy)-7-{[(4-{[3-(methyloxy)phenyl]acetyl}morpholin-2-yl)methyl]oxy}quinazolin-4-amine |
| 363 | N-(3,4-dichlorophenyl)-6-(methyloxy)-7-({[4-(2-methylpentanoyl)morpholin-2-yl]methyl}oxy)quinazolin-4-amine |
| 364 | 7-[({4-[(4-butylphenyl)carbonyl]morpholin-2-yl}methyl)oxy]-N-(3,4-dichlorophenyl)-6-(methyloxy)quinazolin-4-amine |
| 365 | 7-[({4-[(4-chlorophenyl)acetyl]morpholin-2-yl}methyl)oxy]-N-(3,4-dichlorophenyl)-6-(methyloxy)quinazolin-4-amine |
| 366 | N-(3,4-dichlorophenyl)-6-(methyloxy)-7-({[4-(2-propylpentanoyl)morpholin-2-yl]methyl}oxy)quinazolin-4-amine |
| 367 | N-(3,4-dichlorophenyl)-6-(methyloxy)-7-({[4-(4-methylpentanoyl)morpholin-2-yl]methyl}oxy)quinazolin-4-amine |
| 368 | N-(3,4-dichlorophenyl)-7-[({4-[(2,5-difluorophenyl)carbonyl]morpholin-2-yl}methyl)oxy]-6-(methyloxy)quinazolin-4-amine |
| 369 | 7-({[4-(cyclopentylcarbonyl)morpholin-2-yl]methyl}oxy)-N-(3,4-dichlorophenyl)-6-(methyloxy)quinazolin-4-amine |
| 370 | N-(3,4-dichlorophenyl)-6-(methyloxy)-7-({[4-(2-phenylbutanoyl)morpholin-2-yl]methyl}oxy)quinazolin-4-amine |
| 371 | N-(3,4-dichlorophenyl)-6-(methyloxy)-7-[({4-[(2,3,6-trifluorophenyl)carbonyl]morpholin-2-yl}methyl)oxy]quinazolin-4-amine |
| 372 | N-(3,4-dichlorophenyl)-7-({[4-(furan-3-ylcarbonyl)morpholin-2-yl]methyl}oxy)-6-(methyloxy)quinazolin-4-amine |
| 373 | N-(3,4-dichlorophenyl)-6-(methyloxy)-7-{[(4-propanoylmorpholin-2-yl)methyl]oxy}quinazolin-4-amine |
| 374 | N-(3,4-dichlorophenyl)-7-{[(4-hexanoylmorpholin-2-yl)methyl]oxy}-6-(methyloxy)quinazolin-4-amine |
| 375 | N-(3,4-dichlorophenyl)-7-({[4-(2-ethylhexanoyl)morpholin-2-yl]methyl}oxy)-6-(methyloxy)quinazolin-4-amine |
| 376 | N-(3,4-dichlorophenyl)-6-(methyloxy)-7-({[4-(3-phenylpropanoyl)morpholin-2-yl]methyl}oxy)quinazolin-4-amine |
| 377 | N-(3,4-dichlorophenyl)-7-({[4-(2,2-dimethylpropanoyl)morpholin-2-yl]methyl}oxy)-6-(methyloxy)quinazolin-4-amine |
| 378 | N-(3,4-dichlorophenyl)-6-(methyloxy)-7-({[4-(naphthalen-1-ylcarbonyl)morpholin-2-yl]methyl}oxy)quinazolin-4-amine |
| 379 | 7-[({4-[(2-chloropyridin-3-yl)carbonyl]morpholin-2-yl}methyl)oxy]-N-(3,4-dichlorophenyl)-6-(methyloxy)quinazolin-4-amine |
| 380 | 7-[({4-[(6-chloropyridin-3-yl)carbonyl]morpholin-2-yl}methyl)oxy]-N-(3,4-dichlorophenyl)-6-(methyloxy)quinazolin-4-amine |
| 381 | 7-({[4-(1,3-benzodioxol-5-ylcarbonyl)morpholin-2-yl]methyl}oxy)-N-(3,4-dichlorophenyl)-6-(methyloxy)quinazolin-4-amine |
| 382 | N-(3,4-dichlorophenyl)-6-[(1-methylethyl)oxy]-7-[(morpholin-2-ylmethyl)oxy]quinazolin-4-amine |
| 383 | N-(3,4-dichlorophenyl)-6-{[2-(methyloxy)ethyl]oxy}-7-[(morpholin-2-ylmethyl)oxy]quinazolin-4-amine |
| 384 | N-(3,4-dichlorophenyl)-6-(ethyloxy)-7-[(morpholin-2-ylmethyl)oxy]quinazolin-4-amine |
| 385 | N-(3,4-dichlorophenyl)-6-(ethyloxy)-7-{[(4-methylmorpholin-2-yl)methyl]oxy}quinazolin-4-amine |
| 386 | N-(4-bromo-2-methylphenyl)-7-{[(4-methylmorpholin-2-yl)methyl]oxy}-6-(methyloxy)quinazolin-4-amine |
| 387 | N-(4-chloro-3-methylphenyl)-7-{[(4-methylmorpholin-2-yl)methyl]oxy}-6-(methyloxy)quinazolin-4-amine |
| 388 | N'-cyano-2-({[4-[(3,4-dichlorophenyl)amino]-6-(methyloxy)quinazolin-7-yl]oxy}methyl)-N-methylmorpholine-4-carboximidamide |
| 389 | N-(4-bromo-3-chlorophenyl)-7-{[(4-methylmorpholin-2-yl)methyl]oxy}-6-(methyloxy)quinazolin-4-amine |
| 390 | N-(3,4-dichlorophenyl)-6-[(1-methylethyl)oxy]-7-{[(4-methylmorpholin-2-yl)methyl]oxy}quinazolin-4-amine |
| 391 | N-(3,4-dichlorophenyl)-7-{[(4-methylmorpholin-2-yl)methyl]oxy}-6-{[2-(methyloxy)ethyl]oxy}quinazolin-4-amine |
| 392 | N-(4-bromo-2-chlorophenyl)-7-{[(4-methylmorpholin-2-yl)methyl]oxy}-6-(methyloxy)quinazolin-4-amine |

| Entry | Name |
|---|---|
| 393 | 7-{[(4-acetyl-1,4-oxazepan-2-yl)methyl]oxy}-N-(3,4-dichlorophenyl)-6-(methyloxy)quinazolin-4-amine |
| 394 | 4-[(3,4-dichlorophenyl)amino]-7-{[(4-methylmorpholin-2-yl)methyl]oxy}quinazolin-6-ol |
| 395 | N-(3-bromo-4-chlorophenyl)-7-{[(4-methylmorpholin-2-yl)methyl]oxy}-6-(methyloxy)quinazolin-4-amine |
| 396 | 3-[2-({[4-[(3,4-dichlorophenyl)amino]-6-(methyloxy)quinazolin-7-yl]oxy}methyl)morpholin-4-yl]-3-oxopropanoic acid |
| 397 | methyl 4-[2-({[4-[(3,4-dichlorophenyl)amino]-6-(methyloxy)quinazolin-7-yl]oxy}methyl)morpholin-4-yl]-4-oxobutanoate |
| 398 | N-(3,4-dichlorophenyl)-7-{[(4-methylmorpholin-3-yl)methyl]oxy}-6-(methyloxy)quinazolin-4-amine |
| 399 | N-(3-bromo-2-chlorophenyl)-7-{[(4-methylmorpholin-2-yl)methyl]oxy}-6-(methyloxy)quinazolin-4-amine |
| 400 | N'-cyano-2-({[4-[(3,4-dichlorophenyl)amino]-6-(methyloxy)quinazolin-7-yl]oxy}methyl)-N-[2-(methyloxy)ethyl]morpholine-4-carboximidamide |
| 401 | N'-cyano-2-({[4-[(3,4-dichlorophenyl)amino]-6-(methyloxy)quinazolin-7-yl]oxy}methyl)-N-ethylmorpholine-4-carboximidamide |
| 402 | [(1E)-[2-({[4-[(3,4-dichlorophenyl)amino]-6-(methyloxy)quinazolin-7-yl]oxy}methyl)morpholin-4-yl](piperidin-1-yl)methylidene]cyanamide |
| 403 | [(1E)-[2-({[4-[(3,4-dichlorophenyl)amino]-6-(methyloxy)quinazolin-7-yl]oxy}methyl)morpholin-4-yl](pyrrolidin-1-yl)methylidene]cyanamide |
| 404 | [(1E)-[2-({[4-[(3,4-dichlorophenyl)amino]-6-(methyloxy)quinazolin-7-yl]oxy}methyl)morpholin-4-yl](4-methylpiperazin-1-yl)methylidene]cyanamide |
| 405 | N-(3,4-dichlorophenyl)-7-{[(6-ethyl-4,6-dimethylmorpholin-2-yl)methyl]oxy}-6-(methyloxy)quinazolin-4-amine |
| 406 | N-(4-bromo-3-methylphenyl)-7-{[(4-methylmorpholin-2-yl)methyl]oxy}-6-(methyloxy)quinazolin-4-amine |
| 407 | N-(3,4-dichlorophenyl)-7-{[(6,6-dimethylmorpholin-2-yl)methyl]oxy}-6-(methyloxy)quinazolin-4-amine |
| 408 | N-(3,4-dichlorophenyl)-6-(methyloxy)-7-{[(4,6,6-trimethylmorpholin-2-yl)methyl]oxy}quinazolin-4-amine |
| 409 | N-(3,4-dichlorophenyl)-7-{[2-(5,5-dimethylmorpholin-2-yl)ethyl]oxy}-6-(methyloxy)quinazolin-4-amine |
| 410 | N-(3,4-dichlorophenyl)-6-(methyloxy)-7-{[2-(4,5,5-trimethylmorpholin-2-yl)ethyl]oxy}quinazolin-4-amine |
| 411 | 1,1-dimethylethyl 2-(2-{[4-[(3,4-dichlorophenyl)amino]-6-(methyloxy)quinazolin-7-yl]oxy}ethyl)-5,5-dimethylmorpholine-4-carboxylate |
| 412 | N-(3,4-dichlorophenyl)-6-(methyloxy)-7-{[(4,5,5-trimethylmorpholin-2-yl)methyl]oxy}quinazolin-4-amine |
| 413 | N-(4-bromo-2,3-dichlorophenyl)-7-{[(4-methylmorpholin-2-yl)methyl]oxy}-6-(methyloxy)quinazolin-4-amine |
| 414 | N-(4,5-dichloro-2-fluorophenyl)-7-{[(4-methylmorpholin-2-yl)methyl]oxy}-6-(methyloxy)quinazolin-4-amine |
| 415 | N-(3,4-dichlorophenyl)-6-(methyloxy)-7-{[2-(4,6,6-trimethylmorpholin-2-yl)ethyl]oxy}quinazolin-4-amine |
| 416 | N-(4-bromo-2,3-difluorophenyl)-7-{[(4-methylmorpholin-2-yl)methyl]oxy}-6-(methyloxy)quinazolin-4-amine |
| 417 | N-(4-bromo-2,5-difluorophenyl)-7-{[(4-methylmorpholin-2-yl)methyl]oxy}-6-(methyloxy)quinazolin-4-amine |
| 418 | N-(4-bromo-3,5-difluorophenyl)-7-{[(4-methylmorpholin-2-yl)methyl]oxy}-6-(methyloxy)quinazolin-4-amine |
| 419 | N-(3,4-dichloro-2-methylphenyl)-7-{[(4-methylmorpholin-2-yl)methyl]oxy}-6-(methyloxy)quinazolin-4-amine |
| 420 | N-(3,4-dichlorophenyl)-7-({[(2R,5S,6S)-5,6-dimethylmorpholin-2-yl]methyl}oxy)-6-(methyloxy)quinazolin-4-amine |
| 421 | N-(3,4-dichlorophenyl)-6-(methyloxy)-7-({[(2R,5S,6S)-4,5,6-trimethylmorpholin-2-yl]methyl}oxy)quinazolin-4-amine |
| 422 | N-(3,4-dichlorophenyl)-6-(methyloxy)-7-({[(2S,5S,6S)-4,5,6-trimethylmorpholin-2-yl]methyl}oxy)quinazolin-4-amine |
| 423 | N-(4-bromo-3-chloro-2-methylphenyl)-7-{[(4-methylmorpholin-2-yl)methyl]oxy}-6-(methyloxy)quinazolin-4-amine |
| 424 | N-(4-bromo-5-chloro-2-fluorophenyl)-7-{[(4-methylmorpholin-2-yl)methyl]oxy}-6-(methyloxy)quinazolin-4-amine |
| 425 | N-(4-bromo-3-chloro-2-fluorophenyl)-7-{[(4-methylmorpholin-2-yl)methyl]oxy}-6-(methyloxy)quinazolin-4-amine |
| 426 | N-(3,4-dichloro-2-fluorophenyl)-7-{[(4-methylmorpholin-2-yl)methyl]oxy}-6-(methyloxy)quinazolin-4-amine |
| 427 | N-(3-chloro-2,4-difluorophenyl)-7-{[(4-methylmorpholin-2-yl)methyl]oxy}-6-(methyloxy)quinazolin-4-amine |
| 428 | N-(2,3-dichloro-4-methylphenyl)-7-{[(4-methylmorpholin-2-yl)methyl]oxy}-6-(methyloxy)quinazolin-4-amine |
| 429 | 6-({[4-[(3,4-dichlorophenyl)amino]-6-(methyloxy)quinazolin-7-yl]oxy}methyl)-3,3,4-trimethylmorpholin-2-one |
| 430 | N-(4-bromo-2,3-dichlorophenyl)-6-(methyloxy)-7-{[(4,5,5-trimethylmorpholin-2-yl)methyl]oxy}quinazolin-4-amine |
| 431 | N-(4-bromo-5-chloro-2-fluorophenyl)-6-(methyloxy)-7-{[(4,5,5-trimethylmorpholin-2-yl)methyl]oxy}quinazolin-4-amine |

| Entry | Name |
|---|---|
| 432 | N-(4,5-dichloro-2-fluorophenyl)-6-(methyloxy)-7-{[(4,5,5-trimethylmorpholin-2-yl)methyl]oxy}quinazolin-4-amine |
| 433 | N-(3,4-dichloro-2-fluorophenyl)-6-(methyloxy)-7-{[(4,5,5-trimethylmorpholin-2-yl)methyl]oxy}quinazolin-4-amine |
| 434 | N-(4-bromo-3-chloro-2-fluorophenyl)-6-(methyloxy)-7-{[(4,5,5-trimethylmorpholin-2-yl)methyl]oxy}quinazolin-4-amine |
| 435 | N-(3-chloro-2,4-difluorophenyl)-6-(methyloxy)-7-{[(4,5,5-trimethylmorpholin-2-yl)methyl]oxy}quinazolin-4-amine |
| 436 | (6S)-6-({[4-[(4-bromo-3-chloro-2-fluorophenyl)amino]-6-(methyloxy)quinazolin-7-yl]oxy}methyl)-4-methylpiperazin-2-one |
| 437 | (6S)-6-({[4-[(3,4-dichloro-2-fluorophenyl)amino]-6-(methyloxy)quinazolin-7-yl]oxy}methyl)-4-methylpiperazin-2-one |
| 438 | (6S)-6-({[4-[(4-bromo-3-chloro-2-fluorophenyl)amino]-6-(methyloxy)quinazolin-7-yl]oxy}methyl)-1,4-dimethylpiperazin-2-one |
| 439 | (6S)-6-({[4-[(3,4-dichloro-2-fluorophenyl)amino]-6-(methyloxy)quinazolin-7-yl]oxy}methyl)-1,4-dimethylpiperazin-2-one |
| 440 | N-(4-bromo-3-chlorophenyl)-7-{[(3a'S,4R,6'S,6a'R)-2,2-dimethyltetrahydrospiro[1,3-dioxolane-4,3'-furo[3,2-b]furan]-6'-yl]oxy}-6-(methyloxy)quinazolin-4-amine |
| 441 | 1,4:3,6-dianhydro-2-O-[4-[(4-bromo-3-chlorophenyl)amino]-6-(methyloxy)quinazolin-7-yl]-5-O-methyl-5-C-[(methyloxy)methyl]-L-glucitol |
| 442 | 1,4:3,6-dianhydro-2-O-[4-[(4-bromo-3-chlorophenyl)amino]-6-(methyloxy)quinazolin-7-yl]-5-O-(methylsulfonyl)-L-glucitol |
| 443 | 1,4:3,6-dianhydro-2-O-[4-[(4-bromo-3-chlorophenyl)amino]-6-(methyloxy)quinazolin-7-yl]-L-glucitol |
| 444 | 1,4:3,6-dianhydro-2-O-[4-[(4-bromo-3-chlorophenyl)amino]-6-(methyloxy)quinazolin-7-yl]-5-S-methyl-5-thio-D-iditol |
| 445 | 1,4:3,6-dianhydro-5-O-[4-[(4-bromo-3-chlorophenyl)amino]-6-(methyloxy)quinazolin-7-yl]-2-deoxy-2-morpholin-4-yl-D-iditol |
| 446 | 1,4:3,6-dianhydro-5-O-[4-[(4-bromo-3-chlorophenyl)amino]-6-(methyloxy)quinazolin-7-yl]-2-deoxy-2-(4-methylpiperazin-1-yl)-D-iditol |
| 447 | 1,4:3,6-dianhydro-5-O-[4-[(4-bromo-3-chlorophenyl)amino]-6-(methyloxy)quinazolin-7-yl]-2-deoxy-2-pyrrolidin-1-yl-D-iditol |
| 448 | 2-O-acetyl-1,4:3,6-dianhydro-5-O-[4-[(4-bromo-3-chlorophenyl)amino]-6-(methyloxy)quinazolin-7-yl]-D-iditol |
| 449 | 1,4:3,6-dianhydro-2-O-[4-[(4-bromo-3-chlorophenyl)amino]-6-(methyloxy)quinazolin-7-yl]-D-iditol |
| 450 | 1,4:3,6-dianhydro-5-O-[4-[(4-bromo-3-chlorophenyl)amino]-6-(methyloxy)quinazolin-7-yl]-2-deoxy-2-(methylsulfonyl)-D-iditol |
| 451 | 2-amino-1,4:3,6-dianhydro-5-O-[4-[(4-bromo-3-chlorophenyl)amino]-6-(methyloxy)quinazolin-7-yl]-2-deoxy-D-iditol |
| 452 | 1,4:3,6-dianhydro-5-O-[4-[(4-bromo-3-chlorophenyl)amino]-6-(methyloxy)quinazolin-7-yl]-2-deoxy-2-(dimethylamino)-D-iditol |
| 453 | 1,4:3,6-dianhydro-5-O-[4-[(4-bromo-3-chlorophenyl)amino]-6-(methyloxy)quinazolin-7-yl]-2-deoxy-2-(diethylamino)-D-iditol |
| 454 | 1,4:3,6-dianhydro-5-O-[4-[(4-bromo-3-chlorophenyl)amino]-6-(methyloxy)quinazolin-7-yl]-2-deoxy-2-piperidin-1-yl-D-iditol |
| 455 | 2-(acetylamino)-1,4:3,6-dianhydro-5-O-[4-[(4-bromo-3-chlorophenyl)amino]-6-(methyloxy)quinazolin-7-yl]-2-deoxy-D-iditol |
| 456 | 1,4:3,6-dianhydro-2-O-[4-[(4-bromo-3-chlorophenyl)amino]-6-(methyloxy)quinazolin-7-yl]-5-O-methyl-5-C-(trifluoromethyl)-L-glucitol |
| 457 | 1,4:3,6-dianhydro-5-O-[4-[(4-bromo-3-chlorophenyl)amino]-6-(methyloxy)quinazolin-7-yl]-2-deoxy-2-[(methylsulfonyl)amino]-D-iditol |
| 458 | N-(4-bromo-3-chlorophenyl)-6-(methyloxy)-7-[(1-methylpyrrolidin-3-yl)oxy]quinazolin-4-amine |
| 459 | N-(4-bromo-3-chlorophenyl)-6-(methyloxy)-7-[(3R)-tetrahydrofuran-3-yloxy]quinazolin-4-amine |
| 460 | N-(4-bromo-3-chlorophenyl)-6-(methyloxy)-7-{[(3S,4R)-4-(methyloxy)tetrahydrofuran-3-yl]oxy}quinazolin-4-amine |
| 461 | 1,4:3,6-dianhydro-2-deoxy-2-fluoro-5-O-(6-(methyloxy)-4-{[4-(4-methylpiperazin-1-yl)phenyl]amino}quinazolin-7-yl)-D-iditol |
| 462 | 1,4:3,6-dianhydro-2-deoxy-2-fluoro-5-O-[4-{[3-fluoro-4-(4-methylpiperazin-1-yl)phenyl]amino}-6-(methyloxy)quinazolin-7-yl]-D-iditol |
| 463 | 1,4:3,6-dianhydro-2-deoxy-5-O-[4-{[2,3-dichloro-4-(4-methylpiperazin-1-yl)phenyl]amino}-6-(methyloxy)quinazolin-7-yl]-2-fluoro-D-iditol |
| 464 | 1,4:3,6-dianhydro-2-deoxy-5-O-[4-{[3,4-dichloro-2-(4-methylpiperazin-1-yl)phenyl]amino}-6-(methyloxy)quinazolin-7-yl]-2-fluoro-D-iditol |
| 465 | 1,4:3,6-dianhydro-2-O-[4-[(4-bromo-3-chlorophenyl)amino]-6-(methyloxy)quinazolin-7-yl]-5-C-(trifluoromethyl)-D-glucitol |
| 466 | (3,4-dichlorophenyl)[6-(methyloxy)-7-({[4-(tetrahydrofuran-2-ylmethyl)-1,4-oxazepan-2-yl]methyl}oxy)quinazolin-4-amine |

| Entry | Name |
|---|---|
| 467 | N-(3,4-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine |
| 468 | N-(4-bromo-3-chloro-2-fluorophenyl)-7-({[(3aR,5r,6aS)-2-methyloctahydrocyclopenta[c]pyrrol-5-yl]methyl}oxy)-6-(methyloxy)quinazolin-4-amine |
| 469 | N-(3-chloro-2,4-difluorophenyl)-7-({[(3aR,5r,6aS)-2-methyloctahydrocyclopenta[c]pyrrol-5-yl]methyl}oxy)-6-(methyloxy)quinazolin-4-amine |
| 470 | N-(4,5-dichloro-2-fluorophenyl)-7-({[(3aR,5r,6aS)-2-methyloctahydrocyclopenta[c]pyrrol-5-yl]methyl}oxy)-6-(methyloxy)quinazolin-4-amine |
| 471 | N-(4-bromo-5-chloro-2-fluorophenyl)-7-({[(3aR,5r,6aS)-2-methyloctahydrocyclopenta[c]pyrrol-5-yl]methyl}oxy)-6-(methyloxy)quinazolin-4-amine |
| 472 | N-(4-bromo-2,3-dichlorophenyl)-7-({[(3aR,5r,6aS)-2-methyloctahydrocyclopenta[c]pyrrol-5-yl]methyl}oxy)-6-(methyloxy)quinazolin-4-amine |
| 473 | N-(3,4-dichlorophenyl)-7-({[(3aR,5r,6aS)-2-methyloctahydrocyclopenta[c]pyrrol-5-yl]methyl}oxy)-6-(methyloxy)quinazolin-4-amine |
| 474 | N-(3,4-dichlorophenyl)-7-[(2-{[(3-endo)-8-methyl-8-azabicyclo[3.2.1]oct-3-yl]amino}ethyl)oxy]-6-(methyloxy)quinazolin-4-amine |
| 475 | N-(3,4-dichlorophenyl)-7-({2-[(3-endo)-8-methyl-8-azabicyclo[3.2.1]oct-3-yl]ethyl}oxy)-6-(methyloxy)quinazolin-4-amine |
| 476 | N-(3,4-dichlorophenyl)-7-({[(3-endo)-8-methyl-8-azabicyclo[3.2.1]oct-3-yl]methyl}oxy)-6-(methyloxy)quinazolin-4-amine |
| 477 | N-(3,4-dichlorophenyl)-7-{[(3-exo)-8-methyl-8-azabicyclo[3.2.1]oct-3-yl]oxy}-6-(methyloxy)quinazolin-4-amine |
| 478 | 1,4:3,6-Dianhydro-5-O-[4-[(3,4-dichlorophenyl)amino]-6-(methyloxy)quinazolin-7-yl]-2-O-methyl-D-glucitol |
| 479 | 1,4:3,6-dianhydro-5-O-{4-[(3-chloro-2-fluorophenyl)amino]-6-(methyloxy)quinazolin-7-yl}-2-deoxy-2-fluoro-L-iditol |
| 480 | 1,4:3,6-dianhydro-2-O-[4-[(4-bromo-3-chlorophenyl)amino]-6-(methyloxy)quinazolin-7-yl]-5-O-(methylsulfonyl)-D-glucitol |
| 481 | 1,4:3,6-dianhydro-2-O-[4-[(4-bromo-3-chlorophenyl)amino]-6-(methyloxy)quinazolin-7-yl]-D-glucitol |
| 482 | 1,4:3,6-dianhydro-2-O-[4-[(4-bromo-3-chlorophenyl)amino]-6-(methyloxy)quinazolin-7-yl]-5-S-methyl-5-thio-L-iditol |
| 483 | 1,4:3,6-dianhydro-5-O-[4-[(4-bromo-3-chlorophenyl)amino]-6-(methyloxy)quinazolin-7-yl]-2-deoxy-2-morpholin-4-yl-L-iditol |
| 484 | 1,4:3,6-dianhydro-5-O-[4-[(4-bromo-3-chlorophenyl)amino]-6-(methyloxy)quinazolin-7-yl]-2-deoxy-2-(4-methylpiperazin-1-yl)-L-iditol |
| 485 | 1,4:3,6-dianhydro-5-O-[4-[(4-bromo-3-chlorophenyl)amino]-6-(methyloxy)quinazolin-7-yl]-2-deoxy-2-pyrrolidin-1-yl-L-iditol |
| 486 | 2-O-acetyl-1,4:3,6-dianhydro-5-O-[4-[(4-bromo-3-chlorophenyl)amino]-6-(methyloxy)quinazolin-7-yl]-L-iditol |
| 487 | 1,4:3,6-dianhydro-2-O-[4-[(4-bromo-3-chlorophenyl)amino]-6-(methyloxy)quinazolin-7-yl]-L-iditol |
| 488 | 1,4:3,6-dianhydro-5-O-[4-[(4-bromo-3-chlorophenyl)amino]-6-(methyloxy)quinazolin-7-yl]-2-deoxy-2-(methylsulfonyl)-L-iditol |
| 489 | 2-amino-1,4:3,6-dianhydro-5-O-[4-[(4-bromo-3-chlorophenyl)amino]-6-(methyloxy)quinazolin-7-yl]-2-deoxy-L-iditol |
| 490 | 1,4:3,6-dianhydro-5-O-[4-[(4-bromo-3-chlorophenyl)amino]-6-(methyloxy)quinazolin-7-yl]-2-deoxy-2-(dimethylamino)-L-iditol |
| 491 | 1,4:3,6-dianhydro-5-O-[4-[(4-bromo-3-chlorophenyl)amino]-6-(methyloxy)quinazolin-7-yl]-2-deoxy-2-(diethylamino)-L-iditol |
| 492 | 1,4:3,6-dianhydro-5-O-[4-[(4-bromo-3-chlorophenyl)amino]-6-(methyloxy)quinazolin-7-yl]-2-deoxy-2-piperidin-1-yl-L-iditol |
| 493 | 2-(acetylamino)-1,4:3,6-dianhydro-5-O-[4-[(4-bromo-3-chlorophenyl)amino]-6-(methyloxy)quinazolin-7-yl]-2-deoxy-L-iditol |
| 494 | 1,4:3,6-dianhydro-2-O-[4-[(4-bromo-3-chlorophenyl)amino]-6-(methyloxy)quinazolin-7-yl]-5-O-methyl-5-C-(trifluoromethyl)-D-glucitol |
| 495 | 1,4:3,6-dianhydro-5-O-[4-[(4-bromo-3-chlorophenyl)amino]-6-(methyloxy)quinazolin-7-yl]-2-deoxy-2-[(methylsulfonyl)amino]-L-iditol |
| 496 | 1,4:3,6-dianhydro-2-deoxy-2-fluoro-5-O-(6-(methyloxy)-4-{[4-(4-methylpiperazin-1-yl)phenyl]amino}quinazolin-7-yl)-L-iditol |
| 497 | 1,4:3,6-dianhydro-2-deoxy-2-fluoro-5-O-[4-{[3-fluoro-4-(4-methylpiperazin-1-yl)phenyl]amino}-6-(methyloxy)quinazolin-7-yl]-L-iditol |
| 498 | 1,4:3,6-dianhydro-2-deoxy-5-O-[4-{[2,3-dichloro-4-(4-methylpiperazin-1-yl)phenyl]amino}-6-(methyloxy)quinazolin-7-yl]-2-fluoro-L-iditol |
| 499 | 1,4:3,6-dianhydro-2-deoxy-5-O-[4-{[3,4-dichloro-2-(4-methylpiperazin-1-yl)phenyl]amino}-6-(methyloxy)quinazolin-7-yl]-2-fluoro-L-iditol |
| 500 | 1,4:3,6-Dianhydro-5-O-[4-[(3,4-dichlorophenyl)amino]-6-(methyloxy)quinazolin-7-yl]-2-O-methyl-D-glucitol |
| 501 | 1,4:3,6-Dianhydro-2-O-[4-[(4-bromo-3-chlorophenyl)amino]-6-(methyloxy)quinazolin-7-yl]-5-O-methyl-L-glucitol |

The Compounds in Table 5a can be prepared as pharmaceutically acceptable salts, solvates, hydrates, and/or isomers thereof. All such salt, solvate, hydrate, and isomer combinations of the Compounds in Table 5a can be used to practice the invention.

| Entry | Structure |
|---|---|
| 1 | 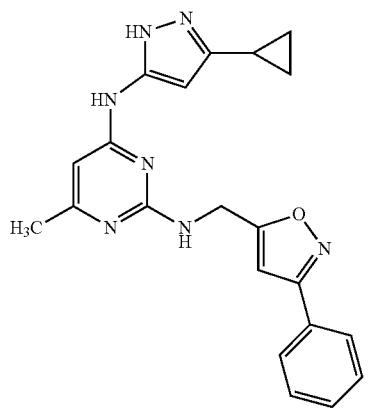 [SMILES: Cc1cc(Nc2cc(C3CC3)n[nH]2)nc(NCc2cc(-c3ccccc3)no2)n1] |
| 2 | 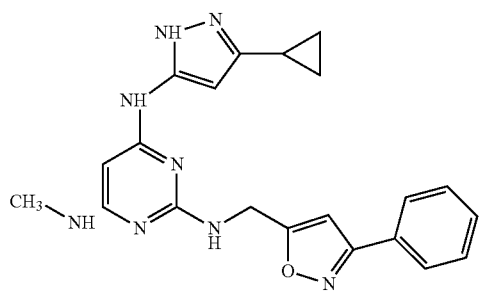 |
| 3 | 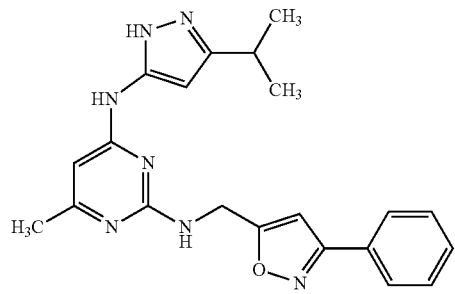 [SMILES: Cc1cc(Nc2cc(C(C)C)n[nH]2)nc(NCc2cc(-c3ccccc3)no2)n1] |
| 4 | 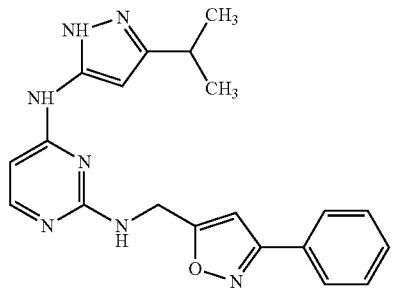 [SMILES: CC(C)c1cc(Nc2ccnc(NCc3cc(-c4ccccc4)no3)n2)[nH]n1] |

| Entry | Structure |
|---|---|
| 5 | 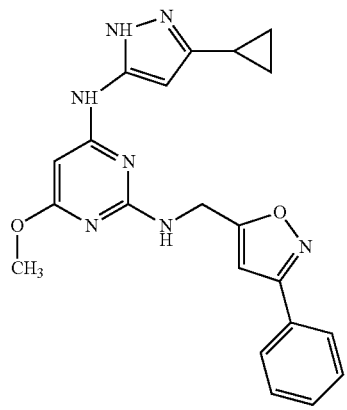 [SMILES: COc1cc(Nc2cc(C3CC3)n[nH]2)nc(NCc2cc(-c3ccccc3)no2)n1] |
| 6 | 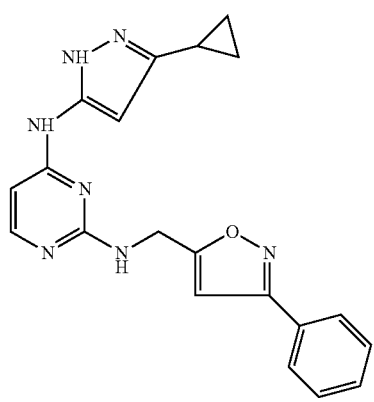 [SMILES: c1ccc(-c2cc(CNc3nccc(Nc4cc(C5CC5)n[nH]4)n3)on2)cc1] |
| 7 | 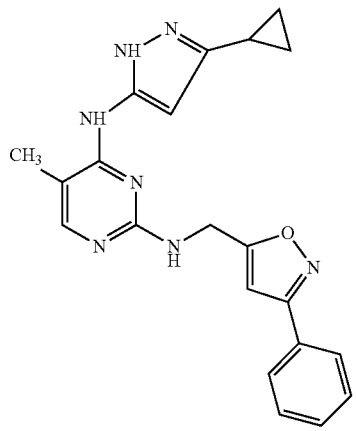 [SMILES: Cc1cnc(NCc2cc(-c3ccccc3)no2)nc1Nc1cc(C2CC2)n[nH]1] |

-continued
| Entry | Structure |
|---|---|
| 8 | 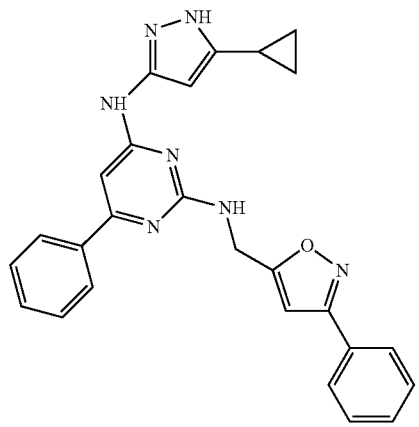 [SMILES: c1ccc(-c2cc(CNc3nc(Nc4cc(C5CC5)[nH]n4)cc(-c4ccccc4)n3)on2)cc1] |
| 9 | 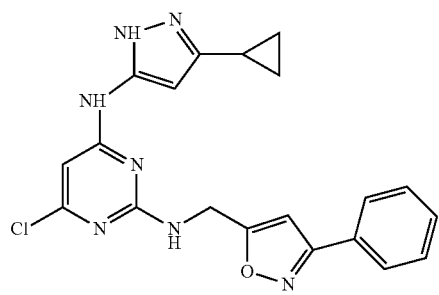 [SMILES: Clc1cc(Nc2cc(C3CC3)n[nH]2)nc(NCc2cc(-c3ccccc3)no2)n1] |
| 10 | 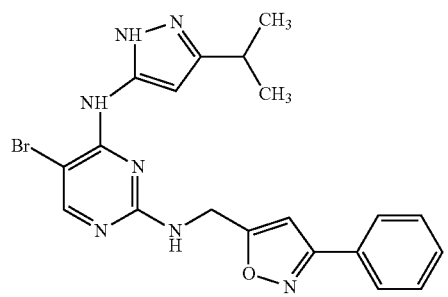 [SMILES: CC(C)c1cc(Nc2nc(NCc3cc(-c4ccccc4)no3)ncc2Br)[nH]n1] |
| 11 | 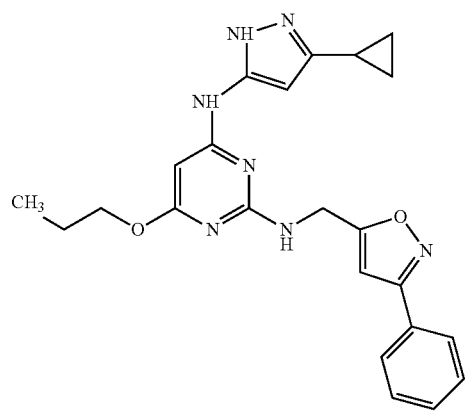 [SMILES: CCCOc1cc(Nc2cc(C3CC3)n[nH]2)nc(NCc2cc(-c3ccccc3)no2)n1] |

-continued
| Entry | Structure |
|---|---|
| 12 | 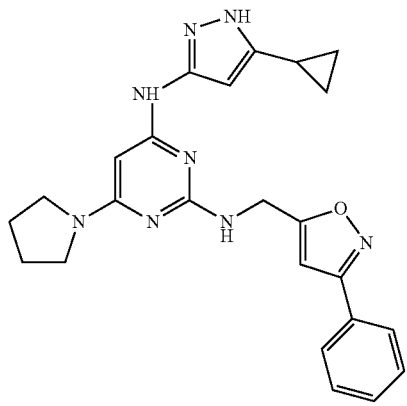 [SMILES: c1ccc(-c2cc(CNc3nc(Nc4cc(C5CC5)[nH]n4)cc(N4CCCC4)n3)on2)cc1] |
| 13 | 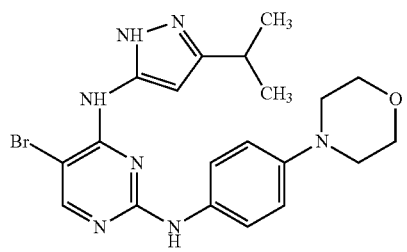 [SMILES: CC(C)c1cc(Nc2nc(Nc3ccc(N4CCOCC4)cc3)ncc2Br)[nH]n1] |
| 14 | 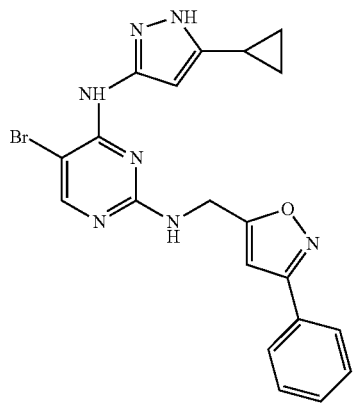 [SMILES: Brc1cnc(NCc2cc(-c3ccccc3)no2)nc1Nc1cc(C2CC2)[nH]n1] |
| 15 | 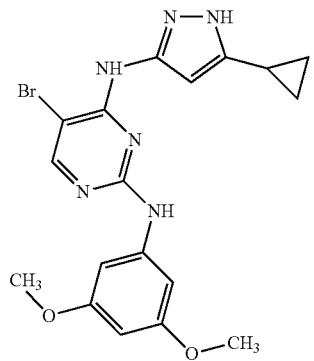 [SMILES: COc1cc(Nc2ncc(Br)c(Nc3cc(C4CC4)[nH]n3)n2)cc(OC)c1] |

| Entry | Structure |
|---|---|
| 16 | 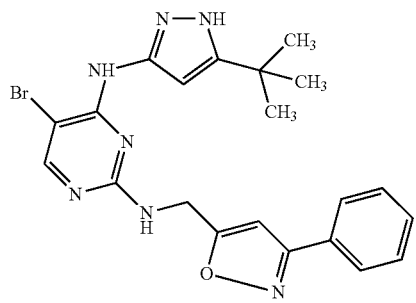 [SMILES: CC(C)(C)c1cc(Nc2nc(NCc3cc(-c4ccccc4)no3)ncc2Br)n[nH]1] |
| 17 | 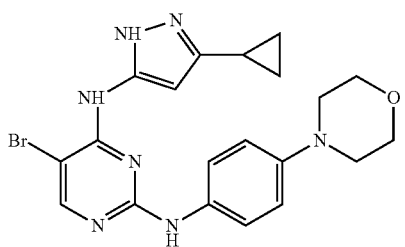 [SMILES: Brc1cnc(Nc2ccc(N3CCOCC3)cc2)nc1Nc1cc(C2CC2)n[nH]1] |
| 18 | 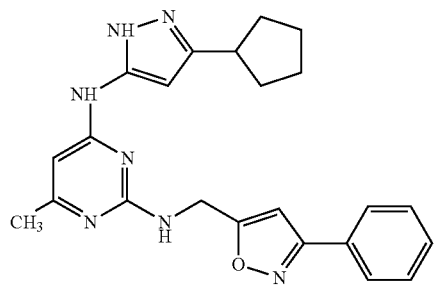 [SMILES: Cc1cc(Nc2cc(C3CCCC3)n[nH]2)nc(NCc2cc(-c3ccccc3)no2)n1] |
| 19 | 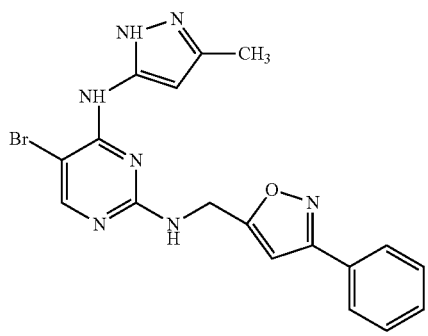 [SMILES: Cc1cc(Nc2nc(NCc3cc(-c4ccccc4)no3)ncc2Br)[nH]n1] |
| 20 | 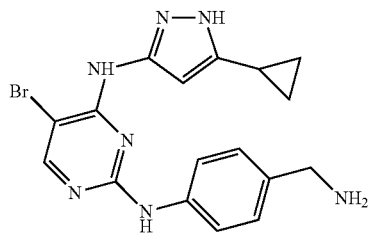 [SMILES: NCc1ccc(Nc2ncc(Br)c(Nc3cc(C4CC4)[nH]n3)n2)cc1] |

-continued
| Entry | Structure |
|---|---|
| 21 | 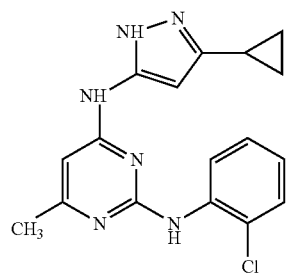 [SMILES: Cc1cc(Nc2cc(C3CC3)n[nH]2)nc(Nc2ccccc2Cl)n1] |
| 22 | 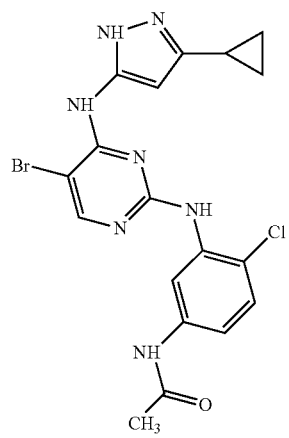 [SMILES: CC(=O)Nc1ccc(Cl)c(Nc2ncc(Br)c(Nc3cc(C4CC4)n[nH]3)n2)c1] |
| 23 | 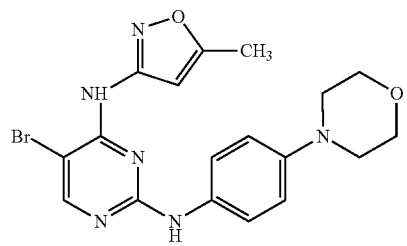 [SMILES: Cc1cc(Nc2nc(Nc3ccc(N4CCOCC4)cc3)ncc2Br)no1] |
| 24 | 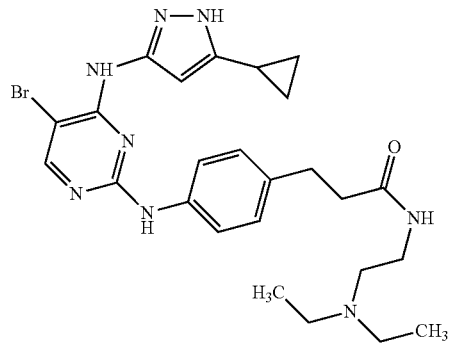 [SMILES: CCN(CC)CCNC(=O)CCc1ccc(Nc2ncc(Br)c(Nc3cc(C4CC4)[nH]n3)n2)cc1] |

| Entry | Structure |
|---|---|
| 25 | 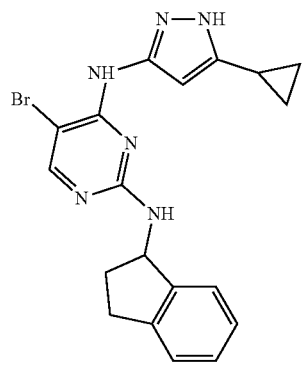 [SMILES: Brc1cnc(NC2CCc3ccccc32)nc1Nc1cc(C2CC2)[nH]n1] |
| 26 | 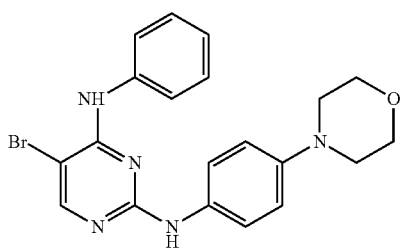 [SMILES: Brc1cnc(Nc2ccc(N3CCOCC3)cc2)nc1Nc1ccccc1] |
| 27 | 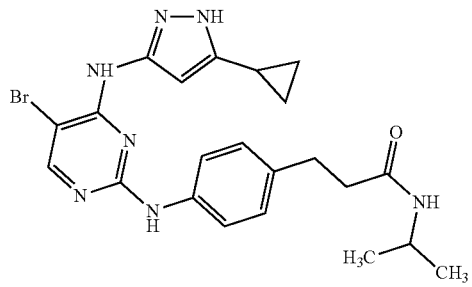 [SMILES: CC(C)NC(=O)CCc1ccc(Nc2ncc(Br)c(Nc3cc(C4CC4)[nH]n3)n2)cc1] |
| 28 | 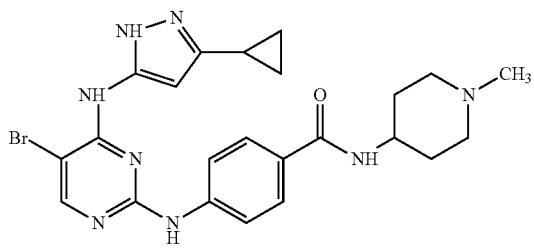 [SMILES: CN1CCC(NC(=O)c2ccc(Nc3ncc(Br)c(Nc4cc(C5CC5)n[nH]4)n3)cc2)CC1] |
| 29 | 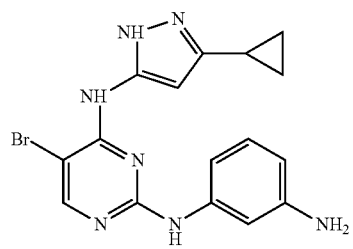 [SMILES: Nc1cccc(Nc2ncc(Br)c(Nc3cc(C4CC4)n[nH]3)n2)c1] |

-continued

| Entry | Structure |
|---|---|
| 30 | 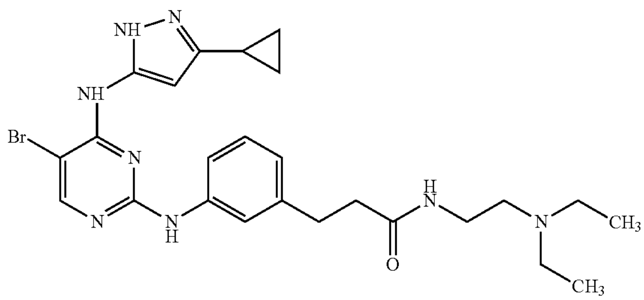 [SMILES: CCN(CC)CCNC(=O)CCc1cccc(Nc2ncc(Br)c(Nc3cc(C4CC4)n[nH]3)n2)c1] |
| 31 | 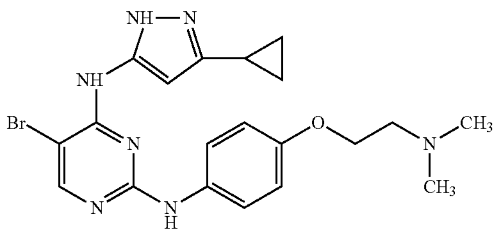 [SMILES: CN(C)CCOc1ccc(Nc2ncc(Br)c(Nc3cc(C4CC4)n[nH]3)n2)cc1] |
| 32 | 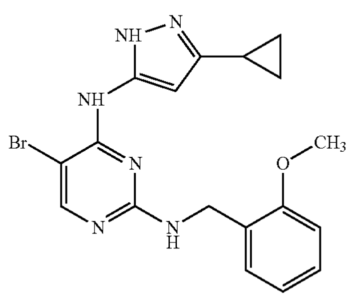 [SMILES: COc1ccccc1CNc1ncc(Br)c(Nc2cc(C3CC3)n[nH]2)n1] |
| 33 | 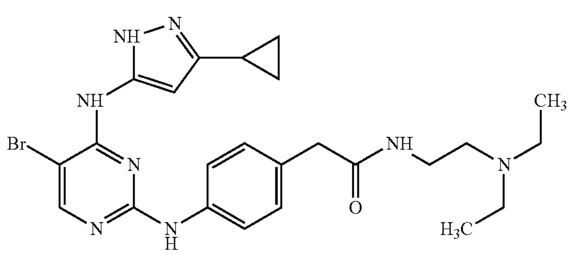 [SMILES: CCN(CC)CCNC(=O)Cc1ccc(Nc2ncc(Br)c(Nc3cc(C4CC4)n[nH]3)n2)cc1] |
| 34 | 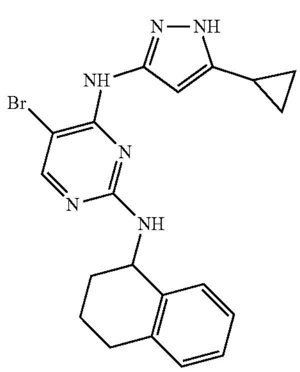 [SMILES: Brc1cnc(NC2CCCc3ccccc32)nc1Nc1cc(C2CC2)[nH]n1] |

| Entry | Structure |
|---|---|
| 35 | 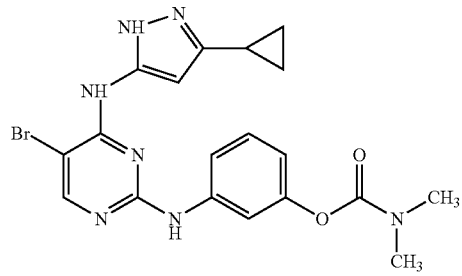 [SMILES: CN(C)C(=O)Oc1cccc(Nc2ncc(Br)c(Nc3cc(C4CC4)n[nH]3)n2)c1] |
| 36 | 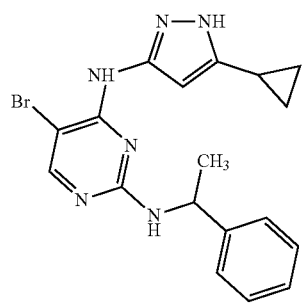 [SMILES: CC(Nc1ncc(Br)c(Nc2cc(C3CC3)[nH]n2)n1)c1ccccc1] |
| 37 | 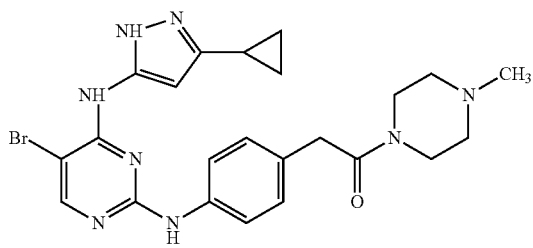 [SMILES: CN1CCN(C(=O)Cc2ccc(Nc3ncc(Br)c(Nc4cc(C5CC5)n[nH]4)n3)cc2)CC1] |
| 38 | 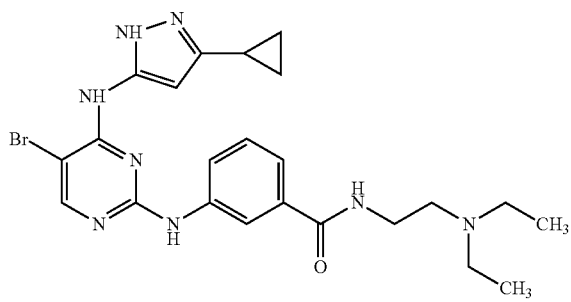 [SMILES: CCN(CC)CCNC(=O)c1cccc(Nc2ncc(Br)c(Nc3cc(C4CC4)n[nH]3)n2)c1] |
| 39 | 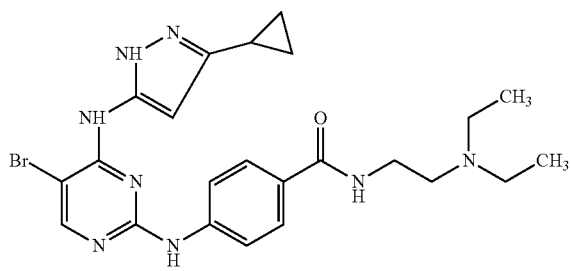 [SMILES: CCN(CC)CCNC(=O)c1ccc(Nc2ncc(Br)c(Nc3cc(C4CC4)n[nH]3)n2)cc1] |

-continued
| Entry | Structure |
|---|---|
| 40 | 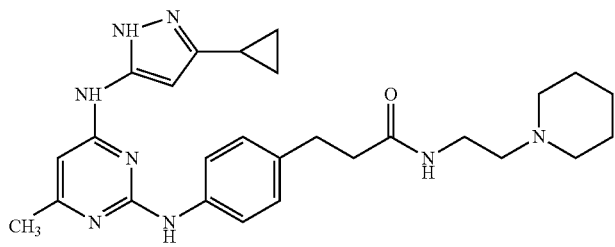 [SMILES: Cc1cc(Nc2cc(C3CC3)n[nH]2)nc(Nc2ccc(CCC(=O)NCCN3CCCCC3)cc2)n1] |
| 41 | 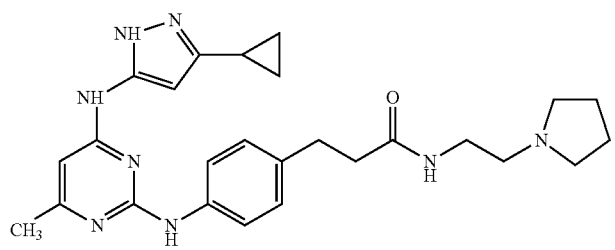 [SMILES: Cc1cc(Nc2cc(C3CC3)n[nH]2)nc(Nc2ccc(CCC(=O)NCCN3CCCC3)cc2)n1] |
| 42 | 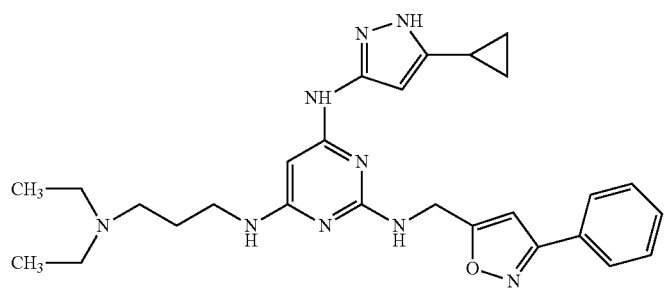 [SMILES: CCN(CC)CCCNc1cc(Nc2cc(C3CC3)[nH]n2)nc(NCc2cc(-c3ccccc3)no2)n1] |
| 43 | 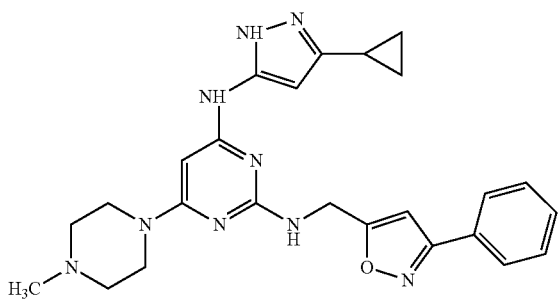 [SMILES: CN1CCN(c2cc(Nc3cc(C4CC4)n[nH]3)nc(NCc3cc(-c4ccccc4)no3)n2)CC1] |
| 44 | 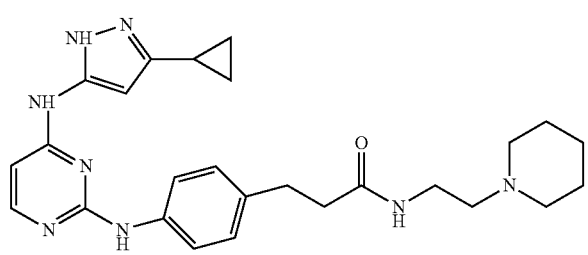 [SMILES: O=C(CCc1ccc(Nc2nccc(Nc3cc(C4CC4)n[nH]3)n2)cc1)NCCN1CCCCC1] |

-continued
| Entry | Structure |
|---|---|
| 45 | 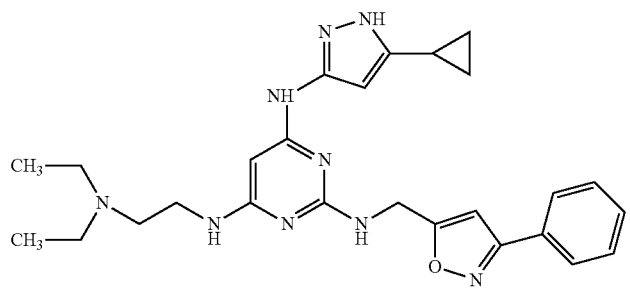 [SMILES: CCN(CC)CCNc1cc(Nc2cc(C3CC3)[nH]n2)nc(NCc2cc(-c3ccccc3)no2)n1] |
| 46 | 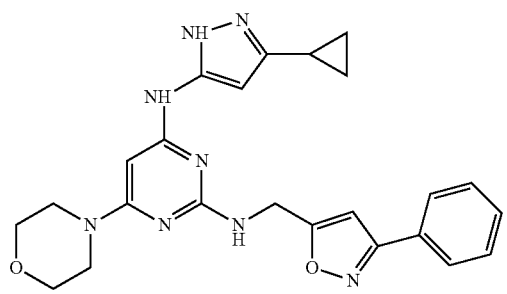 [SMILES: c1ccc(-c2cc(CNc3nc(Nc4cc(C5CC5)n[nH]4)cc(N4CCOCC4)n3)on2)cc1] |
| 47 | 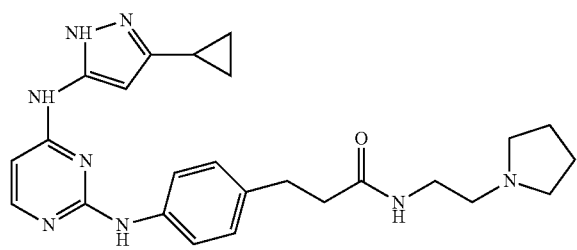 [SMILES: O=C(CCc1ccc(Nc2nccc(Nc3cc(C4CC4)n[nH]3)n2)cc1)NCCN1CCCC1] |
| 48 | 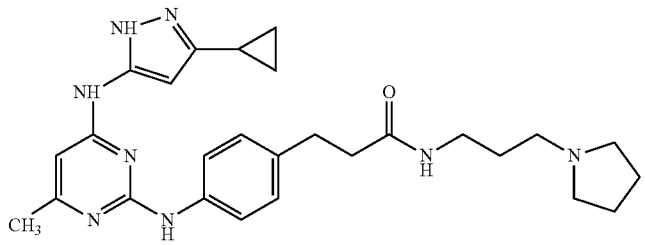 [SMILES: Cc1cc(Nc2cc(C3CC3)n[nH]2)nc(Nc2ccc(CCC(=O)NCCCN3CCCC3)cc2)n1] |
| 49 | 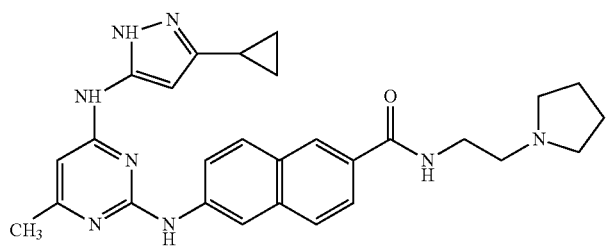 [SMILES: Cc1cc(Nc2cc(C3CC3)n[nH]2)nc(Nc2ccc3cc(C(=O)NCCN4CCCC4)ccc3c2)n1] |

| Entry | Structure |
|---|---|
| 50 | 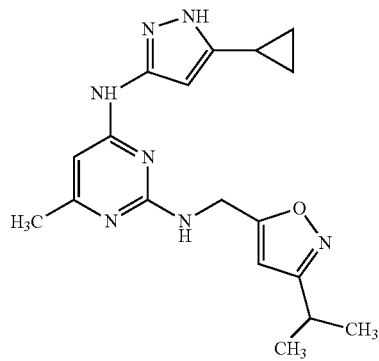 [SMILES: Cc1cc(Nc2cc(C3CC3)[nH]n2)nc(NCc2cc(C(C)C)no2)n1] |
| 51 | 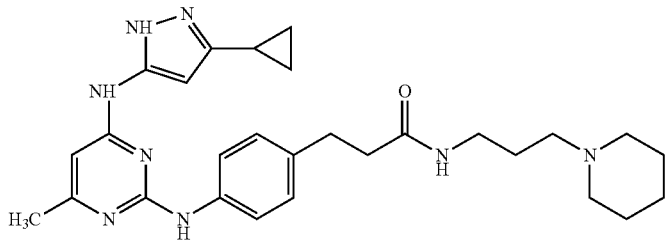 [SMILES: Cc1cc(Nc2cc(C3CC3)n[nH]2)nc(Nc2ccc(CCC(=O)NCCCN3CCCCC3)cc2)n1] |
| 52 | 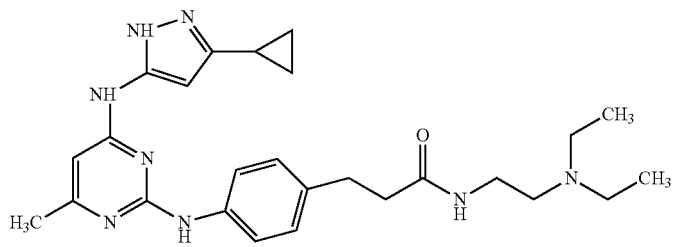 [SMILES: CCN(CC)CCNC(=O)CCc1ccc(Nc2nc(C)cc(Nc3cc(C4CC4)n[nH]3)n2)cc1] |
| 53 | 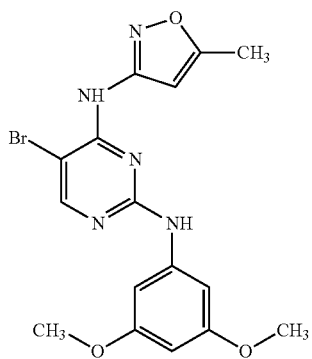 [SMILES: COc1cc(Nc2ncc(Br)c(Nc3cc(C)on3)n2)cc(OC)c1] |

-continued
| Entry | Structure |
|---|---|
| 54 | 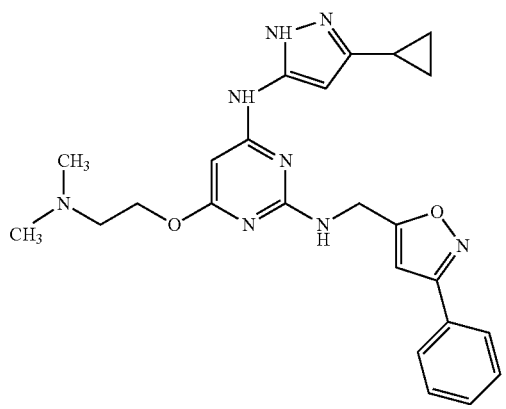 [SMILES: CN(C)CCOc1cc(Nc2cc(C3CC3)n[nH]2)nc(NCc2cc(-c3ccccc3)no2)n1] |
| 55 | 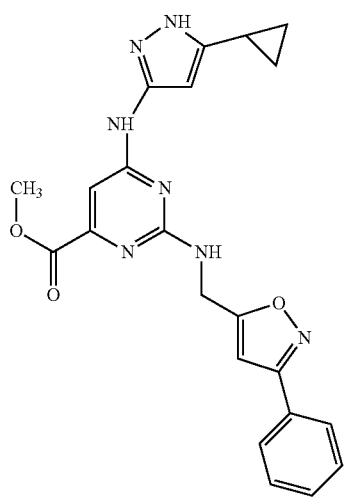 [SMILES: COC(=O)c1cc(Nc2cc(C3CC3)[nH]n2)nc(NCc2cc(-c3ccccc3)no2)n1] |
| 56 | 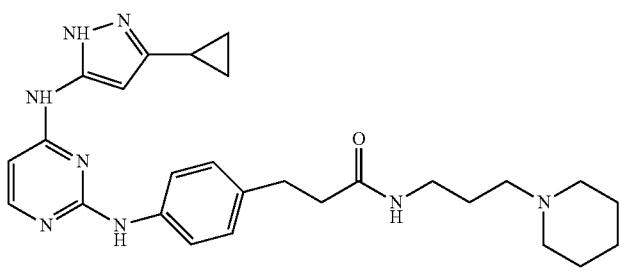 [SMILES: O=C(CCc1ccc(Nc2nccc(Nc3cc(C4CC4)n[nH]3)n2)cc1)NCCCN1CCCCC1] |
| 57 | 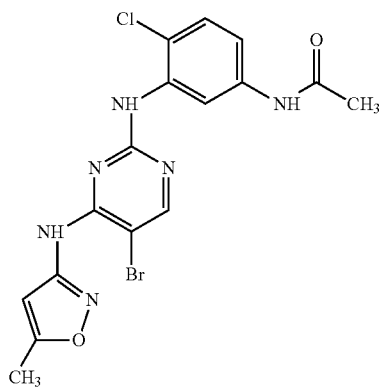 [SMILES: CC(=O)Nc1ccc(Cl)c(Nc2ncc(Br)c(Nc3cc(C)on3)n2)c1] |

| Entry | Structure |
|---|---|
| 58 | 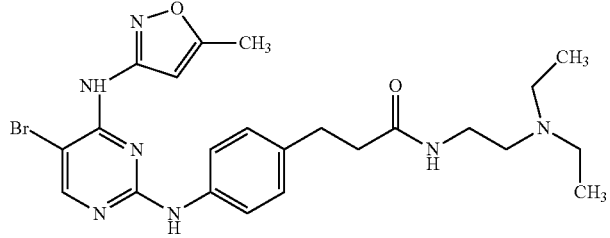 [SMILES: CCN(CC)CCNC(=O)CCc1ccc(Nc2ncc(Br)c(Nc3cc(C)on3)n2)cc1] |
| 59 | 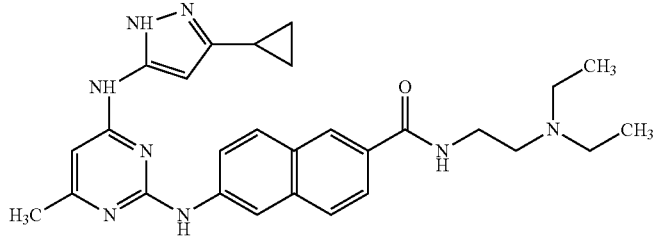 [SMILES: CCN(CC)CCNC(=O)c1ccc2cc(Nc3nc(C)cc(Nc4cc(C5CC5)n[nH]4)n3)ccc2c1] |
| 60 | 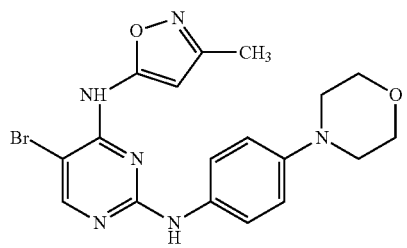 [SMILES: Cc1cc(Nc2nc(Nc3ccc(N4CCOCC4)cc3)ncc2Br)on1] |
| 61 | 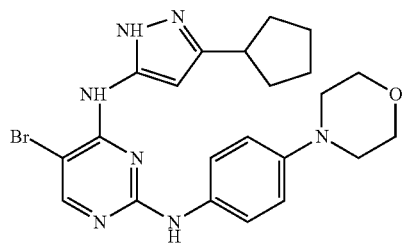 [SMILES: Brc1cnc(Nc2ccc(N3CCOCC3)cc2)nc1Nc1cc(C2CCCC2)n[nH]1] |
| 62 | 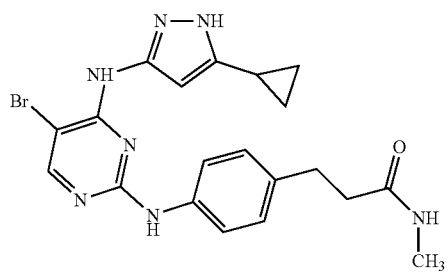 [SMILES: CNC(=O)CCc1ccc(Nc2ncc(Br)c(Nc3cc(C4CC4)[nH]n3)n2)cc1] |
| 63 | 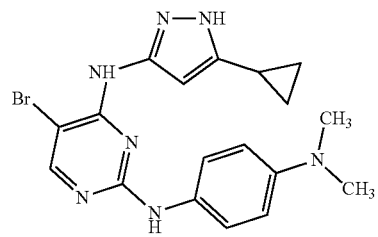 [SMILES: CN(C)c1ccc(Nc2ncc(Br)c(Nc3cc(C4CC4)[nH]n3)n2)cc1] |

-continued
| Entry | Structure |
|---|---|
| 64 | 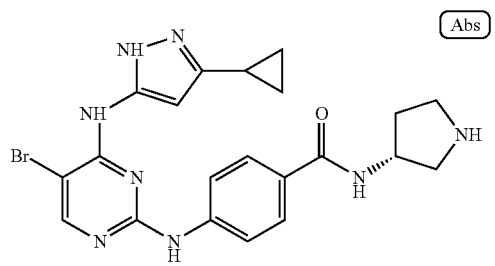 [SMILES: O=C(N[C@@H]1CCNC1)c1ccc(Nc2ncc(Br)c(Nc3cc(C4CC4)n[nH]3)n2)cc1] |
| 65 | 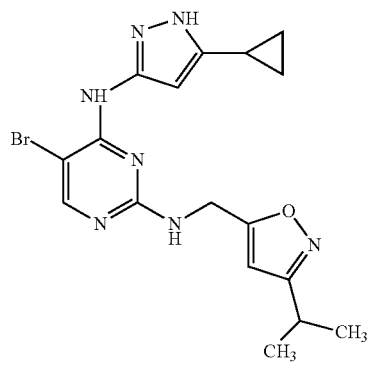 [SMILES: CC(C)c1cc(CNc2ncc(Br)c(Nc3cc(C4CC4)[nH]n3)n2)on1] |
| 66 | 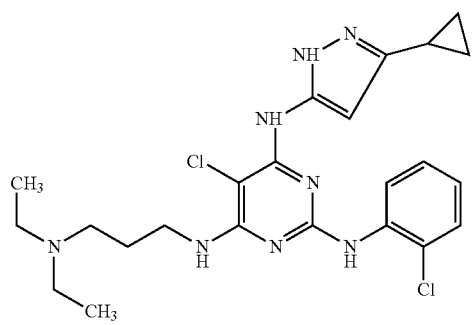 [SMILES: CCN(CC)CCCNc1nc(Nc2ccccc2Cl)nc(Nc2cc(C3CC3)n[nH]2)c1Cl] |
| 67 | 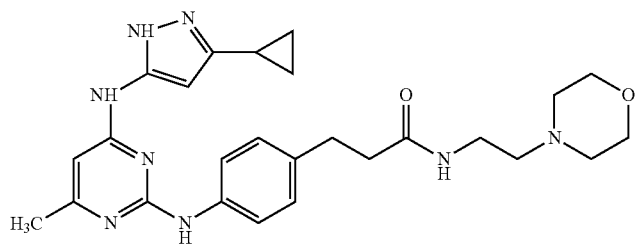 [SMILES: Cc1cc(Nc2cc(C3CC3)n[nH]2)nc(Nc2ccc(CCC(=O)NCCN3CCOCC3)cc2)n1] |
| 68 | 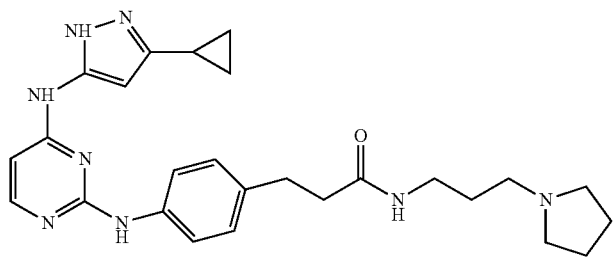 [SMILES: O=C(CCc1ccc(Nc2nccc(Nc3cc(C4CC4)n[nH]3)n2)cc1)NCCCN1CCCC1] |

-continued

| Entry | Structure |
|---|---|
| 69 | 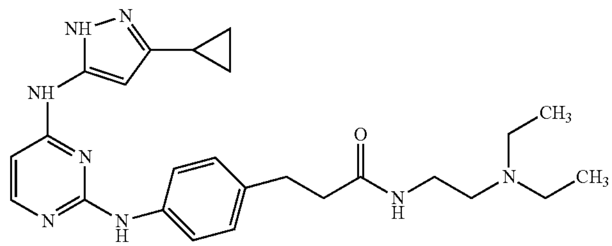 [SMILES: CCN(CC)CCNC(=O)CCc1ccc(Nc2nccc(Nc3cc(C4CC4)n[nH]3)n2)cc1] |
| 70 | 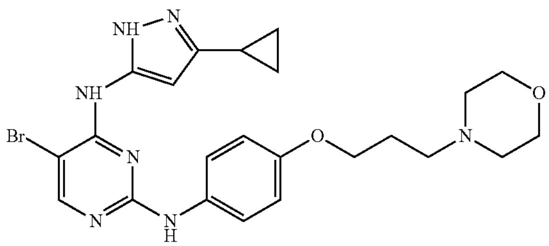 [SMILES: Brc1cnc(Nc2ccc(OCCCN3CCOCC3)cc2)nc1Nc1cc(C2CC2)n[nH]1] |
| 71 | 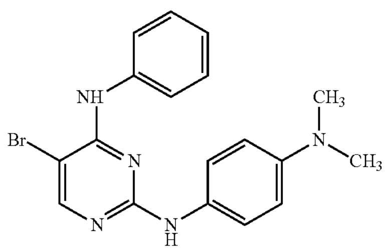 [SMILES: CN(C)c1ccc(Nc2ncc(Br)c(Nc3ccccc3)n2)cc1] |
| 72 | 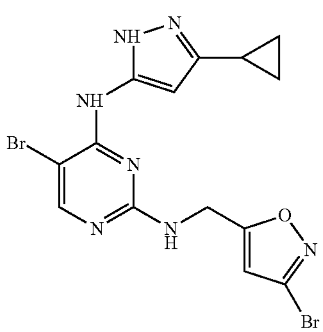 [SMILES: Brc1cc(CNc2ncc(Br)c(Nc3cc(C4CC4)n[nH]3)n2)on1] |
| 73 | 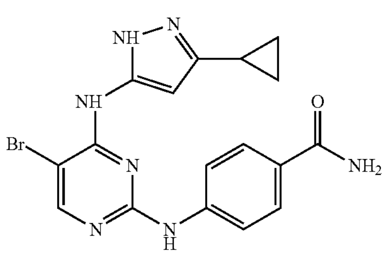 [SMILES: NC(=O)c1ccc(Nc2ncc(Br)c(Nc3cc(C4CC4)n[nH]3)n2)cc1] |
| 74 | 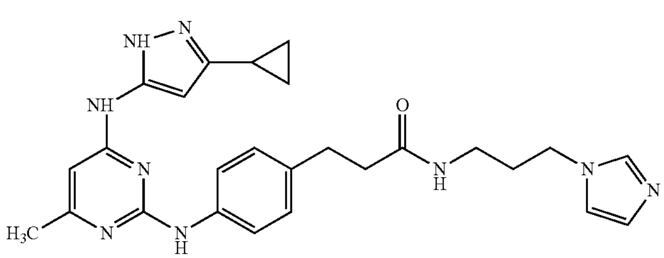 [SMILES: Cc1cc(Nc2cc(C3CC3)n[nH]2)nc(Nc2ccc(CCC(=O)NCCCn3ccnc3)cc2)n1] |

| Entry | Structure |
|---|---|
| 75 | 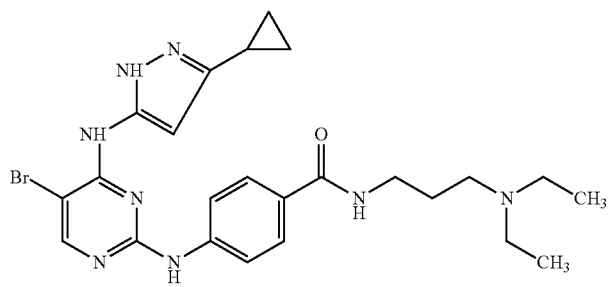 [SMILES: CCN(CC)CCCNC(=O)c1ccc(Nc2ncc(Br)c(Nc3cc(C4CC4)n[nH]3)n2)cc1] |
| 76 | 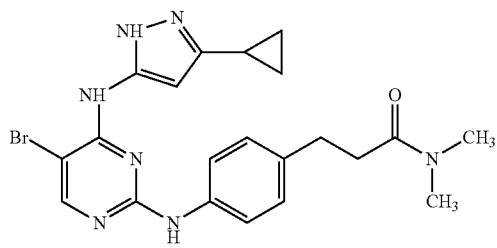 [SMILES: CN(C)C(=O)CCc1ccc(Nc2ncc(Br)c(Nc3cc(C4CC4)n[nH]3)n2)cc1] |
| 77 | 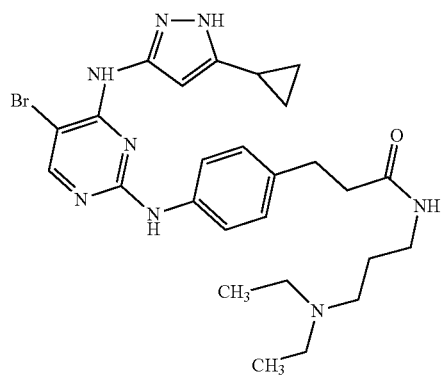 [SMILES: CCN(CC)CCCNC(=O)CCc1ccc(Nc2ncc(Br)c(Nc3cc(C4CC4)[nH]n3)n2)cc1] |
| 78 | 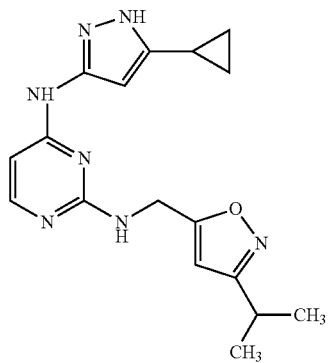 [SMILES: CC(C)c1cc(CNc2nccc(Nc3cc(C4CC4)[nH]n3)n2)on1] |
| 79 | 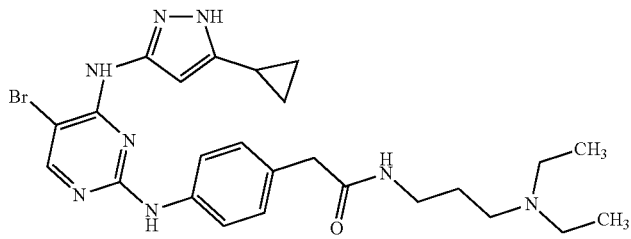 [SMILES: CCN(CC)CCCNC(=O)Cc1ccc(Nc2ncc(Br)c(Nc3cc(C4CC4)[nH]n3)n2)cc1] |

-continued
| Entry | Structure |
|---|---|
| 80 | 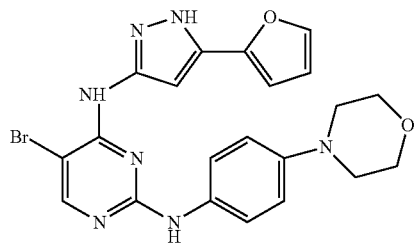 [SMILES: Brc1cnc(Nc2ccc(N3CCOCC3)cc2)nc1Nc1cc(-c2ccco2)[nH]n1] |
| 81 | 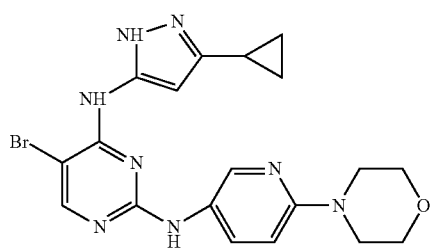 [SMILES: Brc1cnc(Nc2ccc(N3CCOCC3)nc2)nc1Nc1cc(C2CC2)n[nH]1] |
| 82 | 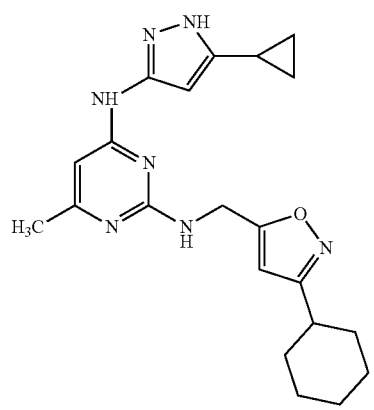 [SMILES: Cc1cc(Nc2cc(C3CC3)[nH]n2)nc(NCc2cc(C3CCCCC3)no2)n1] |
| 83 | 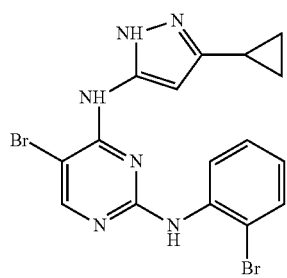 |
| 84 | 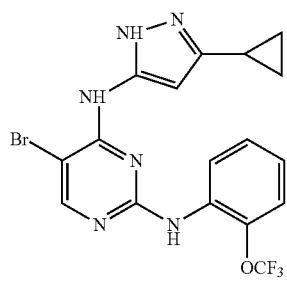 [SMILES: FC(F)(F)Oc1ccccc1Nc1ncc(Br)c(Nc2cc(C3CC3)n[nH]2)n1] |

-continued
| Entry | Structure |
|---|---|
| 85 | 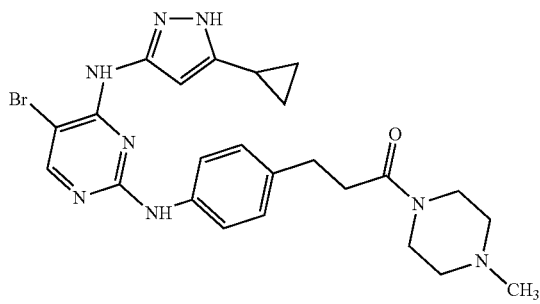 [SMILES: CN1CCN(C(=O)CCc2ccc(Nc3ncc(Br)c(Nc4cc(C5CC5)[nH]n4)n3)cc2)CC1] |
| 86 | 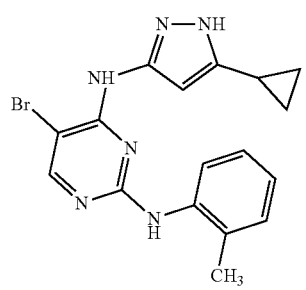 [SMILES: Cc1ccccc1Nc1ncc(Br)c(Nc2cc(C3CC3)[nH]n2)n1] |
| 87 | 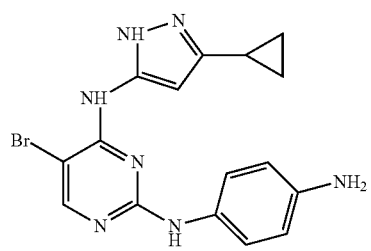 [SMILES: Nc1ccc(Nc2ncc(Br)c(Nc3cc(C4CC4)n[nH]3)n2)cc1] |
| 88 | 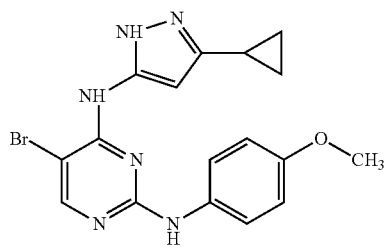 [SMILES: COc1ccc(Nc2ncc(Br)c(Nc3cc(C4CC4)n[nH]3)n2)cc1] |
| 89 | 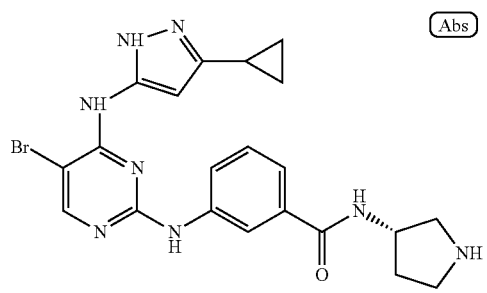 [SMILES: O=C(N[C@H]1CCNC1)c1cccc(Nc2ncc(Br)c(Nc3cc(C4CC4)n[nH]3)n2)c1] |

| Entry | Structure |
|---|---|
| 90 | 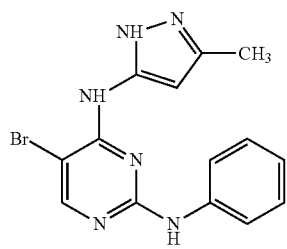 [SMILES: Cc1cc(Nc2nc(Nc3ccccc3)ncc2Br)[nH]n1] |
| 91 | 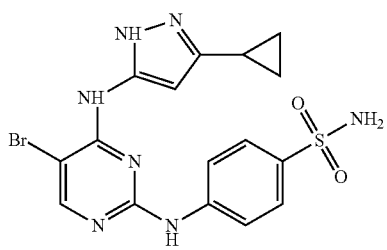 [SMILES: NS(=O)(=O)c1ccc(Nc2ncc(Br)c(Nc3cc(C4CC4)n[nH]3)n2)cc1] |
| 92 | 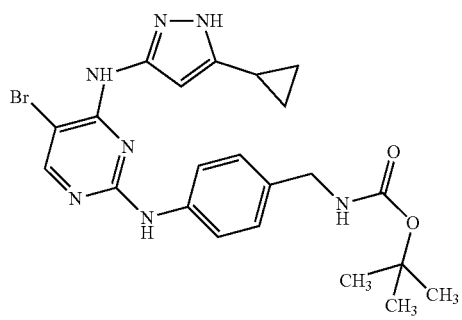 [SMILES: CC(C)(C)OC(=O)NCc1ccc(Nc2ncc(Br)c(Nc3cc(C4CC4)[nH]n3)n2)cc1] |
| 93 | 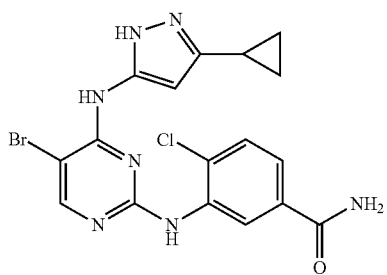 [SMILES: NC(=O)c1ccc(Cl)c(Nc2ncc(Br)c(Nc3cc(C4CC4)n[nH]3)n2)c1] |
| 94 | 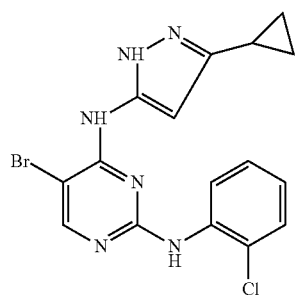 [SMILES: Clc1ccccc1Nc1ncc(Br)c(Nc2cc(C3CC3)n[nH]2)n1] |

| Entry | Structure |
|---|---|
| 95 | 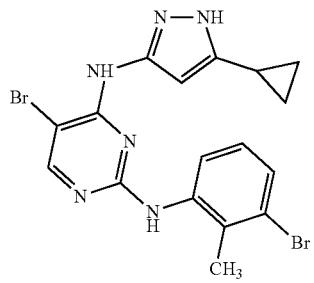 [SMILES: Cc1c(Br)cccc1Nc1ncc(Br)c(Nc2cc(C3CC3)[nH]n2)n1] |
| 96 | 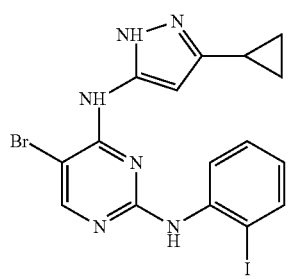 [SMILES: Brc1cnc(Nc2ccccc2I)nc1Nc1cc(C2CC2)n[nH]1] |
| 97 | 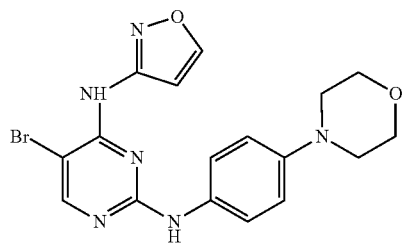 [SMILES: Brc1cnc(Nc2ccc(N3CCOCC3)cc2)nc1Nc1ccon1] |
| 98 | 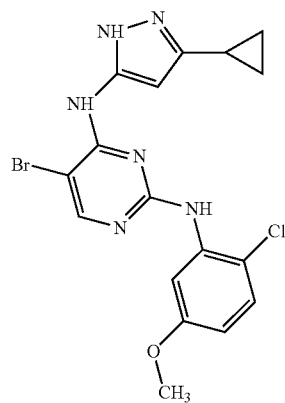 [SMILES: COc1ccc(Cl)c(Nc2ncc(Br)c(Nc3cc(C4CC4)n[nH]3)n2)c1] |
| 99 | 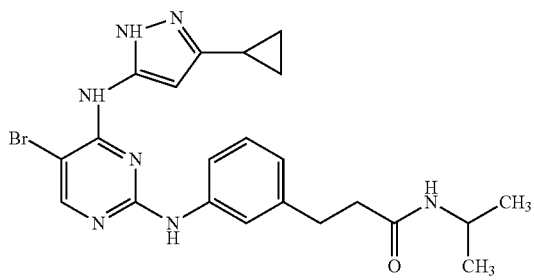 [SMILES: CC(C)NC(=O)CCc1cccc(Nc2ncc(Br)c(Nc3cc(C4CC4)n[nH]3)n2)c1] |

| Entry | Structure |
|---|---|
| 100 | (5-bromo-pyrimidine with 4-NH-(3-cyclopropyl-1H-pyrazol-5-yl) and 2-NH-[3-(3-(4-methylpiperazin-1-yl)-3-oxopropyl)phenyl]) |
| 101 | (5-chloro-pyrimidine with 4-NH-(3-cyclopropyl-1H-pyrazol-5-yl) and 2-NH-(2-chlorophenyl)) |
| 102 | (5-bromo-pyrimidine with 4-NH-(3-cyclopropyl-1H-pyrazol-5-yl) and 2-NH-(2-methoxyphenyl)) |
| 103 | (5-bromo-pyrimidine with 4-NH-(3-cyclopropyl-1H-pyrazol-5-yl) and 2-NH-[4-(2-(methylamino)-2-oxoethyl)phenyl]) |
| 104 | (5-bromo-pyrimidine with 4-NH-(3-cyclopropyl-1H-pyrazol-5-yl) and 2-NH-(2,3-dihydrobenzo[b][1,4]dioxin-6-yl)) |
| 105 | (pyrimidine with 4-NH-(3-cyclopropyl-1H-pyrazol-5-yl) and 2-NH-[4-(3-(2-morpholinoethylamino)-3-oxopropyl)phenyl]) |

-continued

| Entry | Structure |
|---|---|
| 106 | 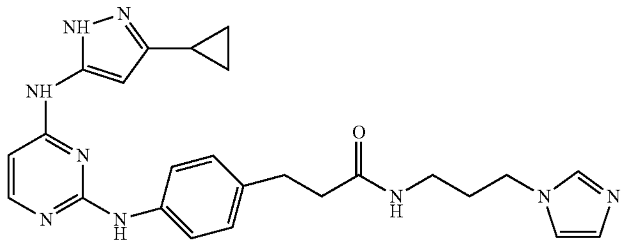 [SMILES: O=C(CCc1ccc(Nc2nccc(Nc3cc(C4CC4)n[nH]3)n2)cc1)NCCCn1ccnc1] |
| 107 | 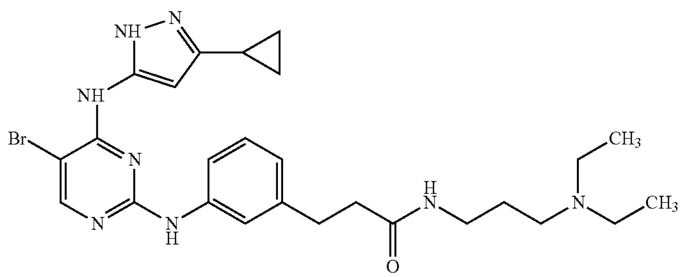 [SMILES: CCN(CC)CCCNC(=O)CCc1cccc(Nc2ncc(Br)c(Nc3cc(C4CC4)n[nH]3)n2)c1] |
| 108 | 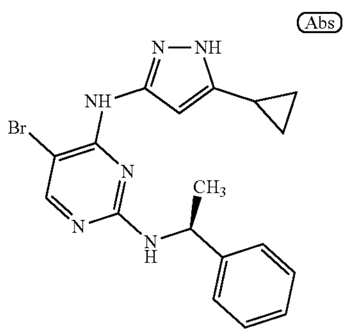 [SMILES: C[C@H](Nc1ncc(Br)c(Nc2cc(C3CC3)[nH]n2)n1)c1ccccc1] |
| 109 | 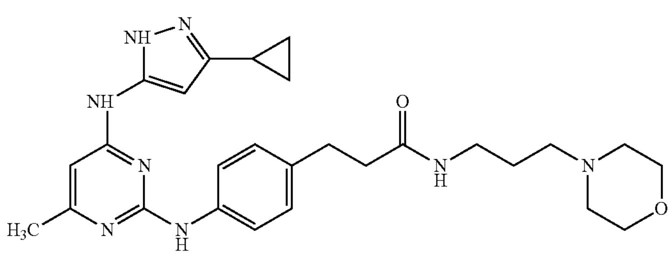 [SMILES: Cc1cc(Nc2cc(C3CC3)n[nH]2)nc(Nc2ccc(CCC(=O)NCCCN3CCOCC3)cc2)n1] |
| 110 | 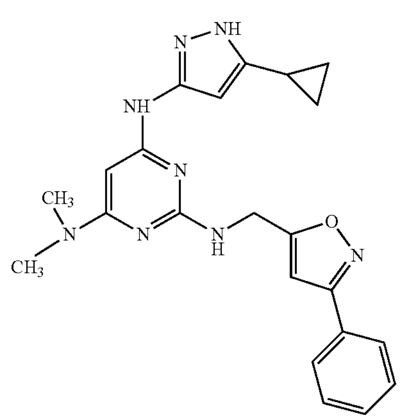 [SMILES: CN(C)c1cc(Nc2cc(C3CC3)[nH]n2)nc(NCc2cc(-c3ccccc3)no2)n1] |

-continued

| Entry | Structure |
|---|---|
| 111 | 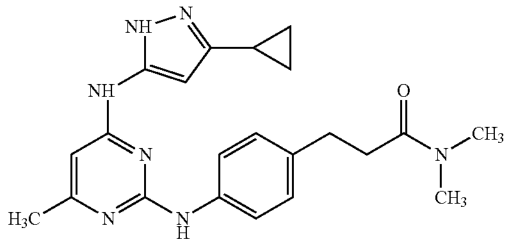 |
| 112 | 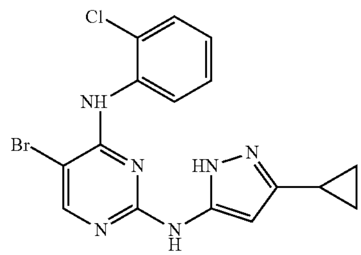 [SMILES: Clc1ccccc1Nc1nc(Nc2cc(C3CC3)n[nH]2)ncc1Br] |
| 113 | 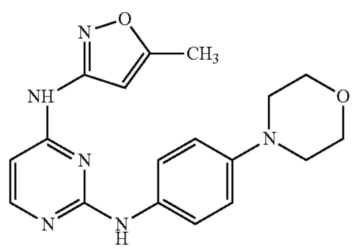 [SMILES: Cc1cc(Nc2ccnc(Nc3ccc(N4CCOCC4)cc3)n2)no1] |
| 114 | 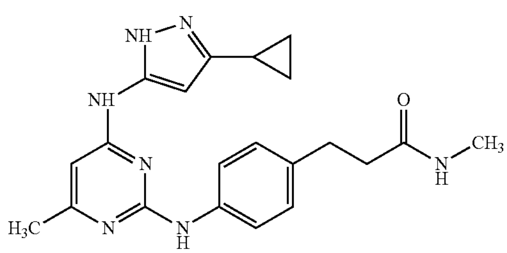 |
| 115 | 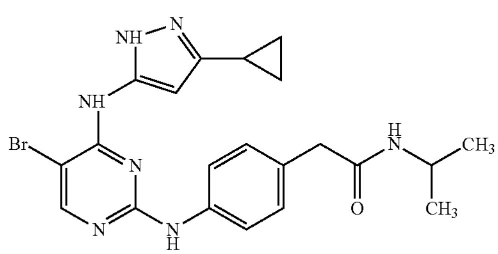 [SMILES: CC(C)NC(=O)Cc1ccc(Nc2ncc(Br)c(Nc3cc(C4CC4)n[nH]3)n2)cc1] |
| 116 | 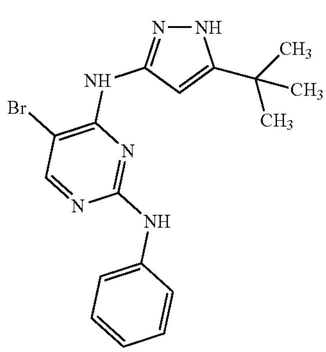 [SMILES: CC(C)(C)c1cc(Nc2nc(Nc3ccccc3)ncc2Br)n[nH]1] |

| Entry | Structure |
|---|---|
| 117 | 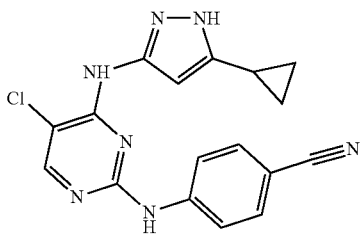 [SMILES: N#Cc1ccc(Nc2ncc(Cl)c(Nc3cc(C4CC4)[nH]n3)n2)cc1] |
| 118 | 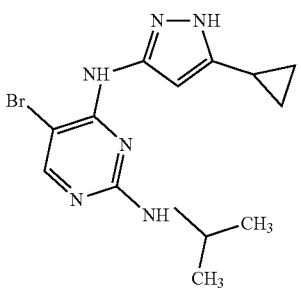 |
| 119 | 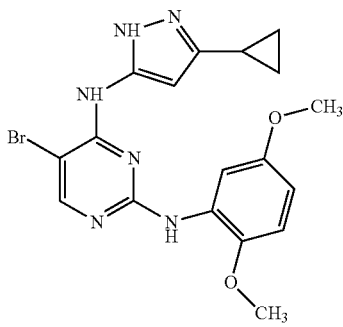 [SMILES: COc1ccc(OC)c(Nc2ncc(Br)c(Nc3cc(C4CC4)n[nH]3)n2)c1] |
| 120 | 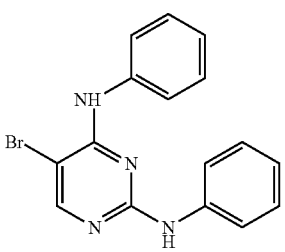 [SMILES: Brc1cnc(Nc2ccccc2)nc1Nc1ccccc1] |
| 121 | 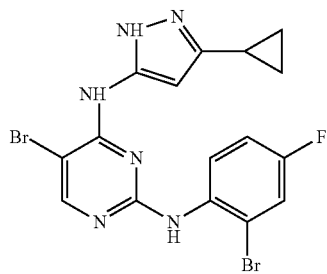 [SMILES: Fc1ccc(Nc2ncc(Br)c(Nc3cc(C4CC4)n[nH]3)n2)c(Br)c1] |

-continued
| Entry | Structure |
|---|---|
| 122 | 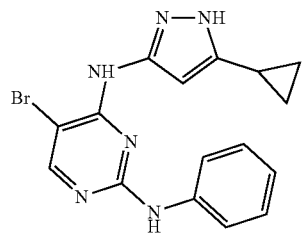 [SMILES: Brc1cnc(Nc2ccccc2)nc1Nc1cc(C2CC2)[nH]n1] |
| 123 | 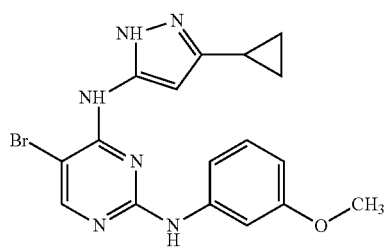 [SMILES: COc1cccc(Nc2ncc(Br)c(Nc3cc(C4CC4)n[nH]3)n2)c1] |
| 124 | 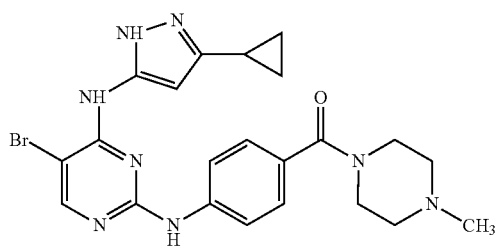 [SMILES: CN1CCN(C(=O)c2ccc(Nc3ncc(Br)c(Nc4cc(C5CC5)n[nH]4)n3)cc2)CC1] |
| 125 | 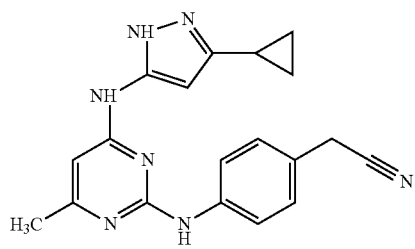 [SMILES: Cc1cc(Nc2cc(C3CC3)n[nH]2)nc(Nc2ccc(CC#N)cc2)n1] |
| 126 | 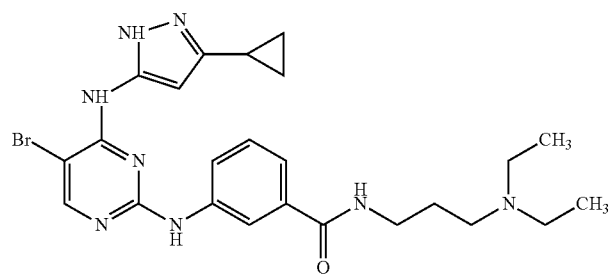 [SMILES: CCN(CC)CCCNC(=O)c1cccc(Nc2ncc(Br)c(Nc3cc(C4CC4)n[nH]3)n2)c1] |
| 127 | 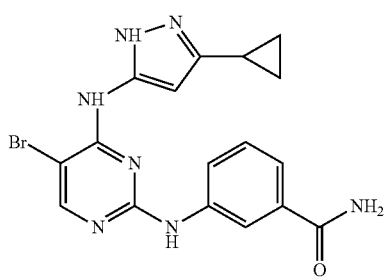 [SMILES: NC(=O)c1cccc(Nc2ncc(Br)c(Nc3cc(C4CC4)n[nH]3)n2)c1] |

-continued
| Entry | Structure |
|---|---|
| 128 | 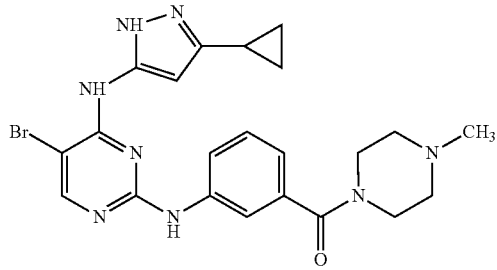 [SMILES: CN1CCN(C(=O)c2cccc(Nc3ncc(Br)c(Nc4cc(C5CC5)n[nH]4)n3)c2)CC1] |
| 129 | 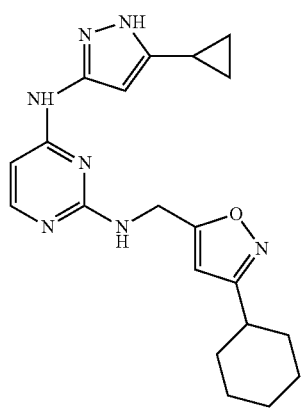 [SMILES: c1cc(Nc2cc(C3CC3)[nH]n2)nc(NCc2cc(C3CCCCC3)no2)n1] |
| 130 | 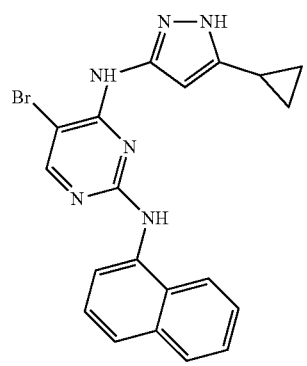 [SMILES: Brc1cnc(Nc2cccc3ccccc23)nc1Nc1cc(C2CC2)[nH]n1] |
| 131 | 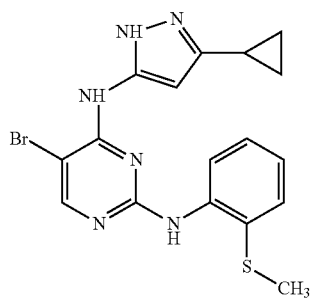 [SMILES: CSc1ccccc1Nc1ncc(Br)c(Nc2cc(C3CC3)n[nH]2)n1] |
| 132 | 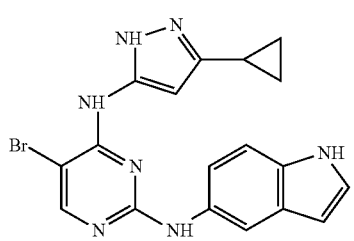 [SMILES: Brc1cnc(Nc2ccc3[nH]ccc3c2)nc1Nc1cc(C2CC2)n[nH]1] |

| Entry | Structure |
|---|---|
| 133 | 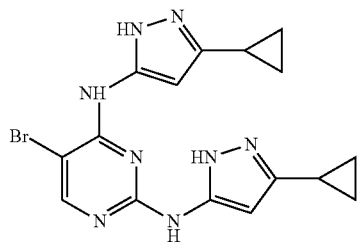 [SMILES: Brc1cnc(Nc2cc(C3CC3)n[nH]2)nc1Nc1cc(C2CC2)n[nH]1] |
| 134 | 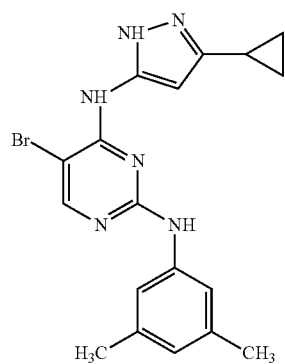 [SMILES: Cc1cc(C)cc(Nc2ncc(Br)c(Nc3cc(C4CC4)n[nH]3)n2)c1] |
| 135 | 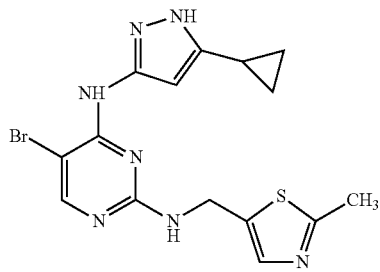 [SMILES: Cc1ncc(CNc2ncc(Br)c(Nc3cc(C4CC4)[nH]n3)n2)s1] |
| 136 | 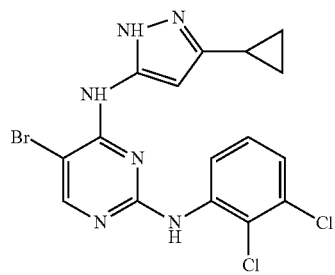 [SMILES: Clc1cccc(Nc2ncc(Br)c(Nc3cc(C4CC4)n[nH]3)n2)c1Cl] |
| 137 | 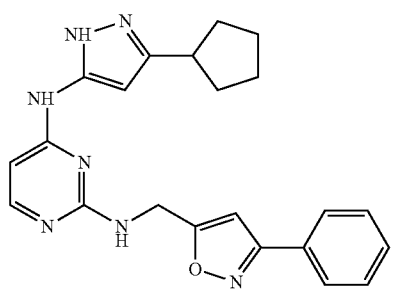 [SMILES: c1ccc(-c2cc(CNc3nccc(Nc4cc(C5CCCC5)n[nH]4)n3)on2)cc1] |

| Entry | Structure |
|---|---|
| 138 | 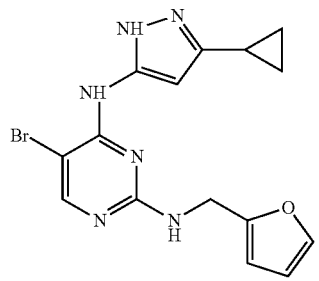 [SMILES: Brc1cnc(NCc2ccco2)nc1Nc1cc(C2CC2)n[nH]1] |
| 139 | 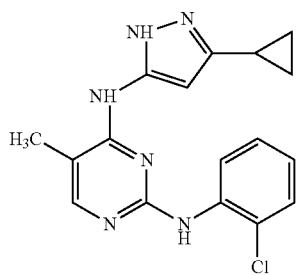 |
| 140 | 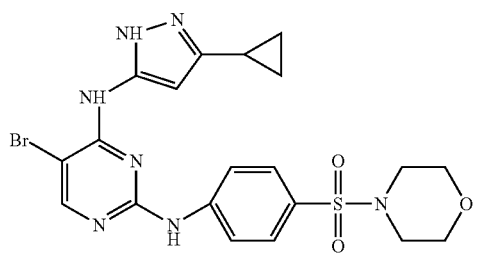 [SMILES: O=S(=O)(c1ccc(Nc2ncc(Br)c(Nc3cc(C4CC4)n[nH]3)n2)cc1)N1CCOCC1] |
| 141 | 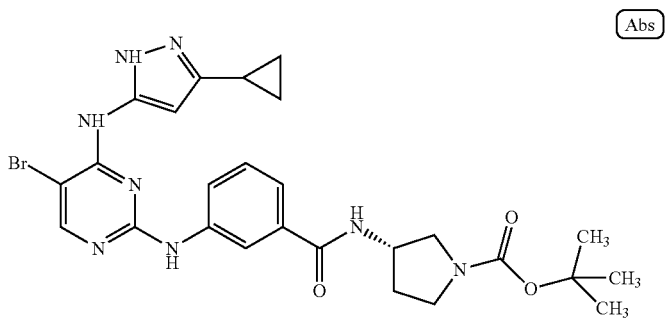 [SMILES: CC(C)(C)OC(=O)N1CC[C@H](NC(=O)c2cccc(Nc3ncc(Br)c(Nc4cc(C5CC5)n[nH]4)n3)c2)C1] [Abs] |
| 142 | 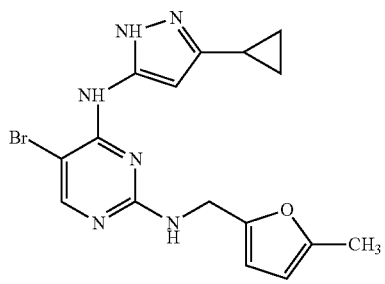 [SMILES: Cc1ccc(CNc2ncc(Br)c(Nc3cc(C4CC4)n[nH]3)n2)o1] |

-continued
| Entry | Structure |
|---|---|
| 143 | 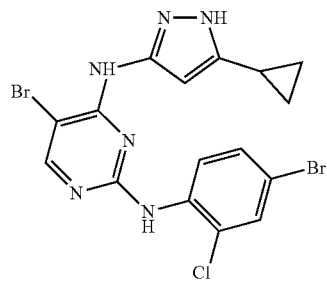 [SMILES: Clc1cc(Br)ccc1Nc1ncc(Br)c(Nc2cc(C3CC3)[nH]n2)n1] |
| 144 | 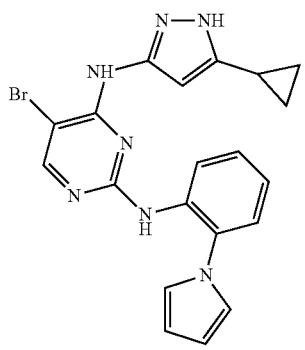 [SMILES: Brc1cnc(Nc2ccccc2-n2cccc2)nc1Nc1cc(C2CC2)[nH]n1] |
| 145 | 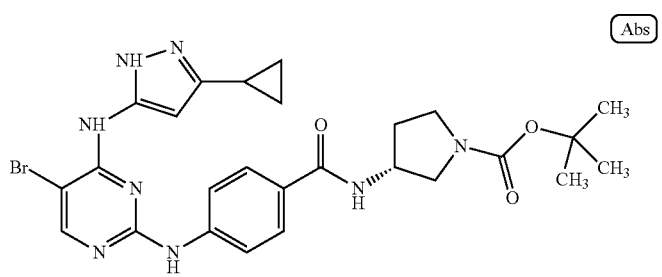 [SMILES: CC(C)(C)OC(=O)N1CC[C@@H](NC(=O)c2ccc(Nc3ncc(Br)c(Nc4cc(C5CC5)n[nH]4)n3)cc2)C1] [Abs] |
| 146 | 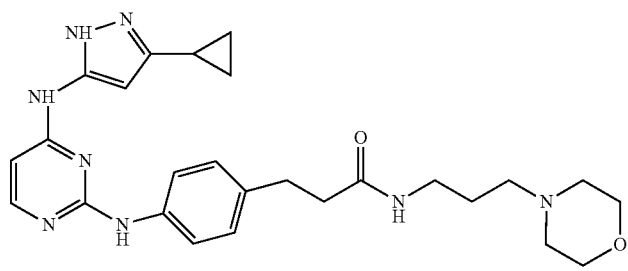 [SMILES: O=C(CCc1ccc(Nc2nccc(Nc3cc(C4CC4)n[nH]3)n2)cc1)NCCCN1CCOCC1] |
| 147 | 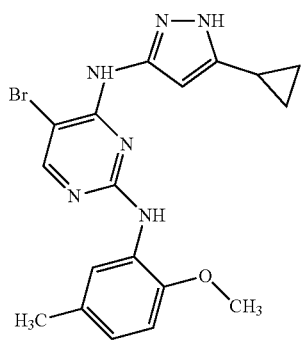 [SMILES: COc1ccc(C)cc1Nc1ncc(Br)c(Nc2cc(C3CC3)[nH]n2)n1] |

| Entry | Structure |
|---|---|
| 148 | 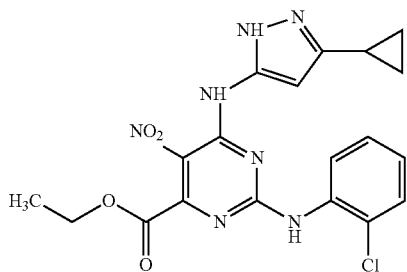 [SMILES: CCOC(=O)c1nc(Nc2ccccc2Cl)nc(Nc2cc(C3CC3)n[nH]2)c1[N+](=O)[O-]] |
| 149 | 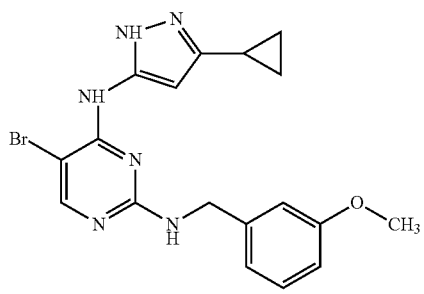 [SMILES: COc1cccc(CNc2ncc(Br)c(Nc3cc(C4CC4)n[nH]3)n2)c1] |
| 150 | 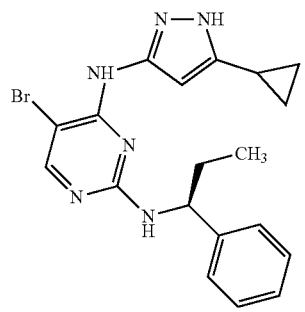 [SMILES: CC[C@H](Nc1ncc(Br)c(Nc2cc(C3CC3)[nH]n2)n1)c1ccccc1] |
| 151 | 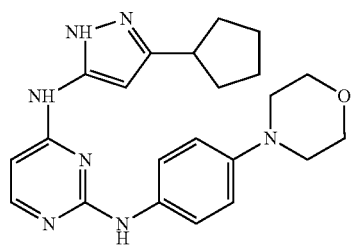 [SMILES: c1cc(Nc2cc(C3CCCC3)n[nH]2)nc(Nc2ccc(N3CCOCC3)cc2)n1] |
| 152 | 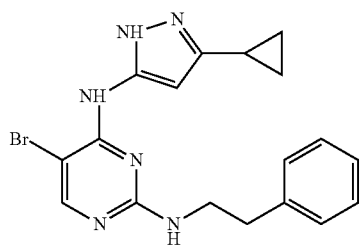 [SMILES: Brc1cnc(NCCc2ccccc2)nc1Nc1cc(C2CC2)n[nH]1] |

-continued

| Entry | Structure |
|---|---|
| 153 | 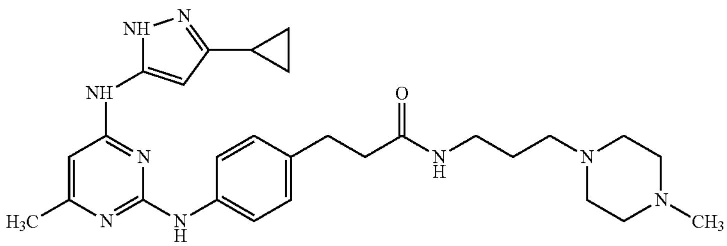 |
| 154 | 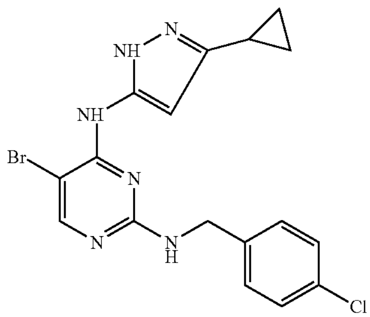 [SMILES: Clc1ccc(CNc2ncc(Br)c(Nc3cc(C4CC4)n[nH]3)n2)cc1] |
| 155 | 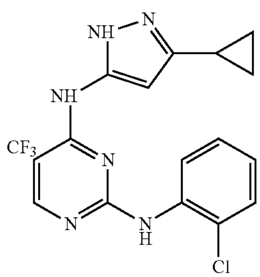 [SMILES: "CF3" ; Clc1ccccc1Nc1nccc(Nc2cc(C3CC3)n[nH]2)n1] |
| 156 | 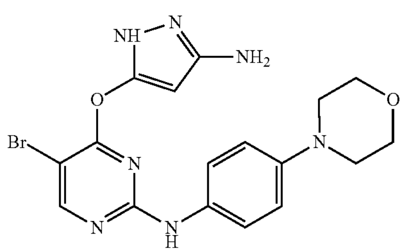 [SMILES: Nc1cc(Oc2nc(Nc3ccc(N4CCOCC4)cc3)ncc2Br)[nH]n1] |
| 157 | 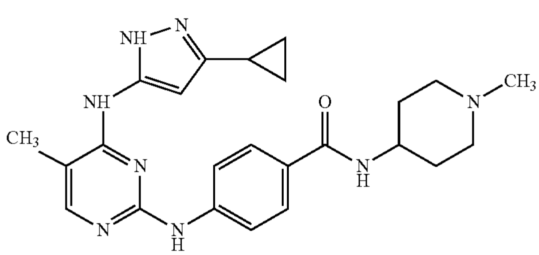 |
| 158 | 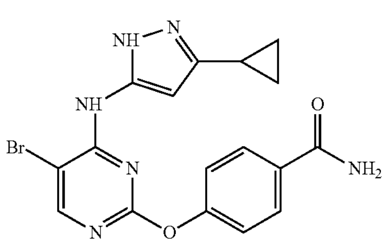 [SMILES: NC(=O)c1ccc(Oc2ncc(Br)c(Nc3cc(C4CC4)n[nH]3)n2)cc1] |

| Entry | Structure |
|---|---|
| 159 | 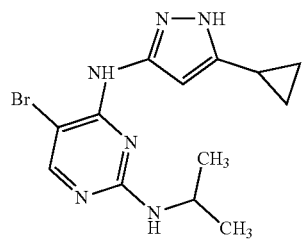 [SMILES: CC(C)Nc1ncc(Br)c(Nc2cc(C3CC3)[nH]n2)n1] |
| 160 | 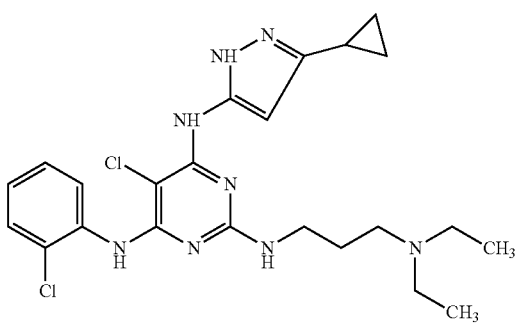 [SMILES: CCN(CC)CCCNc1nc(Nc2cc(C3CC3)n[nH]2)c(Cl)c(Nc2ccccc2Cl)n1] |
| 161 | 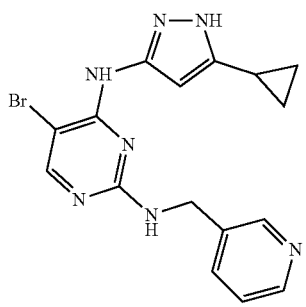 [SMILES: Brc1cnc(NCc2cccnc2)nc1Nc1cc(C2CC2)[nH]n1] |
| 162 | 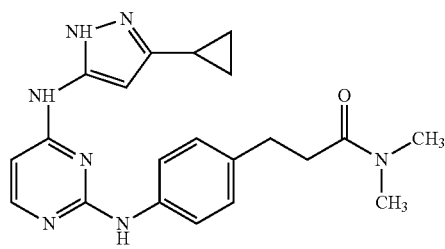 [SMILES: CN(C)C(=O)CCc1ccc(Nc2nccc(Nc3cc(C4CC4)n[nH]3)n2)cc1] |
| 163 | 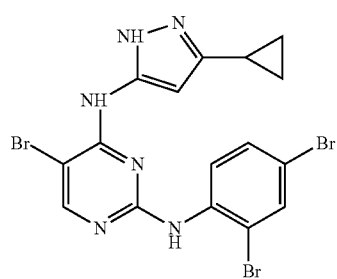 [SMILES: Brc1ccc(Nc2ncc(Br)c(Nc3cc(C4CC4)n[nH]3)n2)c(Br)c1] |

| Entry | Structure |
|---|---|
| 164 | 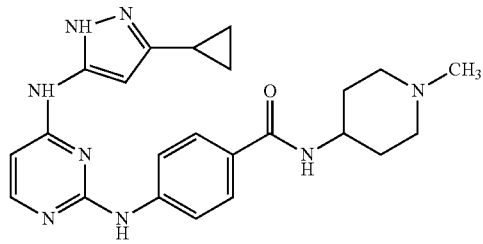 [SMILES: CN1CCC(NC(=O)c2ccc(Nc3nccc(Nc4cc(C5CC5)n[nH]4)n3)cc2)CC1] |
| 165 | 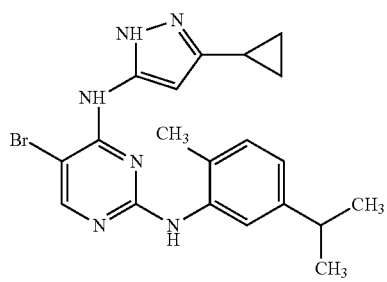 [SMILES: Cc1ccc(C(C)C)cc1Nc1ncc(Br)c(Nc2cc(C3CC3)n[nH]2)n1] |
| 166 | 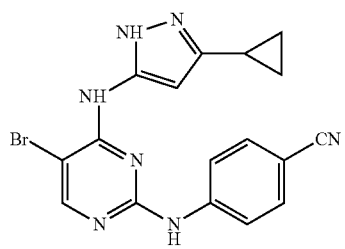 [SMILES: N#Cc1ccc(Nc2ncc(Br)c(Nc3cc(C4CC4)n[nH]3)n2)cc1] |
| 167 | 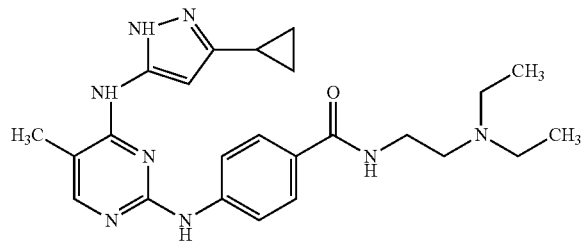 [SMILES: CCN(CC)CCNC(=O)c1ccc(Nc2ncc(C)c(Nc3cc(C4CC4)n[nH]3)n2)cc1] |
| 168 | 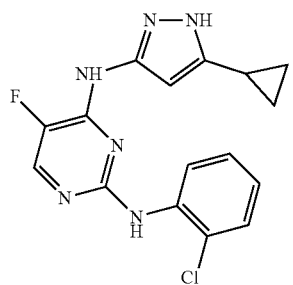 [SMILES: Fc1cnc(Nc2ccccc2Cl)nc1Nc1cc(C2CC2)[nH]n1] |

-continued

| Entry | Structure |
|---|---|
| 169 | 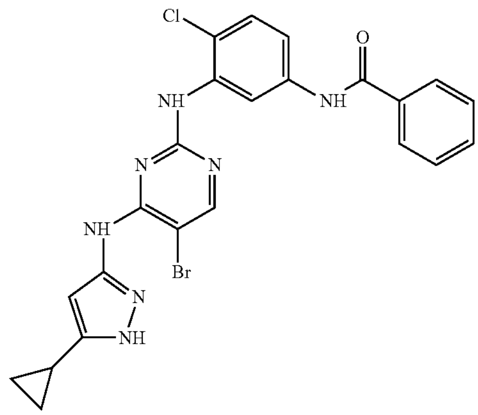 [SMILES: O=C(Nc1ccc(Cl)c(Nc2ncc(Br)c(Nc3cc(C4CC4)[nH]n3)n2)c1)c1ccccc1] |
| 170 | 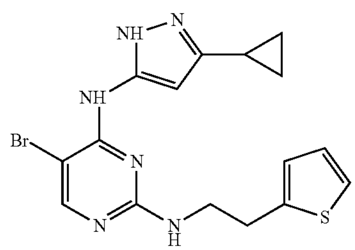 [SMILES: Brc1cnc(NCCc2cccs2)nc1Nc1cc(C2CC2)n[nH]1] |
| 171 | 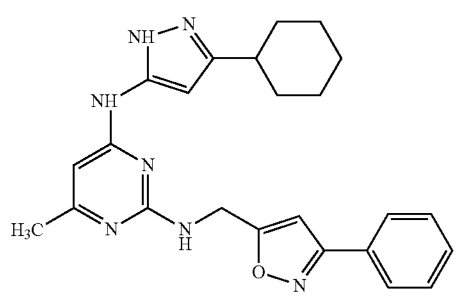 [SMILES: Cc1cc(Nc2cc(C3CCCCC3)n[nH]2)nc(NCc2cc(-c3ccccc3)no2)n1] |
| 172 | 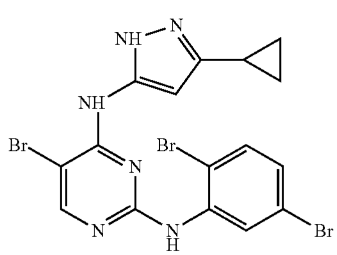 [SMILES: Brc1ccc(Br)c(Nc2ncc(Br)c(Nc3cc(C4CC4)n[nH]3)n2)c1] |
| 173 | 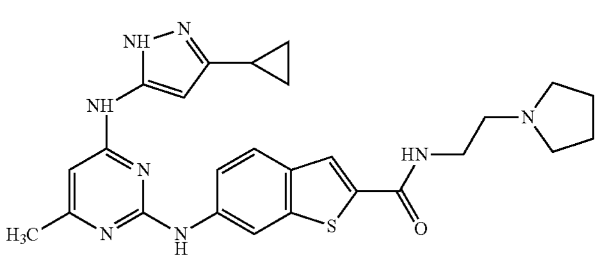 [SMILES: Cc1cc(Nc2cc(C3CC3)n[nH]2)nc(Nc2ccc3cc(C(=O)NCCN4CCCC4)sc3c2)n1] |

| Entry | Structure |
|---|---|
| 174 | 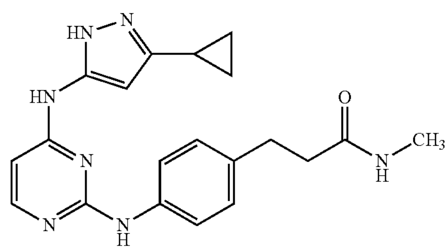 [SMILES: CNC(=O)CCc1ccc(Nc2nccc(Nc3cc(C4CC4)n[nH]3)n2)cc1] |
| 175 | 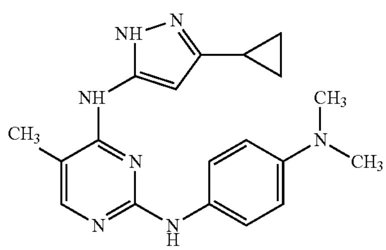 |
| 176 | 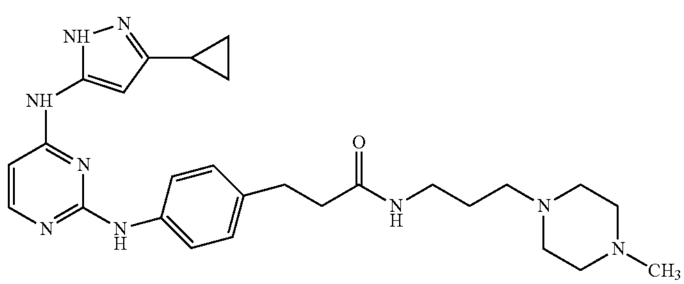 [SMILES: CN1CCN(CCCNC(=O)CCc2ccc(Nc3nccc(Nc4cc(C5CC5)n[nH]4)n3)cc2)CC1] |
| 177 | 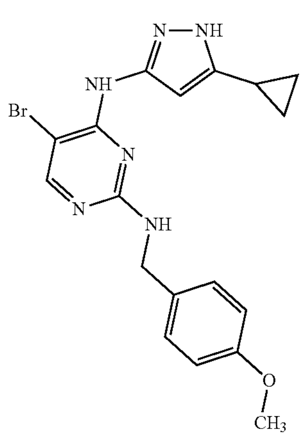 [SMILES: COc1ccc(CNc2ncc(Br)c(Nc3cc(C4CC4)[nH]n3)n2)cc1] |

| Entry | Structure |
|---|---|
| 178 | 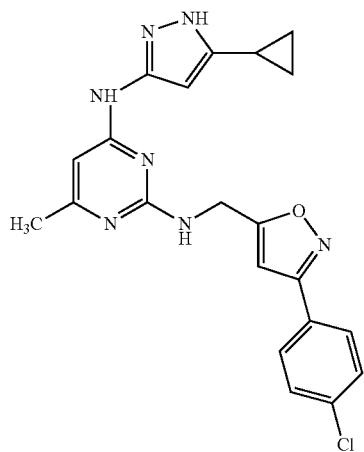 [SMILES: Cc1cc(Nc2cc(C3CC3)[nH]n2)nc(NCc2cc(-c3ccc(Cl)cc3)no2)n1] |
| 179 | 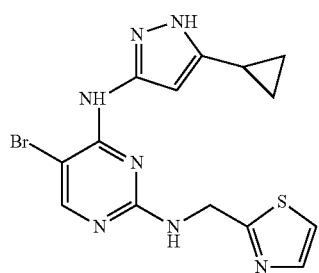 [SMILES: Brc1cnc(NCc2nccs2)nc1Nc1cc(C2CC2)[nH]n1] |
| 180 | 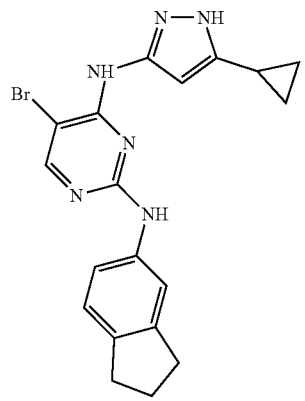 [SMILES: Brc1cnc(Nc2ccc3c(c2)CCC3)nc1Nc1cc(C2CC2)[nH]n1] |
| 181 | 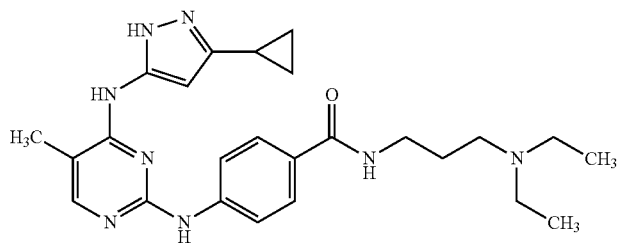 [SMILES: CCN(CC)CCCNC(=O)c1ccc(Nc2ncc(C)c(Nc3cc(C4CC4)n[nH]3)n2)cc1] |

-continued
| Entry | Structure |
|---|---|
| 182 | 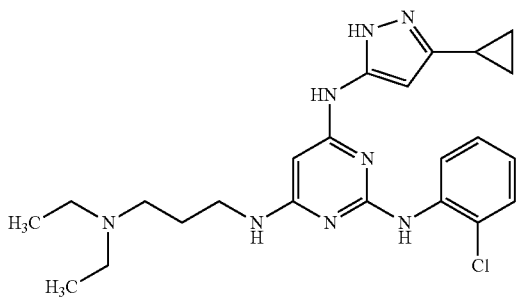 [SMILES: CCN(CC)CCCNc1cc(Nc2cc(C3CC3)n[nH]2)nc(Nc2ccccc2Cl)n1] |
| 183 | 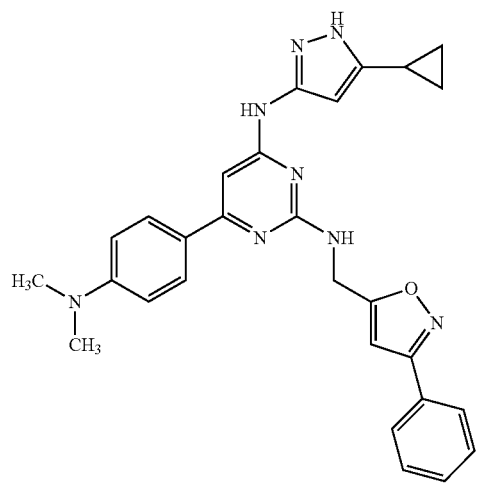 [SMILES: CN(C)c1ccc(-c2cc(Nc3cc(C4CC4)[nH]n3)nc(NCc3cc(-c4ccccc4)no3)n2)cc1] |
| 184 | 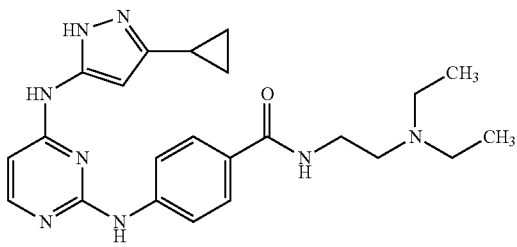 [SMILES: CCN(CC)CCNC(=O)c1ccc(Nc2nccc(Nc3cc(C4CC4)n[nH]3)n2)cc1] |
| 185 | 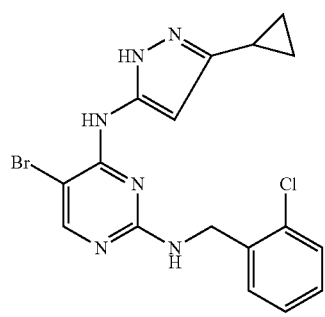 [SMILES: Clc1ccccc1CNc1ncc(Br)c(Nc2cc(C3CC3)n[nH]2)n1] |

| Entry | Structure |
|---|---|
| 186 | 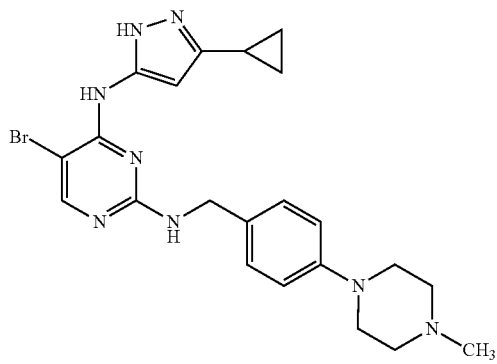 [SMILES: CN1CCN(c2ccc(CNc3ncc(Br)c(Nc4cc(C5CC5)n[nH]4)n3)cc2)CC1] |
| 187 | 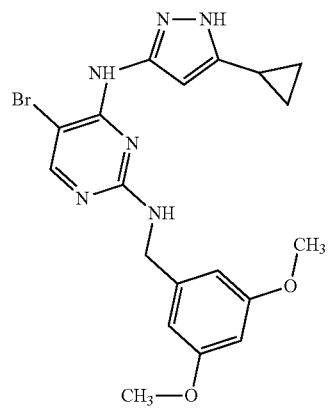 [SMILES: COc1cc(CNc2ncc(Br)c(Nc3cc(C4CC4)[nH]n3)n2)cc(OC)c1] |
| 188 | 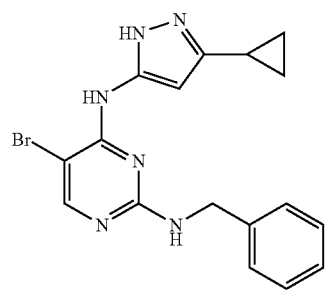 [SMILES: Brc1cnc(NCc2ccccc2)nc1Nc1cc(C2CC2)n[nH]1] |
| 189 | 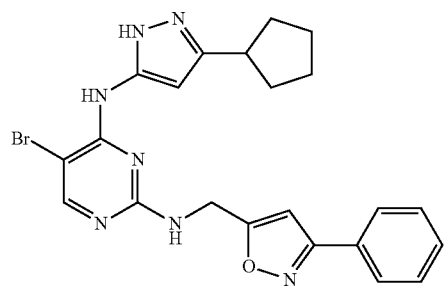 [SMILES: Brc1cnc(NCc2cc(-c3ccccc3)no2)nc1Nc1cc(C2CCCC2)n[nH]1] |

-continued

| Entry | Structure |
|---|---|
| 190 | 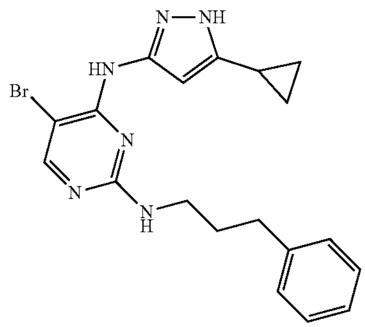 [SMILES: Brc1cnc(NCCCc2ccccc2)nc1Nc1cc(C2CC2)[nH]n1] |
| 191 | 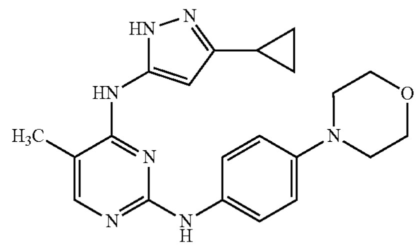 [SMILES: Cc1cnc(Nc2ccc(N3CCOCC3)cc2)nc1Nc1cc(C2CC2)n[nH]1] |
| 192 | 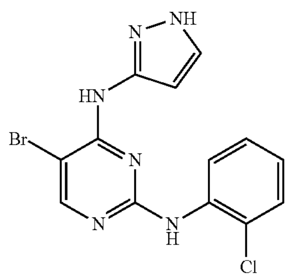 [SMILES: Clc1ccccc1Nc1ncc(Br)c(Nc2cc[nH]n2)n1] |
| 193 | 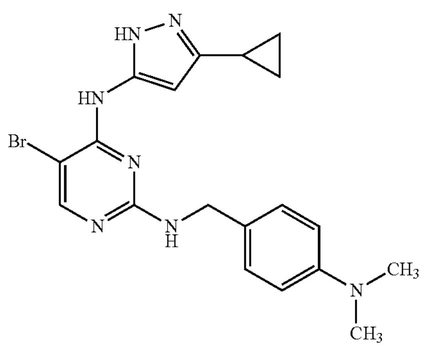 [SMILES: CN(C)c1ccc(CNc2ncc(Br)c(Nc3cc(C4CC4)n[nH]3)n2)cc1] |
| 194 | 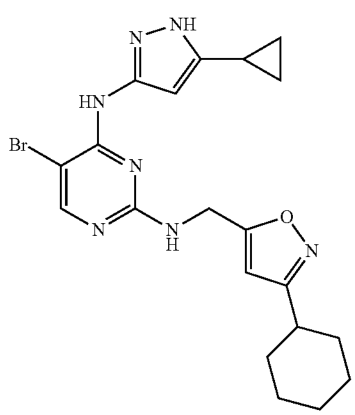 [SMILES: Brc1cnc(NCc2cc(C3CCCCC3)no2)nc1Nc1cc(C2CC2)[nH]n1] |

| Entry | Structure |
|---|---|
| 195 | 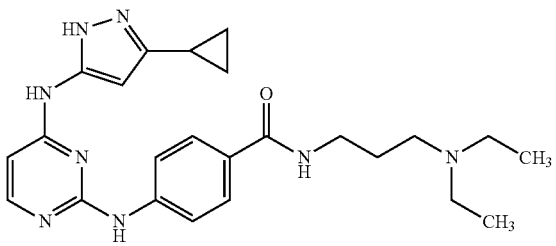 [SMILES: CCN(CC)CCCNC(=O)c1ccc(Nc2nccc(Nc3cc(C4CC4)n[nH]3)n2)cc1] |
| 196 | 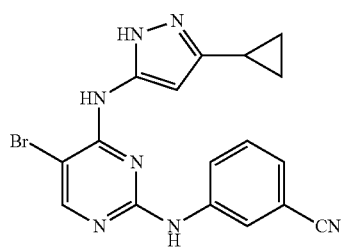 [SMILES: N#Cc1cccc(Nc2ncc(Br)c(Nc3cc(C4CC4)n[nH]3)n2)c1] |
| 197 | 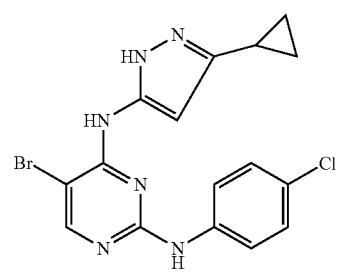 [SMILES: Clc1ccc(Nc2ncc(Br)c(Nc3cc(C4CC4)n[nH]3)n2)cc1] |
| 198 | 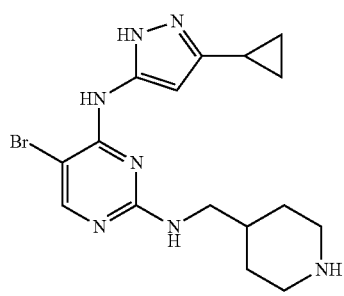 [SMILES: Brc1cnc(NCC2CCNCC2)nc1Nc1cc(C2CC2)n[nH]1] |
| 199 | 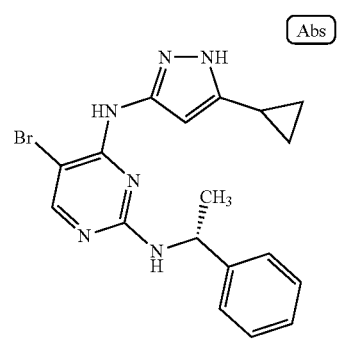 [SMILES: C[C@@H](Nc1ncc(Br)c(Nc2cc(C3CC3)[nH]n2)n1)c1ccccc1] |

| Entry | Structure |
|---|---|
| 200 | 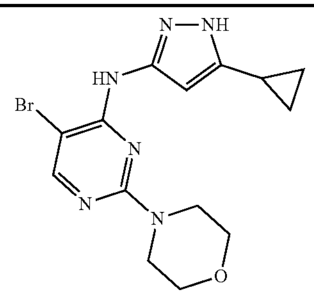 |
| 201 | 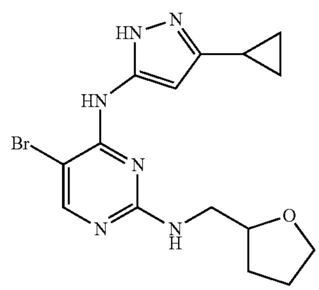 [SMILES: Brc1cnc(NCC2CCCO2)nc1Nc1cc(C2CC2)n[nH]1] |
| 202 | 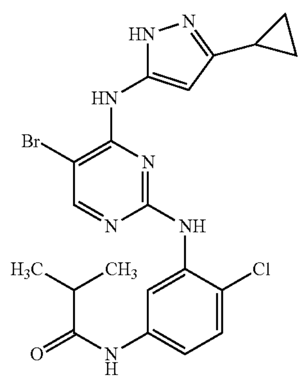 [SMILES: CC(C)C(=O)Nc1ccc(Cl)c(Nc2ncc(Br)c(Nc3cc(C4CC4)n[nH]3)n2)c1] |
| 203 | 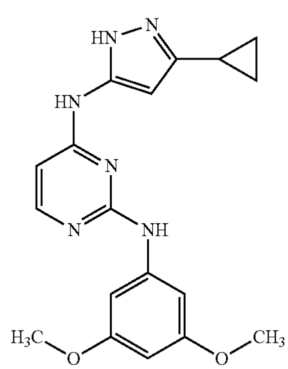 [SMILES: COc1cc(Nc2nccc(Nc3cc(C4CC4)n[nH]3)n2)cc(OC)c1] |
| 204 | 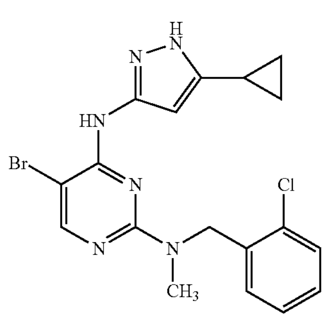 [SMILES: CN(Cc1ccccc1Cl)c1ncc(Br)c(Nc2cc(C3CC3)[nH]n2)n1] |

| Entry | Structure |
|---|---|
| 205 | 5-bromo-N4-(3-chlorophenyl)-N2-(2-chlorophenyl)pyrimidine-2,4-diamine |
| 206 | 5-bromo-N4-(5-cyclopropyl-1H-pyrazol-3-yl)-N2-(2,5-dimethoxybenzyl)pyrimidine-2,4-diamine |
| 207 | N4-(5-cyclopropyl-1H-pyrazol-3-yl)-N2-(2-methoxybenzyl)-6-methylpyrimidine-2,4-diamine |
| 208 | 5-bromo-N4-(5-cyclopropyl-1H-pyrazol-3-yl)-N2-(2-(pyridin-2-yl)ethyl)pyrimidine-2,4-diamine |
| 209 | 5-bromo-N4-(5-cyclopropyl-1H-pyrazol-3-yl)-N2-(2,4-dichlorophenyl)pyrimidine-2,4-diamine |

| Entry | Structure |
|---|---|
| 210 | 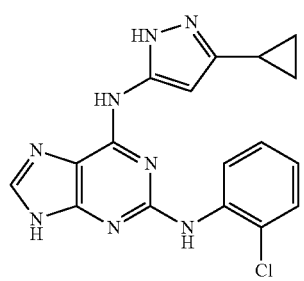 [SMILES: Clc1ccccc1Nc1nc(Nc2cc(C3CC3)n[nH]2)c2nc[nH]c2n1] |
| 211 | 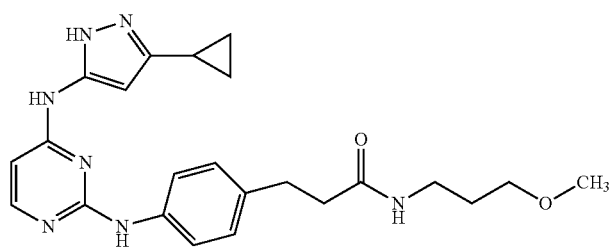 [SMILES: COCCCNC(=O)CCc1ccc(Nc2nccc(Nc3cc(C4CC4)n[nH]3)n2)cc1] |
| 212 | 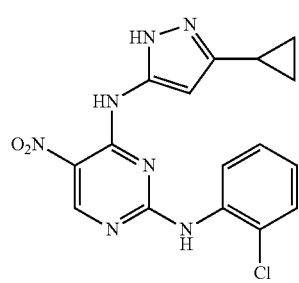 |
| 213 | 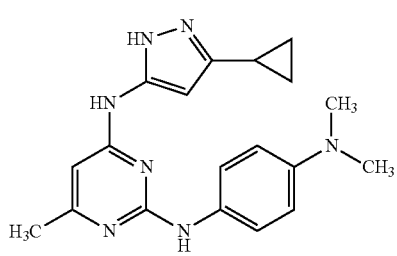 |
| 214 | 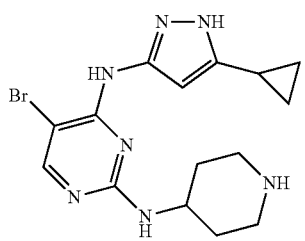 [SMILES: Brc1cnc(NC2CCNCC2)nc1Nc1cc(C2CC2)[nH]n1] |
| 215 | 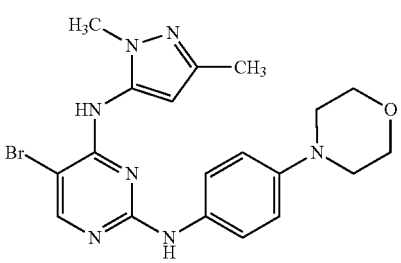 [SMILES: Cc1cc(Nc2nc(Nc3ccc(N4CCOCC4)cc3)ncc2Br)n(C)n1] |

| Entry | Structure |
|---|---|
| 216 | 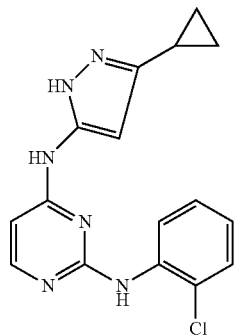 [SMILES: Clc1ccccc1Nc1nccc(Nc2cc(C3CC3)n[nH]2)n1] |
| 217 | 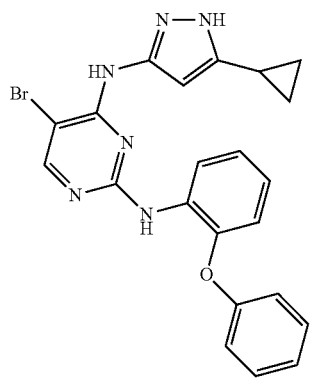 [SMILES: Brc1cnc(Nc2ccccc2Oc2ccccc2)nc1Nc1cc(C2CC2)[nH]n1] |
| 218 | 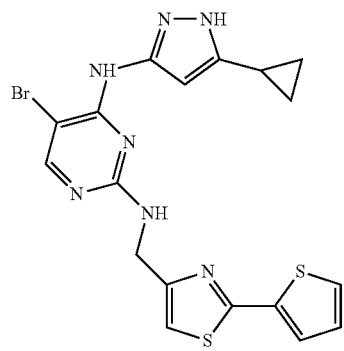 [SMILES: Brc1cnc(NCc2csc(-c3cccs3)n2)nc1Nc1cc(C2CC2)[nH]n1] |
| 219 | 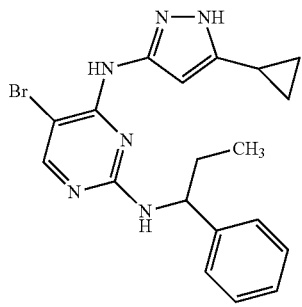 [SMILES: CCC(Nc1ncc(Br)c(Nc2cc(C3CC3)[nH]n2)n1)c1ccccc1] |

-continued

| Entry | Structure |
|---|---|
| 220 | 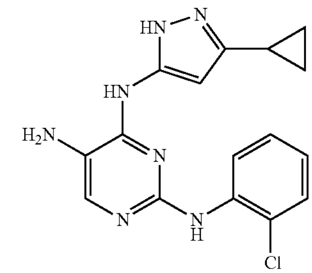 |
| 221 | 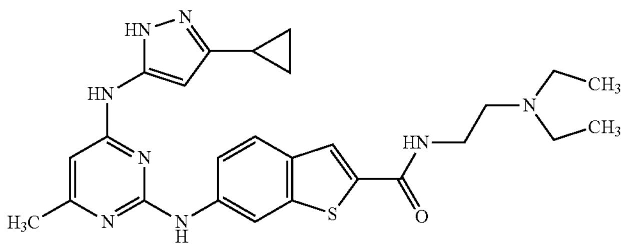 [SMILES: CCN(CC)CCNC(=O)c1cc2ccc(Nc3nc(C)cc(Nc4cc(C5CC5)n[nH]4)n3)cc2s1] |
| 222 | 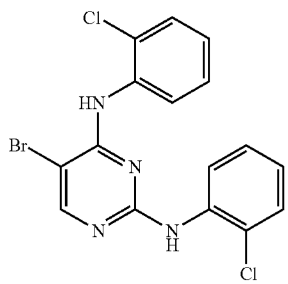 [SMILES: Clc1ccccc1Nc1ncc(Br)c(Nc2ccccc2Cl)n1] |
| 223 | 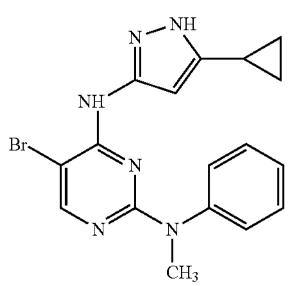 [SMILES: CN(c1ccccc1)c1ncc(Br)c(Nc2cc(C3CC3)[nH]n2)n1] |
| 224 | 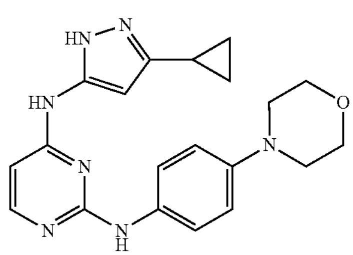 [SMILES: c1cc(Nc2cc(C3CC3)n[nH]2)nc(Nc2ccc(N3CCOCC3)cc2)n1] |
| 225 | 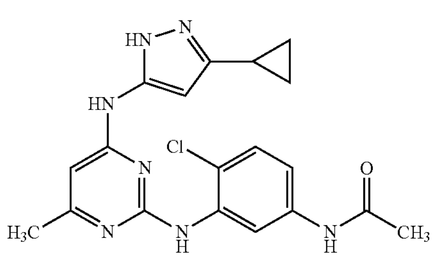 [SMILES: CC(=O)Nc1ccc(Cl)c(Nc2nc(C)cc(Nc3cc(C4CC4)n[nH]3)n2)c1] |

-continued
| Entry | Structure |
|---|---|
| 226 | 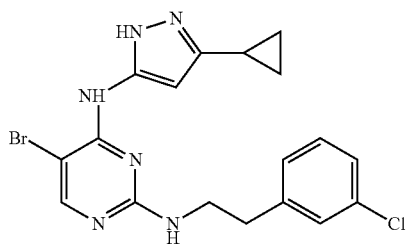 [SMILES: Clc1cccc(CCNc2ncc(Br)c(Nc3cc(C4CC4)n[nH]3)n2)c1] |
| 227 | 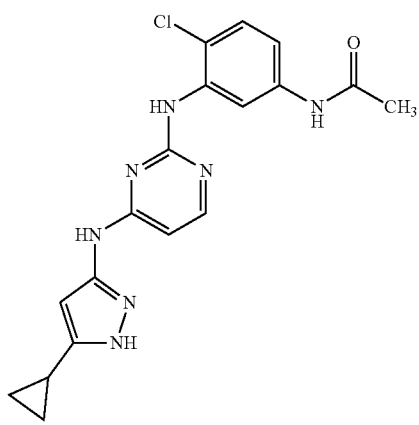 [SMILES: CC(=O)Nc1ccc(Cl)c(Nc2nccc(Nc3cc(C4CC4)[nH]n3)n2)c1] |
| 228 | 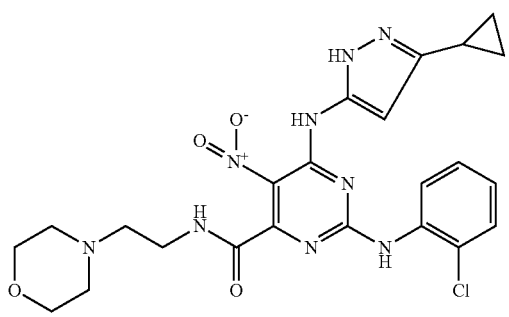 [SMILES: O=C(NCCN1CCOCC1)c1nc(Nc2ccccc2Cl)nc(Nc2cc(C3CC3)n[nH]2)c1[N+](=O)[O-]] |
| 229 | 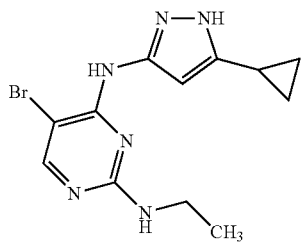 [SMILES: CCNc1ncc(Br)c(Nc2cc(C3CC3)[nH]n2)n1] |
| 230 | 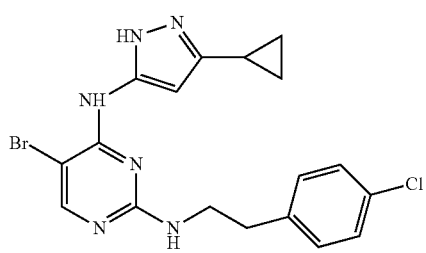 [SMILES: Clc1ccc(CCNc2ncc(Br)c(Nc3cc(C4CC4)n[nH]3)n2)cc1] |

| Entry | Structure |
|---|---|
| 231 | 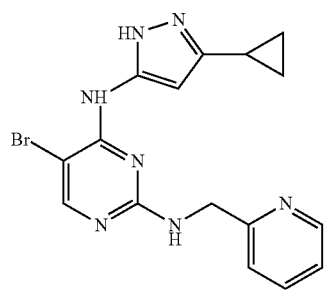 [SMILES: Brc1cnc(NCc2ccccn2)nc1Nc1cc(C2CC2)n[nH]1] |
| 232 | 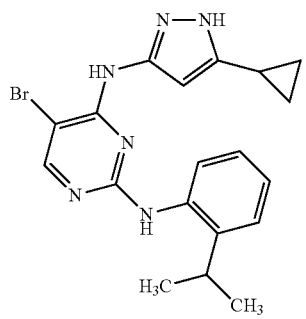 [SMILES: CC(C)c1ccccc1Nc1ncc(Br)c(Nc2cc(C3CC3)[nH]n2)n1] |
| 233 | 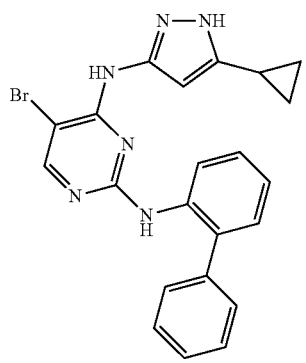 [SMILES: Brc1cnc(Nc2ccccc2-c2ccccc2)nc1Nc1cc(C2CC2)[nH]n1] |
| 234 | 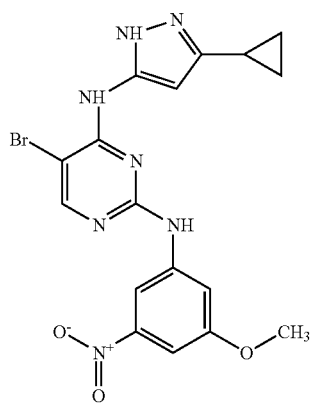 [SMILES: COc1cc(Nc2ncc(Br)c(Nc3cc(C4CC4)n[nH]3)n2)cc([N+](=O)[O-])c1] |

| Entry | Structure |
|---|---|
| 235 | 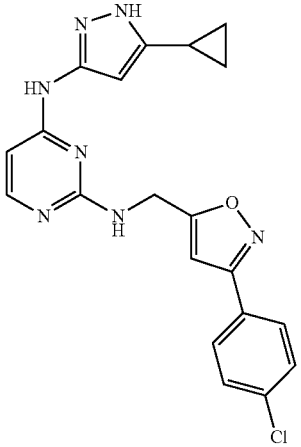 [SMILES: Clc1ccc(-c2cc(CNc3nccc(Nc4cc(C5CC5)[nH]n4)n3)on2)cc1] |
| 236 | 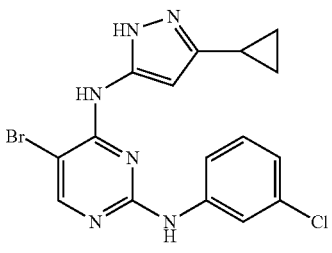 [SMILES: Clc1cccc(Nc2ncc(Br)c(Nc3cc(C4CC4)n[nH]3)n2)c1] |
| 237 | 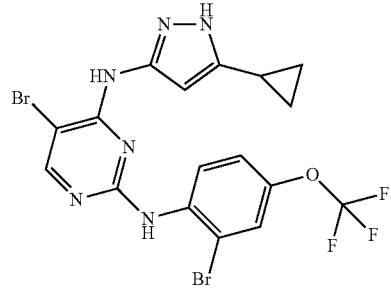 [SMILES: FC(F)(F)Oc1ccc(Nc2ncc(Br)c(Nc3cc(C4CC4)[nH]n3)n2)c(Br)c1] |
| 238 | 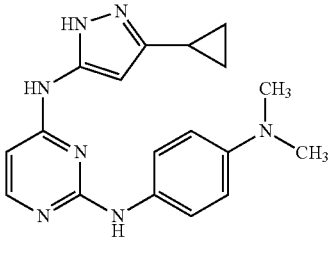 [SMILES: CN(C)c1ccc(Nc2nccc(Nc3cc(C4CC4)n[nH]3)n2)cc1] |
| 239 | 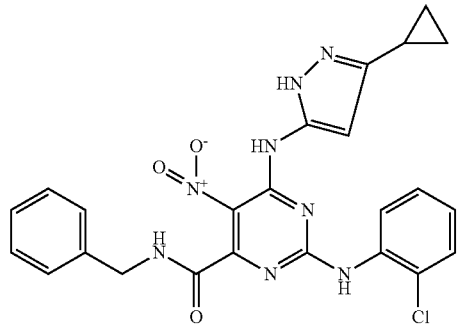 [SMILES: O=C(NCc1ccccc1)c1nc(Nc2ccccc2Cl)nc(Nc2cc(C3CC3)n[nH]2)c1[N+](=O)[O-]] |

| Entry | Structure |
|---|---|
| 240 | 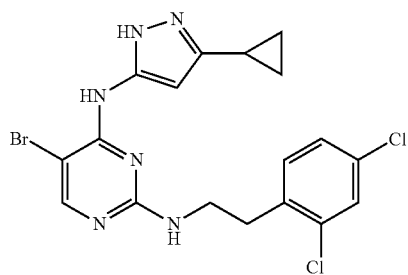 [SMILES: Clc1ccc(CCNc2ncc(Br)c(Nc3cc(C4CC4)n[nH]3)n2)c(Cl)c1] |
| 241 | 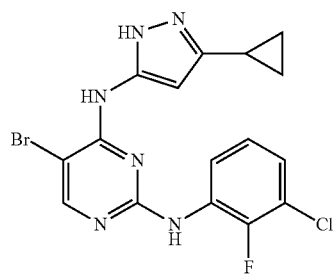 [SMILES: Fc1c(Cl)cccc1Nc1ncc(Br)c(Nc2cc(C3CC3)n[nH]2)n1] |
| 242 | 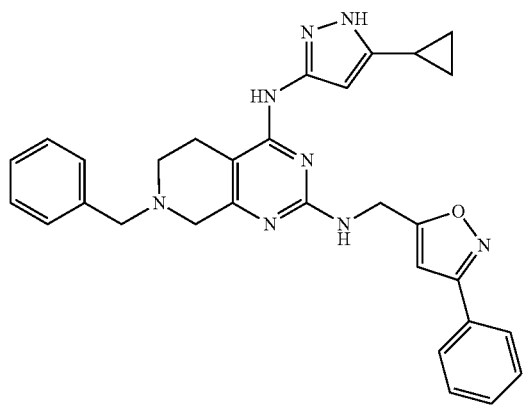 [SMILES: c1ccc(CN2CCc3c(nc(NCc4cc(-c5ccccc5)no4)nc3Nc3cc(C4CC4)[nH]n3)C2)cc1] |
| 243 | 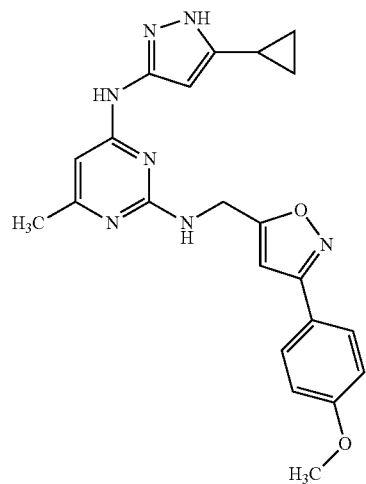 [SMILES: COc1ccc(-c2cc(CNc3nc(C)cc(Nc4cc(C5CC5)[nH]n4)n3)on2)cc1] |

| Entry | Structure |
|---|---|
| 244 | 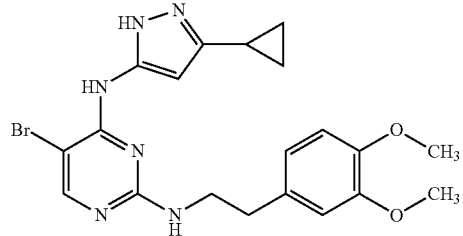 [SMILES: COc1ccc(CCNc2ncc(Br)c(Nc3cc(C4CC4)n[nH]3)n2)cc1OC] |
| 245 | 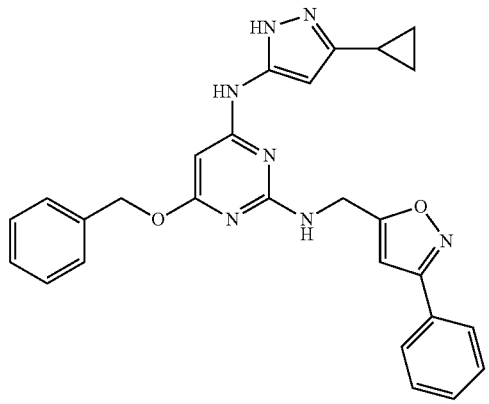 [SMILES: c1ccc(COc2cc(Nc3cc(C4CC4)n[nH]3)nc(NCc3cc(-c4ccccc4)no3)n2)cc1] |
| 246 | 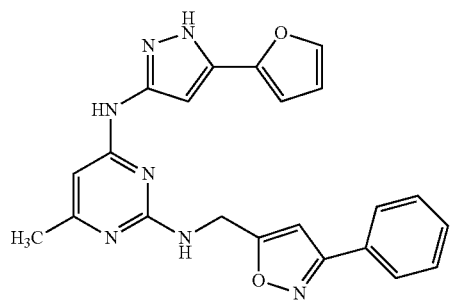 [SMILES: Cc1cc(Nc2cc(-c3ccco3)[nH]n2)nc(NCc2cc(-c3ccccc3)no2)n1] |
| 247 | 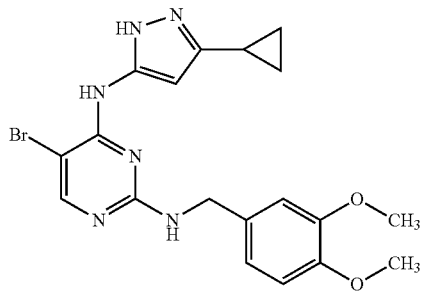 [SMILES: COc1ccc(CNc2ncc(Br)c(Nc3cc(C4CC4)n[nH]3)n2)cc1OC] |
| 248 | 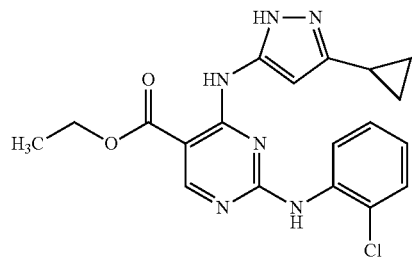 [SMILES: CCOC(=O)c1cnc(Nc2ccccc2Cl)nc1Nc1cc(C2CC2)n[nH]1] |

| Entry | Structure |
|---|---|
| 249 | (5-cyclopropyl-1H-pyrazol-3-yl)amino-5-bromo-2-(4-methylpiperazin-1-yl)pyrimidine |
| 250 | 5-bromo-N4-(5-cyclopropyl-1H-pyrazol-3-yl)-N2-(pyridin-4-ylmethyl)pyrimidine-2,4-diamine |
| 251 | 5-bromo-N4-(5-cyclopropyl-1H-pyrazol-3-yl)-N2-((R)-1-phenylpropyl)pyrimidine-2,4-diamine [Abs] |
| 252 | N4-(5-cyclopropyl-1H-pyrazol-3-yl)-6-methyl-N2-((4-phenylthiazol-2-yl)methyl)pyrimidine-2,4-diamine |
| 253 | 2-(2-chlorophenylamino)-6-(5-cyclopropyl-1H-pyrazol-3-ylamino)-N-isopropyl-5-nitropyrimidine-4-carboxamide |

| Entry | Structure |
|---|---|
| 254 | 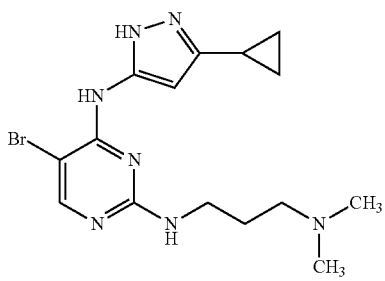 [SMILES: CN(C)CCCNc1ncc(Br)c(Nc2cc(C3CC3)n[nH]2)n1] |
| 255 | 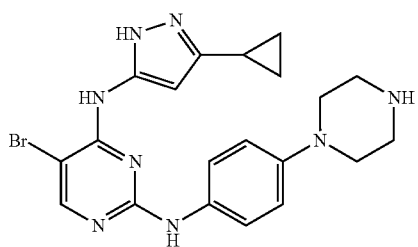 [SMILES: Brc1cnc(Nc2ccc(N3CCNCC3)cc2)nc1Nc1cc(C2CC2)n[nH]1] |
| 256 | 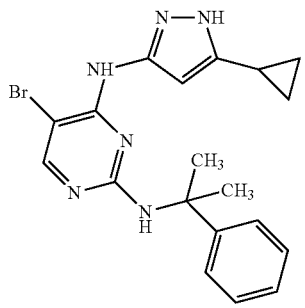 [SMILES: CC(C)(Nc1ncc(Br)c(Nc2cc(C3CC3)[nH]n2)n1)c1ccccc1] |
| 257 | 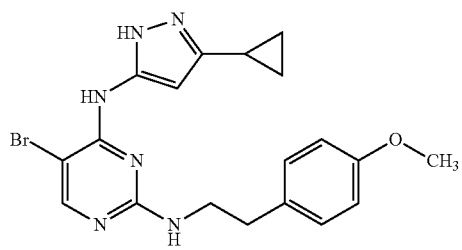 [SMILES: COc1ccc(CCNc2ncc(Br)c(Nc3cc(C4CC4)n[nH]3)n2)cc1] |
| 258 | 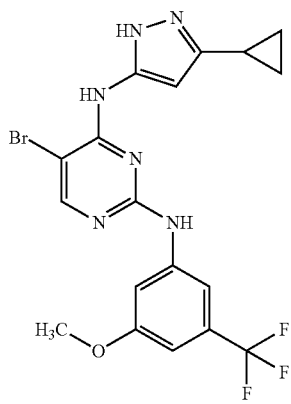 [SMILES: COc1cc(Nc2ncc(Br)c(Nc3cc(C4CC4)n[nH]3)n2)cc(C(F)(F)F)c1] |

-continued
| Entry | Structure |
|---|---|
| 259 | 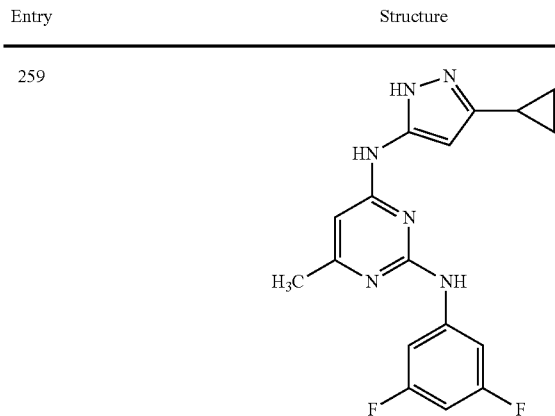 |
| 260 | 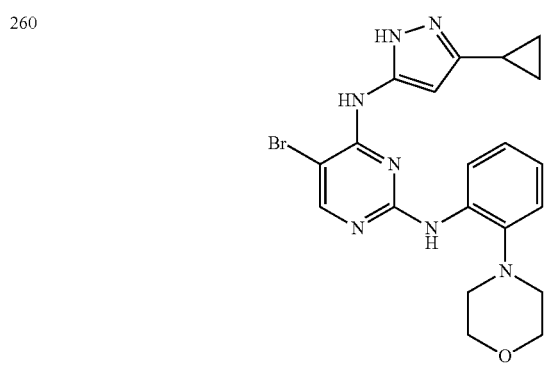 |
| 261 | 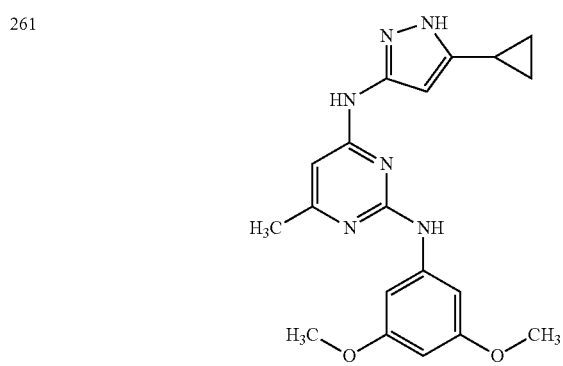 |
| 262 | 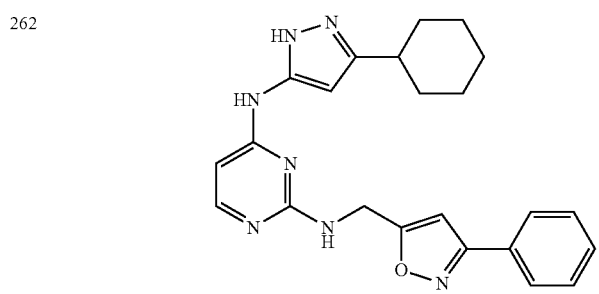 |

| Entry | Structure |
|---|---|
| 263 | *5-bromo-N4-(5-cyclopropyl-1H-pyrazol-3-yl)-N2-(3-(trifluoromethyl)benzyl)pyrimidine-2,4-diamine* |
| 264 | *5-bromo-N4-(5-cyclopropyl-1H-pyrazol-3-yl)-N2-(3-(trifluoromethoxy)phenyl)pyrimidine-2,4-diamine* |
| 265 | *N4-(5-cyclopropyl-1H-pyrazol-3-yl)-N2-((3-(4-methoxyphenyl)isoxazol-5-yl)methyl)pyrimidine-2,4-diamine* |
| 266 | *5-bromo-N4-(5-cyclopropyl-1H-pyrazol-3-yl)-N2-((2-phenyl-2H-1,2,3-triazol-4-yl)methyl)pyrimidine-2,4-diamine* |

| Entry | Structure |
|---|---|
| 267 | 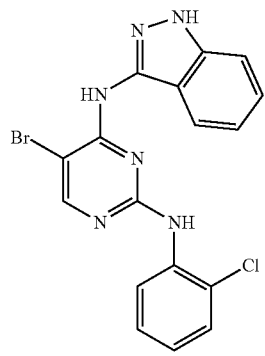 [SMILES: Clc1ccccc1Nc1ncc(Br)c(Nc2n[nH]c3ccccc23)n1] |
| 268 | 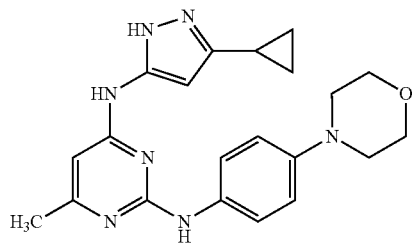 [SMILES: Cc1cc(Nc2cc(C3CC3)n[nH]2)nc(Nc2ccc(N3CCOCC3)cc2)n1] |
| 269 | 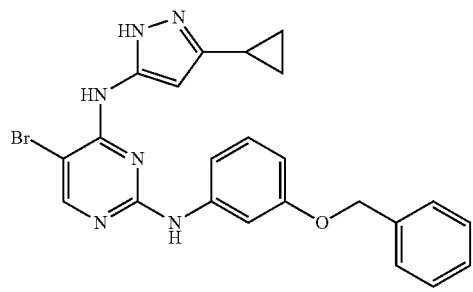 [SMILES: Brc1cnc(Nc2cccc(OCc3ccccc3)c2)nc1Nc1cc(C2CC2)n[nH]1] |
| 270 | 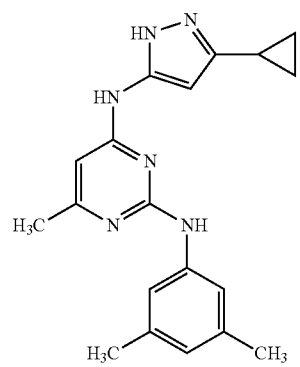 [SMILES: Cc1cc(C)cc(Nc2nc(C)cc(Nc3cc(C4CC4)n[nH]3)n2)c1] |

| Entry | Structure |
|---|---|
| 271 | 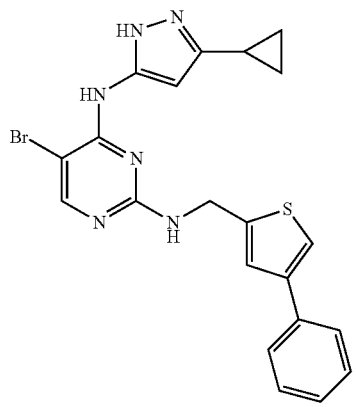 [SMILES: Brc1cnc(NCc2cc(-c3ccccc3)cs2)nc1Nc1cc(C2CC2)n[nH]1] |
| 272 | 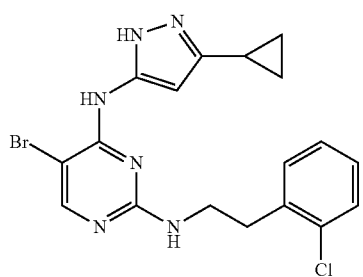 [SMILES: Clc1ccccc1CCNc1ncc(Br)c(Nc2cc(C3CC3)n[nH]2)n1] |
| 273 | 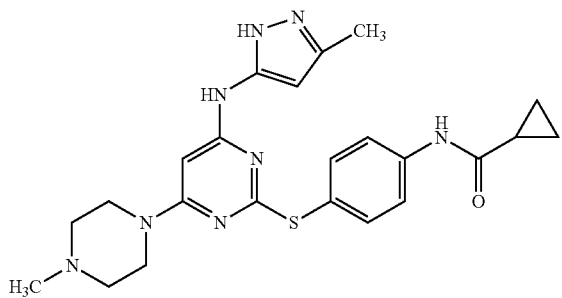 [SMILES: Cc1cc(Nc2cc(N3CCN(C)CC3)nc(Sc3ccc(NC(=O)C4CC4)cc3)n2)[nH]n1] |
| 274 | 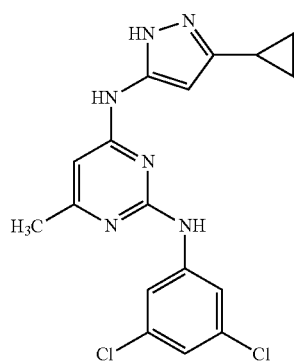 [SMILES: Cc1cc(Nc2cc(C3CC3)n[nH]2)nc(Nc2cc(Cl)cc(Cl)c2)n1] |

-continued
| Entry | Structure |
|---|---|
| 275 | 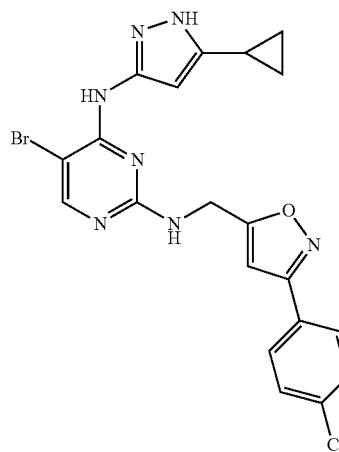 |
| 276 | 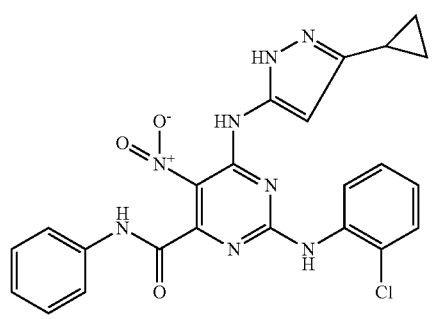 [SMILES: O=C(Nc1ccccc1)c1nc(Nc2ccccc2Cl)nc(Nc2cc(C3CC3)n[nH]2)c1[N+](=O)[O-]] |
| 277 | 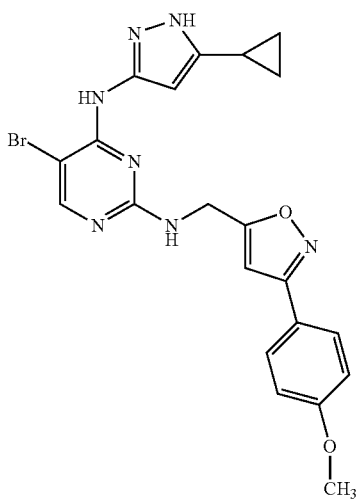 [SMILES: COc1ccc(-c2cc(CNc3ncc(Br)c(Nc4cc(C5CC5)[nH]n4)n3)on2)cc1] |

| Entry | Structure |
|---|---|
| 278 | 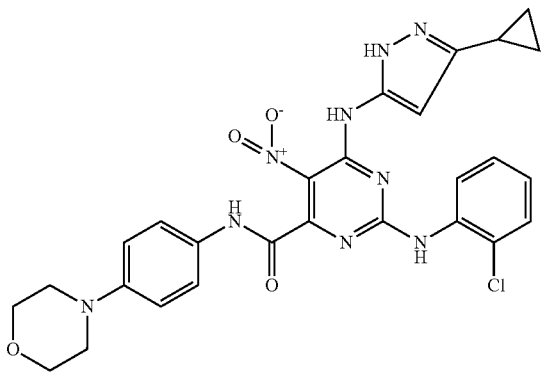 [SMILES: O=C(Nc1ccc(N2CCOCC2)cc1)c1nc(Nc2ccccc2Cl)nc(Nc2cc(C3CC3)n[nH]2)c1[N+](=O)[O-]] |
| 279 | 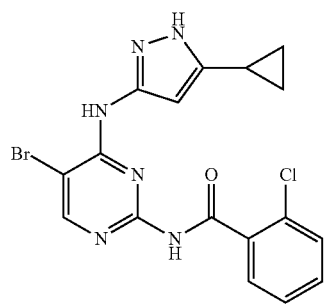 [SMILES: O=C(Nc1ncc(Br)c(Nc2cc(C3CC3)[nH]n2)n1)c1ccccc1Cl] |
| 280 | 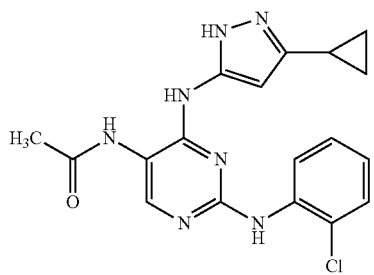 [SMILES: CC(=O)Nc1cnc(Nc2ccccc2Cl)nc1Nc1cc(C2CC2)n[nH]1] |
| 281 | 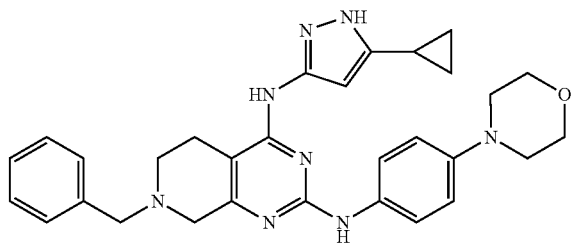 [SMILES: c1ccc(CN2CCc3c(nc(Nc4ccc(N5CCOCC5)cc4)nc3Nc3cc(C4CC4)[nH]n3)C2)cc1] |
| 282 | 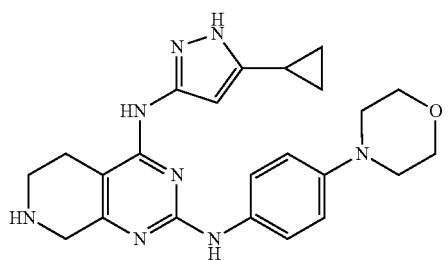 [SMILES: c1cc(N2CCOCC2)ccc1Nc1nc2c(c(Nc3cc(C4CC4)[nH]n3)n1)CCNC2] |

-continued
| Entry | Structure |
|---|---|
| 283 | 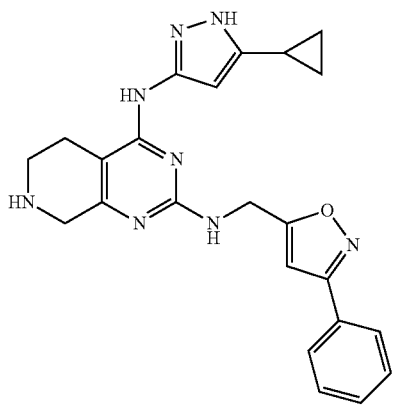 [SMILES: c1ccc(-c2cc(CNc3nc4c(c(Nc5cc(C6CC6)[nH]n5)n3)CCNC4)on2)cc1] |
| 284 | 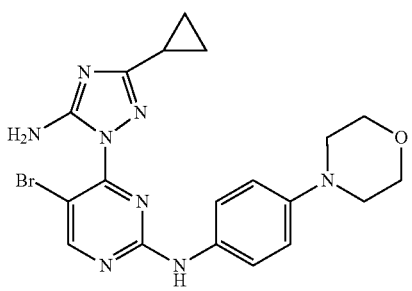 [SMILES: Nc1nc(C2CC2)nn1-c1nc(Nc2ccc(N3CCOCC3)cc2)ncc1Br] |
| 285 | 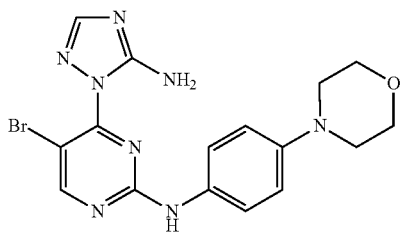 [SMILES: Nc1ncnn1-c1nc(Nc2ccc(N3CCOCC3)cc2)ncc1Br] |
| 286 | 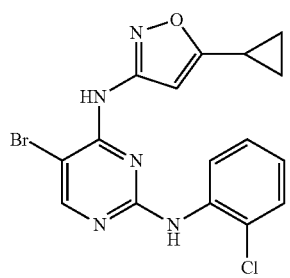 [SMILES: Clc1ccccc1Nc1ncc(Br)c(Nc2cc(C3CC3)on2)n1] |
| 287 | 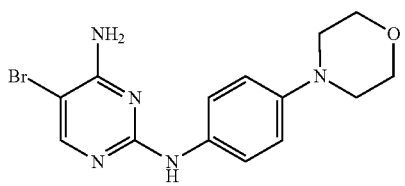 [SMILES: Nc1nc(Nc2ccc(N3CCOCC3)cc2)ncc1Br] |

| Entry | Structure |
|---|---|
| 288 | 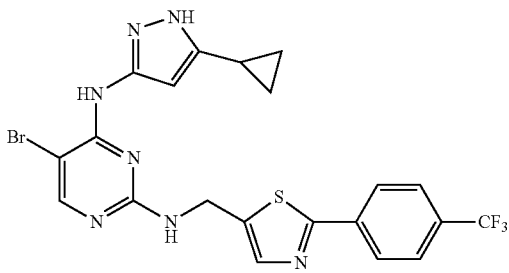 [SMILES: FC(F)(F)c1ccc(-c2ncc(CNc3ncc(Br)c(Nc4cc(C5CC5)[nH]n4)n3)s2)cc1] |
| 289 | 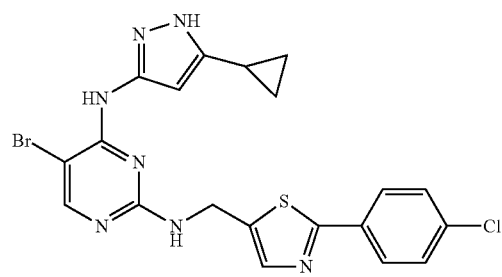 [SMILES: Clc1ccc(-c2ncc(CNc3ncc(Br)c(Nc4cc(C5CC5)[nH]n4)n3)s2)cc1] |
| 290 | 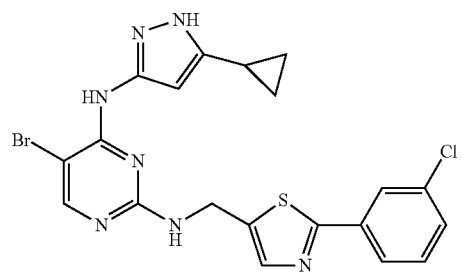 [SMILES: Clc1cccc(-c2ncc(CNc3ncc(Br)c(Nc4cc(C5CC5)[nH]n4)n3)s2)c1] |
| 291 | 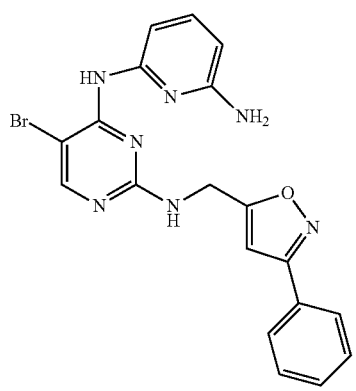 [SMILES: Nc1cccc(Nc2nc(NCc3cc(-c4ccccc4)no3)ncc2Br)n1] |
| 292 | 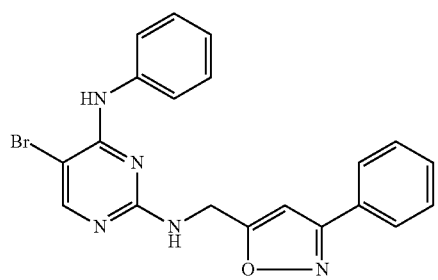 [SMILES: Brc1cnc(NCc2cc(-c3ccccc3)no2)nc1Nc1ccccc1] |

-continued
| Entry | Structure |
|---|---|
| 293 | 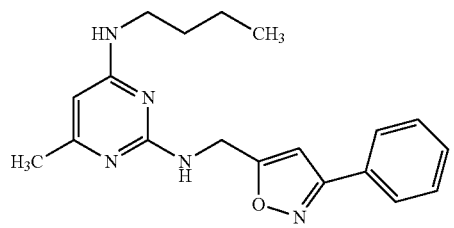 [SMILES: CCCCNc1cc(C)nc(NCc2cc(-c3ccccc3)no2)n1] |
| 294 | 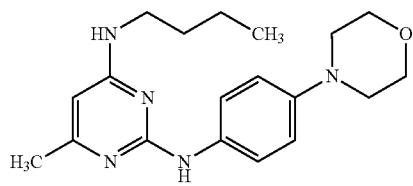 [SMILES: CCCCNc1cc(C)nc(Nc2ccc(N3CCOCC3)cc2)n1] |
| 295 | 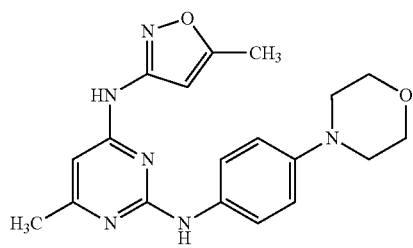 [SMILES: Cc1cc(Nc2cc(C)on2)nc(Nc2ccc(N3CCOCC3)cc2)n1] |
| 296 | 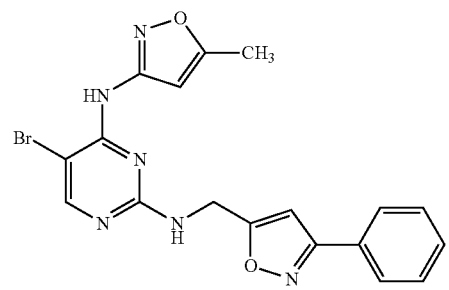 [SMILES: Cc1cc(Nc2nc(NCc3cc(-c4ccccc4)no3)ncc2Br)no1] |
| 297 | 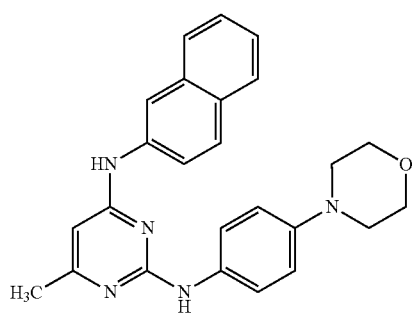 [SMILES: Cc1cc(Nc2ccc3ccccc3c2)nc(Nc2ccc(N3CCOCC3)cc2)n1] |

-continued

| Entry | Structure |
|---|---|
| 298 | (structure) |
| 299 | (structure) |
| 300 | (structure) |

| Entry | Structure |
|---|---|
| 301 | 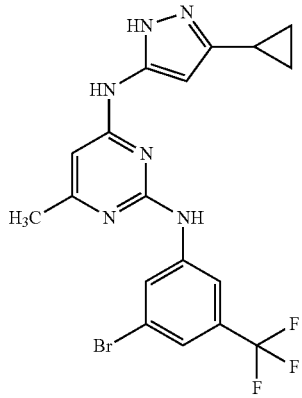 [SMILES: Cc1cc(Nc2cc(C3CC3)n[nH]2)nc(Nc2cc(Br)cc(C(F)(F)F)c2)n1] |
| 302 | 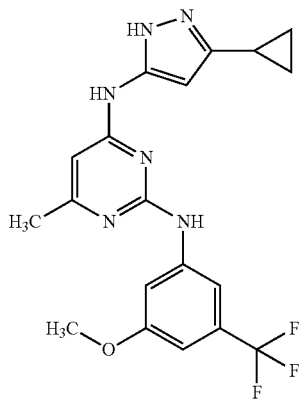 [SMILES: COc1cc(Nc2nc(C)cc(Nc3cc(C4CC4)n[nH]3)n2)cc(C(F)(F)F)c1] |
| 303 | 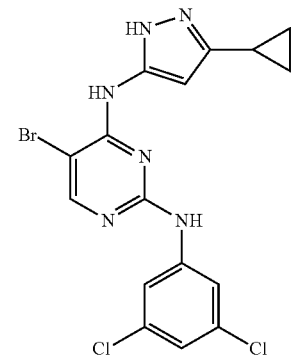 [SMILES: Clc1cc(Cl)cc(Nc2ncc(Br)c(Nc3cc(C4CC4)n[nH]3)n2)c1] |
| 304 | 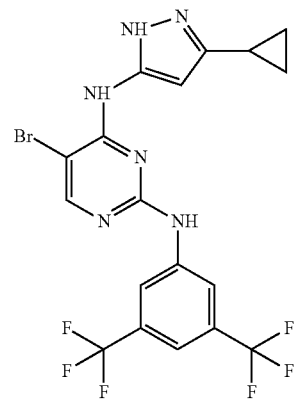 [SMILES: FC(F)(F)c1cc(Nc2ncc(Br)c(Nc3cc(C4CC4)n[nH]3)n2)cc(C(F)(F)F)c1] |

-continued
| Entry | Structure |
|---|---|
| 305 | 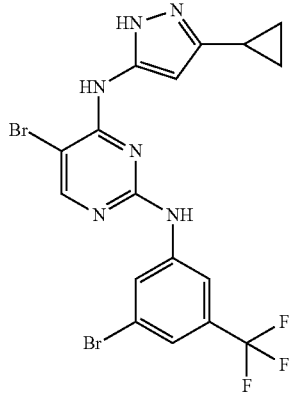 [SMILES: FC(F)(F)c1cc(Br)cc(Nc2ncc(Br)c(Nc3cc(C4CC4)n[nH]3)n2)c1] |
| 306 | 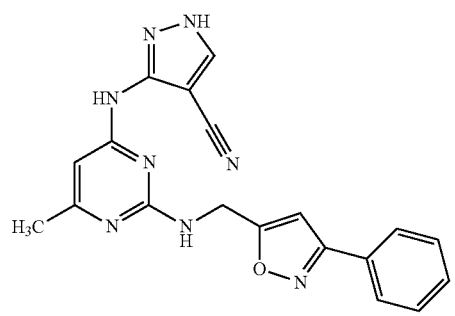 [SMILES: Cc1cc(Nc2n[nH]cc2C#N)nc(NCc2cc(-c3ccccc3)no2)n1] |
| 307 | 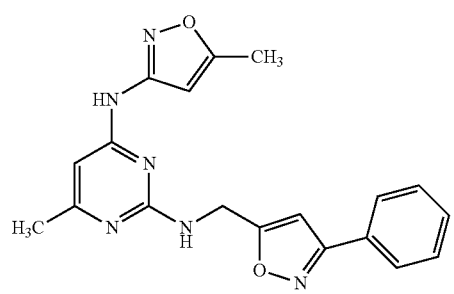 [SMILES: Cc1cc(Nc2cc(C)on2)nc(NCc2cc(-c3ccccc3)no2)n1] |
| 308 | 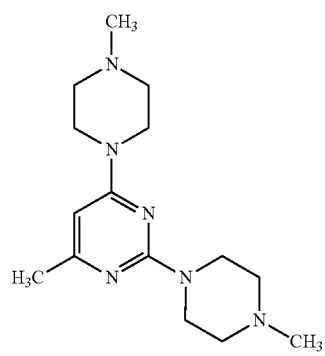 |
| 309 | 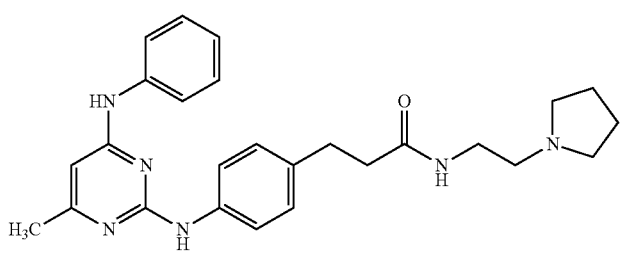 [SMILES: Cc1cc(Nc2ccccc2)nc(Nc2ccc(CCC(=O)NCCN3CCCC3)cc2)n1] |

-continued

| Entry | Structure |
|---|---|
| 310 | (structure) |
| 311 | (structure) |
| 312 | (structure) |
| 313 | (structure) |
| 314 | (structure) |

| Entry | Structure |
|---|---|
| 315 | 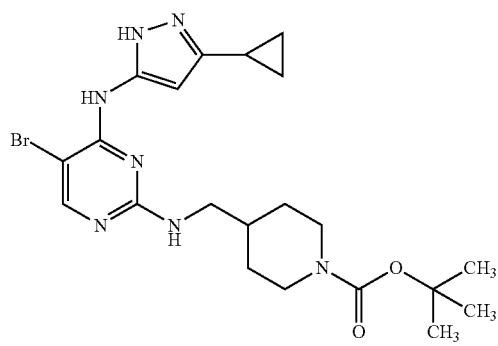 [SMILES: CC(C)(C)OC(=O)N1CCC(CNc2ncc(Br)c(Nc3cc(C4CC4)n[nH]3)n2)CC1] |
| 316 | 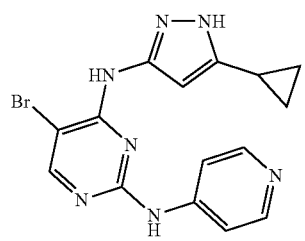 [SMILES: Brc1cnc(Nc2ccncc2)nc1Nc1cc(C2CC2)[nH]n1] |
| 317 | 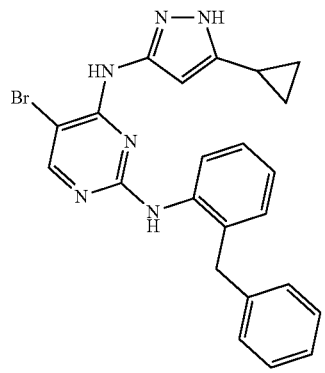 [SMILES: Brc1cnc(Nc2ccccc2Cc2ccccc2)nc1Nc1cc(C2CC2)[nH]n1] |
| 318 | 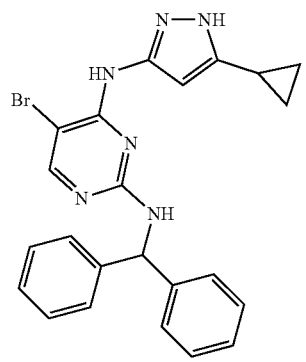 [SMILES: Brc1cnc(NC(c2ccccc2)c2ccccc2)nc1Nc1cc(C2CC2)[nH]n1] |
| 319 | 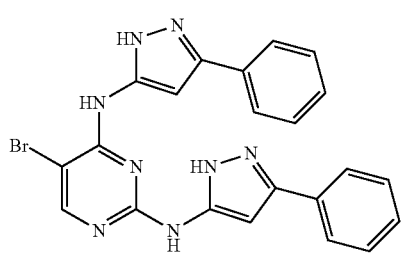 [SMILES: Brc1cnc(Nc2cc(-c3ccccc3)n[nH]2)nc1Nc1cc(-c2ccccc2)n[nH]1] |

| Entry | Structure |
|---|---|
| 320 | 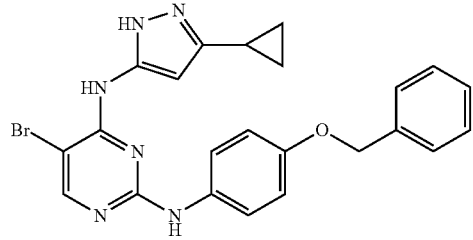 [SMILES: Brc1cnc(Nc2ccc(OCc3ccccc3)cc2)nc1Nc1cc(C2CC2)n[nH]1] |
| 321 | 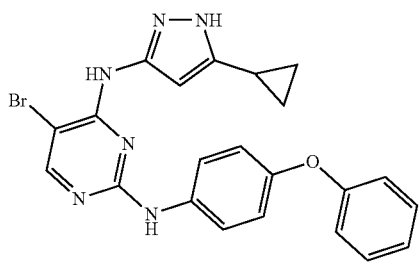 [SMILES: Brc1cnc(Nc2ccc(Oc3ccccc3)cc2)nc1Nc1cc(C2CC2)[nH]n1] |
| 322 | 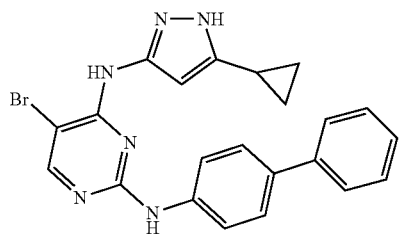 [SMILES: Brc1cnc(Nc2ccc(-c3ccccc3)cc2)nc1Nc1cc(C2CC2)[nH]n1] |
| 323 | 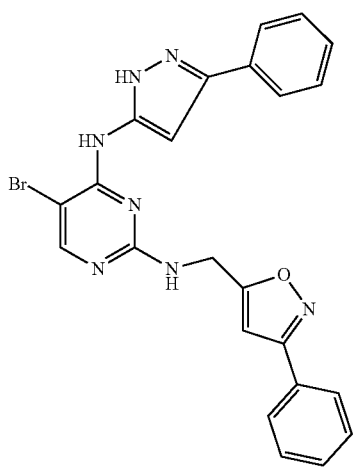 [SMILES: Brc1cnc(NCc2cc(-c3ccccc3)no2)nc1Nc1cc(-c2ccccc2)n[nH]1] |
| 324 | 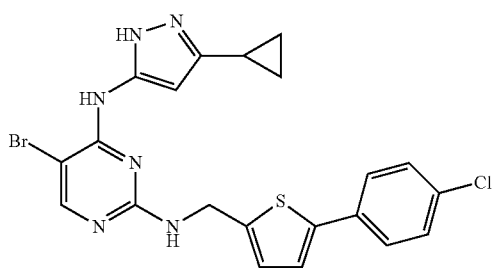 [SMILES: Clc1ccc(-c2ccc(CNc3ncc(Br)c(Nc4cc(C5CC5)n[nH]4)n3)s2)cc1] |

-continued

| Entry | Structure |
|---|---|
| 325 | 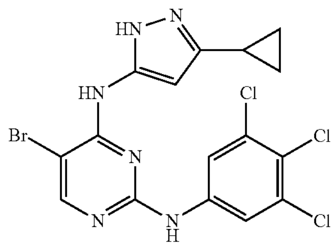 [SMILES: Clc1cc(Nc2ncc(Br)c(Nc3cc(C4CC4)n[nH]3)n2)cc(Cl)c1Cl] |
| 326 | 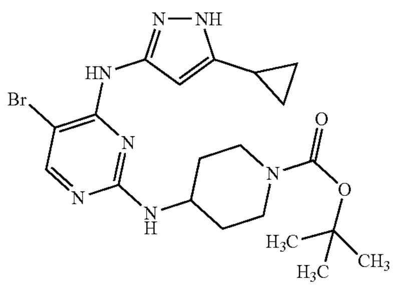 [SMILES: CC(C)(C)OC(=O)N1CCC(Nc2ncc(Br)c(Nc3cc(C4CC4)[nH]n3)n2)CC1] |
| 327 | 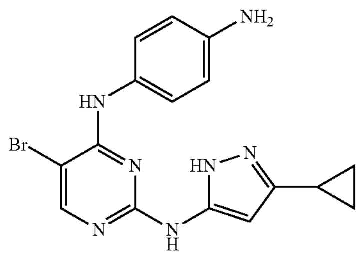 [SMILES: Nc1ccc(Nc2nc(Nc3cc(C4CC4)n[nH]3)ncc2Br)cc1] |
| 328 | 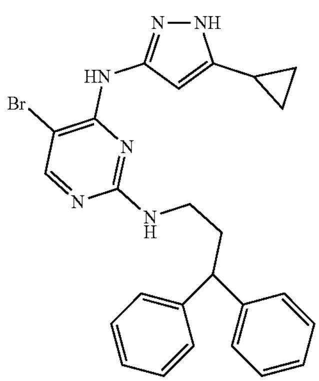 [SMILES: Brc1cnc(NCCC(c2ccccc2)c2ccccc2)nc1Nc1cc(C2CC2)[nH]n1] |
| 329 | 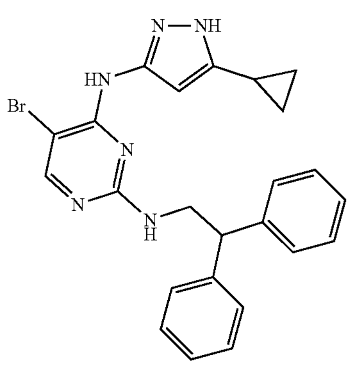 [SMILES: Brc1cnc(NCC(c2ccccc2)c2ccccc2)nc1Nc1cc(C2CC2)[nH]n1] |

-continued
| Entry | Structure |
|---|---|
| 330 | 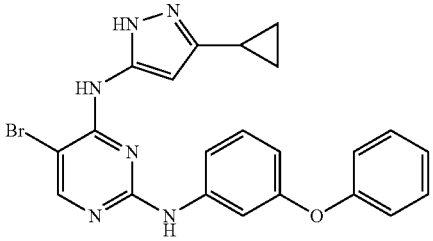 [SMILES: Brc1cnc(Nc2cccc(Oc3ccccc3)c2)nc1Nc1cc(C2CC2)n[nH]1] |
| 331 | 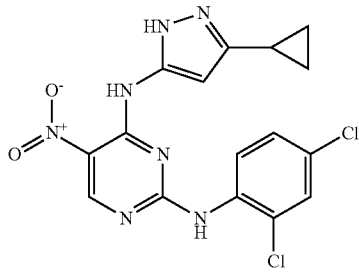 [SMILES: O=[N+]([O-])c1cnc(Nc2ccc(Cl)cc2Cl)nc1Nc1cc(C2CC2)n[nH]1] |
| 332 | 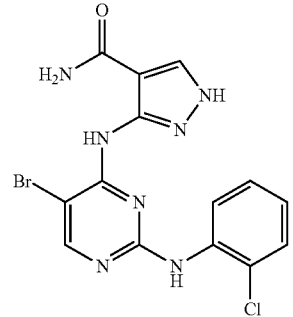 [SMILES: NC(=O)c1c[nH]nc1Nc1nc(Nc2ccccc2Cl)ncc1Br] |
| 333 | 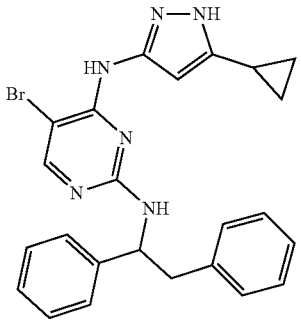 [SMILES: Brc1cnc(NC(Cc2ccccc2)c2ccccc2)nc1Nc1cc(C2CC2)[nH]n1] |
| 334 | 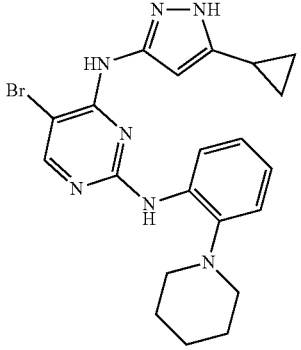 [SMILES: Brc1cnc(Nc2ccccc2N2CCCCC2)nc1Nc1cc(C2CC2)[nH]n1] |

| Entry | Structure |
|---|---|
| 335 | 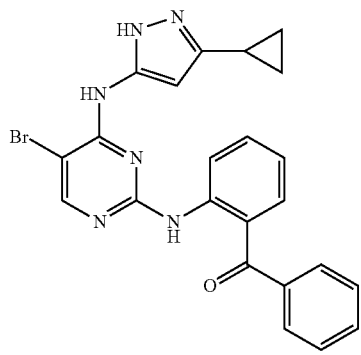 [SMILES: O=C(c1ccccc1)c1ccccc1Nc1ncc(Br)c(Nc2cc(C3CC3)n[nH]2)n1] |
| 336 | 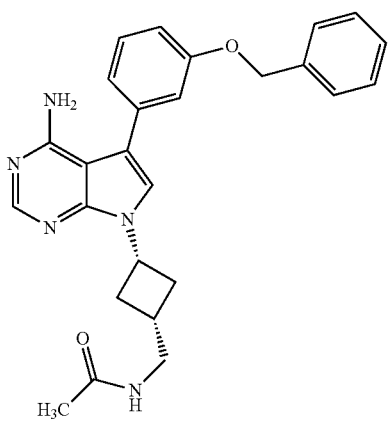 [SMILES: CC(=O)NC[C@H]1C[C@@H](n2cc(-c3cccc(OCc4ccccc4)c3)c3c(N)ncnc32)C1] |
| 337 | 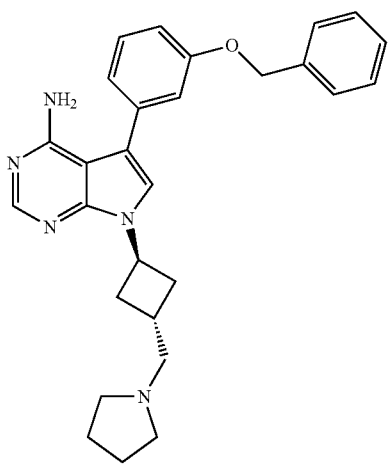 [SMILES: Nc1ncnc2c1c(-c1cccc(OCc3ccccc3)c1)cn2[C@H]1C[C@H](CN2CCCC2)C1] |

-continued
| Entry | Structure |
|---|---|
| 338 | 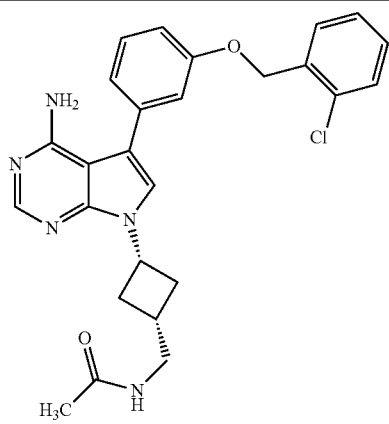 |
| 339 | 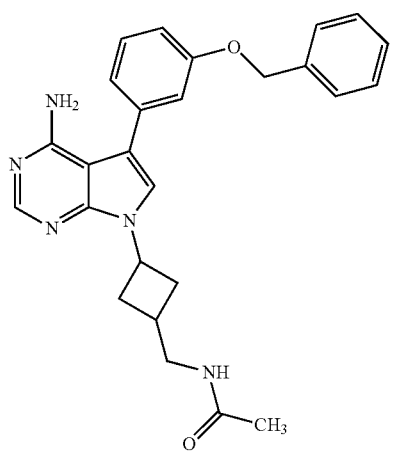 [SMILES: CC(=O)NCC1CC(n2cc(-c3cccc(OCc4ccccc4)c3)c3c(N)ncnc32)C1] |
| 340 | 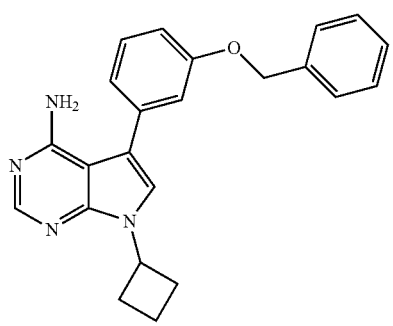 [SMILES: Nc1ncnc2c1c(-c1cccc(OCc3ccccc3)c1)cn2C1CCC1] |
| 341 | 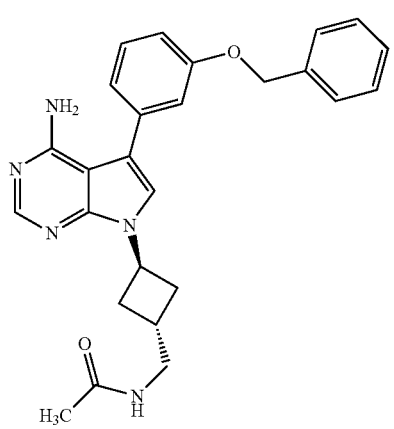 [SMILES: CC(=O)NC[C@H]1C[C@H](n2cc(-c3cccc(OCc4ccccc4)c3)c3c(N)ncnc32)C1] |

| Entry | Structure |
|---|---|
| 342 | 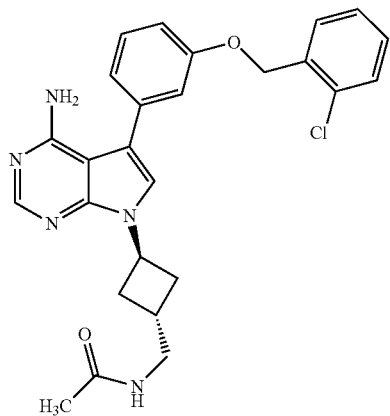 |
| 343 | 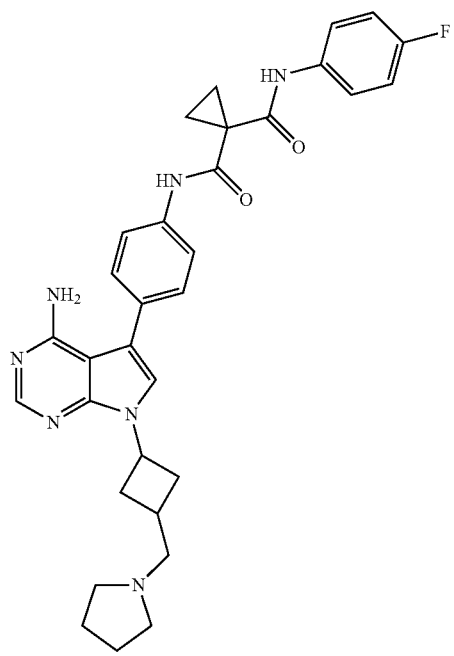 [SMILES: Nc1ncnc2c1c(-c1ccc(NC(=O)C3(C(=O)Nc4ccc(F)cc4)CC3)cc1)cn2C1CC(CN2CCCC2)C1] |
| 344 | 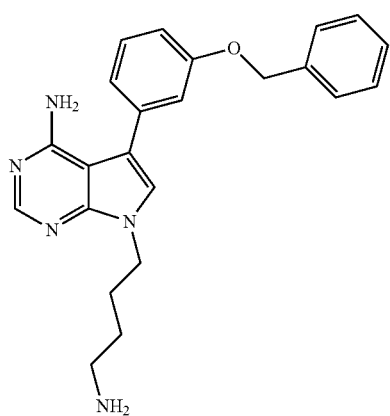 [SMILES: NCCCCn1cc(-c2cccc(OCc3ccccc3)c2)c2c(N)ncnc21] |

| Entry | Structure |
|---|---|
| 345 | 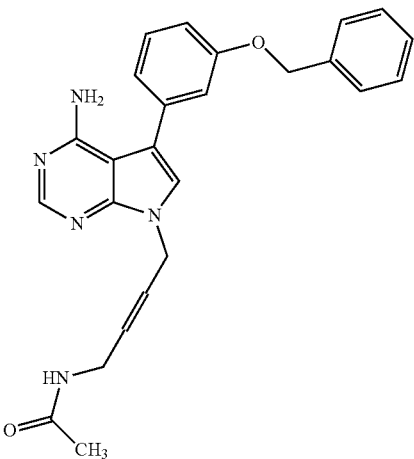 [SMILES: CC(=O)NCC=CCn1cc(-c2cccc(OCc3ccccc3)c2)c2c(N)ncnc21] |
| 346 | 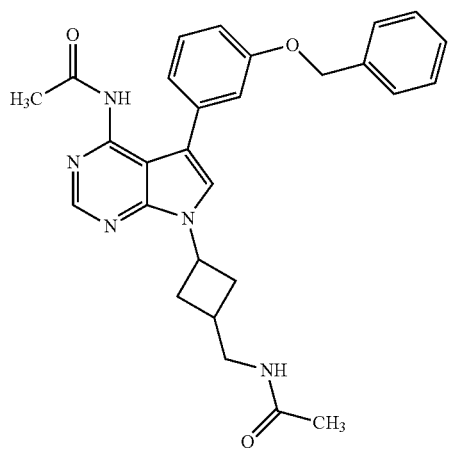 [SMILES: CC(=O)NCC1CC(n2cc(-c3cccc(OCc4ccccc4)c3)c3c(NC(C)=O)ncnc32)C1] |
| 347 | 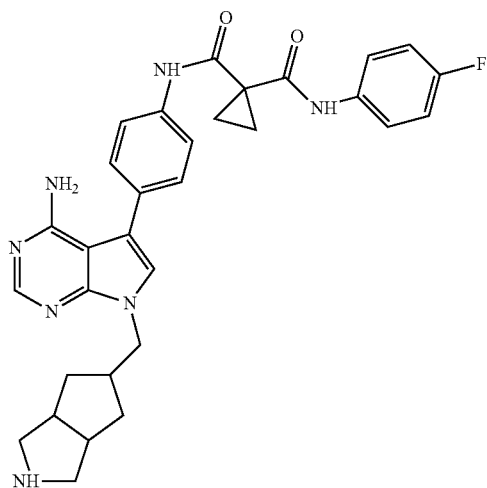 [SMILES: Nc1ncnc2c1c(-c1ccc(NC(=O)C3(C(=O)Nc4ccc(F)cc4)CC3)cc1)cn2CC1CC2CNCC2C1] |

| Entry | Structure |
|---|---|
| 348 | 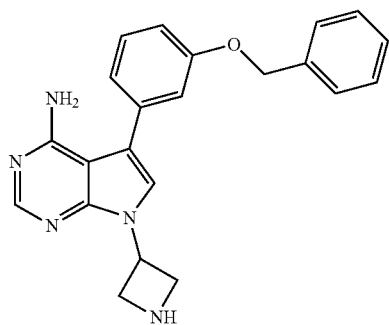 [SMILES: Nc1ncnc2c1c(-c1cccc(OCc3ccccc3)c1)cn2C1CNC1] |
| 349 | 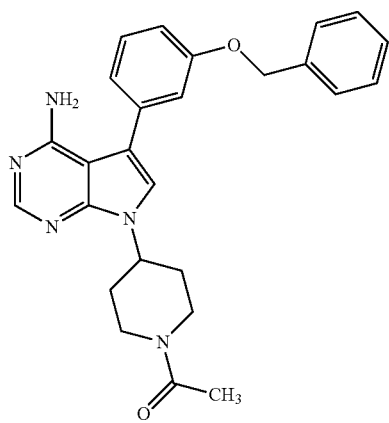 [SMILES: CC(=O)N1CCC(n2cc(-c3cccc(OCc4ccccc4)c3)c3c(N)ncnc32)CC1] |
| 350 | 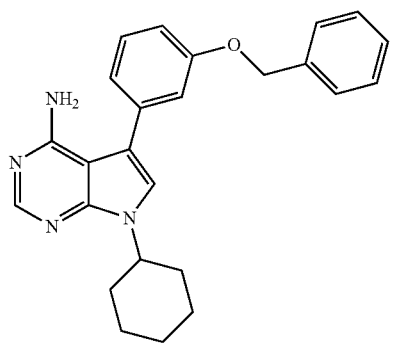 [SMILES: Nc1ncnc2c1c(-c1cccc(OCc3ccccc3)c1)cn2C1CCCCC1] |
| 351 | 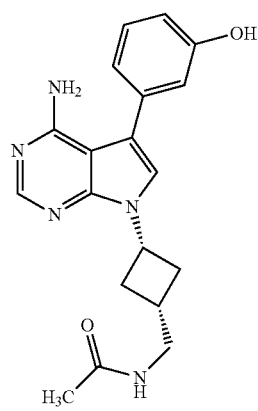 [SMILES: CC(=O)NC[C@H]1C[C@@H](n2cc(-c3cccc(O)c3)c3c(N)ncnc32)C1] |

-continued
| Entry | Structure |
|---|---|
| 352 | 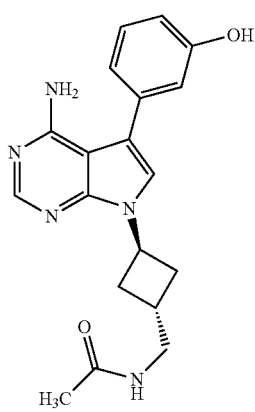 [SMILES: CC(=O)NC[C@H]1C[C@H](n2cc(-c3cccc(O)c3)c3c(N)ncnc32)C1] |
| 353 | 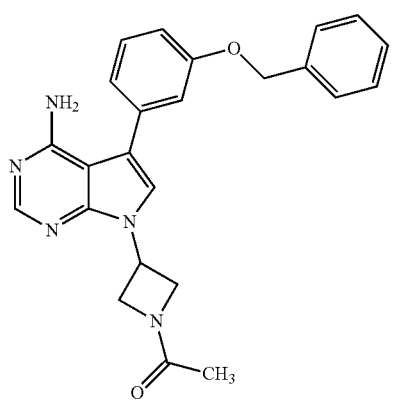 [SMILES: CC(=O)N1CC(n2cc(-c3cccc(OCc4ccccc4)c3)c3c(N)ncnc32)C1] |
| 354 | 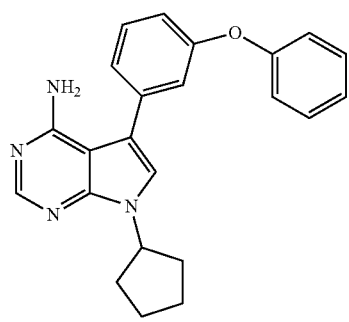 [SMILES: Nc1ncnc2c1c(-c1cccc(Oc3ccccc3)c1)cn2C1CCCC1] |
| 355 | 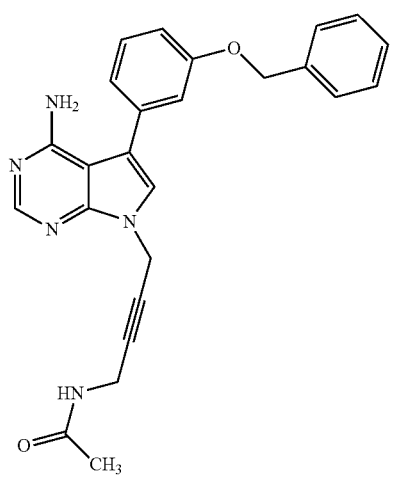 [SMILES: CC(=O)NCC#CCn1cc(-c2cccc(OCc3ccccc3)c2)c2c(N)ncnc21] |

-continued
| Entry | Structure |
|---|---|
| 356 | 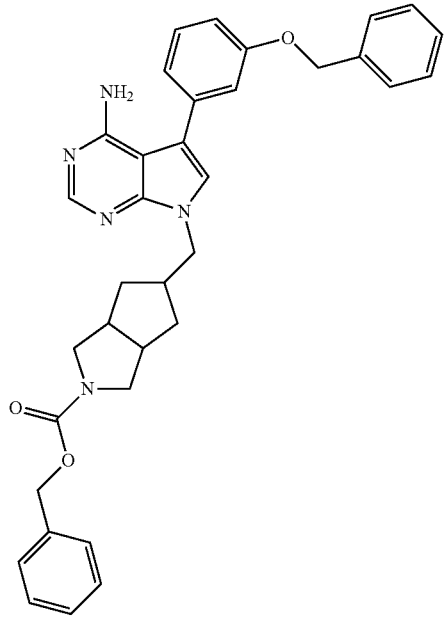 [SMILES: Nc1ncnc2c1c(-c1cccc(OCc3ccccc3)c1)cn2CC1CC2CN(C(=O)OCc3ccccc3)CC2C1] |
| 357 | 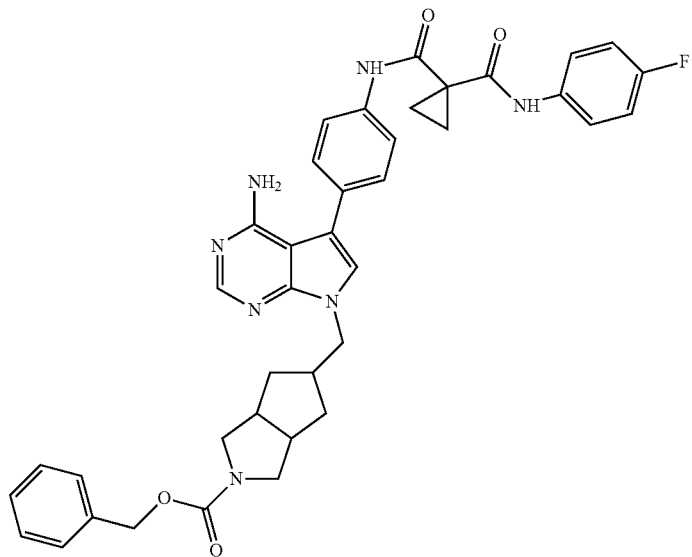 [SMILES: Nc1ncnc2c1c(-c1ccc(NC(=O)C3(C(=O)Nc4ccc(F)cc4)CC3)cc1)cn2CC1CC2CN(C(=O)OCc3ccccc3)CC2C1] |
| 358 | 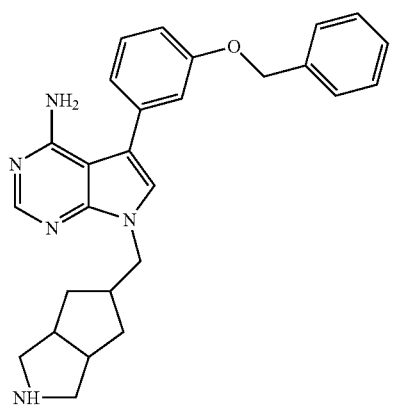 [SMILES: Nc1ncnc2c1c(-c1cccc(OCc3ccccc3)c1)cn2CC1CC2CNCC2C1] |

-continued
| Entry | Structure |
|---|---|
| 495 | 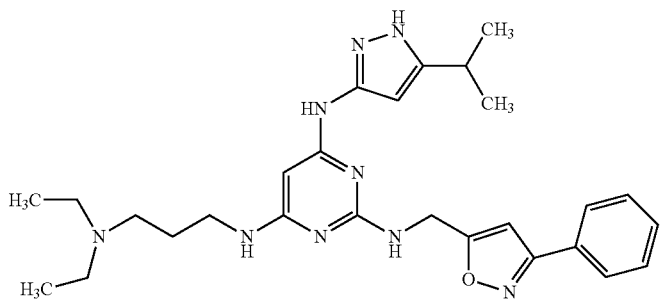 [SMILES: CCN(CC)CCCNc1cc(Nc2cc(C(C)C)[nH]n2)nc(NCc2cc(-c3ccccc3)no2)n1] |
| 496 | 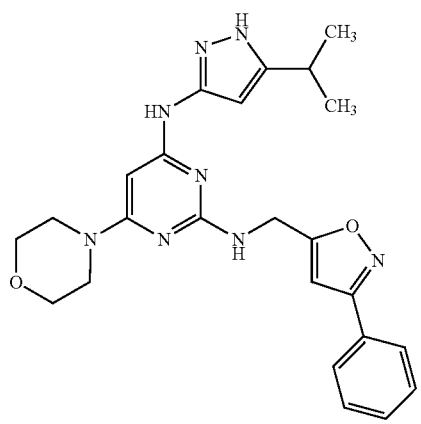 [SMILES: CC(C)c1cc(Nc2cc(N3CCOCC3)nc(NCc3cc(-c4ccccc4)no3)n2)n[nH]1] |
| 497 | 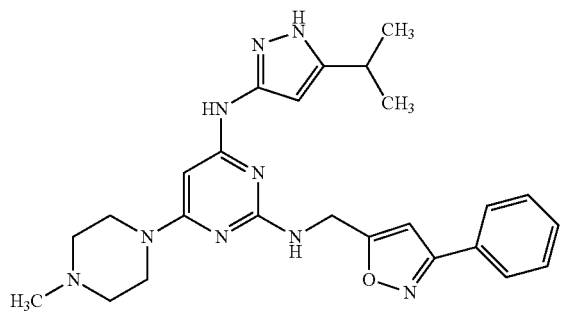 [SMILES: CC(C)c1cc(Nc2cc(N3CCN(C)CC3)nc(NCc3cc(-c4ccccc4)no3)n2)n[nH]1] |
| 498 | 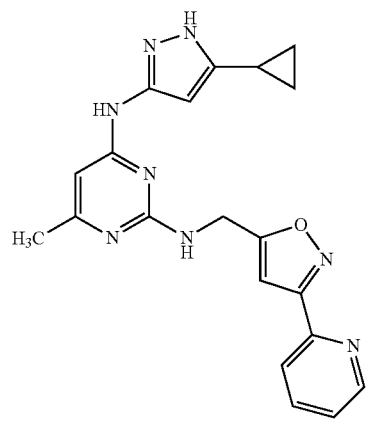 [SMILES: Cc1cc(Nc2cc(C3CC3)[nH]n2)nc(NCc2cc(-c3ccccn3)no2)n1] |

| Entry | Structure |
|---|---|
| 499 | 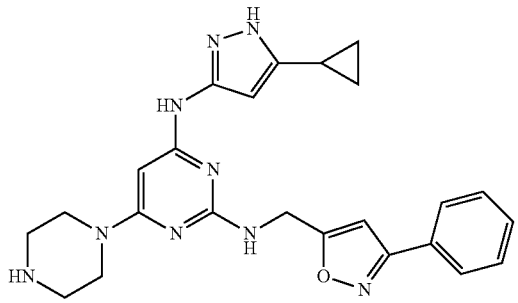 [SMILES: c1ccc(-c2cc(CNc3nc(Nc4cc(C5CC5)[nH]n4)cc(N4CCNCC4)n3)on2)cc1] |
| 500 | 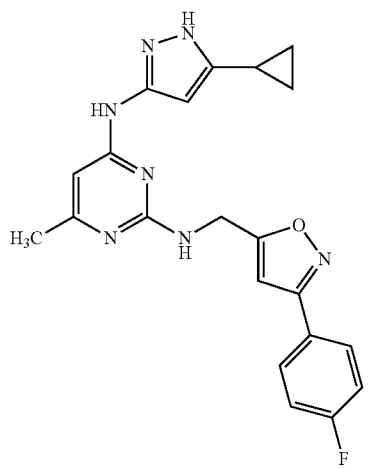 [SMILES: Cc1cc(Nc2cc(C3CC3)[nH]n2)nc(NCc2cc(-c3ccc(F)cc3)no2)n1] |
| 501 | 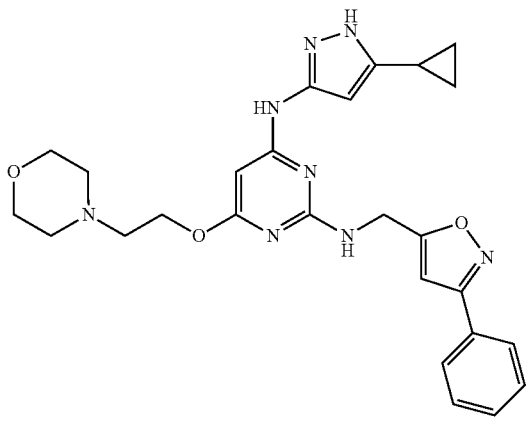 [SMILES: c1ccc(-c2cc(CNc3nc(Nc4cc(C5CC5)[nH]n4)cc(OCCN4CCOCC4)n3)on2)cc1] |
| 502 | Chiral 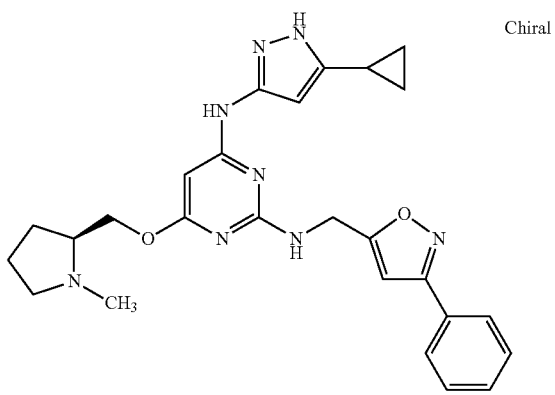 [SMILES: CN1CCC[C@H]1COc1cc(Nc2cc(C3CC3)[nH]n2)nc(NCc2cc(-c3ccccc3)no2)n1] |

-continued
| Entry | Structure |
|---|---|
| 503 | 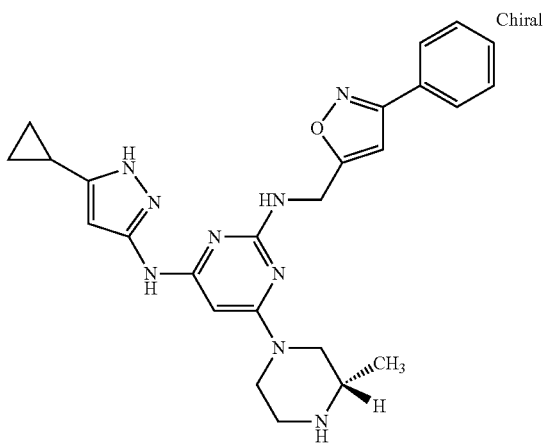 [SMILES: C[C@H]1CN(c2cc(Nc3cc(C4CC4)[nH]n3)nc(NCc3cc(-c4ccccc4)no3)n2)CCN1] Chiral |
| 504 | 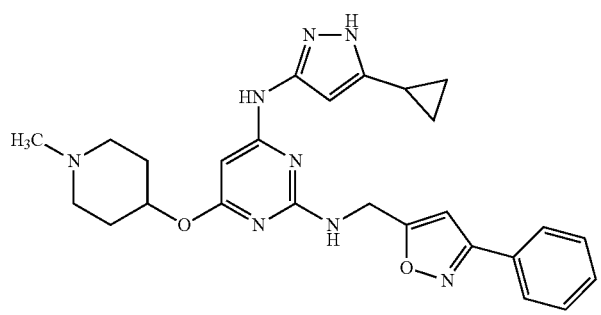 [SMILES: CN1CCC(Oc2cc(Nc3cc(C4CC4)[nH]n3)nc(NCc3cc(-c4ccccc4)no3)n2)CC1] |
| 505 | 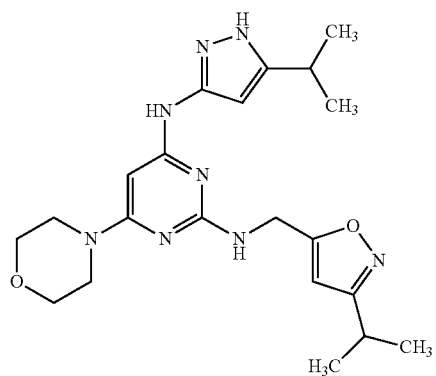 [SMILES: CC(C)c1cc(CNc2nc(Nc3cc(C(C)C)[nH]n3)cc(N3CCOCC3)n2)on1] |
| 506 | 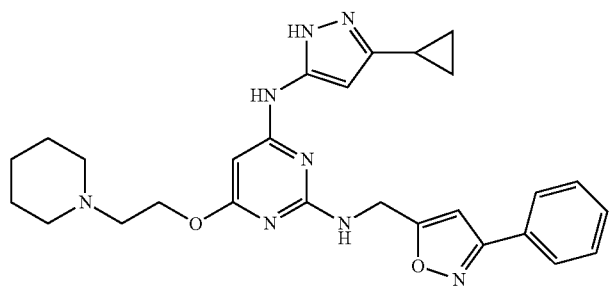 [SMILES: c1ccc(-c2cc(CNc3nc(Nc4cc(C5CC5)n[nH]4)cc(OCCN4CCCCC4)n3)on2)cc1] |

| Entry | Structure |
|---|---|
| 507 | 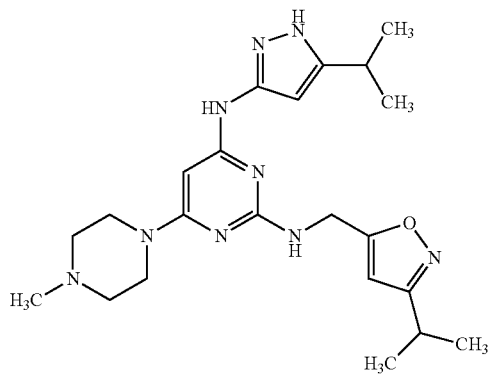 [SMILES: CC(C)c1cc(CNc2nc(Nc3cc(C(C)C)[nH]n3)cc(N3CCN(C)CC3)n2)on1] |
| 508 | 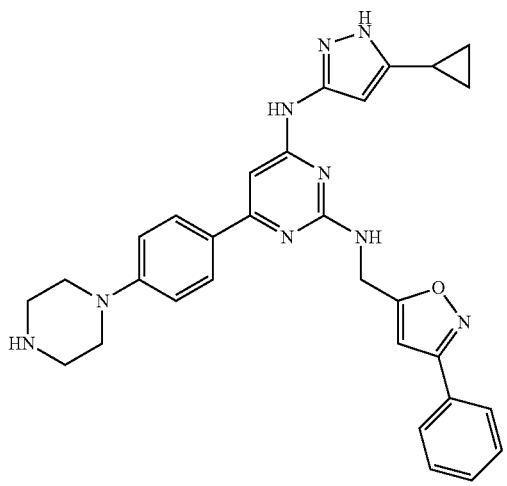 [SMILES: c1ccc(-c2cc(CNc3nc(Nc4cc(C5CC5)[nH]n4)cc(-c4ccc(N5CCNCC5)cc4)n3)on2)cc1] |
| 509 | 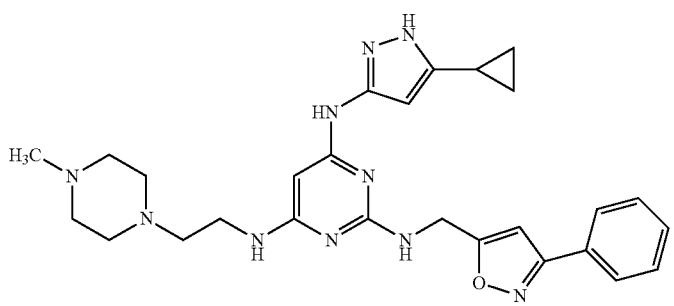 [SMILES: CN1CCN(CCNc2cc(Nc3cc(C4CC4)[nH]n3)nc(NCc3cc(-c4ccccc4)no3)n2)CC1] |
| 510 | 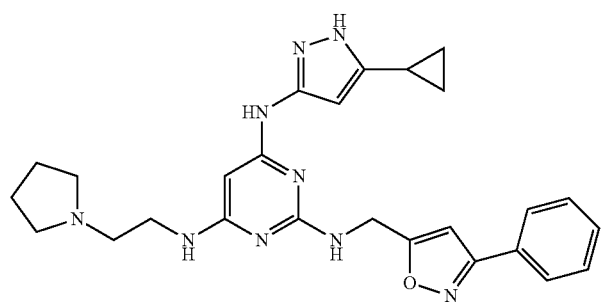 [SMILES: c1ccc(-c2cc(CNc3nc(NCCN4CCCC4)cc(Nc4cc(C5CC5)[nH]n4)n3)on2)cc1] |

-continued
| Entry | Structure |
|---|---|
| 511 | 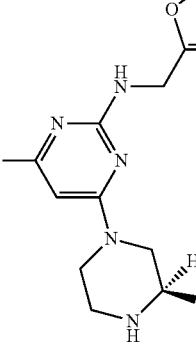 Chiral |
| 512 | 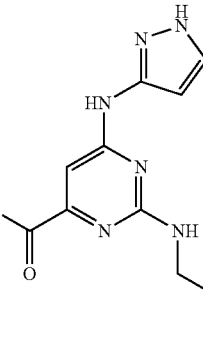 |
| 513 | 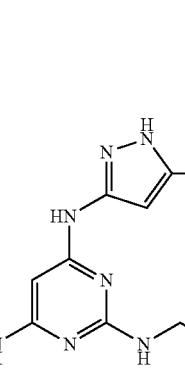 |
| 514 | 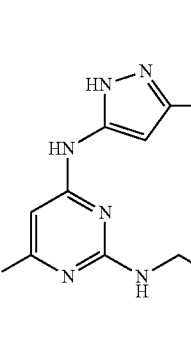 |

| Entry | Structure |
|---|---|
| 515 | 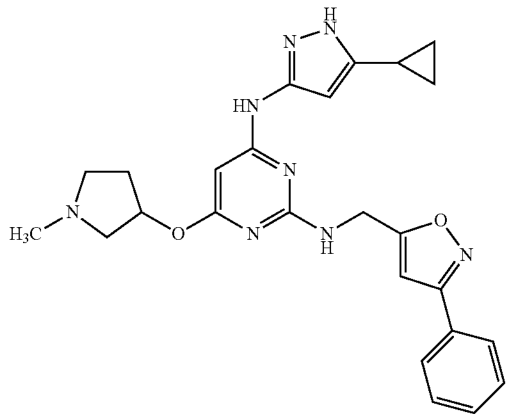 [SMILES: CN1CCC(Oc2cc(Nc3cc(C4CC4)[nH]n3)nc(NCc3cc(-c4ccccc4)no3)n2)C1] |
| 516 | 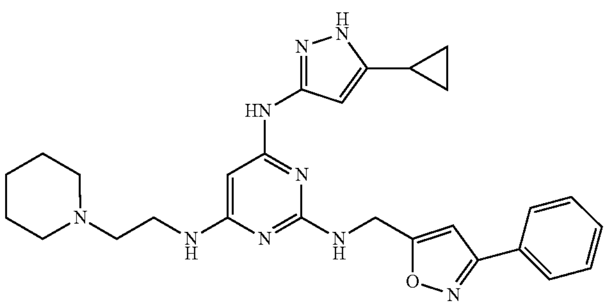 [SMILES: c1ccc(-c2cc(CNc3nc(NCCN4CCCCC4)cc(Nc4cc(C5CC5)[nH]n4)n3)on2)cc1] |
| 517 | 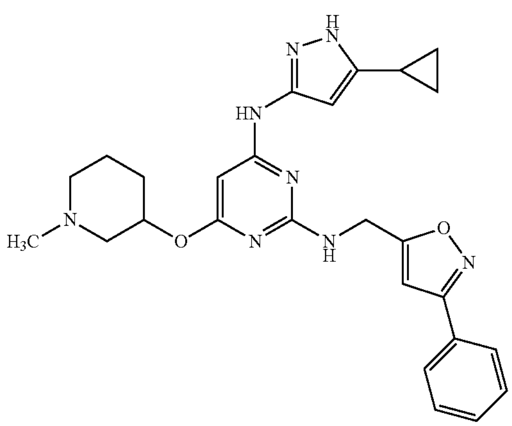 [SMILES: CN1CCCC(Oc2cc(Nc3cc(C4CC4)[nH]n3)nc(NCc3cc(-c4ccccc4)no3)n2)C1] |
| 518 | 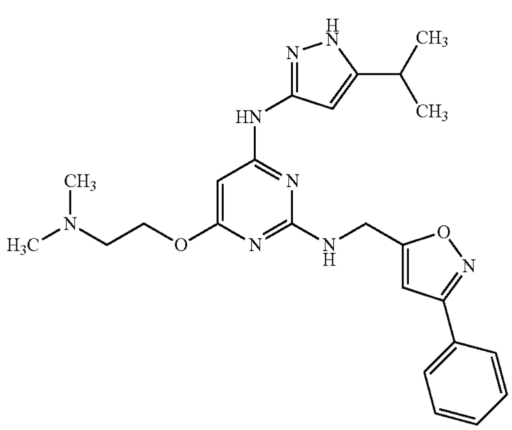 [SMILES: CC(C)c1cc(Nc2cc(OCCN(C)C)nc(NCc3cc(-c4ccccc4)no3)n2)n[nH]1] |

-continued

| Entry | Structure |
|---|---|
| 519 | 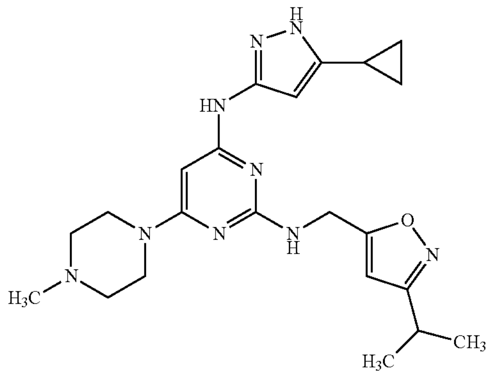 [SMILES: CC(C)c1cc(CNc2nc(Nc3cc(C4CC4)[nH]n3)cc(N3CCN(C)CC3)n2)on1] |
| 520 | 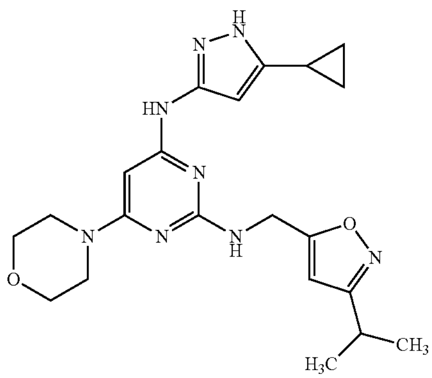 [SMILES: CC(C)c1cc(CNc2nc(Nc3cc(C4CC4)[nH]n3)cc(N3CCOCC3)n2)on1] |
| 521 | 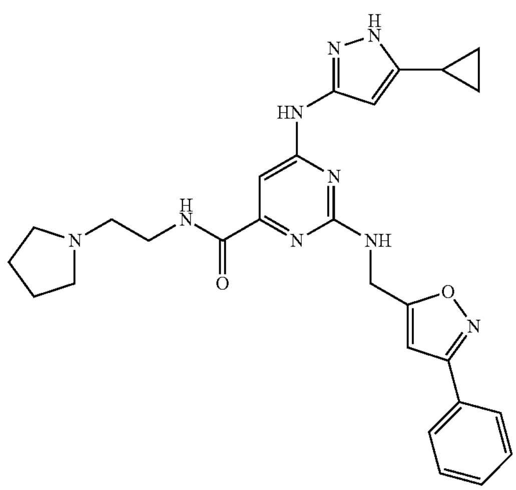 [SMILES: O=C(NCCN1CCCC1)c1cc(Nc2cc(C3CC3)[nH]n2)nc(NCc2cc(-c3ccccc3)no2)n1] |
| 522 | 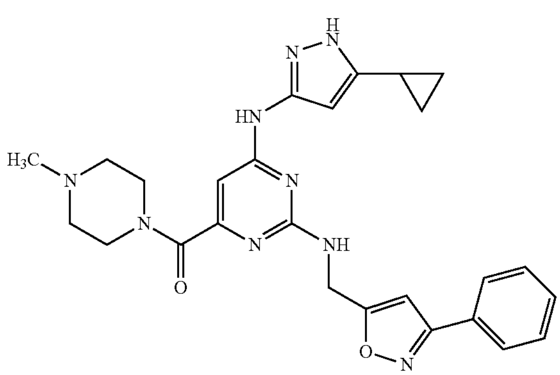 [SMILES: CN1CCN(C(=O)c2cc(Nc3cc(C4CC4)[nH]n3)nc(NCc3cc(-c4ccccc4)no3)n2)CC1] |

-continued
| Entry | Structure |
|---|---|
| 523 | 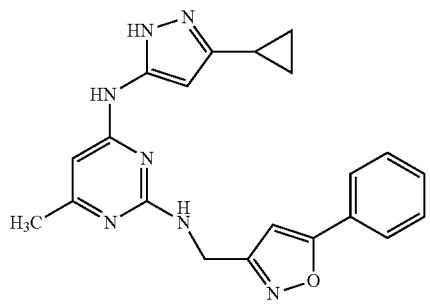 [SMILES: Cc1cc(Nc2cc(C3CC3)n[nH]2)nc(NCc2cc(-c3ccccc3)on2)n1] |
| 524 | 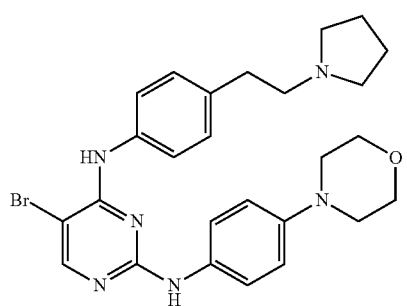 [SMILES: Brc1cnc(Nc2ccc(N3CCOCC3)cc2)nc1Nc1ccc(CCN2CCCC2)cc1] |
| 525 | 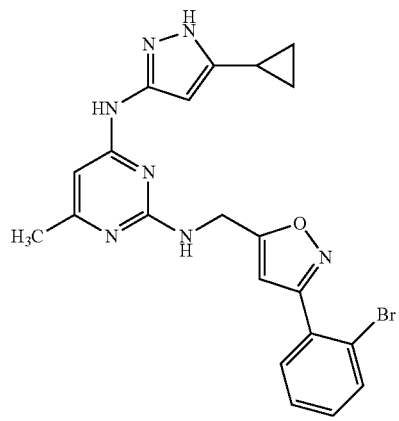 [SMILES: Cc1cc(Nc2cc(C3CC3)[nH]n2)nc(NCc2cc(-c3ccccc3Br)no2)n1] |
| 526 | 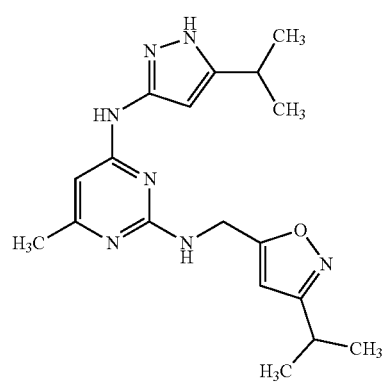 [SMILES: Cc1cc(Nc2cc(C(C)C)[nH]n2)nc(NCc2cc(C(C)C)no2)n1] |

-continued
| Entry | Structure |
|---|---|
| 527 | 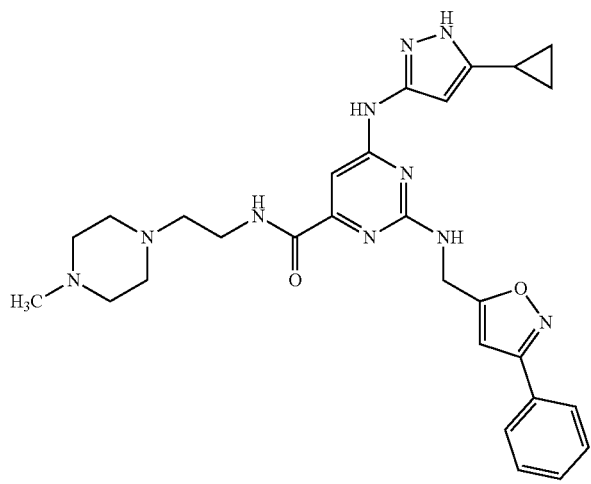 [SMILES: CN1CCN(CCNC(=O)c2cc(Nc3cc(C4CC4)[nH]n3)nc(NCc3cc(-c4ccccc4)no3)n2)CC1] |
| 528 | 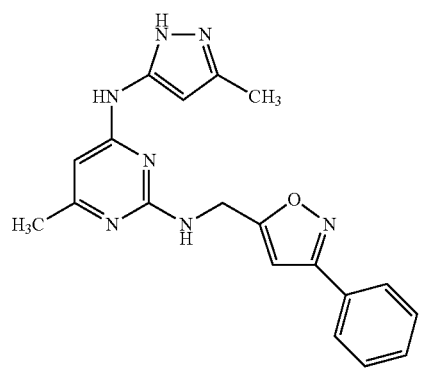 [SMILES: Cc1cc(Nc2cc(C)nc(NCc3cc(-c4ccccc4)no3)n2)[nH]n1] |
| 529 | 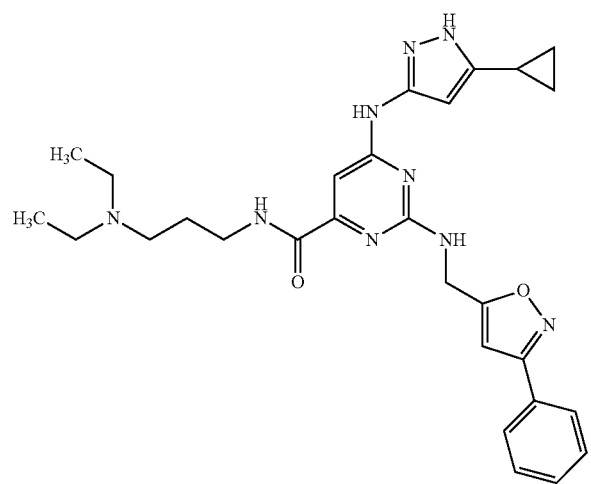 [SMILES: CCN(CC)CCCNC(=O)c1cc(Nc2cc(C3CC3)[nH]n2)nc(NCc2cc(-c3ccccc3)no2)n1] |

-continued
| Entry | Structure |
|---|---|
| 530 | 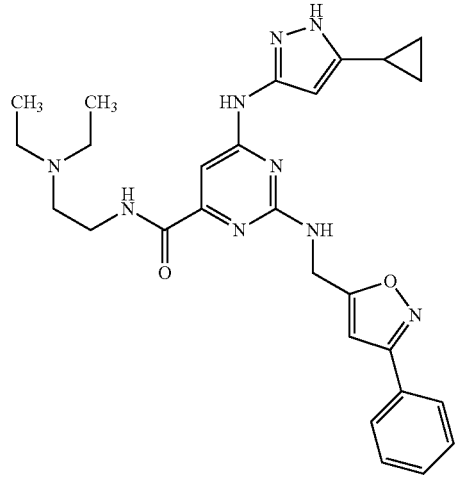 [SMILES: CCN(CC)CCNC(=O)c1cc(Nc2cc(C3CC3)[nH]n2)nc(NCc2cc(-c3ccccc3)no2)n1] |
| 531 | 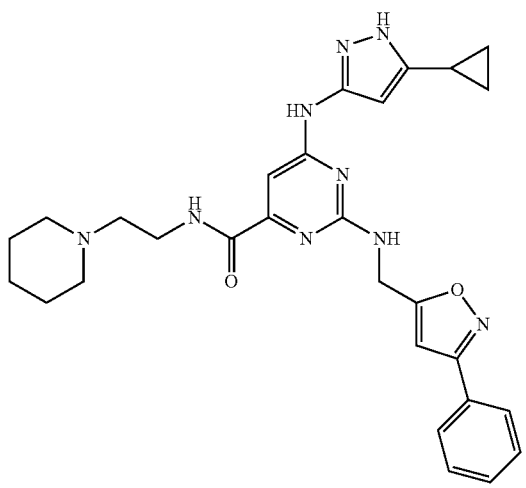 [SMILES: O=C(NCCN1CCCCC1)c1cc(Nc2cc(C3CC3)[nH]n2)nc(NCc2cc(-c3ccccc3)no2)n1] |
| 532 | 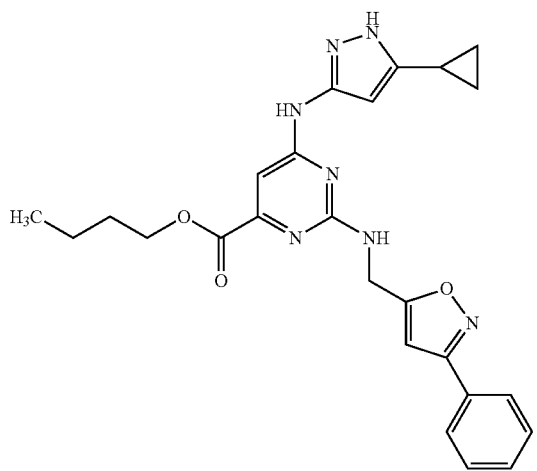 [SMILES: CCCCOC(=O)c1cc(Nc2cc(C3CC3)[nH]n2)nc(NCc2cc(-c3ccccc3)no2)n1] |

| Entry | Structure |
|---|---|
| 533 | 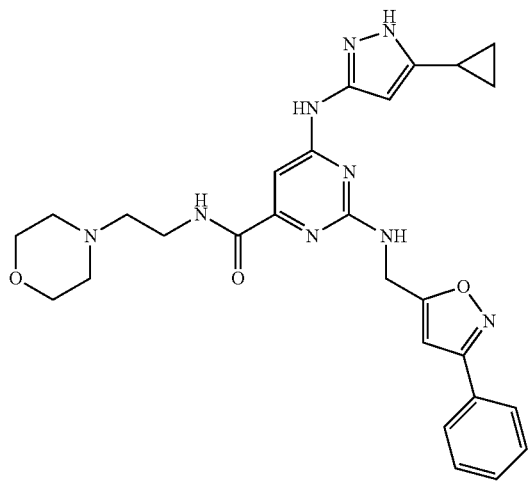 [SMILES: O=C(NCCN1CCOCC1)c1cc(Nc2cc(C3CC3)[nH]n2)nc(NCc2cc(-c3ccccc3)no2)n1] |
| 534 | 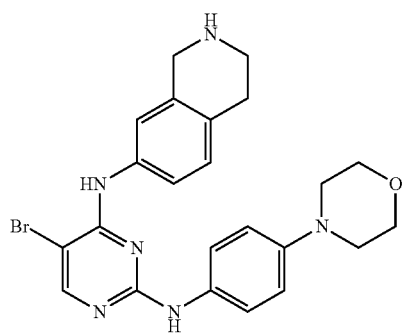 [SMILES: Brc1cnc(Nc2ccc(N3CCOCC3)cc2)nc1Nc1ccc2c(c1)CNCC2] |
| 535 | 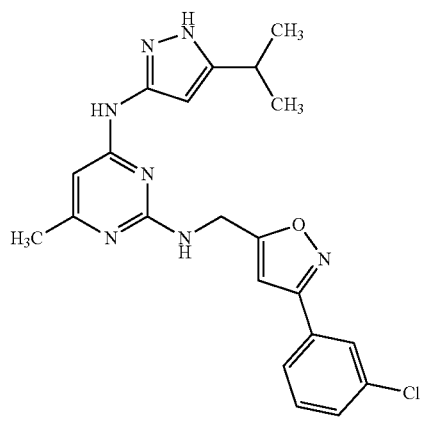 [SMILES: Cc1cc(Nc2cc(C(C)C)[nH]n2)nc(NCc2cc(-c3cccc(Cl)c3)no2)n1] |
| 536 | 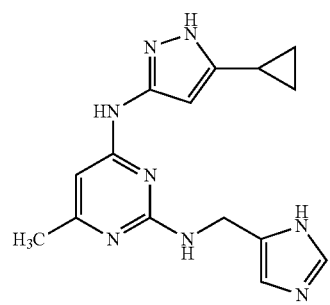 [SMILES: Cc1cc(Nc2cc(C3CC3)[nH]n2)nc(NCc2cnc[nH]2)n1] |

711
-continued
| Entry | Structure |
|---|---|
| 537 | 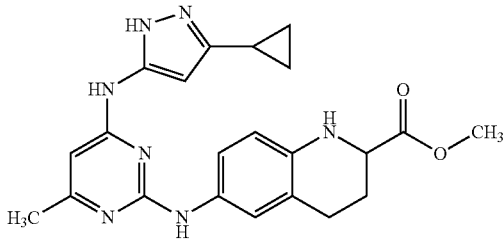 |
| 538 | 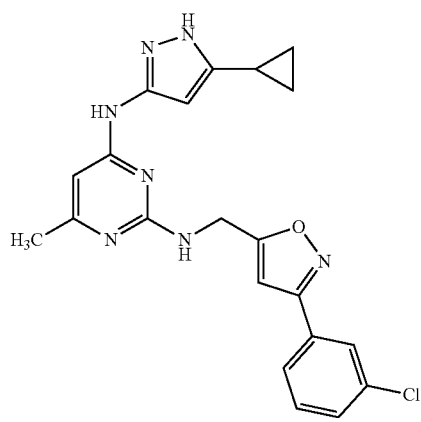 [SMILES: Cc1cc(Nc2cc(C3CC3)[nH]n2)nc(NCc2cc(-c3cccc(Cl)c3)no2)n1] |
| 539 | 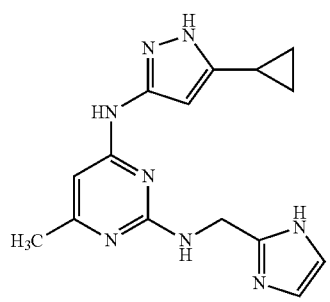 [SMILES: Cc1cc(Nc2cc(C3CC3)[nH]n2)nc(NCc2ncc[nH]2)n1] |
| 540 | 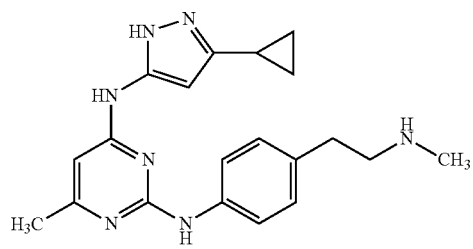 |
| 541 | 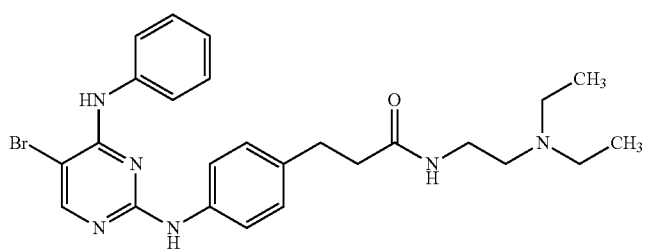 [SMILES: CCN(CC)CCNC(=O)CCc1ccc(Nc2ncc(Br)c(Nc3ccccc3)n2)cc1] |

713
-continued
| Entry | Structure |
|---|---|
| 542 | 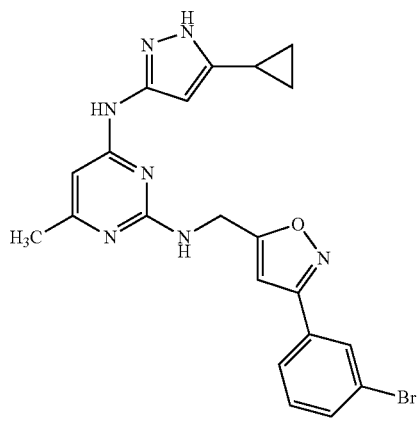 [SMILES: Cc1cc(Nc2cc(C3CC3)[nH]n2)nc(NCc2cc(-c3cccc(Br)c3)no2)n1] |
| 543 | 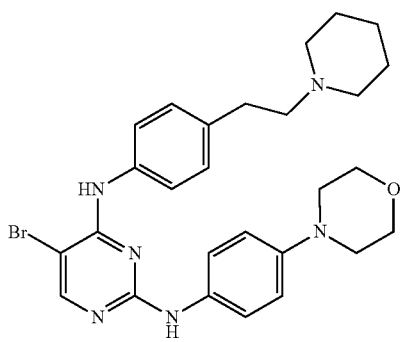 [SMILES: Brc1cnc(Nc2ccc(N3CCOCC3)cc2)nc1Nc1ccc(CCN2CCCCC2)cc1] |
| 544 | 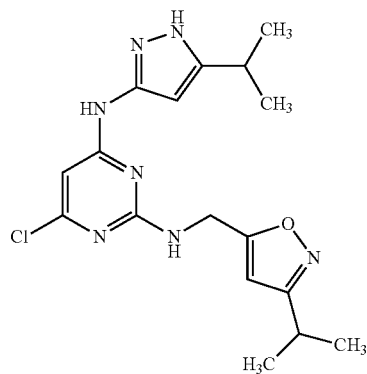 [SMILES: CC(C)c1cc(CNc2nc(Cl)cc(Nc3cc(C(C)C)[nH]n3)n2)on1] |
| 545 | 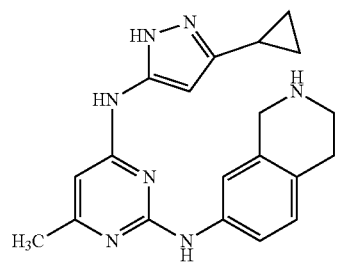 [SMILES: Cc1cc(Nc2cc(C3CC3)n[nH]2)nc(Nc2ccc3c(c2)CNCC3)n1] |
714

| Entry | Structure |
|---|---|
| 546 | 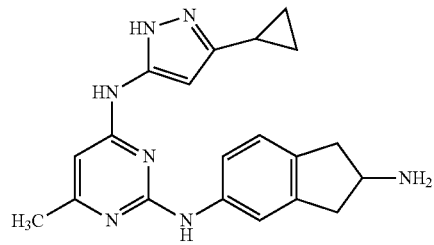 [SMILES: Cc1cc(Nc2cc(C3CC3)n[nH]2)nc(Nc2ccc3c(c2)CC(N)C3)n1] |
| 547 | 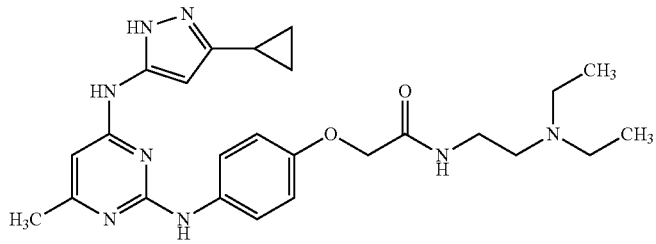 [SMILES: CCN(CC)CCNC(=O)COc1ccc(Nc2nc(C)cc(Nc3cc(C4CC4)n[nH]3)n2)cc1] |
| 548 | 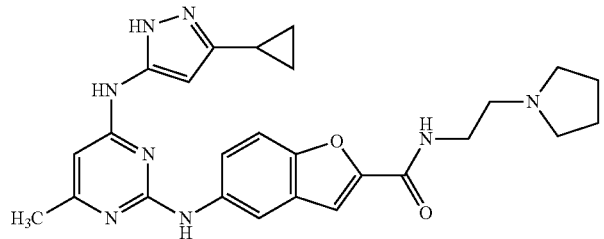 [SMILES: Cc1cc(Nc2cc(C3CC3)n[nH]2)nc(Nc2ccc3oc(C(=O)NCCN4CCCC4)cc3c2)n1] |
| 549 | 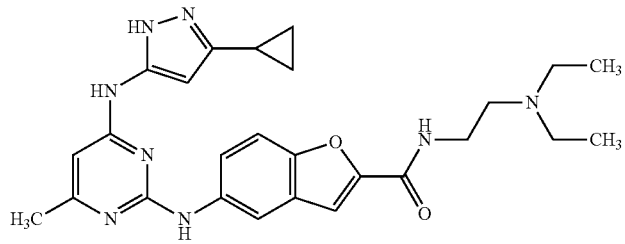 [SMILES: CCN(CC)CCNC(=O)c1cc2cc(Nc3nc(C)cc(Nc4cc(C5CC5)n[nH]4)n3)ccc2o1] |
| 550 | 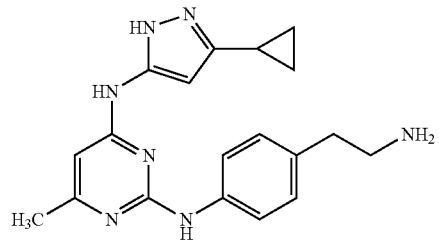 [SMILES: Cc1cc(Nc2cc(C3CC3)n[nH]2)nc(Nc2ccc(CCN)cc2)n1] |
| 551 | 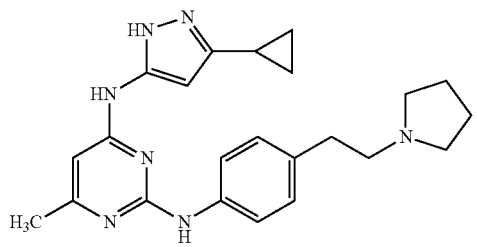 [SMILES: Cc1cc(Nc2cc(C3CC3)n[nH]2)nc(Nc2ccc(CCN3CCCC3)cc2)n1] |

| Entry | Structure |
|---|---|
| 552 | 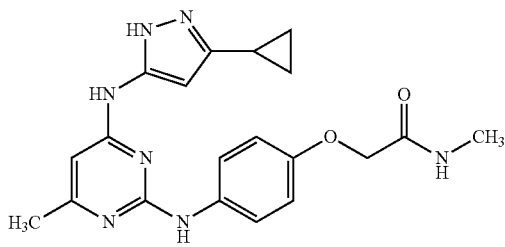 |
| 553 | 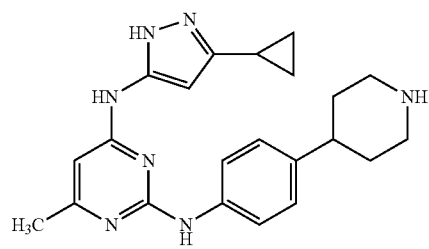 [SMILES: Cc1cc(Nc2cc(C3CC3)n[nH]2)nc(Nc2ccc(C3CCNCC3)cc2)n1] |
| 554 | 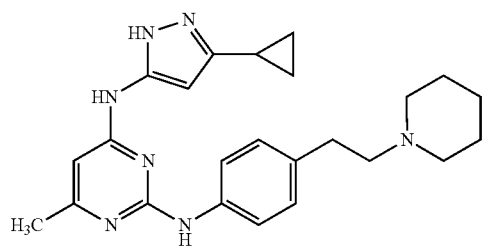 [SMILES: Cc1cc(Nc2cc(C3CC3)n[nH]2)nc(Nc2ccc(CCN3CCCCC3)cc2)n1] |
| 555 | 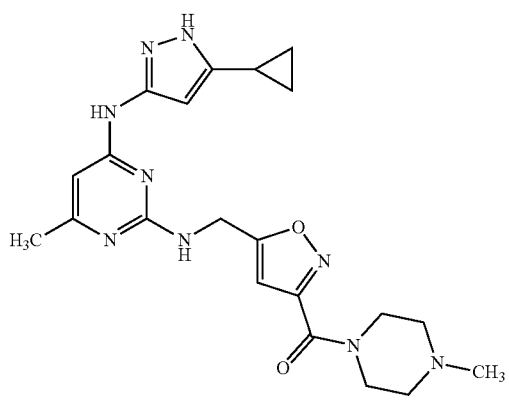 |
| 556 | 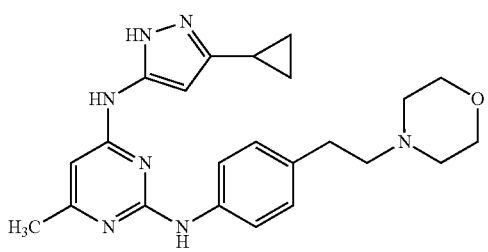 [SMILES: Cc1cc(Nc2cc(C3CC3)n[nH]2)nc(Nc2ccc(CCN3CCOCC3)cc2)n1] |

-continued
| Entry | Structure |
|---|---|
| 557 | 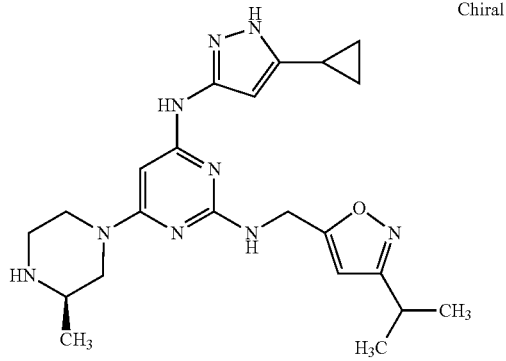 [SMILES: CC(C)c1cc(CNc2nc(Nc3cc(C4CC4)[nH]n3)cc(N3CCN[C@H](C)C3)n2)on1] Chiral |
| 558 | 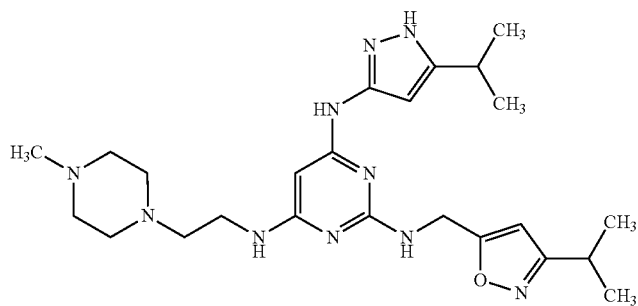 [SMILES: CC(C)c1cc(CNc2nc(NCCN3CCN(C)CC3)cc(Nc3cc(C(C)C)[nH]n3)n2)on1] |
| 559 | 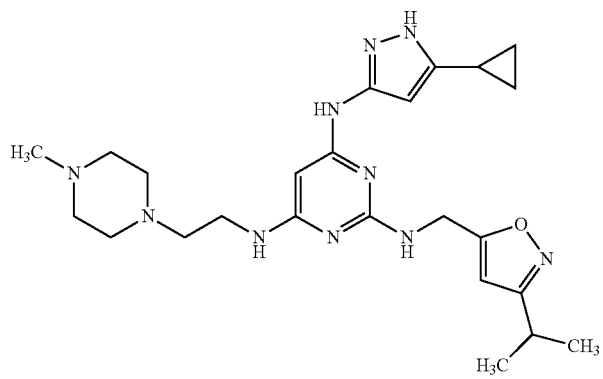 [SMILES: CC(C)c1cc(CNc2nc(NCCN3CCN(C)CC3)cc(Nc3cc(C4CC4)[nH]n3)n2)on1] |
| 560 | 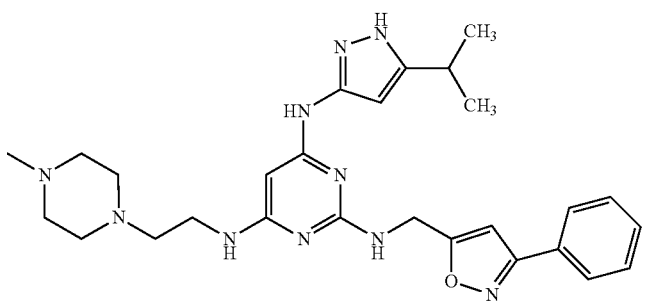 [SMILES: CC(C)c1cc(Nc2cc(NCCN3CCN(C)CC3)nc(NCc3cc(-c4ccccc4)no3)n2)n[nH]1] |

| Entry | Structure |
|---|---|
| 561 | 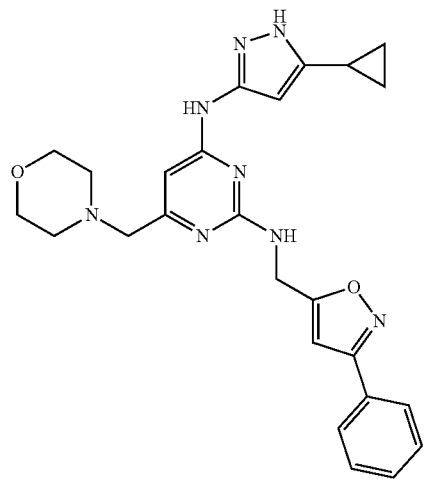 [SMILES: c1ccc(-c2cc(CNc3nc(CN4CCOCC4)cc(Nc4cc(C5CC5)[nH]n4)n3)on2)cc1] |
| 562 | 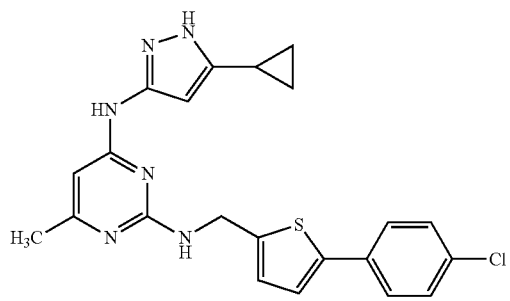 [SMILES: Cc1cc(Nc2cc(C3CC3)[nH]n2)nc(NCc2ccc(-c3ccc(Cl)cc3)s2)n1] |
| 563 | 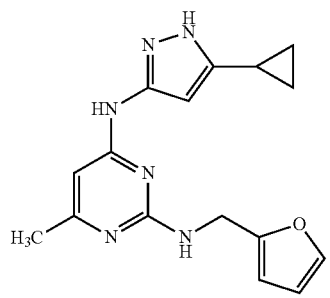 [SMILES: Cc1cc(Nc2cc(C3CC3)[nH]n2)nc(NCc2ccco2)n1] |
| 564 | 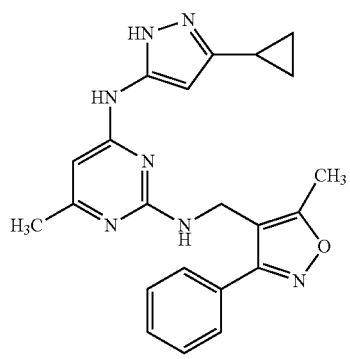 [SMILES: Cc1cc(Nc2cc(C3CC3)n[nH]2)nc(NCc2c(-c3ccccc3)noc2C)n1] |

-continued

| Entry | Structure |
|---|---|
| 565 | 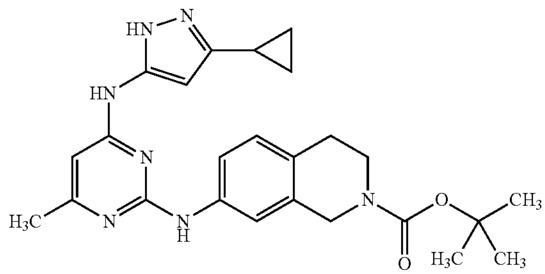 [SMILES: Cc1cc(Nc2cc(C3CC3)n[nH]2)nc(Nc2ccc3c(c2)CN(C(=O)OC(C)(C)C)CC3)n1] |
| 566 | 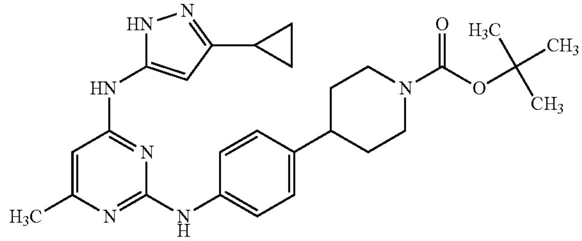 [SMILES: Cc1cc(Nc2cc(C3CC3)n[nH]2)nc(Nc2ccc(C3CCN(C(=O)OC(C)(C)C)CC3)cc2)n1] |
| 567 | 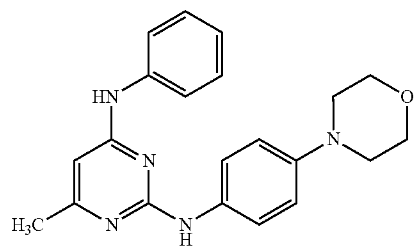 [SMILES: Cc1cc(Nc2ccccc2)nc(Nc2ccc(N3CCOCC3)cc2)n1] |
| 568 | 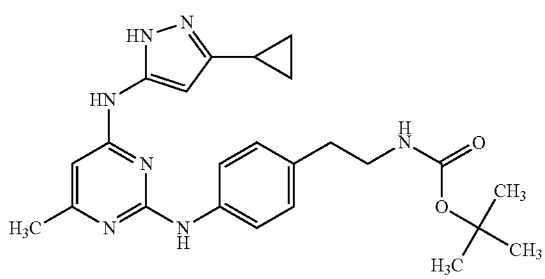 [SMILES: Cc1cc(Nc2cc(C3CC3)n[nH]2)nc(Nc2ccc(CCNC(=O)OC(C)(C)C)cc2)n1] |
| 569 | 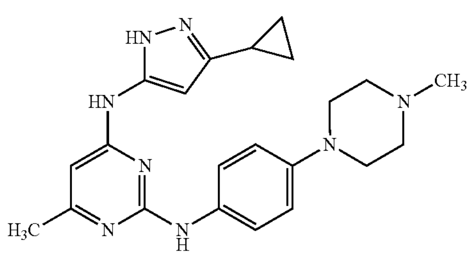 |
| 570 | 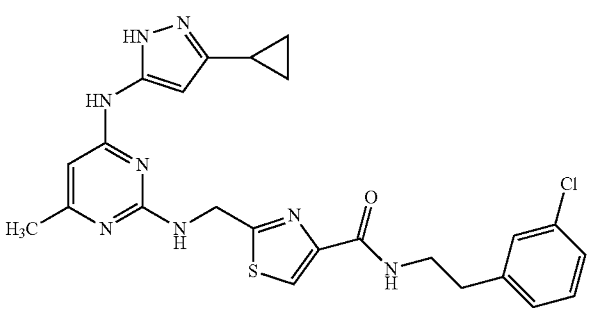 [SMILES: Cc1cc(Nc2cc(C3CC3)n[nH]2)nc(NCc2nc(C(=O)NCCc3cccc(Cl)c3)cs2)n1] |

-continued

| Entry | Structure |
|---|---|
| 571 | 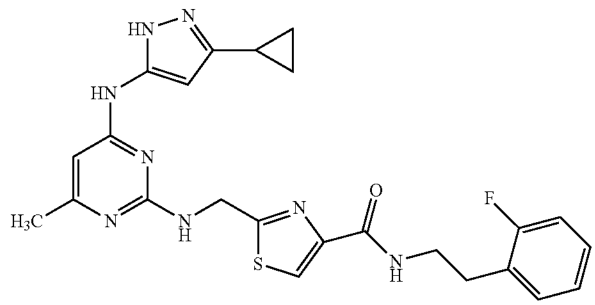 [SMILES: Cc1cc(Nc2cc(C3CC3)n[nH]2)nc(NCc2nc(C(=O)NCCc3ccccc3F)cs2)n1] |
| 572 | 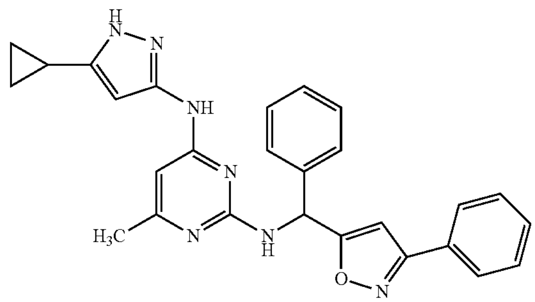 [SMILES: Cc1cc(Nc2cc(C3CC3)[nH]n2)nc(NC(c2ccccc2)c2cc(-c3ccccc3)no2)n1] |

The Compounds in Table 5b can be prepared as pharmaceutically acceptable salts, solvates, hydrates, and/or isomers thereof. All such salt, solvate, hydrate, and isomer combinations of the Compounds in Table 5b can be used to practice the invention.

| Entry | Structure | Name |
|---|---|---|
| 573 | 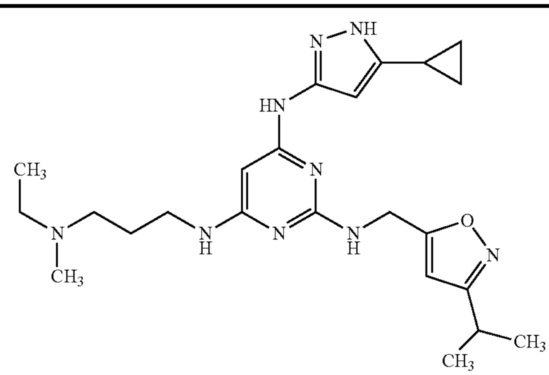 | $N^4$-(5-cyclopropyl-1H-pyrazol-3-yl)-$N^6$-[3-(diethylamino)propyl]-$N^2$-{[3-(1-methylethyl)isoxazol-5-yl]methyl}pyrimidine-2,4,6-triamine |
| 574 | 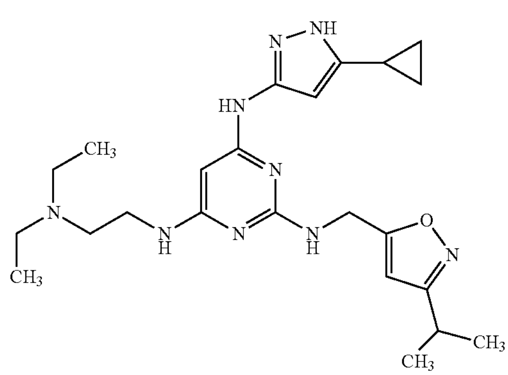 [SMILES: CCN(CC)CCNc1cc(Nc2cc(C3CC3)[nH]n2)nc(NCc2cc(C(C)C)no2)n1] | $N^4$-(5-cyclopropyl-1H-pyrazol-3-yl)-$N^6$-[2-(diethylamino)ethyl]-$N^2$-{[3-(1-methylethyl)isoxazol-5-yl]methyl}pyrimidine-2,4,6-triamine |

-continued

| Entry | Structure | | Name |
|---|---|---|---|
| 575 | 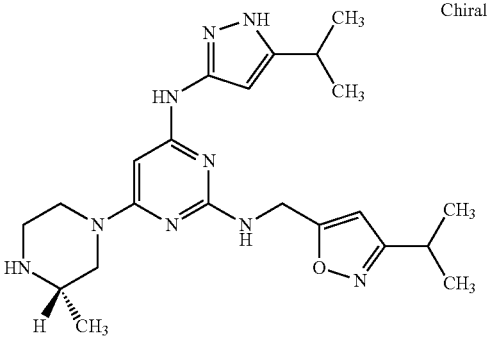 [SMILES: CC(C)c1cc(CNc2nc(Nc3cc(C(C)C)[nH]n3)cc(N3CCN[C@@H](C)C3)n2)on1] | Chiral | $N^2$-{[3-(1-methylethyl)isoxazol-5-yl]methyl}-$N^4$-[5-(1-methylethyl)-1H-pyrazol-3-yl]-6-[(3S)-3-methylpiperazin-1-yl]pyrimidine-2,4-diamine |
| 576 | 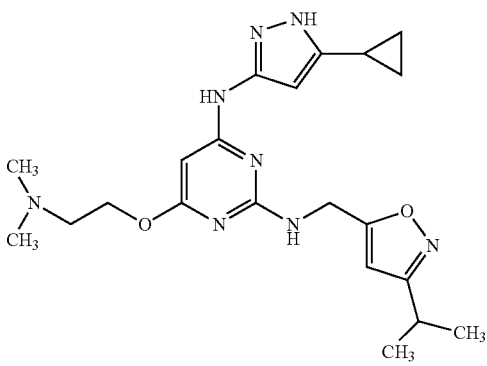 [SMILES: CC(C)c1cc(CNc2nc(Nc3cc(C4CC4)[nH]n3)cc(OCCN(C)C)n2)on1] | | $N^4$-(5-cyclopropyl-1H-pyrazol-3-yl)-6-{[2-(dimethylamino)ethyl]oxy}-$N^2$-{[3-(1-methylethyl)isoxazol-5-yl]methyl}pyrimidine-2,4-diamine |
| 577 | 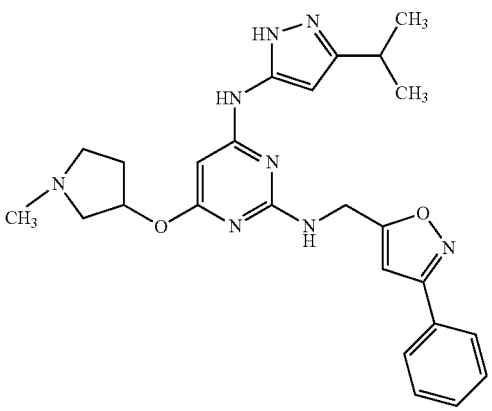 [SMILES: CC(C)c1cc(Nc2cc(OC3CCN(C)C3)nc(NCc3cc(-c4ccccc4)no3)n2)[nH]n1] | | $N^4$-[3-(1-methylethyl)-1H-pyrazol-5-yl]-6-[(1-methylpyrrolidin-3-yl)oxy]-$N^2$-[(3-phenylisoxazol-5-yl)methyl]pyrimidine-2,4-diamine |
| 578 | 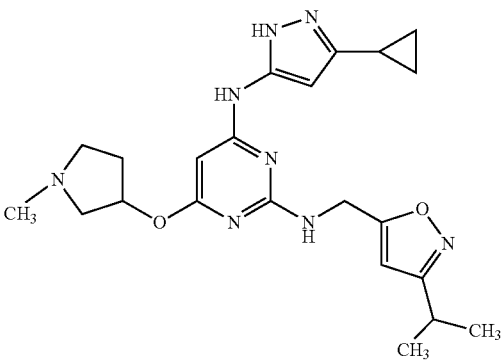 [SMILES: CC(C)c1cc(CNc2nc(Nc3cc(C4CC4)n[nH]3)cc(OC3CCN(C)C3)n2)on1] | | $N^4$-(3-cyclopropyl-1H-pyrazol-5-yl)-$N^2$-{[3-(1-methylethyl)isoxazol-5-yl]methyl}-6-[(1-methylpyrrolidin-3-yl)oxy]pyrimidine-2,4-diamine |

| Entry | Structure | Name |
|---|---|---|
| 579 | 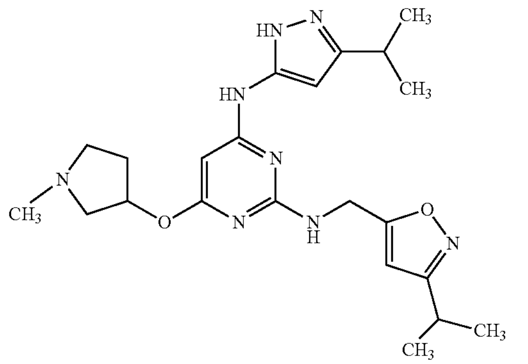 [SMILES: CC(C)c1cc(Nc2cc(OC3CCN(C)C3)nc(NCc3cc(C(C)C)no3)n2)[nH]n1] | $N^2$-{[3-(1-methylethyl)isoxazol-5-yl]methyl}-$N^4$-[3-(1-methylethyl)-1H-pyrazol-5-yl]-6-[(1-methylpyrrolidin-3-yl)oxy]pyrimidine-2,4-diamine |
| 580 | 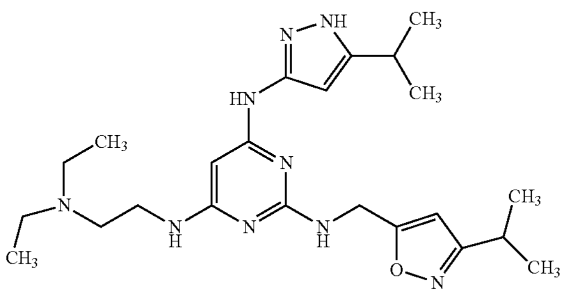 [SMILES: CCN(CC)CCNc1cc(Nc2cc(C(C)C)[nH]n2)nc(NCc2cc(C(C)C)no2)n1] | $N^4$-[2-(diethylamino)ethyl]-$N^2$-{[3-(1-methylethyl)isoxazol-5-yl]methyl}-$N^6$-[5-(1-methylethyl)-1H-pyrazol-3-yl]pyrimidine-2,4,6-triamine |
| 581 | 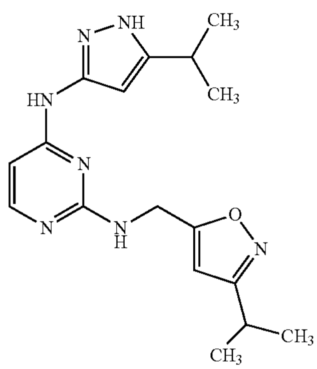 [SMILES: CC(C)c1cc(CNc2nccc(Nc3cc(C(C)C)[nH]n3)n2)on1] | $N^2$-{[3-(1-methylethyl)isoxazol-5-yl]methyl}-$N^4$-[5-(1-methylethyl)-1H-pyrazol-3-yl]pyrimidine-2,4-diamine |
| 582 | 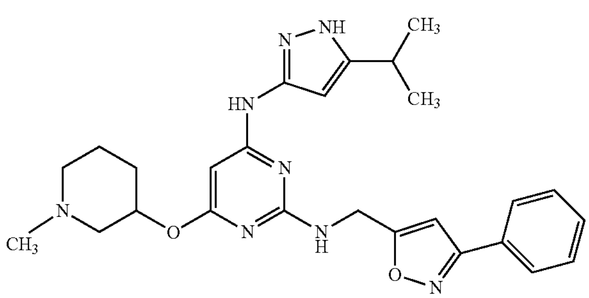 [SMILES: CC(C)c1cc(Nc2cc(OC3CCCN(C)C3)nc(NCc3cc(-c4ccccc4)no3)n2)n[nH]1] | $N^4$-[5-(1-methylethyl)-1H-pyrazol-3-yl]-6-[(1-methylpiperidin-3-yl)oxy]-$N^2$-[(3-phenylisoxazol-5-yl)methyl]pyrimidine-2,4-diamine |
| 583 | 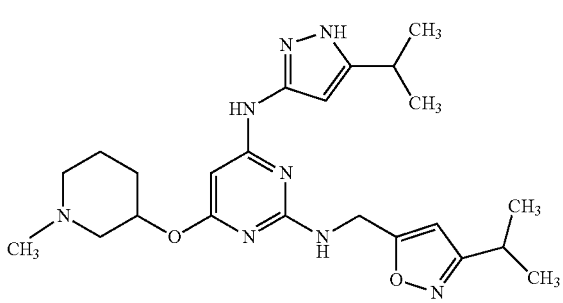 [SMILES: CC(C)c1cc(CNc2nc(Nc3cc(C(C)C)[nH]n3)cc(OC3CCCN(C)C3)n2)on1] | $N^2$-{[3-(1-methylethyl)isoxazol-5-yl]methyl}-$N^4$-[5-(1-methylethyl)-1H-pyrazol-3-yl]-6-[(1-methylpiperidin-3-yl)oxy]pyrimidine-2,4-diamine |

| Entry | Structure | Name |
|---|---|---|
| 584 | 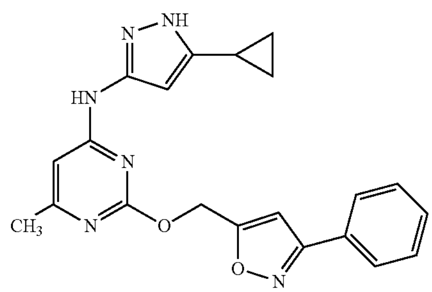 [SMILES: Cc1cc(Nc2cc(C3CC3)[nH]n2)nc(OCc2cc(-c3ccccc3)no2)n1] | N-(5-cyclopropyl-1H-pyrazol-3-yl)-6-methyl-2-{[(3-phenylisoxazol-5-yl)methyl]oxy}pyrimidin-4-amine |
| 585 | 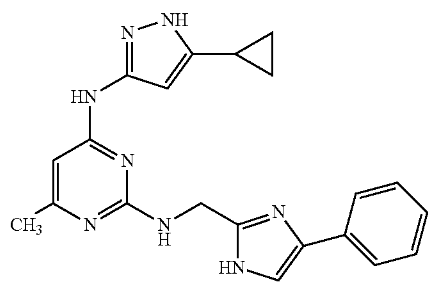 [SMILES: Cc1cc(Nc2cc(C3CC3)[nH]n2)nc(NCc2nc(-c3ccccc3)c[nH]2)n1] | $N^4$-(5-cyclopropyl-1H-pyrazol-3-yl)-6-methyl-$N^2$-[(4-phenyl-1H-imidazol-2-yl)methyl]pyrimidine-2,4-diamine |
| 586 | 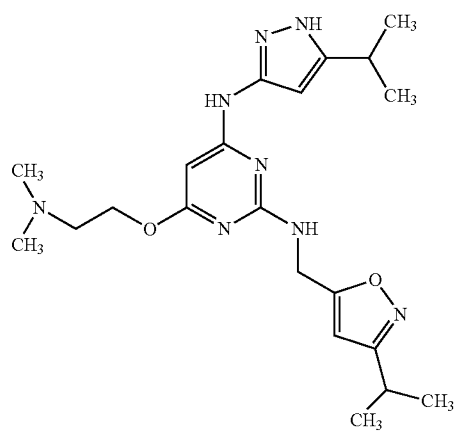 [SMILES: CC(C)c1cc(CNc2nc(Nc3cc(C(C)C)[nH]n3)cc(OCCN(C)C)n2)on1] | 6-{[2-(dimethylamino)ethyl]oxy}-$N^2$-{[3-(1-methylethyl)isoxazol-5-yl]methyl}-$N^4$-[5-(1-methylethyl)-1H-pyrazol-3-yl]pyrimidine-2,4-diamine |
| 587 | 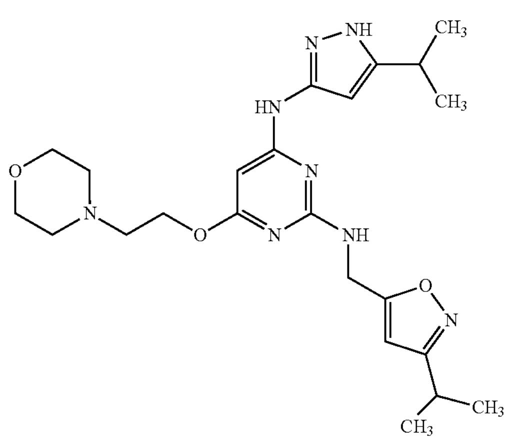 [SMILES: CC(C)c1cc(CNc2nc(Nc3cc(C(C)C)[nH]n3)cc(OCCN3CCOCC3)n2)on1] | $N^2$-{[3-(1-methylethyl)isoxazol-5-yl]methyl}-$N^4$-[5-(1-methylethyl)-1H-pyrazol-3-yl]-6-[(2-morpholin-4-ylethyl)oxy]pyrimidine-2,4-diamine |

| Entry | Structure | Name |
|---|---|---|
| 588 | 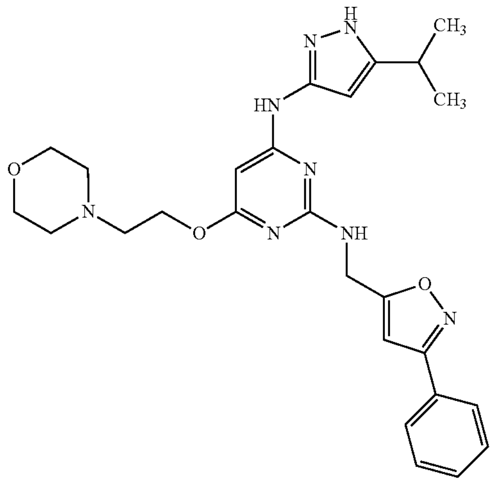 [SMILES: CC(C)c1cc(Nc2cc(OCCN3CCOCC3)nc(NCc3cc(-c4ccccc4)no3)n2)n[nH]1] | $N^4$-[5-(1-methylethyl)-1H-pyrazol-3-yl]-6-[(2-morpholin-4-ylethyl)oxy]-$N^2$-[(3-phenylisoxazol-5-yl)methyl]pyrimidine-2,4-diamine |
| 589 | 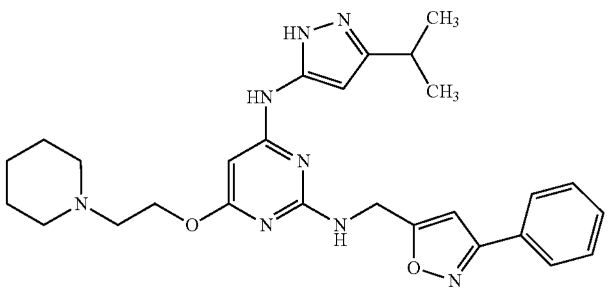 [SMILES: CC(C)c1cc(Nc2cc(OCCN3CCCCC3)nc(NCc3cc(-c4ccccc4)no3)n2)[nH]n1] | $N^4$-[3-(1-methylethyl)-1H-pyrazol-5-yl]-$N^2$-[(3-phenylisoxazol-5-yl)methyl]-6-[(2-piperidin-1-ylethyl)oxy]pyrimidine-2,4-diamine |
| 590 | 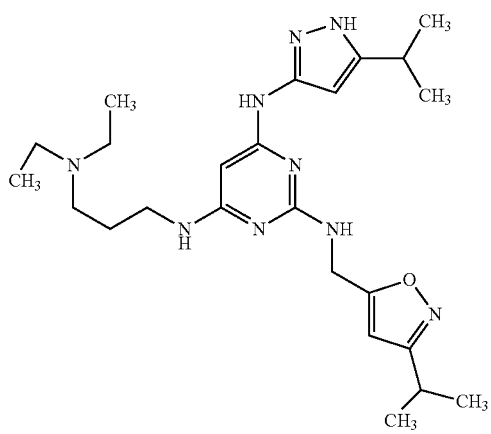 [SMILES: CCN(CC)CCCNc1cc(Nc2cc(C(C)C)[nH]n2)nc(NCc2cc(C(C)C)no2)n1] | $N^4$-[3-(diethylamino)propyl]-$N^2$-{[3-(1-methylethyl)isoxazol-5-yl]methyl}-$N^6$-[5-(1-methylethyl)-1H-pyrazol-3-yl]pyrimidine-2,4,6-triamine |
| 591 | Chiral | $N^4$-[5-(1-methylethyl)-1H-pyrazol-3-yl]-6-[(3S)-3-methylpiperazin-1-yl]-$N^2$-[(3-phenylisoxazol-5-yl)methyl]pyrimidine-2,4-diamine |

| Entry | Structure | Name |
|---|---|---|
| 592 | 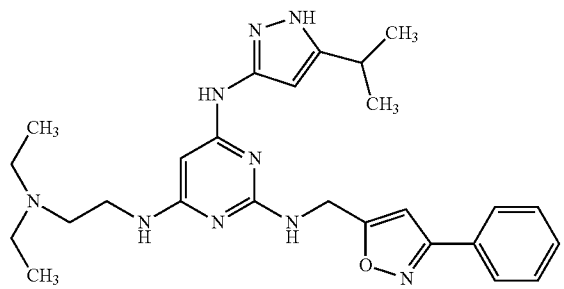 [SMILES: CCN(CC)CCNc1cc(Nc2cc(C(C)C)[nH]n2)nc(NCc2cc(-c3ccccc3)no2)n1] | $N^4$-[2-(diethylamino)ethyl]-$N^6$-[5-(1-methylethyl)-1H-pyrazol-3-yl]-$N^2$-[(3-phenylisoxazol-5-yl)methyl]pyrimidine-2,4,6-triamine |
| 593 | 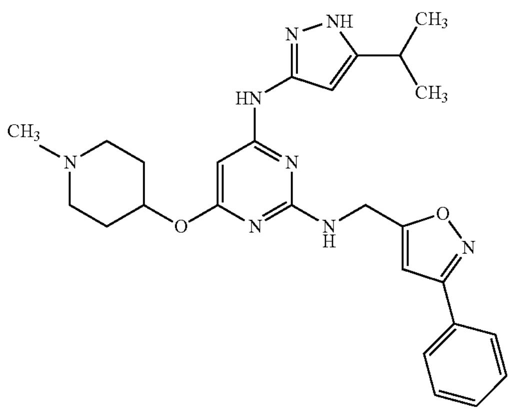 [SMILES: CC(C)c1cc(Nc2cc(OC3CCN(C)CC3)nc(NCc3cc(-c4ccccc4)no3)n2)n[nH]1] | $N^4$-[5-(1-methylethyl)-1H-pyrazol-3-yl]-6-[(1-methylpiperidin-4-yl)oxy]-$N^2$-[(3-phenylisoxazol-5-yl)methyl]pyrimidine-2,4-diamine |
| 594 | 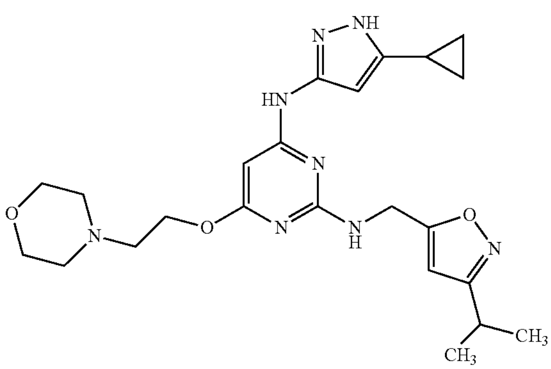 [SMILES: CC(C)c1cc(CNc2nc(Nc3cc(C4CC4)[nH]n3)cc(OCCN3CCOCC3)n2)on1] | $N^4$-(5-cyclopropyl-1H-pyrazol-3-yl)-$N^2$-{[3-(1-methylethyl)isoxazol-5-yl]methyl}-6-[(2-morpholin-4-ylethyl)oxy]pyrimidine-2,4-diamine |
| 595 | 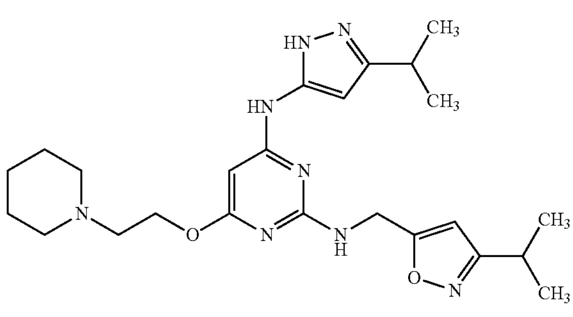 [SMILES: CC(C)c1cc(Nc2cc(OCCN3CCCCC3)nc(NCc3cc(C(C)C)no3)n2)[nH]n1] | $N^2$-{[3-(1-methylethyl)isoxazol-5-yl]methyl}-$N^4$-[3-(1-methylethyl)-1H-pyrazol-5-yl]-6-[(2-piperidin-1-ylethyl)oxy]pyrimidine-2,4-diamin |

| Entry | Structure | Name |
|---|---|---|
| 596 | 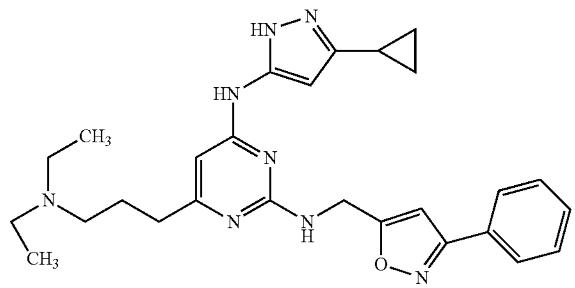 [SMILES: CCN(CC)CCCc1cc(Nc2cc(C3CC3)n[nH]2)nc(NCc2cc(-c3ccccc3)no2)n1] | N⁴-(3-cyclopropyl-1H-pyrazol-5-yl)-6-[3-(diethylamino)propyl]-N²-[(3-phenylisoxazol-5-yl)methyl]pyrimidine-2,4-diamine |
| 597 | 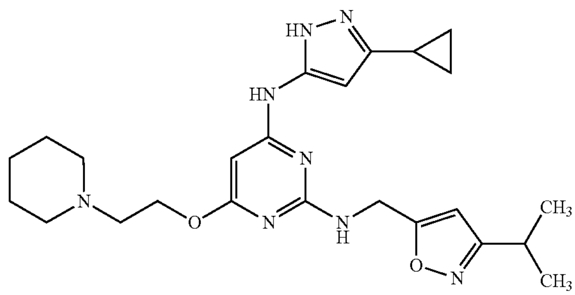 [SMILES: CC(C)c1cc(CNc2nc(Nc3cc(C4CC4)n[nH]3)cc(OCCN3CCCCC3)n2)on1] | N⁴-(3-cyclopropyl-1H-pyrazol-5-yl)-N²-{[3-(1-methylethyl)isoxazol-5-yl]methyl}-6-[(2-piperidin-1-ylethyl)oxy]pyrimidine-2,4-diamine |
| 598 | 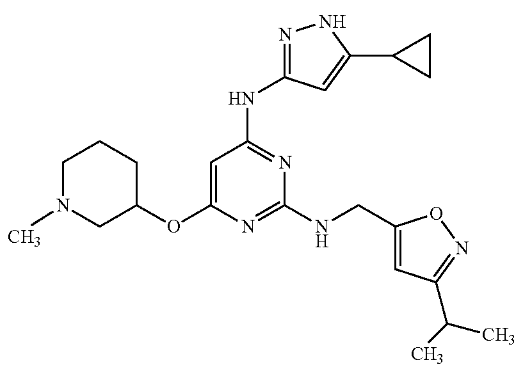 [SMILES: CC(C)c1cc(CNc2nc(Nc3cc(C4CC4)[nH]n3)cc(OC3CCCN(C)C3)n2)on1] | N⁴-(5-cyclopropyl-1H-pyrazol-3-yl)-N²-{[3-(1-methylethyl)isoxazol-5-yl]methyl}-6-[(1-methylpiperidin-3-yl)oxy]pyrimidine-2,4-diamine |
| 599 | 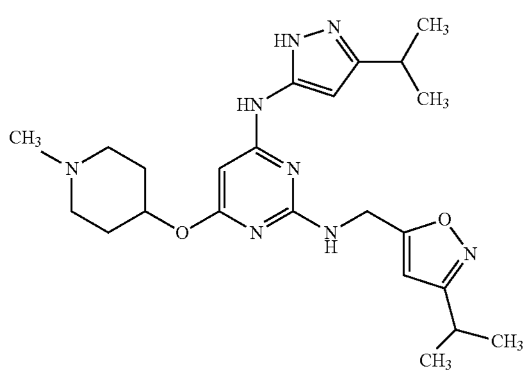 [SMILES: CC(C)c1cc(Nc2cc(OC3CCN(C)CC3)nc(NCc3cc(C(C)C)no3)n2)[nH]n1] | N²-{[3-(1-methylethyl)isoxazol-5-yl]methyl}-N⁴-[3-(1-methylethyl)-1H-pyrazol-5-yl]-6-[(1-methylpiperidin-4-yl)oxy]pyrimidine-2,4-diamine |

| Entry | Structure | Name |
|---|---|---|
| 600 | 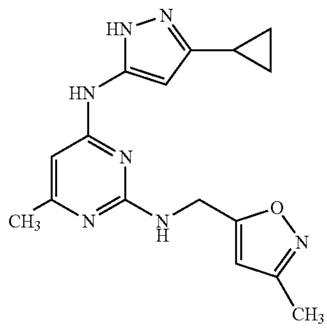 [SMILES: Cc1cc(CNc2nc(C)cc(Nc3cc(C4CC4)n[nH]3)n2)on1] | $N^4$-(3-cyclopropyl-1H-pyrazol-5-yl)-6-methyl-$N^2$-[(3-methylisoxazol-5-yl)methyl]pyrimidine-2,4-diamine |
| 601 | 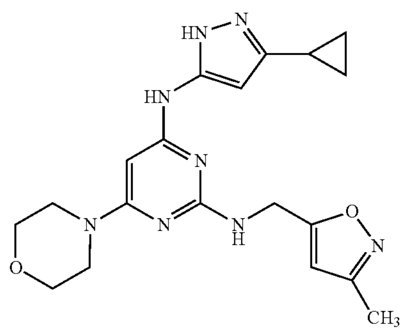 [SMILES: Cc1cc(CNc2nc(Nc3cc(C4CC4)n[nH]3)cc(N3CCOCC3)n2)on1] | $N^4$-(3-cyclopropyl-1H-pyrazol-5-yl)-$N^2$-[(3-methylisoxazol-5-yl)methyl]-6-morpholin-4-ylpyrimidine-2,4-diamine |
| 602 | 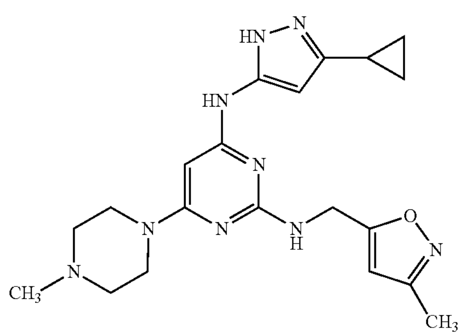 [SMILES: Cc1cc(CNc2nc(Nc3cc(C4CC4)n[nH]3)cc(N3CCN(C)CC3)n2)on1] | $N^4$-(3-cyclopropyl-1H-pyrazol-5-yl)-$N^2$-[(3-methylisoxazol-5-yl)methyl]-6-(4-methylpiperazin-1-yl)pyrimidine-2,4-diamine |
| 603 | 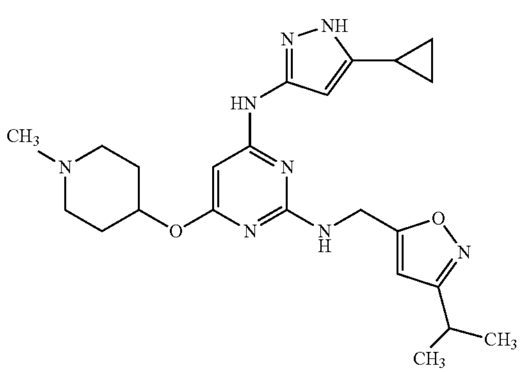 [SMILES: CC(C)c1cc(CNc2nc(Nc3cc(C4CC4)[nH]n3)cc(OC3CCN(C)CC3)n2)on1] | $N^4$-(5-cyclopropyl-1H-pyrazol-3-yl)-$N^2$-{[3-(1-methylethyl)isoxazol-5-yl]methyl}-6-[(1-methylpiperidin-4-yl)oxy]pyrimidine-2,4-diamine |

| Entry | Structure | Name |
|---|---|---|
| 604 | 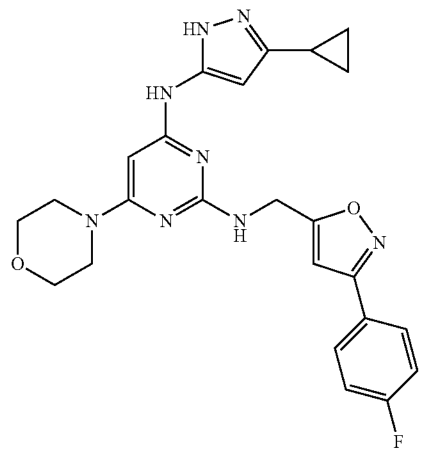 [SMILES: Fc1ccc(-c2cc(CNc3nc(Nc4cc(C5CC5)n[nH]4)cc(N4CCOCC4)n3)on2)cc1] | $N^4$-(3-cyclopropyl-1H-pyrazol-5-yl)-$N^2$-{[3-(4-fluorophenyl)isoxazol-5-yl]methyl}-6-morpholin-4-ylpyrimidine-2,4-diamine |
| 605 | 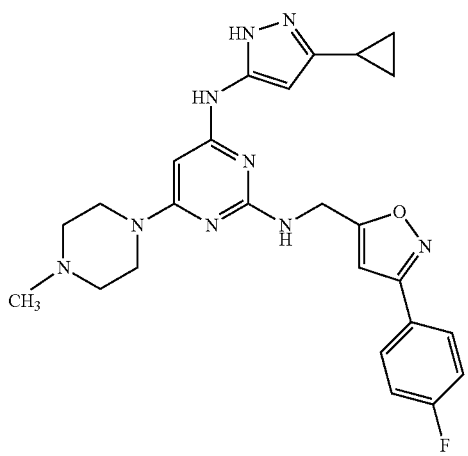 [SMILES: CN1CCN(c2cc(Nc3cc(C4CC4)n[nH]3)nc(NCc3cc(-c4ccc(F)cc4)no3)n2)CC1] | $N^4$-(3-cyclopropyl-1H-pyrazol-5-yl)-$N^2$-{[3-(4-fluorophenyl)isoxazol-5-yl]methyl}-6-(4-methylpiperazin-1-yl)pyrimidine-2,4-diamine |
| 606 | 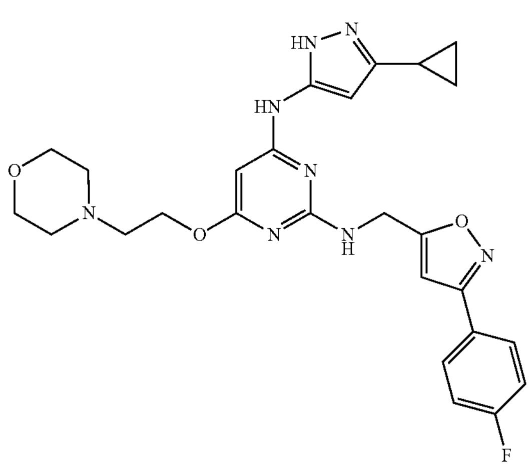 [SMILES: Fc1ccc(-c2cc(CNc3nc(Nc4cc(C5CC5)n[nH]4)cc(OCCN4CCOCC4)n3)on2)cc1] | $N^4$-(3-cyclopropyl-1H-pyrazol-5-yl)-$N^2$-{[3-(4-fluorophenyl)isoxazol-5-yl]methyl}-6-[(2-morpholin-4-ylethyl)oxy]pyrimidine-2,4-diamine |

| Entry | Structure | Name |
|---|---|---|
| 607 | 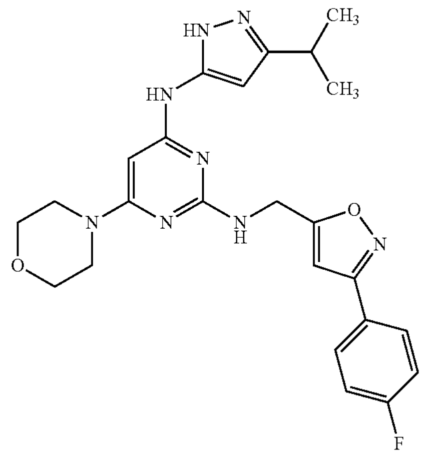 [SMILES: CC(C)c1cc(Nc2cc(N3CCOCC3)nc(NCc3cc(-c4ccc(F)cc4)no3)n2)[nH]n1] | $N^2$-{[3-(4-fluorophenyl)isoxazol-5-yl]methyl}-$N^4$-[3-(1-methylethyl)-1H-pyrazol-5-yl]-6-morpholin-4-ylpyrimidine-2,4-diamine |
| 608 | 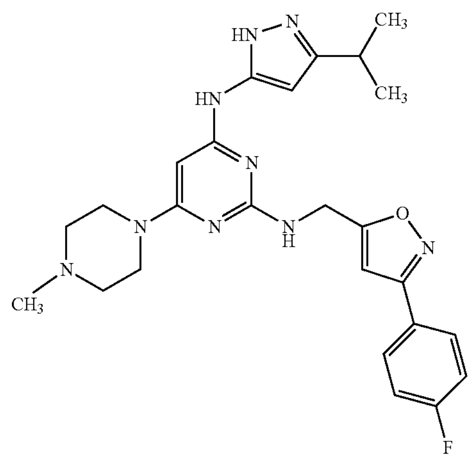 [SMILES: CC(C)c1cc(Nc2cc(N3CCN(C)CC3)nc(NCc3cc(-c4ccc(F)cc4)no3)n2)[nH]n1] | $N^2$-{[3-(4-fluorophenyl)isoxazol-5-yl]methyl}-$N^4$-[3-(1-methylethyl)-1H-pyrazol-5-yl]-6-(4-methylpiperazin-1-yl)pyrimidine-2,4-diamine |
| 609 | 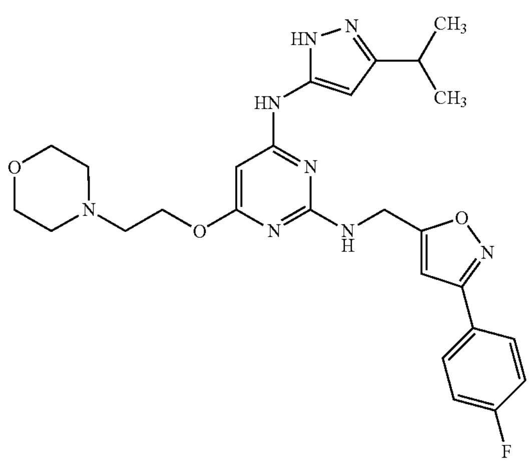 [SMILES: CC(C)c1cc(Nc2cc(OCCN3CCOCC3)nc(NCc3cc(-c4ccc(F)cc4)no3)n2)[nH]n1] | $N^2$-{[3-(4-fluorophenyl)isoxazol-5-yl]methyl}-$N^4$-[3-(1-methylethyl)-1H-pyrazol-5-yl]-6-[(2-morpholin-4-ylethyl)oxy]pyrimidine-2,4-diamine |

-continued

| Entry | Structure | Name |
|---|---|---|
| 610 | 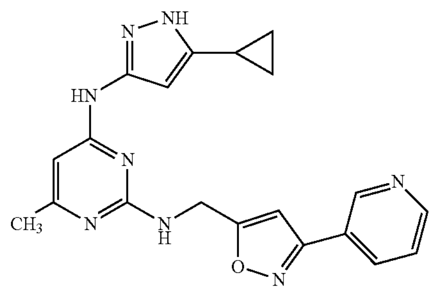 [SMILES: Cc1cc(Nc2cc(C3CC3)[nH]n2)nc(NCc2cc(-c3cccnc3)no2)n1] | $N^4$-(5-cyclopropyl-1H-pyrazol-3-yl)-6-methyl-$N^2$-[(3-pyridin-3-ylisoxazol-5-yl)methyl]pyrimidine-2,4-diamine |
| 611 | 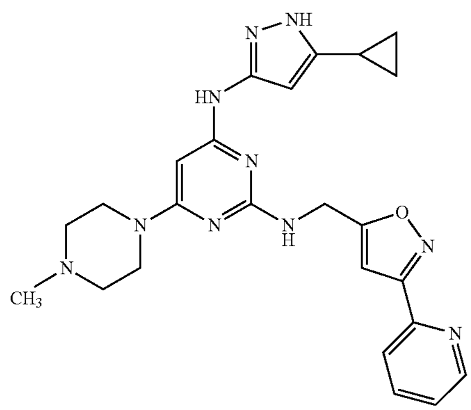 [SMILES: CN1CCN(c2cc(Nc3cc(C4CC4)[nH]n3)nc(NCc3cc(-c4ccccn4)no3)n2)CC1] | $N^4$-(5-cyclopropyl-1H-pyrazol-3-yl)-6-(4-methylpiperazin-1-yl)-$N^2$-[(3-pyridin-2-ylisoxazol-5-yl)methyl]pyrimidine-2,4-diamine |
| 612 | 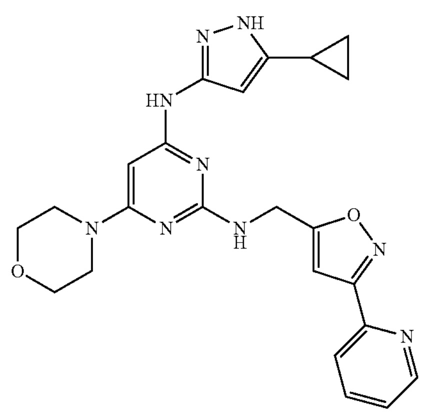 [SMILES: c1ccc(-c2cc(CNc3nc(Nc4cc(C5CC5)[nH]n4)cc(N4CCOCC4)n3)on2)nc1] | $N^4$-(5-cyclopropyl-1H-pyrazol-3-yl)-6-morpholin-4-yl-$N^2$-[(3-pyridin-2-ylisoxazol-5-yl)methyl]pyrimidine-2,4-diamine |
| 613 | 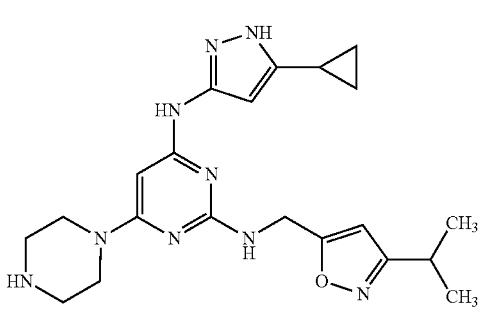 [SMILES: CC(C)c1cc(CNc2nc(Nc3cc(C4CC4)[nH]n3)cc(N3CCNCC3)n2)on1] | $N^4$-(5-cyclopropyl-1H-pyrazol-3-yl)-$N^2$-{[3-(1-methylethyl)isoxazol-5-yl]methyl}-6-piperazin-1-ylpyrimidine-2,4-diamine |

| Entry | Structure | Name |
|---|---|---|
| 614 | 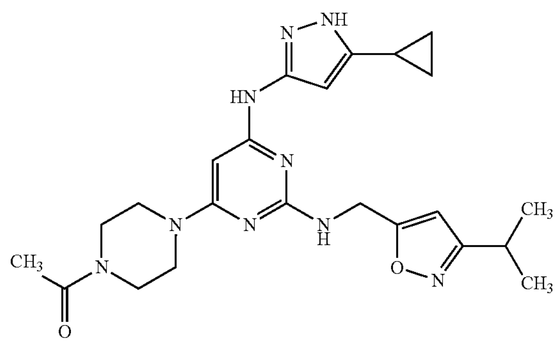 [SMILES: CC(=O)N1CCN(c2cc(Nc3cc(C4CC4)[nH]n3)nc(NCc3cc(C(C)C)no3)n2)CC1] | 6-(4-acetylpiperazin-1-yl)-N4-(5-cyclopropyl-1H-pyrazol-3-yl)-N2-{[3-(1-methylethyl)isoxazol-5-yl]methyl}pyrimidine-2,4-diamine |
| 615 | 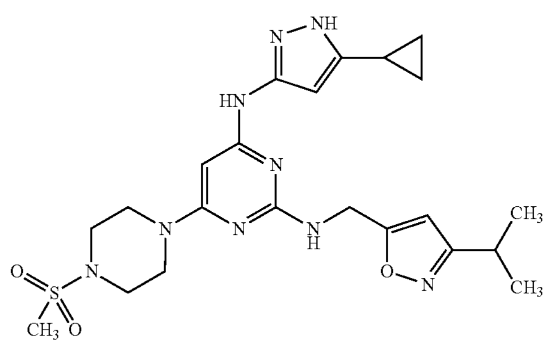 [SMILES: CC(C)c1cc(CNc2nc(Nc3cc(C4CC4)[nH]n3)cc(N3CCN(S(C)(=O)=O)CC3)n2)on1] | N4-(5-cyclopropyl-1H-pyrazol-3-yl)-N2-{[3-(1-methylethyl)isoxazol-5-yl]methyl}-6-[4-(methylsulfonyl)piperazin-1-yl]pyrimidine-2,4-diamine |
| 616 | 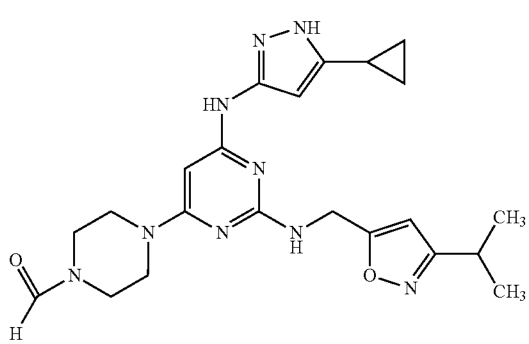 [SMILES: CC(C)c1cc(CNc2nc(Nc3cc(C4CC4)[nH]n3)cc(N3CCN(C=O)CC3)n2)on1] | 4-{6-[(5-cyclopropyl-1H-pyrazol-3-yl)amino]-2-({[3-(1-methylethyl)isoxazol-5-yl]methyl}amino)pyrimidin-4-yl}piperazine-1-carbaldehyde |
| 617 | 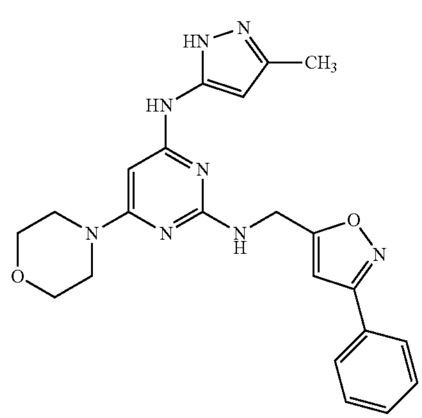 [SMILES: Cc1cc(Nc2cc(N3CCOCC3)nc(NCc3cc(-c4ccccc4)no3)n2)[nH]n1] | N4-(3-methyl-1H-pyrazol-5-yl)-6-morpholin-4-yl-N2-[(3-phenylisoxazol-5-yl)methyl]pyrimidine-2,4-diamine |

| Entry | Structure | Name |
|---|---|---|
| 618 | 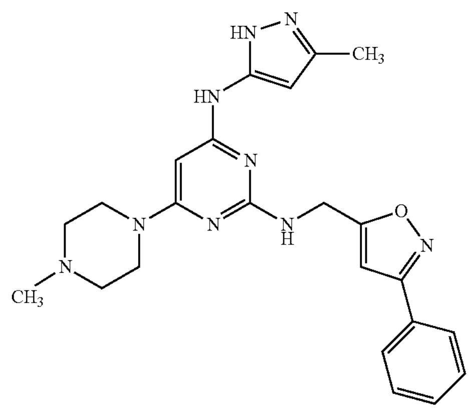 [SMILES: Cc1cc(Nc2cc(N3CCN(C)CC3)nc(NCc3cc(-c4ccccc4)no3)n2)[nH]n1] | 6-(4-methylpiperazin-1-yl)-N$^4$-(3-methyl-1H-pyrazol-5-yl)-N$^2$-[(3-phenylisoxazol-5-yl)methyl]pyrimidine-2,4-diamine |
| 619 | 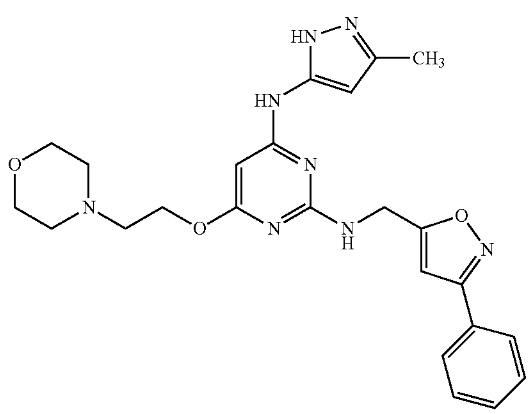 [SMILES: Cc1cc(Nc2cc(OCCN3CCOCC3)nc(NCc3cc(-c4ccccc4)no3)n2)[nH]n1] | N$^4$-(3-methyl-1H-pyrazol-5-yl)-6-[(2-morpholin-4-ylethyl)oxy]-N$^2$-[(3-phenylisoxazol-5-yl)methyl]pyrimidine-2,4-diamine |
| 620 | 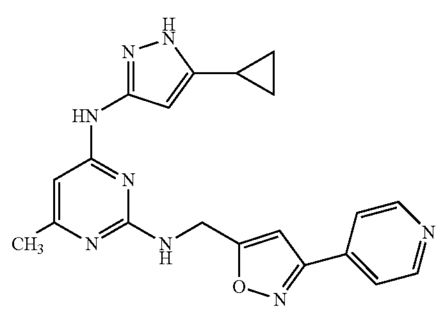 [SMILES: Cc1cc(Nc2cc(C3CC3)[nH]n2)nc(NCc2cc(-c3ccncc3)no2)n1] | N$^4$-(5-cyclopropyl-1H-pyrazol-3-yl)-6-methyl-N$^2$-[(3-pyridin-4-ylisoxazol-5-yl)methyl]pyrimidine-2,4-diamine |
| 621 | 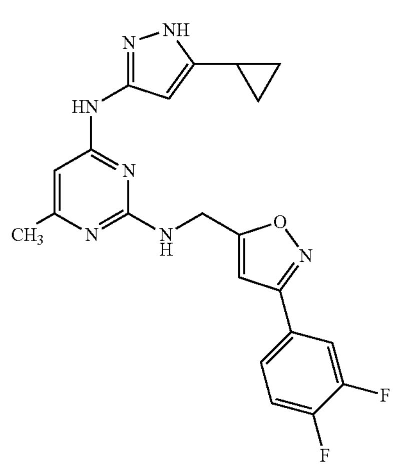 [SMILES: Cc1cc(Nc2cc(C3CC3)[nH]n2)nc(NCc2cc(-c3ccc(F)c(F)c3)no2)n1] | N$^4$-(5-cyclopropyl-1H-pyrazol-3-yl)-N$^2$-{[3-(3,4-difluorophenyl)isoxazol-5-yl]methyl}-6-methylpyrimidine-2,4-diamine |

| Entry | Structure | Name |
|---|---|---|
| 622 | 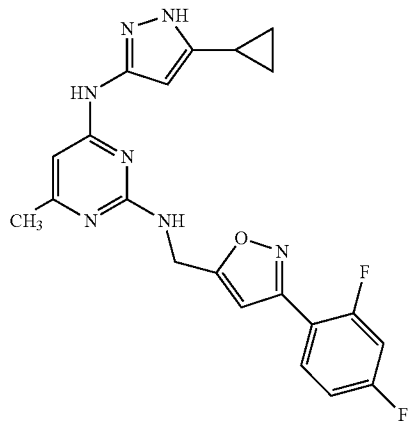 [SMILES: Cc1cc(Nc2cc(C3CC3)[nH]n2)nc(NCc2cc(-c3ccc(F)cc3F)no2)n1] | $N^4$-(5-cyclopropyl-1H-pyrazol-3-yl)-$N^2$-{[3-(2,4-difluorophenyl)isoxazol-5-yl]methyl}-6-methylpyrimidine-2,4-diamine |
| 623 | 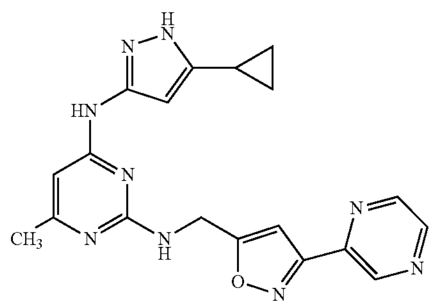 [SMILES: Cc1cc(Nc2cc(C3CC3)[nH]n2)nc(NCc2cc(-c3cnccn3)no2)n1] | $N^4$-(5-cyclopropyl-1H-pyrazol-3-yl)-6-methyl-$N^2$-[(3-pyrazin-2-ylisoxazol-5-yl)methyl]pyrimidine-2,4-diamine |
| 624 | 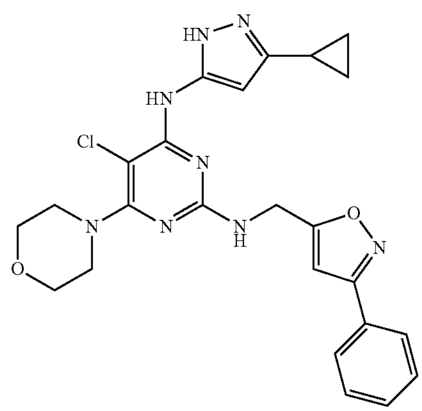 [SMILES: Clc1c(Nc2cc(C3CC3)n[nH]2)nc(NCc2cc(-c3ccccc3)no2)nc1N1CCOCC1] | 5-chloro-$N^4$-(3-cyclopropyl-1H-pyrazol-5-yl)-6-morpholin-4-yl-$N^2$-[(3-phenylisoxazol-5-yl)methyl]pyrimidine-2,4-diamine |
| 625 | 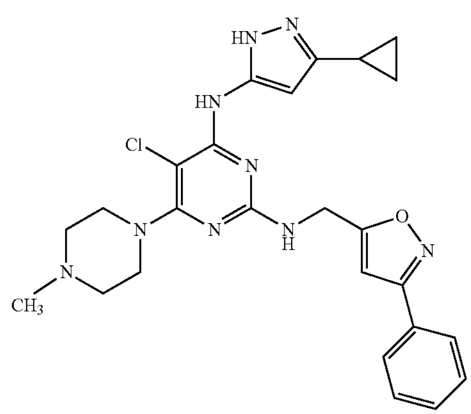 [SMILES: CN1CCN(c2nc(NCc3cc(-c4ccccc4)no3)nc(Nc3cc(C4CC4)n[nH]3)c2Cl)CC1] | 5-chloro-$N^4$-(3-cyclopropyl-1H-pyrazol-5-yl)-6-(4-methylpiperazin-1-yl)-$N^2$-[(3-phenylisoxazol-5-yl)methyl]pyrimidine-2,4-diamine |

| Entry | Structure | Name |
|---|---|---|
| 626 | 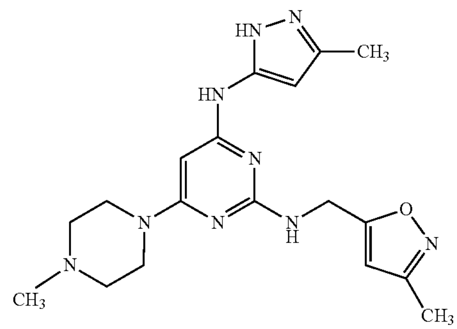 [SMILES: Cc1cc(Nc2cc(N3CCN(C)CC3)nc(NCc3cc(C)no3)n2)[nH]n1] | $N^2$-[(3-methylisoxazol-5-yl)methyl]-6-(4-methylpiperazin-1-yl)-$N^4$-(3-methyl-1H-pyrazol-5-yl)pyrimidine-2,4-diamine |
| 627 | 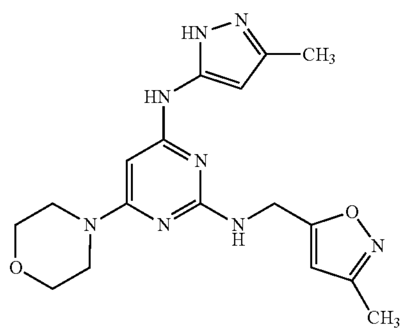 [SMILES: Cc1cc(Nc2cc(N3CCOCC3)nc(NCc3cc(C)no3)n2)[nH]n1] | $N^2$-[(3-methylisoxazol-5-yl)methyl]-$N^4$-(3-methyl-1H-pyrazol-5-yl)-6-morpholin-4-ylpyrimidine-2,4-diamine |
| 628 | 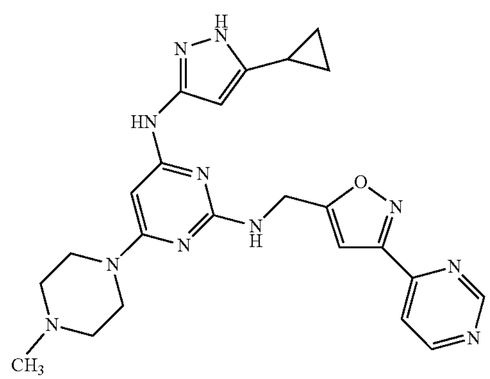 [SMILES: CN1CCN(c2cc(Nc3cc(C4CC4)[nH]n3)nc(NCc3cc(-c4ccncn4)no3)n2)CC1] | $N^4$-(5-cyclopropyl-1H-pyrazol-3-yl)-6-(4-methylpiperazin-1-yl)-$N^2$-[(3-pyrimidin-4-ylisoxazol-5-yl)methyl]pyrimidine-2,4-diamine |
| 629 | 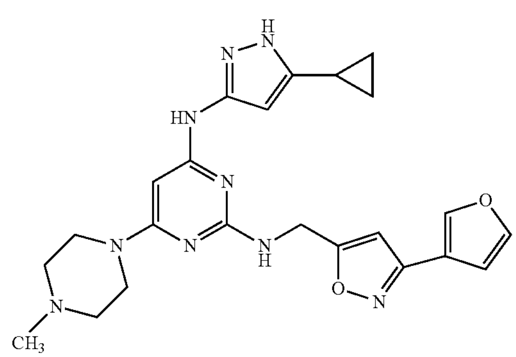 [SMILES: CN1CCN(c2cc(Nc3cc(C4CC4)[nH]n3)nc(NCc3cc(-c4ccoc4)no3)n2)CC1] | $N^4$-(5-cyclopropyl-1H-pyrazol-3-yl)-$N^2$-[(3-furan-3-ylisoxazol-5-yl)methyl]-6-(4-methylpiperazin-1-yl)pyrimidine-2,4-diamine |

| Entry | Structure | Name |
|---|---|---|
| 630 | 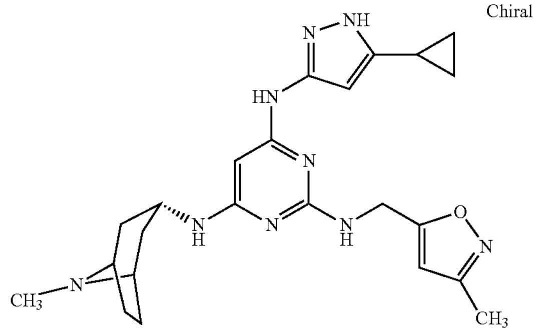 | $N^4$-(5-cyclopropyl-1H-pyrazol-3-yl)-$N^6$-(8-methyl-8-azabicyclo[3.2.1]oct-3-yl)-$N^2$-[(3-methylisoxazol-5-yl)methyl]pyrimidine-2,4,6-triamine |
| 631 | 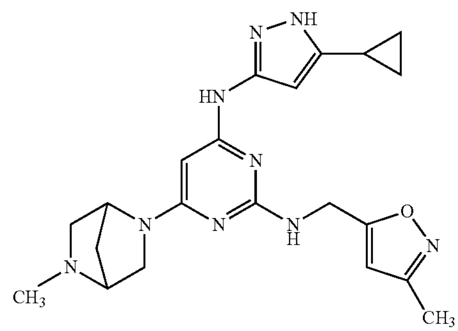 [SMILES: Cc1cc(CNc2nc(Nc3cc(C4CC4)[nH]n3)cc(N3CC4CC3CN4C)n2)on1] | $N^4$-(5-cyclopropyl-1H-pyrazol-3-yl)-6-(5-methyl-2,5-diazabicyclo[2.2.1]hept-2-yl)-$N^2$-[(3-methylisoxazol-5-yl)methyl]pyrimidine-2,4-diamine |
| 632 | 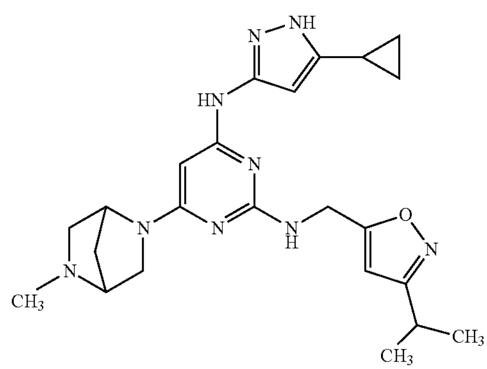 [SMILES: CC(C)c1cc(CNc2nc(Nc3cc(C4CC4)[nH]n3)cc(N3CC4CC3CN4C)n2)on1] | $N^4$-(5-cyclopropyl-1H-pyrazol-3-yl)-6-(5-methyl-2,5-diazabicyclo[2.2.1]hept-2-yl)-$N^2$-{[3-(1-methylethyl)isoxazol-5-yl]methyl}pyrimidine-2,4-diamine |
| 633 | 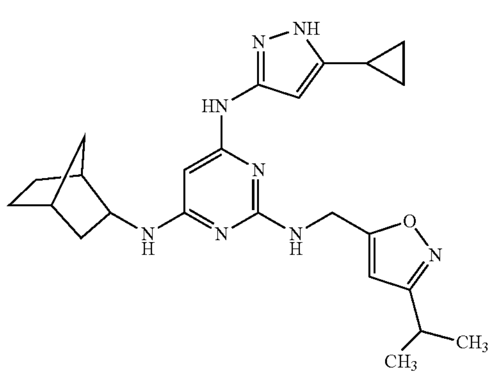 [SMILES: CC(C)c1cc(CNc2nc(Nc3cc(C4CC4)[nH]n3)cc(NC3CC4CCC3C4)n2)on1] | $N^4$-bicyclo[2.2.1]hept-2-yl-$N^6$-(5-cyclopropyl-1H-pyrazol-3-yl)-$N^2$-{[3-(1-methylethyl)isoxazol-5-yl]methyl}pyrimidine-2,4,6-triamine |

| Entry | Structure | Name |
|---|---|---|
| 634 | 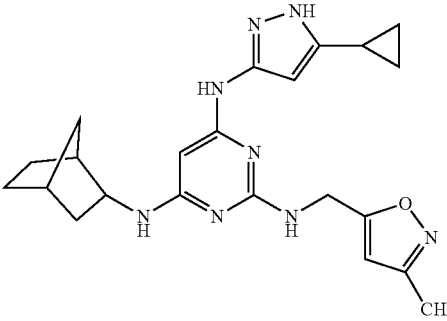 | $N^4$-bicyclo[2.2.1]hept-2-yl-$N^6$-(5-cyclopropyl-1H-pyrazol-3-yl)-$N^2$-[(3-methylisoxazol-5-yl)methyl]pyrimidine-2,4,6-triamine |
| 635 | 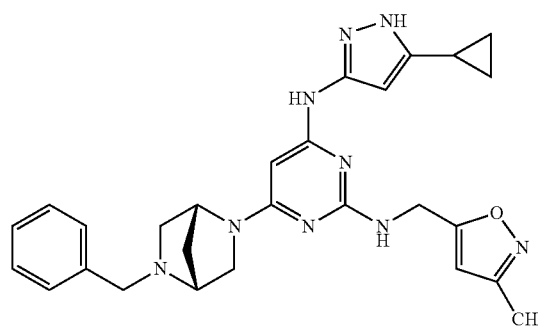 | $N^4$-(5-cyclopropyl-1H-pyrazol-3-yl)-$N^2$-[(3-methylisoxazol-5-yl)methyl]-6-[(1R,4R)-5-(phenylmethyl)-2,5-diazabicyclo[2.2.1]hept-2-yl]pyrimidine-2,4-diamine |
| 636 | 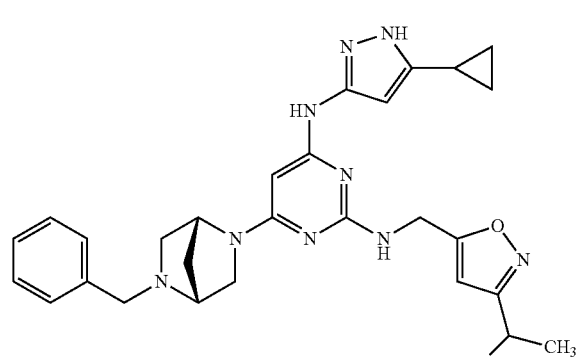 | $N^4$-(5-cyclopropyl-1H-pyrazol-3-yl)-$N^2$-{[3-(1-methylethyl)isoxazol-5-yl]methyl}-6-[(1R,4R)-5-(phenylmethyl)-2,5-diazabicyclo[2.2.1]hept-2-yl]pyrimidine-2,4-diamine |
| 637 | 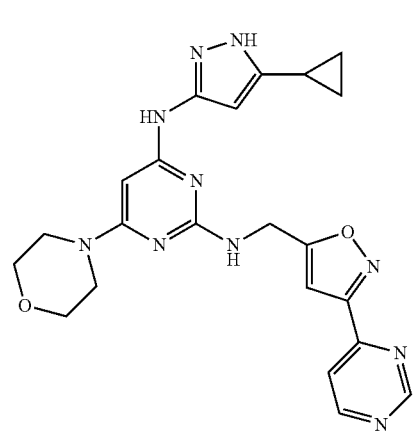 [SMILES: c1cc(-c2cc(CNc3nc(Nc4cc(C5CC5)[nH]n4)cc(N4CCOCC4)n3)on2)ncn1] | $N^4$-(5-cyclopropyl-1H-pyrazol-3-yl)-6-morpholin-4-yl-$N^2$-[(3-pyrimidin-4-ylisoxazol-5-yl)methyl]pyrimidine-2,4-diamine |

| Entry | Structure | Name |
|---|---|---|
| 638 | 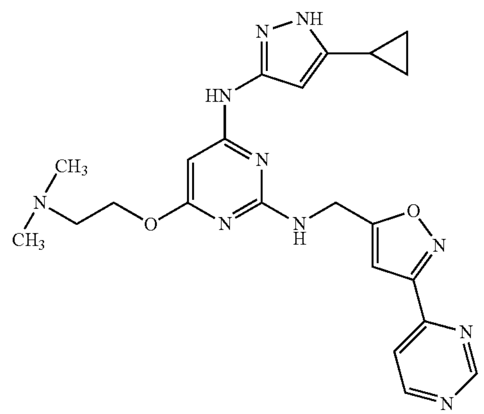 [SMILES: CN(C)CCOc1cc(Nc2cc(C3CC3)[nH]n2)nc(NCc2cc(-c3ccncn3)no2)n1] | $N^4$-(5-cyclopropyl-1H-pyrazol-3-yl)-6-{[2-(dimethylamino)ethyl]oxy}-$N^2$-[(3-pyrimidin-4-ylisoxazol-5-yl)methyl]pyrimidine-2,4-diamine |
| 639 | 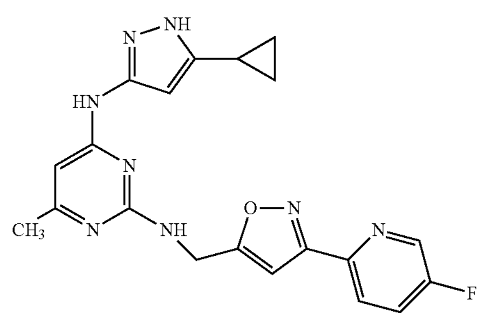 [SMILES: Cc1cc(Nc2cc(C3CC3)[nH]n2)nc(NCc2cc(-c3ccc(F)cn3)no2)n1] | $N^4$-(5-cyclopropyl-1H-pyrazol-3-yl)-$N^2$-{[3-(5-fluoropyridin-2-yl)isoxazol-5-yl]methyl}-6-methylpyrimidine-2,4-diamine |
| 640 | 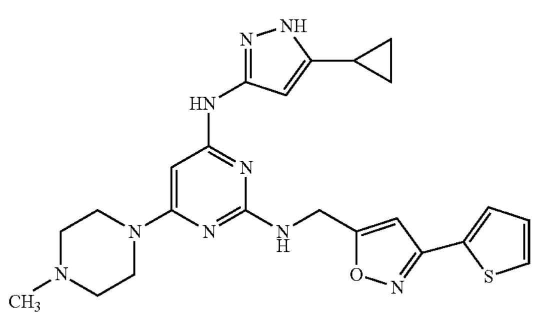 [SMILES: CN1CCN(c2cc(Nc3cc(C4CC4)[nH]n3)nc(NCc3cc(-c4cccs4)no3)n2)CC1] | $N^4$-(5-cyclopropyl-1H-pyrazol-3-yl)-6-(4-methylpiperazin-1-yl)-$N^2$-{[3-(2-thienyl)isoxazol-5-yl]methyl}pyrimidine-2,4-diamine |
| 641 | 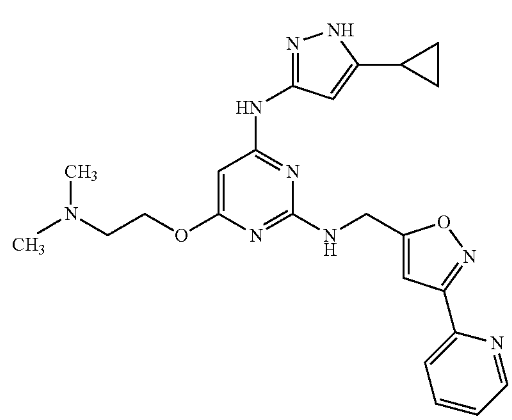 [SMILES: CN(C)CCOc1cc(Nc2cc(C3CC3)[nH]n2)nc(NCc2cc(-c3ccccn3)no2)n1] | $N^4$-(5-cyclopropyl-1H-pyrazol-3-yl)-6-{[2-(dimethylamino)ethyl]oxy}-$N^2$-[(3-pyridin-2-ylisoxazol-5-yl)methyl]pyrimidine-2,4-diamine |

| Entry | Structure | Name |
|---|---|---|
| 642 | 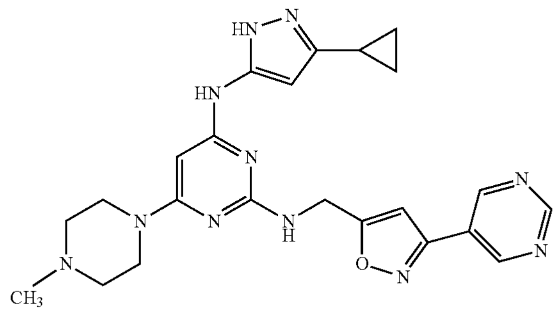 [SMILES: CN1CCN(c2cc(Nc3cc(C4CC4)n[nH]3)nc(NCc3cc(-c4cncnc4)no3)n2)CC1] | $N^4$-(3-cyclopropyl-1H-pyrazol-5-yl)-6-(4-methylpiperazin-1-yl)-$N^2$-[(3-pyrimidin-5-ylisoxazol-5-yl)methyl]pyrimidine-2,4-diamine |
| 643 | 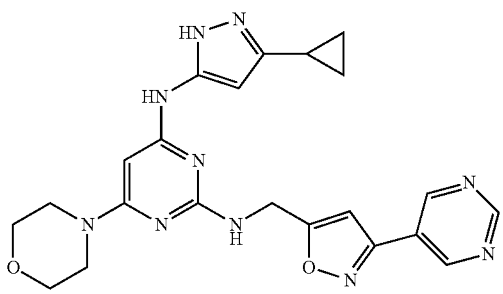 [SMILES: c1ncc(-c2cc(CNc3nc(Nc4cc(C5CC5)n[nH]4)cc(N4CCOCC4)n3)on2)cn1] | $N^4$-(3-cyclopropyl-1H-pyrazol-5-yl)-6-morpholin-4-yl-$N^2$-[(3-pyrimidin-5-ylisoxazol-5-yl)methyl]pyrimidine-2,4-diamine |
| 644 | 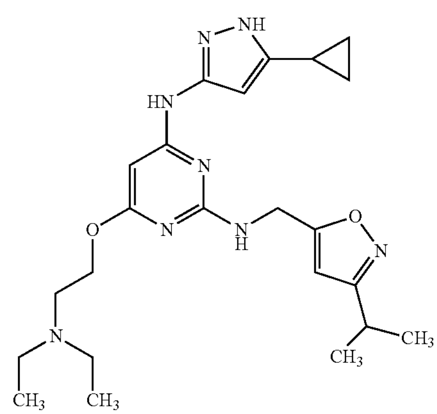 [SMILES: CCN(CC)CCOc1cc(Nc2cc(C3CC3)[nH]n2)nc(NCc2cc(C(C)C)no2)n1] | $N^4$-(5-cyclopropyl-1H-pyrazol-3-yl)-6-{[2-(diethylamino)ethyl]oxy}-$N^2$-{[3-(1-methylethyl)isoxazol-5-yl]methyl}pyrimidine-2,4-diamine |
| 645 | 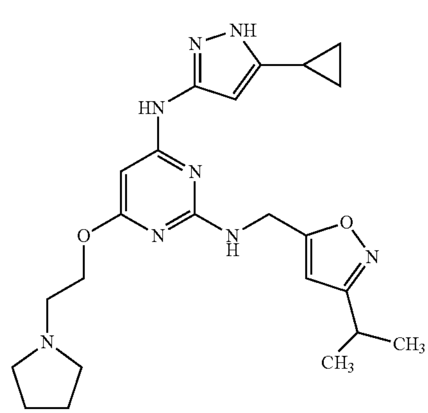 [SMILES: CC(C)c1cc(CNc2nc(Nc3cc(C4CC4)[nH]n3)cc(OCCN3CCCC3)n2)on1] | $N^4$-(5-cyclopropyl-1H-pyrazol-3-yl)-$N^2$-{[3-(1-methylethyl)isoxazol-5-yl]methyl}-6-[(2-pyrrolidin-1-ylethyl)oxy]pyrimidine-2,4-diamine |

| Entry | Structure | Name |
|---|---|---|
| 646 | 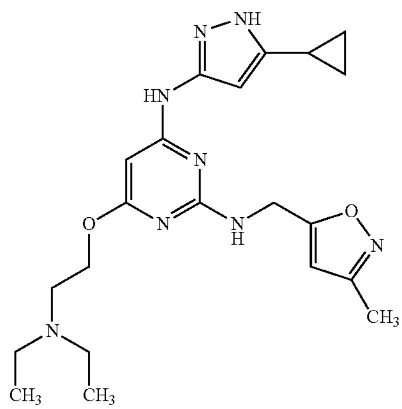 [SMILES: CCN(CC)CCOc1cc(Nc2cc(C3CC3)[nH]n2)nc(NCc2cc(C)no2)n1] | $N^4$-(5-cyclopropyl-1H-pyrazol-3-yl)-6-{[2-(diethylamino)ethyl]oxy}-$N^2$-[(3-methylisoxazol-5-yl)methyl]pyrimidine-2,4-diamine |
| 647 | 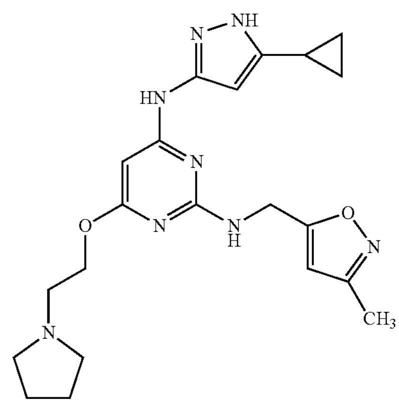 [SMILES: Cc1cc(CNc2nc(Nc3cc(C4CC4)[nH]n3)cc(OCCN3CCCC3)n2)on1] | $N^4$-(5-cyclopropyl-1H-pyrazol-3-yl)-$N^2$-[(3-methylisoxazol-5-yl)methyl]-6-[(2-pyrrolidin-1-ylethyl)oxy]pyrimidine-2,4-diamine |
| 648 | 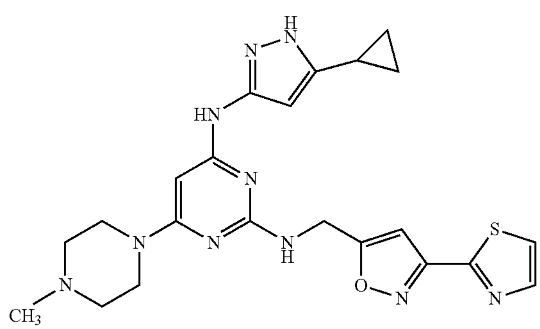 [SMILES: CN1CCN(c2cc(Nc3cc(C4CC4)[nH]n3)nc(NCc3cc(-c4nccs4)no3)n2)CC1] | $N^4$-(5-cyclopropyl-1H-pyrazol-3-yl)-6-(4-methylpiperazin-1-yl)-$N^2$-{[3-(1,3-thiazol-2-yl)isoxazol-5-yl]methyl}pyrimidine-2,4-diamine |
| 649 | 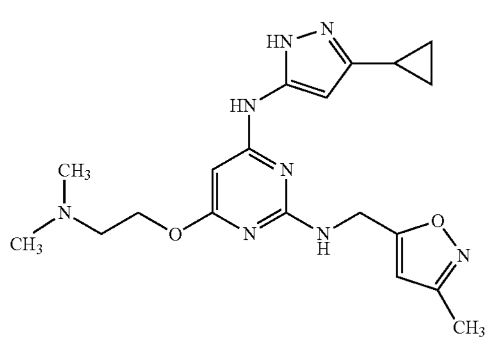 [SMILES: Cc1cc(CNc2nc(Nc3cc(C4CC4)n[nH]3)cc(OCCN(C)C)n2)on1] | $N^4$-(3-cyclopropyl-1H-pyrazol-5-yl)-6-[2-(dimethylamino)ethoxy]-$N^2$-[(3-methylisoxazol-5-yl)methyl]pyrimidine-2,4-diamine |

| Entry | Structure | Name |
|---|---|---|
| 650 | 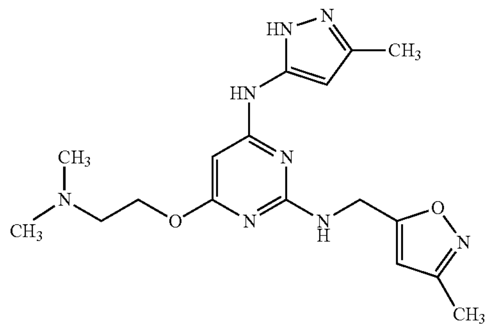 [SMILES: Cc1cc(Nc2cc(OCCN(C)C)nc(NCc3cc(C)no3)n2)[nH]n1] | 6-{[2-(dimethylamino)ethyl]oxy}-$N^2$-[(3-methylisoxazol-5-yl)methyl]-$N^4$-(3-methyl-1H-pyrazol-5-yl)pyrimidine-2,4-diamine |
| 651 | 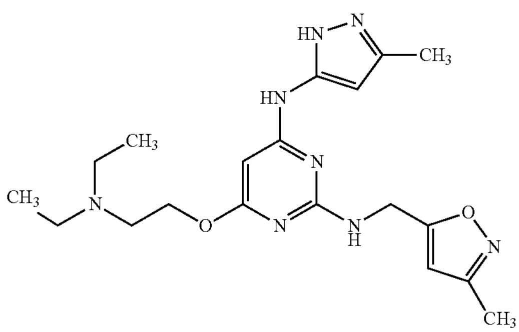 [SMILES: CCN(CC)CCOc1cc(Nc2cc(C)n[nH]2)nc(NCc2cc(C)no2)n1] | 6-{[2-(diethylamino)ethyl]oxy}-$N^2$-[(3-methylisoxazol-5-yl)methyl]-$N^4$-(3-methyl-1H-pyrazol-5-yl)pyrimidine-2,4-diamine |
| 652 | 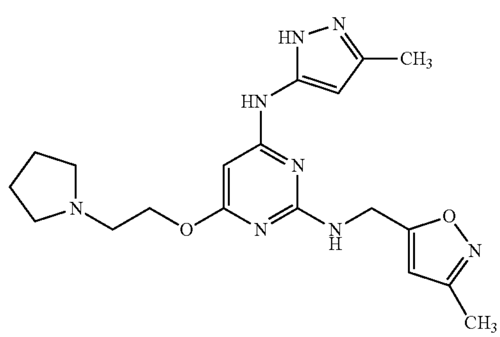 [SMILES: Cc1cc(Nc2cc(OCCN3CCCC3)nc(NCc3cc(C)no3)n2)[nH]n1] | $N^2$-[(3-methylisoxazol-5-yl)methyl]-$N^4$-(3-methyl-1H-pyrazol-5-yl)-6-[(2-pyrrolidin-1-ylethyl)oxy]pyrimidine-2,4-diamine |
| 653 | 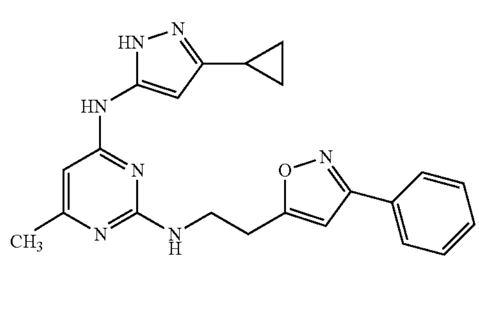 [SMILES: Cc1cc(Nc2cc(C3CC3)n[nH]2)nc(NCCc2cc(-c3ccccc3)no2)n1] | $N^4$-(3-cyclopropyl-1H-pyrazol-5-yl)-6-methyl-$N^2$-[2-(3-phenylisoxazol-5-yl)ethyl]pyrimidine-2,4-diamine |

| Entry | Structure | Name |
|---|---|---|
| 654 | 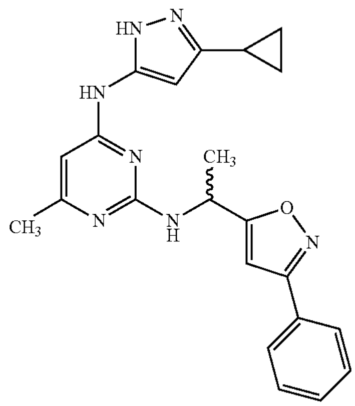 [SMILES: Cc1cc(Nc2cc(C3CC3)n[nH]2)nc(NC(C)c2cc(-c3ccccc3)no2)n1] | $N^4$-(3-cyclopropyl-1H-pyrazol-5-yl)-6-methyl-$N^2$-[1-(3-phenylisoxazol-5-yl)ethyl]pyrimidine-2,4-diamine |
| 655 | 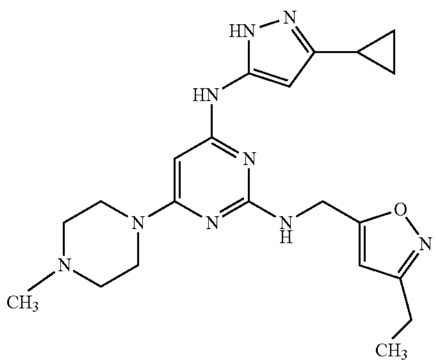 [SMILES: CCc1cc(CNc2nc(Nc3cc(C4CC4)n[nH]3)cc(N3CCN(C)CC3)n2)on1] | $N^4$-(3-cyclopropyl-1H-pyrazol-5-yl)-$N^2$-[(3-ethylisoxazol-5-yl)methyl]-6-(4-methylpiperazin-1-yl)pyrimidine-2,4-diamine |
| 656 | 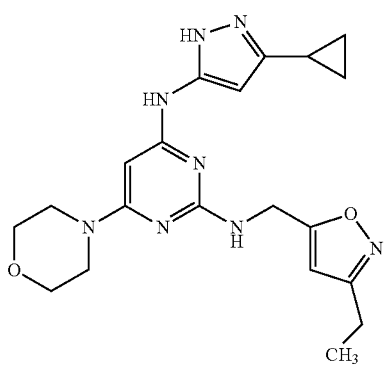 [SMILES: CCc1cc(CNc2nc(Nc3cc(C4CC4)n[nH]3)cc(N3CCOCC3)n2)on1] | $N^4$-(3-cyclopropyl-1H-pyrazol-5-yl)-$N^2$-[(3-ethylisoxazol-5-yl)methyl]-6-morpholin-4-ylpyrimidine-2,4-diamine |
| 657 | 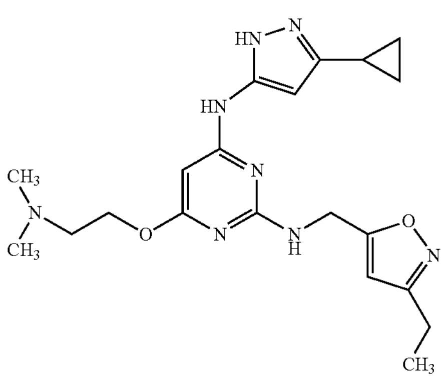 [SMILES: CCc1cc(CNc2nc(Nc3cc(C4CC4)n[nH]3)cc(OCCN(C)C)n2)on1] | $N^4$-(3-cyclopropyl-1H-pyrazol-5-yl)-6-{[2-(dimethylamino)ethyl]oxy}-$N^2$-[(3-ethylisoxazol-5-yl)methyl]pyrimidine-2,4-diamine |

-continued

| Entry | Structure | Name |
|---|---|---|
| 658 | 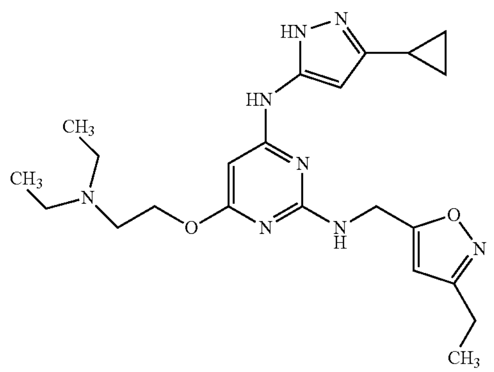 [SMILES: CCc1cc(CNc2nc(Nc3cc(C4CC4)n[nH]3)cc(OCCN(CC)CC)n2)on1] | $N^4$-(3-cyclopropyl-1H-pyrazol-5-yl)-6-{[2-(diethylamino)ethyl]oxy}-$N^2$-[(3-ethylisoxazol-5-yl)methyl]pyrimidine-2,4-diamine |
| 659 | 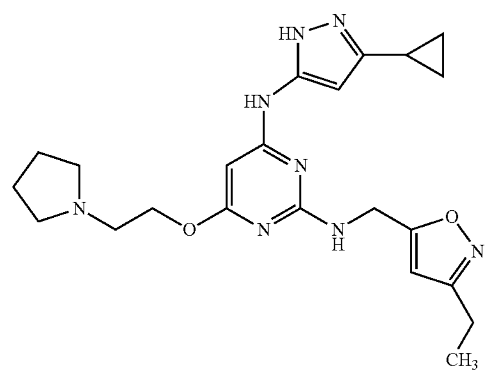 [SMILES: CCc1cc(CNc2nc(Nc3cc(C4CC4)n[nH]3)cc(OCCN3CCCC3)n2)on1] | $N^4$-(3-cyclopropyl-1H-pyrazol-5-yl)-$N^2$-[(3-ethylisoxazol-5-yl)methyl]-6-[(2-pyrrolidin-1-ylethyl)oxy]pyrimidine-2,4-diamine |
| 660 | 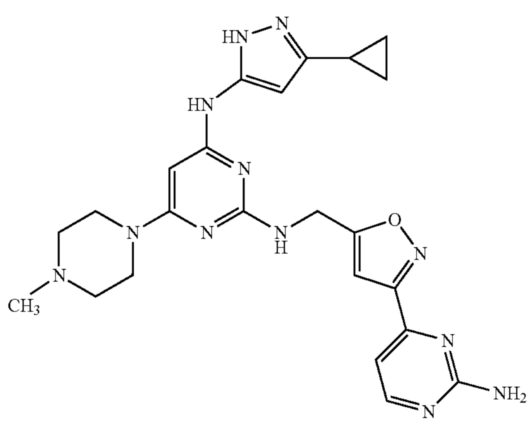 [SMILES: CN1CCN(c2cc(Nc3cc(C4CC4)n[nH]3)nc(NCc3cc(-c4ccnc(N)n4)no3)n2)CC1] | $N^2$-{[3-(2-aminopyrimidin-4-yl)isoxazol-5-yl]methyl}-$N^4$-(3-cyclopropyl-1H-pyrazol-5-yl)-6-(4-methylpiperazin-1-yl)pyrimidine-2,4-diamine |
| 661 | 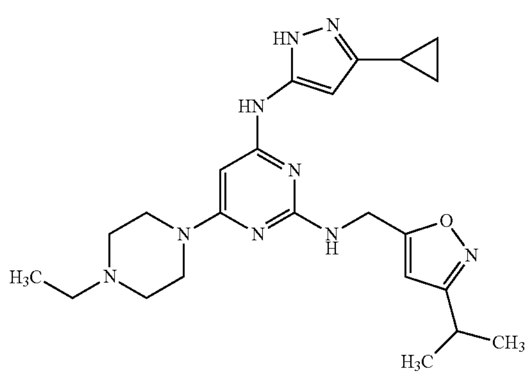 [SMILES: CCN1CCN(c2cc(Nc3cc(C4CC4)n[nH]3)nc(NCc3cc(C(C)C)no3)n2)CC1] | $N^4$-(3-cyclopropyl-1H-pyrazol-5-yl)-6-(4-ethylpiperazin-1-yl)-$N^2$-{[3-(1-methylethyl)isoxazol-5-yl]methyl}pyrimidine-2,4-diamine |

| Entry | Structure | Name |
|---|---|---|
| 662 | 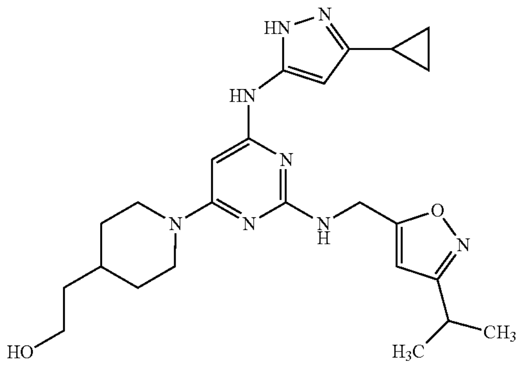 | 2-(1-{6-[(3-cyclopropyl-1H-pyrazol-5-yl)amino]-2-({[3-(1-methylethyl)isoxazol-5-yl]methyl}amino)pyrimidin-4-yl}piperidin-4-yl)ethanol |
| 663 | 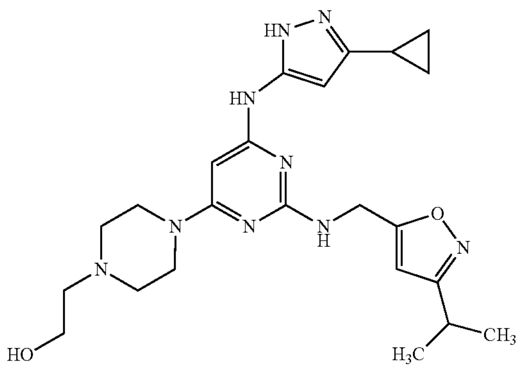 [SMILES: CC(C)c1cc(CNc2nc(Nc3cc(C4CC4)n[nH]3)cc(N3CCC(CCO)CC3)n2)on1] | 2-(4-{6-[(3-cyclopropyl-1H-pyrazol-5-yl)amino]-2-({[3-(1-methylethyl)isoxazol-5-yl]methyl}amino)pyrimidin-4-yl}piperazin-1-yl)ethanol |

The Compounds in Table 6 can be prepared as pharmaceutically acceptable salts, solvates, hydrates, and/or isomers thereof. All such salt, solvate, hydrate, and isomer combinations of the Compounds in Table 6 can be used to practice the invention.

| Entry | Name |
|---|---|
| 1 | 6-(2-butyl-1-hydroxy-3-oxo-2,3-dihydro-1H-isoindol-1-yl)-2H-1,4-benzoxazin-3(4H)-one |
| 2 | 6-[1-hydroxy-3-oxo-2-(2-phenylethyl)-2,3-dihydro-1H-isoindol-1-yl]-2H-1,4-benzoxazin-3(4H)-one |
| 3 | 6-(1-hydroxy-2-{[4-(methyloxy)phenyl]methyl}-3-oxo-2,3-dihydro-1H-isoindol-1-yl)-2H-1,4-benzoxazin-3(4H)-one |
| 4 | 6-(1-hydroxy-2-{[3-(methyloxy)phenyl]methyl}-3-oxo-2,3-dihydro-1H-isoindol-1-yl)-2H-1,4-benzoxazin-3(4H)-one |
| 5 | 6-{2-[(4-fluorophenyl)methyl]-1-hydroxy-3-oxo-2,3-dihydro-1H-isoindol-1-yl}-2H-1,4-benzoxazin-3(4H)-one |
| 6 | 6-(1-hydroxy-3-oxo-2-phenyl-2,3-dihydro-1H-isoindol-1-yl)-2H-1,4-benzoxazin-3(4H)-one |
| 7 | 6-{2-[(3-bromophenyl)methyl]-1-hydroxy-3-oxo-2,3-dihydro-1H-isoindol-1-yl}-2H-1,4-benzoxazin-3(4H)-one |
| 8 | 6-{2-[(4-bromophenyl)methyl]-1-hydroxy-3-oxo-2,3-dihydro-1H-isoindol-1-yl}-2H-1,4-benzoxazin-3(4H)-one |
| 9 | 6-[1-hydroxy-3-oxo-2-(3-phenylpropyl)-2,3-dihydro-1H-isoindol-1-yl]-2H-1,4-benzoxazin-3(4H)-one |
| 10 | 6-{2-[(3,4-dichlorophenyl)methyl]-1-hydroxy-3-oxo-2,3-dihydro-1H-isoindol-1-yl}-2H-1,4-benzoxazin-3(4H)-one |
| 11 | 6-{1-hydroxy-2-[(4-methylphenyl)methyl]-3-oxo-2,3-dihydro-1H-isoindol-1-yl}-2H-1,4-benzoxazin-3(4H)-one |
| 12 | 6-{2-[(4-chlorophenyl)methyl]-1-hydroxy-3-oxo-2,3-dihydro-1H-isoindol-1-yl}-2H-1,4-benzoxazin-3(4H)-one |
| 13 | 6-[1-hydroxy-2-(1-methylethyl)-3-oxo-2,3-dihydro-1H-isoindol-1-yl]-2H-1,4-benzoxazin-3(4H)-one |
| 14 | methyl {5-[1-hydroxy-3-oxo-2-(phenylmethyl)-2,3-dihydro-1H-isoindol-1-yl]-1H-benzimidazol-2-yl}carbamate |

| Entry | Name |
|---|---|
| 15 | 6-{2-[(3,4-dimethylphenyl)methyl]-1-hydroxy-3-oxo-2,3-dihydro-1H-isoindol-1-yl}-2H-1,4-benzoxazin-3(4H)-one |
| 16 | 6-(2-{[4-chloro-3-(trifluoromethyl)phenyl]methyl}-1-hydroxy-3-oxo-2,3-dihydro-1H-isoindol-1-yl)-2H-1,4-benzoxazin-3(4H)-one |
| 17 | 6-(2-{[4-(dimethylamino)phenyl]methyl}-1-hydroxy-3-oxo-2,3-dihydro-1H-isoindol-1-yl)-2H-1,4-benzoxazin-3(4H)-one |
| 18 | 6-[2-(3-chlorophenyl)-1-hydroxy-3-oxo-2,3-dihydro-1H-isoindol-1-yl]-2H-1,4-benzoxazin-3(4H)-one |
| 19 | 6-[2-(4-chlorophenyl)-1-hydroxy-3-oxo-2,3-dihydro-1H-isoindol-1-yl]-2H-1,4-benzoxazin-3(4H)-one |
| 20 | 6-[2-(3,4-dichlorophenyl)-1-hydroxy-3-oxo-2,3-dihydro-1H-isoindol-1-yl]-2H-1,4-benzoxazin-3(4H)-one |
| 21 | 6-[1-hydroxy-2-(4-methylphenyl)-3-oxo-2,3-dihydro-1H-isoindol-1-yl]-2H-1,4-benzoxazin-3(4H)-one |
| 22 | 3-(2-{[3,5-bis(methyloxy)phenyl]amino}-1H-benzimidazol-5-yl)-3-(methyloxy)-2-(phenylmethyl)-2,3-dihydro-1H-isoindol-1-one |
| 23 | 3-(2-{[3,5-bis(methyloxy)phenyl]amino}-1H-benzimidazol-5-yl)-2-(1-methylethyl)-3-(methyloxy)-2,3-dihydro-1H-isoindol-1-one |
| 24 | 3-(2-{[3,5-bis(methyloxy)phenyl]amino}-1H-benzimidazol-5-yl)-3-hydroxy-2-phenyl-2,3-dihydro-1H-isoindol-1-one |
| 25 | 3-(2-{[3,5-bis(methyloxy)phenyl]amino}-1H-benzimidazol-5-yl)-3-hydroxy-2-(phenylmethyl)-2,3-dihydro-1H-isoindol-1-one |
| 26 | methyl {5-[1-hydroxy-3-oxo-2-(phenylmethyl)-2,3-dihydro-1H-isoindol-1-yl]-1-methyl-1H-benzimidazol-2-yl}carbamate |
| 27 | 3-(1H-benzimidazol-5-yl)-3-hydroxy-2-(phenylmethyl)-2,3-dihydro-1H-isoindol-1-one |
| 28 | 5-[1-hydroxy-3-oxo-2-(phenylmethyl)-2,3-dihydro-1H-isoindol-1-yl]-N-methyl-1H-benzimidazole-2-carboxamide |
| 29 | 3-hydroxy-3-(2-methyl-1H-benzimidazol-5-yl)-2-(phenylmethyl)-2,3-dihydro-1H-isoindol-1-one |
| 30 | 7-[1-hydroxy-3-oxo-2-(phenylmethyl)-2,3-dihydro-1H-isoindol-1-yl]-3,4-dihydroquinoxalin-2(1H)-one |
| 31 | 7-[2-(3-chlorophenyl)-1-hydroxy-3-oxo-2,3-dihydro-1H-isoindol-1-yl]-3,4-dihydroquinoxalin-2(1H)-one |
| 32 | 1,1-dimethylethyl 4-{[1-hydroxy-3-oxo-1-(3-oxo-3,4-dihydro-2H-1,4-benzoxazin-6-yl)-1,3-dihydro-2H-isoindol-2-yl]methyl}piperidine-1-carboxylate |
| 33 | 6-(1-hydroxy-2-{[2-(methyloxy)phenyl]methyl}-3-oxo-2,3-dihydro-1H-isoindol-1-yl)-2H-1,4-benzoxazin-3(4H)-one |
| 34 | 6-{2-[(3-chlorophenyl)methyl]-1-hydroxy-3-oxo-2,3-dihydro-1H-isoindol-1-yl}-2H-1,4-benzoxazin-3(4H)-one |
| 35 | 6-{2-[(2-chlorophenyl)methyl]-1-hydroxy-3-oxo-2,3-dihydro-1H-isoindol-1-yl}-2H-1,4-benzoxazin-3(4H)-one |
| 36 | 6-{2-[(3-fluorophenyl)methyl]-1-hydroxy-3-oxo-2,3-dihydro-1H-isoindol-1-yl}-2H-1,4-benzoxazin-3(4H)-one |
| 37 | 6-{2-[(2-bromophenyl)methyl]-1-hydroxy-3-oxo-2,3-dihydro-1H-isoindol-1-yl}-2H-1,4-benzoxazin-3(4H)-one |
| 38 | 6-{2-[(2-fluorophenyl)methyl]-1-hydroxy-3-oxo-2,3-dihydro-1H-isoindol-1-yl}-2H-1,4-benzoxazin-3(4H)-one |
| 39 | 6-[2-(3-fluorophenyl)-1-hydroxy-3-oxo-2,3-dihydro-1H-isoindol-1-yl]-2H-1,4-benzoxazin-3(4H)-one |
| 40 | 6-[1-hydroxy-2-(3-iodophenyl)-3-oxo-2,3-dihydro-1H-isoindol-1-yl]-2H-1,4-benzoxazin-3(4H)-one |
| 41 | 6-[2-(3-bromophenyl)-1-hydroxy-3-oxo-2,3-dihydro-1H-isoindol-1-yl]-2H-1,4-benzoxazin-3(4H)-one |
| 42 | 6-[1-hydroxy-2-(3-nitrophenyl)-3-oxo-2,3-dihydro-1H-isoindol-1-yl]-2H-1,4-benzoxazin-3(4H)-one |
| 43 | 6-{1-hydroxy-2-[3-(methyloxy)phenyl]-3-oxo-2,3-dihydro-1H-isoindol-1-yl}-2H-1,4-benzoxazin-3(4H)-one |
| 44 | 6-[1-hydroxy-2-(3-methylphenyl)-3-oxo-2,3-dihydro-1H-isoindol-1-yl]-2H-1,4-benzoxazin-3(4H)-one |
| 45 | 3-hydroxy-3-(1H-indol-5-yl)-2-(phenylmethyl)-2,3-dihydro-1H-isoindol-1-one |
| 46 | methyl [6-(1-hydroxy-3-oxo-2-phenyl-2,3-dihydro-1H-isoindol-1-yl)-1H-benzimidazol-2-yl]carbamate |
| 47 | 6-[2-(2-aminophenyl)-1-hydroxy-3-oxo-2,3-dihydro-1H-isoindol-1-yl]-2H-1,4-benzoxazin-3(4H)-one |
| 48 | 6-{[2-(3-phenyl-1,2,4-oxadiazol-5-yl)phenyl]carbonyl}-2H-1,4-benzoxazin-3(4H)-one |
| 49 | 6-{[2-(1H-benzimidazol-2-yl)phenyl]carbonyl}-2H-1,4-benzoxazin-3(4H)-one |
| 50 | 6-(1-hydroxy-3-oxo-2-{[2-(trifluoromethyl)phenyl]methyl}-2,3-dihydro-1H-isoindol-1-yl)-2H-1,4-benzoxazin-3(4H)-one |
| 51 | 6-{2-[(5-bromo-2-fluorophenyl)methyl]-1-hydroxy-3-oxo-2,3-dihydro-1H-isoindol-1-yl}-2H-1,4-benzoxazin-3(4H)-one |
| 52 | 6-{1-hydroxy-2-[(3-nitrophenyl)methyl]-3-oxo-2,3-dihydro-1H-isoindol-1-yl}-2H-1,4-benzoxazin-3(4H)-one |
| 53 | 6-(1-hydroxy-3-oxo-2-{[3-(trifluoromethyl)phenyl]methyl}-2,3-dihydro-1H-isoindol-1-yl)-2H-1,4-benzoxazin-3(4H)-one |
| 54 | 6-(2-{[2,3-bis(methyloxy)phenyl]methyl}-1-hydroxy-3-oxo-2,3-dihydro-1H-isoindol-1-yl)-2H-1,4-benzoxazin-3(4H)-one |

-continued

| Entry | Name |
|---|---|
| 55 | 6-{1-hydroxy-2-[(3-iodophenyl)methyl]-3-oxo-2,3-dihydro-1H-isoindol-1-yl}-2H-1,4-benzoxazin-3(4H)-one |
| 56 | 6-[1-hydroxy-3-oxo-2-({3-[(trifluoromethyl)oxy]phenyl}methyl)-2,3-dihydro-1H-isoindol-1-yl]-2H-1,4-benzoxazin-3(4H)-one |
| 57 | 6-(1-hydroxy-2-{[2-(methylthio)phenyl]methyl}-3-oxo-2,3-dihydro-1H-isoindol-1-yl)-2H-1,4-benzoxazin-3(4H)-one |
| 58 | 6-[2-(3,4-difluorophenyl)-1-hydroxy-3-oxo-2,3-dihydro-1H-isoindol-1-yl]-2H-1,4-benzoxazin-3(4H)-one |
| 59 | 6-{1-hydroxy-2-[3-(1-methylethyl)phenyl]-3-oxo-2,3-dihydro-1H-isoindol-1-yl}-2H-1,4-benzoxazin-3(4H)-one |
| 60 | 6-(1-hydroxy-3-oxo-2-{3-[(trifluoromethyl)oxy]phenyl}-2,3-dihydro-1H-isoindol-1-yl)-2H-1,4-benzoxazin-3(4H)-one |
| 61 | 6-{1-hydroxy-3-oxo-2-[3-(trifluoromethyl)phenyl]-2,3-dihydro-1H-isoindol-1-yl}-2H-1,4-benzoxazin-3(4H)-one |
| 62 | 3-[1-hydroxy-3-oxo-1-(3-oxo-3,4-dihydro-2H-1,4-benzoxazin-6-yl)-1,3-dihydro-2H-isoindol-2-yl]benzenesulfonamide |
| 63 | 6-{2-[5-chloro-2-(methyloxy)phenyl]-1-hydroxy-3-oxo-2,3-dihydro-1H-isoindol-1-yl}-2H-1,4-benzoxazin-3(4H)-one |
| 64 | 6-{2-[4-fluoro-3-(trifluoromethyl)phenyl]-1-hydroxy-3-oxo-2,3-dihydro-1H-isoindol-1-yl}-2H-1,4-benzoxazin-3(4H)-one |
| 65 | 3-hydroxy-3-(1H-indol-6-yl)-2-(phenylmethyl)-2,3-dihydro-1H-isoindol-1-one |
| 66 | 6-[2-(3-fluoro-5-iodophenyl)-1-hydroxy-3-oxo-2,3-dihydro-1H-isoindol-1-yl]-2H-1,4-benzoxazin-3(4H)-one |
| 67 | 6-[2-(3-aminophenyl)-1-hydroxy-3-oxo-2,3-dihydro-1H-isoindol-1-yl]-2H-1,4-benzoxazin-3(4H)-one |
| 68 | 6-[2-(3,5-difluorophenyl)-1-hydroxy-3-oxo-2,3-dihydro-1H-isoindol-1-yl]-2H-1,4-benzoxazin-3(4H)-one |
| 69 | 6-{1-hydroxy-2-[3-(methylsulfonyl)phenyl]-3-oxo-2,3-dihydro-1H-isoindol-1-yl}-2H-1,4-benzoxazin-3(4H)-one |
| 70 | ethyl 3-[1-hydroxy-3-oxo-1-(3-oxo-3,4-dihydro-2H-1,4-benzoxazin-6-yl)-1,3-dihydro-2H-isoindol-2-yl]benzoate |
| 71 | 3-[1-hydroxy-3-oxo-1-(3-oxo-3,4-dihydro-2H-1,4-benzoxazin-6-yl)-1,3-dihydro-2H-isoindol-2-yl]benzonitrile |
| 72 | 6-[2-(2-chlorophenyl)-1-hydroxy-3-oxo-2,3-dihydro-1H-isoindol-1-yl]-2H-1,4-benzoxazin-3(4H)-one |
| 73 | 6-[2-(3-amino-5-chlorophenyl)-1-hydroxy-3-oxo-2,3-dihydro-1H-isoindol-1-yl]-2H-1,4-benzoxazin-3(4H)-one |
| 74 | 6-[2-(5-chloro-2-methylphenyl)-1-hydroxy-3-oxo-2,3-dihydro-1H-isoindol-1-yl]-2H-1,4-benzoxazin-3(4H)-one |
| 75 | 6-[2-(3-chloro-2-methylphenyl)-1-hydroxy-3-oxo-2,3-dihydro-1H-isoindol-1-yl]-2H-1,4-benzoxazin-3(4H)-one |
| 76 | 6-[2-(3-ethylphenyl)-1-hydroxy-3-oxo-2,3-dihydro-1H-isoindol-1-yl]-2H-1,4-benzoxazin-3(4H)-one |
| 77 | 6-[2-(3-ethynylphenyl)-1-hydroxy-3-oxo-2,3-dihydro-1H-isoindol-1-yl]-2H-1,4-benzoxazin-3(4H)-one |
| 78 | 6-[1-hydroxy-2-(3-hydroxyphenyl)-3-oxo-2,3-dihydro-1H-isoindol-1-yl]-2H-1,4-benzoxazin-3(4H)-one |
| 79 | 6-{1-hydroxy-3-oxo-2-[3-(phenyloxy)phenyl]-2,3-dihydro-1H-isoindol-1-yl}-2H-1,4-benzoxazin-3(4H)-one |
| 80 | 6-(1-hydroxy-3-oxo-2-{3-[(phenylmethyl)oxy]phenyl}-2,3-dihydro-1H-isoindol-1-yl)-2H-1,4-benzoxazin-3(4H)-one |
| 81 | 3-[1-hydroxy-3-oxo-1-(3-oxo-3,4-dihydro-2H-1,4-benzoxazin-6-yl)-1,3-dihydro-2H-isoindol-2-yl]benzamide |
| 82 | 6-{1-hydroxy-2-[3-(hydroxymethyl)phenyl]-3-oxo-2,3-dihydro-1H-isoindol-1-yl}-2H-1,4-benzoxazin-3(4H)-one |
| 83 | 6-[2-(2-fluorophenyl)-1-hydroxy-3-oxo-2,3-dihydro-1H-isoindol-1-yl]-2H-1,4-benzoxazin-3(4H)-one |
| 84 | 3-hydroxy-3-[2-(methylamino)-1H-benzimidazol-5-yl]-2-(phenylmethyl)-2,3-dihydro-1H-isoindol-1-one |
| 85 | 6-(2-biphenyl-3-yl-1-hydroxy-3-oxo-2,3-dihydro-1H-isoindol-1-yl)-2H-1,4-benzoxazin-3(4H)-one |
| 86 | 6-(2-{3-[(dimethylamino)methyl]phenyl}-1-hydroxy-3-oxo-2,3-dihydro-1H-isoindol-1-yl)-2H-1,4-benzoxazin-3(4H)-one |
| 87 | 6-[2-(3,5-dichlorophenyl)-1-hydroxy-3-oxo-2,3-dihydro-1H-isoindol-1-yl]-2H-1,4-benzoxazin-3(4H)-one |
| 88 | 6-(1-hydroxy-3-oxo-2-piperidin-4-yl-2,3-dihydro-1H-isoindol-1-yl)-2H-1,4-benzoxazin-3(4H)-one |
| 89 | 6-[2-(3-{[2-(dimethylamino)ethyl]oxy}phenyl)-1-hydroxy-3-oxo-2,3-dihydro-1H-isoindol-1-yl]-2H-1,4-benzoxazin-3(4H)-one |
| 90 | 6-[1-hydroxy-2-(2-methylphenyl)-3-oxo-2,3-dihydro-1H-isoindol-1-yl]-2H-1,4-benzoxazin-3(4H)-one |
| 91 | N-methyl-2-[(3-oxo-3,4-dihydro-2H-1,4-benzoxazin-6-yl)carbonyl]-N-phenylbenzamide |
| 92 | methyl {5-[1-(ethyloxy)-3-oxo-2-(phenylmethyl)-2,3-dihydro-1H-isoindol-1-yl]-1H-benzimidazol-2-yl}carbamate |
| 93 | phenylmethyl 2-[(2-{[(methyloxy)carbonyl]amino}-1H-benzimidazol-5-yl)carbonyl]benzoate |

-continued

| Entry | Name |
|---|---|
| 94 | 3-hydroxy-3-(1H-indazol-5-yl)-2-(phenylmethyl)-2,3-dihydro-1H-isoindol-1-one |
| 95 | 3-hydroxy-3-(1H-indazol-6-yl)-2-(phenylmethyl)-2,3-dihydro-1H-isoindol-1-one |
| 96 | ethyl {5-[1-hydroxy-3-oxo-2-(phenylmethyl)-2,3-dihydro-1H-isoindol-1-yl]-1H-benzimidazol-2-yl}carbamate |
| 97 | 2-methylpropyl {5-[1-hydroxy-3-oxo-2-(phenylmethyl)-2,3-dihydro-1H-isoindol-1-yl]-1H-benzimidazol-2-yl}carbamate |
| 98 | methyl {5-[1-hydroxy-3-oxo-2-(2-thienylmethyl)-2,3-dihydro-1H-isoindol-1-yl]-1H-benzimidazol-2-yl}carbamate |
| 99 | methyl {5-[1-hydroxy-3-oxo-2-(2-phenylethyl)-2,3-dihydro-1H-isoindol-1-yl]-1H-benzimidazol-2-yl}carbamate |
| 100 | 3-[2-amino-1-(1,1-dimethylethyl)-1H-benzimidazol-5-yl]-3-hydroxy-2-(phenylmethyl)-2,3-dihydro-1H-isoindol-1-one |
| 101 | 3-(2-amino-1H-benzimidazol-5-yl)-3-hydroxy-2-(phenylmethyl)-2,3-dihydro-1H-isoindol-1-one |
| 102 | methyl [5-(1-hydroxy-3-oxo-2,3-dihydro-1H-isoindol-1-yl)-1H-benzimidazol-2-yl]carbamate |
| 103 | 3-(methyloxy)butyl {5-[1-hydroxy-3-oxo-2-(phenylmethyl)-2,3-dihydro-1H-isoindol-1-yl]-1H-benzimidazol-2-yl}carbamate |
| 104 | methyl (5-{1-hydroxy-3-oxo-2-[(1R)-1-phenylethyl]-2,3-dihydro-1H-isoindol-1-yl}-1H-benzimidazol-2-yl)carbamate |
| 105 | methyl (5-{1-hydroxy-3-oxo-2-[(1S)-1-phenylethyl]-2,3-dihydro-1H-isoindol-1-yl)-1H-benzimidazol-2-yl)carbamate |
| 106 | 2-(methyloxy)ethyl {5-[1-hydroxy-3-oxo-2-(phenylmethyl)-2,3-dihydro-1H-isoindol-1-yl]-1H-benzimidazol-2-yl}carbamate |
| 107 | methyl {6-[1-hydroxy-3-oxo-2-(phenylmethyl)-2,3-dihydro-1H-isoindol-1-yl]-1-methyl-1H-benzimidazol-2-yl}carbamate |
| 108 | prop-2-yn-1-yl {5-[1-hydroxy-3-oxo-2-(phenylmethyl)-2,3-dihydro-1H-isoindol-1-yl]-1H-benzimidazol-2-yl}carbamate |
| 109 | but-2-yn-1-yl {5-[1-hydroxy-3-oxo-2-(phenylmethyl)-2,3-dihydro-1H-isoindol-1-yl]-1H-benzimidazol-2-yl}carbamate |
| 110 | 1-methylethyl {5-[1-hydroxy-3-oxo-2-(phenylmethyl)-2,3-dihydro-1H-isoindol-1-yl]-1H-benzimidazol-2-yl}carbamate |
| 111 | methyl {5-[2-(2,3-dihydro-1H-inden-2-yl)-1-hydroxy-3-oxo-2,3-dihydro-1H-isoindol-1-yl]-1H-benzimidazol-2-yl}carbamate |
| 112 | methyl {5-[1-hydroxy-3-oxo-2-(pyridin-4-ylmethyl)-2,3-dihydro-1H-isoindol-1-yl]-1H-benzimidazol-2-yl}carbamate |
| 113 | methyl {5-[1-hydroxy-3-oxo-2-(pyridin-3-ylmethyl)-2,3-dihydro-1H-isoindol-1-yl]-1H-benzimidazol-2-yl}carbamate |
| 114 | methyl (6-{2-[(3-fluorophenyl)methyl]-1-hydroxy-3-oxo-2,3-dihydro-1H-isoindol-1-yl}-1H-benzimidazol-2-yl)carbamate |
| 115 | methyl {5-[1-hydroxy-2-(3-methylphenyl)-3-oxo-2,3-dihydro-1H-isoindol-1-yl]-1H-benzimidazol-2-yl}carbamate |
| 116 | methyl [5-(1-hydroxy-2-{[2-(methyloxy)phenyl]methyl}-3-oxo-2,3-dihydro-1H-isoindol-1-yl)-1H-benzimidazol-2-yl]carbamate |
| 117 | methyl [5-(1-hydroxy-2-{[3-(methyloxy)phenyl]methyl}-3-oxo-2,3-dihydro-1H-isoindol-1-yl)-1H-benzimidazol-2-yl]carbamate |
| 118 | methyl [5-(1-hydroxy-2-{[4-(methyloxy)phenyl]methyl}-3-oxo-2,3-dihydro-1H-isoindol-1-yl)-1H-benzimidazol-2-yl]carbamate |
| 119 | methyl (6-{2-[(4-fluorophenyl)methyl]-1-hydroxy-3-oxo-2,3-dihydro-1H-isoindol-1-yl}-1H-benzimidazol-2-yl)carbamate |
| 120 | methyl (6-{2-[(3-bromophenyl)methyl]-1-hydroxy-3-oxo-2,3-dihydro-1H-isoindol-1-yl}-1H-benzimidazol-2-yl)carbamate |
| 121 | methyl (5-{1-hydroxy-2-[(3-iodophenyl)methyl]-3-oxo-2,3-dihydro-1H-isoindol-1-yl}-1H-benzimidazol-2-yl)carbamate |
| 122 | methyl (5-{2-[(3-chlorophenyl)methyl]-1-hydroxy-3-oxo-2,3-dihydro-1H-isoindol-1-yl}-1H-benzimidazol-2-yl)carbamate |
| 123 | methyl (5-{2-[(2-fluorophenyl)methyl]-1-hydroxy-3-oxo-2,3-dihydro-1H-isoindol-1-yl}-1H-benzimidazol-2-yl)carbamate |
| 124 | methyl {5-[1-hydroxy-3-oxo-2-(pyridin-2-ylmethyl)-2,3-dihydro-1H-isoindol-1-yl]-1H-benzimidazol-2-yl}carbamate |
| 125 | phenylmethyl {5-[1-hydroxy-3-oxo-2-(phenylmethyl)-2,3-dihydro-1H-isoindol-1-yl]-1H-benzimidazol-2-yl}carbamate |
| 126 | 2-fluoroethyl {5-[1-hydroxy-3-oxo-2-(phenylmethyl)-2,3-dihydro-1H-isoindol-1-yl]-1H-benzimidazol-2-yl}carbamate |
| 127 | propyl {5-[1-hydroxy-3-oxo-2-(phenylmethyl)-2,3-dihydro-1H-isoindol-1-yl]-1H-benzimidazol-2-yl}carbamate |
| 128 | methyl (5-{1-hydroxy-2-[4-(methyloxy)phenyl]-3-oxo-2,3-dihydro-1H-isoindol-1-yl}-1H-benzimidazol-2-yl)carbamate |
| 129 | methyl (5-{2-[(2-chlorophenyl)methyl]-1-hydroxy-3-oxo-2,3-dihydro-1H-isoindol-1-yl}-1H-benzimidazol-2-yl)carbamate |
| 130 | methyl (5-{2-[(2-bromophenyl)methyl]-1-hydroxy-3-oxo-2,3-dihydro-1H-isoindol-1-yl}-1H-benzimidazol-2-yl)carbamate |
| 131 | methyl (5-{1-hydroxy-2-[(3-methylphenyl)methyl]-3-oxo-2,3-dihydro-1H-isoindol-1-yl}-1H-benzimidazol-2-yl)carbamate |
| 132 | methyl (5-{1-hydroxy-2-[(4-methylphenyl)methyl]-3-oxo-2,3-dihydro-1H-isoindol-1-yl}-1H-benzimidazol-2-yl)carbamate |
| 133 | methyl (5-{1-hydroxy-2-[(2-methylphenyl)methyl]-3-oxo-2,3-dihydro-1H-isoindol-1-yl}-1H-benzimidazol-2-yl)carbamate |

| Entry | Name |
|---|---|
| 134 | methyl {5-[2-(3-bromophenyl)-1-hydroxy-3-oxo-2,3-dihydro-1H-isoindol-1-yl]-1H-benzimidazol-2-yl}carbamate |
| 135 | methyl {5-[2-(3-chlorophenyl)-1-hydroxy-3-oxo-2,3-dihydro-1H-isoindol-1-yl]-1H-benzimidazol-2-yl}carbamate |
| 136 | methyl {5-[2-(3-fluorophenyl)-1-hydroxy-3-oxo-2,3-dihydro-1H-isoindol-1-yl]-1H-benzimidazol-2-yl}carbamate |
| 137 | methyl (5-{1-hydroxy-2-[3-(methyloxy)phenyl]-3-oxo-2,3-dihydro-1H-isoindol-1-yl}-1H-benzimidazol-2-yl)carbamate |
| 138 | methyl {5-[2-(4-bromophenyl)-1-hydroxy-3-oxo-2,3-dihydro-1H-isoindol-1-yl]-1H-benzimidazol-2-yl}carbamate |
| 139 | methyl {5-[2-(4-chlorophenyl)-1-hydroxy-3-oxo-2,3-dihydro-1H-isoindol-1-yl]-1H-benzimidazol-2-yl}carbamate |
| 140 | methyl {5-[2-(4-fluorophenyl)-1-hydroxy-3-oxo-2,3-dihydro-1H-isoindol-1-yl]-1H-benzimidazol-2-yl}carbamate |
| 141 | methyl {5-[2-(3,5-dimethylphenyl)-1-hydroxy-3-oxo-2,3-dihydro-1H-isoindol-1-yl]-1H-benzimidazol-2-yl}carbamate |
| 142 | methyl {5-[2-(2-fluorophenyl)-1-hydroxy-3-oxo-2,3-dihydro-1H-isoindol-1-yl]-1H-benzimidazol-2-yl}carbamate |
| 143 | methyl {5-[2-(2-chlorophenyl)-1-hydroxy-3-oxo-2,3-dihydro-1H-isoindol-1-yl]-1H-benzimidazol-2-yl}carbamate |
| 144 | methyl {5-[1-hydroxy-2-(2-methylphenyl)-3-oxo-2,3-dihydro-1H-isoindol-1-yl]-1H-benzimidazol-2-yl}carbamate |
| 145 | methyl (5-{1-hydroxy-2-[2-(methyloxy)phenyl]-3-oxo-2,3-dihydro-1H-isoindol-1-yl}-1H-benzimidazol-2-yl)carbamate |
| 146 | methyl {5-[1-hydroxy-2-(4-methylphenyl)-3-oxo-2,3-dihydro-1H-isoindol-1-yl]-1H-benzimidazol-2-yl}carbamate |
| 147 | methyl (5-{1-hydroxy-3-oxo-2-[3-(trifluoromethyl)phenyl]-2,3-dihydro-1H-isoindol-1-yl}-1H-benzimidazol-2-yl)carbamate |
| 148 | but-2-yn-1-yl (5-{1-hydroxy-3-oxo-2-[(1R)-1-phenylethyl]-2,3-dihydro-1H-isoindol-1-yl}-1H-benzimidazol-2-yl)carbamate |
| 149 | N-ethyl-N'-{5-[1-hydroxy-3-oxo-2-(phenylmethyl)-2,3-dihydro-1H-isoindol-1-yl]-1H-benzimidazol-2-yl}urea |
| 150 | phenylmethyl (5-{1-hydroxy-3-oxo-2-[(1R)-1-phenylethyl]-2,3-dihydro-1H-isoindol-1-yl}-1H-benzimidazol-2-yl)carbamate |
| 151 | methyl {6-[2-(3-amino-5-chlorophenyl)-1-hydroxy-3-oxo-2,3-dihydro-1H-isoindol-1-yl]-1H-benzimidazol-2-yl}carbamate |
| 152 | piperidin-4-ylmethyl {5-[1-hydroxy-3-oxo-2-(phenylmethyl)-2,3-dihydro-1H-isoindol-1-yl]-1H-benzimidazol-2-yl}carbamate |
| 153 | methyl {5-[2-(cyclopropylmethyl)-1-hydroxy-3-oxo-2,3-dihydro-1H-isoindol-1-yl]-1H-benzimidazol-2-yl}carbamate |
| 154 | methyl {5-[2-(2,2-dimethylpropyl)-1-hydroxy-3-oxo-2,3-dihydro-1H-isoindol-1-yl]-1H-benzimidazol-2-yl}carbamate |
| 155 | methyl {5-[2-(3,5-dichlorophenyl)-1-hydroxy-3-oxo-2,3-dihydro-1H-isoindol-1-yl]-1H-benzimidazol-2-yl}carbamate |
| 156 | methyl {5-[2-(3,5-difluorophenyl)-1-hydroxy-3-oxo-2,3-dihydro-1H-isoindol-1-yl]-1H-benzimidazol-2-yl}carbamate |
| 157 | N-ethyl-N'-(5-{1-hydroxy-3-oxo-2-[(1R)-1-phenylethyl]-2,3-dihydro-1H-isoindol-1-yl}-1H-benzimidazol-2-yl)urea |
| 158 | N'-{5-[1-hydroxy-3-oxo-2-(phenylmethyl)-2,3-dihydro-1H-isoindol-1-yl]-1H-benzimidazol-2-yl}-N,N-dimethylurea |
| 159 | methyl {5-[2-(3-{[2-(dimethylamino)ethyl]oxy}phenyl)-1-hydroxy-3-oxo-2,3-dihydro-1H-isoindol-1-yl]-1H-benzimidazol-2-yl}carbamate |
| 160 | 3-(4-methylpiperazin-1-yl)propyl {6-[1-hydroxy-3-oxo-2-(phenylmethyl)-2,3-dihydro-1H-isoindol-1-yl]-1H-benzimidazol-2-yl}carbamate |
| 161 | methyl {5-[2-(cyclohexylmethyl)-1-hydroxy-3-oxo-2,3-dihydro-1H-isoindol-1-yl]-1H-benzimidazol-2-yl}carbamate |
| 162 | methyl {5-[1-hydroxy-2-(2-methylpropyl)-3-oxo-2,3-dihydro-1H-isoindol-1-yl]-1H-benzimidazol-2-yl}carbamate |
| 163 | methyl {5-[1-hydroxy-3-oxo-2-(1,3-thiazol-2-ylmethyl)-2,3-dihydro-1H-isoindol-1-yl]-1H-benzimidazol-2-yl}carbamate |
| 164 | methyl {5-[2-(3,4-difluorophenyl)-1-hydroxy-3-oxo-2,3-dihydro-1H-isoindol-1-yl]-1H-benzimidazol-2-yl}carbamate |
| 165 | methyl (5-{2-[1-(3,5-difluorophenyl)ethyl]-1-hydroxy-3-oxo-2,3-dihydro-1H-isoindol-1-yl}-1H-benzimidazol-2-yl)carbamate |
| 166 | methyl (5-{2-[1-(3-fluorophenyl)ethyl]-1-hydroxy-3-oxo-2,3-dihydro-1H-isoindol-1-yl}-1H-benzimidazol-2-yl)carbamate |
| 167 | methyl [5-(2-cyclohexyl-1-hydroxy-3-oxo-2,3-dihydro-1H-isoindol-1-yl)-1H-benzimidazol-2-yl]carbamate |
| 168 | methyl {5-[2-(2,5-difluorophenyl)-1-hydroxy-3-oxo-2,3-dihydro-1H-isoindol-1-yl]-1H-benzimidazol-2-yl}carbamate |
| 169 | N-{5-[1-hydroxy-3-oxo-2-(phenylmethyl)-2,3-dihydro-1H-isoindol-1-yl]-1H-benzimidazol-2-yl}-N'-(phenylmethyl)urea |
| 170 | piperidin-4-yl {5-[1-hydroxy-3-oxo-2-(phenylmethyl)-2,3-dihydro-1H-isoindol-1-yl]-1H-benzimidazol-2-yl}carbamate |
| 171 | N-{5-[1-hydroxy-3-oxo-2-(phenylmethyl)-2,3-dihydro-1H-isoindol-1-yl]-1H-benzimidazol-2-yl}-N'-methylurea |
| 172 | methyl (5-{2-[1-(2-fluorophenyl)ethyl]-1-hydroxy-3-oxo-2,3-dihydro-1H-isoindol-1-yl}-1H-benzimidazol-2-yl)carbamate |

-continued

| Entry | Name |
|---|---|
| 173 | methyl (5-{1-hydroxy-3-oxo-2-[1-(2-thienyl)ethyl]-2,3-dihydro-1H-isoindol-1-yl}-1H-benzimidazol-2-yl)carbamate |
| 174 | methyl (5-{2-[1-(3-chlorophenyl)ethyl]-1-hydroxy-3-oxo-2,3-dihydro-1H-isoindol-1-yl}-1H-benzimidazol-2-yl)carbamate |
| 175 | methyl (5-{1-hydroxy-2-[3-methyl-5-(trifluoromethyl)phenyl]-3-oxo-2,3-dihydro-1H-isoindol-1-yl}-1H-benzimidazol-2-yl)carbamate |
| 176 | N-{5-[1-hydroxy-3-oxo-2-(phenylmethyl)-2,3-dihydro-1H-isoindol-1-yl]-1H-benzimidazol-2-yl}propanamide |
| 177 | methyl {5-[2-(3,4-dichlorophenyl)-1-hydroxy-3-oxo-2,3-dihydro-1H-isoindol-1-yl]-1H-benzimidazol-2-yl}carbamate |
| 178 | methyl {5-[2-(3-ethylphenyl)-1-hydroxy-3-oxo-2,3-dihydro-1H-isoindol-1-yl]-1H-benzimidazol-2-yl}carbamate |
| 179 | methyl {5-[2-(3-ethynylphenyl)-1-hydroxy-3-oxo-2,3-dihydro-1H-isoindol-1-yl]-1H-benzimidazol-2-yl}carbamate |
| 180 | methyl {5-[2-(4-chloro-3-methylphenyl)-1-hydroxy-3-oxo-2,3-dihydro-1H-isoindol-1-yl]-1H-benzimidazol-2-yl}carbamate |
| 181 | methyl [5-(1-hydroxy-3-oxo-2-{1-[3-(trifluoromethyl)phenyl]ethyl}-2,3-dihydro-1H-isoindol-1-yl)-1H-benzimidazol-2-yl]carbamate |
| 182 | methyl (5-{1-hydroxy-3-oxo-2-[(1R)-1-phenylpropyl]-2,3-dihydro-1H-isoindol-1-yl}-1H-benzimidazol-2-yl)carbamate |
| 183 | methyl [5-(1-hydroxy-3-oxo-2-{2-[(trifluoromethyl)oxy]phenyl}-2,3-dihydro-1H-isoindol-1-yl)-1H-benzimidazol-2-yl]carbamate |
| 184 | methyl {5-[2-(2,3-difluorophenyl)-1-hydroxy-3-oxo-2,3-dihydro-1H-isoindol-1-yl]-1H-benzimidazol-2-yl}carbamate |
| 185 | cyclohexyl {5-[1-hydroxy-3-oxo-2-(phenylmethyl)-2,3-dihydro-1H-isoindol-1-yl]-1H-benzimidazol-2-yl}carbamate |
| 186 | tetrahydrofuran-2-ylmethyl {5-[1-hydroxy-3-oxo-2-(phenylmethyl)-2,3-dihydro-1H-isoindol-1-yl]-1H-benzimidazol-2-yl}carbamate |
| 187 | cyclopropylmethyl {5-[1-hydroxy-3-oxo-2-(phenylmethyl)-2,3-dihydro-1H-isoindol-1-yl]-1H-benzimidazol-2-yl}carbamate |
| 188 | N-{5-[1-hydroxy-3-oxo-2-(phenylmethyl)-2,3-dihydro-1H-isoindol-1-yl]-1H-benzimidazol-2-yl}morpholine-4-carboxamide |
| 189 | methyl {5-[2-(cyclopentylmethyl)-1-hydroxy-3-oxo-2,3-dihydro-1H-isoindol-1-yl]-1H-benzimidazol-2-yl}carbamate |
| 190 | methyl {5-[2-(2,3-dimethylphenyl)-1-hydroxy-3-oxo-2,3-dihydro-1H-isoindol-1-yl]-1H-benzimidazol-2-yl}carbamate |
| 191 | methyl {5-[2-(2,3-dihydro-1H-inden-1-yl)-1-hydroxy-3-oxo-2,3-dihydro-1H-isoindol-1-yl]-1H-benzimidazol-2-yl}carbamate |
| 192 | methyl (2S)-cyclohexyl[1-hydroxy-1-(2-{[(methyloxy)carbonyl]amino}-1H-benzimidazol-5-yl)-3-oxo-1,3-dihydro-2H-isoindol-2-yl]ethanoate |
| 193 | methyl {5-[2-(2,6-difluorophenyl)-1-hydroxy-3-oxo-2,3-dihydro-1H-isoindol-1-yl]-1H-benzimidazol-2-yl}carbamate |
| 194 | methyl {5-[2-(3-chloro-4-fluorophenyl)-1-hydroxy-3-oxo-2,3-dihydro-1H-isoindol-1-yl]-1H-benzimidazol-2-yl}carbamate |
| 195 | but-3-en-1-yl {5-[1-hydroxy-3-oxo-2-(phenylmethyl)-2,3-dihydro-1H-isoindol-1-yl]-1H-benzimidazol-2-yl}carbamate |
| 196 | 2,2,2-trifluoroethyl {5-[1-hydroxy-3-oxo-2-(phenylmethyl)-2,3-dihydro-1H-isoindol-1-yl]-1H-benzimidazol-2-yl}carbamate |
| 197 | methyl {5-[2-(5-chloro-2-fluorophenyl)-1-hydroxy-3-oxo-2,3-dihydro-1H-isoindol-1-yl]-1H-benzimidazol-2-yl}carbamate |
| 198 | methyl (5-{2-[1-(5-chloro-2-methylphenyl)ethyl]-1-hydroxy-3-oxo-2,3-dihydro-1H-isoindol-1-yl}-1H-benzimidazol-2-yl)carbamate |
| 199 | methyl (5-{1-hydroxy-3-oxo-2-[(1S)-1-phenylpropyl]-2,3-dihydro-1H-isoindol-1-yl}-1H-benzimidazol-2-yl)carbamate |
| 200 | methyl (5-{2-[1-(3-chloro-2-methylphenyl)ethyl]-1-hydroxy-3-oxo-2,3-dihydro-1H-isoindol-1-yl}-1H-benzimidazol-2-yl)carbamate |
| 201 | methyl (5-{1-hydroxy-2-[1-(5-methyl-2-thienyl)ethyl]-3-oxo-2,3-dihydro-1H-isoindol-1-yl}-1H-benzimidazol-2-yl)carbamate |
| 202 | methyl (5-{2-[1-(5-chloro-2-thienyl)ethyl]-1-hydroxy-3-oxo-2,3-dihydro-1H-isoindol-1-yl}-1H-benzimidazol-2-yl)carbamate |
| 203 | methyl {5-[1-hydroxy-2-(3-iodophenyl)-3-oxo-2,3-dihydro-1H-isoindol-1-yl]-1H-benzimidazol-2-yl}carbamate |
| 204 | methyl (5-{1-hydroxy-2-[3-(1-methylethyl)phenyl]-3-oxo-2,3-dihydro-1H-isoindol-1-yl}-1H-benzimidazol-2-yl)carbamate |
| 205 | methyl {5-[2-(furan-2-ylmethyl)-1-hydroxy-3-oxo-2,3-dihydro-1H-isoindol-1-yl]-1H-benzimidazol-2-yl}carbamate |
| 206 | methyl {5-[1-hydroxy-3-oxo-2-(3-thienylmethyl)-2,3-dihydro-1H-isoindol-1-yl]-1H-benzimidazol-2-yl}carbamate |
| 207 | methyl {5-[2-(cyclobutylmethyl)-1-hydroxy-3-oxo-2,3-dihydro-1H-isoindol-1-yl]-1H-benzimidazol-2-yl}carbamate |
| 208 | 3,3,3-trifluoro-2-hydroxy-N-{5-[1-hydroxy-3-oxo-2-(phenylmethyl)-2,3-dihydro-1H-isoindol-1-yl]-1H-benzimidazol-2-yl}-2-(trifluoromethyl)propanamide |
| 209 | methyl (5-{1-hydroxy-2-[1-(4-methyl-2-thienyl)ethyl]-3-oxo-2,3-dihydro-1H-isoindol-1-yl}-1H-benzimidazol-2-yl)carbamate |
| 210 | methyl (5-{2-[1-(4-bromo-2-thienyl)ethyl]-1-hydroxy-3-oxo-2,3-dihydro-1H-isoindol-1-yl}-1H-benzimidazol-2-yl)carbamate |
| 211 | methyl {5-[1-hydroxy-2-(3-{[2-(methyloxy)ethyl]oxy}phenyl)-3-oxo-2,3-dihydro-1H-isoindol-1-yl]-1H-benzimidazol-2-yl}carbamate |

-continued

| Entry | Name |
|---|---|
| 212 | tetrahydrofuran-3-ylmethyl {5-[1-hydroxy-3-oxo-2-(phenylmethyl)-2,3-dihydro-1H-isoindol-1-yl]-1H-benzimidazol-2-yl}carbamate |
| 213 | N-{5-[1-hydroxy-3-oxo-2-(phenylmethyl)-2,3-dihydro-1H-isoindol-1-yl]-1H-benzimidazol-2-yl}piperidine-1-carboxamide |
| 214 | methyl {5-[2-(3-bromo-4-fluorophenyl)-1-hydroxy-3-oxo-2,3-dihydro-1H-isoindol-1-yl]-1H-benzimidazol-2-yl}carbamate |
| 215 | 2,3-dihydroxypropyl {5-[1-hydroxy-3-oxo-2-(phenylmethyl)-2,3-dihydro-1H-isoindol-1-yl]-1H-benzimidazol-2-yl}carbamate |
| 216 | methyl {5-[1-hydroxy-3-oxo-2-(tetrahydrofuran-2-ylmethyl)-2,3-dihydro-1H-isoindol-1-yl]-1H-benzimidazol-2-yl}carbamate |
| 217 | methyl (5-{2-[3-(aminocarbonyl)phenyl]-1-hydroxy-3-oxo-2,3-dihydro-1H-isoindol-1-yl}-1H-benzimidazol-2-yl)carbamate |
| 218 | 4,4,4-trifluoro-3-hydroxy-N-{5-[1-hydroxy-3-oxo-2-(phenylmethyl)-2,3-dihydro-1H-isoindol-1-yl]-1H-benzimidazol-2-yl}-3-(trifluoromethyl)butanamide |
| 219 | methyl (5-{1-hydroxy-2-[3-(methylsulfonyl)phenyl]-3-oxo-2,3-dihydro-1H-isoindol-1-yl}-1H-benzimidazol-2-yl)carbamate |
| 220 | methyl (5-{1-hydroxy-3-oxo-2-[3-(phenyloxy)phenyl]-2,3-dihydro-1H-isoindol-1-yl}-1H-benzimidazol-2-yl)carbamate |
| 221 | methyl [5-(1-hydroxy-3-oxo-2-{3-[(phenylmethyl)oxy]phenyl}-2,3-dihydro-1H-isoindol-1-yl)-1H-benzimidazol-2-yl]carbamate |
| 222 | methyl [5-(2-biphenyl-3-yl-1-hydroxy-3-oxo-2,3-dihydro-1H-isoindol-1-yl)-1H-benzimidazol-2-yl]carbamate |
| 223 | 2,2-dimethyl-3-[(phenylmethyl)oxy]propyl {5-[1-hydroxy-3-oxo-2-(phenylmethyl)-2,3-dihydro-1H-isoindol-1-yl]-1H-benzimidazol-2-yl}carbamate |
| 224 | methyl {5-[2-(3-chloro-2-fluorophenyl)-1-hydroxy-3-oxo-2,3-dihydro-1H-isoindol-1-yl]-1H-benzimidazol-2-yl}carbamate |
| 225 | methyl {5-[2-(3-cyanophenyl)-1-hydroxy-3-oxo-2,3-dihydro-1H-isoindol-1-yl]-1H-benzimidazol-2-yl}carbamate |
| 226 | methyl {5-[2-(3-ethynyl-4-fluorophenyl)-1-hydroxy-3-oxo-2,3-dihydro-1H-isoindol-1-yl]-1H-benzimidazol-2-yl}carbamate |
| 227 | methyl {5-[2-(4-fluoro-3-methylphenyl)-1-hydroxy-3-oxo-2,3-dihydro-1H-isoindol-1-yl]-1H-benzimidazol-2-yl}carbamate |
| 228 | methyl {6-[2-(3,4-dichloro-2-fluorophenyl)-1-hydroxy-3-oxo-2,3-dihydro-1H-isoindol-1-yl]-1H-benzimidazol-2-yl}carbamate |
| 229 | [(4S)-2,2-dimethyl-1,3-dioxolan-4-yl]methyl {5-[1-hydroxy-3-oxo-2-(phenylmethyl)-2,3-dihydro-1H-isoindol-1-yl]-1H-benzimidazol-2-yl}carbamate |
| 230 | methyl {5-[2-(5-bromo-2-fluorophenyl)-1-hydroxy-3-oxo-2,3-dihydro-1H-isoindol-1-yl]-1H-benzimidazol-2-yl}carbamate |
| 231 | methyl (5-{2-[3-(acetylamino)phenyl]-1-hydroxy-3-oxo-2,3-dihydro-1H-isoindol-1-yl}-1H-benzimidazol-2-yl)carbamate |
| 232 | methyl (5-{1-hydroxy-3-oxo-2-[3-(phenylmethyl)phenyl]-2,3-dihydro-1H-isoindol-1-yl}-1H-benzimidazol-2-yl)carbamate |
| 233 | methyl (5-{2-[1-(4-chloro-2-thienyl)ethyl]-1-hydroxy-3-oxo-2,3-dihydro-1H-isoindol-1-yl}-1H-benzimidazol-2-yl)carbamate |
| 234 | methyl (5-{1-hydroxy-3-oxo-2-[3-(phenylcarbonyl)phenyl]-2,3-dihydro-1H-isoindol-1-yl}-1H-benzimidazol-2-yl)carbamate |
| 235 | methyl [5-(2-{3-[(dimethylamino)methyl]phenyl}-1-hydroxy-3-oxo-2,3-dihydro-1H-isoindol-1-yl)-1H-benzimidazol-2-yl]carbamate |
| 236 | methyl (5-{2-[3-(aminosulfonyl)phenyl]-1-hydroxy-3-oxo-2,3-dihydro-1H-isoindol-1-yl}-1H-benzimidazol-2-yl)carbamate |
| 237 | methyl {5-[2-(3-acetylphenyl)-1-hydroxy-3-oxo-2,3-dihydro-1H-isoindol-1-yl]-1H-benzimidazol-2-yl}carbamate |
| 238 | methyl {5-[2-(3-ethyl-4-fluorophenyl)-1-hydroxy-3-oxo-2,3-dihydro-1H-isoindol-1-yl]-1H-benzimidazol-2-yl}carbamate |
| 239 | methyl {5-[2-(3-chloro-5-fluorophenyl)-1-hydroxy-3-oxo-2,3-dihydro-1H-isoindol-1-yl]-1H-benzimidazol-2-yl}carbamate |
| 240 | N-{6-[1-hydroxy-3-oxo-2-(phenylmethyl)-2,3-dihydro-1H-isoindol-1-yl]-1H-benzimidazol-2-yl}-2-methylpropanamide |
| 241 | methyl (5-{2-[1-(3-chloro-2-thienyl)ethyl]-1-hydroxy-3-oxo-2,3-dihydro-1H-isoindol-1-yl}-1H-benzimidazol-2-yl)carbamate |
| 242 | methyl [5-(1-hydroxy-3-oxo-2-pyridin-3-yl-2,3-dihydro-1H-isoindol-1-yl)-1H-benzimidazol-2-yl]carbamate |
| 243 | methyl (5-{1-hydroxy-3-oxo-2-[3-(phenylamino)phenyl]-2,3-dihydro-1H-isoindol-1-yl}-1H-benzimidazol-2-yl)carbamate |
| 244 | methyl {5-[2-(5-bromo-2,4-difluorophenyl)-1-hydroxy-3-oxo-2,3-dihydro-1H-isoindol-1-yl]-1H-benzimidazol-2-yl}carbamate |
| 245 | methyl {5-[2-(5-chloro-2,4-difluorophenyl)-1-hydroxy-3-oxo-2,3-dihydro-1H-isoindol-1-yl]-1H-benzimidazol-2-yl}carbamate |
| 246 | methyl {5-[2-(3,5-dichloro-4-fluorophenyl)-1-hydroxy-3-oxo-2,3-dihydro-1H-isoindol-1-yl]-1H-benzimidazol-2-yl}carbamate |
| 247 | 2,2-dimethyl-3-(methyloxy)propyl {5-[1-hydroxy-3-oxo-2-(phenylmethyl)-2,3-dihydro-1H-isoindol-1-yl]-1H-benzimidazol-2-yl}carbamate |
| 248 | 3-hydroxy-2,2-dimethylpropyl {5-[1-hydroxy-3-oxo-2-(phenylmethyl)-2,3-dihydro-1H-isoindol-1-yl]-1H-benzimidazol-2-yl}carbamate |
| 249 | methyl (5-{2-[1-(5-bromo-2-thienyl)ethyl]-1-hydroxy-3-oxo-2,3-dihydro-1H-isoindol-1-yl}-1H-benzimidazol-2-yl)carbamate |
| 250 | methyl {5-[2-(4,5-dichloro-2-fluorophenyl)-1-hydroxy-3-oxo-2,3-dihydro-1H-isoindol-1-yl]-1H-benzimidazol-2-yl}carbamate |

| Entry | Name |
|---|---|
| 251 | methyl {5-[2-(3-bromo-2-fluorophenyl)-1-hydroxy-3-oxo-2,3-dihydro-1H-isoindol-1-yl]-1H-benzimidazol-2-yl}carbamate |
| 252 | methyl {5-[2-(3-chloro-2,4-difluorophenyl)-1-hydroxy-3-oxo-2,3-dihydro-1H-isoindol-1-yl]-1H-benzimidazol-2-yl}carbamate |
| 253 | N-{6-[1-hydroxy-3-oxo-2-(phenylmethyl)-2,3-dihydro-1H-isoindol-1-yl]-1H-benzimidazol-2-yl}pent-4-ynamide |
| 254 | methyl (6-{1-methyl-3-oxo-2-[3-(trifluoromethyl)phenyl]-2,3-dihydro-1H-isoindol-1-yl}-1H-benzimidazol-2-yl)carbamate |
| 255 | methyl [5-(1-hydroxy-3-oxo-2-{3-[(1,1,2,2-tetrafluoroethyl)oxy]phenyl}-2,3-dihydro-1H-isoindol-1-yl)-1H-benzimidazol-2-yl]carbamate |
| 256 | methyl {5-[1-hydroxy-3-oxo-2-(3-piperidin-4-ylphenyl)-2,3-dihydro-1H-isoindol-1-yl]-1H-benzimidazol-2-yl}carbamate |
| 257 | methyl {5-[2-(3-ethenylphenyl)-1-hydroxy-3-oxo-2,3-dihydro-1H-isoindol-1-yl]-1H-benzimidazol-2-yl}carbamate |
| 258 | methyl (5-{2-[3-(dimethylamino)phenyl]-1-hydroxy-3-oxo-2,3-dihydro-1H-isoindol-1-yl}-1H-benzimidazol-2-yl)carbamate |
| 259 | 2,2-difluoro-N-{6-[1-hydroxy-3-oxo-2-(phenylmethyl)-2,3-dihydro-1H-isoindol-1-yl]-1H-benzimidazol-2-yl}cyclopropanecarboxamide |
| 260 | N-ethyl-N'-{6-[2-(4-fluorophenyl)-1-hydroxy-3-oxo-2,3-dihydro-1H-isoindol-1-yl]-1H-benzimidazol-2-yl}urea |
| 261 | methyl {5-[2-(3-aminophenyl)-1-hydroxy-3-oxo-2,3-dihydro-1H-isoindol-1-yl]-1H-benzimidazol-2-yl}carbamate |
| 262 | N-{5-[1-hydroxy-3-oxo-2-(phenylmethyl)-2,3-dihydro-1H-isoindol-1-yl]-1H-benzimidazol-2-yl}-4-[(phenylmethyl)oxy]butanamide |
| 263 | N-{5-[1-hydroxy-3-oxo-2-(phenylmethyl)-2,3-dihydro-1H-isoindol-1-yl]-1H-benzimidazol-2-yl}-4-piperidin-1-ylbutanamide |
| 264 | N-{5-[1-hydroxy-3-oxo-2-(phenylmethyl)-2,3-dihydro-1H-isoindol-1-yl]-1H-benzimidazol-2-yl}-4-(4-methylpiperazin-1-yl)butanamide |
| 265 | N-{6-[2-(4-fluorophenyl)-1-hydroxy-3-oxo-2,3-dihydro-1H-isoindol-1-yl]-1H-benzimidazol-2-yl}butanamide |
| 266 | methyl {6-[2-(3-bromophenyl)-5,6-dichloro-1-hydroxy-3-oxo-2,3-dihydro-1H-isoindol-1-yl]-1H-benzimidazol-2-yl}carbamate |
| 267 | methyl [5-(1-hydroxy-2-{3-[methyl(phenyl)amino]phenyl}-3-oxo-2,3-dihydro-1H-isoindol-1-yl)-1H-benzimidazol-2-yl]carbamate |
| 268 | methyl {5-[1-hydroxy-3-oxo-2-(phenylsulfonyl)-2,3-dihydro-1H-isoindol-1-yl]-1H-benzimidazol-2-yl}carbamate |
| 269 | methyl {5-[(2-{[(phenylamino)carbonyl]amino}phenyl)carbonyl]-1H-benzimidazol-2-yl}carbamate |
| 270 | methyl (5-{[2-({[(phenylmethyl)oxy]carbonyl}amino)phenyl]carbonyl}-1H-benzimidazol-2-yl)carbamate |
| 271 | methyl [5-({2-[(2-phenylhydrazino)carbonyl]phenyl}carbonyl)-1H-benzimidazol-2-yl]carbamate |
| 272 | methyl {5-[(2-{[(phenyloxy)amino]carbonyl}phenyl)carbonyl]-1H-benzimidazol-2-yl}carbamate |
| 273 | but-2-yn-1-yl {5-[2-(4-fluorophenyl)-1-hydroxy-3-oxo-2,3-dihydro-1H-isoindol-1-yl]-1H-benzimidazol-2-yl}carbamate |
| 274 | N-{5-[1-hydroxy-3-oxo-2-(phenylmethyl)-2,3-dihydro-1H-isoindol-1-yl]-1H-benzimidazol-2-yl}-3-piperidin-1-ylpropanamide |
| 275 | N-{6-[2-(4-fluorophenyl)-1-hydroxy-3-oxo-2,3-dihydro-1H-isoindol-1-yl]-1H-benzimidazol-2-yl}propanamide |
| 276 | N-(4-fluorophenyl)-2-{[2-(pent-4-ynylamino)-1H-benzimidazol-6-yl]carbonyl}benzamide |
| 277 | 4-(diethylamino)-N-{5-[1-hydroxy-3-oxo-2-(phenylmethyl)-2,3-dihydro-1H-isoindol-1-yl]-1H-benzimidazol-2-yl}butanamide |
| 278 | N-{5-[1-hydroxy-3-oxo-2-(phenylmethyl)-2,3-dihydro-1H-isoindol-1-yl]-1H-benzimidazol-2-yl}-4-pyrrolidin-1-ylbutanamide |
| 279 | 3-piperidin-1-ylpropyl {6-[2-(4-fluorophenyl)-1-hydroxy-3-oxo-2,3-dihydro-1H-isoindol-1-yl]-1H-benzimidazol-2-yl}carbamate |
| 280 | 3-(4-methylpiperazin-1-yl)propyl {6-[2-(4-fluorophenyl)-1-hydroxy-3-oxo-2,3-dihydro-1H-isoindol-1-yl]-1H-benzimidazol-2-yl}carbamate |
| 281 | methyl {5-[2-(3-bromophenyl)-3-oxo-2,3-dihydro-1H-isoindol-1-yl]-1H-benzimidazol-2-yl}carbamate |
| 282 | methyl {5-[2-(3-ethynyl-2-fluorophenyl)-1-hydroxy-3-oxo-2,3-dihydro-1H-isoindol-1-yl]-1H-benzimidazol-2-yl}carbamate |
| 283 | 2-piperidin-1-ylethyl {5-[2-(4-fluorophenyl)-1-hydroxy-3-oxo-2,3-dihydro-1H-isoindol-1-yl]-1H-benzimidazol-2-yl}carbamate |
| 284 | methyl {5-[2-(3-chloro-2-methylphenyl)-1-hydroxy-3-oxo-2,3-dihydro-1H-isoindol-1-yl]-1H-benzimidazol-2-yl}carbamate |
| 285 | methyl {5-[2-(5-chloro-2-methylphenyl)-1-hydroxy-3-oxo-2,3-dihydro-1H-isoindol-1-yl]-1H-benzimidazol-2-yl}carbamate |
| 286 | N-{6-[1-hydroxy-3-oxo-2-(phenylmethyl)-2,3-dihydro-1H-isoindol-1-yl]-1H-benzimidazol-2-yl}-2,2-dimethyl-3-piperidin-1-ylpropanamide |
| 287 | N-{5-[2-(4-fluorophenyl)-1-hydroxy-3-oxo-2,3-dihydro-1H-isoindol-1-yl]-1H-benzimidazol-2-yl}-4-piperidin-1-ylbutanamide |
| 288 | N-{5-[2-(3-chloro-2-fluorophenyl)-1-hydroxy-3-oxo-2,3-dihydro-1H-isoindol-1-yl]-1H-benzimidazol-2-yl}-4-piperidin-1-ylbutanamide |
| 289 | methyl [6-({2-[(phenylcarbonyl)amino]phenyl}carbonyl)-1H-benzimidazol-2-yl]carbamate |

| Entry | Name |
|---|---|
| 290 | methyl {5-[1-hydroxy-2-(3-morpholin-4-ylphenyl)-3-oxo-2,3-dihydro-1H-isoindol-1-yl]-1H-benzimidazol-2-yl}carbamate |
| 291 | 2-(dimethylamino)ethyl {6-[2-(3-chloro-2-fluorophenyl)-1-hydroxy-3-oxo-2,3-dihydro-1H-isoindol-1-yl]-1H-benzimidazol-2-yl}carbamate |
| 292 | 2-(diethylamino)ethyl {5-[2-(3-chloro-2-fluorophenyl)-1-hydroxy-3-oxo-2,3-dihydro-1H-isoindol-1-yl]-1H-benzimidazol-2-yl}carbamate |
| 293 | 2-piperidin-1-ylethyl {5-[2-(3-chloro-2-fluorophenyl)-1-hydroxy-3-oxo-2,3-dihydro-1H-isoindol-1-yl]-1H-benzimidazol-2-yl}carbamate |
| 294 | 3-piperidin-1-ylpropyl {6-[2-(3-chloro-2-fluorophenyl)-1-hydroxy-3-oxo-2,3-dihydro-1H-isoindol-1-yl]-1H-benzimidazol-2-yl}carbamate |
| 295 | 2-piperidin-1-ylethyl {6-[2-(3-bromophenyl)-3-oxo-2,3-dihydro-1H-isoindol-1-yl]-1H-benzimidazol-2-yl}carbamate |
| 296 | methyl {6-[2-(3-bromophenyl)-4,7-difluoro-1-hydroxy-3-oxo-2,3-dihydro-1H-isoindol-1-yl]-1H-benzimidazol-2-yl}carbamate |
| 297 | 2-[methyl(phenylmethyl)amino]ethyl {5-[2-(3-chloro-2-fluorophenyl)-1-hydroxy-3-oxo-2,3-dihydro-1H-isoindol-1-yl]-1H-benzimidazol-2-yl}carbamate |
| 298 | methyl {5-[1-hydroxy-3-oxo-2-(3-pyrrolidin-1-ylphenyl)-2,3-dihydro-1H-isoindol-1-yl]-1H-benzimidazol-2-yl}carbamate |
| 299 | methyl {5-[2-(5-chloro-2,3-difluorophenyl)-1-hydroxy-3-oxo-2,3-dihydro-1H-isoindol-1-yl]-1H-benzimidazol-2-yl}carbamate |
| 300 | methyl {5-[1-hydroxy-3-oxo-2-(pyrrolidin-2-ylmethyl)-2,3-dihydro-1H-isoindol-1-yl]-1H-benzimidazol-2-yl}carbamate |
| 301 | methyl {5-[1-hydroxy-3-oxo-2-(pyrrolidin-3-ylmethyl)-2,3-dihydro-1H-isoindol-1-yl]-1H-benzimidazol-2-yl}carbamate |
| 302 | (1-methylpiperidin-2-yl)methyl {6-[2-(3-chloro-2-fluorophenyl)-1-hydroxy-3-oxo-2,3-dihydro-1H-isoindol-1-yl]-1H-benzimidazol-2-yl}carbamate |
| 303 | [(2S)-1-methylpyrrolidin-2-yl]methyl {6-[2-(3-chloro-2-fluorophenyl)-1-hydroxy-3-oxo-2,3-dihydro-1H-isoindol-1-yl]-1H-benzimidazol-2-yl}carbamate |
| 304 | octahydro-2H-quinolizin-1-ylmethyl {6-[2-(3-chloro-2-fluorophenyl)-1-hydroxy-3-oxo-2,3-dihydro-1H-isoindol-1-yl]-1H-benzimidazol-2-yl}carbamate |
| 305 | methyl {5-[2-(5-bromo-2-methylphenyl)-1-hydroxy-3-oxo-2,3-dihydro-1H-isoindol-1-yl]-1H-benzimidazol-2-yl}carbamate |
| 306 | 5-[2-(3-chloro-2-fluorophenyl)-1-hydroxy-3-oxo-2,3-dihydro-1H-isoindol-1-yl]-1,3-dihydro-2H-benzimidazol-2-one |
| 307 | methyl {5-[2-(3-bromo-2,5-difluorophenyl)-1-hydroxy-3-oxo-2,3-dihydro-1H-isoindol-1-yl]-1H-benzimidazol-2-yl}carbamate |
| 308 | 2-morpholin-4-ylethyl {6-[2-(3-chloro-2-fluorophenyl)-1-hydroxy-3-oxo-2,3-dihydro-1H-isoindol-1-yl]-1H-benzimidazol-2-yl}carbamate |
| 309 | (1-methylpiperidin-3-yl)methyl {6-[2-(3-chloro-2-fluorophenyl)-1-hydroxy-3-oxo-2,3-dihydro-1H-isoindol-1-yl]-1H-benzimidazol-2-yl}carbamate |
| 310 | methyl (5-{2-[5-chloro-2-(methyloxy)phenyl]-1-hydroxy-3-oxo-2,3-dihydro-1H-isoindol-1-yl}-1H-benzimidazol-2-yl)carbamate |
| 311 | methyl [5-(2-{3-[cyclohexyl(methyl)amino]phenyl}-1-hydroxy-3-oxo-2,3-dihydro-1H-isoindol-1-yl)-1H-benzimidazol-2-yl]carbamate |
| 312 | 8-azabicyclo[3.2.1]oct-3-ylmethyl {6-[2-(3-chloro-2-fluorophenyl)-1-hydroxy-3-oxo-2,3-dihydro-1H-isoindol-1-yl]-1H-benzimidazol-2-yl}carbamate |
| 313 | methyl {6-[1-(3-bromophenyl)-5-oxopyrrolidin-2-yl]-1H-benzimidazol-2-yl}carbamate |
| 314 | (1-methylpiperidin-4-yl)methyl {5-[1-hydroxy-3-oxo-2-(phenylmethyl)-2,3-dihydro-1H-isoindol-1-yl]-1H-benzimidazol-2-yl}carbamate |
| 315 | 1,1-dimethylethyl 4-({[({5-[1-hydroxy-3-oxo-2-(phenylmethyl)-2,3-dihydro-1H-isoindol-1-yl]-1H-benzimidazol-2-yl}amino)carbonyl]oxy}methyl)piperidine-1-carboxylate |
| 316 | (1-methylpiperidin-4-yl)methyl {5-[2-(3-chloro-2-fluorophenyl)-1-hydroxy-3-oxo-2,3-dihydro-1H-isoindol-1-yl]-1H-benzimidazol-2-yl}carbamate |
| 317 | 2-(1-methylpiperidin-4-yl)ethyl {5-[2-(3-chloro-2-fluorophenyl)-1-hydroxy-3-oxo-2,3-dihydro-1H-isoindol-1-yl]-1H-benzimidazol-2-yl}carbamate |
| 318 | methyl ({6-[2-(3-chloro-2-fluorophenyl)-1-hydroxy-3-oxo-2,3-dihydro-1H-isoindol-1-yl]-1H-benzimidazol-2-yl}amino)(oxo)acetate |
| 319 | N-(5-{1-hydroxy-3-oxo-2-[3-(phenyloxy)phenyl]-2,3-dihydro-1H-isoindol-1-yl}-1H-benzimidazol-2-yl)-4-piperidin-1-ylbutanamide |
| 320 | methyl {6-[2-(3-bromophenyl)-1-methyl-3-oxo-2,3-dihydro-1H-isoindol-1-yl]-1H-benzimidazol-2-yl}carbamate |
| 321 | 4-(diethylamino)but-2-yn-1-yl {6-[2-(3-chloro-2-fluorophenyl)-1-hydroxy-3-oxo-2,3-dihydro-1H-isoindol-1-yl]-1H-benzimidazol-2-yl}carbamate |
| 322 | methyl {5-[2-(3-chloro-2,6-difluorophenyl)-1-hydroxy-3-oxo-2,3-dihydro-1H-isoindol-1-yl]-1H-benzimidazol-2-yl}carbamate |
| 323 | 2-(2-oxopyrrolidin-1-yl)ethyl {6-[2-(3-chloro-2-fluorophenyl)-1-hydroxy-3-oxo-2,3-dihydro-1H-isoindol-1-yl]-1H-benzimidazol-2-yl}carbamate |
| 324 | 2-(2,5-dioxopyrrolidin-1-yl)ethyl {6-[2-(3-chloro-2-fluorophenyl)-1-hydroxy-3-oxo-2,3-dihydro-1H-isoindol-1-yl]-1H-benzimidazol-2-yl}carbamate |
| 325 | 2,2,3,3-tetrafluorocyclobutyl {5-[2-(3-chloro-2-fluorophenyl)-1-hydroxy-3-oxo-2,3-dihydro-1H-isoindol-1-yl]-1H-benzimidazol-2-yl}carbamate |
| 326 | 1-acetyl-N-{5-[2-(3-chloro-2-fluorophenyl)-1-hydroxy-3-oxo-2,3-dihydro-1H-isoindol-1-yl]-1H-benzimidazol-2-yl}piperidine-4-carboxamide |
| 327 | N-{5-[2-(3-chloro-2-fluorophenyl)-1-hydroxy-3-oxo-2,3-dihydro-1H-isoindol-1-yl]-1H-benzimidazol-2-yl}cyclobutanecarboxamide |

| Entry | Name |
|---|---|
| 328 | methyl [5-(2-{3-[ethyl(phenyl)amino]phenyl}-1-hydroxy-3-oxo-2,3-dihydro-1H-isoindol-1-yl]-1H-benzimidazol-2-yl]carbamate |
| 329 | N-{6-[2-(3-chloro-2-fluorophenyl)-1-hydroxy-3-oxo-2,3-dihydro-1H-isoindol-1-yl]-1H-benzimidazol-2-yl}-2,2-difluorocyclopropanecarboxamide |
| 330 | cyclobutyl {6-[2-(3-chloro-2-fluorophenyl)-1-hydroxy-3-oxo-2,3-dihydro-1H-isoindol-1-yl]-1H-benzimidazol-2-yl}carbamate |
| 331 | 2,2-difluoroethyl {6-[2-(3-chloro-2-fluorophenyl)-1-hydroxy-3-oxo-2,3-dihydro-1H-isoindol-1-yl]-1H-benzimidazol-2-yl}carbamate |
| 332 | 2-(3-chloro-2-fluorophenyl)-3-hydroxy-3-[2-(pyridin-2-ylamino)-1H-benzimidazol-5-yl]-2,3-dihydro-1H-isoindol-1-one |
| 333 | 1-methylethyl {6-[2-(3-chloro-2-fluorophenyl)-1-hydroxy-3-oxo-2,3-dihydro-1H-isoindol-1-yl]-1H-benzimidazol-2-yl}carbamate |
| 334 | cyclopropylmethyl {6-[2-(3-chloro-2-fluorophenyl)-1-hydroxy-3-oxo-2,3-dihydro-1H-isoindol-1-yl]-1H-benzimidazol-2-yl}carbamate |
| 335 | N-{5-[2-(3-chloro-2-fluorophenyl)-1-hydroxy-3-oxo-2,3-dihydro-1H-isoindol-1-yl]-1H-benzimidazol-2-yl}cyclopropanecarboxamide |
| 336 | 2-(methyloxy)ethyl {5-[2-(3-chloro-2-fluorophenyl)-1-hydroxy-3-oxo-2,3-dihydro-1H-isoindol-1-yl]-1H-benzimidazol-2-yl}carbamate |
| 337 | tetrahydrofuran-2-ylmethyl {6-[2-(3-chloro-2-fluorophenyl)-1-hydroxy-3-oxo-2,3-dihydro-1H-isoindol-1-yl]-1H-benzimidazol-2-yl}carbamate |
| 338 | N-{5-[2-(3-chloro-2-fluorophenyl)-1-hydroxy-3-oxo-2,3-dihydro-1H-isoindol-1-yl]-1H-benzimidazol-2-yl}-2-(2-thienyl)acetamide |
| 339 | methyl {6-[2-(3-chloro-2-fluorophenyl)-4,7-difluoro-1-hydroxy-3-oxo-2,3-dihydro-1H-isoindol-1-yl]-1H-benzimidazol-2-yl}carbamate |
| 340 | ethyl {6-[2-(3-chloro-2-fluorophenyl)-1-hydroxy-3-oxo-2,3-dihydro-1H-isoindol-1-yl]-1H-benzimidazol-2-yl}carbamate |
| 341 | 2-fluoroethyl {6-[2-(3-chloro-2-fluorophenyl)-1-hydroxy-3-oxo-2,3-dihydro-1H-isoindol-1-yl]-1H-benzimidazol-2-yl}carbamate |
| 342 | methyl (5-{1-hydroxy-3-oxo-2-[2-(phenyloxy)phenyl]-2,3-dihydro-1H-isoindol-1-yl}-1H-benzimidazol-2-yl)carbamate |
| 343 | N'-{5-[2-(3-chloro-2-fluorophenyl)-1-hydroxy-3-oxo-2,3-dihydro-1H-isoindol-1-yl]-1H-benzimidazol-2-yl}-N,N-diethylpentanediamide |
| 344 | cyclobutylmethyl {6-[2-(3-chloro-2-fluorophenyl)-1-hydroxy-3-oxo-2,3-dihydro-1H-isoindol-1-yl]-1H-benzimidazol-2-yl}carbamate |
| 345 | 2,2,2-trifluoroethyl {6-[2-(3-chloro-2-fluorophenyl)-1-hydroxy-3-oxo-2,3-dihydro-1H-isoindol-1-yl]-1H-benzimidazol-2-yl}carbamate |
| 346 | methyl (5-{2-[3-(1,1-dimethylethyl)phenyl]-1-hydroxy-3-oxo-2,3-dihydro-1H-isoindol-1-yl}-1H-benzimidazol-2-yl)carbamate |
| 347 | methyl {6-[2-(3-chloro-2-fluorophenyl)-7-fluoro-1-hydroxy-3-oxo-2,3-dihydro-1H-isoindol-1-yl]-1H-benzimidazol-2-yl}carbamate |
| 348 | 2-(3-chloro-2-fluorophenyl)-3-hydroxy-3-[2-(phenylamino)-1H-benzimidazol-5-yl]-2,3-dihydro-1H-isoindol-1-one |
| 349 | methyl {6-[4,7-dichloro-2-(3-chloro-2-fluorophenyl)-1-hydroxy-3-oxo-2,3-dihydro-1H-isoindol-1-yl]-1H-benzimidazol-2-yl}carbamate |
| 350 | phenylmethyl 2-[(2-{[(ethyloxy)carbonyl]amino}-1,3-benzoxazol-5-yl)carbonyl]benzoate |
| 351 | methyl {5-[2-(5-chloro-3-ethynyl-2-methylphenyl)-1-hydroxy-3-oxo-2,3-dihydro-1H-isoindol-1-yl]-1H-benzimidazol-2-yl}carbamate |
| 352 | methyl {5-[2-(5-ethynyl-2,4-difluorophenyl)-1-hydroxy-3-oxo-2,3-dihydro-1H-isoindol-1-yl]-1H-benzimidazol-2-yl}carbamate |
| 353 | methyl {5-[2-(3-ethynyl-2,4-difluorophenyl)-1-hydroxy-3-oxo-2,3-dihydro-1H-isoindol-1-yl]-1H-benzimidazol-2-yl}carbamate |
| 354 | 2-(3-chloro-2-fluorophenyl)-3-hydroxy-3-[2-(pyrimidin-2-ylamino)-1H-benzimidazol-5-yl]-2,3-dihydro-1H-isoindol-1-one |
| 355 | methyl {5-[2-(3-ethynyl-2-fluorophenyl)-4,7-difluoro-1-hydroxy-3-oxo-2,3-dihydro-1H-isoindol-1-yl]-1H-benzimidazol-2-yl}carbamate |
| 356 | 2-(3-chloro-2-fluorophenyl)-3-hydroxy-3-[2-(1,3-thiazol-2-ylamino)-1H-benzimidazol-5-yl]-2,3-dihydro-1H-isoindol-1-one |
| 357 | ethyl {5-[2-(3-chloro-2-fluorophenyl)-1-hydroxy-3-oxo-2,3-dihydro-1H-isoindol-1-yl]-1,3-benzoxazol-2-yl}carbamate |
| 358 | methyl {5-[2-(5-chloro-3-iodo-2-methylphenyl)-1-hydroxy-3-oxo-2,3-dihydro-1H-isoindol-1-yl]-1H-benzimidazol-2-yl}carbamate |
| 359 | methyl {5-[2-(3-ethyl-2-fluorophenyl)-1-hydroxy-3-oxo-2,3-dihydro-1H-isoindol-1-yl]-1H-benzimidazol-2-yl}carbamate |
| 360 | methyl {5-[2-(5-ethynyl-2-methylphenyl)-1-hydroxy-3-oxo-2,3-dihydro-1H-isoindol-1-yl]-1H-benzimidazol-2-yl}carbamate |
| 361 | 2-(3-chloro-2-fluorophenyl)-3-hydroxy-3-[2-(pyrazin-2-ylamino)-1H-benzimidazol-5-yl]-2,3-dihydro-1H-isoindol-1-one |
| 362 | methyl {5-[2-(2-fluoro-3-iodophenyl)-1-hydroxy-3-oxo-2,3-dihydro-1H-isoindol-1-yl]-1H-benzimidazol-2-yl}carbamate |
| 363 | methyl {6-[2-(5-ethynyl-2-fluorophenyl)-1-hydroxy-3-oxo-2,3-dihydro-1H-isoindol-1-yl]-1H-benzimidazol-2-yl}carbamate |
| 364 | 2-(3-ethynyl-2-fluorophenyl)-3-hydroxy-3-[2-(pyrimidin-2-ylamino)-1H-benzimidazol-5-yl]-2,3-dihydro-1H-isoindol-1-one |
| 365 | methyl {5-[2-(2,5-dimethylphenyl)-1-hydroxy-3-oxo-2,3-dihydro-1H-isoindol-1-yl]-1H-benzimidazol-2-yl}carbamate |
| 366 | methyl {5-[2-(3-ethenyl-2-fluorophenyl)-1-hydroxy-3-oxo-2,3-dihydro-1H-isoindol-1-yl]-1H-benzimidazol-2-yl}carbamate |

| Entry | Name |
|---|---|
| 367 | methyl (6-{2-[2-fluoro-3-(methyloxy)phenyl]-1-hydroxy-3-oxo-2,3-dihydro-1H-isoindol-1-yl}-1H-benzimidazol-2-yl)carbamate |
| 368 | methyl (5-{1-hydroxy-2-[2-methyl-5-(methyloxy)phenyl]-3-oxo-2,3-dihydro-1H-isoindol-1-yl}-1H-benzimidazol-2-yl)carbamate |
| 369 | methyl {5-[2-(3-ethynyl-2-fluorophenyl)-7-fluoro-1-hydroxy-3-oxo-2,3-dihydro-1H-isoindol-1-yl]-1H-benzimidazol-2-yl}carbamate |
| 370 | methyl {5-[2-(2-fluoro-3-prop-1-yn-1-ylphenyl)-1-hydroxy-3-oxo-2,3-dihydro-1H-isoindol-1-yl]-1H-benzimidazol-2-yl}carbamate |
| 371 | methyl {5-[2-(5-chloro-2-methylphenyl)-7-fluoro-1-hydroxy-3-oxo-2,3-dihydro-1H-isoindol-1-yl]-1H-benzimidazol-2-yl}carbamate |
| 372 | methyl {5-[2-(3-ethynyl-2-methylphenyl)-1-hydroxy-3-oxo-2,3-dihydro-1H-isoindol-1-yl]-1H-benzimidazol-2-yl}carbamate |
| 373 | 3-hydroxy-2-[3-(methyloxy)phenyl]-3-[2-(pyrimidin-2-ylamino)-1H-benzimidazol-6-yl]-2,3-dihydro-1H-isoindol-1-one |
| 374 | 3-hydroxy-2-(3-methylphenyl)-3-[2-(pyrimidin-2-ylamino)-1H-benzimidazol-6-yl]-2,3-dihydro-1H-isoindol-1-one |
| 375 | 2-(5-chloro-2-methylphenyl)-3-hydroxy-3-[2-(pyrimidin-2-ylamino)-1H-benzimidazol-6-yl]-2,3-dihydro-1H-isoindol-1-one |
| 376 | methyl {6-[2-(5-chloro-2-methylphenyl)-4,7-difluoro-1-hydroxy-3-oxo-2,3-dihydro-1H-isoindol-1-yl]-1H-benzimidazol-2-yl}carbamate |
| 377 | methyl {5-[2-(3-ethynyl-2-fluorophenyl)-3-oxo-2,3-dihydro-1H-isoindol-1-yl]-1H-benzimidazol-2-yl}carbamate |
| 378 | 2-(3-chloro-2-fluorophenyl)-3-{2-[(6-chloropyridazin-3-yl)amino]-1H-benzimidazol-5-yl}-3-hydroxy-2,3-dihydro-1H-isoindol-1-one |
| 379 | 2-(3-chloro-2-fluorophenyl)-4,7-difluoro-3-hydroxy-3-[2-(pyrimidin-2-ylamino)-1H-benzimidazol-5-yl]-2,3-dihydro-1H-isoindol-1-one |
| 380 | methyl {5-[2-(2-fluoro-5-methylphenyl)-1-hydroxy-3-oxo-2,3-dihydro-1H-isoindol-1-yl]-1H-benzimidazol-2-yl}carbamate |
| 381 | methyl (5-{2-[2-fluoro-5-(methyloxy)phenyl]-1-hydroxy-3-oxo-2,3-dihydro-1H-isoindol-1-yl}-1H-benzimidazol-2-yl)carbamate |
| 382 | methyl (5-{1-hydroxy-2-[5-methyl-2-(methyloxy)phenyl]-3-oxo-2,3-dihydro-1H-isoindol-1-yl}-1H-benzimidazol-2-yl)carbamate |
| 383 | methyl {5-[2-(3-ethynyl-5-methylphenyl)-1-hydroxy-3-oxo-2,3-dihydro-1H-isoindol-1-yl]-1H-benzimidazol-2-yl}carbamate |
| 384 | 2-(3-chloro-2-fluorophenyl)-3-{2-[(5-chloropyrimidin-2-yl)amino]-1H-benzimidazol-5-yl}-3-hydroxy-2,3-dihydro-1H-isoindol-1-one |
| 385 | 2-(3-chloro-2-fluorophenyl)-3-hydroxy-3-{2-[(4-methylpyrimidin-2-yl)amino]-1H-benzimidazol-5-yl}-2,3-dihydro-1H-isoindol-1-one |
| 386 | 3-(2-{[4,6-bis(methyloxy)pyrimidin-2-yl]amino}-1H-benzimidazol-5-yl)-2-(3-chloro-2-fluorophenyl)-3-hydroxy-2,3-dihydro-1H-isoindol-1-one |
| 387 | 2-(3-chloro-2-fluorophenyl)-3-hydroxy-3-(2-{[4-methyl-6-(methyloxy)pyrimidin-2-yl]amino}-1H-benzimidazol-5-yl)-2,3-dihydro-1H-isoindol-1-one |
| 388 | 3-hydroxy-2-(3-methylphenyl)-3-[2-(pyrazin-2-ylamino)-1H-benzimidazol-6-yl]-2,3-dihydro-1H-isoindol-1-one |
| 389 | 2-(5-chloro-2-methylphenyl)-3-hydroxy-3-[2-(pyrazin-2-ylamino)-1H-benzimidazol-6-yl]-2,3-dihydro-1H-isoindol-1-one |
| 390 | methyl {6-[2-(2-fluoro-3-methylphenyl)-1-hydroxy-3-oxo-2,3-dihydro-1H-isoindol-1-yl]-1H-benzimidazol-2-yl}carbamate |
| 391 | 3-hydroxy-2-[3-(methyloxy)phenyl]-3-[2-(pyrazin-2-ylamino)-1H-benzimidazol-5-yl]-2,3-dihydro-1H-isoindol-1-one |
| 392 | methyl {6-[(2-{[(2-thienylmethyl)amino]carbonyl}phenyl)carbonyl]-1H-benzimidazol-2-yl}carbamate |
| 393 | methyl {6-[(2-{[(3-methylphenyl)amino]carbonyl}phenyl)carbonyl]-1H-benzimidazol-2-yl}carbamate |
| 394 | methyl {6-[(2-{[(3-bromophenyl)amino]carbonyl}phenyl)carbonyl]-1H-benzimidazol-2-yl}carbamate |
| 395 | methyl {6-[(2-{[(3-chlorophenyl)amino]carbonyl}phenyl)carbonyl]-1H-benzimidazol-2-yl}carbamate |
| 396 | methyl {6-[(2-{[(3-fluorophenyl)amino]carbonyl}phenyl)carbonyl]-1H-benzimidazol-2-yl}carbamate |
| 397 | methyl (6-{[2-({[3-(methyloxy)phenyl]amino}carbonyl)phenyl]carbonyl}-1H-benzimidazol-2-yl)carbamate |
| 398 | methyl (6-{[2-({[3-(trifluoromethyl)phenyl]amino}carbonyl)phenyl]carbonyl}-1H-benzimidazol-2-yl)carbamate |
| 399 | methyl {6-[(2-{[(3-ethylphenyl)amino]carbonyl}phenyl)carbonyl]-1H-benzimidazol-2-yl}carbamate |
| 400 | methyl {6-[(2-{[(3-ethynylphenyl)amino]carbonyl}phenyl)carbonyl]-1H-benzimidazol-2-yl}carbamate |
| 401 | methyl {6-[(2-{[(3-chloro-4-fluorophenyl)amino]carbonyl}phenyl)carbonyl]-1H-benzimidazol-2-yl}carbamate |
| 402 | methyl {6-[(2-{[(5-chloro-2-fluorophenyl)amino]carbonyl}phenyl)carbonyl]-1H-benzimidazol-2-yl}carbamate |
| 403 | methyl {6-[(2-{[(3-iodophenyl)amino]carbonyl}phenyl)carbonyl]-1H-benzimidazol-2-yl}carbamate |
| 404 | methyl (6-{[2-({[3-(1-methylethyl)phenyl]amino}carbonyl)phenyl]carbonyl}-1H-benzimidazol-2-yl)carbamate |

| Entry | Name |
|---|---|
| 405 | methyl {6-[(2-{[(3-thienylmethyl)amino]carbonyl}phenyl)carbonyl]-1H-benzimidazol-2-yl}carbamate |
| 406 | methyl {6-[(2-{[(3-bromo-4-fluorophenyl)amino]carbonyl}phenyl)carbonyl]-1H-benzimidazol-2-yl}carbamate |
| 407 | methyl {6-[(2-{[(3-chloro-2-fluorophenyl)amino]carbonyl}phenyl)carbonyl]-1H-benzimidazol-2-yl}carbamate |
| 408 | methyl {6-[(2-{[(4-fluoro-3-methylphenyl)amino]carbonyl}phenyl)carbonyl]-1H-benzimidazol-2-yl}carbamate |
| 409 | methyl {6-[(2-{[(5-bromo-2-fluorophenyl)amino]carbonyl}phenyl)carbonyl]-1H-benzimidazol-2-yl}carbamate |
| 410 | methyl {6-[(2-{[(5-bromo-2,4-difluorophenyl)amino]carbonyl}phenyl)carbonyl]-1H-benzimidazol-2-yl}carbamate |
| 411 | methyl {6-[(2-{[(5-chloro-2,4-difluorophenyl)amino]carbonyl}phenyl)carbonyl]-1H-benzimidazol-2-yl}carbamate |
| 412 | methyl {6-[(2-{[(3-bromo-2-fluorophenyl)amino]carbonyl}phenyl)carbonyl]-1H-benzimidazol-2-yl}carbamate |
| 413 | methyl {6-[(2-{[(3-ethenylphenyl)amino]carbonyl}phenyl)carbonyl]-1H-benzimidazol-2-yl}carbamate |
| 414 | methyl {6-[(2-{[(3-ethynyl-2-fluorophenyl)amino]carbonyl}phenyl)carbonyl]-1H-benzimidazol-2-yl}carbamate |
| 415 | methyl {6-[(2-{[(5-chloro-2-methylphenyl)amino]carbonyl}phenyl)carbonyl]-1H-benzimidazol-2-yl}carbamate |
| 416 | methyl {6-[(2-{[(5-bromo-2-methylphenyl)amino]carbonyl}phenyl)carbonyl]-1H-benzimidazol-2-yl}carbamate |
| 417 | methyl {6-[(2-{[(2-fluoro-3-iodophenyl)amino]carbonyl}phenyl)carbonyl]-1H-benzimidazol-2-yl}carbamate |
| 418 | methyl {6-[(2-{[(3-ethenyl-2-fluorophenyl)amino]carbonyl}phenyl)carbonyl]-1H-benzimidazol-2-yl}carbamate |
| 419 | methyl {6-[(2-{[(2-fluoro-5-methylphenyl)amino]carbonyl}phenyl)carbonyl]-1H-benzimidazol-2-yl}carbamate |

The Compounds in Table 7 can be prepared as pharmaceutically acceptable salts, solvates, hydrates, and/or isomers thereof. All such salt, solvate, hydrate, and isomer combinations of the Compounds in Table 7 can be used to practice the invention.

| Entry | Name |
|---|---|
| 1 | (3Z)-3-[[5-(methyloxy)-1H-benzimidazol-2-yl](phenyl)methylidene]-5-{[1-(phenylmethyl)pyrrolidin-3-yl]amino}-1,3-dihydro-2H-indol-2-one |
| 2 | (3Z)-5-[(1-ethylpiperidin-3-yl)amino]-3-[[5-(methyloxy)-1H-benzimidazol-2-yl](phenyl)methylidene]-1,3-dihydro-2H-indol-2-one |
| 3 | (3Z)-5-[(1-ethylpiperidin-4-yl)amino]-3-[[5-(methyloxy)-1H-benzimidazol-2-yl](phenyl)methylidene]-1,3-dihydro-2H-indol-2-one |
| 4 | (3Z)-5-[(1-ethylpiperidin-4-yl)amino]-3-[1H-imidazol-2-yl(phenyl)methylidene]-1,3-dihydro-2H-indol-2-one |
| 5 | (3Z)-5-[(1-ethylpiperidin-4-yl)amino]-3-{[5-(methyloxy)-1H-benzimidazol-2-yl][4-(methyloxy)phenyl]methylidene}-1,3-dihydro-2H-indol-2-one |
| 6 | (3Z)-5-[(1-ethylpiperidin-4-yl)amino]-3-[[5-(methyloxy)-1H-benzimidazol-2-yl](4-methylphenyl)methylidene]-1,3-dihydro-2H-indol-2-one |
| 7 | (3Z)-3-[1H-benzimidazol-2-yl(4-nitrophenyl)methylidene]-5-[(1-ethylpiperidin-4-yl)amino]-1,3-dihydro-2H-indol-2-one |
| 8 | (3Z)-3-{1H-benzimidazol-2-yl[4-(methyloxy)phenyl]methylidene}-5-[(1-ethylpiperidin-4-yl)amino]-1,3-dihydro-2H-indol-2-one |
| 9 | (3Z)-3-[1H-benzimidazol-2-yl(phenyl)methylidene]-5-[(1-ethylpiperidin-4-yl)amino]-1,3-dihydro-2H-indol-2-one |
| 10 | (3Z)-3-[[5-(methyloxy)-1H-benzimidazol-2-yl](phenyl)methylidene]-5-[(2,2,6,6-tetramethylpiperidin-4-yl)amino]-1,3-dihydro-2H-indol-2-one |
| 11 | (3Z)-3-[(4-aminophenyl)(1H-benzimidazol-2-yl)methylidene]-5-[(1-ethylpiperidin-4-yl)amino]-1,3-dihydro-2H-indol-2-one |
| 12 | (3Z)-3-[1H-benzimidazol-2-yl(4-methylphenyl)methylidene]-5-[(1-ethylpiperidin-4-yl)amino]-1,3-dihydro-2H-indol-2-one |
| 13 | (3Z)-5-[(1-ethylpiperidin-4-yl)amino]-3-[1H-imidazol-2-yl(4-methylphenyl)methylidene]-1,3-dihydro-2H-indol-2-one |
| 14 | (3Z)-5-[(1-ethylpiperidin-4-yl)oxy]-3-[[5-(methyloxy)-1H-benzimidazol-2-yl](phenyl)methylidene]-1,3-dihydro-2H-indol-2-one |
| 15 | (3Z)-5-[(1-ethylpiperidin-4-yl)amino]-3-{1H-imidazol-2-yl[4-(methyloxy)phenyl]methylidene}-1,3-dihydro-2H-indol-2-one |
| 16 | (3Z)-3-[1H-benzimidazol-2-yl(4-fluorophenyl)methylidene]-5-[(1-ethylpiperidin-4-yl)amino]-1,3-dihydro-2H-indol-2-one |

-continued

| Entry | Name |
|---|---|
| 17 | (3Z)-3-[1H-benzimidazol-2-yl(3,5-difluorophenyl)methylidene]-5-[(1-ethylpiperidin-4-yl)amino]-1,3-dihydro-2H-indol-2-one |
| 18 | (3Z)-3-[1H-benzimidazol-2-yl(3-fluorophenyl)methylidene]-5-[(1-ethylpiperidin-4-yl)amino]-1,3-dihydro-2H-indol-2-one |
| 19 | (3Z)-3-[1H-benzimidazol-2-yl(3-nitrophenyl)methylidene]-5-[(1-ethylpiperidin-4-yl)amino]-1,3-dihydro-2H-indol-2-one |
| 20 | 3-((Z)-1H-benzimidazol-2-yl{5-[(1-ethylpiperidin-4-yl)amino]-2-oxo-1,2-dihydro-3H-indol-3-ylidene}methyl)benzonitrile |
| 21 | (3Z)-3-[(3-aminophenyl)(1H-benzimidazol-2-yl)methylidene]-5-[(1-ethylpiperidin-4-yl)amino]-1,3-dihydro-2H-indol-2-one |
| 22 | (3Z)-3-[1H-benzimidazol-2-yl(phenyl)methylidene]-5-(piperidin-4-ylamino)-1,3-dihydro-2H-indol-2-one |
| 23 | 3-((Z)-1H-benzimidazol-2-yl{5-[(1-ethylpiperidin-4-yl)amino]-2-oxo-1,2-dihydro-3H-indol-3-ylidene}methyl)benzenecarboximidamide |
| 24 | (3Z)-3-[1H-benzimidazol-2-yl(phenyl)methylidene]-5-({1-[2-(methyloxy)ethyl]piperidin-4-yl}amino)-1,3-dihydro-2H-indol-2-one |
| 25 | (3Z)-3-[1H-benzimidazol-2-yl(phenyl)methylidene]-5-[(2,2,6,6-tetramethylpiperidin-4-yl)amino]-1,3-dihydro-2H-indol-2-one |
| 26 | (3Z)-3-{1H-benzimidazol-2-yl[3-(methyloxy)phenyl]methylidene}-5-[(1-ethylpiperidin-4-yl)amino]-1,3-dihydro-2H-indol-2-one |
| 27 | (3Z)-3-[1H-benzimidazol-2-yl(3-chlorophenyl)methylidene]-5-[(1-ethylpiperidin-4-yl)amino]-1,3-dihydro-2H-indol-2-one |
| 28 | 2-(2-{2-[(Z)-{5-[(1-ethylpiperidin-4-yl)amino]-2-oxo-1,2-dihydro-3H-indol-3-ylidene}(phenyl)methyl]-1H-imidazol-4-yl}ethyl)-1H-isoindole-1,3(2H)-dione |
| 29 | (3Z)-3-[1H-benzimidazol-2-yl(phenyl)methylidene]-5-({1-[2-(dimethylamino)ethyl]piperidin-4-yl}amino)-1,3-dihydro-2H-indol-2-one |
| 30 | (3Z)-3-[1H-benzimidazol-2-yl(phenyl)methylidene]-5-{[1-(methylsulfonyl)piperidin-4-yl]amino}-1,3-dihydro-2H-indol-2-one |
| 31 | (3Z)-5-(8-azabicyclo[3.2.1]oct-3-ylamino)-3-[1H-benzimidazol-2-yl(phenyl)methylidene]-1,3-dihydro-2H-indol-2-one |
| 32 | (3Z)-3-{1H-benzimidazol-2-yl[3-(methyloxy)phenyl]methylidene}-5-[(1-ethylpiperidin-4-yl)oxy]-1,3-dihydro-2H-indol-2-one |
| 33 | (3Z)-3-[1H-benzimidazol-2-yl(3,5-difluorophenyl)methylidene]-5-[(1-ethylpiperidin-4-yl)oxy]-1,3-dihydro-2H-indol-2-one |
| 34 | (3Z)-3-[1H-benzimidazol-2-yl(phenyl)methylidene]-5-{[1-(phenylmethyl)piperidin-4-yl]oxy}-1,3-dihydro-2H-indol-2-one |
| 35 | (3Z)-3-[1H-benzimidazol-2-yl(3-chlorophenyl)methylidene]-5-[(1-ethylpiperidin-4-yl)oxy]-1,3-dihydro-2H-indol-2-one |
| 36 | (3Z)-3-[1H-benzimidazol-2-yl(3,5-difluorophenyl)methylidene]-5-({1-[2-(methyloxy)ethyl]piperidin-4-yl}oxy)-1,3-dihydro-2H-indol-2-one |
| 37 | (3Z)-3-[1H-benzimidazol-2-yl(3-chlorophenyl)methylidene]-5-({1-[2-(methyloxy)ethyl]piperidin-4-yl}oxy)-1,3-dihydro-2H-indol-2-one |
| 38 | (3Z)-3-[1H-benzimidazol-2-yl(3-chlorophenyl)methylidene]-5-({1-[2-(methyloxy)ethyl]piperidin-4-yl}amino)-1,3-dihydro-2H-indol-2-one |
| 39 | (3Z)-3-{1H-benzimidazol-2-yl[3-(methyloxy)phenyl]methylidene}-5-({1-[2-(methyloxy)ethyl]piperidin-4-yl}amino)-1,3-dihydro-2H-indol-2-one |
| 40 | (3Z)-3-[(3-chlorophenyl)(1H-imidazol-2-yl)methylidene]-5-({1-[2-(methyloxy)ethyl]piperidin-4-yl}amino)-1,3-dihydro-2H-indol-2-one |
| 41 | (3Z)-3-[(3-fluorophenyl)(1H-imidazol-2-yl)methylidene]-5-({1-[2-(methyloxy)ethyl]piperidin-4-yl}amino)-1,3-dihydro-2H-indol-2-one |
| 42 | (3Z)-3-[1H-benzimidazol-2-yl(3,5-difluorophenyl)methylidene]-5-({1-[2-(methyloxy)ethyl]piperidin-4-yl}amino)-1,3-dihydro-2H-indol-2-one |
| 43 | (3Z)-3-[1H-benzimidazol-2-yl(3-chlorophenyl)methylidene]-5-[(1-ethylpiperidin-4-yl)(methyl)amino]-1,3-dihydro-2H-indol-2-one |
| 44 | (3Z)-3-[(3-chlorophenyl)(1H-imidazol-2-yl)methylidene]-5-[(1-ethylpiperidin-4-yl)oxy]-1,3-dihydro-2H-indol-2-one |
| 45 | (3Z)-3-[1H-benzimidazol-2-yl(4-chlorophenyl)methylidene]-5-[(1-ethylpiperidin-4-yl)amino]-1,3-dihydro-2H-indol-2-one |
| 46 | (3Z)-3-[1H-benzimidazol-2-yl(3-fluorophenyl)methylidene]-5-({1-[2-(methyloxy)ethyl]piperidin-4-yl}amino)-1,3-dihydro-2H-indol-2-one |
| 47 | (3Z)-3-[1H-benzimidazol-2-yl(4-fluorophenyl)methylidene]-5-({1-[2-(methyloxy)ethyl]piperidin-4-yl}amino)-1,3-dihydro-2H-indol-2-one |
| 48 | (3Z)-3-[(3-chlorophenyl)(1H-imidazol-2-yl)methylidene]-5-[(1-ethylpiperidin-4-yl)amino]-1,3-dihydro-2H-indol-2-one |
| 49 | (3Z)-5-[(1-ethylpiperidin-4-yl)amino]-3-[(3-fluorophenyl)(1H-imidazol-2-yl)methylidene]-1,3-dihydro-2H-indol-2-one |
| 50 | (3Z)-3-[1H-benzimidazol-2-yl(3-fluoro-4-methylphenyl)methylidene]-5-[(1-ethylpiperidin-4-yl)amino]-1,3-dihydro-2H-indol-2-one |
| 51 | (3Z)-5-[(1-ethylpiperidin-4-yl)amino]-3-[(3-fluorophenyl)(4-methyl-1H-imidazol-2-yl)methylidene]-1,3-dihydro-2H-indol-2-one |
| 52 | (3Z)-3-[1H-benzimidazol-2-yl(4-fluoro-3-methylphenyl)methylidene]-5-[(1-ethylpiperidin-4-yl)amino]-1,3-dihydro-2H-indol-2-one |
| 53 | (3Z)-3-[(3-chloro-4-fluorophenyl)(1H-imidazol-2-yl)methylidene]-5-[(1-ethylpiperidin-4-yl)amino]-1,3-dihydro-2H-indol-2-one |
| 54 | (3Z)-3-[(3,4-difluorophenyl)(1H-imidazol-2-yl)methylidene]-5-[(1-ethylpiperidin-4-yl)amino]-1,3-dihydro-2H-indol-2-one |
| 55 | (3Z)-3-[(5-chloro-1H-benzimidazol-2-yl)(phenyl)methylidene]-5-[(1-ethylpiperidin-4-yl)amino]-1,3-dihydro-2H-indol-2-one |

-continued

| Entry | Name |
|---|---|
| 56 | (3Z)-3-[(5-chloro-1H-benzimidazol-2-yl)(3,5-difluorophenyl)methylidene]-5-[(1-ethylpiperidin-4-yl)amino]-1,3-dihydro-2H-indol-2-one |
| 57 | (3Z)-5-[(1-ethylpiperidin-4-yl)amino]-3-[(3-fluoro-4-methylphenyl)(1H-imidazol-2-yl)methylidene]-1,3-dihydro-2H-indol-2-one |
| 58 | (3Z)-5-[(1-ethylpiperidin-4-yl)amino]-3-[(4-fluorophenyl)(1H-imidazol-2-yl)methylidene]-1,3-dihydro-2H-indol-2-one |
| 59 | (3Z)-5-[(1-ethylpiperidin-4-yl)amino]-3-[1H-imidazol-2-yl(4-propylphenyl)methylidene]-1,3-dihydro-2H-indol-2-one |
| 60 | (3Z)-5-[(1-ethylpiperidin-4-yl)amino]-3-{1H-imidazol-2-yl[4-(trifluoromethyl)phenyl]methylidene}-1,3-dihydro-2H-indol-2-one |
| 61 | (3E)-3-[(3,5-difluorophenyl)(5-fluoro-1H-benzimidazol-2-yl)methylidene]-5-[(1-ethylpiperidin-4-yl)amino]-1,3-dihydro-2H-indol-2-one |
| 62 | (3Z)-3-[(3,5-difluorophenyl)(5-fluoro-1H-benzimidazol-2-yl)methylidene]-5-[(1-ethylpiperidin-4-yl)amino]-1,3-dihydro-2H-indol-2-one |
| 63 | (3Z)-3-[(3-fluoro-4-methylphenyl)(1H-imidazol-2-yl)methylidene]-5-({1-[2-(methyloxy)ethyl]piperidin-4-yl}amino)-1,3-dihydro-2H-indol-2-one |
| 64 | (3Z)-5-[(1-ethylpiperidin-4-yl)amino]-3-[(4-methyl-1H-imidazol-2-yl)(4-methylphenyl)methylidene]-1,3-dihydro-2H-indol-2-one |
| 65 | (3Z)-5-[(1-ethylpiperidin-4-yl)amino]-3-[[3-fluoro-4-(trifluoromethyl)phenyl](1H-imidazol-2-yl)methylidene]-1,3-dihydro-2H-indol-2-one |
| 66 | (3Z)-3-[(4-chlorophenyl)(1H-imidazol-2-yl)methylidene]-5-[(1-ethylpiperidin-4-yl)amino]-1,3-dihydro-2H-indol-2-one |
| 67 | (3Z)-5-[(1-ethylpiperidin-4-yl)amino]-3-[(3-fluoro-4-methylphenyl)(4-methyl-1H-imidazol-2-yl)methylidene]-1,3-dihydro-2H-indol-2-one |
| 68 | (3Z)-5-[(1-ethylpiperidin-4-yl)amino]-3-{1H-imidazol-2-yl[6-(trifluoromethyl)pyridin-3-yl]methylidene}-1,3-dihydro-2H-indol-2-one |
| 69 | (3Z)-3-[1H-imidazol-2-yl(4-methylphenyl)methylidene]-5-({1-[2-(methyloxy)ethyl]piperidin-4-yl}amino)-1,3-dihydro-2H-indol-2-one |
| 70 | (3Z)-3-[(3-fluorophenyl)(4-methyl-1H-imidazol-2-yl)methylidene]-5-({1-[2-(methyloxy)ethyl]piperidin-4-yl}amino)-1,3-dihydro-2H-indol-2-one |
| 71 | (3Z)-3-{1H-imidazol-2-yl[4-(trifluoromethyl)phenyl]methylidene}-5-({1-[2-(methyloxy)ethyl]piperidin-4-yl}amino)-1,3-dihydro-2H-indol-2-one |
| 72 | (3Z)-3-[(5-chloro-1H-benzimidazol-2-yl)(phenyl)methylidene]-5-({1-[2-(methyloxy)ethyl]piperidin-4-yl}amino)-1,3-dihydro-2H-indol-2-one |
| 73 | (3Z)-3-[(3,5-difluorophenyl)(1H-imidazol-2-yl)methylidene]-5-[(1-ethylpiperidin-4-yl)amino]-1,3-dihydro-2H-indol-2-one |
| 74 | (3Z)-3-[(3,5-difluorophenyl)(4-methyl-1H-imidazol-2-yl)methylidene]-5-[(1-ethylpiperidin-4-yl)amino]-1,3-dihydro-2H-indol-2-one |
| 75 | (3Z)-3-[(3,5-difluorophenyl)(1H-imidazol-2-yl)methylidene]-5-({1-[2-(methyloxy)ethyl]piperidin-4-yl}amino)-1,3-dihydro-2H-indol-2-one |
| 76 | (3Z)-3-[(3,5-difluorophenyl)(4-methyl-1H-imidazol-2-yl)methylidene]-5-({1-[2-(methyloxy)ethyl]piperidin-4-yl}amino)-1,3-dihydro-2H-indol-2-one |
| 77 | (3Z)-3-[(4-methyl-1H-imidazol-2-yl)(4-methylphenyl)methylidene]-5-({1-[2-(methyloxy)ethyl]piperidin-4-yl}amino)-1,3-dihydro-2H-indol-2-one |
| 78 | (3Z)-3-[(4-fluorophenyl)(1H-imidazol-2-yl)methylidene]-5-({1-[2-(methyloxy)ethyl]piperidin-4-yl}amino)-1,3-dihydro-2H-indol-2-one |
| 79 | (3Z)-3-[(3,4-difluorophenyl)(1H-imidazol-2-yl)methylidene]-5-({1-[2-(methyloxy)ethyl]piperidin-4-yl}amino)-1,3-dihydro-2H-indol-2-one |
| 80 | (3Z)-3-[(3-chloro-4-fluorophenyl)(1H-imidazol-2-yl)methylidene]-5-({1-[2-(methyloxy)ethyl]piperidin-4-yl}amino)-1,3-dihydro-2H-indol-2-one |
| 81 | (3Z)-3-[(3-fluorophenyl)(1H-imidazol-2-yl)methylidene]-5-(piperidin-4-ylamino)-1,3-dihydro-2H-indol-2-one |
| 82 | (3Z)-3-[(3-fluorophenyl)(1H-imidazol-2-yl)methylidene]-5-{[1-(2-piperidin-1-ylethyl)piperidin-4-yl]amino}-1,3-dihydro-2H-indol-2-one |
| 83 | (3Z)-3-[(3-fluorophenyl)(1H-imidazol-2-yl)methylidene]-5-{[1-(2-morpholin-4-ylethyl)piperidin-4-yl]amino}-1,3-dihydro-2H-indol-2-one |
| 84 | (3Z)-5-({1-[2-(diethylamino)ethyl]piperidin-4-yl}amino)-3-[(3-fluorophenyl)(1H-imidazol-2-yl)methylidene]-1,3-dihydro-2H-indol-2-one |
| 85 | (3Z)-3-[(3-fluorophenyl)(1H-imidazol-2-yl)methylidene]-5-{[1-(2-pyrrolidin-1-ylethyl)piperidin-4-yl]amino}-1,3-dihydro-2H-indol-2-one |
| 86 | (3Z)-3-[1H-imidazol-2-yl(4-methylphenyl)methylidene]-5-[(1-methylpiperidin-4-yl)amino]-1,3-dihydro-2H-indol-2-one |
| 87 | (3Z)-3-[(3-fluorophenyl)(1H-1,2,4-triazol-5-yl)methylidene]-5-({1-[2-(methyloxy)ethyl]piperidin-4-yl}amino)-1,3-dihydro-2H-indol-2-one |
| 88 | ethyl 2-{(Z)-(3-fluorophenyl)[5-({1-[2-(methyloxy)ethyl]piperidin-4-yl}amino)-2-oxo-1,2-dihydro-3H-indol-3-ylidene]methyl}-4-methyl-1H-imidazole-5-carboxylate |
| 89 | (3Z)-3-[1H-imidazol-2-yl(phenyl)methylidene]-5-({1-[2-(methyloxy)ethyl]piperidin-4-yl}amino)-1,3-dihydro-2H-indol-2-one |
| 90 | (3Z)-3-{1H-imidazol-2-yl[4-(methyloxy)phenyl]methylidene}-5-({1-[2-(methyloxy)ethyl]piperidin-4-yl}amino)-1,3-dihydro-2H-indol-2-one |
| 91 | (3Z)-3-[(4-chlorophenyl)(1H-imidazol-2-yl)methylidene]-5-({1-[2-(methyloxy)ethyl]piperidin-4-yl}amino)-1,3-dihydro-2H-indol-2-one |
| 92 | (3Z)-3-[[3-fluoro-4-(trifluoromethyl)phenyl](1H-imidazol-2-yl)methylidene]-5-({1-[2-(methyloxy)ethyl]piperidin-4-yl}amino)-1,3-dihydro-2H-indol-2-one |
| 93 | (3Z)-3-[(3-fluorophenyl)(1H-imidazol-2-yl)methylidene]-5-{[1-(methylsulfonyl)piperidin-4-yl]amino}-1,3-dihydro-2H-indol-2-one |
| 94 | (3Z)-3-[1H-imidazol-2-yl(4-propylphenyl)methylidene]-5-({1-[2-(methyloxy)ethyl]piperidin-4-yl}amino)-1,3-dihydro-2H-indol-2-one |

-continued

| Entry | Name |
|---|---|
| 95 | (3Z)-5-[(1-ethylpiperidin-4-yl)amino]-3-[(3-fluorophenyl)(4-phenyl-1H-imidazol-2-yl)methylidene]-1,3-dihydro-2H-indol-2-one |
| 96 | (3Z)-3-[(3-fluorophenyl)(4-phenyl-1H-imidazol-2-yl)methylidene]-5-({1-[2-(methyloxy)ethyl]piperidin-4-yl}amino)-1,3-dihydro-2H-indol-2-one |
| 97 | (3Z)-3-[(3-fluoro-4-methylphenyl)(4-methyl-1H-imidazol-2-yl)methylidene]-5-({1-[2-(methyloxy)ethyl]piperidin-4-yl}amino)-1,3-dihydro-2H-indol-2-one |
| 98 | (3Z)-3-{1H-imidazol-2-yl[6-(trifluoromethyl)pyridin-3-yl]methylidene}-5-({1-[2-(methyloxy)ethyl]piperidin-4-yl}amino)-1,3-dihydro-2H-indol-2-one |
| 99 | (3Z)-5-[(1-ethylpiperidin-4-yl)amino]-3-[(3-fluorophenyl)(1H-1,2,4-triazol-5-yl)methylidene]-1,3-dihydro-2H-indol-2-one |
| 100 | (3Z)-5-[(1-ethylpiperidin-4-yl)amino]-3-[[2-fluoro-4-(trifluoromethyl)phenyl](1H-imidazol-2-yl)methylidene]-1,3-dihydro-2H-indol-2-one |
| 101 | (3Z)-5-[(1-ethylpiperidin-4-yl)amino]-3-{(4-methyl-1H-imidazol-2-yl)[4-(trifluoromethyl)phenyl]methylidene}-1,3-dihydro-2H-indol-2-one |
| 102 | (3Z)-3-[(4-chlorophenyl)(4-methyl-1H-imidazol-2-yl)methylidene]-5-[(1-ethylpiperidin-4-yl)amino]-1,3-dihydro-2H-indol-2-one |
| 103 | (3Z)-5-[(1-ethylpiperidin-4-yl)amino]-3-[[3-fluoro-4-(trifluoromethyl)phenyl](4-methyl-1H-imidazol-2-yl)methylidene]-1,3-dihydro-2H-indol-2-one |
| 104 | (3Z)-3-[(3,4-difluorophenyl)(4-methyl-1H-imidazol-2-yl)methylidene]-5-[(1-ethylpiperidin-4-yl)amino]-1,3-dihydro-2H-indol-2-one |
| 105 | (3Z)-3-[(3-chloro-4-fluorophenyl)(4-methyl-1H-imidazol-2-yl)methylidene]-5-[(1-ethylpiperidin-4-yl)amino]-1,3-dihydro-2H-indol-2-one |
| 106 | (3Z)-5-[(1-ethylpiperidin-4-yl)amino]-3-[(4-fluorophenyl)(4-methyl-1H-imidazol-2-yl)methylidene]-1,3-dihydro-2H-indol-2-one |
| 107 | (3Z)-5-[(1-ethylpiperidin-4-yl)amino]-3-[(2-fluorophenyl)(1H-imidazol-2-yl)methylidene]-1,3-dihydro-2H-indol-2-one |
| 108 | (3Z)-5-[(1-ethylpiperidin-4-yl)amino]-3-[[2-fluoro-4-(trifluoromethyl)phenyl](4-methyl-1H-imidazol-2-yl)methylidene]-1,3-dihydro-2H-indol-2-one |
| 109 | (3Z)-3-[(2,3-difluorophenyl)(1H-imidazol-2-yl)methylidene]-5-[(1-ethylpiperidin-4-yl)amino]-1,3-dihydro-2H-indol-2-one |
| 110 | (3Z)-3-[(2,3-difluorophenyl)(4-methyl-1H-imidazol-2-yl)methylidene]-5-[(1-ethylpiperidin-4-yl)amino]-1,3-dihydro-2H-indol-2-one |
| 111 | (3Z)-3-[(2,4-difluorophenyl)(4-methyl-1H-imidazol-2-yl)methylidene]-5-[(1-ethylpiperidin-4-yl)amino]-1,3-dihydro-2H-indol-2-one |
| 112 | (3Z)-3-[(2,4-difluorophenyl)(1H-imidazol-2-yl)methylidene]-5-[(1-ethylpiperidin-4-yl)amino]-1,3-dihydro-2H-indol-2-one |
| 113 | (3Z)-3-[(2-fluorophenyl)(4-methyl-1H-imidazol-2-yl)methylidene]-5-[(1-ethylpiperidin-4-yl)amino]-1,3-dihydro-2H-indol-2-one |
| 114 | (3Z)-3-[(3-trifluoromethylphenyl)(1H-imidazol-2-yl)methylidene]-5-[(1-ethylpiperidin-4-yl)amino]-1,3-dihydro-2H-indol-2-one |
| 115 | (3Z)-3-[(3-trifluoromethylphenyl)(4-methyl-1H-imidazol-2-yl)methylidene]-5-[(1-ethylpiperidin-4-yl)amino]-1,3-dihydro-2H-indol-2-one |
| 116 | (3Z)-3-[(2,4-dichloro-5-fluorophenyl)(1H-imidazol-2-yl)methylidene]-5-[(1-ethylpiperidin-4-yl)amino]-1,3-dihydro-2H-indol-2-one |
| 117 | (3Z)-3-[(2,4-dichloro-5-fluorophenyl)(4-methyl-1H-imidazol-2-yl)methylidene]-5-[(1-ethylpiperidin-4-yl)amino]-1,3-dihydro-2H-indol-2-one |
| 118 | (3Z)-3-[(4-chloro-2-fluorophenyl)(4-methyl-1H-imidazol-2-yl)methylidene]-5-[(1-ethylpiperidin-4-yl)amino]-1,3-dihydro-2H-indol-2-one |

The Compounds in Table 8 can be prepared as pharmaceutically acceptable salts, solvates, hydrates, and/or isomers thereof. All such salt, solvate, hydrate, and isomer combinations of the Compounds in Table 8 can be used to practice the invention.

| Entry | Name |
|---|---|
| 1 | N-[5-chloro-2-(methyloxy)phenyl]-2-{[3-(1H-tetrazol-1-yl)phenyl]oxy}acetamide |
| 2 | N-phenyl-2-{[3-(1H-tetrazol-1-yl)phenyl]oxy}acetamide |
| 3 | N-(2-methylphenyl)-2-{[3-(1H-tetrazol-1-yl)phenyl]oxy}acetamide |
| 4 | N-(2-chlorophenyl)-2-{[3-(1H-tetrazol-1-yl)phenyl]oxy}acetamide |
| 5 | N-[4-chloro-3-(trifluoromethyl)phenyl]-2-{[3-(1H-tetrazol-1-yl)phenyl]oxy}acetamide |
| 6 | ethyl 2-[({[3-(1H-tetrazol-1-yl)phenyl]oxy}acetyl)amino]-4,5,6,7-tetrahydro-1-benzothiophene-3-carboxylate |
| 7 | N-(3-chloro-2-methylphenyl)-2-{[3-(1H-tetrazol-1-yl)phenyl]oxy}acetamide |
| 8 | N-(3-fluorophenyl)-2-{[3-(1H-tetrazol-1-yl)phenyl]oxy}acetamide |
| 9 | N-[4-chloro-3-(trifluoromethyl)phenyl]-2-{[3-(2H-tetrazol-5-yl)phenyl]oxy}acetamide |

-continued

| Entry | Name |
|---|---|
| 10 | N-(4-chloro-2-fluorophenyl)-2-{[3-(1H-tetrazol-1-yl)phenyl]oxy}acetamide |
| 11 | N-(4-bromo-3-methylphenyl)-2-{[3-(1H-tetrazol-1-yl)phenyl]oxy}acetamide |
| 12 | N-(4-morpholin-4-ylphenyl)-2-{[3-(1H-tetrazol-1-yl)phenyl]oxy}acetamide |
| 13 | N-[4-fluoro-3-(trifluoromethyl)phenyl]-2-{[3-(1H-tetrazol-1-yl)phenyl]oxy}acetamide |
| 14 | N-[4-bromo-3-(trifluoromethyl)phenyl]-2-{[3-(1H-tetrazol-1-yl)phenyl]oxy}acetamide |
| 15 | N-[4-chloro-3-(trifluoromethyl)phenyl]-2-{[4-(1H-tetrazol-1-yl)phenyl]oxy}acetamide |
| 16 | N-[4-chloro-3-(trifluoromethyl)phenyl]-2-{[3-(1H-tetrazol-1-yl)phenyl]oxy}propanamide |
| 17 | N-[4-chloro-3-(trifluoromethyl)phenyl]-2-{[3-(5-methyl-1H-tetrazol-1-yl)phenyl]oxy}acetamide |
| 18 | N-[4-chloro-3-(trifluoromethyl)phenyl]-2-{[2-methyl-5-(1H-tetrazol-1-yl)phenyl]oxy}acetamide |
| 19 | N-(4-chlorophenyl)-N-methyl-2-{[3-(1H-tetrazol-1-yl)phenyl]oxy}acetamide |
| 20 | N-[4-chloro-2-(trifluoromethyl)phenyl]-2-{[3-(1H-tetrazol-1-yl)phenyl]oxy}acetamide |
| 21 | N-[4-chloro-3-(trifluoromethyl)phenyl]-2-{[3-(2,5-dioxopyrrolidin-1-yl)phenyl]oxy}acetamide |
| 22 | (2E)—N-[4-chloro-3-(trifluoromethyl)phenyl]-3-[3-(1H-tetrazol-1-yl)phenyl]prop-2-enamide |
| 23 | N-[4-fluoro-3-(trifluoromethyl)phenyl]-2-{[4-(1H-tetrazol-1-yl)phenyl]oxy}acetamide |
| 24 | N-[4-chloro-3-(trifluoromethyl)phenyl]-2-{[3-(2-methyl-2H-tetrazol-5-yl)phenyl]oxy}acetamide |
| 25 | N-[4-chloro-3-(trifluoromethyl)phenyl]-2-{[2,4-dichloro-5-(1H-tetrazol-1-yl)phenyl]oxy}acetamide |
| 26 | N-[4-chloro-3-(trifluoromethyl)phenyl]-2-{[3-(1H-tetrazol-1-yl)phenyl]thio}acetamide |
| 27 | N-[4-chloro-3-(trifluoromethyl)phenyl]-N~2~-[3-(1H-tetrazol-1-yl)phenyl]glycinamide |
| 28 | N-[4-chloro-3-(trifluoromethyl)phenyl]-2-{[2-(1H-tetrazol-1-yl)phenyl]oxy}acetamide |
| 29 | methyl 1-{3-[(2-{[4-chloro-3-(trifluoromethyl)phenyl]amino}-2-oxoethyl)oxy]phenyl}-1H-1,2,3-triazole-4-carboxylate |
| 30 | 1,1-dimethylethyl {4-[({[3-(1H-tetrazol-1-yl)phenyl]oxy}acetyl)amino]phenyl}carbamate |
| 31 | 1,1-dimethylethyl {4-[({[4-(1H-tetrazol-1-yl)phenyl]oxy}acetyl)amino]phenyl}carbamate |
| 32 | N-{4-[(1-ethylpiperidin-4-yl)amino]phenyl}-2-{[3-(1H-tetrazol-1-yl)phenyl]oxy}acetamide |
| 33 | N-{4-[(1-ethylpiperidin-3-yl)amino]phenyl}-2-{[3-(1H-tetrazol-1-yl)phenyl]oxy}acetamide |
| 34 | N-(4-aminophenyl)-2-{[4-(1H-tetrazol-1-yl)phenyl]oxy}acetamide |
| 35 | N-{4-[(1-ethylpiperidin-4-yl)amino]phenyl}-2-{[4-(1H-tetrazol-1-yl)phenyl]oxy}acetamide |
| 36 | N-{4-[(1-ethylpiperidin-3-yl)amino]phenyl}-2-{[4-(1H-tetrazol-1-yl)phenyl]oxy}acetamide |
| 37 | N-[4-chloro-3-(trifluoromethyl)phenyl]-2-[(3-pyridin-4-ylphenyl)oxy]acetamide |
| 38 | N-[4-chloro-3-(trifluoromethyl)phenyl]-N~2~-methyl-N~2~-[3-(1H-tetrazol-1-yl)phenyl]glycinamide |
| 39 | N-1,3-benzothiazol-2-yl-2-{[3-(1H-tetrazol-1-yl)phenyl]oxy}acetamide |
| 40 | N-quinolin-8-yl-2-{[3-(1H-tetrazol-1-yl)phenyl]oxy}acetamide |
| 41 | N-(2,3-dihydro-1,4-benzodioxin-6-yl)-2-{[3-(1H-tetrazol-1-yl)phenyl]oxy}acetamide |
| 42 | N-isoquinolin-5-yl-2-{[3-(1H-tetrazol-1-yl)phenyl]oxy}acetamide |
| 43 | N-{3-[(phenylmethyl)oxy]phenyl}-2-{[3-(1H-tetrazol-1-yl)phenyl]oxy}acetamide |
| 44 | N-[5-methyl-2-(methyloxy)phenyl]-2-{[3-(1H-tetrazol-1-yl)phenyl]oxy}acetamide |
| 45 | N-[2,5-bis(methyloxy)phenyl]-2-{[3-(1H-tetrazol-1-yl)phenyl]oxy}acetamide |
| 46 | N-(6-fluoro-1,3-benzothiazol-2-yl)-2-{[3-(1H-tetrazol-1-yl)phenyl]oxy}acetamide |
| 47 | methyl 3-[({[3-(1H-tetrazol-1-yl)phenyl]oxy}acetyl)amino]benzoate |
| 48 | 5-chloro-2-[({[3-(1H-tetrazol-1-yl)phenyl]oxy}acetyl)amino]benzamide |
| 49 | N-[5-chloro-2,4-bis(methyloxy)phenyl]-2-{[3-(1H-tetrazol-1-yl)phenyl]oxy}acetamide |
| 50 | N-[2-(phenyloxy)phenyl]-2-{[3-(1H-tetrazol-1-yl)phenyl]oxy}acetamide |
| 51 | N-[3-(aminosulfonyl)phenyl]-2-{[3-(1H-tetrazol-1-yl)phenyl]oxy}acetamide |

| Entry | Name |
|---|---|
| 52 | N-[2-(methyloxy)-5-(trifluoromethyl)phenyl]-2-{[3-(1H-tetrazol-1-yl)phenyl]oxy}acetamide |
| 53 | N-(4-{[(4-methylphenyl)sulfonyl]amino}phenyl)-2-{[3-(1H-tetrazol-1-yl)phenyl]oxy}acetamide |
| 54 | N-(5-phenyl-1H-pyrazol-3-yl)-2-{[3-(1H-tetrazol-1-yl)phenyl]oxy}acetamide |
| 55 | N-1,3-benzothiazol-2-yl-2-{[4-(1H-tetrazol-1-yl)phenyl]oxy}acetamide |
| 56 | N-quinolin-8-yl-2-{[4-(1H-tetrazol-1-yl)phenyl]oxy}acetamide |
| 57 | 1,1-dimethylethyl 2-{3-[(2-{[4-chloro-3-(trifluoromethyl)phenyl]amino}-2-oxoethyl)oxy]phenyl}-1H-pyrrole-1-carboxylate |
| 58 | N-[4-chloro-3-(trifluoromethyl)phenyl]-2-{[3-(1H-pyrrol-2-yl)phenyl]oxy}acetamide |
| 59 | N-[4-chloro-3-(trifluoromethyl)phenyl]-2-[(3-pyrimidin-5-ylphenyl)oxy]acetamide |
| 60 | N-[4-chloro-3-(trifluoromethyl)phenyl]-2-{[3-(1H-1,2,3-triazol-1-yl)phenyl]oxy}acetamide |
| 61 | 4-chloro-N-(2-{[3-(1H-tetrazol-1-yl)phenyl]oxy}ethyl)-3-(trifluoromethyl)aniline |
| 62 | N-[4-chloro-3-(trifluoromethyl)phenyl]-N-(2-{[3-(1H-tetrazol-1-yl)phenyl]oxy}ethyl)formamide |
| 63 | N-[4-chloro-3-(trifluoromethyl)phenyl]-2-[(3-pyridin-3-ylphenyl)oxy]acetamide |
| 64 | N-[4-chloro-3-(trifluoromethyl)phenyl]-2-[(3-furan-3-ylphenyl)oxy]acetamide |
| 65 | (2E)—N-[4-fluoro-3-(trifluoromethyl)phenyl]-3-[3-(1H-tetrazol-1-yl)phenyl]prop-2-enamide |
| 66 | N-[4-fluoro-3-(trifluoromethyl)phenyl]-3-[3-(1H-tetrazol-1-yl)phenyl]propanamide |
| 67 | N-[4-chloro-3-(trifluoromethyl)phenyl]-2-{[6-(1H-tetrazol-1-yl)pyrimidin-4-yl]oxy}acetamide |
| 68 | N-[4-chloro-3-(trifluoromethyl)phenyl]-2-{[3-(3,5-dimethylisoxazol-4-yl)phenyl]oxy}acetamide |
| 69 | N-[4-chloro-3-(trifluoromethyl)phenyl]-2-[(3-quinolin-7-ylphenyl)oxy]acetamide |
| 70 | N-[4-chloro-3-(trifluoromethyl)phenyl]-2-[(3-furan-2-ylphenyl)oxy]acetamide |
| 71 | N-[4-chloro-3-(trifluoromethyl)phenyl]-2-[3-(1H-tetrazol-1-yl)phenyl]hydrazinecarboxamide |
| 72 | N-[4-chloro-3-(trifluoromethyl)phenyl]-2-[(3-dibenzo[b,d]furan-4-ylphenyl)oxy]acetamide |
| 73 | N-[4-chloro-3-(trifluoromethyl)phenyl]-2-[(4-pyrimidin-5-ylphenyl)oxy]acetamide |
| 74 | N-methyl-N-[4-(methyloxy)phenyl]-2-{[3-(1H-tetrazol-1-yl)phenyl]oxy}acetamide |
| 75 | N-[4-chloro-3-(trifluoromethyl)phenyl]-N'-{[3-(1H-tetrazol-1-yl)phenyl]methyl}urea |
| 76 | N-[4-chloro-3-(trifluoromethyl)phenyl]-N-methyl-2-{[3-(1H-tetrazol-1-yl)phenyl]oxy}acetamide |
| 77 | N-[4-fluoro-3-(trifluoromethyl)phenyl]-N~2~-[3-(1H-tetrazol-1-yl)phenyl]glycinamide |
| 78 | N-[4-fluoro-3-(trifluoromethyl)phenyl]-2-{[3-(pyridin-2-ylamino)phenyl]oxy}acetamide |
| 79 | N-[2-fluoro-5-(trifluoromethyl)phenyl]-2-[3-(1H-tetrazol-1-yl)phenyl]hydrazinecarboxamide |
| 80 | N-[4-chloro-3-(trifluoromethyl)phenyl]-2-[(4-pyridin-3-ylphenyl)oxy]acetamide |
| 81 | N-[4-chloro-3-(trifluoromethyl)phenyl]-N'-[(3-pyrimidin-5-ylphenyl)methyl]urea |
| 82 | N-[4-chloro-3-(trifluoromethyl)phenyl]-N'-[(4-pyrimidin-5-ylphenyl)methyl]urea |
| 83 | N-[4-chloro-3-(trifluoromethyl)phenyl]-N'-[(4-pyridin-3-ylphenyl)methyl]urea |
| 84 | [3-(1H-tetrazol-1-yl)phenyl]methyl [4-chloro-3-(trifluoromethyl)phenyl]carbamate |
| 85 | N-[4-fluoro-3-(trifluoromethyl)phenyl]-2-[(4-pyrimidin-5-ylphenyl)oxy]acetamide |
| 86 | N~2~-[4-chloro-3-(trifluoromethyl)phenyl]-N-[3-(1H-tetrazol-1-yl)phenyl]glycinamide |
| 87 | 2-{[4-chloro-3-(trifluoromethyl)phenyl]oxy}-N-[3-(1H-tetrazol-1-yl)phenyl]acetamide |
| 88 | N-[4-chloro-3-(trifluoromethyl)phenyl]-2-{[3-methyl-4-(1H-tetrazol-1-yl)phenyl]oxy}acetamide |
| 89 | N-[4-chloro-3-(trifluoromethyl)phenyl]-2-{[4-(1H-1,2,3-triazol-1-yl)phenyl]oxy}acetamide |
| 90 | N-[4-chloro-3-(trifluoromethyl)phenyl]-2-{[3-fluoro-4-(1H-tetrazol-1-yl)phenyl]oxy}acetamide |

-continued

| Entry | Name |
|---|---|
| 91 | N-[4-chloro-3-(trifluoromethyl)phenyl]-2-{[2-fluoro-4-(1H-tetrazol-1-yl)phenyl]oxy}acetamide |
| 92 | N-({[4-chloro-3-(trifluoromethyl)phenyl]amino}carbonyl)-3-(1H-tetrazol-1-yl)benzenesulfonamide |
| 93 | N-({[4-chloro-3-(trifluoromethyl)phenyl]amino}carbonyl)-N-methyl-3-(1H-tetrazol-1-yl)benzenesulfonamide |
| 94 | N-[4-fluoro-3-(trifluoromethyl)phenyl]-2-[(4-pyridin-3-ylphenyl)oxy]acetamide |
| 95 | 2-({4-[2,4-bis(methyloxy)pyrimidin-5-yl]phenyl}oxy)-N-[4-fluoro-3-(trifluoromethyl)phenyl]acetamide |
| 96 | 2-({4-[2,4-bis(methyloxy)pyrimidin-5-yl]phenyl}oxy)-N-[4-chloro-3-(trifluoromethyl)phenyl]acetamide |
| 97 | N-[4-chloro-3-(trifluoromethyl)phenyl]-2-[(4-pyridin-4-ylphenyl)oxy]acetamide |
| 98 | N-[4-chloro-3-(trifluoromethyl)phenyl]-N~2~-[3-(methyloxy)-4-(1H-tetrazol-1-yl)phenyl]glycinamide |
| 99 | N-[4-chloro-3-(trifluoromethyl)phenyl]-N~2~-[4-(methyloxy)-3-(1H-tetrazol-1-yl)phenyl]glycinamide |
| 100 | N-[4-chloro-3-(trifluoromethyl)phenyl]-N~2~-[4-(1H-tetrazol-1-yl)phenyl]glycinamide |
| 101 | N-[4-chloro-3-(trifluoromethyl)phenyl]-2-(2,3,5,6-tetrafluoro-4-pyrimidin-5-ylphenyl)hydrazinecarboxamide |
| 102 | N-[4-chloro-3-(trifluoromethyl)phenyl]-N'-{[4-(1H-tetrazol-1-yl)phenyl]methyl}urea |
| 103 | N-[4-chloro-3-(trifluoromethyl)phenyl]-2-(4-pyrimidin-5-ylphenyl)hydrazinecarboxamide |
| 104 | N-[4-chloro-3-(trifluoromethyl)phenyl]-N'-[(3-pyridin-3-ylphenyl)methyl]urea |
| 105 | N-[4-chloro-3-(trifluoromethyl)phenyl]-2-methyl-2-{[3-(1H-tetrazol-1-yl)phenyl]oxy}propanamide |
| 106 | N-[4-chloro-3-(trifluoromethyl)phenyl]-2-{[4-(1H-tetrazol-1-yl)phenyl]oxy}propanamide |
| 107 | N-({4-[2,4-bis(methyloxy)pyrimidin-5-yl]phenyl}methyl)-N'-[4-chloro-3-(trifluoromethyl)phenyl]urea |
| 108 | N-[4-chloro-3-(trifluoromethyl)phenyl]-N'-({3-[2-(methyloxy)pyrimidin-5-yl]phenyl}methyl)urea |
| 109 | N-[4-chloro-3-(trifluoromethyl)phenyl]-N'-({3-[6-(methyloxy)pyridin-3-yl]phenyl}methyl)urea |
| 110 | N-[4-chloro-3-(trifluoromethyl)phenyl]-N'-({4-[2-(methyloxy)pyrimidin-5-yl]phenyl}methyl)urea |
| 111 | N-[4-chloro-3-(trifluoromethyl)phenyl]-N'-({4-[6-(methyloxy)pyridin-3-yl]phenyl}methyl)urea |
| 112 | 1,1-dimethylethyl 2-{4-[(2-{[4-chloro-3-(trifluoromethyl)phenyl]amino}-2-oxoethyl)oxy]phenyl}-1H-indole-1-carboxylate |
| 113 | N-({[4-chloro-3-(trifluoromethyl)phenyl]amino}carbonyl)-4-(1H-tetrazol-1-yl)benzenesulfonamide |
| 114 | N-[4-chloro-3-(trifluoromethyl)phenyl]-N~2~-[3-(2H-tetrazol-5-yl)phenyl]glycinamide |
| 115 | N-[4-chloro-3-(trifluoromethyl)phenyl]-2-{[2,6-difluoro-4-(1H-tetrazol-1-yl)phenyl]oxy}acetamide |
| 116 | (3-pyridin-3-ylphenyl)methyl [4-chloro-3-(trifluoromethyl)phenyl]carbamate |
| 117 | (3-pyrimidin-5-ylphenyl)methyl [4-chloro-3-(trifluoromethyl)phenyl]carbamate |
| 118 | (3-pyridin-4-ylphenyl)methyl [4-chloro-3-(trifluoromethyl)phenyl]carbamate |
| 119 | N-[4-chloro-3-(trifluoromethyl)phenyl]-2-[4-(1H-tetrazol-1-yl)phenyl]hydrazinecarboxamide |
| 120 | N-[4-chloro-3-(trifluoromethyl)phenyl]-2-(4-pyridin-3-ylphenyl)hydrazinecarboxamide |
| 121 | (4-pyridin-3-ylphenyl)methyl [4-chloro-3-(trifluoromethyl)phenyl]carbamate |
| 122 | (4-pyridin-4-ylphenyl)methyl [4-chloro-3-(trifluoromethyl)phenyl]carbamate |
| 123 | (4-pyrimidin-5-ylphenyl)methyl [4-chloro-3-(trifluoromethyl)phenyl]carbamate |
| 124 | N-[4-chloro-3-(trifluoromethyl)phenyl]-N'-[(4-pyridin-4-ylphenyl)methyl]urea |
| 125 | N-[4-chloro-3-(trifluoromethyl)phenyl]-2-(3-pyridin-3-ylphenyl)hydrazinecarboxamide |
| 126 | N-[4-chloro-3-(trifluoromethyl)phenyl]-2-(3-pyrimidin-5-ylphenyl)hydrazinecarboxamide |
| 127 | N-[5-chloro-2,4-bis(methyloxy)phenyl]-N'-[(4-pyrimidin-5-ylphenyl)methyl]urea |
| 128 | N-[5-chloro-2,4-bis(methyloxy)phenyl]-N'-[(4-pyridin-3-ylphenyl)methyl]urea |

| Entry | Name |
|---|---|
| 129 | (4-pyrimidin-5-ylphenyl)methyl [5-chloro-2,4-bis(methyloxy)phenyl]carbamate |
| 130 | (4-pyridin-3-ylphenyl)methyl [5-chloro-2,4-bis(methyloxy)phenyl]carbamate |
| 131 | 1-(4-pyridin-3-ylphenyl)ethyl [4-chloro-3-(trifluoromethyl)phenyl]carbamate |
| 132 | 1-(4-pyrimidin-5-ylphenyl)ethyl [4-chloro-3-(trifluoromethyl)phenyl]carbamate |
| 133 | N-[5-chloro-2,4-bis(methyloxy)phenyl]-N'-[(3-pyridin-3-ylphenyl)methyl]urea |
| 134 | N-[5-chloro-2,4-bis(methyloxy)phenyl]-N'-[(3-pyrimidin-5-ylphenyl)methyl]urea |
| 135 | (3-pyridin-3-ylphenyl)methyl [5-chloro-2,4-bis(methyloxy)phenyl]carbamate |
| 136 | (3-pyrimidin-5-ylphenyl)methyl [5-chloro-2,4-bis(methyloxy)phenyl]carbamate |
| 137 | N-[4-chloro-3-(trifluoromethyl)phenyl]-2-methyl-2-(3-pyrimidin-5-ylphenyl)hydrazinecarboxamide |
| 138 | N-[4-fluoro-3-(trifluoromethyl)phenyl]-N'-[(4-pyridin-3-ylphenyl)methyl]urea |
| 139 | N-{[3-(6-aminopyridin-3-yl)phenyl]methyl}-N'-[4-chloro-3-(trifluoromethyl)phenyl]urea |
| 140 | N-{[4-(6-aminopyridin-3-yl)phenyl]methyl}-N'-[4-chloro-3-(trifluoromethyl)phenyl]urea |
| 141 | N-{[3-(2-aminopyrimidin-5-yl)phenyl]methyl}-N'-[4-chloro-3-(trifluoromethyl)phenyl]urea |
| 142 | N-{[4-(2-aminopyrimidin-5-yl)phenyl]methyl}-N'-[4-chloro-3-(trifluoromethyl)phenyl]urea |
| 143 | N-[4-chloro-3-(trifluoromethyl)phenyl]-N'-[1-(4-pyridin-3-ylphenyl)ethyl]urea |
| 144 | N-[4-chloro-3-(trifluoromethyl)phenyl]-N'-[1-(4-pyrimidin-5-ylphenyl)ethyl]urea |
| 145 | N-[4-chloro-3-(trifluoromethyl)phenyl]-2-{[4-(1H-indol-2-yl)phenyl]oxy}acetamide |
| 146 | N-[4-chloro-3-(trifluoromethyl)phenyl]-2-(isoquinolin-7-yloxy)acetamide |
| 147 | N-[4-chloro-3-(trifluoromethyl)phenyl]-2-(4-pyridin-4-ylphenyl)hydrazinecarboxamide |
| 148 | N-[4-chloro-3-(trifluoromethyl)phenyl]-2-(3-pyridin-4-ylphenyl)hydrazinecarboxamide |
| 149 | N-[4-chloro-3-(trifluoromethyl)phenyl]-N'-[(3-pyridin-4-ylphenyl)methyl]urea |
| 150 | N-[4-chloro-3-(trifluoromethyl)phenyl]-N'-[(3-quinoxalin-6-ylphenyl)methyl]urea |
| 151 | methyl 3-amino-6-(3-{[({[4-chloro-3-(trifluoromethyl)phenyl]amino}carbonyl)amino]methyl}phenyl)pyrazine-2-carboxylate |
| 152 | N-[4-chloro-3-(trifluoromethyl)phenyl]-N'-[(4-quinoxalin-6-ylphenyl)methyl]urea |
| 153 | N-{[3-(2-amino-5-methylpyridin-3-yl)phenyl]methyl}-N'-[4-chloro-3-(trifluoromethyl)phenyl]urea |
| 154 | methyl 3-amino-6-(4-{[({[4-chloro-3-(trifluoromethyl)phenyl]amino}carbonyl)amino]methyl}phenyl)pyrazine-2-carboxylate |
| 155 | [3-(1H-tetrazol-1-yl)phenyl]methyl [3-chloro-4-(methyloxy)phenyl]carbamate |
| 156 | N-[3-chloro-4-(methyloxy)phenyl]-N'-{[3-(1H-tetrazol-1-yl)phenyl]methyl}urea |
| 157 | N-[4-chloro-3-(trifluoromethyl)phenyl]-2-{[4-(5-hydroxy-1H-tetrazol-1-yl)phenyl]oxy}acetamide |
| 158 | N-{[3-(2-amino-5-chloropyridin-3-yl)phenyl]methyl}-N'-[4-chloro-3-(trifluoromethyl)phenyl]urea |
| 159 | N-{[4-(2-amino-5-chloropyridin-3-yl)phenyl]methyl}-N'-[4-chloro-3-(trifluoromethyl)phenyl]urea |
| 160 | N-{[3-(6-chloropyridin-3-yl)phenyl]methyl}-N'-[4-chloro-3-(trifluoromethyl)phenyl]urea |
| 161 | N-{[4-(6-chloropyridin-3-yl)phenyl]methyl}-N'-[4-chloro-3-(trifluoromethyl)phenyl]urea |
| 162 | N-[4-chloro-3-(trifluoromethyl)phenyl]-N'-{[4-(pyrimidin-2-yloxy)phenyl]methyl}urea |
| 163 | N-({[4-chloro-3-(trifluoromethyl)phenyl]amino}carbonyl)-3-(1H-tetrazol-1-yl)benzamide |
| 164 | 3-amino-6-(3-{[({[4-chloro-3-(trifluoromethyl)phenyl]amino}carbonyl)amino]methyl}phenyl)-N-[2-(dimethylamino)ethyl]pyrazine-2-carboxamide |
| 165 | N-[4-chloro-3-(trifluoromethyl)phenyl]-N'-{[3-(6-fluoropyridin-3-yl)phenyl]methyl}urea |
| 166 | N-[4-chloro-3-(trifluoromethyl)phenyl]-N'-({3-[2-(methyloxy)pyridin-3-yl]phenyl}methyl)urea |
| 167 | N-[4-chloro-3-(trifluoromethyl)phenyl]-N'-{[4-(6-fluoropyridin-3-yl)phenyl]methyl}urea |

| Entry | Name |
|---|---|
| 168 | N-[4-chloro-3-(trifluoromethyl)phenyl]-N'-({4-[2-(methyloxy)pyridin-3-yl]phenyl}methyl)urea |
| 169 | N-[4-chloro-3-(trifluoromethyl)phenyl]-N'-{[4-(6-methylpyridin-3-yl)phenyl]methyl}urea |
| 170 | N-{[4-(2-amino-5-fluoropyridin-3-yl)phenyl]methyl}-N'-[4-chloro-3-(trifluoromethyl)phenyl]urea |
| 171 | N-[4-chloro-3-(trifluoromethyl)phenyl]-N'-{[3-(6-methylpyridin-3-yl)phenyl]methyl}urea |
| 172 | N-{[4-(2-aminopyridin-3-yl)phenyl]methyl}-N'-[4-chloro-3-(trifluoromethyl)phenyl]urea |
| 173 | N-{[3-(2-aminopyridin-3-yl)phenyl]methyl}-N'-[4-chloro-3-(trifluoromethyl)phenyl]urea |
| 174 | [3-(6-methylpyridin-3-yl)phenyl]methyl [4-chloro-3-(trifluoromethyl)phenyl]carbamate |
| 175 | [3-(2-amino-5-fluoropyridin-3-yl)phenyl]methyl [4-chloro-3-(trifluoromethyl)phenyl]carbamate |
| 176 | [3-(2-aminopyridin-3-yl)phenyl]methyl [4-chloro-3-(trifluoromethyl)phenyl]carbamate |
| 177 | (3-pyrazin-2-ylphenyl)methyl [4-chloro-3-(trifluoromethyl)phenyl]carbamate |
| 178 | N-[4-chloro-3-(trifluoromethyl)phenyl]-N'-({3-[6-(hydroxymethyl)pyridin-3-yl]phenyl}methyl)urea |
| 179 | N-{[3-(6-acetylpyridin-3-yl)phenyl]methyl}-N'-[4-chloro-3-(trifluoromethyl)phenyl]urea |
| 180 | N-[4-chloro-3-(trifluoromethyl)phenyl]-N'-{[3-(6-cyanopyridin-3-yl)phenyl]methyl}urea |
| 181 | 1,1-dimethylethyl (3S)-3-({[3-amino-6-(3-{[({[4-chloro-3-(trifluoromethyl)phenyl]amino}carbonyl)amino]methyl}phenyl)pyrazin-2-yl]carbonyl}amino)piperidine-1-carboxylate |
| 182 | 3-amino-6-(3-{[({[4-chloro-3-(trifluoromethyl)phenyl]amino}carbonyl)amino]methyl}phenyl)-N-[(3S)-piperidin-3-yl]pyrazine-2-carboxamide |
| 183 | 1,1-dimethylethyl (3S)-3-({[3-amino-6-(4-{[({[4-chloro-3-(trifluoromethyl)phenyl]amino}carbonyl)amino]methyl}phenyl)pyrazin-2-yl]carbonyl}amino)piperidine-1-carboxylate |
| 184 | 3-amino-6-(4-{[({[4-chloro-3-(trifluoromethyl)phenyl]amino}carbonyl)amino]methyl}phenyl)-N-[(3S)-piperidin-3-yl]pyrazine-2-carboxamide |
| 185 | [3-(7H-pyrrolo[2,3-d]pyrimidin-4-yl)phenyl]methyl [4-chloro-3-(trifluoromethyl)phenyl]carbamate |
| 186 | N-{[3-(2-amino-5-fluoropyridin-3-yl)phenyl]methyl}-N'-[4-chloro-3-(trifluoromethyl)phenyl]urea |
| 187 | [6-(1H-tetrazol-1-yl)pyridin-2-yl]methyl [4-chloro-3-(trifluoromethyl)phenyl]carbamate |
| 188 | [3-(1H-benzimidazol-2-yl)phenyl]methyl [4-chloro-3-(trifluoromethyl)phenyl]carbamate |
| 189 | [3-(6-amino-2-methylpyridin-3-yl)phenyl]methyl [4-chloro-3-(trifluoromethyl)phenyl]carbamate |
| 190 | N-[4-chloro-3-(trifluoromethyl)phenyl]-N'-({3-[5-(methylthio)pyridin-3-yl]phenyl}methyl)urea |
| 191 | [4-(6-methylpyridin-3-yl)phenyl]methyl [4-chloro-3-(trifluoromethyl)phenyl]carbamate |
| 192 | [4-(2-amino-5-fluoropyridin-3-yl)phenyl]methyl [4-chloro-3-(trifluoromethyl)phenyl]carbamate |
| 193 | [4-(2-aminopyridin-3-yl)phenyl]methyl [4-chloro-3-(trifluoromethyl)phenyl]carbamate |
| 194 | (4-pyrazin-2-ylphenyl)methyl [4-chloro-3-(trifluoromethyl)phenyl]carbamate |
| 195 | [4-(7H-pyrrolo[2,3-d]pyrimidin-4-yl)phenyl]methyl [4-chloro-3-(trifluoromethyl)phenyl]carbamate |
| 196 | [4-(6-amino-2-methylpyridin-3-yl)phenyl]methyl [4-chloro-3-(trifluoromethyl)phenyl]carbamate |
| 197 | [3-(1H-tetrazol-1-yl)phenyl]methyl 1,3-benzothiazol-2-ylcarbamate |
| 198 | [3-(1H-tetrazol-1-yl)phenyl]methyl (5-bromopyridin-2-yl)carbamate |
| 199 | (3-pyridin-3-ylphenyl)methyl (3,5-dimethylphenyl)carbamate |
| 200 | (3-pyridin-3-ylphenyl)methyl [5-chloro-2-(methyloxy)phenyl]carbamate |
| 201 | [4-(1H-tetrazol-1-yl)phenyl]methyl [4-chloro-3-(trifluoromethyl)phenyl]carbamate |
| 202 | (3-pyrimidin-5-ylphenyl)methyl [5-chloro-2-(methyloxy)phenyl]carbamate |
| 203 | (4-pyrimidin-5-ylphenyl)methyl (3,4-dimethylphenyl)carbamate |
| 204 | (3-pyridin-3-ylphenyl)methyl (3,4-dimethylphenyl)carbamate |
| 205 | 1,1-dimethylethyl 3-({[3-amino-6-(3-{[({[4-chloro-3-(trifluoromethyl)phenyl]amino}carbonyl)amino]methyl}phenyl)pyrazin-2-yl]carbonyl}amino)piperidine-1-carboxylate |

| Entry | Name |
|---|---|
| 206 | 1,1-dimethylethyl 3-({[3-amino-6-(4-{[({[4-chloro-3-(trifluoromethyl)phenyl]amino}carbonyl)amino]methyl}phenyl)pyrazin-2-yl]carbonyl}amino)piperidine-1-carboxylate |
| 207 | 3-amino-6-(3-{[({[4-chloro-3-(trifluoromethyl)phenyl]amino}carbonyl)amino]methyl}phenyl)-N-piperidin-3-ylpyrazine-2-carboxamide |
| 208 | 3-amino-6-(4-{[({[4-chloro-3-(trifluoromethyl)phenyl]amino}carbonyl)amino]methyl}phenyl)-N-piperidin-3-ylpyrazine-2-carboxamide |
| 209 | 1,1-dimethylethyl 4-{[3-amino-6-(3-{[({[4-chloro-3-(trifluoromethyl)phenyl]amino}carbonyl)amino]methyl}phenyl)pyrazin-2-yl]carbonyl}piperazine-1-carboxylate |
| 210 | 1,1-dimethylethyl 4-{[3-amino-6-(4-{[({[4-chloro-3-(trifluoromethyl)phenyl]amino}carbonyl)amino]methyl}phenyl)pyrazin-2-yl]carbonyl}piperazine-1-carboxylate |
| 211 | N-({3-[5-amino-6-(piperazin-1-ylcarbonyl)pyrazin-2-yl]phenyl}methyl)-N'-[4-chloro-3-(trifluoromethyl)phenyl]urea |
| 212 | N-({4-[5-amino-6-(piperazin-1-ylcarbonyl)pyrazin-2-yl]phenyl}methyl)-N'-[4-chloro-3-(trifluoromethyl)phenyl]urea |
| 213 | N-[4-chloro-3-(trifluoromethyl)phenyl]-N'-{[3-(1H-pyrazol-4-yl)phenyl]methyl}urea |
| 214 | N-[4-chloro-3-(trifluoromethyl)phenyl]-N'-{[4-(1H-pyrazol-4-yl)phenyl]methyl}urea |
| 215 | [3-(2-piperazin-1-ylpyrimidin-5-yl)phenyl]methyl [4-chloro-3-(trifluoromethyl)phenyl]carbamate |
| 216 | [4-(2-piperazin-1-ylpyrimidin-5-yl)phenyl]methyl [4-chloro-3-(trifluoromethyl)phenyl]carbamate |
| 217 | N-{[3-(2-chloropyridin-3-yl)phenyl]methyl}-N'-[4-chloro-3-(trifluoromethyl)phenyl]urea |
| 218 | N-{[4-(2-chloropyridin-3-yl)phenyl]methyl}-N'-[4-chloro-3-(trifluoromethyl)phenyl]urea |
| 219 | N-[4-chloro-3-(trifluoromethyl)phenyl]-N'-{[3-(2-fluoropyridin-3-yl)phenyl]methyl}urea |
| 220 | N-[4-chloro-3-(trifluoromethyl)phenyl]-N'-{[4-(2-fluoropyridin-3-yl)phenyl]methyl}urea |
| 221 | [3-(1H-tetrazol-1-yl)phenyl]methyl [3-(trifluoromethyl)phenyl]carbamate |
| 222 | [3-(1H-tetrazol-1-yl)phenyl]methyl [6-(trifluoromethyl)pyridin-2-yl]carbamate |
| 223 | [3-(1H-tetrazol-1-yl)phenyl]methyl [4-(trifluoromethyl)pyridin-2-yl]carbamate |
| 224 | N-[4-chloro-3-(trifluoromethyl)phenyl]-N'-({3-[5-(methylthio)pyridin-2-yl]phenyl}methyl)urea |
| 225 | [3-(2,6-dimethylpyridin-3-yl)phenyl]methyl [4-chloro-3-(trifluoromethyl)phenyl]carbamate |
| 226 | {3-[5-(methyloxy)pyridin-3-yl]phenyl}methyl [4-chloro-3-(trifluoromethyl)phenyl]carbamate |
| 227 | 2,3'-bipyridin-6-ylmethyl [4-chloro-3-(trifluoromethyl)phenyl]carbamate |
| 228 | (6-pyrimidin-5-ylpyridin-2-yl)methyl [4-chloro-3-(trifluoromethyl)phenyl]carbamate |
| 229 | N-[4-chloro-3-(trifluoromethyl)phenyl]-N'-[(3-isoquinolin-4-ylphenyl)methyl]urea |
| 230 | N-[4-chloro-3-(trifluoromethyl)phenyl]-N'-[(4-isoquinolin-4-ylphenyl)methyl]urea |
| 231 | [6-(1H-tetrazol-1-yl)pyridin-2-yl]methyl [4-(trifluoromethyl)pyridin-2-yl]carbamate |
| 232 | [3-(1H-pyrazol-4-yl)phenyl]methyl [4-chloro-3-(trifluoromethyl)phenyl]carbamate |
| 233 | [4-(1H-pyrazol-4-yl)phenyl]methyl [4-chloro-3-(trifluoromethyl)phenyl]carbamate |

The Compounds in Table 9 can be prepared as pharmaceutically acceptable salts, solvates, hydrates, and/or isomers thereof. All such salt, solvate, hydrate, and isomer combinations of the Compounds in Table 9 can be used to practice the invention.

| Entry | Name |
|---|---|
| 1 | 4-((E)-2-{3-[6-(4-methylpiperazin-1-yl)-1H-benzimidazol-2-yl]-1H-pyrazol-5-yl}ethenyl)phenol |
| 2 | N-[4-chloro-3-(trifluoromethyl)phenyl]-N'-(4-{3-[5-(4-ethylpiperazin-1-yl)-1H-benzimidazol-2-yl]-1H-pyrazol-5-yl}phenyl)urea |

-continued

| Entry | Name |
|---|---|
| 3 | N-(3-ethylphenyl)-N'-(4-{3-[5-(4-ethylpiperazin-1-yl)-1H-benzimidazol-2-yl]-1H-pyrazol-5-yl}phenyl)urea |
| 4 | N-(4-{3-[5-(4-ethylpiperazin-1-yl)-1H-benzimidazol-2-yl]-1H-pyrazol-5-yl}phenyl)-N'-[3-(trifluoromethyl)phenyl]urea |
| 5 | N-(3-acetylphenyl)-N'-(4-{3-[5-(4-methylpiperazin-1-yl)-1H-benzimidazol-2-yl]-1H-pyrazol-5-yl}phenyl)urea |
| 6 | N-(3,4-dichlorophenyl)-N'-(4-{3-[5-(4-methylpiperazin-1-yl)-1H-benzimidazol-2-yl]-1H-pyrazol-5-yl}phenyl)urea |
| 7 | N-(3-bromophenyl)-N'-(4-{3-[6-(4-methylpiperazin-1-yl)-1H-benzimidazol-2-yl]-1H-pyrazol-5-yl}phenyl)urea |
| 8 | N-[4-fluoro-3-(trifluoromethyl)phenyl]-N'-(4-{3-[5-(4-methylpiperazin-1-yl)-1H-benzimidazol-2-yl]-1H-pyrazol-5-yl}phenyl)urea |
| 9 | N-(4-{3-[5-(4-methylpiperazin-1-yl)-1H-benzimidazol-2-yl]-1H-pyrazol-5-yl}phenyl)-N'-[4-(phenyloxy)phenyl]urea |
| 10 | N-(3-chlorophenyl)-N'-(4-{3-[5-(4-methylpiperazin-1-yl)-1H-benzimidazol-2-yl]-1H-pyrazol-5-yl}phenyl)urea |
| 11 | N-[3,5-bis(methyloxy)phenyl]-N'-(4-{3-[6-(4-methylpiperazin-1-yl)-1H-benzimidazol-2-yl]-1H-pyrazol-5-yl}phenyl)urea |
| 12 | N-(4-{3-[5-(4-methylpiperazin-1-yl)-1H-benzimidazol-2-yl]-1H-pyrazol-5-yl}phenyl)-N'-{4-[(trifluoromethyl)oxy]phenyl}urea |
| 13 | N-(4-{3-[6-(4-methylpiperazin-1-yl)-1H-benzimidazol-2-yl]-1H-pyrazol-5-yl}phenyl)-N'-[4-(trifluoromethyl)phenyl]urea |
| 14 | N-[4-chloro-3-(trifluoromethyl)phenyl]-N'-(4-{3-[5-(4-methylpiperazin-1-yl)-1H-benzimidazol-2-yl]-1H-pyrazol-5-yl}phenyl)urea |
| 15 | N-(4-{3-[5-(4-methylpiperazin-1-yl)-1H-benzimidazol-2-yl]-1H-pyrazol-5-yl}phenyl)-N'-[3-(trifluoromethyl)phenyl]urea |
| 16 | N-[4-chloro-3-(trifluoromethyl)phenyl]-N'-(4-{3-[4-(4-methylpiperazin-1-yl)phenyl]-1H-pyrazol-5-yl}phenyl)urea |
| 17 | N-(3,4-dimethylphenyl)-N'-(4-{5-[4-(4-methylpiperazin-1-yl)phenyl]-1H-pyrazol-3-yl}phenyl)urea |
| 18 | N-(4-chlorophenyl)-N'-(4-{3-[5-(4-methylpiperazin-1-yl)-1H-benzimidazol-2-yl]-1H-pyrazol-5-yl}phenyl)urea |
| 19 | N-(3,5-difluorophenyl)-N'-(4-{3-[5-(4-methylpiperazin-1-yl)-1H-benzimidazol-2-yl]-1H-pyrazol-5-yl}phenyl)urea |
| 20 | N-[3-(methyloxy)phenyl]-N'-(4-{3-[5-(4-methylpiperazin-1-yl)-1H-benzimidazol-2-yl]-1H-pyrazol-5-yl}phenyl)urea |
| 21 | N-[4-chloro-3-(trifluoromethyl)phenyl]-N'-(4-{3-[4-(4-ethylpiperazin-1-yl)phenyl]-1H-pyrazol-5-yl}phenyl)urea |
| 22 | N-(3-fluorophenyl)-N'-(4-{3-[5-(4-methylpiperazin-1-yl)-1H-benzimidazol-2-yl]-1H-pyrazol-5-yl}phenyl)urea |
| 23 | N-(4-fluorophenyl)-N'-(4-{3-[5-(4-methylpiperazin-1-yl)-1H-benzimidazol-2-yl]-1H-pyrazol-5-yl}phenyl)urea |
| 24 | N-(3-cyanophenyl)-N'-(4-{3-[6-(4-methylpiperazin-1-yl)-1H-benzimidazol-2-yl]-1H-pyrazol-5-yl}phenyl)urea |
| 25 | N-(3,4-difluorophenyl)-N'-(4-{3-[5-(4-methylpiperazin-1-yl)-1H-benzimidazol-2-yl]-1H-pyrazol-5-yl}phenyl)urea |
| 26 | N-[3,4-bis(methyloxy)phenyl]-N'-(4-{3-[5-(4-methylpiperazin-1-yl)-1H-benzimidazol-2-yl]-1H-pyrazol-5-yl}phenyl)urea |
| 27 | N-[5-chloro-2-(methyloxy)phenyl]-N'-(4-{5-[4-(4-methylpiperazin-1-yl)phenyl]-1H-pyrazol-3-yl}phenyl)urea |
| 28 | N-(4-{5-[4-(4-methylpiperazin-1-yl)phenyl]-1H-pyrazol-3-yl}phenyl)-N'-[4-(phenyloxy)phenyl]urea |
| 29 | N-(2,4-difluorophenyl)-N'-(4-{3-[6-(4-ethylpiperazin-1-yl)-1H-benzimidazol-2-yl]-1H-pyrazol-5-yl}phenyl)urea |
| 30 | N-{4-[3-(1H-benzimidazol-2-yl)-1H-pyrazol-5-yl]phenyl}-N'-[4-chloro-3-(trifluoromethyl)phenyl]urea |
| 31 | N-{4-[3-(1H-benzimidazol-2-yl)-1H-pyrazol-5-yl]phenyl}-N'-[2-fluoro-5-(trifluoromethyl)phenyl]urea |
| 32 | N-(2,4-difluorophenyl)-N'-(4-{3-[5-(4-methylpiperazin-1-yl)-1H-benzimidazol-2-yl]-1H-pyrazol-5-yl}phenyl)urea |
| 33 | N-{4-[3-(1H-benzimidazol-2-yl)-1H-pyrazol-5-yl]phenyl}-N'-phenylurea |
| 34 | N-[3,5-bis(trifluoromethyl)phenyl]-N'-(4-{3-[5-(4-methylpiperazin-1-yl)-1H-benzimidazol-2-yl]-1H-pyrazol-5-yl}phenyl)urea |
| 35 | N-(2-fluorophenyl)-N'-(4-{3-[5-(4-methylpiperazin-1-yl)-1H-benzimidazol-2-yl]-1H-pyrazol-5-yl}phenyl)urea |
| 36 | 4-((E)-2-{5-[(E)-2-phenylethenyl]-1H-pyrazol-3-yl}ethenyl)phenol |
| 37 | 2-(methyloxy)-4-((E)-2-{5-[(E)-2-phenylethenyl]-1H-pyrazol-3-yl}ethenyl)phenol |
| 38 | N-(5-fluoro-2-methylphenyl)-N'-(4-{3-[6-(4-methylpiperazin-1-yl)-1H-benzimidazol-2-yl]-1H-pyrazol-5-yl}phenyl)urea |
| 39 | N-(4-{3-[5-(4-methylpiperazin-1-yl)-1H-benzimidazol-2-yl]-1H-pyrazol-5-yl}phenyl)-N'-phenylurea |
| 40 | N-[4-chloro-3-(trifluoromethyl)phenyl]-N'-(4-{3-[3-(4-methylpiperazin-1-yl)phenyl]-1H-pyrazol-5-yl}phenyl)urea |
| 41 | N-(2,4-difluorophenyl)-N'-(4-{3-[4-(4-methylpiperazin-1-yl)phenyl]-1H-pyrazol-5-yl}phenyl)urea |
| 42 | N-(2,3-dihydro-1,4-benzodioxin-6-yl)-N'-(4-{5-[4-(4-methylpiperazin-1-yl)phenyl]-1H-pyrazol-3-yl}phenyl)urea |

-continued

| Entry | Name |
|---|---|
| 43 | N-[2,4-bis(methyloxy)phenyl]-N'-(4-{5-[4-(4-methylpiperazin-1-yl)phenyl]-1H-pyrazol-3-yl}phenyl)urea |
| 44 | 4-((E)-2-{3-[(E)-2-(4-fluorophenyl)ethenyl]-1H-pyrazol-5-yl}ethenyl)-2-(methyloxy)phenol |
| 45 | 4-{(E)-2-[3-(1-benzofuran-2-yl)-1H-pyrazol-5-yl]ethenyl}phenol |
| 46 | N-(4-{3-[4-(4-methylpiperazin-1-yl)phenyl]-1H-pyrazol-5-yl}phenyl)-N'-(2-phenylethyl)ethanediamide |
| 47 | 4-{(E)-2-[3-(1H-benzimidazol-2-yl)-1H-pyrazol-5-yl]ethenyl}phenol |
| 48 | 4-((E)-2-{3-[(E)-2-(4-chlorophenyl)ethenyl]-1H-pyrazol-5-yl}ethenyl)-2-(methyloxy)phenol |
| 49 | 4-{(E)-2-[3-(1-benzothien-2-yl)-1H-pyrazol-5-yl]ethenyl}phenol |
| 50 | N-[4-chloro-3-(trifluoromethyl)phenyl]-N'-[4-(3-phenyl-1H-pyrazol-5-yl)phenyl]urea |
| 51 | 4-((E)-2-{3-[4-(4-methylpiperazin-1-yl)phenyl]-1H-pyrazol-5-yl}ethenyl)phenol |
| 52 | 1,1-dimethylethyl {4-[3-(1H-benzimidazol-2-yl)-1H-pyrazol-5-yl]phenyl}carbamate |
| 53 | N-(5-fluoro-2-methylphenyl)-N'-(4-{5-[4-(4-methylpiperazin-1-yl)phenyl]-1H-pyrazol-3-yl}phenyl)urea |
| 54 | 4-[(E)-2-(3-phenyl-1H-pyrazol-5-yl)ethenyl]phenol |
| 55 | 2-(methyloxy)-4-[(E)-2-(5-phenyl-1H-pyrazol-3-yl)ethenyl]phenol |
| 56 | 4-[(E)-2-(5-naphthalen-2-yl-1H-pyrazol-3-yl)ethenyl]phenol |
| 57 | 4-{(E)-2-[5-(2-fluorophenyl)-1H-pyrazol-3-yl]ethenyl}phenol |
| 58 | 4-((E)-2-{3-[3-(4-methylpiperazin-1-yl)phenyl]-1H-pyrazol-5-yl}ethenyl)phenol |
| 59 | 4-((E)-2-{3-[(E)-2-(2,4-difluorophenyl)ethenyl]-1H-pyrazol-5-yl}ethenyl)-2-(methyloxy)phenol |
| 60 | 4-{(E)-2-[5-(4-fluorophenyl)-1H-pyrazol-3-yl]ethenyl}phenol |
| 61 | 4-{(E)-2-[3-(4-chlorophenyl)-1H-pyrazol-5-yl]ethenyl}phenol |
| 62 | 4-[(E)-2-(5-pyridin-2-yl-1H-pyrazol-3-yl)ethenyl]phenol |
| 63 | 4-{(E)-2-[3-(5-chloro-1-benzofuran-2-yl)-1H-pyrazol-5-yl]ethenyl}phenol |
| 64 | N-(1,1-dimethylethyl)-N'-(4-{3-[5-(4-ethylpiperazin-1-yl)-1H-benzimidazol-2-yl]-1H-pyrazol-5-yl}phenyl)urea |
| 65 | 4-[(E)-2-(3-pyridin-4-yl-1H-pyrazol-5-yl)ethenyl]phenol |
| 66 | 4-{(E)-2-[3-(3-chlorophenyl)-1H-pyrazol-5-yl]ethenyl}phenol |
| 67 | 4-((E)-2-{5-[2-(methyloxy)phenyl]-1H-pyrazol-3-yl}ethenyl)phenol |
| 68 | 4-{(E)-2-[3-(2-chlorophenyl)-1H-pyrazol-5-yl]ethenyl}phenol |
| 69 | 4-[(E)-2-(3-pyridin-3-yl-1H-pyrazol-5-yl)ethenyl]phenol |
| 70 | 4-((E)-2-{5-[3-(methyloxy)phenyl]-1H-pyrazol-3-yl}ethenyl)phenol |
| 71 | 1,1-dimethylethyl (4-{3-[(E)-2-phenylethenyl]-1H-pyrazol-5-yl}phenyl)carbamate |
| 72 | 4-{(E)-2-[3-(3,4-dichlorophenyl)-1H-pyrazol-5-yl]ethenyl}phenol |
| 73 | 2-{5-[(E)-2-phenylethenyl]-1H-pyrazol-3-yl}-1-benzofuran-6-ol |
| 74 | 4-{(E)-2-[5-(3-fluorophenyl)-1H-pyrazol-3-yl]ethenyl}phenol |
| 75 | 2-(5-phenyl-1H-pyrazol-3-yl)-1H-benzimidazole |
| 76 | N-phenyl-N'-[4-(3-phenyl-1H-pyrazol-5-yl)phenyl]urea |
| 77 | 4-[3-(1H-benzimidazol-2-yl)-1H-pyrazol-5-yl]aniline |
| 78 | 4-[(E)-2-(5-biphenyl-3-yl-1H-pyrazol-3-yl)ethenyl]phenol |
| 79 | 4-((E)-2-{5-[5-(4-methylpiperazin-1-yl)-1H-benzimidazol-2-yl]-1H-pyrazol-3-yl}ethenyl)phenol |

General Administration

In one aspect, the invention provides pharmaceutical compositions comprising an inhibitor of PI3K according to the invention and a pharmaceutically acceptable carrier, excipient, or diluent. In certain other specific embodiments, administration may specifically be by the oral route. Administration of the compounds of the invention, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semisolid, lyophilized powder, or liquid dosage forms, such as for example, tablets, suppositories, pills, soft elastic and hard gelatin capsules, powders, solutions, suspensions, or aerosols, or the like, specifically in unit dosage forms suitable for simple administration of precise dosages. When treating brain cancers, including glioblastomas, the administration may specifically be by placing a gliadel, a dissolvable material that contains the chemotherapy drug (in particular BCNU), directly into brain tumors during an operation.

The compositions will include a compound of Formula I or II as the/an active agent and can include a conventional pharmaceutical carrier or excipient and in addition may include other medicinal agents and pharmaceutical agents that are generally administered to a patient being treated for cancer.

Adjuvants include preserving, wetting, suspending, sweetening, flavoring, perfuming, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylalted hydroxytoluene, etc.

The choice of formulation depends on various factors such as the mode of drug administration (e.g., for oral administration, formulations in the form of tablets, pills or capsules) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and non-aqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

One specific route of administration is oral, using a convenient daily dosage regimen that can be adjusted according to the degree of severity of the disease-state to be treated.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, cellulose derivatives, starch, alignates, gelatin, polyvinylpyrrolidone, sucrose, and gum acacia, (c) humectants, as for example, glycerol, (d) disintegrating agents, as for example, agar-agar, calcium carbonate, potato or tapioca starch, alginic acid, croscarmellose sodium, complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, magnesium stearate and the like (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid dosage forms as described above can be prepared with coatings and shells, such as enteric coatings and others well known in the art. They may contain pacifying agents, and can also be of such composition that they release the active compound or compounds in a certain part of the intestinal tract in a delayed manner. Examples of embedded compositions that can be used are polymeric substances and waxes. The active compounds can also be in microencapsulated form, if appropriate, with one or more of the above-mentioned excipients.

Liquid dosage forms for oral administration include pharmaceutically acceptable emulsions, solutions, suspensions, syrups, and elixirs. Such dosage forms are prepared, for example, by dissolving, dispersing, etc., a compound(s) of the invention, or a pharmaceutically acceptable salt or solvate thereof, and optional pharmaceutical adjuvants in a carrier, such as, for example, water, saline, aqueous dextrose, glycerol, ethanol and the like; solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide; oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan; or mixtures of these substances, and the like, to thereby form a solution or suspension.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are, for example, suppositories that can be prepared by mixing the compounds of the present invention with for example suitable non-irritating excipients or carriers such as cocoa butter, polyethyleneglycol or a suppository wax, which are solid at ordinary temperatures but liquid at body temperature and therefore, melt while in a suitable body cavity and release the active component therein.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Compressed gases may be used to disperse a compound of this invention in aerosol form. Inert gases suitable for this purpose are nitrogen, carbon dioxide, etc.

Generally, depending on the intended mode of administration, the pharmaceutically acceptable compositions will contain about 1% to about 99% by weight of a compound(s) of the invention, or a pharmaceutically acceptable salt or solvate thereof, and 99% to 1% by weight of a suitable pharmaceutical excipient. In one example, the composition will be between about 5% and about 75% by weight of a compound(s) of the invention, or a pharmaceutically acceptable salt or solvate thereof, with the rest being suitable pharmaceutical excipients.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt or solvate thereof, for treatment of a disease-state in accordance with the teachings of this invention.

The compounds of the invention, or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-states, and the host undergoing therapy. The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is an example. The specific dosage used, however, can vary. For example, the dosage can depend on a number of factors including the requirements of the patient, the severity of the condition being treated, and the pharmacological activity of the compound being used. The determination of optimum dosages for a particular patient is well known to one of ordinary skill in the art.

If formulated as a fixed dose, such combination products employ the compounds of this invention within the dosage range described above and the other pharmaceutically active agent(s) within its approved dosage range. Compounds of the instant invention may alternatively be used sequentially with known pharmaceutically acceptable agent(s) when a combination formulation is inappropriate.

Representative pharmaceutical formulations containing a compound of Formula I or II are described below in the Pharmaceutical Composition Examples.

UTILITY

Certain compounds of Formula I have been tested using the assay described in Biological Example 1 and have been determined to be PI3K inhibitors. As such compounds of Formula I are useful for treating diseases, particularly cancer in which PI3K activity contributes to the pathology and/or symptomatology of the disease. For example, cancer in which PI3K activity contributes to its pathology and/or symptomatology include breast cancer, colon cancer, rectal cancer, endometrial cancer, gastric carcinoma, glioblastoma, hepatocellular carcinoma, small cell lung cancer, non-small cell lung cancer, melanoma, ovarian cancer, pancreatic cancer, prostate carcinoma, acute myelogenous leukemia (AML), chronic myelogenous leukemia (CML), and thyroid carcinoma, and the like.

Suitable in vitro assays for measuring PI3K activity and the inhibition thereof by compounds are known. Typically, the assay will measure PI3K-induced ATP consumption. For further details of an in vitro assay for measuring PI3K activity see Biological Examples, Example 1 infra. Cellular activity can be determined using assays as described in Biological Examples 2, 3, and 4 infra. Suitable in vivo models of cancer are known to those of ordinary skill in the art. For further details of in vivo assays see Biological Examples 5-10, infra. Examples describing the administration of a Compound of Formula I in combination with anticancer agents are described in Biological Examples 11-14, infra. Following the examples disclosed herein, as well as that disclosed in the art, a person of ordinary skill in the art can determine what combinations of a Compound of Formula I and anti-cancer agents would be effective for treating cancer.

Preparations of the Intermediates and Compounds of the Invention

Compounds of this invention can be made by the synthetic procedures described in WO 2007/044729, the disclosure of which is incorporated by reference herein.

The starting materials and reagents used in preparing these compounds are either available from commercial suppliers such as Aldrich Chemical Co. (Milwaukee, Wis.), or Bachem (Torrance, Calif.), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4$^{th}$ Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure. The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure and over a temperature range from about −78° C. to about 150° C., in another embodiment from about 0° C. to about 125° C. and most specifically at about room (or ambient) temperature, e.g., about 20° C. Unless otherwise stated (as in the case of a hydrogenation), all reactions are performed under an atmosphere of nitrogen.

Prodrugs can be prepared by techniques known to one skilled in the art. These techniques generally modify appropriate functional groups in a given compound. These modified functional groups regenerate original functional groups by routine manipulation or in vivo. Amides and esters of the compounds of the present invention may be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

The compounds of the invention, or their pharmaceutically acceptable salts, may have asymmetric carbon atoms or quaternized nitrogen atoms in their structure. Compounds of Formula I that may be prepared through the syntheses described herein may exist as single stereoisomers, racemates, and as mixtures of enantiomers and diastereomers. The compounds may also exist as geometric isomers. All such single stereoisomers, racemates and mixtures thereof, and geometric isomers are intended to be within the scope of this invention. Some of the compounds of the invention may exist as tautomers. For example, where a ketone or aldehyde is present, the molecule may exist in the enol form; where an amide is present, the molecule may exist as the imidic acid; and where an enamine is present, the molecule may exist as an imine. All such tautomers are within the scope of the invention.

In particular, in this application B can be 2-hydroxy-pyridinyl, also described as its structure:

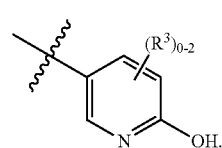

Both 2-hydroxy-pyridinyl and the above structure 14 include, and are equivalent to, pyridin-2(1H)-one and its structure 15:

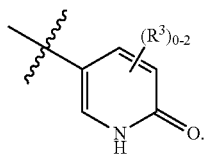

Regardless of which structure or which terminology is used, each tautomer is included within the scope of the Invention.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. When compounds of Formula I contain groups such as hydroxy, carboxy, thiol or any group containing a nitrogen atom(s), these groups can be protected with a suitable "protecting group" or "protective group". A comprehensive list of suitable protective groups can be found in T. W. Greene, *Protective Groups in Organic Synthesis*, John Wiley & Sons, Inc. 1991, the disclosure of which is incorporated herein by reference in its entirety. The protected derivatives of compounds of Formula I can be prepared by methods well known in the art.

Methods for the preparation and/or separation and isolation of single stereoisomers from racemic mixtures or non-racemic mixtures of stereoisomers are well known in the art. For example, optically active (R)- and (S)-isomers may be prepared using chiral synthons or chiral reagents, or resolved using conventional techniques. Enantiomers (R- and S-isomers) may be resolved by methods known to one of ordinary skill in the art, for example by: formation of diastereoisomeric salts or complexes which may be separated, for example, by crystallization; via formation of diastereoisomeric derivatives which may be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer may be synthesized by asymmetric synthesis using optically active reagents, substrates, catalysts or solvents or by converting on enantiomer to the other by asymmetric transformation. For a mixture of enantiomers, enriched in a particular enantiomer, the major component enantiomer may be further enriched (with concomitant loss in yield) by recrystallization.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

In Compounds of Formula I

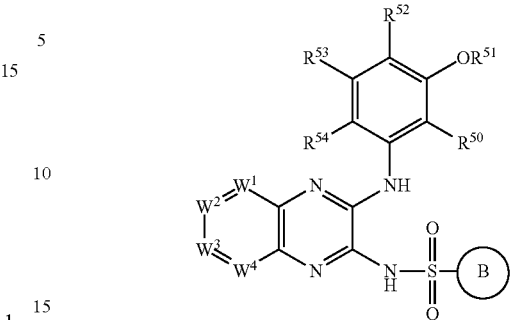

the hydrogen on the —NHS(O)$_2$— group is highly acidic. Thus, intermediates leading to Compounds of Formula I, as well as Compounds of Formula I themselves, can be recovered as uncharged or zwitterionic molecules, or cationic salts such a sodium or potassium, depending on the substitutions on the B ring and on reaction conditions. In the examples that follow, unless otherwise specified, the final form of the compound was assumed to be the uncharged molecule in the absence of analytical techniques that would have determined otherwise.

Compounds of Formula I can be prepared using methods known to one of ordinary skill in the art. In another embodiment, fusion of appropriate reagents at 180° C. in the presence of a base such as K$_2$CO$_3$ and metallic copper is known to provide intermediates of formula 1 (see S. H. Dandegaonker and C. K. Mesta, *J. Med. Chem.* 1965, 8, 884).

Alternatively, the intermediate of formula 3 can be prepared according to the scheme below where each LG$^1$ is a leaving group (in one embodiment halo, in another embodiment chloro) and all other groups are as defined in the Detailed Description of the Invention.

Scheme 1

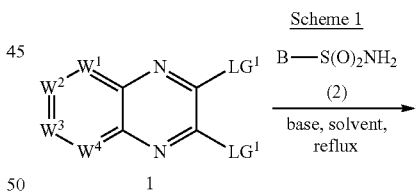

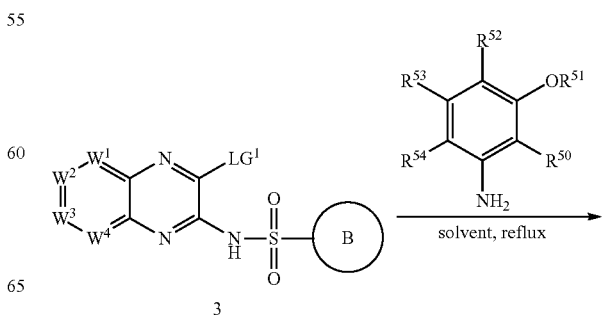

-continued

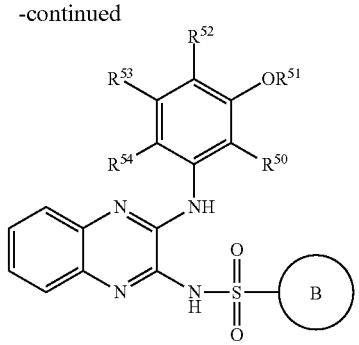

In scheme 1, an intermediate of formula 3 can be prepared by briefly heating commercially available 2,3-dichloroquinoxaline and an intermediate of formula 2 (which are commercially available or can be prepared by one of ordinary skill in the art), a base such as $K_2CO_3$, in a solvent, such as DMF or DMSO. Upon completion (about 2 hours), the reaction mixture is then poured into water and followed by 2 N HCl. The product is then extracted into a solvent such as ethyl acetate and washed with water and brine. The organic layers are combined and dried over a drying agent such as sodium sulfate, filtered, and concentrated under vacuum.

The intermediate of formula 3 is then treated with an intermediate of formula 4 in a solvent such as DMF or p-xylene at reflux temperature. Upon completion of the reaction (about 16 hours or less), the reaction is allowed to cool, extracted into DCM, washed with 2 N HCl and brine, dried over a drying agent such as sodium sulfate or magnesium sulfate, filtered, and concentrated to give a compound of Formula I.

Alternatively, other methods to prepare quinoxaline derivatives are known to one skilled in the art and include, but are not limited to S. V. Litvinenko, V. I. Savich, D. D. Bobrovnik, *Chem. Heterocycl. Compd.* (Engl. Transl), 1994, 30, 340 and W. C. Lumma, R. D. Hartman, *J. Med. Chem.* 1981, 24, 93.

The following compounds were prepared in a manner similar to that described above.

Example 1

N-(3-{[2,5-bis(methoxy)phenyl]amino}quinoxalin-2-yl)-3-nitrobenzenesulfonamide

Example 2

N-(3-{[2,5-bis(methoxy)phenyl]amino}quinoxalin-2-yl)-4-chlorobenzenesulfonamide

Example 3

N-(3-chloroquinoxalin-2-yl)-3-nitrobenzenesulfonamide

Example 4

4-chloro-N-(3-chloroquinoxalin-2-yl)benzenesulfonamide

Example 5

4-chloro-N-(3-(2,5-dimethoxyphenylamino)quinoxalin-2-yl)benzenesulfonamide $^1$H NMR (400 MHz, DMSO-$d_6$) δ 9.18 (s, 1H), 8.78 (s, 1H), 8.40-8.60 (m, 3H), 7.98 (t, 2H), 7.62 (d, 1H), 7.41 (m, 2H), 6.98 (d, 1H), 6.59 (d, 1H), 3.78 (s, 3H), 3.76 (s, 3H); MS (EI) m/z for $C_{22}H_{19}N_5O_6S$: 482.1 (MH$^+$).

Example 6

N-(3-(2,5-dimethoxyphenylamino)quinoxalin-2-yl)-3-nitrobenzenesulfonamide $^1$H NMR (400 MHz, CDCl$_3$) δ 12.68 (br s, 1H), 9.18 (s, 1H), 8.55 (s, 1H), 8.08 (d, 2H), 7.98 (d, 1H), 7.78 (d, 2H), 7.62 (dd, 1H), 7.40 (m, 2H), 7.00 (d, 1H), 6.60 (dd, 1H), 3.78 (s, 6H); MS (EI) m/z for $C_{22}H_{19}ClN_4O_4S$: 471.1 (MH$^+$).

Example 7

N-(3-(N-(3-(2-chloro-5-methoxyphenylamino)quinoxalin-2-yl)sulfamoyl)-4-methylphenyl)-2-(dimethylamino)acetamide $^1$H NMR (400 MHz, DMSO-$d_6$) δ 12.0 (br s, 1H), 10.6 (s, 1H), 10.0 (br s, 1H), 9.52 (s, 1H), 8.91 (d, 1H), 8.25 (d, 1H), 7.69 (dd, 1H), 7.47 (m, 1H), 7.39 (d, 1H), 7.16 (m, 3H), 6.01 (dd, 1H); MS (EI) m/z for $C_{26}H_{27}ClN_6O_4S$: 555 (MH$^+$).

Compounds of Formula I where B is phenyl substituted with $R^{3a}$ where $R^{3a}$ is alkylamino or dialkylamino or B is heteroaryl substituted with $R^3$ where $R^3$ is amino, alkylamino, or dialkylamino, and all other groups are as defined in the Summary of the Invention can be prepared according to Scheme 2.

Scheme 2

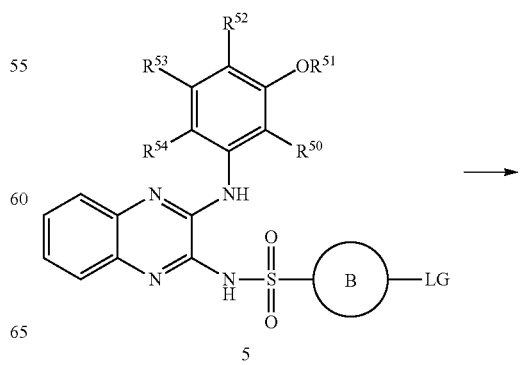

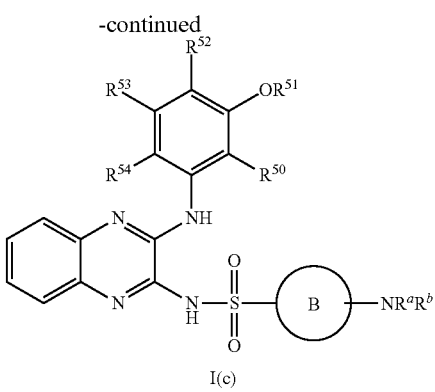

I(c)

LG is a leaving group such as chloro. 5 is reacted with NHR$^a$R$^b$ or HO—C$_1$-C$_6$-alkylene-NHR$^a$R$^b$ where R$^a$ and R$^b$ are independently hydrogen or alkyl. The reaction is carried out in the presence of a base, such as KHCO$_3$, in a solvent such as DMF.

Compounds of Formula I where B is phenyl substituted with R$^{1a}$ where R$^{3a}$ is aminoalkyloxy, alkylaminoalkyloxy, or dialkylaminoalkyloxy or B is heteroaryl substituted with R$^3$ where R$^3$ is aminoalkyloxy, alkylaminoalkyloxy, or dialkylaminoalkyloxy, and all other groups are as defined in the Summary of the Invention can be prepared according to Scheme 3.

Scheme 3

5 →

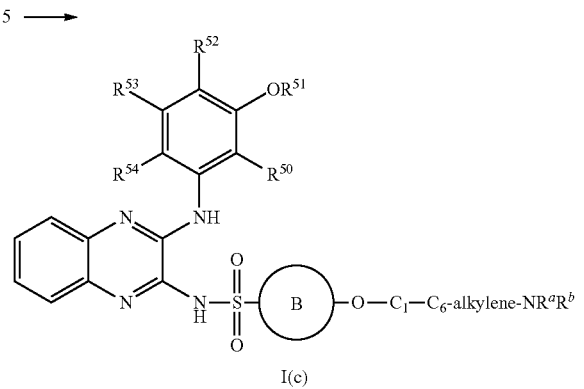

I(c)

The reaction is carried out in the presence of a base such as NaH in a solvent such as DMF.

Compounds of Formula I where B is phenyl substituted with R$^{3a}$ or B is heteroaryl substituted with R$^3$ where R$^{3a}$ and R$^3$ are i. —N(R$^7$)C(O)—C$_1$-C$_6$-alkylene-N(R$^{7a}$)(R$^{7b}$) where R$^7$, R$^{7a}$, and R$^{7b}$ are as defined in the Summary of the Invention;
ii. —NR$^9$C(O)R$^{9a}$ where R$^9$ is as defined in the Summary of the Invention;
iii. —NR$^{11}$C(O)NR$^{11a}$R$^{11b}$ where R$^{11a}$, R$^{11a}$, and R$^{11b}$ are as defined in the Summary of the Invention;
iv. —NR$^{13}$C(O)OR$^{13a}$ where R$^{13}$ and R$^{13a}$ are as defined in the Summary of the Invention;
v. —N(R$^{18}$)C(O)—C$_1$-C$_6$-alkylene-N(R$^{18b}$)C(O)R$^{18a}$ where R$^{18}$, R$^{18a}$, and R$^{18b}$ are as defined in the Summary of the Invention;
vi. —N(R$^{20}$)C(O)—C$_1$-C$_6$-alkylene-C(O)R$^{20a}$ where R$^{20}$ and R$^{20a}$ as defined in the Summary of the Invention;
vii. —NR$^{21}$S(O)$_2$—C$_1$-C$_6$-alkylene-N(R$^{21b}$)R$^{21a}$ where R$^{21}$, R$^{21a}$, and R$^{21b}$ are as defined in the Summary of the Invention;
viii. —N(R$^{22}$)C(O)—C$_0$-C$_6$-alkylene-N(R$^{22b}$)—N(R$^{22c}$)(R$^{22a}$), where R$^{22}$, R$^{22a}$ and R$^{22b}$ are as defined in the Summary of the Invention;
ix. —NR$^{24}$C(O)—C$_1$-C$_6$-alkylene-OR$^{24a}$ where R$^{24}$ and R$^{24a}$ are as defined in the Summary of the Invention;

and where the alkylene in R$^3$ and R$^{3a}$ are independently optionally substituted as described in the Summary of the Invention can be prepared according to Scheme 4 by reacting with an intermediate of formula 9(a), 9(b), 9(c), 9(d), 9(e), 9(f), or 9(g):

9(a) HOC(O)—C$_1$-C$_6$-alkylene-N(R$^{7a}$)(R$^{7b}$) where R$^a$ is R$^{7a}$ or a N-protecting group, such as Boc or Fmoc;
9(b) HOC(O)R$^{9a}$;
9(c) HOC(O)NR$^{11a}$R$^{11b}$;
9(d) HOC(O)OR$^{13a}$;
9(e) HOC(O)—C$_1$-C$_6$-alkylene-N(R$^{18b}$)C(O)R$^{18a}$;
9(f) HOC(O)—C$_1$-C$_6$-alkylene-C(O)R$^{20a}$;
9(g) LG-S(O)$_2$—C$_1$-C$_6$-alkylene-N(R$^{21b}$)R$^a$ where R$^a$ is R$^{21a}$ or a N-protecting group, such as Boc or Fmoc.

Scheme 4

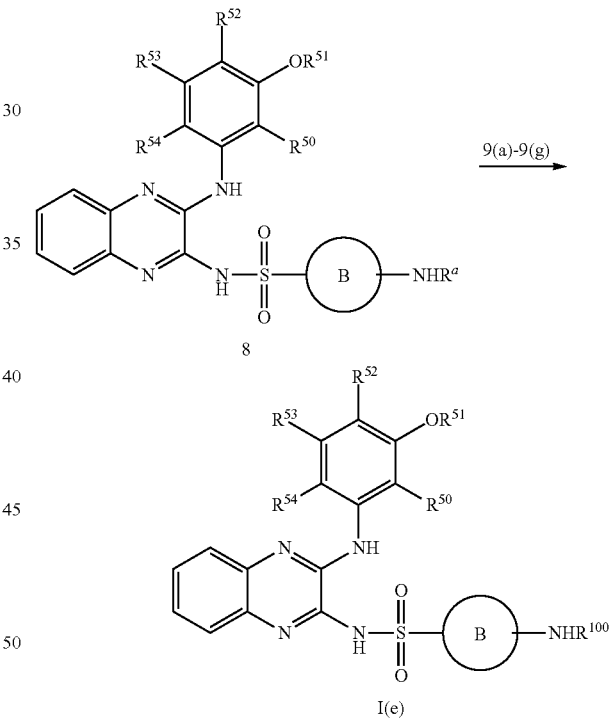

I(e)

R$^{100}$ in Scheme 4 is —C(O)R$^{9a}$, —C(O)NR$^{11a}$R$^{11b}$, —C(O)OR$^{13a}$, —C(O)—C$_1$-C$_6$-alkylene-N(R$^{18b}$)C(O)R$^{18a}$, —C(O)—C$_1$-C$_6$-alkylene-C(O)R$^{20a}$, or —S(O)$_2$—C$_1$-C$_6$-alkylene-N(R$^{21b}$)R$^a$. The reaction is carried out under standard amide coupling conditions known to one of ordinary skill in the art. In particular, the reaction is carried out in the presence of a coupling agent such as HATU, a base such as DIEA, and in a solvent such as DMF. Where applicable, the N-protecting group is then removed using procedures known to one of ordinary skill in the art, such as treating with acid where PG is Boc.

Proceeding as described for Scheme 4, compounds of the invention where B is phenyl substituted with R$^{3a}$ or B is heteroaryl substituted with $R^3$ where $R^{3a}$ and $R^3$ are
a) —C(O)$NR^8R^{8a}$;
b) —C(O)N($R^{10}$)—$C_1$-$C_6$-alkylene-N($R^{10a}$)$R^{10b}$;
c) —C(O)$R^{12}$ where $R^{12}$ is an N-substituted heterocycloalkyl;
d) —C(O)N($R^{14}$)N($R^{14a}$)($R^{14b}$);
e) —C(O)N($R^{16}$)—$C_1$-$C_6$-alkylene-C(O)O$R^{16a}$; or
f) —C(O)N($R^{19}$)—$C_1$-$C_6$-alkylene-C(O)$R^{19a}$; or can be prepared by exchanging the starting materials as necessary. In particular, the intermediate of formula 11:

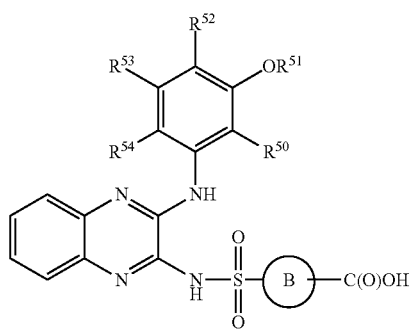

11 is used instead of 8.

Compounds of Formula I where B is phenyl substituted with $R^{3a}$ or B is heteroaryl substituted with $R^3$ where $R^{3a}$ and $R^3$ are —NHC(O)$CH_2NR^{7a}R^{7b}$ where $R^{7a}$ and $R^{7b}$ are as defined in the Summary of the Invention can be prepared according to Scheme 5.

Scheme 5

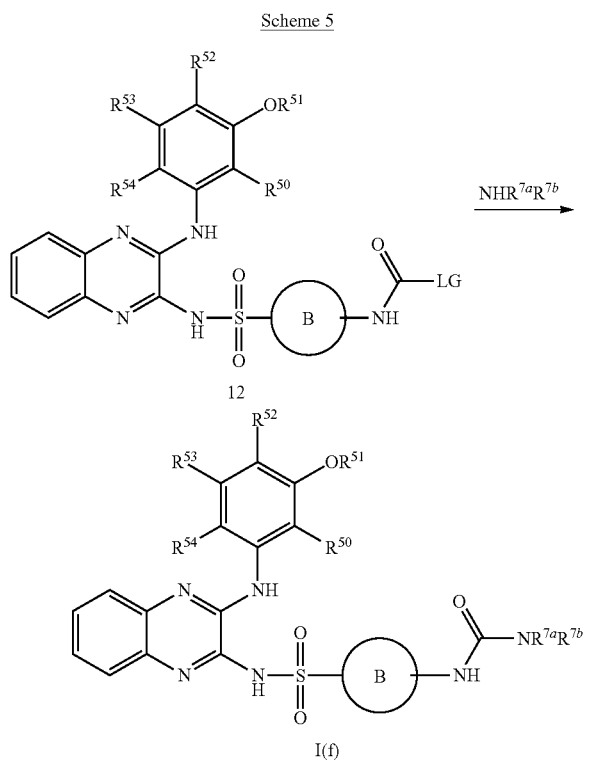

LG is a leaving group such as bromo or chloro. 12 is reacted with NH($R^{7b}$)$R^{7a}$ in the presence of a base, such as DIEA, in a solvent such as ACN.

Compounds of Formula I can be prepared according to Scheme 6.

Scheme 6

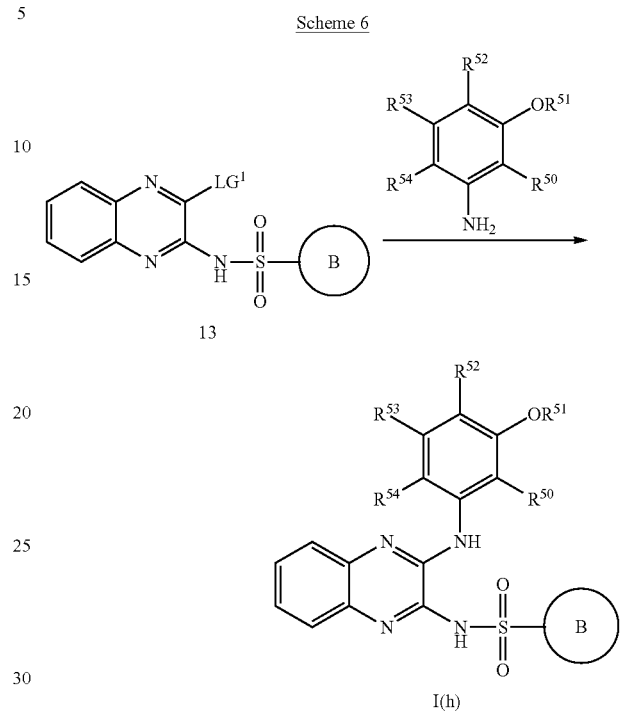

LG in Scheme 6 is a leaving group such as chloro. The reaction can be carried out by irradiating in a solvent such as DMA. Alternatively, the reaction can be carried out in the presence of acetic acid in a solvent such as DMA and by heating.

Example 8

6-chloro-N-(3-(3,5-dimethoxyphenylamino)quinoxalin-2-yl)pyridine-3-sulfonamide

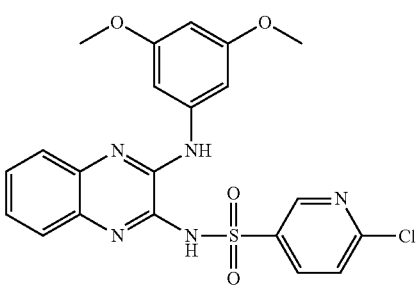

6-chloropyridine-3-sulfonamide 6-chloropyridine-3-sulfonyl chloride (4.1 g, 19.3 mmol) was stirred in ammonium hydroxide (30 mL) at room temperature for 2 hr. The reaction mixture was diluted with EtOAc (150 mL) and any insoluble material filtered. The filtrate was transferred to a separatory funnel and the phases were separated. The aqueous phase was further extracted with EtOAc (1×15 mL). The combined EtOAc extractions were washed with $H_2O$ (1×50 mL) and saturated NaCl (1×50 mL), dried over $Na_2SO_4$, and concentrated in vacuo to give 6-chloropyridine-3-sulfonamide (2.58 g, 69%). MS (EI) m/z for $C_5H_5Cl_2N_2O_2S$: 190.9 (MH$^-$).

6-chloro-N-(3-chloroquinoxalin-2-yl)pyridine-3-sulfonamide 2,3-dichloroquinoxaline (1.09 g, 5.48 mmol), 6-chloropyridine-3-sulfonamide (1.05 g, 5.45 mmol), $K_2CO_3$ (753 mg, 5.45 mmol) and dry DMSO (30 mL) were combined and heated to 150° C. with vigorous stirring for 3-4 hr. The reaction mixture was allowed to cool to room temperature, then poured into 1% AcOH in ice water (300 mL) with vigorous stirring. The resulting solids were filtered, washed with $H_2O$ and dried under high vacuum to give 6-chloro-N-(3-chloroquinoxalin-2-yl)pyridine-3-sulfonamide (1.87 g, 96%). MS (EI) m/z for $C_{13}H_8Cl_2N_4O_2S$: 354.99 (MH$^+$).

6-chloro-N-(3-(3,5-dimethoxyphenylamino)quinoxalin-2-yl)pyridine-3-sulfonamide 6-Chloro-N-(3-chloroquinoxalin-2-yl)pyridine-3-sulfonamide (775 mg, 2.2 mmol), 3,5-dimethoxyaniline (355 mg, 2.3 mmol) and toluene (12 mL) were combined and heated to 125° C. with stirring overnight. The reaction was allowed to cool to room temperature and diluted with $Et_2O$ with vigorous stirring. The resulting solids were filtered, washed with $Et_2O$ and dried to give 6-chloro-N-(3-(3,5-dimethoxyphenylamino)quinoxalin-2-yl)pyridine-3-sulfonamide (920 mg, 89%). $^1$H NMR (400 MHz, DMSO-d$_6$) δ 12.20 (br s, 1H), 9.12 (d, 1H), 9.01 (br s, 1H), 8.53 (dd, 1H), 7.91 (br d, 1H), 7.77 (d, 1H), 7.60 (dd, 1H), 7.40 (m, 4H), 6.26 (m, 1H), 3.78 (s, 6H). MS (EI) m/z for $C_{21}H_{18}ClN_5O_4S$: 472.0 (MH$^+$).

Example 9

N-(3-(3,5-dimethoxyphenylamino)quinoxalin-2-yl)-6-(2-(dimethylamino)-ethylamino)pyridine-3-sulfonamide

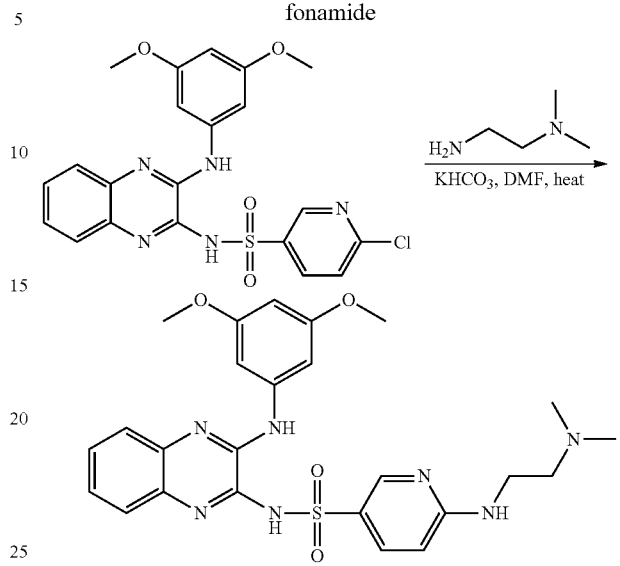

6-chloro-N-(3-(3,5-dimethoxyphenylamino)quinoxalin-2-yl)-pyridine-3-sulfonamide (100 mg, 0.21 mmol), prepared using procedures similar to those used in Example 8, KHCO$_3$ (40 mg, 0.40 mmol), $N^1,N^1$-dimethylethane-1,2-diamine (225 μL, 2.0 mmol) and dry DMF (1.0 mL) were combined and heated to 130° C. with stirring overnight. The reaction mixture was concentrated in vacuo and purified by preparative HPLC to give N-(3-(3,5-dimethoxyphenylamino)-quinoxalin-2-yl)-6-(2-(dimethylamino)ethylamino)pyridine-3-sulfonamide (21.0 mg, 19%). $^1$H NMR (400 MHz, DMSO-d$_6$) δ 8.76 (br s, 1H), 8.63 (d, 1H), 8.07 (dd, 1H), 7.40 (m, 1H), 7.34 (m, 1H), 7.28 (d, 2H), 7.14 (m, 4H), 6.47 (d, 1H), 6.12 (m, 1H), 3.75 (s, 6H), 3.35 (m, 2H), 3.14 (m, 2H), 2.74 (s, 6H). MS (EI) m/z for $C_{25}H_{29}N_7O_4S$: 524.1 (MH$^+$).

Example 10

N-(3-(3,5-dimethoxyphenylamino)quinoxalin-2-yl)-6-(dimethylamino)pyridine-3-sulfonamide was prepared using procedures similar to those used in Example 9. $^1$H NMR (400 MHz, DMSO-d$_6$) δ 12.00 (br s, 1H), 8.92 (br s, 1H), 8.74 (d, 1H), 8.10 (dd, 1H), 7.38 (br s, 1H), 7.54 (m, 1H), 7.33 (m, 4H), 6.70 (d, 1H), 6.22 (s, 1H), 3.77 (s, 6H), 3.08 (s, 6H). MS (EI) m/z for $C_{23}H_{24}N_6O_4S$: 481.1 (MH$^+$).

Example 11

N-(3-(3,5-dimethoxyphenylamino)quinoxalin-2-yl)-6-(2-(dimethylamino)-ethoxy)pyridine-3-sulfonamide

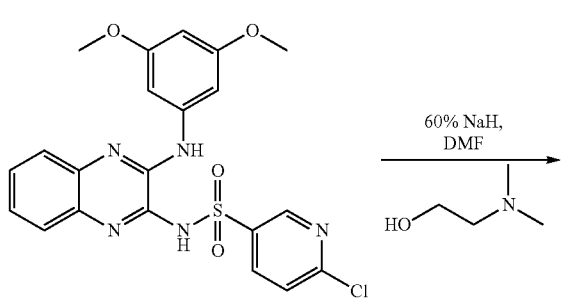

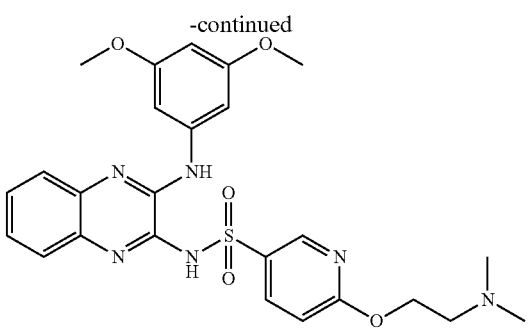

N-(3-(3,5-dimethoxyphenylamino)quinoxalin-2-yl)pyridine-3-sulfonamide (100 mg, 0.21 mmol), prepared using procedures similar to those described above in Example 1,2-(dimethylamino)ethanol (50 μL, 0.50 mmol) and dry DMF were combined and 60% NaH in oil (80 mg, 2.0 mmol) was added. The mixture was stirred at room temperature overnight. The reaction mixture was concentrated in vacuo and purified by preparative HPLC to give N-(3-(3,5-dimethoxyphenylamino)quinoxalin-2-yl)-6-(2-(dimethylamino)ethoxy)pyridine-3-sulfonamide (23 mg, 21%). $^1$H NMR (400 MHz, DMSO-d$_6$) δ 8.78 (d, 1H), 8.73 (s, 1H), 8.38 (dd, 1H), 7.40 (dd, 1H), 7.31 (m, 3H), 7.14 (m, 2H), 6.85 (d, 1H), 6.12 (m, 1H), 4.56 (m, 2H), 3.76 (s, 6H), 3.43 (m, 2H), 2.77 (s, 6H). MS (EI) m/z for C$_{25}$H$_{28}$N$_6$O$_5$S: 525.1 (MH$^+$).

Example 12

N-(3-(3,5-dimethoxyphenylamino)quinoxalin-2-yl)-6-oxo-1,6-dihydropyridine-3-sulfonamide

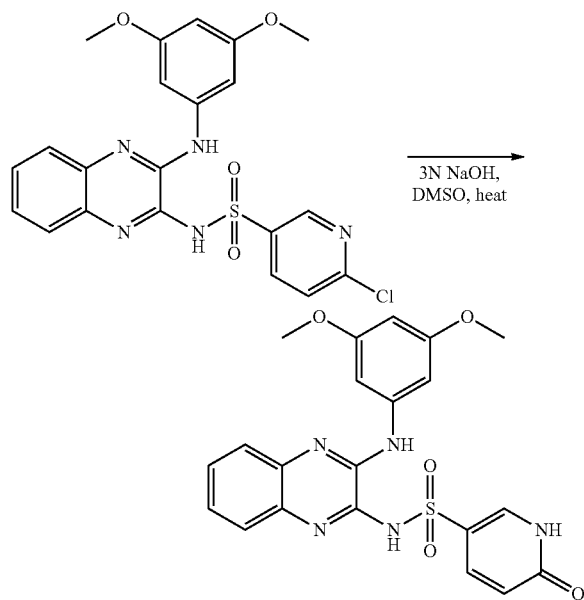

N-(3-(3,5-dimethoxyphenylamino)quinoxalin-2-yl)pyridine-3-sulfonamide (220 mg, 0.47 mmol), prepared using procedures similar to those described above in Example 8, DMSO (5 mL), and 3N NaOH (5 mL) are combined and heated to 100° C. overnight with stirring. Upon cooling to room temperature, the reaction mixture was diluted with H$_2$O and the pH was adjusted to 7.0 with 1N HCl. The resulting solid was filtered, washed with H$_2$O, and air-dried. The solid was then sonicated in EtOAc, filtered, washed with EtOAc, and dried under high vacuum to give N-(3-(3,5-dimethoxyphenylamino)quinoxalin-2-yl)-6-oxo-1,6-dihydropyridine-3-sulfonamide (190 mg, 90%). $^1$H NMR (400 MHz, DMSO-d$_6$) δ 12.23 (br s, 1H), 12.10 (br s, 1H), 8.97 (s, 1H), 8.23 (s, 1H), 7.95 (m, 2H), 7.59 (m, 1H), 7.37 (m, 4H), 6.43 (d, 1H), 6.25 (s, 1H), 3.77 (s, 6H). MS (EI) m/z for C$_{21}$H$_{19}$N$_5$O$_5$S: 454.0 (MH$^+$).

Example 13

N-(3-(2-chloro-5-methoxyphenylamino)quinoxalin-2-yl)-6-oxo-1,6-dihydropyridine-3-sulfonamide The title compound was prepared according to the above Example 12. $^1$H NMR (400 MHz, DMSO-d$_6$) δ 12.22 (br s, 1H), 12.10 (br s, 1H), 9.16 (s, 1H), 8.60 (s, 1H), 8.14 (d, 1H), 7.94 (m, 1H), 7.85 (dd, 1H), 7.62 (m, 1H), 7.40 (m, 3H) 6.69 (dd, 1H), 6.43 (d, 1H), 3.81 (s, 3H). MS (EI) m/z for C$_{20}$H$_{16}$ClN$_5$O$_4$S: 456.0 (MH$^-$).

Example 14

3-amino-N-(3-(3,5-dimethoxyphenylamino)quinoxalin-2-yl)benzenesulfonamide

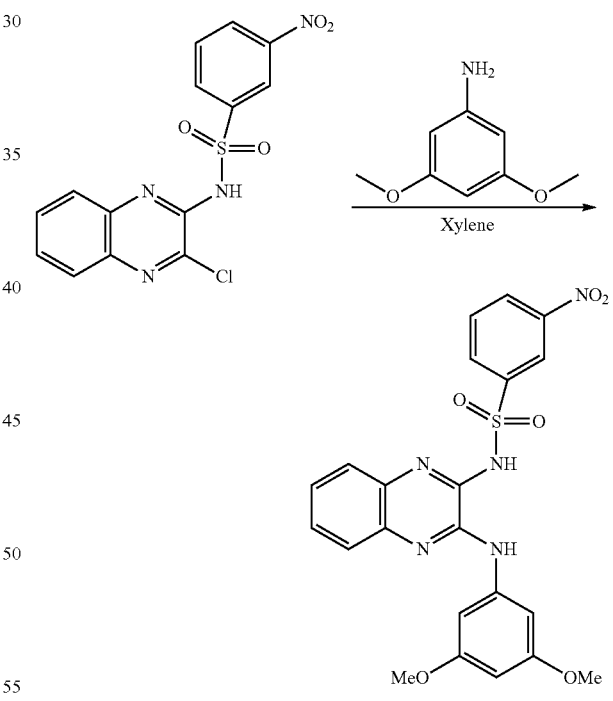

N-(3-(3,5-dimethoxyphenylamino)quinoxalin-2-yl)-3-nitrobenzenesulfonamide

A flask was charged with N-(3-chloroquinoxalin-2-yl)-3-nitrobenzenesulfonamide (5 g, 13.7 mmol), prepared using procedures similar to those in Example 1, 3,5-dimethoxyaniline (4.2 g, 27.4 mmol), and 80 mL of xylene. The reaction mixture was stirred under an N$_2$ atmosphere at 150° C. for 3 hours, after which time, solvent was removed on a rotary evaporator, and 10 mL of Dichloromethane and 50 mL of methanol were added. The slurry was heated to reflux and filtered while hot, resulting in 4.6 g (69.7%) of N-(3-(3,5-dimethoxyphenylamino)quinoxalin-2-yl)-3-nitrobenzenesulfonamide MS (EI) m/z for $C_{22}H_{19}N_5O_6S$: 482.2 (MH$^+$).

Example 15

3-amino-N-(3-(3,5-dimethoxyphenylamino)quinoxalin-2-yl)benzenesulfonamide

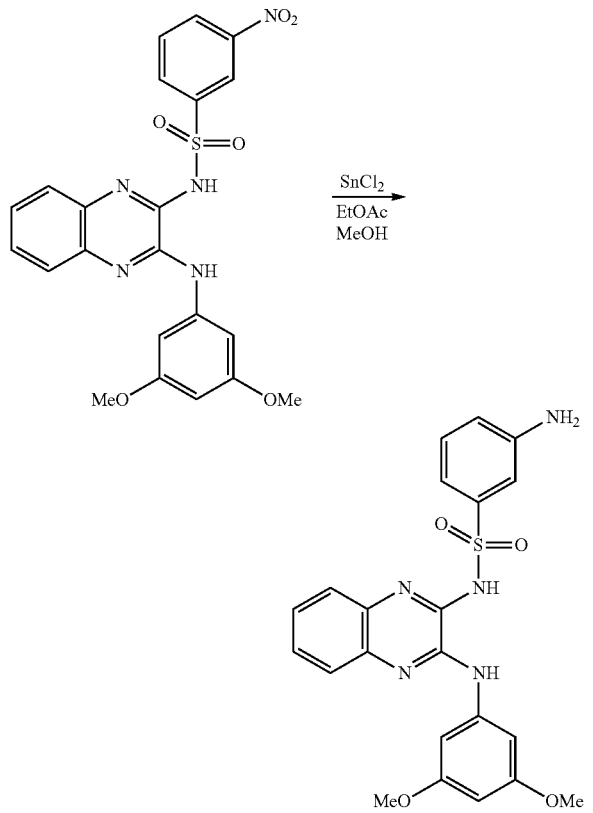

A flask was charged with N-(3-(3,5-dimethoxyphenylamino)quinoxalin-2-yl)-3-nitro-benzenesulfonamide (3.4 g, 7.06 mmol), prepared using procedures similar to those in Example 14, tin chloride solvate (6.4 g, 28.2 mmol), and 30 mL of DMA. A few drops of water were added and the reaction mixture was stirred at 80° C. for 3 hours, after which time, solvent was removed on a rotary evaporator, and 50 mL of water and 10 mL of Methanol were added. The slurry was filtered, and the filtrate was washed with MeOH, water, and diethyl ether (20 mL of each), resulting in 3.25 g 3-amino-N-(3-(3,5-dimethoxy-phenylamino)quinoxalin-2-yl)benzenesulfonamide. $^1$H NMR (400 MHz, DMSO) δ 12.2 (br s, 1H), 8.85 (s, 1H), 7.90 (br s, 1H), 7.50-7.60 (m, 1H), 7.3-7.4 (m, 4H), 7.2 (m, 3H), 6.74 (m, 1H), 6.24 (m, 1H), 5.56 (br s, 2H), 3.76 (s, 6H). MS (EI) m/z for $C_{22}H_{21}N_5O_4S$: 452.0 (MH$^+$).

The following compounds were made using procedures similar to those used in Example 15.

Example 16

Proceeding as above, 3-amino-N-(3-(2,5-dimethoxy-phenylamino)quinoxalin-2-yl)benzenesulfonamide was prepared. $^1$H NMR (400 MHz, DMSO) δ 12.4 (br s, 1H), 9.20 (s, 1H), 8.56 (d, 1H), 7.95 (d, 1H), 7.62 (m, 1H), 7.38 (m, 2H), 7.24 (q, 2H), 7.14 (d, 1H), 6.98 (d, 1H), 6.8 (m, 1H), 6.60 (m, 1H), 5.6 (br s, 2H), 3.78 (d, 6H). MS (EI) m/z for $C_{22}H_{21}N_5O_4S$: 452.3 (MH$^+$).

Example 17

Proceeding as above, 3-amino-N-(3-(2-chloro-5-hydroxy-phenylamino)quinoxalin-2-yl)benzenesulfonamide was prepared. MS (EI) m/z for $C_{20}H_{16}ClN_5O_3S$ 1.0×$C_2H_1O_2F_3$: 442.2, 444.2 (MH$^+$).

Example 18

Proceeding as above, 3-amino-N-(3-(6-methoxyquinolin-8-ylamino)quinoxalin-2-yl)benzenesulfonamide was prepared. MS (EI) m/z for $C_{24}H_{20}N_6O_3S$: 473.0 (MH$^+$).

Example 19

3-amino-N-(3-(3-fluoro-5-methoxy-phenylamino)quinoxalin-2-yl)benzenesulfonamide

MS (EI) m/z for $C_{21}H_{18}FN_5O_3S$: 439.99 (MH$^+$).

Example 20

3-amino-N-(3-(2-chloro-5-methoxy-phenylamino)quinoxalin-2-yl)benzenesulfonamide

MS (EI) m/z for $C_{21}H_{18}ClN_5O_3S$: 457.02 (MH$^+$).

Example 21

3-amino-N-(3-(5-methoxy-2-methyl-phenylamino)quinoxalin-2-yl)benzenesulfonamide

MS (EI) m/z for $C_{22}H_{21}N_5O_3S$: 436.32 (MH$^+$).

Example 22a and Example 22b 3-amino-N-(3-(3-methoxy-5-nitro-phenylamino)quinoxalin-2-yl)benzenesulfonamide and 3-amino-N-(3-(3-amino-5-methoxy-phenylamino)quinoxalin-2-yl)benzenesulfonamide

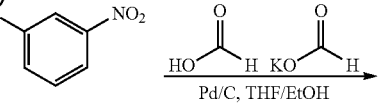

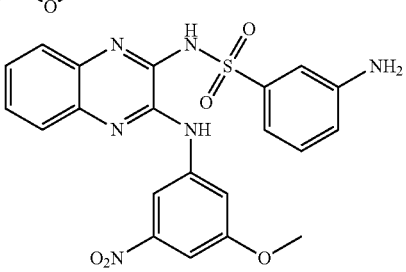

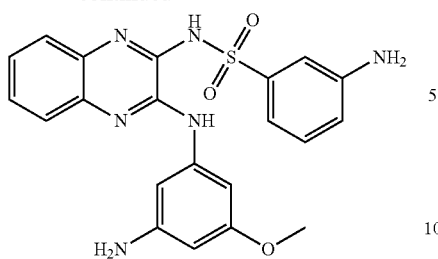

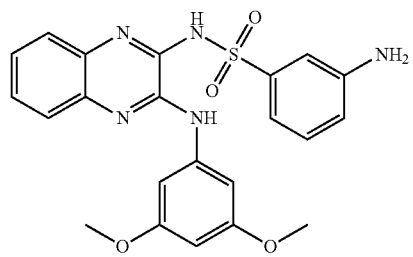

To a mixture of N-(3-{[3-(methyloxy)-5-nitrophenyl]amino}quinoxalin-2-yl)-3-nitrobenzenesulfonamide (400 mg), THF (2 mL) and EtOH (2 mL) was added formic acid (938 μL), potassium formate (203 mg). After the mixture was flushed with $N_2$, 10% wt Pd/C (50 mg) was added. The resulting mixture was heated at 60° C. with stirring. LC/MS analysis indicated that the reaction mixture contained the complete reduced di-amino compound as the major product and the partially reduced mono-amino compound as a minor product. A portion of the crude mixture was purified by HPLC to give the two products. Product A: 3-amino-N-(3-(3-methoxy-5-nitro-phenylamino)quinoxalin-2-yl)benzenesulfonamide. $^1$H NMR (400 MHz, DMSO) δ 12.2 (br s, 1H), 9.51 (s, 1H), 8.77 (s, 1H), 8.21 (s, 1H), 7.92 (s, 1H), 7.48 (m, 1H), 7.43-7.38 (m, 3H), 7.24-7.16 (m, 3H), 6.75 (d, 1H), 5.57 (br s, 2H), 3.90 (s, 3H). MS (EI) for $C_{21}H_{18}N_6O_5S$: 467.00 (MH+). Product B: 3-amino-N-(3-(3-amino-5-methoxy-phenylamino)quinoxalin-2-yl)benzenesulfonamide. $^1$H NMR (400 MHz, DMSO) δ 12.0 (br. s, 1H), 8.53 (s, 1H), 7.84 (s, 1H), 7.56 (d, 1H), 7.37-7.30 (m, 2H), 7.21-7.17 (m, 3H), 6.87 (s, 1H), 6.81 (s, 1H), 6.74 (br s, 2H), 5.91 (s, 1H), 5.56 (br s, 3H), 3.69 (s, 3H). MS (EI) for $C_{21}H_{20}N_6O_3S$: 437.2 (MH+).

Example 23a and Example 23b

N-(3-(3,5-dimethoxy-phenylamino)quinoxalin-2-yl)-3-(hydroxyamino)-benzenesulfonamide and 3-amino-N-(3-{[3,5-(dimethoxy)phenyl]amino}quinoxalin-2-yl)benzenesulfonamide To a solution N-(3-(3,5-dimethoxyphenylamino)quinoxalin-2-yl)-3-nitrobenzenesulfonamide (1.3 g) in 20 mL of THF and 10 mL of MeOH was added 10% wt Pd/C (100 mg). The mixture was stirred under a $H_2$ balloon overnight. A portion of the reaction mixture was taken out and filtered, then purified by HPLC to afford two products. Product A: N-(3-{[3,5-bis(methyloxy)phenyl]amino}quinoxalin-2-yl)-3-(hydroxyamino)benzenesulfonamide. MS (EI) for $C_{22}H_{21}N_5O_5S$: 468.1 (MH+). Product B: 3-amino-N-(3-(3,5-dimethoxy-phenylamino)quinoxalin-2-yl)benzenesulfonamide. $^1$H NMR (400 MHz, DMSO) δ 12.2 (br s, 1H), 8.85 (s, 1H), 7.90 (br s, 1H), 7.50-7.60 (m, 1H), 7.3-7.4 (m, 4H), 7.2 (m, 3H), 6.74 (m, 1H), 6.24 (m, 1H), 5.56 (br s, 2H), 3.76 (s, 6H). MS (EI) for $C_{22}H_{21}N_5O_4S$: 452.0 (MH+).

Example 24

(S)-2-amino-N-(3-(N-(3-(3,5-dimethoxyphenylamino)quinoxalin-2-yl)sulfamoyl)phenyl)propanamide hydrochloride

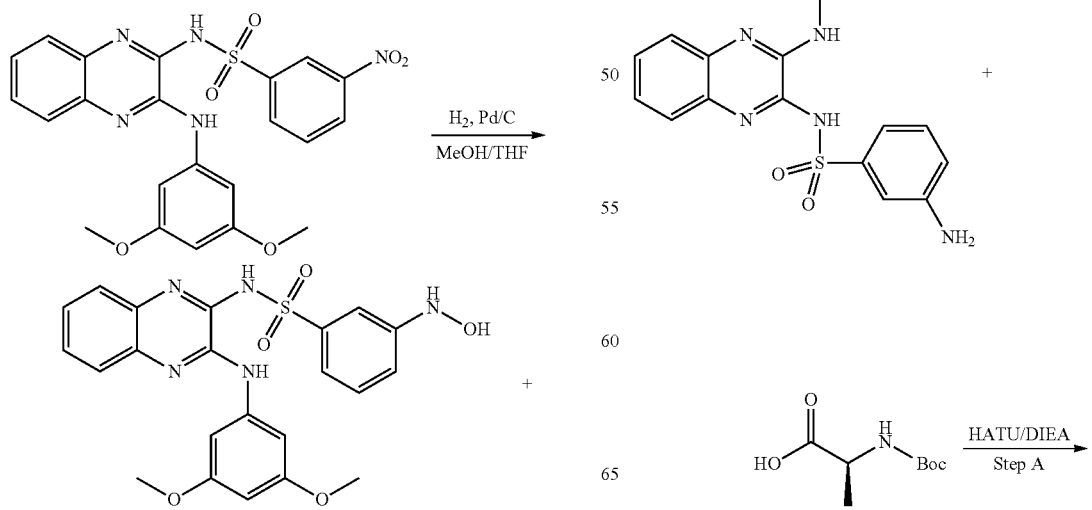

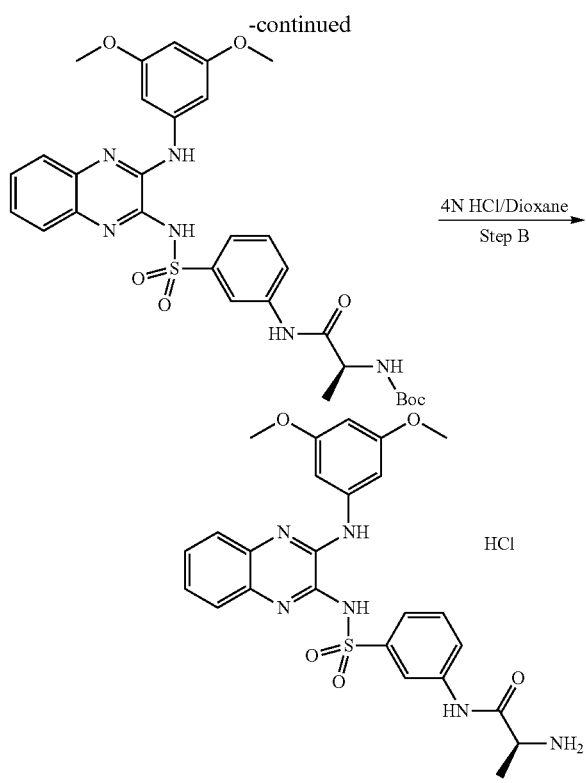

(S)-tert-butyl 1-(3-(N-(3-(3,5-dimethoxyphenylamino)quinoxalin-2-yl)sulfamoyl)phenylamino)-1-oxopropan-2-ylcarbamate 3-amino-N-(3-(3,5-dimethoxy-phenylamino)quinoxalin-2-yl)benzenesulfonamide (1.1 mmol, 500 mg), prepared using procedures similar to those described above in Example 15, (L)-Boc-Ala-OH (1.5 mmol, 284 mg), dichloromethane (15 mL), DMF (10 mL), DIEA (2 mmol, 330 μL), and HATU (2 mmol, 760 mg) stirred at room temperature over night. The crude mixture was column purified using 1/1 ethyl acetate/hexanes on silica to gave 160 mg.

(S)-2-amino-N-(3-(N-(3-(3,5-dimethoxyphenylamino)quinoxalin-2-yl)sulfamoyl)phenyl)propanamide hydrochloride 4 N HCl is dioxane (10 mL) was added to a solution of (S)-tert-butyl 1-(3-(N-(3-(3,5-dimethoxyphenylamino)quinoxalin-2-yl)sulfamoyl)phenylamino)-1-oxopropan-2-ylcarbamate (160 mg) and DCM (15 mL). The mixture was stirred at room temperature for 3 hours. The solvent decanted and ether added to the solid, ether decanted to gave 80 mg product as HCl salt. $^1$H NMR (400 MHz, CD$_3$OD) δ 8.50-8.49 (t, 1H), 7.89-7.87 (m, 1H), 7.74-7.72 (m, 1H), 7.61-7.5 (m, 3H), 7.40-7.36 (m, 2H), 7.21-7.20 (d, 2H), 6.23-6.21 (t, 1H), 4.09-4.03 (q, 1H), 3.78 (s, 6H), 1.60-1.58 (d, 3H); MS (EI) m/z for C$_{25}$H$_{26}$N$_6$O$_5$S.HCl: 523.1 (MH$^+$).

The following compounds were prepared as the free amine and/or HCl salt using procedures similar to those in Example 24. Where the deprotection step is not necessary, Step B in the above scheme was not preformed.

Example 25

N-(2-chloro-5-(N-(3-(2-chloro-5-methoxy-phenylamino)quinoxalin-2-yl)sulfamoyl)phenyl)-2-(methylamino)acetamide The title compound was prepared according to the Examples above. $^1$H NMR (400 MHz, DMSO-d$_6$) δ 10.50 (s, 1H), 9.14 (s, 1H), 9.03 (m, 2H), 8.63 (d, 1H), 8.44 (d, 1H), 7.98 (m, 1H), 7.91 (dd, 1H), 7.80 (d, 1H), 7.67 (m, 1H), 7.44 (m, 3H), 6.71 (dd, 1H), 4.06 (m, 2H), 3.83 (s, 3H), 2.64 (t, 3H). MS (EI) m/z for C$_{24}$H$_{22}$Cl$_2$N$_6$O$_4$S: 561.0 (MH$^+$).

Example 26

(S)-2-amino-N-(3-(N-(3-(2-chloro-5-methoxy-phenylamino)quinoxalin-2-yl)sulfamoyl)phenyl)propanamide hydrochloride $^1$H NMR (400 MHz, CD$_3$OD) δ 8.72-8.71 (d, 1H), 8.48-8.46 (t, 1H), 7.86-7.84 (m, 1H), 7.80-7.78 (m, 1H), 7.63-7.59 (m, 2H), 7.58-7.55 (t, 1H), 7.41-7.38 (m, 2H), 7.24-7.22 (d, 1H), 6.60-6.58 (dd, 1H), 4.10-4.04 (q, 1H), 3.83 (s, 3H), 1.61-1.60 (d, 3H); MS (EI) m/z for C$_{24}$H$_{23}$ClN$_6$O$_4$S.HCl: 527.2 (MH$^+$).

Example 27

(S)-2-amino-N-(3-(N-(3-(2-chloro-5-methoxyphenylamino)quinoxalin-2-yl)sulfamoyl)phenyl)butanamide hydrochloride $^1$H NMR (400 MHz, CD$_3$OD) δ 8.74-8.73 (d, 1H), 8.80-8.47 (t, 1H), 7.87-7.85 (m, 1H), 7.80-7.78 (m, 1H), 7.67-7.61 (m, 2H), 7.59-7.55 (t, 1H), 7.42-7.39 (m, 2H), 7.26-7.24 (d, 1H), 6.62-6.59 (dd, 1H), 3.96-3.93 (t, 1H), 3.84 (s, 3H), 2.02-1.94 (m, 2H, 1.09-1.06 (t, 3H); MS (EI) m/z for C$_{25}$H$_{25}$ClN$_6$O$_4$S.HCl: 541.3 (MH$^+$).

Example 28

(S)—N-(3-(N-(3-(2-chloro-5-methoxyphenylamino)quinoxalin-2-yl)sulfamoyl)phenyl)pyrrolidine-2-carboxamide hydrochloride $^1$H NMR (400 MHz, CD$_3$OD) δ 8.78-8.77 (d, 1H), 8.47-8.46 (t, 1H), 7.87-7.85 (m, 1H), 7.80-7.75 (m, 1H), 7.69-7.65 (m, 2H), 7.59-7.55 (t, 1H), 7.45-7.41 (m, 2H), 7.31-7.28 (d, 1H), 6.65-6.63 (dd, 1H), 4.42-4.38 (m, 1H), 3.86 (s, 3H), 3.48-3.42 (m, 2H), 2.55-2.49 (m, 1H), 2.18-2.08 (m, 3H); MS (EI) m/z for C$_{26}$H$_{25}$ClN$_6$O$_4$S.HCl: 553.3 (MH$^+$).

Example 29

(S)—N-(3-(N-(3-(3,5-dimethoxy-phenylamino)quinoxalin-2-yl)sulfamoyl)phenyl)pyrrolidine-2-carboxamide hydrochloride. $^1$H NMR (400 MHz, CD$_3$OD) δ 10.62 (br s, 1H), 8.50-8.49 (t, 1H), 7.90-7.87 (m, 1H), 7.76-7.73 (m, 1H), 7.63-7.58 (m, 3H), 7.43-7.35 (m, 2H), 7.14 (s, 2H), 6.27-6.26 (t, 1H), 4.43-4.38 (m, 1H), 3.78 (s, 6H), 3.48-3.41 (m, 1H), 3.40-3.36 (m, 1H(, 2.54-2.48 (m, 1H), 2.19-2.05 (m, 3H); MS (EI) m/z for C$_{27}$H$_{28}$N$_6$O$_5$S.HCl: 549.3 (MH$^+$).

Example 30

(R)-2-amino-N-(3-(N-(3-(3,5-dimethoxy-phenylamino)quinoxalin-2-yl)sulfamoyl)phenyl)-3-hydroxypropanamide hydrochloride $^1$H NMR (400 MHz, CD$_3$OD) δ 8.49-8.48 (t, 1H), 7.89-7.87 (m, 1H), 7.75-7.72 (m, 1H), 7.65-7.62 (m, 2H), 7.62-7.55 (t, 1H), 7.44-7.38 (m, 2H), 7.23-7.22 (d, 2H), 6.27-6.26 (t, 1H), 4.07-4.05 (m, 1H), 3.99-3.93 (m, 2H), 3.80 (s, 6H); MS (EI) m/z for C$_{25}$H$_{26}$N$_6$O$_6$S.HCl: 539.1 (MH$^+$).

Example 31

N-(3-(N-(3-(2-chloro-5-methoxy-phenylamino)quinoxalin-2-yl)sulfamoyl)phenyl)piperidine-3-carboxamide hydrochloride. $^1$H NMR (400 MHz, CD$_3$OD) δ 8.79-8.78 (d, 1H), 8.45 (m, 1H), 7.83-7.81 (d, 1H), 7.76-7.74 (m, 1H), 7.636 (m, 2H), 7.54-7.50 (t, 1H), 7.41 (m, 2H), 7.30-7.28 (d, 1H), 6.65-6.62 (dd, 1H), 3.86 (s, 3H), 3.40-3.32 (m, 2H), 3.20-3.13 (m, 3H), 2.93 (m, 1H), 2.15-2.11 (m, 1H), 1.98-1.93 (m, 2H), 1.83 (m, 1H); MS (EI) m/z for C$_{27}$H$_{27}$ClN$_6$O$_4$S.HCl: 567.3 (MH$^+$).

Example 32

(S)-2-amino-N-(3-(N-(3-(3,5-dimethoxyphenylamino)quinoxalin-2-yl)sulfamoyl)phenyl)butanamide hydrochloride MS (EI) m/z for C$_{26}$H$_{28}$N$_6$O$_5$S.HCl: 537.1 (MH$^+$).

Example 33

(R)—N-(3-(N-(3-(3,5-dimethoxy-phenylamino)quinoxalin-2-yl)sulfamoyl)phenyl)pyrrolidine-2-carboxamide hydrochloride MS (EI) m/z for C$_{27}$H$_{28}$N$_6$O$_5$S.HCl: 549.1 (MH$^+$).

Example 34

(R)—N-(3-(N-(3-(2-chloro-5-methoxy-phenylamino)quinoxalin-2-yl)sulfamoyl)phenyl)pyrrolidine-2-carboxamide hydrochloride MS (EI) m/z for C$_{26}$H$_{25}$ClN$_6$O$_4$S.HCl: 553 (MH$^+$).

Example 35

(R)-2-amino-N-(3-(N-(3-(3,5-dimethoxyphenylamino)quinoxalin-2-yl)sulfamoyl)phenyl)propanamide $^1$H NMR (400 MHz, DMSO-d$_6$) δ 10.2 (br s, 1H), 8.82 (s, 1H), 8.27 (m, 1H), 7.75 (m, 2H), 7.33 (m, 5H), 7.13 (m, 2H), 6.14 (t, 1H), 3.77 (s, 6H), 1.39 (d, 3H); MS (EI) m/z for C$_{25}$H$_{26}$N$_6$O$_5$S: 523 (MH$^+$).

Example 36

N-(3-(N-(3-(2-chloro-5-methoxy-phenylamino)quinoxalin-2-yl)sulfamoyl)phenyl)-2-(methylamino)acetamide $^1$H NMR (400 MHz, DMSO-d$_6$) δ 10.6 (s, 1H), 9.48 (s, 1H), 8.95 (br s, 1H), 8.75 (br s, 1H), 8.19 (br s, 1H), 7.77 (dd, 1H), 7.69 (dd, 1H), 7.41 (m, 4H), 7.17 (m, 2H), 6.60 (dd, 1H), 3.91 (s, 2H), 3.82 (s, 6H), 2.62 (s, 3H); MS (EI) m/z for C$_{24}$H$_{23}$ClN$_6$O$_4$S: 527 (MH$^+$).

Example 37

(R)-2-amino-N-(3-(N-(3-(2-chloro-5-methoxy-phenylamino)quinoxalin-2-yl)sulfamoyl)phenyl)propanamide $^1$H NMR (400 MHz, DMSO-d$_6$) δ 10.5 (s, 1H), 9.47 (s, 1H), 8.95 (d, 1H), 8.22 (d, 2H), 8.14 (br s, 2H), 7.76 (m, 2H), 7.40 (m, 4H), 7.17 (m, 2H), 6.60 (m, 1H), 3.97 (q, 1H), 3.96 (s, 3H), 1.45 (d, 3H); MS (EI) m/z for C$_{24}$H$_{23}$ClN$_6$O$_4$S: 527 (MH$^+$).

Example 38

2-amino-N-(3-(N-(3-(2-chloro-5-methoxy-phenylamino)quinoxalin-2-yl)sulfamoyl)phenyl)-2-methylpropanamide $^1$H NMR (400 MHz, DMSO-d$_6$) δ 10.1 (s, 1H), 9.46 (s, 1H), 8.95 (d, 1H), 8.50 (br s, 1H), 8.27 (m, 1H), 7.81 (m, 2H), 7.47 (m, 1H), 7.37 (m, 3H), 7.17 (m, 2H), 6.61 (dd, 1H), 3.83 (s, 3H), 1.60 (s, 6H); MS (EI) m/z for C$_{25}$H$_{25}$ClN$_6$O$_4$S: 541 (MH$^+$).

Example 39

2-amino-N-(3-(N-(3-(3,5-dimethoxy-phenylamino)quinoxalin-2-yl)sulfamoyl)phenyl)-2-methylpropanamide $^1$H NMR (400 MHz, DMSO-d$_6$) δ 10.33 (s, 1H), 8.89 (s, 1H), 8.32 (br s, 4H), 7.92 (m, 3H), 7.59 (m, 2H), 7.37 (m, 4H), 6.24 (s, 1H), 3.76 (s, 6H), 1.61 (s, 6H); MS (EI) m/z for C$_{26}$H$_{28}$N$_6$O$_5$S: 537 (MH$^+$).

Example 40

N-(3-(N-(3-(3,5-dimethoxy-phenylamino)quinoxalin-2-yl)sulfamoyl)-4-methylphenyl)-2-(dimethylamino)acetamide $^1$H NMR (400 MHz, DMSO-d$_6$) δ 10.58 (s, 1H), 9.80 (br s, 1H), 8.85 (s, 1H), 8.25 (s, 1H), 7.67 (dd, 1H), 7.30 (m, 7H), 6.16 (m, 1H), 4.02 (br s, 2H), 3.77 (s, 6H), 2.81 (s, 6H), 2.54 (s, 3H); MS (EI) m/z for C$_{27}$H$_{30}$N$_6$O$_5$S: 551 (MH$^+$).

Example 41

N-(3-(N-(3-(2-chloro-5-methoxy-phenylamino)quinoxalin-2-yl)sulfamoyl)phenyl)-2-((2-(dimethylamino)ethyl)(methyl)amino)acetamide $^1$H NMR (400 MHz, DMSO-d$_6$) δ 10.0 (s, 1H), 9.48 (s, 1H), 8.96 (d, 1H), 8.16 (m, 1H), 7.76 (m, 2H), 7.39 (m, 4H), 7.17 (m, 2H), 6.61 (dd, 1H), 3.82 (s, 3H), 3.40 (br s, 2H), 2.94 (br s, 2H), 2.71 (br t, 2H), 2.60 (s, 6H), 2.33 (s, 3H); MS (EI) m/z for C$_{28}$H$_{32}$ClN$_7$O$_4$S: 598 (MH$^+$).

Example 42

2-amino-N-(3-(N-(3-(2-chloro-5-methoxyphenylamino)quinoxalin-2-yl)sulfamoyl)phenyl)acetamide $^1$H NMR (400 MHz, DMSO-d$_6$) δ 10.5 (s, 1H), 9.48 (s, 1H), 8.94 (s, 1H), 8.15 (s, 1H), 8.06 (br s, 3H), 7.74 (m, 2H), 7.39 (m, 4H), 7.18 (m, 2H), 6.61 (dd, 1H), 3.83 (s, 3H), 3.77 (s, 2H); MS (EI) m/z for C$_{23}$H$_{21}$ClN$_6$O$_4$S: 513 (MH$^+$).

Example 43

N-(3-(N-(3-(2-acetyl-5-methoxyphenylamino)quinoxalin-2-yl)sulfamoyl)phenyl)-2-(dimethylamino)acetamide $^1$H NMR (400 MHz, DMSO-d$_6$) δ 12.4 (s, 1H), 10.5 (s, 1H), 9.27 (s, 1H), 8.25 (s, 1H), 8.01 (d, 1H), 7.82 (d, 1H), 7.71 (d, 1H), 7.42 (m, 3H), 7.21 (m, 2H), 6.63 (dd, 1H), 3.91 (m, 5H), 2.75 (s, 6H), 2.61 (s, 3H); MS (EI) m/z for C$_{27}$H$_{28}$N$_6$O$_5$S: 549 (MH$^+$).

Example 44

N-(3-(N-(3-(2-chloro-5-methoxy-phenylamino)quinoxalin-2-yl)sulfamoyl)phenyl)formamide $^1$H NMR (400 MHz, DMSO-d$_6$) δ 12.6 (s, 1H), 10.5 (s, 1H), 9.16 (s, 1H), 8.53 (br s, 1H), 8.35 (m, 2H), 8.02 (s, 1H), 7.56 (m, 7H), 6.70 (dd, 1H), 3.83 (s, 3H); MS (EI) m/z for C$_{22}$H$_{18}$ClN$_5$O$_4$S: 484 (MH$^+$).

Example 45

2-amino-N-(5-(N-(3-(3,5-dimethoxy-phenylamino)quinoxalin-2-yl)sulfamoyl)-2-methylphenyl)acetamide $^1$H NMR (400 MHz, DMSO-d$_6$) δ 12.4 (s, 1H), 10.1 (br s, 1H), 8.82 (s, 1H), 8.20 (m, 3H), 7.82 (m, 1H), 7.30 (m, 6H), 6.20 (s, 1H), 3.85 (s, 2H), 3.77 (s, 6H), 2.26 (s, 3H); MS (EI) m/z for C$_{25}$H$_{26}$N$_6$O$_5$S: 523 (MH$^+$).

Example 46

N-(3-(N-(3-(2-chloro-5-methoxy-phenylamino)quinoxalin-2-yl)sulfamoyl)phenyl)-2-methyl-2-(methylamino)propanamide $^1$H NMR (400 MHz, DMSO-d$_6$) δ 10.09 (s, 1H), 9.46 (s, 1H), 8.95 (m, 3H), 8.28 (s, 1H), 7.81 (m, 2H), 7.41 (m, 4H), 7.17 (m, 2H), 6.60 (dd, 1H), 3.82 (s, 3H), 2.53 (s, 3H), 1.60 (s, 6H); MS (EI) m/z for C$_{26}$H$_{27}$ClN$_6$O$_4$S: 555 (MH$^+$).

Example 47

(S)—N-(3-(N-(3-(2-chloro-5-methoxy-phenylamino)quinoxalin-2-yl)sulfamoyl)phenyl)-2-(methylamino)propanamide $^1$H NMR (400 MHz, DMSO-d$_6$) δ 10.61 (s, 1H), 9.47 (s, 1H), 8.95 (s, 1H), 8.82 (br s, 2H), 8.27 (m, 1H), 7.74 (m, 2H), 7.42 (m, 4H), 7.17 (m, 2H), 6.60 (dd, 1H), 3.90 (m, 1H), 3.82 (s, 3H), 2.59 (s, 3H), 1.49 (d, 3H); MS (EI) m/z for C$_{25}$H$_{25}$ClN$_6$O$_4$S: 541 (MH$^+$).

Example 48

3-amino-N-(5-(N-(3-(2-chloro-5-methoxyphenylamino)quinoxalin-2-yl)sulfamoyl)-2-methylphenyl)propanamide $^1$H NMR (400 MHz, DMSO-d$_6$) δ 12.25 (s, 1H), 9.77 (s, 1H), 8.82 (s, 1H), 7.84 (m, 5H), 7.50 (d, 1H), 7.37 (m, 5H), 6.22 (m, 1H), 3.74 (s, 6H), 3.08 (m, 2H), 2.77 (m, 2H), 2.27 (s, 3H); MS (EI) m/z for C$_{26}$H$_{28}$N$_6$O$_5$S: 537 (MH$^+$).

Example 49

1-amino-N-(3-(N-(3-(2-chloro-5-methoxy-phenylamino)quinoxalin-2-yl)sulfamoyl)phenyl)cyclopropanecarboxamide $^1$H NMR (400 MHz, DMSO-d$_6$) δ 9.54 (br s, 1H), 9.42 (s, 1H), 8.91 (s, 1H), 8.21 (s, 1H), 8.20 (br s, 2H), 7.81 (m, 2H), 7.48 (m, 4H), 7.22 (m, 2H), 6.61 (dd, 1H), 3.82 (s, 3H), 1.63 (m, 2H), 1.26 (m, 2H); MS (EI) m/z for C$_{25}$H$_{23}$ClN$_6$O$_4$S: 539 (MH$^+$).

Example 50

(S)-2-amino-N-(3-(N-(3-(2-chloro-5-methoxy-phenylamino)quinoxalin-2-yl)sulfamoyl)phenyl)-6-(dimethylamino)hexanamide $^1$H NMR (400 MHz, DMSO-d$_6$) δ 9.47 (br s, 1H), 8.95 (d, 1H), 8.26 (m, 1H), 7.73 (m, 2H), 7.30 (m, 4H), 7.26 (m, 4H), 7.16 (m, 2H), 6.59 (dd, 1H), 3.82 (s, 3H), 3.34 (m, 1H), 2.20 (m, 2H), 2.09 (s, 6H), 1.50 (m, 6H); MS (EI) m/z for C$_{29}$H$_{34}$ClN$_7$O$_4$S: 610 (MH$^+$).

Example 51

1-amino-N-(3-(N-(3-(2-chloro-5-methoxy-phenylamino)quinoxalin-2-yl)sulfamoyl)phenyl)cyclopentanecarboxamide $^1$H NMR (400 MHz, DMSO-d$_5$) δ 10.12 (br s, 1H), 9.46 (s, 1H), 8.95 (d, 1H), 8.26 (m, 1H), 8.16 (m, 3H), 7.84 (m, 2H), 7.35 (m, 6H), 6.60 (dd, 1H), 3.82 (s, 3H), 2.34 (m, 2H), 1.91 (m, 6H); MS (EI) m/z for C$_{27}$H$_{27}$ClN$_6$O$_4$S: 567 (MH$^+$).

Example 52

N-(5-(N-(3-(2-chloro-5-methoxyphenylamino)quinoxalin-2-yl)sulfamoyl)-2-methylphenyl)-2-(dimethylamino)acetamide $^1$H NMR (400 MHz, DMSO-d$_6$) δ 12.0 (br s, 1H), 9.98 (s, 1H), 9.43 (s, 1H), 8.91 (m, 1H), 8.08 (s, 1H), 7.84 (dd, 1H), 7.32 (m, 6H), 6.61 (dd, 1H), 4.07 (s, 2H), 3.82 (s, 3H), 2.82 (s, 6H), 2.21 (s, 3H); MS (EI) m/z for C$_{26}$H$_{27}$ClN$_6$O$_4$S: 555 (MH$^+$).

Example 53

1-amino-N-(3-(N-(3-(3,5-dimethoxy-phenylamino)quinoxalin-2-yl)sulfamoyl)phenyl)cyclobutanecarboxamide $^1$H NMR (400 MHz, DMSO-d$_6$) δ 10.34 (br s, 1H), 8.81 (s, 1H), 8.49 (br s, 3H), 8.34 (s, 1H), 7.83 (m, 2H), 7.43 (m, 3H), 7.31 (m, 2H), 7.16 (m, 2H), 6.16 (s, 1H), 3.77 (s, 6H), 2.83 (m, 2H), 2.25 (m, 3H), 2.05 (m, 1H); MS (EI) m/z for $C_{27}H_{28}N_6O_5S$: 549 (MH$^+$).

Example 54

N-(3-(3,5-dimethoxyphenylamino)quinoxalin-2-yl)-3-(3-(2-(dimethylamino)ethyl)ureido)benzenesulfonamide $^1$H NMR (400 MHz, DMSO-d$_6$) δ 8.91 (br s, 1H), 8.81 (s, 1H), 8.08 (s, 1H), 7.60 (s, 1H), 7.38 (m, 9H), 6.28 (m, 1H), 6.15 (s, 1H), 3.78 (s, 6H), 3.40 (m, 2H), 3.08 (m, 2H), 2.74 (s, 6H); MS (EI) m/z for $C_{27}H_{31}N_7O_5S$: 566 (MH$^+$).

Example 55

1-amino-N-(3-(N-(3-(3,5-dimethoxy-phenylamino)quinoxalin-2-yl)sulfamoyl)phenyl)cyclopentanecarboxamide $^1$H NMR (400 MHz, DMSO-d$_6$) δ 12.40 (br s, 1H), 10.58 (s, 1H), 8.46 (m, 4H), 7.80 (m, 3H), 7.59 (m, 2H), 7.34 (m, 4H), 6.25 (m, 1H), 3.76 (s, 6H), 2.35 (m, 2H), 1.90 (m, 8H); MS (EI) m/z for $C_{28}H_{30}N_6O_5S$: 563 (MH$^+$).

Example 56

1-amino-N-(3-(N-(3-(3,5-dimethoxy-phenylamino)quinoxalin-2-yl)sulfamoyl)phenyl)cyclopropanecarboxamide $^1$H NMR (400 MHz, DMSO-d$_6$) δ 9.54 (br s, 1H), 8.84 (s, 1H), 8.29 (s, 1H), 7.75 (m, 2H), 7.39 (m, 6H), 7.17 (m, 2H), 6.16 (m, 1H), 3.78 (s, 6H), 1.52 (m, 2H), 1.17 (m, 2H); MS (EI) m/z for $C_{26}H_{26}N_6O_5S$: 535 (MH$^+$).

Example 57

2-(dimethylamino)ethyl 3-(N-(3-(3,5-dimethoxy-phenylamino)quinoxalin-2-yl)sulfamoyl)phenylcarbamate $^1$H NMR (400 MHz, DMSO-d$_6$) δ 9.78 (br s, 1H), 8.79 (s, 1H), 8.19 (s, 1H), 7.66 (d, 1H), 7.31 (m, 9H), 6.14 (m, 1H), 4.17 (t, 2H), 3.78 (s, 6H), 2.54 (t, 2H), 2.21 (s, 6H): MS (EI) m/z for $C_{27}H_{30}N_6O_6S$: 567 (MH$^+$).

Example 58

4-amino-N-(3-(N-(3-(3,5-dimethoxy-phenylamino)quinoxalin-2-yl)sulfamoyl)phenyl)tetrahydro-2H-pyran-4-carboxamide $^1$H NMR (400 MHz, DMSO-d$_6$) δ 12.2 (br s, 1H), 10.6 (s, 1H), 8.74 (m, 5H), 7.93 (m, 2H), 7.47 (m, 6H), 6.24 (m, 1H), 3.77 (m, 10H), 2.45 (m, 2H), 1.81 (m, 2H); MS (EI) m/z for $C_{28}H_{30}N_6O_6S$: 579 (MH$^+$).

Example 59

N-(3-(2-chloro-5-methoxy-phenylamino)quinoxalin-2-yl)-N-3-(2-(dimethylamino)ethyl)benzene-1,3-disulfonamide $^1$H NMR (400 MHz, DMSO-d$_6$) δ 9.35 (m, 2H), 8.92 (m, 1H), 8.64 (s, 1H), 8.30 (m, 1H), 8.11 (s, 1H), 7.86 (m, 1H), 7.68 (m, 1H), 7.49 (s, 1H), 7.42 (m, 2H), 7.21 (m, 2H), 6.61 (m, 1H), 3.82 (s, 3H), 3.05 (m, 4H), 2.74 (s, 6H); MS (EI) m/z for $C_{25}H_{27}ClN_6O_5S_2$: 591 (MH$^+$).

Example 60

N-(3-(2-chloro-5-methoxy-phenylamino)quinoxalin-2-yl)-N3-(3-(dimethylamino)propyl)benzene-1,3-disulfonamide $^1$H NMR (400 MHz, DMSO-d$_6$) δ 9.38 (m, 2H), 8.90 (m, 1H), 8.60 (s, 1H), 8.32 (m, 1H), 8.12 (s, 1H), 7.88 (m, 1H), 7.72 (m, 1H), 7.59 (s, 1H), 7.40 (m, 2H), 7.20 (m, 2H), 6.67 (m, 1H), 3.82 (s, 3H), 2.97 (m, 2H), 2.78 (m, 2H), 2.71 (s, 6H), 1.70 (m, 2H); MS (EI) m/z for $C_{26}H_{29}ClN_6O_5S_2$: 605 (MH$^+$).

Example 61

N-(3-(N-(3-(2-chloro-5-methoxy-phenylamino)quinoxalin-2-yl)sulfamoyl)-4-methylphenyl)-2-(methylamino)acetamide MS (EI) m/z for $C_{25}H_{25}ClN_6O_4S$: 541.0 (MH$^+$).

Example 62

(S)-2-amino-N-(3-(N-(3-(2-chloro-5-methoxy-phenylamino)quinoxalin-2-yl)sulfamoyl)-4-methylphenyl)propanamide MS (EI) m/z for $C_{25}H_{25}ClN_6O_4S$: 541.2 (MH$^+$).

Example 63

(R)-2-amino-N-(3-(N-(3-(2-chloro-5-methoxy-phenylamino)quinoxalin-2-yl)sulfamoyl)-4-methylphenyl)propanamide MS (EI) m/z for $C_{25}H_{25}ClN_6O_4S$: 541.0 (MH$^+$).

Example 64

(S)—N-(3-(N-(3-(3,5-dimethoxy-phenylamino)quinoxalin-2-yl)sulfamoyl)phenyl)-2-(methylamino)propanamide MS (EI) m/z for $C_{26}H_{28}N_6O_5S$: 537.1 (MH$^+$).

Example 65

(R)—N-(3-(N-(3-(2-chloro-5-methoxy-phenylamino)quinoxalin-2-yl)sulfamoyl)phenyl)-2-(methylamino)propanamide MS (EI) m/z for $C_{25}H_{25}ClN_6O_4S$: 541.1 (MH$^+$).

Example 66

(R)—N-(3-(N-(3-(3,5-dimethoxy-phenylamino)quinoxalin-2-yl)sulfamoyl)phenyl)-2-(methylamino)propanamide MS (EI) m/z for $C_{26}H_{28}N_6O_5S$: 537.3 (MH$^+$).

Example 67

N-(3-(N-(3-(3,5-dimethoxy-phenylamino)quinoxalin-2-yl)sulfamoyl)phenyl)piperidine-2-carboxamide MS (EI) m/z for $C_{28}H_{30}N_6O_5S$: 563.1 (MH$^+$).

Example 68

N-(3-(N-(3-(3,5-dimethoxy-phenylamino)quinoxalin-2-yl)sulfamoyl)phenyl)-2-(2-(dimethylamino)ethylamino)acetamide MS (EI) m/z for $C_{28}H_{33}N_7O_5S$: 580.1 (MH$^+$).

Example 69

N-(3-(N-(3-(3,5-dimethoxy-phenylamino)quinoxalin-2-yl)sulfamoyl)phenyl)-2-(4-(methylamino)piperidin-1-yl)acetamide MS (EI) m/z for $C_{30}H_{35}N_7O_6S$: 606.1 (MH$^+$).

Example 70

N-(3-(N-(3-(3,5-dimethoxy-phenylamino)quinoxalin-2-yl)sulfamoyl)phenyl)-2-(4-(dimethylamino)piperidin-1-yl)acetamide MS (EI) m/z for $C_{31}H_{37}N_7O_5S$: 620.1 (MH$^+$).

Example 71

N-(3-(N-(3-(3,5-dimethoxyphenylamino)quinoxalin-2-yl)sulfamoyl)phenyl)-2-(dimethylamino)acetamide $^1$H NMR (400 MHz, DMSO) δ 12.4 (br s, 1H), 10.9 (s, 1H), 9.8 (s, 1H), 8.9 (s, 1H), 8.3 (br s, 1H), 7.9 (d, 2H), 7.8 (d, 1H), 7.6 (t, 2H), 7.4 (q, 2H), 7.3 (s, 1H), 6.25 (s, 1H), 4.15 (s, 2H), 3.8 (s, 6H), 2.9 (s, 6H). MS (EI) m/z for $C_{26}H_{28}N_6O_5S$ 2.0× $C_2H_1O_2F_3$: 537.1 (MH$^+$).

Example 72

N-(3-(N-(3-(2-chloro-5-methoxy-phenylamino)quinoxalin-2-yl)sulfamoyl)phenyl)-2-(ethylamino)acetamide $^1$H NMR (400 MHz, DMSO) δ 10.8 (s, 1H), 9.20 (s, 1H), 8.84 (br s, 2H), 8.64 (br s, 1H), 8.30 (s, 1H), 7.9-8.0 (br s, 1H), 7.80 (t, 2H), 7.55-7.68 (m, 2H), 7.4 (d, 3H), 6.70 (m, 1H), 3.97 (br s, 2H), 3.83 (s, 3H), 3.04 (br s, 2H), 1.3 (t, 3H). MS (EI) m/z for $C_{25}H_{25}ClN_6O_4S$ 2.0×$C_2H_1O_2F_3$: 541.3, 543.2 (MH$^+$).

Example 73

2-(azetidin-1-yl)-N-(3-(N-(3-(2-chloro-5-methoxyphenylamino)quinoxalin-2-yl)sulfamoyl)phenyl)acetamide $^1$H NMR (400 MHz, DMSO) δ 10.8 (s, 1H), 10.2 (s, 1H), 9.2 (s, 1H), 8.7 (s, 1H), 8.3 (s, 1H), 7.9-8.0 (br s, 1H), 7.80 (d, 1H), 7.72 (d, 1H), 7.65 (br s, 1H), 7.56 (t, 1H), 7.40 (d, 3H), 6.70 (m, 1H), 4.28 (s, 2H), 4.15 (m, 4H), 3.82 (s, 3H), 2.32 (br s, 1H). MS (EI) m/z for $C_{26}H_{25}ClN_6O_4S$ 2.0×$C_2H_1O_2F_3$: 553.3, 555.2 (MH$^+$).

Example 74

N-(3-(N-(3-(2-bromo-5-methoxy-phenylamino)quinoxalin-2-yl)sulfamoyl)phenyl)-2-(methylamino)acetamide The title compound was prepared according to the Examples above. $^1$H NMR (400 MHz, DMSO) δ 10.6 (s, 1H), 9.5 (s, 1H), 8.95 (d, 1H), 8.18 (t, 1H), 7.78 (m, 1H), 7.70 (m, 1H), 7.54 (d, 1H), 7.46 (m, 1H), 7.38 (t, 1H), 7.32 (d, 1H), 7.12-7.22 (m, 2H), 6.56 (m, 1H), 3.90 (s, 2H), 3.82 (s, 3H), 2.62 (s, 3H). MS (EI) m/z for $C_{24}H_{23}BrN_6O_4S$: 572.77, 570.90 (MH$^+$).

Example 75

2-(dimethylamino)-N-(3-(N-(3-(6-methoxy-quinolin-8-ylamino)quinoxalin-2-yl)sulfamoyl)phenyl)acetamide The title compound was prepared according to the Examples above. $^1$H NMR (400 MHz, DMSO) δ 10.9 (s, 1H), 10.6 (s, 1H), 9.13 (s, 1H), 8.80 (d, 1H), 8.26-8.30 (m, 2H), 7.85 (d, 1H), 7.70 (d, 1H), 7.60 (q, 1H), 7.54 (m, 1H), 7.44 (t, 2H), 7.20 (t, 2H), 6.80 (d, 1H), 4.00 (s, 2H), 3.94 (s, 3H), 2.78 (s, 6H). MS (EI) m/z for $C_{28}H_{27}N_7O_4S$: 558.3 (MH$^+$).

Example 76

N-(3-(N-(3-(2-bromo-5-methoxy-phenylamino)quinoxalin-2-yl)sulfamoyl)phenyl)-2-(dimethylamino)acetamide $^1$H NMR (400 MHz, DMSO) δ 10.6 (s, 1H), 9.4 (s, 1H), 8.9 (s, 1H), 8.25 (s, 1H), 7.78 (d, 1H), 7.70 (d, 1H), 7.54 (d, 1H), 7.48 (d, 1H), 7.40 (t, 2H), 6.56 (d, 1H), 4.02 (s, 2H), 3.82 (s, 3H), 2.80 (s, 6H). MS (EI) m/z for $C_{25}H_{25}BrN_6O_4S$: 586.79, 584.91 (MH$^+$).

Example 77

N-(3-(N-(3-(2-chloro-5-methoxy-phenylamino)quinoxalin-2-yl)sulfamoyl)phenyl)-2-(2-fluoroethylamino)acetamide $^1$H NMR (400 MHz, DMSO) δ 10.6 (s, 1H), 9.4 (s, 1H), 8.9 (d, 1H), 8.20 (s, 1H), 7.78 (d, 1H), 7.70 (d, 1H), 7.48 (m, 1H), 7.36-7.44 (m, 3H), 7.20 (q, 3H), 6.6 (m, 1H), 4.78 (t, 1H), 4.66 (t, 1H), 3.94 (s, 2H), 3.82 (s, 3H), 3.4 (t, 1H), 3.3 (t, 1H). MS (EI) m/z for $C_{25}H_{24}ClFN_6O_4S$: 559.2, 561.2 (MH$^+$).

Example 78

N-(3-(N-(3-(3,5-dimethoxy-phenylamino)quinoxalin-2-yl)sulfamoyl)phenyl)formamide $^1$H NMR (400 MHz, DMSO) δ 12.4 (br s, 1H), 10.5 (s, 1H), 8.90 (s, 1H), 8.3 (s, 1H), 7.9 (br s, 1H), 7.85 (d, 1H), 7.75 (d, 1H), 7.5-7.6 (m, 2H), 7.3-7.4 (m, 4H), 6.2 (s, 1H), 3.8 (s, 3H). MS (EI) m/z for $C_{23}H_{21}N_5O_5S$: 480.1 (MH$^+$).

Example 79

N-(3-(N-(3-(2-chloro-5-methoxy-phenylamino)quinoxalin-2-yl)sulfamoyl)phenyl)-2-(3-(dimethylamino)azetidin-1-yl)acetamide $^1$H NMR (400 MHz, DMSO) δ 10.2 (br s, 1H), 9.5 (s, 1H), 8.95 (d, 1H), 8.2 (s, 1H), 7.75 (d, 1H), 7.65 (d, 1H), 7.45 (d, 1H), 7.40 (d, 1H), 7.30-7.35 (t, 1H), 7.1-7.2 (q, 2H), 6.60 (m, 1H), 3.82 (s, 3H). MS (EI) m/z for $C_{28}H_{30}ClN_7O_4S$: 480.1 (MH$^+$).

Example 80

N-(3-(N-(3-(3,5-dimethoxy-phenylamino)quinoxalin-2-yl)sulfamoyl)phenyl)-2-(pyrrolidin-1-yl)acetamide MS (EI) m/z for $C_{28}H_{30}N_6O_5S$: 563.18 (MH$^+$).

Example 81

N-(3-(N-(3-(2-chloro-5-methoxyphenylamino)quinoxalin-2-yl)sulfamoyl)phenyl)-2-(ethyl(methyl)amino)acetamide $^1$H NMR (400 MHz, DMSO) δ 12.0 (s, 1H), 10.6 (s, 1H), 9.65 (s, 1H), 9.5 (s, 1H), 8.95 (s, 1H), 8.25 (s, 1H), 7.8 (d, 1H), 7.70 (d, 1H), 7.45-7.50 (d, 1H), 7.3-7.4 (m, 3H), 7.2 (t, 2H), 6.60 (d, 1H), 4.02 (br s, 2H), 3.82 (s, 3H), 3.14 (br s, 2H), 2.80 (s, 3H) 1.2 (t, 3H). MS (EI) m/z for $C_{26}H_{27}ClN_6O_4S$: 555.2, 557.3 (MH$^+$).

Example 82

N-(3-(N-(3-(2-chloro-5-methoxy-phenylamino)quinoxalin-2-yl)sulfamoyl)phenyl)-2-(3-(piperidin-1-yl)azetidin-1-yl)acetamide MS (EI) m/z for $C_{31}H_{34}ClN_7O_4S$ 2.0×$C_2H_1O_2F_3$: 636.3, 638.3 (MH$^+$).

Example 83

N-(3-(N-(3-(3-fluoro-5-methoxy-phenylamino)quinoxalin-2-yl)sulfamoyl)phenyl)-2-(methylamino)acetamide MS (EI) m/z for $C_{24}H_{23}FN_6O_4S$: 511.04 (MH$^+$).

Example 84

N-(3-(N-(3-(3,5-dimethoxy-phenylamino)quinoxalin-2-yl)sulfamoyl)phenyl)-1-methylpiperidine-4-carboxamide MS (EI) m/z for $C_{29}H_{32}N_6O_5S$ 1.0×$C_2H_4O_2$: 577.2 (MH$^+$).

Example 85

N-(3-(N-(3-(3-methoxyphenylamino)quinoxalin-2-yl)sulfamoyl)phenyl)-2-(methylamino)acetamide $^1$H NMR (400 MHz, DMSO) δ 10.6 (s, 1H), 8.82 (s, 1H), 8.22 (t, 1H), 7.86 (t, 1H), 7.76 (m, 1H), 7.66 (m, 1H), 7.46 (m, 1H), 7.41 (m, 1H), 7.38 (t, 1H), 7.28 (m 1H), 7.24 (t, 1H), 7.12 (m, 2H), 6.56 (d, 1H), 3.88 (s, 2H), 3.80 (s, 3H), 2.60 (s, 3H). MS (EI) m/z for $C_{24}H_{24}N_6O_4S$: 492.99 (MH$^+$).

Example 86

N-(3-(N-(3-(2-chloro-5-methoxy-phenylamino)quinoxalin-2-yl)sulfamoyl)phenyl)-2-(2,2,2-trifluoroethylamino)acetamide $^1$H NMR (400 MHz, DMSO) δ 10.4 (s, 1H), 9.2 (s, 1H), 8.65 (s, 1H), 8.4 (s, 1H), 8.00 (m, 1H), 7.80 (d, 1H), 7.75 (d, 1H), 7.65 (q, 1H), 7.55 (t, 1H), 7.40-7.5 (m, 3H), 6.7 (m, 1H), 3.82 (s, 3H), 3.62 (br s, 2H), 3.55 (br d, 2H). MS (EI) m/z for $C_{25}H_{22}ClF_3N_6O_4S$ 1.0×$C_2H_1O_2F_3$: 595.0, 597.0 (MH$^+$).

Example 87

N-(3-(N-(3-(3,5-dimethoxy-phenylamino)quinoxalin-2-yl)sulfamoyl)phenyl)-3-(piperidin-1-yl)propanamide MS (EI) m/z for $C_{30}H_{34}N_6O_5S$: 591.2 (MH$^+$).

Example 88

N-(3-(N-(3-(3,5-dimethoxy-phenylamino)quinoxalin-2-yl)sulfamoyl)phenyl)-4-(dimethylamino)butanamide MS (EI) m/z for $C_{28}H_{32}N_6O_5S$ 1.0×$C_2H_4O_2$: 565.2 (MH$^+$).

Example 89

2-(dimethylamino)-N-(3-(N-(3-(3-fluoro-5-methoxyphenylamino)quinoxalin-2-yl)sulfamoyl)phenyl)acetamide $^1$H NMR (400 MHz, DMSO) δ 10.9 (s, 1H), 9.8 (br s, 1H), 9.1 (s, 1H), 8.34 (s, 1H), 7.90 (d, 1H), 7.76 (d, 1H), 7.52-7.68 (m, 4H), 7.40 (m, 2H), 6.54 (m, 1H), 4.16 (s, 2H), 3.82 (s, 3H), 2.86 (s, 6H). MS (EI) m/z for $C_{25}H_{25}FN_6O_4S$: 525.05 (MH$^+$).

Example 90

N-(3-(N-(3-(3,5-dimethoxy-phenylamino)quinoxalin-2-yl)sulfamoyl)phenyl)-2-(piperidin-1-yl)acetamide MS (EI) m/z for $C_{29}H_{32}N_6O_5S$: 577.37 (MH$^+$).

Example 91

2-(dimethylamino)-N-(3-(N-(3-(3-methoxy-phenylamino)quinoxalin-2-yl)sulfamoyl)phenyl)acetamide $^1$H NMR (400 MHz, DMSO) δ 10.5 (s, 1H), 8.8 (s, 1H), 8.25 (s, 1H), 7.83 (t, 1H), 7.76 (d, 1H), 7.64 (d, 1H), 7.3-7.48 (m, 4H), 7.22 (t, 1H), 7.12 (t, 2H), 6.56 (m, 1H), 3.96 (s, 2H), 3.78 (s, 3H), 2.76 (s, 6H). MS (EI) m/z for $C_{25}H_{26}N_6O_4S$: 507.1 (MH$^+$).

Example 92

N-(3-(N-(3-(2-chloro-5-hydroxy-phenylamino)quinoxalin-2-yl)sulfamoyl)phenyl)-2-(dimethylamino)acetamide $^1$H NMR (400 MHz, DMSO) δ 10.8 (s, 1H), 9.9 (s, 1H), 9.8 (s, 1H), 9.1 (s, 1H), 8.55 (s, 1H), 8.34 (s, 1H), 7.9-8.0 (br s, 1H), 7.82 (d, 1H), 7.76 (d, 1H), 7.52-7.66 (m, 2H), 7.42 (t, 1H), 7.26 (d, 1H), 6.50 (m, 1H), 4.16 (s, 2H), 2.86 (s, 6H). MS (EI) m/z for $C_{24}H_{23}ClN_6O_4S$: 527.1, 529.0 (MH$^+$).

Example 93

N-(3-(N-(3-(3,5-dimethoxy-phenylamino)quinoxalin-2-yl)sulfamoyl)phenyl)-2-morpholinoacetamide MS (EI) m/z for $C_{28}H_{30}N_6O_6S$: 579.1 (MH$^+$).

Example 94

N-(3-(N-(3-(3,5-dimethoxy-phenylamino)quinoxalin-2-yl)sulfamoyl)phenyl)acetamide MS (EI) m/z for $C_{24}H_{23}N_5O_5S$: 494.0 (MH$^+$).

Example 97

2-amino-N-(3-(N-(3-(2-chloro-5-methoxy-phenylamino)quinoxalin-2-yl)sulfamoyl)-4-methylphenyl)-2-methylpropanamide MS (EI) m/z for $C_{26}H_{27}ClN_6O_4S$: 556.12 (MH$^+$).

Example 98

N-(3-(N-(3-(2-chloro-5-methoxy-phenylamino)quinoxalin-2-yl)sulfamoyl)phenyl)-2-(dimethylamino)acetamide MS (EI) m/z for $C_{25}H_{25}ClN_6O_4S$: 542.05 (MH$^+$).

Example 99

2-amino-N-(3-(N-(3-(3,5-dimethoxy-phenylamino)quinoxalin-2-yl)sulfamoyl)phenyl)acetamide MS (EI) m/z for $C_{24}H_{24}N_6O_5S$: 509.59 (MH$^+$).

Example 100

3-(N-(3-(2-chloro-5-methoxy-phenylamino)quinoxalin-2-yl)sulfamoyl)benzoic acid

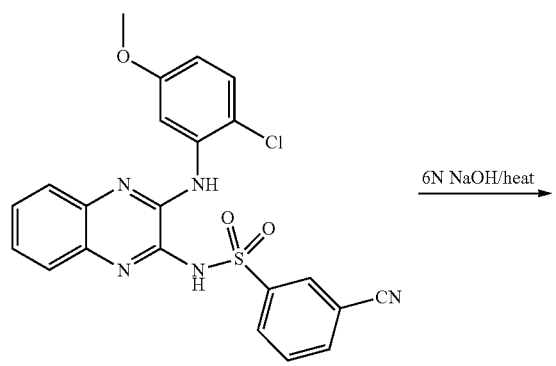

6N NaOH/heat

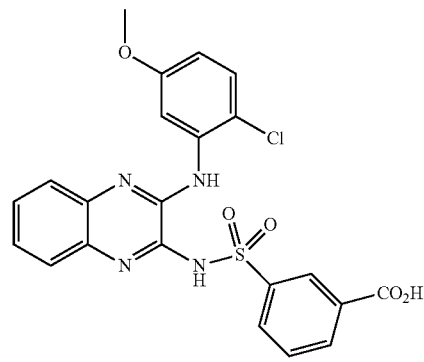

To a solution of N-(3-{[2-chloro-5-(methoxy)-phenyl]amino}quinoxalin-2-yl)-3-cyanobenzenesulfonamide (6.02 g, 12.95 mmol), prepared using procedures similar to those in Example 115 or Example 423, in methanol (20 mL) and 1,4-dioxane (20 mL) was added 6.0 N aqueous sodium hydroxide (40 mL) at room temperature. The solution was stirred at 90° C. for 3.5 h. The reaction was cooled to room temperature and neutralized slowly by adding 2.0 N hydrochloric acid until the pH of the solution became in the 2-3 range at 0° C. The solution was diluted with ethyl acetate (300 mL). The organic layer was washed with saturated aqueous sodium chloride (50 mL) and dried over magnesium sulfate. Filtration and concentration at reduced pressure afforded 3-{[(3-{[2-chloro-5-(methoxy)-phenyl]amino}quinoxalin-2-yl)amino]sulfonyl}benzoic acid (5.921 g, 94%). MS (EI) m/z for $C_{22}H_{17}ClN_4O_5S$: 485.0 (MH$^+$).

The following compounds were prepared using procedures similar to those used in Example 100.

Example 101

Proceeding as above, 3-(N-(3-(3,5-dimethoxyphenylamino)quinoxalin-2-yl)sulfamoyl)benzoic acid was prepared. MS (EI) m/z for $C_{23}H_{20}N_4O_6S$: 481.0 (MH$^+$).

Example 102

3-(N-(3-(2-chloro-5-methoxyphenylamino)quinoxalin-2-yl)sulfamoyl)-N-(2-methyl-1-(piperidin-1-yl)propan-2-yl)benzamide MS (EI) m/z for $C_{31}H_{35}ClN_6O_4S$: 623.06 (MH$^+$).

Example 103

3-(N-(3-(2-chloro-5-methoxy-phenylamino)quinoxalin-2-yl)sulfamoyl)-N-(2-methyl-1-oxo-1-(piperidin-1-yl)propan-2-yl)benzamide MS (EI) m/z for $C_{31}H_{33}ClN_6O_5S$: 637.65 (MH$^+$).

Example 104

3-{[(3-{[2-chloro-5-(methoxy)phenyl]amino}quinoxalin-2-yl)amino]sulfonyl}-N-[2-(dimethylamino)ethyl]benzamide

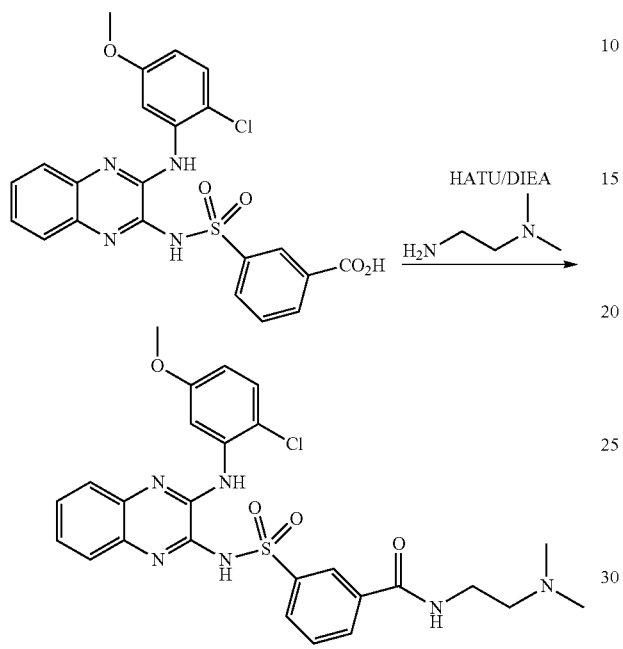

To a solution of 3-{[(3-{[2-chloro-5-(methoxy)phenyl]amino}quinoxalin-2-yl)amino]sulfonyl}benzoic acid (0.20 g, 0.42 mmol), prepared using procedures similar to Example 100, in dimethylformamide (4 mL) were added 2-(7-aza-1H-benzotriazole-1-yl)-1,1,3,3-tetramethyluronium hexafluorophosphate (HATU, 0.32 g, 0.83 mmol) and N-ethyldiisopropylamine (DIEA, 0.13 g, 1.04 mmol) at room temperature. The reaction was stirred for 15 min before N,N-dimethylethane-1,2-diamine (73 mg, 0.83 mmol) was added. The reaction mixture was allowed to stir overnight. The reaction was diluted with ethyl acetate (200 mL) and washed with water (50 mL), saturated aqueous sodium bicarbonate (40 mL), 1.0 N aqueous hydrochloric acid (30 mL), and saturated aqueous sodium chloride (25 mL). The organic layer was dried over magnesium sulfate, filtered and concentrated at reduced pressure to afford 3-{[(3-{[2-chloro-5-(methoxy)phenyl]amino}quinoxalin-2-yl)amino]sulfonyl}-N-[2-(dimethylamino)ethyl]benzamide (0.20 g, 87%) as yellow solid. MS (EI) m/z for $C_{26}H_{27}ClN_6O_4S$: 555.1 (MH$^+$).

The following compounds were prepared using procedures similar to those in Example 104.

Example 105

5-(N-(3-(2-chloro-5-methoxy-phenylamino)quinoxalin-2-yl)sulfamoyl)-N-(2-(dimethylamino)ethyl)-2-methoxybenzamide $^1$H NMR (400 MHz, DMSO-d$_6$) δ 9.45 (s, 1H), 8.95 (d, 1H), 8.57 (d, 1H), 8.28 (t, 1H), 8.14 (dd, 1H), 7.46 (dd, 1H), 7.39 (m, 2H), 7.17 (m, 4H), 6.60 (dd, 1H), 3.89 (s, 3H), 3.82 (s, 3H), 3.38 (m, 2H), 2.43 (m, 2H), 2.21 (s, 6H). MS (EI) m/z for $C_{27}H_{29}ClN_6O_5S$: 585.3 (MH$^+$).

Example 106

5-(N-(3-(2-chloro-5-methoxy-phenylamino)quinoxalin-2-yl)sulfamoyl)-N-(2-(dimethylamino)ethyl)-2-fluorobenzamide $^1$H NMR (400 MHz, DMSO-d$_6$) δ 9.40 (br s, 1H), 9.16 (s, 1H), 8.73 (m, 1H), 8.67 (d, 1H), 8.36 (dd, 1H), 8.26 (m, 1H), 7.94 (br s, 1H), 7.66 (m, 1H), 7.59 (t, 1H), 7.43 (m, 3H), 6.71 (dd, 1H), 3.83 (s, 3H), 3.62 (m, 2H), 3.27 (m, 2H), 2.85 (d, 6H). MS (EI) m/z for $C_{26}H_{26}ClFN_6O_4S$: 573.1 (MH$^+$).

Example 107

3-(N-(3-(3,5-dimethoxyphenylamino)quinoxalin-2-yl)sulfamoyl)-N-(2-(dimethylamino)ethyl)benzamide MS (EI) m/z for $C_{27}H_{30}N_6O_5S$: 551.1 (MH$^+$).

Example 108

3-(N-(3-(2-chloro-5-methoxy-phenylamino)quinoxalin-2-yl)sulfamoyl)-N-(2-(dimethylamino)ethyl)-N-methylbenzamide MS (EI) m/z for $C_{27}H_{29}ClN_6O_4S$: 569.1 (MH$^+$).

Example 109

3-(N-(3-(3,5-dimethoxyphenylamino)quinoxalin-2-yl)sulfamoyl)-N-(2-(dimethylamino)ethyl)-N-methylbenzamide MS (EI) m/z for $C_{28}H_{32}N_6O_5S$: 565.1 (MH$^+$).

Example 110

3-(N-(3-(2-chloro-5-methoxy-phenylamino)quinoxalin-2-yl)sulfamoyl)benzamide

MS (EI) m/z for $C_{22}H_{18}ClN_5O_4S$: 484.0 (MH$^+$).

Example 111

3-(N-(3-(2-chloro-5-methoxy-phenylamino)quinoxalin-2-yl)sulfamoyl)-N-(2-morpholinoethyl)benzamide MS (EI) m/z for $C_{28}H_{29}ClN_6O_5S$: 597.0 (MH$^+$).

Example 112

3-(N-(3-(2-chloro-5-methoxy-phenylamino)quinoxalin-2-yl)sulfamoyl)-N-methylbenzamide MS (EI) m/z for $C_{23}H_{20}ClN_5O_4S$: 498.0 (MH$^+$).

Example 113

3-(N-(3-(2-chloro-5-methoxy-phenylamino)quinoxalin-2-yl)sulfamoyl)-N-morpholinobenzamide MS (EI) m/z for $C_{26}H_{25}ClN_6O_5S$: 569.0 (MH$^+$).

Example 114

N-(3-{[2-chloro-5-(methoxy)phenyl]amino}quinoxalin-2-yl)-3-{5-[(dimethylamino)methyl]-1,3,4-oxadiazol-2-yl}benzenesulfonamide

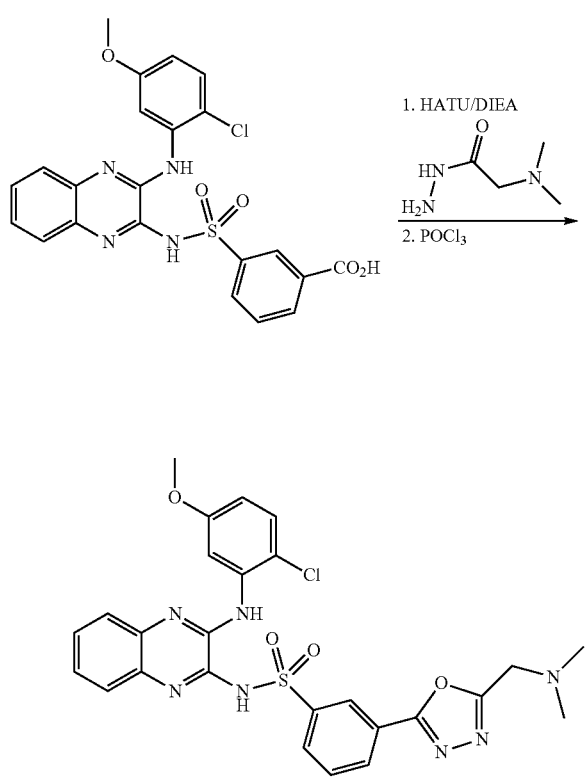

To a solution of 3-{[(3-{[2-chloro-5-(methoxy)phenyl]amino}quinoxalin-2-yl)amino]sulfonyl}benzoic acid (0.25 g, 0.52 mmol), prepared as described above in Example 100, in dimethylformamide (2.6 mL) were added 2-(7-aza-1H-benzotriazole-1-yl)-1,1,3,3-tetramethyluronium hexafluorophosphate (HATU, 0.25 g, 0.67 mmol) and N-ethyldiisopropylamine (DIEA, 0.11 g, 0.88 mmol) at room temperature. The reaction was stirred for 15 min before 2-(dimethylamino)acetohydrazide (78 mg, 0.67 mmol) was added. The reaction mixture was allowed to stir overnight. The reaction was diluted with ethyl acetate (200 mL) and washed with water (30 mL), saturated aqueous sodium bicarbonate (30 mL), 1.0 N aqueous hydrochloric acid (20 mL), and saturated aqueous sodium chloride (25 mL). The organic layer was dried over magnesium sulfate, filtered and concentrated at reduced pressure to afford 180 mg of a coupled intermediate which was then heated in phosphorus oxychloride (5 mL) at 100° C. for 4 h. The reaction was cooled to room temperature and treated with ice water (50 mL) and extracted with dichloromethane (3×50 mL). The organic layer was dried over magnesium sulfate, filtered and concentrated at reduced pressure to afford a crude product which was subjected to reverse phase HPLC to afford N-(3-{[2-chloro-5-(methoxy)-phenyl]amino}quinoxalin-2-yl)-3-{5-[(dimethylamino)methyl]-1,3,4-oxadiazol-2-yl}-benzenesulfonamide (16 mg, 5%) as yellow solid. MS (EI) m/z for $C_{26}H_{24}ClN_7O_4S$: 566.0 (MH$^+$).

Example 115

N-(3-(3-methoxy-5-nitro-phenylamino)-quinoxalin-2-yl)-3-nitrobenzenesulfonamide

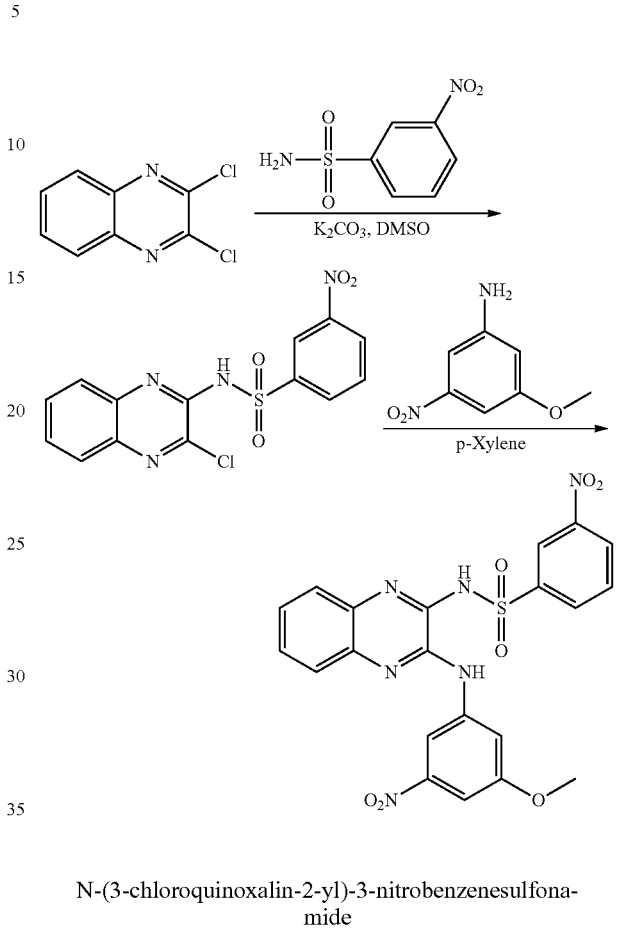

N-(3-chloroquinoxalin-2-yl)-3-nitrobenzenesulfonamide 2,3-Dichloroquinoxaline (26.1 g, 131.1 mmol), m-Nitrobenzene sulfonamide (26.5 g, 131.1 mmol) and potassium carbonate (18.1 g, 131.1) were dissolved in anhydrous DMSO (500 mL). The reaction was heated to 150° C. for 2 h. The reaction mixture was poured into water (400 mL), followed by addition of 2M HCl (60 mL). The product was extracted with EtOAc (3×500 mL). The organic layers were combined and washed water (2×500 mL) and brine (2×500 mL). The product was then dried with sodium sulfate to give N-(3-chloroquinoxalin-2-yl)-3-nitrobenzenesulfonamide. MS (EI) m/z for $C_{14}H_9ClN_4O_4S$: 364.94, 366.97 (MH$^+$)

N-(3-(3-methoxy-5-nitrophenylamino)quinoxalin-2-yl)-3-nitro-benzenesulfonamide

N-(3-chloroquinoxalin-2-yl)-3-nitrobenzenesulfonamide (700 mg, 1.92 mmol), 3-methoxy-5-nitroaniline (645 mg, 3.84 mmol) and p-xylene (7 mL) were combined and heated to 140° C., then stirred for 16 hours at 130° C. The reaction was allowed to cool, placed in a sep. funnel, diluted with DCM, and washed with 2M HCl and brine and concentrated in vacuo. The resulting solid was washed with Et$_2$O to give N-(3-(3-methoxy-5-nitro-phenylamino)quinoxalin-2-yl)-3-nitrobenzenesulfonamide (400 mg, 42%). MS (EI) m/z for $C_{21}H_{16}N_6O_7S$: 496.94 (MH$^+$).

The following compounds were prepared using procedures similar to those in Example 115.

Example 116

N-(3-(2-chloro-5-methoxyphenylamino)quinoxalin-2-yl)-3-cyanobenzenesulfonamide

MS (EI) m/z for $C_{22}H_{16}ClN_5O_3S$: 465.9 (MH$^+$).

Example 117

3-cyano-N-(3-(3,5-dimethoxy-phenylamino)quinoxalin-2-yl)benzenesulfonamide

MS (EI) m/z for $C_{23}H_{19}N_5O_4S$: 462.3 (MH$^+$).

Example 118

N-(3-(2,5-dimethoxy-phenylamino)quinoxalin-2-yl)-3-fluorobenzenesulfonamide

MS (EI) m/z for $C_{22}H_{19}FN_4O_4S$: 456.0 (MH$^+$).

Example 119

3-bromo-N-(3-(3,5-dimethoxy-phenylamino)quinoxalin-2-yl)benzenesulfonamide

MS (EI) m/z for $C_{22}H_{19}BrN_4O_4S$: 516.9 (MH$^+$).

Example 120

3-bromo-N-(3-(2,5-dimethoxy-phenylamino)quinoxalin-2-yl)benzenesulfonamide

MS (EI) m/z for $C_{22}H_{19}BrN_4O_4S$: 516.9 (MH$^+$).

Example 121

N-(3-(3-methoxyphenylamino)quinoxalin-2-yl)benzenesulfonamide

MS (EI) m/z for $C_{21}H_{18}N_4O_3S$: 407.0 (MH$^+$).

Example 122

N-(3-(4-fluoro-3-methoxyphenylamino)quinoxalin-2-yl)benzenesulfonamide

MS (EI) m/z for $C_{21}H_{17}FN_4O_3S$: 425.0 (MH$^+$).

Example 123

N-(3-(2,5-dimethoxy-phenylamino)quinoxalin-2-yl)-4-methoxybenzenesulfonamide

MS (EI) m/z for $C_{23}H_{22}N_4O_5S$: 467.0 (MH$^+$).

Example 124

N-(3-(3,5-dimethoxy-phenylamino)quinoxalin-2-yl)-4-methoxybenzenesulfonamide

MS (EI) m/z for $C_{23}H_{22}N_4O_5S$: 467.0 (MH$^+$).

Example 125

N-(3-(4-chloro-3-methoxy-phenylamino)quinoxalin-2-yl)benzenesulfonamide

MS (EI) m/z for $C_{21}H_{17}ClN_4O_3S$: 440.9 (MH$^+$).

Example 126

N-(3-(3,5-dimethoxy-phenylamino)quinoxalin-2-yl)thiophene-2-sulfonamide

MS (EI) m/z for $C_{20}H_{18}N_4O_4S_2$: 443.0 (MH$^+$).

Example 127

N-(3-(6-methoxyquinolin-8-ylamino)quinoxalin-2-yl)-3-nitrobenzenesulfonamide

MS (EI) m/z for $C_{24}H_{18}N_6O_5S$: 502.95 (MH$^+$).

Example 128

3-nitro-N-(3-(pyridin-4-ylamino)quinoxalin-2-yl)benzenesulfonamide

MS (EI) m/z for $C_{19}H_{14}N_6O_4S$: 423.2 (MH$^+$).

Example 129

N-(3-(2-chloropyridin-4-ylamino)quinoxalin-2-yl)-3-nitrobenzenesulfonamide

MS (EI) m/z for $C_{19}H_{13}ClN_6O_4S$: 456.93, 458.90 (MH$^+$).

Example 130

N-(3-(4,6-dimethoxypyrimidin-2-ylamino)quinoxalin-2-yl)-3-nitrobenzenesulfonamide MS (EI) m/z for $C_{20}H_{17}N_7O_6S$: 484.03 (MH$^+$).

Example 131

N-(3-(4-hydroxy-6-methoxypyrimidin-2-ylamino)quinoxalin-2-yl)-3-nitrobenzenesulfonamide MS (EI) m/z for $C_{19}H_{15}N_7O_6S$: 469.97 (MH$^+$).

Example 132

N-(3-(3,5-dimethoxy-phenylamino)quinoxalin-2-yl)-2-fluorobenzenesulfonamide

MS (EI) m/z for $C_{22}H_{19}FN_4O_4S$: 455.3 (MH$^+$).

Example 133

N-(3-(2-bromo-5-methoxy-phenylamino)quinoxalin-2-yl)-3-nitrobenzenesulfonamide

MS (EI) m/z for $C_{21}H_{16}BrN_5O_5S$: 531.82, 532.84 (MH$^+$).

Example 134

N-(3-(3,5-dimethoxy-phenylamino)quinoxalin-2-yl)-4-methylbenzenesulfonamide

MS (EI) m/z for $C_{23}H_{22}N_4O_4S$: 451.0 (MH$^+$).

Example 136

N-(3-(2,5-dimethoxy-phenylamino)quinoxalin-2-yl)-4-methylbenzenesulfonamide

MS (EI) m/z for $C_{23}H_{22}N_4O_4S$: 451.0 (MH$^+$).

Example 137

N-(3-(3-fluoro-5-methoxy-phenylamino)quinoxalin-2-yl)-3-nitrobenzenesulfonamide

MS (EI) m/z for $C_{21}H_{16}FN_5O_5S$: 470.0 (MH$^+$).

Example 138

4-bromo-N-(3-(3,5-dimethoxy-phenylamino)quinoxalin-2-yl)benzenesulfonamide

MS (EI) m/z for $C_{22}H_{19}BrN_4O_4S$: 516.9, 514.9 (MH$^+$).

Example 139

N-(3-(3-methoxyphenylamino)quinoxalin-2-yl)-3-nitro-benzenesulfonamide

MS (EI) m/z for $C_{21}H_{17}N_5O_5S$: 451.93 (MH$^+$).

Example 140

N-(3-(2-chloro-5-hydroxy-phenylamino)quinoxalin-2-yl)-3-nitrobenzenesulfonamide.
MS (EI) m/z for $C_{20}H_{14}ClN_5O_5S$: 472.15, 474.13 (MH$^+$).

Example 141

3-acetyl-N-(3-(2-chloro-5-methoxy-phenylamino)quinoxalin-2-yl)benzenesulfonamide MS (EI) m/z for $C_{23}H_{19}ClN_4O_4S$: 483.08 (MH$^+$).

Example 142

N-(3-(3,5-dimethoxy-phenylamino)quinoxalin-2-yl)benzenesulfonamide

MS (EI) m/z for $C_{22}H_{20}N_4O_4S$: 437.49 (MH$^+$).

Example 143

N-(3-(5-methoxy-2-methyl-phenylamino)quinoxalin-2-yl)benzenesulfonamide

MS (EI) m/z for $C_{22}H_{20}N_4O_3S$: 421.46 (MH$^+$).

Example 144

N-(3-(2-chloro-5-methoxy-phenylamino)quinoxalin-2-yl)benzenesulfonamide

MS (EI) m/z for $C_{21}H_{17}ClN_4O_3S$: 440.59 (MH$^+$).

Example 145

N-(3-(2,5-dimethoxy-phenylamino)quinoxalin-2-yl)benzenesulfonamide

MS (EI) m/z for $C_{22}H_{20}N_4O_4S$: 437.53 (MH$^+$).

Example 146

4-chloro-N-(3-(3,5-dimethoxy-phenylamino)quinoxalin-2-yl)benzenesulfonamide

MS (EI) m/z for $C_{22}H_{19}ClN_4O_4S$: 470.54 (MH$^+$).

Example 147

N-(3-(5-methoxy-2-methyl-phenylamino)quinoxalin-2-yl)-3-nitrobenzenesulfonamide

MS (EI) m/z for $C_{22}H_{19}N_5O_5S$: 466.32 (MH$^+$).

Example 148

N-(3-(2-chloro-5-methoxy-phenylamino)quinoxalin-2-yl)-3-nitrobenzenesulfonamide

MS (EI) m/z for $C_{21}H_{16}ClN_5O_5S$: 485.86 (MH$^+$).

Example 149

N-(3-(4-chloro-2,5-dimethoxy-phenylamino)quinoxalin-2-yl)benzenesulfonamide

MS (EI) m/z for $C_{22}H_{19}ClN_4O_4S$: 470.99 (MH$^+$).

Example 150

N-(3-{[3,5-bis(methoxy)phenyl]amino}quinoxalin-2-yl)-3-(2H-tetrazol-5-yl)benzenesulfonamide

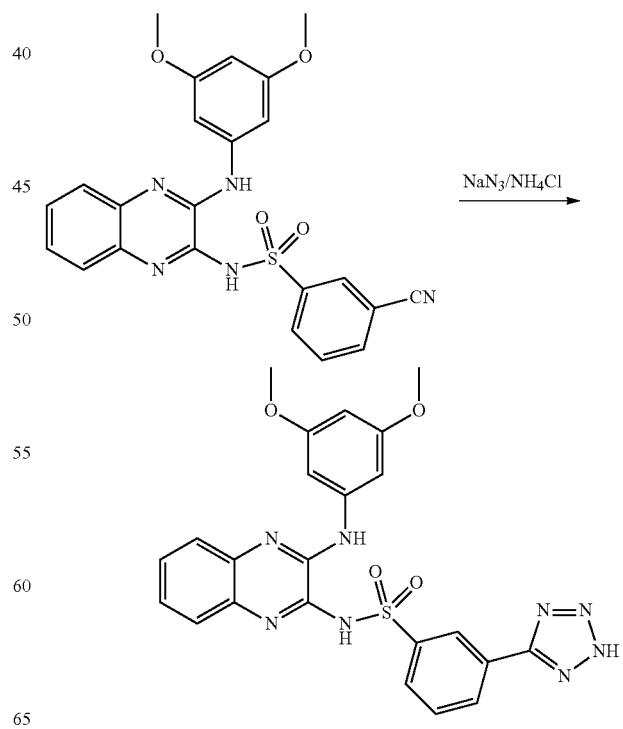

To a stirred solution of 3-cyano-N-(3-(3,5-dimethoxyphenylamino)quinoxalin-2-yl)benzenesulfonamide (0.20 g, 0.44 mmol), prepared using procedures similar to those described in Example 115, in dimethylformamide (1.2 mL) at 50° C. were added sodium azide (0.11 g, 1.76 mmol) and ammonium chloride (94 mg, 1.76 mmol). The crude mixture was heated at 100° C. overnight. The reaction was cooled to room temperature treated with ice water (20 mL) followed by concentrated hydrochloric acid (10 mL). The solid obtained was filtered under reduced pressure and washed with hexane (20 mL), diethyl ether (20 mL), and ethyl acetate (5 mL) to afford N-(3-{[3,5-bis(methoxy)phenyl]amino}quinoxalin-2-yl)-3-(2H-tetrazol-5-yl)benzenesulfonamide (55 mg, 25%) as light yellow solid. MS (EI) m/z for $C_{23}H_{20}N_8O_4S$: 505.0 ($MH^+$).

Example 151

N-(3-(2,6-dichloropyridin-4-ylamino)quinoxalin-2-yl)-3-nitrobenzenesulfonamide

A mixture of N-(3-chloroquinoxalin-2-yl)-3-nitrobenzenesulfonamide (1 g), 2,6-dichloropyridin-4-amine (760 mg) and p-xylene (10 mL) was heated at 135° C. with stirring overnight. Upon cooling to room temperature, the mixture was dissolved in dichloromethane, washed with 2 N HCl (2×) and brine, concentrated in vacuo to give a crude product of N-{3-[(2,6-dichloropyridin-4-yl)amino]quinoxalin-2-yl}-3-nitrobenzenesulfonamide. A small portion of this crude product was purified by HPLC to give N-{3-[(2,6-dichloropyridin-4-yl)amino]quinoxalin-2-yl}-3-nitrobenzenesulfonamide. $^1$H NMR (400 MHz, DMSO) δ 9.71 (s, 1H), 8.90 (s, 1H), 8.50 (d, 2H), 8.8.41 (d, 1H), 8.30 (s, 2H), 7.88-7.78 (m, 27.65 (d, 1H), 7.47-7.37 (m, 2H); MS (EI) m/z for $C_{19}H_{12}C_{12}N_6O_4S$: 491.1, 493.1 ($MH^+$).

Example 152

N-(3-(2-chloro-6-methoxypyridin-4-ylamino)quinoxalin-2-yl)-3-nitrobenzenesulfonamide To a crude product of N-{3-[(2,6-dichloropyridin-4-yl)amino]quinoxalin-2-yl}-3-nitrobenzenesulfonamide (1.24 g) prepared using procedures similar to those for Example 151, was added anhydrous DMSO (10 mL), followed by sodium methoxide (273 mg). The resulting mixture was heated at 100° C. for 3 days. The mixture was diluted with EtOAc and water, and the pH was adjusted to about 4 by adding acetic acid. The product was extracted with EtOAc (3×). The combined extracts were washed with brine to give the crude product. A portion of the crude product was purified by prep HPLC to give N-(3-{[2-chloro-6-(methyloxy)pyridin-4-yl]amino}quinoxalin-2-yl)-3-nitrobenzenesulfonamide. $^1$H NMR (400 MHz, DMSO) δ 9.44 (s, 1H), 8.90 (s, 1H), 8.50 (d, 1H), 8.42 (d, 1H), 7.88-7.84 (m, 2H), 7.77 (s, 1H), 7.74 (s, 1H), 7.64 (d, 1H), 7.45-7.38 (m, 2H), 3.82 (s, 3H); MS (EI) m/z for $C_{20}H_{15}ClN_6O_5S$: 496.94 ($MH^+$).

Example 153

2-(dimethylamino)-N-(3-(N-(3-(3-(2-(dimethylamino)acetamido)-5-methoxy-phenylamino)quinoxalin-2-yl)sulfamoyl)phenyl)acetamide

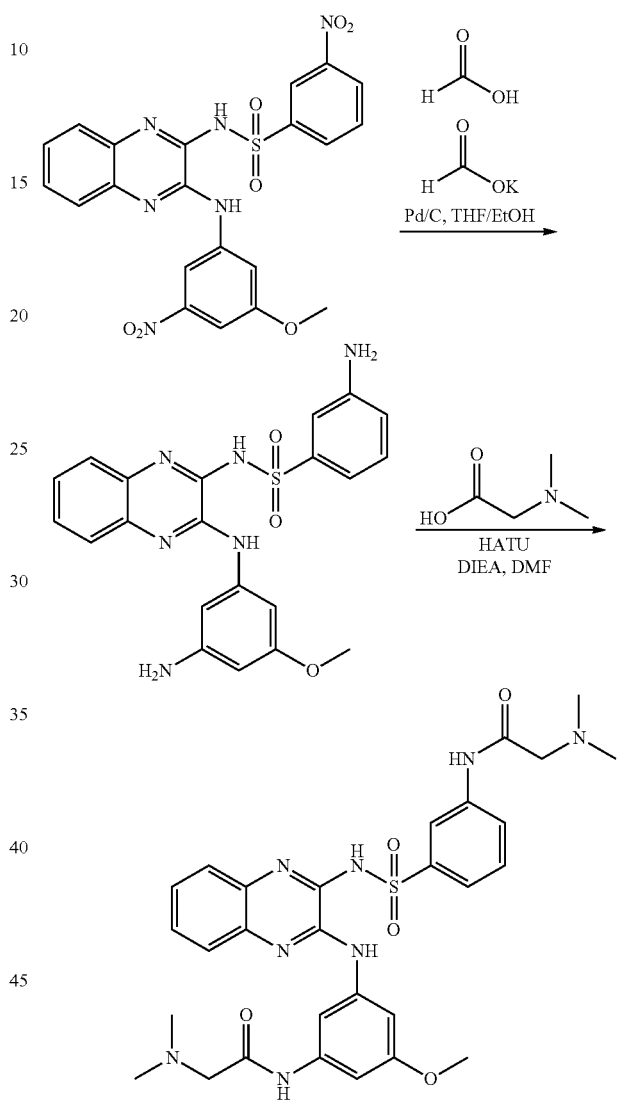

3-amino-N-(3-(3-amino-5-methoxyphenylamino)quinoxalin-2-yl)benzenesulfonamide

N-(3-(3-Methoxy-5-nitrophenylamino)quinoxalin-2-yl)-3-nitrobenzenesulfonamide (400 mg, 0.81 mmol), prepared as described above in Example 115, was dissolved in 1:1 THF:EtOH (4 mL), to which was added formic acid (938 μl, 2.42 mmol) and potassium formate (203 mg, 2.42 mmol). The system was flushed with nitrogen, and then 10% wt Pd/C (50 mg) was added. The reaction was then heated to 60° C. Once the reaction was determined complete by LC-MS, it was allowed to cool, and DMF was added for solubility. The solution was then filtered through a nylon fit to remove the catalyst. The filtrate was diluted water and the pH adjusted to 7 and extracted with DCM (2×) and EtOAc (2×). All organic layers were combined and evaporated to dryness to give 3-amino-N-(3-(3-amino-5-methoxyphenylamino)quinoxalin-2-yl)benzenesulfonamide (330 mg, 93%). MS (EI) m/z for $C_{21}H_{20}N_6O_3S$: 437.06 (MH$^+$)

2-(dimethylamino)-N-(3-(N-(3-(3-(2-(dimethylamino)-acetamido)-5-methoxyphenylamino)quinoxalin-2-yl)-sulfamoyl)phenyl)acetamide 3-Amino-N-(3-(3-amino-5-methoxyphenylamino)quinoxalin-2-yl)benzenesulfonamide (330 mg, 0.76 mmol), DMF (4 mL), N,N-Dimethylglycine (312 mg, 3.02 mmol), HATU (1.15 g, 3.02 mmol) and 1.29 (mL) (7.56 mmol) DIEA (1.29 mL, 7.56 mmol) were combined and heated to 90° C., followed by heating at 50° C. for over 16 hours. The reaction was allowed to cool, placed into a sep. funnel diluted with water and aqueous LiCl and extracted with EtOAc. The final compound was then purified by prep. HPLC to give 2-(dimethylamino)-N-(3-(N-(3-(3-(2-(dimethylamino)acetamido)-5-methoxy-phenylamino)-quinoxalin-2-yl)sulfamoyl)phenyl)acetamide. $^1$H NMR (400 MHz, CD$_3$OD) δ 8.45 (t, 1H), 7.93 (t, 1H), 7.85-7.88 (m, 1H), 7.70-7.74 (m, 1H), 7.65-7.68 (m, 1H), 7.58-7.62 (m, 1H), 7.58 (t, 1H), 7.34-7.42 (m, 3H), 7.0 (t, 1H), 4.05 (d, 2H), 3.8 (s, 3H), 2.9-3.0 (d, 12H). MS (EI) m/z for $C_{29}H_{34}N_8O_5S$: 607.2 (MH$^+$).

The following title compounds were prepared using procedures similar to those in Example 153.

Example 154

N-(3-(2,5-dimethoxyphenylamino)-7-methylquinoxalin-2-yl)benzenesulfonamide

MS (EI) m/z for $C_{23}H_{22}N_4O_4S$: 451.0 (MH$^+$).

Example 155a and Example 155b

N-(3-(3,5-dimethoxy-phenylamino)quinoxalin-2-yl)-3-(methylamino)benzenesulfonamide and N-(3-(3,5-dimethoxy-phenylamino)quinoxalin-2-yl)-3-(dimethylamino)benzenesulfonamide

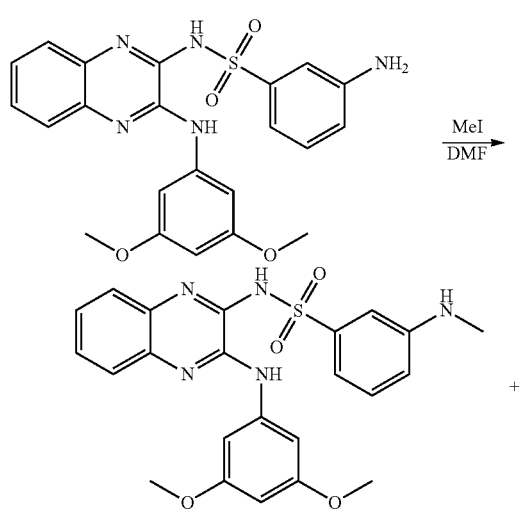

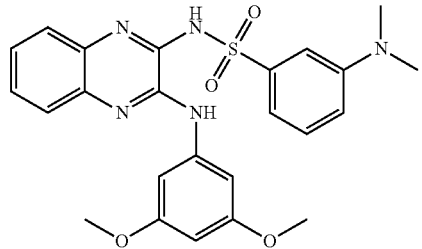

To a solution of 3-amino-N-(3-(3,5-dimethoxy-phenylamino)quinoxalin-2-yl)benzenesulfonamide (414 mg) in DMF (4.5 mL) was added iodomethane (114 μl). The reaction mixture was heated at 35-50° C. until the formation of both mono-methylated and di-methylated products was detected by LC/MS. The mixture was diluted with EtOAc, washed with water, 10% LiCl (2x) and brine. After removal of solvent in vacuo, the crude mixture was purified by flash silica column chromatography eluting with 15% EtOAc in hexanes, affording the mono-methylated and di-methylated products. Product A: N-(3-(3,5-dimethoxyphenylamino)quinoxalin-2-yl)-3-(methylamino)-benzenesulfonamide (35 mg). $^1$H NMR (400 MHz, DMSO) δ 12.2 (s, 1H), 8.93 (s, 1H), 7.85 (d, 1H), 7.58 (d, 1H), 7.40-7.20 (m, 7H), 6.76 (m, 1H), 6.24 (m, 1H), 6.16 (br s, 1H), 3.77 (s, 6H), 2.71 (s, 3H). MS (EI) for $C_{23}H_{23}N_5O_4S$: 466.05 (MH+). Product B: N-(3-(3,5-dimethoxyphenylamino)quinoxalin-2-yl)-3-(dimethylamino)benzenesulfonamide (33 mg). $^1$H NMR (400 MHz, DMSO) δ 1220 (s, 1H), 8.98 (s, 1H), 7.98 (d, 1H), 7.56 (d, 1H), 7.42-7.32 (m, 7H), 6.74 (m, 1H), 6.24 (m, 1H), 3.77 (s, 6H), 2.97 (s, 6H). MS (EI) for $C_{24}H_{25}N_5O_4S$: 480.04 (MH+).

Example 156

N-(3-{[(2-{[3,5-bis(methoxy)phenyl]amino}pyrido[2,3-b]pyrazin-3-yl)amino]sulfonyl}phenyl)-N-2-[2-(dimethylamino)ethyl]-N-2-methylglycinamide

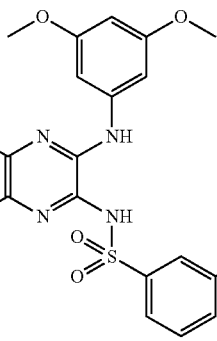

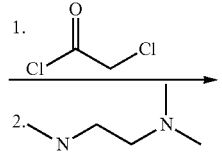

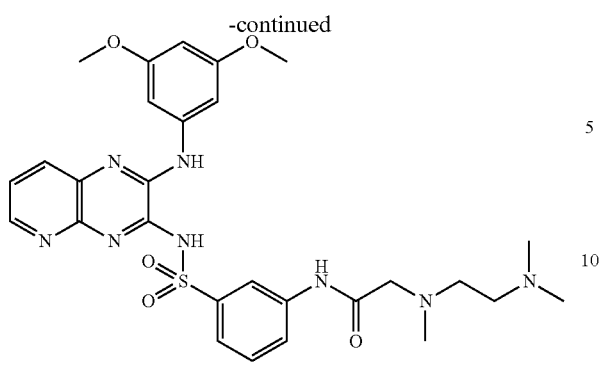

To a THF suspension (1.3 mL) of 3-amino-N-(3-{[3,5-(dimethoxy)-phenyl]amino}-quinoxalin-2-yl)benzenesulfonamide (126 mg, 0.28 mmol), prepared using procedures similar to those described for Example 15, was added 0.143 mL of 2M aqueous $Na_2CO_3$. To this yellow suspension is added dropwise 33 μL (0.42 mmol) of chloroacetyl chloride. The reaction mixture turns clear after a few minutes and is allowed to stir at 23° C. for 1 h. To the reaction is added a DMSO (1 mL) solution containing 180 μL (1.4 mmol) of N,N',N' trimethylethelyenediamine. The reaction is then warmed to 60° C. and stirred for 18 h. The product is isolated by preparative RP-HPLC ($NH_4OAc$/ACN) gradient, the appropriate fractions were pooled and lyophilize to give a solid yellow as the acetic acid salt: 59 mg (51%). $^1$H-NMR (400 MHz, $CDCL_3$): δ 10.1 (br s, 1H), 8.37 (br s, 2H), 8.18 (d, 1H), 7.97 (d, 1H), 7.60 (br d, 1H), 7.27 (s, 2H), 7.20 (br s, 3H), 6.15 (s, 1H), 3.82 (m, 2H), 3.65 (s, 6H), 3.20 (br m, 2H), 2.82 (br s, 8H), 2.42 (s, 3H), 2.02 (s, 3H). MS (EI) m/z for $C_{28}H_{34}N_8O_5S$: 595.84 (MH$^+$).

The following title compounds were prepared using similar procedures to those in Example 156.

Example 157

N-(3-(N-(3-(3,5-dimethoxy-phenylamino)quinoxalin-2-yl)sulfamoyl)phenyl)-2-((3-(dimethylamino)propyl)(methyl)amino)acetamide MS (EI) m/z for $C_{30}H_{37}N_7O_5S$: 608.1 (MH$^+$).

Example 158

2-(1,4'-bipiperidin-1'-yl)-N-(3-(N-(3-(3,5-dimethoxy-phenylamino)quinoxalin-2-yl)sulfamoyl)phenyl)acetamide MS (EI) m/z for $C_{34}H_{41}N_7O_5S$: 660.1 (MH$^+$).

Example 159 tert-butyl 2-(3-(N-(3-(3,5-dimethoxy-phenylamino)quinoxalin-2-yl)sulfamoyl)phenylcarbamoyl)piperidine-1-carboxylate MS (EI) m/z for $C_{33}H_{38}N_6O_7S$: 663.1 (MH$^+$).

Example 160

3-(N-(3-(2-chloro-5-methoxy-phenylamino)quinoxalin-2-yl)sulfamoyl)-N-(1-(dimethylamino)propan-2-yl)benzamide MS (EI) m/z for $C_{27}H_{29}ClN_6O_4S$: 569.0 (MH$^+$).

Example 161

N-(3-(3,5-dimethoxy-phenylamino)quinoxalin-2-yl)-3-ureidobenzenesulfonamide

MS (EI) m/z for $C_{23}H_{22}N_6O_5S$: 495.40 (MH$^+$).

Example 162

2-(dimethylamino)-N-(3-(N-(3-(5-methoxy-2-methylphenylamino)quinoxalin-2-yl)sulfamoyl)phenyl)acetamide MS (EI) m/z for $C_{26}H_{28}N_6O_4S$: 521.69 (MH$^+$).

Example 163

N-(3-(N-(3-(3,5-dimethoxy-phenylamino)quinoxalin-2-yl)sulfamoyl)phenyl)-2-(4-methylpiperazin-1-yl)acetamide MS (EI) m/z for $C_{29}H_{33}N_7O_5S$: 592.61 (MH$^+$).

Example 164

2-acetamido-N-(3-(N-(3-(3,5-dimethoxyphenylamino)quinoxalin-2-yl)sulfamoyl)phenyl)acetamide MS (EI) m/z for $C_{26}H_{26}N_6O_6S$: 550.59 (MH$^+$).

Example 165 tert-butyl 2-(3-(N-(3-(3,5-dimethoxy-phenylamino)quinoxalin-2-yl)sulfamoyl)phenylamino)-2-oxoethylcarbamate MS (EI) m/z for $C_{29}H_{32}N_6O_7S$: 609.32 (MH$^+$).

Example 166

N-(2-(3,5-dimethoxy-phenylamino)pyrido[2,3-b]pyrazin-3-yl)-3-nitrobenzenesulfonamide

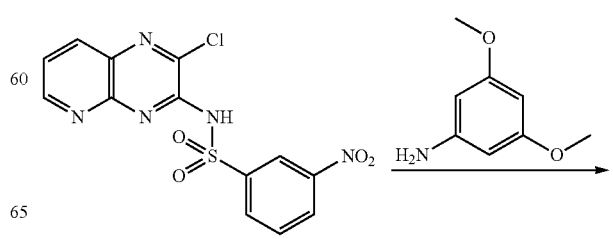

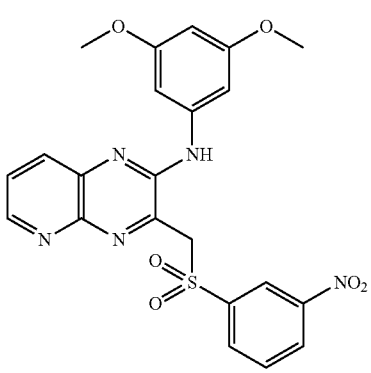

To a xylene suspension (15 mL) of N-(2-chloropyrido[2,3-b]pyrazin-3-yl)-3-nitrobenzenesulfonamide (1 g, 2.7 mmol) (prepared using procedures similar to those in Asier, et al *J. Org Chem* 2005, 70(7), 2878 and Leeson, et al *J. Med. Chem.* 1991, 34, 1243) was added 420 mg (2.7 mmol) of 3,5 dimethoxyaniline. After refluxing the reaction for 1 h, the reaction is cooled, the precipitate is collected by filtration and dried under vacuum to give 830 mg of the product as a ~6:1 mixture of isomers with the major being N-(2-(3,5-dimethoxy-phenylamino)pyrido[2,3-b]pyrazin-3-yl)-3-nitrobenzenesulfonamide which was assigned by known chemical reactivity. Analytical HPLC, ret. time=3.3 min (14%), 3.05 min (86%), (conditions: Phenomenex Gemini C18 50×4.6 column, gradient 5% to 95% MeCN/H$_2$O, in the presence of 0.1% TFA, 5 min run at 3.5 ml/min flow rate, λ=254 nm). $^1$H-NMR (400 MHz, DMSO-d6): major isomer δ 9.14 (br s, 1H), 8.69 (dd, 1H), 8.60 (dd, 1H), 8.33 (dt, 2H), 7.77 (t, 1H), 7.49 (dd, 1H), 7.37 d, 2H), 7.05 (s, 1H), 6.26 (t, 1H), 3.77 (s, 6H); MS (EI) m/z for C$_{21}$H$_{18}$N$_6$O$_6$S: 483.08 (MH$^+$).

Example 167

3-amino-N-(2-(3,5-dimethoxy-phenylamino)pyrido[2,3-b]pyrazin-3-yl)benzenesulfonamide To a 1:1 THF/EtOH suspension (1 mL) of N-(3-(3,5-dimethoxyphenylamino)-pyrido[3,2-b]pyrazin-2-yl)-3-nitrobenzenesulfonamide (190 mg, 0.21 mmol) (prepared using procedures similar to those in Examples 166) was added 47 μL (1.26 mmol) of formic acid plus 99 mg (1.17 mmol) of potassium formate and 50 mg of 10% palladium on charcoal. After refluxing the reaction for 1 h, hot filtration through celite (washing with a small portion of DMF), dilution with 30 mL of water, the pH was adjusted to 5.5 with 5% NaHCO$_3$, the product is isolated as a precipitate 140 mg (80%) of white powder. Analytical HPLC, ret. time=2.6 min (90%), 3.05 min (10%), 100% pure (conditions: YMC C18 5×4.6 column, gradient 10% to 90% MeCN/H$_2$O, in the presence of 0.1% TFA, 9 min run at 1 ml/min flow rate, λ=254 nm). $^1$H-NMR (400 MHz, CDCL$_3$): δ 8.48 (br s, 1H), 8.34 (dd, 1H), 7.92 (dd, 1H), 7.41 (dd, 1H), 7.15 (m, 3H), 7.13 (d, 2H), 6.86 (dd, 1H), 6.28 (t, 1H), 3.83 (s, 6H); MS (EI) m/z for C$_{21}$H$_{20}$N$_6$O$_4$S: 453.03 (MH$^+$).

Example 168

3-amino-N-(3-{[3,5-bis(methoxy)phenyl]amino}pyrido[2,3-b]pyrazin-2-yl)benzenesulfonamide

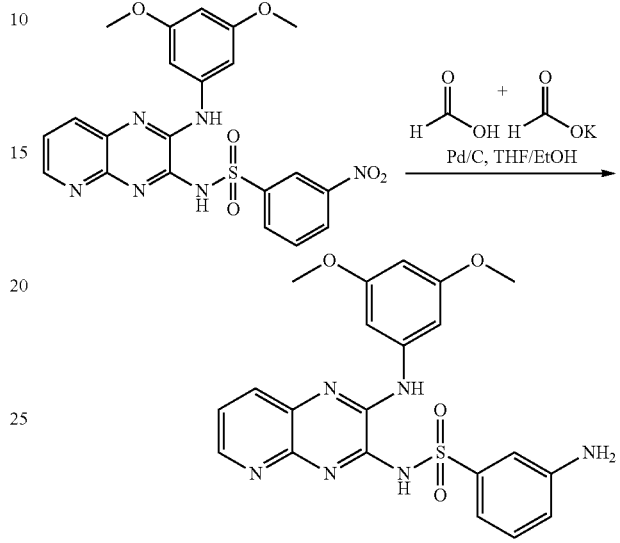

To a 1:1 THF/EtOH suspension (1 mL) of 3-nitro-N-(3-{[3,5-bis(methoxy)-phenyl]amino}pyrido[2,3-b]pyrazin-2-yl)benzenesulfonamide (100 mg, 0.21 mmol) (prepared using procedures similar to those used in Example 166) was added 46 μL (0.63 mmol) of formic acid plus 100 mg (0.63 mmol) of potassium formate and 100 mg of 10% palladium on charcoal. After refluxing the reaction for 1 h, hot filtration through celite, and concentration, the product is isolated by preparative RP-HPLC (NH$_4$OAc/ACN) gradient. The appropriate fractions were pooled and lyophilize to give solid yellow product: 3.2 mg (4%). $^1$H-NMR (400 MHz, CDCl$_3$): δ 8.62 (d, 1H), 8.52 (s, 1H), 7.62 (d, 1H), 7.3 (m, 4H), 7.18 (d, 2H), 6.88 (d, 1H), 6.27 (t, 1H), 3.96 (br s, 2H), 3.83 (s, 6H). MS (EI) m/z for C$_{21}$H$_{20}$N$_6$O$_4$S: 453.22 (MH$^+$).

Example 169

N-(3-{[2-chloro-5-(methoxy)phenyl]amino}quinoxalin-2-yl)-3-(1-{[2-(dimethylamino)-ethyl]amino}ethyl)benzenesulfonamide trifluoroacetic acid salt

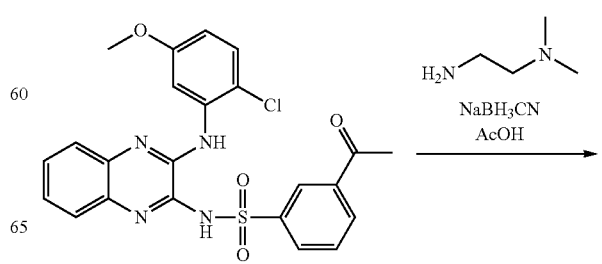

867
-continued

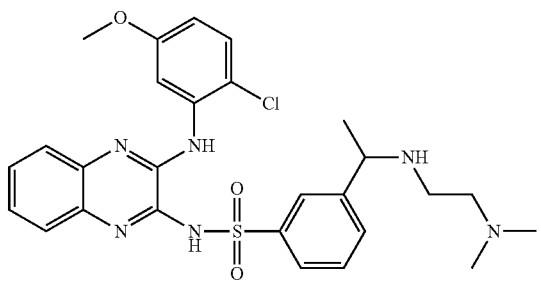

To a dichloroethane solution (0.6 mL) of 3-acetyl-N-(3-{[2-chloro-5-(methoxy)-phenyl]amino}quinoxalin-2-yl)benzenesulfonamide (150 mg, 0.31 mmol), prepared using procedures similar to those in Example 115, and 51 μL (0.37 mmol) of N,N-dimethylethylenediamine was added 19 μL of acetic acid followed by 132 mg (0.62 mmol) of sodium cyanoborohydride. The reaction mixture was refluxed for 18 h under a nitrogen atmosphere. After concentration (in vacuo), the product is isolated by preparative RP-HPLC (0.1% TFA/ACN) gradient, followed by lyophilization of appropriate fractions to give solid yellow solid: 189 mg (90%). $^1$H-NMR (400 MHz, $d_3$-MeOD): δ 8.74 (s, 1H), 8.18 (s, 1H), 8.12 (d, 1H), 7.71 (m, 3H), 7.48 (m, 4H), 7.28 (d, 1H), 6.63 (d, 1H), 4.38 (q, 1H), 3.80 (s, 3H), 3.30 (m, 3H), 3.12 (m, 1H), 2.84 (s, 3H), 1.60 (d, 3H). MS (EI) m/z for $C_{27}H_{31}ClN_6O_3S$: 555.56 (MH$^+$).

Example 170

N,N-{[(3-{[(3-{[2-chloro-5-(methoxy)phenyl]amino}quinoxalin-2-yl)amino]sulfonyl}-4-methylphenyl)amino](dimethylamino)methylidene}-N-methylmethanaminium

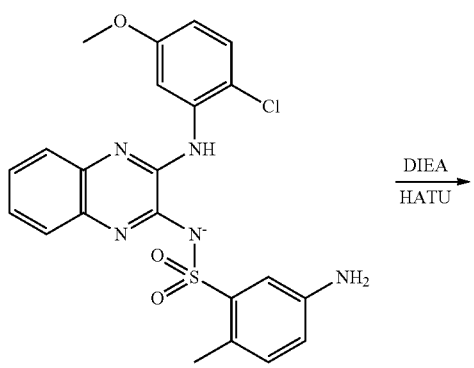

868
-continued

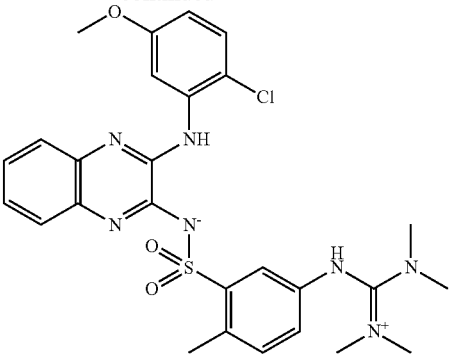

To a dimethylformamide solution (1 mL) of 3-amino-N-(3-{[2-chloro-5-(methoxy)-phenyl]amino}quinoxalin-2-yl) 2-methylbenzenesulfonamide (200 mg, 0.40 mmol), prepared using procedures similar to those described in Example 115, is added 312 μL (1.8 mmol) of DIEA and 122 mg (0.6 mmol) of HATU. After stirring for 18 h at 60° C., the product was precipitated from a 1:1 mixture of hexane/ethyl acetate, filtered and dried to afford 60 mg (26%). $^1$H NMR (400 MHz, DMSO-$d_6$): δ 9.26 (b rs, 1H), 8.96 (br s, 1H), 7.80 (s, 1H), 7.51 (br s, 1H), 7.45 (d, 1H), 7.18 (brm, 4H), 6.91 (br s, 1H), 6.60 (br d, 1H), 3.82 (s, 3H), 3.36 (s, 3H), 2.85 (s, 6H), 2.58 (s, 3H). MS (EI) m/z for $C_{27}H_{31}ClN_7O_3S^+$: 569.32 (MH$^+$).

Example 171

2-Bromo-N-(3-(N-(3-(3,5-dimethoxyphenylamino)quinoxalin-2-yl)sulfamoyl)phenyl)acetamide

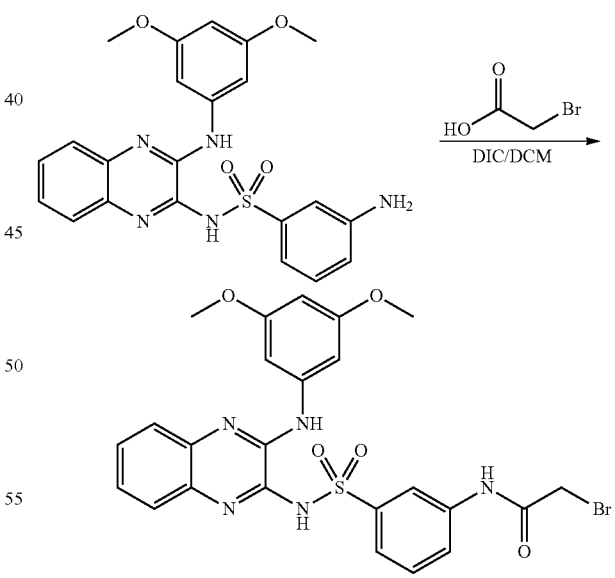

In a 50 mL round-bottom flask was added 2-bromoacetic acid (1.87 g, 13.5 mmol), N,N-diisopropylcarbodiimide (860 mg, 6.8 mmol) and 10 mL DCM. To this mixture was added 3-amino-N-(3-(3,5-dimethoxyphenylamino) quinoxalin-2-yl)benzenesulfonamide (2.03 g, 4.5 mmol), prepared using procedures similar to those in Example 168. The reaction was stirred overnight at room temperature. Complete consumption of the starting aniline was confirmed by LCMS. The solvent was evaporated off to yield the crude product (2-bromo-N-(3-(N-(3-(3,5-dimethoxyphenylamino) quinoxalin-2-yl)sulfamoyl)phenyl)acetamide). This was used directly in the next step without further purification.

General Alkylation Procedure 1

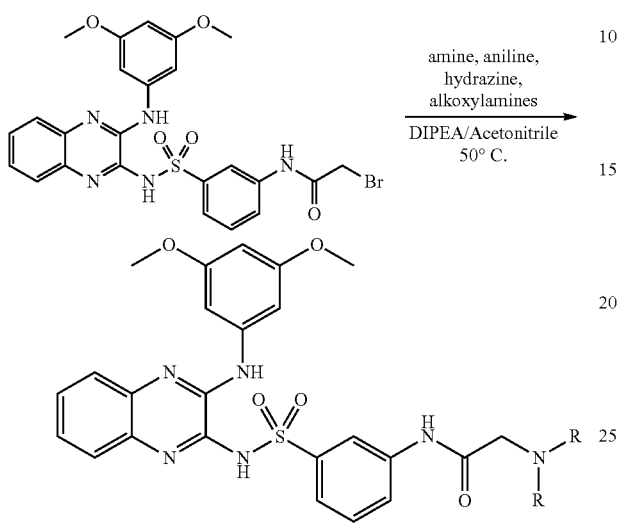

Into a 2-dram vial was placed 2-bromo-N-(3-(N-(3-(3,5-dimethoxy-phenylamino)quinoxalin-2-yl) sulfamoyl)phenyl)acetamide (86 mg, 0.15 mmol), prepared using procedures similar to those in Example 171,along with 2 mL of acetonitrile. Eight equivalents (1.2 mmol) of the desired amine, aniline, hydrazine or alkoxyamine were added followed by the addition of Hunig's Base (41 µL, 0.25 mmol). The reaction then was stirred at 50° C. for one hour (overnight for aniline reagents). Preparative reverse-phase HPLC was used to isolate the desired product directly from the crude reaction mixture. A Waters Fractionlynx preparative reverse-phase HPLC—equipped with a Waters SunFire Prep C18, OCD 5 µM, 30×70 mm column and running a 5-100% gradient with a binary solvent system of 25 mM ammonium acetate in water/acetonitrile—was used to carry out the purification.

The following title compounds were prepared according to General Library Alkylation Procedure 1.

Example 172

N-(3-(N-(3-(3,5-dimethoxy-phenylamino)quinoxalin-2-yl)sulfamoyl)phenyl)-2-(methylamino)acetamide $^1$H-NMR (400 MHz, d$_6$-DMSO): 8.81 (s, 1H), 8.23 (t, 1H), 7.75 (d, 1H), 7.66 (d, 1H), 7.41-7.38 (m, 1H), 7.35 (m, 1H), 7.32 (d, 2H), 7.29-7.27 (m, 1H), 7.14-7.11 (m, 2H), 6.14 (t, 1H), 3.80 (s, 1H), 3.78 (s, 6H), 2.58 (s, 3H), 1.91 (s, 2H); MS (EI) m/z C$_{25}$H$_{26}$N$_6$O$_5$S: 523.6 (MH$^+$).

Example 173

2-(cyclopropylmethylamino)-N-(3-(N-(3-(3,5-dimethoxyphenylamino)quinoxalin-2-yl)sulfamoyl)phenyl)acetamide $^1$H-NMR (400 MHz, d$_6$-DMSO): 10.58 (s, 1H), 8.81 (s, 1H), 8.20 (t, 1H), 7.76 (d, 1H), 7.67 (d, 1H), 7.42-7.36 (m, 2H), 7.32 (d, 2H), 7.27 (s, 1H), 7.14-7.12 (m, 2H), 6.15 (t, 1H), 3.93 (s, 2H), 3.78 (s, 6H), 2.89 (s, 1H), 2.88 (s, 1H), 1.05-1.00 (m, 1H), 0.59 (d, 1H), 0.57 (d, 1H), 0.35 (d, 1H), 0.34 (d, 1H); MS (EI) m/z C$_{28}$H$_{30}$N$_6$O$_5$S: 563.6 (MH$^+$).

Example 174

N-(3-(N-(3-(3,5-dimethoxy-phenylamino)quinoxalin-2-yl)sulfamoyl)phenyl)-2-(2-hydroxy-propylamino)acetamide $^1$H-NMR (400 MHz, d$_6$-DMSO): 10.49 ppm (s, 1H), 8.81 ppm (s, 1H), 8.23 ppm (t, 1H), 8.13 ppm (s, 1H), 7.76 ppm (d, 1H), 7.765-7.763 (dd, 1H), 7.41-7.37 ppm (m, 2H), 7.33-7.32 ppm (d, 1H), 7.30-7.28 ppm (m, 1H), 7.16-7.09 ppm (m, 2H), 6.55 ppm (s, 1H), 6.14 ppm (t, 1H), 5.49 ppm (d, 2H), 5.25 ppm (s, 1H), 3.85 ppm (s, 1H), 3.78 ppm (s, 6H) 3.67-3.59 ppm (m, 1H), 3.00-2.89 ppm (dd, 1H), 2.79-2.76 ppm (m, 1H), 1.10 ppm (d, 1H), 1.01-0.99 ppm (d, 1H); MS (EI) m/z C$_{27}$H$_{30}$N$_6$O$_6$S: 566.6 (MH$^+$).

Example 175

N-(3-(N-(3-(3,5-dimethoxy-phenylamino)quinoxalin-2-yl)sulfamoyl)phenyl)-2-(3-fluorobenzylamino)acetamide $^1$H-NMR (400 MHz, d$_6$-DMSO): 10.42 ppm (s, 1H), 8.82 ppm (s, 1H), 8.23 ppm (s, 1H), 8.14 ppm (s, 1H), 7.75 ppm (d, 1H), 7.65 ppm (d, 1H), 7.49-7.32 ppm (m, 6H), 7.25-7.20 ppm (m, 1H), 7.14-7.12 ppm (m, 2H), 6.55 ppm (s, 1H), 6.15 ppm (t, 1H), 4.14 ppm (s, 2H), 3.78 ppm (s, 6H), 3.74 ppm (s, 2H); MS (EI) m/z C$_{31}$H$_{29}$FN$_6$O$_5$S: 616.7 (MH$^+$).

Example 176

2-(benzylamino)-N-(3-(N-(3-(3,5-dimethoxy-phenylamino)quinoxalin-2-yl)sulfamoyl)phenyl)acetamide MS (EI) m/z C$_{31}$H$_{30}$N$_6$O$_5$S: 599 (MH$^+$).

Example 177

2-(diethylamino)-N-(3-(N-(3-(3,5-dimethoxy-phenylamino)quinoxalin-2-yl)sulfamoyl)phenyl)acetamide MS (EI) m/z C$_{28}$H$_{32}$N$_6$O$_5$S: 565 (MH$^+$).

Example 178

2-(4-(3,4-dichlorophenyl)piperazin-1-yl)-N-(3-(N-(3-(3,5-dimethoxyphenylamino)quinoxalin-2-yl)sulfamoyl)phenyl)acetamide MS (EI) m/z C$_{34}$H$_{33}$Cl$_2$N$_7$O$_5$S: 722 (MH$^+$).

Example 179

N-(3-(N-(3-(3,5-dimethoxy-phenylamino)quinoxalin-2-yl)sulfamoyl)phenyl)-2-(2,2-dimethylhydrazinyl)acetamide MS (EI) m/z C$_{26}$H$_{29}$N$_7$O$_5$S: 552 (MH$^+$).

Example 180

N-(3-(N-(3-(3,5-dimethoxy-phenylamino)quinoxalin-2-yl)sulfamoyl)phenyl)-2-(p-tolylamino)acetamide MS (EI) m/z $C_{31}H_{30}N_6O_5S$: 599 (MH$^+$).

Example 181

2-(benzyloxyamino)-N-(3-(N-(3-(3,5-dimethoxyphenylamino)quinoxalin-2-yl)sulfamoyl)phenyl)acetamide MS (EI) m/z $C_{31}H_{30}N_6O_6S$: 615 (MH$^+$).

Example 182

2-(2-chlorophenylamino)-N-(3-(N-(3-(3,5-dimethoxyphenylamino)quinoxalin-2-yl)sulfamoyl)phenyl)acetamide MS (EI) m/z $C_{30}H_{27}ClN_6O_5S$: 619 (MH$^+$).

Example 183

N-(3-(N-(3-(3,5-dimethoxyphenylamino)quinoxalin-2-yl)sulfamoyl)phenyl)-2-(isopropylamino)acetamide MS (EI) m/z $C_{27}H_{30}N_6O_5S$: 551 (MH$^+$).

Example 184

2-(4-cyclopentylpiperazin-1-yl)-N-(3-(N-(3-(3,5-dimethoxyphenylamino)quinoxalin-2-yl)sulfamoyl)phenyl)acetamide MS (EI) m/z $C_{33}H_{39}N_7O_5S$: 646 (MH$^+$).

Example 185

N-(3-(N-(3-(3,5-dimethoxy-phenylamino)quinoxalin-2-yl)sulfamoyl)phenyl)-2-(4-propylpiperidin-1-yl)acetamide MS (EI) m/z $C_{32}H_{38}N_6O_5S$: 619 (MH$^+$).

Example 186

N-(3-(N-(3-(3,5-dimethoxy-phenylamino)quinoxalin-2-yl)sulfamoyl)phenyl)-2-(isobutoxyamino)acetamide MS (EI) m/z $C_{28}H_{32}N_6O_6S$: 581 (MH$^+$).

Example 187

2-(3-tert-butylphenylamino)-N-(3-(N-(3-(3,5-dimethoxyphenylamino)quinoxalin-2-yl)sulfamoyl)phenyl)acetamide MS (EI) m/z $C_{34}H_{36}N_6O_5S$: 641 (MH$^+$).

Example 188

N-(3-(N-(3-(3,5-dimethoxy-phenylamino)quinoxalin-2-yl)sulfamoyl)phenyl)-2-(2-phenylpropan-2-ylamino)acetamide MS (EI) m/z $C_{33}H_{34}N_6O_5S$: 627 (MH$^+$).

Example 189

N-(3-(N-(3-(3,5-dimethoxy-phenylamino)quinoxalin-2-yl)sulfamoyl)phenyl)-2-(3-fluoro-4-hydroxyphenylamino)acetamide MS (EI) m/z $C_{30}H_{27}FN_6O_6S$: 619 (MH$^+$).

Example 190

N-(3-(N-(3-(3,5-dimethoxy-phenylamino)quinoxalin-2-yl)sulfamoyl)phenyl)-2-(2-(methylthio)benzylamino)acetamide MS (EI) m/z $C_{32}H_{32}N_6O_5S_2$: 645 (MH$^+$).

Example 191

N-(3-(N-(3-(3,5-dimethoxy-phenylamino)quinoxalin-2-yl)sulfamoyl)phenyl)-2-(5-fluoro-2-methylbenzylamino)acetamide

MS (EI) $C_{32}H_{31}FN_6O_5S$: 631 (MH$^+$).

Example 192

N-(3-(N-(3-(3,5-dimethoxy-phenylamino)quinoxalin-2-yl)sulfamoyl)phenyl)-2-(2-phenylpyrrolidin-1-yl)acetamide MS (EI) m/z $C_{34}H_{34}N_6O_5S$: 639 (MH$^+$).

Example 193

2-(2-benzylpyrrolidin-1-yl)-N-(3-(N-(3-(3,5-dimethoxy-phenylamino)quinoxalin-2-yl)sulfamoyl)phenyl)acetamide MS (EI) m/z $C_{35}H_{36}N_6O_5S$: 653 (MH$^+$).

Example 194

N-(3-(N-(3-(3,5-dimethoxy-phenylamino)quinoxalin-2-yl)sulfamoyl)phenyl)-2-(2-phenylmorpholino)acetamide MS (EI) m/z $C_{34}H_{34}N_6O_6S$: 655 (MH$^+$).

Example 195

N-(3-(N-(3-(3,5-dimethoxy-phenylamino)quinoxalin-2-yl)sulfamoyl)phenyl)-2-(2-(pyridin-4-yl)piperidin-1-yl)acetamide MS (EI) m/z $C_{34}H_{35}N_7O_5S$: 654 (MH$^+$).

Example 196

N-(3-(N-(3-(3,5-dimethoxy-phenylamino)quinoxalin-2-yl)sulfamoyl)phenyl)-2-(o-tolylamino)acetamide MS (EI) m/z $C_{31}H_{30}N_6O_5S$: 599 (MH$^+$).

Example 197

N-(3-(N-(3-(3,5-dimethoxy-phenylamino)quinoxalin-2-yl)sulfamoyl)phenyl)-2-(2,4-dimethylbenzylamino)acetamide MS (EI) m/z $C_{33}H_{34}N_6O_5S$: 627 (MH$^+$).

Example 198

N-(3-(N-(3-(3,5-dimethoxy-phenylamino)quinoxalin-2-yl)sulfamoyl)phenyl)-2-(methyl(pyridin-3-ylmethyl)amino)acetamide MS (EI) m/z $C_{31}H_{31}N_7O_5S$: 614 (MH$^+$).

Example 199

2-(3-chloro-4-methylbenzylamino)-N-(3-(N-(3-(3,5-dimethoxyphenylamino)quinoxalin-2-yl)sulfamoyl)phenyl)acetamide MS (EI) m/z $C_{32}H_{31}ClN_6O_5S$: 647 (MH$^+$).

Example 200

N-(3-(N-(3-(3,5-dimethoxy-phenylamino)quinoxalin-2-yl)sulfamoyl)phenyl)-2-((2-(dimethylamino)ethyl)(methyl)amino)acetamide MS (EI) m/z $C_{29}H_{35}N_7O_5S$: 594 (MH$^+$).

Example 201

2-(4-acetylpiperazin-1-yl)-N-(3-(N-(3-(3,5-dimethoxyphenylamino)quinoxalin-2-yl)sulfamoyl)phenyl)acetamide MS (EI) m/z $C_{30}H_{33}N_7O_6S$: 620 (MH$^+$).

Example 202

N-(3-(N-(3-(3,5-dimethoxyphenylamino)quinoxalin-2-yl)sulfamoyl)phenyl)-2-(methyl(1-methylpyrrolidin-3-yl)amino)acetamide MS (EI) m/z $C_{30}H_{35}N_7O_5S$: 606 (MH$^+$).

Example 203

N-(3-(N-(3-(3,5-dimethoxyphenylamino)quinoxalin-2-yl)sulfamoyl)phenyl)-2-(4-methyl-1,4-diazepan-1-yl)acetamide MS (EI) m/z $C_{30}H_{35}N_7O_5S$: 606 (MH$^+$).

Example 204

2-(4-allylpiperazin-1-yl)-N-(3-(N-(3-(3,5-dimethoxyphenylamino)quinoxalin-2-yl)sulfamoyl)phenyl)acetamide MS (EI) m/z $C_{31}H_{35}N_7O_5S$: 618 (MH$^+$).

Example 205

N-(3-(N-(3-(3,5-dimethoxyphenylamino)quinoxalin-2-yl)sulfamoyl)phenyl)-2-(4-isopropylpiperazin-1-yl)acetamide MS (EI) m/z $C_{31}H_{37}N_7O_5S$: 620 (MH$^+$).

Example 206

N-(3-(N-(3-(3,5-dimethoxy-phenylamino)quinoxalin-2-yl)sulfamoyl)phenyl)-2-(3-(dimethylamino)pyrrolidin-1-yl)acetamide MS (EI) m/z $C_{30}H_{35}N_7O_5S$: 606 (MH$^+$).

Example 207

N-(3-(N-(3-(3,5-dimethoxy-phenylamino)quinoxalin-2-yl)sulfamoyl)phenyl)-2-(3-(dimethylamino)azetidin-1-yl)acetamide MS (EI) m/z $C_{29}H_{33}N_7O_5S$: 592 (MH$^+$).

Example 208

N-(3-(N-(3-(3,5-dimethoxy-phenylamino)quinoxalin-2-yl)sulfamoyl)phenyl)-2-(4-oxopiperidin-1-yl)acetamide MS (EI) m/z $C_{29}H_{30}N_6O_6S$: 591 (MH$^+$).

Example 209

N-(3-(N-(3-(3,5-dimethoxy-phenylamino)quinoxalin-2-yl)sulfamoyl)phenyl)-2-((2-methoxyethyl)(methyl)amino)acetamide MS (EI) m/z $C_{28}H_{32}N_6O_6S$: 581 (MH$^+$).

Example 210

N-(3-(N-(3-(3,5-dimethoxy-phenylamino)quinoxalin-2-yl)sulfamoyl)phenyl)-2-(4-methylbenzyloxyamino)acetamide MS (EI) m/z $C_{32}H_{32}N_6O_6S$: 629 (MH$^+$).

Example 211

N-(3-(N-(3-(3,5-dimethoxy-phenylamino)quinoxalin-2-yl)sulfamoyl)phenyl)-2-(2-methoxybenzyloxyamino)acetamide MS (EI) m/z $C_{32}H_{32}N_6O_7S$: 645 (MH$^+$).

Example 212

N-(3-(N-(3-(3,5-dimethoxy-phenylamino)quinoxalin-2-yl)sulfamoyl)phenyl)-2-(propylamino)acetamide MS (EI) m/z $C_{27}H_{30}N_6O_5S$: 551 (MH$^+$).

Example 213

N-(3-(N-(3-(3,5-dimethoxy-phenylamino)quinoxa-lin-2-yl)sulfamoyl)phenyl)-2-(ethyl(methyl)amino)acetamide MS (EI) m/z $C_{27}H_{30}N_6O_5S$: 551 (MH$^+$).

Example 214

2-(allyl(methyl)amino)-N-(3-(N-(3-(3,5-dimethoxy-phenylamino)quinoxalin-2-yl)sulfamoyl)phenyl)acetamide MS (EI) m/z $C_{28}H_{30}N_6O_5S$: 563 (MH$^+$).

Example 215

2-(tert-butylamino)-N-(3-(N-(3-(3,5-dimethoxy-phenylamino)quinoxalin-2-yl)sulfamoyl)phenyl)acetamide MS (EI) m/z $C_{28}H_{32}N_6O_5S$: 565 (MH$^+$).

Example 216

N-(3-(N-(3-(3,5-dimethoxy-phenylamino)quinoxa-lin-2-yl)sulfamoyl)phenyl)-2-(isobutylamino)acetamide MS (EI) m/z $C_{28}H_{32}N_6O_5S$: 565 (MH$^+$).

Example 217

2-(butylamino)-N-(3-(N-(3-(3,5-dimethoxy-pheny-lamino)quinoxalin-2-yl)sulfamoyl)phenyl)acetamide MS (EI) m/z $C_{28}H_{32}N_6O_5S$: 565 (MH$^+$).

Example 218

N-(3-(N-(3-(3,5-dimethoxy-phenylamino)quinoxa-lin-2-yl)sulfamoyl)phenyl)-2-(isopropyl(methyl)amino)acetamide MS (EI) m/z $C_{28}H_{32}N_6O_5S$: 565 (MH$^+$).

Example 219

N-(3-(N-(3-(3,5-dimethoxy-phenylamino)quinoxa-lin-2-yl)sulfamoyl)phenyl)-2-(4-formylpiperazin-1-yl)acetamide MS (EI) m/z $C_{29}H_{31}N_7O_6S$: 606 (MH$^+$).

Example 220

N-(3-(N-(3-(3,5-dimethoxy-phenylamino)quinoxa-lin-2-yl)sulfamoyl)phenyl)-2-(4-ethylpiperazin-1-yl)acetamide MS (EI) m/z $C_{30}H_{35}N_7O_5S$: 606 (MH$^+$).

Example 221

N-(3-(N-(3-(3,5-dimethoxy-phenylamino)quinoxa-lin-2-yl)sulfamoyl)phenyl)-2-(4-formyl-1,4-diaz-epan-1-yl)acetamide MS (EI) m/z $C_{30}H_{33}N_7O_6S$: 620 (MH$^+$).

Example 222

N-(3-(N-(3-(3,5-dimethoxy-phenylamino)quinoxa-lin-2-yl)sulfamoyl)phenyl)-2-(ethyl(2-hydroxyethyl)amino)acetamide MS (EI) m/z $C_{28}H_{32}N_6O_6S$: 581 (MH$^+$).

Example 223

(S)—N-(3-(N-(3-(3,5-dimethoxy-phenylamino)qui-noxalin-2-yl)sulfamoyl)phenyl)-2-(3-hydroxypyrroli-din-1-yl)acetamide MS (EI) m/z $C_{28}H_{30}N_6O_6S$: 579 (MH$^+$).

Example 224

N-(3-(N-(3-(3,5-dimethoxy-phenylamino)quinoxa-lin-2-yl)sulfamoyl)phenyl)-2-(2,6-dimethylmor-pholino)acetamide MS (EI) m/z $C_{30}H_{34}N_6O_6S$: 607 (MH$^+$).

Example 225

N-(3-(N-(3-(3,5-dimethoxy-phenylamino)quinoxa-tin-2-yl)sulfamoyl)phenyl)-2-(2-methylbenzylamino)acetamide MS (EI) m/z $C_{32}H_{32}N_6O_5S$: 613 (MH$^+$).

Example 226

N-(3-(N-(3-(3,5-dimethoxy-phenylamino)quinoxa-lin-2-yl)sulfamoyl)phenyl)-2-(2-methoxy-ethy-lamino)acetamide MS (EI) m/z $C_{27}H_{30}N_6O_6S$: 567 (MH$^+$).

Example 227

N-(3-(N-(3-(3,5-dimethoxyphenylamino)quinoxalin-2-yl)sulfamoyl)phenyl)-2-(thiazolidin-3-yl)aceta-mide MS (EI) m/z $C_{27}H_{28}N_6O_5S_2$: 581 (MH$^+$).

Example 228

N-(3-(N-(3-(3,5-dimethoxy-phenylamino)quinoxa-lin-2-yl)sulfamoyl)phenyl)-2-(3-(hydroxymethyl)piperidin-1-yl)acetamide MS (EI) m/z $C_{30}H_{34}N_6O_6S$: 607 (MH$^+$).

Example 229

N-(3-(N-(3-(3,5-dimethoxy-phenylamino)quinoxa-lin-2-yl)sulfamoyl)phenyl)-2-(2-phenylpropylamino)acetamide MS (EI) m/z $C_{33}H_{34}N_6O_5S$: 627 (MH$^+$).

Example 230

N-(3-(N-(3-(3,5-dimethoxy-phenylamino)quinoxalin-2-yl)sulfamoyl)phenyl)-2-(isobutyl(methyl)amino)acetamide MS (EI) m/z $C_{29}H_{34}N_6O_5S$: 579 (MH$^+$).

Example 231

N-(3-(N-(3-(3,5-dimethoxy-phenylamino)quinoxalin-2-yl)sulfamoyl)phenyl)-2-(phenylamino)acetamide MS (EI) m/z $C_{30}H_{28}N_6O_5S$: 585 (MH$^+$).

Example 232

N-(3-(N-(3-(3,5-dimethoxy-phenylamino)quinoxalin-2-yl)sulfamoyl)phenyl)-2-(2-propylphenylamino)acetamide MS (EI) m/z $C_{33}H_{34}N_6O_5S$: 627 (MH$^+$).

Example 233

N-(3-(N-(3-(3,5-dimethoxy-phenylamino)quinoxalin-2-yl)sulfamoyl)phenyl)-2-(2-isopropylphenylamino)acetamide MS (EI) m/z $C_{33}H_{34}N_6O_5S$: 627 (MH$^+$).

Example 234

N-(3-(N-(3-(3,5-dimethoxy-phenylamino)quinoxalin-2-yl)sulfamoyl)phenyl)-2-(2-fluoro-4-methylphenylamino)acetamide MS (EI) m/z $C_{31}H_{29}FN_6O_5S$: 617 (MH$^+$).

Example 235

2-(4-chlorophenylamino)-N-(3-(N-(3-(3,5-dimethoxy-phenylamino)quinoxalin-2-yl)sulfamoyl)phenyl)acetamide MS (EI) m/z $C_{30}H_{27}ClN_6O_5S$: 619 (MH$^+$).

Example 236

N-(3-(N-(3-(3,5-dimethoxy-phenylamino)quinoxalin-2-yl)sulfamoyl)phenyl)-2-(2-methoxyphenylamino)acetamide MS (EI) m/z $C_{31}H_{30}N_6O_6S$: 615 (MH$^+$).

Example 237

2-(3-chlorophenylamino)-N-(3-(N-(3-(3,5-dimethoxy-phenylamino)quinoxalin-2-yl)sulfamoyl)phenyl)acetamide MS (EI) m/z $C_{30}H_{27}ClN_6O_5S$: 619 (MH$^+$).

Example 238

N-(3-(N-(3-(3,5-dimethoxy-phenylamino)quinoxalin-2-yl)sulfamoyl)phenyl)-2-(2,3-dimethylphenylamino)acetamide MS (EI) m/z $C_{32}H_{32}N_6O_5S$: 613 (MH$^+$).

Example 239

N-(3-(N-(3-(3,5-dimethoxy-phenylamino)quinoxalin-2-yl)sulfamoyl)phenyl)-2-(2-fluorophenylamino)acetamide MS (EI) m/z $C_{30}H_{27}FN_6O_5S$: 603 (MH$^+$).

Example 240

N-(3-(N-(3-(3,5-dimethoxy-phenylamino)quinoxalin-2-yl)sulfamoyl)phenyl)-2-(3-fluorophenylamino)acetamide MS (EI) m/z $C_{30}H_{27}FN_6O_5S$: 603 (MH$^+$).

Example 241

N-(3-(N-(3-(3,5-dimethoxy-phenylamino)quinoxalin-2-yl)sulfamoyl)phenyl)-2-(thiophen-2-ylmethylamino)acetamide MS (EI) m/z $C_{29}H_{28}N_6O_5S_2$: 605 (MH$^+$).

Example 242

2-(cyclohexyl(ethyl)amino)-N-(3-(N-(3-(3,5-dimethoxyphenylamino)quinoxalin-2-yl)sulfamoyl)phenyl)acetamide MS (EI) m/z $C_{32}H_{38}N_6O_5S$: 619 (MH$^+$).

Example 243

2-((cyclopropylmethyl)(propyl)amino)-N-(3-(N-(3-(3,5-dimethoxyphenylamino)quinoxalin-2-yl)sulfamoyl)phenyl)acetamide MS (EI) m/z $C_{31}H_{36}N_6O_5S$: 605 (MH$^+$).

Example 244

2-(allyl(cyclopentyl)amino)-N-(3-(N-(3-(3,5-dimethoxyphenylamino)quinoxalin-2-yl)sulfamoyl)phenyl)acetamide MS (EI) m/z $C_{32}H_{36}N_6O_5S$: 617 (MH$^+$).

Example 245

N-(3-(N-(3-(3,5-dimethoxy-phenylamino)quinoxalin-2-yl)sulfamoyl)phenyl)-2-(ethyl(isopropyl)amino)acetamide MS (EI) m/z $C_{29}H_{34}N_6O_5S$: 579 (MH$^+$).

Example 246

N-(3-(N-(3-(3,5-dimethoxy-phenylamino)quinoxalin-2-yl)sulfamoyl)phenyl)-2-(ethyl(phenyl)amino)acetamide MS (EI) m/z $C_{32}H_{32}N_6O_5S$: 613 (MH$^+$).

Example 247

N-(3-(N-(3-(3,5-dimethoxy-phenylamino)quinoxalin-2-yl)sulfamoyl)phenyl)-2-(2-methylpyrrolidin-1-yl)acetamide
MS (EI) m/z $C_{29}H_{32}N_6O_5S$: 577 (MH$^+$).

Example 248

N-(3-(N-(3-(3,5-dimethoxy-phenylamino)quinoxalin-2-yl)sulfamoyl)phenyl)-2-(2-methylpiperidin-1-yl)acetamide MS (EI) m/z $C_{30}H_{34}N_6O_5S$: 591 (MH$^+$).

Example 249

N-(3-(N-(3-(3,5-dimethoxy-phenylamino)quinoxalin-2-yl)sulfamoyl)phenyl)-2-(pyridin-2-ylmethylamino)acetamide
MS (EI) m/z $C_{30}H_{29}N_7O_5S$: 600 (MH$^+$).

Example 250

2-(benzyl(methyl)amino)-N-(3-(N-(3-(3,5-dimethoxy-phenylamino)quinoxalin-2-yl)sulfamoyl)phenyl)acetamide MS (EI) m/z $C_{32}H_{32}N_6O_5S$: 613 (MH$^+$).

Example 251

N-(3-(N-(3-(3,5-dimethoxy-phenylamino)quinoxalin-2-yl)sulfamoyl)phenyl)-2-(1-phenylethylamino)acetamide MS (EI) m/z $C_{32}H_{32}N_6O_5S$: 613 (MH$^+$).

Example 252

N-(3-(N-(3-(3,5-dimethoxy-phenylamino)quinoxalin-2-yl)sulfamoyl)phenyl)-2-(3-methylpiperidin-1-yl)acetamide MS (EI) m/z $C_{30}H_{34}N_6O_5S$: 591 (MH$^+$).

Example 253

N-(3-(N-(3-(3,5-dimethoxy-phenylamino)quinoxalin-2-yl)sulfamoyl)phenyl)-2-(4-methylpiperidin-1-yl)acetamide MS (EI) m/z $C_{30}H_{34}N_6O_5S$: 591 (MH$^+$).

Example 254

2-(3,4-dihydroisoquinolin-2(1H)-yl)-N-(3-(N-(3-(3,5-dimethoxyphenylamino)quinoxalin-2-yl)sulfamoyl)phenyl)acetamide MS (EI) m/z $C_{33}H_{32}N_6O_5S$: 625 (MH$^+$).

Example 255

N-(3-(N-(3-(3,5-dimethoxy-phenylamino)quinoxalin-2-yl)sulfamoyl)phenyl)-2-(2,6-dimethylpiperidin-1-yl)acetamide MS (EI) m/z $C_{31}H_{36}N_6O_5S$: 605 (MH$^+$).

Example 256

N-(3-(N-(3-(3,5-dimethoxy-phenylamino)quinoxalin-2-yl)sulfamoyl)phenyl)-2-(3-hydroxybenzylamino)acetamide MS (EI) m/z $C_{31}H_{30}N_6O_6S$: 615 (MH$^+$)

General Library Acylation Procedure 1

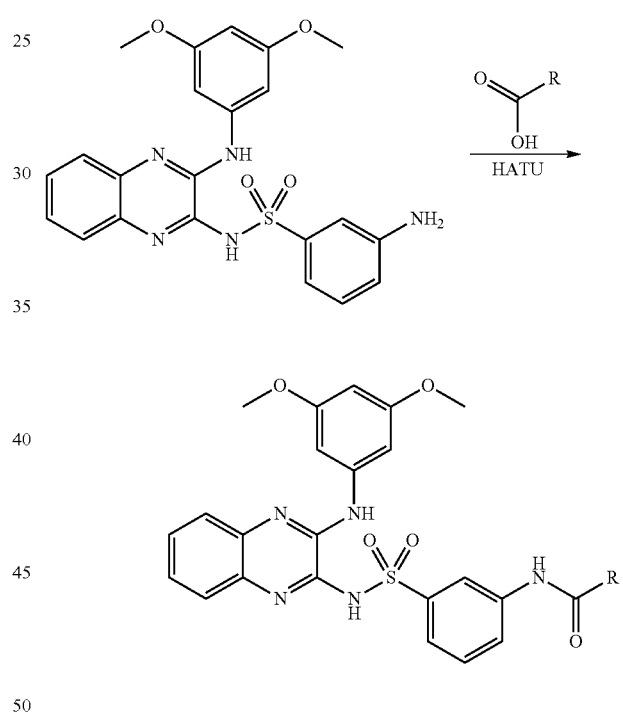

Into a 2-dram vial were added 3-amino-N-(3-(3,5-dimethoxy-phenylamino)quinoxalin-2-yl)benzenesulfonamide (54 mg, 0.12 mmol), prepared using procedures similar to those described in Example 15, DMA (2 mL) and the desired carboxylic acid (0.17 mmol). DIEA (70 μL, 0.4 mmol) followed by HATU (53 mg, 0.14 mmol) were added to the vial and the reaction mixture stirred at 50° C. overnight. Preparative reverse-phase HPLC was used to isolate the desired product directly from the crude reaction mixture. A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification.

The following title compounds were prepared according to General Library Acylation Procedure 1.

Example 257

N-(3-(N-(3-(2-chloro-5-methoxy-phenylamino)quinoxalin-2-yl)sulfamoyl)phenyl)morpholine-4-carboxamide MS (EI) m/z for $C_{26}H_{25}ClN_6O_5S$: 567 (MH$^-$).

Example 258

N-(3-(N-(3-(3,5-dimethoxy-phenylamino)quinoxalin-2-yl)sulfamoyl)phenyl)-2-(dimethylamino)acetamide MS (EI) m/z for $C_{26}H_{28}N_6O_5S$: 535.1 (MH$^-$).

Example 259

N-(3-(N-(3-(3,5-dimethoxy-phenylamino)quinoxalin-2-yl)sulfamoyl)phenyl)propionamide $^1$H-NMR (400 MHz, d$_6$-DMSO): 12.37 (s, 1H), 10.20 (s, 1H), 8.88 (s, 1H), 8.37 (s, 1H), 7.93 (s, 1H), 7.77 (t, 2H), 7.59 (t, 1H), 7.51 (t, 1H), 7.41-7.34 (m, 4H), 6.24 (t, 1H), 3.76 (s, 6H), 2.36-2.31 (dd, 2H), 1.10 (s, 1H), 1.08 (s, 1H), 1.06 (s, 1H); MS (EI) m/z $C_{25}H_{25}N_5O_5S$: 508.6 (MH$^+$).

Example 260

N-(3-(N-(3-(3,5-dimethoxy-phenylamino)quinoxalin-2-yl)sulfamoyl)Phenyl)pyridazine-4-carboxamide $^1$H-NMR (400 MHz, d$_6$-DMSO): 11.01 (s, 1H), 9.66 (dd, 1H), 9.52 (dd, 1H), 8.90 (s, 1H), 8.55 (s, 1H), 8.13 (dd, 1H), 7.99 (d, 1H), 7.93 (d, 1H), 7.65-7.58 (m, 2H), 7.42-7.35 (m, 4H), 6.24 (t, 1H), 3.75 (s, 6H); MS (EI) m/z $C_{27}H_{23}N_7O_5S$: 558.6 (MH$^+$).

Example 261

N-(3-(N-(3-(3,5-dimethoxy-phenylamino)quinoxalin-2-yl)sulfamoyl)phenyl)-2-methylnicotinamide $^1$H-NMR (400 MHz, d$_6$-DMSO): 10.78 ppm (s, 1H), 8.90 ppm (s, 1H), 8.58-8.57 ppm (dd, 2H), 7.90-7.86 ppm (m, 4H), 7.60-7.56 ppm (m, 2H), 7.42-7.34 (m, 5H), 6.23 ppm (t, 1H), 3.74 ppm (s, 6H), 2.57 ppm (s, 3H); MS (EI) m/z $C_{29}H_{26}N_5O_5S$: 570.6 (MH$^+$).

Example 262

N-(3-(N-(3-(3,5-dimethoxy-phenylamino)quinoxalin-2-yl)sulfamoyl)phenyl)-2-(o-tolyloxy)acetamide $^1$H-NMR (400 MHz, d$_6$-DMSO): 12.37 ppm (s, 1H), 10.41 ppm (s, 1H), 8.90 ppm (s, 1H), 8.41 ppm (s, 1H), 7.93 ppm (s, 1H), 7.90-7.8 ppm (m, 2H), 7.59-7.53 ppm (m, 2H), 7.42-7.33 ppm (m, 4H), 7.17-7.12 ppm (m, 2H), 6.89-6.85 ppm (m, 2H), 6.24 ppm (t, 1H), 4.74 ppm (s, 2H), 3.76 ppm (s, 6H), 2.33 ppm (s, 2H); MS (EI) m/z $C_{31}H_{29}N_5O_6S$: 599.7 (MH$^+$).

Example 263

N-(3-(N-(3-(3,5-dimethoxy-phenylamino)quinoxalin-2-yl)sulfamoyl)phenyl)-3-methoxy-4-methylbenzamide MS (EI) m/z $C_{31}H_{29}N_5O_6S$: 600 (MH$^+$).

Example 264

N-(3-(N-(3-(3,5-dimethoxy-phenylamino)quinoxalin-2-yl)sulfamoyl)phenyl)-3-methoxy-4-methylbenzamide MS (EI) m/z $C_{28}H_{24}N_6O_5S$: 557 (MH$^+$).

Example 265

N-(3-(N-(3-(3,5-dimethoxy-phenylamino)quinoxalin-2-yl)sulfamoyl)phenyl)thiazole-4-carboxamide MS (EI) m/z $C_{26}H_{22}N_6O_5S_2$: 563 (MH$^+$).

Example 266

2-bromo-N-(3-(N-(3-(3,5-dimethoxy-phenylamino)quinoxalin-2-yl)sulfamoyl)phenyl)thiophene-3-carboxamide MS (EI) m/z $C_{27}H_{22}BrN_5O_5S_2$ 640 (MH$^+$).

Example 267

N-(3-(N-(3-(3,5-dimethoxy-phenylamino)quinoxalin-2-yl)sulfamoyl)phenyl)pivalamide MS (EI) m/z $C_{27}H_{29}N_5O_5S$: 536 (MH$^+$).

Example 268

N-(3-(N-(3-(3,5-dimethoxy-phenylamino)quinoxalin-2-yl)sulfamoyl)phenyl)pent-4-enamide MS (EI) m/z $C_{27}H_{27}N_5O_5S$: 534 (MH$^+$).

Example 269

N-(3-(N-(3-(3,5-dimethoxy-phenylamino)quinoxalin-2-yl)sulfamoyl)phenyl)benzamide MS (EI) m/z $C_{29}H_{25}N_5O_5S$: 556 (MH$^+$).

Example 270

N-(3-(N-(3-(3,5-dimethoxy-phenylamino)quinoxalin-2-yl)sulfamoyl)phenyl)butyramide MS (EI) m/z $C_{26}H_{27}N_5O_5S$: 522 (MH$^+$).

Example 271

N-(3-(N-(3-(3,5-dimethoxy-phenylamino)quinoxalin-2-yl)sulfamoyl)phenyl)-2-methoxyacetamide MS (EI) m/z $C_{25}H_{25}N_5O_6S$: 524 (MH$^+$).

Example 272

N-(3-(N-(3-(3,5-dimethoxy-phenylamino)quinoxalin-2-yl)sulfamoyl)phenyl)cyclobutanecarboxamide MS (EI) m/z $C_{27}H_{27}N_5O_5S$: 534 (MH$^+$).

Example 273

N-(3-(N-(3-(3,5-dimethoxy-phenylamino)quinoxalin-2-yl)sulfamoyl)phenyl)-2-methylcyclopropanecarboxamide MS (EI) m/z $C_{27}H_{27}N_5O_5S$: 534 (MH$^+$).

Example 274

N-(3-(N-(3-(3,5-dimethoxy-phenylamino)quinoxalin-2-yl)sulfamoyl)phenyl)-1-methylcyclopropanecarboxamide MS (EI) m/z $C_{27}H_{27}N_5O_5S$: 534 (MH$^+$).

Example 275

N-(3-(N-(3-(3,5-dimethoxy-phenylamino)quinoxalin-2-yl)sulfamoyl)phenyl)-3-methylbutanamide MS (EI) m/z $C_{27}H_{29}N_5O_5S$: 536 (MH$^+$).

Example 276

N-(3-(N-(3-(3,5-dimethoxy-phenylamino)quinoxalin-2-yl)sulfamoyl)phenyl)-2-ethoxyacetamide MS (EI) m/z $C_{26}H_{27}N_5O_6S$: 538 (MH$^+$).

Example 277

N-(3-(N-(3-(3,5-dimethoxy-phenylamino)quinoxalin-2-yl)sulfamoyl)phenyl)-3-methoxypropanamide MS (EI) m/z $C_{26}H_{27}N_5O_6S$: 538 (MH$^+$).

Example 278

N-(3-(N-(3-(3,5-dimethoxy-phenylamino)quinoxalin-2-yl)sulfamoyl)phenyl)-2-hydroxyacetamide MS (EI) m/z $C_{24}H_{23}N_5O_6S$: 510 (MH$^+$).

Example 279

N-(3-(N-(3-(3,5-dimethoxy-phenylamino)quinoxalin-2-yl)sulfamoyl)phenyl)isobutyramide MS (EI) m/z $C_{26}H_{27}N_5O_5S$: 522 (MH$^+$).

Example 280

N-(3-(N-(3-(3,5-dimethoxy-phenylamino)quinoxalin-2-yl)sulfamoyl)phenyl)-1-hydroxycyclopropanecarboxamide MS (EI) m/z $C_{26}H_{25}N_5O_6S$: 536 (MH$^+$).

Example 281

N-(3-(N-(3-(3,5-dimethoxy-phenylamino)quinoxalin-2-yl)sulfamoyl)phenyl)furan-3-carboxamide MS (EI) m/z $C_{27}H_{23}N_5O_6S$: 546 (MH$^+$).

Example 282

N-(3-(N-(3-(3,5-dimethoxy-phenylamino)quinoxalin-2-yl)sulfamoyl)phenyl)tetrahydrofuran-3-carboxamide MS (EI) m/z $C_{27}H_{27}N_5O_6S$: 550 (MH$^+$).

Example 283

N-(3-(N-(3-(3,5-dimethoxy-phenylamino)quinoxalin-2-yl)sulfamoyl)phenyl)tetrahydrofuran-2-carboxamide MS (EI) m/z $C_{27}H_{27}N_5O_6S$: 550 (MH$^+$).

Example 284

N-(3-(N-(3-(3,5-dimethoxy-phenylamino)quinoxalin-2-yl)sulfamoyl)phenyl)furan-2-carboxamide MS (EI) m/z $C_{27}H_{23}N_5O_6S$: 546 (MH$^+$).

Example 285

N-(3-(N-(3-(3,5-dimethoxy-phenylamino)quinoxalin-2-yl)sulfamoyl)phenyl)isonicotinamide MS (EI) m/z $C_{28}H_{24}N_6O_5S$: 557 (MH$^+$).

Example 286

N-(3-(N-(3-(3,5-dimethoxy-phenylamino)quinoxalin-2-yl)sulfamoyl)phenyl)-1H-pyrrole-2-carboxamide MS (EI) m/z $C_{27}H_{24}N_6O_5S$: 545 (MH$^+$).

Example 287

N-(3-(N-(3-(3,5-dimethoxy-phenylamino)quinoxalin-2-yl)sulfamoyl)phenyl)pyrazine-2-carboxamide MS (EI) m/z $C_{27}H_{23}N_7O_5S$: 558 (MH$^+$).

Example 288

N-(3-(N-(3-(3,5-dimethoxy-phenylamino)quinoxalin-2-yl)sulfamoyl)phenyl)-1-methyl-1H-pyrrole-2-carboxamide MS (EI) m/z $C_{28}H_{26}N_6O_5S$: 559 (MH$^+$).

Example 289

N-(3-(N-(3-(3,5-dimethoxy-phenylamino)quinoxalin-2-yl)sulfamoyl)phenyl)-5-methylisoxazole-3-carboxamide MS (EI) m/z $C_{27}H_{24}N_6O_6S$: 561 (MH$^+$).

Example 290

N-(3-(N-(3-(3,5-dimethoxy-phenylamino)quinoxalin-2-yl)sulfamoyl)phenyl)thiophene-2-carboxamide MS (EI) m/z $C_{27}H_{23}N_5O_5S_2$: 562 (MH$^+$).

Example 291

(S)—N-(3-(N-(3-(3,5-dimethoxy-phenylamino)quinoxalin-2-yl)sulfamoyl)phenyl)-1-methylpyrrolidine-2-carboxamide MS (EI) m/z $C_{28}H_{30}N_6O_5S$: 563 (MH$^+$).

Example 292

N-(3-(N-(3-(3,5-dimethoxy-phenylamino)quinoxalin-2-yl)sulfamoyl)phenyl)-2-methylbenzamide MS (EI) m/z $C_{30}H_{27}N_5O_5S$: 570 (MH$^+$).

Example 293

N-(3-(N-(3-(3,5-dimethoxy-phenylamino)quinoxalin-2-yl)sulfamoyl)phenyl)-2-phenylacetamide MS (EI) m/z $C_{30}H_{27}N_5O_5S$: 570 (MH$^+$).

Example 294

N-(3-(N-(3-(3,5-dimethoxy-phenylamino)quinoxalin-2-yl)sulfamoyl)phenyl)-3-methylpicolinamide MS (EI) m/z $C_{29}H_{26}N_6O_5S$: 571 (MH$^+$).

Example 295

N-(3-(N-(3-(3,5-dimethoxy-phenylamino)quinoxalin-2-yl)sulfamoyl)phenyl)-2-(pyridin-3-yl)acetamide MS (EI) m/z $C_{29}H_{26}N_6O_5S$: 571 (MH$^+$).

Example 296

N-(3-(N-(3-(3,5-dimethoxy-phenylamino)quinoxalin-2-yl)sulfamoyl)phenyl)-6-hydroxypicolinamide MS (EI) m/z $C_{28}H_{24}N_6O_6S$: 573 (MH$^+$).

Example 297

N-(3-(N-(3-(3,5-dimethoxy-phenylamino)quinoxalin-2-yl)sulfamoyl)phenyl)-2-fluorobenzamide MS (EI) m/z $C_{29}H_{24}FN_5O_5S$: 574 (MH$^+$).

Example 298

N-(3-(N-(3-(3,5-dimethoxy-phenylamino)quinoxalin-2-yl)sulfamoyl)phenyl)-4-fluorobenzamide MS (EI) m/z $C_{29}H_{24}FN_5O_5S$: 574 (MH$^+$).

Example 299

N-(3-(N-(3-(3,5-dimethoxy-phenylamino)quinoxalin-2-yl)sulfamoyl)phenyl)-3-fluorobenzamide MS (EI) m/z $C_{29}H_{24}FN_5O_5S$: 574 (MH$^+$).

Example 300

2-cyclohexyl-N-(3-(N-(3-(3,5-dimethoxy-phenylamino)quinoxalin-2-yl)sulfamoyl)phenyl)acetamide MS (EI) m/z $C_{30}H_{33}N_5O_5S$: 576 (MH$^+$).

Example 301

N-(3-(N-(3-(3,5-dimethoxy-phenylamino)quinoxalin-2-yl)sulfamoyl)phenyl)-2-(2-oxocyclopentyl)acetamide MS (EI) m/z $C_{29}H_{29}N_5O_6S$: 576 (MH$^+$).

Example 302

4-cyclopropyl-N-(3-(N-(3-(3,5-dimethoxy-phenylamino)quinoxalin-2-yl)sulfamoyl)phenyl)-4-oxobutanamide MS (EI) m/z $C_{29}H_{29}N_5O_6S$: 576 (MH$^+$).

Example 303

N-(3-(N-(3-(3,5-dimethoxy-phenylamino)quinoxalin-2-yl)sulfamoyl)phenyl)-3-oxocyclohexanecarboxamide MS (EI) m/z $C_{29}H_{29}N_5O_6S$: 576 (MH$^+$).

Example 304

N-(3-(N-(3-(3,5-dimethoxy-phenylamino)quinoxalin-2-yl)sulfamoyl)phenyl)-3-(pyridin-3-yl)propanamide MS (EI) m/z $C_{30}H_{28}N_6O_5S$: 585 (MH$^+$).

Example 305

N-(3-(N-(3-(3,5-dimethoxy-phenylamino)quinoxalin-2-yl)sulfamoyl)phenyl)-2-methoxybenzamide MS (EI) m/z $C_{30}H_{27}N_5O_6S$: 586 (MH$^+$).

Example 306

N-(3-(N-(3-(3,5-dimethoxy-phenylamino)quinoxalin-2-yl)sulfamoyl)phenyl)-3-methoxybenzamide MS (EI) m/z $C_{30}H_{27}N_5O_6S$: 586 (MH$^+$).

Example 307

N-(3-(N-(3-(3,5-dimethoxy-phenylamino)quinoxalin-2-yl)sulfamoyl)phenyl)-2-phenoxyacetamide MS (EI) m/z $C_{30}H_{27}N_5O_6S$: 586 (MH$^+$).

Example 308

N-(3-(N-(3-(3,5-dimethoxy-phenylamino)quinoxalin-2-yl)sulfamoyl)phenyl)-4-methoxybenzamide MS (EI) m/z $C_{30}H_{27}N_5O_6S$: 586 (MH$^+$).

Example 309

N-(3-(N-(3-(3,5-dimethoxy-phenylamino)quinoxalin-2-yl)sulfamoyl)phenyl)-2-(4-fluorophenyl)acetamide MS (EI) m/z $C_{30}H_{26}FN_5O_5S$: 588 (MH$^+$).

Example 310

N-(3-(N-(3-(3,5-dimethoxy-phenylamino)quinoxalin-2-yl)sulfamoyl)phenyl)-2-(2-fluorophenyl)acetamide MS (EI) m/z $C_{30}H_{26}FN_5O_5S$: 588 (MH$^+$).

Example 311

N-(3-(N-(3-(3,5-dimethoxy-phenylamino)quinoxalin-2-yl)sulfamoyl)phenyl)-2-(3-fluorophenyl)acetamide MS (EI) m/z $C_{30}H_{26}FN_5O_5S$: 588 (MH$^+$).

Example 312

2-chloro-N-(3-(N-(3-(3,5-dimethoxy-phenylamino)quinoxalin-2-yl)sulfamoyl)phenyl)benzamide MS (EI) m/z $C_{29}H_{24}ClN_5O_5S$: 590 (MH$^+$).

Example 313

4-chloro-N-(3-(N-(3-(3,5-dimethoxy-phenylamino)quinoxalin-2-yl)sulfamoyl)phenyl)benzamide MS (EI) m/z $C_{29}H_{24}ClN_5O_5S$: 590 (MH$^+$).

Example 314

3-chloro-N-(3-(N-(3-(3,5-dimethoxy-phenylamino)quinoxalin-2-yl)sulfamoyl)phenyl)benzamide MS (EI) m/z $C_{29}H_{24}ClN_5O_5S$: 590 (MH$^+$).

Example 315

(1R,2R)—N-(3-(N-(3-(3,5-dimethoxy-phenylamino)quinoxalin-2-yl)sulfamoyl)phenyl)-2-phenylcyclopropanecarboxamide MS (EI) m/z $C_{32}H_{29}N_5O_5S$: 596 (MH$^+$).

Example 316

N-(3-(N-(3-(3,5-dimethoxy-phenylamino)quinoxalin-2-yl)sulfamoyl)phenyl)-1-phenylcyclopropanecarboxamide MS (EI) m/z $C_{32}H_{29}N_5O_5S$: 596 (MH$^+$).

Example 317

N-(3-(N-(3-(3,5-dimethoxy-phenylamino)quinoxalin-2-yl)sulfamoyl)phenyl)-2-(1H-imidazol-4-yl)acetamide MS (EI) m/z $C_{27}H_{25}N_7O_5S$: 560 (MH$^+$).

Example 318

N-(3-(N-(3-(3,5-dimethoxy-phenylamino)quinoxalin-2-yl)sulfamoyl)phenyl)-4-methoxy-2-methylbenzamide MS (EI) m/z $C_{31}H_{29}N_5O_6S$: 600 (MH$^+$).

Example 319

N-(3-(N-(3-(3,5-dimethoxy-phenylamino)quinoxalin-2-yl)sulfamoyl)phenyl)-2-(4-fluorophenoxy)acetamide MS (EI) m/z $C_{30}H_{26}FN_5O_6S$: 604 (MH$^+$).

Example 320

N-(3-(N-(3-(3,5-dimethoxy-phenylamino)quinoxalin-2-yl)sulfamoyl)phenyl)-5-fluoro-2-methoxybenzamide MS (EI) m/z $C_{30}H_{26}FN_5O_6S$: 604 (MH$^+$).

Example 321

2-(4-chlorophenyl)-N-(3-(N-(3-(3,5-dimethoxy-phenylamino)quinoxalin-2-yl)sulfamoyl)phenyl)acetamide MS (EI) m/z $C_{30}H_{26}ClN_5O_5S$: 604 (MH$^+$).

Example 322

2-(2-chlorophenyl)-N-(3-(N-(3-(3,5-dimethoxy-phenylamino)quinoxalin-2-yl)sulfamoyl)phenyl)acetamide MS (EI) m/z $C_{30}H_{26}ClN_5O_5S$: 604 (MH$^+$).

Example 323

2-(3-chlorophenyl)-N-(3-(N-(3-(3,5-dimethoxy-phenylamino)quinoxalin-2-yl)sulfamoyl)phenyl)acetamide MS (EI) m/z $C_{30}H_{26}ClN_5O_5S$: 604 (MH$^+$).

Example 324

1-acetyl-N-(3-(N-(3-(3,5-dimethoxy-phenylamino)quinoxalin-2-yl)sulfamoyl)phenyl)piperidine-4-carboxamide MS (EI) m/z $C_{30}H_{32}N_6O_6S$: 605 (MH$^+$).

Example 325

N-(3-(N-(3-(3,5-dimethoxy-phenylamino)quinoxalin-2-yl)sulfamoyl)phenyl)-2-(pyridin-4-yl)acetamide MS (EI) m/z $C_{29}H_{26}N_6O_5S$: 571 (MH$^+$).

Example 326

N-(3-(N-(3-(3,5-dimethoxy-phenylamino)quinoxalin-2-yl)sulfamoyl)phenyl)-2-(pyridin-2-yl)acetamide MS (EI) m/z $C_{29}H_{26}N_6O_5S$: 571 (MH$^+$).

Example 327

2,4-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 328

3,4-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 329

2,5-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 330

3,5-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 331

2,3-dichloro-N-(3-(N-(3-(3,5-dimethoxy-phenylamino)quinoxalin-2-yl)sulfamoyl)phenyl)benzamide MS (EI) m/z $C_{29}H_{23}Cl_2N_5O_5S$: 624 (MH$^+$).

Example 332

N-(3-(N-(3-(3,5-dimethoxy-phenylamino)quinoxalin-2-yl)sulfamoyl)phenyl)pentanamide MS (EI) m/z $C_{27}H_{29}N_5O_5S$: 536 (MH$^+$).

Example 333

N-(3-(N-(3-(3,5-dimethoxy-phenylamino)quinoxalin-2-yl)sulfamoyl)phenyl)-2-methylbutanamide MS (EI) m/z $C_{27}H_{29}N_5O_5S$: 536 (MH$^+$).

Example 334

N-(3-(N-(3-(3,5-dimethoxy-phenylamino)quinoxalin-2-yl)sulfamoyl)phenyl)-1H-imidazole-2-carboxamide MS (EI) m/z $C_{26}H_{23}N_7O_5S$: 546 (MH$^+$).

Example 335

N-(3-(N-(3-(3,5-dimethoxy-phenylamino)quinoxalin-2-yl)sulfamoyl)phenyl)-1H-imidazole-4-carboxamide MS (EI) m/z $C_{26}H_{23}N_7O_5S$: 546 (MH$^+$).

Example 336

N-(3-(N-(3-(3,5-dimethoxy-phenylamino)quinoxalin-2-yl)sulfamoyl)phenyl)isoxazole-5-carboxamide MS (EI) m/z $C_{26}H_{22}N_6O_6S$: 547 (MH$^+$).

Example 337

N-(3-(N-(3-(3,5-dimethoxy-phenylamino)quinoxalin-2-yl)sulfamoyl)phenyl)-3,3-dimethylbutanamide MS (EI) m/z $C_{28}H_{31}N_5O_5S$: 550 (MH$^+$).

Example 338

N-(3-(N-(3-(3,5-dimethoxy-phenylamino)quinoxalin-2-yl)sulfamoyl)phenyl)-2-methylpentanamide MS (EI) m/z $C_{28}H_{31}N_5O_5S$: 550 (MH$^+$).

Example 339

N-(3-(N-(3-(3,5-dimethoxy-phenylamino)quinoxalin-2-yl)sulfamoyl)phenyl)-2,2-dimethylbutanamide MS (EI) m/z $C_{28}H_{31}N_5O_5S$: 550 (MH$^+$).

Example 340

N-(3-(N-(3-(3,5-dimethoxy-phenylamino)quinoxalin-2-yl)sulfamoyl)phenyl)-4-methylpentanamide MS (EI) m/z $C_{28}H_{31}N_5O_5S$: 550 (MH$^+$).

Example 341

N-(3-(N-(3-(3,5-dimethoxy-phenylamino)quinoxalin-2-yl)sulfamoyl)phenyl)pyrimidine-5-carboxamide MS (EI) m/z $C_{27}H_{23}N_7O_5S$: 558 (MH$^+$).

Example 342

N-(3-(N-(3-(3,5-dimethoxy-phenylamino)quinoxalin-2-yl)sulfamoyl)phenyl)-3-methylfuran-2-carboxamide MS (EI) m/z $C_{28}H_{25}N_5O_6S$: 560 (MH$^+$).

Example 343

N-(3-(N-(3-(3,5-dimethoxy-phenylamino)quinoxalin-2-yl)sulfamoyl)phenyl)thiophene-3-carboxamide MS (EI) m/z $C_{27}H_{23}N_5O_5S_2$: 562 (MH$^+$).

Example 344

N-(3-(N-(3-(3,5-dimethoxy-phenylamino)quinoxalin-2-yl)sulfamoyl)phenyl)-3-oxocyclopentanecarboxamide MS (EI) m/z $C_{28}H_{27}N_5O_6S$: 562 (MH$^+$).

Example 345

N-(3-(N-(3-(3,5-dimethoxy-phenylamino)quinoxalin-2-yl)sulfamoyl)phenyl)-2-(2-methoxyethoxy)acetamide MS (EI) m/z $C_{27}H_{29}N_5O_7S$: 568 (MH$^+$).

Example 346

N-(3-(N-(3-(3,5-dimethoxy-phenylamino)quinoxalin-2-yl)sulfamoyl)phenyl)-4-methylbenzamide MS (EI) m/z $C_{30}H_{27}N_5O_5S$: 570 (MH$^+$).

Example 347

N-(3-(N-(3-(3,5-dimethoxy-phenylamino)quinoxalin-2-yl)sulfamoyl)phenyl)-2-(3-methylisoxazol-4-yl)acetamide MS (EI) m/z $C_{28}H_{26}N_6O_6S$: 575 (MH$^+$).

Example 348

3-cyclopentyl-N-(3-(N-(3-(3,5-dimethoxy-phenylamino)quinoxalin-2-yl)sulfamoyl)phenyl)propanamide MS (EI) m/z $C_{30}H_{33}N_5O_5S$: 576 (MH$^+$).

Example 349

N-(3-(N-(3-(3,5-dimethoxy-phenylamino)quinoxalin-2-yl)sulfamoyl)phenyl)-2-o-tolylacetamide MS (EI) m/z $C_{31}H_{29}N_5O_5S$: 584 (MH$^+$).

Example 350

N-(3-(N-(3-(3,5-dimethoxy-phenylamino)quinoxalin-2-yl)sulfamoyl)phenyl)-2-methoxynicotinamide MS (EI) m/z $C_{29}H_{26}N_6O_6S$: 587 (MH$^+$).

Example 351

N-(3-(N-(3-(3,5-dimethoxy-phenylamino)quinoxalin-2-yl)sulfamoyl)phenyl)-4-fluoro-3-methylbenzamide MS (EI) m/z $C_{30}H_{26}FN_5O_5S$: 588 (MH$^+$).

Example 352

N-(3-(N-(3-(3,5-dimethoxy-phenylamino)quinoxalin-2-yl)sulfamoyl)phenyl)-3-fluoro-2-methylbenzamide MS (EI) m/z $C_{30}H_{26}FN_5O_5S$: 588 (MH$^+$).

Example 353

N-(3-(N-(3-(3,5-dimethoxy-phenylamino)quinoxalin-2-yl)sulfamoyl)phenyl)-3-fluoro-4-methylbenzamide MS (EI) m/z $C_{30}H_{26}FN_5O_5S$: 588 (MH$^+$).

Example 354

N-(3-(N-(3-(3,5-dimethoxy-phenylamino)quinoxalin-2-yl)sulfamoyl)phenyl)-2-fluoro-5-methylbenzamide MS (EI) m/z $C_{30}H_{26}FN_5O_5S$: 588 (MH$^+$).

Example 355

N-(3-(N-(3-(3,5-dimethoxy-phenylamino)quinoxalin-2-yl)sulfamoyl)phenyl)-5-fluoro-2-methylbenzamide MS (EI) m/z $C_{30}H_{26}FN_5O_5S$: 588 (MH$^+$).

Example 356

6-chloro-N-(3-(N-(3-(3,5-dimethoxy-phenylamino)quinoxalin-2-yl)sulfamoyl)phenyl)nicotinamide MS (EI) m/z $C_{28}H_{23}ClN_6O_5S$: 591 (MH$^+$).

Example 357

2-chloro-N-(3-(N-(3-(3,5-dimethoxy-phenylamino)quinoxalin-2-yl)sulfamoyl)phenyl)nicotinamide MS (EI) m/z $C_{28}H_{23}ClN_6O_5S$: 591 (MH$^+$).

Example 358

2-chloro-N-(3-(N-(3-(3,5-dimethoxy-phenylamino)quinoxalin-2-yl)sulfamoyl)phenyl)isonicotinamide MS (EI) m/z $C_{28}H_{23}ClN_6O_5S$: 591 (MH$^+$).

Example 359

N-(3-(N-(3-(3,5-dimethoxy-phenylamino)quinoxalin-2-yl)sulfamoyl)phenyl)-4-(dimethylamino)benzamide MS (EI) m/z $C_{31}H_{30}N_6O_5S$: 599 (MH$^+$).

Example 360

N-(3-(N-(3-(3,5-dimethoxy-phenylamino)quinoxalin-2-yl)sulfamoyl)phenyl)-3-(dimethylamino)benzamide MS (EI) m/z $C_{31}H_{30}N_6O_5S$: 599 (MH$^+$).

Example 361

N-(3-(N-(3-(3,5-dimethoxy-phenylamino)quinoxalin-2-yl)sulfamoyl)phenyl)benzo[d][1,3]-dioxole-5-carboxamide MS (EI) m/z $C_{30}H_{25}N_5O_7S$: 600 (MH$^+$).

Example 362

N-(3-(N-(3-(3,5-dimethoxy-phenylamino)quinoxalin-2-yl)sulfamoyl)phenyl)-2-(m-tolyloxy)acetamide MS (EI) m/z $C_{31}H_{29}N_5O_6S$: 600 (MH$^+$).

Example 363

N-(3-(N-(3-(3,5-dimethoxy-phenylamino)quinoxalin-2-yl)sulfamoyl)phenyl)-2-(4-methoxyphenyl)acetamide MS (EI) m/z $C_{31}H_{29}N_5O_6S$: 600 (MH$^+$).

Example 364

N-(3-(N-(3-(3,5-dimethoxy-phenylamino)quinoxalin-2-yl)sulfamoyl)phenyl)-2-(2-methoxyphenyl)acetamide MS (EI) m/z $C_{31}H_{29}N_5O_6S$: 600 (MH$^+$).

Example 365

N-(3-(N-(3-(3,5-dimethoxy-phenylamino)quinoxalin-2-yl)sulfamoyl)phenyl)-2-(3-methoxyphenyl)acetamide MS (EI) m/z $C_{31}H_{29}N_5O_6S$: 600 (MH$^+$).

Example 366

N-(3-(N-(3-(3,5-dimethoxy-phenylamino)quinoxalin-2-yl)sulfamoyl)phenyl)-2-methoxy-4-methylbenzamide MS (EI) m/z $C_{31}H_{29}N_5O_6S$: 600 (MH$^+$).

Example 367

N-(3-(N-(3-(3,5-dimethoxy-phenylamino)quinoxalin-2-yl)sulfamoyl)phenyl)-3-fluoro-4-methoxybenzamide MS (EI) m/z $C_{30}H_{26}FN_5O_6S$: 604 (MH$^+$).

Example 368

N-(3-(N-(3-(3,5-dimethoxy-phenylamino)quinoxalin-2-yl)sulfamoyl)phenyl)-2-fluoro-6-methoxybenzamide MS (EI) m/z $C_{30}H_{26}FN_5O_6S$: 604 (MH$^+$).

Example 369

N-(3-(N-(3-(3,5-dimethoxy-phenylamino)quinoxalin-2-yl)sulfamoyl)phenyl)-3-(4-methoxyphenyl)propanamide MS (EI) m/z $C_{32}H_{31}N_5O_6S$: 614 (MH$^+$).

Example 370

N-(3-(N-(3-(3,5-dimethoxy-phenylamino)quinoxalin-2-yl)sulfamoyl)phenyl)-3-(2-methoxyphenyl)propanamide MS (EI) m/z $C_{32}H_{31}N_5O_6S$: 614 (MH$^+$).

Example 371

N-(3-(N-(3-(3,5-dimethoxy-phenylamino)quinoxalin-2-yl)sulfamoyl)phenyl)-3-(3-methoxyphenyl)propanamide MS (EI) m/z $C_{32}H_{31}N_5O_6S$: 614 (MH$^+$).

Example 372

N-(3-(N-(3-(3,5-dimethoxy-phenylamino)quinoxalin-2-yl)sulfamoyl)phenyl)azetidine-3-carboxamide

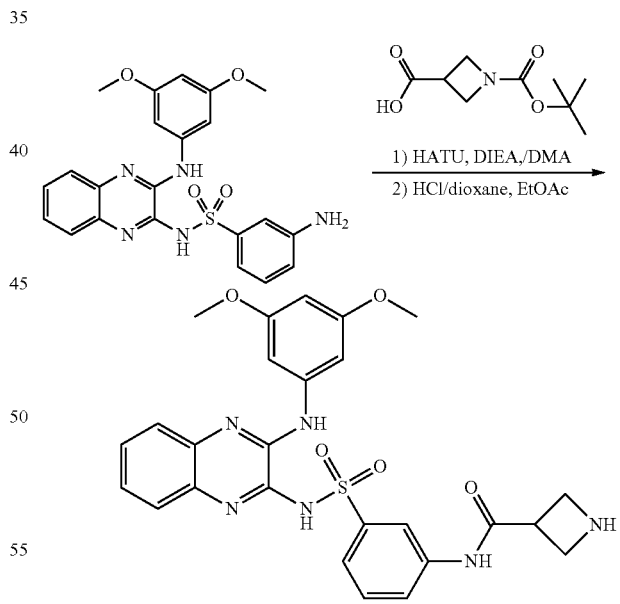

Into a 20 mL vial was added 3-amino-N-(3-(3,5-dimethoxy-phenylamino)quinoxalin-2-yl)benzenesulfonamide (0.24 mmol, 1 equiv), prepared using procedures similar to those described in Example 15, DMA (5 mL) and 1-(tert-butoxycarbonyl)azetidine-3-carboxylic acid (0.336 mmol, 1.4 equiv). Hunig's Base (0.792 mmol, 3.3 equiv) and HATU (0.288 mmol, 1.2 equiv) were added to the vial and the reaction mixture was then stirred at room temperature overnight. Completion of the reaction was indicated by LCMS. The solvent was removed by rotary evaporation. The crude mixture was carried forward without further purification. The residue was suspended in 5 mL ethyl acetate and chilled in an ice bath. A solution of 4 N HCl in dioxane (3 mL, 5 equiv) was added with stirring. The reaction mixture was then stirred at room temperature overnight. The solid materials were collected by filtration, washed with ethylacetate then purified further by preparative reverse-phase HPLC (ammonium acetate/ACN). A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification. N-(3-(N-(3-(3,5-dimethoxy-phenylamino)quinoxalin-2-yl)sulfamoyl)phenyl)azetidine-3-carboxamide was obtained (26 mg, 20%). $^1$H-NMR (400 MHz, $d_6$-DMSO): 10.26 (s, 1H), 8.81 (s, 1H), 8.25 (t, 8.14 (s, 1H), 7.74 (d, 1H), 7.69 (d, 1H), 7.41-7.39 (m, 1H), 7.36 (d, 1H), 7.32 (d, 2H), 7.30-7.28 (dd, 1H), 7.14-7.11 (m, 2H), 6.14 (t, 1H), 4.09 (d, 4H), 3.78 (s, 6H); MS (EI) m/z $C_{26}H_{26}N_6O_5S$: 535.6 (MH$^+$).

formed by adding ethyl acetate and dichloromethane to the dried crude product, filtration yielded N-(3-chloroquinoxalin-2-yl)-benzenesulfonamide which was used without further purification. MS (EI) m/z $C_{14}H_{10}ClN_3O_2S$: 319.9 (MH$^+$).

A CEM microwave reaction vessel was charged with N-(3-chloroquinoxalin-2-yl)benzenesulfonamide (52 mg, 0.16 mmol), prepared using procedures similar to those described in the above step, 4-fluoroaniline (36 mg, 0.32 mmol), and 0.8 mL of dimethylacetamide. The vessel was sealed and the reaction mixture was heated under microwave radiation for 25 m at 120° C. in a CEM Discover microwave instrument. Methanol (1 mL) was added to the reaction mixture and after 20 minutes the product precipitated out of the solution. Filtration yielded N-(3-(4-fluorophenylamino)quinoxalin-2-yl) benzenesulfonamide (39 mg, 62%). $^1$H-NMR (400 MHz, $d_o$-DMSO): δ 12.30 (s, 1H), 9.11 (s, 1H), 8.16-8.10 (d, 2H), 8.02-7.90 (m, 3H), 7.68-7.58 (m, 3H), 7.55-7.51 (m, 1H), 7.41-7.32 (m, 2H), 7.25-7.16 (m, 2H); MS (EI) m/z $C_{20}H_{15}FN_4O_2S$: 395.0 (MH$^+$).

Example 373

N-(3-(4-fluorophenylamino)quinoxalin-2-yl)benzenesulfonamide

Example 374

N-(3-(N-(3-chloroquinoxalin-2-yl)sulfamoyl)phenyl)-2-(dimethylamino)acetamide

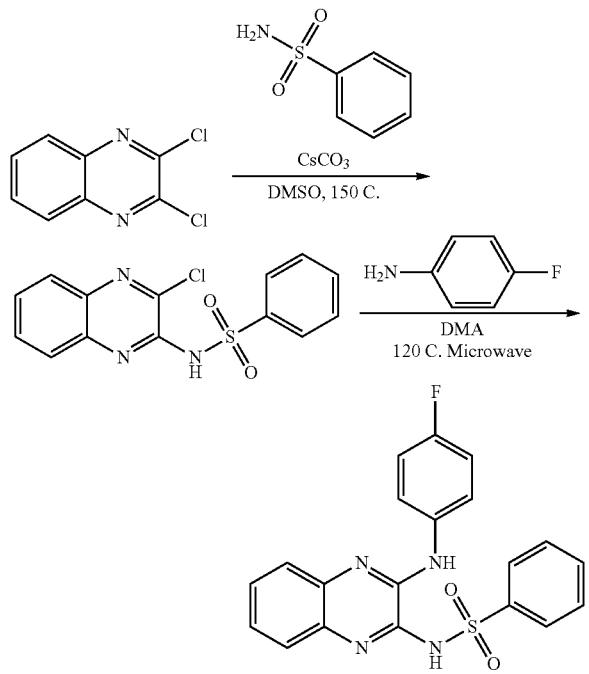

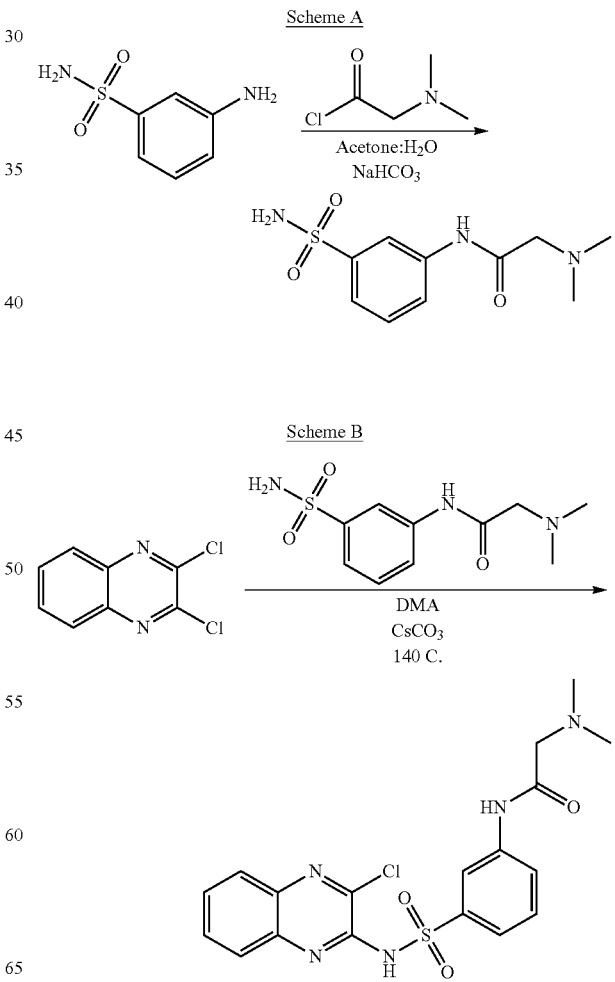

A flask was charged with 2,3-dichloroquinoxaline (3.5 g, 18 mmol), 85 mL of dimethylsulfoxide, benzene sulfonamide (2.8 g, 18 mmol), and cesium carbonate (5.8 g, 18 mmol). The reaction mixture was stirred under an N$_2$ atmosphere for 15 h at 150° C., after which time, it was transferred to a separatory funnel and 100 mL of water were added. Concentrated HCl was then added in order to acidify the reaction mixture to pH<2. The aqueous layer was subsequently washed three times with 90 mL ethyl acetate. The ethyl acetate layers were then washed two times with 150 mL water, three times with 100 mL brine and then dried over sodium sulfate. The ethyl acetate was removed on a rotary-evaporator. A slurry was Scheme A A flask was charged with 3-aminobenzene sulfonamide (3.3 g, 19 mmol), and 20 mL of 1:1 acetone:$H_2O$. The solution was stirred at room temperature until the aminobenzene sulfonamide had dissolved. The flask was then cooled in an ice bath and dimethylamino-acetyl chloride HCl (4.6 g, 29 mmol) was added. To the resulting slurry sodium bicarbonate (4.8 g, 57 mmol) was added over a 15 m period. After 30 min the reaction was removed from the ice bath and allowed to stir at room temperature for 15 h. The reaction mixture was then filtered and washed with methanol and acetonitrile. The filtrate was dried on a rotary evaporator to yield 2-(dimethylamino)-N-(3-sulfamoyl-phenyl)acetamide, which was submitted to the next step without further purification. MS (EI) m/z $C_{10}H_{15}N_3O_3S$: 258.0 ($MH^+$).

Scheme B

A flask was charged with dichloroquinozaline (1.0 g, 5.8 mmol), 10 mL of dimethylacetamide, 2-(dimethylamino)-N-(3-sulfamoylphenyl)acetamide (0.70 g, 2.7 mmol), and cesium carbonate (1.8 g, 5.5 mmol). The reaction mixture was stirred for 3 h at 140° C. and then filtered. The solvent was evaporated from the filtrate on a rotary-evaporator to yield (N-(3-(N-(3-chloroquinoxalin-2-yl)sulfamoyl)phenyl)-2-(dimethylamino)acetamide) which was submitted to the next step without further purification. MS (EI) m/z $C_{18}H_{18}ClN_5O_3S$: 420.0 ($MH^+$).

General Amination Procedure 1a

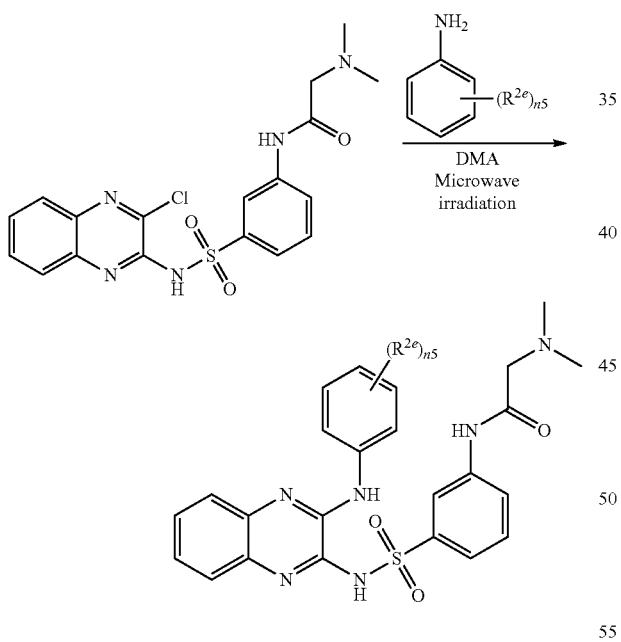

A CEM microwave reaction vessel was charged with N-(3-(N-(3-chloroquinoxalin-2-yl)sulfamoyl)phenyl)-2-(dimethylamino)acetamide (30 mg, 0.071 mmol), prepared using procedures similar to those described in Example 374, the desired aniline (16 mg, 0.14 mmol, 2 eq), and 0.5 mL of dimethylacetamide. The vessel was sealed and the reaction mixture was heated under microwave radiation for 70 min at 140° C. in a CEM Discover microwave instrument. The solvent was then removed by rotary-evaporation. Purification of the final product was accomplished by preparatory reverse-phase HPLC with the eluents 25 mM aqueous $NH_4OAc/ACN$ to the desired product.

The following compounds were prepared according to the above General Amination Procedure 1a.

Example 375

2-(dimethylamino)-N-(3-(N-(3-(3-fluorophenylamino)quinoxalin-2-yl)sulfamoyl)phenyl)acetamide $^1$H-NMR (400 MHz, $CDCl_3$): 9.40 ppm (s, 1H), 8.43 ppm (s, 1H), 8.22 ppm (s, 1H), 8.07-8.02 ppm (d, 1H), 7.97-7.93 ppm (d, 1H), 7.76-7.71 (m, 2H), 7.53-7.48 ppm (t, 1H), 7.45-7.36 ppm (m, 4H), 7.35-7.28 ppm (m, 2H), 6.84-6.77 ppm (t, 1H), 3.10 ppm (s, 2H), 2.38 ppm (s, 6H); MS (EI) m/z $C_{24}H_{23}FN_6O_3S$: 495 ($MH^+$).

Example 376

2-(dimethylamino)-N-(3-(N-(3-(4-fluorophenylamino)quinoxalin-2-yl)sulfamoyl)phenyl)acetamide MS (EI) m/z $C_{24}H_{23}FN_6O_3S$: 495 ($MH^+$).

Example 377

N-(3-(N-(3-(4-chloro-phenylamino)quinoxalin-2-yl)sulfamoyl)phenyl)-2-(dimethylamino)acetamide MS (EI) m/z $C_{24}H_{23}ClN_6O_3S$: 511 ($MH^+$).

General Amination Procedure 1b

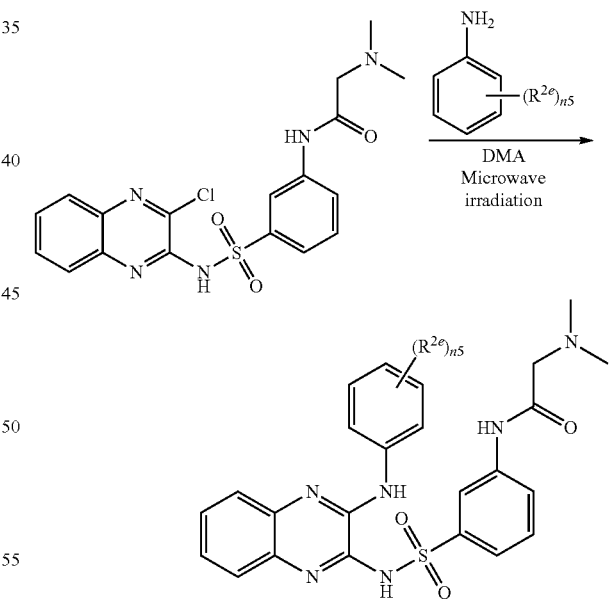

A CEM microwave reaction vessel was charged with N-(3-(N-(3-chloroquinoxalin-2-yl)sulfamoyl)phenyl)-2-(dimethylamino)acetamide (62 mg, 0.147 mmol), prepared using procedures similar to those in Example 374, the desired aniline (0.567 mmol, 4 eq), and 1.0 mL of toluene. The vessel was sealed and the reaction mixture was heated under microwave radiation for 60 min at 180° C. in a CEM Discover microwave instrument. The solvent was removed on a rotary-evaporator. Purification of the final product was done by preparatory HPLC with NH$_4$OAc/ACN as eluent to yield the desired product.

The following compounds were prepared according to the above General Amination Procedure 1b.

Example 378

N-(3-(N-(3-(3-chloro-phenylamino)quinoxalin-2-yl) sulfamoyl)phenyl)-2-(dimethylamino)acetamide MS (EI) m/z C$_{24}$H$_{23}$ClN$_6$O$_3$S: 511 (MH$^+$).

Example 379

2-(dimethylamino)-N-(3-(N-(3-(4-fluoro-3-methoxyphenylamino)quinoxalin-2-yl)sulfamoyl)phenyl) acetamide 2-(dimethylamino)-N-(3-(N-(3-(4-fluoro-3-methoxyphenylamino)quinoxalin-2-yl)sulfamoyl)phenyl). $^1$H-NMR (400 MHz, CDCl$_3$): δ 9.47 (s, 1H), 8.36 (s, 1H), 8.29 (s, 1H), 7.91-7.87 (d, 1H), 7.80-7.73 (m, 2H), 7.66-7.63 (d, 1H), 7.53-7.47 (t, 1H), 7.43-7.30 (m, 4H), 7.10-7.04 (t, 1H), 6.55-5.95 (br s, 1H), 3.96 (s, 3H), 3.12 (s, 2H), 2.39 (s, 6H), 2.08 (s, 3H(AcOH); MS (EI) m/z C$_{25}$H$_{25}$FN$_6$O$_4$S: 525 (MH$^+$).

Example 380

N-(3-(3,5-dimethoxy-phenylamino)quinoxalin-2-yl)-4-isopropoxybenzenesulfonamide

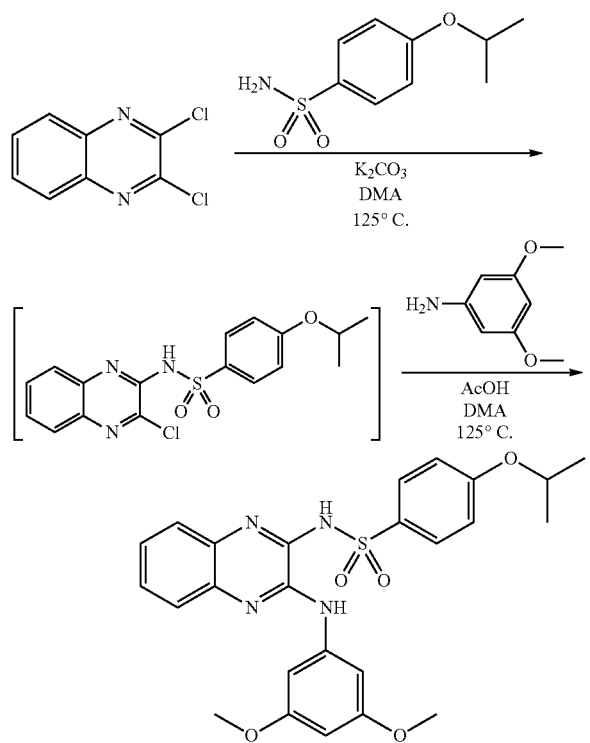

N-(3-(3,5-dimethoxy-phenylamino)quinoxalin-2-yl)-4-isopropoxybenzenesulfonamide A solution of 2,3-dichloroquinoxaline (2.0 mL, 0.38 M) was combined with K$_2$CO$_3$ (105 mg, 0.76 mmol) in a glass vial. A solution of 4-isopropoxybenzene sulfonamide (1.75 mL, 0.43 M) was added and the solution was stirred overnight at 125° C. After cooling, acetic acid (45 mL, 0.79 mmol) and 3,5-dimethoxyaniline (230 mg, 1.5 mmol) were added. The reaction mixture was stirred again at 125° C. overnight. Upon cooling, the reaction mixture was diluted with 8 mL of methanol and then 8 mL of water. The precipitate was collected by filtration and recrystallized from N,N-dimethylacetamide/water to give N-(3-(3,5-dimethoxy-phenylamino)quinoxalin-2-yl)-4-isopropoxy-benzenesulfonamide (45 mg, 12%). $^1$H-NMR (400 MHz, d$_6$-DMSO): 12.16 (bs, 1H), 8.93 (s, 1H), 8.03 (d, 2H), 7.92 (bs, 1H), 7.56 (d, 1H), 7.36 (m, 4H), 7.07 (d, 2H), 6.24 (s, 1H), 4.72 (m, 1H), 3.76 (s, 6H), 1.27 (d, 6H); MS (EI) m/z C$_{25}$H$_{26}$N$_4$O$_5$S: 495 (MH$^+$).

Examples 381-411 were synthesized proceeding as above in Example 423. In the cases where the product did not precipitate, the mixture was purified by reverse phase HPLC.

Example 381

3-chloro-N-(3-(3,5-dimethoxy-phenylamino)quinoxalin-2-yl)-4-methylbenzenesulfonamide $^1$H-NMR (400 MHz, d$_6$-DMSO): 12.31 (bs, 1H), 8.96 (s, 1H), 8.18 (s, 1H), 7.98 (d, 1H), 7.92 (bs, 1H), 7.58 (d, 2H), 7.43-7.33 (m, 4H), 6.24 (t, 1H), 3.76 (s, 6H), 2.39 (s, 3H); MS (EI) m/z C$_{23}$H$_{21}$ClN$_4$O$_4$S: 485 (MH$^+$).

Example 382

N-(3-(3,5-dimethoxy-phenylamino)quinoxalin-2-yl) naphthalene-1-sulfonamide

MS (EI) m/z C$_{26}$H$_{22}$N$_4$O$_4$S: 487 (MH$^+$).

Example 383

N-(3-(3,5-dimethoxy-phenylamino)quinoxalin-2-yl)-4-fluorobenzenesulfonamide

MS (EI) m/z C$_{22}$H$_{19}$FN$_4$O$_4$S: 455 (MH$^+$).

Example 384

N-(3-(3,5-dimethoxy-phenylamino)quinoxalin-2-yl)-3-fluorobenzenesulfonamide

MS (EI) m/z C$_{22}$H$_{19}$FN$_4$O$_4$S: 455 (MH$^+$).

Example 385

N-(3-(3,5-dimethoxy-phenylamino)quinoxalin-2-yl)-3-(trifluoromethyl)benzenesulfonamide MS (EI) m/z C$_{23}$H$_{19}$F$_3$N$_4$O$_4$S: 505 (MH$^+$).

Example 386

N-(3-(3,5-dimethoxy-phenylamino)quinoxalin-2-yl)-4-(trifluoromethyl)benzenesulfonamide MS (EI) m/z C$_{23}$H$_{19}$F$_3$N$_4$O$_4$S: 505 (MH$^+$).

Example 387

N-(3-(3,5-dimethoxy-phenylamino)quinoxalin-2-yl)-4-(trifluoromethoxy)benzenesulfonamide MS (EI) m/z $C_{23}H_{19}F_3N_4O_5S$: 521 (MH$^+$).

Example 388

N-(4-(N-(3-(3,5-dimethoxy-phenylamino)quinoxalin-2-yl)sulfamoyl)phenyl)acetamide MS (EI) m/z $C_{24}H_{23}N_5O_5S$: 494 (MH$^+$).

Example 389

N-(3-(3,5-dimethoxy-phenylamino)quinoxalin-2-yl)-4-fluoro-2-methylbenzenesulfonamide MS (EI) m/z $C_{23}H_{21}FN_4O_4S$: 469 (MH$^+$).

Example 390

N-(3-(3,5-dimethoxy-phenylamino)quinoxalin-2-yl)-2-methylbenzenesulfonamide

MS (EI) m/z $C_{23}H_{22}N_4O_4S$: 451 (MH$^+$).

Example 391

2-chloro-N-(3-(3,5-dimethoxy-phenylamino)quinoxalin-2-yl)benzenesulfonamide

MS (EI) m/z $C_{22}H_{19}ClN_4O_4S$: 471 (MH$^+$).

Example 392

N-(3-(3,5-dimethoxy-phenylamino)quinoxalin-2-yl)-3,5-difluorobenzenesulfonamide

MS (EI) m/z $C_{22}H_{18}F_2N_4O_4S$: 473 (MH$^+$).

Example 393

3,5-dichloro-N-(3-(3,5-dimethoxy-phenylamino)quinoxalin-2-yl)benzenesulfonamide

MS (EI) m/z $C_{22}H_{18}Cl_2N_4O_4S$: 505 (MH$^+$).

Example 394

N-(3-(3,5-dimethoxy-phenylamino)quinoxalin-2-yl)-3-fluoro-4-methylbenzenesulfonamide MS (EI) m/z $C_{23}H_{21}FN_4O_4S$: 469 (MH$^+$).

Example 395

N-(3-(3,5-dimethoxy-phenylamino)quinoxalin-2-yl)-2-(trifluoromethyl)benzenesulfonamide MS (EI) m/z $C_{23}H_{19}F_3N_4O_4S$: 505 (MH$^+$).

Example 396

4-cyano-N-(3-(3,5-dimethoxy-phenylamino)quinoxalin-2-yl)benzenesulfonamide

MS (EI) m/z $C_{23}H_{19}N_5O_4S$: 462 (MH$^+$).

Example 397

N-(3-(3,5-dimethoxy-phenylamino)quinoxalin-2-yl)-1-phenylmethanesulfonamide

MS (EI) m/z $C_{23}H_{22}N_4O_4S$: 451 (MH$^+$).

Example 398

4,5-dichloro-N-(3-(3,5-dimethoxy-phenylamino)quinoxalin-2-yl)thiophene-2-sulfonamide MS (EI) m/z $C_{20}H_{16}Cl_2N_4O_4S_2$: 511 (MH$^+$).

Example 399

1-(3-chlorophenyl)-N-(3-(3,5-dimethoxy-phenylamino)quinoxalin-2-yl)methanesulfonamide MS (EI) m/z $C_{23}H_{21}ClN_4O_4S$: 485 (MH$^+$).

Example 400

N-(3-(3,5-dimethoxy-phenylamino)quinoxalin-2-yl)-2,5-dimethylthiophene-3-sulfonamide MS (EI) m/z $C_{22}H_{22}N_4O_4S_2$: 471 (MH$^+$).

Example 401

N-(3-(3,5-dimethoxy-phenylamino)quinoxalin-2-yl)-3,5-bis(trifluoromethyl)benzenesulfonamide MS (EI) m/z $C_{24}H_{18}F_6N_4O_4S$: 573 (MH$^+$).

Example 402

N-(3-(3,5-dimethoxy-phenylamino)quinoxalin-2-yl)-4-fluoro-3-(trifluoromethyl)benzenesulfonamide MS (EI) m/z $C_{23}H_{18}F_4N_4O_4S$: 523 (MH$^+$).

Example 403

5-chloro-N-(3-(3,5-dimethoxy-phenylamino)quinoxalin-2-yl)-1,3-dimethyl-1H-pyrazole-4-sulfonamide MS (EI) m/z $C_{21}H_{21}ClN_6O_4S$: 489 (MH$^+$).

Example 404

5-chloro-N-(3-(3,5-dimethoxy-phenylamino)quinoxalin-2-yl)-2-methoxybenzenesulfonamide MS (EI) m/z $C_{23}H_{21}ClN_4O_5S$: 501 (MH$^+$).

Example 405

5-bromo-N-(3-(3,5-dimethoxy-phenylamino)quinoxalin-2-yl)-2-methoxybenzenesulfonamide MS (EI) m/z $C_{23}H_{21}BrN_4O_5S$: 545 (MH$^+$).

Example 406

2,5-dichloro-N-(3-(3,5-dimethoxy-phenylamino)quinoxalin-2-yl)thiophene-3-sulfonamide MS (EI) m/z $C_{20}H_{16}Cl_2N_4O_4S_2$: 511 (MH+).

Example 407

N-(3-(3,5-dimethoxy-phenylamino)quinoxalin-2-yl)-3,5-dimethylisoxazole-4-sulfonamide MS (EI) m/z $C_{21}H_{21}N_5O_5S$: 456 (MH+).

Example 408

N-(3-(3,5-dimethoxy-phenylamino)quinoxalin-2-yl)-2,5-dimethoxybenzenesulfonamide MS (EI) m/z $C_{24}H_{24}N_4O_6S$: 497 (MH+).

Example 409

3-chloro-N-(3-(3,5-dimethoxy-phenylamino)quinoxalin-2-yl)-4-fluorobenzenesulfonamide MS (EI) m/z $C_{22}H_{18}ClFN_4O_4S$: 489 (MH+).

Example 410

4-(difluoromethoxy)-N-(3-(3,5-dimethoxy-phenylamino)quinoxalin-2-yl)benzenesulfonamide MS (EI) m/z $C_{23}H_{20}F_2N_4O_5S$: 503 (MIT).

Example 411

N-(3-(3,5-dimethoxy-phenylamino)quinoxalin-2-yl)-3-(methylsulfonyl)benzenesulfonamide MS (EI) m/z $C_{23}H_{22}N_4O_6S_2$: 515 (MH+).

General Acylation Procedure 2

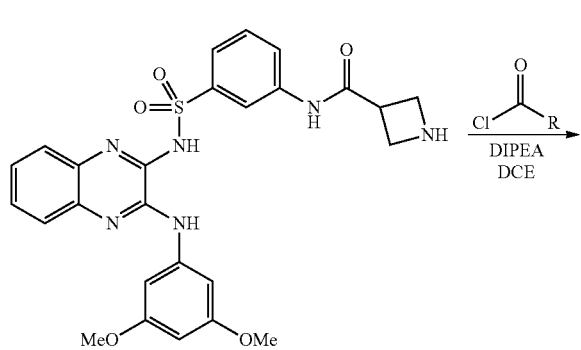

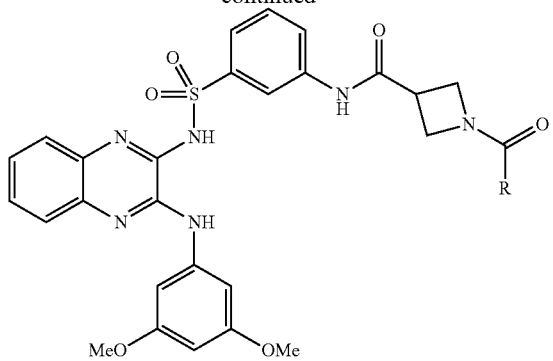

N-(3-(N-(3-(3,5-dimethoxy-phenylamino)quinoxalin-2-yl)-sulfamoyl)phenyl)azetidine-3-carboxamide (125 mg, 0.23 mmol), prepared using procedures similar to those described in Example 372, was dissolved into 5 mL DCE in a 10 mL round-bottom flask. DIEA (1.17 mmol, 5.0 equiv.) was then added with stirring followed by acid chloride (0.47 mmol, 2.0 equiv.). The reaction was then stirred at room temperature for 1 hour or until complete as indicated by LCMS. The solvent was subsequently removed under reduced pressure on a rotary evaporator. The crude material was then redissolved in methanol. Purification of the final product was accomplished by preparatory reverse-phase HPLC with the eluents 25 mM aqueous NH$_4$OAc/CAN. A Waters Fractionlynx preparative reverse-phase HPLC; equipped with a Waters SunFire Prep C18, OCD 5 µM, 30×70 mm column and running a 5-100% gradient with a binary solvent system of 25 mM ammonium acetate in water/acetonitrile; was used to carry out the purification.

The following compounds were prepared according to General Acylation Procedure 2.

Example 412

N-(3-(N-(3-(3,5-dimethoxy-phenylamino)quinoxalin-2-yl)sulfamoyl)phenyl)-1-propionylazetidine-3-carboxamide $^1$H-NMR (400 MHz, d$_6$-DMSO): 12.40 (s, 1H), 10.45 (s, 1H), 8.88 (s, 1H), 8.40 (s, 1H), 7.93 (s, 1H), 7.82 (d, 1H), 7.77 (d, 1H), 7.60-7.45 (m, 2H), 7.41-7.30 (m, 4H), 6.24 (s, 1H), 4.26 (t, 1H), 4.22-4.17 (m, 1H), 3.99 (t, 1H), 3.95-3.89 (m, 1H), 3.76 (s, 6H), 3.59-3.45 (m, 1H), 2.05 (dd, 2H), 0.95 (t, 3H); MS (EI) m/z $C_{29}H_{30}N_6O_6S$: 591 (MH+).

Example 413

1-acetyl-N-(3-{[(3-{[3,5-bis(methoxy)-phenyl]amino}quinoxalin-2-yl)amino]sulfonyl}phenyl)azetidine-3-carboxamide MS (EI) m/z $C_{28}H_{28}N_6O_6S$: 577 (MH+).

Example 414

1-(cyclopropanecarbonyl)-N-(3-(N-(3-(3,5-dimethoxy-phenylamino)quinoxalin-2-yl)sulfamoyl)phenyl)azetidine-3-carboxamide MS (EI) m/z $C_{30}H_{30}N_6O_6S$: 603 (MH+).

General Reductive Amination Procedure 1

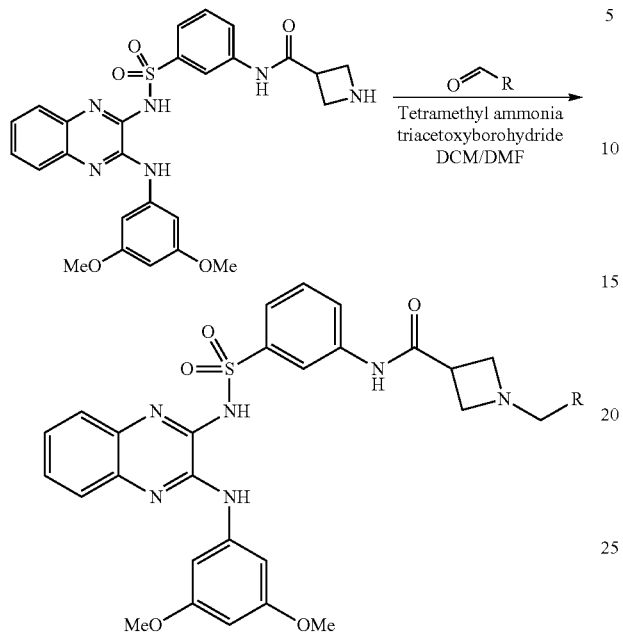

To a solution of N-(3-(N-(3-(3,5-dimethoxy-phenylamino)quinoxalin-2-yl)sulfamoyl)phenyl)azetidine-3-carboxamide (110 mg, 0.19 mmol), prepared using procedures similar to those described in Example 372, in 3 mL of DCE and 200 μL of DMF, aldehyde (0.77 mmol, 4.0 eq.) was added slowly followed by tetramethylammonium triacetoxyborohydride (1.16 mmol, 6.0 eq). The reaction was stirred at room temperature overnight. LC/MS indicated the reaction was completed. The solvent was subsequently removed under reduced pressure on a rotary evaporator. The crude material was then redissolved in methanol. Purification of the final product was accomplished by preparatory reverse-phase HPLC with the eluents 25 mM aqueous NH$_4$OAc/CAN. A Waters Fractionlynx preparative reverse-phase HPLC; equipped with a Waters SunFire Prep C18, OCD 5 μM, 30×70 mm column and running a 5-100% gradient with a binary solvent system of 25 mM ammonium acetate in water/acetonitrile; was used to carry out the purification.

The following title compounds were prepared according to General Reductive Amination Procedure 1.

Example 415

N-(3-(N-(3-(3,5-dimethoxy-phenylamino)quinoxalin-2-yl)sulfamoyl)phenyl)-1-ethylazetidine-3-carboxamide $^1$H-NMR (400 MHz, d$_6$-DMSO): 10.29 (s, 1H), 8.82 (s, 1H), 8.25 (t, 1H), 7.75-7.68 (m, 2H), 7.43-7.38 (m, 1H), 7.375-7.340 (m, 1H), 7.338-7.310 (d, 2H), 7.305-7.262 (m, 1H), 7.15-7.08 (m, 2H), 6.56 (s, 1H), 6.15 (t, 1H), 4.15-4.08 (m, 2H), 4.06-3.95 (m, 2H), 3.78 (s, 6H), 3.65-3.56 (m, 1H), 3.12-3.04 (m, 2H), 1.03 (t, 3H); MS (EI) m/z C$_{28}$H$_{30}$N$_6$O$_5$S: 563 (MH$^+$).

Example 416

1-(cyclopropylmethyl)-N-(3-(N-(3-(3,5-dimethoxy-phenylamino)quinoxalin-2-yl)sulfamoyl)phenyl)azetidine-3-carboxamide MS (EI) m/z C$_{30}$H$_{32}$N$_6$O$_5$S: 589 (MH$^+$).

Example 417

1-benzyl-N-(3-(N-(3-(3,5-dimethoxy-phenylamino)quinoxalin-2-yl)sulfamoyl)phenyl)azetidine-3-carboxamide MS (EI) m/z C$_{33}$H$_{32}$N$_6$O$_5$S: 625 (MH$^+$).

Example 418

N-(3-(N-(3-(3,5-dimethoxy-phenylamino)quinoxalin-2-yl)sulfamoyl)phenyl)-1-(furan-2-ylmethyl)azetidine-3-carboxamide MS (EI) m/z C$_{31}$H$_{30}$N$_6$O$_6$S: 615 (MH$^+$).

Example 419

1-((1H-imidazol-5-yl)methyl)-N-(3-(N-(3-(3,5-dimethoxy-phenylamino)quinoxalin-2-yl)sulfamoyl)phenyl)azetidine-3-carboxamide MS (EI) m/z C$_{30}$H$_{30}$N$_8$O$_5$S: 615 (MH$^+$).

General Amide Formation Procedure 1a

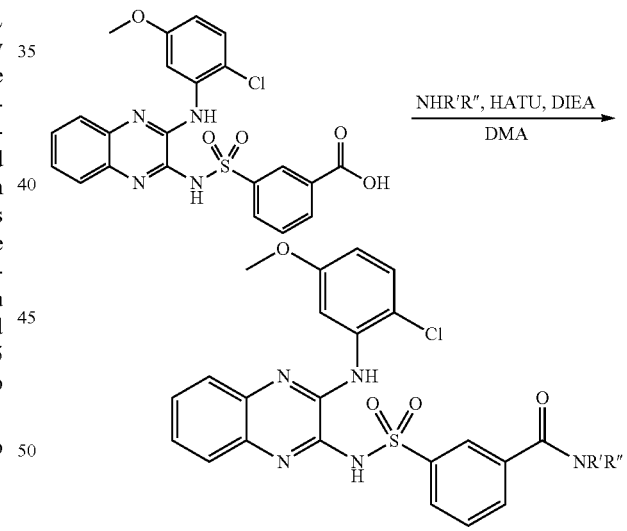

Into a small 1 dram vial was added 3-(N-(3-(2-chloro-5-methoxy-phenylamino)-quinoxalin-2-yl)sulfamoyl)benzoic acid (61 mg, 0.13 mmol, 1.1 equiv), prepared using procedures described for Example 100. The acid was dissolved in DMA (1 mL) and DIEA (42 μL, 0.24 mmol, 2 equiv) was added then added to the solution. The amine reagent (1 mL of 0.12 M solution in DMA) was added to solution with stirring followed by HATU (64 mg, 0.17 mmol, 1.4 equiv). The reaction was stirred overnight at room temperature. Upon completion as indicated by LCMS analysis, 2 mL of methanol was added to the solution. Preparative reverse-phase HPLC was used to isolate the desired product. A Waters Fractionlynx preparative reverse-phase HPLC—equipped with a Waters SunFire Prep C18, OCD 5 μM, 30×70 mm column and running a 5-100% gradient with a binary solvent system of 25 mM ammonium acetate in water/acetonitrile—was used to carry out the purification.

The following compounds were prepared according to General Amide Formation Procedure 1.

Example 420

3-(N-(3-(2-chloro-5-methoxy-phenylamino)quinoxalin-2-yl)sulfamoyl)-N-(3-(dimethylamino)propyl)benzamide 3-(N-(3-(2-chloro-5-methoxyphenylamino)quinoxalin-2-yl)sulfamoyl)-N-(3-(dimethylamino)propyl)benzamide: $^1$H NMR (400 MHz, d$_6$-DMSO): 9.44 (s, 1H), 8.94 (s, 1H), 8.79 (t, 1H), 8.54 (s, 1H), 8.24 (d, 1H), 7.87 (d, 1H), 7.48 (m, 3H), 7.33 (d, 1H), 7.18 (m, 2H), 6.60 (dd, 1H), 3.82 (1H), 3.04 (m, 3H), 2.51 (m, 5H), 1.91 (s, 1H), 1.86 (m, 3H); MS (EI) m/z for $C_{27}H_{29}ClN_6O_4S$: 569 (MH$^+$).

Example 421

3-(N-(3-(2-chloro-5-methoxy-phenylamino)quinoxalin-2-yl)sulfamoyl)-N-(1-methylazetidin-3-yl)benzamide 3-(N-(3-(2-chloro-5-methoxyphenylamino)quinoxalin-2-yl)sulfamoyl)-N-(1-methylazetidin-3-yl)benzamide: $^1$H NMR (400 MHz, d$_6$-DMSO): 9.43 (s, 1H), 9.23 (d, 1H), 8.94 (d, 1H), 8.58 (s, 1H), 8.29 (d, 1H), 7.89 (d, 1H), 7.56 (t, 1H), 7.47 (d, 1H), 7.44 (d, 1H), 7.33 (d, 1H), 7.18 (m, 2H), 6.60 (dd, 1H), 4.81 (m, 1H), 4.33 (m, 2H), 4.19 (m, 2H), 3.82 (s, 1H), 2.51 (s, 3H); MS (EI) m/z for $C_{26}H_{25}ClN_6O_4S$: 553 (MH$^+$).

Example 422

3-(N-(3-(2-chloro-5-methoxy-phenylamino)quinoxalin-2-yl)sulfamoyl)-N-(pyridin-4-ylmethyl)benzamide MS (EI) m/z $C_{28}H_{23}ClN_6O_4S$: 575 (MH$^+$).

Example 423

3-(N-(3-(2-chloro-5-methoxy-phenylamino)quinoxalin-2-yl)sulfamoyl)-N-(3-(dimethylamino)propyl)benzamide MS (EI) m/z $C_{28}H_{26}ClN_7O_4S$: 592 (MH$^+$).

Example 424

N-(3-(2-chloro-5-methoxy-phenylamino)quinoxalin-2-yl)-3-(2,2-dimethylhydrazinecarbonyl)benzenesulfonamide MS (EI) m/z $C_{24}H_{23}ClN_6O_4S$: 527 (MH$^+$).

Example 425

3-(N-(3-(2-chloro-5-methoxy-phenylamino)quinoxalin-2-yl)sulfamoyl)-N-(2-methoxyethyl)benzamide MS (EI) m/z $C_{25}H_{24}ClN_5O_5S$: 542 (MH$^+$).

Example 426

N-(3-(2-chloro-5-methoxy-phenylamino)quinoxalin-2-yl)-3-(4-methylpiperazine-1-carbonyl)benzenesulfonamide MS (EI) m/z $C_{27}H_{27}ClN_6O_4S$: 567 (MH$^+$).

Example 427

3-(N-(3-(2-chloro-5-methoxy-phenylamino)quinoxalin-2-yl)sulfamoyl)-N-(2-(pyrrolidin-1-yl)ethyl)benzamide MS (EI) m/z $C_{28}H_{29}ClN_6O_4S$: 581 (MH$^+$).

Example 428

3-(N-(3-(2-chloro-5-methoxy-phenylamino)quinoxalin-2-yl)sulfamoyl)-N-(2-(pyridin-4-yl)ethyl)benzamide MS (EI) m/z $C_{29}H_{25}ClN_6O_4S$: 589 (MH$^+$).

Example 429

N-(2-(1H-imidazol-4-yl)ethyl)-3-(N-(3-(2-chloro-5-methoxyphenylamino)quinoxalin-2-yl)sulfamoyl)benzamide MS (EI) m/z $C_{27}H_{24}ClN_7O_4S$: 578 (MH$^+$).

Example 430

3-(N-(3-(2-chloro-5-methoxy-phenylamino)quinoxalin-2-yl)sulfamoyl)-N-(piperidin-1-yl)benzamide MS (EI) m/z $C_{27}H_{27}ClN_6O_4S$: 567 (MH$^+$).

Example 431

3-(N-(3-(2-chloro-5-methoxy-phenylamino)quinoxalin-2-yl)sulfamoyl)-N-(2-hydroxyethyl)benzamide MS (EI) m/z $C_{24}H_{22}ClN_5O_5S$: 528 (MH$^+$).

Example 432

3-(N-(3-(2-chloro-5-methoxy-phenylamino)quinoxalin-2-yl)sulfamoyl)-N-(3-ethoxypropyl)benzamide MS (EI) m/z $C_{27}H_{28}ClN_5O_5S$: 570 (MH$^+$).

Example 433

3-(N-(3-(2-chloro-5-methoxy-phenylamino)quinoxalin-2-yl)sulfamoyl)-N-(3-(pyrrolidin-1-yl)propyl)benzamide MS (EI) m/z $C_{29}H_{31}ClN_6O_4S$: 595 (MH$^+$).

Example 434

3-(N-(3-(2-chloro-5-methoxy-phenylamino)quinoxalin-2-yl)sulfamoyl)-N-(3-(diethylamino)propyl)benzamide MS (EI) m/z $C_{29}H_{33}ClN_6O_4S$: 597 (MH$^+$).

Example 435

3-(N-(3-(2-chloro-5-methoxy-phenylamino)quinoxalin-2-yl)sulfamoyl)-N-(3-(2-oxopyrrolidin-1-yl)propyl)benzamide MS (EI) m/z $C_{29}H_{29}ClN_6O_5S$: 609 (MH$^+$).

Example 436

3-(N-(3-(2-chloro-5-methoxy-phenylamino)quinoxalin-2-yl)sulfamoyl)-N-(pyridin-2-ylmethyl)benzamide MS (EI) m/z $C_{28}H_{23}ClN_6O_4S$: 575 (MH$^+$).

Example 437

3-(N-(3-(2-chloro-5-methoxy-phenylamino)quinoxalin-2-yl)sulfamoyl)-N-(2-cyanoethyl)-N-methylbenzamide MS (EI) m/z $C_{26}H_{23}ClN_6O_4S$: 551 (MH$^+$).

Example 438

3-(N-(3-(2-chloro-5-methoxyphenylamino)quinoxalin-2-yl)sulfamoyl)-N-(2-cyanoethyl)-N-ethylbenzamide MS (EI) m/z $C_{27}H_{25}ClN_6O_4S$: 565 (MH$^+$).

Example 439

3-(N-(3-(2-chloro-5-methoxy-phenylamino)quinoxalin-2-yl)sulfamoyl)-N-(2-(ethylthio)ethyl)benzamide MS (EI) m/z $C_{26}H_{26}ClN_5O_4S_2$: 572 (MH$^+$).

Example 440

3-(N-(3-(2-chloro-5-methoxy-phenylamino)quinoxalin-2-yl)sulfamoyl)-N-(3-propoxypropyl)benzamide MS (EI) m/z $C_{28}H_{30}ClN_5O_5S$: 584 (MH$^+$).

Example 441

3-(N-(3-(2-chloro-5-methoxy-phenylamino)quinoxalin-2-yl)sulfamoyl)-N-(5-(diethylamino)pentan-2-yl)benzamide MS (EI) m/z $C_{31}H_{37}ClN_6O_4S$: 625 (MH$^+$).

Example 442

3-(N-(3-(2-chloro-5-methoxy-phenylamino)quinoxalin-2-yl)sulfamoyl)-N-(3-methoxypropyl)benzamide MS (EI) m/z $C_{26}H_{26}ClN_5O_5S$: 556 (MH$^+$).

Example 443

3-(N-(3-(2-chloro-5-methoxy-phenylamino)quinoxalin-2-yl)sulfamoyl)-N-(3-morpholinopropyl)benzamide MS (EI) m/z $C_{29}H_{31}ClN_6O_5S$: 611 (MH$^+$).

Example 444

3-(N-(3-(2-chloro-5-methoxy-phenylamino)quinoxalin-2-yl)sulfamoyl)-N-(pyridin-3-ylmethyl)benzamide MS (EI) m/z $C_{28}H_{23}ClN_6O_4S$: 575 (MH$^+$)

Example 445

3-(N-(3-(2-chloro-5-methoxyphenylamino)quinoxalin-2-yl)sulfamoyl)-N-(2-cyanoethyl)benzamide
MS (EI) m/z $C_{25}H_{21}ClN_6O_4S$: 537 (MH$^+$).

Example 446

3-(N-(3-(2-chloro-5-methoxy-phenylamino)quinoxalin-2-yl)sulfamoyl)-N-(1-methoxypropan-2-yl)benzamide MS (EI) m/z $C_{26}H_{26}ClN_5O_5S$: 556 (MH$^+$).

Example 447

3-(N-(3-(2-chloro-5-methoxy-phenylamino)quinoxalin-2-yl)sulfamoyl)-N-(2-(methylthio)ethyl)benzamide MS (EI) m/z $C_{25}H_{24}ClN_5O_4S_2$: 558 (MH$^+$).

Example 448

3-(N-(3-(2-chloro-5-methoxy-phenylamino)quinoxalin-2-yl)sulfamoyl)-N-(3-(dimethylamino)propyl)-N-methylbenzamide MS (EI) m/z $C_{28}H_{31}ClN_6O_4S$: 583 (MH$^+$).

Example 449

3-(N-(3-(2-chloro-5-methoxy-phenylamino)quinoxalin-2-yl)sulfamoyl)-N-(3-isopropoxypropyl)benzamide MS (EI) m/z $C_{28}H_{30}ClN_5O_5S$: 584 (MH$^+$).

Example 450

3-(N-(3-(2-chloro-5-methoxy-phenylamino)quinoxalin-2-yl)sulfamoyl)-N-(2-(dimethylamino)ethyl)-N-ethylbenzamide MS (EI) m/z $C_{28}H_{31}ClN_6O_4S$: 583 (MH$^+$).

Example 451

N-(3-butoxypropyl)-3-(N-(3-(2-chloro-5-methoxyphenylamino)quinoxalin-2-yl)sulfamoyl)benzamide MS (EI) m/z $C_{29}H_{32}ClN_5O_5S$: 598 (MH$^+$).

Example 452

3-(N-(3-(2-chloro-5-methoxy-phenylamino)quinoxalin-2-yl)sulfamoyl)-N-(2-(diethylamino)ethyl)benzamide MS (EI) m/z $C_{28}H_{31}ClN_6O_4S$: 583 (MH$^+$).

Example 453 methyl 3-(3-(N-(3-(2-chloro-5-methoxy-phenylamino)quinoxalin-2-yl)sulfamoyl)benzamido)propanoate. MS (EI) m/z $C_{26}H_{24}ClN_5O_6S$: 570 (MH$^+$)

Example 454

3-(N-(3-(2-chloro-5-methoxy-phenylamino)quinoxalin-2-yl)sulfamoyl)-N-methyl-N-propylbenzamide MS (EI) m/z $C_{26}H_{26}ClN_5O_4S$: 540 (MH$^+$).

Example 455 ethyl 3-(3-(N-(3-(2-chloro-5-methoxy-phenylamino)quinoxalin-2-yl)sulfamoyl)benzamido)propanoate MS (EI) m/z $C_{27}H_{26}ClN_5O_6S$: 584 (MH$^+$).

Example 456

3-(N-(3-(2-chloro-5-methoxy-phenylamino)quinoxalin-2-yl)sulfamoyl)-N-(2-(piperidin-1-yl)ethyl)benzamide MS (EI) m/z $C_{29}H_{31}ClN_6O_4S$: 595 (MH$^+$).

Example 457

3-(N-(3-(2-chloro-5-methoxy-phenylamino)quinoxalin-2-yl)sulfamoyl)-N-((1-ethylpyrrolidin-2-yl)methyl)benzamide MS (EI) m/z $C_{29}H_{31}ClN_6O_4S$: 595 (MH$^+$).

Example 458

N-(2-(bis(2-hydroxyethyl)amino)ethyl)-3-(N-(3-(2-chloro-5-methoxyphenylamino)quinoxalin-2-yl)sulfamoyl)benzamide MS (EI) m/z $C_{28}H_3ClN_6O_6S$: 615 (MH$^+$).

Example 459

N-(3-(2-chloro-5-methoxy-phenylamino)quinoxalin-2-yl)-3-(3-(diethylamino)pyrrolidine-1-carbonyl)benzenesulfonamide MS (EI) m/z $C_{30}H_{33}ClN_6O_4S$: 609 (MH$^+$).

Example 460

3-(N-(3-(2-chloro-5-methoxy-phenylamino)quinoxalin-2-yl)sulfamoyl)-N-methyl-N-(1-methylpyrrolidin-3-yl)benzamide MS (EI) m/z $C_{28}H_{29}ClN_6O_4S$: 581 (MH$^+$).

Example 461

N-(3-(2-chloro-5-methoxy-phenylamino)quinoxalin-2-yl)-3-(3-(dimethylamino)pyrrolidine-1-carbonyl)benzenesulfonamide MS (EI) m/z $C_{28}H_{29}ClN_6O_4S$: 581 (MH$^+$).

Example 462

3-(N-(3-(2-chloro-5-methoxy-phenylamino)quinoxalin-2-yl)sulfamoyl)-N-(2-methyl-1-morpholinopropan-2-yl)benzamide MS (EI) m/z $C_{30}H_{33}ClN_6O_5S$: 625 (MH$^+$).

Example 463

3-(N-(3-(2-chloro-5-methoxy-phenylamino)quinoxalin-2-yl)sulfamoyl)-N-(1H-pyrrol-1-yl)benzamide MS (EI) m/z $C_{26}H_{21}ClN_6O_4S$: 549 (MH$^+$).

Example 464

3-(N-(3-(2-chloro-5-methoxy-phenylamino)quinoxalin-2-yl)sulfamoyl)-N-(3-oxopyrazolidin-4-yl)benzamide MS (EI) m/z $C_{25}H_{22}ClN_7O_5S$: 568 (MH$^+$).

Example 465

N-(3-(2-chloro-5-methoxy-phenylamino)quinoxalin-2-yl)-3-(2-((dimethylamino)methyl)piperidine-1-carbonyl)benzenesulfonamide MS (EI) m/z $C_{30}H_{33}ClN_6O_4S$: 609 (MH$^+$).

Example 466

N-(3-(2-chloro-5-methoxy-phenylamino)quinoxalin-2-yl)-3-(2-(piperidin-1-ylmethyl)piperidine-1-carbonyl)benzenesulfonamide MS (EI) m/z $C_{33}H_{37}ClN_6O_4S$: 649 (MH$^+$).

Example 467

3-(N-(3-(2-chloro-5-methoxy-phenylamino)quinoxalin-2-yl)sulfamoyl)-N-(1-ethylpiperidin-3-yl)benzamide MS (EI) m/z $C_{29}H_{31}ClN_6O_4S$: 595 (MH$^+$).

General Amide Formation Procedure 1b

The procedure outlined in General Amide Formation Procedure 1a was used to incorporate a number of amines that contained a second amine group protected as the tert-butylcarbamate (i.e. where R', within NHR'R", contained a Boc-protected amine group). The deprotection was carried out after HPLC purification of the Boc-protected precursor.

Into a small 1 dram vial was added 3-(N-(3-(2-chloro-5-methoxy-phenylamino)quinoxalin-2-yl)sulfamoyl)benzoic acid (61 mg, 0.13 mmol, 1.1 equiv). The acid was dissolved in 1 mL of DMA and DIEA (42 µL, 0.24 mmol, 2 equiv) was added then added to the solution. The mono-Boc-protected diamine reagent (1 mL of 0.12 M solution in DMA, 1 equiv) was added to solution with stirring followed by HATU (64 mg, 0.17 mmol, 1.4 equiv). The reaction was stirred overnight at room temperature. Upon completion as indicated by LCMS analysis, 2 mL of methanol was added to the solution. Preparative reverse-phase HPLC was used to isolate the desired product directly from this crude reaction solution. A Waters Fractionlynx preparative reverse-phase HPLC; equipped with a Waters SunFire Prep C18, OCD 5 µM, 30×70 mm column and running a 5-100% gradient with a binary solvent system of 25 mM ammonium acetate in water/acetonitrile; was used to carry out the purification. The product fractions were combined and concentrated to dryness under reduced pressure by rotary evaporation. A solution of 4 N HCl in dioxane (2 mL) was added. The solution was then stirred at room temperature until no starting material was detected. The deprotected product precipitated out of solution as an HCL salt and was collected by filtration, washed with ether and dried under vacuum.

The following compounds were prepared according to the above General Amide Formation Procedure 1b.

Example 468

3-(N-(3-(2-chloro-5-methoxy-phenylamino)quinoxalin-2-yl)sulfamoyl)-N-(piperidin-3-yl)benzamide 3-(N-(3-(2-chloro-5-methoxyphenylamino)quinoxalin-2-yl)sulfamoyl)-N-(piperidin-3-yl)benzamide: $^1$H NMR (400 MHz, $d_6$-DMSO): 12.82 (s, 1H), 9.12 (s, 1H), 9.04 (s, 1H), 8.85 (d, 1H), 8.65 (s, 1H), 8.55 (s, 1H), 8.18 (m, 1H), 7.98 (s, 1H), 7.69 (m, 2H), 7.43 (m, 2H), 6.69 (dd, 1H), 4.21 (s, 1H), 3.83 (s, 3H), 3.69 (m, 1H), 3.48 (m, 1H), 3.18 (s, 1H), 2.84 (q, 2H), 1.91 (s, 2H); MS (EI) m/z for $C_{27}H_{27}ClN_6O_4S$: 567 (MH$^+$).

Example 469

3-(N-(3-(2-chloro-5-methoxy-phenylamino)quinoxalin-2-yl)sulfamoyl)-N-(piperidin-2-ylmethyl)benzamide 3-(N-(3-(2-chloro-5-methoxyphenylamino)quinoxalin-2-yl)sulfamoyl)-N-(piperidin-2-ylmethyl)benzamide: NMR (400 MHz, $d_6$-DMSO): 12.78 (s, 1H), 9.16 (s, 1H), 9.09 (s, 1H), 8.79 (s, 1H), 8.59 (d, 2H), 8.22 (t, 2H), 7.99 (s, 1H), 7.74 (t, 1H), 7.66 (s, 1H), 7.42 (m, 2H), 6.69 (dd, 1H), 3.82 (s, 3H), 3.69 (dd, 1H), 3.57 (m, 1H), 3.50 (m, 3H), 3.22 (s, 2H), 2.82 (d, 1H), 1.68 (m, 5H); MS (EI) m/z for $C_{28}H_{29}ClN_6O_4S$: 581 (MH$^+$).

Example 470

3-(3-aminopyrrolidine-1-carbonyl)-N-(3-(2-chloro-5-methoxy-phenylamino)quinoxalin-2-yl)benzenesulfonamide MS (EI) m/z $C_{26}H_{25}ClN_6O_4S$: 553 (MH$^+$).

Example 471

3-(3-aminoazetidine-1-carbonyl)-N-(3-(2-chloro-5-methoxy-phenylamino)quinoxalin-2-yl)benzenesulfonamide MS (EI) m/z $C_{25}H_{23}ClN_6O_4S$: 539 (MH$^+$).

Example 472

3-(3-aminopiperidine-1-carbonyl)-N-(3-(2-chloro-5-methoxy-phenylamino)quinoxalin-2-yl)benzenesulfonamide MS (EI) m/z $C_{27}H_{27}ClN_6O_4S$: 567 (MH$^+$).

Example 473

3-(N-(3-(2-chloro-5-methoxy-phenylamino)quinoxalin-2-yl)sulfamoyl)-N-(pyrrolidin-3-yl)benzamide MS (EI) m/z $C_{26}H_{25}ClN_6O_4S$: 553 (MH$^+$).

Example 474

N-(3-(2-chloro-5-methoxy-phenylamino)quinoxalin-2-yl)-3-(3-(methylamino)pyrrolidine-1-carbonyl)benzenesulfonamide MS (EI) m/z $C_{27}H_{27}ClN_6O_4S$: 567 (MH$^+$).

Example 475

N-(2-aminoethyl)-3-(N-(3-(2-chloro-5-methoxy-phenylamino)quinoxalin-2-yl)sulfamoyl)benzamide MS (EI) m/z $C_{24}H_{23}ClN_6O_4S$: 527 (MH$^+$).

Example 476

3-(4-amino-3-oxopyrazolidine-1-carbonyl)-N-(3-(2-chloro-5-methoxyphenylamino)quinoxalin-2-yl)benzenesulfonamide MS (EI) m/z $C_{25}H_{22}ClN_7O_5S$: 568 (MH$^+$).

Example 477

3-(N-(3-(2-chloro-5-methoxyphenylamino)quinoxalin-2-yl)sulfamoyl)-N-((1-methylpiperidin-2-yl)methyl)benzamide 3-(N-(3-(2-chloro-5-methoxyphenylamino)quinoxalin-2-yl)sulfamoyl)-N-(piperidin-2-ylmethyl)benzamide (299 mg, 0.51 mmol, 1 equiv), prepared using procedures similar to those described for Example 514, was dissolved in 2.3 mL of DMA. Formic acid (388 µL, 10.28 mmol, 20 equiv) was added to solution with stirring followed by the addition of formaldehyde (508 µL of 37% aq. solution). The reaction was then stirred at room temperature overnight. Analysis of an aliquot of the reaction mixture by LCMS indicated the complete consumption of starting material. The reaction was diluted with methanol (2 mL). Preparative reverse-phase HPLC was used to isolate the desired product directly from the crude reaction mixture. A Waters Fractionlynx preparative reverse-phase HPLC; equipped with a Waters SunFire Prep C18, OCD 5 µM, 30×70 mm column and running a 5-100% gradient with a binary solvent system of 25 mM ammonium acetate in water/acetonitrile; was used to carry out the purification. $^1$H NMR (400 MHz, $d_6$-DMSO): 9.44 (s, 1H), 8.94 (s, 1H), 8.79 (t, 1H), 8.57 (s, 1H), 8.27 (d, 1H), 7.90 (d, 1H) 7.54 (t, 1H), 7.46 (d, 1H), 7.39 (d, 1H), 7.33 (d, 1H), 7.18 (m, 2H), 6.60 (dd, 1H), 3.82 (s, 3H), 3.59 (m, 2H), 3.00 (s, 1H), 2.90 (s, 3H), 1.62 (m, 7H); MS (EI) m/z for $C_{29}H_{31}ClN_6O_4S$: 595 (MH$^+$).

Example 478

3-(N-(3-(2-chloro-5-methoxyphenylamino)quinoxalin-2-yl)sulfamoyl)-N-(1-methylpiperidin-3-yl)benzamide The title compound was prepared using similar procedures to those used in Example 522. $^1$H NMR (400 MHz, $d_6$-DMSO): 9.43 (s, 1H), 8.93 (s, 1H), 8.59 (s, 1H), 8.24 (d, 1H), 7.87 (d, 1H), 7.47 (m, 2H), 7.40 (d, 1H), 7.33 (d, 1H), 7.19 (m, 2H), 6.60 (dd, 1H), 4.21 (s, 1H), 3.82 (s, 1H), 2.76 (s, 1H), 2.50 (m, 7H), 1.91 (m, 2H), 1.63 (m, 2H); MS (EI) m/z for $C_{28}H_{29}ClN_6O_4S$: 581 (MH$^+$).

BIOLOGICAL EXAMPLES

Biological Example 1

PI3Kalpha Luciferase-Coupled Chemiluminescence Assay Protocol

PI3Kα activity is measured as the percent of ATP consumed following the kinase reaction using luciferase-luciferin-coupled chemiluminescence. Reactions were conducted in 384-well white, medium binding microtiter plates (Greiner). Kinase reactions were initiated by combining test compounds, ATP, substrate (PIP2), and kinase in a 20 μL volume in a buffer solution. The standard PI3Kalpha assay buffer is composed 50 mM Tris, pH 7.5, 1 mM EGTA, 10 mM $MgCl_2$, 1 mM DTT and 0.03% CHAPS. The standard assay concentrations for enzyme, ATP, and substrate are 0.5-1.1 nM, 1 μM, and 7.5 μM, respectively. The reaction mixture was incubated at ambient temperature for approximately 2 h. Following the kinase reaction, a 100 μL aliquot of luciferase-luciferin mix (Promega Kinase-Glo) was added and the chemiluminescence signal measured using a Victor2 plate reader (Perkin Elmer). Total ATP consumption was limited to 40-60% and $IC_{50}$ values of control compounds correlate well with literature references.

Certain compounds of the invention demonstrated the ability to bind to PI3K when tested in this assay. The following embodiments are directed to the compounds themselves as well as their use in a method of treating. For example, in one embodiment of the invention, the PI3K inhibitor is selected from the compounds in Table 1 having a PI3K-binding affinity of about 8 μM or less. In another embodiment, the PI3K inhibitor is selected from the compounds in Table 1 having a PI3K-binding affinity of about 4 μM or less. In another embodiment, the PI3K inhibitor is selected from the compounds in Table 1 having a PI3K-binding affinity of about 3 μM or less. In another embodiment, the PI3K inhibitor is selected from the compounds in Table 1 having a PI3K-binding affinity of about 2 μM or less. In another embodiment, the PI3K inhibitor is selected from the compounds in Table 1 having a PI3K-binding affinity of about 1.5 μM or less. In another embodiment, the PI3K inhibitor is selected from the compounds in Table 1 having a PI3K-binding affinity of about 1.5 μM or less. In another embodiment, the PI3K inhibitor is selected from the compounds in Table 1 having a PI3K-binding affinity of about 0.750 μM or less. In another embodiment, the PI3K inhibitor is selected from the compounds in Table 1 having a PI3K-binding affinity of about 0.5 μM or less. In another embodiment, the PI3K inhibitor is selected from the compounds in Table 1 having a PI3K-binding affinity of about 0.3 μM or less. In another embodiment, the PI3K inhibitor is selected from the compounds in Table 1 having a PI3K-binding affinity of about 0.2 μM or less. In another embodiment, the PI3K inhibitor is selected from the compounds in Table 1 having a PI3K-binding affinity of about 0.1 μM or less. In another embodiment, the PI3K inhibitor is selected from the compounds in Table 1 having a PI3K-binding affinity of about 0.075 μM or less. In another embodiment, the PI3K inhibitor is selected from the compounds in Table 1 having a PI3K-binding affinity of about 0.050 μM or less.

Biological Example 2

Phospho AKT Assay

PC-3 cells were seeded on 6-well plates at 150,000 cells/well. Cells were cultured for 3 days, then treated with compounds in serum-free medium for 3 hr. EGF (100 ng/ml) was added for the last 10 min. Cells were lysed in TENN buffer. Phospho T308 Akt and total Akt were quantfied by ELISA performed according to the Biosource assay protocol. The readings of phospho Akt were normalized to total Akt readings.

Biological Example 3

Phospho S6 Assay

PC-3 cells were seeded on 96-well plates at 8,000 cells/well. For each experiment, cells were seeded and treated in duplicated plates: one plate for phospho S6 CellELISA, and one plate for total S6 CellELISA. Cells were cultured on the plates for 3 days, then treated with compounds in serum-free medium for 3 hr in triplicate. Cells were fixed with 4% formaldehyde, quenched with 0.6% H2O2, blocked with 5% BSA, incubated with either phospho S6 antibody or total S6 antibody overnight, incubated with goat-anti-rabbit-IgG-HRP for 1 hr, and developed in chemiluminescent substrate.

Biological Example 4

$PIP_3$ Assay

MCF-7 cells grown in 10-cm dishes were starved for 3 hours in DMEM, and then treated with compounds for 20 minutes. In the last 2 minutes of the incubation with the compounds, EGF (100 ng/ml) was added to stimulate the production of PIP3. The medium was aspirated and the cells were scraped with 10% trichloroacetic acid. The lipids were extracted from the pellet after the cell lysates were centrifuged. PIP3 in the cellular lipid extraction was quantified with the AlphaScreen [Registered TM of PerkinElmer] assay in which Grp1-PH is used as the PIP3 specific probe. The amount of cellular PIP3 was calculated from the standard curve of $diC_8$ PI (3,4,5) P3.

Biological Example 5-10

In Vivo Models

Compound A is a Compound of Formula I. Compound B is N-(3,4-dichloro-2-fluorophenyl)-7-({[(3aR,5r,6aS)-2-methyloctahydrocyclopenta-[c]pyrrol-5-yl]methyl}oxy)-6-(methyloxy)quinazolin-4-amine.

Female and male athymic nude mice (NCr) 5-8 weeks of age and weighing approximately 20-25 g were used in the following model. Prior to initiation of a study, the animals were allowed to acclimate for a minimum of 48 h. During these studies, animals were provided food and water ad libitum and housed in a room conditioned at 70-75° F. and 60% relative humidity. A 12 h light and 12 h dark cycle was maintained with automatic timers. All animals were examined daily for compound-induced or tumor-related deaths.

PC-3 human prostate adenocarcinoma cells were cultured in vitro in DMEM (Mediatech) supplemented with 20% Fetal Bovine Serum (Hyclone), Penicillin-Streptomycin and non-essential amino acids at 37° C. in a humidified 5% $CO_2$ atmosphere. On day 0, cells were harvested by trypsinization and 3×10⁶ cells (passage 13, 99% viability) in 0.1 mL of ice-cold Hank's balanced salt solution were implanted subcutaneously into the hindflank of 5-8 week old male nude mice. A transponder was implanted in each mouse for identification, and animals were monitored daily for clinical symptoms and survival. Body weights were recorded daily. Experiments were conducted with Compound A as a single agent as well as Compound A in combination with Taxol and Compound A in combination with Rapamycin. This model can be used to assess the desirability of treating with Compound A in combination with other anti-cancer agents.

U-87 MG human glioblastoma cells were cultured in vitro in DMEM (Mediatech) supplemented with 10% Fetal Bovine Serum (Hyclone), Penicillin-Streptomycin and non-essential amino acids at 37° C. in a humidified 5% $CO_2$ atmosphere. On day 0, cells were harvested by trypsinization and 2×10⁶ cells (passage 5, 96% viability) in 0.1 mL of ice-cold Hank's balanced salt solution were implanted intradermally into the hindflank of 5-8 week old female nude mice. A transponder was implanted in each mouse for identification, and animals were monitored daily for clinical symptoms and survival. Body weights were recorded daily. Experiments were conducted with Compound A as a single agent and the results are not included. This model can be used to assess the desirability of treating with Compound A in combination with other anti-cancer agents.

A549 human lung carcinoma cells were cultured in vitro in DMEM (Mediatech) supplemented with 10% Fetal Bovine Serum (Hyclone), Penicillin-Streptomycin and non-essential amino acids at 37° C. in a humidified 5% $CO_2$ atmosphere. On day 0, cells were harvested by trypsinization and 10×10⁶ cells (passage 12, 99% viability) in 0.1 mL of ice-cold Hank's balanced salt solution were implanted intradermally into the hindflank of 5-8 week old female nude mice. A transponder was implanted in each mouse for identification, and animals were monitored daily for clinical symptoms and survival. Body weights were recorded daily. Experiments were conducted with Compound A as a single agent as well as Compound A in combination with Compound B. This model can be used to assess the desirability of treating with Compound A in combination with other anti-cancer agents.

MDA-MB-468 human breast adenocarcinoma cells, passage number <6, were maintained and propagated in log-phase growth in Dulbecco's Modification of Eagles's Medium (DMEM; Mediatech) containing L-Glutamine supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization, and 10×10⁶ cells (passage 10, 98% viability) in 50% cold Hanks balanced salt solution/50% Matrigel (100 μL total volume per mouse) were implanted subcutaneously into the mammary fat pads of female nude mice. Experiments were conducted with Compound A as a single agent as well as Compound A in combination with erlotinib. This model can be used to assess the desirability of treating with Compound A in combination with other anti-cancer agents.

Calu-6 human lung anaplastic carcinoma cells were cultured in vitro in DMEM (Mediatech) supplemented with 10% Fetal Bovine Serum (Hyclone), Penicillin-Streptomycin and non-essential amino acids at 37° C. in a humidified, 5% $CO_2$ atmosphere. On day 0, cells were harvested by trypsinization, and 5×10⁶ cells (passage #8, 96% viability) in 0.1 mL ice-cold Hank's balanced salt solution were implanted intradermally in the hind-flank of 5-8 week old female athymic nude mice. A transponder was implanted in each mouse for identification, and animals were monitored daily for clinical symptoms and survival. Body weights were recorded daily. Experiments were conducted with Compound A as a single agent as well as Compound A in combination with carboplatin. This model can be used to assess the desirability of treating with Compound A in combination with other anti-cancer agents.

MCF7 human mammary adenocarcinoma cells were cultured in vitro in DMEM (Cellgro) supplemented with 10% Fetal Bovine Serum (Cellgro), Penicillin-Streptomycin and non-essential amino acids at 37° C. in a humidified 5% $CO_2$ atmosphere. On day 0, cells were harvested by trypsinization, and 5×10⁶ cells (passage 10 and 95.4% viability for Study 1, passage 9 and 90% viability for Study 2) in 100 μL of a solution made of 50% cold Hanks balanced salt solution with 50% growth factor reduced matrigel (R&D Systems for Study 1 and Becton Dickinson for Study 2) implanted subcutaneously into the hindflank of female nude mice.

For subcutaneous or intradermal tumors, the mean tumor weight of each animal in the respective control and treatment groups was determined twice weekly during the study. Tumor weight (TW) was determined by measuring perpendicular diameters with a caliper, using the following formula:

$$\text{tumor weight (mg)} = [\text{tumor volume} = \text{length (mm)} \times \text{width}^2 \text{ (mm}^2\text{)}]/2$$

These data were recorded and plotted on a tumor weight vs. days post-implantation line graph and presented graphically as an indication of tumor growth rates. Percent inhibition of tumor growth (TGI) is determined with the following formula:

$$\left(1 - \left(\frac{(X_f - X_0)}{(Y_f - X_0)}\right)\right) * 100$$

where $X_0$=average TW of all tumors on group day
$X_f$=TW of treated group on Day f
$Y_f$=TW of vehicle control group on Day f
If tumors regress below their starting sizes, then the percent tumor regression is determined with the following formula:

$$\left(\frac{(X_0 - X_f)}{X_0}\right) * 100$$

Tumor size is calculated individually for each tumor to obtain a mean±SEM value for each experimental group. Statistical significance is determined using the 2-tailed Student's t-test (significance defined as P<0.05).

Biological Examples 11-16

Compound A is a Compound of Formula I and is an inhibitor of class I PI3-kinases. Compound B is N-(3,4-dichloro-2-fluorophenyl)-7-({[(3aR,5r,6aS)-2-methyloctahydrocyclopenta-[c]pyrrol-5-yl]methyl}oxy)-6-(methyloxy)quinazolin-4-amine.

Prostate Cancer Xenograft Model—A Compound of Formula I in Combination with Taxol Compound A was tested alone and in combination with taxol in a prostate carcinoma tumor model. PC-3 is a human prostate carcinoma cell line that harbors a homozygous deletion mutation in PTEN, which results in constitutive activation of the PI3K pathway. In single-dose pharmacodynamic experiments, oral administration of Compound A results in a dose-dependent decrease in the phosphorylation of AKT, p70S6K, and S6 in PC-3 tumors grown ectopically in mice. Repeat-dose administration of a Compound A also inhibits the growth of these tumors, but does not induce regressions.

Oral administration of Compound A at 100 mg/kg qd or 300 mg/kg biweekly (biw) resulted in substantial tumor growth inhibition in mice. See FIG. 1. Comparable tumor growth inhibition was achieved with 7.5 mg/kg taxol administered i.v. twice weekly. While tumor growth was inhibited substantially with Compound A alone, the combination of either dose of Compound A with taxol was superior to either agent alone and induced significant regression of the tumors. Body weight loss and dose skipping was minimal in all groups, and was not exacerbated in the combination group indicating that the combination was well tolerated. These results support the use of a Compound of Formula I in combination with taxol in tumors with constitutively activated PI3K signaling.

Prostate Cancer Xenograft Model—A Compound of Formula I in Combination with Rapamycin Compound A was tested alone and in combination with rapamycin in a prostate carcinoma tumor model (PC-3 cell line). Oral administration of Compound A at 100 mg/kg qd resulted in substantial tumor growth inhibition. See FIG. 2. Comparable tumor growth inhibition was achieved with 5 mg/kg rapamycin administered i.p. daily. While tumor growth was inhibited substantially with Compound A alone, the combination of Compound A with rapamycin was superior to either agent alone and induced significant regression of the tumors. Body weight loss and dose skipping was minimal with each agent alone, but body weight loss was exacerbated in the combination group necessitating dose skipping. The fact that tumor regression was observed despite dose skipping suggests that using an intermittent dosing schedule would maintain efficacy and improve tolerability. These results support the use of a Compound of Formula I in combination with rapamycin in tumors with constitutively activated PI3K signaling.

Non-Small Cell Lung Cancer Xenograft Model—A Compound of Formula I in Combination with Carboplatin Compound A was tested both as a single agent and in combination with carboplatin in a NSCLC tumor model.

Calu-6 is a human NSCLC cell line that harbors a heterozygous activating mutation in K-Ras (Q61K). Oral administration of a Compound A at 100 mg/kg qd or 300 mg/kg every fourth day (q4d) to mice bearing Calu-6 tumors resulted in substantial tumor growth inhibition. See FIG. 3. Both dose schedules resulted in similar inhibition of tumor growth. Significant tumor growth inhibition was also observed with 50 mg/kg carboplatin administered i.v. q4d, but was not as pronounced as with Compound A. While tumor growth was inhibited substantially with Compound A alone, the combination of the two agents was superior to either agent alone and resulted in almost complete inhibition of tumor growth. Body weight loss and dose skipping was minimal in all groups, and was not exacerbated in the combination group indicating that the combination was well tolerated. These results support the use of a Compound of Formula I both as a single agent and in combination with platins in tumors with activating mutations in K-Ras.

Non-Small Cell Lung Cancer Xenograft Model—A Compound of Formula I in Combination with Compound B Compound A was tested both as a single agent and in combination with Compound B. The A549 human non-small cell lung carcinoma cell line harbors a homozygous stop mutation in the gene encoding LKB1, and an activating G12S mutation in K-Ras, promoting activation of both PI3K and mTOR. A549 cells also express wild-type EGFR.

As a single agent, Compound B, an inhibitor of EGFR, was orally administered once-daily at 30 mg/kg and Compound A was orally administered either at 30 mg/kg qd or 100 mg/kg q2d. Combination therapies consisted of Compound B with Compound A at 30 mg/kg or 100 mg/kg. Administration of each agent in the combination groups was separated by 6 h. Single agent administration of Compound B for 18 days caused a significant tumor growth inhibition of 80%. See FIG. 4a. A significant tumor growth inhibition of 96% was observed with Compound A at 100 mg/kg q2d, whereas Compound A at 30 mg/kg qd lead to a lower but still significant TGI of 76%. The combination of Compound B 30 mg/kg qd with Compound A 30 mg/kg qd or with Compound A 100 mg/kg q2d resulted in significant efficacy associated with 15% and 39% regression, respectively, which was significantly higher than either of the single agent treatments alone.

As a single agent Compound B dosed at 30 mg/kg qd was generally well tolerated, with a body weight loss of 1.5-6.9% and no dose omission. Administration of Compound A dosed at 30 mg/kg qd was well tolerated with 4 doses skipped at the beginning of the study, which were not compound-related. Compound A dosed at 100 mg/kg q2d was also well tolerated with 1 dose skipped at the beginning of the study, which was not compound-related. The combination of Compound B at 30 mg/kg qd with Compound A at 30 mg/kg qd was fairly well tolerated with body weight loss of 1 to 8% and 2 doses skipped). However, the combination of Compound B at 30 mg/kg qd with Compound A at 100 mg/kg q2d was associated with body weight loss of 2 to 11% and 13 doses skipped within the first 10 days; however, body weights at the end of the study were not significantly different from the vehicle-treated control group. Single agent administration of Compound B and Compound A were well tolerated with minimal dose skipping. When administered in combination, minor body weight loss was observed that necessitated dose skipping primarily in the 100 mg/kg q2d group.

Breast Cancer Xenograft Model—A Compound of Formula I in Combination with Compound B Compound A was tested both as a single agent and in combination with Compound B, an EGFR inhibitor, in a breast tumor model. The MCF7 human breast carcinoma cell line harbors a heterozygous, activating mutation in PI3K (PI3KCA/E545K) and expresses wild-type EGFR.

Compound B was administered orally once-daily (qd) at 30 mg/kg, and Compound A was administered once-daily at 30 mg/kg or once every other day (q2d) at 100 mg/kg. Combination therapies consisted of Compound B together with Compound A at 30 mg/kg qd or 100 mg/kg q2d. Single agent administration of Compound B at 30 mg/kg qd for 14 days caused a tumor growth inhibition of 38%-61%. See FIGS. 4b-1 and 4b-2. A significant tumor growth inhibition of 83%-91% was observed with Compound A at 100 mg/kg q2d, whereas Compound A at 30 mg/kg qd lead to a lower but still significant TGI of 57%. The combination of Compound B at 30 mg/kg qd with Compound A at 100 mg/kg q2d resulted in a significant efficacy associated with 16-22% regression, which was significantly higher than either of the single agent treatments alone. Combining Compound B at 30 mg/kg qd with Compound A at 30 mg/kg qd lead to a lower but still significant tumor growth inhibition of 66%, but did not add any benefit to the anti-tumor efficacy of the single treatments.

As a single agent Compound B dosed at 30 mg/kg qd was generally well tolerated, with a non significant final body weight loss of 4.5 to 6.1% and 7 to 13 dose omissions. Administration of Compound A at 30 mg/kg qd and 100 mg/kg q2d was well tolerated with minimal dose skipping and body weight loss. The combination of Compound B at 30 mg/kg qd with Compound A at 30 mg/kg qd lead to a body weight loss of 4 to 13% throughout the study and 14 doses skipped mostly within the first 9 days. The combination of Compound B at 30 mg/kg qd with Compound A at 100 mg/kg q2d was associated with a body weight loss of 3.7 to 13% throughout the study and 20 to 32 dose omissions.

Breast Cancer Xenograft Model—A Compound of Formula I in Combination with Erlotinib Compound A was tested both as a single agent and in combination with erlotinib, in an erolitinib-resistant tumor model with elevated PI3K signaling.

MDA-MB-468 is a human breast carcinoma cell line that has an increase in the copy number of the EGFR gene and a homozygous deletion of PTEN. In vitro treatment of these cells with EGFR inhibitors such as erlotinib inhibits EGFR activity but fails to downregulate the PI3K pathway. Oral administration of erlotinib at 100 mg/kg qd to mice bearing MDA-MB-468 tumors resulted in significant but incomplete tumor growth inhibition. See FIG. 5. Oral administration of Compound A at 100 mg/kg qd resulted in a similar level of tumor growth inhibition. While tumor growth was inhibited substantially with Compound A alone, the combination of the two agents was superior to either agent alone and resulted in a regression of the tumors.

Mice administered Compound A at 100 mg/kg qd exhibited a modest (~3%) loss in body weight comparable to vehicle controls. Mice administered erlotinib exhibited an apparent decrease in their rate of body weight gain relative to vehicle controls. Coadministration with erlotinib resulted in a substantial loss in body weight in mice treated with Compound A (19% body weight loss from start of dosing). Consistent with these data, only minimal dose-skipping was required when Compound A was administered as monotherapy (1-3 doses skipped), but substantial dose-skipping was required for Compound A when erlotinib was coadministered. The fact that tumor regression was observed despite dose skipping suggests that use of an intermittent dosing schedule could maintain efficacy and improve tolerability. These results support the use of a Compound of Formula I in combination with erlotinib in tumors expressing EGF receptors and harboring PTEN deletions.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled. All patents, patent applications and publications cited in this application are hereby incorporated by reference in their entirety for all purposes to the same extent as if each individual patent, patent application or publication were so individually denoted.

What is claimed is:

1. A method of treating cancer which method comprises administering to a patient a therapeutically effective amount of a compound that is:

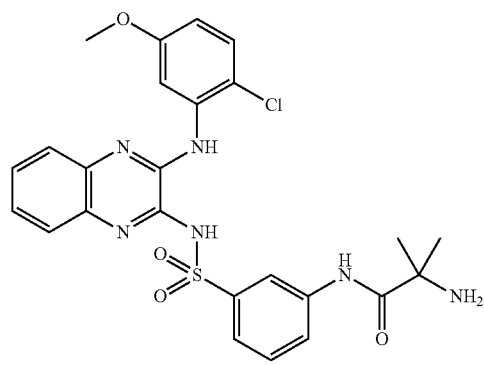 [SMILES: COc1ccc(Cl)c(Nc2nc3ccccc3nc2NS(=O)(=O)c2cccc(NC(=O)C(C)(C)N)c2)c1]

or a single isomer or tautomer thereof where the compound is optionally as a pharmaceutically acceptable salt in combination with one or more chemotherapeutic agents.

2. The method of claim 1 where the cancer is selected from breast cancer, colon cancer, rectal cancer, endometrial cancer, gastrointestinal carcinoid tumors, gastrointestinal stromal tumors, glioblastoma, hepatocellular carcinoma, small cell lung cancer, non-small cell lung cancer, melanoma, ovarian cancer, cervical cancer, pancreatic cancer, prostate carcinoma, acute myelogenous leukemia, chronic myelogenous leukemia, non-Hodgkin's lymphoma, and thyroid carcinoma.

3. The method of claim 1 where the treatment is one chemotherapeutic agent and the chemotherapeutic agent is a platin.

4. The method of claim 1 where the treatment is one chemotherapeutic agent and the chemotherapeutic agent is a taxane.

5. The method of claim 1 where the treatment is one chemotherapeutic agent and the chemotherapeutic agent is rapamycin or a rapamycin analogue.

6. The method of claim 1 where the treatment is one or two chemotherapeutic agents independently selected from rapamycin, a rapamycin analogue, an alkylating agent, a taxane, a platin, an EGFR inhibitor, and an ErbB2 inhibitor.

7. The method of claim 6 where the treatment is one or two chemotherapeutic agents independently selected from rapamycin, paclitaxel, carboplatin, lapatinib, and erlotinib.

8. The method of claim 1, where the treatment is one chemotherapeutic agent where the chemotherapeutic agent is erlotinib.

9. The method of claim 1, where the treatment is one chemotherapeutic agent where the chemotherapeutic agent is lapatinib.

10. The method of claim 1, where the treatment is one chemotherapeutic agent where the chemotherapeutic agent is carboplatin.

11. The method of claim 1, where the treatment is one chemotherapeutic agent where the chemotherapeutic agent is paclitaxel.

12. The method of claim 1, where the treatment is one chemotherapeutic agent where the chemotherapeutic agent is rapamycin.

13. The method of claim 1, where the treatment is one or two agents independently selected from rapamycin, temozolomide, paclitaxel, docetaxel, carboplatin, erlotinib, and lapatinib.

* * * * *